(12) United States Patent
Olland et al.

(10) Patent No.: US 7,155,346 B2
(45) Date of Patent: Dec. 26, 2006

(54) CRYSTAL STRUCTURE OF YQEJ AND USES THEREOF

(75) Inventors: Andrea M. Olland, Medford, MA (US); Mark L. Stahl, Lexington, MA (US); Francis X. Sullivan, Boulder, CO (US); Kathryn W. Underwood, Quincy, MA (US); Rajiv Chopra, Andover, MA (US)

(73) Assignees: Wyeth, Madison, NJ (US); Millennium Pharmaceuticals, Inc., Cambridge, MA (US)

( * ) Notice: Subject to any disclaimer, the term of this patent is extended or adjusted under 35 U.S.C. 154(b) by 353 days.

(21) Appl. No.: 10/209,041

(22) Filed: Jul. 31, 2002

(65) Prior Publication Data

US 2003/0124699 A1 Jul. 3, 2003

Related U.S. Application Data

(60) Provisional application No. 60/313,153, filed on Aug. 17, 2001, provisional application No. 60/340,613, filed on Dec. 7, 2001.

(51) Int. Cl.
G01N 33/48 (2006.01)
C12Q 1/48 (2006.01)

(52) U.S. Cl. ............... 702/19; 435/15; 702/27

(58) Field of Classification Search ............ 702/19, 702/27; 435/15, 4, 32
See application file for complete search history.

(56) References Cited

U.S. PATENT DOCUMENTS 5,130,105 A 7/1992 Carter et al.

6,664,074 B1* 12/2003 Youngman et al. .......... 435/32

OTHER PUBLICATIONS

Balducci, E., et al. (1995) Anal. Biochem. 228(1), 64-8.
Balducci, E., et al. (1995) Biochem. J. 310(Pt 2), 395-400.
Begley, T. P., (2001) Vitam. Horm. 61, 103-19.
Bell, C. E., Yeates, T. O., and Eisenberg, D. (1997) Protein Sci. 6(10), 2084-2096.
Brick, P., et al., (1988) J. Mol. Biol. 208, 83-98.
D'Angelo, I., et al. (2000) Structure Fold. Des. 8(9), 993-1004.
Emanuelli, M., et al. (1992) Arch. Biochem. Biophys. 298(1), 29-34.
Emanuelli, M., et al. (1999) FEBS Lett. 455(1-2), 13-7.
Emanuelli, M., et al. (2001) J. Biol. Chem. 276(1), 406-12.
Holm, L., and Sander, C. (1995) Trends Biochem. Sci. 20, 478-480.
Hughes, K. T., et al. (1983) J. Bacteriol. 155(1), 213-21.
Izard, T., and Geerlof, A. (1999) EMBO J. 18(8), 2021-30.
Lawrence, M. C., and Colman, P. M. (1993) J. Mol. Biol. 234, 946-950.
Magni, G., et al. (1999) Adv. Enzymol. Relat. Areas Mol Biol 73, 135-82.
Mehl, R. A., Kinsland, C., and Begley, T. P. (2000) J. Bacteriol. 182(15), 4372-4.
Natalini, P., et al. (1986) Biochemistry 25(12), 3725-9.
Petit, M. A., and Ehrlich, S. D. (2000) Nucleic Acids Res 28(23), 4642-8.
Raffaelli, et al., (1999) FEBS Lett. 444(2-3), 222-6.
Raffaelli, N., et al. (1997) J. Bacteriol. 179(24), 7718-23.

(Continued)

*Primary Examiner*—Nashaat T. Nashed
(74) *Attorney, Agent, or Firm*—Fish & Richardson P.C.

(57) ABSTRACT

This invention is directed to the crystal structure of yqeJ, and to the use of this structure in rational drug design methods to identify agents that may interact with active sites of yqeJ. Such agents may be useful as antibacterial agents.

16 Claims, 243 Drawing Sheets

OTHER PUBLICATIONS

Raffaelli, N., et al. (1999) J. Bacteriol. 181(17), 5509-11.
Raffaelli, N., et al. (1999) Mol. Cell. Biochem. 193(1-2), 99-102.
Rizzi, M., et al., (1996) EMBO J. 15(19), 5125-34.
Rould, M. A., Perona, J. J., and Steitz, T. A. (1991) Nature 352(6332), 213-8.
Saridakis, V., et al. (2001) J. Biol. Chem. 276(10), 7225-32.
Schweiger, M., et al. (2001) FEBS Lett. 492(1-2), 95-100.
von Delft, F., et al.,(2001) Structure (Camb) 9(5), 439-50.
Weber, C. H., et al. (1999) Structure 7, 1113-1124.
Ziegler, M. (2000) Eur. J. Biochem. 267(6), 1550-64.
Bacon et al. "A Fast Algorithm for Rendering Space-Filling Molecule Pictures" *J. Mol. Graph.* 6:219-220 (1988).
"The *CCP4* Suite: Programs for Protein Crystallography" *Acta. Cryst.* D50:760-763 (1994).
De La Fortelle et al. "Maximum-Likelihood Heavy-Atom Parameter Refinement for Multiple Isomorphous Replacement and Multiwavelength Anomalous Diffraction Methods" *Methods Enzymol.* 276:472-494 (1997).
Kraulis "*MOLSCRIPT*: a program to produce both detailed and schematic plots of protein structures" *J. Appl. Cryst.* 24:946-950 (1991).
Perrakis et al. "Automated protein model building combined with iterative structure refinement" *Nature Struct. Biol.* 6(5):458-463 (1999).
Philo "Measuring Sedimentation, Diffusion, and Molecular Weights of Small Molecules by Direct Fitting of Sedimentation Velocity Concentration Profiles" *Modern Analytical Ultracentrifugation* 156-170, (Schuster) Birkhäuser, Boston, MA (1994).
Rossman et al. "Evolutionary and Structural Relationships among Dehydrogenases" *The Enzymes* 61-102, Academic Press, New York (1975).
Terwilliger et al. "Automated MAD and MIR structure solution" *Acta. Cryst.* D55:849-861 (1999).
Weeks et al. "The design and implementation of *SnB* version 2.0" *J. of Appl. Cryst.* 32:120-124 (1999).
Makino et al., "Automated Flexible Ligand Docking Method and Its Application for Database Search" *J. Computational Chem.* 18(14):1812-1825 (1997).
Rice et al., "Single-wavelength anomalous diffraction phasing revisited" *Acta. Cryst.* D56:1413-1420 (2000).
Rould, "Screening for Heavy-Atom Derivatives and Obtaining Accurate Isomorphous Differences" *Methods Enzymology* 276:461-472 (1997).
Tapia et al., "Computer Assisted Simulations and Molecular Graphics Methods in Molecular Design. 1. Theory and Applications to Enzyme Active-Site Directed Drug Design" *Molecular Engin.* 3:377-414 (1994).
Walters et al., "Virtual screening—an overview" *DDT* 3(4):160-178 (1998).

\* cited by examiner

NAMN R=OH
NMN R=NH₂

ATP pyrophosphate

NAAD R=OH
NAD R=NH₂

β-strand 1    α-helix A    β-strand 2

```
B_subtilis       1  ----------------------------------------MKKIGIF GGTFDPFHNGHLLMANEVLYQAGLDEIWF
E_coli           1  ----------------------------------------MKSLQALF GGTFDPVHYGHLKPVETLANLIGLTRVTI
B_halodurans     1  ----------------------------------------MKRIGLL GGTFDPFHIGHLLAQEAIHCADLDEVWF
L_lactis         1  ----------------------------------------MDKGNRKKVGLL GGNFNPIHHAHLMADQVAQQMNLDKVLL
M_leprae         1  ---------------------------------------------M GGTFDPIHYGHLVAASEVAHMFELDEVMF
S_coelicolor     1  MGEHDTPTGPAHAPARGTQNAVPARATGPVQGPVNGPADGPSAGKRRLGVM GGTFDPIHYGHLVAASEVAAQFQLDEVVF
M_tuberculosis   1  ----------------------------------------------M GGTFDPIHYGHLVAASEVADLFDLDEVVF
T_pallidum       1  ----------------------------------------MKLALF GGSYDPVHLGHLLLADAVRHHAGYDRVLF
B_burgdorferi    1  ----------------------------------------MRIAIL GGTYNPVHIGHIFLAKEIEYLLNIDRVIF
N_meningitidis   1  ----------------------------------------MKKIGLF GGTFDPIHNGHLHIARAFADEIGLDAVVF
P_aeruginosa     1  ----------------------------------------MGKRIGLF GGTFDPVHIGHMRSAVEMAEQFALDELRL
```

α-helix B    β-strand 3    α-helix C    β-strand 4    α-turn

```
B_subtilis      37  MPNQIPPHKQNEDYTDSFHRVEMLKLAIQSNPS-FKLELVEMEREGPSYTFDTVSLLKQRY---PNDQLFPIIGADMIEY
E_coli          38  IPNNVPPHRP-QPEANSVQRKHMLELAIADKPL-GTLDERELKRNAPSYTAQTLKEWRQEQG---PDVPLAPILGQDSLLT
B_halodurans    37  VPVGIPPHKEREEIASNDDRLAMIKRAIKGKETLGNICTIELEREGKSYTIDTVRTLTKKH---PDVRFFPIIGGDMVKS
L_lactis        42  MPENIPPLVDEKETISAKHRVKMLELAIKENPR-LGLELIEHERGGKSMSYDTLKLLTEAN---PDTDYYFIIGSDMVEY
M_leprae        31  VPSGQPWQKG-RHVSAAEDRYLMTVIATASNPR-FSVSRVDHDRTGPTYTRDTVHDLHALN---PDSELYFITGADALAS
S_coelicolor    81  VPTGQPWQKSHRAVSAAEDRYLMTVIATASNPQ-GSVSRIDHDRGCPTYTKDTLRDLRALN---PDADDLFPITGADALAQ
M_tuberculosis  31  VPSGQPWQKG-RQVSAAEHRYLMTVIATASNPR-FSVSRVDHDRGCPTYTKDTLADLHALH---PDSELYETTGADALAS
T_pallidum      36  VPTFVSPFKEKEGSASAHDRVRMLHLAIGTTPY-GSVEECERRRGCISYTAEIVQHVREKYGAQLEGKLALVLGEDAARS
B_burgdorferi   36  IPTCNPAHKLIDENVSVSNRIDMLKLALENEDK-MFIDDCDTINGGITYTVDTISCVKKKY---KNDKLFLIIGDDLFQN
N_meningitidis  37  LPTGGPYHKD-AASASAADRLAMVELATAEDAR-GAVSDCDTVRECATYTFDTVQIFRQQF---PSAQLWWLMGSDSLMK
P_aeruginosa    38  LPNARPPHRE-TPQVSAAQRLAMVERAVAGVER-LTVDPRELQRDKPSLTIDTLESVRAELA-ADDQLFMLIGWDAFCG
```

α-helix D    β-strand 5                      β-strand 6    α-helix E

```
B_subtilis     113  LPKWYKLDELLNLIQFIGVKRPGFHVETPY----------P--------------LLFADVPEFEVSSIMIRERFKSKKP
E_coli         114  FPTWYEYETILDNAHLIVCRRPGYPLEMAQPQYQQWLEDHLTHNPEDLHLQPAGKIYLAETPWFNISATIIRERLQNGES
B_halodurans   114  LPTWKGIDELLATVTFIGFKRPGVLLDSPY----------QD----Q-------LMLVEGPEVNVSST---I-------
L_lactis       118  LPKWYKIDELLKLVTFIALRKKDTISKSPY----------P--------------VTWLDAPLLPISSMLREMFAKNIE
M_leprae       106  ILSWQGWDELFDLARFVGVSRPGYELGQEH----------ITGVMGELP---ADALTLVEIPALAISSTDCRQRVEQRQP
S_coelicolor   157  ILTWRDSEELFSLAHFIGVTRPGHTLTDAG----------LP--KGGVS-------LVEVPALAISSTDCRARVAKGDP
M_tuberculosis 106  IMSWQGWEELFELARFVGVSRPGYELRNEH----------ITSLLGQLA---------------------
T_pallidum     115  VPHWHAFDSWSTHVDEVVGARPVTSGDGGN---------------------------
B_burgdorferi  112  FDSWKDPQSIVSSVELVVAHRIYKERLKSSFKH---------------------
N_meningitidis 112  LHTWKKWQMFVRETNIAVAMRQGDSLHQTP----------R-----EL----------------
P_aeruginosa   114  LPTWHRWEALLDHCHIVVLQRFDADSEPPE-SLRDLLAARSVADPQALK-GPGGQITFVWQTPLAVSAAQIRALLGAGRS
```

α-helix F

```
B_subtilis     169  TDYLIPDKVKKYVEENGLYES-------------------------------
E_coli         194  CEDLLPEPVLTYINQQGLYR--------------------------------
B_halodurans   160  --------------------------------------------------
L_lactis       174  PTYFLPQNVIDYIKTEKLYKKR-------------------------------
M_leprae       173  LWYLMPDGVVQYVFKRRLYRGPHGVAGTGRLTTPSLVVGNNTMIRERMTEGKPISYLLPLDV
S_coelicolor   217  VWYLVPDGVVRYIDKRHLYRGE------------------------------
M_tuberculosis 144  --------------------------------------------------
T_pallidum     144  --------------------------------------------------
B_burgdorferi  144  --------------------------------------------------
N_meningitidis 144  --------------------------------------------------
P_aeruginosa   192  VRFLVPDAVLNYIEAHHLYRAPH-----------------------------
```

Figure 2

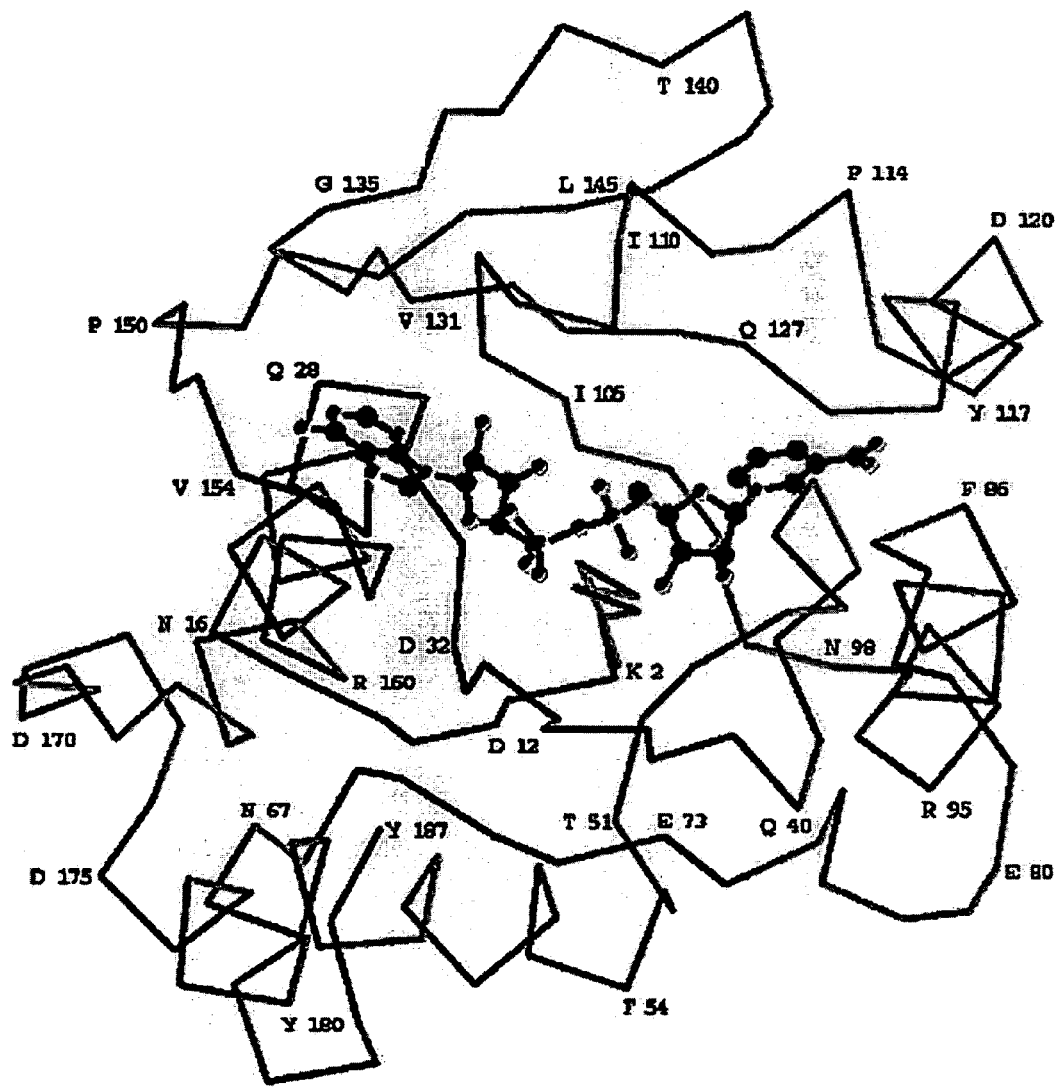
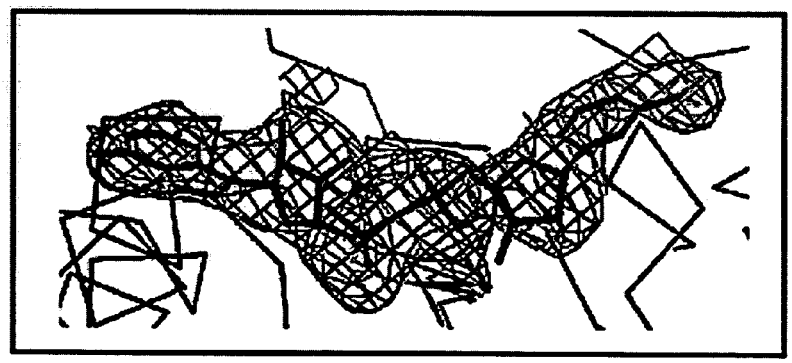
Figure 8A

Figure 9 (1 of 92)

|  | | Atom Type | Res. | MOL. | Res. No. | X | Y | Z | OCC. | B | |
|---|---|---|---|---|---|---|---|---|---|---|---|
| ATOM | 1 | CB | SER | A | 1 | 44.683 | -5.215 | 1.526 | 1.00 | 37.99 | A |
| ATOM | 2 | OG | SER | A | 1 | 44.384 | -4.990 | 0.159 | 1.00 | 40.08 | A |
| ATOM | 3 | C | SER | A | 1 | 44.545 | -2.769 | 2.020 | 1.00 | 35.73 | A |
| ATOM | 4 | O | SER | A | 1 | 44.779 | -1.915 | 1.165 | 1.00 | 36.87 | A |
| ATOM | 5 | N | SER | A | 1 | 45.730 | -4.270 | 3.564 | 1.00 | 38.12 | A |
| ATOM | 6 | CA | SER | A | 1 | 45.412 | -4.014 | 2.130 | 1.00 | 36.87 | A |
| ATOM | 7 | N | LYS | A | 2 | 43.541 | -2.675 | 2.887 | 1.00 | 32.84 | A |
| ATOM | 8 | CA | LYS | A | 2 | 42.644 | -1.520 | 2.913 | 1.00 | 31.33 | A |
| ATOM | 9 | CB | LYS | A | 2 | 41.177 | -1.954 | 2.839 | 1.00 | 31.86 | A |
| ATOM | 10 | CG | LYS | A | 2 | 40.660 | -2.348 | 1.473 | 1.00 | 32.81 | A |
| ATOM | 11 | CD | LYS | A | 2 | 39.166 | -2.620 | 1.580 | 1.00 | 33.87 | A |
| ATOM | 12 | CE | LYS | A | 2 | 38.510 | -2.704 | 0.225 | 1.00 | 35.62 | A |
| ATOM | 13 | NZ | LYS | A | 2 | 37.039 | -2.830 | 0.356 | 1.00 | 37.05 | A |
| ATOM | 14 | C | LYS | A | 2 | 42.821 | -0.713 | 4.199 | 1.00 | 28.85 | A |
| ATOM | 15 | O | LYS | A | 2 | 42.952 | -1.271 | 5.290 | 1.00 | 26.45 | A |
| ATOM | 16 | N | LYS | A | 3 | 42.817 | 0.605 | 4.064 | 1.00 | 26.71 | A |
| ATOM | 17 | CA | LYS | A | 3 | 42.934 | 1.477 | 5.220 | 1.00 | 25.60 | A |
| ATOM | 18 | CB | LYS | A | 3 | 43.918 | 2.606 | 4.918 | 1.00 | 26.55 | A |
| ATOM | 19 | CG | LYS | A | 3 | 45.364 | 2.099 | 4.835 | 1.00 | 27.91 | A |
| ATOM | 20 | CD | LYS | A | 3 | 46.336 | 3.171 | 4.365 | 1.00 | 32.34 | A |
| ATOM | 21 | CE | LYS | A | 3 | 46.410 | 4.343 | 5.333 | 1.00 | 35.16 | A |
| ATOM | 22 | NZ | LYS | A | 3 | 47.348 | 5.402 | 4.849 | 1.00 | 37.90 | A |
| ATOM | 23 | C | LYS | A | 3 | 41.519 | 1.988 | 5.469 | 1.00 | 23.98 | A |
| ATOM | 24 | O | LYS | A | 3 | 40.960 | 2.735 | 4.659 | 1.00 | 23.18 | A |
| ATOM | 25 | N | ILE | A | 4 | 40.941 | 1.556 | 6.584 | 1.00 | 21.86 | A |
| ATOM | 26 | CA | ILE | A | 4 | 39.569 | 1.902 | 6.929 | 1.00 | 20.02 | A |
| ATOM | 27 | CB | ILE | A | 4 | 38.772 | 0.619 | 7.267 | 1.00 | 20.63 | A |
| ATOM | 28 | CG2 | ILE | A | 4 | 37.293 | 0.951 | 7.436 | 1.00 | 18.05 | A |
| ATOM | 29 | CG1 | ILE | A | 4 | 38.991 | -0.448 | 6.185 | 1.00 | 19.75 | A |
| ATOM | 30 | CD1 | ILE | A | 4 | 38.467 | -0.072 | 4.830 | 1.00 | 21.08 | A |
| ATOM | 31 | C | ILE | A | 4 | 39.382 | 2.879 | 8.091 | 1.00 | 19.91 | A |
| ATOM | 32 | O | ILE | A | 4 | 39.929 | 2.683 | 9.178 | 1.00 | 18.56 | A |
| ATOM | 33 | N | GLY | A | 5 | 38.579 | 3.916 | 7.860 | 1.00 | 19.30 | A |
| ATOM | 34 | CA | GLY | A | 5 | 38.293 | 1.882 | 8.909 | 1.00 | 19.98 | A |

Figure 9 (2 of 92)

| ATOM | 35 | C | GLY | A | 5 | 36.953 | 4.591 | 9.581 | 1.00 | 21.12 | A |
|---|---|---|---|---|---|---|---|---|---|---|---|
| ATOM | 36 | O | GLY | A | 5 | 35.898 | 4.748 | 8.955 | 1.00 | 22.71 | A |
| ATOM | 37 | N | ILE | A | 6 | 36.981 | 4.153 | 10.841 | 1.00 | 19.98 | A |
| ATOM | 38 | CA | ILE | A | 6 | 35.746 | 3.863 | 11.576 | 1.00 | 20.04 | A |
| ATOM | 39 | CB | ILE | A | 6 | 35.991 | 2.914 | 12.774 | 1.00 | 20.90 | A |
| ATOM | 40 | CG2 | ILE | A | 6 | 34.666 | 2.602 | 13.455 | 1.00 | 19.25 | A |
| ATOM | 41 | CG1 | ILE | A | 6 | 36.652 | 1.609 | 12.309 | 1.00 | 21.29 | A |
| ATOM | 42 | CD1 | ILE | A | 6 | 35.821 | 0.785 | 11.346 | 1.00 | 22.69 | A |
| ATOM | 43 | C | ILE | A | 6 | 35.177 | 5.180 | 12.111 | 1.00 | 18.69 | A |
| ATOM | 44 | O | ILE | A | 6 | 35.810 | 5.854 | 12.929 | 1.00 | 19.20 | A |
| ATOM | 45 | N | PHE | A | 7 | 33.970 | 5.517 | 11.662 | 1.00 | 17.88 | A |
| ATOM | 46 | CA | PHE | A | 7 | 33.299 | 6.760 | 12.017 | 1.00 | 15.97 | A |
| ATOM | 47 | CB | PHE | A | 7 | 33.059 | 7.542 | 10.716 | 1.00 | 19.01 | A |
| ATOM | 48 | CG | PHE | A | 7 | 32.347 | 8.860 | 10.889 | 1.00 | 18.70 | A |
| ATOM | 49 | CD1 | PHE | A | 7 | 32.539 | 9.640 | 12.021 | 1.00 | 20.52 | A |
| ATOM | 50 | CD2 | PHE | A | 7 | 31.506 | 9.335 | 9.880 | 1.00 | 20.73 | A |
| ATOM | 51 | CE1 | PHE | A | 7 | 31.900 | 10.880 | 12.151 | 1.00 | 22.05 | A |
| ATOM | 52 | CE2 | PHE | A | 7 | 30.864 | 10.569 | 9.994 | 1.00 | 19.99 | A |
| ATOM | 53 | CZ | PHE | A | 7 | 31.061 | 11.345 | 11.134 | 1.00 | 20.35 | A |
| ATOM | 54 | C | PHE | A | 7 | 31.994 | 6.493 | 12.765 | 1.00 | 17.47 | A |
| ATOM | 55 | O | PHE | A | 7 | 30.958 | 6.214 | 12.161 | 1.00 | 15.95 | A |
| ATOM | 56 | N | GLY | A | 8 | 32.052 | 6.578 | 14.092 | 1.00 | 17.52 | A |
| ATOM | 57 | CA | GLY | A | 8 | 30.873 | 6.328 | 14.897 | 1.00 | 17.72 | A |
| ATOM | 58 | C | GLY | A | 8 | 30.007 | 7.556 | 15.101 | 1.00 | 16.90 | A |
| ATOM | 59 | O | GLY | A | 8 | 30.471 | 8.677 | 14.946 | 1.00 | 15.27 | A |
| ATOM | 60 | N | GLY | A | 9 | 28.741 | 7.335 | 15.445 | 1.00 | 17.64 | A |
| ATOM | 61 | CA | GLY | A | 9 | 27.816 | 8.437 | 15.674 | 1.00 | 16.61 | A |
| ATOM | 62 | C | GLY | A | 9 | 26.396 | 7.924 | 15.859 | 1.00 | 16.96 | A |
| ATOM | 63 | O | GLY | A | 9 | 26.156 | 6.715 | 15.760 | 1.00 | 16.11 | A |
| ATOM | 64 | N | THR | A | 10 | 25.452 | 8.817 | 16.156 | 1.00 | 16.90 | A |
| ATOM | 65 | CA | THR | A | 10 | 24.064 | 8.386 | 16.305 | 1.00 | 16.95 | A |
| ATOM | 66 | CB | THR | A | 10 | 23.244 | 9.291 | 17.259 | 1.00 | 19.15 | A |
| ATOM | 67 | OG1 | THR | A | 10 | 23.183 | 10.622 | 16.728 | 1.00 | 19.14 | A |
| ATOM | 68 | CG2 | THR | A | 10 | 23.861 | 9.307 | 18.647 | 1.00 | 15.61 | A |
| ATOM | 69 | C | THR | A | 10 | 23.422 | 8.464 | 14.933 | 1.00 | 18.10 | A |
| ATOM | 70 | O | THR | A | 10 | 22.540 | 7.664 | 14.603 | 1.00 | 18.51 | A |
| ATOM | 71 | N | PHE | A | 11 | 23.887 | 9.424 | 14.131 | 1.00 | 16.92 | A |
| ATOM | 72 | CA | PHE | A | 11 | 23.357 | 9.635 | 12.787 | 1.00 | 17.31 | A |
| ATOM | 73 | CB | PHE | A | 11 | 23.863 | 8.538 | 11.849 | 1.00 | 15.51 | A |
| ATOM | 74 | CG | PHE | A | 11 | 25.368 | 8.415 | 11.824 | 1.00 | 17.21 | A |
| ATOM | 75 | CD1 | PHE | A | 11 | 26.002 | 7.308 | 12.387 | 1.00 | 16.75 | A |
| ATOM | 76 | CD2 | PHE | A | 11 | 26.153 | 9.423 | 11.269 | 1.00 | 15.57 | A |
| ATOM | 77 | CE1 | PHE | A | 11 | 27.397 | 7.208 | 12.399 | 1.00 | 15.85 | A |
| ATOM | 78 | CE2 | PHE | A | 11 | 27.546 | 9.335 | 11.274 | 1.00 | 19.34 | A |
| ATOM | 79 | CZ | PHE | A | 11 | 28.172 | 8.220 | 11.843 | 1.00 | 18.30 | A |
| ATOM | 80 | C | PHE | A | 11 | 21.836 | 9.624 | 12.888 | 1.00 | 17.52 | A |
| ATOM | 81 | O | PHE | A | 11 | 21.142 | 8.885 | 12.186 | 1.00 | 18.29 | A |
| ATOM | 82 | N | ASP | A | 12 | 21.330 | 10.460 | 13.785 | 1.00 | 17.83 | A |
| ATOM | 83 | CA | ASP | A | 12 | 19.895 | 10.557 | 14.037 | 1.00 | 16.89 | A |
| ATOM | 84 | CB | ASP | A | 12 | 19.613 | 9.976 | 15.427 | 1.00 | 17.71 | A |
| ATOM | 85 | CG | ASP | A | 12 | 18.131 | 9.941 | 15.767 | 1.00 | 21.82 | A |
| ATOM | 86 | OD1 | ASP | A | 12 | 17.299 | 9.762 | 14.843 | 1.00 | 19.78 | A |
| ATOM | 87 | OD2 | ASP | A | 12 | 17.812 | 10.074 | 16.973 | 1.00 | 22.75 | A |
| ATOM | 88 | C | ASP | A | 12 | 19.439 | 12.015 | 13.940 | 1.00 | 16.01 | A |
| ATOM | 89 | O | ASP | A | 12 | 19.046 | 12.633 | 14.933 | 1.00 | 15.72 | A |
| ATOM | 90 | N | PRO | A | 13 | 19.418 | 12.564 | 12.716 | 1.00 | 16.03 | A |
| ATOM | 91 | CD | PRO | A | 13 | 18.738 | 13.848 | 12.460 | 1.00 | 16.56 | A |
| ATOM | 92 | CA | PRO | A | 13 | 19.788 | 11.914 | 11.452 | 1.00 | 16.39 | A |
| ATOM | 93 | CB | PRO | A | 13 | 18.716 | 12.429 | 10.511 | 1.00 | 16.27 | A |
| ATOM | 94 | CG | PRO | A | 13 | 18.656 | 13.897 | 10.919 | 1.00 | 17.29 | A |
| ATOM | 95 | C | PRO | A | 13 | 21.179 | 12.275 | 10.931 | 1.00 | 15.98 | A |
| ATOM | 96 | O | PRO | A | 13 | 21.858 | 13.142 | 11.487 | 1.00 | 17.80 | A |
| ATOM | 97 | N | PRO | A | 14 | 21.621 | 11.603 | 9.855 | 1.00 | 16.45 | A |
| ATOM | 98 | CD | PRO | A | 14 | 20.951 | 10.515 | 9.127 | 1.00 | 18.09 | A |
| ATOM | 99 | CA | PRO | A | 14 | 22.929 | 11.885 | 9.262 | 1.00 | 16.62 | A |
| ATOM | 100 | CB | PRO | A | 14 | 23.125 | 10.745 | 8.260 | 1.00 | 18.66 | A |

Figure 9 (3 of 92)

| ATOM | 101 | CG  | PRO | A | 14 | 22.114 | 9.710  | 8.663  | 1.00 | 20.95 | A |
|------|-----|-----|-----|---|----|--------|--------|--------|------|-------|---|
| ATOM | 102 | C   | PRO | A | 14 | 22.708 | 13.216 | 8.545  | 1.00 | 16.42 | A |
| ATOM | 103 | O   | PRO | A | 14 | 21.604 | 13.475 | 8.054  | 1.00 | 13.88 | A |
| ATOM | 104 | N   | HIS | A | 15 | 23.738 | 14.053 | 8.488  | 1.00 | 15.95 | A |
| ATOM | 105 | CA  | HIS | A | 15 | 23.620 | 15.358 | 7.852  | 1.00 | 14.00 | A |
| ATOM | 106 | CB  | HIS | A | 15 | 23.315 | 16.402 | 8.917  | 1.00 | 14.54 | A |
| ATOM | 107 | CG  | HIS | A | 15 | 24.300 | 16.405 | 10.042 | 1.00 | 15.88 | A |
| ATOM | 108 | CD2 | HIS | A | 15 | 24.162 | 16.084 | 11.350 | 1.00 | 15.17 | A |
| ATOM | 109 | ND1 | HIS | A | 15 | 25.619 | 16.765 | 9.871  | 1.00 | 15.52 | A |
| ATOM | 110 | CE1 | HIS | A | 15 | 26.249 | 16.671 | 11.028 | 1.00 | 16.39 | A |
| ATOM | 111 | NE2 | HIS | A | 15 | 25.387 | 16.259 | 11.941 | 1.00 | 17.33 | A |
| ATOM | 112 | C   | HIS | A | 15 | 24.910 | 15.711 | 7.110  | 1.00 | 13.55 | A |
| ATOM | 113 | O   | HIS | A | 15 | 25.883 | 14.958 | 7.156  | 1.00 | 12.75 | A |
| ATOM | 114 | N   | ASN | A | 16 | 24.914 | 16.855 | 6.437  | 1.00 | 12.46 | A |
| ATOM | 115 | CA  | ASN | A | 16 | 26.075 | 17.285 | 5.652  | 1.00 | 14.17 | A |
| ATOM | 116 | CB  | ASN | A | 16 | 25.777 | 18.604 | 4.924  | 1.00 | 13.04 | A |
| ATOM | 117 | CG  | ASN | A | 16 | 24.663 | 18.471 | 3.899  | 1.00 | 14.00 | A |
| ATOM | 118 | OD1 | ASN | A | 16 | 24.339 | 17.368 | 3.462  | 1.00 | 12.06 | A |
| ATOM | 119 | ND2 | ASN | A | 16 | 24.085 | 19.602 | 3.495  | 1.00 | 11.18 | A |
| ATOM | 120 | C   | ASN | A | 16 | 27.373 | 17.430 | 6.445  | 1.00 | 14.15 | A |
| ATOM | 121 | O   | ASN | A | 16 | 28.456 | 17.254 | 5.892  | 1.00 | 15.23 | A |
| ATOM | 122 | N   | GLY | A | 17 | 27.264 | 17.761 | 7.730  | 1.00 | 14.71 | A |
| ATOM | 123 | CA  | GLY | A | 17 | 28.452 | 17.909 | 8.553  | 1.00 | 14.41 | A |
| ATOM | 124 | C   | GLY | A | 17 | 29.161 | 16.572 | 8.662  | 1.00 | 15.34 | A |
| ATOM | 125 | O   | GLY | A | 17 | 30.394 | 16.511 | 8.667  | 1.00 | 12.60 | A |
| ATOM | 126 | N   | HIS | A | 18 | 28.377 | 15.496 | 8.744  | 1.00 | 16.58 | A |
| ATOM | 127 | CA  | HIS | A | 18 | 28.924 | 14.140 | 8.833  | 1.00 | 16.93 | A |
| ATOM | 128 | CB  | HIS | A | 18 | 27.809 | 13.113 | 9.026  | 1.00 | 16.74 | A |
| ATOM | 129 | CG  | HIS | A | 18 | 27.158 | 13.164 | 10.371 | 1.00 | 19.14 | A |
| ATOM | 130 | CD2 | HIS | A | 18 | 27.686 | 13.188 | 11.616 | 1.00 | 18.03 | A |
| ATOM | 131 | ND1 | HIS | A | 18 | 25.790 | 13.117 | 10.534 | 1.00 | 18.13 | A |
| ATOM | 132 | CE1 | HIS | A | 18 | 25.504 | 13.105 | 11.823 | 1.00 | 17.95 | A |
| ATOM | 133 | NE2 | HIS | A | 18 | 26.637 | 13.147 | 12.500 | 1.00 | 19.65 | A |
| ATOM | 134 | C   | HIS | A | 18 | 29.660 | 13.794 | 7.550  | 1.00 | 16.02 | A |
| ATOM | 135 | O   | HIS | A | 18 | 30.792 | 13.315 | 7.578  | 1.00 | 17.19 | A |
| ATOM | 136 | N   | LEU | A | 19 | 28.991 | 14.025 | 6.428  | 1.00 | 15.79 | A |
| ATOM | 137 | CA  | LEU | A | 19 | 29.553 | 13.736 | 5.115  | 1.00 | 16.14 | A |
| ATOM | 138 | CB  | LEU | A | 19 | 28.519 | 14.039 | 4.024  | 1.00 | 15.07 | A |
| ATOM | 139 | CG  | LEU | A | 19 | 27.211 | 13.244 | 4.140  | 1.00 | 13.97 | A |
| ATOM | 140 | CD1 | LEU | A | 19 | 26.197 | 13.763 | 3.119  | 1.00 | 13.12 | A |
| ATOM | 141 | CD2 | LEU | A | 19 | 27.491 | 11.747 | 3.934  | 1.00 | 14.26 | A |
| ATOM | 142 | C   | LEU | A | 19 | 30.827 | 14.538 | 4.883  | 1.00 | 16.73 | A |
| ATOM | 143 | O   | LEU | A | 19 | 31.821 | 14.003 | 4.391  | 1.00 | 16.83 | A |
| ATOM | 144 | N   | LEU | A | 20 | 30.805 | 15.816 | 5.251  | 1.00 | 16.81 | A |
| ATOM | 145 | CA  | LEU | A | 20 | 31.982 | 16.658 | 5.084  | 1.00 | 17.03 | A |
| ATOM | 146 | CB  | LEU | A | 20 | 31.681 | 18.099 | 5.520  | 1.00 | 16.75 | A |
| ATOM | 147 | CG  | LEU | A | 20 | 32.894 | 19.031 | 5.571  | 1.00 | 18.42 | A |
| ATOM | 148 | CD1 | LEU | A | 20 | 33.486 | 19.176 | 4.171  | 1.00 | 15.95 | A |
| ATOM | 149 | CD2 | LEU | A | 20 | 32.487 | 20.397 | 6.138  | 1.00 | 17.13 | A |
| ATOM | 150 | C   | LEU | A | 20 | 33.145 | 16.101 | 5.913  | 1.00 | 17.11 | A |
| ATOM | 151 | O   | LEU | A | 20 | 34.206 | 15.784 | 5.377  | 1.00 | 16.36 | A |
| ATOM | 152 | N   | MET | A | 21 | 32.941 | 15.976 | 7.222  | 1.00 | 17.66 | A |
| ATOM | 153 | CA  | MET | A | 21 | 33.988 | 15.461 | 8.106  | 1.00 | 17.40 | A |
| ATOM | 154 | CB  | MET | A | 21 | 33.431 | 15.213 | 9.509  | 1.00 | 14.99 | A |
| ATOM | 155 | CG  | MET | A | 21 | 34.507 | 15.145 | 10.575 | 1.00 | 15.83 | A |
| ATOM | 156 | SD  | MET | A | 21 | 33.977 | 14.355 | 12.125 | 1.00 | 13.48 | A |
| ATOM | 157 | CE  | MET | A | 21 | 34.405 | 12.918 | 11.720 | 1.00 | 1.18  | A |
| ATOM | 158 | C   | MET | A | 21 | 34.578 | 14.160 | 7.559  | 1.00 | 18.20 | A |
| ATOM | 159 | O   | MET | A | 21 | 35.793 | 14.027 | 7.433  | 1.00 | 19.00 | A |
| ATOM | 160 | N   | ALA | A | 22 | 33.710 | 13.207 | 7.227  | 1.00 | 18.81 | A |
| ATOM | 161 | CA  | ALA | A | 22 | 34.144 | 11.915 | 6.698  | 1.00 | 19.82 | A |
| ATOM | 162 | CB  | ALA | A | 22 | 32.933 | 11.039 | 6.423  | 1.00 | 20.05 | A |
| ATOM | 163 | C   | ALA | A | 22 | 35.005 | 12.020 | 5.433  | 1.00 | 19.91 | A |
| ATOM | 164 | O   | ALA | A | 22 | 36.002 | 11.312 | 5.293  | 1.00 | 18.35 | A |
| ATOM | 165 | N   | ASN | A | 23 | 34.626 | 12.909 | 4.521  | 1.00 | 19.01 | A |
| ATOM | 166 | CA  | ASN | A | 23 | 35.369 | 13.069 | 3.281  | 1.00 | 19.71 | A |

Figure 9 (4 of 92)

| ATOM | 167 | CB | ASN | A | 23 | 34.584 | 13.948 | 2.307 | 1.00 | 18.80 | A |
|---|---|---|---|---|---|---|---|---|---|---|---|
| ATOM | 168 | CG | ASN | A | 23 | 35.007 | 13.729 | 0.861 | 1.00 | 19.89 | A |
| ATOM | 169 | OD1 | ASN | A | 23 | 35.522 | 14.636 | 0.197 | 1.00 | 20.00 | A |
| ATOM | 170 | ND2 | ASN | A | 23 | 34.796 | 12.518 | 0.370 | 1.00 | 16.50 | A |
| ATOM | 171 | C | ASN | A | 23 | 36.740 | 13.676 | 3.563 | 1.00 | 20.75 | A |
| ATOM | 172 | O | ASN | A | 23 | 37.755 | 13.244 | 3.004 | 1.00 | 20.44 | A |
| ATOM | 173 | N | GLU | A | 24 | 36.767 | 14.663 | 4.454 | 1.00 | 20.42 | A |
| ATOM | 174 | CA | GLU | A | 24 | 38.009 | 15.321 | 4.822 | 1.00 | 20.33 | A |
| ATOM | 175 | CB | GLU | A | 24 | 37.721 | 16.466 | 5.800 | 1.00 | 21.87 | A |
| ATOM | 176 | CG | GLU | A | 24 | 36.989 | 17.638 | 5.174 | 1.00 | 21.12 | A |
| ATOM | 177 | CD | GLU | A | 24 | 37.780 | 18.261 | 4.038 | 1.00 | 22.44 | A |
| ATOM | 178 | OE1 | GLU | A | 24 | 38.959 | 18.604 | 4.258 | 1.00 | 23.52 | A |
| ATOM | 179 | OE2 | GLU | A | 24 | 37.230 | 18.411 | 2.928 | 1.00 | 21.70 | A |
| ATOM | 180 | C | GLU | A | 24 | 38.990 | 14.325 | 5.442 | 1.00 | 19.42 | A |
| ATOM | 181 | O | GLU | A | 24 | 40.158 | 14.275 | 5.062 | 1.00 | 20.42 | A |
| ATOM | 182 | N | VAL | A | 25 | 38.515 | 13.533 | 6.396 | 1.00 | 19.37 | A |
| ATOM | 183 | CA | VAL | A | 25 | 39.362 | 12.538 | 7.049 | 1.00 | 18.86 | A |
| ATOM | 184 | CB | VAL | A | 25 | 38.556 | 11.755 | 8.114 | 1.00 | 18.33 | A |
| ATOM | 185 | CG1 | VAL | A | 25 | 39.331 | 10.530 | 8.569 | 1.00 | 19.61 | A |
| ATOM | 186 | CG2 | VAL | A | 25 | 38.261 | 12.657 | 9.310 | 1.00 | 19.03 | A |
| ATOM | 187 | C | VAL | A | 25 | 39.921 | 11.560 | 6.001 | 1.00 | 19.76 | A |
| ATOM | 188 | O | VAL | A | 25 | 41.128 | 11.307 | 5.938 | 1.00 | 18.27 | A |
| ATOM | 189 | N | LEU | A | 26 | 39.022 | 11.009 | 5.192 | 1.00 | 20.61 | A |
| ATOM | 190 | CA | LEU | A | 26 | 39.379 | 10.074 | 4.136 | 1.00 | 21.66 | A |
| ATOM | 191 | CB | LEU | A | 26 | 38.198 | 9.916 | 3.177 | 1.00 | 20.90 | A |
| ATOM | 192 | CG | LEU | A | 26 | 38.420 | 9.096 | 1.901 | 1.00 | 24.75 | A |
| ATOM | 193 | CD1 | LEU | A | 26 | 38.343 | 7.606 | 2.229 | 1.00 | 24.46 | A |
| ATOM | 194 | CD2 | LEU | A | 26 | 37.350 | 9.466 | 0.860 | 1.00 | 24.98 | A |
| ATOM | 195 | C | LEU | A | 26 | 40.592 | 10.596 | 3.370 | 1.00 | 23.44 | A |
| ATOM | 196 | O | LEU | A | 26 | 41.620 | 9.935 | 3.276 | 1.00 | 23.13 | A |
| ATOM | 197 | N | TYR | A | 27 | 40.451 | 11.797 | 2.825 | 1.00 | 26.12 | A |
| ATOM | 198 | CA | TYR | A | 27 | 41.505 | 12.431 | 2.056 | 1.00 | 28.85 | A |
| ATOM | 199 | CB | TYR | A | 27 | 40.984 | 13.734 | 1.439 | 1.00 | 31.83 | A |
| ATOM | 200 | CG | TYR | A | 27 | 42.082 | 14.633 | 0.912 | 1.00 | 34.85 | A |
| ATOM | 201 | CD1 | TYR | A | 27 | 42.741 | 14.336 | -0.284 | 1.00 | 38.12 | A |
| ATOM | 202 | CE1 | TYR | A | 27 | 43.792 | 15.139 | -0.754 | 1.00 | 39.59 | A |
| ATOM | 203 | CD2 | TYR | A | 27 | 42.492 | 15.756 | 1.631 | 1.00 | 36.84 | A |
| ATOM | 204 | CE2 | TYR | A | 27 | 43.536 | 16.564 | 1.175 | 1.00 | 39.11 | A |
| ATOM | 205 | CZ | TYR | A | 27 | 44.182 | 16.247 | -0.018 | 1.00 | 40.66 | A |
| ATOM | 206 | OH | TYR | A | 27 | 45.222 | 17.034 | -0.468 | 1.00 | 43.32 | A |
| ATOM | 207 | C | TYR | A | 27 | 42.747 | 12.738 | 2.889 | 1.00 | 29.13 | A |
| ATOM | 208 | O | TYR | A | 27 | 43.861 | 12.367 | 2.527 | 1.00 | 29.10 | A |
| ATOM | 209 | N | GLN | A | 28 | 42.550 | 13.418 | 4.008 | 1.00 | 28.80 | A |
| ATOM | 210 | CA | GLN | A | 28 | 43.667 | 13.803 | 4.849 | 1.00 | 28.49 | A |
| ATOM | 211 | CB | GLN | A | 28 | 43.197 | 14.802 | 5.894 | 1.00 | 28.91 | A |
| ATOM | 212 | CG | GLN | A | 28 | 42.893 | 16.139 | 5.274 | 1.00 | 29.62 | A |
| ATOM | 213 | CD | GLN | A | 28 | 42.406 | 17.142 | 6.275 | 1.00 | 30.64 | A |
| ATOM | 214 | OE1 | GLN | A | 28 | 43.030 | 17.340 | 7.319 | 1.00 | 32.08 | A |
| ATOM | 215 | NE2 | GLN | A | 28 | 41.289 | 17.797 | 5.966 | 1.00 | 28.12 | A |
| ATOM | 216 | C | GLN | A | 28 | 44.460 | 12.693 | 5.506 | 1.00 | 27.72 | A |
| ATOM | 217 | O | GLN | A | 28 | 45.663 | 12.845 | 5.706 | 1.00 | 27.82 | A |
| ATOM | 218 | N | ALA | A | 29 | 43.807 | 11.587 | 5.847 | 1.00 | 25.96 | A |
| ATOM | 219 | CA | ALA | A | 29 | 44.509 | 10.469 | 6.475 | 1.00 | 25.66 | A |
| ATOM | 220 | CB | ALA | A | 29 | 43.648 | 9.850 | 7.580 | 1.00 | 23.71 | A |
| ATOM | 221 | C | ALA | A | 29 | 44.857 | 9.417 | 5.427 | 1.00 | 25.73 | A |
| ATOM | 222 | O | ALA | A | 29 | 45.273 | 8.309 | 5.762 | 1.00 | 26.08 | A |
| ATOM | 223 | N | GLY | A | 30 | 44.683 | 9.775 | 4.157 | 1.00 | 25.33 | A |
| ATOM | 224 | CA | GLY | A | 30 | 44.975 | 8.856 | 3.073 | 1.00 | 23.70 | A |
| ATOM | 225 | C | GLY | A | 30 | 44.318 | 7.504 | 3.272 | 1.00 | 24.16 | A |
| ATOM | 226 | O | GLY | A | 30 | 44.955 | 6.465 | 3.094 | 1.00 | 24.99 | A |
| ATOM | 227 | N | LEU | A | 31 | 43.042 | 7.514 | 3.645 | 1.00 | 22.78 | A |
| ATOM | 228 | CA | LEU | A | 31 | 42.308 | 6.275 | 3.874 | 1.00 | 22.19 | A |
| ATOM | 229 | CB | LEU | A | 31 | 41.256 | 6.478 | 4.976 | 1.00 | 22.70 | A |
| ATOM | 230 | CG | LEU | A | 31 | 41.734 | 7.102 | 6.297 | 1.00 | 23.47 | A |
| ATOM | 231 | CD1 | LEU | A | 31 | 40.601 | 7.085 | 7.332 | 1.00 | 21.45 | A |
| ATOM | 232 | CD2 | LEU | A | 31 | 42.934 | 6.326 | -6.822 | 1.00 | 20.64 | A |

Figure 9 (5 of 92)

| ATOM | 233 | C | LEU | A | 31 | 41.626 | 5.824 | 2.584 | 1.00 | 21.91 | A |
|---|---|---|---|---|---|---|---|---|---|---|---|
| ATOM | 234 | O | LEU | A | 31 | 41.556 | 6.576 | 1.615 | 1.00 | 20.08 | A |
| ATOM | 235 | N | ASP | A | 32 | 41.132 | 4.591 | 2.572 | 1.00 | 22.60 | A |
| ATOM | 236 | CA | ASP | A | 32 | 40.455 | 4.061 | 1.397 | 1.00 | 23.30 | A |
| ATOM | 237 | CB | ASP | A | 32 | 40.797 | 2.585 | 1.213 | 1.00 | 25.23 | A |
| ATOM | 238 | CG | ASP | A | 32 | 42.236 | 2.376 | 0.830 | 1.00 | 27.00 | A |
| ATOM | 239 | OD1 | ASP | A | 32 | 42.610 | 2.835 | -0.266 | 1.00 | 29.31 | A |
| ATOM | 240 | OD2 | ASP | A | 32 | 42.991 | 1.769 | 1.621 | 1.00 | 27.72 | A |
| ATOM | 241 | C | ASP | A | 32 | 38.950 | 4.206 | 1.536 | 1.00 | 24.37 | A |
| ATOM | 242 | O | ASP | A | 32 | 38.260 | 4.573 | 0.587 | 1.00 | 24.55 | A |
| ATOM | 243 | N | GLU | A | 33 | 38.446 | 3.912 | 2.729 | 1.00 | 22.99 | A |
| ATOM | 244 | CA | GLU | A | 33 | 37.014 | 3.994 | 2.989 | 1.00 | 22.23 | A |
| ATOM | 245 | CB | GLU | A | 33 | 36.361 | 2.608 | 2.870 | 1.00 | 23.06 | A |
| ATOM | 246 | CG | GLU | A | 33 | 36.505 | 1.907 | 1.524 | 1.00 | 24.94 | A |
| ATOM | 247 | CD | GLU | A | 33 | 36.009 | 0.469 | 1.579 | 1.00 | 27.15 | A |
| ATOM | 248 | OE1 | GLU | A | 33 | 36.103 | -0.245 | 0.556 | 1.00 | 29.59 | A |
| ATOM | 249 | OE2 | GLU | A | 33 | 35.528 | 0.049 | 2.653 | 1.00 | 25.79 | A |
| ATOM | 250 | C | GLU | A | 33 | 36.734 | 4.511 | 4.386 | 1.00 | 20.74 | A |
| ATOM | 251 | O | GLU | A | 33 | 37.565 | 4.411 | 5.279 | 1.00 | 21.29 | A |
| ATOM | 252 | N | ILE | A | 34 | 35.542 | 5.065 | 4.554 | 1.00 | 20.56 | A |
| ATOM | 253 | CA | ILE | A | 34 | 35.079 | 5.557 | 5.837 | 1.00 | 17.64 | A |
| ATOM | 254 | CB | ILE | A | 34 | 34.653 | 7.034 | 5.787 | 1.00 | 17.15 | A |
| ATOM | 255 | CG2 | ILE | A | 34 | 34.049 | 7.432 | 7.133 | 1.00 | 14.06 | A |
| ATOM | 256 | CG1 | ILE | A | 34 | 35.845 | 7.918 | 5.418 | 1.00 | 14.62 | A |
| ATOM | 257 | CD1 | ILE | A | 34 | 37.013 | 7.816 | 6.381 | 1.00 | 17.03 | A |
| ATOM | 258 | C | ILE | A | 34 | 33.836 | 4.733 | 6.111 | 1.00 | 18.54 | A |
| ATOM | 259 | O | ILE | A | 34 | 32.935 | 4.656 | 5.271 | 1.00 | 18.34 | A |
| ATOM | 260 | N | TRP | A | 35 | 33.791 | 4.109 | 7.280 | 1.00 | 17.15 | A |
| ATOM | 261 | CA | TRP | A | 35 | 32.655 | 3.298 | 7.656 | 1.00 | 17.29 | A |
| ATOM | 262 | CB | TRP | A | 35 | 33.136 | 1.965 | 8.228 | 1.00 | 16.94 | A |
| ATOM | 263 | CG | TRP | A | 35 | 33.812 | 1.063 | 7.229 | 1.00 | 19.20 | A |
| ATOM | 264 | CD2 | TRP | A | 35 | 34.282 | -0.268 | 7.469 | 1.00 | 18.13 | A |
| ATOM | 265 | CE2 | TRP | A | 35 | 34.799 | -0.758 | 6.245 | 1.00 | 19.92 | A |
| ATOM | 266 | CE3 | TRP | A | 35 | 34.315 | -1.097 | 8.601 | 1.00 | 16.76 | A |
| ATOM | 267 | CD1 | TRP | A | 35 | 34.060 | 1.324 | 5.903 | 1.00 | 20.22 | A |
| ATOM | 268 | NE1 | TRP | A | 35 | 34.651 | 0.232 | 5.309 | 1.00 | 19.48 | A |
| ATOM | 269 | CZ2 | TRP | A | 35 | 35.343 | -2.042 | 6.122 | 1.00 | 19.12 | A |
| ATOM | 270 | CZ3 | TRP | A | 35 | 34.855 | -2.374 | 8.478 | 1.00 | 18.76 | A |
| ATOM | 271 | CH2 | TRP | A | 35 | 35.362 | -2.833 | 7.246 | 1.00 | 19.53 | A |
| ATOM | 272 | C | TRP | A | 35 | 31.807 | 4.030 | 8.693 | 1.00 | 17.94 | A |
| ATOM | 273 | O | TRP | A | 35 | 32.277 | 4.325 | 9.795 | 1.00 | 16.36 | A |
| ATOM | 274 | N | PHE | A | 36 | 30.565 | 4.334 | 8.329 | 1.00 | 16.50 | A |
| ATOM | 275 | CA | PHE | A | 36 | 29.646 | 5.008 | 9.241 | 1.00 | 17.33 | A |
| ATOM | 276 | CB | PHE | A | 36 | 28.542 | 5.735 | 8.457 | 1.00 | 14.70 | A |
| ATOM | 277 | CG | PHE | A | 36 | 29.034 | 6.938 | 7.681 | 1.00 | 13.30 | A |
| ATOM | 278 | CD1 | PHE | A | 36 | 30.016 | 6.799 | 6.703 | 1.00 | 11.79 | A |
| ATOM | 279 | CD2 | PHE | A | 36 | 28.507 | 8.206 | 7.921 | 1.00 | 13.43 | A |
| ATOM | 280 | CE1 | PHE | A | 36 | 30.465 | 7.899 | 5.970 | 1.00 | 11.65 | A |
| ATOM | 281 | CE2 | PHE | A | 36 | 28.953 | 9.322 | 7.191 | 1.00 | 12.33 | A |
| ATOM | 282 | CZ | PHE | A | 36 | 29.933 | 9.161 | 6.215 | 1.00 | 12.36 | A |
| ATOM | 283 | C | PHE | A | 36 | 29.064 | 3.898 | 10.115 | 1.00 | 18.05 | A |
| ATOM | 284 | O | PHE | A | 36 | 28.377 | 3.002 | 9.621 | 1.00 | 18.07 | A |
| ATOM | 285 | N | MET | A | 37 | 29.359 | 3.964 | 11.410 | 1.00 | 17.04 | A |
| ATOM | 286 | CA | MET | A | 37 | 28.931 | 2.948 | 12.364 | 1.00 | 16.61 | A |
| ATOM | 287 | CB | MET | A | 37 | 30.189 | 2.373 | 13.045 | 1.00 | 15.80 | A |
| ATOM | 288 | CG | MET | A | 37 | 30.006 | 1.150 | 13.956 | 1.00 | 11.58 | A |
| ATOM | 289 | SD | MET | A | 37 | 31.591 | 0.502 | 14.623 | 1.00 | 1.29 | A |
| ATOM | 290 | CE | MET | A | 37 | 32.029 | 1.824 | 15.831 | 1.00 | 5.77 | A |
| ATOM | 291 | C | MET | A | 37 | 27.923 | 3.470 | 13.398 | 1.00 | 20.24 | A |
| ATOM | 292 | O | MET | A | 37 | 28.295 | 4.076 | 14.405 | 1.00 | 20.90 | A |
| ATOM | 293 | N | PRO | A | 38 | 26.622 | 3.244 | 13.149 | 1.00 | 21.44 | A |
| ATOM | 294 | CD | PRO | A | 38 | 26.094 | 2.504 | 11.993 | 1.00 | 21.23 | A |
| ATOM | 295 | CA | PRO | A | 38 | 25.534 | 3.673 | 14.037 | 1.00 | 22.14 | A |
| ATOM | 296 | CB | PRO | A | 38 | 24.282 | 3.124 | 13.353 | 1.00 | 24.19 | A |
| ATOM | 297 | CG | PRO | A | 38 | 24.684 | 2.996 | 11.927 | 1.00 | 23.67 | A |
| ATOM | 298 | C | PRO | A | 38 | 25.725 | 3.035 | 15.405 | 1.00 | 23.62 | A |

Figure 9 (6 of 92)

| | | | | | | | | | | |
|---|---|---|---|---|---|---|---|---|---|---|
| ATOM | 299 | O | PRO | A | 38 | 25.947 | 1.824 | 15.499 | 1.00 21.29 | A |
| ATOM | 300 | N | ASN | A | 39 | 25.623 | 3.838 | 16.460 | 1.00 24.47 | A |
| ATOM | 301 | CA | ASN | A | 39 | 25.806 | 3.325 | 17.811 | 1.00 27.54 | A |
| ATOM | 302 | CB | ASN | A | 39 | 26.166 | 4.462 | 18.779 | 1.00 26.72 | A |
| ATOM | 303 | CG | ASN | A | 39 | 24.955 | 5.294 | 19.200 | 1.00 27.68 | A |
| ATOM | 304 | OD1 | ASN | A | 39 | 24.168 | 5.754 | 18.366 | 1.00 22.77 | A |
| ATOM | 305 | ND2 | ASN | A | 39 | 24.810 | 5.495 | 20.507 | 1.00 28.68 | A |
| ATOM | 306 | C | ASN | A | 39 | 24.574 | 2.590 | 18.320 | 1.00 31.08 | A |
| ATOM | 307 | O | ASN | A | 39 | 23.440 | 2.892 | 17.941 | 1.00 29.85 | A |
| ATOM | 308 | N | GLN | A | 40 | 24.817 | 1.608 | 19.177 | 1.00 36.09 | A |
| ATOM | 309 | CA | GLN | A | 40 | 23.751 | 0.817 | 19.765 | 1.00 40.86 | A |
| ATOM | 310 | CB | GLN | A | 40 | 24.353 | -0.336 | 20.561 | 1.00 41.50 | A |
| ATOM | 311 | CG | GLN | A | 40 | 23.362 | -1.079 | 21.421 | 1.00 43.62 | A |
| ATOM | 312 | CD | GLN | A | 40 | 24.036 | -2.141 | 22.255 | 1.00 45.14 | A |
| ATOM | 313 | OE1 | GLN | A | 40 | 24.609 | -3.093 | 21.720 | 1.00 46.54 | A |
| ATOM | 314 | NE2 | GLN | A | 40 | 23.986 | -1.981 | 23.574 | 1.00 45.36 | A |
| ATOM | 315 | C | GLN | A | 40 | 22.925 | 1.699 | 20.686 | 1.00 43.08 | A |
| ATOM | 316 | O | GLN | A | 40 | 23.461 | 2.595 | 21.341 | 1.00 44.03 | A |
| ATOM | 317 | N | ILE | A | 41 | 21.623 | 1.446 | 20.734 | 1.00 45.43 | A |
| ATOM | 318 | CA | ILE | A | 41 | 20.731 | 2.221 | 21.582 | 1.00 48.02 | A |
| ATOM | 319 | CB | ILE | A | 41 | 19.250 | 1.958 | 21.214 | 1.00 49.00 | A |
| ATOM | 320 | CG2 | ILE | A | 41 | 18.325 | 2.692 | 22.175 | 1.00 49.79 | A |
| ATOM | 321 | CG1 | ILE | A | 41 | 18.995 | 2.396 | 19.768 | 1.00 47.95 | A |
| ATOM | 322 | CD1 | ILE | A | 41 | 19.410 | 3.824 | 19.474 | 1.00 47.99 | A |
| ATOM | 323 | C | ILE | A | 41 | 20.962 | 1.869 | 23.048 | 1.00 49.73 | A |
| ATOM | 324 | O | ILE | A | 41 | 20.673 | 0.753 | 23.483 | 1.00 49.40 | A |
| ATOM | 325 | N | PRO | A | 42 | 21.499 | 2.823 | 23.828 | 1.00 51.44 | A |
| ATOM | 326 | CD | PRO | A | 42 | 21.945 | 4.164 | 23.409 | 1.00 51.56 | A |
| ATOM | 327 | CA | PRO | A | 42 | 21.770 | 2.607 | 25.254 | 1.00 52.02 | A |
| ATOM | 328 | CB | PRO | A | 42 | 22.378 | 3.938 | 25.700 | 1.00 52.36 | A |
| ATOM | 329 | CG | PRO | A | 42 | 23.003 | 4.474 | 24.435 | 1.00 52.60 | A |
| ATOM | 330 | C | PRO | A | 42 | 20.489 | 2.281 | 26.014 | 1.00 52.49 | A |
| ATOM | 331 | O | PRO | A | 42 | 19.473 | 2.957 | 25.843 | 1.00 52.33 | A |
| ATOM | 332 | N | ASP | A | 52 | 12.865 | 3.982 | 14.720 | 1.00 44.41 | A |
| ATOM | 333 | CA | ASP | A | 52 | 13.878 | 3.399 | 15.591 | 1.00 42.91 | A |
| ATOM | 334 | CB | ASP | A | 52 | 13.445 | 1.997 | 16.037 | 1.00 45.33 | A |
| ATOM | 335 | CG | ASP | A | 52 | 14.268 | 1.474 | 17.200 | 1.00 46.64 | A |
| ATOM | 336 | OD1 | ASP | A | 52 | 14.131 | 2.012 | 18.321 | 1.00 47.85 | A |
| ATOM | 337 | OD2 | ASP | A | 52 | 15.055 | 0.527 | 16.992 | 1.00 47.83 | A |
| ATOM | 338 | C | ASP | A | 52 | 15.201 | 3.319 | 14.837 | 1.00 40.76 | A |
| ATOM | 339 | O | ASP | A | 52 | 15.550 | 4.230 | 14.082 | 1.00 41.93 | A |
| ATOM | 340 | N | SER | A | 53 | 15.937 | 2.232 | 15.039 | 1.00 36.37 | A |
| ATOM | 341 | CA | SER | A | 53 | 17.211 | 2.067 | 14.359 | 1.00 32.42 | A |
| ATOM | 342 | CB | SER | A | 53 | 17.980 | 0.892 | 14.960 | 1.00 33.02 | A |
| ATOM | 343 | OG | SER | A | 53 | 18.470 | 1.221 | 16.252 | 1.00 33.55 | A |
| ATOM | 344 | C | SER | A | 53 | 16.992 | 1.853 | 12.866 | 1.00 29.87 | A |
| ATOM | 345 | O | SER | A | 53 | 17.835 | 2.218 | 12.044 | 1.00 28.68 | A |
| ATOM | 346 | N | PHE | A | 54 | 15.850 | 1.267 | 12.523 | 1.00 27.26 | A |
| ATOM | 347 | CA | PHE | A | 54 | 15.503 | 1.003 | 11.132 | 1.00 26.55 | A |
| ATOM | 348 | CB | PHE | A | 54 | 14.076 | 0.448 | 11.041 | 1.00 28.83 | A |
| ATOM | 349 | CG | PHE | A | 54 | 13.545 | 0.358 | 9.635 | 1.00 30.77 | A |
| ATOM | 350 | CD1 | PHE | A | 54 | 14.045 | -0.590 | 8.743 | 1.00 32.34 | A |
| ATOM | 351 | CD2 | PHE | A | 54 | 12.553 | 1.235 | 9.197 | 1.00 32.46 | A |
| ATOM | 352 | CE1 | PHE | A | 54 | 13.566 | -0.665 | 7.430 | 1.00 32.50 | A |
| ATOM | 353 | CE2 | PHE | A | 54 | 12.066 | 1.170 | 7.887 | 1.00 33.32 | A |
| ATOM | 354 | CZ | PHE | A | 54 | 12.575 | 0.218 | 7.001 | 1.00 33.37 | A |
| ATOM | 355 | C | PHE | A | 54 | 15.600 | 2.274 | 10.300 | 1.00 24.04 | A |
| ATOM | 356 | O | PHE | A | 54 | 16.186 | 2.276 | 9.219 | 1.00 22.26 | A |
| ATOM | 357 | N | HIS | A | 55 | 15.021 | 3.352 | 10.820 | 1.00 23.41 | A |
| ATOM | 358 | CA | HIS | A | 55 | 15.008 | 4.641 | 10.129 | 1.00 24.50 | A |
| ATOM | 359 | CB | HIS | A | 55 | 14.017 | 5.591 | 10.822 | 1.00 23.11 | A |
| ATOM | 360 | CG | HIS | A | 55 | 12.577 | 5.245 | 10.578 | 1.00 23.62 | A |
| ATOM | 361 | CD2 | HIS | A | 55 | 11.962 | 4.697 | 9.503 | 1.00 25.30 | A |
| ATOM | 362 | ND1 | HIS | A | 55 | 11.582 | 5.488 | 11.501 | 1.00 26.84 | A |
| ATOM | 363 | CE1 | HIS | A | 55 | 10.418 | 5.105 | 11.007 | 1.00 24.91 | A |
| ATOM | 364 | NE2 | HIS | A | 55 | 10.620 | 4.622 | 9.795 | 1.00 25.91 | A |

Figure 9 (7 of 92)

| | | | | | | | | | |
|---|---|---|---|---|---|---|---|---|---|
| ATOM | 365 | C | HIS A | 55 | 16.390 | 5.286 | 10.015 | 1.00 24.62 | A |
| ATOM | 366 | O | HIS A | 55 | 16.739 | 5.829 | 8.961 | 1.00 26.02 | A |
| ATOM | 367 | N | ARG A | 56 | 17.175 | 5.221 | 11.088 | 1.00 23.22 | A |
| ATOM | 368 | CA | ARG A | 56 | 18.525 | 5.792 | 11.081 | 1.00 24.59 | A |
| ATOM | 369 | CB | ARG A | 56 | 19.201 | 5.590 | 12.444 | 1.00 23.70 | A |
| ATOM | 370 | CG | ARG A | 56 | 18.462 | 6.222 | 13.616 | 1.00 26.71 | A |
| ATOM | 371 | CD | ARG A | 56 | 18.841 | 5.535 | 14.916 | 1.00 26.81 | A |
| ATOM | 372 | NE | ARG A | 56 | 20.273 | 5.612 | 15.144 | 1.00 28.68 | A |
| ATOM | 373 | CZ | ARG A | 56 | 20.965 | 4.772 | 15.908 | 1.00 28.00 | A |
| ATOM | 374 | NH1 | ARG A | 56 | 20.356 | 3.771 | 16.527 | 1.00 26.51 | A |
| ATOM | 375 | NH2 | ARG A | 56 | 22.272 | 4.942 | 16.056 | 1.00 26.92 | A |
| ATOM | 376 | C | ARG A | 56 | 19.369 | 5.108 | 10.004 | 1.00 21.92 | A |
| ATOM | 377 | O | ARG A | 56 | 20.139 | 5.753 | 9.296 | 1.00 21.99 | A |
| ATOM | 378 | N | VAL A | 57 | 19.215 | 3.794 | 9.892 | 1.00 19.91 | A |
| ATOM | 379 | CA | VAL A | 57 | 19.961 | 3.007 | 8.921 | 1.00 20.54 | A |
| ATOM | 380 | CB | VAL A | 57 | 19.728 | 1.498 | 9.158 | 1.00 20.83 | A |
| ATOM | 381 | CG1 | VAL A | 57 | 20.344 | 0.685 | 8.042 | 1.00 21.85 | A |
| ATOM | 382 | CG2 | VAL A | 57 | 20.335 | 1.096 | 10.492 | 1.00 21.51 | A |
| ATOM | 383 | C | VAL A | 57 | 19.587 | 3.359 | 7.483 | 1.00 20.36 | A |
| ATOM | 384 | O | VAL A | 57 | 20.456 | 3.466 | 6.614 | 1.00 18.35 | A |
| ATOM | 385 | N | GLU A | 58 | 18.294 | 3.533 | 7.234 | 1.00 20.56 | A |
| ATOM | 386 | CA | GLU A | 58 | 17.835 | 3.880 | 5.896 | 1.00 19.75 | A |
| ATOM | 387 | CB | GLU A | 58 | 16.306 | 3.802 | 5.817 | 1.00 21.37 | A |
| ATOM | 388 | CG | GLU A | 58 | 15.756 | 2.385 | 5.821 | 1.00 23.88 | A |
| ATOM | 389 | CD | GLU A | 58 | 16.412 | 1.504 | 4.772 | 1.00 27.43 | A |
| ATOM | 390 | OE1 | GLU A | 58 | 16.360 | 1.853 | 3.567 | 1.00 28.53 | A |
| ATOM | 391 | OE2 | GLU A | 58 | 16.988 | 0.460 | 5.157 | 1.00 29.07 | A |
| ATOM | 392 | C | GLU A | 58 | 18.314 | 5.277 | 5.501 | 1.00 18.33 | A |
| ATOM | 393 | O | GLU A | 58 | 18.675 | 5.500 | 4.350 | 1.00 17.68 | A |
| ATOM | 394 | N | MET A | 59 | 18.329 | 6.216 | 6.449 | 1.00 17.62 | A |
| ATOM | 395 | CA | MET A | 59 | 18.793 | 7.569 | 6.137 | 1.00 16.36 | A |
| ATOM | 396 | CB | MET A | 59 | 18.460 | 8.545 | 7.286 | 1.00 14.74 | A |
| ATOM | 397 | CG | MET A | 59 | 16.939 | 8.846 | 7.442 | 1.00 13.47 | A |
| ATOM | 398 | SD | MET A | 59 | 16.459 | 10.074 | 8.697 | 1.00 4.48 | A |
| ATOM | 399 | CE | MET A | 59 | 16.583 | 9.157 | 10.127 | 1.00 9.90 | A |
| ATOM | 400 | C | MET A | 59 | 20.304 | 7.533 | 5.851 | 1.00 16.76 | A |
| ATOM | 401 | O | MET A | 59 | 20.795 | 8.214 | 4.946 | 1.00 14.87 | A |
| ATOM | 402 | N | LEU A | 60 | 21.035 | 6.716 | 6.606 | 1.00 16.98 | A |
| ATOM | 403 | CA | LEU A | 60 | 22.479 | 6.590 | 6.404 | 1.00 18.65 | A |
| ATOM | 404 | CB | LEU A | 60 | 23.095 | 5.655 | 7.440 | 1.00 18.40 | A |
| ATOM | 405 | CG | LEU A | 60 | 23.622 | 6.328 | 8.707 | 1.00 20.90 | A |
| ATOM | 406 | CD1 | LEU A | 60 | 24.037 | 5.261 | 9.714 | 1.00 20.64 | A |
| ATOM | 407 | CD2 | LEU A | 60 | 24.803 | 7.236 | 8.354 | 1.00 20.06 | A |
| ATOM | 408 | C | LEU A | 60 | 22.754 | 6.049 | 5.008 | 1.00 19.02 | A |
| ATOM | 409 | O | LEU A | 60 | 23.603 | 6.577 | 4.291 | 1.00 17.69 | A |
| ATOM | 410 | N | LYS A | 61 | 22.035 | 4.994 | 4.627 | 1.00 20.13 | A |
| ATOM | 411 | CA | LYS A | 61 | 22.209 | 4.415 | 3.303 | 1.00 20.53 | A |
| ATOM | 412 | CB | LYS A | 61 | 21.208 | 3.285 | 3.060 | 1.00 21.67 | A |
| ATOM | 413 | CG | LYS A | 61 | 21.407 | 2.058 | 3.923 | 1.00 23.42 | A |
| ATOM | 414 | CD | LYS A | 61 | 20.493 | 0.924 | 3.464 | 1.00 26.89 | A |
| ATOM | 415 | CE | LYS A | 61 | 20.717 | -0.340 | 4.285 | 1.00 28.17 | A |
| ATOM | 416 | NZ | LYS A | 61 | 19.783 | -1.439 | 3.904 | 1.00 29.18 | A |
| ATOM | 417 | C | LYS A | 61 | 22.006 | 5.511 | 2.264 | 1.00 20.19 | A |
| ATOM | 418 | O | LYS A | 61 | 22.798 | 5.646 | 1.333 | 1.00 21.84 | A |
| ATOM | 419 | N | LEU A | 62 | 20.946 | 6.296 | 2.425 | 1.00 19.86 | A |
| ATOM | 420 | CA | LEU A | 62 | 20.661 | 7.393 | 1.493 | 1.00 20.55 | A |
| ATOM | 421 | CB | LEU A | 62 | 19.323 | 8.056 | 1.829 | 1.00 19.61 | A |
| ATOM | 422 | CG | LEU A | 62 | 18.065 | 7.256 | 1.499 | 1.00 20.77 | A |
| ATOM | 423 | CD1 | LEU A | 62 | 16.851 | 7.993 | 2.009 | 1.00 22.09 | A |
| ATOM | 424 | CD2 | LEU A | 62 | 17.975 | 7.045 | -0.006 | 1.00 20.57 | A |
| ATOM | 425 | C | LEU A | 62 | 21.748 | 8.462 | 1.514 | 1.00 20.91 | A |
| ATOM | 426 | O | LEU A | 62 | 22.166 | 8.958 | 0.468 | 1.00 19.74 | A |
| ATOM | 427 | N | ALA A | 63 | 22.207 | 8.813 | 2.712 | 1.00 19.39 | A |
| ATOM | 428 | CA | ALA A | 63 | 23.226 | 9.839 | 2.859 | 1.00 18.41 | A |
| ATOM | 429 | CB | ALA A | 63 | 23.467 | 10.119 | 4.341 | 1.00 16.56 | A |
| ATOM | 430 | C | ALA A | 63 | 24.554 | 9.521 | 2.178 | 1.00 19.10 | A |

Figure 9 (8 of 92)

| | | | | | | | | | | | |
|---|---|---|---|---|---|---|---|---|---|---|---|
| ATOM | 431 | O   | ALA | A | 63 | 25.162 | 10.397 | 1.566  | 1.00 | 17.83 | A |
| ATOM | 432 | N   | ILE | A | 64 | 24.999 | 8.273  | 2.268  | 1.00 | 20.17 | A |
| ATOM | 433 | CA  | ILE | A | 64 | 26.289 | 7.900  | 1.700  | 1.00 | 22.83 | A |
| ATOM | 434 | CB  | ILE | A | 64 | 26.998 | 6.890  | 2.601  | 1.00 | 23.15 | A |
| ATOM | 435 | CG2 | ILE | A | 64 | 27.170 | 7.480  | 4.000  | 1.00 | 20.46 | A |
| ATOM | 436 | CG1 | ILE | A | 64 | 26.186 | 5.591  | 2.640  | 1.00 | 21.95 | A |
| ATOM | 437 | CD1 | ILE | A | 64 | 26.856 | 4.464  | 3.411  | 1.00 | 23.49 | A |
| ATOM | 438 | C   | ILE | A | 64 | 26.288 | 7.317  | 0.298  | 1.00 | 25.91 | A |
| ATOM | 439 | O   | ILE | A | 64 | 27.355 | 7.046  | -0.247 | 1.00 | 25.40 | A |
| ATOM | 440 | N   | GLN | A | 65 | 25.103 | 7.113  | -0.273 | 1.00 | 27.83 | A |
| ATOM | 441 | CA  | GLN | A | 65 | 24.976 | 6.538  | -1.611 | 1.00 | 30.68 | A |
| ATOM | 442 | CB  | GLN | A | 65 | 23.511 | 6.553  | -2.064 | 1.00 | 31.43 | A |
| ATOM | 443 | CG  | GLN | A | 65 | 22.711 | 5.349  | -1.615 | 1.00 | 34.85 | A |
| ATOM | 444 | CD  | GLN | A | 65 | 21.259 | 5.415  | -2.060 | 1.00 | 37.47 | A |
| ATOM | 445 | OE1 | GLN | A | 65 | 20.447 | 4.566  | -1.685 | 1.00 | 39.33 | A |
| ATOM | 446 | NE2 | GLN | A | 65 | 20.928 | 6.422  | -2.862 | 1.00 | 36.49 | A |
| ATOM | 447 | C   | GLN | A | 65 | 25.814 | 7.211  | -2.684 | 1.00 | 30.91 | A |
| ATOM | 448 | O   | GLN | A | 65 | 26.316 | 6.551  | -3.589 | 1.00 | 30.88 | A |
| ATOM | 449 | N   | SER | A | 66 | 25.960 | 8.524  | -2.581 | 1.00 | 32.83 | A |
| ATOM | 450 | CA  | SER | A | 66 | 26.707 | 9.286  | -3.568 | 1.00 | 33.88 | A |
| ATOM | 451 | CB  | SER | A | 66 | 26.344 | 10.764 | -3.462 | 1.00 | 35.45 | A |
| ATOM | 452 | OG  | SER | A | 66 | 27.106 | 11.525 | -4.384 | 1.00 | 39.73 | A |
| ATOM | 453 | C   | SER | A | 66 | 28.218 | 9.146  | -3.483 | 1.00 | 33.65 | A |
| ATOM | 454 | O   | SER | A | 66 | 28.928 | 9.501  | -4.420 | 1.00 | 34.64 | A |
| ATOM | 455 | N   | ASN | A | 67 | 28.720 | 8.640  | -2.366 | 1.00 | 32.31 | A |
| ATOM | 456 | CA  | ASN | A | 67 | 30.158 | 8.500  | -2.216 | 1.00 | 30.88 | A |
| ATOM | 457 | CB  | ASN | A | 67 | 30.616 | 9.268  | -0.980 | 1.00 | 31.19 | A |
| ATOM | 458 | CG  | ASN | A | 67 | 32.110 | 9.477  | -0.947 | 1.00 | 31.17 | A |
| ATOM | 459 | OD1 | ASN | A | 67 | 32.591 | 10.471 | -0.406 | 1.00 | 32.90 | A |
| ATOM | 460 | ND2 | ASN | A | 67 | 32.857 | 8.537  | -1.516 | 1.00 | 30.51 | A |
| ATOM | 461 | C   | ASN | A | 67 | 30.562 | 7.035  | -2.127 | 1.00 | 29.78 | A |
| ATOM | 462 | O   | ASN | A | 67 | 30.242 | 6.349  | -1.162 | 1.00 | 29.79 | A |
| ATOM | 463 | N   | PRO | A | 68 | 31.285 | 6.541  | -3.141 | 1.00 | 29.33 | A |
| ATOM | 464 | CD  | PRO | A | 68 | 31.693 | 7.285  | -4.341 | 1.00 | 29.05 | A |
| ATOM | 465 | CA  | PRO | A | 68 | 31.751 | 5.152  | -3.218 | 1.00 | 30.16 | A |
| ATOM | 466 | CB  | PRO | A | 68 | 32.441 | 5.090  | -4.582 | 1.00 | 29.54 | A |
| ATOM | 467 | CG  | PRO | A | 68 | 31.782 | 6.184  | -5.353 | 1.00 | 31.41 | A |
| ATOM | 468 | C   | PRO | A | 68 | 32.698 | 4.755  | -2.093 | 1.00 | 29.31 | A |
| ATOM | 469 | O   | PRO | A | 68 | 32.861 | 3.571  | -1.796 | 1.00 | 30.18 | A |
| ATOM | 470 | N   | SER | A | 69 | 33.320 | 5.750  | -1.474 | 1.00 | 28.29 | A |
| ATOM | 471 | CA  | SER | A | 69 | 34.266 | 5.507  | -0.390 | 1.00 | 27.93 | A |
| ATOM | 472 | CB  | SER | A | 69 | 35.291 | 6.644  | -0.339 | 1.00 | 28.39 | A |
| ATOM | 473 | OG  | SER | A | 69 | 36.059 | 6.684  | -1.530 | 1.00 | 31.12 | A |
| ATOM | 474 | C   | SER | A | 69 | 33.587 | 5.364  | 0.971  | 1.00 | 25.71 | A |
| ATOM | 475 | O   | SER | A | 69 | 34.228 | 4.998  | 1.954  | 1.00 | 25.25 | A |
| ATOM | 476 | N   | PHE | A | 70 | 32.288 | 5.648  | 1.022  | 1.00 | 24.83 | A |
| ATOM | 477 | CA  | PHE | A | 70 | 31.531 | 5.558  | 2.270  | 1.00 | 22.81 | A |
| ATOM | 478 | CB  | PHE | A | 70 | 30.541 | 6.722  | 2.384  | 1.00 | 22.34 | A |
| ATOM | 479 | CG  | PHE | A | 70 | 31.191 | 8.073  | 2.455  | 1.00 | 22.36 | A |
| ATOM | 480 | CD1 | PHE | A | 70 | 30.413 | 9.227  | 2.445  | 1.00 | 22.74 | A |
| ATOM | 481 | CD2 | PHE | A | 70 | 32.577 | 8.199  | 2.545  | 1.00 | 22.61 | A |
| ATOM | 482 | CE1 | PHE | A | 70 | 31.007 | 10.485 | 2.524  | 1.00 | 22.81 | A |
| ATOM | 483 | CE2 | PHE | A | 70 | 33.177 | 9.452  | 2.625  | 1.00 | 20.72 | A |
| ATOM | 484 | CZ  | PHE | A | 70 | 32.391 | 10.595 | 2.614  | 1.00 | 21.36 | A |
| ATOM | 485 | C   | PHE | A | 70 | 30.768 | 4.254  | 2.353  | 1.00 | 22.36 | A |
| ATOM | 486 | O   | PHE | A | 70 | 30.040 | 3.891  | 1.428  | 1.00 | 22.34 | A |
| ATOM | 487 | N   | LYS | A | 71 | 30.934 | 3.555  | 3.471  | 1.00 | 21.11 | A |
| ATOM | 488 | CA  | LYS | A | 71 | 30.265 | 2.283  | 3.685  | 1.00 | 21.85 | A |
| ATOM | 489 | CB  | LYS | A | 71 | 31.285 | 1.140  | 3.766  | 1.00 | 22.42 | A |
| ATOM | 490 | CG  | LYS | A | 71 | 32.348 | 1.134  | 2.667  | 1.00 | 24.75 | A |
| ATOM | 491 | CD  | LYS | A | 71 | 31.739 | 0.984  | 1.281  | 1.00 | 27.50 | A |
| ATOM | 492 | CE  | LYS | A | 71 | 32.823 | 0.855  | 0.216  | 1.00 | 29.05 | A |
| ATOM | 493 | NZ  | LYS | A | 71 | 32.261 | 0.813  | -1.161 | 1.00 | 28.97 | A |
| ATOM | 494 | C   | LYS | A | 71 | 29.498 | 2.338  | 4.994  | 1.00 | 21.75 | A |
| ATOM | 495 | O   | LYS | A | 71 | 29.780 | 3.168  | 5.861  | 1.00 | 21.45 | A |
| ATOM | 496 | N   | LEU | A | 72 | 28.540 | 1.436  | 5.130  | 1.00 | 20.45 | A |

Figure 9 (9 of 92)

| ATOM | 497 | CA | LEU | A | 72 | 27.728 | 1.337 | 6.329 | 1.00 | 23.70 | A |
| ATOM | 498 | CB | LEU | A | 72 | 26.266 | 1.133 | 5.939 | 1.00 | 23.54 | A |
| ATOM | 499 | CG | LEU | A | 72 | 25.257 | 0.962 | 7.072 | 1.00 | 25.04 | A |
| ATOM | 500 | CD1 | LEU | A | 72 | 25.179 | 2.245 | 7.889 | 1.00 | 26.20 | A |
| ATOM | 501 | CD2 | LEU | A | 72 | 23.899 | 0.627 | 6.485 | 1.00 | 28.03 | A |
| ATOM | 502 | C | LEU | A | 72 | 28.222 | 0.139 | 7.148 | 1.00 | 23.97 | A |
| ATOM | 503 | O | LEU | A | 72 | 28.411 | -0.948 | 6.605 | 1.00 | 23.66 | A |
| ATOM | 504 | N | GLU | A | 73 | 28.441 | 0.340 | 8.445 | 1.00 | 23.15 | A |
| ATOM | 505 | CA | GLU | A | 73 | 28.903 | -0.737 | 9.318 | 1.00 | 20.83 | A |
| ATOM | 506 | CB | GLU | A | 73 | 30.302 | -0.424 | 9.866 | 1.00 | 22.76 | A |
| ATOM | 507 | CG | GLU | A | 73 | 30.795 | -1.448 | 10.891 | 1.00 | 22.69 | A |
| ATOM | 508 | CD | GLU | A | 73 | 30.698 | -2.867 | 10.363 | 1.00 | 22.87 | A |
| ATOM | 509 | OE1 | GLU | A | 73 | 31.337 | -3.163 | 9.335 | 1.00 | 26.67 | A |
| ATOM | 510 | OE2 | GLU | A | 73 | 29.978 | -3.683 | 10.965 | 1.00 | 23.10 | A |
| ATOM | 511 | C | GLU | A | 73 | 27.910 | -0.887 | 10.460 | 1.00 | 19.84 | A |
| ATOM | 512 | O | GLU | A | 73 | 27.835 | -0.028 | 11.337 | 1.00 | 19.29 | A |
| ATOM | 513 | N | LEU | A | 74 | 27.162 | -1.989 | 10.451 | 1.00 | 18.15 | A |
| ATOM | 514 | CA | LEU | A | 74 | 26.128 | -2.243 | 11.447 | 1.00 | 19.14 | A |
| ATOM | 515 | CB | LEU | A | 74 | 24.861 | -2.746 | 10.745 | 1.00 | 18.10 | A |
| ATOM | 516 | CG | LEU | A | 74 | 24.297 | -1.853 | 9.636 | 1.00 | 18.10 | A |
| ATOM | 517 | CD1 | LEU | A | 74 | 23.020 | -2.482 | 9.101 | 1.00 | 16.37 | A |
| ATOM | 518 | CD2 | LEU | A | 74 | 24.012 | -0.447 | 10.181 | 1.00 | 18.21 | A |
| ATOM | 519 | C | LEU | A | 74 | 26.461 | -3.209 | 12.581 | 1.00 | 18.85 | A |
| ATOM | 520 | O | LEU | A | 74 | 25.555 | -3.714 | 13.227 | 1.00 | 20.14 | A |
| ATOM | 521 | N | VAL | A | 75 | 27.738 | -3.453 | 12.845 | 1.00 | 18.43 | A |
| ATOM | 522 | CA | VAL | A | 75 | 28.105 | -4.389 | 13.904 | 1.00 | 17.60 | A |
| ATOM | 523 | CB | VAL | A | 75 | 29.638 | -4.445 | 14.086 | 1.00 | 17.68 | A |
| ATOM | 524 | CG1 | VAL | A | 75 | 30.168 | -3.068 | 14.443 | 1.00 | 17.77 | A |
| ATOM | 525 | CG2 | VAL | A | 75 | 30.000 | -5.461 | 15.167 | 1.00 | 16.13 | A |
| ATOM | 526 | C | VAL | A | 75 | 27.443 | -4.104 | 15.262 | 1.00 | 20.29 | A |
| ATOM | 527 | O | VAL | A | 75 | 27.095 | -5.038 | 15.994 | 1.00 | 19.68 | A |
| ATOM | 528 | N | GLU | A | 76 | 27.248 | -2.834 | 15.607 | 1.00 | 19.57 | A |
| ATOM | 529 | CA | GLU | A | 76 | 26.633 | -2.533 | 16.899 | 1.00 | 21.05 | A |
| ATOM | 530 | CB | GLU | A | 76 | 26.891 | -1.076 | 17.311 | 1.00 | 19.58 | A |
| ATOM | 531 | CG | GLU | A | 76 | 28.366 | -0.679 | 17.388 | 1.00 | 18.98 | A |
| ATOM | 532 | CD | GLU | A | 76 | 28.596 | 0.550 | 18.272 | 1.00 | 19.14 | A |
| ATOM | 533 | OE1 | GLU | A | 76 | 29.675 | 1.163 | 18.178 | 1.00 | 20.96 | A |
| ATOM | 534 | OE2 | GLU | A | 76 | 27.701 | 0.898 | 19.070 | 1.00 | 17.90 | A |
| ATOM | 535 | C | GLU | A | 76 | 25.127 | -2.817 | 16.930 | 1.00 | 21.06 | A |
| ATOM | 536 | O | GLU | A | 76 | 24.521 | -2.857 | 18.004 | 1.00 | 20.64 | A |
| ATOM | 537 | N | MET | A | 77 | 24.530 | -3.013 | 15.754 | 1.00 | 21.54 | A |
| ATOM | 538 | CA | MET | A | 77 | 23.101 | -3.312 | 15.646 | 1.00 | 21.33 | A |
| ATOM | 539 | CB | MET | A | 77 | 22.564 | -2.931 | 14.255 | 1.00 | 20.71 | A |
| ATOM | 540 | CG | MET | A | 77 | 22.531 | -1.437 | 13.911 | 1.00 | 24.54 | A |
| ATOM | 541 | SD | MET | A | 77 | 21.503 | -0.462 | 14.995 | 1.00 | 19.14 | A |
| ATOM | 542 | CE | MET | A | 77 | 22.742 | 0.036 | 16.212 | 1.00 | 23.85 | A |
| ATOM | 543 | C | MET | A | 77 | 22.811 | -4.805 | 15.880 | 1.00 | 21.22 | A |
| ATOM | 544 | O | MET | A | 77 | 21.668 | -5.178 | 16.149 | 1.00 | 20.14 | A |
| ATOM | 545 | N | GLU | A | 78 | 23.840 | -5.649 | 15.781 | 1.00 | 21.82 | A |
| ATOM | 546 | CA | GLU | A | 78 | 23.693 | -7.103 | 15.951 | 1.00 | 22.68 | A |
| ATOM | 547 | CB | GLU | A | 78 | 25.003 | -7.824 | 15.581 | 1.00 | 21.69 | A |
| ATOM | 548 | CG | GLU | A | 78 | 25.451 | -7.627 | 14.133 | 1.00 | 21.93 | A |
| ATOM | 549 | CD | GLU | A | 78 | 26.861 | -8.131 | 13.869 | 1.00 | 21.71 | A |
| ATOM | 550 | OE1 | GLU | A | 78 | 27.536 | -7.555 | 12.993 | 1.00 | 21.48 | A |
| ATOM | 551 | OE2 | GLU | A | 78 | 27.301 | -9.098 | 14.526 | 1.00 | 23.27 | A |
| ATOM | 552 | C | GLU | A | 78 | 23.263 | -7.586 | 17.338 | 1.00 | 24.85 | A |
| ATOM | 553 | O | GLU | A | 78 | 23.714 | -7.075 | 18.362 | 1.00 | 23.56 | A |
| ATOM | 554 | N | ARG | A | 79 | 22.390 | -8.588 | 17.349 | 1.00 | 27.25 | A |
| ATOM | 555 | CA | ARG | A | 79 | 21.902 | -9.206 | 18.579 | 1.00 | 29.90 | A |
| ATOM | 556 | CB | ARG | A | 79 | 21.042 | -10.422 | 18.210 | 1.00 | 32.92 | A |
| ATOM | 557 | CG | ARG | A | 79 | 20.744 | -11.417 | 19.322 | 1.00 | 38.39 | A |
| ATOM | 558 | CD | ARG | A | 79 | 19.694 | -12.429 | 18.847 | 1.00 | 40.84 | A |
| ATOM | 559 | NE | ARG | A | 79 | 19.704 | -13.669 | 19.619 | 1.00 | 44.32 | A |
| ATOM | 560 | CZ | ARG | A | 79 | 20.708 | -14.543 | 19.615 | 1.00 | 47.25 | A |
| ATOM | 561 | NH1 | ARG | A | 79 | 20.638 | -15.650 | 20.346 | 1.00 | 47.51 | A |
| ATOM | 562 | NH2 | ARG | A | 79 | 21.787 | -14.313 | 18.876 | 1.00 | 47.83 | A |

Figure 9 (10 of 92)

| | | | | | | | | | | |
|---|---|---|---|---|---|---|---|---|---|---|
| ATOM | 563 | C | ARG | A | 79 | 23.125 | -9.620 | 19.398 | 1.00 29.92 | A |
| ATOM | 564 | O | ARG | A | 79 | 24.026 | -10.279 | 18.883 | 1.00 28.98 | A |
| ATOM | 565 | N | GLU | A | 80 | 23.160 | -9.212 | 20.664 | 1.00 31.59 | A |
| ATOM | 566 | CA | GLU | A | 80 | 24.287 | -9.513 | 21.546 | 1.00 33.37 | A |
| ATOM | 567 | CB | GLU | A | 80 | 24.485 | -11.030 | 21.676 | 1.00 36.36 | A |
| ATOM | 568 | CG | GLU | A | 80 | 23.293 | -11.777 | 22.256 | 1.00 41.02 | A |
| ATOM | 569 | CD | GLU | A | 80 | 23.559 | -13.263 | 22.405 | 1.00 43.19 | A |
| ATOM | 570 | OE1 | GLU | A | 80 | 23.948 | -13.902 | 21.402 | 1.00 45.51 | A |
| ATOM | 571 | OE2 | GLU | A | 80 | 23.379 | -13.793 | 23.523 | 1.00 45.66 | A |
| ATOM | 572 | C | GLU | A | 80 | 25.568 | -8.878 | 21.001 | 1.00 32.13 | A |
| ATOM | 573 | O | GLU | A | 80 | 26.677 | -9.334 | 21.291 | 1.00 32.63 | A |
| ATOM | 574 | N | GLY | A | 81 | 25.408 | -7.822 | 20.213 | 1.00 30.00 | A |
| ATOM | 575 | CA | GLY | A | 81 | 26.558 | -7.149 | 19.633 | 1.00 28.28 | A |
| ATOM | 576 | C | GLY | A | 81 | 27.316 | -6.265 | 20.607 | 1.00 26.52 | A |
| ATOM | 577 | O | GLY | A | 81 | 26.798 | -5.924 | 21.669 | 1.00 24.43 | A |
| ATOM | 578 | N | PRO | A | 82 | 28.551 | -5.868 | 20.264 | 1.00 24.88 | A |
| ATOM | 579 | CD | PRO | A | 82 | 29.242 | -6.164 | 18.996 | 1.00 24.75 | A |
| ATOM | 580 | CA | PRO | A | 82 | 29.380 | -5.016 | 21.120 | 1.00 24.24 | A |
| ATOM | 581 | CB | PRO | A | 82 | 30.759 | -5.162 | 20.498 | 1.00 23.86 | A |
| ATOM | 582 | CG | PRO | A | 82 | 30.426 | -5.193 | 19.029 | 1.00 24.11 | A |
| ATOM | 583 | C | PRO | A | 82 | 28.913 | -3.558 | 21.130 | 1.00 24.45 | A |
| ATOM | 584 | O | PRO | A | 82 | 28.287 | -3.089 | 20.174 | 1.00 24.70 | A |
| ATOM | 585 | N | SER | A | 83 | 29.221 | -2.848 | 22.214 | 1.00 23.30 | A |
| ATOM | 586 | CA | SER | A | 83 | 28.857 | -1.442 | 22.334 | 1.00 22.28 | A |
| ATOM | 587 | CB | SER | A | 83 | 27.657 | -1.273 | 23.279 | 1.00 20.83 | A |
| ATOM | 588 | OG | SER | A | 83 | 27.947 | -1.728 | 24.588 | 1.00 23.12 | A |
| ATOM | 589 | C | SER | A | 83 | 30.057 | -0.613 | 22.817 | 1.00 21.88 | A |
| ATOM | 590 | O | SER | A | 83 | 30.171 | 0.569 | 22.494 | 1.00 20.36 | A |
| ATOM | 591 | N | TYR | A | 84 | 30.946 | -1.228 | 23.592 | 1.00 21.02 | A |
| ATOM | 592 | CA | TYR | A | 84 | 32.140 | -0.526 | 24.065 | 1.00 20.90 | A |
| ATOM | 593 | CB | TYR | A | 84 | 32.681 | -1.156 | 25.357 | 1.00 21.81 | A |
| ATOM | 594 | CG | TYR | A | 84 | 31.871 | -0.808 | 26.588 | 1.00 22.05 | A |
| ATOM | 595 | CD1 | TYR | A | 84 | 30.837 | -1.629 | 27.024 | 1.00 23.06 | A |
| ATOM | 596 | CE1 | TYR | A | 84 | 30.054 | -1.278 | 28.130 | 1.00 24.34 | A |
| ATOM | 597 | CD2 | TYR | A | 84 | 32.112 | 0.377 | 27.288 | 1.00 24.27 | A |
| ATOM | 598 | CE2 | TYR | A | 84 | 31.337 | 0.738 | 28.390 | 1.00 25.59 | A |
| ATOM | 599 | CZ | TYR | A | 84 | 30.310 | -0.094 | 28.804 | 1.00 26.40 | A |
| ATOM | 600 | OH | TYR | A | 84 | 29.537 | 0.270 | 29.882 | 1.00 29.14 | A |
| ATOM | 601 | C | TYR | A | 84 | 33.202 | -0.585 | 22.966 | 1.00 19.45 | A |
| ATOM | 602 | O | TYR | A | 84 | 33.433 | -1.638 | 22.373 | 1.00 19.07 | A |
| ATOM | 603 | N | THR | A | 85 | 33.836 | 0.552 | 22.698 | 1.00 18.59 | A |
| ATOM | 604 | CA | THR | A | 85 | 34.853 | 0.656 | 21.652 | 1.00 19.23 | A |
| ATOM | 605 | CB | THR | A | 85 | 35.640 | 1.968 | 21.788 | 1.00 17.43 | A |
| ATOM | 606 | OG1 | THR | A | 85 | 34.721 | 3.041 | 22.016 | 1.00 19.82 | A |
| ATOM | 607 | CG2 | THR | A | 85 | 36.421 | 2.257 | 20.511 | 1.00 18.51 | A |
| ATOM | 608 | C | THR | A | 85 | 35.844 | -0.505 | 21.591 | 1.00 18.46 | A |
| ATOM | 609 | O | THR | A | 85 | 36.079 | -1.073 | 20.520 | 1.00 19.14 | A |
| ATOM | 610 | N | PHE | A | 86 | 36.433 | -0.856 | 22.727 | 1.00 17.95 | A |
| ATOM | 611 | CA | PHE | A | 86 | 37.389 | -1.961 | 22.751 | 1.00 19.66 | A |
| ATOM | 612 | CB | PHE | A | 86 | 37.849 | -2.254 | 24.185 | 1.00 21.57 | A |
| ATOM | 613 | CG | PHE | A | 86 | 38.927 | -3.305 | 24.270 | 1.00 22.86 | A |
| ATOM | 614 | CD1 | PHE | A | 86 | 40.261 | -2.975 | 24.051 | 1.00 24.25 | A |
| ATOM | 615 | CD2 | PHE | A | 86 | 38.601 | -4.628 | 24.541 | 1.00 23.72 | A |
| ATOM | 616 | CE1 | PHE | A | 86 | 41.264 | -3.951 | 24.103 | 1.00 24.83 | A |
| ATOM | 617 | CE2 | PHE | A | 86 | 39.596 | -5.618 | 24.595 | 1.00 25.82 | A |
| ATOM | 618 | CZ | PHE | A | 86 | 40.931 | -5.274 | 24.374 | 1.00 23.63 | A |
| ATOM | 619 | C | PHE | A | 86 | 36.760 | -3.223 | 22.154 | 1.00 19.61 | A |
| ATOM | 620 | O | PHE | A | 86 | 37.349 | -3.867 | 21.286 | 1.00 19.47 | A |
| ATOM | 621 | N | ASP | A | 87 | 35.564 | -3.565 | 22.626 | 1.00 19.51 | A |
| ATOM | 622 | CA | ASP | A | 87 | 34.841 | -4.750 | 22.154 | 1.00 20.26 | A |
| ATOM | 623 | CB | ASP | A | 87 | 33.557 | -4.920 | 22.967 | 1.00 19.79 | A |
| ATOM | 624 | CG | ASP | A | 87 | 33.831 | -5.217 | 24.429 | 1.00 22.96 | A |
| ATOM | 625 | OD1 | ASP | A | 87 | 32.945 | -4.959 | 25.266 | 1.00 25.35 | A |
| ATOM | 626 | OD2 | ASP | A | 87 | 34.931 | -5.715 | 24.747 | 1.00 23.10 | A |
| ATOM | 627 | C | ASP | A | 87 | 34.498 | -4.664 | 20.662 | 1.00 19.90 | A |
| ATOM | 628 | O | ASP | A | 87 | 34.723 | -5.605 | 19.896 | 1.00 18.98 | A |

Figure 9 (11 of 92)

| ATOM | 629 | N | THR | A | 88 | 33.958 | -3.524 | 20.254 | 1.00 | 19.74 | A |
|---|---|---|---|---|---|---|---|---|---|---|---|
| ATOM | 630 | CA | THR | A | 88 | 33.586 | -3.315 | 18.861 | 1.00 | 18.89 | A |
| ATOM | 631 | CB | THR | A | 88 | 32.924 | -1.949 | 18.695 | 1.00 | 18.60 | A |
| ATOM | 632 | OG1 | THR | A | 88 | 31.722 | -1.928 | 19.473 | 1.00 | 19.42 | A |
| ATOM | 633 | CG2 | THR | A | 88 | 32.596 | -1.675 | 17.230 | 1.00 | 18.67 | A |
| ATOM | 634 | C | THR | A | 88 | 34.787 | -3.410 | 17.932 | 1.00 | 18.59 | A |
| ATOM | 635 | O | THR | A | 88 | 34.750 | -4.102 | 16.911 | 1.00 | 19.63 | A |
| ATOM | 636 | N | VAL | A | 89 | 35.859 | -2.718 | 18.292 | 1.00 | 17.71 | A |
| ATOM | 637 | CA | VAL | A | 89 | 37.055 | -2.727 | 17.470 | 1.00 | 16.31 | A |
| ATOM | 638 | CB | VAL | A | 89 | 38.096 | -1.708 | 17.986 | 1.00 | 18.10 | A |
| ATOM | 639 | CG1 | VAL | A | 89 | 39.408 | -1.847 | 17.216 | 1.00 | 16.31 | A |
| ATOM | 640 | CG2 | VAL | A | 89 | 37.537 | -0.287 | 17.836 | 1.00 | 16.70 | A |
| ATOM | 641 | C | VAL | A | 89 | 37.679 | -4.111 | 17.427 | 1.00 | 17.46 | A |
| ATOM | 642 | O | VAL | A | 89 | 38.138 | -4.557 | 16.375 | 1.00 | 14.73 | A |
| ATOM | 643 | N | SER | A | 90 | 37.696 | -4.800 | 18.563 | 1.00 | 17.99 | A |
| ATOM | 644 | CA | SER | A | 90 | 38.288 | -6.128 | 18.590 | 1.00 | 20.30 | A |
| ATOM | 645 | CB | SER | A | 90 | 38.245 | -6.699 | 20.009 | 1.00 | 20.14 | A |
| ATOM | 646 | OG | SER | A | 90 | 39.015 | -5.894 | 20.893 | 1.00 | 19.49 | A |
| ATOM | 647 | C | SER | A | 90 | 37.569 | -7.053 | 17.602 | 1.00 | 21.58 | A |
| ATOM | 648 | O | SER | A | 90 | 38.213 | -7.804 | 16.860 | 1.00 | 22.64 | A |
| ATOM | 649 | N | LEU | A | 91 | 36.241 | -6.983 | 17.574 | 1.00 | 20.38 | A |
| ATOM | 650 | CA | LEU | A | 91 | 35.475 | -7.820 | 16.661 | 1.00 | 20.50 | A |
| ATOM | 651 | CB | LEU | A | 91 | 33.981 | -7.727 | 16.980 | 1.00 | 21.68 | A |
| ATOM | 652 | CG | LEU | A | 91 | 33.054 | -8.574 | 16.097 | 1.00 | 24.52 | A |
| ATOM | 653 | CD1 | LEU | A | 91 | 33.475 | -10.050 | 16.155 | 1.00 | 22.26 | A |
| ATOM | 654 | CD2 | LEU | A | 91 | 31.603 | -8.396 | 16.569 | 1.00 | 22.94 | A |
| ATOM | 655 | C | LEU | A | 91 | 35.730 | -7.423 | 15.209 | 1.00 | 21.02 | A |
| ATOM | 656 | O | LEU | A | 91 | 35.868 | -8.278 | 14.337 | 1.00 | 21.32 | A |
| ATOM | 657 | N | LEU | A | 92 | 35.803 | -6.125 | 14.941 | 1.00 | 20.96 | A |
| ATOM | 658 | CA | LEU | A | 92 | 36.051 | -5.680 | 13.577 | 1.00 | 21.22 | A |
| ATOM | 659 | CB | LEU | A | 92 | 35.869 | -4.159 | 13.465 | 1.00 | 19.49 | A |
| ATOM | 660 | CG | LEU | A | 92 | 34.426 | -3.632 | 13.569 | 1.00 | 20.71 | A |
| ATOM | 661 | CD1 | LEU | A | 92 | 34.407 | -2.113 | 13.395 | 1.00 | 16.69 | A |
| ATOM | 662 | CD2 | LEU | A | 92 | 33.555 | -4.283 | 12.498 | 1.00 | 19.46 | A |
| ATOM | 663 | C | LEU | A | 92 | 37.450 | -6.093 | 13.104 | 1.00 | 21.87 | A |
| ATOM | 664 | O | LEU | A | 92 | 37.627 | -6.465 | 11.948 | 1.00 | 22.08 | A |
| ATOM | 665 | N | LYS | A | 93 | 38.443 | -6.031 | 13.985 | 1.00 | 21.17 | A |
| ATOM | 666 | CA | LYS | A | 93 | 39.792 | -6.428 | 13.599 | 1.00 | 24.20 | A |
| ATOM | 667 | CB | LYS | A | 93 | 40.786 | -6.135 | 14.728 | 1.00 | 24.83 | A |
| ATOM | 668 | CG | LYS | A | 93 | 41.175 | -4.665 | 14.841 | 1.00 | 27.84 | A |
| ATOM | 669 | CD | LYS | A | 93 | 42.059 | -4.396 | 16.055 | 1.00 | 27.48 | A |
| ATOM | 670 | CE | LYS | A | 93 | 43.393 | -5.109 | 15.948 | 1.00 | 28.03 | A |
| ATOM | 671 | NZ | LYS | A | 93 | 44.156 | -4.648 | 14.757 | 1.00 | 29.99 | A |
| ATOM | 672 | C | LYS | A | 93 | 39.821 | -7.918 | 13.257 | 1.00 | 25.14 | A |
| ATOM | 673 | O | LYS | A | 93 | 40.554 | -8.350 | 12.371 | 1.00 | 26.53 | A |
| ATOM | 674 | N | GLN | A | 94 | 39.006 | -8.691 | 13.963 | 1.00 | 25.34 | A |
| ATOM | 675 | CA | GLN | A | 94 | 38.917 | -10.131 | 13.757 | 1.00 | 27.52 | A |
| ATOM | 676 | CB | GLN | A | 94 | 38.125 | -10.764 | 14.903 | 1.00 | 29.41 | A |
| ATOM | 677 | CG | GLN | A | 94 | 38.113 | -12.279 | 14.897 | 1.00 | 35.80 | A |
| ATOM | 678 | CD | GLN | A | 94 | 37.327 | -12.854 | 16.062 | 1.00 | 39.68 | A |
| ATOM | 679 | OE1 | GLN | A | 94 | 36.092 | -12.923 | 16.028 | 1.00 | 40.88 | A |
| ATOM | 680 | NE2 | GLN | A | 94 | 38.040 | -13.256 | 17.113 | 1.00 | 41.31 | A |
| ATOM | 681 | C | GLN | A | 94 | 38.249 | -10.455 | 12.420 | 1.00 | 26.53 | A |
| ATOM | 682 | O | GLN | A | 94 | 38.638 | -11.398 | 11.724 | 1.00 | 24.51 | A |
| ATOM | 683 | N | ARG | A | 95 | 37.245 | -9.665 | 12.060 | 1.00 | 24.91 | A |
| ATOM | 684 | CA | ARG | A | 95 | 36.539 | -9.872 | 10.808 | 1.00 | 22.89 | A |
| ATOM | 685 | CB | ARG | A | 95 | 35.157 | -9.202 | 10.871 | 1.00 | 21.60 | A |
| ATOM | 686 | CG | ARG | A | 95 | 34.200 | -9.881 | 11.837 | 1.00 | 21.58 | A |
| ATOM | 687 | CD | ARG | A | 95 | 32.865 | -9.160 | 11.925 | 1.00 | 18.03 | A |
| ATOM | 688 | NE | ARG | A | 95 | 31.894 | -9.887 | 12.737 | 1.00 | 17.74 | A |
| ATOM | 689 | CZ | ARG | A | 95 | 30.668 | -9.446 | 13.003 | 1.00 | 18.42 | A |
| ATOM | 690 | NH1 | ARG | A | 95 | 29.846 | -10.169 | 13.749 | 1.00 | 16.68 | A |
| ATOM | 691 | NH2 | ARG | A | 95 | 30.261 | -8.276 | 12.522 | 1.00 | 18.34 | A |
| ATOM | 692 | C | ARG | A | 95 | 37.320 | -9.352 | 9.616 | 1.00 | 22.31 | A |
| ATOM | 693 | O | ARG | A | 95 | 37.095 | -9.786 | 8.505 | 1.00 | 22.78 | A |
| ATOM | 694 | N | TYR | A | 96 | 38.233 | -8.417 | 9.849 | 1.00 | 21.17 | A |

Figure 9 (12 of 92)

| ATOM | 695 | CA | TYR | A | 96 | 39.028 | -7.851 | 8.767 | 1.00 | 21.67 | A |
|---|---|---|---|---|---|---|---|---|---|---|---|
| ATOM | 696 | CB | TYR | A | 96 | 38.542 | -6.441 | 8.441 | 1.00 | 22.10 | A |
| ATOM | 697 | CG | TYR | A | 96 | 37.103 | -6.387 | 7.978 | 1.00 | 21.45 | A |
| ATOM | 698 | CD1 | TYR | A | 96 | 36.057 | -6.272 | 8.893 | 1.00 | 19.79 | A |
| ATOM | 699 | CE1 | TYR | A | 96 | 34.726 | -6.222 | 8.468 | 1.00 | 20.30 | A |
| ATOM | 700 | CD2 | TYR | A | 96 | 36.787 | -6.459 | 6.620 | 1.00 | 22.47 | A |
| ATOM | 701 | CE2 | TYR | A | 96 | 35.453 | -6.411 | 6.180 | 1.00 | 21.85 | A |
| ATOM | 702 | CZ | TYR | A | 96 | 34.433 | -6.287 | 7.111 | 1.00 | 20.69 | A |
| ATOM | 703 | OH | TYR | A | 96 | 33.124 | -6.181 | 6.692 | 1.00 | 19.70 | A |
| ATOM | 704 | C | TYR | A | 96 | 40.503 | -7.841 | 9.142 | 1.00 | 22.77 | A |
| ATOM | 705 | O | TYR | A | 96 | 41.147 | -6.803 | 9.180 | 1.00 | 19.67 | A |
| ATOM | 706 | N | PRO | A | 97 | 41.056 | -9.032 | 9.411 | 1.00 | 24.96 | A |
| ATOM | 707 | CD | PRO | A | 97 | 40.426 | -10.331 | 9.079 | 1.00 | 25.21 | A |
| ATOM | 708 | CA | PRO | A | 97 | 42.467 | -9.212 | 9.806 | 1.00 | 27.34 | A |
| ATOM | 709 | CB | PRO | A | 97 | 42.587 | -10.732 | 9.965 | 1.00 | 26.55 | A |
| ATOM | 710 | CG | PRO | A | 97 | 41.105 | -11.234 | 10.046 | 1.00 | 27.44 | A |
| ATOM | 711 | C | PRO | A | 97 | 43.559 | -8.663 | 8.884 | 1.00 | 28.93 | A |
| ATOM | 712 | O | PRO | A | 97 | 44.677 | -8.405 | 9.331 | 1.00 | 30.40 | A |
| ATOM | 713 | N | ASN | A | 98 | 43.264 | -8.534 | 7.598 | 1.00 | 30.40 | A |
| ATOM | 714 | CA | ASN | A | 98 | 44.284 | -8.049 | 6.696 | 1.00 | 31.58 | A |
| ATOM | 715 | CB | ASN | A | 98 | 44.285 | -8.874 | 5.411 | 1.00 | 35.65 | A |
| ATOM | 716 | CG | ASN | A | 98 | 44.371 | -10.364 | 5.686 | 1.00 | 40.05 | A |
| ATOM | 717 | OD1 | ASN | A | 98 | 43.340 | -11.043 | 5.737 | 1.00 | 41.50 | A |
| ATOM | 718 | ND2 | ASN | A | 98 | 45.593 | -10.883 | 5.876 | 1.00 | 40.72 | A |
| ATOM | 719 | C | ASN | A | 98 | 44.175 | -6.574 | 6.372 | 1.00 | 31.85 | A |
| ATOM | 720 | O | ASN | A | 98 | 44.916 | -6.080 | 5.545 | 1.00 | 31.44 | A |
| ATOM | 721 | N | ASP | A | 99 | 43.265 | -5.861 | 7.019 | 1.00 | 30.48 | A |
| ATOM | 722 | CA | ASP | A | 99 | 43.114 | -4.451 | 6.742 | 1.00 | 28.69 | A |
| ATOM | 723 | CB | ASP | A | 99 | 41.636 | -4.135 | 6.510 | 1.00 | 28.58 | A |
| ATOM | 724 | CG | ASP | A | 99 | 41.064 | -4.802 | 5.253 | 1.00 | 28.49 | A |
| ATOM | 725 | OD1 | ASP | A | 99 | 41.601 | -4.628 | 4.136 | 1.00 | 27.54 | A |
| ATOM | 726 | OD2 | ASP | A | 99 | 40.040 | -5.500 | 5.376 | 1.00 | 27.94 | A |
| ATOM | 727 | C | ASP | A | 99 | 43.625 | -3.617 | 7.909 | 1.00 | 27.47 | A |
| ATOM | 728 | O | ASP | A | 99 | 43.736 | -4.121 | 9.035 | 1.00 | 27.53 | A |
| ATOM | 729 | N | GLN | A | 100 | 43.906 | -2.340 | 7.655 | 1.00 | 25.38 | A |
| ATOM | 730 | CA | GLN | A | 100 | 44.355 | -1.449 | 8.718 | 1.00 | 24.68 | A |
| ATOM | 731 | CB | GLN | A | 100 | 45.556 | -0.624 | 8.248 | 1.00 | 25.94 | A |
| ATOM | 732 | CG | GLN | A | 100 | 45.970 | 0.507 | 9.214 | 1.00 | 30.18 | A |
| ATOM | 733 | CD | GLN | A | 100 | 47.368 | 1.062 | 8.920 | 1.00 | 31.72 | A |
| ATOM | 734 | OE1 | GLN | A | 100 | 47.745 | 1.251 | 7.759 | 1.00 | 30.25 | A |
| ATOM | 735 | NE2 | GLN | A | 100 | 48.137 | 1.334 | 9.977 | 1.00 | 32.85 | A |
| ATOM | 736 | C | GLN | A | 100 | 43.193 | -0.532 | 9.125 | 1.00 | 23.54 | A |
| ATOM | 737 | O | GLN | A | 100 | 42.758 | 0.322 | 8.345 | 1.00 | 22.09 | A |
| ATOM | 738 | N | LEU | A | 101 | 42.704 | -0.710 | 10.350 | 1.00 | 21.54 | A |
| ATOM | 739 | CA | LEU | A | 101 | 41.595 | 0.099 | 10.855 | 1.00 | 20.47 | A |
| ATOM | 740 | CB | LEU | A | 101 | 40.672 | -0.741 | 11.745 | 1.00 | 19.37 | A |
| ATOM | 741 | CG | LEU | A | 101 | 40.220 | -2.104 | 11.209 | 1.00 | 19.60 | A |
| ATOM | 742 | CD1 | LEU | A | 101 | 39.144 | -2.691 | 12.129 | 1.00 | 18.40 | A |
| ATOM | 743 | CD2 | LEU | A | 101 | 39.687 | -1.964 | 9.797 | 1.00 | 19.64 | A |
| ATOM | 744 | C | LEU | A | 101 | 42.047 | 1.326 | 11.637 | 1.00 | 21.18 | A |
| ATOM | 745 | O | LEU | A | 101 | 43.081 | 1.306 | 12.301 | 1.00 | 21.36 | A |
| ATOM | 746 | N | PHE | A | 102 | 41.257 | 2.393 | 11.547 | 1.00 | 20.42 | A |
| ATOM | 747 | CA | PHE | A | 102 | 41.532 | 3.642 | 12.248 | 1.00 | 20.29 | A |
| ATOM | 748 | CB | PHE | A | 102 | 41.909 | 4.756 | 11.268 | 1.00 | 19.96 | A |
| ATOM | 749 | CG | PHE | A | 102 | 43.179 | 4.509 | 10.514 | 1.00 | 21.56 | A |
| ATOM | 750 | CD1 | PHE | A | 102 | 43.236 | 3.549 | 9.506 | 1.00 | 21.93 | A |
| ATOM | 751 | CD2 | PHE | A | 102 | 44.322 | 5.243 | 10.808 | 1.00 | 20.61 | A |
| ATOM | 752 | CE1 | PHE | A | 102 | 44.424 | 3.329 | 8.798 | 1.00 | 24.02 | A |
| ATOM | 753 | CE2 | PHE | A | 102 | 45.515 | 5.030 | 10.107 | 1.00 | 22.41 | A |
| ATOM | 754 | CZ | PHE | A | 102 | 45.565 | 4.072 | 9.101 | 1.00 | 21.17 | A |
| ATOM | 755 | C | PHE | A | 102 | 40.254 | 4.048 | 12.967 | 1.00 | 19.74 | A |
| ATOM | 756 | O | PHE | A | 102 | 39.160 | 3.797 | 12.471 | 1.00 | 20.12 | A |
| ATOM | 757 | N | PHE | A | 103 | 40.389 | 4.666 | 14.134 | 1.00 | 18.89 | A |
| ATOM | 758 | CA | PHE | A | 103 | 39.216 | 5.105 | 14.880 | 1.00 | 18.47 | A |
| ATOM | 759 | CB | PHE | A | 103 | 39.222 | 4.510 | 16.284 | 1.00 | 19.58 | A |
| ATOM | 760 | CG | PHE | A | 103 | 37.874 | 4.533 | 16.946 | 1.00 | 22.72 | A |

Figure 9 (13 of 92)

| | | | | | | | | | | |
|---|---|---|---|---|---|---|---|---|---|---|
| ATOM | 761 | CD1 | PHE | A | 103 | 36.885 | 3.626 | 16.569 | 1.00 24.54 | A |
| ATOM | 762 | CD2 | PHE | A | 103 | 37.577 | 5.482 | 17.919 | 1.00 24.19 | A |
| ATOM | 763 | CE1 | PHE | A | 103 | 35.613 | 3.668 | 17.156 | 1.00 26.48 | A |
| ATOM | 764 | CE2 | PHE | A | 103 | 36.313 | 5.532 | 18.509 | 1.00 25.28 | A |
| ATOM | 765 | CZ | PHE | A | 103 | 35.330 | 4.624 | 18.127 | 1.00 25.75 | A |
| ATOM | 766 | C | PHE | A | 103 | 39.183 | 6.636 | 14.962 | 1.00 18.11 | A |
| ATOM | 767 | O | PHE | A | 103 | 40.124 | 7.265 | 15.455 | 1.00 18.02 | A |
| ATOM | 768 | N | ILE | A | 104 | 38.093 | 7.226 | 14.482 | 1.00 16.62 | A |
| ATOM | 769 | CA | ILE | A | 104 | 37.936 | 8.680 | 14.472 | 1.00 17.56 | A |
| ATOM | 770 | CB | ILE | A | 104 | 37.076 | 9.119 | 13.249 | 1.00 17.52 | A |
| ATOM | 771 | CG2 | ILE | A | 104 | 36.944 | 10.638 | 13.198 | 1.00 17.85 | A |
| ATOM | 772 | CG1 | ILE | A | 104 | 37.721 | 8.614 | 11.953 | 1.00 18.03 | A |
| ATOM | 773 | CD1 | ILE | A | 104 | 36.816 | 8.684 | 10.753 | 1.00 16.41 | A |
| ATOM | 774 | C | ILE | A | 104 | 37.303 | 9.237 | 15.754 | 1.00 16.31 | A |
| ATOM | 775 | O | ILE | A | 104 | 36.260 | 8.766 | 16.195 | 1.00 18.28 | A |
| ATOM | 776 | N | ILE | A | 105 | 37.948 | 10.236 | 16.347 | 1.00 14.39 | A |
| ATOM | 777 | CA | ILE | A | 105 | 37.445 | 10.893 | 17.555 | 1.00 14.81 | A |
| ATOM | 778 | CB | ILE | A | 105 | 38.105 | 10.352 | 18.853 | 1.00 15.51 | A |
| ATOM | 779 | CG2 | ILE | A | 105 | 37.639 | 8.925 | 19.150 | 1.00 15.67 | A |
| ATOM | 780 | CG1 | ILE | A | 105 | 39.626 | 10.407 | 18.709 | 1.00 14.52 | A |
| ATOM | 781 | CD1 | ILE | A | 105 | 40.371 | 10.452 | 20.042 | 1.00 17.60 | A |
| ATOM | 782 | C | ILE | A | 105 | 37.820 | 12.367 | 17.458 | 1.00 15.63 | A |
| ATOM | 783 | O | ILE | A | 105 | 38.561 | 12.773 | 16.552 | 1.00 14.91 | A |
| ATOM | 784 | N | GLY | A | 106 | 37.303 | 13.165 | 18.386 | 1.00 16.24 | A |
| ATOM | 785 | CA | GLY | A | 106 | 37.639 | 14.572 | 18.408 | 1.00 16.79 | A |
| ATOM | 786 | C | GLY | A | 106 | 39.058 | 14.611 | 18.937 | 1.00 20.15 | A |
| ATOM | 787 | O | GLY | A | 106 | 39.400 | 13.854 | 19.847 | 1.00 19.33 | A |
| ATOM | 788 | N | ALA | A | 107 | 39.893 | 15.474 | 18.373 | 1.00 20.89 | A |
| ATOM | 789 | CA | ALA | A | 107 | 41.285 | 15.557 | 18.804 | 1.00 23.38 | A |
| ATOM | 790 | CB | ALA | A | 107 | 42.034 | 16.556 | 17.920 | 1.00 23.08 | A |
| ATOM | 791 | C | ALA | A | 107 | 41.450 | 15.939 | 20.280 | 1.00 23.62 | A |
| ATOM | 792 | O | ALA | A | 107 | 42.486 | 15.659 | 20.886 | 1.00 26.30 | A |
| ATOM | 793 | N | ASP | A | 108 | 40.432 | 16.573 | 20.850 | 1.00 20.81 | A |
| ATOM | 794 | CA | ASP | A | 108 | 40.485 | 17.008 | 22.242 | 1.00 20.97 | A |
| ATOM | 795 | CB | ASP | A | 108 | 39.712 | 18.321 | 22.409 | 1.00 20.00 | A |
| ATOM | 796 | CG | ASP | A | 108 | 38.222 | 18.146 | 22.175 | 1.00 21.99 | A |
| ATOM | 797 | OD1 | ASP | A | 108 | 37.845 | 17.416 | 21.236 | 1.00 21.02 | A |
| ATOM | 798 | OD2 | ASP | A | 108 | 37.421 | 18.738 | 22.923 | 1.00 26.47 | A |
| ATOM | 799 | C | ASP | A | 108 | 39.909 | 15.989 | 23.208 | 1.00 19.36 | A |
| ATOM | 800 | O | ASP | A | 108 | 39.990 | 16.178 | 24.418 | 1.00 19.99 | A |
| ATOM | 801 | N | MET | A | 109 | 39.334 | 14.910 | 22.691 | 1.00 19.11 | A |
| ATOM | 802 | CA | MET | A | 109 | 38.723 | 13.925 | 23.576 | 1.00 17.26 | A |
| ATOM | 803 | CB | MET | A | 109 | 38.305 | 12.651 | 22.813 | 1.00 16.03 | A |
| ATOM | 804 | CG | MET | A | 109 | 37.388 | 11.700 | 23.643 | 1.00 15.74 | A |
| ATOM | 805 | SD | MET | A | 109 | 36.740 | 10.231 | 22.784 | 1.00 8.28 | A |
| ATOM | 806 | CE | MET | A | 109 | 38.004 | 9.070 | 23.104 | 1.00 11.10 | A |
| ATOM | 807 | C | MET | A | 109 | 39.633 | 13.535 | 24.726 | 1.00 16.72 | A |
| ATOM | 808 | O | MET | A | 109 | 39.196 | 13.509 | 25.879 | 1.00 14.79 | A |
| ATOM | 809 | N | ILE | A | 110 | 40.900 | 13.262 | 24.415 | 1.00 15.52 | A |
| ATOM | 810 | CA | ILE | A | 110 | 41.856 | 12.808 | 25.425 | 1.00 15.49 | A |
| ATOM | 811 | CB | ILE | A | 110 | 42.585 | 11.546 | 24.930 | 1.00 14.28 | A |
| ATOM | 812 | CG2 | ILE | A | 110 | 41.582 | 10.417 | 24.723 | 1.00 14.88 | A |
| ATOM | 813 | CG1 | ILE | A | 110 | 43.333 | 11.859 | 23.626 | 1.00 15.03 | A |
| ATOM | 814 | CD1 | ILE | A | 110 | 44.197 | 10.722 | 23.106 | 1.00 16.31 | A |
| ATOM | 815 | C | ILE | A | 110 | 42.914 | 13.817 | 25.871 | 1.00 16.31 | A |
| ATOM | 816 | O | ILE | A | 110 | 43.823 | 13.476 | 26.632 | 1.00 15.04 | A |
| ATOM | 817 | N | GLU | A | 111 | 42.783 | 15.054 | 25.406 | 1.00 16.89 | A |
| ATOM | 818 | CA | GLU | A | 111 | 43.726 | 16.120 | 25.717 | 1.00 18.06 | A |
| ATOM | 819 | CB | GLU | A | 111 | 43.275 | 17.417 | 25.042 | 1.00 21.05 | A |
| ATOM | 820 | CG | GLU | A | 111 | 44.331 | 18.512 | 25.022 | 1.00 28.77 | A |
| ATOM | 821 | CD | GLU | A | 111 | 43.802 | 19.806 | 24.428 | 1.00 31.59 | A |
| ATOM | 822 | OE1 | GLU | A | 111 | 42.939 | 19.723 | 23.527 | 1.00 32.38 | A |
| ATOM | 823 | OE2 | GLU | A | 111 | 44.253 | 20.898 | 24.851 | 1.00 33.31 | A |
| ATOM | 824 | C | GLU | A | 111 | 43.928 | 16.404 | 27.204 | 1.00 16.46 | A |
| ATOM | 825 | O | GLU | A | 111 | 45.022 | 16.761 | 27.623 | 1.00 13.59 | A |
| ATOM | 826 | N | TYR | A | 112 | 42.874 | 16.238 | 27.992 | 1.00 15.56 | A |

Figure 9 (14 of 92)

| | | | | | | | | | | |
|---|---|---|---|---|---|---|---|---|---|---|
| ATOM | 827 | CA | TYR | A | 112 | 42.932 | 16.535 | 29.420 | 1.00 16.70 | A |
| ATOM | 828 | CB | TYR | A | 112 | 41.656 | 17.290 | 29.819 | 1.00 16.74 | A |
| ATOM | 829 | CG | TYR | A | 112 | 41.291 | 18.361 | 28.818 | 1.00 19.23 | A |
| ATOM | 830 | CD1 | TYR | A | 112 | 40.160 | 18.235 | 28.010 | 1.00 19.77 | A |
| ATOM | 831 | CE1 | TYR | A | 112 | 39.872 | 19.188 | 27.020 | 1.00 21.13 | A |
| ATOM | 832 | CD2 | TYR | A | 112 | 42.125 | 19.467 | 28.623 | 1.00 19.34 | A |
| ATOM | 833 | CE2 | TYR | A | 112 | 41.848 | 20.419 | 27.645 | 1.00 20.95 | A |
| ATOM | 834 | CZ | TYR | A | 112 | 40.723 | 20.271 | 26.850 | 1.00 22.23 | A |
| ATOM | 835 | OH | TYR | A | 112 | 40.466 | 21.207 | 25.882 | 1.00 26.11 | A |
| ATOM | 836 | C | TYR | A | 112 | 43.119 | 15.336 | 30.346 | 1.00 15.92 | A |
| ATOM | 837 | O | TYR | A | 112 | 43.129 | 15.492 | 31.560 | 1.00 16.72 | A |
| ATOM | 838 | N | LEU | A | 113 | 43.263 | 14.144 | 29.786 | 1.00 16.46 | A |
| ATOM | 839 | CA | LEU | A | 113 | 43.434 | 12.957 | 30.616 | 1.00 17.68 | A |
| ATOM | 840 | CB | LEU | A | 113 | 42.949 | 11.717 | 29.858 | 1.00 16.56 | A |
| ATOM | 841 | CG | LEU | A | 113 | 41.455 | 11.646 | 29.526 | 1.00 15.86 | A |
| ATOM | 842 | CD1 | LEU | A | 113 | 41.194 | 10.475 | 28.603 | 1.00 15.31 | A |
| ATOM | 843 | CD2 | LEU | A | 113 | 40.639 | 11.498 | 30.807 | 1.00 14.84 | A |
| ATOM | 844 | C | LEU | A | 113 | 44.880 | 12.743 | 31.047 | 1.00 18.20 | A |
| ATOM | 845 | O | LEU | A | 113 | 45.803 | 13.062 | 30.306 | 1.00 18.55 | A |
| ATOM | 846 | N | PRO | A | 114 | 45.093 | 12.223 | 32.271 | 1.00 18.79 | A |
| ATOM | 847 | CD | PRO | A | 114 | 44.082 | 12.042 | 33.333 | 1.00 18.38 | A |
| ATOM | 848 | CA | PRO | A | 114 | 46.444 | 11.960 | 32.787 | 1.00 19.61 | A |
| ATOM | 849 | CB | PRO | A | 114 | 46.243 | 12.005 | 34.302 | 1.00 18.74 | A |
| ATOM | 850 | CG | PRO | A | 114 | 44.876 | 11.382 | 34.450 | 1.00 18.42 | A |
| ATOM | 851 | C | PRO | A | 114 | 46.835 | 10.562 | 32.297 | 1.00 20.27 | A |
| ATOM | 852 | O | PRO | A | 114 | 45.997 | 9.856 | 31.738 | 1.00 19.17 | A |
| ATOM | 853 | N | LYS | A | 115 | 48.084 | 10.156 | 32.508 | 1.00 21.74 | A |
| ATOM | 854 | CA | LYS | A | 115 | 48.526 | 8.834 | 32.064 | 1.00 21.16 | A |
| ATOM | 855 | CB | LYS | A | 115 | 49.915 | 8.518 | 32.624 | 1.00 24.08 | A |
| ATOM | 856 | CG | LYS | A | 115 | 50.521 | 7.236 | 32.063 | 1.00 25.63 | A |
| ATOM | 857 | CD | LYS | A | 115 | 50.624 | 7.312 | 30.544 | 1.00 28.05 | A |
| ATOM | 858 | CE | LYS | A | 115 | 51.386 | 6.129 | 29.976 | 1.00 31.19 | A |
| ATOM | 859 | NZ | LYS | A | 115 | 51.492 | 6.219 | 28.488 | 1.00 32.70 | A |
| ATOM | 860 | C | LYS | A | 115 | 47.533 | 7.768 | 32.517 | 1.00 21.26 | A |
| ATOM | 861 | O | LYS | A | 115 | 47.187 | 7.697 | 33.699 | 1.00 21.18 | A |
| ATOM | 862 | N | TRP | A | 116 | 47.081 | 6.938 | 31.579 | 1.00 21.16 | A |
| ATOM | 863 | CA | TRP | A | 116 | 46.102 | 5.896 | 31.878 | 1.00 22.01 | A |
| ATOM | 864 | CB | TRP | A | 116 | 44.701 | 6.464 | 31.668 | 1.00 24.03 | A |
| ATOM | 865 | CG | TRP | A | 116 | 43.619 | 5.653 | 32.278 | 1.00 25.39 | A |
| ATOM | 866 | CD2 | TRP | A | 116 | 42.226 | 5.958 | 32.266 | 1.00 26.72 | A |
| ATOM | 867 | CE2 | TRP | A | 116 | 41.574 | 4.962 | 33.024 | 1.00 28.28 | A |
| ATOM | 868 | CE3 | TRP | A | 116 | 41.462 | 6.981 | 31.689 | 1.00 27.98 | A |
| ATOM | 869 | CD1 | TRP | A | 116 | 43.758 | 4.512 | 33.016 | 1.00 25.51 | A |
| ATOM | 870 | NE1 | TRP | A | 116 | 42.534 | 4.091 | 33.470 | 1.00 26.99 | A |
| ATOM | 871 | CZ2 | TRP | A | 116 | 40.192 | 4.958 | 33.224 | 1.00 29.02 | A |
| ATOM | 872 | CZ3 | TRP | A | 116 | 40.088 | 6.978 | 31.886 | 1.00 31.06 | A |
| ATOM | 873 | CH2 | TRP | A | 116 | 39.466 | 5.970 | 32.650 | 1.00 30.77 | A |
| ATOM | 874 | C | TRP | A | 116 | 46.303 | 4.683 | 30.971 | 1.00 22.76 | A |
| ATOM | 875 | O | TRP | A | 116 | 46.150 | 4.789 | 29.760 | 1.00 21.83 | A |
| ATOM | 876 | N | TYR | A | 117 | 46.623 | 3.529 | 31.554 | 1.00 24.23 | A |
| ATOM | 877 | CA | TYR | A | 117 | 46.869 | 2.329 | 30.756 | 1.00 26.11 | A |
| ATOM | 878 | CB | TYR | A | 117 | 47.484 | 1.214 | 31.608 | 1.00 26.17 | A |
| ATOM | 879 | CG | TYR | A | 117 | 48.847 | 1.550 | 32.179 | 1.00 26.19 | A |
| ATOM | 880 | CD1 | TYR | A | 117 | 49.753 | 2.331 | 31.462 | 1.00 26.06 | A |
| ATOM | 881 | CE1 | TYR | A | 117 | 51.015 | 2.641 | 31.988 | 1.00 26.80 | A |
| ATOM | 882 | CD2 | TYR | A | 117 | 49.235 | 1.079 | 33.438 | 1.00 26.31 | A |
| ATOM | 883 | CE2 | TYR | A | 117 | 50.496 | 1.379 | 33.972 | 1.00 26.13 | A |
| ATOM | 884 | CZ | TYR | A | 117 | 51.377 | 2.162 | 33.240 | 1.00 26.63 | A |
| ATOM | 885 | OH | TYR | A | 117 | 52.610 | 2.482 | 33.758 | 1.00 26.74 | A |
| ATOM | 886 | C | TYR | A | 117 | 45.655 | 1.777 | 30.028 | 1.00 27.26 | A |
| ATOM | 887 | O | TYR | A | 117 | 45.799 | 1.102 | 29.008 | 1.00 27.76 | A |
| ATOM | 888 | N | LYS | A | 118 | 44.463 | 2.043 | 30.547 | 1.00 27.79 | A |
| ATOM | 889 | CA | LYS | A | 118 | 43.262 | 1.556 | 29.889 | 1.00 28.62 | A |
| ATOM | 890 | CB | LYS | A | 118 | 42.047 | 1.751 | 30.793 | 1.00 31.51 | A |
| ATOM | 891 | CG | LYS | A | 118 | 41.642 | 0.474 | 31.511 | 1.00 35.71 | A |
| ATOM | 892 | CD | LYS | A | 118 | 40.980 | 0.760 | 32.850 | 1.00 40.36 | A |

Figure 9 (15 of 92)

| | | | | | | | | | | |
|---|---|---|---|---|---|---|---|---|---|---|
| ATOM | 893 | CE | LYS | A | 118 | 42.006 | 1.244 | 33.872 | 1.00 42.66 | A |
| ATOM | 894 | NZ | LYS | A | 118 | 41.393 | 1.645 | 35.172 | 1.00 43.78 | A |
| ATOM | 895 | C | LYS | A | 118 | 43.095 | 2.300 | 28.568 | 1.00 27.49 | A |
| ATOM | 896 | O | LYS | A | 118 | 42.582 | 1.752 | 27.590 | 1.00 26.49 | A |
| ATOM | 897 | N | LEU | A | 119 | 43.548 | 3.550 | 28.543 | 1.00 25.31 | A |
| ATOM | 898 | CA | LEU | A | 119 | 43.478 | 4.352 | 27.334 | 1.00 24.41 | A |
| ATOM | 899 | CB | LEU | A | 119 | 43.611 | 5.842 | 27.667 | 1.00 22.32 | A |
| ATOM | 900 | CG | LEU | A | 119 | 43.783 | 6.752 | 26.445 | 1.00 21.37 | A |
| ATOM | 901 | CD1 | LEU | A | 119 | 42.587 | 6.585 | 25.523 | 1.00 19.48 | A |
| ATOM | 902 | CD2 | LEU | A | 119 | 43.925 | 8.196 | 26.872 | 1.00 17.07 | A |
| ATOM | 903 | C | LEU | A | 119 | 44.616 | 3.923 | 26.403 | 1.00 25.16 | A |
| ATOM | 904 | O | LEU | A | 119 | 44.415 | 3.744 | 25.201 | 1.00 24.15 | A |
| ATOM | 905 | N | ASP | A | 120 | 45.813 | 3.760 | 26.962 | 1.00 24.91 | A |
| ATOM | 906 | CA | ASP | A | 120 | 46.960 | 3.345 | 26.161 | 1.00 27.17 | A |
| ATOM | 907 | CB | ASP | A | 120 | 48.194 | 3.121 | 27.039 | 1.00 28.19 | A |
| ATOM | 908 | CG | ASP | A | 120 | 48.763 | 4.409 | 27.588 | 1.00 29.07 | A |
| ATOM | 909 | OD1 | ASP | A | 120 | 48.423 | 5.492 | 27.065 | 1.00 28.06 | A |
| ATOM | 910 | OD2 | ASP | A | 120 | 49.568 | 4.334 | 28.538 | 1.00 31.85 | A |
| ATOM | 911 | C | ASP | A | 120 | 46.633 | 2.051 | 25.441 | 1.00 27.26 | A |
| ATOM | 912 | O | ASP | A | 120 | 46.965 | 1.874 | 24.267 | 1.00 26.25 | A |
| ATOM | 913 | N | GLU | A | 121 | 45.970 | 1.155 | 26.163 | 1.00 27.62 | A |
| ATOM | 914 | CA | GLU | A | 121 | 45.588 | -0.144 | 25.629 | 1.00 29.37 | A |
| ATOM | 915 | CB | GLU | A | 121 | 44.902 | -0.959 | 26.725 | 1.00 32.88 | A |
| ATOM | 916 | CG | GLU | A | 121 | 44.465 | -2.350 | 26.316 | 1.00 38.65 | A |
| ATOM | 917 | CD | GLU | A | 121 | 43.983 | -3.161 | 27.508 | 1.00 42.10 | A |
| ATOM | 918 | OE1 | GLU | A | 121 | 42.810 | -3.600 | 27.507 | 1.00 41.77 | A |
| ATOM | 919 | OE2 | GLU | A | 121 | 44.785 | -3.351 | 28.450 | 1.00 44.49 | A |
| ATOM | 920 | C | GLU | A | 121 | 44.665 | 0.007 | 24.429 | 1.00 29.02 | A |
| ATOM | 921 | O | GLU | A | 121 | 44.809 | -0.703 | 23.424 | 1.00 27.05 | A |
| ATOM | 922 | N | LEU | A | 122 | 43.719 | 0.936 | 24.533 | 1.00 27.94 | A |
| ATOM | 923 | CA | LEU | A | 122 | 42.783 | 1.174 | 23.445 | 1.00 28.13 | A |
| ATOM | 924 | CB | LEU | A | 122 | 41.648 | 2.092 | 23.914 | 1.00 28.63 | A |
| ATOM | 925 | CG | LEU | A | 122 | 40.546 | 2.412 | 22.900 | 1.00 26.84 | A |
| ATOM | 926 | CD1 | LEU | A | 122 | 39.996 | 1.126 | 22.313 | 1.00 28.09 | A |
| ATOM | 927 | CD2 | LEU | A | 122 | 39.434 | 3.200 | 23.586 | 1.00 27.05 | A |
| ATOM | 928 | C | LEU | A | 122 | 43.507 | 1.793 | 22.250 | 1.00 27.61 | A |
| ATOM | 929 | O | LEU | A | 122 | 43.215 | 1.465 | 21.100 | 1.00 25.90 | A |
| ATOM | 930 | N | LEU | A | 123 | 44.469 | 2.669 | 22.529 | 1.00 27.21 | A |
| ATOM | 931 | CA | LEU | A | 123 | 45.221 | 3.332 | 21.470 | 1.00 28.50 | A |
| ATOM | 932 | CB | LEU | A | 123 | 46.006 | 4.519 | 22.043 | 1.00 29.65 | A |
| ATOM | 933 | CG | LEU | A | 123 | 45.155 | 5.652 | 22.633 | 1.00 30.47 | A |
| ATOM | 934 | CD1 | LEU | A | 123 | 46.048 | 6.742 | 23.216 | 1.00 30.86 | A |
| ATOM | 935 | CD2 | LEU | A | 123 | 44.258 | 6.226 | 21.551 | 1.00 30.55 | A |
| ATOM | 936 | C | LEU | A | 123 | 46.164 | 2.388 | 20.725 | 1.00 28.86 | A |
| ATOM | 937 | O | LEU | A | 123 | 46.467 | 2.604 | 19.551 | 1.00 29.61 | A |
| ATOM | 938 | N | ASN | A | 124 | 46.636 | 1.348 | 21.404 | 1.00 28.52 | A |
| ATOM | 939 | CA | ASN | A | 124 | 47.529 | 0.384 | 20.771 | 1.00 27.92 | A |
| ATOM | 940 | CB | ASN | A | 124 | 48.385 | -0.327 | 21.814 | 1.00 29.90 | A |
| ATOM | 941 | CG | ASN | A | 124 | 49.286 | 0.620 | 22.555 | 1.00 34.64 | A |
| ATOM | 942 | OD1 | ASN | A | 124 | 49.983 | 1.438 | 21.945 | 1.00 36.78 | A |
| ATOM | 943 | ND2 | ASN | A | 124 | 49.284 | 0.523 | 23.879 | 1.00 37.18 | A |
| ATOM | 944 | C | ASN | A | 124 | 46.722 | -0.652 | 20.004 | 1.00 26.39 | A |
| ATOM | 945 | O | ASN | A | 124 | 47.246 | -1.344 | 19.131 | 1.00 25.38 | A |
| ATOM | 946 | N | LEU | A | 125 | 45.443 | -0.759 | 20.340 | 1.00 23.76 | A |
| ATOM | 947 | CA | LEU | A | 125 | 44.572 | -1.717 | 19.679 | 1.00 23.27 | A |
| ATOM | 948 | CB | LEU | A | 125 | 43.232 | -1.795 | 20.414 | 1.00 20.48 | A |
| ATOM | 949 | CG | LEU | A | 125 | 42.454 | -3.118 | 20.464 | 1.00 24.86 | A |
| ATOM | 950 | CD1 | LEU | A | 125 | 40.987 | -2.835 | 20.203 | 1.00 20.58 | A |
| ATOM | 951 | CD2 | LEU | A | 125 | 43.004 | -4.122 | 19.455 | 1.00 23.01 | A |
| ATOM | 952 | C | LEU | A | 125 | 44.337 | -1.265 | 18.236 | 1.00 22.66 | A |
| ATOM | 953 | O | LEU | A | 125 | 44.331 | -2.074 | 17.311 | 1.00 21.78 | A |
| ATOM | 954 | N | ILE | A | 126 | 44.176 | 0.041 | 18.054 | 1.00 22.88 | A |
| ATOM | 955 | CA | ILE | A | 126 | 43.894 | 0.601 | 16.741 | 1.00 23.88 | A |
| ATOM | 956 | CB | ILE | A | 126 | 42.356 | 0.568 | 16.500 | 1.00 25.94 | A |
| ATOM | 957 | CG2 | ILE | A | 126 | 41.642 | 1.228 | 17.677 | 1.00 24.29 | A |
| ATOM | 958 | CG1 | ILE | A | 126 | 41.992 | 1.242 | 15.178 | 1.00 24.79 | A |

Figure 9 (16 of 92)

| | | | | | | | | | | |
|---|---|---|---|---|---|---|---|---|---|---|
| ATOM | 959 | CD1 | ILE | A | 126 | 40.541 | 1.047 | 14.789 | 1.00 24.66 | A |
| ATOM | 960 | C | ILE | A | 126 | 44.407 | 2.035 | 16.632 | 1.00 24.34 | A |
| ATOM | 961 | O | ILE | A | 126 | 44.460 | 2.756 | 17.625 | 1.00 23.98 | A |
| ATOM | 962 | N | GLN | A | 127 | 44.779 | 2.448 | 15.422 | 1.00 24.95 | A |
| ATOM | 963 | CA | GLN | A | 127 | 45.284 | 3.799 | 15.206 | 1.00 23.61 | A |
| ATOM | 964 | CB | GLN | A | 127 | 45.980 | 3.887 | 13.846 | 1.00 24.22 | A |
| ATOM | 965 | CG | GLN | A | 127 | 46.397 | 5.298 | 13.449 | 1.00 25.91 | A |
| ATOM | 966 | CD | GLN | A | 127 | 47.529 | 5.841 | 14.299 | 1.00 28.13 | A |
| ATOM | 967 | OE1 | GLN | A | 127 | 48.637 | 5.295 | 14.295 | 1.00 29.28 | A |
| ATOM | 968 | NE2 | GLN | A | 127 | 47.261 | 6.921 | 15.033 | 1.00 25.51 | A |
| ATOM | 969 | C | GLN | A | 127 | 44.163 | 4.842 | 15.276 | 1.00 24.25 | A |
| ATOM | 970 | O | GLN | A | 127 | 43.231 | 4.825 | 14.472 | 1.00 24.49 | A |
| ATOM | 971 | N | PHE | A | 128 | 44.262 | 5.751 | 16.238 | 1.00 22.68 | A |
| ATOM | 972 | CA | PHE | A | 128 | 43.264 | 6.800 | 16.398 | 1.00 23.09 | A |
| ATOM | 973 | CB | PHE | A | 128 | 43.194 | 7.248 | 17.865 | 1.00 25.06 | A |
| ATOM | 974 | CG | PHE | A | 128 | 42.270 | 6.419 | 18.712 | 1.00 28.83 | A |
| ATOM | 975 | CD1 | PHE | A | 128 | 42.384 | 5.033 | 18.746 | 1.00 30.66 | A |
| ATOM | 976 | CD2 | PHE | A | 128 | 41.278 | 7.030 | 19.471 | 1.00 30.94 | A |
| ATOM | 977 | CE1 | PHE | A | 128 | 41.519 | 4.264 | 19.524 | 1.00 32.05 | A |
| ATOM | 978 | CE2 | PHE | A | 128 | 40.408 | 6.273 | 20.252 | 1.00 32.66 | A |
| ATOM | 979 | CZ | PHE | A | 128 | 40.530 | 4.884 | 20.277 | 1.00 33.51 | A |
| ATOM | 980 | C | PHE | A | 128 | 43.567 | 8.020 | 15.530 | 1.00 21.53 | A |
| ATOM | 981 | O | PHE | A | 128 | 44.728 | 8.387 | 15.334 | 1.00 19.33 | A |
| ATOM | 982 | N | ILE | A | 129 | 42.511 | 8.628 | 14.999 | 1.00 19.67 | A |
| ATOM | 983 | CA | ILE | A | 129 | 42.644 | 9.838 | 14.202 | 1.00 19.41 | A |
| ATOM | 984 | CB | ILE | A | 129 | 42.010 | 9.696 | 12.803 | 1.00 18.70 | A |
| ATOM | 985 | CG2 | ILE | A | 129 | 42.036 | 11.045 | 12.087 | 1.00 19.45 | A |
| ATOM | 986 | CG1 | ILE | A | 129 | 42.791 | 8.676 | 11.972 | 1.00 17.38 | A |
| ATOM | 987 | CD1 | ILE | A | 129 | 42.175 | 8.398 | 10.609 | 1.00 15.52 | A |
| ATOM | 988 | C | ILE | A | 129 | 41.898 | 10.914 | 14.974 | 1.00 20.02 | A |
| ATOM | 989 | O | ILE | A | 129 | 40.750 | 10.720 | 15.366 | 1.00 21.24 | A |
| ATOM | 990 | N | GLY | A | 130 | 42.558 | 12.038 | 15.210 | 1.00 21.78 | A |
| ATOM | 991 | CA | GLY | A | 130 | 41.925 | 13.116 | 15.940 | 1.00 21.21 | A |
| ATOM | 992 | C | GLY | A | 130 | 41.504 | 14.228 | 15.003 | 1.00 20.69 | A |
| ATOM | 993 | O | GLY | A | 130 | 42.339 | 14.812 | 14.312 | 1.00 19.77 | A |
| ATOM | 994 | N | VAL | A | 131 | 40.204 | 14.502 | 14.964 | 1.00 19.02 | A |
| ATOM | 995 | CA | VAL | A | 131 | 39.664 | 15.556 | 14.113 | 1.00 21.95 | A |
| ATOM | 996 | CB | VAL | A | 131 | 38.182 | 15.280 | 13.745 | 1.00 21.78 | A |
| ATOM | 997 | CG1 | VAL | A | 131 | 37.546 | 16.534 | 13.169 | 1.00 21.42 | A |
| ATOM | 998 | CG2 | VAL | A | 131 | 38.096 | 14.138 | 12.736 | 1.00 21.26 | A |
| ATOM | 999 | C | VAL | A | 131 | 39.734 | 16.875 | 14.869 | 1.00 23.24 | A |
| ATOM | 1000 | O | VAL | A | 131 | 39.466 | 16.925 | 16.068 | 1.00 24.84 | A |
| ATOM | 1001 | N | LYS | A | 132 | 40.098 | 17.943 | 14.170 | 1.00 25.25 | A |
| ATOM | 1002 | CA | LYS | A | 132 | 40.186 | 19.254 | 14.799 | 1.00 27.20 | A |
| ATOM | 1003 | CB | LYS | A | 132 | 41.535 | 19.414 | 15.516 | 1.00 25.68 | A |
| ATOM | 1004 | CG | LYS | A | 132 | 42.760 | 19.393 | 14.628 | 1.00 25.88 | A |
| ATOM | 1005 | CD | LYS | A | 132 | 44.025 | 19.446 | 15.482 | 1.00 26.74 | A |
| ATOM | 1006 | CE | LYS | A | 132 | 45.276 | 19.563 | 14.630 | 1.00 26.30 | A |
| ATOM | 1007 | NZ | LYS | A | 132 | 45.242 | 20.795 | 13.795 | 1.00 28.46 | A |
| ATOM | 1008 | C | LYS | A | 132 | 39.997 | 20.358 | 13.770 | 1.00 28.51 | A |
| ATOM | 1009 | O | LYS | A | 132 | 40.033 | 20.105 | 12.572 | 1.00 26.70 | A |
| ATOM | 1010 | N | ARG | A | 133 | 39.778 | 21.580 | 14.243 | 1.00 33.50 | A |
| ATOM | 1011 | CA | ARG | A | 133 | 39.586 | 22.713 | 13.344 | 1.00 37.57 | A |
| ATOM | 1012 | CB | ARG | A | 133 | 38.944 | 23.884 | 14.088 | 1.00 39.46 | A |
| ATOM | 1013 | CG | ARG | A | 133 | 37.691 | 23.531 | 14.850 | 1.00 41.47 | A |
| ATOM | 1014 | CD | ARG | A | 133 | 36.939 | 24.781 | 15.256 | 1.00 44.45 | A |
| ATOM | 1015 | NE | ARG | A | 133 | 35.970 | 24.505 | 16.308 | 1.00 49.08 | A |
| ATOM | 1016 | CZ | ARG | A | 133 | 36.300 | 24.229 | 17.565 | 1.00 50.76 | A |
| ATOM | 1017 | NH1 | ARG | A | 133 | 35.360 | 23.986 | 18.467 | 1.00 52.80 | A |
| ATOM | 1018 | NH2 | ARG | A | 133 | 37.574 | 24.207 | 17.926 | 1.00 53.48 | A |
| ATOM | 1019 | C | ARG | A | 133 | 40.932 | 23.152 | 12.779 | 1.00 38.81 | A |
| ATOM | 1020 | O | ARG | A | 133 | 41.973 | 22.916 | 13.391 | 1.00 39.16 | A |
| ATOM | 1021 | N | PRO | A | 134 | 40.931 | 23.783 | 11.593 | 1.00 41.18 | A |
| ATOM | 1022 | CD | PRO | A | 134 | 39.798 | 23.998 | 10.677 | 1.00 41.24 | A |
| ATOM | 1023 | CA | PRO | A | 134 | 42.185 | 24.240 | 10.983 | 1.00 43.20 | A |
| ATOM | 1024 | CB | PRO | A | 134 | 41.708 | 24.987 | 9.745 | 1.00 41.93 | A |

Figure 9 (17 of 92)

```
ATOM   1025  CG   PRO A 134      40.499  24.197   9.347  1.00 42.12      A
ATOM   1026  C    PRO A 134      42.948  25.134  11.956  1.00 45.47      A
ATOM   1027  O    PRO A 134      42.367  26.019  12.589  1.00 44.54      A
ATOM   1028  N    GLY A 135      44.251  24.901  12.069  1.00 47.77      A
ATOM   1029  CA   GLY A 135      45.045  25.671  13.004  1.00 51.12      A
ATOM   1030  C    GLY A 135      44.726  25.125  14.382  1.00 53.65      A
ATOM   1031  O    GLY A 135      44.272  23.985  14.499  1.00 55.10      A
ATOM   1032  N    PHE A 136      44.942  25.925  15.420  1.00 55.40      A
ATOM   1033  CA   PHE A 136      44.668  25.495  16.790  1.00 57.27      A
ATOM   1034  CB   PHE A 136      43.164  25.368  17.026  1.00 59.02      A
ATOM   1035  CG   PHE A 136      42.815  25.053  18.448  1.00 61.58      A
ATOM   1036  CD1  PHE A 136      43.089  25.972  19.461  1.00 62.60      A
ATOM   1037  CD2  PHE A 136      42.257  23.820  18.786  1.00 62.12      A
ATOM   1038  CE1  PHE A 136      42.817  25.666  20.796  1.00 64.18      A
ATOM   1039  CE2  PHE A 136      41.980  23.500  20.117  1.00 62.97      A
ATOM   1040  CZ   PHE A 136      42.260  24.424  21.125  1.00 64.25      A
ATOM   1041  C    PHE A 136      45.348  24.166  17.128  1.00 57.34      A
ATOM   1042  O    PHE A 136      45.026  23.116  16.564  1.00 56.96      A
ATOM   1043  N    HIS A 137      46.270  24.215  18.081  1.00 57.55      A
ATOM   1044  CA   HIS A 137      47.023  23.035  18.470  1.00 57.44      A
ATOM   1045  CB   HIS A 137      48.423  23.453  18.920  1.00 57.79      A
ATOM   1046  CG   HIS A 137      49.199  24.166  17.859  1.00 58.23      A
ATOM   1047  CD2  HIS A 137      50.306  23.804  17.168  1.00 58.70      A
ATOM   1048  ND1  HIS A 137      48.828  25.399  17.369  1.00 58.97      A
ATOM   1049  CE1  HIS A 137      49.672  25.767  16.422  1.00 59.20      A
ATOM   1050  NE2  HIS A 137      50.578  24.817  16.280  1.00 58.94      A
ATOM   1051  C    HIS A 137      46.397  22.141  19.524  1.00 57.35      A
ATOM   1052  O    HIS A 137      45.547  22.562  20.310  1.00 56.69      A
ATOM   1053  N    VAL A 138      46.846  20.891  19.523  1.00 57.62      A
ATOM   1054  CA   VAL A 138      46.372  19.895  20.463  1.00 59.28      A
ATOM   1055  CB   VAL A 138      45.564  18.779  19.753  1.00 59.05      A
ATOM   1056  CG1  VAL A 138      45.486  17.534  20.635  1.00 59.55      A
ATOM   1057  CG2  VAL A 138      44.161  19.274  19.452  1.00 59.38      A
ATOM   1058  C    VAL A 138      47.511  19.243  21.227  1.00 60.12      A
ATOM   1059  O    VAL A 138      48.258  18.431  20.677  1.00 60.46      A
ATOM   1060  N    GLU A 139      47.657  19.624  22.490  1.00 61.30      A
ATOM   1061  CA   GLU A 139      48.667  19.014  23.341  1.00 63.19      A
ATOM   1062  CB   GLU A 139      48.719  19.716  24.696  1.00 64.12      A
ATOM   1063  CG   GLU A 139      48.585  21.227  24.636  1.00 65.39      A
ATOM   1064  CD   GLU A 139      49.826  21.903  24.092  1.00 66.85      A
ATOM   1065  OE1  GLU A 139      50.919  21.670  24.655  1.00 67.40      A
ATOM   1066  OE2  GLU A 139      49.707  22.668  23.108  1.00 66.55      A
ATOM   1067  C    GLU A 139      47.983  17.667  23.507  1.00 63.82      A
ATOM   1068  O    GLU A 139      46.751  17.615  23.460  1.00 64.64      A
ATOM   1069  N    THR A 140      48.728  16.581  23.699  1.00 63.99      A
ATOM   1070  CA   THR A 140      48.042  15.302  23.834  1.00 64.14      A
ATOM   1071  CB   THR A 140      47.168  15.027  22.572  1.00 64.93      A
ATOM   1072  OG1  THR A 140      46.111  14.116  22.901  1.00 65.82      A
ATOM   1073  CG2  THR A 140      48.020  14.422  21.451  1.00 64.86      A
ATOM   1074  C    THR A 140      48.893  14.059  24.066  1.00 63.51      A
ATOM   1075  O    THR A 140      48.436  12.963  23.773  1.00 64.26      A
ATOM   1076  N    PRO A 141      50.097  14.198  24.648  1.00 62.66      A
ATOM   1077  CD   PRO A 141      50.284  15.155  25.746  1.00 62.82      A
ATOM   1078  CA   PRO A 141      50.966  13.030  24.882  1.00 61.33      A
ATOM   1079  CB   PRO A 141      51.255  13.098  26.391  1.00 61.98      A
ATOM   1080  CG   PRO A 141      50.335  14.220  26.916  1.00 62.54      A
ATOM   1081  C    PRO A 141      50.411  11.666  24.460  1.00 59.66      A
ATOM   1082  O    PRO A 141      50.337  10.734  25.265  1.00 60.84      A
ATOM   1083  N    TYR A 142      50.045  11.552  23.187  1.00 57.47      A
ATOM   1084  CA   TYR A 142      49.473  10.326  22.653  1.00 55.06      A
ATOM   1085  CB   TYR A 142      47.970  10.283  22.942  1.00 54.51      A
ATOM   1086  CG   TYR A 142      47.625  10.101  24.402  1.00 54.17      A
ATOM   1087  CD1  TYR A 142      46.987  11.111  25.126  1.00 54.30      A
ATOM   1088  CE1  TYR A 142      46.661  10.941  26.468  1.00 53.70      A
ATOM   1089  CD2  TYR A 142      47.930   8.911  25.060  1.00 54.85      A
ATOM   1090  CE2  TYR A 142      47.610   8.727  26.400  1.00 54.68      A
```

Figure 9 (18 of 92)

```
ATOM   1091  CZ   TYR A 142      46.974    9.746   27.100  1.00 54.87      A
ATOM   1092  OH   TYR A 142      46.645    9.561   28.427  1.00 54.72      A
ATOM   1093  C    TYR A 142      49.700   10.223   21.151  1.00 53.86      A
ATOM   1094  O    TYR A 142      49.936   11.227   20.479  1.00 53.93      A
ATOM   1095  N    PRO A 143      49.632    8.998   20.605  1.00 52.66      A
ATOM   1096  CD   PRO A 143      49.345   -7.735   21.313  1.00 52.30      A
ATOM   1097  CA   PRO A 143      49.829    8.761   19.171  1.00 51.71      A
ATOM   1098  CB   PRO A 143      49.362    7.317   18.999  1.00 52.17      A
ATOM   1099  CG   PRO A 143      49.763    6.690   20.301  1.00 52.01      A
ATOM   1100  C    PRO A 143      49.018    9.742   18.320  1.00 50.10      A
ATOM   1101  O    PRO A 143      49.469   10.847   18.020  1.00 51.20      A
ATOM   1102  N    LEU A 144      47.821    9.320   17.935  1.00 47.54      A
ATOM   1103  CA   LEU A 144      46.917   10.137   17.132  1.00 43.87      A
ATOM   1104  CB   LEU A 144      46.347   11.299   17.961  1.00 42.91      A
ATOM   1105  CG   LEU A 144      45.457   11.078   19.185  1.00 42.42      A
ATOM   1106  CD1  LEU A 144      44.833   12.409   19.558  1.00 43.32      A
ATOM   1107  CD2  LEU A 144      44.366   10.075   18.896  1.00 42.98      A
ATOM   1108  C    LEU A 144      47.466   10.733   15.843  1.00 41.19      A
ATOM   1109  O    LEU A 144      48.520   11.373   15.824  1.00 40.93      A
ATOM   1110  N    LEU A 145      46.736   10.505   14.760  1.00 37.90      A
ATOM   1111  CA   LEU A 145      47.070   11.096   13.477  1.00 34.56      A
ATOM   1112  CB   LEU A 145      46.796   10.141   12.313  1.00 33.71      A
ATOM   1113  CG   LEU A 145      47.508    8.791   12.205  1.00 36.13      A
ATOM   1114  CD1  LEU A 145      47.393    8.327   10.754  1.00 34.02      A
ATOM   1115  CD2  LEU A 145      48.983    8.895   12.611  1.00 35.87      A
ATOM   1116  C    LEU A 145      46.008   12.184   13.498  1.00 32.20      A
ATOM   1117  O    LEU A 145      44.905   11.945   13.984  1.00 31.34      A
ATOM   1118  N    PHE A 146      46.318   13.374   13.007  1.00 29.82      A
ATOM   1119  CA   PHE A 146      45.319   14.425   13.042  1.00 28.21      A
ATOM   1120  CB   PHE A 146      45.891   15.684   13.702  1.00 28.72      A
ATOM   1121  CG   PHE A 146      46.226   15.506   15.158  1.00 30.43      A
ATOM   1122  CD1  PHE A 146      47.502   15.116   15.553  1.00 30.65      A
ATOM   1123  CD2  PHE A 146      45.254   15.694   16.135  1.00 30.57      A
ATOM   1124  CE1  PHE A 146      47.806   14.916   16.904  1.00 31.41      A
ATOM   1125  CE2  PHE A 146      45.546   15.496   17.491  1.00 31.34      A
ATOM   1126  CZ   PHE A 146      46.824   15.106   17.876  1.00 31.49      A
ATOM   1127  C    PHE A 146      44.744   14.760   11.674  1.00 27.34      A
ATOM   1128  O    PHE A 146      45.392   14.566   10.639  1.00 26.52      A
ATOM   1129  N    ALA A 147      43.506   15.241   11.686  1.00 24.98      A
ATOM   1130  CA   ALA A 147      42.821   15.632   10.469  1.00 22.96      A
ATOM   1131  CB   ALA A 147      41.795   14.585   10.090  1.00 22.23      A
ATOM   1132  C    ALA A 147      42.139   16.973   10.706  1.00 23.68      A
ATOM   1133  O    ALA A 147      41.288   17.102   11.591  1.00 22.58      A
ATOM   1134  N    ASP A 148      42.523   17.980    9.928  1.00 23.80      A
ATOM   1135  CA   ASP A 148      41.909   19.292   10.062  1.00 24.80      A
ATOM   1136  CB   ASP A 148      42.831   20.394    9.537  1.00 28.62      A
ATOM   1137  CG   ASP A 148      44.183   20.393   10.213  1.00 31.95      A
ATOM   1138  OD1  ASP A 148      45.140   19.855    9.614  1.00 35.93      A
ATOM   1139  OD2  ASP A 148      44.285   20.917   11.344  1.00 33.21      A
ATOM   1140  C    ASP A 148      40.626   19.276    9.247  1.00 24.72      A
ATOM   1141  O    ASP A 148      40.631   18.883    8.084  1.00 26.55      A
ATOM   1142  N    VAL A 149      39.526   19.687    9.857  1.00 22.59      A
ATOM   1143  CA   VAL A 149      38.250   19.712    9.154  1.00 21.45      A
ATOM   1144  CB   VAL A 149      37.289   18.611    9.697  1.00 22.30      A
ATOM   1145  CG1  VAL A 149      35.951   18.656    8.964  1.00 22.26      A
ATOM   1146  CG2  VAL A 149      37.928   17.234    9.524  1.00 20.54      A
ATOM   1147  C    VAL A 149      37.617   21.089    9.334  1.00 19.86      A
ATOM   1148  O    VAL A 149      37.548   21.606   10.445  1.00 17.50      A
ATOM   1149  N    PRO A 150      37.201   21.722    8.228  1.00 19.42      A
ATOM   1150  CD   PRO A 150      37.359   21.298    6.825  1.00 20.31      A
ATOM   1151  CA   PRO A 150      36.574   23.041    8.306  1.00 19.62      A
ATOM   1152  CB   PRO A 150      36.119   23.289    6.872  1.00 19.79      A
ATOM   1153  CG   PRO A 150      37.164   22.600    6.072  1.00 20.59      A
ATOM   1154  C    PRO A 150      35.397   22.951    9.265  1.00 19.91      A
ATOM   1155  O    PRO A 150      34.688   21.948    9.284  1.00 19.42      A
ATOM   1156  N    GLU A 151      35.186   23.989   10.063  1.00 19.79      A
```

Figure 9 (19 of 92)

| | | | | | | | | | | |
|---|---|---|---|---|---|---|---|---|---|---|
| ATOM | 1157 | CA | GLU | A | 151 | 34.080 | 23.972 | 11.003 | 1.00 21.01 | A |
| ATOM | 1158 | CB | GLU | A | 151 | 34.242 | 25.102 | 12.031 | 1.00 22.29 | A |
| ATOM | 1159 | CG | GLU | A | 151 | 33.186 | 25.110 | 13.124 | 1.00 27.77 | A |
| ATOM | 1160 | CD | GLU | A | 151 | 33.408 | 26.200 | 14.167 | 1.00 30.48 | A |
| ATOM | 1161 | OE1 | GLU | A | 151 | 32.555 | 26.329 | 15.069 | 1.00 34.19 | A |
| ATOM | 1162 | OE2 | GLU | A | 151 | 34.426 | 26.923 | 14.095 | 1.00 32.83 | A |
| ATOM | 1163 | C | GLU | A | 151 | 32.745 | 24.112 | 10.264 | 1.00 19.25 | A |
| ATOM | 1164 | O | GLU | A | 151 | 32.560 | 25.015 | 9.450 | 1.00 17.81 | A |
| ATOM | 1165 | N | PHE | A | 152 | 31.830 | 23.189 | 10.535 | 1.00 18.30 | A |
| ATOM | 1166 | CA | PHE | A | 152 | 30.496 | 23.213 | 9.934 | 1.00 18.25 | A |
| ATOM | 1167 | CB | PHE | A | 152 | 30.351 | 22.107 | 8.872 | 1.00 16.40 | A |
| ATOM | 1168 | CG | PHE | A | 152 | 29.119 | 22.240 | 8.010 | 1.00 16.38 | A |
| ATOM | 1169 | CD1 | PHE | A | 152 | 28.849 | 21.302 | 7.014 | 1.00 15.91 | A |
| ATOM | 1170 | CD2 | PHE | A | 152 | 28.230 | 23.300 | 8.185 | 1.00 17.16 | A |
| ATOM | 1171 | CE1 | PHE | A | 152 | 27.711 | 21.414 | 6.202 | 1.00 16.93 | A |
| ATOM | 1172 | CE2 | PHE | A | 152 | 27.090 | 23.424 | 7.380 | 1.00 18.81 | A |
| ATOM | 1173 | CZ | PHE | A | 152 | 26.831 | 22.474 | 6.385 | 1.00 16.71 | A |
| ATOM | 1174 | C | PHE | A | 152 | 29.574 | 22.962 | 11.118 | 1.00 17.10 | A |
| ATOM | 1175 | O | PHE | A | 152 | 29.390 | 21.824 | 11.546 | 1.00 16.20 | A |
| ATOM | 1176 | N | GLU | A | 153 | 29.020 | 24.047 | 11.648 | 1.00 19.28 | A |
| ATOM | 1177 | CA | GLU | A | 153 | 28.149 | 24.027 | 12.826 | 1.00 22.32 | A |
| ATOM | 1178 | CB | GLU | A | 153 | 28.006 | 25.458 | 13.374 | 1.00 22.80 | A |
| ATOM | 1179 | CG | GLU | A | 153 | 27.180 | 25.601 | 14.656 | 1.00 26.33 | A |
| ATOM | 1180 | CD | GLU | A | 153 | 27.129 | 27.041 | 15.185 | 1.00 27.08 | A |
| ATOM | 1181 | OE1 | GLU | A | 153 | 26.497 | 27.257 | 16.242 | 1.00 30.39 | A |
| ATOM | 1182 | OE2 | GLU | A | 153 | 27.715 | 27.950 | 14.555 | 1.00 23.77 | A |
| ATOM | 1183 | C | GLU | A | 153 | 26.770 | 23.414 | 12.609 | 1.00 23.12 | A |
| ATOM | 1184 | O | GLU | A | 153 | 25.750 | 24.091 | 12.711 | 1.00 25.26 | A |
| ATOM | 1185 | N | VAL | A | 154 | 26.743 | 22.127 | 12.301 | 1.00 22.52 | A |
| ATOM | 1186 | CA | VAL | A | 154 | 25.490 | 21.426 | 12.100 | 1.00 21.36 | A |
| ATOM | 1187 | CB | VAL | A | 154 | 25.239 | 21.099 | 10.591 | 1.00 21.52 | A |
| ATOM | 1188 | CG1 | VAL | A | 154 | 26.418 | 20.328 | 10.004 | 1.00 18.56 | A |
| ATOM | 1189 | CG2 | VAL | A | 154 | 23.941 | 20.301 | 10.438 | 1.00 21.18 | A |
| ATOM | 1190 | C | VAL | A | 154 | 25.609 | 20.148 | 12.911 | 1.00 20.38 | A |
| ATOM | 1191 | O | VAL | A | 154 | 26.682 | 19.551 | 12.975 | 1.00 22.28 | A |
| ATOM | 1192 | N | SER | A | 155 | 24.514 | 19.746 | 13.547 | 1.00 20.09 | A |
| ATOM | 1193 | CA | SER | A | 155 | 24.484 | 18.536 | 14.371 | 1.00 19.74 | A |
| ATOM | 1194 | CB | SER | A | 155 | 24.724 | 18.889 | 15.840 | 1.00 17.93 | A |
| ATOM | 1195 | OG | SER | A | 155 | 23.638 | 19.656 | 16.342 | 1.00 17.62 | A |
| ATOM | 1196 | C | SER | A | 155 | 23.113 | 17.877 | 14.245 | 1.00 19.10 | A |
| ATOM | 1197 | O | SER | A | 155 | 22.161 | 18.503 | 13.772 | 1.00 18.84 | A |
| ATOM | 1198 | N | SER | A | 156 | 23.000 | 16.628 | 14.681 | 1.00 19.56 | A |
| ATOM | 1199 | CA | SER | A | 156 | 21.721 | 15.935 | 14.586 | 1.00 20.51 | A |
| ATOM | 1200 | CB | SER | A | 156 | 21.892 | 14.457 | 14.912 | 1.00 21.21 | A |
| ATOM | 1201 | OG | SER | A | 156 | 22.670 | 13.826 | 13.910 | 1.00 20.06 | A |
| ATOM | 1202 | C | SER | A | 156 | 20.684 | 16.566 | 15.508 | 1.00 22.61 | A |
| ATOM | 1203 | O | SER | A | 156 | 19.484 | 16.527 | 15.229 | 1.00 19.81 | A |
| ATOM | 1204 | N | THR | A | 157 | 21.155 | 17.155 | 16.603 | 1.00 24.04 | A |
| ATOM | 1205 | CA | THR | A | 157 | 20.268 | 17.813 | 17.548 | 1.00 25.65 | A |
| ATOM | 1206 | CB | THR | A | 157 | 21.034 | 18.222 | 18.819 | 1.00 27.15 | A |
| ATOM | 1207 | OG1 | THR | A | 157 | 21.538 | 17.043 | 19.466 | 1.00 26.27 | A |
| ATOM | 1208 | CG2 | THR | A | 157 | 20.120 | 18.976 | 19.775 | 1.00 27.27 | A |
| ATOM | 1209 | C | THR | A | 157 | 19.625 | 19.048 | 16.911 | 1.00 25.81 | A |
| ATOM | 1210 | O | THR | A | 157 | 18.402 | 19.217 | 16.966 | 1.00 28.38 | A |
| ATOM | 1211 | N | MET | A | 158 | 20.439 | 19.910 | 16.305 | 1.00 24.48 | A |
| ATOM | 1212 | CA | MET | A | 158 | 19.911 | 21.106 | 15.655 | 1.00 22.25 | A |
| ATOM | 1213 | CB | MET | A | 158 | 21.015 | 21.912 | 14.964 | 1.00 25.03 | A |
| ATOM | 1214 | CG | MET | A | 158 | 20.616 | 22.275 | 13.511 | 1.00 23.82 | A |
| ATOM | 1215 | SD | MET | A | 158 | 21.866 | 22.941 | 12.551 | 1.00 33.45 | A |
| ATOM | 1216 | CE | MET | A | 158 | 21.360 | 24.647 | 12.447 | 1.00 33.78 | A |
| ATOM | 1217 | C | MET | A | 158 | 18.913 | 20.698 | 14.582 | 1.00 20.05 | A |
| ATOM | 1218 | O | MET | A | 158 | 17.838 | 21.281 | 14.470 | 1.00 21.84 | A |
| ATOM | 1219 | N | ILE | A | 159 | 19.290 | 19.714 | 13.769 | 1.00 17.78 | A |
| ATOM | 1220 | CA | ILE | A | 159 | 18.411 | 19.270 | 12.696 | 1.00 18.85 | A |
| ATOM | 1221 | CB | ILE | A | 159 | 19.026 | 18.113 | 11.870 | 1.00 15.88 | A |
| ATOM | 1222 | CG2 | ILE | A | 159 | 18.064 | 17.715 | 10.768 | 1.00 13.63 | A |

Figure 9 (20 of 92)

| ATOM | 1223 | CG1 | ILE A 159 | 20.379 | 18.538 | 11.270 | 1.00 | 16.65 | A |
|---|---|---|---|---|---|---|---|---|---|
| ATOM | 1224 | CD1 | ILE A 159 | 20.325 | 19.765 | 10.389 | 1.00 | 14.56 | A |
| ATOM | 1225 | C | ILE A 159 | 17.052 | 18.815 | 13.223 | 1.00 | 20.26 | A |
| ATOM | 1226 | O | ILE A 159 | 16.016 | 19.245 | 12.717 | 1.00 | 20.72 | A |
| ATOM | 1227 | N | ARG A 160 | 17.051 | 17.947 | 14.232 | 1.00 | 20.45 | A |
| ATOM | 1228 | CA | ARG A 160 | 15.791 | 17.466 | 14.776 | 1.00 | 23.79 | A |
| ATOM | 1229 | CB | ARG A 160 | 16.022 | 16.476 | 15.932 | 1.00 | 22.66 | A |
| ATOM | 1230 | CG | ARG A 160 | 16.754 | 15.199 | 15.521 | 1.00 | 20.38 | A |
| ATOM | 1231 | CD | ARG A 160 | 16.623 | 14.103 | 16.578 | 1.00 | 23.19 | A |
| ATOM | 1232 | NE | ARG A 160 | 17.193 | 14.488 | 17.870 | 1.00 | 23.23 | A |
| ATOM | 1233 | CZ | ARG A 160 | 18.468 | 14.330 | 18.208 | 1.00 | 22.36 | A |
| ATOM | 1234 | NH1 | ARG A 160 | 18.886 | 14.718 | 19.403 | 1.00 | 21.28 | A |
| ATOM | 1235 | NH2 | ARG A 160 | 19.321 | 13.766 | 17.362 | 1.00 | 23.53 | A |
| ATOM | 1236 | C | ARG A 160 | 14.940 | 18.638 | 15.247 | 1.00 | 26.07 | A |
| ATOM | 1237 | O | ARG A 160 | 13.748 | 18.691 | 14.947 | 1.00 | 27.94 | A |
| ATOM | 1238 | N | GLU A 161 | 15.552 | 19.585 | 15.960 | 1.00 | 27.08 | A |
| ATOM | 1239 | CA | GLU A 161 | 14.819 | 20.749 | 16.455 | 1.00 | 29.31 | A |
| ATOM | 1240 | CB | GLU A 161 | 15.714 | 21.613 | 17.357 | 1.00 | 32.63 | A |
| ATOM | 1241 | CG | GLU A 161 | 16.457 | 20.794 | 18.422 | 1.00 | 40.60 | A |
| ATOM | 1242 | CD | GLU A 161 | 17.120 | 21.638 | 19.514 | 1.00 | 44.86 | A |
| ATOM | 1243 | OE1 | GLU A 161 | 17.767 | 22.661 | 19.189 | 1.00 | 46.29 | A |
| ATOM | 1244 | OE2 | GLU A 161 | 17.003 | 21.257 | 20.704 | 1.00 | 46.62 | A |
| ATOM | 1245 | C | GLU A 161 | 14.276 | 21.576 | 15.290 | 1.00 | 28.75 | A |
| ATOM | 1246 | O | GLU A 161 | 13.200 | 22.165 | 15.395 | 1.00 | 28.33 | A |
| ATOM | 1247 | N | ARG A 162 | 15.009 | 21.621 | 14.179 | 1.00 | 26.49 | A |
| ATOM | 1248 | CA | ARG A 162 | 14.530 | 22.368 | 13.024 | 1.00 | 25.77 | A |
| ATOM | 1249 | CB | ARG A 162 | 15.641 | 22.544 | 11.980 | 1.00 | 25.60 | A |
| ATOM | 1250 | CG | ARG A 162 | 16.725 | 23.513 | 12.436 | 1.00 | 22.57 | A |
| ATOM | 1251 | CD | ARG A 162 | 17.575 | 24.010 | 11.290 | 1.00 | 21.23 | A |
| ATOM | 1252 | NE | ARG A 162 | 18.382 | 25.155 | 11.706 | 1.00 | 19.90 | A |
| ATOM | 1253 | CZ | ARG A 162 | 18.704 | 26.172 | 10.914 | 1.00 | 18.10 | A |
| ATOM | 1254 | NH1 | ARG A 162 | 18.293 | 26.189 | 9.651 | 1.00 | 15.80 | A |
| ATOM | 1255 | NH2 | ARG A 162 | 19.428 | 27.180 | 11.389 | 1.00 | 19.44 | A |
| ATOM | 1256 | C | ARG A 162 | 13.315 | 21.680 | 12.409 | 1.00 | 25.85 | A |
| ATOM | 1257 | O | ARG A 162 | 12.355 | 22.340 | 12.010 | 1.00 | 24.70 | A |
| ATOM | 1258 | N | PHE A 163 | 13.344 | 20.353 | 12.331 | 1.00 | 25.64 | A |
| ATOM | 1259 | CA | PHE A 163 | 12.197 | 19.637 | 11.777 | 1.00 | 25.78 | A |
| ATOM | 1260 | CB | PHE A 163 | 12.499 | 18.141 | 11.656 | 1.00 | 24.34 | A |
| ATOM | 1261 | CG | PHE A 163 | 13.229 | 17.778 | 10.391 | 1.00 | 22.67 | A |
| ATOM | 1262 | CD1 | PHE A 163 | 12.630 | 17.978 | 9.151 | 1.00 | 22.70 | A |
| ATOM | 1263 | CD2 | PHE A 163 | 14.514 | 17.252 | 10.436 | 1.00 | 21.43 | A |
| ATOM | 1264 | CE1 | PHE A 163 | 13.308 | 17.655 | 7.966 | 1.00 | 23.99 | A |
| ATOM | 1265 | CE2 | PHE A 163 | 15.198 | 16.926 | 9.258 | 1.00 | 23.49 | A |
| ATOM | 1266 | CZ | PHE A 163 | 14.597 | 17.127 | 8.025 | 1.00 | 21.95 | A |
| ATOM | 1267 | C | PHE A 163 | 10.990 | 19.868 | 12.680 | 1.00 | 26.81 | A |
| ATOM | 1268 | O | PHE A 163 | 9.874 | 20.084 | 12.203 | 1.00 | 26.84 | A |
| ATOM | 1269 | N | LYS A 164 | 11.222 | 19.860 | 13.988 | 1.00 | 28.48 | A |
| ATOM | 1270 | CA | LYS A 164 | 10.141 | 20.065 | 14.946 | 1.00 | 31.32 | A |
| ATOM | 1271 | CB | LYS A 164 | 10.636 | 19.786 | 16.367 | 1.00 | 33.62 | A |
| ATOM | 1272 | CG | LYS A 164 | 9.578 | 20.025 | 17.432 | 1.00 | 38.02 | A |
| ATOM | 1273 | CD | LYS A 164 | 10.007 | 19.495 | 18.795 | 1.00 | 41.70 | A |
| ATOM | 1274 | CE | LYS A 164 | 8.935 | 19.776 | 19.846 | 1.00 | 46.09 | A |
| ATOM | 1275 | NZ | LYS A 164 | 9.301 | 19.270 | 21.201 | 1.00 | 49.08 | A |
| ATOM | 1276 | C | LYS A 164 | 9.568 | 21.469 | 14.855 | 1.00 | 32.00 | A |
| ATOM | 1277 | O | LYS A 164 | 8.346 | 21.667 | 14.867 | 1.00 | 31.63 | A |
| ATOM | 1278 | N | SER A 165 | 10.453 | 22.453 | 14.757 | 1.00 | 32.62 | A |
| ATOM | 1279 | CA | SER A 165 | 10.022 | 23.849 | 14.661 | 1.00 | 33.75 | A |
| ATOM | 1280 | CB | SER A 165 | 11.137 | 24.774 | 15.151 | 1.00 | 35.83 | A |
| ATOM | 1281 | OG | SER A 165 | 11.687 | 24.306 | 16.371 | 1.00 | 40.13 | A |
| ATOM | 1282 | C | SER A 165 | 9.621 | 24.256 | 13.245 | 1.00 | 33.32 | A |
| ATOM | 1283 | O | SER A 165 | 9.166 | 25.381 | 13.022 | 1.00 | 32.97 | A |
| ATOM | 1284 | N | LYS A 166 | 9.775 | 23.341 | 12.298 | 1.00 | 31.74 | A |
| ATOM | 1285 | CA | LYS A 166 | 9.433 | 23.610 | 10.906 | 1.00 | 32.18 | A |
| ATOM | 1286 | CB | LYS A 166 | 7.974 | 24.092 | 10.777 | 1.00 | 33.67 | A |
| ATOM | 1287 | CG | LYS A 166 | 6.981 | 23.045 | 11.274 | 1.00 | 36.57 | A |
| ATOM | 1288 | CD | LYS A 166 | 7.053 | 21.783 | 10.461 | 1.00 | 38.79 | A |

Figure 9 (21 of 92)

| ATOM | 1289 | CE | LYS | A | 166 | 5.886 | 21.642 | 9.502 | 1.00 | 41.75 | A |
|---|---|---|---|---|---|---|---|---|---|---|---|
| ATOM | 1290 | NZ | LYS | A | 166 | 5.875 | 22.680 | 8.430 | 1.00 | 44.26 | A |
| ATOM | 1291 | C | LYS | A | 166 | 10.387 | 24.600 | 10.238 | 1.00 | 30.60 | A |
| ATOM | 1292 | O | LYS | A | 166 | 10.025 | 25.263 | 9.252 | 1.00 | 27.92 | A |
| ATOM | 1293 | N | LYS | A | 167 | 11.624 | 24.653 | 10.739 | 1.00 | 29.15 | A |
| ATOM | 1294 | CA | LYS | A | 167 | 12.639 | 25.551 | 10.174 | 1.00 | 28.58 | A |
| ATOM | 1295 | CB | LYS | A | 167 | 13.702 | 25.880 | 11.206 | 1.00 | 28.48 | A |
| ATOM | 1296 | CG | LYS | A | 167 | 13.204 | 26.640 | 12.436 | 1.00 | 29.63 | A |
| ATOM | 1297 | CD | LYS | A | 167 | 14.355 | 26.704 | 13.419 | 1.00 | 32.29 | A |
| ATOM | 1298 | CE | LYS | A | 167 | 14.131 | 27.734 | 14.506 | 1.00 | 33.49 | A |
| ATOM | 1299 | NZ | LYS | A | 167 | 15.335 | 27.838 | 15.408 | 1.00 | 37.11 | A |
| ATOM | 1300 | C | LYS | A | 167 | 13.297 | 24.844 | 8.993 | 1.00 | 27.78 | A |
| ATOM | 1301 | O | LYS | A | 167 | 13.288 | 23.613 | 8.923 | 1.00 | 28.05 | A |
| ATOM | 1302 | N | PRO | A | 168 | 13.886 | 25.610 | 8.060 | 1.00 | 27.76 | A |
| ATOM | 1303 | CD | PRO | A | 168 | 13.975 | 27.080 | 8.089 | 1.00 | 27.82 | A |
| ATOM | 1304 | CA | PRO | A | 168 | 14.554 | 25.079 | 6.861 | 1.00 | 26.62 | A |
| ATOM | 1305 | CB | PRO | A | 168 | 15.004 | 26.341 | 6.116 | 1.00 | 27.70 | A |
| ATOM | 1306 | CG | PRO | A | 168 | 14.064 | 27.404 | 6.618 | 1.00 | 30.22 | A |
| ATOM | 1307 | C | PRO | A | 168 | 15.741 | 24.181 | 7.178 | 1.00 | 24.40 | A |
| ATOM | 1308 | O | PRO | A | 168 | 16.430 | 24.395 | 8.167 | 1.00 | 24.43 | A |
| ATOM | 1309 | N | THR | A | 169 | 15.974 | 23.174 | 6.345 | 1.00 | 22.82 | A |
| ATOM | 1310 | CA | THR | A | 169 | 17.111 | 22.283 | 6.543 | 1.00 | 23.24 | A |
| ATOM | 1311 | CB | THR | A | 169 | 16.664 | 20.845 | 6.907 | 1.00 | 23.02 | A |
| ATOM | 1312 | OG1 | THR | A | 169 | 15.782 | 20.338 | 5.898 | 1.00 | 23.12 | A |
| ATOM | 1313 | CG2 | THR | A | 169 | 15.967 | 20.842 | 8.254 | 1.00 | 23.86 | A |
| ATOM | 1314 | C | THR | A | 169 | 17.965 | 22.254 | 5.283 | 1.00 | 20.96 | A |
| ATOM | 1315 | O | THR | A | 169 | 18.918 | 21.469 | 5.174 | 1.00 | 19.19 | A |
| ATOM | 1316 | N | ASP | A | 170 | 17.630 | 23.134 | 4.339 | 1.00 | 20.25 | A |
| ATOM | 1317 | CA | ASP | A | 170 | 18.369 | 23.216 | 3.078 | 1.00 | 20.58 | A |
| ATOM | 1318 | CB | ASP | A | 170 | 17.838 | 24.349 | 2.182 | 1.00 | 22.48 | A |
| ATOM | 1319 | CG | ASP | A | 170 | 16.329 | 24.340 | 2.045 | 1.00 | 26.15 | A |
| ATOM | 1320 | OD1 | ASP | A | 170 | 15.642 | 24.861 | 2.956 | 1.00 | 28.63 | A |
| ATOM | 1321 | OD2 | ASP | A | 170 | 15.833 | 23.810 | 1.029 | 1.00 | 25.44 | A |
| ATOM | 1322 | C | ASP | A | 170 | 19.835 | 23.497 | 3.357 | 1.00 | 17.83 | A |
| ATOM | 1323 | O | ASP | A | 170 | 20.156 | 24.310 | 4.216 | 1.00 | 17.04 | A |
| ATOM | 1324 | N | TYR | A | 171 | 20.708 | 22.820 | 2.618 | 1.00 | 18.10 | A |
| ATOM | 1325 | CA | TYR | A | 171 | 22.156 | 22.985 | 2.728 | 1.00 | 17.01 | A |
| ATOM | 1326 | CB | TYR | A | 171 | 22.509 | 24.467 | 2.548 | 1.00 | 17.29 | A |
| ATOM | 1327 | CG | TYR | A | 171 | 21.792 | 25.106 | 1.362 | 1.00 | 17.50 | A |
| ATOM | 1328 | CD1 | TYR | A | 171 | 20.789 | 26.062 | 1.557 | 1.00 | 16.45 | A |
| ATOM | 1329 | CE1 | TYR | A | 171 | 20.106 | 26.630 | 0.474 | 1.00 | 15.09 | A |
| ATOM | 1330 | CD2 | TYR | A | 171 | 22.095 | 24.729 | 0.045 | 1.00 | 17.55 | A |
| ATOM | 1331 | CE2 | TYR | A | 171 | 21.418 | 25.289 | -1.045 | 1.00 | 15.75 | A |
| ATOM | 1332 | CZ | TYR | A | 171 | 20.427 | 26.239 | -0.823 | 1.00 | 16.28 | A |
| ATOM | 1333 | OH | TYR | A | 171 | 19.766 | 26.811 | -1.889 | 1.00 | 16.67 | A |
| ATOM | 1334 | C | TYR | A | 171 | 22.754 | 22.430 | 4.023 | 1.00 | 18.04 | A |
| ATOM | 1335 | O | TYR | A | 171 | 23.973 | 22.512 | 4.239 | 1.00 | 18.37 | A |
| ATOM | 1336 | N | LEU | A | 172 | 21.898 | 21.860 | 4.875 | 1.00 | 16.86 | A |
| ATOM | 1337 | CA | LEU | A | 172 | 22.344 | 21.265 | 6.136 | 1.00 | 17.13 | A |
| ATOM | 1338 | CB | LEU | A | 172 | 21.491 | 21.775 | 7.307 | 1.00 | 17.39 | A |
| ATOM | 1339 | CG | LEU | A | 172 | 21.608 | 23.274 | 7.621 | 1.00 | 17.75 | A |
| ATOM | 1340 | CD1 | LEU | A | 172 | 20.624 | 23.657 | 8.724 | 1.00 | 18.65 | A |
| ATOM | 1341 | CD2 | LEU | A | 172 | 23.040 | 23.596 | 8.048 | 1.00 | 15.39 | A |
| ATOM | 1342 | C | LEU | A | 172 | 22.271 | 19.737 | 6.068 | 1.00 | 17.22 | A |
| ATOM | 1343 | O | LEU | A | 172 | 23.088 | 19.047 | 6.672 | 1.00 | 15.82 | A |
| ATOM | 1344 | N | ILE | A | 173 | 21.293 | 19.207 | 5.333 | 1.00 | 17.60 | A |
| ATOM | 1345 | CA | ILE | A | 173 | 21.150 | 17.756 | 5.190 | 1.00 | 18.95 | A |
| ATOM | 1346 | CB | ILE | A | 173 | 19.975 | 17.181 | 6.031 | 1.00 | 19.96 | A |
| ATOM | 1347 | CG2 | ILE | A | 173 | 20.216 | 17.418 | 7.510 | 1.00 | 20.79 | A |
| ATOM | 1348 | CG1 | ILE | A | 173 | 18.654 | 17.812 | 5.585 | 1.00 | 19.92 | A |
| ATOM | 1349 | CD1 | ILE | A | 173 | 17.452 | 17.233 | 6.294 | 1.00 | 20.91 | A |
| ATOM | 1350 | C | ILE | A | 173 | 20.884 | 17.414 | 3.732 | 1.00 | 19.30 | A |
| ATOM | 1351 | O | ILE | A | 173 | 20.337 | 18.218 | 2.992 | 1.00 | 18.40 | A |
| ATOM | 1352 | N | PRO | A | 174 | 21.274 | 16.210 | 3.305 | 1.00 | 20.11 | A |
| ATOM | 1353 | CD | PRO | A | 174 | 22.015 | 15.184 | 4.058 | 1.00 | 19.12 | A |
| ATOM | 1354 | CA | PRO | A | 174 | 21.059 | 15.794 | 1.916 | 1.00 | 21.10 | A |

Figure 9 (22 of 92)

| ATOM | 1355 | CB  | PRO A 174 | 21.655 | 14.387 | 1.874  | 1.00 | 18.81 | A |
| ATOM | 1356 | CG  | PRO A 174 | 22.701 | 14.421 | 2.949  | 1.00 | 19.48 | A |
| ATOM | 1357 | C   | PRO A 174 | 19.573 | 15.790 | 1.586  | 1.00 | 22.80 | A |
| ATOM | 1358 | O   | PRO A 174 | 18.736 | 15.471 | 2.435  | 1.00 | 21.17 | A |
| ATOM | 1359 | N   | ASP A 175 | 19.251 | 16.149 | 0.351  | 1.00 | 24.64 | A |
| ATOM | 1360 | CA  | ASP A 175 | 17.864 | 16.172 | -0.086 | 1.00 | 26.08 | A |
| ATOM | 1361 | CB  | ASP A 175 | 17.794 | 16.494 | -1.578 | 1.00 | 30.46 | A |
| ATOM | 1362 | CG  | ASP A 175 | 17.311 | 17.900 | -1.842 | 1.00 | 33.98 | A |
| ATOM | 1363 | OD1 | ASP A 175 | 18.099 | 18.849 | -1.663 | 1.00 | 35.49 | A |
| ATOM | 1364 | OD2 | ASP A 175 | 16.132 | 18.051 | -2.219 | 1.00 | 38.72 | A |
| ATOM | 1365 | C   | ASP A 175 | 17.144 | 14.850 | 0.178  | 1.00 | 24.12 | A |
| ATOM | 1366 | O   | ASP A 175 | 16.031 | 14.831 | 0.698  | 1.00 | 23.66 | A |
| ATOM | 1367 | N   | LYS A 176 | 17.784 | 13.746 | -0.189 | 1.00 | 23.71 | A |
| ATOM | 1368 | CA  | LYS A 176 | 17.196 | 12.425 | -0.011 | 1.00 | 23.29 | A |
| ATOM | 1369 | CB  | LYS A 176 | 18.143 | 11.348 | -0.531 | 1.00 | 25.22 | A |
| ATOM | 1370 | CG  | LYS A 176 | 18.242 | 11.281 | -2.046 | 1.00 | 27.67 | A |
| ATOM | 1371 | CD  | LYS A 176 | 19.230 | 10.195 | -2.458 | 1.00 | 31.16 | A |
| ATOM | 1372 | CE  | LYS A 176 | 19.386 | 10.109 | -3.969 | 1.00 | 34.79 | A |
| ATOM | 1373 | NZ  | LYS A 176 | 20.473 | 9.147  | -4.352 | 1.00 | 38.06 | A |
| ATOM | 1374 | C   | LYS A 176 | 16.851 | 12.146 | 1.443  | 1.00 | 22.57 | A |
| ATOM | 1375 | O   | LYS A 176 | 15.873 | 11.464 | 1.732  | 1.00 | 22.51 | A |
| ATOM | 1376 | N   | VAL A 177 | 17.658 | 12.671 | 2.361  | 1.00 | 20.53 | A |
| ATOM | 1377 | CA  | VAL A 177 | 17.396 | 12.480 | 3.782  | 1.00 | 19.74 | A |
| ATOM | 1378 | CB  | VAL A 177 | 18.612 | 12.914 | 4.650  | 1.00 | 16.95 | A |
| ATOM | 1379 | CG1 | VAL A 177 | 18.282 | 12.766 | 6.128  | 1.00 | 15.73 | A |
| ATOM | 1380 | CG2 | VAL A 177 | 19.828 | 12.055 | 4.304  | 1.00 | 16.85 | A |
| ATOM | 1381 | C   | VAL A 177 | 16.151 | 13.257 | 4.189  | 1.00 | 19.95 | A |
| ATOM | 1382 | O   | VAL A 177 | 15.257 | 12.734 | 4.888  | 1.00 | 19.06 | A |
| ATOM | 1383 | N   | LYS A 178 | 16.079 | 14.510 | 3.764  | 1.00 | 20.66 | A |
| ATOM | 1384 | CA  | LYS A 178 | 14.908 | 15.330 | 4.066  | 1.00 | 22.30 | A |
| ATOM | 1385 | CB  | LYS A 178 | 15.105 | 16.730 | 3.450  | 1.00 | 22.59 | A |
| ATOM | 1386 | CG  | LYS A 178 | 13.847 | 17.597 | 3.420  | 1.00 | 22.97 | A |
| ATOM | 1387 | CD  | LYS A 178 | 14.045 | 18.811 | 2.541  | 1.00 | 27.42 | A |
| ATOM | 1388 | CE  | LYS A 178 | 12.713 | 19.509 | 2.341  | 1.00 | 31.30 | A |
| ATOM | 1389 | NZ  | LYS A 178 | 11.668 | 18.597 | 1.752  | 1.00 | 35.01 | A |
| ATOM | 1390 | C   | LYS A 178 | 13.676 | 14.628 | 3.530  | 1.00 | 24.17 | A |
| ATOM | 1391 | O   | LYS A 178 | 12.662 | 14.533 | 4.205  | 1.00 | 22.76 | A |
| ATOM | 1392 | N   | LYS A 179 | 13.796 | 14.109 | 2.317  | 1.00 | 26.28 | A |
| ATOM | 1393 | CA  | LYS A 179 | 12.683 | 13.400 | 1.696  | 1.00 | 29.17 | A |
| ATOM | 1394 | CB  | LYS A 179 | 13.052 | 12.896 | 0.273  | 1.00 | 31.48 | A |
| ATOM | 1395 | CG  | LYS A 179 | 12.138 | 11.818 | -0.328 | 1.00 | 37.22 | A |
| ATOM | 1396 | CD  | LYS A 179 | 11.097 | 12.375 | -1.297 | 1.00 | 40.74 | A |
| ATOM | 1397 | CE  | LYS A 179 | 10.380 | 11.241 | -2.018 | 1.00 | 42.28 | A |
| ATOM | 1398 | NZ  | LYS A 179 | 11.170 | 10.102 | -2.549 | 1.00 | 42.99 | A |
| ATOM | 1399 | C   | LYS A 179 | 12.230 | 12.245 | 2.573  | 1.00 | 28.51 | A |
| ATOM | 1400 | O   | LYS A 179 | 11.043 | 12.074 | 2.805  | 1.00 | 29.46 | A |
| ATOM | 1401 | N   | TYR A 180 | 13.180 | 11.487 | 3.106  | 1.00 | 26.92 | A |
| ATOM | 1402 | CA  | TYR A 180 | 12.837 | 10.343 | 3.947  | 1.00 | 24.94 | A |
| ATOM | 1403 | CB  | TYR A 180 | 14.076 | 9.519  | 4.287  | 1.00 | 25.27 | A |
| ATOM | 1404 | CG  | TYR A 180 | 13.815 | 8.212  | 4.992  | 1.00 | 24.54 | A |
| ATOM | 1405 | CD1 | TYR A 180 | 13.579 | 7.038  | 4.275  | 1.00 | 23.25 | A |
| ATOM | 1406 | CE1 | TYR A 180 | 13.366 | 5.817  | 4.938  | 1.00 | 23.91 | A |
| ATOM | 1407 | CD2 | TYR A 180 | 13.834 | 8.149  | 6.376  | 1.00 | 23.11 | A |
| ATOM | 1408 | CE2 | TYR A 180 | 13.625 | 6.945  | 7.055  | 1.00 | 23.33 | A |
| ATOM | 1409 | CZ  | TYR A 180 | 13.386 | 5.781  | 6.322  | 1.00 | 24.12 | A |
| ATOM | 1410 | OH  | TYR A 180 | 13.113 | 4.586  | 6.935  | 1.00 | 24.02 | A |
| ATOM | 1411 | C   | TYR A 180 | 12.170 | 10.757 | 5.242  | 1.00 | 25.48 | A |
| ATOM | 1412 | O   | TYR A 180 | 11.210 | 10.120 | 5.696  | 1.00 | 25.76 | A |
| ATOM | 1413 | N   | VAL A 181 | 12.677 | 11.833 | 5.830  | 1.00 | 25.72 | A |
| ATOM | 1414 | CA  | VAL A 181 | 12.144 | 12.350 | 7.077  | 1.00 | 26.11 | A |
| ATOM | 1415 | CB  | VAL A 181 | 12.967 | 13.562 | 7.588  | 1.00 | 27.01 | A |
| ATOM | 1416 | CG1 | VAL A 181 | 12.221 | 14.240 | 8.742  | 1.00 | 24.52 | A |
| ATOM | 1417 | CG2 | VAL A 181 | 14.351 | 13.075 | 8.086  | 1.00 | 22.76 | A |
| ATOM | 1418 | C   | VAL A 181 | 10.695 | 12.760 | 6.923  | 1.00 | 29.14 | A |
| ATOM | 1419 | O   | VAL A 181 | 9.851  | 12.392 | 7.737  | 1.00 | 27.77 | A |
| ATOM | 1420 | N   | GLU A 182 | 10.409 | 13.486 | 5.851  | 1.00 | 32.19 | A |

Figure 9 (23 of 92)

| | | | | | | | | | | |
|---|---|---|---|---|---|---|---|---|---|---|
| ATOM | 1421 | CA | GLU | A | 182 | 9.072 | 13.969 | 5.606 | 1.00 35.27 | A |
| ATOM | 1422 | CB | GLU | A | 182 | 9.115 | 15.123 | 4.602 | 1.00 37.15 | A |
| ATOM | 1423 | CG | GLU | A | 182 | 9.869 | 14.853 | 3.317 | 1.00 40.92 | A |
| ATOM | 1424 | CD | GLU | A | 182 | 9.879 | 16.072 | 2.402 | 1.00 43.33 | A |
| ATOM | 1425 | OE1 | GLU | A | 182 | 9.682 | 17.198 | 2.915 | 1.00 43.47 | A |
| ATOM | 1426 | OE2 | GLU | A | 182 | 10.095 | 15.910 | 1.177 | 1.00 42.81 | A |
| ATOM | 1427 | C | GLU | A | 182 | 8.104 | 12.895 | 5.153 | 1.00 36.33 | A |
| ATOM | 1428 | O | GLU | A | 182 | 6.911 | 12.999 | 5.430 | 1.00 38.02 | A |
| ATOM | 1429 | N | GLU | A | 183 | 8.595 | 11.862 | 4.474 | 1.00 36.02 | A |
| ATOM | 1430 | CA | GLU | A | 183 | 7.704 | 10.793 | 4.030 | 1.00 36.97 | A |
| ATOM | 1431 | CB | GLU | A | 183 | 8.384 | 9.919 | 2.986 | 1.00 38.59 | A |
| ATOM | 1432 | CG | GLU | A | 183 | 8.763 | 10.656 | 1.732 | 1.00 42.05 | A |
| ATOM | 1433 | CD | GLU | A | 183 | 8.898 | 9.723 | 0.560 | 1.00 42.93 | A |
| ATOM | 1434 | OE1 | GLU | A | 183 | 9.694 | 8.766 | 0.653 | 1.00 43.46 | A |
| ATOM | 1435 | OE2 | GLU | A | 183 | 8.200 | 9.947 | -0.451 | 1.00 45.07 | A |
| ATOM | 1436 | C | GLU | A | 183 | 7.283 | 9.925 | 5.209 | 1.00 36.19 | A |
| ATOM | 1437 | O | GLU | A | 183 | 6.166 | 9.400 | 5.244 | 1.00 37.46 | A |
| ATOM | 1438 | N | ASN | A | 184 | 8.181 | 9.782 | 6.177 | 1.00 33.22 | A |
| ATOM | 1439 | CA | ASN | A | 184 | 7.893 | 8.972 | 7.351 | 1.00 31.32 | A |
| ATOM | 1440 | CB | ASN | A | 184 | 9.094 | 8.078 | 7.681 | 1.00 30.55 | A |
| ATOM | 1441 | CG | ASN | A | 184 | 9.506 | 7.202 | 6.505 | 1.00 30.96 | A |
| ATOM | 1442 | OD1 | ASN | A | 184 | 10.245 | 7.633 | 5.620 | 1.00 30.93 | A |
| ATOM | 1443 | ND2 | ASN | A | 184 | 9.013 | 5.975 | 6.485 | 1.00 29.69 | A |
| ATOM | 1444 | C | ASN | A | 184 | 7.500 | 9.813 | 8.562 | 1.00 29.51 | A |
| ATOM | 1445 | O | ASN | A | 184 | 7.390 | 9.301 | 9.674 | 1.00 29.24 | A |
| ATOM | 1446 | N | GLY | A | 185 | 7.284 | 11.106 | 8.329 | 1.00 28.54 | A |
| ATOM | 1447 | CA | GLY | A | 185 | 6.875 | 12.011 | 9.388 | 1.00 26.51 | A |
| ATOM | 1448 | C | GLY | A | 185 | 7.712 | 11.934 | 10.647 | 1.00 27.56 | A |
| ATOM | 1449 | O | GLY | A | 185 | 7.175 | 11.891 | 11.752 | 1.00 28.09 | A |
| ATOM | 1450 | N | LEU | A | 186 | 9.030 | 11.935 | 10.487 | 1.00 25.62 | A |
| ATOM | 1451 | CA | LEU | A | 186 | 9.932 | 11.846 | 11.627 | 1.00 25.17 | A |
| ATOM | 1452 | CB | LEU | A | 186 | 11.230 | 11.149 | 11.211 | 1.00 24.14 | A |
| ATOM | 1453 | CG | LEU | A | 186 | 11.091 | 9.834 | 10.439 | 1.00 24.02 | A |
| ATOM | 1454 | CD1 | LEU | A | 186 | 12.481 | 9.324 | 10.082 | 1.00 24.64 | A |
| ATOM | 1455 | CD2 | LEU | A | 186 | 10.341 | 8.808 | 11.274 | 1.00 23.80 | A |
| ATOM | 1456 | C | LEU | A | 186 | 10.277 | 13.211 | 12.205 | 1.00 25.26 | A |
| ATOM | 1457 | O | LEU | A | 186 | 10.059 | 14.241 | 11.575 | 1.00 25.21 | A |
| ATOM | 1458 | N | TYR | A | 187 | 10.802 | 13.190 | 13.423 | 1.00 25.80 | A |
| ATOM | 1459 | CA | TYR | A | 187 | 11.259 | 14.377 | 14.134 | 1.00 29.65 | A |
| ATOM | 1460 | CB | TYR | A | 187 | 12.537 | 14.892 | 13.470 | 1.00 25.57 | A |
| ATOM | 1461 | CG | TYR | A | 187 | 13.586 | 13.820 | 13.275 | 1.00 23.69 | A |
| ATOM | 1462 | CD1 | TYR | A | 187 | 14.086 | 13.094 | 14.362 | 1.00 20.93 | A |
| ATOM | 1463 | CE1 | TYR | A | 187 | 15.075 | 12.134 | 14.187 | 1.00 19.95 | A |
| ATOM | 1464 | CD2 | TYR | A | 187 | 14.099 | 13.548 | 12.008 | 1.00 20.82 | A |
| ATOM | 1465 | CE2 | TYR | A | 187 | 15.083 | 12.593 | 11.825 | 1.00 17.58 | A |
| ATOM | 1466 | CZ | TYR | A | 187 | 15.572 | 11.895 | 12.918 | 1.00 19.14 | A |
| ATOM | 1467 | OH | TYR | A | 187 | 16.596 | 10.995 | 12.747 | 1.00 20.78 | A |
| ATOM | 1468 | C | TYR | A | 187 | 10.293 | 15.542 | 14.321 | 1.00 33.65 | A |
| ATOM | 1469 | O | TYR | A | 187 | 10.719 | 16.649 | 14.645 | 1.00 34.09 | A |
| ATOM | 1470 | N | GLU | A | 188 | 9.000 | 15.317 | 14.126 | 1.00 38.67 | A |
| ATOM | 1471 | CA | GLU | A | 188 | 8.054 | 16.407 | 14.319 | 1.00 43.78 | A |
| ATOM | 1472 | CB | GLU | A | 188 | 7.011 | 16.395 | 13.206 | 1.00 43.03 | A |
| ATOM | 1473 | CG | GLU | A | 188 | 7.571 | 16.949 | 11.904 | 1.00 45.38 | A |
| ATOM | 1474 | CD | GLU | A | 188 | 7.164 | 16.145 | 10.683 | 1.00 48.45 | A |
| ATOM | 1475 | OE1 | GLU | A | 188 | 5.942 | 16.002 | 10.438 | 1.00 48.36 | A |
| ATOM | 1476 | OE2 | GLU | A | 188 | 8.073 | 15.659 | 9.968 | 1.00 49.17 | A |
| ATOM | 1477 | C | GLU | A | 188 | 7.414 | 16.306 | 15.697 | 1.00 45.94 | A |
| ATOM | 1478 | O | GLU | A | 188 | 6.302 | 16.769 | 15.917 | 1.00 48.11 | A |
| ATOM | 1479 | N | SER | A | 189 | 8.157 | 15.710 | 16.625 | 1.00 49.16 | A |
| ATOM | 1480 | CA | SER | A | 189 | 7.716 | 15.515 | 18.003 | 1.00 52.51 | A |
| ATOM | 1481 | CB | SER | A | 189 | 8.825 | 14.835 | 18.816 | 1.00 52.99 | A |
| ATOM | 1482 | OG | SER | A | 189 | 8.430 | 14.629 | 20.164 | 1.00 55.34 | A |
| ATOM | 1483 | C | SER | A | 189 | 7.324 | 16.823 | 18.678 | 1.00 54.06 | A |
| ATOM | 1484 | O | SER | A | 189 | 7.355 | 17.868 | 17.994 | 1.00 55.46 | A |
| ATOM | 1485 | OXT | SER | A | 189 | 6.987 | 16.783 | 19.884 | 1.00 56.96 | A |
| ATOM | 1486 | CB | SER | B | 1 | 5.682 | 46.494 | -1.161 | 1.00 37.40 | B |

Figure 9 (24 of 92)

| | | | | | | | | | | |
|---|---|---|---|---|---|---|---|---|---|---|
| ATOM | 1487 | OG | SER | B | 1 | 6.876 | 46.768 | -0.449 | 1.00 38.60 | B |
| ATOM | 1488 | C | SER | B | 1 | 6.508 | 44.213 | -1.715 | 1.00 36.94 | B |
| ATOM | 1489 | O | SER | B | 1 | 5.877 | 43.569 | -0.874 | 1.00 37.31 | B |
| ATOM | 1490 | N | SER | B | 1 | 4.678 | 45.251 | -3.055 | 1.00 35.74 | B |
| ATOM | 1491 | CA | SER | B | 1 | 5.937 | 45.503 | -2.297 | 1.00 36.56 | B |
| ATOM | 1492 | N | LYS | B | 2 | 7.703 | 43.839 | -2.162 | 1.00 34.91 | B |
| ATOM | 1493 | CA | LYS | B | 2 | 8.355 | 42.629 | -1.669 | 1.00 33.01 | B |
| ATOM | 1494 | CB | LYS | B | 2 | 9.007 | 41.847 | -2.803 | 1.00 32.97 | B |
| ATOM | 1495 | CG | LYS | B | 2 | 8.126 | 41.485 | -3.963 | 1.00 36.21 | B |
| ATOM | 1496 | CD | LYS | B | 2 | 8.992 | 40.810 | -5.015 | 1.00 38.08 | B |
| ATOM | 1497 | CE | LYS | B | 2 | 8.249 | 40.563 | -6.309 | 1.00 39.36 | B |
| ATOM | 1498 | NZ | LYS | B | 2 | 9.167 | 39.990 | -7.331 | 1.00 39.86 | B |
| ATOM | 1499 | C | LYS | B | 2 | 9.458 | 42.964 | -0.680 | 1.00 31.14 | B |
| ATOM | 1500 | O | LYS | B | 2 | 9.973 | 44.081 | -0.653 | 1.00 30.52 | B |
| ATOM | 1501 | N | LYS | B | 3 | 9.813 | 41.978 | 0.132 | 1.00 29.12 | B |
| ATOM | 1502 | CA | LYS | B | 3 | 10.899 | 42.135 | 1.082 | 1.00 28.24 | B |
| ATOM | 1503 | CB | LYS | B | 3 | 10.549 | 41.465 | 2.411 | 1.00 29.27 | B |
| ATOM | 1504 | CG | LYS | B | 3 | 9.437 | 42.187 | 3.163 | 1.00 30.79 | B |
| ATOM | 1505 | CD | LYS | B | 3 | 9.216 | 41.597 | 4.541 | 1.00 32.32 | B |
| ATOM | 1506 | CE | LYS | B | 3 | 8.158 | 42.370 | 5.310 | 1.00 33.45 | B |
| ATOM | 1507 | NZ | LYS | B | 3 | 8.017 | 41.872 | 6.712 | 1.00 34.83 | B |
| ATOM | 1508 | C | LYS | B | 3 | 12.065 | 41.442 | 0.378 | 1.00 26.51 | B |
| ATOM | 1509 | O | LYS | B | 3 | 12.027 | 40.237 | 0.105 | 1.00 25.75 | B |
| ATOM | 1510 | N | ILE | B | 4 | 13.086 | 42.224 | 0.055 | 1.00 24.42 | B |
| ATOM | 1511 | CA | ILE | B | 4 | 14.235 | 41.715 | -0.673 | 1.00 22.51 | B |
| ATOM | 1512 | CB | ILE | B | 4 | 14.397 | 42.467 | -2.030 | 1.00 22.84 | B |
| ATOM | 1513 | CG2 | ILE | B | 4 | 15.594 | 41.910 | -2.808 | 1.00 21.48 | B |
| ATOM | 1514 | CG1 | ILE | B | 4 | 13.097 | 42.368 | -2.839 | 1.00 22.30 | B |
| ATOM | 1515 | CD1 | ILE | B | 4 | 12.617 | 40.935 | -3.107 | 1.00 21.20 | B |
| ATOM | 1516 | C | ILE | B | 4 | 15.554 | 41.818 | 0.070 | 1.00 20.82 | B |
| ATOM | 1517 | O | ILE | B | 4 | 15.939 | 42.890 | 0.531 | 1.00 20.53 | B |
| ATOM | 1518 | N | GLY | B | 5 | 16.245 | 40.690 | 0.176 | 1.00 20.10 | B |
| ATOM | 1519 | CA | GLY | B | 5 | 17.544 | 40.680 | 0.817 | 1.00 18.63 | B |
| ATOM | 1520 | C | GLY | B | 5 | 18.581 | 40.791 | -0.287 | 1.00 18.43 | B |
| ATOM | 1521 | O | GLY | B | 5 | 18.547 | 40.021 | -1.257 | 1.00 18.42 | B |
| ATOM | 1522 | N | ILE | B | 6 | 19.491 | 41.752 | -0.152 | 1.00 16.58 | B |
| ATOM | 1523 | CA | ILE | B | 6 | 20.540 | 41.983 | -1.145 | 1.00 15.07 | B |
| ATOM | 1524 | CB | ILE | B | 6 | 20.793 | 43.503 | -1.315 | 1.00 14.57 | B |
| ATOM | 1525 | CG2 | ILE | B | 6 | 21.937 | 43.748 | -2.292 | 1.00 11.18 | B |
| ATOM | 1526 | CG1 | ILE | B | 6 | 19.496 | 44.192 | -1.772 | 1.00 16.70 | B |
| ATOM | 1527 | CD1 | ILE | B | 6 | 18.962 | 43.699 | -3.118 | 1.00 16.11 | B |
| ATOM | 1528 | C | ILE | B | 6 | 21.821 | 41.287 | -0.688 | 1.00 15.42 | B |
| ATOM | 1529 | O | ILE | B | 6 | 22.307 | 41.530 | 0.414 | 1.00 13.77 | B |
| ATOM | 1530 | N | PHE | B | 7 | 22.378 | 40.437 | -1.543 | 1.00 14.46 | B |
| ATOM | 1531 | CA | PHE | B | 7 | 23.573 | 39.682 | -1.184 | 1.00 15.97 | B |
| ATOM | 1532 | CB | PHE | B | 7 | 23.203 | 38.188 | -1.177 | 1.00 15.96 | B |
| ATOM | 1533 | CG | PHE | B | 7 | 24.234 | 37.285 | -0.550 | 1.00 18.73 | B |
| ATOM | 1534 | CD1 | PHE | B | 7 | 25.539 | 37.721 | -0.306 | 1.00 21.09 | B |
| ATOM | 1535 | CD2 | PHE | B | 7 | 23.903 | 35.971 | -0.238 | 1.00 20.31 | B |
| ATOM | 1536 | CE1 | PHE | B | 7 | 26.495 | 36.859 | 0.234 | 1.00 21.55 | B |
| ATOM | 1537 | CE2 | PHE | B | 7 | 24.858 | 35.097 | 0.306 | 1.00 22.22 | B |
| ATOM | 1538 | CZ | PHE | B | 7 | 26.152 | 35.543 | 0.541 | 1.00 20.59 | B |
| ATOM | 1539 | C | PHE | B | 7 | 24.743 | 39.955 | -2.140 | 1.00 15.74 | B |
| ATOM | 1540 | O | PHE | B | 7 | 24.861 | 39.324 | -3.192 | 1.00 17.04 | B |
| ATOM | 1541 | N | GLY | B | 8 | 25.597 | 40.904 | -1.767 | 1.00 16.22 | B |
| ATOM | 1542 | CA | GLY | B | 8 | 26.748 | 41.237 | -2.589 | 1.00 17.51 | B |
| ATOM | 1543 | C | GLY | B | 8 | 27.872 | 40.234 | -2.398 | 1.00 18.86 | B |
| ATOM | 1544 | O | GLY | B | 8 | 27.885 | 39.486 | -1.415 | 1.00 17.36 | B |
| ATOM | 1545 | N | GLY | B | 9 | 28.814 | 40.209 | -3.336 | 1.00 18.69 | B |
| ATOM | 1546 | CA | GLY | B | 9 | 29.931 | 39.281 | -3.241 | 1.00 20.27 | B |
| ATOM | 1547 | C | GLY | B | 9 | 30.644 | 39.101 | -4.568 | 1.00 21.18 | B |
| ATOM | 1548 | O | GLY | B | 9 | 30.144 | 39.536 | -5.604 | 1.00 21.62 | B |
| ATOM | 1549 | N | THR | B | 10 | 31.815 | 38.472 | -4.546 | 1.00 21.88 | B |
| ATOM | 1550 | CA | THR | B | 10 | 32.577 | 38.245 | -5.777 | 1.00 23.10 | B |
| ATOM | 1551 | CB | THR | B | 10 | 34.094 | 38.205 | -5.506 | 1.00 24.73 | B |
| ATOM | 1552 | OG1 | THR | B | 10 | 34.510 | 39.437 | -4.904 | 1.00 24.60 | B |

Figure 9 (25 of 92)

| | | | | | | | | | | |
|---|---|---|---|---|---|---|---|---|---|---|
| ATOM | 1553 | CG2 | THR | B | 10 | 34.865 | 38.005 | -6.810 | 1.00 27.22 | B |
| ATOM | 1554 | C | THR | B | 10 | 32.159 | 36.906 | -6.371 | 1.00 22.74 | B |
| ATOM | 1555 | O | THR | B | 10 | 32.094 | 36.738 | -7.591 | 1.00 21.29 | B |
| ATOM | 1556 | N | PHE | B | 11 | 31.870 | 35.961 | -5.483 | 1.00 22.85 | B |
| ATOM | 1557 | CA | PHE | B | 11 | 31.444 | 34.618 | -5.865 | 1.00 23.51 | B |
| ATOM | 1558 | CB | PHE | B | 11 | 30.023 | 34.653 | -6.446 | 1.00 22.19 | B |
| ATOM | 1559 | CG | PHE | B | 11 | 29.033 | 35.375 | -5.582 | 1.00 22.48 | B |
| ATOM | 1560 | CD1 | PHE | B | 11 | 28.577 | 36.645 | -5.932 | 1.00 24.07 | B |
| ATOM | 1561 | CD2 | PHE | B | 11 | 28.567 | 34.798 | -4.402 | 1.00 24.05 | B |
| ATOM | 1562 | CE1 | PHE | B | 11 | 27.664 | 37.334 | -5.112 | 1.00 22.15 | B |
| ATOM | 1563 | CE2 | PHE | B | 11 | 27.664 | 35.470 | -3.581 | 1.00 23.10 | B |
| ATOM | 1564 | CZ | PHE | B | 11 | 27.210 | 36.746 | -3.937 | 1.00 23.01 | B |
| ATOM | 1565 | C | PHE | B | 11 | 32.389 | 33.954 | -6.868 | 1.00 24.15 | B |
| ATOM | 1566 | O | PHE | B | 11 | 31.969 | 33.544 | -7.955 | 1.00 23.82 | B |
| ATOM | 1567 | N | ASP | B | 12 | 33.668 | 33.857 | -6.519 | 1.00 24.22 | B |
| ATOM | 1568 | CA | ASP | B | 12 | 34.608 | 33.204 | -7.411 | 1.00 25.22 | B |
| ATOM | 1569 | CB | ASP | B | 12 | 35.544 | 34.230 | -8.066 | 1.00 30.25 | B |
| ATOM | 1570 | CG | ASP | B | 12 | 36.595 | 34.761 | -7.124 | 1.00 35.22 | B |
| ATOM | 1571 | OD1 | ASP | B | 12 | 36.241 | 35.182 | -6.002 | 1.00 39.25 | B |
| ATOM | 1572 | OD2 | ASP | B | 12 | 37.782 | 34.760 | -7.517 | 1.00 38.93 | B |
| ATOM | 1573 | C | ASP | B | 12 | 35.387 | 32.144 | -6.637 | 1.00 24.12 | B |
| ATOM | 1574 | O | ASP | B | 12 | 36.530 | 32.355 | -6.226 | 1.00 24.98 | B |
| ATOM | 1575 | N | PRO | B | 13 | 34.765 | 30.975 | -6.433 | 1.00 21.65 | B |
| ATOM | 1576 | CD | PRO | B | 13 | 35.433 | 29.750 | -5.955 | 1.00 21.10 | B |
| ATOM | 1577 | CA | PRO | B | 13 | 33.412 | 30.669 | -6.900 | 1.00 20.77 | B |
| ATOM | 1578 | CB | PRO | B | 13 | 33.559 | 29.240 | -7.382 | 1.00 20.45 | B |
| ATOM | 1579 | CG | PRO | B | 13 | 34.393 | 28.657 | -6.253 | 1.00 22.16 | B |
| ATOM | 1580 | C | PRO | B | 13 | 32.364 | 30.757 | -5.791 | 1.00 21.13 | B |
| ATOM | 1581 | O | PRO | B | 13 | 32.690 | 30.971 | -4.618 | 1.00 19.58 | B |
| ATOM | 1582 | N | PRO | B | 14 | 31.082 | 30.592 | -6.155 | 1.00 21.07 | B |
| ATOM | 1583 | CD | PRO | B | 14 | 30.530 | 30.303 | -7.490 | 1.00 21.36 | B |
| ATOM | 1584 | CA | PRO | B | 14 | 30.022 | 30.642 | -5.149 | 1.00 19.94 | B |
| ATOM | 1585 | CB | PRO | B | 14 | 28.740 | 30.686 | -5.979 | 1.00 21.19 | B |
| ATOM | 1586 | CG | PRO | B | 14 | 29.191 | 30.937 | -7.404 | 1.00 22.46 | B |
| ATOM | 1587 | C | PRO | B | 14 | 30.140 | 29.300 | -4.423 | 1.00 20.40 | B |
| ATOM | 1588 | O | PRO | B | 14 | 30.588 | 28.320 | -5.022 | 1.00 19.71 | B |
| ATOM | 1589 | N | HIS | B | 15 | 29.748 | 29.238 | -3.156 | 1.00 19.67 | B |
| ATOM | 1590 | CA | HIS | B | 15 | 29.822 | 27.974 | -2.435 | 1.00 19.50 | B |
| ATOM | 1591 | CB | HIS | B | 15 | 31.121 | 27.898 | -1.628 | 1.00 19.45 | B |
| ATOM | 1592 | CG | HIS | B | 15 | 31.434 | 29.141 | -0.856 | 1.00 21.43 | B |
| ATOM | 1593 | CD2 | HIS | B | 15 | 32.352 | 30.112 | -1.070 | 1.00 21.25 | B |
| ATOM | 1594 | ND1 | HIS | B | 15 | 30.776 | 29.485 | 0.306 | 1.00 22.27 | B |
| ATOM | 1595 | CE1 | HIS | B | 15 | 31.279 | 30.613 | 0.775 | 1.00 22.75 | B |
| ATOM | 1596 | NE2 | HIS | B | 15 | 32.237 | 31.014 | -0.042 | 1.00 21.44 | B |
| ATOM | 1597 | C | HIS | B | 15 | 28.615 | 27.727 | -1.539 | 1.00 19.79 | B |
| ATOM | 1598 | O | HIS | B | 15 | 27.661 | 28.501 | -1.540 | 1.00 20.55 | B |
| ATOM | 1599 | N | ASN | B | 16 | 28.661 | 26.638 | -0.781 | 1.00 19.65 | B |
| ATOM | 1600 | CA | ASN | B | 16 | 27.559 | 26.277 | 0.094 | 1.00 18.48 | B |
| ATOM | 1601 | CB | ASN | B | 16 | 27.735 | 24.838 | 0.599 | 1.00 19.30 | B |
| ATOM | 1602 | CG | ASN | B | 16 | 27.651 | 23.814 | -0.531 | 1.00 19.40 | B |
| ATOM | 1603 | OD1 | ASN | B | 16 | 27.036 | 24.076 | -1.561 | 1.00 18.15 | B |
| ATOM | 1604 | ND2 | ASN | B | 16 | 28.257 | 22.647 | -0.336 | 1.00 16.66 | B |
| ATOM | 1605 | C | ASN | B | 16 | 27.401 | 27.242 | 1.256 | 1.00 18.58 | B |
| ATOM | 1606 | O | ASN | B | 16 | 26.316 | 27.357 | 1.827 | 1.00 20.65 | B |
| ATOM | 1607 | N | GLY | B | 17 | 28.477 | 27.938 | 1.606 | 1.00 16.61 | B |
| ATOM | 1608 | CA | GLY | B | 17 | 28.394 | 28.898 | 2.690 | 1.00 16.00 | B |
| ATOM | 1609 | C | GLY | B | 17 | 27.497 | 30.042 | 2.256 | 1.00 16.96 | B |
| ATOM | 1610 | O | GLY | B | 17 | 26.730 | 30.574 | 3.062 | 1.00 15.76 | B |
| ATOM | 1611 | N | HIS | B | 18 | 27.592 | 30.417 | 0.977 | 1.00 15.07 | B |
| ATOM | 1612 | CA | HIS | B | 18 | 26.769 | 31.488 | 0.412 | 1.00 14.87 | B |
| ATOM | 1613 | CB | HIS | B | 18 | 27.178 | 31.774 | -1.040 | 1.00 15.04 | B |
| ATOM | 1614 | CG | HIS | B | 18 | 28.527 | 32.402 | -1.180 | 1.00 12.43 | B |
| ATOM | 1615 | CD2 | HIS | B | 18 | 29.102 | 33.431 | -0.519 | 1.00 14.30 | B |
| ATOM | 1616 | ND1 | HIS | B | 18 | 29.444 | 31.990 | -2.121 | 1.00 15.34 | B |
| ATOM | 1617 | CE1 | HIS | B | 18 | 30.528 | 32.739 | -2.036 | 1.00 14.59 | B |
| ATOM | 1618 | NE2 | HIS | B | 18 | 30.346 | 33.623 | -1.072 | 1.00 15.61 | B |

Figure 9 (26 of 92)

| ATOM | 1619 | C | HIS | B | 18 | 25.308 | 31.060 | 0.422 | 1.00 | 15.77 | B |
|---|---|---|---|---|---|---|---|---|---|---|---|
| ATOM | 1620 | O | HIS | B | 18 | 24.433 | 31.805 | 0.870 | 1.00 | 17.42 | B |
| ATOM | 1621 | N | LEU | B | 19 | 25.050 | 29.852 | -0.081 | 1.00 | 14.83 | B |
| ATOM | 1622 | CA | LEU | B | 19 | 23.694 | 29.335 | -0.136 | 1.00 | 13.28 | B |
| ATOM | 1623 | CB | LEU | B | 19 | 23.670 | 27.958 | -0.809 | 1.00 | 12.34 | B |
| ATOM | 1624 | CG | LEU | B | 19 | 24.144 | 28.016 | -2.262 | 1.00 | 13.49 | B |
| ATOM | 1625 | CD1 | LEU | B | 19 | 24.122 | 26.638 | -2.895 | 1.00 | 14.34 | B |
| ATOM | 1626 | CD2 | LEU | B | 19 | 23.242 | 28.988 | -3.032 | 1.00 | 12.43 | B |
| ATOM | 1627 | C | LEU | B | 19 | 23.083 | 29.249 | 1.250 | 1.00 | 13.91 | B |
| ATOM | 1628 | O | LEU | B | 19 | 21.947 | 29.670 | 1.449 | 1.00 | 12.02 | B |
| ATOM | 1629 | N | LEU | B | 20 | 23.842 | 28.719 | 2.210 | 1.00 | 13.84 | B |
| ATOM | 1630 | CA | LEU | B | 20 | 23.346 | 28.599 | 3.581 | 1.00 | 14.05 | B |
| ATOM | 1631 | CB | LEU | B | 20 | 24.376 | 27.885 | 4.462 | 1.00 | 13.20 | B |
| ATOM | 1632 | CG | LEU | B | 20 | 24.034 | 27.818 | 5.958 | 1.00 | 12.58 | B |
| ATOM | 1633 | CD1 | LEU | B | 20 | 22.765 | 27.017 | 6.166 | 1.00 | 10.68 | B |
| ATOM | 1634 | CD2 | LEU | B | 20 | 25.187 | 27.179 | 6.715 | 1.00 | 13.16 | B |
| ATOM | 1635 | C | LEU | B | 20 | 22.991 | 29.955 | 4.205 | 1.00 | 15.18 | B |
| ATOM | 1636 | O | LEU | B | 20 | 21.887 | 30.137 | 4.730 | 1.00 | 16.53 | B |
| ATOM | 1637 | N | MET | B | 21 | 23.921 | 30.906 | 4.151 | 1.00 | 13.76 | B |
| ATOM | 1638 | CA | MET | B | 21 | 23.681 | 32.232 | 4.720 | 1.00 | 13.62 | B |
| ATOM | 1639 | CB | MET | B | 21 | 24.923 | 33.124 | 4.536 | 1.00 | 12.57 | B |
| ATOM | 1640 | CG | MET | B | 21 | 24.799 | 34.512 | 5.161 | 1.00 | 15.32 | B |
| ATOM | 1641 | SD | MET | B | 21 | 26.218 | 35.612 | 4.890 | 1.00 | 7.64 | B |
| ATOM | 1642 | CE | MET | B | 21 | 25.568 | 36.617 | 3.726 | 1.00 | 13.18 | B |
| ATOM | 1643 | C | MET | B | 21 | 22.444 | 32.896 | 4.097 | 1.00 | 13.21 | B |
| ATOM | 1644 | O | MET | B | 21 | 21.578 | 33.425 | 4.804 | 1.00 | 14.40 | B |
| ATOM | 1645 | N | ALA | B | 22 | 22.356 | 32.853 | 2.773 | 1.00 | 13.01 | B |
| ATOM | 1646 | CA | ALA | B | 22 | 21.232 | 33.445 | 2.054 | 1.00 | 12.66 | B |
| ATOM | 1647 | CB | ALA | B | 22 | 21.416 | 33.241 | 0.551 | 1.00 | 8.88 | B |
| ATOM | 1648 | C | ALA | B | 22 | 19.887 | 32.856 | 2.496 | 1.00 | 12.43 | B |
| ATOM | 1649 | O | ALA | B | 22 | 18.918 | 33.589 | 2.711 | 1.00 | 13.55 | B |
| ATOM | 1650 | N | ASN | B | 23 | 19.838 | 31.536 | 2.639 | 1.00 | 12.27 | B |
| ATOM | 1651 | CA | ASN | B | 23 | 18.614 | 30.855 | 3.032 | 1.00 | 14.02 | B |
| ATOM | 1652 | CB | ASN | B | 23 | 18.778 | 29.347 | 2.874 | 1.00 | 14.26 | B |
| ATOM | 1653 | CG | ASN | B | 23 | 17.449 | 28.641 | 2.703 | 1.00 | 15.86 | B |
| ATOM | 1654 | OD1 | ASN | B | 23 | 17.095 | 27.736 | 3.471 | 1.00 | 18.27 | B |
| ATOM | 1655 | ND2 | ASN | B | 23 | 16.702 | 29.053 | 1.692 | 1.00 | 12.78 | B |
| ATOM | 1656 | C | ASN | B | 23 | 18.201 | 31.166 | 4.467 | 1.00 | 14.57 | B |
| ATOM | 1657 | O | ASN | B | 23 | 17.007 | 31.302 | 4.776 | 1.00 | 13.07 | B |
| ATOM | 1658 | N | GLU | B | 24 | 19.189 | 31.269 | 5.344 | 1.00 | 15.00 | B |
| ATOM | 1659 | CA | GLU | B | 24 | 18.920 | 31.569 | 6.743 | 1.00 | 15.23 | B |
| ATOM | 1660 | CB | GLU | B | 24 | 20.191 | 31.371 | 7.568 | 1.00 | 15.54 | B |
| ATOM | 1661 | CG | GLU | B | 24 | 20.624 | 29.904 | 7.674 | 1.00 | 17.90 | B |
| ATOM | 1662 | CD | GLU | B | 24 | 19.564 | 29.016 | 8.322 | 1.00 | 19.75 | B |
| ATOM | 1663 | OE1 | GLU | B | 24 | 19.072 | 29.358 | 9.418 | 1.00 | 19.42 | B |
| ATOM | 1664 | OE2 | GLU | B | 24 | 19.226 | 27.966 | 7.742 | 1.00 | 22.30 | B |
| ATOM | 1665 | C | GLU | B | 24 | 18.395 | 32.995 | 6.878 | 1.00 | 15.11 | B |
| ATOM | 1666 | O | GLU | B | 24 | 17.451 | 33.250 | 7.626 | 1.00 | 17.81 | B |
| ATOM | 1667 | N | VAL | B | 25 | 19.006 | 33.922 | 6.148 | 1.00 | 14.65 | B |
| ATOM | 1668 | CA | VAL | B | 25 | 18.576 | 35.313 | 6.170 | 1.00 | 12.85 | B |
| ATOM | 1669 | CB | VAL | B | 25 | 19.494 | 36.183 | 5.264 | 1.00 | 14.07 | B |
| ATOM | 1670 | CG1 | VAL | B | 25 | 18.881 | 37.576 | 5.043 | 1.00 | 12.01 | B |
| ATOM | 1671 | CG2 | VAL | B | 25 | 20.879 | 36.320 | 5.919 | 1.00 | 11.83 | B |
| ATOM | 1672 | C | VAL | B | 25 | 17.136 | 35.347 | 5.648 | 1.00 | 13.78 | B |
| ATOM | 1673 | O | VAL | B | 25 | 16.256 | 35.938 | 6.265 | 1.00 | 14.73 | B |
| ATOM | 1674 | N | LEU | B | 26 | 16.911 | 34.671 | 4.527 | 1.00 | 13.56 | B |
| ATOM | 1675 | CA | LEU | B | 26 | 15.606 | 34.599 | 3.886 | 1.00 | 17.36 | B |
| ATOM | 1676 | CB | LEU | B | 26 | 15.649 | 33.613 | 2.709 | 1.00 | 16.11 | B |
| ATOM | 1677 | CG | LEU | B | 26 | 14.278 | 33.279 | 2.116 | 1.00 | 15.29 | B |
| ATOM | 1678 | CD1 | LEU | B | 26 | 13.727 | 34.504 | 1.411 | 1.00 | 18.21 | B |
| ATOM | 1679 | CD2 | LEU | B | 26 | 14.388 | 32.091 | 1.153 | 1.00 | 14.92 | B |
| ATOM | 1680 | C | LEU | B | 26 | 14.472 | 34.192 | 4.820 | 1.00 | 19.95 | B |
| ATOM | 1681 | O | LEU | B | 26 | 13.432 | 34.859 | 4.881 | 1.00 | 19.77 | B |
| ATOM | 1682 | N | TYR | B | 27 | 14.652 | 33.092 | 5.538 | 1.00 | 20.39 | B |
| ATOM | 1683 | CA | TYR | B | 27 | 13.599 | 32.652 | 6.431 | 1.00 | 22.64 | B |
| ATOM | 1684 | CB | TYR | B | 27 | 13.663 | 31.137 | 6.640 | 1.00 | 26.44 | B |

Figure 9 (27 of 92)

```
ATOM   1685  CG   TYR B  27      13.258  30.371   5.399  1.00 33.25           B
ATOM   1686  CD1  TYR B  27      14.194  30.058   4.410  1.00 33.97           B
ATOM   1687  CE1  TYR B  27      13.819  29.398   3.240  1.00 36.53           B
ATOM   1688  CD2  TYR B  27      11.928  30.001   5.188  1.00 35.23           B
ATOM   1689  CE2  TYR B  27      11.541  29.340   4.016  1.00 37.84           B
ATOM   1690  CZ   TYR B  27      12.495  29.044   3.048  1.00 37.45           B
ATOM   1691  OH   TYR B  27      12.127  28.399   1.885  1.00 40.70           B
ATOM   1692  C    TYR B  27      13.569  33.370   7.772  1.00 21.74           B
ATOM   1693  O    TYR B  27      12.502  33.743   8.238  1.00 20.62           B
ATOM   1694  N    GLN B  28      14.725  33.586   8.386  1.00 20.35           B
ATOM   1695  CA   GLN B  28      14.742  34.256   9.683  1.00 19.38           B
ATOM   1696  CB   GLN B  28      16.127  34.137  10.313  1.00 18.73           B
ATOM   1697  CG   GLN B  28      16.493  32.711  10.674  1.00 17.52           B
ATOM   1698  CD   GLN B  28      17.823  32.611  11.389  1.00 17.51           B
ATOM   1699  OE1  GLN B  28      18.076  33.337  12.345  1.00 14.41           B
ATOM   1700  NE2  GLN B  28      18.677  31.693  10.933  1.00 15.78           B
ATOM   1701  C    GLN B  28      14.308  35.722   9.628  1.00 20.56           B
ATOM   1702  O    GLN B  28      13.761  36.248  10.598  1.00 20.90           B
ATOM   1703  N    ALA B  29      14.530  36.383   8.496  1.00 19.89           B
ATOM   1704  CA   ALA B  29      14.141  37.784   8.375  1.00 20.30           B
ATOM   1705  CB   ALA B  29      15.179  38.542   7.587  1.00 18.93           B
ATOM   1706  C    ALA B  29      12.772  37.926   7.719  1.00 19.87           B
ATOM   1707  O    ALA B  29      12.287  39.035   7.501  1.00 19.47           B
ATOM   1708  N    GLY B  30      12.157  36.789   7.410  1.00 20.06           B
ATOM   1709  CA   GLY B  30      10.846  36.788   6.781  1.00 20.94           B
ATOM   1710  C    GLY B  30      10.802  37.498   5.436  1.00 20.20           B
ATOM   1711  O    GLY B  30       9.842  38.204   5.143  1.00 18.71           B
ATOM   1712  N    LEU B  31      11.831  37.302   4.612  1.00 19.77           B
ATOM   1713  CA   LEU B  31      11.894  37.949   3.301  1.00 19.40           B
ATOM   1714  CB   LEU B  31      13.348  38.215   2.899  1.00 16.80           B
ATOM   1715  CG   LEU B  31      14.264  38.878   3.926  1.00 17.28           B
ATOM   1716  CD1  LEU B  31      15.616  39.120   3.264  1.00 16.82           B
ATOM   1717  CD2  LEU B  31      13.672  40.193   4.425  1.00 14.38           B
ATOM   1718  C    LEU B  31      11.233  37.120   2.217  1.00 18.65           B
ATOM   1719  O    LEU B  31      10.955  35.942   2.407  1.00 20.67           B
ATOM   1720  N    ASP B  32      11.000  37.748   1.070  1.00 19.28           B
ATOM   1721  CA   ASP B  32      10.378  37.087  -0.069  1.00 18.63           B
ATOM   1722  CB   ASP B  32       9.552  38.103  -0.868  1.00 20.58           B
ATOM   1723  CG   ASP B  32       8.322  38.574  -0.118  1.00 24.31           B
ATOM   1724  OD1  ASP B  32       7.396  37.758   0.046  1.00 25.37           B
ATOM   1725  OD2  ASP B  32       8.278  39.749   0.311  1.00 26.14           B
ATOM   1726  C    ASP B  32      11.436  36.467  -0.984  1.00 17.29           B
ATOM   1727  O    ASP B  32      11.303  35.329  -1.449  1.00 15.21           B
ATOM   1728  N    GLU B  33      12.490  37.230  -1.241  1.00 18.38           B
ATOM   1729  CA   GLU B  33      13.556  36.772  -2.117  1.00 17.61           B
ATOM   1730  CB   GLU B  33      13.312  37.270  -3.540  1.00 20.16           B
ATOM   1731  CG   GLU B  33      11.960  36.907  -4.118  1.00 24.97           B
ATOM   1732  CD   GLU B  33      11.718  37.562  -5.473  1.00 28.01           B
ATOM   1733  OE1  GLU B  33      10.682  37.263  -6.104  1.00 29.05           B
ATOM   1734  OE2  GLU B  33      12.564  38.377  -5.903  1.00 26.56           B
ATOM   1735  C    GLU B  33      14.907  37.280  -1.673  1.00 16.77           B
ATOM   1736  O    GLU B  33      15.007  38.233  -0.895  1.00 16.34           B
ATOM   1737  N    ILE B  34      15.945  36.630  -2.186  1.00 15.13           B
ATOM   1738  CA   ILE B  34      17.320  37.019  -1.917  1.00 15.28           B
ATOM   1739  CB   ILE B  34      18.122  35.894  -1.215  1.00 13.94           B
ATOM   1740  CG2  ILE B  34      19.586  36.298  -1.118  1.00 15.94           B
ATOM   1741  CG1  ILE B  34      17.540  35.605   0.180  1.00 14.28           B
ATOM   1742  CD1  ILE B  34      17.770  36.707   1.212  1.00 12.27           B
ATOM   1743  C    ILE B  34      17.914  37.257  -3.301  1.00 15.54           B
ATOM   1744  O    ILE B  34      17.772  36.420  -4.195  1.00 14.34           B
ATOM   1745  N    TRP B  35      18.553  38.405  -3.489  1.00 16.26           B
ATOM   1746  CA   TRP B  35      19.165  38.717  -4.777  1.00 19.17           B
ATOM   1747  CB   TRP B  35      18.756  40.120  -5.243  1.00 19.21           B
ATOM   1748  CG   TRP B  35      17.300  40.245  -5.588  1.00 22.38           B
ATOM   1749  CD2  TRP B  35      16.619  41.426  -6.027  1.00 22.79           B
ATOM   1750  CE2  TRP B  35      15.263  41.075  -6.237  1.00 24.73           B
```

Figure 9 (28 of 92)

| | | | | | | | | | | |
|---|---|---|---|---|---|---|---|---|---|---|
| ATOM | 1751 | CE3 | TRP | B | 35 | 17.021 | 42.749 | -6.263 | 1.00 24.28 | B |
| ATOM | 1752 | CD1 | TRP | B | 35 | 16.358 | 39.253 | -5.551 | 1.00 24.14 | B |
| ATOM | 1753 | NE1 | TRP | B | 35 | 15.132 | 39.743 | -5.941 | 1.00 23.06 | B |
| ATOM | 1754 | CZ2 | TRP | B | 35 | 14.305 | 42.000 | -6.671 | 1.00 24.44 | B |
| ATOM | 1755 | CZ3 | TRP | B | 35 | 16.070 | 43.672 | -6.693 | 1.00 25.12 | B |
| ATOM | 1756 | CH2 | TRP | B | 35 | 14.726 | 43.291 | -6.892 | 1.00 27.51 | B |
| ATOM | 1757 | C | TRP | B | 35 | 20.683 | 38.638 | -4.683 | 1.00 19.24 | B |
| ATOM | 1758 | O | TRP | B | 35 | 21.308 | 39.409 | -3.958 | 1.00 19.91 | B |
| ATOM | 1759 | N | PHE | B | 36 | 21.278 | 37.698 | -5.405 | 1.00 19.25 | B |
| ATOM | 1760 | CA | PHE | B | 36 | 22.726 | 37.570 | -5.396 | 1.00 18.90 | B |
| ATOM | 1761 | CB | PHE | B | 36 | 23.143 | 36.150 | -5.766 | 1.00 17.88 | B |
| ATOM | 1762 | CG | PHE | B | 36 | 22.801 | 35.125 | -4.713 | 1.00 18.14 | B |
| ATOM | 1763 | CD1 | PHE | B | 36 | 21.474 | 34.790 | -4.445 | 1.00 16.79 | B |
| ATOM | 1764 | CD2 | PHE | B | 36 | 23.809 | 34.497 | -3.986 | 1.00 20.89 | B |
| ATOM | 1765 | CE1 | PHE | B | 36 | 21.155 | 33.839 | -3.468 | 1.00 16.85 | B |
| ATOM | 1766 | CE2 | PHE | B | 36 | 23.502 | 33.542 | -3.002 | 1.00 19.23 | B |
| ATOM | 1767 | CZ | PHE | B | 36 | 22.171 | 33.213 | -2.745 | 1.00 18.66 | B |
| ATOM | 1768 | C | PHE | B | 36 | 23.266 | 38.582 | -6.396 | 1.00 20.02 | B |
| ATOM | 1769 | O | PHE | B | 36 | 22.849 | 38.603 | -7.556 | 1.00 18.57 | B |
| ATOM | 1770 | N | MET | B | 37 | 24.195 | 39.420 | -5.942 | 1.00 19.10 | B |
| ATOM | 1771 | CA | MET | B | 37 | 24.741 | 40.464 | -6.796 | 1.00 19.51 | B |
| ATOM | 1772 | CB | MET | B | 37 | 24.343 | 41.822 | -6.233 | 1.00 17.88 | B |
| ATOM | 1773 | CG | MET | B | 37 | 22.850 | 41.924 | -5.879 | 1.00 19.63 | B |
| ATOM | 1774 | SD | MET | B | 37 | 22.199 | 43.567 | -6.233 | 1.00 17.10 | B |
| ATOM | 1775 | CE | MET | B | 37 | 22.873 | 43.690 | -7.839 | 1.00 3.35 | B |
| ATOM | 1776 | C | MET | B | 37 | 26.256 | 40.403 | -6.987 | 1.00 19.80 | B |
| ATOM | 1777 | O | MET | B | 37 | 27.021 | 40.922 | -6.171 | 1.00 18.96 | B |
| ATOM | 1778 | N | PRO | B | 38 | 26.705 | 39.777 | -8.087 | 1.00 19.26 | B |
| ATOM | 1779 | CD | PRO | B | 38 | 25.876 | 39.183 | -9.147 | 1.00 17.72 | B |
| ATOM | 1780 | CA | PRO | B | 38 | 28.127 | 39.634 | -8.410 | 1.00 20.89 | B |
| ATOM | 1781 | CB | PRO | B | 38 | 28.112 | 38.840 | -9.721 | 1.00 19.29 | B |
| ATOM | 1782 | CG | PRO | B | 38 | 26.802 | 38.153 | -9.706 | 1.00 17.99 | B |
| ATOM | 1783 | C | PRO | B | 38 | 28.764 | 40.998 | -8.602 | 1.00 22.94 | B |
| ATOM | 1784 | O | PRO | B | 38 | 28.233 | 41.829 | -9.332 | 1.00 21.40 | B |
| ATOM | 1785 | N | ASN | B | 39 | 29.894 | 41.240 | -7.948 | 1.00 26.41 | B |
| ATOM | 1786 | CA | ASN | B | 39 | 30.563 | 42.528 | -8.116 | 1.00 30.86 | B |
| ATOM | 1787 | CB | ASN | B | 39 | 31.252 | 42.954 | -6.813 | 1.00 29.49 | B |
| ATOM | 1788 | CG | ASN | B | 39 | 32.300 | 41.959 | -6.347 | 1.00 30.42 | B |
| ATOM | 1789 | OD1 | ASN | B | 39 | 32.585 | 41.858 | -5.148 | 1.00 31.40 | B |
| ATOM | 1790 | ND2 | ASN | B | 39 | 32.889 | 41.226 | -7.288 | 1.00 27.86 | B |
| ATOM | 1791 | C | ASN | B | 39 | 31.580 | 42.405 | -9.244 | 1.00 33.78 | B |
| ATOM | 1792 | O | ASN | B | 39 | 31.745 | 41.328 | -9.819 | 1.00 32.62 | B |
| ATOM | 1793 | N | GLN | B | 40 | 32.237 | 43.513 | -9.578 | 1.00 38.32 | B |
| ATOM | 1794 | CA | GLN | B | 40 | 33.259 | 43.509 | -10.620 | 1.00 42.86 | B |
| ATOM | 1795 | CB | GLN | B | 40 | 32.660 | 43.781 | -12.004 | 1.00 43.67 | B |
| ATOM | 1796 | CG | GLN | B | 40 | 33.692 | 43.730 | -13.139 | 1.00 46.25 | B |
| ATOM | 1797 | CD | GLN | B | 40 | 34.330 | 42.349 | -13.319 | 1.00 47.90 | B |
| ATOM | 1798 | OE1 | GLN | B | 40 | 35.140 | 41.899 | -12.497 | 1.00 47.32 | B |
| ATOM | 1799 | NE2 | GLN | B | 40 | 33.958 | 41.669 | -14.403 | 1.00 48.80 | B |
| ATOM | 1800 | C | GLN | B | 40 | 34.338 | 44.536 | -10.324 | 1.00 45.14 | B |
| ATOM | 1801 | O | GLN | B | 40 | 34.065 | 45.630 | -9.822 | 1.00 46.10 | B |
| ATOM | 1802 | N | ILE | B | 41 | 35.570 | 44.153 | -10.629 | 1.00 47.77 | B |
| ATOM | 1803 | CA | ILE | B | 41 | 36.732 | 44.991 | -10.414 | 1.00 49.93 | B |
| ATOM | 1804 | CB | ILE | B | 41 | 37.986 | 44.112 | -10.182 | 1.00 49.49 | B |
| ATOM | 1805 | CG2 | ILE | B | 41 | 39.255 | 44.888 | -10.517 | 1.00 50.54 | B |
| ATOM | 1806 | CG1 | ILE | B | 41 | 38.005 | 43.597 | -8.743 | 1.00 49.36 | B |
| ATOM | 1807 | CD1 | ILE | B | 41 | 36.893 | 42.618 | -8.416 | 1.00 47.73 | B |
| ATOM | 1808 | C | ILE | B | 41 | 36.974 | 45.843 | -11.647 | 1.00 51.70 | B |
| ATOM | 1809 | O | ILE | B | 41 | 36.645 | 45.439 | -12.761 | 1.00 51.14 | B |
| ATOM | 1810 | N | PRO | B | 42 | 37.516 | 47.055 | -11.461 | 1.00 53.81 | B |
| ATOM | 1811 | CD | PRO | B | 42 | 37.772 | 47.822 | -10.229 | 1.00 54.38 | B |
| ATOM | 1812 | CA | PRO | B | 42 | 37.770 | 47.865 | -12.655 | 1.00 55.45 | B |
| ATOM | 1813 | CB | PRO | B | 42 | 38.139 | 49.236 | -12.079 | 1.00 55.22 | B |
| ATOM | 1814 | CG | PRO | B | 42 | 37.538 | 49.232 | -10.694 | 1.00 55.05 | B |
| ATOM | 1815 | C | PRO | B | 42 | 38.993 | 47.149 | -13.232 | 1.00 56.96 | B |
| ATOM | 1816 | O | PRO | B | 42 | 39.946 | 46.902 | -12.496 | 1.00 57.39 | B |

Figure 9 (29 of 92)

| ATOM | 1817 | N | PRO | B | 43 | 38.987 | 46.799 | -14.532 | 1.00 | 57.40 | B |
|---|---|---|---|---|---|---|---|---|---|---|---|
| ATOM | 1818 | CD | PRO | B | 43 | 38.107 | 47.287 | -15.603 | 1.00 | 57.73 | B |
| ATOM | 1819 | CA | PRO | B | 43 | 40.150 | 46.101 | -15.101 | 1.00 | 57.94 | B |
| ATOM | 1820 | CB | PRO | B | 43 | 40.017 | 46.355 | -16.611 | 1.00 | 57.89 | B |
| ATOM | 1821 | CG | PRO | B | 43 | 39.095 | 47.545 | -16.707 | 1.00 | 57.75 | B |
| ATOM | 1822 | C | PRO | B | 43 | 41.509 | 46.517 | -14.533 | 1.00 | 58.27 | B |
| ATOM | 1823 | O | PRO | B | 43 | 42.251 | 47.287 | -15.145 | 1.00 | 58.73 | B |
| ATOM | 1824 | N | HIS | B | 44 | 41.813 | 45.986 | -13.349 | 1.00 | 58.43 | B |
| ATOM | 1825 | CA | HIS | B | 44 | 43.057 | 46.256 | -12.635 | 1.00 | 58.60 | B |
| ATOM | 1826 | CB | HIS | B | 44 | 42.895 | 47.434 | -11.665 | 1.00 | 59.32 | B |
| ATOM | 1827 | CG | HIS | B | 44 | 42.517 | 48.722 | -12.325 | 1.00 | 60.09 | B |
| ATOM | 1828 | CD2 | HIS | B | 44 | 41.552 | 49.626 | -12.030 | 1.00 | 60.65 | B |
| ATOM | 1829 | ND1 | HIS | B | 44 | 43.187 | 49.224 | -13.421 | 1.00 | 60.84 | B |
| ATOM | 1830 | CE1 | HIS | B | 44 | 42.651 | 50.378 | -13.772 | 1.00 | 60.57 | B |
| ATOM | 1831 | NE2 | HIS | B | 44 | 41.656 | 50.646 | -12.944 | 1.00 | 60.45 | B |
| ATOM | 1832 | C | HIS | B | 44 | 43.440 | 45.020 | -11.834 | 1.00 | 58.14 | B |
| ATOM | 1833 | O | HIS | B | 44 | 42.858 | 44.753 | -10.783 | 1.00 | 58.34 | B |
| ATOM | 1834 | N | THR | B | 51 | 38.711 | 35.819 | -11.549 | 1.00 | 42.64 | B |
| ATOM | 1835 | CA | THR | B | 51 | 37.896 | 35.141 | -12.548 | 1.00 | 42.74 | B |
| ATOM | 1836 | CB | THR | B | 51 | 37.014 | 34.065 | -11.892 | 1.00 | 42.66 | B |
| ATOM | 1837 | OG1 | THR | B | 51 | 37.852 | 33.060 | -11.310 | 1.00 | 43.20 | B |
| ATOM | 1838 | CG2 | THR | B | 51 | 36.099 | 33.421 | -12.917 | 1.00 | 42.14 | B |
| ATOM | 1839 | C | THR | B | 51 | 37.001 | 36.111 | -13.317 | 1.00 | 42.99 | B |
| ATOM | 1840 | O | THR | B | 51 | 36.465 | 37.064 | -12.749 | 1.00 | 42.81 | B |
| ATOM | 1841 | N | ASP | B | 52 | 36.844 | 35.863 | -14.614 | 1.00 | 43.19 | B |
| ATOM | 1842 | CA | ASP | B | 52 | 36.011 | 36.710 | -15.458 | 1.00 | 43.45 | B |
| ATOM | 1843 | CB | ASP | B | 52 | 36.009 | 36.174 | -16.893 | 1.00 | 46.07 | B |
| ATOM | 1844 | CG | ASP | B | 52 | 35.602 | 37.224 | -17.916 | 1.00 | 48.60 | B |
| ATOM | 1845 | OD1 | ASP | B | 52 | 34.463 | 37.745 | -17.835 | 1.00 | 49.54 | B |
| ATOM | 1846 | OD2 | ASP | B | 52 | 36.431 | 37.524 | -18.805 | 1.00 | 49.01 | B |
| ATOM | 1847 | C | ASP | B | 52 | 34.592 | 36.727 | -14.897 | 1.00 | 42.20 | B |
| ATOM | 1848 | O | ASP | B | 52 | 34.151 | 35.769 | -14.261 | 1.00 | 42.13 | B |
| ATOM | 1849 | N | SER | B | 53 | 33.881 | 37.819 | -15.143 | 1.00 | 40.96 | B |
| ATOM | 1850 | CA | SER | B | 53 | 32.525 | 37.981 | -14.648 | 1.00 | 39.49 | B |
| ATOM | 1851 | CB | SER | B | 53 | 32.075 | 39.420 | -14.884 | 1.00 | 40.04 | B |
| ATOM | 1852 | OG | SER | B | 53 | 31.045 | 39.760 | -13.977 | 1.00 | 41.63 | B |
| ATOM | 1853 | C | SER | B | 53 | 31.492 | 37.021 | -15.237 | 1.00 | 39.00 | B |
| ATOM | 1854 | O | SER | B | 53 | 30.670 | 36.459 | -14.508 | 1.00 | 37.41 | B |
| ATOM | 1855 | N | PHE | B | 54 | 31.517 | 36.834 | -16.552 | 1.00 | 37.82 | B |
| ATOM | 1856 | CA | PHE | B | 54 | 30.535 | 35.949 | -17.162 | 1.00 | 37.70 | B |
| ATOM | 1857 | CB | PHE | B | 54 | 30.707 | 35.895 | -18.690 | 1.00 | 39.01 | B |
| ATOM | 1858 | CG | PHE | B | 54 | 31.719 | 34.898 | -19.161 | 1.00 | 40.94 | B |
| ATOM | 1859 | CD1 | PHE | B | 54 | 31.348 | 33.581 | -19.427 | 1.00 | 42.94 | B |
| ATOM | 1860 | CD2 | PHE | B | 54 | 33.045 | 35.272 | -19.335 | 1.00 | 42.92 | B |
| ATOM | 1861 | CE1 | PHE | B | 54 | 32.289 | 32.652 | -19.861 | 1.00 | 43.86 | B |
| ATOM | 1862 | CE2 | PHE | B | 54 | 33.997 | 34.354 | -19.768 | 1.00 | 43.36 | B |
| ATOM | 1863 | CZ | PHE | B | 54 | 33.620 | 33.041 | -20.032 | 1.00 | 44.51 | B |
| ATOM | 1864 | C | PHE | B | 54 | 30.651 | 34.564 | -16.548 | 1.00 | 36.05 | B |
| ATOM | 1865 | O | PHE | B | 54 | 29.674 | 33.823 | -16.481 | 1.00 | 35.05 | B |
| ATOM | 1866 | N | HIS | B | 55 | 31.852 | 34.232 | -16.086 | 1.00 | 34.81 | B |
| ATOM | 1867 | CA | HIS | B | 55 | 32.103 | 32.943 | -15.453 | 1.00 | 34.47 | B |
| ATOM | 1868 | CB | HIS | B | 55 | 33.611 | 32.693 | -15.329 | 1.00 | 35.78 | B |
| ATOM | 1869 | CG | HIS | B | 55 | 34.206 | 31.990 | -16.510 | 1.00 | 37.39 | B |
| ATOM | 1870 | CD2 | HIS | B | 55 | 33.714 | 31.010 | -17.303 | 1.00 | 38.21 | B |
| ATOM | 1871 | ND1 | HIS | B | 55 | 35.472 | 32.263 | -16.981 | 1.00 | 37.09 | B |
| ATOM | 1872 | CE1 | HIS | B | 55 | 35.731 | 31.483 | -18.015 | 1.00 | 37.65 | B |
| ATOM | 1873 | NE2 | HIS | B | 55 | 34.681 | 30.713 | -18.231 | 1.00 | 37.60 | B |
| ATOM | 1874 | C | HIS | B | 55 | 31.464 | 32.911 | -14.070 | 1.00 | 32.84 | B |
| ATOM | 1875 | O | HIS | B | 55 | 30.758 | 31.965 | -13.723 | 1.00 | 33.33 | B |
| ATOM | 1876 | N | ARG | B | 56 | 31.711 | 33.951 | -13.281 | 1.00 | 30.77 | B |
| ATOM | 1877 | CA | ARG | B | 56 | 31.151 | 34.013 | -11.940 | 1.00 | 30.83 | B |
| ATOM | 1878 | CB | ARG | B | 56 | 31.724 | 35.218 | -11.188 | 1.00 | 30.19 | B |
| ATOM | 1879 | CG | ARG | B | 56 | 33.216 | 35.072 | -10.930 | 1.00 | 29.94 | B |
| ATOM | 1880 | CD | ARG | B | 56 | 33.789 | 36.208 | -10.112 | 1.00 | 31.15 | B |
| ATOM | 1881 | NE | ARG | B | 56 | 33.930 | 37.444 | -10.874 | 1.00 | 30.51 | B |
| ATOM | 1882 | CZ | ARG | B | 56 | 33.265 | 38.565 | -10.612 | 1.00 | 31.05 | B |

Figure 9 (30 of 92)

| | | | | | | | | | | |
|---|---|---|---|---|---|---|---|---|---|---|
| ATOM | 1883 | NH1 | ARG | B | 56 | 32.399 | 38.613 | -9.602 | 1.00 29.14 | B |
| ATOM | 1884 | NH2 | ARG | B | 56 | 33.477 | 39.644 | -11.355 | 1.00 29.48 | B |
| ATOM | 1885 | C | ARG | B | 56 | 29.631 | 34.072 | -12.001 | 1.00 30.44 | B |
| ATOM | 1886 | O | ARG | B | 56 | 28.941 | 33.521 | -11.140 | 1.00 29.93 | B |
| ATOM | 1887 | N | VAL | B | 57 | 29.109 | 34.724 | -13.035 | 1.00 29.93 | B |
| ATOM | 1888 | CA | VAL | B | 57 | 27.667 | 34.824 | -13.197 | 1.00 29.18 | B |
| ATOM | 1889 | CB | VAL | B | 57 | 27.293 | 35.831 | -14.306 | 1.00 28.38 | B |
| ATOM | 1890 | CG1 | VAL | B | 57 | 25.805 | 35.829 | -14.523 | 1.00 29.06 | B |
| ATOM | 1891 | CG2 | VAL | B | 57 | 27.750 | 37.227 | -13.916 | 1.00 28.66 | B |
| ATOM | 1892 | C | VAL | B | 57 | 27.112 | 33.445 | -13.549 | 1.00 28.68 | B |
| ATOM | 1893 | O | VAL | B | 57 | 26.069 | 33.034 | -13.032 | 1.00 27.88 | B |
| ATOM | 1894 | N | GLU | B | 58 | 27.813 | 32.723 | -14.420 | 1.00 27.40 | B |
| ATOM | 1895 | CA | GLU | B | 58 | 27.348 | 31.395 | -14.800 | 1.00 27.26 | B |
| ATOM | 1896 | CB | GLU | B | 58 | 28.219 | 30.789 | -15.910 | 1.00 29.75 | B |
| ATOM | 1897 | CG | GLU | B | 58 | 27.990 | 31.395 | -17.294 | 1.00 32.26 | B |
| ATOM | 1898 | CD | GLU | B | 58 | 26.511 | 31.555 | -17.634 | 1.00 35.15 | B |
| ATOM | 1899 | OE1 | GLU | B | 58 | 25.753 | 30.567 | -17.521 | 1.00 34.53 | B |
| ATOM | 1900 | OE2 | GLU | B | 58 | 26.110 | 32.677 | -18.019 | 1.00 35.83 | B |
| ATOM | 1901 | C | GLU | B | 58 | 27.337 | 30.473 | -13.585 | 1.00 23.84 | B |
| ATOM | 1902 | O | GLU | B | 58 | 26.336 | 29.818 | -13.320 | 1.00 23.59 | B |
| ATOM | 1903 | N | MET | B | 59 | 28.443 | 30.427 | -12.844 | 1.00 22.60 | B |
| ATOM | 1904 | CA | MET | B | 59 | 28.497 | 29.579 | -11.658 | 1.00 22.40 | B |
| ATOM | 1905 | CB | MET | B | 59 | 29.867 | 29.696 | -10.957 | 1.00 19.05 | B |
| ATOM | 1906 | CG | MET | B | 59 | 31.018 | 29.004 | -11.720 | 1.00 10.45 | B |
| ATOM | 1907 | SD | MET | B | 59 | 32.632 | 28.952 | -10.935 | 1.00 8.45 | B |
| ATOM | 1908 | CE | MET | B | 59 | 32.988 | 30.638 | -10.778 | 1.00 10.85 | B |
| ATOM | 1909 | C | MET | B | 59 | 27.350 | 29.936 | -10.695 | 1.00 24.00 | B |
| ATOM | 1910 | O | MET | B | 59 | 26.711 | 29.050 | -10.131 | 1.00 24.71 | B |
| ATOM | 1911 | N | LEU | B | 60 | 27.066 | 31.225 | -10.531 | 1.00 25.00 | B |
| ATOM | 1912 | CA | LEU | B | 60 | 25.982 | 31.639 | -9.638 | 1.00 27.04 | B |
| ATOM | 1913 | CB | LEU | B | 60 | 25.867 | 33.166 | -9.586 | 1.00 27.13 | B |
| ATOM | 1914 | CG | LEU | B | 60 | 26.514 | 33.827 | -8.369 | 1.00 28.02 | B |
| ATOM | 1915 | CD1 | LEU | B | 60 | 26.241 | 35.310 | -8.415 | 1.00 29.17 | B |
| ATOM | 1916 | CD2 | LEU | B | 60 | 25.951 | 33.227 | -7.077 | 1.00 26.22 | B |
| ATOM | 1917 | C | LEU | B | 60 | 24.639 | 31.051 | -10.052 | 1.00 27.77 | B |
| ATOM | 1918 | O | LEU | B | 60 | 23.926 | 30.472 | -9.225 | 1.00 28.59 | B |
| ATOM | 1919 | N | LYS | B | 61 | 24.290 | 31.207 | -11.328 | 1.00 26.70 | B |
| ATOM | 1920 | CA | LYS | B | 61 | 23.030 | 30.679 | -11.834 | 1.00 27.16 | B |
| ATOM | 1921 | CB | LYS | B | 61 | 22.959 | 30.786 | -13.360 | 1.00 27.23 | B |
| ATOM | 1922 | CG | LYS | B | 61 | 22.869 | 32.196 | -13.902 | 1.00 28.51 | B |
| ATOM | 1923 | CD | LYS | B | 61 | 22.740 | 32.153 | -15.415 | 1.00 31.17 | B |
| ATOM | 1924 | CE | LYS | B | 61 | 22.823 | 33.531 | -16.032 | 1.00 32.41 | B |
| ATOM | 1925 | NZ | LYS | B | 61 | 22.798 | 33.436 | -17.521 | 1.00 32.65 | B |
| ATOM | 1926 | C | LYS | B | 61 | 22.900 | 29.218 | -11.450 | 1.00 26.89 | B |
| ATOM | 1927 | O | LYS | B | 61 | 21.837 | 28.765 | -11.039 | 1.00 27.84 | B |
| ATOM | 1928 | N | LEU | B | 62 | 23.994 | 28.483 | -11.600 | 1.00 26.47 | B |
| ATOM | 1929 | CA | LEU | B | 62 | 24.004 | 27.067 | -11.281 | 1.00 26.75 | B |
| ATOM | 1930 | CB | LEU | B | 62 | 25.314 | 26.438 | -11.758 | 1.00 27.95 | B |
| ATOM | 1931 | CG | LEU | B | 62 | 25.528 | 26.418 | -13.275 | 1.00 30.35 | B |
| ATOM | 1932 | CD1 | LEU | B | 62 | 26.867 | 25.770 | -13.604 | 1.00 30.12 | B |
| ATOM | 1933 | CD2 | LEU | B | 62 | 24.391 | 25.654 | -13.937 | 1.00 29.94 | B |
| ATOM | 1934 | C | LEU | B | 62 | 23.825 | 26.825 | -9.790 | 1.00 26.81 | B |
| ATOM | 1935 | O | LEU | B | 62 | 23.096 | 25.924 | -9.383 | 1.00 26.05 | B |
| ATOM | 1936 | N | ALA | B | 63 | 24.479 | 27.647 | -8.976 | 1.00 25.90 | B |
| ATOM | 1937 | CA | ALA | B | 63 | 24.398 | 27.500 | -7.531 | 1.00 24.98 | B |
| ATOM | 1938 | CB | ALA | B | 63 | 25.390 | 28.442 | -6.861 | 1.00 25.27 | B |
| ATOM | 1939 | C | ALA | B | 63 | 23.002 | 27.746 | -6.975 | 1.00 25.85 | B |
| ATOM | 1940 | O | ALA | B | 63 | 22.564 | 27.050 | -6.054 | 1.00 24.07 | B |
| ATOM | 1941 | N | ILE | B | 64 | 22.295 | 28.721 | -7.534 | 1.00 25.98 | B |
| ATOM | 1942 | CA | ILE | B | 64 | 20.969 | 29.050 | -7.025 | 1.00 26.45 | B |
| ATOM | 1943 | CB | ILE | B | 64 | 20.732 | 30.568 | -7.014 | 1.00 26.25 | B |
| ATOM | 1944 | CG2 | ILE | B | 64 | 21.833 | 31.258 | -6.227 | 1.00 24.81 | B |
| ATOM | 1945 | CG1 | ILE | B | 64 | 20.665 | 31.095 | -8.445 | 1.00 25.09 | B |
| ATOM | 1946 | CD1 | ILE | B | 64 | 20.286 | 32.550 | -8.524 | 1.00 26.82 | B |
| ATOM | 1947 | C | ILE | B | 64 | 19.784 | 28.416 | -7.730 | 1.00 27.41 | B |
| ATOM | 1948 | O | ILE | B | 64 | 18.654 | 28.598 | -7.294 | 1.00 27.97 | B |

Figure 9 (31 of 92)

| | | | | | | | | | | |
|---|---|---|---|---|---|---|---|---|---|---|
| ATOM | 1949 | N | GLN | B | 65 | 20.033 | 27.676 | -8.807 | 1.00 29.80 | B |
| ATOM | 1950 | CA | GLN | B | 65 | 18.960 | 27.029 | -9.561 | 1.00 31.38 | B |
| ATOM | 1951 | CB | GLN | B | 65 | 19.538 | 25.987 | -10.526 | 1.00 33.75 | B |
| ATOM | 1952 | CG | GLN | B | 65 | 20.241 | 26.576 | -11.726 | 1.00 38.14 | B |
| ATOM | 1953 | CD | GLN | B | 65 | 20.577 | 25.544 | -12.791 | 1.00 40.21 | B |
| ATOM | 1954 | OE1 | GLN | B | 65 | 21.160 | 25.876 | -13.822 | 1.00 42.56 | B |
| ATOM | 1955 | NE2 | GLN | B | 65 | 20.206 | 24.290 | -12.549 | 1.00 40.12 | B |
| ATOM | 1956 | C | GLN | B | 65 | 17.878 | 26.351 | -8.722 | 1.00 32.05 | B |
| ATOM | 1957 | O | GLN | B | 65 | 16.685 | 26.633 | -8.877 | 1.00 33.96 | B |
| ATOM | 1958 | N | SER | B | 66 | 18.303 | 25.452 | -7.839 | 1.00 31.12 | B |
| ATOM | 1959 | CA | SER | B | 66 | 17.394 | 24.688 | -6.997 | 1.00 30.85 | B |
| ATOM | 1960 | CB | SER | B | 66 | 18.181 | 23.611 | -6.249 | 1.00 32.02 | B |
| ATOM | 1961 | OG | SER | B | 66 | 19.123 | 24.199 | -5.366 | 1.00 32.10 | B |
| ATOM | 1962 | C | SER | B | 66 | 16.559 | 25.469 | -5.989 | 1.00 30.24 | B |
| ATOM | 1963 | O | SER | B | 66 | 15.607 | 24.923 | -5.422 | 1.00 29.74 | B |
| ATOM | 1964 | N | ASN | B | 67 | 16.907 | 26.731 | -5.747 | 1.00 28.69 | B |
| ATOM | 1965 | CA | ASN | B | 67 | 16.156 | 27.534 | -4.784 | 1.00 26.29 | B |
| ATOM | 1966 | CB | ASN | B | 67 | 17.112 | 28.148 | -3.765 | 1.00 25.54 | B |
| ATOM | 1967 | CG | ASN | B | 67 | 16.392 | 28.730 | -2.559 | 1.00 25.10 | B |
| ATOM | 1968 | OD1 | ASN | B | 67 | 16.928 | 28.729 | -1.454 | 1.00 26.99 | B |
| ATOM | 1969 | ND2 | ASN | B | 67 | 15.184 | 29.235 | -2.766 | 1.00 24.56 | B |
| ATOM | 1970 | C | ASN | B | 67 | 15.342 | 28.626 | -5.481 | 1.00 25.97 | B |
| ATOM | 1971 | O | ASN | B | 67 | 15.890 | 29.586 | -6.014 | 1.00 24.66 | B |
| ATOM | 1972 | N | PRO | B | 68 | 14.012 | 28.487 | -5.472 | 1.00 26.35 | B |
| ATOM | 1973 | CD | PRO | B | 68 | 13.298 | 27.309 | -4.954 | 1.00 26.22 | B |
| ATOM | 1974 | CA | PRO | B | 68 | 13.074 | 29.428 | -6.092 | 1.00 26.36 | B |
| ATOM | 1975 | CB | PRO | B | 68 | 11.718 | 28.776 | -5.838 | 1.00 26.89 | B |
| ATOM | 1976 | CG | PRO | B | 68 | 12.060 | 27.313 | -5.797 | 1.00 27.93 | B |
| ATOM | 1977 | C | PRO | B | 68 | 13.121 | 30.861 | -5.563 | 1.00 26.09 | B |
| ATOM | 1978 | O | PRO | B | 68 | 12.821 | 31.805 | -6.297 | 1.00 26.45 | B |
| ATOM | 1979 | N | SER | B | 69 | 13.500 | 31.024 | -4.300 | 1.00 24.31 | B |
| ATOM | 1980 | CA | SER | B | 69 | 13.552 | 32.346 | -3.692 | 1.00 23.86 | B |
| ATOM | 1981 | CB | SER | B | 69 | 13.313 | 32.218 | -2.188 | 1.00 24.97 | B |
| ATOM | 1982 | OG | SER | B | 69 | 12.083 | 31.560 | -1.931 | 1.00 27.49 | B |
| ATOM | 1983 | C | SER | B | 69 | 14.872 | 33.089 | -3.955 | 1.00 23.91 | B |
| ATOM | 1984 | O | SER | B | 69 | 15.026 | 34.254 | -3.567 | 1.00 22.70 | B |
| ATOM | 1985 | N | PHE | B | 70 | 15.815 | 32.414 | -4.610 | 1.00 19.68 | B |
| ATOM | 1986 | CA | PHE | B | 70 | 17.112 | 33.012 | -4.925 | 1.00 20.59 | B |
| ATOM | 1987 | CB | PHE | B | 70 | 18.243 | 31.982 | -4.766 | 1.00 18.97 | B |
| ATOM | 1988 | CG | PHE | B | 70 | 18.498 | 31.552 | -3.338 | 1.00 17.87 | B |
| ATOM | 1989 | CD1 | PHE | B | 70 | 19.403 | 30.525 | -3.065 | 1.00 17.51 | B |
| ATOM | 1990 | CD2 | PHE | B | 70 | 17.855 | 32.178 | -2.268 | 1.00 15.59 | B |
| ATOM | 1991 | CE1 | PHE | B | 70 | 19.669 | 30.124 | -1.744 | 1.00 17.06 | B |
| ATOM | 1992 | CE2 | PHE | B | 70 | 18.114 | 31.786 | -0.938 | 1.00 18.48 | B |
| ATOM | 1993 | CZ | PHE | B | 70 | 19.022 | 30.758 | -0.678 | 1.00 15.23 | B |
| ATOM | 1994 | C | PHE | B | 70 | 17.118 | 33.535 | -6.356 | 1.00 21.30 | B |
| ATOM | 1995 | O | PHE | B | 70 | 16.647 | 32.860 | -7.273 | 1.00 20.85 | B |
| ATOM | 1996 | N | LYS | B | 71 | 17.647 | 34.739 | -6.546 | 1.00 21.33 | B |
| ATOM | 1997 | CA | LYS | B | 71 | 17.711 | 35.331 | -7.873 | 1.00 23.21 | B |
| ATOM | 1998 | CB | LYS | B | 71 | 16.569 | 36.334 | -8.083 | 1.00 24.39 | B |
| ATOM | 1999 | CG | LYS | B | 71 | 15.286 | 35.737 | -8.684 | 1.00 30.37 | B |
| ATOM | 2000 | CD | LYS | B | 71 | 14.370 | 35.126 | -7.632 | 1.00 34.47 | B |
| ATOM | 2001 | CE | LYS | B | 71 | 13.184 | 34.400 | -8.272 | 1.00 36.17 | B |
| ATOM | 2002 | NZ | LYS | B | 71 | 13.603 | 33.129 | -8.955 | 1.00 38.15 | B |
| ATOM | 2003 | C | LYS | B | 71 | 19.037 | 36.025 | -8.135 | 1.00 23.26 | B |
| ATOM | 2004 | O | LYS | B | 71 | 19.712 | 36.488 | -7.212 | 1.00 24.18 | B |
| ATOM | 2005 | N | LEU | B | 72 | 19.406 | 36.078 | -9.408 | 1.00 22.38 | B |
| ATOM | 2006 | CA | LEU | B | 72 | 20.627 | 36.730 | -9.842 | 1.00 23.79 | B |
| ATOM | 2007 | CB | LEU | B | 72 | 21.257 | 35.967 | -11.008 | 1.00 25.20 | B |
| ATOM | 2008 | CG | LEU | B | 72 | 22.418 | 36.670 | -11.729 | 1.00 27.23 | B |
| ATOM | 2009 | CD1 | LEU | B | 72 | 23.615 | 36.807 | -10.797 | 1.00 26.16 | B |
| ATOM | 2010 | CD2 | LEU | B | 72 | 22.802 | 35.861 | -12.970 | 1.00 29.79 | B |
| ATOM | 2011 | C | LEU | B | 72 | 20.255 | 38.130 | -10.312 | 1.00 24.41 | B |
| ATOM | 2012 | O | LEU | B | 72 | 19.338 | 38.289 | -11.113 | 1.00 24.17 | B |
| ATOM | 2013 | N | GLU | B | 73 | 20.952 | 39.141 | -9.806 | 1.00 23.62 | B |
| ATOM | 2014 | CA | GLU | B | 73 | 20.689 | 40.513 | -10.219 | 1.00 25.90 | B |

Figure 9 (32 of 92)

| ATOM | 2015 | CB | GLU | B | 73 | 20.076 | 41.311 | -9.064 | 1.00 | 25.22 | B |
|---|---|---|---|---|---|---|---|---|---|---|---|
| ATOM | 2016 | CG | GLU | B | 73 | 19.597 | 42.707 | -9.427 | 1.00 | 29.32 | B |
| ATOM | 2017 | CD | GLU | B | 73 | 18.481 | 42.716 | -10.472 | 1.00 | 30.44 | B |
| ATOM | 2018 | OE1 | GLU | B | 73 | 17.622 | 41.811 | -10.458 | 1.00 | 29.79 | B |
| ATOM | 2019 | OE2 | GLU | B | 73 | 18.453 | 43.654 | -11.294 | 1.00 | 34.94 | B |
| ATOM | 2020 | C | GLU | B | 73 | 22.023 | 41.111 | -10.659 | 1.00 | 27.47 | B |
| ATOM | 2021 | O | GLU | B | 73 | 23.033 | 40.984 | -9.959 | 1.00 | 26.02 | B |
| ATOM | 2022 | N | LEU | B | 74 | 22.020 | 41.748 | -11.827 | 1.00 | 28.15 | B |
| ATOM | 2023 | CA | LEU | B | 74 | 23.228 | 42.332 | -12.394 | 1.00 | 31.23 | B |
| ATOM | 2024 | CB | LEU | B | 74 | 23.402 | 41.837 | -13.830 | 1.00 | 32.61 | B |
| ATOM | 2025 | CG | LEU | B | 74 | 23.438 | 40.327 | -14.083 | 1.00 | 34.10 | B |
| ATOM | 2026 | CD1 | LEU | B | 74 | 23.449 | 40.079 | -15.582 | 1.00 | 34.74 | B |
| ATOM | 2027 | CD2 | LEU | B | 74 | 24.662 | 39.712 | -13.422 | 1.00 | 34.27 | B |
| ATOM | 2028 | C | LEU | B | 74 | 23.276 | 43.859 | -12.404 | 1.00 | 31.95 | B |
| ATOM | 2029 | O | LEU | B | 74 | 23.978 | 44.440 | -13.226 | 1.00 | 34.07 | B |
| ATOM | 2030 | N | VAL | B | 75 | 22.557 | 44.515 | -11.501 | 1.00 | 34.04 | B |
| ATOM | 2031 | CA | VAL | B | 75 | 22.553 | 45.978 | -11.495 | 1.00 | 36.34 | B |
| ATOM | 2032 | CB | VAL | B | 75 | 21.583 | 46.551 | -10.435 | 1.00 | 36.73 | B |
| ATOM | 2033 | CG1 | VAL | B | 75 | 20.217 | 45.893 | -10.566 | 1.00 | 38.69 | B |
| ATOM | 2034 | CG2 | VAL | B | 75 | 22.148 | 46.363 | -9.051 | 1.00 | 39.11 | B |
| ATOM | 2035 | C | VAL | B | 75 | 23.929 | 46.611 | -11.279 | 1.00 | 37.04 | B |
| ATOM | 2036 | O | VAL | B | 75 | 24.161 | 47.745 | -11.697 | 1.00 | 37.97 | B |
| ATOM | 2037 | N | GLU | B | 76 | 24.842 | 45.891 | -10.634 | 1.00 | 37.61 | B |
| ATOM | 2038 | CA | GLU | B | 76 | 26.176 | 46.438 | -10.399 | 1.00 | 37.62 | B |
| ATOM | 2039 | CB | GLU | B | 76 | 26.890 | 45.665 | -9.284 | 1.00 | 35.75 | B |
| ATOM | 2040 | CG | GLU | B | 76 | 28.305 | 46.163 | -8.997 | 1.00 | 32.78 | B |
| ATOM | 2041 | CD | GLU | B | 76 | 28.741 | 45.963 | -7.542 | 1.00 | 32.94 | B |
| ATOM | 2042 | OE1 | GLU | B | 76 | 29.964 | 45.830 | -7.313 | 1.00 | 30.31 | B |
| ATOM | 2043 | OE2 | GLU | B | 76 | 27.874 | 45.959 | -6.634 | 1.00 | 28.53 | B |
| ATOM | 2044 | C | GLU | B | 76 | 26.983 | 46.384 | -11.692 | 1.00 | 38.54 | B |
| ATOM | 2045 | O | GLU | B | 76 | 28.053 | 46.988 | -11.805 | 1.00 | 37.69 | B |
| ATOM | 2046 | N | MET | B | 77 | 26.439 | 45.675 | -12.675 | 1.00 | 39.07 | B |
| ATOM | 2047 | CA | MET | B | 77 | 27.087 | 45.529 | -13.968 | 1.00 | 41.59 | B |
| ATOM | 2048 | CB | MET | B | 77 | 26.851 | 44.117 | -14.508 | 1.00 | 43.59 | B |
| ATOM | 2049 | CG | MET | B | 77 | 26.926 | 43.014 | -13.456 | 1.00 | 46.94 | B |
| ATOM | 2050 | SD | MET | B | 77 | 28.555 | 42.831 | -12.756 | 1.00 | 50.84 | B |
| ATOM | 2051 | CE | MET | B | 77 | 29.327 | 41.902 | -14.081 | 1.00 | 49.69 | B |
| ATOM | 2052 | C | MET | B | 77 | 26.511 | 46.543 | -14.956 | 1.00 | 42.20 | B |
| ATOM | 2053 | O | MET | B | 77 | 26.921 | 46.590 | -16.115 | 1.00 | 41.34 | B |
| ATOM | 2054 | N | GLU | B | 78 | 25.558 | 47.352 | -14.498 | 1.00 | 42.79 | B |
| ATOM | 2055 | CA | GLU | B | 78 | 24.919 | 48.334 | -15.374 | 1.00 | 43.27 | B |
| ATOM | 2056 | CB | GLU | B | 78 | 23.535 | 47.820 | -15.785 | 1.00 | 44.55 | B |
| ATOM | 2057 | CG | GLU | B | 78 | 23.505 | 46.321 | -16.067 | 1.00 | 46.37 | B |
| ATOM | 2058 | CD | GLU | B | 78 | 22.101 | 45.776 | -16.229 | 1.00 | 47.70 | B |
| ATOM | 2059 | OE1 | GLU | B | 78 | 21.206 | 46.190 | -15.460 | 1.00 | 48.05 | B |
| ATOM | 2060 | OE2 | GLU | B | 78 | 21.896 | 44.921 | -17.114 | 1.00 | 48.77 | B |
| ATOM | 2061 | C | GLU | B | 78 | 24.788 | 49.712 | -14.722 | 1.00 | 43.02 | B |
| ATOM | 2062 | O | GLU | B | 78 | 23.851 | 50.458 | -15.006 | 1.00 | 42.65 | B |
| ATOM | 2063 | N | ARG | B | 79 | 25.735 | 50.051 | -13.856 | 1.00 | 44.20 | B |
| ATOM | 2064 | CA | ARG | B | 79 | 25.710 | 51.337 | -13.169 | 1.00 | 44.94 | B |
| ATOM | 2065 | CB | ARG | B | 79 | 26.595 | 51.280 | -11.917 | 1.00 | 44.66 | B |
| ATOM | 2066 | CG | ARG | B | 79 | 26.123 | 50.279 | -10.869 | 1.00 | 45.07 | B |
| ATOM | 2067 | CD | ARG | B | 79 | 27.066 | 50.221 | -9.673 | 1.00 | 45.85 | B |
| ATOM | 2068 | NE | ARG | B | 79 | 28.443 | 49.955 | -10.079 | 1.00 | 46.58 | B |
| ATOM | 2069 | CZ | ARG | B | 79 | 29.439 | 50.830 | -9.974 | 1.00 | 47.21 | B |
| ATOM | 2070 | NH1 | ARG | B | 79 | 29.220 | 52.037 | -9.470 | 1.00 | 47.75 | B |
| ATOM | 2071 | NH2 | ARG | B | 79 | 30.656 | 50.501 | -10.376 | 1.00 | 47.92 | B |
| ATOM | 2072 | C | ARG | B | 79 | 26.160 | 52.487 | -14.069 | 1.00 | 45.53 | B |
| ATOM | 2073 | O | ARG | B | 79 | 25.794 | 53.643 | -13.842 | 1.00 | 43.94 | B |
| ATOM | 2074 | N | GLU | B | 80 | 26.940 | 52.164 | -15.098 | 1.00 | 47.20 | B |
| ATOM | 2075 | CA | GLU | B | 80 | 27.451 | 53.177 | -16.018 | 1.00 | 49.35 | B |
| ATOM | 2076 | CB | GLU | B | 80 | 28.644 | 52.638 | -16.810 | 1.00 | 51.05 | B |
| ATOM | 2077 | CG | GLU | B | 80 | 29.916 | 52.487 | -15.998 | 1.00 | 53.90 | B |
| ATOM | 2078 | CD | GLU | B | 80 | 31.146 | 52.347 | -16.873 | 1.00 | 54.98 | B |
| ATOM | 2079 | OE1 | GLU | B | 80 | 31.404 | 53.270 | -17.679 | 1.00 | 55.70 | B |
| ATOM | 2080 | OE2 | GLU | B | 80 | 31.854 | 51.321 | -16.755 | 1.00 | 55.51 | B |

Figure 9 (33 of 92)

| ATOM | 2081 | C   | GLU | B | 80 | 26.441 | 53.751 | -17.001 | 1.00 | 49.19 | B |
|------|------|-----|-----|---|----|--------|--------|---------|------|-------|---|
| ATOM | 2082 | O   | GLU | B | 80 | 25.843 | 53.031 | -17.801 | 1.00 | 49.87 | B |
| ATOM | 2083 | N   | GLY | B | 81 | 26.264 | 55.065 | -16.925 | 1.00 | 48.51 | B |
| ATOM | 2084 | CA  | GLY | B | 81 | 25.367 | 55.758 | -17.825 | 1.00 | 47.83 | B |
| ATOM | 2085 | C   | GLY | B | 81 | 26.253 | 56.606 | -18.719 | 1.00 | 46.95 | B |
| ATOM | 2086 | O   | GLY | B | 81 | 27.442 | 56.755 | -18.428 | 1.00 | 46.76 | B |
| ATOM | 2087 | N   | PRO | B | 82 | 25.721 | 57.176 | -19.811 | 1.00 | 45.47 | B |
| ATOM | 2088 | CD  | PRO | B | 82 | 24.351 | 57.017 | -20.330 | 1.00 | 45.12 | B |
| ATOM | 2089 | CA  | PRO | B | 82 | 26.531 | 58.006 | -20.712 | 1.00 | 43.58 | B |
| ATOM | 2090 | CB  | PRO | B | 82 | 25.503 | 58.526 | -21.718 | 1.00 | 44.05 | B |
| ATOM | 2091 | CG  | PRO | B | 82 | 24.517 | 57.393 | -21.791 | 1.00 | 44.92 | B |
| ATOM | 2092 | C   | PRO | B | 82 | 27.294 | 59.140 | -20.021 | 1.00 | 41.24 | B |
| ATOM | 2093 | O   | PRO | B | 82 | 28.368 | 59.536 | -20.477 | 1.00 | 42.20 | B |
| ATOM | 2094 | N   | SER | B | 83 | 26.758 | 59.652 | -18.917 | 1.00 | 38.09 | B |
| ATOM | 2095 | CA  | SER | B | 83 | 27.415 | 60.750 | -18.219 | 1.00 | 35.80 | B |
| ATOM | 2096 | CB  | SER | B | 83 | 26.740 | 62.074 | -18.593 | 1.00 | 36.60 | B |
| ATOM | 2097 | OG  | SER | B | 83 | 25.407 | 62.126 | -18.102 | 1.00 | 37.41 | B |
| ATOM | 2098 | C   | SER | B | 83 | 27.447 | 60.634 | -16.698 | 1.00 | 33.78 | B |
| ATOM | 2099 | O   | SER | B | 83 | 28.075 | 61.455 | -16.028 | 1.00 | 35.74 | B |
| ATOM | 2100 | N   | TYR | B | 84 | 26.778 | 59.628 | -16.149 | 1.00 | 30.23 | B |
| ATOM | 2101 | CA  | TYR | B | 84 | 26.730 | 59.457 | -14.702 | 1.00 | 26.96 | B |
| ATOM | 2102 | CB  | TYR | B | 84 | 25.446 | 60.082 | -14.148 | 1.00 | 25.79 | B |
| ATOM | 2103 | CG  | TYR | B | 84 | 25.292 | 59.949 | -12.649 | 1.00 | 24.25 | B |
| ATOM | 2104 | CD1 | TYR | B | 84 | 26.004 | 60.770 | -11.777 | 1.00 | 25.20 | B |
| ATOM | 2105 | CE1 | TYR | B | 84 | 25.847 | 60.660 | -10.386 | 1.00 | 25.25 | B |
| ATOM | 2106 | CD2 | TYR | B | 84 | 24.420 | 59.005 | -12.100 | 1.00 | 25.32 | B |
| ATOM | 2107 | CE2 | TYR | B | 84 | 24.259 | 58.884 | -10.717 | 1.00 | 24.78 | B |
| ATOM | 2108 | CZ  | TYR | B | 84 | 24.973 | 59.717 | -9.869  | 1.00 | 25.82 | B |
| ATOM | 2109 | OH  | TYR | B | 84 | 24.803 | 59.610 | -8.508  | 1.00 | 28.73 | B |
| ATOM | 2110 | C   | TYR | B | 84 | 26.790 | 57.991 | -14.296 | 1.00 | 25.70 | B |
| ATOM | 2111 | O   | TYR | B | 84 | 26.258 | 57.126 | -14.987 | 1.00 | 24.78 | B |
| ATOM | 2112 | N   | THR | B | 85 | 27.430 | 57.720 | -13.163 | 1.00 | 23.86 | B |
| ATOM | 2113 | CA  | THR | B | 85 | 27.555 | 56.354 | -12.667 | 1.00 | 23.42 | B |
| ATOM | 2114 | CB  | THR | B | 85 | 29.034 | 55.923 | -12.584 | 1.00 | 24.28 | B |
| ATOM | 2115 | OG1 | THR | B | 85 | 29.633 | 56.018 | -13.883 | 1.00 | 23.23 | B |
| ATOM | 2116 | CG2 | THR | B | 85 | 29.143 | 54.481 | -12.071 | 1.00 | 23.51 | B |
| ATOM | 2117 | C   | THR | B | 85 | 26.936 | 56.185 | -11.286 | 1.00 | 21.70 | B |
| ATOM | 2118 | O   | THR | B | 85 | 27.375 | 56.801 | -10.315 | 1.00 | 20.49 | B |
| ATOM | 2119 | N   | PHE | B | 86 | 25.909 | 55.347 | -11.214 | 1.00 | 21.08 | B |
| ATOM | 2120 | CA  | PHE | B | 86 | 25.218 | 55.059 | -9.961  | 1.00 | 20.91 | B |
| ATOM | 2121 | CB  | PHE | B | 86 | 23.846 | 54.434 | -10.234 | 1.00 | 20.52 | B |
| ATOM | 2122 | CG  | PHE | B | 86 | 22.801 | 55.398 | -10.717 | 1.00 | 19.48 | B |
| ATOM | 2123 | CD1 | PHE | B | 86 | 21.945 | 56.022 | -9.811  | 1.00 | 20.82 | B |
| ATOM | 2124 | CD2 | PHE | B | 86 | 22.620 | 55.624 | -12.079 | 1.00 | 19.89 | B |
| ATOM | 2125 | CE1 | PHE | B | 86 | 20.911 | 56.854 | -10.255 | 1.00 | 21.51 | B |
| ATOM | 2126 | CE2 | PHE | B | 86 | 21.592 | 56.453 | -12.533 | 1.00 | 20.21 | B |
| ATOM | 2127 | CZ  | PHE | B | 86 | 20.735 | 57.068 | -11.621 | 1.00 | 19.88 | B |
| ATOM | 2128 | C   | PHE | B | 86 | 26.018 | 54.018 | -9.194  | 1.00 | 21.00 | B |
| ATOM | 2129 | O   | PHE | B | 86 | 26.819 | 53.287 | -9.785  | 1.00 | 20.14 | B |
| ATOM | 2130 | N   | ASP | B | 87 | 25.825 | 53.961 | -7.880  | 1.00 | 19.67 | B |
| ATOM | 2131 | CA  | ASP | B | 87 | 26.465 | 52.907 | -7.116  | 1.00 | 19.61 | B |
| ATOM | 2132 | CB  | ASP | B | 87 | 26.862 | 53.362 | -5.698  | 1.00 | 20.91 | B |
| ATOM | 2133 | CG  | ASP | B | 87 | 25.703 | 53.911 | -4.890  | 1.00 | 22.11 | B |
| ATOM | 2134 | OD1 | ASP | B | 87 | 25.954 | 54.390 | -3.757  | 1.00 | 23.78 | B |
| ATOM | 2135 | OD2 | ASP | B | 87 | 24.557 | 53.866 | -5.368  | 1.00 | 23.17 | B |
| ATOM | 2136 | C   | ASP | B | 87 | 25.346 | 51.865 | -7.115  | 1.00 | 19.42 | B |
| ATOM | 2137 | O   | ASP | B | 87 | 24.229 | 52.167 | -7.539  | 1.00 | 17.78 | B |
| ATOM | 2138 | N   | THR | B | 88 | 25.619 | 50.646 | -6.674  | 1.00 | 20.09 | B |
| ATOM | 2139 | CA  | THR | B | 88 | 24.584 | 49.622 | -6.704  | 1.00 | 20.35 | B |
| ATOM | 2140 | CB  | THR | B | 88 | 25.166 | 48.258 | -6.302  | 1.00 | 19.66 | B |
| ATOM | 2141 | OG1 | THR | B | 88 | 26.214 | 47.922 | -7.214  | 1.00 | 18.70 | B |
| ATOM | 2142 | CG2 | THR | B | 88 | 24.100 | 47.168 | -6.367  | 1.00 | 18.24 | B |
| ATOM | 2143 | C   | THR | B | 88 | 23.351 | 49.923 | -5.859  | 1.00 | 20.21 | B |
| ATOM | 2144 | O   | THR | B | 88 | 22.233 | 49.680 | -6.289  | 1.00 | 21.40 | B |
| ATOM | 2145 | N   | VAL | B | 89 | 23.558 | 50.464 | -4.666  | 1.00 | 20.86 | B |
| ATOM | 2146 | CA  | VAL | B | 89 | 22.471 | 50.783 | -3.757  | 1.00 | 20.11 | B |

Figure 9 (34 of 92)

| | | | | | | | | | | |
|---|---|---|---|---|---|---|---|---|---|---|
| ATOM | 2147 | CB | VAL | B | 89 | 23.031 | 51.331 | -2.422 | 1.00 20.34 | B |
| ATOM | 2148 | CG1 | VAL | B | 89 | 21.907 | 51.863 | -1.552 | 1.00 20.63 | B |
| ATOM | 2149 | CG2 | VAL | B | 89 | 23.782 | 50.221 | -1.687 | 1.00 19.25 | B |
| ATOM | 2150 | C | VAL | B | 89 | 21.474 | 51.785 | -4.336 | 1.00 21.95 | B |
| ATOM | 2151 | O | VAL | B | 89 | 20.261 | 51.584 | -4.251 | 1.00 22.06 | B |
| ATOM | 2152 | N | SER | B | 90 | 21.987 | 52.865 | -4.915 | 1.00 20.58 | B |
| ATOM | 2153 | CA | SER | B | 90 | 21.132 | 53.893 | -5.496 | 1.00 21.50 | B |
| ATOM | 2154 | CB | SER | B | 90 | 21.966 | 55.127 | -5.841 | 1.00 22.65 | B |
| ATOM | 2155 | OG | SER | B | 90 | 22.457 | 55.752 | -4.666 | 1.00 24.51 | B |
| ATOM | 2156 | C | SER | B | 90 | 20.377 | 53.420 | -6.742 | 1.00 20.38 | B |
| ATOM | 2157 | O | SER | B | 90 | 19.222 | 53.787 | -6.947 | 1.00 19.93 | B |
| ATOM | 2158 | N | LEU | B | 91 | 21.025 | 52.614 | -7.574 | 1.00 19.20 | B |
| ATOM | 2159 | CA | LEU | B | 91 | 20.375 | 52.125 | -8.784 | 1.00 20.68 | B |
| ATOM | 2160 | CB | LEU | B | 91 | 21.389 | 51.433 | -9.690 | 1.00 19.11 | B |
| ATOM | 2161 | CG | LEU | B | 91 | 20.831 | 50.950 | -11.025 | 1.00 20.18 | B |
| ATOM | 2162 | CD1 | LEU | B | 91 | 20.147 | 52.110 | -11.753 | 1.00 22.03 | B |
| ATOM | 2163 | CD2 | LEU | B | 91 | 21.960 | 50.374 | -11.862 | 1.00 21.54 | B |
| ATOM | 2164 | C | LEU | B | 91 | 19.241 | 51.164 | -8.446 | 1.00 21.78 | B |
| ATOM | 2165 | O | LEU | B | 91 | 18.216 | 51.125 | -9.139 | 1.00 22.32 | B |
| ATOM | 2166 | N | LEU | B | 92 | 19.430 | 50.383 | -7.383 | 1.00 21.64 | B |
| ATOM | 2167 | CA | LEU | B | 92 | 18.408 | 49.441 | -6.943 | 1.00 20.93 | B |
| ATOM | 2168 | CB | LEU | B | 92 | 18.941 | 48.555 | -5.809 | 1.00 19.58 | B |
| ATOM | 2169 | CG | LEU | B | 92 | 19.859 | 47.380 | -6.178 | 1.00 18.90 | B |
| ATOM | 2170 | CD1 | LEU | B | 92 | 20.659 | 46.939 | -4.959 | 1.00 16.45 | B |
| ATOM | 2171 | CD2 | LEU | B | 92 | 19.028 | 46.224 | -6.719 | 1.00 17.76 | B |
| ATOM | 2172 | C | LEU | B | 92 | 17.180 | 50.218 | -6.468 | 1.00 21.61 | B |
| ATOM | 2173 | O | LEU | B | 92 | 16.046 | 49.865 | -6.800 | 1.00 21.09 | B |
| ATOM | 2174 | N | LYS | B | 93 | 17.404 | 51.276 | -5.693 | 1.00 21.47 | B |
| ATOM | 2175 | CA | LYS | B | 93 | 16.294 | 52.085 | -5.194 | 1.00 25.24 | B |
| ATOM | 2176 | CB | LYS | B | 93 | 16.787 | 53.142 | -4.199 | 1.00 26.32 | B |
| ATOM | 2177 | CG | LYS | B | 93 | 17.050 | 52.601 | -2.803 | 1.00 29.66 | B |
| ATOM | 2178 | CD | LYS | B | 93 | 16.499 | 53.549 | -1.734 | 1.00 35.51 | B |
| ATOM | 2179 | CE | LYS | B | 93 | 17.216 | 54.899 | -1.755 | 1.00 37.34 | B |
| ATOM | 2180 | NZ | LYS | B | 93 | 16.690 | 55.816 | -0.706 | 1.00 40.18 | B |
| ATOM | 2181 | C | LYS | B | 93 | 15.588 | 52.771 | -6.353 | 1.00 25.41 | B |
| ATOM | 2182 | O | LYS | B | 93 | 14.386 | 53.041 | -6.307 | 1.00 26.23 | B |
| ATOM | 2183 | N | GLN | B | 94 | 16.359 | 53.047 | -7.392 | 1.00 24.73 | B |
| ATOM | 2184 | CA | GLN | B | 94 | 15.856 | 53.698 | -8.581 | 1.00 26.14 | B |
| ATOM | 2185 | CB | GLN | B | 94 | 17.049 | 54.066 | -9.460 | 1.00 27.47 | B |
| ATOM | 2186 | CG | GLN | B | 94 | 16.806 | 55.139 | -10.464 | 1.00 31.47 | B |
| ATOM | 2187 | CD | GLN | B | 94 | 16.619 | 56.514 | -9.850 | 1.00 32.88 | B |
| ATOM | 2188 | OE1 | GLN | B | 94 | 16.811 | 56.711 | -8.650 | 1.00 33.56 | B |
| ATOM | 2189 | NE2 | GLN | B | 94 | 16.248 | 57.477 | -10.683 | 1.00 32.56 | B |
| ATOM | 2190 | C | GLN | B | 94 | 14.911 | 52.746 | -9.319 | 1.00 25.98 | B |
| ATOM | 2191 | O | GLN | B | 94 | 13.801 | 53.121 | -9.696 | 1.00 27.70 | B |
| ATOM | 2192 | N | ARG | B | 95 | 15.352 | 51.505 | -9.503 | 1.00 24.77 | B |
| ATOM | 2193 | CA | ARG | B | 95 | 14.562 | 50.512 | -10.210 | 1.00 23.08 | B |
| ATOM | 2194 | CB | ARG | B | 95 | 15.465 | 49.387 | -10.710 | 1.00 23.29 | B |
| ATOM | 2195 | CG | ARG | B | 95 | 16.486 | 49.846 | -11.741 | 1.00 24.00 | B |
| ATOM | 2196 | CD | ARG | B | 95 | 17.385 | 48.705 | -12.184 | 1.00 23.68 | B |
| ATOM | 2197 | NE | ARG | B | 95 | 18.299 | 49.125 | -13.246 | 1.00 25.26 | B |
| ATOM | 2198 | CZ | ARG | B | 95 | 19.171 | 48.318 | -13.841 | 1.00 26.50 | B |
| ATOM | 2199 | NH1 | ARG | B | 95 | 19.961 | 48.780 | -14.800 | 1.00 23.64 | B |
| ATOM | 2200 | NH2 | ARG | B | 95 | 19.255 | 47.047 | -13.473 | 1.00 24.45 | B |
| ATOM | 2201 | C | ARG | B | 95 | 13.409 | 49.909 | -9.419 | 1.00 23.04 | B |
| ATOM | 2202 | O | ARG | B | 95 | 12.392 | 49.534 | -10.003 | 1.00 21.58 | B |
| ATOM | 2203 | N | TYR | B | 96 | 13.549 | 49.815 | -8.100 | 1.00 20.94 | B |
| ATOM | 2204 | CA | TYR | B | 96 | 12.491 | 49.217 | -7.286 | 1.00 21.29 | B |
| ATOM | 2205 | CB | TYR | B | 96 | 12.924 | 47.816 | -6.824 | 1.00 20.63 | B |
| ATOM | 2206 | CG | TYR | B | 96 | 13.505 | 46.955 | -7.931 | 1.00 20.82 | B |
| ATOM | 2207 | CD1 | TYR | B | 96 | 14.880 | 46.889 | -8.139 | 1.00 22.04 | B |
| ATOM | 2208 | CE1 | TYR | B | 96 | 15.420 | 46.130 | -9.177 | 1.00 22.11 | B |
| ATOM | 2209 | CD2 | TYR | B | 96 | 12.676 | 46.237 | -8.791 | 1.00 20.56 | B |
| ATOM | 2210 | CE2 | TYR | B | 96 | 13.199 | 45.479 | -9.830 | 1.00 23.06 | B |
| ATOM | 2211 | CZ | TYR | B | 96 | 14.574 | 45.431 | -10.019 | 1.00 23.58 | B |
| ATOM | 2212 | OH | TYR | B | 96 | 15.107 | 44.706 | -11.061 | 1.00 23.85 | B |

Figure 9 (35 of 92)

```
ATOM   2213  C   TYR B  96     12.169  50.078  -6.074  1.00 21.53      B
ATOM   2214  O   TYR B  96     12.299  49.628  -4.935  1.00 21.80      B
ATOM   2215  N   PRO B  97     11.707  51.317  -6.304  1.00 23.48      B
ATOM   2216  CD  PRO B  97     11.287  51.834  -7.621  1.00 22.68      B
ATOM   2217  CA  PRO B  97     11.362  52.276  -5.244  1.00 25.08      B
ATOM   2218  CB  PRO B. 97     10.985  53.531  -6.032  1.00 22.36      B
ATOM   2219  CG  PRO B  97     10.333  52.954  -7.241  1.00 21.03      B
ATOM   2220  C   PRO B  97     10.267  51.868  -4.263  1.00 26.86      B
ATOM   2221  O   PRO B  97     10.169  52.434  -3.177  1.00 28.23      B
ATOM   2222  N   ASN B  98      9.451  50.893  -4.641  1.00 29.97      B
ATOM   2223  CA  ASN B  98      8.360  50.444  -3.781  1.00 32.98      B
ATOM   2224  CB  ASN B  98      7.141  50.104  -4.640  1.00 38.00      B
ATOM   2225  CG  ASN B  98      5.893  49.855  -3.813  1.00 42.83      B
ATOM   2226  OD1 ASN B  98      5.878  50.085  -2.602  1.00 45.76      B
ATOM   2227  ND2 ASN B  98      4.832  49.393  -4.470  1.00 45.42      B
ATOM   2228  C   ASN B  98      8.701  49.245  -2.893  1.00 32.91      B
ATOM   2229  O   ASN B  98      8.003  48.982  -1.914  1.00 33.37      B
ATOM   2230  N   ASP B  99      9.766  48.520  -3.226  1.00 30.88      B
ATOM   2231  CA  ASP B  99     10.151  47.353  -2.441  1.00 29.35      B
ATOM   2232  CB  ASP B  99     10.947  46.363  -3.292  1.00 30.06      B
ATOM   2233  CG  ASP B  99     10.121  45.754  -4.400  1.00 31.03      B
ATOM   2234  OD1 ASP B  99      8.970  45.365  -4.129  1.00 32.21      B
ATOM   2235  OD2 ASP B  99     10.624  45.653  -5.538  1.00 29.91      B
ATOM   2236  C   ASP B  99     10.968  47.689  -1.209  1.00 29.21      B
ATOM   2237  O   ASP B  99     11.560  48.764  -1.111  1.00 30.06      B
ATOM   2238  N   GLN B 100     10.986  46.755  -0.265  1.00 28.69      B
ATOM   2239  CA  GLN B 100     11.748  46.903   0.967  1.00 28.18      B
ATOM   2240  CB  GLN B 100     11.000  46.262   2.136  1.00 29.92      B
ATOM   2241  CG  GLN B 100      9.867  47.098   2.710  1.00 33.00      B
ATOM   2242  CD  GLN B 100      9.019  46.314   3.702  1.00 35.42      B
ATOM   2243  OE1 GLN B 100      8.260  45.419   3.322  1.00 37.42      B
ATOM   2244  NE2 GLN B 100      9.156  46.639   4.980  1.00 38.22      B
ATOM   2245  C   GLN B 100     13.069  46.178   0.741  1.00 26.77      B
ATOM   2246  O   GLN B 100     13.103  44.950   0.647  1.00 25.10      B
ATOM   2247  N   LEU B 101     14.150  46.941   0.644  1.00 25.02      B
ATOM   2248  CA  LEU B 101     15.464  46.364   0.410  1.00 25.39      B
ATOM   2249  CB  LEU B 101     16.278  47.246  -0.546  1.00 26.33      B
ATOM   2250  CG  LEU B 101     15.629  47.705  -1.863  1.00 27.00      B
ATOM   2251  CD1 LEU B 101     16.604  48.621  -2.604  1.00 27.00      B
ATOM   2252  CD2 LEU B 101     15.252  46.512  -2.731  1.00 26.40      B
ATOM   2253  C   LEU B 101     16.217  46.210   1.720  1.00 24.17      B
ATOM   2254  O   LEU B 101     16.360  47.163   2.482  1.00 25.05      B
ATOM   2255  N   PHE B 102     16.696  45.001   1.974  1.00 21.81      B
ATOM   2256  CA  PHE B 102     17.440  44.723   3.185  1.00 20.96      B
ATOM   2257  CB  PHE B 102     16.827  43.539   3.943  1.00 19.79      B
ATOM   2258  CG  PHE B 102     15.406  43.759   4.383  1.00 22.15      B
ATOM   2259  CD1 PHE B 102     14.364  43.765   3.460  1.00 21.59      B
ATOM   2260  CD2 PHE B 102     15.107  43.955   5.727  1.00 22.86      B
ATOM   2261  CE1 PHE B 102     13.042  43.961   3.871  1.00 21.75      B
ATOM   2262  CE2 PHE B 102     13.792  44.151   6.143  1.00 23.02      B
ATOM   2263  CZ  PHE B 102     12.760  44.154   5.213  1.00 22.05      B
ATOM   2264  C   PHE B 102     18.859  44.373   2.792  1.00 19.83      B
ATOM   2265  O   PHE B 102     19.078  43.445   2.025  1.00 21.42      B
ATOM   2266  N   PHE B 103     19.821  45.128   3.301  1.00 19.67      B
ATOM   2267  CA  PHE B 103     21.212  44.850   3.016  1.00 19.48      B
ATOM   2268  CB  PHE B 103     21.974  46.157   2.800  1.00 18.88      B
ATOM   2269  CG  PHE B 103     21.520  46.911   1.578  1.00 20.25      B
ATOM   2270  CD1 PHE B 103     20.455  47.810   1.647  1.00 21.10      B
ATOM   2271  CD2 PHE B 103     22.120  46.676   0.343  1.00 19.64      B
ATOM   2272  CE1 PHE B 103     19.991  48.462   0.503  1.00 20.44      B
ATOM   2273  CE2 PHE B 103     21.665  47.322  -0.810  1.00 21.38      B
ATOM   2274  CZ  PHE B 103     20.599  48.214  -0.732  1.00 20.06      B
ATOM   2275  C   PHE B 103     21.768  44.042   4.191  1.00 19.79      B
ATOM   2276  O   PHE B 103     21.355  44.233   5.337  1.00 18.19      B
ATOM   2277  N   ILE B 104     22.694  43.135   3.896  1.00 19.51      B
ATOM   2278  CA  ILE B 104     23.271  42.256   4.904  1.00 18.52      B
```

Figure 9 (36 of 92)

| | | | | | | | | | | |
|---|---|---|---|---|---|---|---|---|---|---|
| ATOM | 2279 | CB | ILE | B | 104 | 23.459 | 40.848 | 4.298 | 1.00 17.89 | B |
| ATOM | 2280 | CG2 | ILE | B | 104 | 23.926 | 39.868 | 5.359 | 1.00 18.21 | B |
| ATOM | 2281 | CG1 | ILE | B | 104 | 22.128 | 40.397 | 3.678 | 1.00 17.74 | B |
| ATOM | 2282 | CD1 | ILE | B | 104 | 22.186 | 39.068 | 2.955 | 1.00 17.45 | B |
| ATOM | 2283 | C | ILE | B | 104 | 24.591 | 42.763 | 5.487 | 1.00 19.94 | B |
| ATOM | 2284 | O | ILE | B | 104 | 25.521 | 43.102 | 4.752 | 1.00 19.28 | B |
| ATOM | 2285 | N | ILE | B | 105 | 24.655 | 42.805 | 6.818 | 1.00 19.81 | B |
| ATOM | 2286 | CA | ILE | B | 105 | 25.832 | 43.267 | 7.553 | 1.00 20.18 | B |
| ATOM | 2287 | CB | ILE | B | 105 | 25.466 | 44.456 | 8.491 | 1.00 21.23 | B |
| ATOM | 2288 | CG2 | ILE | B | 105 | 26.709 | 44.949 | 9.231 | 1.00 20.94 | B |
| ATOM | 2289 | CG1 | ILE | B | 105 | 24.868 | 45.603 | 7.676 | 1.00 22.76 | B |
| ATOM | 2290 | CD1 | ILE | B | 105 | 25.816 | 46.186 | 6.644 | 1.00 23.39 | B |
| ATOM | 2291 | C | ILE | B | 105 | 26.429 | 42.145 | 8.416 | 1.00 19.01 | B |
| ATOM | 2292 | O | ILE | B | 105 | 25.726 | 41.505 | 9.194 | 1.00 20.86 | B |
| ATOM | 2293 | N | GLY | B | 106 | 27.726 | 41.915 | 8.279 | 1.00 18.30 | B |
| ATOM | 2294 | CA | GLY | B | 106 | 28.371 | 40.880 | 9.062 | 1.00 19.61 | B |
| ATOM | 2295 | C | GLY | B | 106 | 28.638 | 41.355 | 10.475 | 1.00 20.76 | B |
| ATOM | 2296 | O | GLY | B | 106 | 29.009 | 42.506 | 10.689 | 1.00 20.30 | B |
| ATOM | 2297 | N | ALA | B | 107 | 28.436 | 40.469 | 11.442 | 1.00 21.94 | B |
| ATOM | 2298 | CA | ALA | B | 107 | 28.655 | 40.785 | 12.853 | 1.00 22.49 | B |
| ATOM | 2299 | CB | ALA | B | 107 | 27.369 | 41.309 | 13.473 | 1.00 21.86 | B |
| ATOM | 2300 | C | ALA | B | 107 | 29.078 | 39.493 | 13.543 | 1.00 24.57 | B |
| ATOM | 2301 | O | ALA | B | 107 | 28.564 | 39.143 | 14.606 | 1.00 25.12 | B |
| ATOM | 2302 | N | ASP | B | 108 | 30.023 | 38.787 | 12.935 | 1.00 25.66 | B |
| ATOM | 2303 | CA | ASP | B | 108 | 30.464 | 37.521 | 13.488 | 1.00 27.73 | B |
| ATOM | 2304 | CB | ASP | B | 108 | 30.395 | 36.438 | 12.411 | 1.00 29.68 | B |
| ATOM | 2305 | CG | ASP | B | 108 | 30.300 | 35.048 | 13.000 | 1.00 31.40 | B |
| ATOM | 2306 | OD1 | ASP | B | 108 | 31.068 | 34.163 | 12.569 | 1.00 31.92 | B |
| ATOM | 2307 | OD2 | ASP | B | 108 | 29.448 | 34.846 | 13.897 | 1.00 33.01 | B |
| ATOM | 2308 | C | ASP | B | 108 | 31.862 | 37.540 | 14.079 | 1.00 29.02 | B |
| ATOM | 2309 | O | ASP | B | 108 | 32.278 | 36.568 | 14.706 | 1.00 28.97 | B |
| ATOM | 2310 | N | MET | B | 109 | 32.585 | 38.640 | 13.892 | 1.00 28.91 | B |
| ATOM | 2311 | CA | MET | B | 109 | 33.949 | 38.744 | 14.400 | 1.00 29.84 | B |
| ATOM | 2312 | CB | MET | B | 109 | 34.877 | 39.307 | 13.309 | 1.00 29.14 | B |
| ATOM | 2313 | CG | MET | B | 109 | 34.881 | 38.529 | 11.983 | 1.00 28.29 | B |
| ATOM | 2314 | SD | MET | B | 109 | 35.624 | 36.875 | 12.105 | 1.00 25.25 | B |
| ATOM | 2315 | CE | MET | B | 109 | 36.430 | 36.727 | 10.560 | 1.00 30.79 | B |
| ATOM | 2316 | C | MET | B | 109 | 34.034 | 39.633 | 15.638 | 1.00 32.06 | B |
| ATOM | 2317 | O | MET | B | 109 | 34.846 | 39.381 | 16.524 | 1.00 33.68 | B |
| ATOM | 2318 | N | ILE | B | 110 | 33.198 | 40.669 | 15.695 | 1.00 32.70 | B |
| ATOM | 2319 | CA | ILE | B | 110 | 33.195 | 41.611 | 16.814 | 1.00 33.21 | B |
| ATOM | 2320 | CB | ILE | B | 110 | 33.573 | 43.040 | 16.330 | 1.00 33.93 | B |
| ATOM | 2321 | CG2 | ILE | B | 110 | 33.100 | 44.087 | 17.326 | 1.00 36.60 | B |
| ATOM | 2322 | CG1 | ILE | B | 110 | 35.086 | 43.138 | 16.136 | 1.00 34.48 | B |
| ATOM | 2323 | CD1 | ILE | B | 110 | 35.554 | 44.523 | 15.722 | 1.00 34.74 | B |
| ATOM | 2324 | C | ILE | B | 110 | 31.871 | 41.685 | 17.565 | 1.00 32.19 | B |
| ATOM | 2325 | O | ILE | B | 110 | 30.805 | 41.477 | 16.992 | 1.00 32.69 | B |
| ATOM | 2326 | N | GLU | B | 111 | 31.966 | 42.018 | 18.849 | 1.00 31.80 | B |
| ATOM | 2327 | CA | GLU | B | 111 | 30.823 | 42.123 | 19.751 | 1.00 32.33 | B |
| ATOM | 2328 | CB | GLU | B | 111 | 31.331 | 42.125 | 21.199 | 1.00 33.33 | B |
| ATOM | 2329 | CG | GLU | B | 111 | 30.245 | 42.131 | 22.265 | 1.00 33.96 | B |
| ATOM | 2330 | CD | GLU | B | 111 | 30.762 | 42.550 | 23.637 | 1.00 32.28 | B |
| ATOM | 2331 | OE1 | GLU | B | 111 | 31.945 | 42.297 | 23.946 | 1.00 30.64 | B |
| ATOM | 2332 | OE2 | GLU | B | 111 | 29.974 | 43.126 | 24.412 | 1.00 32.27 | B |
| ATOM | 2333 | C | GLU | B | 111 | 29.956 | 43.362 | 19.541 | 1.00 32.42 | B |
| ATOM | 2334 | O | GLU | B | 111 | 28.776 | 43.375 | 19.901 | 1.00 33.81 | B |
| ATOM | 2335 | N | TYR | B | 112 | 30.536 | 44.410 | 18.975 | 1.00 31.24 | B |
| ATOM | 2336 | CA | TYR | B | 112 | 29.790 | 45.647 | 18.780 | 1.00 31.41 | B |
| ATOM | 2337 | CB | TYR | B | 112 | 30.396 | 46.741 | 19.673 | 1.00 32.47 | B |
| ATOM | 2338 | CG | TYR | B | 112 | 29.798 | 48.124 | 19.523 | 1.00 32.15 | B |
| ATOM | 2339 | CD1 | TYR | B | 112 | 30.460 | 49.111 | 18.795 | 1.00 31.96 | B |
| ATOM | 2340 | CE1 | TYR | B | 112 | 29.935 | 50.394 | 18.675 | 1.00 31.83 | B |
| ATOM | 2341 | CD2 | TYR | B | 112 | 28.587 | 48.452 | 20.129 | 1.00 31.34 | B |
| ATOM | 2342 | CE2 | TYR | B | 112 | 28.049 | 49.733 | 20.015 | 1.00 32.16 | B |
| ATOM | 2343 | CZ | TYR | B | 112 | 28.730 | 50.699 | 19.285 | 1.00 31.73 | B |
| ATOM | 2344 | OH | TYR | B | 112 | 28.200 | 51.962 | 19.154 | 1.00 31.47 | B |

Figure 9 (37 of 92)

| ATOM | 2345 | C | TYR | B | 112 | 29.750 | 46.097 | 17.326 | 1.00 | 30.75 | B |
|---|---|---|---|---|---|---|---|---|---|---|---|
| ATOM | 2346 | O | TYR | B | 112 | 30.689 | 45.876 | 16.558 | 1.00 | 31.53 | B |
| ATOM | 2347 | N | LEU | B | 113 | 28.636 | 46.711 | 16.953 | 1.00 | 30.39 | B |
| ATOM | 2348 | CA | LEU | B | 113 | 28.452 | 47.206 | 15.596 | 1.00 | 30.20 | B |
| ATOM | 2349 | CB | LEU | B | 113 | 27.226 | 46.549 | 14.963 | 1.00 | 32.40 | B |
| ATOM | 2350 | CG | LEU | B | 113 | 27.028 | 46.856 | 13.482 | 1.00 | 32.04 | B |
| ATOM | 2351 | CD1 | LEU | B | 113 | 27.424 | 45.635 | 12.673 | 1.00 | 32.43 | B |
| ATOM | 2352 | CD2 | LEU | B | 113 | 25.576 | 47.234 | 13.225 | 1.00 | 33.49 | B |
| ATOM | 2353 | C | LEU | B | 113 | 28.253 | 48.713 | 15.671 | 1.00 | 28.74 | B |
| ATOM | 2354 | O | LEU | B | 113 | 27.283 | 49.192 | 16.257 | 1.00 | 27.10 | B |
| ATOM | 2355 | N | PRO | B | 114 | 29.172 | 49.483 | 15.069 | 1.00 | 28.35 | B |
| ATOM | 2356 | CD | PRO | B | 114 | 30.351 | 49.047 | 14.298 | 1.00 | 27.57 | B |
| ATOM | 2357 | CA | PRO | B | 114 | 29.071 | 50.941 | 15.094 | 1.00 | 28.39 | B |
| ATOM | 2358 | CB | PRO | B | 114 | 30.455 | 51.381 | 14.626 | 1.00 | 27.76 | B |
| ATOM | 2359 | CG | PRO | B | 114 | 30.809 | 50.325 | 13.642 | 1.00 | 26.79 | B |
| ATOM | 2360 | C | PRO | B | 114 | 27.953 | 51.509 | 14.223 | 1.00 | 28.60 | B |
| ATOM | 2361 | O | PRO | B | 114 | 27.504 | 50.870 | 13.261 | 1.00 | 27.48 | B |
| ATOM | 2362 | N | LYS | B | 115 | 27.514 | 52.715 | 14.576 | 1.00 | 27.87 | B |
| ATOM | 2363 | CA | LYS | B | 115 | 26.470 | 53.410 | 13.833 | 1.00 | 28.12 | B |
| ATOM | 2364 | CB | LYS | B | 115 | 25.773 | 54.422 | 14.743 | 1.00 | 28.67 | B |
| ATOM | 2365 | CG | LYS | B | 115 | 24.350 | 54.726 | 14.327 | 1.00 | 29.26 | B |
| ATOM | 2366 | CD | LYS | B | 115 | 23.568 | 55.463 | 15.412 | 1.00 | 30.38 | B |
| ATOM | 2367 | CE | LYS | B | 115 | 24.028 | 56.902 | 15.573 | 1.00 | 29.67 | B |
| ATOM | 2368 | NZ | LYS | B | 115 | 23.098 | 57.665 | 16.459 | 1.00 | 29.43 | B |
| ATOM | 2369 | C | LYS | B | 115 | 27.184 | 54.122 | 12.686 | 1.00 | 28.87 | B |
| ATOM | 2370 | O | LYS | B | 115 | 27.295 | 55.351 | 12.662 | 1.00 | 28.91 | B |
| ATOM | 2371 | N | TRP | B | 116 | 27.677 | 53.335 | 11.737 | 1.00 | 28.76 | B |
| ATOM | 2372 | CA | TRP | B | 116 | 28.420 | 53.881 | 10.613 | 1.00 | 30.25 | B |
| ATOM | 2373 | CB | TRP | B | 116 | 29.356 | 52.821 | 10.038 | 1.00 | 28.44 | B |
| ATOM | 2374 | CG | TRP | B | 116 | 28.633 | 51.671 | 9.430 | 1.00 | 29.84 | B |
| ATOM | 2375 | CD2 | TRP | B | 116 | 28.331 | 51.493 | 8.044 | 1.00 | 29.57 | B |
| ATOM | 2376 | CE2 | TRP | B | 116 | 27.607 | 50.288 | 7.925 | 1.00 | 30.64 | B |
| ATOM | 2377 | CE3 | TRP | B | 116 | 28.602 | 52.237 | 6.889 | 1.00 | 29.58 | B |
| ATOM | 2378 | CD1 | TRP | B | 116 | 28.094 | 50.596 | 10.082 | 1.00 | 30.32 | B |
| ATOM | 2379 | NE1 | TRP | B | 116 | 27.477 | 49.761 | 9.184 | 1.00 | 31.13 | B |
| ATOM | 2380 | CZ2 | TRP | B | 116 | 27.148 | 49.808 | 6.694 | 1.00 | 30.32 | B |
| ATOM | 2381 | CZ3 | TRP | B | 116 | 28.145 | 51.760 | 5.664 | 1.00 | 31.44 | B |
| ATOM | 2382 | CH2 | TRP | B | 116 | 27.426 | 50.556 | 5.580 | 1.00 | 29.82 | B |
| ATOM | 2383 | C | TRP | B | 116 | 27.555 | 54.445 | 9.497 | 1.00 | 31.22 | B |
| ATOM | 2384 | O | TRP | B | 116 | 28.051 | 55.161 | 8.631 | 1.00 | 32.12 | B |
| ATOM | 2385 | N | TYR | B | 117 | 26.268 | 54.130 | 9.510 | 1.00 | 33.15 | B |
| ATOM | 2386 | CA | TYR | B | 117 | 25.377 | 54.627 | 8.470 | 1.00 | 36.67 | B |
| ATOM | 2387 | CB | TYR | B | 117 | 24.828 | 53.471 | 7.624 | 1.00 | 37.89 | B |
| ATOM | 2388 | CG | TYR | B | 117 | 23.891 | 53.956 | 6.540 | 1.00 | 40.58 | B |
| ATOM | 2389 | CD1 | TYR | B | 117 | 24.361 | 54.769 | 5.507 | 1.00 | 40.95 | B |
| ATOM | 2390 | CE1 | TYR | B | 117 | 23.500 | 55.279 | 4.537 | 1.00 | 42.07 | B |
| ATOM | 2391 | CD2 | TYR | B | 117 | 22.525 | 53.656 | 6.575 | 1.00 | 41.51 | B |
| ATOM | 2392 | CE2 | TYR | B | 117 | 21.648 | 54.162 | 5.604 | 1.00 | 42.24 | B |
| ATOM | 2393 | CZ | TYR | B | 117 | 22.146 | 54.972 | 4.589 | 1.00 | 43.33 | B |
| ATOM | 2394 | OH | TYR | B | 117 | 21.303 | 55.480 | 3.625 | 1.00 | 44.17 | B |
| ATOM | 2395 | C | TYR | B | 117 | 24.209 | 55.440 | 9.009 | 1.00 | 36.43 | B |
| ATOM | 2396 | O | TYR | B | 117 | 23.509 | 55.014 | 9.926 | 1.00 | 35.02 | B |
| ATOM | 2397 | N | LYS | B | 118 | 23.998 | 56.608 | 8.409 | 1.00 | 38.98 | B |
| ATOM | 2398 | CA | LYS | B | 118 | 22.916 | 57.506 | 8.804 | 1.00 | 41.22 | B |
| ATOM | 2399 | CB | LYS | B | 118 | 23.287 | 58.947 | 8.436 | 1.00 | 42.85 | B |
| ATOM | 2400 | CG | LYS | B | 118 | 24.221 | 59.604 | 9.446 | 1.00 | 45.20 | B |
| ATOM | 2401 | CD | LYS | B | 118 | 24.959 | 60.807 | 8.875 | 1.00 | 47.00 | B |
| ATOM | 2402 | CE | LYS | B | 118 | 26.059 | 60.369 | 7.913 | 1.00 | 48.42 | B |
| ATOM | 2403 | NZ | LYS | B | 118 | 26.873 | 61.515 | 7.408 | 1.00 | 48.31 | B |
| ATOM | 2404 | C | LYS | B | 118 | 21.570 | 57.130 | 8.184 | 1.00 | 40.94 | B |
| ATOM | 2405 | O | LYS | B | 118 | 21.424 | 57.071 | 6.964 | 1.00 | 41.66 | B |
| ATOM | 2406 | N | ILE | B | 126 | 15.168 | 51.275 | 2.940 | 1.00 | 35.56 | B |
| ATOM | 2407 | CA | ILE | B | 126 | 16.472 | 50.640 | 3.100 | 1.00 | 36.06 | B |
| ATOM | 2408 | CB | ILE | B | 126 | 17.619 | 51.582 | 2.661 | 1.00 | 36.35 | B |
| ATOM | 2409 | CG2 | ILE | B | 126 | 18.959 | 51.034 | 3.125 | 1.00 | 36.94 | B |
| ATOM | 2410 | CG1 | ILE | B | 126 | 17.614 | 51.731 | 1.139 | 1.00 | 37.09 | B |

Figure 9 (38 of 92)

| ATOM | 2411 | CD1 | ILE | B | 126 | 18.638 | 52.716 | 0.629 | 1.00 | 39.10 | B |
|------|------|-----|-----|---|-----|--------|--------|-------|------|-------|---|
| ATOM | 2412 | C | ILE | B | 126 | 16.717 | 50.211 | 4.541 | 1.00 | 35.07 | B |
| ATOM | 2413 | O | ILE | B | 126 | 16.832 | 51.040 | 5.439 | 1.00 | 36.22 | B |
| ATOM | 2414 | N | GLN | B | 127 | 16.795 | 48.906 | 4.753 | 1.00 | 32.99 | B |
| ATOM | 2415 | CA | GLN | B | 127 | 17.033 | 48.376 | 6.077 | 1.00 | 31.18 | B |
| ATOM | 2416 | CB | GLN | B | 127 | 15.800 | 47.632 | 6.570 | 1.00 | 33.09 | B |
| ATOM | 2417 | CG | GLN | B | 127 | 14.616 | 48.541 | 6.834 | 1.00 | 36.47 | B |
| ATOM | 2418 | CD | GLN | B | 127 | 13.420 | 47.785 | 7.354 | 1.00 | 39.37 | B |
| ATOM | 2419 | OE1 | GLN | B | 127 | 12.744 | 47.082 | 6.604 | 1.00 | 42.70 | B |
| ATOM | 2420 | NE2 | GLN | B | 127 | 13.160 | 47.908 | 8.649 | 1.00 | 40.87 | B |
| ATOM | 2421 | C | GLN | B | 127 | 18.233 | 47.446 | 6.080 | 1.00 | 30.59 | B |
| ATOM | 2422 | O | GLN | B | 127 | 18.781 | 47.103 | 5.030 | 1.00 | 28.70 | B |
| ATOM | 2423 | N | PHE | B | 128 | 18.642 | 47.040 | 7.272 | 1.00 | 29.34 | B |
| ATOM | 2424 | CA | PHE | B | 128 | 19.771 | 46.144 | 7.405 | 1.00 | 29.38 | B |
| ATOM | 2425 | CB | PHE | B | 128 | 20.931 | 46.889 | 8.067 | 1.00 | 31.05 | B |
| ATOM | 2426 | CG | PHE | B | 128 | 21.493 | 47.990 | 7.215 | 1.00 | 36.05 | B |
| ATOM | 2427 | CD1 | PHE | B | 128 | 22.454 | 47.717 | 6.247 | 1.00 | 37.30 | B |
| ATOM | 2428 | CD2 | PHE | B | 128 | 21.029 | 49.294 | 7.346 | 1.00 | 37.63 | B |
| ATOM | 2429 | CE1 | PHE | B | 128 | 22.946 | 48.725 | 5.419 | 1.00 | 36.64 | B |
| ATOM | 2430 | CE2 | PHE | B | 128 | 21.513 | 50.310 | 6.521 | 1.00 | 39.28 | B |
| ATOM | 2431 | CZ | PHE | B | 128 | 22.475 | 50.021 | 5.556 | 1.00 | 38.96 | B |
| ATOM | 2432 | C | PHE | B | 128 | 19.403 | 44.907 | 8.209 | 1.00 | 27.31 | B |
| ATOM | 2433 | O | PHE | B | 128 | 18.446 | 44.918 | 8.977 | 1.00 | 26.22 | B |
| ATOM | 2434 | N | ILE | B | 129 | 20.159 | 43.837 | 7.993 | 1.00 | 26.31 | B |
| ATOM | 2435 | CA | ILE | B | 129 | 19.981 | 42.582 | 8.711 | 1.00 | 26.06 | B |
| ATOM | 2436 | CB | ILE | B | 129 | 19.339 | 41.478 | 7.850 | 1.00 | 26.62 | B |
| ATOM | 2437 | CG2 | ILE | B | 129 | 19.203 | 40.218 | 8.676 | 1.00 | 25.77 | B |
| ATOM | 2438 | CG1 | ILE | B | 129 | 17.966 | 41.909 | 7.348 | 1.00 | 26.24 | B |
| ATOM | 2439 | CD1 | ILE | B | 129 | 17.350 | 40.922 | 6.376 | 1.00 | 27.86 | B |
| ATOM | 2440 | C | ILE | B | 129 | 21.383 | 42.110 | 9.063 | 1.00 | 26.45 | B |
| ATOM | 2441 | O | ILE | B | 129 | 22.251 | 42.000 | 8.189 | 1.00 | 26.12 | B |
| ATOM | 2442 | N | GLY | B | 130 | 21.619 | 41.848 | 10.339 | 1.00 | 24.65 | B |
| ATOM | 2443 | CA | GLY | B | 130 | 22.927 | 41.380 | 10.725 | 1.00 | 24.37 | B |
| ATOM | 2444 | C | GLY | B | 130 | 22.981 | 39.867 | 10.673 | 1.00 | 24.49 | B |
| ATOM | 2445 | O | GLY | B | 130 | 21.961 | 39.196 | 10.853 | 1.00 | 23.89 | B |
| ATOM | 2446 | N | VAL | B | 131 | 24.162 | 39.328 | 10.381 | 1.00 | 23.77 | B |
| ATOM | 2447 | CA | VAL | B | 131 | 24.342 | 37.883 | 10.366 | 1.00 | 22.90 | B |
| ATOM | 2448 | CB | VAL | B | 131 | 24.680 | 37.332 | 8.965 | 1.00 | 20.70 | B |
| ATOM | 2449 | CG1 | VAL | B | 131 | 23.450 | 37.403 | 8.081 | 1.00 | 17.48 | B |
| ATOM | 2450 | CG2 | VAL | B | 131 | 25.843 | 38.097 | 8.357 | 1.00 | 23.35 | B |
| ATOM | 2451 | C | VAL | B | 131 | 25.473 | 37.543 | 11.319 | 1.00 | 22.57 | B |
| ATOM | 2452 | O | VAL | B | 131 | 26.571 | 38.082 | 11.211 | 1.00 | 21.84 | B |
| ATOM | 2453 | N | LYS | B | 132 | 25.181 | 36.656 | 12.262 | 1.00 | 22.92 | B |
| ATOM | 2454 | CA | LYS | B | 132 | 26.152 | 36.235 | 13.258 | 1.00 | 24.02 | B |
| ATOM | 2455 | CB | LYS | B | 132 | 25.977 | 37.071 | 14.525 | 1.00 | 22.69 | B |
| ATOM | 2456 | CG | LYS | B | 132 | 24.594 | 36.955 | 15.153 | 1.00 | 24.33 | B |
| ATOM | 2457 | CD | LYS | B | 132 | 24.430 | 37.915 | 16.332 | 1.00 | 25.95 | B |
| ATOM | 2458 | CE | LYS | B | 132 | 23.181 | 37.604 | 17.142 | 1.00 | 23.23 | B |
| ATOM | 2459 | NZ | LYS | B | 132 | 23.244 | 36.214 | 17.682 | 1.00 | 23.30 | B |
| ATOM | 2460 | C | LYS | B | 132 | 25.910 | 34.765 | 13.570 | 1.00 | 24.08 | B |
| ATOM | 2461 | O | LYS | B | 132 | 24.944 | 34.178 | 13.090 | 1.00 | 23.41 | B |
| ATOM | 2462 | N | ARG | B | 133 | 26.786 | 34.163 | 14.365 | 1.00 | 24.63 | B |
| ATOM | 2463 | CA | ARG | B | 133 | 26.599 | 32.763 | 14.726 | 1.00 | 25.56 | B |
| ATOM | 2464 | CB | ARG | B | 133 | 27.899 | 32.149 | 15.233 | 1.00 | 26.82 | B |
| ATOM | 2465 | CG | ARG | B | 133 | 28.924 | 31.840 | 14.174 | 1.00 | 29.36 | B |
| ATOM | 2466 | CD | ARG | B | 133 | 30.267 | 31.715 | 14.845 | 1.00 | 30.32 | B |
| ATOM | 2467 | NE | ARG | B | 133 | 30.661 | 33.000 | 15.410 | 1.00 | 32.57 | B |
| ATOM | 2468 | CZ | ARG | B | 133 | 31.539 | 33.152 | 16.391 | 1.00 | 33.90 | B |
| ATOM | 2469 | NH1 | ARG | B | 133 | 32.120 | 32.088 | 16.932 | 1.00 | 35.05 | B |
| ATOM | 2470 | NH2 | ARG | B | 133 | 31.849 | 34.371 | 16.816 | 1.00 | 34.04 | B |
| ATOM | 2471 | C | ARG | B | 133 | 25.583 | 32.725 | 15.848 | 1.00 | 24.71 | B |
| ATOM | 2472 | O | ARG | B | 133 | 25.479 | 33.677 | 16.625 | 1.00 | 23.58 | B |
| ATOM | 2473 | N | PRO | B | 134 | 24.814 | 31.631 | 15.946 | 1.00 | 24.87 | B |
| ATOM | 2474 | CD | PRO | B | 134 | 24.756 | 30.440 | 15.077 | 1.00 | 24.07 | B |
| ATOM | 2475 | CA | PRO | B | 134 | 23.828 | 31.562 | 17.027 | 1.00 | 24.41 | B |
| ATOM | 2476 | CB | PRO | B | 134 | 23.116 | 30.226 | 16.768 | 1.00 | 25.41 | B |

Figure 9 (39 of 92)

```
ATOM   2477  CG   PRO B 134      24.117  29.422  15.973  1.00 25.25      B
ATOM   2478  C    PRO B 134      24.560  31.612  18.368  1.00 26.40      B
ATOM   2479  O    PRO B 134      25.654  31.062  18.496  1.00 25.37      B
ATOM   2480  N    GLY B 135      23.970  32.292  19.348  1.00 27.91      B
ATOM   2481  CA   GLY B 135      24.592  32.410  20.656  1.00 29.99      B
ATOM   2482  C    GLY B 135      25.542  33.597  20.752  1.00 32.32      B
ATOM   2483  O    GLY B 135      25.783  34.121  21.839  1.00 33.37      B
ATOM   2484  N    PHE B 136      26.088  34.023  19.617  1.00 32.73      B
ATOM   2485  CA   PHE B 136      27.011  35.152  19.592  1.00 33.06      B
ATOM   2486  CB   PHE B 136      27.667  35.268  18.209  1.00 32.86      B
ATOM   2487  CG   PHE B 136      28.821  36.234  18.157  1.00 34.77      B
ATOM   2488  CD1  PHE B 136      29.997  35.977  18.861  1.00 34.03      B
ATOM   2489  CD2  PHE B 136      28.736  37.401  17.400  1.00 34.65      B
ATOM   2490  CE1  PHE B 136      31.069  36.866  18.808  1.00 34.73      B
ATOM   2491  CE2  PHE B 136      29.801  38.297  17.341  1.00 34.43      B
ATOM   2492  CZ   PHE B 136      30.971  38.029  18.047  1.00 34.32      B
ATOM   2493  C    PHE B 136      26.237  36.427  19.922  1.00 33.06      B
ATOM   2494  O    PHE B 136      25.318  36.812  19.201  1.00 33.20      B
ATOM   2495  N    HIS B 137      26.607  37.071  21.024  1.00 32.68      B
ATOM   2496  CA   HIS B 137      25.947  38.293  21.462  1.00 32.22      B
ATOM   2497  CB   HIS B 137      26.067  38.435  22.978  1.00 34.07      B
ATOM   2498  CG   HIS B 137      25.335  37.374  23.739  1.00 35.31      B
ATOM   2499  CD2  HIS B 137      25.787  36.320  24.458  1.00 36.53      B
ATOM   2500  ND1  HIS B 137      23.960  37.316  23.796  1.00 35.91      B
ATOM   2501  CE1  HIS B 137      23.595  36.271  24.518  1.00 38.15      B
ATOM   2502  NE2  HIS B 137      24.685  35.650  24.932  1.00 37.04      B
ATOM   2503  C    HIS B 137      26.527  39.527  20.785  1.00 31.72      B
ATOM   2504  O    HIS B 137      27.744  39.730  20.763  1.00 31.92      B
ATOM   2505  N    VAL B 138      25.643  40.355  20.243  1.00 29.14      B
ATOM   2506  CA   VAL B 138      26.059  41.566  19.561  1.00 29.71      B
ATOM   2507  CB   VAL B 138      25.881  41.432  18.028  1.00 28.19      B
ATOM   2508  CG1  VAL B 138      26.148  42.773  17.349  1.00 27.60      B
ATOM   2509  CG2  VAL B 138      26.831  40.365  17.489  1.00 27.55      B
ATOM   2510  C    VAL B 138      25.268  42.770  20.039  1.00 30.17      B
ATOM   2511  O    VAL B 138      24.041  42.740  20.080  1.00 30.81      B
ATOM   2512  N    GLU B 139      25.980  43.830  20.405  1.00 31.46      B
ATOM   2513  CA   GLU B 139      25.331  45.054  20.854  1.00 32.71      B
ATOM   2514  CB   GLU B 139      25.928  45.532  22.180  1.00 34.23      B
ATOM   2515  CG   GLU B 139      25.765  44.537  23.323  1.00 34.25      B
ATOM   2516  CD   GLU B 139      26.290  45.070  24.640  1.00 34.59      B
ATOM   2517  OE1  GLU B 139      25.492  45.633  25.418  1.00 34.68      B
ATOM   2518  OE2  GLU B 139      27.506  44.936  24.889  1.00 35.01      B
ATOM   2519  C    GLU B 139      25.543  46.106  19.780  1.00 32.68      B
ATOM   2520  O    GLU B 139      26.597  46.159  19.145  1.00 32.84      B
ATOM   2521  N    THR B 140      24.533  46.937  19.572  1.00 32.79      B
ATOM   2522  CA   THR B 140      24.620  47.975  18.561  1.00 33.75      B
ATOM   2523  CB   THR B 140      24.434  47.372  17.146  1.00 34.28      B
ATOM   2524  OG1  THR B 140      24.550  48.405  16.158  1.00 35.17      B
ATOM   2525  CG2  THR B 140      23.064  46.698  17.031  1.00 34.26      B
ATOM   2526  C    THR B 140      23.549  49.031  18.812  1.00 33.20      B
ATOM   2527  O    THR B 140      22.480  48.730  19.343  1.00 31.57      B
ATOM   2528  N    PRO B 141      23.837  50.292  18.452  1.00 34.11      B
ATOM   2529  CD   PRO B 141      25.126  50.800  17.945  1.00 35.61      B
ATOM   2530  CA   PRO B 141      22.886  51.392  18.640  1.00 35.10      B
ATOM   2531  CB   PRO B 141      23.743  52.630  18.387  1.00 34.11      B
ATOM   2532  CG   PRO B 141      24.737  52.149  17.379  1.00 35.65      B
ATOM   2533  C    PRO B 141      21.703  51.290  17.677  1.00 36.18      B
ATOM   2534  O    PRO B 141      20.684  51.958  17.847  1.00 36.06      B
ATOM   2535  N    TYR B 142      21.852  50.441  16.668  1.00 37.78      B
ATOM   2536  CA   TYR B 142      20.820  50.231  15.659  1.00 38.92      B
ATOM   2537  CB   TYR B 142      21.412  49.612  14.389  1.00 38.90      B
ATOM   2538  CG   TYR B 142      22.275  50.503  13.533  1.00 39.82      B
ATOM   2539  CD1  TYR B 142      23.577  50.122  13.198  1.00 38.67      B
ATOM   2540  CE1  TYR B 142      24.350  50.888  12.333  1.00 39.75      B
ATOM   2541  CD2  TYR B 142      21.768  51.683  12.986  1.00 40.07      B
ATOM   2542  CE2  TYR B 142      22.535  52.459  12.116  1.00 40.99      B
```

Figure 9 (40 of 92)

| | | | | | | | | | |
|---|---|---|---|---|---|---|---|---|---|
| ATOM | 2543 | CZ | TYR | B 142 | 23.823 | 52.052 | 11.794 | 1.00 39.81 | B |
| ATOM | 2544 | OH | TYR | B 142 | 24.577 | 52.801 | 10.927 | 1.00 40.10 | B |
| ATOM | 2545 | C | TYR | B 142 | 19.740 | 49.271 | 16.115 | 1.00 39.17 | B |
| ATOM | 2546 | O | TYR | B 142 | 20.034 | 48.258 | 16.745 | 1.00 39.74 | B |
| ATOM | 2547 | N | PRO | B 143 | 18.469 | 49.596 | 15.841 | 1.00 39.38 | B |
| ATOM | 2548 | CD | PRO | B 143 | 17.903 | 50.935 | 15.606 | 1.00 39.97 | B |
| ATOM | 2549 | CA | PRO | B 143 | 17.425 | 48.654 | 16.249 | 1.00 39.42 | B |
| ATOM | 2550 | CB | PRO | B 143 | 16.154 | 49.502 | 16.209 | 1.00 38.95 | B |
| ATOM | 2551 | CG | PRO | B 143 | 16.665 | 50.898 | 16.464 | 1.00 40.30 | B |
| ATOM | 2552 | C | PRO | B 143 | 17.513 | 47.688 | 15.062 | 1.00 39.13 | B |
| ATOM | 2553 | O | PRO | B 143 | 16.835 | 47.874 | 14.055 | 1.00 41.73 | B |
| ATOM | 2554 | N | LEU | B 144 | 18.377 | 46.685 | 15.175 | 1.00 37.00 | B |
| ATOM | 2555 | CA | LEU | B 144 | 18.627 | 45.746 | 14.085 | 1.00 34.34 | B |
| ATOM | 2556 | CB | LEU | B 144 | 20.121 | 45.781 | 13.762 | 1.00 34.39 | B |
| ATOM | 2557 | CG | LEU | B 144 | 20.657 | 44.855 | 12.676 | 1.00 34.02 | B |
| ATOM | 2558 | CD1 | LEU | B 144 | 20.263 | 45.404 | 11.324 | 1.00 34.44 | B |
| ATOM | 2559 | CD2 | LEU | B 144 | 22.165 | 44.746 | 12.787 | 1.00 33.79 | B |
| ATOM | 2560 | C | LEU | B 144 | 18.204 | 44.299 | 14.315 | 1.00 32.59 | B |
| ATOM | 2561 | O | LEU | B 144 | 18.388 | 43.759 | 15.403 | 1.00 32.84 | B |
| ATOM | 2562 | N | LEU | B 145 | 17.644 | 43.675 | 13.279 | 1.00 29.91 | B |
| ATOM | 2563 | CA | LEU | B 145 | 17.223 | 42.277 | 13.347 | 1.00 28.55 | B |
| ATOM | 2564 | CB | LEU | B 145 | 15.982 | 42.048 | 12.477 | 1.00 31.12 | B |
| ATOM | 2565 | CG | LEU | B 145 | 15.506 | 40.600 | 12.286 | 1.00 34.89 | B |
| ATOM | 2566 | CD1 | LEU | B 145 | 15.316 | 39.917 | 13.641 | 1.00 35.91 | B |
| ATOM | 2567 | CD2 | LEU | B 145 | 14.196 | 40.592 | 11.502 | 1.00 35.61 | B |
| ATOM | 2568 | C | LEU | B 145 | 18.375 | 41.399 | 12.847 | 1.00 26.57 | B |
| ATOM | 2569 | O | LEU | B 145 | 18.985 | 41.691 | 11.822 | 1.00 22.81 | B |
| ATOM | 2570 | N | PHE | B 146 | 18.676 | 40.328 | 13.573 | 1.00 24.49 | B |
| ATOM | 2571 | CA | PHE | B 146 | 19.764 | 39.446 | 13.181 | 1.00 24.42 | B |
| ATOM | 2572 | CB | PHE | B 146 | 20.731 | 39.197 | 14.343 | 1.00 23.97 | B |
| ATOM | 2573 | CG | PHE | B 146 | 21.506 | 40.407 | 14.768 | 1.00 24.62 | B |
| ATOM | 2574 | CD1 | PHE | B 146 | 20.930 | 41.363 | 15.599 | 1.00 26.54 | B |
| ATOM | 2575 | CD2 | PHE | B 146 | 22.823 | 40.578 | 14.361 | 1.00 23.58 | B |
| ATOM | 2576 | CE1 | PHE | B 146 | 21.658 | 42.470 | 16.022 | 1.00 26.70 | B |
| ATOM | 2577 | CE2 | PHE | B 146 | 23.558 | 41.679 | 14.775 | 1.00 24.43 | B |
| ATOM | 2578 | CZ | PHE | B 146 | 22.976 | 42.627 | 15.608 | 1.00 26.06 | B |
| ATOM | 2579 | C | PHE | B 146 | 19.301 | 38.091 | 12.688 | 1.00 24.52 | B |
| ATOM | 2580 | O | PHE | B 146 | 18.180 | 37.651 | 12.959 | 1.00 24.66 | B |
| ATOM | 2581 | N | ALA | B 147 | 20.189 | 37.440 | 11.953 | 1.00 22.40 | B |
| ATOM | 2582 | CA | ALA | B 147 | 19.933 | 36.107 | 11.442 | 1.00 21.88 | B |
| ATOM | 2583 | CB | ALA | B 147 | 19.927 | 36.104 | 9.909 | 1.00 19.62 | B |
| ATOM | 2584 | C | ALA | B 147 | 21.090 | 35.274 | 11.981 | 1.00 21.68 | B |
| ATOM | 2585 | O | ALA | B 147 | 22.267 | 35.583 | 11.728 | 1.00 21.29 | B |
| ATOM | 2586 | N | ASP | B 148 | 20.743 | 34.246 | 12.753 | 1.00 21.01 | B |
| ATOM | 2587 | CA | ASP | B 148 | 21.719 | 33.349 | 13.345 | 1.00 19.33 | B |
| ATOM | 2588 | CB | ASP | B 148 | 21.140 | 32.703 | 14.617 | 1.00 20.99 | B |
| ATOM | 2589 | CG | ASP | B 148 | 21.082 | 33.670 | 15.798 | 1.00 21.97 | B |
| ATOM | 2590 | OD1 | ASP | B 148 | 20.260 | 33.452 | 16.712 | 1.00 24.93 | B |
| ATOM | 2591 | OD2 | ASP | B 148 | 21.861 | 34.644 | 15.823 | 1.00 21.83 | B |
| ATOM | 2592 | C | ASP | B 148 | 22.059 | 32.281 | 12.313 | 1.00 18.54 | B |
| ATOM | 2593 | O | ASP | B 148 | 21.297 | 31.323 | 12.118 | 1.00 17.79 | B |
| ATOM | 2594 | N | VAL | B 149 | 23.202 | 32.457 | 11.657 | 1.00 15.90 | B |
| ATOM | 2595 | CA | VAL | B 149 | 23.656 | 31.538 | 10.630 | 1.00 15.11 | B |
| ATOM | 2596 | CB | VAL | B 149 | 24.326 | 32.312 | 9.464 | 1.00 17.79 | B |
| ATOM | 2597 | CG1 | VAL | B 149 | 24.843 | 31.335 | 8.407 | 1.00 16.60 | B |
| ATOM | 2598 | CG2 | VAL | B 149 | 23.333 | 33.311 | 8.850 | 1.00 16.31 | B |
| ATOM | 2599 | C | VAL | B 149 | 24.668 | 30.536 | 11.189 | 1.00 14.89 | B |
| ATOM | 2600 | O | VAL | B 149 | 25.667 | 30.923 | 11.793 | 1.00 11.74 | B |
| ATOM | 2601 | N | PRO | B 150 | 24.412 | 29.230 | 11.010 | 1.00 15.09 | B |
| ATOM | 2602 | CD | PRO | B 150 | 23.193 | 28.549 | 10.531 | 1.00 14.63 | B |
| ATOM | 2603 | CA | PRO | B 150 | 25.387 | 28.268 | 11.536 | 1.00 16.59 | B |
| ATOM | 2604 | CB | PRO | B 150 | 24.795 | 26.911 | 11.136 | 1.00 14.70 | B |
| ATOM | 2605 | CG | PRO | B 150 | 23.321 | 27.163 | 11.179 | 1.00 14.77 | B |
| ATOM | 2606 | C | PRO | B 150 | 26.766 | 28.504 | 10.902 | 1.00 18.41 | B |
| ATOM | 2607 | O | PRO | B 150 | 26.871 | 28.797 | 9.705 | 1.00 16.14 | B |
| ATOM | 2608 | N | GLU | B 151 | 27.819 | 28.385 | 11.705 | 1.00 18.58 | B |

Figure 9 (41 of 92)

| | | | | | | | | | | |
|---|---|---|---|---|---|---|---|---|---|---|
| ATOM | 2609 | CA | GLU | B | 151 | 29.178 | 28.575 | 11.204 | 1.00 20.32 | B |
| ATOM | 2610 | CB | GLU | B | 151 | 30.183 | 28.474 | 12.362 | 1.00 23.29 | B |
| ATOM | 2611 | CG | GLU | B | 151 | 31.648 | 28.412 | 11.928 | 1.00 27.81 | B |
| ATOM | 2612 | CD | GLU | B | 151 | 32.196 | 29.754 | 11.473 | 1.00 30.61 | B |
| ATOM | 2613 | OE1 | GLU | B | 151 | 32.436 | 30.618 | 12.344 | 1.00 33.76 | B |
| ATOM | 2614 | OE2 | GLU | B | 151 | 32.386 | 29.950 | 10.252 | 1.00 32.69 | B |
| ATOM | 2615 | C | GLU | B | 151 | 29.527 | 27.536 | 10.132 | 1.00 18.86 | B |
| ATOM | 2616 | O | GLU | B | 151 | 29.227 | 26.352 | 10.279 | 1.00 19.41 | B |
| ATOM | 2617 | N | PHE | B | 152 | 30.161 | 27.990 | 9.056 | 1.00 18.79 | B |
| ATOM | 2618 | CA | PHE | B | 152 | 30.584 | 27.113 | 7.963 | 1.00 21.69 | B |
| ATOM | 2619 | CB | PHE | B | 152 | 29.492 | 27.042 | 6.885 | 1.00 20.49 | B |
| ATOM | 2620 | CG | PHE | B | 152 | 29.641 | 25.882 | 5.926 | 1.00 19.46 | B |
| ATOM | 2621 | CD1 | PHE | B | 152 | 28.651 | 25.619 | 4.984 | 1.00 20.79 | B |
| ATOM | 2622 | CD2 | PHE | B | 152 | 30.769 | 25.064 | 5.952 | 1.00 18.17 | B |
| ATOM | 2623 | CE1 | PHE | B | 152 | 28.780 | 24.554 | 4.076 | 1.00 21.37 | B |
| ATOM | 2624 | CE2 | PHE | B | 152 | 30.913 | 24.002 | 5.056 | 1.00 20.01 | B |
| ATOM | 2625 | CZ | PHE | B | 152 | 29.914 | 23.744 | 4.112 | 1.00 19.12 | B |
| ATOM | 2626 | C | PHE | B | 152 | 31.861 | 27.752 | 7.405 | 1.00 23.06 | B |
| ATOM | 2627 | O | PHE | B | 152 | 31.797 | 28.621 | 6.539 | 1.00 24.95 | B |
| ATOM | 2628 | N | GLU | B | 153 | 33.012 | 27.315 | 7.917 | 1.00 23.98 | B |
| ATOM | 2629 | CA | GLU | B | 153 | 34.317 | 27.861 | 7.530 | 1.00 24.83 | B |
| ATOM | 2630 | CB | GLU | B | 153 | 35.398 | 27.391 | 8.498 | 1.00 26.19 | B |
| ATOM | 2631 | CG | GLU | B | 153 | 35.012 | 27.497 | 9.954 | 1.00 31.17 | B |
| ATOM | 2632 | CD | GLU | B | 153 | 36.168 | 27.167 | 10.886 | 1.00 35.50 | B |
| ATOM | 2633 | OE1 | GLU | B | 153 | 36.945 | 26.230 | 10.574 | 1.00 36.68 | B |
| ATOM | 2634 | OE2 | GLU | B | 153 | 36.290 | 27.841 | 11.938 | 1.00 37.84 | B |
| ATOM | 2635 | C | GLU | B | 153 | 34.746 | 27.510 | 6.119 | 1.00 25.09 | B |
| ATOM | 2636 | O | GLU | B | 153 | 35.711 | 26.766 | 5.909 | 1.00 25.21 | B |
| ATOM | 2637 | N | VAL | B | 154 | 34.025 | 28.053 | 5.152 | 1.00 23.96 | B |
| ATOM | 2638 | CA | VAL | B | 154 | 34.326 | 27.806 | 3.757 | 1.00 23.96 | B |
| ATOM | 2639 | CB | VAL | B | 154 | 33.268 | 26.886 | 3.098 | 1.00 23.38 | B |
| ATOM | 2640 | CG1 | VAL | B | 154 | 31.866 | 27.469 | 3.288 | 1.00 22.67 | B |
| ATOM | 2641 | CG2 | VAL | B | 154 | 33.586 | 26.716 | 1.611 | 1.00 22.30 | B |
| ATOM | 2642 | C | VAL | B | 154 | 34.343 | 29.140 | 3.051 | 1.00 23.78 | B |
| ATOM | 2643 | O | VAL | B | 154 | 33.508 | 30.006 | 3.308 | 1.00 23.58 | B |
| ATOM | 2644 | N | SER | B | 155 | 35.308 | 29.317 | 2.165 | 1.00 23.46 | B |
| ATOM | 2645 | CA | SER | B | 155 | 35.395 | 30.563 | 1.438 | 1.00 23.77 | B |
| ATOM | 2646 | CB | SER | B | 155 | 36.440 | 31.474 | 2.081 | 1.00 23.34 | B |
| ATOM | 2647 | OG | SER | B | 155 | 37.713 | 30.855 | 2.031 | 1.00 23.98 | B |
| ATOM | 2648 | C | SER | B | 155 | 35.787 | 30.270 | 0.005 | 1.00 23.02 | B |
| ATOM | 2649 | O | SER | B | 155 | 36.216 | 29.162 | -0.320 | 1.00 21.85 | B |
| ATOM | 2650 | N | SER | B | 156 | 35.632 | 31.271 | -0.849 | 1.00 22.17 | B |
| ATOM | 2651 | CA | SER | B | 156 | 36.000 | 31.127 | -2.241 | 1.00 23.86 | B |
| ATOM | 2652 | CB | SER | B | 156 | 35.566 | 32.372 | -3.022 | 1.00 23.42 | B |
| ATOM | 2653 | OG | SER | B | 156 | 34.150 | 32.467 | -3.067 | 1.00 19.41 | B |
| ATOM | 2654 | C | SER | B | 156 | 37.518 | 30.935 | -2.324 | 1.00 25.33 | B |
| ATOM | 2655 | O | SER | B | 156 | 38.003 | 30.050 | -3.025 | 1.00 25.74 | B |
| ATOM | 2656 | N | THR | B | 157 | 38.260 | 31.759 | -1.591 | 1.00 26.24 | B |
| ATOM | 2657 | CA | THR | B | 157 | 39.720 | 31.675 | -1.583 | 1.00 27.96 | B |
| ATOM | 2658 | CB | THR | B | 157 | 40.344 | 32.655 | -0.554 | 1.00 29.04 | B |
| ATOM | 2659 | OG1 | THR | B | 157 | 39.806 | 33.968 | -0.746 | 1.00 31.47 | B |
| ATOM | 2660 | CG2 | THR | B | 157 | 41.853 | 32.710 | -0.720 | 1.00 26.82 | B |
| ATOM | 2661 | C | THR | B | 157 | 40.165 | 30.264 | -1.205 | 1.00 27.88 | B |
| ATOM | 2662 | O | THR | B | 157 | 41.006 | 29.666 | -1.870 | 1.00 28.10 | B |
| ATOM | 2663 | N | MET | B | 158 | 39.602 | 29.744 | -0.120 | 1.00 28.09 | B |
| ATOM | 2664 | CA | MET | B | 158 | 39.945 | 28.411 | 0.361 | 1.00 27.42 | B |
| ATOM | 2665 | CB | MET | B | 158 | 39.189 | 28.130 | 1.665 | 1.00 28.64 | B |
| ATOM | 2666 | CG | MET | B | 158 | 39.432 | 26.754 | 2.260 | 1.00 25.75 | B |
| ATOM | 2667 | SD | MET | B | 158 | 37.859 | 25.923 | 2.589 | 1.00 29.41 | B |
| ATOM | 2668 | CE | MET | B | 158 | 37.318 | 25.857 | 1.103 | 1.00 3.88 | B |
| ATOM | 2669 | C | MET | B | 158 | 39.617 | 27.354 | -0.693 | 1.00 27.27 | B |
| ATOM | 2670 | O | MET | B | 158 | 40.356 | 26.388 | -0.873 | 1.00 27.85 | B |
| ATOM | 2671 | N | ILE | B | 159 | 38.509 | 27.550 | -1.394 | 1.00 26.97 | B |
| ATOM | 2672 | CA | ILE | B | 159 | 38.085 | 26.620 | -2.434 | 1.00 28.02 | B |
| ATOM | 2673 | CB | ILE | B | 159 | 36.639 | 26.928 | -2.867 | 1.00 25.68 | B |
| ATOM | 2674 | CG2 | ILE | B | 159 | 36.314 | 26.237 | -4.180 | 1.00 26.27 | B |

Figure 9 (42 of 92)

| | | | | | | | | | | | |
|---|---|---|---|---|---|---|---|---|---|---|---|
| ATOM | 2675 | CG1 | ILE | B | 159 | 35.681 | 26.479 | -1.761 | 1.00 | 27.43 | B |
| ATOM | 2676 | CD1 | ILE | B | 159 | 34.264 | 26.946 | -1.958 | 1.00 | 27.43 | B |
| ATOM | 2677 | C | ILE | B | 159 | 39.014 | 26.660 | -3.653 | 1.00 | 28.66 | B |
| ATOM | 2678 | O | ILE | B | 159 | 39.330 | 25.618 | -4.236 | 1.00 | 28.93 | B |
| ATOM | 2679 | N | ARG | B | 160 | 39.448 | 27.855 | -4.043 | 1.00 | 29.25 | B |
| ATOM | 2680 | CA | ARG | B | 160 | 40.343 | 27.970 | -5.188 | 1.00 | 31.08 | B |
| ATOM | 2681 | CB | ARG | B | 160 | 40.653 | 29.441 | -5.495 | 1.00 | 30.98 | B |
| ATOM | 2682 | CG | ARG | B | 160 | 39.461 | 30.230 | -6.037 | 1.00 | 31.37 | B |
| ATOM | 2683 | CD | ARG | B | 160 | 39.911 | 31.533 | -6.700 | 1.00 | 31.10 | B |
| ATOM | 2684 | NE | ARG | B | 160 | 40.646 | 32.394 | -5.780 | 1.00 | 29.77 | B |
| ATOM | 2685 | CZ | ARG | B | 160 | 40.076 | 33.193 | -4.884 | 1.00 | 31.59 | B |
| ATOM | 2686 | NH1 | ARG | B | 160 | 40.831 | 33.937 | -4.083 | 1.00 | 29.73 | B |
| ATOM | 2687 | NH2 | ARG | B | 160 | 38.752 | 33.259 | -4.795 | 1.00 | 30.73 | B |
| ATOM | 2688 | C | ARG | B | 160 | 41.634 | 27.208 | -4.900 | 1.00 | 31.82 | B |
| ATOM | 2689 | O | ARG | B | 160 | 42.092 | 26.421 | -5.731 | 1.00 | 32.25 | B |
| ATOM | 2690 | N | GLU | B | 161 | 42.203 | 27.430 | -3.716 | 1.00 | 32.54 | B |
| ATOM | 2691 | CA | GLU | B | 161 | 43.437 | 26.756 | -3.318 | 1.00 | 34.73 | B |
| ATOM | 2692 | CB | GLU | B | 161 | 43.825 | 27.137 | -1.882 | 1.00 | 37.02 | B |
| ATOM | 2693 | CG | GLU | B | 161 | 43.967 | 28.641 | -1.663 | 1.00 | 43.79 | B |
| ATOM | 2694 | CD | GLU | B | 161 | 44.383 | 29.020 | -0.238 | 1.00 | 48.29 | B |
| ATOM | 2695 | OE1 | GLU | B | 161 | 43.776 | 28.508 | 0.738 | 1.00 | 49.30 | B |
| ATOM | 2696 | OE2 | GLU | B | 161 | 45.312 | 29.849 | -0.097 | 1.00 | 49.07 | B |
| ATOM | 2697 | C | GLU | B | 161 | 43.258 | 25.245 | -3.424 | 1.00 | 33.52 | B |
| ATOM | 2698 | O | GLU | B | 161 | 44.163 | 24.533 | -3.864 | 1.00 | 33.87 | B |
| ATOM | 2699 | N | ARG | B | 162 | 42.081 | 24.759 | -3.044 | 1.00 | 31.53 | B |
| ATOM | 2700 | CA | ARG | B | 162 | 41.808 | 23.330 | -3.112 | 1.00 | 31.53 | B |
| ATOM | 2701 | CB | ARG | B | 162 | 40.460 | 23.008 | -2.462 | 1.00 | 31.79 | B |
| ATOM | 2702 | CG | ARG | B | 162 | 40.461 | 23.185 | -0.950 | 1.00 | 31.42 | B |
| ATOM | 2703 | CD | ARG | B | 162 | 39.257 | 22.514 | -0.302 | 1.00 | 30.06 | B |
| ATOM | 2704 | NE | ARG | B | 162 | 39.396 | 22.456 | 1.152 | 1.00 | 25.67 | B |
| ATOM | 2705 | CZ | ARG | B | 162 | 39.079 | 21.393 | 1.883 | 1.00 | 25.92 | B |
| ATOM | 2706 | NH1 | ARG | B | 162 | 38.603 | 20.301 | 1.291 | 1.00 | 24.81 | B |
| ATOM | 2707 | NH2 | ARG | B | 162 | 39.242 | 21.416 | 3.204 | 1.00 | 22.31 | B |
| ATOM | 2708 | C | ARG | B | 162 | 41.833 | 22.791 | -4.539 | 1.00 | 31.03 | B |
| ATOM | 2709 | O | ARG | B | 162 | 42.424 | 21.744 | -4.795 | 1.00 | 30.48 | B |
| ATOM | 2710 | N | PHE | B | 163 | 41.188 | 23.497 | -5.464 | 1.00 | 30.39 | B |
| ATOM | 2711 | CA | PHE | B | 163 | 41.162 | 23.065 | -6.858 | 1.00 | 30.94 | B |
| ATOM | 2712 | CB | PHE | B | 163 | 40.353 | 24.043 | -7.717 | 1.00 | 28.66 | B |
| ATOM | 2713 | CG | PHE | B | 163 | 38.885 | 23.738 | -7.775 | 1.00 | 28.16 | B |
| ATOM | 2714 | CD1 | PHE | B | 163 | 38.434 | 22.521 | -8.284 | 1.00 | 27.08 | B |
| ATOM | 2715 | CD2 | PHE | B | 163 | 37.947 | 24.669 | -7.333 | 1.00 | 27.33 | B |
| ATOM | 2716 | CE1 | PHE | B | 163 | 37.070 | 22.238 | -8.353 | 1.00 | 26.68 | B |
| ATOM | 2717 | CE2 | PHE | B | 163 | 36.582 | 24.392 | -7.399 | 1.00 | 25.12 | B |
| ATOM | 2718 | CZ | PHE | B | 163 | 36.144 | 23.177 | -7.909 | 1.00 | 26.54 | B |
| ATOM | 2719 | C | PHE | B | 163 | 42.583 | 22.989 | -7.401 | 1.00 | 32.61 | B |
| ATOM | 2720 | O | PHE | B | 163 | 42.966 | 22.020 | -8.054 | 1.00 | 32.82 | B |
| ATOM | 2721 | N | LYS | B | 164 | 43.358 | 24.026 | -7.115 | 1.00 | 34.44 | B |
| ATOM | 2722 | CA | LYS | B | 164 | 44.735 | 24.112 | -7.575 | 1.00 | 36.96 | B |
| ATOM | 2723 | CB | LYS | B | 164 | 45.305 | 25.491 | -7.232 | 1.00 | 37.86 | B |
| ATOM | 2724 | CG | LYS | B | 164 | 46.806 | 25.618 | -7.450 | 1.00 | 40.72 | B |
| ATOM | 2725 | CD | LYS | B | 164 | 47.318 | 26.974 | -6.994 | 1.00 | 42.94 | B |
| ATOM | 2726 | CE | LYS | B | 164 | 48.836 | 27.048 | -7.072 | 1.00 | 44.06 | B |
| ATOM | 2727 | NZ | LYS | B | 164 | 49.324 | 28.386 | -6.655 | 1.00 | 45.06 | B |
| ATOM | 2728 | C | LYS | B | 164 | 45.616 | 23.017 | -6.974 | 1.00 | 37.32 | B |
| ATOM | 2729 | O | LYS | B | 164 | 46.393 | 22.374 | -7.689 | 1.00 | 36.91 | B |
| ATOM | 2730 | N | SER | B | 165 | 45.486 | 22.796 | -5.668 | 1.00 | 36.37 | B |
| ATOM | 2731 | CA | SER | B | 165 | 46.294 | 21.788 | -4.989 | 1.00 | 36.51 | B |
| ATOM | 2732 | CB | SER | B | 165 | 46.499 | 22.177 | -3.523 | 1.00 | 36.88 | B |
| ATOM | 2733 | OG | SER | B | 165 | 45.265 | 22.283 | -2.842 | 1.00 | 39.69 | B |
| ATOM | 2734 | C | SER | B | 165 | 45.727 | 20.375 | -5.076 | 1.00 | 35.66 | B |
| ATOM | 2735 | O | SER | B | 165 | 46.263 | 19.449 | -4.471 | 1.00 | 35.12 | B |
| ATOM | 2736 | N | LYS | B | 166 | 44.644 | 20.216 | -5.827 | 1.00 | 36.18 | B |
| ATOM | 2737 | CA | LYS | B | 166 | 44.012 | 18.911 | -6.018 | 1.00 | 36.38 | B |
| ATOM | 2738 | CB | LYS | B | 166 | 45.051 | 17.913 | -6.541 | 1.00 | 37.61 | B |
| ATOM | 2739 | CG | LYS | B | 166 | 45.706 | 18.347 | -7.847 | 1.00 | 39.09 | B |
| ATOM | 2740 | CD | LYS | B | 166 | 44.675 | 18.518 | -8.947 | 1.00 | 39.27 | B |

Figure 9 (43 of 92)

| ATOM | 2741 | CE  | LYS | B | 166 | 43.946 | 17.210 | -9.218  | 1.00 | 40.45 | B |
|------|------|-----|-----|---|-----|--------|--------|---------|------|-------|---|
| ATOM | 2742 | NZ  | LYS | B | 166 | 42.853 | 17.378 | -10.214 | 1.00 | 40.94 | B |
| ATOM | 2743 | C   | LYS | B | 166 | 43.288 | 18.313 | -4.804  | 1.00 | 35.58 | B |
| ATOM | 2744 | O   | LYS | B | 166 | 42.982 | 17.121 | -4.788  | 1.00 | 35.37 | B |
| ATOM | 2745 | N   | LYS | B | 167 | 43.012 | 19.133 | -3.795  | 1.00 | 35.82 | B |
| ATOM | 2746 | CA  | LYS | B | 167 | 42.298 | 18.666 | -2.607  | 1.00 | 34.81 | B |
| ATOM | 2747 | CB  | LYS | B | 167 | 42.540 | 19.611 | -1.433  | 1.00 | 37.27 | B |
| ATOM | 2748 | CG  | LYS | B | 167 | 43.983 | 19.713 | -0.971  | 1.00 | 39.82 | B |
| ATOM | 2749 | CD  | LYS | B | 167 | 44.083 | 20.650 | 0.225   | 1.00 | 42.30 | B |
| ATOM | 2750 | CE  | LYS | B | 167 | 45.486 | 20.685 | 0.808   | 1.00 | 44.98 | B |
| ATOM | 2751 | NZ  | LYS | B | 167 | 45.537 | 21.570 | 2.011   | 1.00 | 46.74 | B |
| ATOM | 2752 | C   | LYS | B | 167 | 40.797 | 18.620 | -2.912  | 1.00 | 33.51 | B |
| ATOM | 2753 | O   | LYS | B | 167 | 40.324 | 19.291 | -3.828  | 1.00 | 33.76 | B |
| ATOM | 2754 | N   | PRO | B | 168 | 40.030 | 17.825 | -2.149  | 1.00 | 31.95 | B |
| ATOM | 2755 | CD  | PRO | B | 168 | 40.525 | 16.820 | -1.193  | 1.00 | 32.01 | B |
| ATOM | 2756 | CA  | PRO | B | 168 | 38.579 | 17.687 | -2.333  | 1.00 | 29.87 | B |
| ATOM | 2757 | CB  | PRO | B | 168 | 38.192 | 16.686 | -1.251  | 1.00 | 30.48 | B |
| ATOM | 2758 | CG  | PRO | B | 168 | 39.392 | 15.812 | -1.180  | 1.00 | 32.04 | B |
| ATOM | 2759 | C   | PRO | B | 168 | 37.781 | 18.985 | -2.208  | 1.00 | 28.10 | B |
| ATOM | 2760 | O   | PRO | B | 168 | 38.200 | 19.923 | -1.528  | 1.00 | 26.82 | B |
| ATOM | 2761 | N   | THR | B | 169 | 36.633 | 19.031 | -2.881  | 1.00 | 25.51 | B |
| ATOM | 2762 | CA  | THR | B | 169 | 35.752 | 20.191 | -2.822  | 1.00 | 25.26 | B |
| ATOM | 2763 | CB  | THR | B | 169 | 35.711 | 20.980 | -4.169  | 1.00 | 23.99 | B |
| ATOM | 2764 | OG1 | THR | B | 169 | 35.125 | 20.166 | -5.189  | 1.00 | 26.35 | B |
| ATOM | 2765 | CG2 | THR | B | 169 | 37.108 | 21.389 | -4.598  | 1.00 | 23.54 | B |
| ATOM | 2766 | C   | THR | B | 169 | 34.335 | 19.725 | -2.480  | 1.00 | 24.67 | B |
| ATOM | 2767 | O   | THR | B | 169 | 33.439 | 20.548 | -2.292  | 1.00 | 22.92 | B |
| ATOM | 2768 | N   | ASP | B | 170 | 34.150 | 18.407 | -2.389  | 1.00 | 22.60 | B |
| ATOM | 2769 | CA  | ASP | B | 170 | 32.845 | 17.823 | -2.070  | 1.00 | 22.96 | B |
| ATOM | 2770 | CB  | ASP | B | 170 | 32.937 | 16.308 | -1.875  | 1.00 | 25.62 | B |
| ATOM | 2771 | CG  | ASP | B | 170 | 33.660 | 15.607 | -3.005  | 1.00 | 29.03 | B |
| ATOM | 2772 | OD1 | ASP | B | 170 | 34.889 | 15.801 | -3.131  | 1.00 | 31.84 | B |
| ATOM | 2773 | OD2 | ASP | B | 170 | 33.002 | 14.858 | -3.755  | 1.00 | 27.76 | B |
| ATOM | 2774 | C   | ASP | B | 170 | 32.268 | 18.401 | -0.788  | 1.00 | 21.48 | B |
| ATOM | 2775 | O   | ASP | B | 170 | 32.997 | 18.629 | 0.181   | 1.00 | 19.42 | B |
| ATOM | 2776 | N   | TYR | B | 171 | 30.953 | 18.609 | -0.801  | 1.00 | 19.93 | B |
| ATOM | 2777 | CA  | TYR | B | 171 | 30.196 | 19.133 | 0.331   | 1.00 | 20.77 | B |
| ATOM | 2778 | CB  | TYR | B | 171 | 30.438 | 18.264 | 1.580   | 1.00 | 20.03 | B |
| ATOM | 2779 | CG  | TYR | B | 171 | 30.258 | 16.777 | 1.302   | 1.00 | 22.54 | B |
| ATOM | 2780 | CD1 | TYR | B | 171 | 31.344 | 15.906 | 1.319   | 1.00 | 21.98 | B |
| ATOM | 2781 | CE1 | TYR | B | 171 | 31.193 | 14.554 | 0.978   | 1.00 | 23.55 | B |
| ATOM | 2782 | CD2 | TYR | B | 171 | 29.009 | 16.263 | 0.942   | 1.00 | 22.75 | B |
| ATOM | 2783 | CE2 | TYR | B | 171 | 28.846 | 14.920 | 0.598   | 1.00 | 23.54 | B |
| ATOM | 2784 | CZ  | TYR | B | 171 | 29.939 | 14.071 | 0.616   | 1.00 | 23.78 | B |
| ATOM | 2785 | OH  | TYR | B | 171 | 29.781 | 12.743 | 0.271   | 1.00 | 21.58 | B |
| ATOM | 2786 | C   | TYR | B | 171 | 30.481 | 20.599 | 0.639   | 1.00 | 21.60 | B |
| ATOM | 2787 | O   | TYR | B | 171 | 29.836 | 21.191 | 1.507   | 1.00 | 21.72 | B |
| ATOM | 2788 | N   | LEU | B | 172 | 31.436 | 21.188 | -0.076  | 1.00 | 21.91 | B |
| ATOM | 2789 | CA  | LEU | B | 172 | 31.778 | 22.593 | 0.131   | 1.00 | 22.12 | B |
| ATOM | 2790 | CB  | LEU | B | 172 | 33.294 | 22.779 | 0.102   | 1.00 | 22.29 | B |
| ATOM | 2791 | CG  | LEU | B | 172 | 34.101 | 22.043 | 1.178   | 1.00 | 23.12 | B |
| ATOM | 2792 | CD1 | LEU | B | 172 | 35.589 | 22.272 | 0.935   | 1.00 | 21.22 | B |
| ATOM | 2793 | CD2 | LEU | B | 172 | 33.708 | 22.543 | 2.568   | 1.00 | 21.66 | B |
| ATOM | 2794 | C   | LEU | B | 172 | 31.130 | 23.476 | -0.934  | 1.00 | 22.22 | B |
| ATOM | 2795 | O   | LEU | B | 172 | 30.743 | 24.614 | -0.660  | 1.00 | 21.57 | B |
| ATOM | 2796 | N   | ILE | B | 173 | 31.016 | 22.940 | -2.148  | 1.00 | 22.40 | B |
| ATOM | 2797 | CA  | ILE | B | 173 | 30.415 | 23.652 | -3.272  | 1.00 | 21.94 | B |
| ATOM | 2798 | CB  | ILE | B | 173 | 31.488 | 24.102 | -4.311  | 1.00 | 23.60 | B |
| ATOM | 2799 | CG2 | ILE | B | 173 | 32.425 | 25.110 | -3.687  | 1.00 | 20.55 | B |
| ATOM | 2800 | CG1 | ILE | B | 173 | 32.286 | 22.893 | -4.821  | 1.00 | 23.84 | B |
| ATOM | 2801 | CD1 | ILE | B | 173 | 33.221 | 23.227 | -5.968  | 1.00 | 23.21 | B |
| ATOM | 2802 | C   | ILE | B | 173 | 29.409 | 22.753 | -3.990  | 1.00 | 22.80 | B |
| ATOM | 2803 | O   | ILE | B | 173 | 29.538 | 21.527 | -3.983  | 1.00 | 22.63 | B |
| ATOM | 2804 | N   | PRO | B | 174 | 28.386 | 23.351 | -4.621  | 1.00 | 23.53 | B |
| ATOM | 2805 | CD  | PRO | B | 174 | 28.091 | 24.785 | -4.767  | 1.00 | 21.35 | B |
| ATOM | 2806 | CA  | PRO | B | 174 | 27.392 | 22.536 | -5.328  | 1.00 | 24.18 | B |

Figure 9 (44 of 92)

| | | | | | | | | | | |
|---|---|---|---|---|---|---|---|---|---|---|
| ATOM | 2807 | CB | PRO | B | 174 | 26.404 | 23.576 | -5.863 | 1.00 22.63 | B |
| ATOM | 2808 | CG | PRO | B | 174 | 26.609 | 24.771 | -4.979 | 1.00 22.46 | B |
| ATOM | 2809 | C | PRO | B | 174 | 28.065 | 21.748 | -6.462 | 1.00 25.29 | B |
| ATOM | 2810 | O | PRO | B | 174 | 28.976 | 22.254 | -7.122 | 1.00 24.78 | B |
| ATOM | 2811 | N | ASP | B | 175 | 27.620 | 20.516 | -6.684 | 1.00 27.57 | B |
| ATOM | 2812 | CA | ASP | B | 175 | 28.189 | 19.683 | -7.741 | 1.00 31.03 | B |
| ATOM | 2813 | CB | ASP | B | 175 | 27.427 | 18.358 | -7.849 | 1.00 32.88 | B |
| ATOM | 2814 | CG | ASP | B | 175 | 27.880 | 17.347 | -6.822 | 1.00 36.59 | B |
| ATOM | 2815 | OD1 | ASP | B | 175 | 29.096 | 17.054 | -6.778 | 1.00 37.98 | B |
| ATOM | 2816 | OD2 | ASP | B | 175 | 27.028 | 16.845 | -6.059 | 1.00 39.19 | B |
| ATOM | 2817 | C | ASP | B | 175 | 28.212 | 20.362 | -9.107 | 1.00 31.05 | B |
| ATOM | 2818 | O | ASP | B | 175 | 29.192 | 20.252 | -9.841 | 1.00 31.98 | B |
| ATOM | 2819 | N | LYS | B | 176 | 27.137 | 21.061 | -9.452 | 1.00 30.44 | B |
| ATOM | 2820 | CA | LYS | B | 176 | 27.080 | 21.738 | -10.738 | 1.00 30.95 | B |
| ATOM | 2821 | CB | LYS | B | 176 | 25.675 | 22.298 | -10.976 | 1.00 32.58 | B |
| ATOM | 2822 | CG | LYS | B | 176 | 24.644 | 21.207 | -11.262 | 1.00 34.56 | B |
| ATOM | 2823 | CD | LYS | B | 176 | 23.280 | 21.763 | -11.644 | 1.00 37.46 | B |
| ATOM | 2824 | CE | LYS | B | 176 | 22.661 | 22.556 | -10.503 | 1.00 38.77 | B |
| ATOM | 2825 | NZ | LYS | B | 176 | 21.249 | 22.940 | -10.797 | 1.00 41.08 | B |
| ATOM | 2826 | C | LYS | B | 176 | 28.132 | 22.835 | -10.887 | 1.00 30.06 | B |
| ATOM | 2827 | O | LYS | B | 176 | 28.628 | 23.075 | -11.985 | 1.00 30.15 | B |
| ATOM | 2828 | N | VAL | B | 177 | 28.481 | 23.497 | -9.788 | 1.00 29.38 | B |
| ATOM | 2829 | CA | VAL | B | 177 | 29.483 | 24.552 | -9.843 | 1.00 26.92 | B |
| ATOM | 2830 | CB | VAL | B | 177 | 29.485 | 25.398 | -8.557 | 1.00 24.31 | B |
| ATOM | 2831 | CG1 | VAL | B | 177 | 30.664 | 26.347 | -8.568 | 1.00 22.22 | B |
| ATOM | 2832 | CG2 | VAL | B | 177 | 28.185 | 26.176 | -8.446 | 1.00 20.91 | B |
| ATOM | 2833 | C | VAL | B | 177 | 30.853 | 23.918 | -10.033 | 1.00 28.32 | B |
| ATOM | 2834 | O | VAL | B | 177 | 31.688 | 24.422 | -10.782 | 1.00 28.58 | B |
| ATOM | 2835 | N | LYS | B | 178 | 31.079 | 22.804 | -9.348 | 1.00 29.98 | B |
| ATOM | 2836 | CA | LYS | B | 178 | 32.339 | 22.084 | -9.459 | 1.00 31.49 | B |
| ATOM | 2837 | CB | LYS | B | 178 | 32.333 | 20.880 | -8.521 | 1.00 32.98 | B |
| ATOM | 2838 | CG | LYS | B | 178 | 33.380 | 19.823 | -8.841 | 1.00 35.37 | B |
| ATOM | 2839 | CD | LYS | B | 178 | 33.210 | 18.622 | -7.928 | 1.00 37.36 | B |
| ATOM | 2840 | CE | LYS | B | 178 | 34.158 | 17.509 | -8.302 | 1.00 38.92 | B |
| ATOM | 2841 | NZ | LYS | B | 178 | 33.987 | 16.345 | -7.392 | 1.00 41.61 | B |
| ATOM | 2842 | C | LYS | B | 178 | 32.516 | 21.608 | -10.900 | 1.00 32.38 | B |
| ATOM | 2843 | O | LYS | B | 178 | 33.617 | 21.661 | -11.463 | 1.00 31.19 | B |
| ATOM | 2844 | N | LYS | B | 179 | 31.419 | 21.142 | -11.486 | 1.00 32.03 | B |
| ATOM | 2845 | CA | LYS | B | 179 | 31.428 | 20.651 | -12.856 | 1.00 34.22 | B |
| ATOM | 2846 | CB | LYS | B | 179 | 30.049 | 20.086 | -13.216 | 1.00 34.36 | B |
| ATOM | 2847 | CG | LYS | B | 179 | 29.933 | 19.573 | -14.643 | 1.00 39.78 | B |
| ATOM | 2848 | CD | LYS | B | 179 | 28.552 | 18.983 | -14.923 | 1.00 40.92 | B |
| ATOM | 2849 | CE | LYS | B | 179 | 28.426 | 18.534 | -16.374 | 1.00 43.41 | B |
| ATOM | 2850 | NZ | LYS | B | 179 | 27.065 | 18.003 | -16.696 | 1.00 43.17 | B |
| ATOM | 2851 | C | LYS | B | 179 | 31.800 | 21.779 | -13.810 | 1.00 34.59 | B |
| ATOM | 2852 | O | LYS | B | 179 | 32.540 | 21.573 | -14.772 | 1.00 35.64 | B |
| ATOM | 2853 | N | TYR | B | 180 | 31.289 | 22.976 | -13.536 | 1.00 34.24 | B |
| ATOM | 2854 | CA | TYR | B | 180 | 31.581 | 24.126 | -14.380 | 1.00 34.84 | B |
| ATOM | 2855 | CB | TYR | B | 180 | 30.780 | 25.349 | -13.929 | 1.00 32.57 | B |
| ATOM | 2856 | CG | TYR | B | 180 | 30.921 | 26.530 | -14.863 | 1.00 30.96 | B |
| ATOM | 2857 | CD1 | TYR | B | 180 | 30.135 | 26.635 | -16.010 | 1.00 30.48 | B |
| ATOM | 2858 | CE1 | TYR | B | 180 | 30.268 | 27.723 | -16.877 | 1.00 29.62 | B |
| ATOM | 2859 | CD2 | TYR | B | 180 | 31.846 | 27.537 | -14.607 | 1.00 29.86 | B |
| ATOM | 2860 | CE2 | TYR | B | 180 | 31.989 | 28.625 | -15.466 | 1.00 30.50 | B |
| ATOM | 2861 | CZ | TYR | B | 180 | 31.197 | 28.711 | -16.596 | 1.00 29.03 | B |
| ATOM | 2862 | OH | TYR | B | 180 | 31.330 | 29.788 | -17.434 | 1.00 29.62 | B |
| ATOM | 2863 | C | TYR | B | 180 | 33.071 | 24.438 | -14.302 | 1.00 35.08 | B |
| ATOM | 2864 | O | TYR | B | 180 | 33.729 | 24.645 | -15.322 | 1.00 34.86 | B |
| ATOM | 2865 | N | VAL | B | 181 | 33.597 | 24.470 | -13.082 | 1.00 35.35 | B |
| ATOM | 2866 | CA | VAL | B | 181 | 35.012 | 24.744 | -12.872 | 1.00 35.95 | B |
| ATOM | 2867 | CB | VAL | B | 181 | 35.381 | 24.612 | -11.380 | 1.00 34.98 | B |
| ATOM | 2868 | CG1 | VAL | B | 181 | 36.878 | 24.792 | -11.188 | 1.00 33.83 | B |
| ATOM | 2869 | CG2 | VAL | B | 181 | 34.607 | 25.640 | -10.565 | 1.00 34.35 | B |
| ATOM | 2870 | C | VAL | B | 181 | 35.857 | 23.761 | -13.683 | 1.00 37.54 | B |
| ATOM | 2871 | O | VAL | B | 181 | 36.844 | 24.146 | -14.309 | 1.00 35.84 | B |
| ATOM | 2872 | N | GLU | B | 182 | 35.450 | 22.493 | -13.674 | 1.00 39.96 | B |

Figure 9 (45 of 92)

| | | | | | | | | | | |
|---|---|---|---|---|---|---|---|---|---|---|
| ATOM | 2873 | CA | GLU | B | 182 | 36.166 | 21.446 | -14.395 | 1.00 43.07 | B |
| ATOM | 2874 | CB | GLU | B | 182 | 35.638 | 20.071 | -13.978 | 1.00 43.93 | B |
| ATOM | 2875 | CG | GLU | B | 182 | 35.710 | 19.810 | -12.483 | 1.00 46.03 | B |
| ATOM | 2876 | CD | GLU | B | 182 | 35.088 | 18.479 | -12.079 | 1.00 47.62 | B |
| ATOM | 2877 | OE1 | GLU | B | 182 | 33.988 | 18.155 | -12.581 | 1.00 48.58 | B |
| ATOM | 2878 | OE2 | GLU | B | 182 | 35.690 | 17.765 | -11.245 | 1.00 47.12 | B |
| ATOM | 2879 | C | GLU | B | 182 | 36.064 | 21.589 | -15.915 | 1.00 44.29 | B |
| ATOM | 2880 | O | GLU | B | 182 | 37.072 | 21.547 | -16.616 | 1.00 45.34 | B |
| ATOM | 2881 | N | GLU | B | 183 | 34.846 | 21.763 | -16.419 | 1.00 45.24 | B |
| ATOM | 2882 | CA | GLU | B | 183 | 34.628 | 21.884 | -17.856 | 1.00 45.82 | B |
| ATOM | 2883 | CB | GLU | B | 183 | 33.135 | 21.803 | -18.175 | 1.00 46.85 | B |
| ATOM | 2884 | CG | GLU | B | 183 | 32.445 | 20.562 | -17.635 | 1.00 48.76 | B |
| ATOM | 2885 | CD | GLU | B | 183 | 30.988 | 20.491 | -18.047 | 1.00 50.58 | B |
| ATOM | 2886 | OE1 | GLU | B | 183 | 30.317 | 21.548 | -18.025 | 1.00 50.36 | B |
| ATOM | 2887 | OE2 | GLU | B | 183 | 30.511 | 19.384 | -18.382 | 1.00 50.52 | B |
| ATOM | 2888 | C | GLU | B | 183 | 35.191 | 23.164 | -18.459 | 1.00 46.36 | B |
| ATOM | 2889 | O | GLU | B | 183 | 35.184 | 23.326 | -19.679 | 1.00 47.23 | B |
| ATOM | 2890 | N | ASN | B | 184 | 35.681 | 24.067 | -17.614 | 1.00 45.66 | B |
| ATOM | 2891 | CA | ASN | B | 184 | 36.234 | 25.330 | -18.090 | 1.00 44.03 | B |
| ATOM | 2892 | CB | ASN | B | 184 | 35.352 | 26.491 | -17.622 | 1.00 44.20 | B |
| ATOM | 2893 | CG | ASN | B | 184 | 34.022 | 26.547 | -18.360 | 1.00 44.09 | B |
| ATOM | 2894 | OD1 | ASN | B | 184 | 33.959 | 26.974 | -19.514 | 1.00 44.64 | B |
| ATOM | 2895 | ND2 | ASN | B | 184 | 32.957 | 26.105 | -17.701 | 1.00 42.12 | B |
| ATOM | 2896 | C | ASN | B | 184 | 37.674 | 25.554 | -17.640 | 1.00 43.60 | B |
| ATOM | 2897 | O | ASN | B | 184 | 38.231 | 26.638 | -17.827 | 1.00 43.53 | B |
| ATOM | 2898 | N | GLY | B | 185 | 38.269 | 24.523 | -17.050 | 1.00 43.34 | B |
| ATOM | 2899 | CA | GLY | B | 185 | 39.646 | 24.607 | -16.589 | 1.00 42.37 | B |
| ATOM | 2900 | C | GLY | B | 185 | 39.957 | 25.763 | -15.661 | 1.00 42.25 | B |
| ATOM | 2901 | O | GLY | B | 185 | 41.077 | 26.274 | -15.651 | 1.00 43.18 | B |
| ATOM | 2902 | N | LEU | B | 186 | 38.975 | 26.175 | -14.867 | 1.00 41.31 | B |
| ATOM | 2903 | CA | LEU | B | 186 | 39.170 | 27.282 | -13.940 | 1.00 40.57 | B |
| ATOM | 2904 | CB | LEU | B | 186 | 37.817 | 27.840 | -13.497 | 1.00 40.73 | B |
| ATOM | 2905 | CG | LEU | B | 186 | 36.935 | 28.501 | -14.556 | 1.00 41.18 | B |
| ATOM | 2906 | CD1 | LEU | B | 186 | 35.589 | 28.850 | -13.942 | 1.00 40.32 | B |
| ATOM | 2907 | CD2 | LEU | B | 186 | 37.622 | 29.750 | -15.096 | 1.00 40.56 | B |
| ATOM | 2908 | C | LEU | B | 186 | 39.971 | 26.881 | -12.703 | 1.00 40.20 | B |
| ATOM | 2909 | O | LEU | B | 186 | 39.979 | 25.718 | -12.303 | 1.00 40.32 | B |
| ATOM | 2910 | N | TYR | B | 187 | 40.649 | 27.861 | -12.116 | 1.00 40.42 | B |
| ATOM | 2911 | CA | TYR | B | 187 | 41.440 | 27.678 | -10.902 | 1.00 41.58 | B |
| ATOM | 2912 | CB | TYR | B | 187 | 40.497 | 27.333 | -9.741 | 1.00 39.11 | B |
| ATOM | 2913 | CG | TYR | B | 187 | 39.305 | 28.265 | -9.659 | 1.00 37.19 | B |
| ATOM | 2914 | CD1 | TYR | B | 187 | 39.480 | 29.648 | -9.603 | 1.00 36.39 | B |
| ATOM | 2915 | CE1 | TYR | B | 187 | 38.385 | 30.516 | -9.559 | 1.00 36.05 | B |
| ATOM | 2916 | CD2 | TYR | B | 187 | 38.000 | 27.769 | -9.666 | 1.00 37.54 | B |
| ATOM | 2917 | CE2 | TYR | B | 187 | 36.896 | 28.629 | -9.623 | 1.00 35.46 | B |
| ATOM | 2918 | CZ | TYR | B | 187 | 37.099 | 30.000 | -9.570 | 1.00 35.69 | B |
| ATOM | 2919 | OH | TYR | B | 187 | 36.022 | 30.856 | -9.537 | 1.00 34.01 | B |
| ATOM | 2920 | C | TYR | B | 187 | 42.593 | 26.670 | -10.974 | 1.00 43.86 | B |
| ATOM | 2921 | O | TYR | B | 187 | 42.680 | 25.745 | -10.159 | 1.00 43.36 | B |
| ATOM | 2922 | N | GLU | B | 188 | 43.480 | 26.872 | -11.949 | 1.00 46.08 | B |
| ATOM | 2923 | CA | GLU | B | 188 | 44.660 | 26.030 | -12.151 | 1.00 46.97 | B |
| ATOM | 2924 | CB | GLU | B | 188 | 45.807 | 26.531 | -11.268 | 1.00 48.03 | B |
| ATOM | 2925 | CG | GLU | B | 188 | 46.285 | 27.927 | -11.632 | 1.00 50.28 | B |
| ATOM | 2926 | CD | GLU | B | 188 | 46.995 | 28.618 | -10.488 | 1.00 51.28 | B |
| ATOM | 2927 | OE1 | GLU | B | 188 | 48.001 | 28.073 | -9.992 | 1.00 52.81 | B |
| ATOM | 2928 | OE2 | GLU | B | 188 | 46.542 | 29.710 | -10.082 | 1.00 52.42 | B |
| ATOM | 2929 | C | GLU | B | 188 | 44.419 | 24.546 | -11.898 | 1.00 47.32 | B |
| ATOM | 2930 | O | GLU | B | 188 | 43.275 | 24.090 | -12.102 | 1.00 47.57 | B |
| ATOM | 2931 | OXT | GLU | B | 188 | 45.389 | 23.854 | -11.520 | 1.00 47.00 | B |
| ATOM | 2932 | CB | SER | C | 1 | 53.161 | 62.551 | 15.177 | 1.00 35.07 | C |
| ATOM | 2933 | OG | SER | C | 1 | 53.888 | 62.305 | 16.367 | 1.00 35.15 | C |
| ATOM | 2934 | C | SER | C | 1 | 52.781 | 60.089 | 15.041 | 1.00 33.50 | C |
| ATOM | 2935 | O | SER | C | 1 | 53.616 | 59.267 | 15.407 | 1.00 34.47 | C |
| ATOM | 2936 | N | SER | C | 1 | 52.359 | 61.558 | 13.052 | 1.00 34.63 | C |
| ATOM | 2937 | CA | SER | C | 1 | 53.210 | 61.331 | 14.258 | 1.00 34.35 | C |
| ATOM | 2938 | N | LYS | C | 2 | 51.485 | 59.962 | 15.309 | 1.00 31.87 | C |

Figure 9 (46 of 92)

| | | | | | | | | | | |
|---|---|---|---|---|---|---|---|---|---|---|
| ATOM | 2939 | CA | LYS | C | 2 | 50.967 | 58.801 | 16.035 | 1.00 31.37 | C |
| ATOM | 2940 | CB | LYS | C | 2 | 50.273 | 59.232 | 17.325 | 1.00 32.12 | C |
| ATOM | 2941 | CG | LYS | C | 2 | 51.173 | 59.694 | 18.453 | 1.00 35.79 | C |
| ATOM | 2942 | CD | LYS | C | 2 | 50.292 | 60.098 | 19.633 | 1.00 36.54 | C |
| ATOM | 2943 | CE | LYS | C | 2 | 51.083 | 60.348 | 20.898 | 1.00 38.57 | C |
| ATOM | 2944 | NZ | LYS | C | 2 | 50.157 | 60.614 | 22.036 | 1.00 39.81 | C |
| ATOM | 2945 | C | LYS | C | 2 | 49.957 | 57.997 | 15.214 | 1.00 29.15 | C |
| ATOM | 2946 | O | LYS | C | 2 | 49.137 | 58.565 | 14.492 | 1.00 29.13 | C |
| ATOM | 2947 | N | LYS | C | 3 | 50.022 | 56.674 | 15.327 | 1.00 27.04 | C |
| ATOM | 2948 | CA | LYS | C | 3 | 49.075 | 55.802 | 14.641 | 1.00 25.65 | C |
| ATOM | 2949 | CB | LYS | C | 3 | 49.776 | 54.562 | 14.083 | 1.00 26.20 | C |
| ATOM | 2950 | CG | LYS | C | 3 | 50.707 | 54.833 | 12.901 | 1.00 29.61 | C |
| ATOM | 2951 | CD | LYS | C | 3 | 51.268 | 53.521 | 12.348 | 1.00 32.56 | C |
| ATOM | 2952 | CE | LYS | C | 3 | 52.228 | 53.752 | 11.199 | 1.00 34.88 | C |
| ATOM | 2953 | NZ | LYS | C | 3 | 53.342 | 54.642 | 11.619 | 1.00 37.46 | C |
| ATOM | 2954 | C | LYS | C | 3 | 48.065 | 55.400 | 15.719 | 1.00 24.32 | C |
| ATOM | 2955 | O | LYS | C | 3 | 48.390 | 54.643 | 16.636 | 1.00 23.29 | C |
| ATOM | 2956 | N | ILE | C | 4 | 46.850 | 55.920 | 15.614 | 1.00 22.67 | C |
| ATOM | 2957 | CA | ILE | C | 4 | 45.817 | 55.651 | 16.599 | 1.00 21.01 | C |
| ATOM | 2958 | CB | ILE | C | 4 | 45.096 | 56.969 | 17.033 | 1.00 22.05 | C |
| ATOM | 2959 | CG2 | ILE | C | 4 | 44.076 | 56.672 | 18.123 | 1.00 16.38 | C |
| ATOM | 2960 | CG1 | ILE | C | 4 | 46.119 | 58.022 | 17.488 | 1.00 21.88 | C |
| ATOM | 2961 | CD1 | ILE | C | 4 | 47.044 | 57.559 | 18.581 | 1.00 25.85 | C |
| ATOM | 2962 | C | ILE | C | 4 | 44.743 | 54.686 | 16.109 | 1.00 20.94 | C |
| ATOM | 2963 | O | ILE | C | 4 | 44.188 | 54.862 | 15.028 | 1.00 22.32 | C |
| ATOM | 2964 | N | GLY | C | 5 | 44.459 | 53.673 | 16.920 | 1.00 19.35 | C |
| ATOM | 2965 | CA | GLY | C | 5 | 43.417 | 52.714 | 16.599 | 1.00 20.63 | C |
| ATOM | 2966 | C | GLY | C | 5 | 42.170 | 53.060 | 17.405 | 1.00 19.18 | C |
| ATOM | 2967 | O | GLY | C | 5 | 42.176 | 52.940 | 18.635 | 1.00 21.18 | C |
| ATOM | 2968 | N | ILE | C | 6 | 41.119 | 53.512 | 16.723 | 1.00 19.34 | C |
| ATOM | 2969 | CA | ILE | C | 6 | 39.847 | 53.875 | 17.365 | 1.00 19.15 | C |
| ATOM | 2970 | CB | ILE | C | 6 | 38.969 | 54.762 | 16.443 | 1.00 20.81 | C |
| ATOM | 2971 | CG2 | ILE | C | 6 | 37.720 | 55.205 | 17.195 | 1.00 18.72 | C |
| ATOM | 2972 | CG1 | ILE | C | 6 | 39.762 | 55.969 | 15.939 | 1.00 21.74 | C |
| ATOM | 2973 | CD1 | ILE | C | 6 | 40.272 | 56.881 | 17.023 | 1.00 24.32 | C |
| ATOM | 2974 | C | ILE | C | 6 | 39.063 | 52.593 | 17.654 | 1.00 17.29 | C |
| ATOM | 2975 | O | ILE | C | 6 | 38.685 | 51.870 | 16.730 | 1.00 16.41 | C |
| ATOM | 2976 | N | PHE | C | 7 | 38.790 | 52.333 | 18.927 | 1.00 17.05 | C |
| ATOM | 2977 | CA | PHE | C | 7 | 38.094 | 51.110 | 19.335 | 1.00 16.78 | C |
| ATOM | 2978 | CB | PHE | C | 7 | 39.052 | 50.314 | 20.237 | 1.00 19.26 | C |
| ATOM | 2979 | CG | PHE | C | 7 | 38.513 | 49.001 | 20.737 | 1.00 21.07 | C |
| ATOM | 2980 | CD1 | PHE | C | 7 | 37.636 | 48.242 | 19.974 | 1.00 21.39 | C |
| ATOM | 2981 | CD2 | PHE | C | 7 | 38.945 | 48.498 | 21.967 | 1.00 21.27 | C |
| ATOM | 2982 | CE1 | PHE | C | 7 | 37.192 | 46.994 | 20.427 | 1.00 24.24 | C |
| ATOM | 2983 | CE2 | PHE | C | 7 | 38.511 | 47.256 | 22.428 | 1.00 22.65 | C |
| ATOM | 2984 | CZ | PHE | C | 7 | 37.630 | 46.499 | 21.654 | 1.00 22.43 | C |
| ATOM | 2985 | C | PHE | C | 7 | 36.754 | 51.396 | 20.028 | 1.00 17.04 | C |
| ATOM | 2986 | O | PHE | C | 7 | 36.702 | 51.667 | 21.223 | 1.00 13.86 | C |
| ATOM | 2987 | N | GLY | C | 8 | 35.665 | 51.318 | 19.267 | 1.00 16.71 | C |
| ATOM | 2988 | CA | GLY | C | 8 | 34.349 | 51.602 | 19.823 | 1.00 17.90 | C |
| ATOM | 2989 | C | GLY | C | 8 | 33.642 | 50.454 | 20.524 | 1.00 17.67 | C |
| ATOM | 2990 | O | GLY | C | 8 | 34.005 | 49.299 | 20.370 | 1.00 15.76 | C |
| ATOM | 2991 | N | GLY | C | 9 | 32.615 | 50.782 | 21.301 | 1.00 18.78 | C |
| ATOM | 2992 | CA | GLY | C | 9 | 31.876 | 49.754 | 22.005 | 1.00 19.22 | C |
| ATOM. | 2993 | C | GLY | C | 9 | 31.002 | 50.314 | 23.109 | 1.00 20.48 | C |
| ATOM | 2994 | O | GLY | C | 9 | 30.963 | 51.527 | 23.333 | 1.00 17.69 | C |
| ATOM | 2995 | N | THR | C | 10 | 30.281 | 49.428 | 23.790 | 1.00 19.86 | C |
| ATOM | 2996 | CA | THR | C | 10 | 29.427 | 49.837 | 24.895 | 1.00 21.15 | C |
| ATOM | 2997 | CB | THR | C | 10 | 28.183 | 48.934 | 25.031 | 1.00 23.19 | C |
| ATOM | 2998 | OG1 | THR | C | 10 | 28.600 | 47.604 | 25.375 | 1.00 26.06 | C |
| ATOM | 2999 | CG2 | THR | C | 10 | 27.397 | 48.903 | 23.718 | 1.00 21.66 | C |
| ATOM | 3000 | C | THR | C | 10 | 30.237 | 49.716 | 26.184 | 1.00 20.32 | C |
| ATOM | 3001 | O | THR | C | 10 | 30.081 | 50.524 | 27.103 | 1.00 19.91 | C |
| ATOM | 3002 | N | PHE | C | 11 | 31.105 | 48.708 | 26.231 | 1.00 18.97 | C |
| ATOM | 3003 | CA | PHE | C | 11 | 31.941 | 48.453 | 27.404 | 1.00 19.67 | C |
| ATOM | 3004 | CB | PHE | C | 11 | 33.056 | 49.504 | 27.490 | 1.00 16.90 | C |

Figure 9 (47 of 92)

```
ATOM   3005  CG   PHE C  11      33.926  49.564  26.256  1.00 18.29      C
ATOM   3006  CD1  PHE C  11      33.899  50.681  25.421  1.00 18.47      C
ATOM   3007  CD2  PHE C  11      34.747  48.488  25.908  1.00 18.31      C
ATOM   3008  CE1  PHE C  11      34.676  50.729  24.251  1.00 18.88      C
ATOM   3009  CE2  PHE C  11      35.527  48.521  24.741  1.00 18.56      C
ATOM   3010  CZ   PHE C  11      35.487  49.651  23.910  1.00 18.18      C
ATOM   3011  C    PHE C  11      31.032  48.498  28.637  1.00 18.69      C
ATOM   3012  O    PHE C  11      31.237  49.267  29.565  1.00 18.79      C
ATOM   3013  N    ASP C  12      30.014  47.655  28.626  1.00 18.29      C
ATOM   3014  CA   ASP C  12      29.051  47.612  29.711  1.00 18.72      C
ATOM   3015  CB   ASP C  12      27.708  48.134  29.180  1.00 18.94      C
ATOM   3016  CG   ASP C  12      26.606  48.128  30.227  1.00 22.88      C
ATOM   3017  OD1  ASP C  12      26.901  48.391  31.411  1.00 23.12      C
ATOM   3018  OD2  ASP C  12      25.435  47.879  29.853  1.00 23.52      C
ATOM   3019  C    ASP C  12      28.929  46.177  30.223  1.00 17.90      C
ATOM   3020  O    ASP C  12      27.915  45.527  30.024  1.00 16.67      C
ATOM   3021  N    PRO C  13      29.962  45.675  30.917  1.00 17.81      C
ATOM   3022  CD   PRO C  13      29.854  44.363  31.587  1.00 17.99      C
ATOM   3023  CA   PRO C  13      31.223  46.322  31.278  1.00 17.14      C
ATOM   3024  CB   PRO C  13      31.436  45.821  32.691  1.00 18.29      C
ATOM   3025  CG   PRO C  13      31.063  44.363  32.539  1.00 18.92      C
ATOM   3026  C    PRO C  13      32.404  45.939  30.371  1.00 17.93      C
ATOM   3027  O    PRO C  13      32.284  45.074  29.498  1.00 17.22      C
ATOM   3028  N    PRO C  14      33.566  46.592  30.567  1.00 17.95      C
ATOM   3029  CD   PRO C  14      33.861  47.678  31.516  1.00 19.86      C
ATOM   3030  CA   PRO C  14      34.744  46.271  29.750  1.00 17.16      C
ATOM   3031  CB   PRO C  14      35.758  47.357  30.125  1.00 17.49      C
ATOM   3032  CG   PRO C  14      34.964  48.418  30.809  1.00 21.20      C
ATOM   3033  C    PRO C  14      35.203  44.905  30.252  1.00 16.75      C
ATOM   3034  O    PRO C  14      34.996  44.581  31.427  1.00 15.48      C
ATOM   3035  N    HIS C  15      35.838  44.115  29.396  1.00 15.27      C
ATOM   3036  CA   HIS C  15      36.276  42.794  29.819  1.00 15.89      C
ATOM   3037  CB   HIS C  15      35.150  41.784  29.577  1.00 16.30      C
ATOM   3038  CG   HIS C  15      34.679  41.733  28.156  1.00 15.85      C
ATOM   3039  CD2  HIS C  15      33.464  41.983  27.608  1.00 17.76      C
ATOM   3040  ND1  HIS C  15      35.493  41.339  27.117  1.00 15.67      C
ATOM   3041  CE1  HIS C  15      34.800  41.343  25.991  1.00 17.31      C
ATOM   3042  NE2  HIS C  15      33.565  41.731  26.260  1.00 14.81      C
ATOM   3043  C    HIS C  15      37.555  42.342  29.120  1.00 16.00      C
ATOM   3044  O    HIS C  15      38.063  43.037  28.232  1.00 15.15      C
ATOM   3045  N    ASN C  16      38.056  41.170  29.517  1.00 14.01      C
ATOM   3046  CA   ASN C  16      39.291  40.618  28.961  1.00 14.38      C
ATOM   3047  CB   ASN C  16      39.618  39.276  29.635  1.00 15.53      C
ATOM   3048  CG   ASN C  16      39.995  39.440  31.106  1.00 17.06      C
ATOM   3049  OD1  ASN C  16      40.109  40.561  31.603  1.00 18.28      C
ATOM   3050  ND2  ASN C  16      40.201  38.324  31.802  1.00 15.13      C
ATOM   3051  C    ASN C  16      39.299  40.461  27.440  1.00 14.31      C
ATOM   3052  O    ASN C  16      40.352  40.568  26.808  1.00 13.12      C
ATOM   3053  N    GLY C  17      38.129  40.201  26.861  1.00 14.51      C
ATOM   3054  CA   GLY C  17      38.027  40.055  25.421  1.00 13.67      C
ATOM   3055  C    GLY C  17      38.319  41.382  24.742  1.00 15.00      C
ATOM   3056  O    GLY C  17      38.934  41.424  23.672  1.00 13.69      C
ATOM   3057  N    HIS C  18      37.882  42.474  25.366  1.00 14.63      C
ATOM   3058  CA   HIS C  18      38.132  43.808  24.826  1.00 14.17      C
ATOM   3059  CB   HIS C  18      37.402  44.869  25.652  1.00 16.59      C
ATOM   3060  CG   HIS C  18      35.915  44.845  25.501  1.00 18.02      C
ATOM   3061  CD2  HIS C  18      35.131  44.757  24.401  1.00 20.79      C
ATOM   3062  ND1  HIS C  18      35.058  44.971  26.572  1.00 18.38      C
ATOM   3063  CE1  HIS C  18      33.810  44.964  26.140  1.00 19.19      C
ATOM   3064  NE2  HIS C  18      33.826  44.836  24.826  1.00 21.34      C
ATOM   3065  C    HIS C  18      39.629  44.098  24.873  1.00 14.25      C
ATOM   3066  O    HIS C  18      40.216  44.560  23.897  1.00 12.00      C
ATOM   3067  N    LEU C  19      40.238  43.831  26.023  1.00 14.33      C
ATOM   3068  CA   LEU C  19      41.665  44.082  26.211  1.00 15.33      C
ATOM   3069  CB   LEU C  19      42.061  43.790  27.660  1.00 13.54      C
ATOM   3070  CG   LEU C  19      41.330  44.644  28.709  1.00 15.01      C
```

Figure 9 (48 of 92)

| ATOM | 3071 | CD1 | LEU | C | 19 | 41.790 | 44.263 | 30.115 | 1.00 | 14.51 | C |
|---|---|---|---|---|---|---|---|---|---|---|---|
| ATOM | 3072 | CD2 | LEU | C | 19 | 41.610 | 46.122 | 28.450 | 1.00 | 12.70 | C |
| ATOM | 3073 | C | LEU | C | 19 | 42.496 | 43.255 | 25.242 | 1.00 | 15.84 | C |
| ATOM | 3074 | O | LEU | C | 19 | 43.428 | 43.760 | 24.611 | 1.00 | 16.78 | C |
| ATOM | 3075 | N | LEU | C | 20 | 42.142 | 41.986 | 25.107 | 1.00 | 15.07 | C |
| ATOM | 3076 | CA | LEU | C | 20 | 42.848 | 41.100 | 24.200 | 1.00 | 15.44 | C |
| ATOM | 3077 | CB | LEU | C | 20 | 42.261 | 39.688 | 24.300 | 1.00 | 15.42 | C |
| ATOM | 3078 | CG | LEU | C | 20 | 42.749 | 38.704 | 23.237 | 1.00 | 16.20 | C |
| ATOM | 3079 | CD1 | LEU | C | 20 | 44.266 | 38.600 | 23.317 | 1.00 | 15.78 | C |
| ATOM | 3080 | CD2 | LEU | C | 20 | 42.101 | 37.332 | 23.446 | 1.00 | 14.46 | C |
| ATOM | 3081 | C | LEU | C | 20 | 42.800 | 41.567 | 22.734 | 1.00 | 16.80 | C |
| ATOM | 3082 | O | LEU | C | 20 | 43.829 | 41.630 | 22.058 | 1.00 | 16.12 | C |
| ATOM | 3083 | N | MET | C | 21 | 41.606 | 41.884 | 22.244 | 1.00 | 16.52 | C |
| ATOM | 3084 | CA | MET | C | 21 | 41.452 | 42.305 | 20.857 | 1.00 | 16.76 | C |
| ATOM | 3085 | CB | MET | C | 21 | 39.980 | 42.553 | 20.536 | 1.00 | 15.22 | C |
| ATOM | 3086 | CG | MET | C | 21 | 39.684 | 42.603 | 19.045 | 1.00 | 14.98 | C |
| ATOM | 3087 | SD | MET | C | 21 | 38.094 | 43.376 | 18.725 | 1.00 | 14.08 | C |
| ATOM | 3088 | CE | MET | C | 21 | 38.679 | 44.844 | 18.548 | 1.00 | 3.58 | C |
| ATOM | 3089 | C | MET | C | 21 | 42.246 | 43.571 | 20.591 | 1.00 | 15.87 | C |
| ATOM | 3090 | O | MET | C | 21 | 42.925 | 43.692 | 19.571 | 1.00 | 16.05 | C |
| ATOM | 3091 | N | ALA | C | 22 | 42.160 | 44.507 | 21.527 | 1.00 | 15.49 | C |
| ATOM | 3092 | CA | ALA | C | 22 | 42.860 | 45.775 | 21.418 | 1.00 | 17.06 | C |
| ATOM | 3093 | CB | ALA | C | 22 | 42.500 | 46.686 | 22.604 | 1.00 | 15.55 | C |
| ATOM | 3094 | C | ALA | C | 22 | 44.365 | 45.589 | 21.343 | 1.00 | 17.36 | C |
| ATOM | 3095 | O | ALA | C | 22 | 45.030 | 46.249 | 20.542 | 1.00 | 16.90 | C |
| ATOM | 3096 | N | ASN | C | 23 | 44.905 | 44.692 | 22.165 | 1.00 | 16.55 | C |
| ATOM | 3097 | CA | ASN | C | 23 | 46.349 | 44.473 | 22.173 | 1.00 | 17.39 | C |
| ATOM | 3098 | CB | ASN | C | 23 | 46.759 | 43.607 | 23.369 | 1.00 | 17.76 | C |
| ATOM | 3099 | CG | ASN | C | 23 | 48.197 | 43.850 | 23.789 | 1.00 | 20.99 | C |
| ATOM | 3100 | OD1 | ASN | C | 23 | 49.041 | 42.943 | 23.756 | 1.00 | 18.28 | C |
| ATOM | 3101 | ND2 | ASN | C | 23 | 48.487 | 45.089 | 24.186 | 1.00 | 17.71 | C |
| ATOM | 3102 | C | ASN | C | 23 | 46.810 | 43.810 | 20.887 | 1.00 | 17.12 | C |
| ATOM | 3103 | O | ASN | C | 23 | 47.873 | 44.131 | 20.362 | 1.00 | 17.43 | C |
| ATOM | 3104 | N | GLU | C | 24 | 46.005 | 42.881 | 20.381 | 1.00 | 16.88 | C |
| ATOM | 3105 | CA | GLU | C | 24 | 46.351 | 42.189 | 19.154 | 1.00 | 18.16 | C |
| ATOM | 3106 | CB | GLU | C | 24 | 45.373 | 41.037 | 18.909 | 1.00 | 17.19 | C |
| ATOM | 3107 | CG | GLU | C | 24 | 45.490 | 39.912 | 19.928 | 1.00 | 18.17 | C |
| ATOM | 3108 | CD | GLU | C | 24 | 46.858 | 39.231 | 19.906 | 1.00 | 19.96 | C |
| ATOM | 3109 | OE1 | GLU | C | 24 | 47.255 | 38.717 | 18.846 | 1.00 | 18.57 | C |
| ATOM | 3110 | OE2 | GLU | C | 24 | 47.541 | 39.198 | 20.948 | 1.00 | 20.07 | C |
| ATOM | 3111 | C | GLU | C | 24 | 46.363 | 43.166 | 17.974 | 1.00 | 17.81 | C |
| ATOM | 3112 | O | GLU | C | 24 | 47.294 | 43.166 | 17.172 | 1.00 | 16.44 | C |
| ATOM | 3113 | N | VAL | C | 25 | 45.344 | 44.011 | 17.877 | 1.00 | 18.69 | C |
| ATOM | 3114 | CA | VAL | C | 25 | 45.284 | 44.982 | 16.787 | 1.00 | 20.05 | C |
| ATOM | 3115 | CB | VAL | C | 25 | 43.960 | 45.776 | 16.808 | 1.00 | 20.27 | C |
| ATOM | 3116 | CG1 | VAL | C | 25 | 44.011 | 46.892 | 15.773 | 1.00 | 18.61 | C |
| ATOM | 3117 | CG2 | VAL | C | 25 | 42.786 | 44.835 | 16.517 | 1.00 | 20.71 | C |
| ATOM | 3118 | C | VAL | C | 25 | 46.452 | 45.959 | 16.894 | 1.00 | 20.51 | C |
| ATOM | 3119 | O | VAL | C | 25 | 47.079 | 46.317 | 15.886 | 1.00 | 20.34 | C |
| ATOM | 3120 | N | LEU | C | 26 | 46.735 | 46.383 | 18.123 | 1.00 | 20.64 | C |
| ATOM | 3121 | CA | LEU | C | 26 | 47.832 | 47.302 | 18.398 | 1.00 | 22.16 | C |
| ATOM | 3122 | CB | LEU | C | 26 | 47.992 | 47.486 | 19.909 | 1.00 | 21.05 | C |
| ATOM | 3123 | CG | LEU | C | 26 | 49.237 | 48.261 | 20.347 | 1.00 | 22.13 | C |
| ATOM | 3124 | CD1 | LEU | C | 26 | 49.057 | 49.748 | 20.070 | 1.00 | 19.98 | C |
| ATOM | 3125 | CD2 | LEU | C | 26 | 49.480 | 48.021 | 21.836 | 1.00 | 21.01 | C |
| ATOM | 3126 | C | LEU | C | 26 | 49.140 | 46.765 | 17.814 | 1.00 | 23.45 | C |
| ATOM | 3127 | O | LEU | C | 26 | 49.838 | 47.464 | 17.079 | 1.00 | 25.77 | C |
| ATOM | 3128 | N | TYR | C | 27 | 49.466 | 45.521 | 18.143 | 1.00 | 23.72 | C |
| ATOM | 3129 | CA | TYR | C | 27 | 50.688 | 44.902 | 17.654 | 1.00 | 25.88 | C |
| ATOM | 3130 | CB | TYR | C | 27 | 50.982 | 43.616 | 18.431 | 1.00 | 29.67 | C |
| ATOM | 3131 | CG | TYR | C | 27 | 52.092 | 42.798 | 17.807 | 1.00 | 34.82 | C |
| ATOM | 3132 | CD1 | TYR | C | 27 | 53.429 | 43.176 | 17.951 | 1.00 | 36.02 | C |
| ATOM | 3133 | CE1 | TYR | C | 27 | 54.452 | 42.464 | 17.329 | 1.00 | 36.84 | C |
| ATOM | 3134 | CD2 | TYR | C | 27 | 51.804 | 41.676 | 17.022 | 1.00 | 35.30 | C |
| ATOM | 3135 | CE2 | TYR | C | 27 | 52.820 | 40.958 | 16.393 | 1.00 | 37.22 | C |
| ATOM | 3136 | CZ | TYR | C | 27 | 54.141 | 41.362 | 16.551 | 1.00 | 37.92 | C |

Figure 9 (49 of 92)

| ATOM | 3137 | OH | TYR | C | 27 | 55.152 | 40.679 | 15.916 | 1.00 | 40.92 | C |
|---|---|---|---|---|---|---|---|---|---|---|---|
| ATOM | 3138 | C | TYR | C | 27 | 50.662 | 44.570 | 16.166 | 1.00 | 25.37 | C |
| ATOM | 3139 | O | TYR | C | 27 | 51.610 | 44.869 | 15.445 | 1.00 | 26.01 | C |
| ATOM | 3140 | N | GLN | C | 28 | 49.578 | 43.955 | 15.707 | 1.00 | 25.58 | C |
| ATOM | 3141 | CA | GLN | C | 28 | 49.470 | 43.552 | 14.309 | 1.00 | 26.17 | C |
| ATOM | 3142 | CB | GLN | C | 28 | 48.331 | 42.557 | 14.148 | 1.00 | 27.69 | C |
| ATOM | 3143 | CG | GLN | C | 28 | 48.667 | 41.213 | 14.743 | 1.00 | 31.36 | C |
| ATOM | 3144 | CD | GLN | C | 28 | 47.527 | 40.251 | 14.637 | 1.00 | 33.30 | C |
| ATOM | 3145 | OE1 | GLN | C | 28 | 47.029 | 39.988 | 13.543 | 1.00 | 32.68 | C |
| ATOM | 3146 | NE2 | GLN | C | 28 | 47.099 | 39.710 | 15.777 | 1.00 | 33.88 | C |
| ATOM | 3147 | C | GLN | C | 28 | 49.340 | 44.639 | 13.258 | 1.00 | 26.17 | C |
| ATOM | 3148 | O | GLN | C | 28 | 49.720 | 44.428 | 12.107 | 1.00 | 24.96 | C |
| ATOM | 3149 | N | ALA | C | 29 | 48.794 | 45.790 | 13.632 | 1.00 | 26.51 | C |
| ATOM | 3150 | CA | ALA | C | 29 | 48.656 | 46.880 | 12.678 | 1.00 | 25.69 | C |
| ATOM | 3151 | CB | ALA | C | 29 | 47.278 | 47.521 | 12.811 | 1.00 | 25.52 | C |
| ATOM | 3152 | C | ALA | C | 29 | 49.759 | 47.911 | 12.928 | 1.00 | 26.04 | C |
| ATOM | 3153 | O | ALA | C | 29 | 49.733 | 49.014 | 12.378 | 1.00 | 26.06 | C |
| ATOM | 3154 | N | GLY | C | 30 | 50.728 | 47.544 | 13.763 | 1.00 | 25.94 | C |
| ATOM | 3155 | CA | GLY | C | 30 | 51.822 | 48.455 | 14.072 | 1.00 | 24.91 | C |
| ATOM | 3156 | C | GLY | C | 30 | 51.352 | 49.835 | 14.503 | 1.00 | 25.03 | C |
| ATOM | 3157 | O | GLY | C | 30 | 51.817 | 50.855 | 13.985 | 1.00 | 24.38 | C |
| ATOM | 3158 | N | LEU | C | 31 | 50.427 | 49.872 | 15.457 | 1.00 | 24.01 | C |
| ATOM | 3159 | CA | LEU | C | 31 | 49.892 | 51.134 | 15.948 | 1.00 | 24.55 | C |
| ATOM | 3160 | CB | LEU | C | 31 | 48.385 | 50.986 | 16.210 | 1.00 | 25.16 | C |
| ATOM | 3161 | CG | LEU | C | 31 | 47.533 | 50.451 | 15.046 | 1.00 | 26.67 | C |
| ATOM | 3162 | CD1 | LEU | C | 31 | 46.075 | 50.372 | 15.471 | 1.00 | 27.64 | C |
| ATOM | 3163 | CD2 | LEU | C | 31 | 47.674 | 51.357 | 13.831 | 1.00 | 25.96 | C |
| ATOM | 3164 | C | LEU | C | 31 | 50.615 | 51.573 | 17.226 | 1.00 | 23.53 | C |
| ATOM | 3165 | O | LEU | C | 31 | 51.330 | 50.789 | 17.840 | 1.00 | 22.08 | C |
| ATOM | 3166 | N | ASP | C | 32 | 50.427 | 52.827 | 17.622 | 1.00 | 24.02 | C |
| ATOM | 3167 | CA | ASP | C | 32 | 51.067 | 53.346 | 18.834 | 1.00 | 23.76 | C |
| ATOM | 3168 | CB | ASP | C | 32 | 51.525 | 54.789 | 18.620 | 1.00 | 24.14 | C |
| ATOM | 3169 | CG | ASP | C | 32 | 52.572 | 54.912 | 17.531 | 1.00 | 26.03 | C |
| ATOM | 3170 | OD1 | ASP | C | 32 | 53.609 | 54.225 | 17.642 | 1.00 | 24.78 | C |
| ATOM | 3171 | OD2 | ASP | C | 32 | 52.361 | 55.696 | 16.575 | 1.00 | 24.85 | C |
| ATOM | 3172 | C | ASP | C | 32 | 50.114 | 53.298 | 20.023 | 1.00 | 23.69 | C |
| ATOM | 3173 | O | ASP | C | 32 | 50.522 | 53.039 | 21.156 | 1.00 | 22.53 | C |
| ATOM | 3174 | N | GLU | C | 33 | 48.840 | 53.562 | 19.763 | 1.00 | 22.84 | C |
| ATOM | 3175 | CA | GLU | C | 33 | 47.849 | 53.543 | 20.827 | 1.00 | 22.63 | C |
| ATOM | 3176 | CB | GLU | C | 33 | 47.602 | 54.969 | 21.349 | 1.00 | 23.07 | C |
| ATOM | 3177 | CG | GLU | C | 33 | 48.832 | 55.702 | 21.883 | 1.00 | 26.86 | C |
| ATOM | 3178 | CD | GLU | C | 33 | 48.549 | 57.167 | 22.184 | 1.00 | 28.69 | C |
| ATOM | 3179 | OE1 | GLU | C | 33 | 49.455 | 57.867 | 22.684 | 1.00 | 31.16 | C |
| ATOM | 3180 | OE2 | GLU | C | 33 | 47.419 | 57.627 | 21.917 | 1.00 | 30.81 | C |
| ATOM | 3181 | C | GLU | C | 33 | 46.529 | 52.980 | 20.330 | 1.00 | 21.18 | C |
| ATOM | 3182 | O | GLU | C | 33 | 46.281 | 52.918 | 19.123 | 1.00 | 22.03 | C |
| ATOM | 3183 | N | ILE | C | 34 | 45.700 | 52.550 | 21.276 | 1.00 | 20.56 | C |
| ATOM | 3184 | CA | ILE | C | 34 | 44.353 | 52.080 | 20.986 | 1.00 | 18.29 | C |
| ATOM | 3185 | CB | ILE | C | 34 | 44.103 | 50.615 | 21.391 | 1.00 | 19.43 | C |
| ATOM | 3186 | CG2 | ILE | C | 34 | 42.592 | 50.296 | 21.263 | 1.00 | 15.98 | C |
| ATOM | 3187 | CG1 | ILE | C | 34 | 44.921 | 49.667 | 20.508 | 1.00 | 18.62 | C |
| ATOM | 3188 | CD1 | ILE | C | 34 | 44.677 | 49.835 | 19.010 | 1.00 | 19.63 | C |
| ATOM | 3189 | C | ILE | C | 34 | 43.477 | 52.968 | 21.863 | 1.00 | 18.53 | C |
| ATOM | 3190 | O | ILE | C | 34 | 43.721 | 53.088 | 23.070 | 1.00 | 17.99 | C |
| ATOM | 3191 | N | TRP | C | 35 | 42.481 | 53.613 | 21.262 | 1.00 | 16.72 | C |
| ATOM | 3192 | CA | TRP | C | 35 | 41.590 | 54.478 | 22.025 | 1.00 | 17.26 | C |
| ATOM | 3193 | CB | TRP | C | 35 | 41.387 | 55.820 | 21.314 | 1.00 | 16.20 | C |
| ATOM | 3194 | CG | TRP | C | 35 | 42.606 | 56.697 | 21.274 | 1.00 | 18.45 | C |
| ATOM | 3195 | CD2 | TRP | C | 35 | 42.704 | 58.000 | 20.682 | 1.00 | 20.69 | C |
| ATOM | 3196 | CE2 | TRP | C | 35 | 44.028 | 58.455 | 20.887 | 1.00 | 20.56 | C |
| ATOM | 3197 | CE3 | TRP | C | 35 | 41.801 | 58.827 | 19.997 | 1.00 | 21.30 | C |
| ATOM | 3198 | CD1 | TRP | C | 35 | 43.840 | 56.422 | 21.799 | 1.00 | 18.04 | C |
| ATOM | 3199 | NE1 | TRP | C | 35 | 44.700 | 57.475 | 21.569 | 1.00 | 19.91 | C |
| ATOM | 3200 | CZ2 | TRP | C | 35 | 44.473 | 59.697 | 20.432 | 1.00 | 21.16 | C |
| ATOM | 3201 | CZ3 | TRP | C | 35 | 42.246 | 60.067 | 19.541 | 1.00 | 23.45 | C |
| ATOM | 3202 | CH2 | TRP | C | 35 | 43.572 | 60.487 | 19.763 | 1.00 | 21.75 | C |

Figure 9 (50 of 92)

| ATOM | 3203 | C | TRP | C | 35 | 40.245 | 53.804 | 22.212 | 1.00 | 18.88 | C |
| --- | --- | --- | --- | --- | --- | --- | --- | --- | --- | --- | --- |
| ATOM | 3204 | O | TRP | C | 35 | 39.524 | 53.546 | 21.240 | 1.00 | 18.42 | C |
| ATOM | 3205 | N | PHE | C | 36 | 39.911 | 53.510 | 23.462 | 1.00 | 18.11 | C |
| ATOM | 3206 | CA | PHE | C | 36 | 38.633 | 52.882 | 23.765 | 1.00 | 17.38 | C |
| ATOM | 3207 | CB | PHE | C | 36 | 38.694 | 52.182 | 25.125 | 1.00 | 17.06 | C |
| ATOM | 3208 | CG | PHE | C | 36 | 39.589 | 50.967 | 25.142 | 1.00 | 17.68 | C |
| ATOM | 3209 | CD1 | PHE | C | 36 | 40.924 | 51.063 | 24.762 | 1.00 | 16.66 | C |
| ATOM | 3210 | CD2 | PHE | C | 36 | 39.093 | 49.728 | 25.538 | 1.00 | 17.44 | C |
| ATOM | 3211 | CE1 | PHE | C | 36 | 41.753 | 49.949 | 24.773 | 1.00 | 18.52 | C |
| ATOM | 3212 | CE2 | PHE | C | 36 | 39.916 | 48.605 | 25.553 | 1.00 | 17.97 | C |
| ATOM | 3213 | CZ | PHE | C | 36 | 41.248 | 48.713 | 25.171 | 1.00 | 18.08 | C |
| ATOM | 3214 | C | PHE | C | 36 | 37.603 | 54.001 | 23.766 | 1.00 | 17.59 | C |
| ATOM | 3215 | O | PHE | C | 36 | 37.629 | 54.891 | 24.630 | 1.00 | 16.43 | C |
| ATOM | 3216 | N | MET | C | 37 | 36.708 | 53.950 | 22.780 | 1.00 | 15.74 | C |
| ATOM | 3217 | CA | MET | C | 37 | 35.671 | 54.961 | 22.591 | 1.00 | 16.07 | C |
| ATOM | 3218 | CB | MET | C | 37 | 35.727 | 55.463 | 21.136 | 1.00 | 14.35 | C |
| ATOM | 3219 | CG | MET | C | 37 | 34.958 | 56.756 | 20.850 | 1.00 | 9.88 | C |
| ATOM | 3220 | SD | MET | C | 37 | 35.264 | 57.406 | 19.189 | 1.00 | 2.78 | C |
| ATOM | 3221 | CE | MET | C | 37 | 34.434 | 56.147 | 18.207 | 1.00 | 9.25 | C |
| ATOM | 3222 | C | MET | C | 37 | 34.269 | 54.424 | 22.922 | 1.00 | 18.25 | C |
| ATOM | 3223 | O | MET | C | 37 | 33.608 | 53.800 | 22.085 | 1.00 | 16.69 | C |
| ATOM | 3224 | N | PRO | C | 38 | 33.792 | 54.675 | 24.153 | 1.00 | 18.83 | C |
| ATOM | 3225 | CD | PRO | C | 38 | 34.319 | 55.638 | 25.132 | 1.00 | 19.95 | C |
| ATOM | 3226 | CA | PRO | C | 38 | 32.465 | 54.193 | 24.538 | 1.00 | 19.39 | C |
| ATOM | 3227 | CB | PRO | C | 38 | 32.405 | 54.445 | 26.046 | 1.00 | 18.24 | C |
| ATOM | 3228 | CG | PRO | C | 38 | 33.694 | 55.180 | 26.402 | 1.00 | 19.66 | C |
| ATOM | 3229 | C | PRO | C | 38 | 31.373 | 54.959 | 23.802 | 1.00 | 21.60 | C |
| ATOM | 3230 | O | PRO | C | 38 | 31.410 | 56.182 | 23.730 | 1.00 | 20.19 | C |
| ATOM | 3231 | N | ASN | C | 39 | 30.407 | 54.233 | 23.254 | 1.00 | 23.62 | C |
| ATOM | 3232 | CA | ASN | C | 39 | 29.298 | 54.851 | 22.535 | 1.00 | 27.71 | C |
| ATOM | 3233 | CB | ASN | C | 39 | 28.581 | 53.812 | 21.670 | 1.00 | 25.07 | C |
| ATOM | 3234 | CG | ASN | C | 39 | 27.630 | 52.932 | 22.477 | 1.00 | 25.45 | C |
| ATOM | 3235 | OD1 | ASN | C | 39 | 27.879 | 52.620 | 23.645 | 1.00 | 21.91 | C |
| ATOM | 3236 | ND2 | ASN | C | 39 | 26.535 | 52.520 | 21.846 | 1.00 | 25.37 | C |
| ATOM | 3237 | C | ASN | C | 39 | 28.312 | 55.388 | 23.563 | 1.00 | 30.80 | C |
| ATOM | 3238 | O | ASN | C | 39 | 28.486 | 55.198 | 24.763 | 1.00 | 31.16 | C |
| ATOM | 3239 | N | GLN | C | 40 | 27.273 | 56.063 | 23.103 | 1.00 | 35.75 | C |
| ATOM | 3240 | CA | GLN | C | 40 | 26.285 | 56.546 | 24.047 | 1.00 | 41.53 | C |
| ATOM | 3241 | CB | GLN | C | 40 | 26.523 | 58.006 | 24.396 | 1.00 | 43.92 | C |
| ATOM | 3242 | CG | GLN | C | 40 | 25.656 | 58.456 | 25.554 | 1.00 | 47.56 | C |
| ATOM | 3243 | CD | GLN | C | 40 | 25.972 | 59.861 | 25.979 | 1.00 | 50.01 | C |
| ATOM | 3244 | OE1 | GLN | C | 40 | 25.759 | 60.806 | 25.219 | 1.00 | 51.36 | C |
| ATOM | 3245 | NE2 | GLN | C | 40 | 26.498 | 60.016 | 27.195 | 1.00 | 51.30 | C |
| ATOM | 3246 | C | GLN | C | 40 | 24.868 | 56.375 | 23.543 | 1.00 | 43.50 | C |
| ATOM | 3247 | O | GLN | C | 40 | 24.601 | 56.443 | 22.345 | 1.00 | 44.72 | C |
| ATOM | 3248 | N | ILE | C | 41 | 23.963 | 56.152 | 24.482 | 1.00 | 44.93 | C |
| ATOM | 3249 | CA | ILE | C | 41 | 22.558 | 55.970 | 24.168 | 1.00 | 47.27 | C |
| ATOM | 3250 | CB | ILE | C | 41 | 21.985 | 54.768 | 24.948 | 1.00 | 47.26 | C |
| ATOM | 3251 | CG2 | ILE | C | 41 | 22.653 | 54.688 | 26.319 | 1.00 | 48.78 | C |
| ATOM | 3252 | CG1 | ILE | C | 41 | 20.460 | 54.877 | 25.058 | 1.00 | 48.18 | C |
| ATOM | 3253 | CD1 | ILE | C | 41 | 19.723 | 54.867 | 23.720 | 1.00 | 48.10 | C |
| ATOM | 3254 | C | ILE | C | 41 | 21.761 | 57.229 | 24.508 | 1.00 | 48.32 | C |
| ATOM | 3255 | O | ILE | C | 41 | 21.778 | 57.706 | 25.647 | 1.00 | 48.32 | C |
| ATOM | 3256 | N | PRO | C | 42 | 21.060 | 57.791 | 23.509 | 1.00 | 49.34 | C |
| ATOM | 3257 | CD | PRO | C | 42 | 21.103 | 57.398 | 22.087 | 1.00 | 50.03 | C |
| ATOM | 3258 | CA | PRO | C | 42 | 20.246 | 58.998 | 23.688 | 1.00 | 49.65 | C |
| ATOM | 3259 | CB | PRO | C | 42 | 20.051 | 59.488 | 22.257 | 1.00 | 50.05 | C |
| ATOM | 3260 | CG | PRO | C | 42 | 19.955 | 58.199 | 21.490 | 1.00 | 49.53 | C |
| ATOM | 3261 | C | PRO | C | 42 | 18.921 | 58.670 | 24.374 | 1.00 | 50.02 | C |
| ATOM | 3262 | O | PRO | C | 42 | 18.749 | 57.580 | 24.925 | 1.00 | 49.66 | C |
| ATOM | 3263 | N | ASP | C | 52 | 24.951 | 55.790 | 34.939 | 1.00 | 39.43 | C |
| ATOM | 3264 | CA | ASP | C | 52 | 25.333 | 54.675 | 34.080 | 1.00 | 38.64 | C |
| ATOM | 3265 | CB | ASP | C | 52 | 24.202 | 54.368 | 33.094 | 1.00 | 40.89 | C |
| ATOM | 3266 | CG | ASP | C | 52 | 24.463 | 53.126 | 32.262 | 1.00 | 42.32 | C |
| ATOM | 3267 | OD1 | ASP | C | 52 | 24.158 | 52.002 | 32.726 | 1.00 | 46.09 | C |
| ATOM | 3268 | OD2 | ASP | C | 52 | 24.978 | 53.278 | 31.133 | 1.00 | 44.64 | C |

Figure 9 (51 of 92)

| | | | | | | | | | | |
|---|---|---|---|---|---|---|---|---|---|---|
| ATOM | 3269 | C | ASP | C | 52 | 26.636 | 54.981 | 33.327 | 1.00 37.05 | C |
| ATOM | 3270 | O | ASP | C | 52 | 27.647 | 54.315 | 33.547 | 1.00 36.71 | C |
| ATOM | 3271 | N | SER | C | 53 | 26.621 | 55.986 | 32.451 | 1.00 34.63 | C |
| ATOM | 3272 | CA | SER | C | 53 | 27.830 | 56.328 | 31.705 | 1.00 33.42 | C |
| ATOM | 3273 | CB | SER | C | 53 | 27.613 | 57.577 | 30.843 | 1.00 33.90 | C |
| ATOM | 3274 | OG | SER | C | 53 | 26.925 | 57.259 | 29.643 | 1.00 35.19 | C |
| ATOM | 3275 | C | SER | C | 53 | 29.049 | 56.532 | 32.599 | 1.00 31.69 | C |
| ATOM | 3276 | O | SER | C | 53 | 30.130 | 56.041 | 32.285 | 1.00 32.45 | C |
| ATOM | 3277 | N | PHE | C | 54 | 28.898 | 57.239 | 33.716 | 1.00 31.30 | C |
| ATOM | 3278 | CA | PHE | C | 54 | 30.063 | 57.447 | 34.567 | 1.00 30.28 | C |
| ATOM | 3279 | CB | PHE | C | 54 | 29.754 | 58.452 | 35.692 | 1.00 32.36 | C |
| ATOM | 3280 | CG | PHE | C | 54 | 29.090 | 57.859 | 36.894 | 1.00 35.05 | C |
| ATOM | 3281 | CD1 | PHE | C | 54 | 29.852 | 57.366 | 37.950 | 1.00 34.19 | C |
| ATOM | 3282 | CD2 | PHE | C | 54 | 27.698 | 57.813 | 36.983 | 1.00 36.22 | C |
| ATOM | 3283 | CE1 | PHE | C | 54 | 29.239 | 56.836 | 39.081 | 1.00 37.65 | C |
| ATOM | 3284 | CE2 | PHE | C | 54 | 27.069 | 57.283 | 38.111 | 1.00 37.66 | C |
| ATOM | 3285 | CZ | PHE | C | 54 | 27.839 | 56.794 | 39.163 | 1.00 37.47 | C |
| ATOM | 3286 | C | PHE | C | 54 | 30.583 | 56.105 | 35.092 | 1.00 27.74 | C |
| ATOM | 3287 | O | PHE | C | 54 | 31.774 | 55.942 | 35.328 | 1.00 28.47 | C |
| ATOM | 3288 | N | HIS | C | 55 | 29.700 | 55.128 | 35.240 | 1.00 25.56 | C |
| ATOM | 3289 | CA | HIS | C | 55 | 30.143 | 53.816 | 35.689 | 1.00 24.20 | C |
| ATOM | 3290 | CB | HIS | C | 55 | 28.939 | 52.960 | 36.086 | 1.00 24.67 | C |
| ATOM | 3291 | CG | HIS | C | 55 | 28.419 | 53.258 | 37.460 | 1.00 24.77 | C |
| ATOM | 3292 | CD2 | HIS | C | 55 | 29.065 | 53.599 | 38.600 | 1.00 23.71 | C |
| ATOM | 3293 | ND1 | HIS | C | 55 | 27.079 | 53.222 | 37.775 | 1.00 26.23 | C |
| ATOM | 3294 | CE1 | HIS | C | 55 | 26.919 | 53.532 | 39.049 | 1.00 24.49 | C |
| ATOM | 3295 | NE2 | HIS | C | 55 | 28.109 | 53.765 | 39.573 | 1.00 26.35 | C |
| ATOM | 3296 | C | HIS | C | 55 | 30.952 | 53.138 | 34.576 | 1.00 22.75 | C |
| ATOM | 3297 | O | HIS | C | 55 | 31.985 | 52.514 | 34.832 | 1.00 21.04 | C |
| ATOM | 3298 | N | ARG | C | 56 | 30.492 | 53.276 | 33.338 | 1.00 20.35 | C |
| ATOM | 3299 | CA | ARG | C | 56 | 31.200 | 52.679 | 32.212 | 1.00 21.03 | C |
| ATOM | 3300 | CB | ARG | C | 56 | 30.367 | 52.825 | 30.935 | 1.00 21.27 | C |
| ATOM | 3301 | CG | ARG | C | 56 | 29.016 | 52.120 | 31.015 | 1.00 22.32 | C |
| ATOM | 3302 | CD | ARG | C | 56 | 28.050 | 52.681 | 29.984 | 1.00 21.44 | C |
| ATOM | 3303 | NE | ARG | C | 56 | 28.572 | 52.508 | 28.641 | 1.00 20.03 | C |
| ATOM | 3304 | CZ | ARG | C | 56 | 28.306 | 53.316 | 27.621 | 1.00 17.43 | C |
| ATOM | 3305 | NH1 | ARG | C | 56 | 27.519 | 54.371 | 27.781 | 1.00 17.67 | C |
| ATOM | 3306 | NH2 | ARG | C | 56 | 28.828 | 53.056 | 26.433 | 1.00 18.78 | C |
| ATOM | 3307 | C | ARG | C | 56 | 32.560 | 53.360 | 32.054 | 1.00 19.90 | C |
| ATOM | 3308 | O | ARG | C | 56 | 33.579 | 52.696 | 31.802 | 1.00 18.27 | C |
| ATOM | 3309 | N | VAL | C | 57 | 32.577 | 54.683 | 32.209 | 1.00 17.73 | C |
| ATOM | 3310 | CA | VAL | C | 57 | 33.823 | 55.430 | 32.106 | 1.00 18.32 | C |
| ATOM | 3311 | CB | VAL | C | 57 | 33.586 | 56.945 | 32.245 | 1.00 19.39 | C |
| ATOM | 3312 | CG1 | VAL | C | 57 | 34.913 | 57.666 | 32.414 | 1.00 18.15 | C |
| ATOM | 3313 | CG2 | VAL | C | 57 | 32.866 | 57.469 | 31.005 | 1.00 19.03 | C |
| ATOM | 3314 | C | VAL | C | 57 | 34.799 | 54.975 | 33.195 | 1.00 19.09 | C |
| ATOM | 3315 | O | VAL | C | 57 | 35.992 | 54.779 | 32.929 | 1.00 17.65 | C |
| ATOM | 3316 | N | GLU | C | 58 | 34.290 | 54.794 | 34.414 | 1.00 18.91 | C |
| ATOM | 3317 | CA | GLU | C | 58 | 35.140 | 54.356 | 35.521 | 1.00 19.78 | C |
| ATOM | 3318 | CB | GLU | C | 58 | 34.416 | 54.535 | 36.861 | 1.00 21.16 | C |
| ATOM | 3319 | CG | GLU | C | 58 | 34.196 | 56.000 | 37.259 | 1.00 23.93 | C |
| ATOM | 3320 | CD | GLU | C | 58 | 35.499 | 56.804 | 37.312 | 1.00 25.79 | C |
| ATOM | 3321 | OE1 | GLU | C | 58 | 36.412 | 56.417 | 38.067 | 1.00 28.03 | C |
| ATOM | 3322 | OE2 | GLU | C | 58 | 35.616 | 57.822 | 36.600 | 1.00 26.23 | C |
| ATOM | 3323 | C | GLU | C | 58 | 35.636 | 52.912 | 35.373 | 1.00 19.33 | C |
| ATOM | 3324 | O | GLU | C | 58 | 36.790 | 52.622 | 35.690 | 1.00 18.31 | C |
| ATOM | 3325 | N | MET | C | 59 | 34.791 | 52.000 | 34.894 | 1.00 18.06 | C |
| ATOM | 3326 | CA | MET | C | 59 | 35.252 | 50.623 | 34.733 | 1.00 16.46 | C |
| ATOM | 3327 | CB | MET | C | 59 | 34.091 | 49.666 | 34.412 | 1.00 15.98 | C |
| ATOM | 3328 | CG | MET | C | 59 | 33.128 | 49.416 | 35.588 | 1.00 13.70 | C |
| ATOM | 3329 | SD | MET | C | 59 | 31.826 | 48.224 | 35.240 | 1.00 2.03 | C |
| ATOM | 3330 | CE | MET | C | 59 | 30.866 | 49.117 | 34.084 | 1.00 11.12 | C |
| ATOM | 3331 | C | MET | C | 59 | 36.311 | 50.573 | 33.633 | 1.00 16.23 | C |
| ATOM | 3332 | O | MET | C | 59 | 37.282 | 49.829 | 33.738 | 1.00 15.43 | C |
| ATOM | 3333 | N | LEU | C | 60 | 36.133 | 51.381 | 32.589 | 1.00 16.64 | C |
| ATOM | 3334 | CA | LEU | C | 60 | 37.092 | 51.424 | 31.491 | 1.00 17.45 | C |

Figure 9 (52 of 92)

| ATOM | 3335 | CB | LEU | C | 60 | 36.602 | 52.354 | 30.383 | 1.00 | 17.28 | C |
|---|---|---|---|---|---|---|---|---|---|---|---|
| ATOM | 3336 | CG | LEU | C | 60 | 35.868 | 51.682 | 29.218 | 1.00 | 19.32 | C |
| ATOM | 3337 | CD1 | LEU | C | 60 | 35.216 | 52.735 | 28.341 | 1.00 | 17.77 | C |
| ATOM | 3338 | CD2 | LEU | C | 60 | 36.850 | 50.843 | 28.411 | 1.00 | 17.28 | C |
| ATOM | 3339 | C | LEU | C | 60 | 38.456 | 51.890 | 31.991 | 1.00 | 19.29 | C |
| ATOM | 3340 | O | LEU | C | 60 | 39.473 | 51.250 | 31.716 | 1.00 | 18.86 | C |
| ATOM | 3341 | N | LYS | C | 61 | 38.481 | 53.000 | 32.730 | 1.00 | 20.26 | C |
| ATOM | 3342 | CA | LYS | C | 61 | 39.745 | 53.514 | 33.256 | 1.00 | 20.52 | C |
| ATOM | 3343 | CB | LYS | C | 61 | 39.510 | 54.708 | 34.182 | 1.00 | 21.93 | C |
| ATOM | 3344 | CG | LYS | C | 61 | 39.001 | 55.951 | 33.491 | 1.00 | 23.93 | C |
| ATOM | 3345 | CD | LYS | C | 61 | 38.766 | 57.054 | 34.496 | 1.00 | 27.10 | C |
| ATOM | 3346 | CE | LYS | C | 61 | 38.225 | 58.294 | 33.826 | 1.00 | 28.89 | C |
| ATOM | 3347 | NZ | LYS | C | 61 | 37.968 | 59.357 | 34.835 | 1.00 | 31.87 | C |
| ATOM | 3348 | C | LYS | C | 61 | 40.467 | 52.418 | 34.025 | 1.00 | 20.01 | C |
| ATOM | 3349 | O | LYS | C | 61 | 41.680 | 52.240 | 33.882 | 1.00 | 19.88 | C |
| ATOM | 3350 | N | LEU | C | 62 | 39.712 | 51.686 | 34.839 | 1.00 | 19.26 | C |
| ATOM | 3351 | CA | LEU | C | 62 | 40.282 | 50.603 | 35.630 | 1.00 | 19.59 | C |
| ATOM | 3352 | CB | LEU | C | 62 | 39.237 | 50.062 | 36.621 | 1.00 | 18.84 | C |
| ATOM | 3353 | CG | LEU | C | 62 | 38.843 | 50.951 | 37.814 | 1.00 | 20.28 | C |
| ATOM | 3354 | CD1 | LEU | C | 62 | 37.728 | 50.289 | 38.609 | 1.00 | 18.93 | C |
| ATOM | 3355 | CD2 | LEU | C | 62 | 40.052 | 51.188 | 38.721 | 1.00 | 23.42 | C |
| ATOM | 3356 | C | LEU | C | 62 | 40.802 | 49.470 | 34.733 | 1.00 | 20.12 | C |
| ATOM | 3357 | O | LEU | C | 62 | 41.881 | 48.921 | 34.969 | 1.00 | 18.03 | C |
| ATOM | 3358 | N | ALA | C | 63 | 40.039 | 49.135 | 33.695 | 1.00 | 19.87 | C |
| ATOM | 3359 | CA | ALA | C | 63 | 40.428 | 48.068 | 32.781 | 1.00 | 21.77 | C |
| ATOM | 3360 | CB | ALA | C | 63 | 39.274 | 47.757 | 31.818 | 1.00 | 20.27 | C |
| ATOM | 3361 | C | ALA | C | 63 | 41.702 | 48.367 | 31.981 | 1.00 | 22.37 | C |
| ATOM | 3362 | O | ALA | C | 63 | 42.502 | 47.463 | 31.735 | 1.00 | 20.68 | C |
| ATOM | 3363 | N | ILE | C | 64 | 41.893 | 49.626 | 31.588 | 1.00 | 23.28 | C |
| ATOM | 3364 | CA | ILE | C | 64 | 43.052 | 50.003 | 30.776 | 1.00 | 26.72 | C |
| ATOM | 3365 | CB | ILE | C | 64 | 42.675 | 51.095 | 29.766 | 1.00 | 26.97 | C |
| ATOM | 3366 | CG2 | ILE | C | 64 | 41.537 | 50.608 | 28.881 | 1.00 | 26.83 | C |
| ATOM | 3367 | CG1 | ILE | C | 64 | 42.273 | 52.367 | 30.511 | 1.00 | 28.32 | C |
| ATOM | 3368 | CD1 | ILE | C | 64 | 42.025 | 53.560 | 29.607 | 1.00 | 29.79 | C |
| ATOM | 3369 | C | ILE | C | 64 | 44.291 | 50.492 | 31.522 | 1.00 | 28.86 | C |
| ATOM | 3370 | O | ILE | C | 64 | 45.378 | 50.545 | 30.952 | 1.00 | 29.76 | C |
| ATOM | 3371 | N | GLN | C | 65 | 44.117 | 50.852 | 32.789 | 1.00 | 31.41 | C |
| ATOM | 3372 | CA | GLN | C | 65 | 45.197 | 51.359 | 33.640 | 1.00 | 33.00 | C |
| ATOM | 3373 | CB | GLN | C | 65 | 44.880 | 51.073 | 35.108 | 1.00 | 34.58 | C |
| ATOM | 3374 | CG | GLN | C | 65 | 44.123 | 52.171 | 35.814 | 1.00 | 38.89 | C |
| ATOM | 3375 | CD | GLN | C | 65 | 43.982 | 51.908 | 37.306 | 1.00 | 39.40 | C |
| ATOM | 3376 | OE1 | GLN | C | 65 | 43.366 | 52.691 | 38.027 | 1.00 | 41.60 | C |
| ATOM | 3377 | NE2 | GLN | C | 65 | 44.553 | 50.802 | 37.772 | 1.00 | 40.59 | C |
| ATOM | 3378 | C | GLN | C | 65 | 46.596 | 50.831 | 33.371 | 1.00 | 33.06 | C |
| ATOM | 3379 | O | GLN | C | 65 | 47.549 | 51.588 | 33.167 | 1.00 | 33.73 | C |
| ATOM | 3380 | N | SER | C | 66 | 46.702 | 49.514 | 33.404 | 1.00 | 34.25 | C |
| ATOM | 3381 | CA | SER | C | 66 | 47.965 | 48.823 | 33.236 | 1.00 | 34.34 | C |
| ATOM | 3382 | CB | SER | C | 66 | 47.826 | 47.445 | 33.861 | 1.00 | 36.36 | C |
| ATOM | 3383 | OG | SER | C | 66 | 47.507 | 47.598 | 35.236 | 1.00 | 38.68 | C |
| ATOM | 3384 | C | SER | C | 66 | 48.553 | 48.699 | 31.842 | 1.00 | 33.22 | C |
| ATOM | 3385 | O | SER | C | 66 | 49.568 | 48.030 | 31.667 | 1.00 | 34.17 | C |
| ATOM | 3386 | N | ASN | C | 67 | 47.934 | 49.323 | 30.851 | 1.00 | 30.57 | C |
| ATOM | 3387 | CA | ASN | C | 67 | 48.470 | 49.245 | 29.501 | 1.00 | 27.96 | C |
| ATOM | 3388 | CB | ASN | C | 67 | 47.515 | 48.483 | 28.584 | 1.00 | 27.82 | C |
| ATOM | 3389 | CG | ASN | C | 67 | 48.142 | 48.133 | 27.250 | 1.00 | 25.71 | C |
| ATOM | 3390 | OD1 | ASN | C | 67 | 47.787 | 47.128 | 26.638 | 1.00 | 28.32 | C |
| ATOM | 3391 | ND2 | ASN | C | 67 | 49.068 | 48.961 | 26.787 | 1.00 | 25.88 | C |
| ATOM | 3392 | C | ASN | C | 67 | 48.686 | 50.657 | 28.996 | 1.00 | 26.76 | C |
| ATOM | 3393 | O | ASN | C | 67 | 47.752 | 51.323 | 28.561 | 1.00 | 26.87 | C |
| ATOM | 3394 | N | PRO | C | 68 | 49.937 | 51.128 | 29.048 | 1.00 | 27.21 | C |
| ATOM | 3395 | CD | PRO | C | 68 | 51.115 | 50.326 | 29.416 | 1.00 | 26.76 | C |
| ATOM | 3396 | CA | PRO | C | 68 | 50.343 | 52.468 | 28.614 | 1.00 | 27.23 | C |
| ATOM | 3397 | CB | PRO | C | 68 | 51.869 | 52.405 | 28.673 | 1.00 | 27.44 | C |
| ATOM | 3398 | CG | PRO | C | 68 | 52.123 | 51.393 | 29.743 | 1.00 | 29.15 | C |
| ATOM | 3399 | C | PRO | C | 68 | 49.857 | 52.822 | 27.218 | 1.00 | 25.09 | C |
| ATOM | 3400 | O | PRO | C | 68 | 49.644 | 53.990 | 26.910 | 1.00 | 26.89 | C |

Figure 9 (53 of 92)

| | | | | | | | | | | |
|---|---|---|---|---|---|---|---|---|---|---|
| ATOM | 3401 | N | SER | C | 69 | 49.686 | 51.809 | 26.379 | 1.00 23.45 | C |
| ATOM | 3402 | CA | SER | C | 69 | 49.245 | 52.030 | 25.006 | 1.00 22.39 | C |
| ATOM | 3403 | CB | SER | C | 69 | 49.716 | 50.874 | 24.131 | 1.00 21.28 | C |
| ATOM | 3404 | OG | SER | C | 69 | 51.115 | 50.707 | 24.247 | 1.00 23.02 | C |
| ATOM | 3405 | C | SER | C | 69 | 47.737 | 52.205 | 24.851 | 1.00 20.92 | C |
| ATOM | 3406 | O | SER | C | 69 | 47.259 | 52.535 | 23.764 | 1.00 21.89 | C |
| ATOM | 3407 | N | PHE | C | 70 | 46.990 | 51.990 | 25.930 | 1.00 20.69 | C |
| ATOM | 3408 | CA | PHE | C | 70 | 45.531 | 52.124 | 25.892 | 1.00 19.08 | C |
| ATOM | 3409 | CB | PHE | C | 70 | 44.874 | 50.994 | 26.691 | 1.00 17.76 | C |
| ATOM | 3410 | CG | PHE | C | 70 | 44.995 | 49.634 | 26.053 | 1.00 19.33 | C |
| ATOM | 3411 | CD1 | PHE | C | 70 | 44.487 | 48.508 | 26.697 | 1.00 18.74 | C |
| ATOM | 3412 | CD2 | PHE | C | 70 | 45.595 | 49.477 | 24.805 | 1.00 18.96 | C |
| ATOM | 3413 | CE1 | PHE | C | 70 | 44.575 | 47.249 | 26.109 | 1.00 20.79 | C |
| ATOM | 3414 | CE2 | PHE | C | 70 | 45.690 | 48.227 | 24.206 | 1.00 19.20 | C |
| ATOM | 3415 | CZ | PHE | C | 70 | 45.177 | 47.104 | 24.860 | 1.00 20.81 | C |
| ATOM | 3416 | C | PHE | C | 70 | 45.069 | 53.468 | 26.448 | 1.00 20.41 | C |
| ATOM | 3417 | O | PHE | C | 70 | 45.557 | 53.923 | 27.485 | 1.00 19.52 | C |
| ATOM | 3418 | N | LYS | C | 71 | 44.116 | 54.093 | 25.760 | 1.00 22.16 | C |
| ATOM | 3419 | CA | LYS | C | 71 | 43.579 | 55.382 | 26.179 | 1.00 22.97 | C |
| ATOM | 3420 | CB | LYS | C | 71 | 44.085 | 56.490 | 25.257 | 1.00 25.16 | C |
| ATOM | 3421 | CG | LYS | C | 71 | 45.578 | 56.430 | 24.966 | 1.00 29.86 | C |
| ATOM | 3422 | CD | LYS | C | 71 | 46.390 | 56.627 | 26.230 | 1.00 32.97 | C |
| ATOM | 3423 | CE | LYS | C | 71 | 47.883 | 56.610 | 25.936 | 1.00 36.05 | C |
| ATOM | 3424 | NZ | LYS | C | 71 | 48.679 | 56.859 | 27.175 | 1.00 37.84 | C |
| ATOM | 3425 | C | LYS | C | 71 | 42.059 | 55.359 | 26.134 | 1.00 23.39 | C |
| ATOM | 3426 | O | LYS | C | 71 | 41.461 | 54.490 | 25.504 | 1.00 23.14 | C |
| ATOM | 3427 | N | LEU | C | 72 | 41.447 | 56.338 | 26.789 | 1.00 23.92 | C |
| ATOM | 3428 | CA | LEU | C | 72 | 39.999 | 56.470 | 26.840 | 1.00 24.66 | C |
| ATOM | 3429 | CB | LEU | C | 72 | 39.562 | 56.655 | 28.297 | 1.00 26.33 | C |
| ATOM | 3430 | CG | LEU | C | 72 | 38.063 | 56.729 | 28.600 | 1.00 28.14 | C |
| ATOM | 3431 | CD1 | LEU | C | 72 | 37.392 | 55.439 | 28.156 | 1.00 27.04 | C |
| ATOM | 3432 | CD2 | LEU | C | 72 | 37.848 | 56.960 | 30.090 | 1.00 27.44 | C |
| ATOM | 3433 | C | LEU | C | 72 | 39.576 | 57.684 | 26.010 | 1.00 24.91 | C |
| ATOM | 3434 | O | LEU | C | 72 | 40.038 | 58.796 | 26.258 | 1.00 24.92 | C |
| ATOM | 3435 | N | GLU | C | 73 | 38.710 | 57.480 | 25.021 | 1.00 23.98 | C |
| ATOM | 3436 | CA | GLU | C | 73 | 38.244 | 58.590 | 24.185 | 1.00 23.39 | C |
| ATOM | 3437 | CB | GLU | C | 73 | 38.471 | 58.284 | 22.700 | 1.00 24.63 | C |
| ATOM | 3438 | CG | GLU | C | 73 | 37.983 | 59.391 | 21.772 | 1.00 22.67 | C |
| ATOM | 3439 | CD | GLU | C | 73 | 38.542 | 60.753 | 22.161 | 1.00 25.10 | C |
| ATOM | 3440 | OE1 | GLU | C | 73 | 39.782 | 60.927 | 22.135 | 1.00 21.70 | C |
| ATOM | 3441 | OE2 | GLU | C | 73 | 37.740 | 61.646 | 22.498 | 1.00 21.90 | C |
| ATOM | 3442 | C | GLU | C | 73 | 36.763 | 58.816 | 24.451 | 1.00 21.63 | C |
| ATOM | 3443 | O | GLU | C | 73 | 35.929 | 57.995 | 24.083 | 1.00 20.00 | C |
| ATOM | 3444 | N | LEU | C | 74 | 36.439 | 59.943 | 25.081 | 1.00 21.90 | C |
| ATOM | 3445 | CA | LEU | C | 74 | 35.058 | 60.234 | 25.442 | 1.00 20.85 | C |
| ATOM | 3446 | CB | LEU | C | 74 | 35.010 | 60.706 | 26.893 | 1.00 21.09 | C |
| ATOM | 3447 | CG | LEU | C | 74 | 35.717 | 59.833 | 27.932 | 1.00 21.40 | C |
| ATOM | 3448 | CD1 | LEU | C | 74 | 35.683 | 60.538 | 29.273 | 1.00 18.25 | C |
| ATOM | 3449 | CD2 | LEU | C | 74 | 35.038 | 58.466 | 28.016 | 1.00 20.78 | C |
| ATOM | 3450 | C | LEU | C | 74 | 34.329 | 61.244 | 24.567 | 1.00 21.30 | C |
| ATOM | 3451 | O | LEU | C | 74 | 33.340 | 61.837 | 24.996 | 1.00 20.12 | C |
| ATOM | 3452 | N | VAL | C | 75 | 34.791 | 61.436 | 23.338 | 1.00 22.61 | C |
| ATOM | 3453 | CA | VAL | C | 75 | 34.138 | 62.400 | 22.464 | 1.00 22.62 | C |
| ATOM | 3454 | CB | VAL | C | 75 | 34.768 | 62.404 | 21.053 | 1.00 23.07 | C |
| ATOM | 3455 | CG1 | VAL | C | 75 | 34.646 | 61.024 | 20.411 | 1.00 22.31 | C |
| ATOM | 3456 | CG2 | VAL | C | 75 | 34.091 | 63.465 | 20.195 | 1.00 23.84 | C |
| ATOM | 3457 | C | VAL | C | 75 | 32.620 | 62.201 | 22.336 | 1.00 24.03 | C |
| ATOM | 3458 | O | VAL | C | 75 | 31.881 | 63.187 | 22.306 | 1.00 25.09 | C |
| ATOM | 3459 | N | GLU | C | 76 | 32.144 | 60.953 | 22.278 | 1.00 23.17 | C |
| ATOM | 3460 | CA | GLU | C | 76 | 30.698 | 60.712 | 22.137 | 1.00 23.23 | C |
| ATOM | 3461 | CB | GLU | C | 76 | 30.397 | 59.260 | 21.729 | 1.00 24.09 | C |
| ATOM | 3462 | CG | GLU | C | 76 | 31.019 | 58.812 | 20.419 | 1.00 24.44 | C |
| ATOM | 3463 | CD | GLU | C | 76 | 30.393 | 57.533 | 19.877 | 1.00 24.07 | C |
| ATOM | 3464 | OE1 | GLU | C | 76 | 31.050 | 56.867 | 19.061 | 1.00 24.92 | C |
| ATOM | 3465 | OE2 | GLU | C | 76 | 29.250 | 57.196 | 20.255 | 1.00 24.64 | C |
| ATOM | 3466 | C | GLU | C | 76 | 29.890 | 61.019 | 23.394 | 1.00 24.04 | C |

Figure 9 (54 of 92)

| ATOM | 3467 | O | GLU | C | 76 | 28.658 | 61.034 | 23.351 | 1.00 | 23.01 | C |
|---|---|---|---|---|---|---|---|---|---|---|---|
| ATOM | 3468 | N | MET | C | 77 | 30.583 | 61.241 | 24.509 | 1.00 | 24.30 | C |
| ATOM | 3469 | CA | MET | C | 77 | 29.938 | 61.547 | 25.790 | 1.00 | 24.82 | C |
| ATOM | 3470 | CB | MET | C | 77 | 30.849 | 61.136 | 26.957 | 1.00 | 22.52 | C |
| ATOM | 3471 | CG | MET | C | 77 | 31.338 | 59.695 | 26.944 | 1.00 | 25.27 | C |
| ATOM | 3472 | SD | MET | C | 77 | 30.565 | 58.677 | 28.216 | 1.00 | 23.98 | C |
| ATOM | 3473 | CE | MET | C | 77 | 29.046 | 58.421 | 27.435 | 1.00 | 18.71 | C |
| ATOM | 3474 | C | MET | C | 77 | 29.649 | 63.048 | 25.920 | 1.00 | 24.37 | C |
| ATOM | 3475 | O | MET | C | 77 | 28.847 | 63.461 | 26.750 | 1.00 | 24.28 | C |
| ATOM | 3476 | N | GLU | C | 78 | 30.319 | 63.851 | 25.099 | 1.00 | 25.74 | C |
| ATOM | 3477 | CA | GLU | C | 78 | 30.187 | 65.309 | 25.128 | 1.00 | 26.25 | C |
| ATOM | 3478 | CB | GLU | C | 78 | 31.198 | 65.943 | 24.161 | 1.00 | 25.12 | C |
| ATOM | 3479 | CG | GLU | C | 78 | 32.636 | 65.462 | 24.362 | 1.00 | 24.55 | C |
| ATOM | 3480 | CD | GLU | C | 78 | 33.625 | 66.084 | 23.391 | 1.00 | 24.45 | C |
| ATOM | 3481 | OE1 | GLU | C | 78 | 34.769 | 65.596 | 23.320 | 1.00 | 26.13 | C |
| ATOM | 3482 | OE2 | GLU | C | 78 | 33.277 | 67.062 | 22.701 | 1.00 | 25.91 | C |
| ATOM | 3483 | C | GLU | C | 78 | 28.796 | 65.850 | 24.813 | 1.00 | 27.20 | C |
| ATOM | 3484 | O | GLU | C | 78 | 28.027 | 65.255 | 24.056 | 1.00 | 24.36 | C |
| ATOM | 3485 | N | ARG | C | 79 | 28.482 | 66.987 | 25.420 | 1.00 | 29.34 | C |
| ATOM | 3486 | CA | ARG | C | 79 | 27.210 | 67.659 | 25.194 | 1.00 | 33.38 | C |
| ATOM | 3487 | CB | ARG | C | 79 | 27.171 | 68.948 | 26.031 | 1.00 | 34.80 | C |
| ATOM | 3488 | CG | ARG | C | 79 | 25.938 | 69.818 | 25.875 | 1.00 | 40.67 | C |
| ATOM | 3489 | CD | ARG | C | 79 | 25.929 | 70.921 | 26.943 | 1.00 | 43.66 | C |
| ATOM | 3490 | NE | ARG | C | 79 | 25.001 | 72.003 | 26.623 | 1.00 | 47.48 | C |
| ATOM | 3491 | CZ | ARG | C | 79 | 25.175 | 72.859 | 25.619 | 1.00 | 48.88 | C |
| ATOM | 3492 | NH1 | ARG | C | 79 | 24.282 | 73.813 | 25.391 | 1.00 | 49.25 | C |
| ATOM | 3493 | NH2 | ARG | C | 79 | 26.249 | 72.764 | 24.844 | 1.00 | 50.20 | C |
| ATOM | 3494 | C | ARG | C | 79 | 27.187 | 67.965 | 23.695 | 1.00 | 33.59 | C |
| ATOM | 3495 | O | ARG | C | 79 | 28.149 | 68.514 | 23.154 | 1.00 | 33.45 | C |
| ATOM | 3496 | N | GLU | C | 80 | 26.108 | 67.576 | 23.026 | 1.00 | 35.71 | C |
| ATOM | 3497 | CA | GLU | C | 80 | 25.960 | 67.793 | 21.585 | 1.00 | 38.12 | C |
| ATOM | 3498 | CB | GLU | C | 80 | 25.982 | 69.297 | 21.271 | 1.00 | 41.66 | C |
| ATOM | 3499 | CG | GLU | C | 80 | 25.095 | 70.124 | 22.206 | 1.00 | 47.33 | C |
| ATOM | 3500 | CD | GLU | C | 80 | 24.979 | 71.584 | 21.793 | 1.00 | 50.65 | C |
| ATOM | 3501 | OE1 | GLU | C | 80 | 26.016 | 72.208 | 21.476 | 1.00 | 52.57 | C |
| ATOM | 3502 | OE2 | GLU | C | 80 | 23.844 | 72.112 | 21.799 | 1.00 | 52.91 | C |
| ATOM | 3503 | C | GLU | C | 80 | 27.061 | 67.073 | 20.796 | 1.00 | 36.92 | C |
| ATOM | 3504 | O | GLU | C | 80 | 27.393 | 67.460 | 19.673 | 1.00 | 37.01 | C |
| ATOM | 3505 | N | GLY | C | 81 | 27.614 | 66.016 | 21.387 | 1.00 | 34.16 | C |
| ATOM | 3506 | CA | GLY | C | 81 | 28.671 | 65.263 | 20.735 | 1.00 | 32.38 | C |
| ATOM | 3507 | C | GLY | C | 81 | 28.195 | 64.406 | 19.576 | 1.00 | 31.42 | C |
| ATOM | 3508 | O | GLY | C | 81 | 26.999 | 64.151 | 19.441 | 1.00 | 30.53 | C |
| ATOM | 3509 | N | PRO | C | 82 | 29.117 | 63.935 | 18.719 | 1.00 | 30.26 | C |
| ATOM | 3510 | CD | PRO | C | 82 | 30.570 | 64.189 | 18.754 | 1.00 | 28.67 | C |
| ATOM | 3511 | CA | PRO | C | 82 | 28.758 | 63.100 | 17.567 | 1.00 | 28.91 | C |
| ATOM | 3512 | CB | PRO | C | 82 | 30.006 | 63.177 | 16.698 | 1.00 | 29.23 | C |
| ATOM | 3513 | CG | PRO | C | 82 | 31.101 | 63.205 | 17.723 | 1.00 | 29.15 | C |
| ATOM | 3514 | C | PRO | C | 82 | 28.414 | 61.663 | 17.966 | 1.00 | 29.25 | C |
| ATOM | 3515 | O | PRO | C | 82 | 28.762 | 61.218 | 19.058 | 1.00 | 28.99 | C |
| ATOM | 3516 | N | SER | C | 83 | 27.716 | 60.948 | 17.088 | 1.00 | 28.22 | C |
| ATOM | 3517 | CA | SER | C | 83 | 27.350 | 59.557 | 17.355 | 1.00 | 29.06 | C |
| ATOM | 3518 | CB | SER | C | 83 | 25.906 | 59.448 | 17.853 | 1.00 | 29.20 | C |
| ATOM | 3519 | OG | SER | C | 83 | 24.979 | 59.774 | 16.833 | 1.00 | 32.34 | C |
| ATOM | 3520 | C | SER | C | 83 | 27.527 | 58.720 | 16.090 | 1.00 | 28.69 | C |
| ATOM | 3521 | O | SER | C | 83 | 27.784 | 57.522 | 16.165 | 1.00 | 28.01 | C |
| ATOM | 3522 | N | TYR | C | 84 | 27.374 | 59.344 | 14.927 | 1.00 | 27.55 | C |
| ATOM | 3523 | CA | TYR | C | 84 | 27.576 | 58.619 | 13.683 | 1.00 | 27.25 | C |
| ATOM | 3524 | CB | TYR | C | 84 | 26.821 | 59.273 | 12.529 | 1.00 | 27.59 | C |
| ATOM | 3525 | CG | TYR | C | 84 | 25.333 | 59.060 | 12.617 | 1.00 | 28.29 | C |
| ATOM | 3526 | CD1 | TYR | C | 84 | 24.500 | 60.045 | 13.135 | 1.00 | 28.58 | C |
| ATOM | 3527 | CE1 | TYR | C | 84 | 23.131 | 59.841 | 13.241 | 1.00 | 30.27 | C |
| ATOM | 3528 | CD2 | TYR | C | 84 | 24.759 | 57.857 | 12.204 | 1.00 | 28.25 | C |
| ATOM | 3529 | CE2 | TYR | C | 84 | 23.386 | 57.645 | 12.308 | 1.00 | 29.38 | C |
| ATOM | 3530 | CZ | TYR | C | 84 | 22.583 | 58.643 | 12.829 | 1.00 | 28.49 | C |
| ATOM | 3531 | OH | TYR | C | 84 | 21.233 | 58.443 | 12.954 | 1.00 | 32.12 | C |
| ATOM | 3532 | C | TYR | C | 84 | 29.068 | 58.625 | 13.404 | 1.00 | 26.51 | C |

Figure 9 (55 of 92)

| | | | | | | | | | | |
|---|---|---|---|---|---|---|---|---|---|---|
| ATOM | 3533 | O | TYR | C | 84 | 29.727 | 59.650 | 13.549 | 1.00 26.12 | C |
| ATOM | 3534 | N | THR | C | 85 | 29.592 | 57.469 | 13.010 | 1.00 25.51 | C |
| ATOM | 3535 | CA | THR | C | 85 | 31.013 | 57.312 | 12.736 | 1.00 23.20 | C |
| ATOM | 3536 | CB | THR | C | 85 | 31.281 | 55.954 | 12.055 | 1.00 24.03 | C |
| ATOM | 3537 | OG1 | THR | C | 85 | 30.575 | 54.924 | 12.764 | 1.00 21.41 | C |
| ATOM | 3538 | CG2 | THR | C | 85 | 32.778 | 55.638 | 12.055 | 1.00 21.82 | C |
| ATOM | 3539 | C | THR | C | 85 | 31.613 | 58.425 | 11.879 | 1.00 23.58 | C |
| ATOM | 3540 | O | THR | C | 85 | 32.677 | 58.960 | 12.208 | 1.00 22.52 | C |
| ATOM | 3541 | N | PHE | C | 86 | 30.947 | 58.773 | 10.779 | 1.00 22.16 | C |
| ATOM | 3542 | CA | PHE | C | 86 | 31.465 | 59.821 | 9.903 | 1.00 21.76 | C |
| ATOM | 3543 | CB | PHE | C | 86 | 30.499 | 60.100 | 8.755 | 1.00 25.38 | C |
| ATOM | 3544 | CG | PHE | C | 86 | 31.049 | 61.042 | 7.726 | 1.00 27.23 | C |
| ATOM | 3545 | CD1 | PHE | C | 86 | 31.932 | 60.590 | 6.756 | 1.00 29.11 | C |
| ATOM | 3546 | CD2 | PHE | C | 86 | 30.712 | 62.388 | 7.748 | 1.00 28.89 | C |
| ATOM | 3547 | CE1 | PHE | C | 86 | 32.475 | 61.468 | 5.817 | 1.00 31.32 | C |
| ATOM | 3548 | CE2 | PHE | C | 86 | 31.252 | 63.275 | 6.813 | 1.00 30.04 | C |
| ATOM | 3549 | CZ | PHE | C | 86 | 32.133 | 62.813 | 5.849 | 1.00 30.12 | C |
| ATOM | 3550 | C | PHE | C | 86 | 31.709 | 61.125 | 10.667 | 1.00 21.12 | C |
| ATOM | 3551 | O | PHE | C | 86 | 32.740 | 61.769 | 10.502 | 1.00 17.37 | C |
| ATOM | 3552 | N | ASP | C | 87 | 30.748 | 61.501 | 11.500 | 1.00 20.73 | C |
| ATOM | 3553 | CA | ASP | C | 87 | 30.841 | 62.726 | 12.286 | 1.00 21.72 | C |
| ATOM | 3554 | CB | ASP | C | 87 | 29.473 | 63.039 | 12.898 | 1.00 21.42 | C |
| ATOM | 3555 | CG | ASP | C | 87 | 28.405 | 63.268 | 11.839 | 1.00 23.37 | C |
| ATOM | 3556 | OD1 | ASP | C | 87 | 27.205 | 63.153 | 12.144 | 1.00 24.58 | C |
| ATOM | 3557 | OD2 | ASP | C | 87 | 28.770 | 63.571 | 10.689 | 1.00 26.67 | C |
| ATOM | 3558 | C | ASP | C | 87 | 31.900 | 62.587 | 13.377 | 1.00 21.10 | C |
| ATOM | 3559 | O | ASP | C | 87 | 32.742 | 63.467 | 13.565 | 1.00 21.68 | C |
| ATOM | 3560 | N | THR | C | 88 | 31.859 | 61.472 | 14.090 | 1.00 19.90 | C |
| ATOM | 3561 | CA | THR | C | 88 | 32.820 | 61.236 | 15.154 | 1.00 19.81 | C |
| ATOM | 3562 | CB | THR | C | 88 | 32.510 | 59.925 | 15.865 | 1.00 19.88 | C |
| ATOM | 3563 | OG1 | THR | C | 88 | 31.206 | 60.027 | 16.461 | 1.00 18.59 | C |
| ATOM | 3564 | CG2 | THR | C | 88 | 33.565 | 59.635 | 16.945 | 1.00 18.35 | C |
| ATOM | 3565 | C | THR | C | 88 | 34.242 | 61.213 | 14.611 | 1.00 20.52 | C |
| ATOM | 3566 | O | THR | C | 88 | 35.134 | 61.866 | 15.162 | 1.00 20.94 | C |
| ATOM | 3567 | N | VAL | C | 89 | 34.458 | 60.485 | 13.519 | 1.00 20.42 | C |
| ATOM | 3568 | CA | VAL | C | 89 | 35.793 | 60.418 | 12.935 | 1.00 20.16 | C |
| ATOM | 3569 | CB | VAL | C | 89 | 35.874 | 59.378 | 11.800 | 1.00 20.24 | C |
| ATOM | 3570 | CG1 | VAL | C | 89 | 37.212 | 59.486 | 11.084 | 1.00 19.71 | C |
| ATOM | 3571 | CG2 | VAL | C | 89 | 35.739 | 57.980 | 12.381 | 1.00 21.01 | C |
| ATOM | 3572 | C | VAL | C | 89 | 36.211 | 61.784 | 12.414 | 1.00 20.76 | C |
| ATOM | 3573 | O | VAL | C | 89 | 37.357 | 62.195 | 12.596 | 1.00 21.36 | C |
| ATOM | 3574 | N | SER | C | 90 | 35.285 | 62.493 | 11.778 | 1.00 20.41 | C |
| ATOM | 3575 | CA | SER | C | 90 | 35.590 | 63.823 | 11.255 | 1.00 21.47 | C |
| ATOM | 3576 | CB | SER | C | 90 | 34.359 | 64.424 | 10.562 | 1.00 21.05 | C |
| ATOM | 3577 | OG | SER | C | 90 | 34.095 | 63.771 | 9.328 | 1.00 19.41 | C |
| ATOM | 3578 | C | SER | C | 90 | 36.072 | 64.770 | 12.363 | 1.00 21.18 | C |
| ATOM | 3579 | O | SER | C | 90 | 37.039 | 65.504 | 12.177 | 1.00 20.80 | C |
| ATOM | 3580 | N | LEU | C | 91 | 35.401 | 64.754 | 13.513 | 1.00 20.16 | C |
| ATOM | 3581 | CA | LEU | C | 91 | 35.795 | 65.623 | 14.614 | 1.00 20.29 | C |
| ATOM | 3582 | CB | LEU | C | 91 | 34.767 | 65.554 | 15.743 | 1.00 21.20 | C |
| ATOM | 3583 | CG | LEU | C | 91 | 35.035 | 66.481 | 16.934 | 1.00 21.70 | C |
| ATOM | 3584 | CD1 | LEU | C | 91 | 35.183 | 67.922 | 16.447 | 1.00 19.30 | C |
| ATOM | 3585 | CD2 | LEU | C | 91 | 33.901 | 66.358 | 17.945 | 1.00 19.75 | C |
| ATOM | 3586 | C | LEU | C | 91 | 37.175 | 65.245 | 15.141 | 1.00 20.94 | C |
| ATOM | 3587 | O | LEU | C | 91 | 38.033 | 66.106 | 15.344 | 1.00 21.46 | C |
| ATOM | 3588 | N | LEU | C | 92 | 37.394 | 63.955 | 15.361 | 1.00 20.43 | C |
| ATOM | 3589 | CA | LEU | C | 92 | 38.690 | 63.494 | 15.844 | 1.00 20.25 | C |
| ATOM | 3590 | CB | LEU | C | 92 | 38.660 | 61.979 | 16.064 | 1.00 19.75 | C |
| ATOM | 3591 | CG | LEU | C | 92 | 37.657 | 61.492 | 17.122 | 1.00 19.34 | C |
| ATOM | 3592 | CD1 | LEU | C | 92 | 37.706 | 59.978 | 17.225 | 1.00 16.93 | C |
| ATOM | 3593 | CD2 | LEU | C | 92 | 37.977 | 62.122 | 18.464 | 1.00 18.80 | C |
| ATOM | 3594 | C | LEU | C | 92 | 39.809 | 63.868 | 14.864 | 1.00 21.25 | C |
| ATOM | 3595 | O | LEU | C | 92 | 40.924 | 64.210 | 15.272 | 1.00 19.52 | C |
| ATOM | 3596 | N | LYS | C | 93 | 39.528 | 63.801 | 13.568 | 1.00 22.26 | C |
| ATOM | 3597 | CA | LYS | C | 93 | 40.551 | 64.159 | 12.593 | 1.00 24.82 | C |
| ATOM | 3598 | CB | LYS | C | 93 | 40.087 | 63.829 | 11.174 | 1.00 25.53 | C |

Figure 9 (56 of 92)

```
ATOM   3599  CG   LYS C  93      40.354  62.386  10.782  1.00 27.15           C
ATOM   3600  CD   LYS C  93      39.838  62.071   9.391  1.00 27.98           C
ATOM   3601  CE   LYS C  93      40.548  62.874   8.321  1.00 28.33           C
ATOM   3602  NZ   LYS C  93      41.988  62.521   8.258  1.00 31.66           C
ATOM   3603  C    LYS C  93      40.891  65.640  12.697  1.00 24.84           C
ATOM   3604  O    LYS C  93      42.028  66.038  12.461  1.00 24.24           C
ATOM   3605  N    GLN C  94      39.895  66.443  13.057  1.00 25.92           C
ATOM   3606  CA   GLN C  94      40.066  67.878  13.208  1.00 27.11           C
ATOM   3607  CB   GLN C  94      38.692  68.560  13.247  1.00 28.83           C
ATOM   3608  CG   GLN C  94      38.741  70.083  13.299  1.00 32.80           C
ATOM   3609  CD   GLN C  94      37.361  70.722  13.379  1.00 34.79           C
ATOM   3610  OE1  GLN C  94      36.630  70.539  14.355  1.00 35.40           C
ATOM   3611  NE2  GLN C  94      37.000  71.480  12.346  1.00 36.38           C
ATOM   3612  C    GLN C  94      40.844  68.190  14.493  1.00 27.36           C
ATOM   3613  O    GLN C  94      41.569  69.184  14.572  1.00 27.60           C
ATOM   3614  N    ARG C  95      40.695  67.334  15.498  1.00 26.44           C
ATOM   3615  CA   ARG C  95      41.379  67.537  16.771  1.00 25.03           C
ATOM   3616  CB   ARG C  95      40.580  66.893  17.906  1.00 23.61           C
ATOM   3617  CG   ARG C  95      39.256  67.586  18.172  1.00 23.56           C
ATOM   3618  CD   ARG C  95      38.505  66.949  19.315  1.00 20.52           C
ATOM   3619  NE   ARG C  95      37.353  67.757  19.697  1.00 22.09           C
ATOM   3620  CZ   ARG C  95      36.460  67.406  20.616  1.00 20.93           C
ATOM   3621  NH1  ARG C  95      35.445  68.211  20.902  1.00 21.14           C
ATOM   3622  NH2  ARG C  95      36.571  66.244  21.245  1.00 21.46           C
ATOM   3623  C    ARG C  95      42.804  66.988  16.768  1.00 25.67           C
ATOM   3624  O    ARG C  95      43.658  67.465  17.516  1.00 25.09           C
ATOM   3625  N    TYR C  96      43.061  65.991  15.925  1.00 23.60           C
ATOM   3626  CA   TYR C  96      44.390  65.393  15.846  1.00 24.26           C
ATOM   3627  CB   TYR C  96      44.393  64.004  16.489  1.00 23.14           C
ATOM   3628  CG   TYR C  96      43.961  63.997  17.945  1.00 23.36           C
ATOM   3629  CD1  TYR C  96      42.619  63.843  18.299  1.00 22.31           C
ATOM   3630  CE1  TYR C  96      42.219  63.837  19.640  1.00 23.43           C
ATOM   3631  CD2  TYR C  96      44.899  64.148  18.969  1.00 23.00           C
ATOM   3632  CE2  TYR C  96      44.513  64.145  20.309  1.00 24.11           C
ATOM   3633  CZ   TYR C  96      43.176  63.989  20.639  1.00 24.01           C
ATOM   3634  OH   TYR C  96      42.808  63.996  21.965  1.00 23.21           C
ATOM   3635  C    TYR C  96      44.830  65.281  14.393  1.00 25.49           C
ATOM   3636  O    TYR C  96      45.063  64.184  13.892  1.00 22.08           C
ATOM   3637  N    PRO C  97      44.966  66.429  13.708  1.00 27.07           C
ATOM   3638  CD   PRO C  97      44.719  67.764  14.278  1.00 28.29           C
ATOM   3639  CA   PRO C  97      45.371  66.540  12.300  1.00 28.12           C
ATOM   3640  CB   PRO C  97      45.281  68.041  12.022  1.00 28.67           C
ATOM   3641  CG   PRO C  97      44.314  68.543  13.059  1.00 31.62           C
ATOM   3642  C    PRO C  97      46.750  65.996  11.960  1.00 28.23           C
ATOM   3643  O    PRO C  97      47.007  65.642  10.813  1.00 29.06           C
ATOM   3644  N    ASN C  98      47.642  65.932  12.940  1.00 28.61           C
ATOM   3645  CA   ASN C  98      48.982  65.428  12.670  1.00 30.26           C
ATOM   3646  CB   ASN C  98      50.006  66.140  13.551  1.00 33.22           C
ATOM   3647  CG   ASN C  98      49.926  67.642  13.430  1.00 36.69           C
ATOM   3648  OD1  ASN C  98      49.885  68.186  12.323  1.00 39.22           C
ATOM   3649  ND2  ASN C  98      49.906  68.327  14.569  1.00 36.97           C
ATOM   3650  C    ASN C  98      49.122  63.930  12.879  1.00 29.58           C
ATOM   3651  O    ASN C  98      50.160  63.351  12.549  1.00 29.18           C
ATOM   3652  N    ASP C  99      48.086  63.298  13.420  1.00 27.54           C
ATOM   3653  CA   ASP C  99      48.148  61.862  13.687  1.00 26.05           C
ATOM   3654  CB   ASP C  99      47.553  61.579  15.070  1.00 24.73           C
ATOM   3655  CG   ASP C  99      48.294  62.323  16.183  1.00 24.93           C
ATOM   3656  OD1  ASP C  99      49.520  62.129  16.302  1.00 23.46           C
ATOM   3657  OD2  ASP C  99      47.658  63.097  16.927  1.00 24.82           C
ATOM   3658  C    ASP C  99      47.464  61.006  12.626  1.00 25.64           C
ATOM   3659  O    ASP C  99      46.670  61.507  11.827  1.00 25.10           C
ATOM   3660  N    GLN C 100      47.793  59.718  12.597  1.00 24.31           C
ATOM   3661  CA   GLN C 100      47.173  58.815  11.635  1.00 24.62           C
ATOM   3662  CB   GLN C 100      48.218  57.938  10.945  1.00 26.15           C
ATOM   3663  CG   GLN C 100      47.592  56.868  10.060  1.00 32.37           C
ATOM   3664  CD   GLN C 100      48.546  56.317   9.014  1.00 34.75           C
```

Figure 9 (57 of 92)

| | | | | | | | | | | |
|---|---|---|---|---|---|---|---|---|---|---|
| ATOM | 3665 | OE1 | GLN | C | 100 | 49.677 | 55.936 | 9.320 | 1.00 36.41 | C |
| ATOM | 3666 | NE2 | GLN | C | 100 | 48.085 | 56.264 | 7.766 | 1.00 37.73 | C |
| ATOM | 3667 | C | GLN | C | 100 | 46.150 | 57.947 | 12.356 | 1.00 23.80 | C |
| ATOM | 3668 | O | GLN | C | 100 | 46.501 | 57.087 | 13.170 | 1.00 22.33 | C |
| ATOM | 3669 | N | LEU | C | 101 | 44.879 | 58.184 | 12.051 | 1.00 22.62 | C |
| ATOM | 3670 | CA | LEU | C | 101 | 43.793 | 57.453 | 12.686 | 1.00 22.50 | C |
| ATOM | 3671 | CB | LEU | C | 101 | 42.602 | 58.393 | 12.921 | 1.00 24.13 | C |
| ATOM | 3672 | CG | LEU | C | 101 | 42.951 | 59.748 | 13.556 | 1.00 25.37 | C |
| ATOM | 3673 | CD1 | LEU | C | 101 | 41.683 | 60.490 | 13.944 | 1.00 24.41 | C |
| ATOM | 3674 | CD2 | LEU | C | 101 | 43.827 | 59.526 | 14.783 | 1.00 26.41 | C |
| ATOM | 3675 | C | LEU | C | 101 | 43.322 | 56.229 | 11.918 | 1.00 21.70 | C |
| ATOM | 3676 | O | LEU | C | 101 | 43.266 | 56.234 | 10.683 | 1.00 21.45 | C |
| ATOM | 3677 | N | PHE | C | 102 | 42.983 | 55.184 | 12.670 | 1.00 19.42 | C |
| ATOM | 3678 | CA | PHE | C | 102 | 42.473 | 53.933 | 12.112 | 1.00 18.86 | C |
| ATOM | 3679 | CB | PHE | C | 102 | 43.456 | 52.776 | 12.344 | 1.00 18.60 | C |
| ATOM | 3680 | CG | PHE | C | 102 | 44.803 | 52.984 | 11.721 | 1.00 20.58 | C |
| ATOM | 3681 | CD1 | PHE | C | 102 | 45.699 | 53.908 | 12.253 | 1.00 19.57 | C |
| ATOM | 3682 | CD2 | PHE | C | 102 | 45.182 | 52.249 | 10.603 | 1.00 18.89 | C |
| ATOM | 3683 | CE1 | PHE | C | 102 | 46.959 | 54.094 | 11.675 | 1.00 21.99 | C |
| ATOM | 3684 | CE2 | PHE | C | 102 | 46.438 | 52.428 | 10.017 | 1.00 19.72 | C |
| ATOM | 3685 | CZ | PHE | C | 102 | 47.328 | 53.349 | 10.550 | 1.00 19.94 | C |
| ATOM | 3686 | C | PHE | C | 102 | 41.164 | 53.609 | 12.835 | 1.00 18.46 | C |
| ATOM | 3687 | O | PHE | C | 102 | 41.016 | 53.931 | 14.018 | 1.00 16.62 | C |
| ATOM | 3688 | N | PHE | C | 103 | 40.227 | 52.975 | 12.131 | 1.00 17.51 | C |
| ATOM | 3689 | CA | PHE | C | 103 | 38.945 | 52.597 | 12.728 | 1.00 17.32 | C |
| ATOM | 3690 | CB | PHE | C | 103 | 37.778 | 53.224 | 11.963 | 1.00 19.99 | C |
| ATOM | 3691 | CG | PHE | C | 103 | 36.474 | 53.213 | 12.734 | 1.00 23.05 | C |
| ATOM | 3692 | CD1 | PHE | C | 103 | 36.243 | 54.133 | 13.757 | 1.00 24.44 | C |
| ATOM | 3693 | CD2 | PHE | C | 103 | 35.494 | 52.267 | 12.457 | 1.00 22.59 | C |
| ATOM | 3694 | CE1 | PHE | C | 103 | 35.046 | 54.106 | 14.497 | 1.00 24.98 | C |
| ATOM | 3695 | CE2 | PHE | C | 103 | 34.303 | 52.234 | 13.188 | 1.00 24.22 | C |
| ATOM | 3696 | CZ | PHE | C | 103 | 34.082 | 53.152 | 14.207 | 1.00 24.62 | C |
| ATOM | 3697 | C | PHE | C | 103 | 38.794 | 51.071 | 12.738 | 1.00 16.77 | C |
| ATOM | 3698 | O | PHE | C | 103 | 38.921 | 50.414 | 11.700 | 1.00 14.92 | C |
| ATOM | 3699 | N | ILE | C | 104 | 38.513 | 50.518 | 13.917 | 1.00 15.04 | C |
| ATOM | 3700 | CA | ILE | C | 104 | 38.385 | 49.074 | 14.075 | 1.00 15.15 | C |
| ATOM | 3701 | CB | ILE | C | 104 | 38.907 | 48.643 | 15.470 | 1.00 14.52 | C |
| ATOM | 3702 | CG2 | ILE | C | 104 | 38.811 | 47.129 | 15.627 | 1.00 14.40 | C |
| ATOM | 3703 | CG1 | ILE | C | 104 | 40.358 | 49.100 | 15.637 | 1.00 14.29 | C |
| ATOM | 3704 | CD1 | ILE | C | 104 | 40.857 | 49.046 | 17.074 | 1.00 15.97 | C |
| ATOM | 3705 | C | ILE | C | 104 | 36.972 | 48.516 | 13.877 | 1.00 14.88 | C |
| ATOM | 3706 | O | ILE | C | 104 | 36.023 | 48.985 | 14.502 | 1.00 15.31 | C |
| ATOM | 3707 | N | ILE | C | 105 | 36.851 | 47.518 | 13.000 | 1.00 13.74 | C |
| ATOM | 3708 | CA | ILE | C | 105 | 35.572 | 46.860 | 12.727 | 1.00 13.30 | C |
| ATOM | 3709 | CB | ILE | C | 105 | 34.913 | 47.376 | 11.429 | 1.00 14.17 | C |
| ATOM | 3710 | CG2 | ILE | C | 105 | 34.610 | 48.872 | 11.532 | 1.00 13.36 | C |
| ATOM | 3711 | CG1 | ILE | C | 105 | 35.844 | 47.088 | 10.242 | 1.00 12.90 | C |
| ATOM | 3712 | CD1 | ILE | C | 105 | 35.149 | 47.114 | 8.892 | 1.00 13.66 | C |
| ATOM | 3713 | C | ILE | C | 105 | 35.778 | 45.359 | 12.517 | 1.00 14.56 | C |
| ATOM | 3714 | O | ILE | C | 105 | 36.910 | 44.878 | 12.410 | 1.00 15.03 | C |
| ATOM | 3715 | N | GLY | C | 106 | 34.674 | 44.622 | 12.439 | 1.00 14.59 | C |
| ATOM | 3716 | CA | GLY | C | 106 | 34.767 | 43.201 | 12.179 | 1.00 14.10 | C |
| ATOM | 3717 | C | GLY | C | 106 | 35.105 | 43.114 | 10.702 | 1.00 15.43 | C |
| ATOM | 3718 | O | GLY | C | 106 | 34.572 | 43.879 | 9.902 | 1.00 14.69 | C |
| ATOM | 3719 | N | ALA | C | 107 | 35.995 | 42.209 | 10.322 | 1.00 16.61 | C |
| ATOM | 3720 | CA | ALA | C | 107 | 36.373 | 42.103 | 8.916 | 1.00 19.13 | C |
| ATOM | 3721 | CB | ALA | C | 107 | 37.488 | 41.070 | 8.761 | 1.00 18.63 | C |
| ATOM | 3722 | C | ALA | C | 107 | 35.189 | 41.750 | 7.999 | 1.00 19.99 | C |
| ATOM | 3723 | O | ALA | C | 107 | 35.221 | 42.015 | 6.791 | 1.00 22.18 | C |
| ATOM | 3724 | N | ASP | C | 108 | 34.140 | 41.174 | 8.578 | 1.00 19.18 | C |
| ATOM | 3725 | CA | ASP | C | 108 | 32.966 | 40.771 | 7.807 | 1.00 20.28 | C |
| ATOM | 3726 | CB | ASP | C | 108 | 32.406 | 39.463 | 8.374 | 1.00 18.92 | C |
| ATOM | 3727 | CG | ASP | C | 108 | 31.890 | 39.632 | 9.786 | 1.00 19.45 | C |
| ATOM | 3728 | OD1 | ASP | C | 108 | 32.515 | 40.396 | 10.551 | 1.00 19.78 | C |
| ATOM | 3729 | OD2 | ASP | C | 108 | 30.873 | 39.005 | 10.138 | 1.00 21.97 | C |
| ATOM | 3730 | C | ASP | C | 108 | 31.841 | 41.800 | 7.765 | 1.00 19.27 | C |

Figure 9 (58 of 92)

```
ATOM   3731  O    ASP C 108      30.851  41.592   7.064  1.00 21.15           C
ATOM   3732  N    MET C 109      31.973  42.900   8.499  1.00 18.52           C
ATOM   3733  CA   MET C 109      30.903  43.905   8.528  1.00 17.44           C
ATOM   3734  CB   MET C 109      31.326  45.133   9.364  1.00 13.59           C
ATOM   3735  CG   MET C 109      30.185  46.139   9.628  1.00 16.36           C
ATOM   3736  SD   MET C 109      30.664  47.645  10.542  1.00  8.56           C
ATOM   3737  CE   MET C 109      31.143  48.718   9.200  1.00 15.26           C
ATOM   3738  C    MET C 109      30.435  44.353   7.134  1.00 17.37           C
ATOM   3739  O    MET C 109      29.231  44.490   6.900  1.00 16.74           C
ATOM   3740  N    ILE C 110      31.370  44.542   6.202  1.00 16.77           C
ATOM   3741  CA   ILE C 110      31.013  45.006   4.859  1.00 17.41           C
ATOM   3742  CB   ILE C 110      31.828  46.263   4.495  1.00 18.71           C
ATOM   3743  CG2  ILE C 110      31.536  47.363   5.490  1.00 20.14           C
ATOM   3744  CG1  ILE C 110      33.320  45.933   4.503  1.00 18.14           C
ATOM   3745  CD1  ILE C 110      34.222  47.124   4.224  1.00 19.47           C
ATOM   3746  C    ILE C 110      31.188  43.979   3.746  1.00 18.19           C
ATOM   3747  O    ILE C 110      31.153  44.316   2.563  1.00 16.74           C
ATOM   3748  N    GLU C 111      31.369  42.723   4.128  1.00 19.27           C
ATOM   3749  CA   GLU C 111      31.559  41.642   3.170  1.00 21.58           C
ATOM   3750  CB   GLU C 111      31.857  40.335   3.906  1.00 25.13           C
ATOM   3751  CG   GLU C 111      33.326  40.039   4.047  1.00 34.25           C
ATOM   3752  CD   GLU C 111      34.026  40.013   2.704  1.00 37.78           C
ATOM   3753  OE1  GLU C 111      33.671  39.153   1.865  1.00 41.53           C
ATOM   3754  OE2  GLU C 111      34.925  40.858   2.484  1.00 42.02           C
ATOM   3755  C    GLU C 111      30.412  41.374   2.217  1.00 20.01           C
ATOM   3756  O    GLU C 111      30.635  40.995   1.072  1.00 18.95           C
ATOM   3757  N    TYR C 112      29.188  41.559   2.690  1.00 19.01           C
ATOM   3758  CA   TYR C 112      28.012  41.258   1.885  1.00 19.21           C
ATOM   3759  CB   TYR C 112      27.003  40.509   2.764  1.00 18.49           C
ATOM   3760  CG   TYR C 112      27.688  39.529   3.698  1.00 19.33           C
ATOM   3761  CD1  TYR C 112      27.754  39.771   5.074  1.00 18.75           C
ATOM   3762  CE1  TYR C 112      28.458  38.911   5.924  1.00 18.08           C
ATOM   3763  CD2  TYR C 112      28.336  38.398   3.196  1.00 18.02           C
ATOM   3764  CE2  TYR C 112      29.037  37.534   4.036  1.00 18.00           C
ATOM   3765  CZ   TYR C 112      29.096  37.798   5.394  1.00 18.74           C
ATOM   3766  OH   TYR C 112      29.806  36.954   6.214  1.00 22.01           C
ATOM   3767  C    TYR C 112      27.344  42.454   1.214  1.00 19.21           C
ATOM   3768  O    TYR C 112      26.298  42.307   0.589  1.00 20.71           C
ATOM   3769  N    LEU C 113      27.956  43.626   1.333  1.00 18.71           C
ATOM   3770  CA   LEU C 113      27.417  44.844   0.738  1.00 19.05           C
ATOM   3771  CB   LEU C 113      27.873  46.066   1.533  1.00 16.88           C
ATOM   3772  CG   LEU C 113      27.384  46.153   2.977  1.00 17.39           C
ATOM   3773  CD1  LEU C 113      28.182  47.214   3.708  1.00 16.54           C
ATOM   3774  CD2  LEU C 113      25.888  46.470   2.997  1.00 16.45           C
ATOM   3775  C    LEU C 113      27.834  45.045  -0.714  1.00 20.40           C
ATOM   3776  O    LEU C 113      28.970  44.754  -1.091  1.00 20.28           C
ATOM   3777  N    PRO C 114      26.909  45.539  -1.553  1.00 20.67           C
ATOM   3778  CD   PRO C 114      25.464  45.725  -1.305  1.00 20.73           C
ATOM   3779  CA   PRO C 114      27.231  45.777  -2.959  1.00 20.46           C
ATOM   3780  CB   PRO C 114      25.864  45.704  -3.638  1.00 19.87           C
ATOM   3781  CG   PRO C 114      24.974  46.345  -2.621  1.00 20.63           C
ATOM   3782  C    PRO C 114      27.856  47.171  -3.023  1.00 21.94           C
ATOM   3783  O    PRO C 114      27.936  47.866  -1.999  1.00 21.12           C
ATOM   3784  N    LYS C 115      28.287  47.579  -4.212  1.00 22.73           C
ATOM   3785  CA   LYS C 115      28.916  48.883  -4.395  1.00 22.76           C
ATOM   3786  CB   LYS C 115      29.105  49.153  -5.890  1.00 24.69           C
ATOM   3787  CG   LYS C 115      29.874  50.433  -6.203  1.00 26.81           C
ATOM   3788  CD   LYS C 115      31.291  50.378  -5.640  1.00 30.42           C
ATOM   3789  CE   LYS C 115      32.081  51.618  -6.021  1.00 32.02           C
ATOM   3790  NZ   LYS C 115      33.464  51.577  -5.468  1.00 35.15           C
ATOM   3791  C    LYS C 115      28.086  49.997  -3.750  1.00 22.01           C
ATOM   3792  O    LYS C 115      26.906  50.170  -4.064  1.00 20.83           C
ATOM   3793  N    TRP C 116      28.707  50.751  -2.846  1.00 21.49           C
ATOM   3794  CA   TRP C 116      28.002  51.822  -2.150  1.00 21.67           C
ATOM   3795  CB   TRP C 116      27.429  51.270  -0.840  1.00 22.13           C
ATOM   3796  CG   TRP C 116      26.353  52.114  -0.241  1.00 24.90           C
```

Figure 9 (59 of 92)

```
ATOM   3797  CD2 TRP C 116      25.712  51.913   1.023  1.00 25.77           C
ATOM   3798  CE2 TRP C 116      24.757  52.939   1.174  1.00 25.57           C
ATOM   3799  CE3 TRP C 116      25.854  50.965   2.044  1.00 26.86           C
ATOM   3800  CD1 TRP C 116      25.774  53.223  -0.792  1.00 24.96           C
ATOM   3801  NE1 TRP C 116      24.815  53.724   0.052  1.00 23.54           C
ATOM   3802  CZ2 TRP C 116      23.946  53.046   2.304  1.00 26.11           C
ATOM   3803  CZ3 TRP C 116      25.049  51.071   3.170  1.00 28.37           C
ATOM   3804  CH2 TRP C 116      24.107  52.106   3.291  1.00 28.92           C
ATOM   3805  C   TRP C 116      28.921  53.023  -1.873  1.00 21.72           C
ATOM   3806  O   TRP C 116      29.905  52.914  -1.137  1.00 20.76           C
ATOM   3807  N   TYR C 117      28.593  54.173  -2.455  1.00 22.28           C
ATOM   3808  CA  TYR C 117      29.425  55.362  -2.275  1.00 22.84           C
ATOM   3809  CB  TYR C 117      28.943  56.515  -3.163  1.00 20.98           C
ATOM   3810  CG  TYR C 117      29.031  56.249  -4.657  1.00 19.33           C
ATOM   3811  CD1 TYR C 117      30.071  55.490  -5.199  1.00 20.49           C
ATOM   3812  CE1 TYR C 117      30.158  55.264  -6.591  1.00 21.43           C
ATOM   3813  CD2 TYR C 117      28.083  56.779  -5.530  1.00 20.89           C
ATOM   3814  CE2 TYR C 117      28.159  56.563  -6.913  1.00 21.61           C
ATOM   3815  CZ  TYR C 117      29.190  55.803  -7.432  1.00 19.93           C
ATOM   3816  OH  TYR C 117      29.216  55.542  -8.780  1.00 21.90           C
ATOM   3817  C   TYR C 117      29.518  55.838  -0.833  1.00 23.61           C
ATOM   3818  O   TYR C 117      30.566  56.320  -0.417  1.00 23.61           C
ATOM   3819  N   LYS C 118      28.436  55.717  -0.068  1.00 25.60           C
ATOM   3820  CA  LYS C 118      28.480  56.146   1.325  1.00 27.12           C
ATOM   3821  CB  LYS C 118      27.133  55.916   2.012  1.00 30.40           C
ATOM   3822  CG  LYS C 118      26.066  56.917   1.616  1.00 33.89           C
ATOM   3823  CD  LYS C 118      26.505  58.335   1.950  1.00 37.71           C
ATOM   3824  CE  LYS C 118      25.440  59.361   1.568  1.00 41.14           C
ATOM   3825  NZ  LYS C 118      25.906  60.768   1.796  1.00 43.96           C
ATOM   3826  C   LYS C 118      29.569  55.373   2.060  1.00 27.75           C
ATOM   3827  O   LYS C 118      30.318  55.941   2.854  1.00 27.05           C
ATOM   3828  N   LEU C 119      29.651  54.074   1.790  1.00 25.01           C
ATOM   3829  CA  LEU C 119      30.654  53.236   2.423  1.00 26.03           C
ATOM   3830  CB  LEU C 119      30.402  51.757   2.092  1.00 25.13           C
ATOM   3831  CG  LEU C 119      31.406  50.751   2.664  1.00 25.53           C
ATOM   3832  CD1 LEU C 119      31.474  50.895   4.171  1.00 23.78           C
ATOM   3833  CD2 LEU C 119      31.007  49.338   2.286  1.00 24.95           C
ATOM   3834  C   LEU C 119      32.053  53.647   1.959  1.00 26.45           C
ATOM   3835  O   LEU C 119      32.973  53.784   2.768  1.00 26.34           C
ATOM   3836  N   ASP C 120      32.211  53.858   0.658  1.00 27.11           C
ATOM   3837  CA  ASP C 120      33.508  54.254   0.133  1.00 27.96           C
ATOM   3838  CB  ASP C 120      33.461  54.385  -1.390  1.00 30.51           C
ATOM   3839  CG  ASP C 120      33.096  53.085  -2.080  1.00 33.04           C
ATOM   3840  OD1 ASP C 120      33.404  52.000  -1.536  1.00 35.69           C
ATOM   3841  OD2 ASP C 120      32.513  53.151  -3.180  1.00 35.80           C
ATOM   3842  C   ASP C 120      33.958  55.581   0.736  1.00 27.57           C
ATOM   3843  O   ASP C 120      35.137  55.759   1.051  1.00 24.90           C
ATOM   3844  N   GLU C 121      33.020  56.513   0.893  1.00 27.82           C
ATOM   3845  CA  GLU C 121      33.342  57.824   1.453  1.00 28.15           C
ATOM   3846  CB  GLU C 121      32.084  58.695   1.590  1.00 32.05           C
ATOM   3847  CG  GLU C 121      31.185  58.809   0.357  1.00 38.80           C
ATOM   3848  CD  GLU C 121      31.888  59.374  -0.870  1.00 43.90           C
ATOM   3849  OE1 GLU C 121      32.872  60.127  -0.698  1.00 46.72           C
ATOM   3850  OE2 GLU C 121      31.444  59.083  -2.009  1.00 45.89           C
ATOM   3851  C   GLU C 121      33.950  57.631   2.839  1.00 26.50           C
ATOM   3852  O   GLU C 121      34.961  58.253   3.188  1.00 26.10           C
ATOM   3853  N   LEU C 122      33.325  56.757   3.620  1.00 23.13           C
ATOM   3854  CA  LEU C 122      33.785  56.479   4.973  1.00 23.40           C
ATOM   3855  CB  LEU C 122      32.737  55.636   5.702  1.00 21.86           C
ATOM   3856  CG  LEU C 122      32.859  55.426   7.213  1.00 23.39           C
ATOM   3857  CD1 LEU C 122      33.051  56.765   7.953  1.00 20.92           C
ATOM   3858  CD2 LEU C 122      31.587  54.733   7.692  1.00 21.52           C
ATOM   3859  C   LEU C 122      35.147  55.776   4.965  1.00 22.73           C
ATOM   3860  O   LEU C 122      36.037  56.132   5.733  1.00 20.81           C
ATOM   3861  N   LEU C 123      35.311  54.793   4.085  1.00 23.33           C
ATOM   3862  CA  LEU C 123      36.569  54.065   3.990  1.00 25.01           C
```

Figure 9 (60 of 92)

| ATOM | 3863 | CB | LEU | C | 123 | 36.428 | 52.874 | 3.037 | 1.00 | 26.41 | C |
|---|---|---|---|---|---|---|---|---|---|---|---|
| ATOM | 3864 | CG | LEU | C | 123 | 35.487 | 51.718 | 3.385 | 1.00 | 26.95 | C |
| ATOM | 3865 | CD1 | LEU | C | 123 | 35.533 | 50.704 | 2.250 | 1.00 | 27.89 | C |
| ATOM | 3866 | CD2 | LEU | C | 123 | 35.891 | 51.061 | 4.702 | 1.00 | 27.42 | C |
| ATOM | 3867 | C | LEU | C | 123 | 37.731 | 54.952 | 3.518 | 1.00 | 25.76 | C |
| ATOM | 3868 | O | LEU | C | 123 | 38.893 | 54.658 | 3.793 | 1.00 | 24.51 | C |
| ATOM | 3869 | N | ASN | C | 124 | 37.422 | 56.031 | 2.807 | 1.00 | 26.64 | C |
| ATOM | 3870 | CA | ASN | C | 124 | 38.461 | 56.931 | 2.315 | 1.00 | 27.97 | C |
| ATOM | 3871 | CB | ASN | C | 124 | 38.031 | 57.548 | 0.979 | 1.00 | 31.51 | C |
| ATOM | 3872 | CG | ASN | C | 124 | 39.114 | 58.417 | 0.355 | 1.00 | 34.60 | C |
| ATOM | 3873 | OD1 | ASN | C | 124 | 40.284 | 58.354 | 0.740 | 1.00 | 36.43 | C |
| ATOM | 3874 | ND2 | ASN | C | 124 | 38.725 | 59.226 | -0.628 | 1.00 | 38.72 | C |
| ATOM | 3875 | C | ASN | C | 124 | 38.761 | 58.031 | 3.332 | 1.00 | 27.41 | C |
| ATOM | 3876 | O | ASN | C | 124 | 39.778 | 58.716 | 3.243 | 1.00 | 28.14 | C |
| ATOM | 3877 | N | LEU | C | 125 | 37.865 | 58.179 | 4.300 | 1.00 | 26.30 | C |
| ATOM | 3878 | CA | LEU | C | 125 | 37.988 | 59.173 | 5.357 | 1.00 | 26.45 | C |
| ATOM | 3879 | CB | LEU | C | 125 | 36.632 | 59.349 | 6.045 | 1.00 | 26.70 | C |
| ATOM | 3880 | CG | LEU | C | 125 | 36.279 | 60.651 | 6.770 | 1.00 | 29.92 | C |
| ATOM | 3881 | CD1 | LEU | C | 125 | 35.238 | 60.352 | 7.838 | 1.00 | 28.26 | C |
| ATOM | 3882 | CD2 | LEU | C | 125 | 37.494 | 61.263 | 7.408 | 1.00 | 32.13 | C |
| ATOM | 3883 | C | LEU | C | 125 | 39.017 | 58.725 | 6.399 | 1.00 | 25.74 | C |
| ATOM | 3884 | O | LEU | C | 125 | 39.780 | 59.532 | 6.926 | 1.00 | 24.40 | C |
| ATOM | 3885 | N | ILE | C | 126 | 39.030 | 57.430 | 6.687 | 1.00 | 24.42 | C |
| ATOM | 3886 | CA | ILE | C | 126 | 39.932 | 56.879 | 7.689 | 1.00 | 24.78 | C |
| ATOM | 3887 | CB | ILE | C | 126 | 39.254 | 56.965 | 9.085 | 1.00 | 23.78 | C |
| ATOM | 3888 | CG2 | ILE | C | 126 | 37.920 | 56.240 | 9.046 | 1.00 | 25.58 | C |
| ATOM | 3889 | CG1 | ILE | C | 126 | 40.147 | 56.382 | 10.173 | 1.00 | 24.12 | C |
| ATOM | 3890 | CD1 | ILE | C | 126 | 39.549 | 56.518 | 11.572 | 1.00 | 21.33 | C |
| ATOM | 3891 | C | ILE | C | 126 | 40.268 | 55.428 | 7.348 | 1.00 | 24.67 | C |
| ATOM | 3892 | O | ILE | C | 126 | 39.429 | 54.700 | 6.823 | 1.00 | 25.12 | C |
| ATOM | 3893 | N | GLN | C | 127 | 41.495 | 55.010 | 7.643 | 1.00 | 24.54 | C |
| ATOM | 3894 | CA | GLN | C | 127 | 41.916 | 53.647 | 7.348 | 1.00 | 24.15 | C |
| ATOM | 3895 | CB | GLN | C | 127 | 43.438 | 53.510 | 7.493 | 1.00 | 25.51 | C |
| ATOM | 3896 | CG | GLN | C | 127 | 43.959 | 52.100 | 7.246 | 1.00 | 26.33 | C |
| ATOM | 3897 | CD | GLN | C | 127 | 43.819 | 51.661 | 5.794 | 1.00 | 30.30 | C |
| ATOM | 3898 | OE1 | GLN | C | 127 | 44.473 | 52.212 | 4.905 | 1.00 | 29.78 | C |
| ATOM | 3899 | NE2 | GLN | C | 127 | 42.965 | 50.666 | 5.548 | 1.00 | 28.56 | C |
| ATOM | 3900 | C | GLN | C | 127 | 41.222 | 52.637 | 8.257 | 1.00 | 22.96 | C |
| ATOM | 3901 | O | GLN | C | 127 | 41.390 | 52.655 | 9.474 | 1.00 | 22.73 | C |
| ATOM | 3902 | N | PHE | C | 128 | 40.454 | 51.742 | 7.651 | 1.00 | 21.91 | C |
| ATOM | 3903 | CA | PHE | C | 128 | 39.742 | 50.727 | 8.404 | 1.00 | 22.39 | C |
| ATOM | 3904 | CB | PHE | C | 128 | 38.449 | 50.336 | 7.677 | 1.00 | 23.04 | C |
| ATOM | 3905 | CG | PHE | C | 128 | 37.293 | 51.243 | 7.973 | 1.00 | 27.63 | C |
| ATOM | 3906 | CD1 | PHE | C | 128 | 37.351 | 52.598 | 7.661 | 1.00 | 29.01 | C |
| ATOM | 3907 | CD2 | PHE | C | 128 | 36.153 | 50.748 | 8.597 | 1.00 | 29.08 | C |
| ATOM | 3908 | CE1 | PHE | C | 128 | 36.286 | 53.449 | 7.971 | 1.00 | 30.62 | C |
| ATOM | 3909 | CE2 | PHE | C | 128 | 35.087 | 51.588 | 8.911 | 1.00 | 30.42 | C |
| ATOM | 3910 | CZ | PHE | C | 128 | 35.154 | 52.942 | 8.597 | 1.00 | 30.47 | C |
| ATOM | 3911 | C | PHE | C | 128 | 40.575 | 49.480 | 8.644 | 1.00 | 21.06 | C |
| ATOM | 3912 | O | PHE | C | 128 | 41.294 | 49.023 | 7.760 | 1.00 | 20.86 | C |
| ATOM | 3913 | N | ILE | C | 129 | 40.481 | 48.946 | 9.858 | 1.00 | 21.05 | C |
| ATOM | 3914 | CA | ILE | C | 129 | 41.181 | 47.717 | 10.218 | 1.00 | 19.60 | C |
| ATOM | 3915 | CB | ILE | C | 129 | 41.993 | 47.867 | 11.518 | 1.00 | 18.27 | C |
| ATOM | 3916 | CG2 | ILE | C | 129 | 42.548 | 46.515 | 11.943 | 1.00 | 16.17 | C |
| ATOM | 3917 | CG1 | ILE | C | 129 | 43.147 | 48.845 | 11.309 | 1.00 | 16.87 | C |
| ATOM | 3918 | CD1 | ILE | C | 129 | 43.909 | 49.150 | 12.580 | 1.00 | 14.77 | C |
| ATOM | 3919 | C | ILE | C | 129 | 40.092 | 46.678 | 10.457 | 1.00 | 19.84 | C |
| ATOM | 3920 | O | ILE | C | 129 | 39.231 | 46.861 | 11.324 | 1.00 | 19.04 | C |
| ATOM | 3921 | N | GLY | C | 130 | 40.116 | 45.603 | 9.679 | 1.00 | 19.63 | C |
| ATOM | 3922 | CA | GLY | C | 130 | 39.123 | 44.559 | 9.848 | 1.00 | 21.16 | C |
| ATOM | 3923 | C | GLY | C | 130 | 39.664 | 43.425 | 10.704 | 1.00 | 21.65 | C |
| ATOM | 3924 | O | GLY | C | 130 | 40.649 | 42.790 | 10.341 | 1.00 | 22.69 | C |
| ATOM | 3925 | N | VAL | C | 131 | 39.033 | 43.178 | 11.846 | 1.00 | 21.56 | C |
| ATOM | 3926 | CA | VAL | C | 131 | 39.464 | 42.103 | 12.736 | 1.00 | 22.49 | C |
| ATOM | 3927 | CB | VAL | C | 131 | 39.054 | 42.393 | 14.200 | 1.00 | 22.21 | C |
| ATOM | 3928 | CG1 | VAL | C | 131 | 39.119 | 41.123 | 15.028 | 1.00 | 22.03 | C |

Figure 9 (61 of 92)

| ATOM | 3929 | CG2 | VAL | C | 131 | 39.967 | 43.455 | 14.790 | 1.00 | 19.46 | C |
|---|---|---|---|---|---|---|---|---|---|---|---|
| ATOM | 3930 | C | VAL | C | 131 | 38.840 | 40.778 | 12.316 | 1.00 | 24.54 | C |
| ATOM | 3931 | O | VAL | C | 131 | 37.650 | 40.717 | 12.006 | 1.00 | 24.68 | C |
| ATOM | 3932 | N | LYS | C | 132 | 39.645 | 39.720 | 12.305 | 1.00 | 26.09 | C |
| ATOM | 3933 | CA | LYS | C | 132 | 39.156 | 38.395 | 11.932 | 1.00 | 29.72 | C |
| ATOM | 3934 | CB | LYS | C | 132 | 39.324 | 38.159 | 10.427 | 1.00 | 27.45 | C |
| ATOM | 3935 | CG | LYS | C | 132 | 40.758 | 38.184 | 9.907 | 1.00 | 29.65 | C |
| ATOM | 3936 | CD | LYS | C | 132 | 40.759 | 38.034 | 8.387 | 1.00 | 29.39 | C |
| ATOM | 3937 | CE | LYS | C | 132 | 42.166 | 38.000 | 7.810 | 1.00 | 30.92 | C |
| ATOM | 3938 | NZ | LYS | C | 132 | 42.955 | 36.831 | 8.295 | 1.00 | 30.40 | C |
| ATOM | 3939 | C | LYS | C | 132 | 39.882 | 37.307 | 12.713 | 1.00 | 32.29 | C |
| ATOM | 3940 | O | LYS | C | 132 | 40.892 | 37.569 | 13.364 | 1.00 | 31.46 | C |
| ATOM | 3941 | N | ARG | C | 133 | 39.357 | 36.088 | 12.654 | 1.00 | 37.31 | C |
| ATOM | 3942 | CA | ARG | C | 133 | 39.963 | 34.964 | 13.359 | 1.00 | 41.55 | C |
| ATOM | 3943 | CB | ARG | C | 133 | 38.948 | 33.831 | 13.517 | 1.00 | 43.21 | C |
| ATOM | 3944 | CG | ARG | C | 133 | 37.667 | 34.236 | 14.227 | 1.00 | 45.09 | C |
| ATOM | 3945 | CD | ARG | C | 133 | 36.821 | 33.024 | 14.557 | 1.00 | 47.13 | C |
| ATOM | 3946 | NE | ARG | C | 133 | 35.466 | 33.383 | 14.975 | 1.00 | 50.59 | C |
| ATOM | 3947 | CZ | ARG | C | 133 | 34.553 | 33.933 | 14.177 | 1.00 | 51.63 | C |
| ATOM | 3948 | NH1 | ARG | C | 133 | 33.351 | 34.221 | 14.647 | 1.00 | 53.13 | C |
| ATOM | 3949 | NH2 | ARG | C | 133 | 34.835 | 34.195 | 12.907 | 1.00 | 52.98 | C |
| ATOM | 3950 | C | ARG | C | 133 | 41.187 | 34.453 | 12.608 | 1.00 | 43.83 | C |
| ATOM | 3951 | O | ARG | C | 133 | 41.256 | 34.557 | 11.382 | 1.00 | 44.57 | C |
| ATOM | 3952 | N | PRO | C | 134 | 42.178 | 33.905 | 13.338 | 1.00 | 45.88 | C |
| ATOM | 3953 | CD | PRO | C | 134 | 42.228 | 33.728 | 14.800 | 1.00 | 46.29 | C |
| ATOM | 3954 | CA | PRO | C | 134 | 43.396 | 33.380 | 12.716 | 1.00 | 47.45 | C |
| ATOM | 3955 | CB | PRO | C | 134 | 44.024 | 32.569 | 13.838 | 1.00 | 47.11 | C |
| ATOM | 3956 | CG | PRO | C | 134 | 43.694 | 33.402 | 15.034 | 1.00 | 47.09 | C |
| ATOM | 3957 | C | PRO | C | 134 | 43.021 | 32.539 | 11.513 | 1.00 | 49.18 | C |
| ATOM | 3958 | O | PRO | C | 134 | 42.187 | 31.636 | 11.606 | 1.00 | 49.30 | C |
| ATOM | 3959 | N | GLY | C | 135 | 43.640 | 32.842 | 10.381 | 1.00 | 51.38 | C |
| ATOM | 3960 | CA | GLY | C | 135 | 43.309 | 32.131 | 9.165 | 1.00 | 54.26 | C |
| ATOM | 3961 | C | GLY | C | 135 | 42.047 | 32.807 | 8.670 | 1.00 | 56.31 | C |
| ATOM | 3962 | O | GLY | C | 135 | 41.791 | 33.962 | 9.014 | 1.00 | 57.51 | C |
| ATOM | 3963 | N | PHE | C | 136 | 41.252 | 32.107 | 7.872 | 1.00 | 57.40 | C |
| ATOM | 3964 | CA | PHE | C | 136 | 40.012 | 32.676 | 7.358 | 1.00 | 59.03 | C |
| ATOM | 3965 | CB | PHE | C | 136 | 39.088 | 33.059 | 8.510 | 1.00 | 59.32 | C |
| ATOM | 3966 | CG | PHE | C | 136 | 38.561 | 31.884 | 9.251 | 1.00 | 60.37 | C |
| ATOM | 3967 | CD1 | PHE | C | 136 | 39.413 | 31.095 | 10.020 | 1.00 | 60.26 | C |
| ATOM | 3968 | CD2 | PHE | C | 136 | 37.224 | 31.525 | 9.139 | 1.00 | 60.73 | C |
| ATOM | 3969 | CE1 | PHE | C | 136 | 38.942 | 29.968 | 10.661 | 1.00 | 60.77 | C |
| ATOM | 3970 | CE2 | PHE | C | 136 | 36.743 | 30.399 | 9.777 | 1.00 | 61.24 | C |
| ATOM | 3971 | CZ | PHE | C | 136 | 37.607 | 29.621 | 10.538 | 1.00 | 61.14 | C |
| ATOM | 3972 | C | PHE | C | 136 | 40.194 | 33.869 | 6.434 | 1.00 | 60.02 | C |
| ATOM | 3973 | O | PHE | C | 136 | 40.995 | 34.771 | 6.693 | 1.00 | 59.94 | C |
| ATOM | 3974 | N | HIS | C | 137 | 39.420 | 33.868 | 5.356 | 1.00 | 60.82 | C |
| ATOM | 3975 | CA | HIS | C | 137 | 39.504 | 34.927 | 4.375 | 1.00 | 61.83 | C |
| ATOM | 3976 | CB | HIS | C | 137 | 39.907 | 34.340 | 3.024 | 1.00 | 62.32 | C |
| ATOM | 3977 | CG | HIS | C | 137 | 41.101 | 33.440 | 3.092 | 1.00 | 63.11 | C |
| ATOM | 3978 | CD2 | HIS | C | 137 | 42.330 | 33.546 | 2.535 | 1.00 | 63.63 | C |
| ATOM | 3979 | ND1 | HIS | C | 137 | 41.105 | 32.262 | 3.808 | 1.00 | 63.52 | C |
| ATOM | 3980 | CE1 | HIS | C | 137 | 42.286 | 31.680 | 3.688 | 1.00 | 63.55 | C |
| ATOM | 3981 | NE2 | HIS | C | 137 | 43.047 | 32.439 | 2.920 | 1.00 | 63.35 | C |
| ATOM | 3982 | C | HIS | C | 137 | 38.219 | 35.721 | 4.221 | 1.00 | 62.06 | C |
| ATOM | 3983 | O | HIS | C | 137 | 37.124 | 35.162 | 4.116 | 1.00 | 61.80 | C |
| ATOM | 3984 | N | VAL | C | 138 | 38.383 | 37.039 | 4.218 | 1.00 | 62.28 | C |
| ATOM | 3985 | CA | VAL | C | 138 | 37.291 | 37.981 | 4.042 | 1.00 | 62.86 | C |
| ATOM | 3986 | CB | VAL | C | 138 | 37.467 | 39.208 | 4.973 | 1.00 | 63.45 | C |
| ATOM | 3987 | CG1 | VAL | C | 138 | 36.513 | 40.314 | 4.585 | 1.00 | 63.47 | C |
| ATOM | 3988 | CG2 | VAL | C | 138 | 37.213 | 38.795 | 6.417 | 1.00 | 64.11 | C |
| ATOM | 3989 | C | VAL | C | 138 | 37.420 | 38.392 | 2.581 | 1.00 | 62.93 | C |
| ATOM | 3990 | O | VAL | C | 138 | 38.235 | 39.247 | 2.229 | 1.00 | 62.39 | C |
| ATOM | 3991 | N | GLU | C | 139 | 36.627 | 37.749 | 1.733 | 1.00 | 63.21 | C |
| ATOM | 3992 | CA | GLU | C | 139 | 36.655 | 38.004 | 0.301 | 1.00 | 63.87 | C |
| ATOM | 3993 | CB | GLU | C | 139 | 35.563 | 37.178 | -0.388 | 1.00 | 64.42 | C |
| ATOM | 3994 | CG | GLU | C | 139 | 35.619 | 35.687 | -0.079 | 1.00 | 65.84 | C |

Figure 9 (62 of 92)

```
ATOM   3995  CD   GLU C 139      36.952  35.054  -0.451  1.00 66.87           C
ATOM   3996  OE1  GLU C 139      37.444  35.311  -1.571  1.00 68.28           C
ATOM   3997  OE2  GLU C 139      37.504  34.292   0.373  1.00 67.06           C
ATOM   3998  C    GLU C 139      36.517  39.468  -0.111  1.00 63.66           C
ATOM   3999  O    GLU C 139      37.482  40.237  -0.066  1.00 63.97           C
ATOM   4000  N    THR C 140      35.304  39.827  -0.524  1.00 62.96           C
ATOM   4001  CA   THR C 140      34.959  41.169  -0.994  1.00 62.11           C
ATOM   4002  CB   THR C 140      33.675  41.672  -0.327  1.00 63.02           C
ATOM   4003  OG1  THR C 140      32.647  40.679  -0.459  1.00 63.46           C
ATOM   4004  CG2  THR C 140      33.208  42.950  -1.004  1.00 62.80           C
ATOM   4005  C    THR C 140      36.033  42.243  -0.856  1.00 60.76           C
ATOM   4006  O    THR C 140      36.467  42.581   0.246  1.00 60.27           C
ATOM   4007  N    PRO C 141      36.468  42.797  -1.996  1.00 59.92           C
ATOM   4008  CD   PRO C 141      36.151  42.258  -3.330  1.00 60.22           C
ATOM   4009  CA   PRO C 141      37.492  43.839  -2.100  1.00 58.90           C
ATOM   4010  CB   PRO C 141      37.788  43.884  -3.603  1.00 59.74           C
ATOM   4011  CG   PRO C 141      37.433  42.498  -4.068  1.00 59.84           C
ATOM   4012  C    PRO C 141      37.099  45.213  -1.555  1.00 57.47           C
ATOM   4013  O    PRO C 141      36.096  45.804  -1.965  1.00 56.98           C
ATOM   4014  N    TYR C 142      37.918  45.706  -0.630  1.00 55.82           C
ATOM   4015  CA   TYR C 142      37.747  47.010   0.009  1.00 52.71           C
ATOM   4016  CB   TYR C 142      36.702  46.954   1.128  1.00 52.95           C
ATOM   4017  CG   TYR C 142      35.262  46.945   0.670  1.00 52.94           C
ATOM   4018  CD1  TYR C 142      34.481  45.791   0.778  1.00 53.17           C
ATOM   4019  CE1  TYR C 142      33.148  45.783   0.377  1.00 53.04           C
ATOM   4020  CD2  TYR C 142      34.671  48.093   0.144  1.00 52.85           C
ATOM   4021  CE2  TYR C 142      33.338  48.095  -0.262  1.00 53.12           C
ATOM   4022  CZ   TYR C 142      32.583  46.937  -0.144  1.00 53.57           C
ATOM   4023  OH   TYR C 142      31.267  46.928  -0.553  1.00 54.28           C
ATOM   4024  C    TYR C 142      39.088  47.368   0.626  1.00 51.24           C
ATOM   4025  O    TYR C 142      39.888  46.484   0.938  1.00 51.18           C
ATOM   4026  N    PRO C 143      39.358  48.669   0.811  1.00 50.10           C
ATOM   4027  CD   PRO C 143      38.537  49.851   0.511  1.00 49.98           C
ATOM   4028  CA   PRO C 143      40.636  49.072   1.407  1.00 48.92           C
ATOM   4029  CB   PRO C 143      40.601  50.598   1.325  1.00 49.21           C
ATOM   4030  CG   PRO C 143      39.598  50.880   0.245  1.00 49.94           C
ATOM   4031  C    PRO C 143      40.570  48.617   2.848  1.00 47.20           C
ATOM   4032  O    PRO C 143      39.821  49.195   3.634  1.00 48.37           C
ATOM   4033  N    LEU C 144      41.337  47.598   3.209  1.00 44.66           C
ATOM   4034  CA   LEU C 144      41.264  47.121   4.577  1.00 41.74           C
ATOM   4035  CB   LEU C 144      40.124  46.109   4.705  1.00 42.19           C
ATOM   4036  CG   LEU C 144      39.125  46.288   5.844  1.00 42.60           C
ATOM   4037  CD1  LEU C 144      38.304  47.547   5.608  1.00 43.17           C
ATOM   4038  CD2  LEU C 144      38.212  45.080   5.908  1.00 43.90           C
ATOM   4039  C    LEU C 144      42.532  46.487   5.105  1.00 39.71           C
ATOM   4040  O    LEU C 144      43.133  45.629   4.464  1.00 39.44           C
ATOM   4041  N    LEU C 145      42.940  46.917   6.286  1.00 37.55           C
ATOM   4042  CA   LEU C 145      44.104  46.331   6.916  1.00 36.06           C
ATOM   4043  CB   LEU C 145      44.844  47.377   7.748  1.00 36.96           C
ATOM   4044  CG   LEU C 145      46.202  46.972   8.321  1.00 40.74           C
ATOM   4045  CD1  LEU C 145      47.126  46.490   7.205  1.00 41.73           C
ATOM   4046  CD2  LEU C 145      46.809  48.172   9.042  1.00 43.62           C
ATOM   4047  C    LEU C 145      43.470  45.265   7.803  1.00 33.85           C
ATOM   4048  O    LEU C 145      42.448  45.515   8.437  1.00 33.65           C
ATOM   4049  N    PHE C 146      44.045  44.072   7.826  1.00 32.21           C
ATOM   4050  CA   PHE C 146      43.475  43.006   8.631  1.00 31.18           C
ATOM   4051  CB   PHE C 146      43.291  41.745   7.785  1.00 29.25           C
ATOM   4052  CG   PHE C 146      42.392  41.943   6.604  1.00 30.34           C
ATOM   4053  CD1  PHE C 146      42.920  42.261   5.354  1.00 30.62           C
ATOM   4054  CD2  PHE C 146      41.011  41.839   6.743  1.00 29.22           C
ATOM   4055  CE1  PHE C 146      42.078  42.476   4.254  1.00 30.39           C
ATOM   4056  CE2  PHE C 146      40.162  42.050   5.656  1.00 29.79           C
ATOM   4057  CZ   PHE C 146      40.699  42.370   4.407  1.00 30.89           C
ATOM   4058  C    PHE C 146      44.297  42.680   9.860  1.00 30.66           C
ATOM   4059  O    PHE C 146      45.512  42.875   9.882  1.00 31.02           C
ATOM   4060  N    ALA C 147      43.614  42.189  10.888  1.00 29.05           C
```

Figure 9 (63 of 92)

```
ATOM   4061  CA   ALA C 147     44.257  41.813  12.135  1.00 28.12      C
ATOM   4062  CB   ALA C 147     44.016  42.881  13.201  1.00 28.19      C
ATOM   4063  C    ALA C 147     43.690  40.486  12.598  1.00 27.54      C
ATOM   4064  O    ALA C 147     42.486  40.360  12.815  1.00 26.14      C
ATOM   4065  N    ASP C 148     44.559  39.492  12.736  1.00 27.52      C
ATOM   4066  CA   ASP C 148     44.141  38.177  13.195  1.00 29.07      C
ATOM   4067  CB   ASP C 148     45.132  37.103  12.732  1.00 31.55      C
ATOM   4068  CG   ASP C 148     45.047  36.824  11.241  1.00 33.94      C
ATOM   4069  OD1  ASP C 148     45.870  36.027  10.744  1.00 35.62      C
ATOM   4070  OD2  ASP C 148     44.158  37.393  10.568  1.00 35.67      C
ATOM   4071  C    ASP C 148     44.094  38.190  14.714  1.00 28.88      C
ATOM   4072  O    ASP C 148     45.104  38.413  15.366  1.00 32.10      C
ATOM   4073  N    VAL C 149     42.923  37.956  15.284  1.00 27.86      C
ATOM   4074  CA   VAL C 149     42.805  37.945  16.730  1.00 25.30      C
ATOM   4075  CB   VAL C 149     41.856  39.063  17.222  1.00 24.47      C
ATOM   4076  CG1  VAL C 149     41.599  38.917  18.707  1.00 22.88      C
ATOM   4077  CG2  VAL C 149     42.466  40.423  16.930  1.00 20.55      C
ATOM   4078  C    VAL C 149     42.271  36.595  17.188  1.00 26.67      C
ATOM   4079  O    VAL C 149     41.320  36.060  16.610  1.00 24.22      C
ATOM   4080  N    PRO C 150     42.907  36.008  18.212  1.00 26.23      C
ATOM   4081  CD   PRO C 150     44.194  36.418  18.802  1.00 27.41      C
ATOM   4082  CA   PRO C 150     42.481  34.715  18.745  1.00 25.90      C
ATOM   4083  CB   PRO C 150     43.509  34.442  19.836  1.00 26.73      C
ATOM   4084  CG   PRO C 150     44.742  35.107  19.307  1.00 27.47      C
ATOM   4085  C    PRO C 150     41.067  34.847  19.312  1.00 25.73      C
ATOM   4086  O    PRO C 150     40.780  35.777  20.068  1.00 25.39      C
ATOM   4087  N    GLU C 151     40.197  33.912  18.952  1.00 24.12      C
ATOM   4088  CA   GLU C 151     38.818  33.914  19.416  1.00 23.79      C
ATOM   4089  CB   GLU C 151     38.052  32.779  18.719  1.00 26.06      C
ATOM   4090  CG   GLU C 151     36.546  32.752  18.957  1.00 32.24      C
ATOM   4091  CD   GLU C 151     35.852  31.628  18.183  1.00 35.17      C
ATOM   4092  OE1  GLU C 151     34.624  31.460  18.346  1.00 37.96      C
ATOM   4093  OE2  GLU C 151     36.532  30.915  17.408  1.00 36.23      C
ATOM   4094  C    GLU C 151     38.750  33.743  20.938  1.00 23.17      C
ATOM   4095  O    GLU C 151     39.329  32.810  21.502  1.00 20.35      C
ATOM   4096  N    PHE C 152     38.063  34.672  21.593  1.00 22.27      C
ATOM   4097  CA   PHE C 152     37.859  34.638  23.038  1.00 20.27      C
ATOM   4098  CB   PHE C 152     38.712  35.699  23.744  1.00 19.58      C
ATOM   4099  CG   PHE C 152     38.718  35.579  25.252  1.00 19.21      C
ATOM   4100  CD1  PHE C 152     39.515  36.421  26.024  1.00 18.03      C
ATOM   4101  CD2  PHE C 152     37.932  34.627  25.898  1.00 18.73      C
ATOM   4102  CE1  PHE C 152     39.533  36.318  27.415  1.00 20.44      C
ATOM   4103  CE2  PHE C 152     37.939  34.513  27.295  1.00 20.43      C
ATOM   4104  CZ   PHE C 152     38.744  35.361  28.056  1.00 18.72      C
ATOM   4105  C    PHE C 152     36.376  34.967  23.168  1.00 20.15      C
ATOM   4106  O    PHE C 152     35.978  36.125  23.039  1.00 19.08      C
ATOM   4107  N    GLU C 153     35.573  33.933  23.410  1.00 19.97      C
ATOM   4108  CA   GLU C 153     34.120  34.051  23.511  1.00 21.42      C
ATOM   4109  CB   GLU C 153     33.485  32.666  23.293  1.00 22.71      C
ATOM   4110  CG   GLU C 153     31.954  32.636  23.362  1.00 26.09      C
ATOM   4111  CD   GLU C 153     31.370  31.229  23.234  1.00 28.99      C
ATOM   4112  OE1  GLU C 153     30.120  31.109  23.281  1.00 31.07      C
ATOM   4113  OE2  GLU C 153     32.149  30.250  23.087  1.00 26.59      C
ATOM   4114  C    GLU C 153     33.578  34.664  24.806  1.00 21.48      C
ATOM   4115  O    GLU C 153     32.901  34.001  25.589  1.00 21.78      C
ATOM   4116  N    VAL C 154     33.888  35.930  25.038  1.00 20.86      C
ATOM   4117  CA   VAL C 154     33.377  36.615  26.216  1.00 20.00      C
ATOM   4118  CB   VAL C 154     34.521  37.030  27.186  1.00 20.58      C
ATOM   4119  CG1  VAL C 154     35.621  37.770  26.433  1.00 18.06      C
ATOM   4120  CG2  VAL C 154     33.964  37.904  28.306  1.00 20.27      C
ATOM   4121  C    VAL C 154     32.679  37.842  25.657  1.00 19.02      C
ATOM   4122  O    VAL C 154     33.101  38.381  24.638  1.00 18.96      C
ATOM   4123  N    SER C 155     31.590  38.264  26.287  1.00 18.46      C
ATOM   4124  CA   SER C 155     30.877  39.446  25.816  1.00 17.64      C
ATOM   4125  CB   SER C 155     29.702  39.055  24.922  1.00 19.95      C
ATOM   4126  OG   SER C 155     28.668  38.462  25.684  1.00 19.71      C
```

Figure 9 (64 of 92)

| ATOM | 4127 | C | SER | C | 155 | 30.347 | 40.194 | 27.018 | 1.00 | 16.80 | C |
|---|---|---|---|---|---|---|---|---|---|---|---|
| ATOM | 4128 | O | SER | C | 155 | 30.245 | 39.629 | 28.099 | 1.00 | 16.81 | C |
| ATOM | 4129 | N | SER | C | 156 | 30.012 | 41.464 | 26.836 | 1.00 | 17.06 | C |
| ATOM | 4130 | CA | SER | C | 156 | 29.486 | 42.239 | 27.949 | 1.00 | 17.50 | C |
| ATOM | 4131 | CB | SER | C | 156 | 29.288 | 43.697 | 27.542 | 1.00 | 18.47 | C |
| ATOM | 4132 | OG | SER | C | 156 | 30.536 | 44.363 | 27.441 | 1.00 | 18.08 | C |
| ATOM | 4133 | C | SER | C | 156 | 28.165 | 41.630 | 28.411 | 1.00 | 19.49 | C |
| ATOM | 4134 | O | SER | C | 156 | 27.887 | 41.552 | 29.615 | 1.00 | 17.52 | C |
| ATOM | 4135 | N | THR | C | 157 | 27.354 | 41.177 | 27.460 | 1.00 | 18.86 | C |
| ATOM | 4136 | CA | THR | C | 157 | 26.078 | 40.582 | 27.833 | 1.00 | 22.21 | C |
| ATOM | 4137 | CB | THR | C | 157 | 25.218 | 40.255 | 26.605 | 1.00 | 23.54 | C |
| ATOM | 4138 | OG1 | THR | C | 157 | 24.776 | 41.475 | 25.999 | 1.00 | 26.73 | C |
| ATOM | 4139 | CG2 | THR | C | 157 | 24.002 | 39.443 | 27.022 | 1.00 | 25.74 | C |
| ATOM | 4140 | C | THR | C | 157 | 26.243 | 39.322 | 28.673 | 1.00 | 20.09 | C |
| ATOM | 4141 | O | THR | C | 157 | 25.534 | 39.150 | 29.661 | 1.00 | 22.35 | C |
| ATOM | 4142 | N | MET | C | 158 | 27.168 | 38.445 | 28.290 | 1.00 | 19.32 | C |
| ATOM | 4143 | CA | MET | C | 158 | 27.397 | 37.223 | 29.054 | 1.00 | 17.69 | C |
| ATOM | 4144 | CB | MET | C | 158 | 28.521 | 36.377 | 28.465 | 1.00 | 22.87 | C |
| ATOM | 4145 | CG | MET | C | 158 | 29.600 | 36.149 | 29.549 | 1.00 | 23.71 | C |
| ATOM | 4146 | SD | MET | C | 158 | 31.018 | 35.338 | 29.120 | 1.00 | 31.82 | C |
| ATOM | 4147 | CE | MET | C | 158 | 30.892 | 33.925 | 30.111 | 1.00 | 34.45 | C |
| ATOM | 4148 | C | MET | C | 158 | 27.845 | 37.575 | 30.467 | 1.00 | 17.21 | C |
| ATOM | 4149 | O | MET | C | 158 | 27.487 | 36.897 | 31.433 | 1.00 | 16.57 | C |
| ATOM | 4150 | N | ILE | C | 159 | 28.692 | 38.597 | 30.566 | 1.00 | 16.53 | C |
| ATOM | 4151 | CA | ILE | C | 159 | 29.217 | 39.023 | 31.857 | 1.00 | 18.00 | C |
| ATOM | 4152 | CB | ILE | C | 159 | 30.315 | 40.123 | 31.707 | 1.00 | 16.95 | C |
| ATOM | 4153 | CG2 | ILE | C | 159 | 30.849 | 40.519 | 33.079 | 1.00 | 18.43 | C |
| ATOM | 4154 | CG1 | ILE | C | 159 | 31.474 | 39.614 | 30.838 | 1.00 | 18.73 | C |
| ATOM | 4155 | CD1 | ILE | C | 159 | 32.138 | 38.349 | 31.341 | 1.00 | 19.99 | C |
| ATOM | 4156 | C | ILE | C | 159 | 28.109 | 39.553 | 32.754 | 1.00 | 16.28 | C |
| ATOM | 4157 | O | ILE | C | 159 | 28.056 | 39.221 | 33.934 | 1.00 | 17.18 | C |
| ATOM | 4158 | N | ARG | C | 160 | 27.227 | 40.379 | 32.196 | 1.00 | 18.37 | C |
| ATOM | 4159 | CA | ARG | C | 160 | 26.125 | 40.947 | 32.976 | 1.00 | 18.44 | C |
| ATOM | 4160 | CB | ARG | C | 160 | 25.282 | 41.905 | 32.118 | 1.00 | 19.06 | C |
| ATOM | 4161 | CG | ARG | C | 160 | 25.992 | 43.195 | 31.702 | 1.00 | 18.55 | C |
| ATOM | 4162 | CD | ARG | C | 160 | 24.990 | 44.250 | 31.249 | 1.00 | 19.05 | C |
| ATOM | 4163 | NE | ARG | C | 160 | 24.258 | 43.840 | 30.048 | 1.00 | 20.85 | C |
| ATOM | 4164 | CZ | ARG | C | 160 | 24.713 | 43.985 | 28.806 | 1.00 | 20.10 | C |
| ATOM | 4165 | NH1 | ARG | C | 160 | 23.977 | 43.577 | 27.778 | 1.00 | 18.69 | C |
| ATOM | 4166 | NH2 | ARG | C | 160 | 25.893 | 44.557 | 28.586 | 1.00 | 17.98 | C |
| ATOM | 4167 | C | ARG | C | 160 | 25.222 | 39.861 | 33.553 | 1.00 | 20.55 | C |
| ATOM | 4168 | O | ARG | C | 160 | 24.845 | 39.917 | 34.730 | 1.00 | 21.41 | C |
| ATOM | 4169 | N | GLU | C | 161 | 24.877 | 38.870 | 32.736 | 1.00 | 20.46 | C |
| ATOM | 4170 | CA | GLU | C | 161 | 24.009 | 37.795 | 33.205 | 1.00 | 20.93 | C |
| ATOM | 4171 | CB | GLU | C | 161 | 23.541 | 36.930 | 32.034 | 1.00 | 23.62 | C |
| ATOM | 4172 | CG | GLU | C | 161 | 22.778 | 37.693 | 30.945 | 1.00 | 30.10 | C |
| ATOM | 4173 | CD | GLU | C | 161 | 21.704 | 38.645 | 31.484 | 1.00 | 35.16 | C |
| ATOM | 4174 | OE1 | GLU | C | 161 | 21.053 | 38.328 | 32.507 | 1.00 | 37.17 | C |
| ATOM | 4175 | OE2 | GLU | C | 161 | 21.498 | 39.714 | 30.867 | 1.00 | 37.09 | C |
| ATOM | 4176 | C | GLU | C | 161 | 24.727 | 36.941 | 34.243 | 1.00 | 20.63 | C |
| ATOM | 4177 | O | GLU | C | 161 | 24.112 | 36.455 | 35.194 | 1.00 | 18.66 | C |
| ATOM | 4178 | N | ARG | C | 162 | 26.033 | 36.756 | 34.067 | 1.00 | 18.13 | C |
| ATOM | 4179 | CA | ARG | C | 162 | 26.778 | 35.988 | 35.045 | 1.00 | 19.33 | C |
| ATOM | 4180 | CB | ARG | C | 162 | 28.227 | 35.790 | 34.601 | 1.00 | 19.53 | C |
| ATOM | 4181 | CG | ARG | C | 162 | 28.358 | 34.752 | 33.516 | 1.00 | 21.13 | C |
| ATOM | 4182 | CD | ARG | C | 162 | 29.780 | 34.291 | 33.354 | 1.00 | 20.86 | C |
| ATOM | 4183 | NE | ARG | C | 162 | 29.827 | 33.104 | 32.512 | 1.00 | 21.52 | C |
| ATOM | 4184 | CZ | ARG | C | 162 | 30.668 | 32.097 | 32.696 | 1.00 | 21.14 | C |
| ATOM | 4185 | NH1 | ARG | C | 162 | 31.536 | 32.134 | 33.700 | 1.00 | 17.87 | C |
| ATOM | 4186 | NH2 | ARG | C | 162 | 30.641 | 31.055 | 31.875 | 1.00 | 21.33 | C |
| ATOM | 4187 | C | ARG | C | 162 | 26.736 | 36.689 | 36.397 | 1.00 | 19.50 | C |
| ATOM | 4188 | O | ARG | C | 162 | 26.567 | 36.043 | 37.436 | 1.00 | 20.02 | C |
| ATOM | 4189 | N | PHE | C | 163 | 26.891 | 38.009 | 36.394 | 1.00 | 19.23 | C |
| ATOM | 4190 | CA | PHE | C | 163 | 26.839 | 38.742 | 37.655 | 1.00 | 20.01 | C |
| ATOM | 4191 | CB | PHE | C | 163 | 27.170 | 40.229 | 37.451 | 1.00 | 18.61 | C |
| ATOM | 4192 | CG | PHE | C | 163 | 28.655 | 40.542 | 37.468 | 1.00 | 19.93 | C |

Figure 9 (65 of 92)

```
ATOM   4193  CD1 PHE C 163      29.442  40.191  38.562  1.00 20.87      C
ATOM   4194  CD2 PHE C 163      29.251  41.219  36.409  1.00 19.41      C
ATOM   4195  CE1 PHE C 163      30.802  40.516  38.598  1.00 22.72      C
ATOM   4196  CE2 PHE C 163      30.604  41.549  36.431  1.00 20.61      C
ATOM   4197  CZ  PHE C 163      31.383  41.198  37.528  1.00 21.28      C
ATOM   4198  C   PHE C 163      25.436  38.596  38.224  1.00 19.96      C
ATOM   4199  O   PHE C 163      25.258  38.342  39.414  1.00 20.11      C
ATOM   4200  N   LYS C 164      24.438  38.752  37.365  1.00 21.55      C
ATOM   4201  CA  LYS C 164      23.051  38.645  37.796  1.00 23.21      C
ATOM   4202  CB  LYS C 164      22.110  38.967  36.634  1.00 24.38      C
ATOM   4203  CG  LYS C 164      22.182  40.409  36.164  1.00 26.65      C
ATOM   4204  CD  LYS C 164      21.245  40.649  34.977  1.00 29.56      C
ATOM   4205  CE  LYS C 164      21.330  42.087  34.477  1.00 30.43      C
ATOM   4206  NZ  LYS C 164      20.609  42.293  33.179  1.00 33.98      C
ATOM   4207  C   LYS C 164      22.726  37.261  38.354  1.00 23.29      C
ATOM   4208  O   LYS C 164      22.049  37.142  39.371  1.00 23.87      C
ATOM   4209  N   SER C 165      23.216  36.221  37.692  1.00 23.87      C
ATOM   4210  CA  SER C 165      22.964  34.854  38.124  1.00 24.09      C
ATOM   4211  CB  SER C 165      22.958  33.923  36.908  1.00 23.04      C
ATOM   4212  OG  SER C 165      24.167  34.044  36.178  1.00 27.58      C
ATOM   4213  C   SER C 165      23.992  34.367  39.155  1.00 24.48      C
ATOM   4214  O   SER C 165      23.967  33.209  39.564  1.00 24.62      C
ATOM   4215  N   LYS C 166      24.890  35.253  39.573  1.00 24.01      C
ATOM   4216  CA  LYS C 166      25.908  34.896  40.556  1.00 25.39      C
ATOM   4217  CB  LYS C 166      25.242  34.467  41.866  1.00 29.03      C
ATOM   4218  CG  LYS C 166      24.368  35.545  42.499  1.00 33.05      C
ATOM   4219  CD  LYS C 166      23.594  35.011  43.710  1.00 37.55      C
ATOM   4220  CE  LYS C 166      22.674  36.081  44.302  1.00 39.69      C
ATOM   4221  NZ  LYS C 166      21.861  35.569  45.440  1.00 42.14      C
ATOM   4222  C   LYS C 166      26.856  33.790  40.090  1.00 24.18      C
ATOM   4223  O   LYS C 166      27.274  32.943  40.883  1.00 22.84      C
ATOM   4224  N   LYS C 167      27.168  33.776  38.799  1.00 23.44      C
ATOM   4225  CA  LYS C 167      28.101  32.792  38.260  1.00 24.62      C
ATOM   4226  CB  LYS C 167      27.722  32.402  36.832  1.00 25.79      C
ATOM   4227  CG  LYS C 167      26.417  31.643  36.736  1.00 28.52      C
ATOM   4228  CD  LYS C 167      26.124  31.258  35.297  1.00 32.16      C
ATOM   4229  CE  LYS C 167      24.822  30.493  35.193  1.00 34.19      C
ATOM   4230  NZ  LYS C 167      24.518  30.174  33.777  1.00 37.23      C
ATOM   4231  C   LYS C 167      29.484  33.437  38.264  1.00 23.49      C
ATOM   4232  O   LYS C 167      29.604  34.660  38.280  1.00 23.87      C
ATOM   4233  N   PRO C 168      30.544  32.621  38.247  1.00 23.15      C
ATOM   4234  CD  PRO C 168      30.518  31.150  38.230  1.00 23.09      C
ATOM   4235  CA  PRO C 168      31.928  33.113  38.253  1.00 21.84      C
ATOM   4236  CB  PRO C 168      32.756  31.829  38.234  1.00 21.70      C
ATOM   4237  CG  PRO C 168      31.842  30.818  38.862  1.00 23.35      C
ATOM   4238  C   PRO C 168      32.259  33.993  37.059  1.00 21.09      C
ATOM   4239  O   PRO C 168      31.745  33.781  35.957  1.00 19.67      C
ATOM   4240  N   THR C 169      33.121  34.982  37.284  1.00 20.32      C
ATOM   4241  CA  THR C 169      33.552  35.864  36.212  1.00 20.70      C
ATOM   4242  CB  THR C 169      33.051  37.313  36.416  1.00 20.78      C
ATOM   4243  OG1 THR C 169      33.421  37.776  37.719  1.00 22.23      C
ATOM   4244  CG2 THR C 169      31.536  37.371  36.260  1.00 21.23      C
ATOM   4245  C   THR C 169      35.074  35.850  36.128  1.00 20.23      C
ATOM   4246  O   THR C 169      35.670  36.591  35.346  1.00 19.10      C
ATOM   4247  N   ASP C 170      35.697  34.979  36.919  1.00 19.96      C
ATOM   4248  CA  ASP C 170      37.154  34.874  36.925  1.00 20.59      C
ATOM   4249  CB  ASP C 170      37.637  33.765  37.867  1.00 23.03      C
ATOM   4250  CG  ASP C 170      36.897  33.742  39.185  1.00 27.25      C
ATOM   4251  OD1 ASP C 170      35.850  33.054  39.279  1.00 27.76      C
ATOM   4252  OD2 ASP C 170      37.365  34.418  40.126  1.00 31.82      C
ATOM   4253  C   ASP C 170      37.706  34.567  35.539  1.00 18.41      C
ATOM   4254  O   ASP C 170      37.155  33.752  34.799  1.00 16.84      C
ATOM   4255  N   TYR C 171      38.817  35.215  35.213  1.00 17.91      C
ATOM   4256  CA  TYR C 171      39.500  35.021  33.946  1.00 17.31      C
ATOM   4257  CB  TYR C 171      39.811  33.531  33.742  1.00 17.58      C
ATOM   4258  CG  TYR C 171      40.432  32.886  34.971  1.00 19.01      C
```

Figure 9 (66 of 92)

```
ATOM   4259  CD1  TYR C 171     39.717  31.963  35.736  1.00 18.74           C
ATOM   4260  CE1  TYR C 171     40.262  31.403  36.897  1.00 18.71           C
ATOM   4261  CD2  TYR C 171     41.719  33.236  35.395  1.00 20.86           C
ATOM   4262  CE2  TYR C 171     42.275  32.684  36.556  1.00 20.07           C
ATOM   4263  CZ   TYR C 171     41.538  31.769  37.300  1.00 18.30           C
ATOM   4264  OH   TYR C 171     42.065  31.233  38.451  1.00 19.06           C
ATOM   4265  C    TYR C 171     38.720  35.579  32.766  1.00 16.79           C
ATOM   4266  O    TYR C 171     39.142  35.443  31.619  1.00 16.27           C
ATOM   4267  N    LEU C 172     37.587  36.215  33.046  1.00 15.71           C
ATOM   4268  CA   LEU C 172     36.781  36.822  31.986  1.00 16.52           C
ATOM   4269  CB   LEU C 172     35.334  36.327  32.058  1.00 15.59           C
ATOM   4270  CG   LEU C 172     35.148  34.819  31.822  1.00 17.40           C
ATOM   4271  CD1  LEU C 172     33.717  34.394  32.167  1.00 15.62           C
ATOM   4272  CD2  LEU C 172     35.471  34.493  30.371  1.00 15.86           C
ATOM   4273  C    LEU C 172     36.816  38.347  32.079  1.00 17.13           C
ATOM   4274  O    LEU C 172     36.649  39.037  31.079  1.00 17.28           C
ATOM   4275  N    ILE C 173     37.041  38.873  33.282  1.00 18.14           C
ATOM   4276  CA   ILE C 173     37.094  40.324  33.488  1.00 20.24           C
ATOM   4277  CB   ILE C 173     35.770  40.877  34.078  1.00 21.95           C
ATOM   4278  CG2  ILE C 173     34.618  40.570  33.154  1.00 22.13           C
ATOM   4279  CG1  ILE C 173     35.515  40.265  35.458  1.00 20.91           C
ATOM   4280  CD1  ILE C 173     34.274  40.817  36.138  1.00 23.40           C
ATOM   4281  C    ILE C 173     38.213  40.678  34.463  1.00 20.35           C
ATOM   4282  O    ILE C 173     38.587  39.870  35.302  1.00 19.89           C
ATOM   4283  N    PRO C 174     38.761  41.896  34.363  1.00 21.24           C
ATOM   4284  CD   PRO C 174     38.559  42.931  33.336  1.00 21.51           C
ATOM   4285  CA   PRO C 174     39.837  42.273  35.280  1.00 22.14           C
ATOM   4286  CB   PRO C 174     40.290  43.636  34.749  1.00 21.75           C
ATOM   4287  CG   PRO C 174     39.921  43.591  33.291  1.00 22.64           C
ATOM   4288  C    PRO C 174     39.335  42.360  36.724  1.00 22.94           C
ATOM   4289  O    PRO C 174     38.202  42.773  36.977  1.00 20.00           C
ATOM   4290  N    ASP C 175     40.191  41.961  37.658  1.00 23.99           C
ATOM   4291  CA   ASP C 175     39.883  41.998  39.080  1.00 24.57           C
ATOM   4292  CB   ASP C 175     41.133  41.621  39.881  1.00 27.72           C
ATOM   4293  CG   ASP C 175     41.193  40.142  40.210  1.00 30.91           C
ATOM   4294  OD1  ASP C 175     40.757  39.323  39.376  1.00 31.92           C
ATOM   4295  OD2  ASP C 175     41.686  39.796  41.306  1.00 34.15           C
ATOM   4296  C    ASP C 175     39.392  43.368  39.532  1.00 25.12           C
ATOM   4297  O    ASP C 175     38.463  43.472  40.338  1.00 24.10           C
ATOM   4298  N    LYS C 176     40.025  44.423  39.026  1.00 24.77           C
ATOM   4299  CA   LYS C 176     39.638  45.779  39.410  1.00 25.55           C
ATOM   4300  CB   LYS C 176     40.633  46.802  38.855  1.00 28.31           C
ATOM   4301  CG   LYS C 176     41.930  46.910  39.648  1.00 32.49           C
ATOM   4302  CD   LYS C 176     42.955  47.770  38.917  1.00 34.30           C
ATOM   4303  CE   LYS C 176     44.188  48.020  39.779  1.00 37.96           C
ATOM   4304  NZ   LYS C 176     43.880  48.877  40.969  1.00 39.50           C
ATOM   4305  C    LYS C 176     38.241  46.121  38.932  1.00 24.63           C
ATOM   4306  O    LYS C 176     37.516  46.862  39.593  1.00 23.93           C
ATOM   4307  N    VAL C 177     37.867  45.580  37.777  1.00 22.99           C
ATOM   4308  CA   VAL C 177     36.547  45.829  37.223  1.00 22.05           C
ATOM   4309  CB   VAL C 177     36.475  45.370  35.744  1.00 21.80           C
ATOM   4310  CG1  VAL C 177     35.048  45.500  35.211  1.00 19.24           C
ATOM   4311  CG2  VAL C 177     37.430  46.207  34.907  1.00 21.10           C
ATOM   4312  C    VAL C 177     35.528  45.078  38.078  1.00 20.97           C
ATOM   4313  O    VAL C 177     34.473  45.609  38.406  1.00 20.87           C
ATOM   4314  N    LYS C 178     35.859  43.846  38.448  1.00 21.81           C
ATOM   4315  CA   LYS C 178     34.984  43.037  39.290  1.00 23.36           C
ATOM   4316  CB   LYS C 178     35.618  41.666  39.528  1.00 25.04           C
ATOM   4317  CG   LYS C 178     34.821  40.734  40.439  1.00 28.62           C
ATOM   4318  CD   LYS C 178     35.606  39.449  40.698  1.00 31.96           C
ATOM   4319  CE   LYS C 178     34.802  38.435  41.491  1.00 33.73           C
ATOM   4320  NZ   LYS C 178     35.528  37.136  41.634  1.00 37.11           C
ATOM   4321  C    LYS C 178     34.757  43.751  40.635  1.00 23.21           C
ATOM   4322  O    LYS C 178     33.627  43.864  41.110  1.00 22.33           C
ATOM   4323  N    LYS C 179     35.838  44.240  41.234  1.00 22.56           C
ATOM   4324  CA   LYS C 179     35.763  44.944  42.514  1.00 22.93           C
```

Figure 9 (67 of 92)

| ATOM | 4325 | CB  | LYS | C | 179 | 37.173 | 45.331 | 42.986 | 1.00 | 26.35 | C |
| --- | --- | --- | --- | --- | --- | --- | --- | --- | --- | --- | --- |
| ATOM | 4326 | CG  | LYS | C | 179 | 37.202 | 46.130 | 44.286 | 1.00 | 31.15 | C |
| ATOM | 4327 | CD  | LYS | C | 179 | 38.619 | 46.538 | 44.676 | 1.00 | 33.11 | C |
| ATOM | 4328 | CE  | LYS | C | 179 | 38.606 | 47.378 | 45.950 | 1.00 | 36.42 | C |
| ATOM | 4329 | NZ  | LYS | C | 179 | 39.978 | 47.714 | 46.426 | 1.00 | 37.91 | C |
| ATOM | 4330 | C   | LYS | C | 179 | 34.888 | 46.194 | 42.417 | 1.00 | 23.10 | C |
| ATOM | 4331 | O   | LYS | C | 179 | 34.132 | 46.505 | 43.340 | 1.00 | 21.38 | C |
| ATOM | 4332 | N   | TYR | C | 180 | 34.993 | 46.911 | 41.299 | 1.00 | 22.20 | C |
| ATOM | 4333 | CA  | TYR | C | 180 | 34.199 | 48.118 | 41.094 | 1.00 | 21.32 | C |
| ATOM | 4334 | CB  | TYR | C | 180 | 34.683 | 48.867 | 39.853 | 1.00 | 23.30 | C |
| ATOM | 4335 | CG  | TYR | C | 180 | 33.940 | 50.156 | 39.588 | 1.00 | 21.91 | C |
| ATOM | 4336 | CD1 | TYR | C | 180 | 34.447 | 51.383 | 40.022 | 1.00 | 22.60 | C |
| ATOM | 4337 | CE1 | TYR | C | 180 | 33.753 | 52.576 | 39.782 | 1.00 | 22.20 | C |
| ATOM | 4338 | CD2 | TYR | C | 180 | 32.724 | 50.147 | 38.915 | 1.00 | 21.82 | C |
| ATOM | 4339 | CE2 | TYR | C | 180 | 32.024 | 51.319 | 38.675 | 1.00 | 22.88 | C |
| ATOM | 4340 | CZ  | TYR | C | 180 | 32.541 | 52.532 | 39.108 | 1.00 | 23.65 | C |
| ATOM | 4341 | OH  | TYR | C | 180 | 31.834 | 53.688 | 38.857 | 1.00 | 23.27 | C |
| ATOM | 4342 | C   | TYR | C | 180 | 32.723 | 47.766 | 40.922 | 1.00 | 21.62 | C |
| ATOM | 4343 | O   | TYR | C | 180 | 31.839 | 48.504 | 41.366 | 1.00 | 19.91 | C |
| ATOM | 4344 | N   | VAL | C | 181 | 32.466 | 46.640 | 40.260 | 1.00 | 22.41 | C |
| ATOM | 4345 | CA  | VAL | C | 181 | 31.097 | 46.184 | 40.020 | 1.00 | 22.72 | C |
| ATOM | 4346 | CB  | VAL | C | 181 | 31.081 | 44.949 | 39.082 | 1.00 | 21.76 | C |
| ATOM | 4347 | CG1 | VAL | C | 181 | 29.750 | 44.226 | 39.170 | 1.00 | 22.39 | C |
| ATOM | 4348 | CG2 | VAL | C | 181 | 31.329 | 45.397 | 37.646 | 1.00 | 19.42 | C |
| ATOM | 4349 | C   | VAL | C | 181 | 30.405 | 45.828 | 41.327 | 1.00 | 23.81 | C |
| ATOM | 4350 | O   | VAL | C | 181 | 29.250 | 46.189 | 41.547 | 1.00 | 24.79 | C |
| ATOM | 4351 | N   | GLU | C | 182 | 31.124 | 45.119 | 42.190 | 1.00 | 24.65 | C |
| ATOM | 4352 | CA  | GLU | C | 182 | 30.587 | 44.693 | 43.474 | 1.00 | 26.93 | C |
| ATOM | 4353 | CB  | GLU | C | 182 | 31.539 | 43.701 | 44.148 | 1.00 | 27.22 | C |
| ATOM | 4354 | CG  | GLU | C | 182 | 31.888 | 42.484 | 43.310 | 1.00 | 29.00 | C |
| ATOM | 4355 | CD  | GLU | C | 182 | 32.818 | 41.532 | 44.043 | 1.00 | 31.48 | C |
| ATOM | 4356 | OE1 | GLU | C | 182 | 33.759 | 42.019 | 44.706 | 1.00 | 32.17 | C |
| ATOM | 4357 | OE2 | GLU | C | 182 | 32.618 | 40.301 | 43.955 | 1.00 | 33.70 | C |
| ATOM | 4358 | C   | GLU | C | 182 | 30.342 | 45.862 | 44.416 | 1.00 | 27.74 | C |
| ATOM | 4359 | O   | GLU | C | 182 | 29.312 | 45.917 | 45.086 | 1.00 | 27.62 | C |
| ATOM | 4360 | N   | GLU | C | 183 | 31.284 | 46.799 | 44.463 | 1.00 | 28.74 | C |
| ATOM | 4361 | CA  | GLU | C | 183 | 31.145 | 47.950 | 45.346 | 1.00 | 30.97 | C |
| ATOM | 4362 | CB  | GLU | C | 183 | 32.442 | 48.762 | 45.377 | 1.00 | 32.53 | C |
| ATOM | 4363 | CG  | GLU | C | 183 | 33.659 | 47.947 | 45.780 | 1.00 | 35.60 | C |
| ATOM | 4364 | CD  | GLU | C | 183 | 34.920 | 48.784 | 45.908 | 1.00 | 38.27 | C |
| ATOM | 4365 | OE1 | GLU | C | 183 | 35.148 | 49.669 | 45.049 | 1.00 | 38.72 | C |
| ATOM | 4366 | OE2 | GLU | C | 183 | 35.694 | 48.545 | 46.863 | 1.00 | 39.91 | C |
| ATOM | 4367 | C   | GLU | C | 183 | 29.984 | 48.859 | 44.966 | 1.00 | 30.83 | C |
| ATOM | 4368 | O   | GLU | C | 183 | 29.356 | 49.455 | 45.839 | 1.00 | 32.39 | C |
| ATOM | 4369 | N   | ASN | C | 184 | 29.681 | 48.956 | 43.675 | 1.00 | 29.51 | C |
| ATOM | 4370 | CA  | ASN | C | 184 | 28.595 | 49.822 | 43.230 | 1.00 | 28.74 | C |
| ATOM | 4371 | CB  | ASN | C | 184 | 29.055 | 50.622 | 42.011 | 1.00 | 29.77 | C |
| ATOM | 4372 | CG  | ASN | C | 184 | 30.189 | 51.580 | 42.350 | 1.00 | 30.71 | C |
| ATOM | 4373 | OD1 | ASN | C | 184 | 31.371 | 51.265 | 42.170 | 1.00 | 30.24 | C |
| ATOM | 4374 | ND2 | ASN | C | 184 | 29.831 | 52.746 | 42.875 | 1.00 | 29.11 | C |
| ATOM | 4375 | C   | ASN | C | 184 | 27.254 | 49.134 | 42.953 | 1.00 | 28.90 | C |
| ATOM | 4376 | O   | ASN | C | 184 | 26.368 | 49.711 | 42.317 | 1.00 | 29.05 | C |
| ATOM | 4377 | N   | GLY | C | 185 | 27.111 | 47.909 | 43.451 | 1.00 | 28.67 | C |
| ATOM | 4378 | CA  | GLY | C | 185 | 25.882 | 47.154 | 43.276 | 1.00 | 28.68 | C |
| ATOM | 4379 | C   | GLY | C | 185 | 25.382 | 47.036 | 41.849 | 1.00 | 27.78 | C |
| ATOM | 4380 | O   | GLY | C | 185 | 24.176 | 46.973 | 41.615 | 1.00 | 28.39 | C |
| ATOM | 4381 | N   | LEU | C | 186 | 26.303 | 46.996 | 40.893 | 1.00 | 27.26 | C |
| ATOM | 4382 | CA  | LEU | C | 186 | 25.941 | 46.892 | 39.484 | 1.00 | 25.47 | C |
| ATOM | 4383 | CB  | LEU | C | 186 | 27.091 | 47.410 | 38.619 | 1.00 | 25.56 | C |
| ATOM | 4384 | CG  | LEU | C | 186 | 27.462 | 48.885 | 38.790 | 1.00 | 26.19 | C |
| ATOM | 4385 | CD1 | LEU | C | 186 | 28.600 | 49.241 | 37.820 | 1.00 | 25.59 | C |
| ATOM | 4386 | CD2 | LEU | C | 186 | 26.236 | 49.754 | 38.517 | 1.00 | 23.91 | C |
| ATOM | 4387 | C   | LEU | C | 186 | 25.599 | 45.466 | 39.058 | 1.00 | 24.80 | C |
| ATOM | 4388 | O   | LEU | C | 186 | 26.026 | 44.497 | 39.687 | 1.00 | 22.90 | C |
| ATOM | 4389 | N   | TYR | C | 187 | 24.827 | 45.352 | 37.980 | 1.00 | 24.77 | C |
| ATOM | 4390 | CA  | TYR | C | 187 | 24.443 | 44.056 | 37.423 | 1.00 | 25.42 | C |

Figure 9 (68 of 92)

```
ATOM   4391  CB   TYR C 187      25.630  43.445  36.674  1.00 21.37           C
ATOM   4392  CG   TYR C 187      26.324  44.414  35.745  1.00 20.34           C
ATOM   4393  CD1  TYR C 187      25.606  45.129  34.788  1.00 19.96           C
ATOM   4394  CE1  TYR C 187      26.249  46.023  33.923  1.00 20.95           C
ATOM   4395  CD2  TYR C 187      27.708  44.612  35.818  1.00 21.25           C
ATOM   4396  CE2  TYR C 187      28.360  45.501  34.962  1.00 19.64           C
ATOM   4397  CZ   TYR C 187      27.624  46.203  34.019  1.00 19.00           C
ATOM   4398  OH   TYR C 187      28.255  47.095  33.187  1.00 20.00           C
ATOM   4399  C    TYR C 187      23.954  43.086  38.489  1.00 27.44           C
ATOM   4400  O    TYR C 187      24.331  41.907  38.510  1.00 26.67           C
ATOM   4401  N    GLU C 188      23.113  43.601  39.377  1.00 29.30           C
ATOM   4402  CA   GLU C 188      22.546  42.813  40.459  1.00 31.49           C
ATOM   4403  CB   GLU C 188      22.266  43.711  41.667  1.00 32.87           C
ATOM   4404  CG   GLU C 188      23.060  43.339  42.912  1.00 36.55           C
ATOM   4405  CD   GLU C 188      23.346  44.532  43.808  1.00 37.45           C
ATOM   4406  OE1  GLU C 188      22.541  45.490  43.809  1.00 38.50           C
ATOM   4407  OE2  GLU C 188      24.377  44.505  44.520  1.00 38.79           C
ATOM   4408  C    GLU C 188      21.263  42.139  39.990  1.00 31.08           C
ATOM   4409  O    GLU C 188      21.080  40.952  40.324  1.00 33.18           C
ATOM   4410  OXT  GLU C 188      20.455  42.805  39.307  1.00 30.85           C
ATOM   4411  CB   SER D   1      34.127  11.456  50.090  1.00 39.91           D
ATOM   4412  OG   SER D   1      34.347  11.224  48.707  1.00 42.07           D
ATOM   4413  C    SER D   1      34.839  13.814  49.747  1.00 38.96           D
ATOM   4414  O    SER D   1      33.745  14.378  49.688  1.00 40.18           D
ATOM   4415  N    SER D   1      34.773  12.825  52.055  1.00 39.11           D
ATOM   4416  CA   SER D   1      35.037  12.571  50.608  1.00 39.86           D
ATOM   4417  N    LYS D   2      35.904  14.238  49.076  1.00 37.25           D
ATOM   4418  CA   LYS D   2      35.836  15.404  48.206  1.00 35.60           D
ATOM   4419  CB   LYS D   2      37.173  16.140  48.178  1.00 36.72           D
ATOM   4420  CG   LYS D   2      37.683  16.625  49.514  1.00 40.16           D
ATOM   4421  CD   LYS D   2      39.029  17.308  49.320  1.00 43.01           D
ATOM   4422  CE   LYS D   2      39.695  17.666  50.640  1.00 44.48           D
ATOM   4423  NZ   LYS D   2      40.958  18.421  50.403  1.00 44.76           D
ATOM   4424  C    LYS D   2      35.510  14.997  46.776  1.00 33.54           D
ATOM   4425  O    LYS D   2      35.610  13.824  46.402  1.00 32.59           D
ATOM   4426  N    LYS D   3      35.108  15.985  45.986  1.00 30.27           D
ATOM   4427  CA   LYS D   3      34.819  15.780  44.573  1.00 27.38           D
ATOM   4428  CB   LYS D   3      33.505  16.457  44.183  1.00 27.96           D
ATOM   4429  CG   LYS D   3      32.291  15.864  44.873  1.00 31.06           D
ATOM   4430  CD   LYS D   3      31.014  16.570  44.455  1.00 32.44           D
ATOM   4431  CE   LYS D   3      29.834  16.083  45.273  1.00 35.53           D
ATOM   4432  NZ   LYS D   3      28.597  16.856  44.968  1.00 38.33           D
ATOM   4433  C    LYS D   3      36.003  16.474  43.907  1.00 24.83           D
ATOM   4434  O    LYS D   3      36.123  17.700  43.954  1.00 23.74           D
ATOM   4435  N    ILE D   4      36.883  15.684  43.306  1.00 22.06           D
ATOM   4436  CA   ILE D   4      38.081  16.216  42.679  1.00 19.27           D
ATOM   4437  CB   ILE D   4      39.327  15.471  43.202  1.00 19.69           D
ATOM   4438  CG2  ILE D   4      40.589  16.100  42.628  1.00 17.19           D
ATOM   4439  CG1  ILE D   4      39.334  15.479  44.739  1.00 18.80           D
ATOM   4440  CD1  ILE D   4      39.558  16.847  45.367  1.00 21.16           D
ATOM   4441  C    ILE D   4      38.089  16.142  41.153  1.00 18.80           D
ATOM   4442  O    ILE D   4      37.812  15.097  40.564  1.00 19.45           D
ATOM   4443  N    GLY D   5      38.408  17.269  40.525  1.00 16.56           D
ATOM   4444  CA   GLY D   5      38.488  17.311  39.082  1.00 15.37           D
ATOM   4445  C    GLY D   5      39.950  17.167  38.722  1.00 15.69           D
ATOM   4446  O    GLY D   5      40.781  17.943  39.181  1.00 15.86           D
ATOM   4447  N    ILE D   6      40.276  16.155  37.930  1.00 14.89           D
ATOM   4448  CA   ILE D   6      41.655  15.931  37.514  1.00 15.02           D
ATOM   4449  CB   ILE D   6      41.933  14.422  37.332  1.00 16.00           D
ATOM   4450  CG2  ILE D   6      43.386  14.210  36.909  1.00 11.03           D
ATOM   4451  CG1  ILE D   6      41.589  13.671  38.626  1.00 15.10           D
ATOM   4452  CD1  ILE D   6      42.354  14.165  39.857  1.00 16.26           D
ATOM   4453  C    ILE D   6      41.897  16.650  36.182  1.00 15.54           D
ATOM   4454  O    ILE D   6      41.205  16.399  35.203  1.00 16.98           D
ATOM   4455  N    PHE D   7      42.894  17.525  36.146  1.00 15.75           D
ATOM   4456  CA   PHE D   7      43.188  18.292  34.945  1.00 15.40           D
```

Figure 9 (69 of 92)

| ATOM | 4457 | CB | PHE | D | 7 | 43.075 | 19.780 | 35.293 | 1.00 | 17.94 | D |
|---|---|---|---|---|---|---|---|---|---|---|---|
| ATOM | 4458 | CG | PHE | D | 7 | 43.109 | 20.704 | 34.108 | 1.00 | 20.95 | D |
| ATOM | 4459 | CD1 | PHE | D | 7 | 43.523 | 20.261 | 32.854 | 1.00 | 22.95 | D |
| ATOM | 4460 | CD2 | PHE | D | 7 | 42.741 | 22.037 | 34.258 | 1.00 | 22.47 | D |
| ATOM | 4461 | CE1 | PHE | D | 7 | 43.570 | 21.133 | 31.764 | 1.00 | 25.10 | D |
| ATOM | 4462 | CE2 | PHE | D | 7 | 42.785 | 22.920 | 33.173 | 1.00 | 23.75 | D |
| ATOM | 4463 | CZ | PHE | D | 7 | 43.199 | 22.466 | 31.925 | 1.00 | 22.43 | D |
| ATOM | 4464 | C | PHE | D | 7 | 44.584 | 17.962 | 34.395 | 1.00 | 15.13 | D |
| ATOM | 4465 | O | PHE | D | 7 | 45.581 | 18.554 | 34.801 | 1.00 | 15.21 | D |
| ATOM | 4466 | N | GLY | D | 8 | 44.652 | 17.011 | 33.471 | 1.00 | 14.62 | D |
| ATOM | 4467 | CA | GLY | D | 8 | 45.937 | 16.647 | 32.901 | 1.00 | 16.20 | D |
| ATOM | 4468 | C | GLY | D | 8 | 46.371 | 17.649 | 31.849 | 1.00 | 17.24 | D |
| ATOM | 4469 | O | GLY | D | 8 | 45.534 | 18.319 | 31.243 | 1.00 | 17.64 | D |
| ATOM | 4470 | N | GLY | D | 9 | 47.679 | 17.763 | 31.642 | 1.00 | 17.83 | D |
| ATOM | 4471 | CA | GLY | D | 9 | 48.197 | 18.685 | 30.648 | 1.00 | 19.14 | D |
| ATOM | 4472 | C | GLY | D | 9 | 49.717 | 18.747 | 30.632 | 1.00 | 20.94 | D |
| ATOM | 4473 | O | GLY | D | 9 | 50.384 | 18.192 | 31.505 | 1.00 | 18.84 | D |
| ATOM | 4474 | N | THR | D | 10 | 50.266 | 19.416 | 29.622 | 1.00 | 21.34 | D |
| ATOM | 4475 | CA | THR | D | 10 | 51.711 | 19.565 | 29.501 | 1.00 | 22.82 | D |
| ATOM | 4476 | CB | THR | D | 10 | 52.153 | 19.647 | 28.029 | 1.00 | 25.66 | D |
| ATOM | 4477 | OG1 | THR | D | 10 | 51.609 | 18.542 | 27.299 | 1.00 | 28.13 | D |
| ATOM | 4478 | CG2 | THR | D | 10 | 53.670 | 19.588 | 27.936 | 1.00 | 29.76 | D |
| ATOM | 4479 | C | THR | D | 10 | 52.086 | 20.867 | 30.194 | 1.00 | 21.05 | D |
| ATOM | 4480 | O | THR | D | 10 | 53.175 | 21.003 | 30.754 | 1.00 | 21.51 | D |
| ATOM | 4481 | N | PHE | D | 11 | 51.155 | 21.814 | 30.159 | 1.00 | 18.76 | D |
| ATOM | 4482 | CA | PHE | D | 11 | 51.330 | 23.120 | 30.776 | 1.00 | 19.35 | D |
| ATOM | 4483 | CB | PHE | D | 11 | 51.092 | 23.037 | 32.289 | 1.00 | 19.58 | D |
| ATOM | 4484 | CG | PHE | D | 11 | 49.799 | 22.385 | 32.667 | 1.00 | 20.41 | D |
| ATOM | 4485 | CD1 | PHE | D | 11 | 49.790 | 21.108 | 33.219 | 1.00 | 21.09 | D |
| ATOM | 4486 | CD2 | PHE | D | 11 | 48.585 | 23.036 | 32.461 | 1.00 | 21.23 | D |
| ATOM | 4487 | CE1 | PHE | D | 11 | 48.587 | 20.487 | 33.562 | 1.00 | 21.42 | D |
| ATOM | 4488 | CE2 | PHE | D | 11 | 47.377 | 22.421 | 32.799 | 1.00 | 21.87 | D |
| ATOM | 4489 | CZ | PHE | D | 11 | 47.382 | 21.146 | 33.351 | 1.00 | 21.41 | D |
| ATOM | 4490 | C | PHE | D | 11 | 52.698 | 23.747 | 30.538 | 1.00 | 19.67 | D |
| ATOM | 4491 | O | PHE | D | 11 | 53.402 | 24.083 | 31.492 | 1.00 | 20.39 | D |
| ATOM | 4492 | N | ASP | D | 12 | 53.096 | 23.894 | 29.280 | 1.00 | 20.57 | D |
| ATOM | 4493 | CA | ASP | D | 12 | 54.372 | 24.533 | 29.015 | 1.00 | 21.78 | D |
| ATOM | 4494 | CB | ASP | D | 12 | 55.457 | 23.499 | 28.702 | 1.00 | 27.29 | D |
| ATOM | 4495 | CG | ASP | D | 12 | 55.347 | 22.935 | 27.325 | 1.00 | 32.17 | D |
| ATOM | 4496 | OD1 | ASP | D | 12 | 54.251 | 22.456 | 26.967 | 1.00 | 38.13 | D |
| ATOM | 4497 | OD2 | ASP | D | 12 | 56.370 | 22.964 | 26.606 | 1.00 | 35.45 | D |
| ATOM | 4498 | C | ASP | D | 12 | 54.222 | 25.559 | 27.896 | 1.00 | 19.35 | D |
| ATOM | 4499 | O | ASP | D | 12 | 54.512 | 25.303 | 26.728 | 1.00 | 19.09 | D |
| ATOM | 4500 | N | PRO | D | 13 | 53.757 | 26.755 | 28.262 | 1.00 | 17.74 | D |
| ATOM | 4501 | CD | PRO | D | 13 | 53.792 | 27.994 | 27.461 | 1.00 | 16.31 | D |
| ATOM | 4502 | CA | PRO | D | 13 | 53.420 | 27.051 | 29.657 | 1.00 | 16.77 | D |
| ATOM | 4503 | CB | PRO | D | 13 | 53.910 | 28.473 | 29.813 | 1.00 | 15.81 | D |
| ATOM | 4504 | CG | PRO | D | 13 | 53.459 | 29.068 | 28.497 | 1.00 | 16.14 | D |
| ATOM | 4505 | C | PRO | D | 13 | 51.928 | 26.981 | 29.930 | 1.00 | 17.24 | D |
| ATOM | 4506 | O | PRO | D | 13 | 51.127 | 26.779 | 29.019 | 1.00 | 15.59 | D |
| ATOM | 4507 | N | PRO | D | 14 | 51.546 | 27.142 | 31.205 | 1.00 | 17.61 | D |
| ATOM | 4508 | CD | PRO | D | 14 | 52.433 | 27.153 | 32.381 | 1.00 | 19.76 | D |
| ATOM | 4509 | CA | PRO | D | 14 | 50.145 | 27.124 | 31.619 | 1.00 | 18.63 | D |
| ATOM | 4510 | CB | PRO | D | 14 | 50.226 | 27.111 | 33.139 | 1.00 | 19.07 | D |
| ATOM | 4511 | CG | PRO | D | 14 | 51.565 | 26.515 | 33.419 | 1.00 | 23.76 | D |
| ATOM | 4512 | C | PRO | D | 14 | 49.625 | 28.476 | 31.126 | 1.00 | 19.14 | D |
| ATOM | 4513 | O | PRO | D | 14 | 50.370 | 29.463 | 31.142 | 1.00 | 18.50 | D |
| ATOM | 4514 | N | HIS | D | 15 | 48.370 | 28.536 | 30.698 | 1.00 | 16.99 | D |
| ATOM | 4515 | CA | HIS | D | 15 | 47.833 | 29.803 | 30.223 | 1.00 | 18.49 | D |
| ATOM | 4516 | CB | HIS | D | 15 | 47.874 | 29.852 | 28.686 | 1.00 | 18.79 | D |
| ATOM | 4517 | CG | HIS | D | 15 | 47.373 | 28.608 | 28.020 | 1.00 | 19.88 | D |
| ATOM | 4518 | CD2 | HIS | D | 15 | 48.019 | 27.666 | 27.290 | 1.00 | 20.93 | D |
| ATOM | 4519 | ND1 | HIS | D | 15 | 46.053 | 28.216 | 28.066 | 1.00 | 21.61 | D |
| ATOM | 4520 | CE1 | HIS | D | 15 | 45.905 | 27.088 | 27.392 | 1.00 | 19.42 | D |
| ATOM | 4521 | NE2 | HIS | D | 15 | 47.083 | 26.732 | 26.911 | 1.00 | 21.18 | D |
| ATOM | 4522 | C | HIS | D | 15 | 46.428 | 30.075 | 30.742 | 1.00 | 18.19 | D |

Figure 9 (70 of 92)

| ATOM | 4523 | O | HIS | D | 15 | 45.859 | 29.261 | 31.468 | 1.00 | 18.39 | D |
|---|---|---|---|---|---|---|---|---|---|---|---|
| ATOM | 4524 | N | ASN | D | 16 | 45.880 | 31.230 | 30.377 | 1.00 | 17.88 | D |
| ATOM | 4525 | CA | ASN | D | 16 | 44.556 | 31.623 | 30.834 | 1.00 | 17.46 | D |
| ATOM | 4526 | CB | ASN | D | 16 | 44.246 | 33.048 | 30.370 | 1.00 | 17.62 | D |
| ATOM | 4527 | CG | ASN | D | 16 | 45.194 | 34.079 | 30.983 | 1.00 | 18.67 | D |
| ATOM | 4528 | OD1 | ASN | D | 16 | 45.736 | 33.860 | 32.065 | 1.00 | 15.03 | D |
| ATOM | 4529 | ND2 | ASN | D | 16 | 45.378 | 35.215 | 30.301 | 1.00 | 17.12 | D |
| ATOM | 4530 | C | ASN | D | 16 | 43.478 | 30.653 | 30.375 | 1.00 | 17.42 | D |
| ATOM | 4531 | O | ASN | D | 16 | 42.455 | 30.494 | 31.041 | 1.00 | 15.58 | D |
| ATOM | 4532 | N | GLY | D | 17 | 43.713 | 30.000 | 29.241 | 1.00 | 17.89 | D |
| ATOM | 4533 | CA | GLY | D | 17 | 42.749 | 29.032 | 28.746 | 1.00 | 16.67 | D |
| ATOM | 4534 | C | GLY | D | 17 | 42.606 | 27.907 | 29.760 | 1.00 | 17.90 | D |
| ATOM | 4535 | O | GLY | D | 17 | 41.502 | 27.424 | 30.017 | 1.00 | 14.81 | D |
| ATOM | 4536 | N | HIS | D | 18 | 43.729 | 27.492 | 30.347 | 1.00 | 15.67 | D |
| ATOM | 4537 | CA | HIS | D | 18 | 43.710 | 26.419 | 31.348 | 1.00 | 15.70 | D |
| ATOM | 4538 | CB | HIS | D | 18 | 45.140 | 26.065 | 31.780 | 1.00 | 13.46 | D |
| ATOM | 4539 | CG | HIS | D | 18 | 45.973 | 25.446 | 30.701 | 1.00 | 13.74 | D |
| ATOM | 4540 | CD2 | HIS | D | 18 | 45.767 | 24.350 | 29.933 | 1.00 | 14.49 | D |
| ATOM | 4541 | ND1 | HIS | D | 18 | 47.225 | 25.918 | 30.363 | 1.00 | 15.14 | D |
| ATOM | 4542 | CE1 | HIS | D | 18 | 47.756 | 25.135 | 29.440 | 1.00 | 15.52 | D |
| ATOM | 4543 | NE2 | HIS | D | 18 | 46.893 | 24.175 | 29.161 | 1.00 | 16.88 | D |
| ATOM | 4544 | C | HIS | D | 18 | 42.915 | 26.847 | 32.590 | 1.00 | 15.68 | D |
| ATOM | 4545 | O | HIS | D | 18 | 42.078 | 26.094 | 33.099 | 1.00 | 13.65 | D |
| ATOM | 4546 | N | LEU | D | 19 | 43.175 | 28.063 | 33.070 | 1.00 | 13.83 | D |
| ATOM | 4547 | CA | LEU | D | 19 | 42.508 | 28.556 | 34.268 | 1.00 | 15.28 | D |
| ATOM | 4548 | CB | LEU | D | 19 | 43.100 | 29.904 | 34.686 | 1.00 | 15.82 | D |
| ATOM | 4549 | CG | LEU | D | 19 | 44.605 | 29.898 | 34.980 | 1.00 | 17.00 | D |
| ATOM | 4550 | CD1 | LEU | D | 19 | 45.111 | 31.322 | 35.084 | 1.00 | 14.86 | D |
| ATOM | 4551 | CD2 | LEU | D | 19 | 44.880 | 29.134 | 36.281 | 1.00 | 15.64 | D |
| ATOM | 4552 | C | LEU | D | 19 | 41.012 | 28.685 | 34.065 | 1.00 | 15.72 | D |
| ATOM | 4553 | O | LEU | D | 19 | 40.221 | 28.294 | 34.930 | 1.00 | 14.91 | D |
| ATOM | 4554 | N | LEU | D | 20 | 40.626 | 29.241 | 32.923 | 1.00 | 14.44 | D |
| ATOM | 4555 | CA | LEU | D | 20 | 39.216 | 29.406 | 32.600 | 1.00 | 15.70 | D |
| ATOM | 4556 | CB | LEU | D | 20 | 39.053 | 30.108 | 31.246 | 1.00 | 12.48 | D |
| ATOM | 4557 | CG | LEU | D | 20 | 37.619 | 30.259 | 30.725 | 1.00 | 15.51 | D |
| ATOM | 4558 | CD1 | LEU | D | 20 | 36.804 | 31.109 | 31.686 | 1.00 | 12.67 | D |
| ATOM | 4559 | CD2 | LEU | D | 20 | 37.635 | 30.884 | 29.330 | 1.00 | 15.13 | D |
| ATOM | 4560 | C | LEU | D | 20 | 38.504 | 28.055 | 32.557 | 1.00 | 16.76 | D |
| ATOM | 4561 | O | LEU | D | 20 | 37.453 | 27.889 | 33.178 | 1.00 | 17.40 | D |
| ATOM | 4562 | N | MET | D | 21 | 39.069 | 27.094 | 31.818 | 1.00 | 16.65 | D |
| ATOM | 4563 | CA | MET | D | 21 | 38.456 | 25.769 | 31.709 | 1.00 | 16.59 | D |
| ATOM | 4564 | CB | MET | D | 21 | 39.289 | 24.839 | 30.795 | 1.00 | 14.08 | D |
| ATOM | 4565 | CG | MET | D | 21 | 38.624 | 23.460 | 30.529 | 1.00 | 14.08 | D |
| ATOM | 4566 | SD | MET | D | 21 | 39.569 | 22.265 | 29.509 | 1.00 | 5.28 | D |
| ATOM | 4567 | CE | MET | D | 21 | 40.274 | 21.332 | 30.731 | 1.00 | 14.46 | D |
| ATOM | 4568 | C | MET | D | 21 | 38.293 | 25.137 | 33.098 | 1.00 | 16.93 | D |
| ATOM | 4569 | O | MET | D | 21 | 37.227 | 24.611 | 33.434 | 1.00 | 18.35 | D |
| ATOM | 4570 | N | ALA | D | 22 | 39.339 | 25.211 | 33.910 | 1.00 | 16.79 | D |
| ATOM | 4571 | CA | ALA | D | 22 | 39.298 | 24.639 | 35.262 | 1.00 | 17.21 | D |
| ATOM | 4572 | CB | ALA | D | 22 | 40.657 | 24.782 | 35.927 | 1.00 | 14.98 | D |
| ATOM | 4573 | C | ALA | D | 22 | 38.224 | 25.275 | 36.148 | 1.00 | 16.43 | D |
| ATOM | 4574 | O | ALA | D | 22 | 37.476 | 24.580 | 36.836 | 1.00 | 15.48 | D |
| ATOM | 4575 | N | ASN | D | 23 | 38.167 | 26.600 | 36.138 | 1.00 | 16.73 | D |
| ATOM | 4576 | CA | ASN | D | 23 | 37.202 | 27.338 | 36.943 | 1.00 | 16.67 | D |
| ATOM | 4577 | CB | ASN | D | 23 | 37.430 | 28.844 | 36.774 | 1.00 | 17.33 | D |
| ATOM | 4578 | CG | ASN | D | 23 | 36.860 | 29.649 | 37.922 | 1.00 | 18.93 | D |
| ATOM | 4579 | OD1 | ASN | D | 23 | 36.022 | 30.538 | 37.723 | 1.00 | 17.82 | D |
| ATOM | 4580 | ND2 | ASN | D | 23 | 37.305 | 29.337 | 39.137 | 1.00 | 14.33 | D |
| ATOM | 4581 | C | ASN | D | 23 | 35.774 | 26.987 | 36.536 | 1.00 | 16.52 | D |
| ATOM | 4582 | O | ASN | D | 23 | 34.892 | 26.827 | 37.382 | 1.00 | 15.77 | D |
| ATOM | 4583 | N | GLU | D | 24 | 35.548 | 26.869 | 35.233 | 1.00 | 17.80 | D |
| ATOM | 4584 | CA | GLU | D | 24 | 34.222 | 26.535 | 34.713 | 1.00 | 17.18 | D |
| ATOM | 4585 | CB | GLU | D | 24 | 34.195 | 26.707 | 33.197 | 1.00 | 17.61 | D |
| ATOM | 4586 | CG | GLU | D | 24 | 34.385 | 28.147 | 32.733 | 1.00 | 18.76 | D |
| ATOM | 4587 | CD | GLU | D | 24 | 33.270 | 29.059 | 33.199 | 1.00 | 19.47 | D |
| ATOM | 4588 | OE1 | GLU | D | 24 | 32.090 | 28.704 | 33.006 | 1.00 | 18.65 | D |

Figure 9 (71 of 92)

| ATOM | 4589 | OE2 | GLU | D | 24 | 33.572 | 30.136 | 33.749 | 1.00 | 21.23 | D |
|---|---|---|---|---|---|---|---|---|---|---|---|
| ATOM | 4590 | C | GLU | D | 24 | 33.817 | 25.112 | 35.080 | 1.00 | 16.74 | D |
| ATOM | 4591 | O | GLU | D | 24 | 32.672 | 24.862 | 35.456 | 1.00 | 17.43 | D |
| ATOM | 4592 | N | VAL | D | 25 | 34.749 | 24.173 | 34.959 | 1.00 | 15.07 | D |
| ATOM | 4593 | CA | VAL | D | 25 | 34.453 | 22.790 | 35.314 | 1.00 | 14.76 | D |
| ATOM | 4594 | CB | VAL | D | 25 | 35.649 | 21.859 | 34.983 | 1.00 | 14.94 | D |
| ATOM | 4595 | CG1 | VAL | D | 25 | 35.437 | 20.470 | 35.590 | 1.00 | 12.93 | D |
| ATOM | 4596 | CG2 | VAL | D | 25 | 35.799 | 21.740 | 33.471 | 1.00 | 14.82 | D |
| ATOM | 4597 | C | VAL | D | 25 | 34.173 | 22.770 | 36.816 | 1.00 | 15.64 | D |
| ATOM | 4598 | O | VAL | D | 25 | 33.177 | 22.212 | 37.268 | 1.00 | 14.78 | D |
| ATOM | 4599 | N | LEU | D | 26 | 35.050 | 23.416 | 37.576 | 1.00 | 16.13 | D |
| ATOM | 4600 | CA | LEU | D | 26 | 34.920 | 23.476 | 39.025 | 1.00 | 17.68 | D |
| ATOM | 4601 | CB | LEU | D | 26 | 35.914 | 24.485 | 39.598 | 1.00 | 19.01 | D |
| ATOM | 4602 | CG | LEU | D | 26 | 35.767 | 24.759 | 41.098 | 1.00 | 19.61 | D |
| ATOM | 4603 | CD1 | LEU | D | 26 | 36.234 | 23.544 | 41.883 | 1.00 | 19.26 | D |
| ATOM | 4604 | CD2 | LEU | D | 26 | 36.588 | 25.990 | 41.477 | 1.00 | 21.46 | D |
| ATOM | 4605 | C | LEU | D | 26 | 33.514 | 23.862 | 39.466 | 1.00 | 19.95 | D |
| ATOM | 4606 | O | LEU | D | 26 | 32.854 | 23.131 | 40.218 | 1.00 | 19.64 | D |
| ATOM | 4607 | N | TYR | D | 27 | 33.065 | 25.016 | 38.990 | 1.00 | 19.77 | D |
| ATOM | 4608 | CA | TYR | D | 27 | 31.752 | 25.536 | 39.330 | 1.00 | 23.26 | D |
| ATOM | 4609 | CB | TYR | D | 27 | 31.684 | 27.025 | 38.965 | 1.00 | 27.14 | D |
| ATOM | 4610 | CG | TYR | D | 27 | 30.297 | 27.606 | 39.069 | 1.00 | 34.84 | D |
| ATOM | 4611 | CD1 | TYR | D | 27 | 29.763 | 27.963 | 40.309 | 1.00 | 37.46 | D |
| ATOM | 4612 | CE1 | TYR | D | 27 | 28.454 | 28.434 | 40.420 | 1.00 | 39.21 | D |
| ATOM | 4613 | CD2 | TYR | D | 27 | 29.488 | 27.739 | 37.933 | 1.00 | 35.48 | D |
| ATOM | 4614 | CE2 | TYR | D | 27 | 28.183 | 28.206 | 38.033 | 1.00 | 38.67 | D |
| ATOM | 4615 | CZ | TYR | D | 27 | 27.671 | 28.551 | 39.282 | 1.00 | 39.56 | D |
| ATOM | 4616 | OH | TYR | D | 27 | 26.376 | 29.004 | 39.397 | 1.00 | 42.66 | D |
| ATOM | 4617 | C | TYR | D | 27 | 30.580 | 24.794 | 38.673 | 1.00 | 22.00 | D |
| ATOM | 4618 | O | TYR | D | 27 | 29.654 | 24.361 | 39.354 | 1.00 | 23.14 | D |
| ATOM | 4619 | N | GLN | D | 28 | 30.614 | 24.639 | 37.356 | 1.00 | 20.53 | D |
| ATOM | 4620 | CA | GLN | D | 28 | 29.503 | 23.988 | 36.670 | 1.00 | 20.31 | D |
| ATOM | 4621 | CB | GLN | D | 28 | 29.706 | 24.053 | 35.152 | 1.00 | 19.45 | D |
| ATOM | 4622 | CG | GLN | D | 28 | 29.576 | 25.467 | 34.593 | 1.00 | 17.73 | D |
| ATOM | 4623 | CD | GLN | D | 28 | 29.601 | 25.513 | 33.073 | 1.00 | 19.13 | D |
| ATOM | 4624 | OE1 | GLN | D | 28 | 28.841 | 24.807 | 32.407 | 1.00 | 16.21 | D |
| ATOM | 4625 | NE2 | GLN | D | 28 | 30.467 | 26.360 | 32.517 | 1.00 | 19.16 | D |
| ATOM | 4626 | C | GLN | D | 28 | 29.218 | 22.558 | 37.104 | 1.00 | 21.06 | D |
| ATOM | 4627 | O | GLN | D | 28 | 28.067 | 22.129 | 37.092 | 1.00 | 21.66 | D |
| ATOM | 4628 | N | ALA | D | 29 | 30.252 | 21.822 | 37.498 | 1.00 | 20.62 | D |
| ATOM | 4629 | CA | ALA | D | 29 | 30.067 | 20.435 | 37.927 | 1.00 | 21.22 | D |
| ATOM | 4630 | CB | ALA | D | 29 | 31.203 | 19.561 | 37.397 | 1.00 | 20.38 | D |
| ATOM | 4631 | C | ALA | D | 29 | 30.001 | 20.342 | 39.445 | 1.00 | 21.27 | D |
| ATOM | 4632 | O | ALA | D | 29 | 29.920 | 19.249 | 40.003 | 1.00 | 21.47 | D |
| ATOM | 4633 | N | GLY | D | 30 | 30.045 | 21.496 | 40.106 | 1.00 | 21.61 | D |
| ATOM | 4634 | CA | GLY | D | 30 | 29.976 | 21.532 | 41.559 | 1.00 | 21.40 | D |
| ATOM | 4635 | C | GLY | D | 30 | 31.037 | 20.724 | 42.288 | 1.00 | 22.80 | D |
| ATOM | 4636 | O | GLY | D | 30 | 30.718 | 19.991 | 43.230 | 1.00 | 23.16 | D |
| ATOM | 4637 | N | LEU | D | 31 | 32.296 | 20.858 | 41.871 | 1.00 | 21.95 | D |
| ATOM | 4638 | CA | LEU | D | 31 | 33.396 | 20.129 | 42.500 | 1.00 | 22.26 | D |
| ATOM | 4639 | CB | LEU | D | 31 | 34.481 | 19.813 | 41.463 | 1.00 | 20.61 | D |
| ATOM | 4640 | CG | LEU | D | 31 | 33.974 | 19.262 | 40.127 | 1.00 | 20.77 | D |
| ATOM | 4641 | CD1 | LEU | D | 31 | 35.156 | 19.032 | 39.198 | 1.00 | 18.08 | D |
| ATOM | 4642 | CD2 | LEU | D | 31 | 33.194 | 17.968 | 40.344 | 1.00 | 18.87 | D |
| ATOM | 4643 | C | LEU | D | 31 | 34.000 | 20.954 | 43.633 | 1.00 | 22.11 | D |
| ATOM | 4644 | O | LEU | D | 31 | 33.680 | 22.138 | 43.776 | 1.00 | 20.80 | D |
| ATOM | 4645 | N | ASP | D | 32 | 34.866 | 20.329 | 44.434 | 1.00 | 21.99 | D |
| ATOM | 4646 | CA | ASP | D | 32 | 35.522 | 21.018 | 45.548 | 1.00 | 22.56 | D |
| ATOM | 4647 | CB | ASP | D | 32 | 35.708 | 20.070 | 46.733 | 1.00 | 24.51 | D |
| ATOM | 4648 | CG | ASP | D | 32 | 34.397 | 19.558 | 47.272 | 1.00 | 25.85 | D |
| ATOM | 4649 | OD1 | ASP | D | 32 | 33.558 | 20.386 | 47.687 | 1.00 | 27.50 | D |
| ATOM | 4650 | OD2 | ASP | D | 32 | 34.206 | 18.331 | 47.274 | 1.00 | 25.89 | D |
| ATOM | 4651 | C | ASP | D | 32 | 36.885 | 21.568 | 45.142 | 1.00 | 22.81 | D |
| ATOM | 4652 | O | ASP | D | 32 | 37.267 | 22.681 | 45.521 | 1.00 | 23.02 | D |
| ATOM | 4653 | N | GLU | D | 33 | 37.627 | 20.778 | 44.377 | 1.00 | 20.81 | D |
| ATOM | 4654 | CA | GLU | D | 33 | 38.944 | 21.203 | 43.937 | 1.00 | 20.33 | D |

Figure 9 (72 of 92)

| ATOM | 4655 | CB | GLU | D | 33 | 40.031 | 20.630 | 44.854 | 1.00 | 20.62 | D |
| --- | --- | --- | --- | --- | --- | --- | --- | --- | --- | --- | --- |
| ATOM | 4656 | CG | GLU | D | 33 | 39.896 | 20.991 | 46.320 | 1.00 | 23.95 | D |
| ATOM | 4657 | CD | GLU | D | 33 | 40.906 | 20.262 | 47.202 | 1.00 | 25.33 | D |
| ATOM | 4658 | OE1 | GLU | D | 33 | 40.815 | 20.400 | 48.440 | 1.00 | 29.57 | D |
| ATOM | 4659 | OE2 | GLU | D | 33 | 41.789 | 19.557 | 46.665 | 1.00 | 23.48 | D |
| ATOM | 4660 | C | GLU | D | 33 | 39.220 | 20.722 | 42.529 | 1.00 | 17.96 | D |
| ATOM | 4661 | O | GLU | D | 33 | 38.564 | 19.810 | 42.030 | 1.00 | 17.72 | D |
| ATOM | 4662 | N | ILE | D | 34 | 40.194 | 21.358 | 41.895 | 1.00 | 17.33 | D |
| ATOM | 4663 | CA | ILE | D | 34 | 40.636 | 20.968 | 40.561 | 1.00 | 16.45 | D |
| ATOM | 4664 | CB | ILE | D | 34 | 40.476 | 22.098 | 39.509 | 1.00 | 15.67 | D |
| ATOM | 4665 | CG2 | ILE | D | 34 | 41.155 | 21.679 | 38.198 | 1.00 | 13.95 | D |
| ATOM | 4666 | CG1 | ILE | D | 34 | 38.996 | 22.421 | 39.289 | 1.00 | 12.47 | D |
| ATOM | 4667 | CD1 | ILE | D | 34 | 38.183 | 21.243 | 38.810 | 1.00 | 10.52 | D |
| ATOM | 4668 | C | ILE | D | 34 | 42.128 | 20.716 | 40.757 | 1.00 | 16.47 | D |
| ATOM | 4669 | O | ILE | D | 34 | 42.840 | 21.568 | 41.296 | 1.00 | 15.22 | D |
| ATOM | 4670 | N | TRP | D | 35 | 42.601 | 19.550 | 40.339 | 1.00 | 15.41 | D |
| ATOM | 4671 | CA | TRP | D | 35 | 44.016 | 19.244 | 40.483 | 1.00 | 16.97 | D |
| ATOM | 4672 | CB | TRP | D | 35 | 44.197 | 17.856 | 41.110 | 1.00 | 15.66 | D |
| ATOM | 4673 | CG | TRP | D | 35 | 43.791 | 17.795 | 42.558 | 1.00 | 18.24 | D |
| ATOM | 4674 | CD2 | TRP | D | 35 | 43.780 | 16.634 | 43.393 | 1.00 | 18.77 | D |
| ATOM | 4675 | CE2 | TRP | D | 35 | 43.313 | 17.036 | 44.667 | 1.00 | 20.19 | D |
| ATOM | 4676 | CE3 | TRP | D | 35 | 44.120 | 15.288 | 43.190 | 1.00 | 20.05 | D |
| ATOM | 4677 | CD1 | TRP | D | 35 | 43.347 | 18.828 | 43.335 | 1.00 | 19.13 | D |
| ATOM | 4678 | NE1 | TRP | D | 35 | 43.057 | 18.379 | 44.606 | 1.00 | 19.93 | D |
| ATOM | 4679 | CZ2 | TRP | D | 35 | 43.174 | 16.139 | 45.733 | 1.00 | 20.91 | D |
| ATOM | 4680 | CZ3 | TRP | D | 35 | 43.984 | 14.395 | 44.251 | 1.00 | 21.67 | D |
| ATOM | 4681 | CH2 | TRP | D | 35 | 43.514 | 14.826 | 45.506 | 1.00 | 21.02 | D |
| ATOM | 4682 | C | TRP | D | 35 | 44.760 | 19.302 | 39.155 | 1.00 | 18.08 | D |
| ATOM | 4683 | O | TRP | D | 35 | 44.524 | 18.476 | 38.270 | 1.00 | 18.68 | D |
| ATOM | 4684 | N | PHE | D | 36 | 45.647 | 20.284 | 39.009 | 1.00 | 18.32 | D |
| ATOM | 4685 | CA | PHE | D | 36 | 46.439 | 20.401 | 37.789 | 1.00 | 18.91 | D |
| ATOM | 4686 | CB | PHE | D | 36 | 47.049 | 21.800 | 37.678 | 1.00 | 18.00 | D |
| ATOM | 4687 | CG | PHE | D | 36 | 46.030 | 22.875 | 37.429 | 1.00 | 15.93 | D |
| ATOM | 4688 | CD1 | PHE | D | 36 | 45.049 | 23.157 | 38.375 | 1.00 | 14.26 | D |
| ATOM | 4689 | CD2 | PHE | D | 36 | 46.012 | 23.563 | 36.221 | 1.00 | 18.55 | D |
| ATOM | 4690 | CE1 | PHE | D | 36 | 44.061 | 24.102 | 38.121 | 1.00 | 14.00 | D |
| ATOM | 4691 | CE2 | PHE | D | 36 | 45.022 | 24.513 | 35.957 | 1.00 | 16.36 | D |
| ATOM | 4692 | CZ | PHE | D | 36 | 44.047 | 24.779 | 36.911 | 1.00 | 14.87 | D |
| ATOM | 4693 | C | PHE | D | 36 | 47.527 | 19.332 | 37.865 | 1.00 | 20.75 | D |
| ATOM | 4694 | O | PHE | D | 36 | 48.309 | 19.297 | 38.823 | 1.00 | 19.99 | D |
| ATOM | 4695 | N | MET | D | 37 | 47.568 | 18.467 | 36.854 | 1.00 | 20.75 | D |
| ATOM | 4696 | CA | MET | D | 37 | 48.516 | 17.354 | 36.814 | 1.00 | 21.99 | D |
| ATOM | 4697 | CB | MET | D | 37 | 47.735 | 16.041 | 36.800 | 1.00 | 21.67 | D |
| ATOM | 4698 | CG | MET | D | 37 | 46.637 | 15.958 | 37.860 | 1.00 | 23.35 | D |
| ATOM | 4699 | SD | MET | D | 37 | 46.730 | 14.382 | 38.723 | 1.00 | 20.68 | D |
| ATOM | 4700 | CE | MET | D | 37 | 48.497 | 14.342 | 38.855 | 1.00 | 6.40 | D |
| ATOM | 4701 | C | MET | D | 37 | 49.471 | 17.364 | 35.627 | 1.00 | 22.12 | D |
| ATOM | 4702 | O | MET | D | 37 | 49.171 | 16.800 | 34.579 | 1.00 | 20.87 | D |
| ATOM | 4703 | N | PRO | D | 38 | 50.653 | 17.974 | 35.788 | 1.00 | 23.86 | D |
| ATOM | 4704 | CD | PRO | D | 38 | 51.249 | 18.441 | 37.048 | 1.00 | 22.95 | D |
| ATOM | 4705 | CA | PRO | D | 38 | 51.629 | 18.031 | 34.691 | 1.00 | 25.56 | D |
| ATOM | 4706 | CB | PRO | D | 38 | 52.784 | 18.852 | 35.279 | 1.00 | 25.35 | D |
| ATOM | 4707 | CG | PRO | D | 38 | 52.233 | 19.438 | 36.565 | 1.00 | 24.54 | D |
| ATOM | 4708 | C | PRO | D | 38 | 52.113 | 16.640 | 34.287 | 1.00 | 27.77 | D |
| ATOM | 4709 | O | PRO | D | 38 | 52.568 | 15.879 | 35.137 | 1.00 | 26.29 | D |
| ATOM | 4710 | N | ASN | D | 39 | 52.022 | 16.293 | 33.007 | 1.00 | 30.03 | D |
| ATOM | 4711 | CA | ASN | D | 39 | 52.524 | 14.988 | 32.591 | 1.00 | 34.66 | D |
| ATOM | 4712 | CB | ASN | D | 39 | 51.949 | 14.587 | 31.231 | 1.00 | 33.96 | D |
| ATOM | 4713 | CG | ASN | D | 39 | 52.082 | 15.674 | 30.194 | 1.00 | 34.23 | D |
| ATOM | 4714 | OD1 | ASN | D | 39 | 51.250 | 15.778 | 29.293 | 1.00 | 34.26 | D |
| ATOM | 4715 | ND2 | ASN | D | 39 | 53.131 | 16.483 | 30.302 | 1.00 | 32.00 | D |
| ATOM | 4716 | C | ASN | D | 39 | 54.039 | 15.144 | 32.534 | 1.00 | 39.01 | D |
| ATOM | 4717 | O | ASN | D | 39 | 54.537 | 16.268 | 32.429 | 1.00 | 39.01 | D |
| ATOM | 4718 | N | GLN | D | 40 | 54.789 | 14.048 | 32.611 | 1.00 | 43.32 | D |
| ATOM | 4719 | CA | GLN | D | 40 | 56.237 | 14.200 | 32.601 | 1.00 | 48.44 | D |
| ATOM | 4720 | CB | GLN | D | 40 | 56.842 | 13.551 | 33.841 | 1.00 | 49.74 | D |

Figure 9 (73 of 92)

| ATOM | 4721 | CG | GLN | D | 40 | 58.231 | 14.080 | 34.139 | 1.00 | 52.79 | D |
| --- | --- | --- | --- | --- | --- | --- | --- | --- | --- | --- | --- |
| ATOM | 4722 | CD | GLN | D | 40 | 58.808 | 13.536 | 35.425 | 1.00 | 53.94 | D |
| ATOM | 4723 | OE1 | GLN | D | 40 | 59.916 | 13.903 | 35.824 | 1.00 | 55.14 | D |
| ATOM | 4724 | NE2 | GLN | D | 40 | 58.064 | 12.655 | 36.083 | 1.00 | 54.23 | D |
| ATOM | 4725 | C | GLN | D | 40 | 56.991 | 13.728 | 31.367 | 1.00 | 50.94 | D |
| ATOM | 4726 | O | GLN | D | 40 | 57.843 | 14.458 | 30.853 | 1.00 | 52.31 | D |
| ATOM | 4727 | N | ILE | D | 41 | 56.691 | 12.518 | 30.901 | 1.00 | 52.69 | D |
| ATOM | 4728 | CA | ILE | D | 41 | 57.347 | 11.942 | 29.722 | 1.00 | 54.60 | D |
| ATOM | 4729 | CB | ILE | D | 41 | 57.702 | 13.029 | 28.672 | 1.00 | 55.30 | D |
| ATOM | 4730 | CG2 | ILE | D | 41 | 58.381 | 12.390 | 27.472 | 1.00 | 56.15 | D |
| ATOM | 4731 | CG1 | ILE | D | 41 | 56.438 | 13.778 | 28.241 | 1.00 | 56.10 | D |
| ATOM | 4732 | CD1 | ILE | D | 41 | 56.703 | 14.950 | 27.321 | 1.00 | 56.05 | D |
| ATOM | 4733 | C | ILE | D | 41 | 58.629 | 11.197 | 30.093 | 1.00 | 54.61 | D |
| ATOM | 4734 | O | ILE | D | 41 | 59.375 | 11.618 | 30.979 | 1.00 | 55.16 | D |
| ATOM | 4735 | N | THR | D | 51 | 60.049 | 21.534 | 27.788 | 1.00 | 51.60 | D |
| ATOM | 4736 | CA | THR | D | 51 | 60.576 | 22.275 | 28.932 | 1.00 | 51.75 | D |
| ATOM | 4737 | CB | THR | D | 51 | 59.643 | 23.451 | 29.311 | 1.00 | 52.07 | D |
| ATOM | 4738 | OG1 | THR | D | 51 | 59.414 | 24.270 | 28.157 | 1.00 | 53.78 | D |
| ATOM | 4739 | CG2 | THR | D | 51 | 60.269 | 24.302 | 30.409 | 1.00 | 51.25 | D |
| ATOM | 4740 | C | THR | D | 51 | 60.726 | 21.344 | 30.137 | 1.00 | 50.83 | D |
| ATOM | 4741 | O | THR | D | 51 | 59.880 | 20.478 | 30.372 | 1.00 | 50.29 | D |
| ATOM | 4742 | N | ASP | D | 52 | 61.807 | 21.522 | 30.891 | 1.00 | 50.03 | D |
| ATOM | 4743 | CA | ASP | D | 52 | 62.061 | 20.691 | 32.063 | 1.00 | 49.24 | D |
| ATOM | 4744 | CB | ASP | D | 52 | 63.419 | 21.043 | 32.673 | 1.00 | 50.94 | D |
| ATOM | 4745 | CG | ASP | D | 52 | 64.578 | 20.597 | 31.796 | 1.00 | 54.06 | D |
| ATOM | 4746 | OD1 | ASP | D | 52 | 64.712 | 19.376 | 31.553 | 1.00 | 54.41 | D |
| ATOM | 4747 | OD2 | ASP | D | 52 | 65.352 | 21.466 | 31.341 | 1.00 | 56.72 | D |
| ATOM | 4748 | C | ASP | D | 52 | 60.961 | 20.811 | 33.109 | 1.00 | 47.77 | D |
| ATOM | 4749 | O | ASP | D | 52 | 60.445 | 21.901 | 33.367 | 1.00 | 47.51 | D |
| ATOM | 4750 | N | SER | D | 53 | 60.607 | 19.672 | 33.697 | 1.00 | 45.60 | D |
| ATOM | 4751 | CA | SER | D | 53 | 59.561 | 19.596 | 34.707 | 1.00 | 44.75 | D |
| ATOM | 4752 | CB | SER | D | 53 | 59.625 | 18.244 | 35.418 | 1.00 | 46.48 | D |
| ATOM | 4753 | OG | SER | D | 53 | 59.342 | 17.193 | 34.508 | 1.00 | 51.09 | D |
| ATOM | 4754 | C | SER | D | 53 | 59.639 | 20.718 | 35.727 | 1.00 | 42.20 | D |
| ATOM | 4755 | O | SER | D | 53 | 58.632 | 21.351 | 36.047 | 1.00 | 41.71 | D |
| ATOM | 4756 | N | PHE | D | 54 | 60.841 | 20.961 | 36.234 | 1.00 | 39.42 | D |
| ATOM | 4757 | CA | PHE | D | 54 | 61.054 | 22.010 | 37.219 | 1.00 | 36.82 | D |
| ATOM | 4758 | CB | PHE | D | 54 | 62.552 | 22.261 | 37.409 | 1.00 | 38.04 | D |
| ATOM | 4759 | CG | PHE | D | 54 | 62.850 | 23.400 | 38.333 | 1.00 | 38.42 | D |
| ATOM | 4760 | CD1 | PHE | D | 54 | 62.714 | 23.251 | 39.709 | 1.00 | 38.97 | D |
| ATOM | 4761 | CD2 | PHE | D | 54 | 63.199 | 24.646 | 37.825 | 1.00 | 38.28 | D |
| ATOM | 4762 | CE1 | PHE | D | 54 | 62.919 | 24.332 | 40.567 | 1.00 | 39.18 | D |
| ATOM | 4763 | CE2 | PHE | D | 54 | 63.405 | 25.731 | 38.676 | 1.00 | 37.91 | D |
| ATOM | 4764 | CZ | PHE | D | 54 | 63.263 | 25.575 | 40.047 | 1.00 | 37.39 | D |
| ATOM | 4765 | C | PHE | D | 54 | 60.370 | 23.331 | 36.856 | 1.00 | 35.11 | D |
| ATOM | 4766 | O | PHE | D | 54 | 59.573 | 23.861 | 37.626 | 1.00 | 35.26 | D |
| ATOM | 4767 | N | HIS | D | 55 | 60.691 | 23.865 | 35.684 | 1.00 | 32.78 | D |
| ATOM | 4768 | CA | HIS | D | 55 | 60.109 | 25.128 | 35.249 | 1.00 | 30.17 | D |
| ATOM | 4769 | CB | HIS | D | 55 | 60.752 | 25.575 | 33.941 | 1.00 | 29.21 | D |
| ATOM | 4770 | CG | HIS | D | 55 | 62.159 | 26.057 | 34.105 | 1.00 | 28.10 | D |
| ATOM | 4771 | CD2 | HIS | D | 55 | 62.692 | 26.969 | 34.950 | 1.00 | 27.21 | D |
| ATOM | 4772 | ND1 | HIS | D | 55 | 63.203 | 25.586 | 33.340 | 1.00 | 28.76 | D |
| ATOM | 4773 | CE1 | HIS | D | 55 | 64.321 | 26.187 | 33.706 | 1.00 | 28.27 | D |
| ATOM | 4774 | NE2 | HIS | D | 55 | 64.037 | 27.032 | 34.682 | 1.00 | 29.32 | D |
| ATOM | 4775 | C | HIS | D | 55 | 58.600 | 25.048 | 35.100 | 1.00 | 29.70 | D |
| ATOM | 4776 | O | HIS | D | 55 | 57.880 | 25.928 | 35.575 | 1.00 | 29.13 | D |
| ATOM | 4777 | N | ARG | D | 56 | 58.113 | 23.994 | 34.453 | 1.00 | 28.35 | D |
| ATOM | 4778 | CA | ARG | D | 56 | 56.673 | 23.849 | 34.289 | 1.00 | 28.18 | D |
| ATOM | 4779 | CB | ARG | D | 56 | 56.349 | 22.593 | 33.474 | 1.00 | 27.87 | D |
| ATOM | 4780 | CG | ARG | D | 56 | 56.814 | 22.697 | 32.022 | 1.00 | 28.03 | D |
| ATOM | 4781 | CD | ARG | D | 56 | 56.336 | 21.520 | 31.188 | 1.00 | 28.96 | D |
| ATOM | 4782 | NE | ARG | D | 56 | 56.922 | 20.263 | 31.632 | 1.00 | 29.65 | D |
| ATOM | 4783 | CZ | ARG | D | 56 | 56.226 | 19.160 | 31.890 | 1.00 | 28.62 | D |
| ATOM | 4784 | NH1 | ARG | D | 56 | 54.905 | 19.152 | 31.750 | 1.00 | 27.54 | D |
| ATOM | 4785 | NH2 | ARG | D | 56 | 56.855 | 18.065 | 32.292 | 1.00 | 27.06 | D |
| ATOM | 4786 | C | ARG | D | 56 | 55.988 | 23.815 | 35.652 | 1.00 | 26.91 | D |

Figure 9 (74 of 92)

| ATOM | 4787 | O | ARG | D | 56 | 54.917 | 24.392 | 35.819 | 1.00 | 27.37 | D |
|---|---|---|---|---|---|---|---|---|---|---|---|
| ATOM | 4788 | N | VAL | D | 57 | 56.612 | 23.163 | 36.633 | 1.00 | 26.44 | D |
| ATOM | 4789 | CA | VAL | D | 57 | 56.041 | 23.105 | 37.980 | 1.00 | 25.33 | D |
| ATOM | 4790 | CB | VAL | D | 57 | 56.818 | 22.126 | 38.899 | 1.00 | 26.44 | D |
| ATOM | 4791 | CG1 | VAL | D | 57 | 56.383 | 22.318 | 40.351 | 1.00 | 26.24 | D |
| ATOM | 4792 | CG2 | VAL | D | 57 | 56.558 | 20.679 | 38.466 | 1.00 | 26.19 | D |
| ATOM | 4793 | C | VAL | D | 57 | 56.044 | 24.501 | 38.612 | 1.00 | 24.21 | D |
| ATOM | 4794 | O | VAL | D | 57 | 55.068 | 24.903 | 39.245 | 1.00 | 22.62 | D |
| ATOM | 4795 | N | GLU | D | 58 | 57.132 | 25.248 | 38.439 | 1.00 | 22.80 | D |
| ATOM | 4796 | CA | GLU | D | 58 | 57.182 | 26.597 | 38.993 | 1.00 | 23.58 | D |
| ATOM | 4797 | CB | GLU | D | 58 | 58.588 | 27.198 | 38.868 | 1.00 | 27.03 | D |
| ATOM | 4798 | CG | GLU | D | 58 | 59.643 | 26.541 | 39.750 | 1.00 | 29.96 | D |
| ATOM | 4799 | CD | GLU | D | 58 | 59.195 | 26.403 | 41.197 | 1.00 | 32.71 | D |
| ATOM | 4800 | OE1 | GLU | D | 58 | 58.899 | 27.437 | 41.836 | 1.00 | 33.24 | D |
| ATOM | 4801 | OE2 | GLU | D | 58 | 59.135 | 25.254 | 41.690 | 1.00 | 32.64 | D |
| ATOM | 4802 | C | GLU | D | 58 | 56.169 | 27.515 | 38.291 | 1.00 | 21.72 | D |
| ATOM | 4803 | O | GLU | D | 58 | 55.504 | 28.317 | 38.940 | 1.00 | 20.74 | D |
| ATOM | 4804 | N | MET | D | 59 | 56.048 | 27.406 | 36.972 | 1.00 | 20.39 | D |
| ATOM | 4805 | CA | MET | D | 59 | 55.089 | 28.248 | 36.259 | 1.00 | 20.56 | D |
| ATOM | 4806 | CB | MET | D | 59 | 55.235 | 28.082 | 34.732 | 1.00 | 18.67 | D |
| ATOM | 4807 | CG | MET | D | 59 | 56.462 | 28.790 | 34.133 | 1.00 | 15.30 | D |
| ATOM | 4808 | SD | MET | D | 59 | 56.568 | 28.721 | 32.335 | 1.00 | 5.44 | D |
| ATOM | 4809 | CE | MET | D | 59 | 56.984 | 27.093 | 32.072 | 1.00 | 11.48 | D |
| ATOM | 4810 | C | MET | D | 59 | 53.657 | 27.908 | 36.703 | 1.00 | 19.88 | D |
| ATOM | 4811 | O | MET | D | 59 | 52.819 | 28.793 | 36.835 | 1.00 | 18.59 | D |
| ATOM | 4812 | N | LEU | D | 60 | 53.393 | 26.628 | 36.960 | 1.00 | 21.30 | D |
| ATOM | 4813 | CA | LEU | D | 60 | 52.062 | 26.196 | 37.385 | 1.00 | 21.43 | D |
| ATOM | 4814 | CB | LEU | D | 60 | 51.983 | 24.675 | 37.413 | 1.00 | 21.81 | D |
| ATOM | 4815 | CG | LEU | D | 60 | 51.371 | 24.064 | 36.156 | 1.00 | 23.17 | D |
| ATOM | 4816 | CD1 | LEU | D | 60 | 51.462 | 22.562 | 36.226 | 1.00 | 26.02 | D |
| ATOM | 4817 | CD2 | LEU | D | 60 | 49.924 | 24.507 | 36.028 | 1.00 | 22.96 | D |
| ATOM | 4818 | C | LEU | D | 60 | 51.634 | 26.748 | 38.737 | 1.00 | 21.98 | D |
| ATOM | 4819 | O | LEU | D | 60 | 50.473 | 27.126 | 38.926 | 1.00 | 22.00 | D |
| ATOM | 4820 | N | LYS | D | 61 | 52.565 | 26.791 | 39.680 | 1.00 | 22.28 | D |
| ATOM | 4821 | CA | LYS | D | 61 | 52.268 | 27.313 | 41.006 | 1.00 | 22.50 | D |
| ATOM | 4822 | CB | LYS | D | 61 | 53.514 | 27.227 | 41.887 | 1.00 | 25.22 | D |
| ATOM | 4823 | CG | LYS | D | 61 | 54.010 | 25.803 | 42.075 | 1.00 | 27.30 | D |
| ATOM | 4824 | CD | LYS | D | 61 | 55.233 | 25.745 | 42.970 | 1.00 | 30.64 | D |
| ATOM | 4825 | CE | LYS | D | 61 | 55.632 | 24.303 | 43.245 | 1.00 | 30.41 | D |
| ATOM | 4826 | NZ | LYS | D | 61 | 56.941 | 24.223 | 43.965 | 1.00 | 33.70 | D |
| ATOM | 4827 | C | LYS | D | 61 | 51.823 | 28.760 | 40.861 | 1.00 | 23.43 | D |
| ATOM | 4828 | O | LYS | D | 61 | 50.784 | 29.166 | 41.395 | 1.00 | 24.36 | D |
| ATOM | 4829 | N | LEU | D | 62 | 52.599 | 29.532 | 40.110 | 1.00 | 22.00 | D |
| ATOM | 4830 | CA | LEU | D | 62 | 52.287 | 30.933 | 39.891 | 1.00 | 22.25 | D |
| ATOM | 4831 | CB | LEU | D | 62 | 53.362 | 31.571 | 39.005 | 1.00 | 22.57 | D |
| ATOM | 4832 | CG | LEU | D | 62 | 54.764 | 31.652 | 39.621 | 1.00 | 22.28 | D |
| ATOM | 4833 | CD1 | LEU | D | 62 | 55.786 | 32.049 | 38.581 | 1.00 | 23.68 | D |
| ATOM | 4834 | CD2 | LEU | D | 62 | 54.750 | 32.654 | 40.762 | 1.00 | 22.96 | D |
| ATOM | 4835 | C | LEU | D | 62 | 50.912 | 31.078 | 39.245 | 1.00 | 23.55 | D |
| ATOM | 4836 | O | LEU | D | 62 | 50.082 | 31.874 | 39.694 | 1.00 | 23.01 | D |
| ATOM | 4837 | N | ALA | D | 63 | 50.666 | 30.296 | 38.199 | 1.00 | 23.92 | D |
| ATOM | 4838 | CA | ALA | D | 63 | 49.394 | 30.359 | 37.496 | 1.00 | 23.78 | D |
| ATOM | 4839 | CB | ALA | D | 63 | 49.369 | 29.329 | 36.365 | 1.00 | 22.43 | D |
| ATOM | 4840 | C | ALA | D | 63 | 48.185 | 30.159 | 38.409 | 1.00 | 23.21 | D |
| ATOM | 4841 | O | ALA | D | 63 | 47.249 | 30.956 | 38.383 | 1.00 | 22.80 | D |
| ATOM | 4842 | N | ILE | D | 64 | 48.216 | 29.113 | 39.229 | 1.00 | 22.75 | D |
| ATOM | 4843 | CA | ILE | D | 64 | 47.089 | 28.803 | 40.113 | 1.00 | 23.67 | D |
| ATOM | 4844 | CB | ILE | D | 64 | 46.994 | 27.287 | 40.356 | 1.00 | 23.94 | D |
| ATOM | 4845 | CG2 | ILE | D | 64 | 46.901 | 26.557 | 39.013 | 1.00 | 23.56 | D |
| ATOM | 4846 | CG1 | ILE | D | 64 | 48.210 | 26.804 | 41.154 | 1.00 | 23.80 | D |
| ATOM | 4847 | CD1 | ILE | D | 64 | 48.135 | 25.347 | 41.566 | 1.00 | 25.94 | D |
| ATOM | 4848 | C | ILE | D | 64 | 47.010 | 29.488 | 41.479 | 1.00 | 25.91 | D |
| ATOM | 4849 | O | ILE | D | 64 | 45.944 | 29.491 | 42.101 | 1.00 | 26.02 | D |
| ATOM | 4850 | N | GLN | D | 65 | 48.119 | 30.063 | 41.941 | 1.00 | 27.67 | D |
| ATOM | 4851 | CA | GLN | D | 65 | 48.184 | 30.742 | 43.245 | 1.00 | 30.93 | D |
| ATOM | 4852 | CB | GLN | D | 65 | 49.389 | 31.688 | 43.290 | 1.00 | 32.46 | D |

Figure 9 (75 of 92)

| | | | | | | | | | | |
|---|---|---|---|---|---|---|---|---|---|---|
| ATOM | 4853 | CG | GLN | D | 65 | 50.712 | 31.012 | 43.541 | 1.00 34.74 | D |
| ATOM | 4854 | CD | GLN | D | 65 | 51.851 | 32.004 | 43.667 | 1.00 36.44 | D |
| ATOM | 4855 | OE1 | GLN | D | 65 | 53.002 | 31.618 | 43.886 | 1.00 38.03 | D |
| ATOM | 4856 | NE2 | GLN | D | 65 | 51.537 | 33.290 | 43.528 | 1.00 33.63 | D |
| ATOM | 4857 | C | GLN | D | 65 | 46.969 | 31.539 | 43.723 | 1.00 31.26 | D |
| ATOM | 4858 | O | GLN | D | 65 | 46.529 | 31.395 | 44.867 | 1.00 32.67 | D |
| ATOM | 4859 | N | SER | D | 66 | 46.440 | 32.391 | 42.858 | 1.00 31.34 | D |
| ATOM | 4860 | CA | SER | D | 66 | 45.312 | 33.238 | 43.220 | 1.00 31.76 | D |
| ATOM | 4861 | CB | SER | D | 66 | 45.136 | 34.333 | 42.172 | 1.00 31.87 | D |
| ATOM | 4862 | OG | SER | D | 66 | 44.618 | 33.788 | 40.970 | 1.00 32.12 | D |
| ATOM | 4863 | C | SER | D | 66 | 43.977 | 32.534 | 43.412 | 1.00 32.13 | D |
| ATOM | 4864 | O | SER | D | 66 | 43.042 | 33.126 | 43.949 | 1.00 33.41 | D |
| ATOM | 4865 | N | ASN | D | 67 | 43.876 | 31.282 | 42.979 | 1.00 31.36 | D |
| ATOM | 4866 | CA | ASN | D | 67 | 42.624 | 30.543 | 43.101 | 1.00 29.22 | D |
| ATOM | 4867 | CB | ASN | D | 67 | 42.235 | 29.968 | 41.736 | 1.00 29.72 | D |
| ATOM | 4868 | CG | ASN | D | 67 | 40.785 | 29.518 | 41.672 | 1.00 30.23 | D |
| ATOM | 4869 | OD1 | ASN | D | 67 | 40.167 | 29.567 | 40.608 | 1.00 32.16 | D |
| ATOM | 4870 | ND2 | ASN | D | 67 | 40.241 | 29.065 | 42.796 | 1.00 27.75 | D |
| ATOM | 4871 | C | ASN | D | 67 | 42.738 | 29.430 | 44.135 | 1.00 28.67 | D |
| ATOM | 4872 | O | ASN | D | 67 | 43.430 | 28.439 | 43.923 | 1.00 27.50 | D |
| ATOM | 4873 | N | PRO | D | 68 | 42.034 | 29.581 | 45.266 | 1.00 28.59 | D |
| ATOM | 4874 | CD | PRO | D | 68 | 41.185 | 30.755 | 45.529 | 1.00 28.53 | D |
| ATOM | 4875 | CA | PRO | D | 68 | 41.991 | 28.648 | 46.400 | 1.00 29.34 | D |
| ATOM | 4876 | CB | PRO | D | 68 | 41.016 | 29.322 | 47.367 | 1.00 30.02 | D |
| ATOM | 4877 | CG | PRO | D | 68 | 41.145 | 30.781 | 47.028 | 1.00 30.30 | D |
| ATOM | 4878 | C | PRO | D | 68 | 41.559 | 27.211 | 46.095 | 1.00 29.53 | D |
| ATOM | 4879 | O | PRO | D | 68 | 41.954 | 26.286 | 46.808 | 1.00 30.15 | D |
| ATOM | 4880 | N | SER | D | 69 | 40.749 | 27.026 | 45.053 | 1.00 27.32 | D |
| ATOM | 4881 | CA | SER | D | 69 | 40.255 | 25.697 | 44.696 | 1.00 26.65 | D |
| ATOM | 4882 | CB | SER | D | 69 | 38.864 | 25.803 | 44.069 | 1.00 27.87 | D |
| ATOM | 4883 | OG | SER | D | 69 | 37.935 | 26.378 | 44.971 | 1.00 29.57 | D |
| ATOM | 4884 | C | SER | D | 69 | 41.160 | 24.929 | 43.745 | 1.00 25.50 | D |
| ATOM | 4885 | O | SER | D | 69 | 40.866 | 23.786 | 43.385 | 1.00 26.22 | D |
| ATOM | 4886 | N | PHE | D | 70 | 42.246 | 25.559 | 43.324 | 1.00 23.82 | D |
| ATOM | 4887 | CA | PHE | D | 70 | 43.174 | 24.916 | 42.410 | 1.00 23.06 | D |
| ATOM | 4888 | CB | PHE | D | 70 | 43.671 | 25.901 | 41.343 | 1.00 22.74 | D |
| ATOM | 4889 | CG | PHE | D | 70 | 42.608 | 26.341 | 40.360 | 1.00 20.50 | D |
| ATOM | 4890 | CD1 | PHE | D | 70 | 42.909 | 27.283 | 39.378 | 1.00 20.39 | D |
| ATOM | 4891 | CD2 | PHE | D | 70 | 41.318 | 25.822 | 40.413 | 1.00 18.76 | D |
| ATOM | 4892 | CE1 | PHE | D | 70 | 41.943 | 27.705 | 38.463 | 1.00 20.18 | D |
| ATOM | 4893 | CE2 | PHE | D | 70 | 40.336 | 26.236 | 39.498 | 1.00 21.49 | D |
| ATOM | 4894 | CZ | PHE | D | 70 | 40.651 | 27.179 | 38.523 | 1.00 19.64 | D |
| ATOM | 4895 | C | PHE | D | 70 | 44.359 | 24.395 | 43.197 | 1.00 23.62 | D |
| ATOM | 4896 | O | PHE | D | 70 | 44.837 | 25.048 | 44.125 | 1.00 23.00 | D |
| ATOM | 4897 | N | LYS | D | 71 | 44.820 | 23.208 | 42.829 | 1.00 23.06 | D |
| ATOM | 4898 | CA | LYS | D | 71 | 45.960 | 22.609 | 43.488 | 1.00 23.90 | D |
| ATOM | 4899 | CB | LYS | D | 71 | 45.503 | 21.613 | 44.551 | 1.00 24.56 | D |
| ATOM | 4900 | CG | LYS | D | 71 | 45.200 | 22.260 | 45.890 | 1.00 30.83 | D |
| ATOM | 4901 | CD | LYS | D | 71 | 43.734 | 22.136 | 46.286 | 1.00 35.72 | D |
| ATOM | 4902 | CE | LYS | D | 71 | 43.476 | 22.889 | 47.592 | 1.00 39.79 | D |
| ATOM | 4903 | NZ | LYS | D | 71 | 42.067 | 22.780 | 48.074 | 1.00 44.13 | D |
| ATOM | 4904 | C | LYS | D | 71 | 46.859 | 21.918 | 42.484 | 1.00 24.40 | D |
| ATOM | 4905 | O | LYS | D | 71 | 46.414 | 21.464 | 41.424 | 1.00 24.59 | D |
| ATOM | 4906 | N | LEU | D | 72 | 48.136 | 21.859 | 42.821 | 1.00 24.03 | D |
| ATOM | 4907 | CA | LEU | D | 72 | 49.118 | 21.210 | 41.981 | 1.00 25.11 | D |
| ATOM | 4908 | CB | LEU | D | 72 | 50.442 | 21.975 | 42.044 | 1.00 26.73 | D |
| ATOM | 4909 | CG | LEU | D | 72 | 51.563 | 21.538 | 41.102 | 1.00 27.23 | D |
| ATOM | 4910 | CD1 | LEU | D | 72 | 51.036 | 21.440 | 39.680 | 1.00 28.34 | D |
| ATOM | 4911 | CD2 | LEU | D | 72 | 52.697 | 22.554 | 41.181 | 1.00 31.14 | D |
| ATOM | 4912 | C | LEU | D | 72 | 49.290 | 19.808 | 42.547 | 1.00 26.34 | D |
| ATOM | 4913 | O | LEU | D | 72 | 49.386 | 19.633 | 43.757 | 1.00 25.67 | D |
| ATOM | 4914 | N | GLU | D | 73 | 49.306 | 18.810 | 41.674 | 1.00 27.29 | D |
| ATOM | 4915 | CA | GLU | D | 73 | 49.470 | 17.427 | 42.101 | 1.00 30.16 | D |
| ATOM | 4916 | CB | GLU | D | 73 | 48.127 | 16.691 | 42.016 | 1.00 32.88 | D |
| ATOM | 4917 | CG | GLU | D | 73 | 48.119 | 15.283 | 42.599 | 1.00 37.64 | D |
| ATOM | 4918 | CD | GLU | D | 73 | 48.456 | 15.241 | 44.087 | 1.00 39.37 | D |

Figure 9 (76 of 92)

| ATOM | 4919 | OE1 | GLU | D | 73 | 47.855 | 16.005 | 44.871 | 1.00 | 39.44 | D |
|---|---|---|---|---|---|---|---|---|---|---|---|
| ATOM | 4920 | OE2 | GLU | D | 73 | 49.318 | 14.427 | 44.476 | 1.00 | 42.50 | D |
| ATOM | 4921 | C | GLU | D | 73 | 50.499 | 16.796 | 41.175 | 1.00 | 30.26 | D |
| ATOM | 4922 | O | GLU | D | 73 | 50.309 | 16.749 | 39.958 | 1.00 | 29.33 | D |
| ATOM | 4923 | N | LEU | D | 74 | 51.595 | 16.319 | 41.757 | 1.00 | 29.97 | D |
| ATOM | 4924 | CA | LEU | D | 74 | 52.677 | 15.721 | 40.989 | 1.00 | 31.81 | D |
| ATOM | 4925 | CB | LEU | D | 74 | 54.017 | 16.224 | 41.529 | 1.00 | 32.88 | D |
| ATOM | 4926 | CG | LEU | D | 74 | 54.192 | 17.729 | 41.742 | 1.00 | 33.05 | D |
| ATOM | 4927 | CD1 | LEU | D | 74 | 55.498 | 17.970 | 42.484 | 1.00 | 33.45 | D |
| ATOM | 4928 | CD2 | LEU | D | 74 | 54.187 | 18.461 | 40.405 | 1.00 | 32.46 | D |
| ATOM | 4929 | C | LEU | D | 74 | 52.693 | 14.192 | 40.995 | 1.00 | 33.29 | D |
| ATOM | 4930 | O | LEU | D | 74 | 53.764 | 13.591 | 40.886 | 1.00 | 33.99 | D |
| ATOM | 4931 | N | VAL | D | 75 | 51.530 | 13.557 | 41.111 | 1.00 | 34.43 | D |
| ATOM | 4932 | CA | VAL | D | 75 | 51.485 | 12.094 | 41.148 | 1.00 | 35.86 | D |
| ATOM | 4933 | CB | VAL | D | 75 | 50.055 | 11.556 | 41.405 | 1.00 | 36.00 | D |
| ATOM | 4934 | CG1 | VAL | D | 75 | 49.428 | 12.278 | 42.577 | 1.00 | 36.38 | D |
| ATOM | 4935 | CG2 | VAL | D | 75 | 49.210 | 11.693 | 40.166 | 1.00 | 38.52 | D |
| ATOM | 4936 | C | VAL | D | 75 | 52.011 | 11.446 | 39.872 | 1.00 | 36.59 | D |
| ATOM | 4937 | O | VAL | D | 75 | 52.633 | 10.386 | 39.921 | 1.00 | 36.60 | D |
| ATOM | 4938 | N | GLU | D | 76 | 51.756 | 12.078 | 38.730 | 1.00 | 37.42 | D |
| ATOM | 4939 | CA | GLU | D | 76 | 52.214 | 11.545 | 37.453 | 1.00 | 38.40 | D |
| ATOM | 4940 | CB | GLU | D | 76 | 51.600 | 12.341 | 36.301 | 1.00 | 37.79 | D |
| ATOM | 4941 | CG | GLU | D | 76 | 52.203 | 12.030 | 34.945 | 1.00 | 35.81 | D |
| ATOM | 4942 | CD | GLU | D | 76 | 51.161 | 11.856 | 33.854 | 1.00 | 34.46 | D |
| ATOM | 4943 | OE1 | GLU | D | 76 | 51.566 | 11.799 | 32.674 | 1.00 | 35.23 | D |
| ATOM | 4944 | OE2 | GLU | D | 76 | 49.951 | 11.765 | 34.169 | 1.00 | 30.38 | D |
| ATOM | 4945 | C | GLU | D | 76 | 53.735 | 11.591 | 37.368 | 1.00 | 40.41 | D |
| ATOM | 4946 | O | GLU | D | 76 | 54.340 | 10.997 | 36.474 | 1.00 | 41.55 | D |
| ATOM | 4947 | N | MET | D | 77 | 54.343 | 12.289 | 38.322 | 1.00 | 41.70 | D |
| ATOM | 4948 | CA | MET | D | 77 | 55.790 | 12.450 | 38.381 | 1.00 | 43.02 | D |
| ATOM | 4949 | CB | MET | D | 77 | 56.129 | 13.877 | 38.819 | 1.00 | 45.09 | D |
| ATOM | 4950 | CG | MET | D | 77 | 55.266 | 14.962 | 38.176 | 1.00 | 47.42 | D |
| ATOM | 4951 | SD | MET | D | 77 | 55.779 | 15.412 | 36.519 | 1.00 | 48.32 | D |
| ATOM | 4952 | CE | MET | D | 77 | 56.757 | 16.858 | 36.875 | 1.00 | 48.12 | D |
| ATOM | 4953 | C | MET | D | 77 | 56.382 | 11.473 | 39.388 | 1.00 | 43.38 | D |
| ATOM | 4954 | O | MET | D | 77 | 57.602 | 11.322 | 39.479 | 1.00 | 43.32 | D |
| ATOM | 4955 | N | GLU | D | 78 | 55.508 | 10.823 | 40.148 | 1.00 | 43.35 | D |
| ATOM | 4956 | CA | GLU | D | 78 | 55.932 | 9.877 | 41.174 | 1.00 | 43.83 | D |
| ATOM | 4957 | CB | GLU | D | 78 | 55.430 | 10.349 | 42.544 | 1.00 | 43.58 | D |
| ATOM | 4958 | CG | GLU | D | 78 | 55.628 | 11.848 | 42.782 | 1.00 | 44.33 | D |
| ATOM | 4959 | CD | GLU | D | 78 | 54.940 | 12.350 | 44.041 | 1.00 | 44.66 | D |
| ATOM | 4960 | OE1 | GLU | D | 78 | 53.809 | 11.901 | 44.314 | 1.00 | 45.12 | D |
| ATOM | 4961 | OE2 | GLU | D | 78 | 55.518 | 13.207 | 44.748 | 1.00 | 44.60 | D |
| ATOM | 4962 | C | GLU | D | 78 | 55.382 | 8.490 | 40.874 | 1.00 | 44.12 | D |
| ATOM | 4963 | O | GLU | D | 78 | 55.238 | 7.667 | 41.777 | 1.00 | 43.33 | D |
| ATOM | 4964 | N | ARG | D | 79 | 55.077 | 8.235 | 39.605 | 1.00 | 45.56 | D |
| ATOM | 4965 | CA | ARG | D | 79 | 54.532 | 6.946 | 39.192 | 1.00 | 47.48 | D |
| ATOM | 4966 | CB | ARG | D | 79 | 53.944 | 7.035 | 37.782 | 1.00 | 46.67 | D |
| ATOM | 4967 | CG | ARG | D | 79 | 52.764 | 7.972 | 37.629 | 1.00 | 46.31 | D |
| ATOM | 4968 | CD | ARG | D | 79 | 52.219 | 7.917 | 36.206 | 1.00 | 45.26 | D |
| ATOM | 4969 | NE | ARG | D | 79 | 53.268 | 8.115 | 35.205 | 1.00 | 44.88 | D |
| ATOM | 4970 | CZ | ARG | D | 79 | 53.601 | 7.222 | 34.276 | 1.00 | 44.83 | D |
| ATOM | 4971 | NH1 | ARG | D | 79 | 52.972 | 6.057 | 34.207 | 1.00 | 42.83 | D |
| ATOM | 4972 | NH2 | ARG | D | 79 | 54.569 | 7.492 | 33.410 | 1.00 | 45.44 | D |
| ATOM | 4973 | C | ARG | D | 79 | 55.562 | 5.817 | 39.233 | 1.00 | 49.19 | D |
| ATOM | 4974 | O | ARG | D | 79 | 55.195 | 4.641 | 39.206 | 1.00 | 49.44 | D |
| ATOM | 4975 | N | GLU | D | 80 | 56.844 | 6.168 | 39.285 | 1.00 | 51.20 | D |
| ATOM | 4976 | CA | GLU | D | 80 | 57.896 | 5.158 | 39.342 | 1.00 | 52.95 | D |
| ATOM | 4977 | CB | GLU | D | 80 | 59.136 | 5.606 | 38.567 | 1.00 | 54.39 | D |
| ATOM | 4978 | CG | GLU | D | 80 | 59.144 | 5.213 | 37.100 | 1.00 | 56.26 | D |
| ATOM | 4979 | CD | GLU | D | 80 | 60.553 | 5.140 | 36.537 | 1.00 | 57.15 | D |
| ATOM | 4980 | OE1 | GLU | D | 80 | 61.296 | 4.205 | 36.908 | 1.00 | 57.78 | D |
| ATOM | 4981 | OE2 | GLU | D | 80 | 60.921 | 6.021 | 35.732 | 1.00 | 57.66 | D |
| ATOM | 4982 | C | GLU | D | 80 | 58.313 | 4.817 | 40.765 | 1.00 | 53.31 | D |
| ATOM | 4983 | O | GLU | D | 80 | 58.772 | 5.680 | 41.511 | 1.00 | 54.07 | D |
| ATOM | 4984 | N | GLY | D | 81 | 58.150 | 3.548 | 41.130 | 1.00 | 54.16 | D |

Figure 9 (77 of 92)

| ATOM | 4985 | CA  | GLY | D | 81 | 58.538 | 3.087  | 42.452 | 1.00 | 54.21 | D |
| ATOM | 4986 | C   | GLY | D | 81 | 59.637 | 2.052  | 42.266 | 1.00 | 54.68 | D |
| ATOM | 4987 | O   | GLY | D | 81 | 59.767 | 1.119  | 43.064 | 1.00 | 54.57 | D |
| ATOM | 4988 | N   | PRO | D | 82 | 60.497 | 2.261  | 41.249 | 1.00 | 53.94 | D |
| ATOM | 4989 | CD  | PRO | D | 82 | 60.962 | 3.655  | 41.413 | 1.00 | 55.06 | D |
| ATOM | 4990 | CA  | PRO | D | 82 | 61.646 | 1.511  | 40.748 | 1.00 | 53.54 | D |
| ATOM | 4991 | CB  | PRO | D | 82 | 62.707 | 1.890  | 41.763 | 1.00 | 54.08 | D |
| ATOM | 4992 | CG  | PRO | D | 82 | 62.475 | 3.467  | 41.774 | 1.00 | 55.18 | D |
| ATOM | 4993 | C   | PRO | D | 82 | 61.591 | 0.015  | 40.372 | 1.00 | 51.74 | D |
| ATOM | 4994 | O   | PRO | D | 82 | 62.571 | -0.533 | 39.850 | 1.00 | 51.88 | D |
| ATOM | 4995 | N   | SER | D | 83 | 60.446 | -0.625 | 40.596 | 1.00 | 48.78 | D |
| ATOM | 4996 | CA  | SER | D | 83 | 60.248 | -2.029 | 40.229 | 1.00 | 45.58 | D |
| ATOM | 4997 | CB  | SER | D | 83 | 60.166 | -2.915 | 41.470 | 1.00 | 46.90 | D |
| ATOM | 4998 | OG  | SER | D | 83 | 61.453 | -3.166 | 42.008 | 1.00 | 49.57 | D |
| ATOM | 4999 | C   | SER | D | 83 | 58.944 | -2.127 | 39.451 | 1.00 | 42.51 | D |
| ATOM | 5000 | O   | SER | D | 83 | 58.750 | -3.017 | 38.614 | 1.00 | 43.66 | D |
| ATOM | 5001 | N   | TYR | D | 84 | 58.053 | -1.187 | 39.741 | 1.00 | 37.20 | D |
| ATOM | 5002 | CA  | TYR | D | 84 | 56.759 | -1.133 | 39.088 | 1.00 | 31.95 | D |
| ATOM | 5003 | CB  | TYR | D | 84 | 55.692 | -1.802 | 39.958 | 1.00 | 28.43 | D |
| ATOM | 5004 | CG  | TYR | D | 84 | 54.320 | -1.759 | 39.333 | 1.00 | 27.33 | D |
| ATOM | 5005 | CD1 | TYR | D | 84 | 54.039 | -2.492 | 38.178 | 1.00 | 27.00 | D |
| ATOM | 5006 | CE1 | TYR | D | 84 | 52.802 | -2.403 | 37.554 | 1.00 | 26.57 | D |
| ATOM | 5007 | CD2 | TYR | D | 84 | 53.321 | -0.937 | 39.855 | 1.00 | 26.20 | D |
| ATOM | 5008 | CE2 | TYR | D | 84 | 52.077 | -0.838 | 39.239 | 1.00 | 26.18 | D |
| ATOM | 5009 | CZ  | TYR | D | 84 | 51.827 | -1.572 | 38.087 | 1.00 | 27.03 | D |
| ATOM | 5010 | OH  | TYR | D | 84 | 50.621 | -1.455 | 37.446 | 1.00 | 28.28 | D |
| ATOM | 5011 | C   | TYR | D | 84 | 56.372 | 0.318  | 38.843 | 1.00 | 30.59 | D |
| ATOM | 5012 | O   | TYR | D | 84 | 56.569 | 1.176  | 39.701 | 1.00 | 31.33 | D |
| ATOM | 5013 | N   | THR | D | 85 | 55.827 | 0.590  | 37.668 | 1.00 | 27.38 | D |
| ATOM | 5014 | CA  | THR | D | 85 | 55.394 | 1.941  | 37.338 | 1.00 | 26.45 | D |
| ATOM | 5015 | CB  | THR | D | 85 | 56.021 | 2.418  | 36.002 | 1.00 | 26.95 | D |
| ATOM | 5016 | OG1 | THR | D | 85 | 57.442 | 2.522  | 36.152 | 1.00 | 26.26 | D |
| ATOM | 5017 | CG2 | THR | D | 85 | 55.467 | 3.779  | 35.602 | 1.00 | 27.07 | D |
| ATOM | 5018 | C   | THR | D | 85 | 53.870 | 1.960  | 37.232 | 1.00 | 25.01 | D |
| ATOM | 5019 | O   | THR | D | 85 | 53.287 | 1.200  | 36.460 | 1.00 | 24.59 | D |
| ATOM | 5020 | N   | PHE | D | 86 | 53.236 | 2.801  | 38.044 | 1.00 | 23.27 | D |
| ATOM | 5021 | CA  | PHE | D | 86 | 51.780 | 2.954  | 38.046 | 1.00 | 22.39 | D |
| ATOM | 5022 | CB  | PHE | D | 86 | 51.281 | 3.562  | 39.360 | 1.00 | 22.17 | D |
| ATOM | 5023 | CG  | PHE | D | 86 | 51.218 | 2.617  | 40.523 | 1.00 | 22.40 | D |
| ATOM | 5024 | CD1 | PHE | D | 86 | 50.008 | 2.019  | 40.883 | 1.00 | 22.40 | D |
| ATOM | 5025 | CD2 | PHE | D | 86 | 52.338 | 2.391  | 41.315 | 1.00 | 22.97 | D |
| ATOM | 5026 | CE1 | PHE | D | 86 | 49.914 | 1.219  | 42.016 | 1.00 | 21.27 | D |
| ATOM | 5027 | CE2 | PHE | D | 86 | 52.251 | 1.586  | 42.458 | 1.00 | 22.88 | D |
| ATOM | 5028 | CZ  | PHE | D | 86 | 51.039 | 1.002  | 42.807 | 1.00 | 19.81 | D |
| ATOM | 5029 | C   | PHE | D | 86 | 51.416 | 3.978  | 36.978 | 1.00 | 22.46 | D |
| ATOM | 5030 | O   | PHE | D | 86 | 52.249 | 4.781  | 36.565 | 1.00 | 21.28 | D |
| ATOM | 5031 | N   | ASP | D | 87 | 50.172 | 3.952  | 36.524 | 1.00 | 22.04 | D |
| ATOM | 5032 | CA  | ASP | D | 87 | 49.750 | 4.988  | 35.606 | 1.00 | 21.98 | D |
| ATOM | 5033 | CB  | ASP | D | 87 | 48.725 | 4.484  | 34.584 | 1.00 | 21.59 | D |
| ATOM | 5034 | CG  | ASP | D | 87 | 47.484 | 3.887  | 35.216 | 1.00 | 22.83 | D |
| ATOM | 5035 | OD1 | ASP | D | 87 | 46.669 | 3.344  | 34.448 | 1.00 | 22.51 | D |
| ATOM | 5036 | OD2 | ASP | D | 87 | 47.311 | 3.952  | 36.450 | 1.00 | 23.38 | D |
| ATOM | 5037 | C   | ASP | D | 87 | 49.147 | 5.970  | 36.605 | 1.00 | 21.76 | D |
| ATOM | 5038 | O   | ASP | D | 87 | 48.969 | 5.622  | 37.779 | 1.00 | 19.11 | D |
| ATOM | 5039 | N   | THR | D | 88 | 48.855 | 7.188  | 36.166 | 1.00 | 21.68 | D |
| ATOM | 5040 | CA  | THR | D | 88 | 48.321 | 8.197  | 37.071 | 1.00 | 20.99 | D |
| ATOM | 5041 | CB  | THR | D | 88 | 48.178 | 9.540  | 36.354 | 1.00 | 20.23 | D |
| ATOM | 5042 | OG1 | THR | D | 88 | 49.469 | 9.953  | 35.898 | 1.00 | 19.37 | D |
| ATOM | 5043 | CG2 | THR | D | 88 | 47.615 | 10.602 | 37.301 | 1.00 | 20.16 | D |
| ATOM | 5044 | C   | THR | D | 88 | 47.006 | 7.848  | 37.749 | 1.00 | 20.56 | D |
| ATOM | 5045 | O   | THR | D | 88 | 46.870 | 8.022  | 38.960 | 1.00 | 20.00 | D |
| ATOM | 5046 | N   | VAL | D | 89 | 46.047 | 7.357  | 36.975 | 1.00 | 19.19 | D |
| ATOM | 5047 | CA  | VAL | D | 89 | 44.747 | 6.997  | 37.517 | 1.00 | 18.80 | D |
| ATOM | 5048 | CB  | VAL | D | 89 | 43.834 | 6.401  | 36.419 | 1.00 | 20.03 | D |
| ATOM | 5049 | CG1 | VAL | D | 89 | 42.475 | 6.044  | 37.000 | 1.00 | 19.27 | D |
| ATOM | 5050 | CG2 | VAL | D | 89 | 43.672 | 7.404  | 35.271 | 1.00 | 18.49 | D |

Figure 9 (78 of 92)

| ATOM | 5051 | C | VAL | D | 89 | 44.877 | 5.991 | 38.660 | 1.00 | 20.50 | D |
|---|---|---|---|---|---|---|---|---|---|---|---|
| ATOM | 5052 | O | VAL | D | 89 | 44.254 | 6.157 | 39.708 | 1.00 | 20.00 | D |
| ATOM | 5053 | N | SER | D | 90 | 45.689 | 4.954 | 38.467 | 1.00 | 20.29 | D |
| ATOM | 5054 | CA | SER | D | 90 | 45.866 | 3.935 | 39.506 | 1.00 | 22.02 | D |
| ATOM | 5055 | CB | SER | D | 90 | 46.708 | 2.763 | 38.988 | 1.00 | 22.81 | D |
| ATOM | 5056 | OG | SER | D | 90 | 46.026 | 2.067 | 37.962 | 1.00 | 29.14 | D |
| ATOM | 5057 | C | SER | D | 90 | 46.498 | 4.457 | 40.792 | 1.00 | 20.71 | D |
| ATOM | 5058 | O | SER | D | 90 | 46.068 | 4.096 | 41.889 | 1.00 | 20.33 | D |
| ATOM | 5059 | N | LEU | D | 91 | 47.523 | 5.291 | 40.672 | 1.00 | 20.64 | D |
| ATOM | 5060 | CA | LEU | D | 91 | 48.174 | 5.806 | 41.870 | 1.00 | 21.03 | D |
| ATOM | 5061 | CB | LEU | D | 91 | 49.461 | 6.547 | 41.515 | 1.00 | 19.97 | D |
| ATOM | 5062 | CG | LEU | D | 91 | 50.388 | 6.832 | 42.699 | 1.00 | 20.30 | D |
| ATOM | 5063 | CD1 | LEU | D | 91 | 50.732 | 5.526 | 43.422 | 1.00 | 21.97 | D |
| ATOM | 5064 | CD2 | LEU | D | 91 | 51.661 | 7.499 | 42.193 | 1.00 | 23.30 | D |
| ATOM | 5065 | C | LEU | D | 91 | 47.224 | 6.725 | 42.627 | 1.00 | 21.73 | D |
| ATOM | 5066 | O | LEU | D | 91 | 47.242 | 6.767 | 43.853 | 1.00 | 20.55 | D |
| ATOM | 5067 | N | LEU | D | 92 | 46.393 | 7.456 | 41.892 | 1.00 | 21.86 | D |
| ATOM | 5068 | CA | LEU | D | 92 | 45.414 | 8.350 | 42.508 | 1.00 | 22.58 | D |
| ATOM | 5069 | CB | LEU | D | 92 | 44.667 | 9.144 | 41.433 | 1.00 | 21.81 | D |
| ATOM | 5070 | CG | LEU | D | 92 | 45.311 | 10.433 | 40.925 | 1.00 | 21.58 | D |
| ATOM | 5071 | CD1 | LEU | D | 92 | 44.636 | 10.887 | 39.635 | 1.00 | 18.90 | D |
| ATOM | 5072 | CD2 | LEU | D | 92 | 45.188 | 11.503 | 42.001 | 1.00 | 20.98 | D |
| ATOM | 5073 | C | LEU | D | 92 | 44.401 | 7.576 | 43.356 | 1.00 | 23.35 | D |
| ATOM | 5074 | O | LEU | D | 92 | 44.136 | 7.945 | 44.495 | 1.00 | 20.73 | D |
| ATOM | 5075 | N | LYS | D | 93 | 43.830 | 6.511 | 42.793 | 1.00 | 24.06 | D |
| ATOM | 5076 | CA | LYS | D | 93 | 42.844 | 5.695 | 43.507 | 1.00 | 24.60 | D |
| ATOM | 5077 | CB | LYS | D | 93 | 42.272 | 4.624 | 42.570 | 1.00 | 27.04 | D |
| ATOM | 5078 | CG | LYS | D | 93 | 41.614 | 5.221 | 41.327 | 1.00 | 30.41 | D |
| ATOM | 5079 | CD | LYS | D | 93 | 41.259 | 4.168 | 40.286 | 1.00 | 33.84 | D |
| ATOM | 5080 | CE | LYS | D | 93 | 40.009 | 3.390 | 40.651 | 1.00 | 35.20 | D |
| ATOM | 5081 | NZ | LYS | D | 93 | 39.699 | 2.400 | 39.575 | 1.00 | 38.82 | D |
| ATOM | 5082 | C | LYS | D | 93 | 43.531 | 5.043 | 44.694 | 1.00 | 24.18 | D |
| ATOM | 5083 | O | LYS | D | 93 | 42.937 | 4.837 | 45.761 | 1.00 | 22.93 | D |
| ATOM | 5084 | N | GLN | D | 94 | 44.805 | 4.741 | 44.485 | 1.00 | 22.50 | D |
| ATOM | 5085 | CA | GLN | D | 94 | 45.656 | 4.131 | 45.485 | 1.00 | 23.51 | D |
| ATOM | 5086 | CB | GLN | D | 94 | 47.005 | 3.841 | 44.829 | 1.00 | 24.73 | D |
| ATOM | 5087 | CG | GLN | D | 94 | 47.843 | 2.774 | 45.462 | 1.00 | 26.62 | D |
| ATOM | 5088 | CD | GLN | D | 94 | 47.168 | 1.416 | 45.530 | 1.00 | 27.32 | D |
| ATOM | 5089 | OE1 | GLN | D | 94 | 46.146 | 1.169 | 44.882 | 1.00 | 25.67 | D |
| ATOM | 5090 | NE2 | GLN | D | 94 | 47.753 | 0.518 | 46.318 | 1.00 | 25.49 | D |
| ATOM | 5091 | C | GLN | D | 94 | 45.806 | 5.115 | 46.663 | 1.00 | 23.67 | D |
| ATOM | 5092 | O | GLN | D | 94 | 45.690 | 4.726 | 47.824 | 1.00 | 23.49 | D |
| ATOM | 5093 | N | ARG | D | 95 | 46.028 | 6.393 | 46.353 | 1.00 | 21.65 | D |
| ATOM | 5094 | CA | ARG | D | 95 | 46.204 | 7.414 | 47.381 | 1.00 | 22.76 | D |
| ATOM | 5095 | CB | ARG | D | 95 | 47.109 | 8.532 | 46.860 | 1.00 | 23.45 | D |
| ATOM | 5096 | CG | ARG | D | 95 | 48.516 | 8.073 | 46.526 | 1.00 | 25.53 | D |
| ATOM | 5097 | CD | ARG | D | 95 | 49.351 | 9.207 | 45.946 | 1.00 | 27.39 | D |
| ATOM | 5098 | NE | ARG | D | 95 | 50.746 | 8.824 | 45.730 | 1.00 | 28.22 | D |
| ATOM | 5099 | CZ | ARG | D | 95 | 51.652 | 9.613 | 45.160 | 1.00 | 30.52 | D |
| ATOM | 5100 | NH1 | ARG | D | 95 | 52.897 | 9.193 | 44.998 | 1.00 | 30.62 | D |
| ATOM | 5101 | NH2 | ARG | D | 95 | 51.309 | 10.828 | 44.747 | 1.00 | 30.71 | D |
| ATOM | 5102 | C | ARG | D | 95 | 44.914 | 8.029 | 47.932 | 1.00 | 23.15 | D |
| ATOM | 5103 | O | ARG | D | 95 | 44.868 | 8.437 | 49.086 | 1.00 | 22.98 | D |
| ATOM | 5104 | N | TYR | D | 96 | 43.870 | 8.096 | 47.117 | 1.00 | 23.64 | D |
| ATOM | 5105 | CA | TYR | D | 96 | 42.615 | 8.680 | 47.565 | 1.00 | 25.69 | D |
| ATOM | 5106 | CB | TYR | D | 96 | 42.443 | 10.077 | 46.950 | 1.00 | 24.68 | D |
| ATOM | 5107 | CG | TYR | D | 96 | 43.670 | 10.949 | 47.068 | 1.00 | 22.09 | D |
| ATOM | 5108 | CD1 | TYR | D | 96 | 44.617 | 10.989 | 46.045 | 1.00 | 22.96 | D |
| ATOM | 5109 | CE1 | TYR | D | 96 | 45.780 | 11.751 | 46.166 | 1.00 | 19.72 | D |
| ATOM | 5110 | CD2 | TYR | D | 96 | 43.913 | 11.701 | 48.226 | 1.00 | 22.42 | D |
| ATOM | 5111 | CE2 | TYR | D | 96 | 45.072 | 12.466 | 48.360 | 1.00 | 20.20 | D |
| ATOM | 5112 | CZ | TYR | D | 96 | 46.003 | 12.484 | 47.324 | 1.00 | 21.75 | D |
| ATOM | 5113 | OH | TYR | D | 96 | 47.165 | 13.216 | 47.443 | 1.00 | 22.37 | D |
| ATOM | 5114 | C | TYR | D | 96 | 41.440 | 7.793 | 47.168 | 1.00 | 27.29 | D |
| ATOM | 5115 | O | TYR | D | 96 | 40.568 | 8.210 | 46.408 | 1.00 | 29.09 | D |
| ATOM | 5116 | N | PRO | D | 97 | 41.388 | 6.566 | 47.703 | 1.00 | 28.52 | D |

Figure 9 (79 of 92)

| | | | | | | | | | | |
|---|---|---|---|---|---|---|---|---|---|---|
| ATOM | 5117 | CD | PRO | D | 97 | 42.235 | 6.083 | 48.811 | 1.00 27.96 | D |
| ATOM | 5118 | CA | PRO | D | 97 | 40.332 | 5.594 | 47.412 | 1.00 28.61 | D |
| ATOM | 5119 | CB | PRO | D | 97 | 40.745 | 4.388 | 48.255 | 1.00 27.81 | D |
| ATOM | 5120 | CG | PRO | D | 97 | 41.354 | 5.036 | 49.450 | 1.00 26.29 | D |
| ATOM | 5121 | C | PRO | D | 97 | 38.892 | 6.010 | 47.691 | 1.00 29.97 | D |
| ATOM | 5122 | O | PRO | D | 97 | 37.965 | 5.499 | 47.059 | 1.00 29.52 | D |
| ATOM | 5123 | N | ASN | D | 98 | 38.692 | 6.927 | 48.629 | 1.00 31.24 | D |
| ATOM | 5124 | CA | ASN | D | 98 | 37.338 | 7.344 | 48.971 | 1.00 33.33 | D |
| ATOM | 5125 | CB | ASN | D | 98 | 37.203 | 7.479 | 50.486 | 1.00 36.09 | D |
| ATOM | 5126 | CG | ASN | D | 98 | 35.780 | 7.275 | 50.962 | 1.00 39.86 | D |
| ATOM | 5127 | OD1 | ASN | D | 98 | 35.273 | 8.042 | 51.784 | 1.00 41.82 | D |
| ATOM | 5128 | ND2 | ASN | D | 98 | 35.127 | 6.228 | 50.457 | 1.00 41.88 | D |
| ATOM | 5129 | C | ASN | D | 98 | 36.861 | 8.638 | 48.315 | 1.00 33.30 | D |
| ATOM | 5130 | O | ASN | D | 98 | 35.682 | 8.983 | 48.415 | 1.00 33.63 | D |
| ATOM | 5131 | N | ASP | D | 99 | 37.759 | 9.362 | 47.656 | 1.00 32.01 | D |
| ATOM | 5132 | CA | ASP | D | 99 | 37.366 | 10.610 | 47.005 | 1.00 31.10 | D |
| ATOM | 5133 | CB | ASP | D | 99 | 38.582 | 11.514 | 46.781 | 1.00 32.72 | D |
| ATOM | 5134 | CG | ASP | D | 99 | 39.132 | 12.088 | 48.070 | 1.00 34.09 | D |
| ATOM | 5135 | OD1 | ASP | D | 99 | 38.346 | 12.658 | 48.854 | 1.00 35.05 | D |
| ATOM | 5136 | OD2 | ASP | D | 99 | 40.356 | 11.978 | 48.297 | 1.00 37.03 | D |
| ATOM | 5137 | C | ASP | D | 99 | 36.691 | 10.366 | 45.665 | 1.00 29.31 | D |
| ATOM | 5138 | O | ASP | D | 99 | 36.894 | 9.335 | 45.036 | 1.00 29.90 | D |
| ATOM | 5139 | N | GLN | D | 100 | 35.877 | 11.319 | 45.233 | 1.00 27.68 | D |
| ATOM | 5140 | CA | GLN | D | 100 | 35.215 | 11.201 | 43.944 | 1.00 26.55 | D |
| ATOM | 5141 | CB | GLN | D | 100 | 33.838 | 11.849 | 44.002 | 1.00 28.03 | D |
| ATOM | 5142 | CG | GLN | D | 100 | 32.836 | 11.034 | 44.784 | 1.00 31.31 | D |
| ATOM | 5143 | CD | GLN | D | 100 | 31.564 | 11.803 | 45.063 | 1.00 32.67 | D |
| ATOM | 5144 | OE1 | GLN | D | 100 | 31.500 | 12.608 | 45.997 | 1.00 31.04 | D |
| ATOM | 5145 | NE2 | GLN | D | 100 | 30.543 | 11.569 | 44.242 | 1.00 34.22 | D |
| ATOM | 5146 | C | GLN | D | 100 | 36.088 | 11.894 | 42.905 | 1.00 24.35 | D |
| ATOM | 5147 | O | GLN | D | 100 | 36.197 | 13.120 | 42.888 | 1.00 23.62 | D |
| ATOM | 5148 | N | LEU | D | 101 | 36.720 | 11.097 | 42.052 | 1.00 23.79 | D |
| ATOM | 5149 | CA | LEU | D | 101 | 37.602 | 11.621 | 41.015 | 1.00 23.85 | D |
| ATOM | 5150 | CB | LEU | D | 101 | 38.793 | 10.680 | 40.803 | 1.00 23.51 | D |
| ATOM | 5151 | CG | LEU | D | 101 | 39.630 | 10.320 | 42.035 | 1.00 23.72 | D |
| ATOM | 5152 | CD1 | LEU | D | 101 | 40.728 | 9.351 | 41.620 | 1.00 24.06 | D |
| ATOM | 5153 | CD2 | LEU | D | 101 | 40.228 | 11.573 | 42.654 | 1.00 22.78 | D |
| ATOM | 5154 | C | LEU | D | 101 | 36.867 | 11.800 | 39.696 | 1.00 23.13 | D |
| ATOM | 5155 | O | LEU | D | 101 | 36.338 | 10.842 | 39.136 | 1.00 23.27 | D |
| ATOM | 5156 | N | PHE | D | 102 | 36.842 | 13.036 | 39.206 | 1.00 22.58 | D |
| ATOM | 5157 | CA | PHE | D | 102 | 36.185 | 13.350 | 37.940 | 1.00 21.52 | D |
| ATOM | 5158 | CB | PHE | D | 102 | 35.254 | 14.558 | 38.092 | 1.00 20.31 | D |
| ATOM | 5159 | CG | PHE | D | 102 | 34.111 | 14.332 | 39.032 | 1.00 18.97 | D |
| ATOM | 5160 | CD1 | PHE | D | 102 | 34.325 | 14.244 | 40.407 | 1.00 18.88 | D |
| ATOM | 5161 | CD2 | PHE | D | 102 | 32.817 | 14.201 | 38.542 | 1.00 19.78 | D |
| ATOM | 5162 | CE1 | PHE | D | 102 | 33.267 | 14.030 | 41.276 | 1.00 18.78 | D |
| ATOM | 5163 | CE2 | PHE | D | 102 | 31.744 | 13.984 | 39.403 | 1.00 19.32 | D |
| ATOM | 5164 | CZ | PHE | D | 102 | 31.970 | 13.899 | 40.773 | 1.00 19.43 | D |
| ATOM | 5165 | C | PHE | D | 102 | 37.241 | 13.677 | 36.893 | 1.00 21.19 | D |
| ATOM | 5166 | O | PHE | D | 102 | 38.018 | 14.608 | 37.072 | 1.00 20.56 | D |
| ATOM | 5167 | N | PHE | D | 103 | 37.272 | 12.913 | 35.807 | 1.00 20.40 | D |
| ATOM | 5168 | CA | PHE | D | 103 | 38.237 | 13.161 | 34.741 | 1.00 20.42 | D |
| ATOM | 5169 | CB | PHE | D | 103 | 38.800 | 11.841 | 34.209 | 1.00 21.79 | D |
| ATOM | 5170 | CG | PHE | D | 103 | 39.629 | 11.096 | 35.222 | 1.00 22.74 | D |
| ATOM | 5171 | CD1 | PHE | D | 103 | 39.032 | 10.241 | 36.143 | 1.00 23.42 | D |
| ATOM | 5172 | CD2 | PHE | D | 103 | 41.004 | 11.284 | 35.283 | 1.00 24.13 | D |
| ATOM | 5173 | CE1 | PHE | D | 103 | 39.793 | 9.585 | 37.112 | 1.00 23.72 | D |
| ATOM | 5174 | CE2 | PHE | D | 103 | 41.772 | 10.633 | 36.247 | 1.00 25.17 | D |
| ATOM | 5175 | CZ | PHE | D | 103 | 41.164 | 9.782 | 37.162 | 1.00 24.10 | D |
| ATOM | 5176 | C | PHE | D | 103 | 37.560 | 13.973 | 33.646 | 1.00 19.90 | D |
| ATOM | 5177 | O | PHE | D | 103 | 36.360 | 13.846 | 33.407 | 1.00 19.44 | D |
| ATOM | 5178 | N | ILE | D | 104 | 38.339 | 14.819 | 32.986 | 1.00 19.79 | D |
| ATOM | 5179 | CA | ILE | D | 104 | 37.802 | 15.712 | 31.973 | 1.00 18.36 | D |
| ATOM | 5180 | CB | ILE | D | 104 | 38.425 | 17.105 | 32.160 | 1.00 18.01 | D |
| ATOM | 5181 | CG2 | ILE | D | 104 | 37.868 | 18.077 | 31.117 | 1.00 17.03 | D |
| ATOM | 5182 | CG1 | ILE | D | 104 | 38.164 | 17.574 | 33.603 | 1.00 14.65 | D |

Figure 9 (80 of 92)

| ATOM | 5183 | CD1 | ILE | D | 104 | 38.990 | 18.772 | 34.051 | 1.00 | 16.64 | D |
|---|---|---|---|---|---|---|---|---|---|---|---|
| ATOM | 5184 | C | ILE | D | 104 | 37.995 | 15.227 | 30.542 | 1.00 | 19.05 | D |
| ATOM | 5185 | O | ILE | D | 104 | 39.114 | 14.934 | 30.121 | 1.00 | 18.33 | D |
| ATOM | 5186 | N | ILE | D | 105 | 36.884 | 15.151 | 29.808 | 1.00 | 17.12 | D |
| ATOM | 5187 | CA | ILE | D | 105 | 36.879 | 14.690 | 28.428 | 1.00 | 17.53 | D |
| ATOM | 5188 | CB | ILE | D | 105 | 35.834 | 13.548 | 28.228 | 1.00 | 18.64 | D |
| ATOM | 5189 | CG2 | ILE | D | 105 | 35.906 | 13.012 | 26.796 | 1.00 | 17.91 | D |
| ATOM | 5190 | CG1 | ILE | D | 105 | 36.087 | 12.410 | 29.221 | 1.00 | 20.28 | D |
| ATOM | 5191 | CD1 | ILE | D | 105 | 37.439 | 11.713 | 29.053 | 1.00 | 22.00 | D |
| ATOM | 5192 | C | ILE | D | 105 | 36.535 | 15.830 | 27.456 | 1.00 | 18.09 | D |
| ATOM | 5193 | O | ILE | D | 105 | 35.522 | 16.515 | 27.610 | 1.00 | 18.46 | D |
| ATOM | 5194 | N | GLY | D | 106 | 37.383 | 16.034 | 26.459 | 1.00 | 17.93 | D |
| ATOM | 5195 | CA | GLY | D | 106 | 37.107 | 17.069 | 25.484 | 1.00 | 18.93 | D |
| ATOM | 5196 | C | GLY | D | 106 | 36.021 | 16.570 | 24.546 | 1.00 | 20.06 | D |
| ATOM | 5197 | O | GLY | D | 106 | 36.048 | 15.416 | 24.129 | 1.00 | 20.63 | D |
| ATOM | 5198 | N | ALA | D | 107 | 35.052 | 17.426 | 24.235 | 1.00 | 20.60 | D |
| ATOM | 5199 | CA | ALA | D | 107 | 33.961 | 17.074 | 23.325 | 1.00 | 20.26 | D |
| ATOM | 5200 | CB | ALA | D | 107 | 32.747 | 16.571 | 24.111 | 1.00 | 17.86 | D |
| ATOM | 5201 | C | ALA | D | 107 | 33.591 | 18.338 | 22.570 | 1.00 | 19.85 | D |
| ATOM | 5202 | O | ALA | D | 107 | 32.419 | 18.645 | 22.397 | 1.00 | 20.80 | D |
| ATOM | 5203 | N | ASP | D | 108 | 34.598 | 19.068 | 22.119 | 1.00 | 20.41 | D |
| ATOM | 5204 | CA | ASP | D | 108 | 34.356 | 20.323 | 21.435 | 1.00 | 23.48 | D |
| ATOM | 5205 | CB | ASP | D | 108 | 35.146 | 21.428 | 22.134 | 1.00 | 23.87 | D |
| ATOM | 5206 | CG | ASP | D | 108 | 34.639 | 22.813 | 21.787 | 1.00 | 26.52 | D |
| ATOM | 5207 | OD1 | ASP | D | 108 | 35.484 | 23.686 | 21.471 | 1.00 | 24.73 | D |
| ATOM | 5208 | OD2 | ASP | D | 108 | 33.398 | 23.022 | 21.833 | 1.00 | 24.33 | D |
| ATOM | 5209 | C | ASP | D | 108 | 34.684 | 20.324 | 19.942 | 1.00 | 26.07 | D |
| ATOM | 5210 | O | ASP | D | 108 | 34.519 | 21.349 | 19.273 | 1.00 | 27.00 | D |
| ATOM | 5211 | N | MET | D | 109 | 35.141 | 19.188 | 19.419 | 1.00 | 25.74 | D |
| ATOM | 5212 | CA | MET | D | 109 | 35.488 | 19.095 | 18.007 | 1.00 | 27.45 | D |
| ATOM | 5213 | CB | MET | D | 109 | 36.893 | 18.484 | 17.842 | 1.00 | 25.76 | D |
| ATOM | 5214 | CG | MET | D | 109 | 38.030 | 19.293 | 18.490 | 1.00 | 26.03 | D |
| ATOM | 5215 | SD | MET | D | 109 | 38.431 | 20.834 | 17.628 | 1.00 | 17.56 | D |
| ATOM | 5216 | CE | MET | D | 109 | 40.144 | 20.894 | 17.851 | 1.00 | 27.22 | D |
| ATOM | 5217 | C | MET | D | 109 | 34.474 | 18.254 | 17.229 | 1.00 | 28.48 | D |
| ATOM | 5218 | O | MET | D | 109 | 34.137 | 18.581 | 16.093 | 1.00 | 29.51 | D |
| ATOM | 5219 | N | ILE | D | 110 | 34.001 | 17.177 | 17.856 | 1.00 | 28.40 | D |
| ATOM | 5220 | CA | ILE | D | 110 | 33.043 | 16.247 | 17.257 | 1.00 | 29.59 | D |
| ATOM | 5221 | CB | ILE | D | 110 | 33.601 | 14.793 | 17.245 | 1.00 | 30.15 | D |
| ATOM | 5222 | CG2 | ILE | D | 110 | 32.466 | 13.783 | 17.280 | 1.00 | 31.80 | D |
| ATOM | 5223 | CG1 | ILE | D | 110 | 34.452 | 14.555 | 16.008 | 1.00 | 30.50 | D |
| ATOM | 5224 | CD1 | ILE | D | 110 | 35.024 | 13.130 | 15.963 | 1.00 | 29.16 | D |
| ATOM | 5225 | C | ILE | D | 110 | 31.710 | 16.207 | 17.994 | 1.00 | 28.73 | D |
| ATOM | 5226 | O | ILE | D | 110 | 31.646 | 16.332 | 19.214 | 1.00 | 28.45 | D |
| ATOM | 5227 | N | GLU | D | 111 | 30.657 | 15.981 | 17.221 | 1.00 | 28.09 | D |
| ATOM | 5228 | CA | GLU | D | 111 | 29.284 | 15.903 | 17.703 | 1.00 | 28.62 | D |
| ATOM | 5229 | CB | GLU | D | 111 | 28.368 | 15.799 | 16.479 | 1.00 | 30.90 | D |
| ATOM | 5230 | CG | GLU | D | 111 | 26.880 | 15.941 | 16.719 | 1.00 | 33.12 | D |
| ATOM | 5231 | CD | GLU | D | 111 | 26.079 | 15.554 | 15.479 | 1.00 | 32.55 | D |
| ATOM | 5232 | OE1 | GLU | D | 111 | 26.526 | 15.862 | 14.350 | 1.00 | 30.99 | D |
| ATOM | 5233 | OE2 | GLU | D | 111 | 25.002 | 14.946 | 15.631 | 1.00 | 34.80 | D |
| ATOM | 5234 | C | GLU | D | 111 | 29.035 | 14.707 | 18.629 | 1.00 | 28.03 | D |
| ATOM | 5235 | O | GLU | D | 111 | 28.224 | 14.781 | 19.554 | 1.00 | 29.10 | D |
| ATOM | 5236 | N | TYR | D | 112 | 29.742 | 13.611 | 18.377 | 1.00 | 26.66 | D |
| ATOM | 5237 | CA | TYR | D | 112 | 29.556 | 12.385 | 19.140 | 1.00 | 26.05 | D |
| ATOM | 5238 | CB | TYR | D | 112 | 29.204 | 11.256 | 18.166 | 1.00 | 26.84 | D |
| ATOM | 5239 | CG | TYR | D | 112 | 28.945 | 9.911 | 18.800 | 1.00 | 25.88 | D |
| ATOM | 5240 | CD1 | TYR | D | 112 | 29.909 | 8.901 | 18.763 | 1.00 | 26.82 | D |
| ATOM | 5241 | CE1 | TYR | D | 112 | 29.664 | 7.646 | 19.332 | 1.00 | 26.13 | D |
| ATOM | 5242 | CD2 | TYR | D | 112 | 27.731 | 9.639 | 19.421 | 1.00 | 25.42 | D |
| ATOM | 5243 | CE2 | TYR | D | 112 | 27.477 | 8.395 | 19.992 | 1.00 | 27.09 | D |
| ATOM | 5244 | CZ | TYR | D | 112 | 28.446 | 7.405 | 19.944 | 1.00 | 24.81 | D |
| ATOM | 5245 | OH | TYR | D | 112 | 28.191 | 6.194 | 20.528 | 1.00 | 26.76 | D |
| ATOM | 5246 | C | TYR | D | 112 | 30.743 | 11.978 | 20.006 | 1.00 | 26.48 | D |
| ATOM | 5247 | O | TYR | D | 112 | 31.901 | 12.195 | 19.653 | 1.00 | 27.74 | D |
| ATOM | 5248 | N | LEU | D | 113 | 30.434 | 11.395 | 21.157 | 1.00 | 26.04 | D |

Figure 9 (81 of 92)

| ATOM | 5249 | CA | LEU | D | 113 | 31.451 | 10.929 | 22.088 | 1.00 | 26.86 | D |
|------|------|-----|-----|---|-----|--------|--------|--------|------|-------|---|
| ATOM | 5250 | CB | LEU | D | 113 | 31.313 | 11.674 | 23.417 | 1.00 | 28.03 | D |
| ATOM | 5251 | CG | LEU | D | 113 | 32.497 | 11.710 | 24.379 | 1.00 | 26.76 | D |
| ATOM | 5252 | CD1 | LEU | D | 113 | 32.055 | 12.447 | 25.638 | 1.00 | 28.70 | D |
| ATOM | 5253 | CD2 | LEU | D | 113 | 32.958 | 10.306 | 24.721 | 1.00 | 27.77 | D |
| ATOM | 5254 | C | LEU | D | 113 | 31.191 | 9.432 | 22.281 | 1.00 | 26.61 | D |
| ATOM | 5255 | O | LEU | D | 113 | 30.165 | 9.042 | 22.840 | 1.00 | 25.80 | D |
| ATOM | 5256 | N | PRO | D | 114 | 32.121 | 8.576 | 21.814 | 1.00 | 25.92 | D |
| ATOM | 5257 | CD | PRO | D | 114 | 33.435 | 8.954 | 21.255 | 1.00 | 25.54 | D |
| ATOM | 5258 | CA | PRO | D | 114 | 32.004 | 7.116 | 21.920 | 1.00 | 25.53 | D |
| ATOM | 5259 | CB | PRO | D | 114 | 33.163 | 6.620 | 21.066 | 1.00 | 25.47 | D |
| ATOM | 5260 | CG | PRO | D | 114 | 34.223 | 7.657 | 21.356 | 1.00 | 25.25 | D |
| ATOM | 5261 | C | PRO | D | 114 | 32.076 | 6.553 | 23.336 | 1.00 | 25.30 | D |
| ATOM | 5262 | O | PRO | D | 114 | 32.616 | 7.182 | 24.247 | 1.00 | 24.01 | D |
| ATOM | 5263 | N | LYS | D | 115 | 31.519 | 5.358 | 23.502 | 1.00 | 24.75 | D |
| ATOM | 5264 | CA | LYS | D | 115 | 31.545 | 4.668 | 24.784 | 1.00 | 24.60 | D |
| ATOM | 5265 | CB | LYS | D | 115 | 30.347 | 3.717 | 24.900 | 1.00 | 24.87 | D |
| ATOM | 5266 | CG | LYS | D | 115 | 30.017 | 3.324 | 26.332 | 1.00 | 25.38 | D |
| ATOM | 5267 | CD | LYS | D | 115 | 28.688 | 2.587 | 26.446 | 1.00 | 27.77 | D |
| ATOM | 5268 | CE | LYS | D | 115 | 28.731 | 1.210 | 25.803 | 1.00 | 29.50 | D |
| ATOM | 5269 | NZ | LYS | D | 115 | 27.507 | 0.426 | 26.148 | 1.00 | 29.86 | D |
| ATOM | 5270 | C | LYS | D | 115 | 32.860 | 3.887 | 24.789 | 1.00 | 24.23 | D |
| ATOM | 5271 | O | LYS | D | 115 | 32.879 | 2.655 | 24.717 | 1.00 | 23.61 | D |
| ATOM | 5272 | N | TRP | D | 116 | 33.962 | 4.629 | 24.861 | 1.00 | 24.27 | D |
| ATOM | 5273 | CA | TRP | D | 116 | 35.301 | 4.045 | 24.851 | 1.00 | 26.40 | D |
| ATOM | 5274 | CB | TRP | D | 116 | 36.328 | 5.080 | 24.393 | 1.00 | 24.75 | D |
| ATOM | 5275 | CG | TRP | D | 116 | 36.433 | 6.257 | 25.319 | 1.00 | 24.78 | D |
| ATOM | 5276 | CD2 | TRP | D | 116 | 37.410 | 6.457 | 26.345 | 1.00 | 26.00 | D |
| ATOM | 5277 | CE2 | TRP | D | 116 | 37.123 | 7.695 | 26.960 | 1.00 | 25.88 | D |
| ATOM | 5278 | CE3 | TRP | D | 116 | 38.503 | 5.712 | 26.804 | 1.00 | 25.58 | D |
| ATOM | 5279 | CD1 | TRP | D | 116 | 35.613 | 7.349 | 25.355 | 1.00 | 25.49 | D |
| ATOM | 5280 | NE1 | TRP | D | 116 | 36.021 | 8.218 | 26.337 | 1.00 | 25.38 | D |
| ATOM | 5281 | CZ2 | TRP | D | 116 | 37.891 | 8.206 | 28.012 | 1.00 | 26.80 | D |
| ATOM | 5282 | CZ3 | TRP | D | 116 | 39.265 | 6.222 | 27.851 | 1.00 | 27.02 | D |
| ATOM | 5283 | CH2 | TRP | D | 116 | 38.954 | 7.456 | 28.441 | 1.00 | 23.68 | D |
| ATOM | 5284 | C | TRP | D | 116 | 35.773 | 3.477 | 26.184 | 1.00 | 27.02 | D |
| ATOM | 5285 | O | TRP | D | 116 | 36.744 | 2.735 | 26.219 | 1.00 | 26.37 | D |
| ATOM | 5286 | N | TYR | D | 117 | 35.108 | 3.832 | 27.277 | 1.00 | 29.43 | D |
| ATOM | 5287 | CA | TYR | D | 117 | 35.526 | 3.336 | 28.585 | 1.00 | 34.01 | D |
| ATOM | 5288 | CB | TYR | D | 117 | 36.047 | 4.485 | 29.462 | 1.00 | 36.86 | D |
| ATOM | 5289 | CG | TYR | D | 117 | 36.493 | 4.030 | 30.839 | 1.00 | 39.95 | D |
| ATOM | 5290 | CD1 | TYR | D | 117 | 37.594 | 3.189 | 30.990 | 1.00 | 41.26 | D |
| ATOM | 5291 | CE1 | TYR | D | 117 | 37.989 | 2.731 | 32.244 | 1.00 | 43.05 | D |
| ATOM | 5292 | CD2 | TYR | D | 117 | 35.793 | 4.407 | 31.989 | 1.00 | 42.27 | D |
| ATOM | 5293 | CE2 | TYR | D | 117 | 36.182 | 3.953 | 33.258 | 1.00 | 41.93 | D |
| ATOM | 5294 | CZ | TYR | D | 117 | 37.282 | 3.115 | 33.374 | 1.00 | 43.82 | D |
| ATOM | 5295 | OH | TYR | D | 117 | 37.687 | 2.658 | 34.610 | 1.00 | 44.89 | D |
| ATOM | 5296 | C | TYR | D | 117 | 34.427 | 2.619 | 29.340 | 1.00 | 35.09 | D |
| ATOM | 5297 | O | TYR | D | 117 | 33.292 | 3.088 | 29.392 | 1.00 | 35.79 | D |
| ATOM | 5298 | N | LYS | D | 118 | 34.773 | 1.485 | 29.935 | 1.00 | 37.80 | D |
| ATOM | 5299 | CA | LYS | D | 118 | 33.814 | 0.720 | 30.714 | 1.00 | 42.41 | D |
| ATOM | 5300 | CB | LYS | D | 118 | 34.174 | -0.772 | 30.688 | 1.00 | 43.56 | D |
| ATOM | 5301 | CG | LYS | D | 118 | 34.061 | -1.392 | 29.294 | 1.00 | 45.14 | D |
| ATOM | 5302 | CD | LYS | D | 118 | 34.443 | -2.869 | 29.277 | 1.00 | 45.94 | D |
| ATOM | 5303 | CE | LYS | D | 118 | 34.368 | -3.439 | 27.866 | 1.00 | 45.97 | D |
| ATOM | 5304 | NZ | LYS | D | 118 | 34.844 | -4.848 | 27.801 | 1.00 | 47.71 | D |
| ATOM | 5305 | C | LYS | D | 118 | 33.829 | 1.250 | 32.144 | 1.00 | 44.69 | D |
| ATOM | 5306 | O | LYS | D | 118 | 34.674 | 0.862 | 32.953 | 1.00 | 45.34 | D |
| ATOM | 5307 | N | LEU | D | 119 | 32.900 | 2.156 | 32.442 | 1.00 | 46.71 | D |
| ATOM | 5308 | CA | LEU | D | 119 | 32.807 | 2.754 | 33.768 | 1.00 | 47.85 | D |
| ATOM | 5309 | CB | LEU | D | 119 | 32.719 | 4.281 | 33.655 | 1.00 | 49.22 | D |
| ATOM | 5310 | CG | LEU | D | 119 | 31.392 | 4.921 | 33.228 | 1.00 | 49.72 | D |
| ATOM | 5311 | CD1 | LEU | D | 119 | 30.464 | 5.008 | 34.438 | 1.00 | 50.48 | D |
| ATOM | 5312 | CD2 | LEU | D | 119 | 31.642 | 6.320 | 32.671 | 1.00 | 49.85 | D |
| ATOM | 5313 | C | LEU | D | 119 | 31.585 | 2.220 | 34.502 | 1.00 | 49.17 | D |
| ATOM | 5314 | O | LEU | D | 119 | 30.634 | 1.756 | 33.874 | 1.00 | 49.78 | D |

Figure 9 (82 of 92)

| ATOM | 5315 | N | LEU | D | 125 | 33.328 | 5.703 | 41.877 | 1.00 | 43.25 | D |
|---|---|---|---|---|---|---|---|---|---|---|---|
| ATOM | 5316 | CA | LEU | D | 125 | 34.480 | 6.498 | 42.279 | 1.00 | 42.68 | D |
| ATOM | 5317 | CB | LEU | D | 125 | 35.550 | 5.619 | 42.936 | 1.00 | 42.82 | D |
| ATOM | 5318 | CG | LEU | D | 125 | 35.329 | 5.193 | 44.396 | 1.00 | 43.81 | D |
| ATOM | 5319 | CD1 | LEU | D | 125 | 34.705 | 6.349 | 45.180 | 1.00 | 44.28 | D |
| ATOM | 5320 | CD2 | LEU | D | 125 | 34.426 | 3.975 | 44.458 | 1.00 | 43.72 | D |
| ATOM | 5321 | C | LEU | D | 125 | 35.105 | 7.274 | 41.123 | 1.00 | 41.90 | D |
| ATOM | 5322 | O | LEU | D | 125 | 35.674 | 8.351 | 41.327 | 1.00 | 42.73 | D |
| ATOM | 5323 | N | ILE | D | 126 | 35.025 | 6.720 | 39.918 | 1.00 | 39.49 | D |
| ATOM | 5324 | CA | ILE | D | 126 | 35.570 | 7.402 | 38.755 | 1.00 | 38.20 | D |
| ATOM | 5325 | CB | ILE | D | 126 | 36.495 | 6.500 | 37.916 | 1.00 | 38.78 | D |
| ATOM | 5326 | CG2 | ILE | D | 126 | 36.730 | 7.136 | 36.549 | 1.00 | 38.37 | D |
| ATOM | 5327 | CG1 | ILE | D | 126 | 37.830 | 6.303 | 38.634 | 1.00 | 39.26 | D |
| ATOM | 5328 | CD1 | ILE | D | 126 | 38.824 | 5.483 | 37.841 | 1.00 | 41.02 | D |
| ATOM | 5329 | C | ILE | D | 126 | 34.440 | 7.874 | 37.869 | 1.00 | 36.14 | D |
| ATOM | 5330 | O | ILE | D | 126 | 33.573 | 7.095 | 37.472 | 1.00 | 35.90 | D |
| ATOM | 5331 | N | GLN | D | 127 | 34.457 | 9.163 | 37.569 | 1.00 | 33.44 | D |
| ATOM | 5332 | CA | GLN | D | 127 | 33.442 | 9.753 | 36.728 | 1.00 | 31.34 | D |
| ATOM | 5333 | CB | GLN | D | 127 | 32.426 | 10.513 | 37.579 | 1.00 | 32.09 | D |
| ATOM | 5334 | CG | GLN | D | 127 | 31.560 | 9.594 | 38.431 | 1.00 | 34.96 | D |
| ATOM | 5335 | CD | GLN | D | 127 | 30.527 | 10.342 | 39.236 | 1.00 | 37.18 | D |
| ATOM | 5336 | OE1 | GLN | D | 127 | 30.838 | 10.952 | 40.265 | 1.00 | 38.99 | D |
| ATOM | 5337 | NE2 | GLN | D | 127 | 29.283 | 10.310 | 38.768 | 1.00 | 38.68 | D |
| ATOM | 5338 | C | GLN | D | 127 | 34.111 | 10.675 | 35.731 | 1.00 | 30.05 | D |
| ATOM | 5339 | O | GLN | D | 127 | 35.300 | 10.985 | 35.847 | 1.00 | 26.97 | D |
| ATOM | 5340 | N | PHE | D | 128 | 33.343 | 11.099 | 34.739 | 1.00 | 28.60 | D |
| ATOM | 5341 | CA | PHE | D | 128 | 33.863 | 11.967 | 33.708 | 1.00 | 27.82 | D |
| ATOM | 5342 | CB | PHE | D | 128 | 33.905 | 11.212 | 32.381 | 1.00 | 29.66 | D |
| ATOM | 5343 | CG | PHE | D | 128 | 34.836 | 10.033 | 32.393 | 1.00 | 33.00 | D |
| ATOM | 5344 | CD1 | PHE | D | 128 | 36.214 | 10.216 | 32.307 | 1.00 | 33.89 | D |
| ATOM | 5345 | CD2 | PHE | D | 128 | 34.339 | 8.740 | 32.524 | 1.00 | 34.41 | D |
| ATOM | 5346 | CE1 | PHE | D | 128 | 37.086 | 9.128 | 32.352 | 1.00 | 34.37 | D |
| ATOM | 5347 | CE2 | PHE | D | 128 | 35.203 | 7.643 | 32.571 | 1.00 | 35.70 | D |
| ATOM | 5348 | CZ | PHE | D | 128 | 36.581 | 7.840 | 32.484 | 1.00 | 35.81 | D |
| ATOM | 5349 | C | PHE | D | 128 | 32.999 | 13.196 | 33.582 | 1.00 | 26.38 | D |
| ATOM | 5350 | O | PHE | D | 128 | 31.841 | 13.191 | 33.997 | 1.00 | 26.39 | D |
| ATOM | 5351 | N | ILE | D | 129 | 33.584 | 14.251 | 33.025 | 1.00 | 24.79 | D |
| ATOM | 5352 | CA | ILE | D | 129 | 32.898 | 15.513 | 32.794 | 1.00 | 23.06 | D |
| ATOM | 5353 | CB | ILE | D | 129 | 33.319 | 16.593 | 33.811 | 1.00 | 23.13 | D |
| ATOM | 5354 | CG2 | ILE | D | 129 | 32.709 | 17.937 | 33.422 | 1.00 | 23.23 | D |
| ATOM | 5355 | CG1 | ILE | D | 129 | 32.872 | 16.191 | 35.216 | 1.00 | 23.37 | D |
| ATOM | 5356 | CD1 | ILE | D | 129 | 33.323 | 17.146 | 36.295 | 1.00 | 26.20 | D |
| ATOM | 5357 | C | ILE | D | 129 | 33.322 | 15.968 | 31.414 | 1.00 | 22.37 | D |
| ATOM | 5358 | O | ILE | D | 129 | 34.513 | 15.990 | 31.102 | 1.00 | 23.39 | D |
| ATOM | 5359 | N | GLY | D | 130 | 32.358 | 16.313 | 30.573 | 1.00 | 21.17 | D |
| ATOM | 5360 | CA | GLY | D | 130 | 32.708 | 16.770 | 29.244 | 1.00 | 18.62 | D |
| ATOM | 5361 | C | GLY | D | 130 | 32.822 | 18.283 | 29.182 | 1.00 | 19.12 | D |
| ATOM | 5362 | O | GLY | D | 130 | 32.119 | 18.988 | 29.904 | 1.00 | 16.74 | D |
| ATOM | 5363 | N | VAL | D | 131 | 33.730 | 18.787 | 28.350 | 1.00 | 17.73 | D |
| ATOM | 5364 | CA | VAL | D | 131 | 33.872 | 20.226 | 28.186 | 1.00 | 18.27 | D |
| ATOM | 5365 | CB | VAL | D | 131 | 35.275 | 20.744 | 28.604 | 1.00 | 17.55 | D |
| ATOM | 5366 | CG1 | VAL | D | 131 | 35.382 | 20.766 | 30.113 | 1.00 | 17.92 | D |
| ATOM | 5367 | CG2 | VAL | D | 131 | 36.367 | 19.879 | 28.007 | 1.00 | 16.03 | D |
| ATOM | 5368 | C | VAL | D | 131 | 33.629 | 20.553 | 26.720 | 1.00 | 19.30 | D |
| ATOM | 5369 | O | VAL | D | 131 | 34.188 | 19.917 | 25.827 | 1.00 | 18.29 | D |
| ATOM | 5370 | N | LYS | D | 132 | 32.775 | 21.538 | 26.479 | 1.00 | 20.49 | D |
| ATOM | 5371 | CA | LYS | D | 132 | 32.444 | 21.948 | 25.122 | 1.00 | 20.26 | D |
| ATOM | 5372 | CB | LYS | D | 132 | 31.323 | 21.060 | 24.565 | 1.00 | 22.01 | D |
| ATOM | 5373 | CG | LYS | D | 132 | 30.015 | 21.154 | 25.358 | 1.00 | 21.63 | D |
| ATOM | 5374 | CD | LYS | D | 132 | 28.922 | 20.273 | 24.770 | 1.00 | 23.78 | D |
| ATOM | 5375 | CE | LYS | D | 132 | 27.596 | 20.458 | 25.510 | 1.00 | 22.93 | D |
| ATOM | 5376 | NZ | LYS | D | 132 | 27.075 | 21.859 | 25.362 | 1.00 | 23.04 | D |
| ATOM | 5377 | C | LYS | D | 132 | 31.978 | 23.392 | 25.160 | 1.00 | 19.29 | D |
| ATOM | 5378 | O | LYS | D | 132 | 31.632 | 23.902 | 26.218 | 1.00 | 19.33 | D |
| ATOM | 5379 | N | ARG | D | 133 | 31.977 | 24.052 | 24.006 | 1.00 | 20.62 | D |
| ATOM | 5380 | CA | ARG | D | 133 | 31.521 | 25.435 | 23.934 | 1.00 | 21.36 | D |

Figure 9 (83 of 92)

| ATOM | 5381 | CB | ARG | D | 133 | 31.745 | 26.010 | 22.541 | 1.00 | 21.62 | D |
|---|---|---|---|---|---|---|---|---|---|---|---|
| ATOM | 5382 | CG | ARG | D | 133 | 33.172 | 26.314 | 22.178 | 1.00 | 25.49 | D |
| ATOM | 5383 | CD | ARG | D | 133 | 33.284 | 26.337 | 20.670 | 1.00 | 26.05 | D |
| ATOM | 5384 | NE | ARG | D | 133 | 32.991 | 25.009 | 20.141 | 1.00 | 29.83 | D |
| ATOM | 5385 | CZ | ARG | D | 133 | 32.732 | 24.740 | 18.868 | 1.00 | 30.91 | D |
| ATOM | 5386 | NH1 | ARG | D | 133 | 32.717 | 25.712 | 17.967 | 1.00 | 33.59 | D |
| ATOM | 5387 | NH2 | ARG | D | 133 | 32.509 | 23.490 | 18.496 | 1.00 | 31.29 | D |
| ATOM | 5388 | C | ARG | D | 133 | 30.027 | 25.464 | 24.201 | 1.00 | 21.72 | D |
| ATOM | 5389 | O | ARG | D | 133 | 29.318 | 24.493 | 23.919 | 1.00 | 21.03 | D |
| ATOM | 5390 | N | PRO | D | 134 | 29.524 | 26.572 | 24.760 | 1.00 | 21.78 | D |
| ATOM | 5391 | CD | PRO | D | 134 | 30.210 | 27.755 | 25.304 | 1.00 | 21.96 | D |
| ATOM | 5392 | CA | PRO | D | 134 | 28.085 | 26.634 | 25.013 | 1.00 | 23.87 | D |
| ATOM | 5393 | CB | PRO | D | 134 | 27.919 | 27.963 | 25.757 | 1.00 | 23.12 | D |
| ATOM | 5394 | CG | PRO | D | 134 | 29.103 | 28.765 | 25.329 | 1.00 | 22.85 | D |
| ATOM | 5395 | C | PRO | D | 134 | 27.358 | 26.605 | 23.666 | 1.00 | 25.81 | D |
| ATOM | 5396 | O | PRO | D | 134 | 27.782 | 27.261 | 22.712 | 1.00 | 27.15 | D |
| ATOM | 5397 | N | GLY | D | 135 | 26.284 | 25.831 | 23.578 | 1.00 | 27.23 | D |
| ATOM | 5398 | CA | GLY | D | 135 | 25.553 | 25.753 | 22.326 | 1.00 | 30.39 | D |
| ATOM | 5399 | C | GLY | D | 135 | 25.979 | 24.574 | 21.468 | 1.00 | 32.23 | D |
| ATOM | 5400 | O | GLY | D | 135 | 25.191 | 24.071 | 20.668 | 1.00 | 32.49 | D |
| ATOM | 5401 | N | PHE | D | 136 | 27.227 | 24.137 | 21.617 | 1.00 | 32.00 | D |
| ATOM | 5402 | CA | PHE | D | 136 | 27.711 | 22.996 | 20.848 | 1.00 | 32.35 | D |
| ATOM | 5403 | CB | PHE | D | 136 | 29.230 | 22.818 | 21.024 | 1.00 | 32.32 | D |
| ATOM | 5404 | CG | PHE | D | 136 | 29.846 | 21.836 | 20.055 | 1.00 | 31.57 | D |
| ATOM | 5405 | CD1 | PHE | D | 136 | 29.889 | 22.115 | 18.693 | 1.00 | 31.14 | D |
| ATOM | 5406 | CD2 | PHE | D | 136 | 30.365 | 20.622 | 20.506 | 1.00 | 31.61 | D |
| ATOM | 5407 | CE1 | PHE | D | 136 | 30.440 | 21.198 | 17.792 | 1.00 | 32.02 | D |
| ATOM | 5408 | CE2 | PHE | D | 136 | 30.919 | 19.697 | 19.613 | 1.00 | 31.74 | D |
| ATOM | 5409 | CZ | PHE | D | 136 | 30.956 | 19.984 | 18.255 | 1.00 | 31.06 | D |
| ATOM | 5410 | C | PHE | D | 136 | 26.971 | 21.776 | 21.387 | 1.00 | 32.33 | D |
| ATOM | 5411 | O | PHE | D | 136 | 27.079 | 21.443 | 22.570 | 1.00 | 32.90 | D |
| ATOM | 5412 | N | HIS | D | 137 | 26.206 | 21.124 | 20.522 | 1.00 | 31.26 | D |
| ATOM | 5413 | CA | HIS | D | 137 | 25.435 | 19.955 | 20.920 | 1.00 | 33.17 | D |
| ATOM | 5414 | CB | HIS | D | 137 | 24.164 | 19.873 | 20.074 | 1.00 | 35.48 | D |
| ATOM | 5415 | CG | HIS | D | 137 | 23.231 | 21.025 | 20.287 | 1.00 | 38.54 | D |
| ATOM | 5416 | CD2 | HIS | D | 137 | 22.951 | 22.101 | 19.513 | 1.00 | 38.87 | D |
| ATOM | 5417 | ND1 | HIS | D | 137 | 22.482 | 21.174 | 21.435 | 1.00 | 39.90 | D |
| ATOM | 5418 | CE1 | HIS | D | 137 | 21.780 | 22.291 | 21.359 | 1.00 | 40.66 | D |
| ATOM | 5419 | NE2 | HIS | D | 137 | 22.046 | 22.872 | 20.203 | 1.00 | 39.86 | D |
| ATOM | 5420 | C | HIS | D | 137 | 26.251 | 18.675 | 20.793 | 1.00 | 32.17 | D |
| ATOM | 5421 | O | HIS | D | 137 | 26.865 | 18.411 | 19.759 | 1.00 | 33.21 | D |
| ATOM | 5422 | N | VAL | D | 138 | 26.257 | 17.885 | 21.857 | 1.00 | 30.59 | D |
| ATOM | 5423 | CA | VAL | D | 138 | 27.008 | 16.635 | 21.881 | 1.00 | 31.37 | D |
| ATOM | 5424 | CB | VAL | D | 138 | 28.165 | 16.701 | 22.912 | 1.00 | 29.84 | D |
| ATOM | 5425 | CG1 | VAL | D | 138 | 28.846 | 15.341 | 23.031 | 1.00 | 30.96 | D |
| ATOM | 5426 | CG2 | VAL | D | 138 | 29.163 | 17.760 | 22.500 | 1.00 | 30.00 | D |
| ATOM | 5427 | C | VAL | D | 138 | 26.097 | 15.482 | 22.269 | 1.00 | 31.88 | D |
| ATOM | 5428 | O | VAL | D | 138 | 25.325 | 15.593 | 23.217 | 1.00 | 32.54 | D |
| ATOM | 5429 | N | GLU | D | 139 | 26.177 | 14.379 | 21.534 | 1.00 | 31.79 | D |
| ATOM | 5430 | CA | GLU | D | 139 | 25.367 | 13.214 | 21.862 | 1.00 | 33.02 | D |
| ATOM | 5431 | CB | GLU | D | 139 | 24.547 | 12.749 | 20.663 | 1.00 | 34.51 | D |
| ATOM | 5432 | CG | GLU | D | 139 | 23.442 | 13.700 | 20.252 | 1.00 | 35.31 | D |
| ATOM | 5433 | CD | GLU | D | 139 | 22.478 | 13.058 | 19.281 | 1.00 | 35.79 | D |
| ATOM | 5434 | OE1 | GLU | D | 139 | 21.389 | 12.633 | 19.721 | 1.00 | 37.70 | D |
| ATOM | 5435 | OE2 | GLU | D | 139 | 22.818 | 12.965 | 18.086 | 1.00 | 35.82 | D |
| ATOM | 5436 | C | GLU | D | 139 | 26.293 | 12.098 | 22.299 | 1.00 | 32.69 | D |
| ATOM | 5437 | O | GLU | D | 139 | 27.371 | 11.920 | 21.737 | 1.00 | 31.90 | D |
| ATOM | 5438 | N | THR | D | 140 | 25.876 | 11.350 | 23.307 | 1.00 | 32.32 | D |
| ATOM | 5439 | CA | THR | D | 140 | 26.701 | 10.263 | 23.794 | 1.00 | 34.32 | D |
| ATOM | 5440 | CB | THR | D | 140 | 27.821 | 10.800 | 24.712 | 1.00 | 34.71 | D |
| ATOM | 5441 | OG1 | THR | D | 140 | 28.590 | 9.707 | 25.231 | 1.00 | 35.44 | D |
| ATOM | 5442 | CG2 | THR | D | 140 | 27.225 | 11.602 | 25.858 | 1.00 | 34.02 | D |
| ATOM | 5443 | C | THR | D | 140 | 25.869 | 9.247 | 24.560 | 1.00 | 35.12 | D |
| ATOM | 5444 | O | THR | D | 140 | 24.894 | 9.603 | 25.224 | 1.00 | 33.69 | D |
| ATOM | 5445 | N | PRO | D | 141 | 26.233 | 7.958 | 24.456 | 1.00 | 36.70 | D |
| ATOM | 5446 | CD | PRO | D | 141 | 27.296 | 7.371 | 23.617 | 1.00 | 36.29 | D |

Figure 9 (84 of 92)

```
ATOM   5447  CA   PRO D 141      25.484    6.920   25.172  1.00 36.90           D
ATOM   5448  CB   PRO D 141      26.059    5.624   24.600  1.00 36.97           D
ATOM   5449  CG   PRO D 141      27.473    6.005   24.233  1.00 37.40           D
ATOM   5450  C    PRO D 141      25.710    7.072   26.678  1.00 37.93           D
ATOM   5451  O    PRO D 141      24.988    6.496   27.490  1.00 37.70           D
ATOM   5452  N    TYR D 142      26.714    7.874   27.029  1.00 38.93           D
ATOM   5453  CA   TYR D 142      27.073    8.154   28.424  1.00 39.87           D
ATOM   5454  CB   TYR D 142      28.484    8.754   28.505  1.00 39.32           D
ATOM   5455  CG   TYR D 142      29.635    7.805   28.284  1.00 39.10           D
ATOM   5456  CD1  TYR D 142      30.680    8.146   27.421  1.00 39.20           D
ATOM   5457  CE1  TYR D 142      31.792    7.317   27.270  1.00 40.26           D
ATOM   5458  CD2  TYR D 142      29.726    6.603   28.989  1.00 38.86           D
ATOM   5459  CE2  TYR D 142      30.835    5.764   28.847  1.00 40.04           D
ATOM   5460  CZ   TYR D 142      31.864    6.130   27.987  1.00 39.96           D
ATOM   5461  OH   TYR D 142      32.971    5.326   27.859  1.00 41.19           D
ATOM   5462  C    TYR D 142      26.127    9.165   29.075  1.00 40.69           D
ATOM   5463  O    TYR D 142      25.745   10.158   28.452  1.00 40.13           D
ATOM   5464  N    PRO D 143      25.721    8.911   30.330  1.00 41.07           D
ATOM   5465  CD   PRO D 143      25.698    7.581   30.958  1.00 42.60           D
ATOM   5466  CA   PRO D 143      24.829    9.834   31.047  1.00 41.07           D
ATOM   5467  CB   PRO D 143      24.189    8.946   32.113  1.00 41.68           D
ATOM   5468  CG   PRO D 143      24.313    7.552   31.543  1.00 42.67           D
ATOM   5469  C    PRO D 143      25.791   10.855   31.660  1.00 40.60           D
ATOM   5470  O    PRO D 143      25.917   10.958   32.877  1.00 42.32           D
ATOM   5471  N    LEU D 144      26.460   11.602   30.788  1.00 39.14           D
ATOM   5472  CA   LEU D 144      27.488   12.570   31.170  1.00 38.21           D
ATOM   5473  CB   LEU D 144      28.602   12.503   30.117  1.00 38.54           D
ATOM   5474  CG   LEU D 144      29.849   13.373   30.241  1.00 39.30           D
ATOM   5475  CD1  LEU D 144      30.592   13.000   31.504  1.00 39.71           D
ATOM   5476  CD2  LEU D 144      30.733   13.164   29.021  1.00 37.48           D
ATOM   5477  C    LEU D 144      27.114   14.036   31.399  1.00 36.28           D
ATOM   5478  O    LEU D 144      26.309   14.616   30.671  1.00 35.97           D
ATOM   5479  N    LEU D 145      27.725   14.634   32.418  1.00 35.67           D
ATOM   5480  CA   LEU D 145      27.509   16.045   32.716  1.00 34.75           D
ATOM   5481  CB   LEU D 145      27.728   16.335   34.207  1.00 37.74           D
ATOM   5482  CG   LEU D 145      27.729   17.818   34.617  1.00 41.60           D
ATOM   5483  CD1  LEU D 145      26.417   18.468   34.205  1.00 42.14           D
ATOM   5484  CD2  LEU D 145      27.931   17.948   36.126  1.00 41.84           D
ATOM   5485  C    LEU D 145      28.529   16.829   31.889  1.00 32.80           D
ATOM   5486  O    LEU D 145      29.708   16.461   31.823  1.00 31.18           D
ATOM   5487  N    PHE D 146      28.073   17.896   31.244  1.00 29.40           D
ATOM   5488  CA   PHE D 146      28.961   18.716   30.436  1.00 28.36           D
ATOM   5489  CB   PHE D 146      28.431   18.864   29.001  1.00 28.05           D
ATOM   5490  CG   PHE D 146      28.500   17.599   28.179  1.00 28.43           D
ATOM   5491  CD1  PHE D 146      27.471   16.662   28.225  1.00 29.01           D
ATOM   5492  CD2  PHE D 146      29.589   17.355   27.345  1.00 29.02           D
ATOM   5493  CE1  PHE D 146      27.521   15.500   27.446  1.00 29.51           D
ATOM   5494  CE2  PHE D 146      29.651   16.194   26.562  1.00 30.48           D
ATOM   5495  CZ   PHE D 146      28.613   15.267   26.613  1.00 29.40           D
ATOM   5496  C    PHE D 146      29.127   20.106   31.041  1.00 27.84           D
ATOM   5497  O    PHE D 146      28.224   20.633   31.691  1.00 27.83           D
ATOM   5498  N    ALA D 147      30.304   20.684   30.848  1.00 24.92           D
ATOM   5499  CA   ALA D 147      30.569   22.027   31.330  1.00 23.33           D
ATOM   5500  CB   ALA D 147      31.880   22.070   32.103  1.00 23.47           D
ATOM   5501  C    ALA D 147      30.674   22.863   30.061  1.00 22.39           D
ATOM   5502  O    ALA D 147      31.390   22.492   29.122  1.00 21.09           D
ATOM   5503  N    ASP D 148      29.928   23.960   30.011  1.00 19.44           D
ATOM   5504  CA   ASP D 148      29.965   24.847   28.857  1.00 19.51           D
ATOM   5505  CB   ASP D 148      28.611   25.534   28.674  1.00 22.42           D
ATOM   5506  CG   ASP D 148      27.600   24.648   27.967  1.00 25.23           D
ATOM   5507  OD1  ASP D 148      26.396   24.962   28.028  1.00 28.57           D
ATOM   5508  OD2  ASP D 148      28.010   23.648   27.337  1.00 26.69           D
ATOM   5509  C    ASP D 148      31.054   25.887   29.075  1.00 18.38           D
ATOM   5510  O    ASP D 148      30.837   26.895   29.747  1.00 18.08           D
ATOM   5511  N    VAL D 149      32.226   25.627   28.505  1.00 18.15           D
ATOM   5512  CA   VAL D 149      33.381   26.506   28.631  1.00 16.11           D
```

Figure 9 (85 of 92)

```
ATOM   5513  CB   VAL D 149      34.673  25.676  28.722  1.00 16.26           D
ATOM   5514  CG1  VAL D 149      35.876  26.586  28.922  1.00 15.97           D
ATOM   5515  CG2  VAL D 149      34.556  24.677  29.877  1.00 16.19           D
ATOM   5516  C    VAL D 149      33.478  27.443  27.432  1.00 18.01           D
ATOM   5517  O    VAL D 149      33.550  26.993  26.290  1.00 17.95           D
ATOM   5518  N    PRO D 150      33.471  28.766  27.677  1.00 18.46           D
ATOM   5519  CD   PRO D 150      33.462  29.476  28.970  1.00 17.02           D
ATOM   5520  CA   PRO D 150      33.565  29.711  26.559  1.00 17.65           D
ATOM   5521  CB   PRO D 150      33.653  31.070  27.254  1.00 18.59           D
ATOM   5522  CG   PRO D 150      32.943  30.848  28.562  1.00 18.16           D
ATOM   5523  C    PRO D 150      34.818  29.413  25.747  1.00 20.05           D
ATOM   5524  O    PRO D 150      35.854  29.054  26.306  1.00 18.99           D
ATOM   5525  N    GLU D 151      34.731  29.554  24.432  1.00 20.59           D
ATOM   5526  CA   GLU D 151      35.887  29.300  23.591  1.00 22.29           D
ATOM   5527  CB   GLU D 151      35.489  29.374  22.113  1.00 24.30           D
ATOM   5528  CG   GLU D 151      36.676  29.362  21.161  1.00 28.62           D
ATOM   5529  CD   GLU D 151      37.418  28.035  21.159  1.00 30.76           D
ATOM   5530  OE1  GLU D 151      37.097  27.176  20.308  1.00 33.77           D
ATOM   5531  OE2  GLU D 151      38.309  27.843  22.015  1.00 31.33           D
ATOM   5532  C    GLU D 151      36.997  30.318  23.880  1.00 21.09           D
ATOM   5533  O    GLU D 151      36.722  31.496  24.093  1.00 20.78           D
ATOM   5534  N    PHE D 152      38.240  29.842  23.899  1.00 19.60           D
ATOM   5535  CA   PHE D 152      39.423  30.679  24.122  1.00 19.00           D
ATOM   5536  CB   PHE D 152      39.826  30.694  25.609  1.00 19.08           D
ATOM   5537  CG   PHE D 152      40.759  31.833  25.988  1.00 18.76           D
ATOM   5538  CD1  PHE D 152      41.033  32.108  27.328  1.00 20.11           D
ATOM   5539  CD2  PHE D 152      41.331  32.650  25.012  1.00 19.11           D
ATOM   5540  CE1  PHE D 152      41.857  33.182  27.691  1.00 20.22           D
ATOM   5541  CE2  PHE D 152      42.158  33.731  25.358  1.00 18.87           D
ATOM   5542  CZ   PHE D 152      42.422  33.998  26.698  1.00 18.72           D
ATOM   5543  C    PHE D 152      40.501  29.998  23.282  1.00 18.43           D
ATOM   5544  O    PHE D 152      41.078  28.990  23.686  1.00 17.74           D
ATOM   5545  N    GLU D 153      40.745  30.555  22.105  1.00 18.35           D
ATOM   5546  CA   GLU D 153      41.698  30.017  21.145  1.00 20.51           D
ATOM   5547  CB   GLU D 153      41.398  30.631  19.779  1.00 22.73           D
ATOM   5548  CG   GLU D 153      42.025  29.935  18.596  1.00 30.20           D
ATOM   5549  CD   GLU D 153      41.834  30.729  17.308  1.00 33.16           D
ATOM   5550  OE1  GLU D 153      40.740  31.315  17.116  1.00 32.91           D
ATOM   5551  OE2  GLU D 153      42.776  30.757  16.486  1.00 35.93           D
ATOM   5552  C    GLU D 153      43.147  30.287  21.531  1.00 20.10           D
ATOM   5553  O    GLU D 153      43.857  31.017  20.837  1.00 20.58           D
ATOM   5554  N    VAL D 154      43.583  29.707  22.644  1.00 21.09           D
ATOM   5555  CA   VAL D 154      44.955  29.893  23.120  1.00 21.04           D
ATOM   5556  CB   VAL D 154      44.988  30.876  24.325  1.00 20.85           D
ATOM   5557  CG1  VAL D 154      44.197  30.294  25.496  1.00 17.15           D
ATOM   5558  CG2  VAL D 154      46.440  31.168  24.739  1.00 20.39           D
ATOM   5559  C    VAL D 154      45.526  28.535  23.542  1.00 21.08           D
ATOM   5560  O    VAL D 154      44.835  27.733  24.162  1.00 21.09           D
ATOM   5561  N    SER D 155      46.779  28.270  23.186  1.00 22.27           D
ATOM   5562  CA   SER D 155      47.415  27.000  23.550  1.00 21.48           D
ATOM   5563  CB   SER D 155      47.351  26.014  22.381  1.00 21.86           D
ATOM   5564  OG   SER D 155      48.166  26.454  21.305  1.00 25.22           D
ATOM   5565  C    SER D 155      48.873  27.233  23.932  1.00 20.85           D
ATOM   5566  O    SER D 155      49.435  28.289  23.643  1.00 22.08           D
ATOM   5567  N    SER D 156      49.484  26.244  24.575  1.00 20.75           D
ATOM   5568  CA   SER D 156      50.878  26.352  24.983  1.00 21.55           D
ATOM   5569  CB   SER D 156      51.307  25.100  25.751  1.00 21.62           D
ATOM   5570  OG   SER D 156      50.637  25.011  26.994  1.00 19.69           D
ATOM   5571  C    SER D 156      51.768  26.537  23.758  1.00 21.96           D
ATOM   5572  O    SER D 156      52.610  27.435  23.722  1.00 22.59           D
ATOM   5573  N    THR D 157      51.571  25.687  22.754  1.00 23.07           D
ATOM   5574  CA   THR D 157      52.348  25.759  21.522  1.00 23.16           D
ATOM   5575  CB   THR D 157      51.804  24.788  20.467  1.00 23.24           D
ATOM   5576  OG1  THR D 157      51.905  23.443  20.954  1.00 27.48           D
ATOM   5577  CG2  THR D 157      52.597  24.914  19.183  1.00 24.56           D
ATOM   5578  C    THR D 157      52.306  27.170  20.941  1.00 23.43           D
```

Figure 9 (86 of 92)

| ATOM | 5579 | O   | THR | D | 157 | 53.340 | 27.749 | 20.605 | 1.00 | 25.01 | D |
|------|------|-----|-----|---|-----|--------|--------|--------|------|-------|---|
| ATOM | 5580 | N   | MET | D | 158 | 51.099 | 27.712 | 20.826 | 1.00 | 23.57 | D |
| ATOM | 5581 | CA  | MET | D | 158 | 50.890 | 29.050 | 20.290 | 1.00 | 23.37 | D |
| ATOM | 5582 | CB  | MET | D | 158 | 49.390 | 29.361 | 20.291 | 1.00 | 26.14 | D |
| ATOM | 5583 | CG  | MET | D | 158 | 49.031 | 30.710 | 19.705 | 1.00 | 29.90 | D |
| ATOM | 5584 | SD  | MET | D | 158 | 47.854 | 31.575 | 20.756 | 1.00 | 36.04 | D |
| ATOM | 5585 | CE  | MET | D | 158 | 48.848 | 31.894 | 22.027 | 1.00 | 19.97 | D |
| ATOM | 5586 | C   | MET | D | 158 | 51.663 | 30.096 | 21.115 | 1.00 | 22.16 | D |
| ATOM | 5587 | O   | MET | D | 158 | 52.294 | 31.004 | 20.570 | 1.00 | 22.15 | D |
| ATOM | 5588 | N   | ILE | D | 159 | 51.611 | 29.960 | 22.433 | 1.00 | 20.04 | D |
| ATOM | 5589 | CA  | ILE | D | 159 | 52.308 | 30.883 | 23.314 | 1.00 | 20.66 | D |
| ATOM | 5590 | CB  | ILE | D | 159 | 51.824 | 30.690 | 24.764 | 1.00 | 20.49 | D |
| ATOM | 5591 | CG2 | ILE | D | 159 | 52.711 | 31.439 | 25.730 | 1.00 | 18.20 | D |
| ATOM | 5592 | CG1 | ILE | D | 159 | 50.375 | 31.195 | 24.857 | 1.00 | 19.55 | D |
| ATOM | 5593 | CD1 | ILE | D | 159 | 49.726 | 30.972 | 26.187 | 1.00 | 22.23 | D |
| ATOM | 5594 | C   | ILE | D | 159 | 53.836 | 30.762 | 23.205 | 1.00 | 22.11 | D |
| ATOM | 5595 | O   | ILE | D | 159 | 54.532 | 31.778 | 23.177 | 1.00 | 20.17 | D |
| ATOM | 5596 | N   | ARG | D | 160 | 54.359 | 29.537 | 23.126 | 1.00 | 23.58 | D |
| ATOM | 5597 | CA  | ARG | D | 160 | 55.804 | 29.356 | 22.982 | 1.00 | 24.09 | D |
| ATOM | 5598 | CB  | ARG | D | 160 | 56.176 | 27.869 | 22.852 | 1.00 | 24.95 | D |
| ATOM | 5599 | CG  | ARG | D | 160 | 55.944 | 27.015 | 24.100 | 1.00 | 24.86 | D |
| ATOM | 5600 | CD  | ARG | D | 160 | 56.724 | 25.698 | 24.017 | 1.00 | 23.14 | D |
| ATOM | 5601 | NE  | ARG | D | 160 | 56.307 | 24.833 | 22.911 | 1.00 | 22.35 | D |
| ATOM | 5602 | CZ  | ARG | D | 160 | 55.224 | 24.055 | 22.928 | 1.00 | 23.48 | D |
| ATOM | 5603 | NH1 | ARG | D | 160 | 54.927 | 23.306 | 21.875 | 1.00 | 22.27 | D |
| ATOM | 5604 | NH2 | ARG | D | 160 | 54.438 | 24.022 | 23.998 | 1.00 | 22.48 | D |
| ATOM | 5605 | C   | ARG | D | 160 | 56.269 | 30.098 | 21.721 | 1.00 | 25.22 | D |
| ATOM | 5606 | O   | ARG | D | 160 | 57.264 | 30.828 | 21.747 | 1.00 | 24.37 | D |
| ATOM | 5607 | N   | GLU | D | 161 | 55.545 | 29.906 | 20.620 | 1.00 | 25.93 | D |
| ATOM | 5608 | CA  | GLU | D | 161 | 55.883 | 30.564 | 19.357 | 1.00 | 28.35 | D |
| ATOM | 5609 | CB  | GLU | D | 161 | 54.902 | 30.163 | 18.251 | 1.00 | 30.95 | D |
| ATOM | 5610 | CG  | GLU | D | 161 | 55.204 | 28.809 | 17.638 | 1.00 | 37.81 | D |
| ATOM | 5611 | CD  | GLU | D | 161 | 56.636 | 28.720 | 17.139 | 1.00 | 42.31 | D |
| ATOM | 5612 | OE1 | GLU | D | 161 | 57.069 | 29.652 | 16.422 | 1.00 | 46.07 | D |
| ATOM | 5613 | OE2 | GLU | D | 161 | 57.328 | 27.729 | 17.458 | 1.00 | 43.50 | D |
| ATOM | 5614 | C   | GLU | D | 161 | 55.887 | 32.078 | 19.487 | 1.00 | 27.53 | D |
| ATOM | 5615 | O   | GLU | D | 161 | 56.768 | 32.755 | 18.949 | 1.00 | 26.88 | D |
| ATOM | 5616 | N   | ARG | D | 162 | 54.901 | 32.615 | 20.196 | 1.00 | 25.76 | D |
| ATOM | 5617 | CA  | ARG | D | 162 | 54.841 | 34.057 | 20.378 | 1.00 | 25.10 | D |
| ATOM | 5618 | CB  | ARG | D | 162 | 53.559 | 34.448 | 21.102 | 1.00 | 24.00 | D |
| ATOM | 5619 | CG  | ARG | D | 162 | 52.323 | 34.183 | 20.290 | 1.00 | 22.70 | D |
| ATOM | 5620 | CD  | ARG | D | 162 | 51.246 | 35.106 | 20.739 | 1.00 | 25.83 | D |
| ATOM | 5621 | NE  | ARG | D | 162 | 50.067 | 35.075 | 19.884 | 1.00 | 21.65 | D |
| ATOM | 5622 | CZ  | ARG | D | 162 | 49.252 | 36.112 | 19.759 | 1.00 | 20.89 | D |
| ATOM | 5623 | NH1 | ARG | D | 162 | 49.519 | 37.225 | 20.432 | 1.00 | 21.22 | D |
| ATOM | 5624 | NH2 | ARG | D | 162 | 48.180 | 36.044 | 18.983 | 1.00 | 18.64 | D |
| ATOM | 5625 | C   | ARG | D | 162 | 56.050 | 34.563 | 21.152 | 1.00 | 25.06 | D |
| ATOM | 5626 | O   | ARG | D | 162 | 56.575 | 35.632 | 20.854 | 1.00 | 24.52 | D |
| ATOM | 5627 | N   | PHE | D | 163 | 56.487 | 33.799 | 22.152 | 1.00 | 24.96 | D |
| ATOM | 5628 | CA  | PHE | D | 163 | 57.650 | 34.196 | 22.943 | 1.00 | 27.46 | D |
| ATOM | 5629 | CB  | PHE | D | 163 | 57.865 | 33.238 | 24.121 | 1.00 | 25.65 | D |
| ATOM | 5630 | CG  | PHE | D | 163 | 57.159 | 33.655 | 25.382 | 1.00 | 23.44 | D |
| ATOM | 5631 | CD1 | PHE | D | 163 | 57.434 | 34.888 | 25.971 | 1.00 | 21.58 | D |
| ATOM | 5632 | CD2 | PHE | D | 163 | 56.220 | 32.820 | 25.980 | 1.00 | 22.56 | D |
| ATOM | 5633 | CE1 | PHE | D | 163 | 56.782 | 35.280 | 27.137 | 1.00 | 22.77 | D |
| ATOM | 5634 | CE2 | PHE | D | 163 | 55.563 | 33.204 | 27.152 | 1.00 | 21.42 | D |
| ATOM | 5635 | CZ  | PHE | D | 163 | 55.844 | 34.434 | 27.728 | 1.00 | 21.47 | D |
| ATOM | 5636 | C   | PHE | D | 163 | 58.899 | 34.200 | 22.072 | 1.00 | 27.95 | D |
| ATOM | 5637 | O   | PHE | D | 163 | 59.719 | 35.113 | 22.146 | 1.00 | 28.37 | D |
| ATOM | 5638 | N   | LYS | D | 164 | 59.021 | 33.173 | 21.240 | 1.00 | 29.18 | D |
| ATOM | 5639 | CA  | LYS | D | 164 | 60.164 | 33.015 | 20.354 | 1.00 | 31.84 | D |
| ATOM | 5640 | CB  | LYS | D | 164 | 60.081 | 31.649 | 19.667 | 1.00 | 34.81 | D |
| ATOM | 5641 | CG  | LYS | D | 164 | 61.158 | 31.386 | 18.629 | 1.00 | 39.14 | D |
| ATOM | 5642 | CD  | LYS | D | 164 | 60.960 | 30.022 | 17.963 | 1.00 | 42.45 | D |
| ATOM | 5643 | CE  | LYS | D | 164 | 61.986 | 29.785 | 16.851 | 1.00 | 45.17 | D |
| ATOM | 5644 | NZ  | LYS | D | 164 | 61.808 | 28.450 | 16.203 | 1.00 | 44.93 | D |

Figure 9 (87 of 92)

| ATOM | 5645 | C | LYS | D | 164 | 60.262 | 34.122 | 19.307 | 1.00 | 31.97 | D |
|---|---|---|---|---|---|---|---|---|---|---|---|
| ATOM | 5646 | O | LYS | D | 164 | 61.350 | 34.638 | 19.044 | 1.00 | 31.44 | D |
| ATOM | 5647 | N | SER | D | 165 | 59.124 | 34.491 | 18.724 | 1.00 | 31.64 | D |
| ATOM | 5648 | CA | SER | D | 165 | 59.082 | 35.526 | 17.691 | 1.00 | 31.62 | D |
| ATOM | 5649 | CB | SER | D | 165 | 57.988 | 35.201 | 16.676 | 1.00 | 32.25 | D |
| ATOM | 5650 | OG | SER | D | 165 | 56.709 | 35.282 | 17.282 | 1.00 | 34.55 | D |
| ATOM | 5651 | C | SER | D | 165 | 58.861 | 36.938 | 18.237 | 1.00 | 31.27 | D |
| ATOM | 5652 | O | SER | D | 165 | 58.641 | 37.877 | 17.469 | 1.00 | 30.96 | D |
| ATOM | 5653 | N | LYS | D | 166 | 58.920 | 37.078 | 19.558 | 1.00 | 30.49 | D |
| ATOM | 5654 | CA | LYS | D | 166 | 58.740 | 38.367 | 20.224 | 1.00 | 29.98 | D |
| ATOM | 5655 | CB | LYS | D | 166 | 59.783 | 39.372 | 19.718 | 1.00 | 33.15 | D |
| ATOM | 5656 | CG | LYS | D | 166 | 61.222 | 38.853 | 19.736 | 1.00 | 35.55 | D |
| ATOM | 5657 | CD | LYS | D | 166 | 61.683 | 38.490 | 21.144 | 1.00 | 39.19 | D |
| ATOM | 5658 | CE | LYS | D | 166 | 61.782 | 39.729 | 22.026 | 1.00 | 42.43 | D |
| ATOM | 5659 | NZ | LYS | D | 166 | 62.272 | 39.420 | 23.398 | 1.00 | 42.06 | D |
| ATOM | 5660 | C | LYS | D | 166 | 57.335 | 38.962 | 20.061 | 1.00 | 29.47 | D |
| ATOM | 5661 | O | LYS | D | 166 | 57.166 | 40.179 | 20.095 | 1.00 | 27.72 | D |
| ATOM | 5662 | N | LYS | D | 167 | 56.330 | 38.113 | 19.882 | 1.00 | 28.70 | D |
| ATOM | 5663 | CA | LYS | D | 167 | 54.956 | 38.595 | 19.745 | 1.00 | 29.83 | D |
| ATOM | 5664 | CB | LYS | D | 167 | 54.147 | 37.631 | 18.879 | 1.00 | 31.63 | D |
| ATOM | 5665 | CG | LYS | D | 167 | 54.611 | 37.611 | 17.430 | 1.00 | 35.89 | D |
| ATOM | 5666 | CD | LYS | D | 167 | 53.752 | 36.706 | 16.567 | 1.00 | 38.96 | D |
| ATOM | 5667 | CE | LYS | D | 167 | 54.224 | 36.749 | 15.116 | 1.00 | 41.11 | D |
| ATOM | 5668 | NZ | LYS | D | 167 | 53.417 | 35.858 | 14.237 | 1.00 | 44.41 | D |
| ATOM | 5669 | C | LYS | D | 167 | 54.347 | 38.715 | 21.146 | 1.00 | 28.97 | D |
| ATOM | 5670 | O | LYS | D | 167 | 54.819 | 38.073 | 22.081 | 1.00 | 28.90 | D |
| ATOM | 5671 | N | PRO | D | 168 | 53.281 | 39.519 | 21.305 | 1.00 | 27.20 | D |
| ATOM | 5672 | CD | PRO | D | 168 | 52.500 | 40.184 | 20.250 | 1.00 | 27.02 | D |
| ATOM | 5673 | CA | PRO | D | 168 | 52.639 | 39.704 | 22.612 | 1.00 | 25.74 | D |
| ATOM | 5674 | CB | PRO | D | 168 | 51.510 | 40.701 | 22.322 | 1.00 | 26.66 | D |
| ATOM | 5675 | CG | PRO | D | 168 | 51.886 | 41.323 | 21.003 | 1.00 | 26.99 | D |
| ATOM | 5676 | C | PRO | D | 168 | 52.085 | 38.439 | 23.253 | 1.00 | 24.93 | D |
| ATOM | 5677 | O | PRO | D | 168 | 51.736 | 37.473 | 22.570 | 1.00 | 24.93 | D |
| ATOM | 5678 | N | THR | D | 169 | 52.008 | 38.461 | 24.578 | 1.00 | 23.57 | D |
| ATOM | 5679 | CA | THR | D | 169 | 51.448 | 37.355 | 25.336 | 1.00 | 22.74 | D |
| ATOM | 5680 | CB | THR | D | 169 | 52.542 | 36.521 | 26.049 | 1.00 | 21.73 | D |
| ATOM | 5681 | OG1 | THR | D | 169 | 53.272 | 37.349 | 26.960 | 1.00 | 21.83 | D |
| ATOM | 5682 | CG2 | THR | D | 169 | 53.491 | 35.925 | 25.035 | 1.00 | 22.75 | D |
| ATOM | 5683 | C | THR | D | 169 | 50.477 | 37.917 | 26.374 | 1.00 | 22.32 | D |
| ATOM | 5684 | O | THR | D | 169 | 49.876 | 37.162 | 27.131 | 1.00 | 22.52 | D |
| ATOM | 5685 | N | ASP | D | 170 | 50.330 | 39.243 | 26.404 | 1.00 | 21.04 | D |
| ATOM | 5686 | CA | ASP | D | 170 | 49.417 | 39.895 | 27.347 | 1.00 | 22.16 | D |
| ATOM | 5687 | CB | ASP | D | 170 | 49.408 | 41.422 | 27.165 | 1.00 | 23.94 | D |
| ATOM | 5688 | CG | ASP | D | 170 | 50.797 | 42.039 | 27.243 | 1.00 | 28.75 | D |
| ATOM | 5689 | OD1 | ASP | D | 170 | 51.631 | 41.772 | 26.345 | 1.00 | 32.04 | D |
| ATOM | 5690 | OD2 | ASP | D | 170 | 51.051 | 42.796 | 28.200 | 1.00 | 29.50 | D |
| ATOM | 5691 | C | ASP | D | 170 | 47.988 | 39.395 | 27.137 | 1.00 | 20.31 | D |
| ATOM | 5692 | O | ASP | D | 170 | 47.540 | 39.268 | 25.998 | 1.00 | 17.73 | D |
| ATOM | 5693 | N | TYR | D | 171 | 47.297 | 39.139 | 28.252 | 1.00 | 18.59 | D |
| ATOM | 5694 | CA | TYR | D | 171 | 45.910 | 38.665 | 28.298 | 1.00 | 17.83 | D |
| ATOM | 5695 | CB | TYR | D | 171 | 45.009 | 39.573 | 27.448 | 1.00 | 17.23 | D |
| ATOM | 5696 | CG | TYR | D | 171 | 45.208 | 41.050 | 27.763 | 1.00 | 18.18 | D |
| ATOM | 5697 | CD1 | TYR | D | 171 | 45.861 | 41.891 | 26.863 | 1.00 | 19.82 | D |
| ATOM | 5698 | CE1 | TYR | D | 171 | 46.132 | 43.221 | 27.180 | 1.00 | 18.62 | D |
| ATOM | 5699 | CD2 | TYR | D | 171 | 44.820 | 41.582 | 28.997 | 1.00 | 18.96 | D |
| ATOM | 5700 | CE2 | TYR | D | 171 | 45.085 | 42.913 | 29.330 | 1.00 | 18.35 | D |
| ATOM | 5701 | CZ | TYR | D | 171 | 45.743 | 43.725 | 28.418 | 1.00 | 19.65 | D |
| ATOM | 5702 | OH | TYR | D | 171 | 46.037 | 45.029 | 28.732 | 1.00 | 17.86 | D |
| ATOM | 5703 | C | TYR | D | 171 | 45.744 | 37.194 | 27.890 | 1.00 | 18.71 | D |
| ATOM | 5704 | O | TYR | D | 171 | 44.634 | 36.667 | 27.885 | 1.00 | 16.63 | D |
| ATOM | 5705 | N | LEU | D | 172 | 46.856 | 36.535 | 27.569 | 1.00 | 18.68 | D |
| ATOM | 5706 | CA | LEU | D | 172 | 46.834 | 35.124 | 27.186 | 1.00 | 19.49 | D |
| ATOM | 5707 | CB | LEU | D | 172 | 47.631 | 34.906 | 25.894 | 1.00 | 19.35 | D |
| ATOM | 5708 | CG | LEU | D | 172 | 47.097 | 35.631 | 24.650 | 1.00 | 20.12 | D |
| ATOM | 5709 | CD1 | LEU | D | 172 | 48.047 | 35.434 | 23.484 | 1.00 | 19.69 | D |
| ATOM | 5710 | CD2 | LEU | D | 172 | 45.711 | 35.094 | 24.305 | 1.00 | 19.57 | D |

Figure 9 (88 of 92)

| ATOM | 5711 | C | LEU | D | 172 | 47.404 | 34.244 | 28.303 | 1.00 | 20.27 | D |
|---|---|---|---|---|---|---|---|---|---|---|---|
| ATOM | 5712 | O | LEU | D | 172 | 47.019 | 33.077 | 28.440 | 1.00 | 20.91 | D |
| ATOM | 5713 | N | ILE | D | 173 | 48.327 | 34.801 | 29.088 | 1.00 | 19.63 | D |
| ATOM | 5714 | CA | ILE | D | 173 | 48.947 | 34.080 | 30.205 | 1.00 | 20.19 | D |
| ATOM | 5715 | CB | ILE | D | 173 | 50.408 | 33.638 | 29.889 | 1.00 | 20.47 | D |
| ATOM | 5716 | CG2 | ILE | D | 173 | 50.424 | 32.631 | 28.756 | 1.00 | 22.17 | D |
| ATOM | 5717 | CG1 | ILE | D | 173 | 51.260 | 34.861 | 29.531 | 1.00 | 21.16 | D |
| ATOM | 5718 | CD1 | ILE | D | 173 | 52.718 | 34.547 | 29.215 | 1.00 | 21.91 | D |
| ATOM | 5719 | C | ILE | D | 173 | 49.023 | 34.996 | 31.420 | 1.00 | 20.61 | D |
| ATOM | 5720 | O | ILE | D | 173 | 49.009 | 36.214 | 31.282 | 1.00 | 22.65 | D |
| ATOM | 5721 | N | PRO | D | 174 | 49.112 | 34.425 | 32.629 | 1.00 | 21.47 | D |
| ATOM | 5722 | CD | PRO | D | 174 | 48.990 | 33.010 | 33.024 | 1.00 | 21.60 | D |
| ATOM | 5723 | CA | PRO | D | 174 | 49.198 | 35.294 | 33.806 | 1.00 | 21.92 | D |
| ATOM | 5724 | CB | PRO | D | 174 | 49.220 | 34.301 | 34.968 | 1.00 | 22.24 | D |
| ATOM | 5725 | CG | PRO | D | 174 | 48.438 | 33.122 | 34.429 | 1.00 | 21.41 | D |
| ATOM | 5726 | C | PRO | D | 174 | 50.501 | 36.099 | 33.713 | 1.00 | 22.03 | D |
| ATOM | 5727 | O | PRO | D | 174 | 51.511 | 35.585 | 33.240 | 1.00 | 21.08 | D |
| ATOM | 5728 | N | ASP | D | 175 | 50.481 | 37.352 | 34.154 | 1.00 | 23.22 | D |
| ATOM | 5729 | CA | ASP | D | 175 | 51.682 | 38.177 | 34.098 | 1.00 | 25.85 | D |
| ATOM | 5730 | CB | ASP | D | 175 | 51.408 | 39.577 | 34.661 | 1.00 | 29.32 | D |
| ATOM | 5731 | CG | ASP | D | 175 | 50.429 | 40.371 | 33.809 | 1.00 | 33.69 | D |
| ATOM | 5732 | OD1 | ASP | D | 175 | 50.613 | 40.427 | 32.570 | 1.00 | 35.94 | D |
| ATOM | 5733 | OD2 | ASP | D | 175 | 49.477 | 40.947 | 34.380 | 1.00 | 36.58 | D |
| ATOM | 5734 | C | ASP | D | 175 | 52.850 | 37.535 | 34.853 | 1.00 | 25.88 | D |
| ATOM | 5735 | O | ASP | D | 175 | 54.002 | 37.650 | 34.433 | 1.00 | 26.75 | D |
| ATOM | 5736 | N | LYS | D | 176 | 52.558 | 36.848 | 35.955 | 1.00 | 24.87 | D |
| ATOM | 5737 | CA | LYS | D | 176 | 53.615 | 36.203 | 36.735 | 1.00 | 23.89 | D |
| ATOM | 5738 | CB | LYS | D | 176 | 53.065 | 35.693 | 38.067 | 1.00 | 25.31 | D |
| ATOM | 5739 | CG | LYS | D | 176 | 52.573 | 36.804 | 38.984 | 1.00 | 28.24 | D |
| ATOM | 5740 | CD | LYS | D | 176 | 52.140 | 36.262 | 40.338 | 1.00 | 30.52 | D |
| ATOM | 5741 | CE | LYS | D | 176 | 51.064 | 35.194 | 40.203 | 1.00 | 32.92 | D |
| ATOM | 5742 | NZ | LYS | D | 176 | 50.673 | 34.633 | 41.528 | 1.00 | 35.50 | D |
| ATOM | 5743 | C | LYS | D | 176 | 54.275 | 35.059 | 35.976 | 1.00 | 22.23 | D |
| ATOM | 5744 | O | LYS | D | 176 | 55.443 | 34.733 | 36.207 | 1.00 | 21.39 | D |
| ATOM | 5745 | N | VAL | D | 177 | 53.526 | 34.436 | 35.074 | 1.00 | 20.50 | D |
| ATOM | 5746 | CA | VAL | D | 177 | 54.084 | 33.352 | 34.278 | 1.00 | 19.92 | D |
| ATOM | 5747 | CB | VAL | D | 177 | 52.981 | 32.535 | 33.581 | 1.00 | 19.11 | D |
| ATOM | 5748 | CG1 | VAL | D | 177 | 53.608 | 31.496 | 32.663 | 1.00 | 17.31 | D |
| ATOM | 5749 | CG2 | VAL | D | 177 | 52.110 | 31.855 | 34.621 | 1.00 | 19.55 | D |
| ATOM | 5750 | C | VAL | D | 177 | 54.987 | 33.990 | 33.230 | 1.00 | 20.55 | D |
| ATOM | 5751 | O | VAL | D | 177 | 56.091 | 33.503 | 32.961 | 1.00 | 20.80 | D |
| ATOM | 5752 | N | LYS | D | 178 | 54.514 | 35.085 | 32.641 | 1.00 | 20.41 | D |
| ATOM | 5753 | CA | LYS | D | 178 | 55.292 | 35.802 | 31.638 | 1.00 | 21.66 | D |
| ATOM | 5754 | CB | LYS | D | 178 | 54.505 | 37.011 | 31.125 | 1.00 | 23.03 | D |
| ATOM | 5755 | CG | LYS | D | 178 | 55.306 | 37.933 | 30.227 | 1.00 | 27.01 | D |
| ATOM | 5756 | CD | LYS | D | 178 | 54.529 | 39.204 | 29.915 | 1.00 | 30.68 | D |
| ATOM | 5757 | CE | LYS | D | 178 | 55.451 | 40.285 | 29.374 | 1.00 | 33.04 | D |
| ATOM | 5758 | NZ | LYS | D | 178 | 54.737 | 41.576 | 29.183 | 1.00 | 37.47 | D |
| ATOM | 5759 | C | LYS | D | 178 | 56.596 | 36.267 | 32.291 | 1.00 | 21.57 | D |
| ATOM | 5760 | O | LYS | D | 178 | 57.682 | 36.108 | 31.728 | 1.00 | 20.11 | D |
| ATOM | 5761 | N | LYS | D | 179 | 56.481 | 36.833 | 33.489 | 1.00 | 20.90 | D |
| ATOM | 5762 | CA | LYS | D | 179 | 57.649 | 37.311 | 34.216 | 1.00 | 23.10 | D |
| ATOM | 5763 | CB | LYS | D | 179 | 57.224 | 37.909 | 35.559 | 1.00 | 23.64 | D |
| ATOM | 5764 | CG | LYS | D | 179 | 58.386 | 38.411 | 36.395 | 1.00 | 27.82 | D |
| ATOM | 5765 | CD | LYS | D | 179 | 57.931 | 38.978 | 37.730 | 1.00 | 30.59 | D |
| ATOM | 5766 | CE | LYS | D | 179 | 59.126 | 39.515 | 38.511 | 1.00 | 34.30 | D |
| ATOM | 5767 | NZ | LYS | D | 179 | 58.741 | 40.032 | 39.860 | 1.00 | 37.59 | D |
| ATOM | 5768 | C | LYS | D | 179 | 58.655 | 36.183 | 34.448 | 1.00 | 23.47 | D |
| ATOM | 5769 | O | LYS | D | 179 | 59.867 | 36.380 | 34.331 | 1.00 | 25.86 | D |
| ATOM | 5770 | N | TYR | D | 180 | 58.149 | 35.000 | 34.775 | 1.00 | 22.44 | D |
| ATOM | 5771 | CA | TYR | D | 180 | 59.005 | 33.844 | 35.026 | 1.00 | 21.91 | D |
| ATOM | 5772 | CB | TYR | D | 180 | 58.178 | 32.704 | 35.624 | 1.00 | 22.78 | D |
| ATOM | 5773 | CG | TYR | D | 180 | 58.996 | 31.488 | 35.999 | 1.00 | 22.42 | D |
| ATOM | 5774 | CD1 | TYR | D | 180 | 59.613 | 31.396 | 37.248 | 1.00 | 22.80 | D |
| ATOM | 5775 | CE1 | TYR | D | 180 | 60.377 | 30.281 | 37.597 | 1.00 | 22.28 | D |
| ATOM | 5776 | CD2 | TYR | D | 180 | 59.164 | 30.433 | 35.101 | 1.00 | 22.73 | D |

Figure 9 (89 of 92)

| ATOM | 5777 | CE2 | TYR | D | 180 | 59.932 | 29.311 | 35.439 | 1.00 | 22.69 | D |
|------|------|-----|-----|---|-----|--------|--------|--------|------|-------|---|
| ATOM | 5778 | CZ | TYR | D | 180 | 60.531 | 29.246 | 36.691 | 1.00 | 22.39 | D |
| ATOM | 5779 | OH | TYR | D | 180 | 61.272 | 28.144 | 37.039 | 1.00 | 23.01 | D |
| ATOM | 5780 | C | TYR | D | 180 | 59.700 | 33.349 | 33.757 | 1.00 | 21.42 | D |
| ATOM | 5781 | O | TYR | D | 180 | 60.841 | 32.885 | 33.801 | 1.00 | 20.02 | D |
| ATOM | 5782 | N | VAL | D | 181 | 58.995 | 33.423 | 32.632 | 1.00 | 21.25 | D |
| ATOM | 5783 | CA | VAL | D | 181 | 59.543 | 32.984 | 31.351 | 1.00 | 21.90 | D |
| ATOM | 5784 | CB | VAL | D | 181 | 58.461 | 33.011 | 30.235 | 1.00 | 21.44 | D |
| ATOM | 5785 | CG1 | VAL | D | 181 | 59.111 | 32.801 | 28.871 | 1.00 | 19.81 | D |
| ATOM | 5786 | CG2 | VAL | D | 181 | 57.413 | 31.933 | 30.493 | 1.00 | 19.18 | D |
| ATOM | 5787 | C | VAL | D | 181 | 60.696 | 33.887 | 30.916 | 1.00 | 23.33 | D |
| ATOM | 5788 | O | VAL | D | 181 | 61.750 | 33.406 | 30.480 | 1.00 | 22.85 | D |
| ATOM | 5789 | N | GLU | D | 182 | 60.481 | 35.193 | 31.035 | 1.00 | 24.24 | D |
| ATOM | 5790 | CA | GLU | D | 182 | 61.478 | 36.177 | 30.639 | 1.00 | 27.15 | D |
| ATOM | 5791 | CB | GLU | D | 182 | 60.911 | 37.588 | 30.775 | 1.00 | 28.53 | D |
| ATOM | 5792 | CG | GLU | D | 182 | 59.646 | 37.834 | 29.983 | 1.00 | 31.32 | D |
| ATOM | 5793 | CD | GLU | D | 182 | 59.125 | 39.250 | 30.164 | 1.00 | 31.79 | D |
| ATOM | 5794 | OE1 | GLU | D | 182 | 59.253 | 39.784 | 31.284 | 1.00 | 36.46 | D |
| ATOM | 5795 | OE2 | GLU | D | 182 | 58.579 | 39.821 | 29.200 | 1.00 | 30.70 | D |
| ATOM | 5796 | C | GLU | D | 182 | 62.779 | 36.089 | 31.425 | 1.00 | 28.94 | D |
| ATOM | 5797 | O | GLU | D | 182 | 63.857 | 36.039 | 30.836 | 1.00 | 32.05 | D |
| ATOM | 5798 | N | GLU | D | 183 | 62.698 | 36.054 | 32.750 | 1.00 | 29.64 | D |
| ATOM | 5799 | CA | GLU | D | 183 | 63.927 | 36.007 | 33.529 | 1.00 | 31.41 | D |
| ATOM | 5800 | CB | GLU | D | 183 | 63.729 | 36.647 | 34.916 | 1.00 | 32.13 | D |
| ATOM | 5801 | CG | GLU | D | 183 | 62.410 | 36.409 | 35.605 | 1.00 | 33.27 | D |
| ATOM | 5802 | CD | GLU | D | 183 | 62.135 | 37.457 | 36.683 | 1.00 | 34.22 | D |
| ATOM | 5803 | OE1 | GLU | D | 183 | 61.907 | 37.081 | 37.854 | 1.00 | 33.37 | D |
| ATOM | 5804 | OE2 | GLU | D | 183 | 62.143 | 38.667 | 36.360 | 1.00 | 35.99 | D |
| ATOM | 5805 | C | GLU | D | 183 | 64.621 | 34.656 | 33.636 | 1.00 | 31.33 | D |
| ATOM | 5806 | O | GLU | D | 183 | 65.721 | 34.562 | 34.179 | 1.00 | 32.44 | D |
| ATOM | 5807 | N | ASN | D | 184 | 63.997 | 33.613 | 33.098 | 1.00 | 29.88 | D |
| ATOM | 5808 | CA | ASN | D | 184 | 64.618 | 32.297 | 33.101 | 1.00 | 28.13 | D |
| ATOM | 5809 | CB | ASN | D | 184 | 63.663 | 31.240 | 33.661 | 1.00 | 28.92 | D |
| ATOM | 5810 | CG | ASN | D | 184 | 63.598 | 31.265 | 35.175 | 1.00 | 28.14 | D |
| ATOM | 5811 | OD1 | ASN | D | 184 | 64.541 | 30.855 | 35.852 | 1.00 | 28.57 | D |
| ATOM | 5812 | ND2 | ASN | D | 184 | 62.490 | 31.760 | 35.715 | 1.00 | 27.81 | D |
| ATOM | 5813 | C | ASN | D | 184 | 65.026 | 31.954 | 31.671 | 1.00 | 26.38 | D |
| ATOM | 5814 | O | ASN | D | 184 | 65.452 | 30.837 | 31.385 | 1.00 | 26.35 | D |
| ATOM | 5815 | N | GLY | D | 185 | 64.894 | 32.938 | 30.785 | 1.00 | 26.00 | D |
| ATOM | 5816 | CA | GLY | D | 185 | 65.258 | 32.763 | 29.390 | 1.00 | 24.20 | D |
| ATOM | 5817 | C | GLY | D | 185 | 64.608 | 31.574 | 28.715 | 1.00 | 24.82 | D |
| ATOM | 5818 | O | GLY | D | 185 | 65.224 | 30.918 | 27.874 | 1.00 | 24.45 | D |
| ATOM | 5819 | N | LEU | D | 186 | 63.355 | 31.301 | 29.070 | 1.00 | 24.76 | D |
| ATOM | 5820 | CA | LEU | D | 186 | 62.624 | 30.179 | 28.496 | 1.00 | 24.82 | D |
| ATOM | 5821 | CB | LEU | D | 186 | 61.528 | 29.725 | 29.462 | 1.00 | 25.89 | D |
| ATOM | 5822 | CG | LEU | D | 186 | 62.025 | 29.183 | 30.802 | 1.00 | 25.31 | D |
| ATOM | 5823 | CD1 | LEU | D | 186 | 60.844 | 28.868 | 31.705 | 1.00 | 25.30 | D |
| ATOM | 5824 | CD2 | LEU | D | 186 | 62.852 | 27.930 | 30.554 | 1.00 | 24.65 | D |
| ATOM | 5825 | C | LEU | D | 186 | 62.011 | 30.511 | 27.139 | 1.00 | 24.90 | D |
| ATOM | 5826 | O | LEU | D | 186 | 61.724 | 31.672 | 26.835 | 1.00 | 23.38 | D |
| ATOM | 5827 | N | TYR | D | 187 | 61.826 | 29.475 | 26.327 | 1.00 | 25.97 | D |
| ATOM | 5828 | CA | TYR | D | 187 | 61.243 | 29.608 | 24.998 | 1.00 | 29.15 | D |
| ATOM | 5829 | CB | TYR | D | 187 | 59.776 | 30.039 | 25.126 | 1.00 | 26.38 | D |
| ATOM | 5830 | CG | TYR | D | 187 | 59.004 | 29.158 | 26.089 | 1.00 | 25.80 | D |
| ATOM | 5831 | CD1 | TYR | D | 187 | 59.127 | 27.767 | 26.042 | 1.00 | 24.52 | D |
| ATOM | 5832 | CE1 | TYR | D | 187 | 58.438 | 26.953 | 26.938 | 1.00 | 23.98 | D |
| ATOM | 5833 | CD2 | TYR | D | 187 | 58.165 | 29.712 | 27.060 | 1.00 | 26.49 | D |
| ATOM | 5834 | CE2 | TYR | D | 187 | 57.469 | 28.905 | 27.962 | 1.00 | 23.94 | D |
| ATOM | 5835 | CZ | TYR | D | 187 | 57.611 | 27.528 | 27.893 | 1.00 | 25.03 | D |
| ATOM | 5836 | OH | TYR | D | 187 | 56.920 | 26.723 | 28.768 | 1.00 | 22.26 | D |
| ATOM | 5837 | C | TYR | D | 187 | 62.026 | 30.556 | 24.094 | 1.00 | 32.22 | D |
| ATOM | 5838 | O | TYR | D | 187 | 61.470 | 31.474 | 23.481 | 1.00 | 32.73 | D |
| ATOM | 5839 | N | GLU | D | 188 | 63.331 | 30.303 | 24.026 | 1.00 | 37.47 | D |
| ATOM | 5840 | CA | GLU | D | 188 | 64.269 | 31.063 | 23.207 | 1.00 | 40.71 | D |
| ATOM | 5841 | CB | GLU | D | 188 | 64.160 | 30.616 | 21.747 | 1.00 | 42.51 | D |
| ATOM | 5842 | CG | GLU | D | 188 | 64.526 | 29.150 | 21.546 | 1.00 | 47.31 | D |

Figure 9 (90 of 92)

| | | | | | | | | | | |
|---|---|---|---|---|---|---|---|---|---|---|
| ATOM | 5843 | CD | GLU | D | 188 | 64.290 | 28.664 | 20.128 | 1.00 50.02 | D |
| ATOM | 5844 | OE1 | GLU | D | 188 | 64.880 | 29.238 | 19.188 | 1.00 51.24 | D |
| ATOM | 5845 | OE2 | GLU | D | 188 | 63.512 | 27.701 | 19.959 | 1.00 52.29 | D |
| ATOM | 5846 | C | GLU | D | 188 | 64.069 | 32.561 | 23.309 | 1.00 42.60 | D |
| ATOM | 5847 | O | GLU | D | 188 | 63.879 | 33.194 | 22.248 | 1.00 44.21 | D |
| ATOM | 5848 | OXT | GLU | D | 188 | 64.115 | 33.079 | 24.449 | 1.00 44.74 | D |
| ATOM | 5849 | O | HOH | S | 1 | 42.446 | 37.399 | 29.398 | 1.00 11.48 | S |
| ATOM | 5850 | O | HOH | S | 2 | 40.378 | 14.756 | 27.934 | 1.00 19.06 | S |
| ATOM | 5851 | O | HOH | S | 3 | 35.220 | 12.064 | 20.053 | 1.00 21.60 | S |
| ATOM | 5852 | O | HOH | S | 4 | 25.924 | 22.594 | 2.226 | 1.00 14.80 | S |
| ATOM | 5853 | O | HOH | S | 5 | 30.062 | 4.533 | 20.846 | 1.00 17.45 | S |
| ATOM | 5854 | O | HOH | S | 6 | 27.414 | 20.317 | 2.668 | 1.00 16.30 | S |
| ATOM | 5855 | O | HOH | S | 7 | 35.477 | 17.317 | 1.484 | 1.00 20.63 | S |
| ATOM | 5856 | O | HOH | S | 8 | 26.762 | -0.417 | 14.095 | 1.00 16.80 | S |
| ATOM | 5857 | O | HOH | S | 9 | 29.128 | 3.964 | 17.294 | 1.00 22.71 | S |
| ATOM | 5858 | O | HOH | S | 10 | 28.414 | 43.219 | 4.855 | 1.00 18.32 | S |
| ATOM | 5859 | O | HOH | S | 11 | 35.695 | 39.028 | 23.185 | 1.00 23.41 | S |
| ATOM | 5860 | O | HOH | S | 12 | 19.162 | 26.872 | 5.514 | 1.00 15.99 | S |
| ATOM | 5861 | O | HOH | S | 13 | 31.183 | 46.334 | 23.709 | 1.00 23.08 | S |
| ATOM | 5862 | O | HOH | S | 14 | 23.849 | 43.513 | 1.280 | 1.00 16.97 | S |
| ATOM | 5863 | O | HOH | S | 15 | 35.791 | 50.820 | 16.467 | 1.00 17.58 | S |
| ATOM | 5864 | O | HOH | S | 16 | 46.164 | 5.682 | 18.256 | 1.00 22.10 | S |
| ATOM | 5865 | O | HOH | S | 17 | 28.492 | 2.268 | 21.243 | 1.00 25.34 | S |
| ATOM | 5866 | O | HOH | S | 18 | 49.170 | 0.989 | 37.276 | 1.00 20.99 | S |
| ATOM | 5867 | O | HOH | S | 19 | 30.266 | 42.444 | -1.211 | 1.00 29.43 | S |
| ATOM | 5868 | O | HOH | S | 20 | 47.679 | 39.997 | 23.386 | 1.00 22.61 | S |
| ATOM | 5869 | O | HOH | S | 21 | 41.917 | 35.333 | 30.916 | 1.00 23.00 | S |
| ATOM | 5870 | O | HOH | S | 22 | 24.479 | 56.844 | -7.279 | 1.00 26.55 | S |
| ATOM | 5871 | O | HOH | S | 23 | 27.346 | 38.195 | 41.131 | 1.00 22.19 | S |
| ATOM | 5872 | O | HOH | S | 24 | 35.563 | 31.290 | 35.107 | 1.00 22.95 | S |
| ATOM | 5873 | O | HOH | S | 25 | 30.679 | 57.055 | 16.684 | 1.00 28.14 | S |
| ATOM | 5874 | O | HOH | S | 26 | 28.494 | 57.639 | 9.529 | 1.00 21.24 | S |
| ATOM | 5875 | O | HOH | S | 27 | 30.807 | -4.199 | 24.388 | 1.00 22.54 | S |
| ATOM | 5876 | O | HOH | S | 28 | 29.013 | 18.575 | 11.626 | 1.00 24.65 | S |
| ATOM | 5877 | O | HOH | S | 29 | 41.142 | 14.486 | 33.330 | 1.00 22.13 | S |
| ATOM | 5878 | O | HOH | S | 30 | 49.052 | 22.589 | 27.602 | 1.00 29.82 | S |
| ATOM | 5879 | O | HOH | S | 31 | 31.636 | 54.149 | 20.008 | 1.00 23.12 | S |
| ATOM | 5880 | O | HOH | S | 32 | 48.634 | 14.386 | 33.490 | 1.00 21.46 | S |
| ATOM | 5881 | O | HOH | S | 33 | 45.228 | 21.871 | 27.810 | 1.00 23.88 | S |
| ATOM | 5882 | O | HOH | S | 34 | 29.937 | 29.096 | 34.623 | 1.00 27.26 | S |
| ATOM | 5883 | O | HOH | S | 35 | 45.663 | 27.430 | 44.401 | 1.00 21.35 | S |
| ATOM | 5884 | O | HOH | S | 36 | 35.364 | 16.315 | 20.237 | 1.00 24.22 | S |
| ATOM | 5885 | O | HOH | S | 37 | 45.306 | 35.389 | 34.224 | 1.00 27.14 | S |
| ATOM | 5886 | O | HOH | S | 38 | 32.051 | 41.292 | 13.082 | 1.00 28.38 | S |
| ATOM | 5887 | O | HOH | S | 39 | 34.497 | 6.990 | 15.455 | 1.00 23.86 | S |
| ATOM | 5888 | O | HOH | S | 40 | 29.084 | 53.410 | 17.031 | 1.00 18.58 | S |
| ATOM | 5889 | O | HOH | S | 41 | 47.565 | 24.110 | 25.757 | 1.00 23.78 | S |
| ATOM | 5890 | O | HOH | S | 42 | 33.745 | 33.393 | 0.365 | 1.00 25.60 | S |
| ATOM | 5891 | O | HOH | S | 43 | 46.121 | 37.793 | 31.960 | 1.00 20.85 | S |
| ATOM | 5892 | O | HOH | S | 44 | 38.368 | 39.078 | 21.931 | 1.00 25.07 | S |
| ATOM | 5893 | O | HOH | S | 45 | 44.934 | 1.717 | 42.302 | 1.00 27.59 | S |
| ATOM | 5894 | O | HOH | S | 46 | 33.251 | 58.588 | 23.502 | 1.00 25.43 | S |
| ATOM | 5895 | O | HOH | S | 47 | 31.837 | 37.758 | 39.909 | 1.00 22.72 | S |
| ATOM | 5896 | O | HOH | S | 48 | 38.595 | 61.442 | 26.222 | 1.00 20.49 | S |
| ATOM | 5897 | O | HOH | S | 49 | 38.254 | 37.392 | 20.280 | 1.00 20.99 | S |
| ATOM | 5898 | O | HOH | S | 50 | 17.582 | 48.170 | 9.725 | 1.00 22.05 | S |
| ATOM | 5899 | O | HOH | S | 51 | 37.779 | 54.479 | 37.753 | 1.00 35.19 | S |
| ATOM | 5900 | O | HOH | S | 52 | 56.761 | 28.996 | 41.149 | 1.00 31.76 | S |
| ATOM | 5901 | O | HOH | S | 53 | 32.226 | 45.839 | 13.191 | 1.00 28.85 | S |
| ATOM | 5902 | O | HOH | S | 54 | 10.972 | 18.710 | 5.339 | 1.00 31.93 | S |
| ATOM | 5903 | O | HOH | S | 55 | 42.965 | 45.383 | 33.134 | 1.00 20.93 | S |
| ATOM | 5904 | O | HOH | S | 56 | 27.632 | 30.857 | 5.613 | 1.00 24.11 | S |
| ATOM | 5905 | O | HOH | S | 57 | 32.779 | 69.530 | 23.438 | 1.00 21.75 | S |
| ATOM | 5906 | O | HOH | S | 58 | 26.532 | 62.220 | 14.610 | 1.00 26.68 | S |
| ATOM | 5907 | O | HOH | S | 59 | 20.050 | 29.278 | 13.683 | 1.00 27.97 | S |
| ATOM | 5908 | O | HOH | S | 60 | 31.607 | 55.154 | 15.382 | 1.00 25.74 | S |

Figure 9 (91 of 92)

| | | | | | | | | | | |
|---|---|---|---|---|---|---|---|---|---|---|
| ATOM | 5909 | O | HOH | S | 61 | 41.197 | 38.056 | 34.625 | 1.00 | 26.15 | S |
| ATOM | 5910 | O | HOH | S | 62 | 22.501 | 53.107 | -14.871 | 1.00 | 27.24 | S |
| ATOM | 5911 | O | HOH | S | 63 | 16.600 | 20.101 | 3.325 | 1.00 | 29.78 | S |
| ATOM | 5912 | O | HOH | S | 64 | 37.917 | 27.520 | 26.063 | 1.00 | 22.60 | S |
| ATOM | 5913 | O | HOH | S | 65 | 30.708 | 17.009 | 14.327 | 1.00 | 24.10 | S |
| ATOM | 5914 | O | HOH | S | 66 | 32.332 | 14.761 | 21.099 | 1.00 | 28.52 | S |
| ATOM | 5915 | O | HOH | S | 67 | 24.733 | 16.878 | 0.843 | 1.00 | 24.38 | S |
| ATOM | 5916 | O | HOH | S | 68 | 38.506 | 64.294 | 21.516 | 1.00 | 28.93 | S |
| ATOM | 5917 | O | HOH | S | 69 | 31.064 | -6.425 | 10.151 | 1.00 | 35.19 | S |
| ATOM | 5918 | O | HOH | S | 70 | 42.465 | 40.936 | 32.703 | 1.00 | 25.65 | S |
| ATOM | 5919 | O | HOH | S | 71 | 35.749 | 60.582 | 2.295 | 1.00 | 28.55 | S |
| ATOM | 5920 | O | HOH | S | 72 | 9.608 | 20.308 | 9.184 | 1.00 | 25.53 | S |
| ATOM | 5921 | O | HOH | S | 73 | 27.304 | 43.187 | 41.801 | 1.00 | 30.43 | S |
| ATOM | 5922 | O | HOH | S | 74 | 29.558 | 28.927 | 21.583 | 1.00 | 31.27 | S |
| ATOM | 5923 | O | HOH | S | 75 | 31.440 | 18.487 | 10.006 | 1.00 | 28.89 | S |
| ATOM | 5924 | O | HOH | S | 76 | 49.766 | 39.301 | 17.689 | 1.00 | 36.12 | S |
| ATOM | 5925 | O | HOH | S | 77 | 33.654 | 9.370 | 17.767 | 1.00 | 32.20 | S |
| ATOM | 5926 | O | HOH | S | 78 | 33.058 | 51.201 | 16.703 | 1.00 | 17.46 | S |
| ATOM | 5927 | O | HOH | S | 79 | 31.514 | 4.585 | 18.476 | 1.00 | 17.92 | S |
| ATOM | 5928 | O | HOH | S | 80 | 43.736 | 38.777 | 31.454 | 1.00 | 25.47 | S |
| ATOM | 5929 | O | HOH | S | 81 | 31.627 | 53.342 | 17.297 | 1.00 | 25.62 | S |
| ATOM | 5930 | O | HOH | S | 82 | 24.457 | 21.856 | 0.171 | 1.00 | 18.33 | S |
| ATOM | 5931 | O | HOH | S | 83 | 42.694 | 40.566 | 36.770 | 1.00 | 27.10 | S |
| ATOM | 5932 | O | HOH | S | 84 | 42.876 | 36.104 | 33.095 | 1.00 | 24.36 | S |
| ATOM | 5933 | O | HOH | S | 85 | 32.804 | 6.804 | 17.549 | 1.00 | 26.51 | S |
| ATOM | 5934 | O | HOH | S | 86 | 28.553 | 4.742 | -0.685 | 1.00 | 27.19 | S |
| ATOM | 5935 | O | HOH | S | 87 | 26.518 | 19.075 | 0.735 | 1.00 | 23.99 | S |
| ATOM | 5936 | O | HOH | S | 88 | 27.913 | 32.416 | 30.344 | 1.00 | 29.24 | S |
| ATOM | 5937 | O | HOH | S | 89 | 37.701 | -9.883 | 5.880 | 1.00 | 28.21 | S |
| ATOM | 5938 | O | HOH | S | 90 | 16.468 | 28.970 | 10.304 | 1.00 | 29.45 | S |
| ATOM | 5939 | O | HOH | S | 91 | 38.577 | 48.343 | 41.590 | 1.00 | 25.47 | S |
| ATOM | 5940 | O | HOH | S | 92 | 47.594 | 65.606 | 15.924 | 1.00 | 26.34 | S |
| ATOM | 5941 | O | HOH | S | 93 | 17.797 | 51.375 | -14.829 | 1.00 | 24.37 | S |
| ATOM | 5942 | O | HOH | S | 94 | 45.605 | 0.257 | 13.106 | 1.00 | 32.38 | S |
| ATOM | 5943 | O | HOH | S | 95 | 61.899 | 34.321 | 26.319 | 1.00 | 33.61 | S |
| ATOM | 5944 | O | HOH | S | 96 | 31.332 | 0.869 | 20.118 | 1.00 | 33.45 | S |
| ATOM | 5945 | O | HOH | S | 97 | 33.881 | 35.450 | 40.228 | 1.00 | 31.47 | S |
| ATOM | 5946 | O | HOH | S | 98 | 30.365 | 65.927 | 10.632 | 1.00 | 31.34 | S |
| ATOM | 5947 | O | HOH | S | 99 | 36.369 | 16.875 | -4.844 | 1.00 | 28.63 | S |
| ATOM | 5948 | O | HOH | S | 100 | 43.811 | 57.085 | 8.103 | 1.00 | 28.29 | S |
| ATOM | 5949 | O | HOH | S | 101 | 18.731 | 3.503 | 0.027 | 1.00 | 32.42 | S |
| ATOM | 5950 | O | HOH | S | 102 | 31.209 | 50.188 | -1.951 | 1.00 | 31.99 | S |
| ATOM | 5951 | O | HOH | S | 103 | 43.135 | 54.744 | 33.273 | 1.00 | 26.70 | S |
| ATOM | 5952 | O | HOH | S | 104 | 48.030 | 38.377 | 35.363 | 1.00 | 31.48 | S |
| ATOM | 5953 | O | HOH | S | 105 | 30.949 | 36.029 | 0.948 | 1.00 | 29.21 | S |
| ATOM | 5954 | O | HOH | S | 106 | 49.667 | 33.390 | 17.613 | 1.00 | 30.14 | S |
| ATOM | 5955 | O | HOH | S | 107 | 17.386 | 39.932 | 16.015 | 1.00 | 31.18 | S |
| ATOM | 5956 | O | HOH | S | 108 | 19.085 | 25.773 | 14.247 | 1.00 | 26.68 | S |
| ATOM | 5957 | O | HOH | S | 109 | 16.187 | 34.331 | 13.857 | 1.00 | 32.25 | S |
| ATOM | 5958 | O | HOH | S | 110 | 25.277 | 1.591 | 24.905 | 1.00 | 31.69 | S |
| ATOM | 5959 | O | HOH | S | 111 | 40.698 | 63.280 | 22.808 | 1.00 | 32.25 | S |
| ATOM | 5960 | O | HOH | S | 112 | 31.961 | 66.002 | 13.175 | 1.00 | 20.43 | S |
| ATOM | 5961 | O | HOH | S | 113 | 13.880 | 35.523 | 13.193 | 1.00 | 33.37 | S |
| ATOM | 5962 | O | HOH | S | 114 | 41.656 | 55.193 | 3.934 | 1.00 | 31.75 | S |
| ATOM | 5963 | O | HOH | S | 115 | 46.067 | -3.106 | 23.165 | 1.00 | 29.26 | S |
| ATOM | 5964 | O | HOH | S | 116 | 27.877 | 30.586 | 8.300 | 1.00 | 25.89 | S |
| ATOM | 5965 | O | HOH | S | 117 | 48.958 | 23.275 | 45.221 | 1.00 | 25.76 | S |
| ATOM | 5966 | O | HOH | S | 118 | 33.616 | 46.791 | 21.815 | 1.00 | 25.22 | S |
| ATOM | 5967 | O | HOH | S | 119 | 15.415 | 8.177 | 15.604 | 1.00 | 39.70 | S |
| ATOM | 5968 | O | HOH | S | 120 | 36.040 | 37.775 | 38.421 | 1.00 | 37.04 | S |
| ATOM | 5969 | O | HOH | S | 121 | 14.767 | 9.776 | 0.171 | 1.00 | 31.75 | S |
| ATOM | 5970 | O | HOH | S | 122 | 51.489 | 15.155 | 38.031 | 1.00 | 29.92 | S |
| ATOM | 5971 | O | HOH | S | 123 | 34.550 | -8.121 | 20.753 | 1.00 | 24.67 | S |
| ATOM | 5972 | O | HOH | S | 124 | 25.340 | 14.553 | -0.476 | 1.00 | 33.51 | S |
| ATOM | 5973 | O | HOH | S | 125 | 18.064 | 56.506 | -6.247 | 1.00 | 32.85 | S |
| ATOM | 5974 | O | HOH | S | 126 | 27.425 | 56.248 | 6.243 | 1.00 | 35.16 | S |

Figure 9 (92 of 92)

| | | | | | | | | | | | |
|---|---|---|---|---|---|---|---|---|---|---|---|
| ATOM | 5975 | O | HOH | S | 127 | 27.852 | 29.129 | 17.902 | 1.00 | 34.51 | S |
| ATOM | 5976 | O | HOH | S | 128 | 34.882 | 14.311 | 22.062 | 1.00 | 23.69 | S |
| ATOM | 5977 | O | HOH | S | 129 | 12.949 | 20.606 | 6.173 | 1.00 | 27.40 | S |
| ATOM | 5978 | O | HOH | S | 130 | 29.213 | 36.665 | 39.968 | 1.00 | 33.63 | S |
| ATOM | 5979 | O | HOH | S | 131 | 29.075 | 35.679 | 22.508 | 1.00 | 32.30 | S |
| ATOM | 5980 | O | HOH | S | 132 | 30.217 | 38.670 | -0.392 | 1.00 | 32.91 | S |
| ATOM | 5981 | O | HOH | S | 133 | 25.261 | 43.048 | -9.651 | 1.00 | 34.41 | S |
| ATOM | 5982 | O | HOH | S | 134 | 48.657 | 39.038 | 30.772 | 1.00 | 31.85 | S |
| ATOM | 5983 | O | HOH | S | 135 | 36.099 | 0.324 | 25.385 | 1.00 | 28.01 | S |
| ATOM | 5984 | O | HOH | S | 136 | 67.958 | 33.306 | 32.921 | 1.00 | 37.86 | S |
| ATOM | 5985 | O | HOH | S | 137 | 44.925 | 1.597 | 34.231 | 1.00 | 35.21 | S |
| ATOM | 5986 | O | HOH | S | 138 | 31.434 | 4.157 | 42.540 | 1.00 | 45.88 | S |
| ATOM | 5987 | O | HOH | S | 139 | 10.607 | 34.000 | 4.173 | 1.00 | 24.98 | S |

END

Figure 10 (1 of 142)

|  |  | Atom Type | Res. | MOL. | Res. No. | x | y | z | OCC. | B |  |
|---|---|---|---|---|---|---|---|---|---|---|---|
| ATOM | 1 | CB | LYS | A | 2 | 37.607 | 47.246 | 111.087 | 1.00 | 24.06 | A |
| ATOM | 2 | CG | LYS | A | 2 | 36.768 | 46.088 | 110.563 | 1.00 | 19.99 | A |
| ATOM | 3 | CD | LYS | A | 2 | 35.527 | 45.860 | 111.461 | 1.00 | 19.87 | A |
| ATOM | 4 | CE | LYS | A | 2 | 34.845 | 44.512 | 111.190 | 1.00 | 14.79 | A |
| ATOM | 5 | NZ | LYS | A | 2 | 33.485 | 44.446 | 111.779 | 1.00 | 12.26 | A |
| ATOM | 6 | C | LYS | A | 2 | 38.479 | 48.423 | 109.036 | 1.00 | 24.36 | A |
| ATOM | 7 | O | LYS | A | 2 | 37.611 | 49.296 | 109.120 | 1.00 | 25.02 | A |
| ATOM | 8 | N | LYS | A | 2 | 39.854 | 48.275 | 111.175 | 1.00 | 22.07 | A |
| ATOM | 9 | CA | LYS | A | 2 | 38.864 | 47.576 | 110.277 | 1.00 | 23.55 | A |
| ATOM | 10 | N | LYS | A | 3 | 39.114 | 48.157 | 107.891 | 1.00 | 22.19 | A |
| ATOM | 11 | CA | LYS | A | 3 | 38.854 | 48.900 | 106.649 | 1.00 | 17.91 | A |
| ATOM | 12 | CB | LYS | A | 3 | 39.884 | 48.527 | 105.591 | 1.00 | 21.64 | A |
| ATOM | 13 | CG | LYS | A | 3 | 41.323 | 48.536 | 106.053 | 1.00 | 24.65 | A |
| ATOM | 14 | CD | LYS | A | 3 | 42.184 | 47.962 | 104.947 | 1.00 | 25.71 | A |
| ATOM | 15 | CE | LYS | A | 3 | 43.566 | 47.520 | 105.387 | 1.00 | 27.37 | A |
| ATOM | 16 | NZ | LYS | A | 3 | 44.236 | 46.836 | 104.221 | 1.00 | 31.90 | A |
| ATOM | 17 | C | LYS | A | 3 | 37.455 | 48.664 | 106.067 | 1.00 | 12.26 | A |

Figure 10 (2 of 142)

| | | | | | | | | | | |
|---|---|---|---|---|---|---|---|---|---|---|
| ATOM | 18 | O | LYS | A | 3 | 37.184 | 47.632 | 105.453 | 1.00 12.26 | A |
| ATOM | 19 | N | ILE | A | 4 | 36.571 | 49.639 | 106.225 | 1.00 12.26 | A |
| ATOM | 20 | CA | ILE | A | 4 | 35.213 | 49.484 | 105.726 | 1.00 12.26 | A |
| ATOM | 21 | CB | ILE | A | 4 | 34.228 | 49.688 | 106.871 | 1.00 12.58 | A |
| ATOM | 22 | CG2 | ILE | A | 4 | 32.780 | 49.710 | 106.356 | 1.00 12.26 | A |
| ATOM | 23 | CG1 | ILE | A | 4 | 34.458 | 48.577 | 107.889 | 1.00 12.26 | A |
| ATOM | 24 | CD1 | ILE | A | 4 | 34.166 | 48.994 | 109.258 | 1.00 15.92 | A |
| ATOM | 25 | C | ILE | A | 4 | 34.812 | 50.382 | 104.573 | 1.00 12.26 | A |
| ATOM | 26 | O | ILE | A | 4 | 35.225 | 51.542 | 104.490 | 1.00 12.26 | A |
| ATOM | 27 | N | GLY | A | 5 | 33.993 | 49.834 | 103.685 | 1.00 12.26 | A |
| ATOM | 28 | CA | GLY | A | 5 | 33.524 | 50.606 | 102.553 | 1.00 19.90 | A |
| ATOM | 29 | C | GLY | A | 5 | 32.033 | 50.890 | 102.619 | 1.00 22.34 | A |
| ATOM | 30 | O | GLY | A | 5 | 31.197 | 49.998 | 102.404 | 1.00 27.22 | A |
| ATOM | 31 | N | ILE | A | 6 | 31.681 | 52.130 | 102.938 | 1.00 20.62 | A |
| ATOM | 32 | CA | ILE | A | 6 | 30.275 | 52.482 | 102.998 | 1.00 18.60 | A |
| ATOM | 33 | CB | ILE | A | 6 | 30.082 | 53.810 | 103.732 | 1.00 14.68 | A |
| ATOM | 34 | CG2 | ILE | A | 6 | 28.651 | 54.301 | 103.597 | 1.00 12.26 | A |
| ATOM | 35 | CG1 | ILE | A | 6 | 30.450 | 53.598 | 105.192 | 1.00 21.13 | A |
| ATOM | 36 | CD1 | ILE | A | 6 | 30.253 | 54.787 | 106.047 | 1.00 27.92 | A |
| ATOM | 37 | C | ILE | A | 6 | 29.728 | 52.543 | 101.576 | 1.00 15.35 | A |
| ATOM | 38 | O | ILE | A | 6 | 30.234 | 53.266 | 100.716 | 1.00 22.66 | A |
| ATOM | 39 | N | PHE | A | 7 | 28.695 | 51.760 | 101.328 | 1.00 12.26 | A |
| ATOM | 40 | CA | PHE | A | 7 | 28.108 | 51.708 | 100.011 | 1.00 12.26 | A |
| ATOM | 41 | CB | PHE | A | 7 | 28.223 | 50.270 | 99.488 | 1.00 12.26 | A |
| ATOM | 42 | CG | PHE | A | 7 | 27.813 | 50.086 | 98.054 | 1.00 12.26 | A |
| ATOM | 43 | CD1 | PHE | A | 7 | 28.045 | 51.068 | 97.106 | 1.00 12.26 | A |
| ATOM | 44 | CD2 | PHE | A | 7 | 27.246 | 48.894 | 97.647 | 1.00 12.26 | A |
| ATOM | 45 | CE1 | PHE | A | 7 | 27.718 | 50.866 | 95.774 | 1.00 12.26 | A |
| ATOM | 46 | CE2 | PHE | A | 7 | 26.921 | 48.685 | 96.322 | 1.00 12.26 | A |
| ATOM | 47 | CZ | PHE | A | 7 | 27.157 | 49.676 | 95.380 | 1.00 12.26 | A |
| ATOM | 48 | C | PHE | A | 7 | 26.663 | 52.164 | 100.067 | 1.00 12.26 | A |
| ATOM | 49 | O | PHE | A | 7 | 25.744 | 51.364 | 99.913 | 1.00 14.54 | A |
| ATOM | 50 | N | GLY | A | 8 | 26.468 | 53.454 | 100.303 | 1.00 12.26 | A |
| ATOM | 51 | CA | GLY | A | 8 | 25.118 | 53.999 | 100.349 | 1.00 19.94 | A |
| ATOM | 52 | C | GLY | A | 8 | 24.383 | 53.903 | 99.009 | 1.00 20.97 | A |
| ATOM | 53 | O | GLY | A | 8 | 25.013 | 53.900 | 97.943 | 1.00 27.50 | A |
| ATOM | 54 | N | GLY | A | 9 | 23.051 | 53.828 | 99.071 | 1.00 19.62 | A |
| ATOM | 55 | CA | GLY | A | 9 | 22.221 | 53.726 | 97.873 | 1.00 18.62 | A |
| ATOM | 56 | C | GLY | A | 9 | 20.766 | 53.577 | 98.287 | 1.00 21.49 | A |
| ATOM | 57 | O | GLY | A | 9 | 20.499 | 53.233 | 99.439 | 1.00 25.38 | A |
| ATOM | 58 | N | THR | A | 10 | 19.813 | 53.842 | 97.398 | 1.00 21.52 | A |
| ATOM | 59 | CA | THR | A | 10 | 18.417 | 53.689 | 97.801 | 1.00 22.05 | A |
| ATOM | 60 | CB | THR | A | 10 | 17.466 | 54.705 | 97.093 | 1.00 23.31 | A |
| ATOM | 61 | OG1 | THR | A | 10 | 17.036 | 54.180 | 95.830 | 1.00 31.15 | A |
| ATOM | 62 | CG2 | THR | A | 10 | 18.164 | 56.013 | 96.850 | 1.00 22.10 | A |
| ATOM | 63 | C | THR | A | 10 | 17.969 | 52.270 | 97.472 | 1.00 19.72 | A |
| ATOM | 64 | O | THR | A | 10 | 16.931 | 51.813 | 97.940 | 1.00 22.90 | A |
| ATOM | 65 | N | PHE | A | 11 | 18.761 | 51.585 | 96.653 | 1.00 14.01 | A |
| ATOM | 66 | CA | PHE | A | 11 | 18.462 | 50.214 | 96.260 | 1.00 15.05 | A |
| ATOM | 67 | CB | PHE | A | 11 | 18.916 | 49.281 | 97.360 | 1.00 12.26 | A |
| ATOM | 68 | CG | PHE | A | 11 | 20.322 | 49.491 | 97.770 | 1.00 12.26 | A |
| ATOM | 69 | CD1 | PHE | A | 11 | 20.617 | 49.942 | 99.049 | 1.00 12.26 | A |
| ATOM | 70 | CD2 | PHE | A | 11 | 21.357 | 49.216 | 96.888 | 1.00 12.26 | A |
| ATOM | 71 | CE1 | PHE | A | 11 | 21.927 | 50.114 | 99.454 | 1.00 12.26 | A |
| ATOM | 72 | CE2 | PHE | A | 11 | 22.656 | 49.382 | 97.278 | 1.00 12.26 | A |
| ATOM | 73 | CZ | PHE | A | 11 | 22.946 | 49.838 | 98.574 | 1.00 12.30 | A |
| ATOM | 74 | C | PHE | A | 11 | 16.978 | 49.951 | 95.994 | 1.00 15.17 | A |
| ATOM | 75 | O | PHE | A | 11 | 16.372 | 49.098 | 96.646 | 1.00 21.44 | A |
| ATOM | 76 | N | ASP | A | 12 | 16.394 | 50.645 | 95.027 | 1.00 12.26 | A |
| ATOM | 77 | CA | ASP | A | 12 | 14.978 | 50.473 | 94.772 | 1.00 12.26 | A |
| ATOM | 78 | CB | ASP | A | 12 | 14.281 | 51.794 | 95.137 | 1.00 21.59 | A |
| ATOM | 79 | CG | ASP | A | 12 | 12.813 | 51.819 | 94.766 | 1.00 26.34 | A |
| ATOM | 80 | OD1 | ASP | A | 12 | 12.143 | 50.785 | 94.923 | 1.00 33.01 | A |
| ATOM | 81 | OD2 | ASP | A | 12 | 12.315 | 52.884 | 94.333 | 1.00 31.26 | A |
| ATOM | 82 | C | ASP | A | 12 | 14.721 | 50.025 | 93.335 | 1.00 15.16 | A |
| ATOM | 83 | O | ASP | A | 12 | 14.295 | 50.807 | 92.475 | 1.00 13.47 | A |

Figure 10 (3 of 142)

```
ATOM    84  N   PRO A  13      14.935  48.725  93.062  1.00 13.36      A
ATOM    85  CD  PRO A  13      14.580  48.134  91.757  1.00 12.26      A
ATOM    86  CA  PRO A  13      15.381  47.675  93.980  1.00 12.26      A
ATOM    87  CB  PRO A  13      14.617  46.469  93.466  1.00 13.94      A
ATOM    88  CG  PRO A  13      14.782  46.636  91.991  1.00 12.26      A
ATOM    89  C   PRO A  13      16.889  47.467  93.904  1.00 12.26      A
ATOM    90  O   PRO A  13      17.571  48.176  93.188  1.00 15.44      A
ATOM    91  N   PRO A  14      17.430  46.486  94.641  1.00 12.26      A
ATOM    92  CD  PRO A  14      16.841  45.626  95.667  1.00 12.26      A
ATOM    93  CA  PRO A  14      18.870  46.252  94.589  1.00 12.26      A
ATOM    94  CB  PRO A  14      19.177  45.629  95.945  1.00 12.26      A
ATOM    95  CG  PRO A  14      17.898  45.693  96.693  1.00 13.21      A
ATOM    96  C   PRO A  14      19.044  45.233  93.494  1.00 14.43      A
ATOM    97  O   PRO A  14      18.169  44.381  93.335  1.00 12.26      A
ATOM    98  N   HIS A  15      20.140  45.298  92.745  1.00 13.18      A
ATOM    99  CA  HIS A  15      20.351  44.329  91.670  1.00 13.07      A
ATOM   100  CB  HIS A  15      19.995  44.944  90.321  1.00 17.23      A
ATOM   101  CG  HIS A  15      20.574  46.308  90.124  1.00 21.66      A
ATOM   102  CD2 HIS A  15      19.982  47.503  89.894  1.00 26.91      A
ATOM   103  ND1 HIS A  15      21.926  46.560  90.211  1.00 24.08      A
ATOM   104  CE1 HIS A  15      22.141  47.853  90.047  1.00 29.49      A
ATOM   105  NE2 HIS A  15      20.978  48.448  89.854  1.00 29.02      A
ATOM   106  C   HIS A  15      21.779  43.843  91.634  1.00 12.26      A
ATOM   107  O   HIS A  15      22.609  44.277  92.432  1.00 12.26      A
ATOM   108  N   ASN A  16      22.063  42.948  90.700  1.00 12.26      A
ATOM   109  CA  ASN A  16      23.397  42.405  90.575  1.00 12.26      A
ATOM   110  CB  ASN A  16      23.461  41.476  89.378  1.00 19.99      A
ATOM   111  CG  ASN A  16      22.570  40.276  89.551  1.00 24.21      A
ATOM   112  OD1 ASN A  16      22.530  39.659  90.628  1.00 29.42      A
ATOM   113  ND2 ASN A  16      21.846  39.923  88.491  1.00 27.97      A
ATOM   114  C   ASN A  16      24.453  43.485  90.457  1.00 12.26      A
ATOM   115  O   ASN A  16      25.431  43.492  91.199  1.00 12.26      A
ATOM   116  N   GLY A  17      24.255  44.399  89.522  1.00 15.98      A
ATOM   117  CA  GLY A  17      25.212  45.474  89.361  1.00 21.10      A
ATOM   118  C   GLY A  17      25.776  45.967  90.685  1.00 22.48      A
ATOM   119  O   GLY A  17      26.972  46.231  90.781  1.00 23.67      A
ATOM   120  N   HIS A  18      24.927  46.112  91.699  1.00 16.91      A
ATOM   121  CA  HIS A  18      25.382  46.549  93.008  1.00 17.92      A
ATOM   122  CB  HIS A  18      24.202  46.707  93.950  1.00 12.26      A
ATOM   123  CG  HIS A  18      23.277  47.815  93.574  1.00 16.34      A
ATOM   124  CD2 HIS A  18      23.522  49.073  93.139  1.00 18.58      A
ATOM   125  ND1 HIS A  18      21.907  47.697  93.654  1.00 17.64      A
ATOM   126  CE1 HIS A  18      21.348  48.835  93.284  1.00 16.77      A
ATOM   127  NE2 HIS A  18      22.306  49.688  92.967  1.00 18.00      A
ATOM   128  C   HIS A  18      26.308  45.472  93.552  1.00 15.65      A
ATOM   129  O   HIS A  18      27.476  45.734  93.853  1.00 17.42      A
ATOM   130  N   LEU A  19      25.783  44.252  93.652  1.00 12.26      A
ATOM   131  CA  LEU A  19      26.537  43.117  94.170  1.00 12.26      A
ATOM   132  CB  LEU A  19      25.743  41.833  93.961  1.00 12.26      A
ATOM   133  CG  LEU A  19      24.434  41.788  94.737  1.00 14.23      A
ATOM   134  CD1 LEU A  19      23.641  40.569  94.361  1.00 12.26      A
ATOM   135  CD2 LEU A  19      24.741  41.803  96.213  1.00 16.53      A
ATOM   136  C   LEU A  19      27.925  42.959  93.570  1.00 12.26      A
ATOM   137  O   LEU A  19      28.883  42.698  94.291  1.00 12.26      A
ATOM   138  N   LEU A  20      28.033  43.122  92.253  1.00 17.08      A
ATOM   139  CA  LEU A  20      29.316  42.979  91.574  1.00 17.17      A
ATOM   140  CB  LEU A  20      29.134  42.913  90.056  1.00 12.26      A
ATOM   141  CG  LEU A  20      30.422  42.636  89.280  1.00 12.26      A
ATOM   142  CD1 LEU A  20      31.020  41.328  89.756  1.00 12.26      A
ATOM   143  CD2 LEU A  20      30.137  42.566  87.789  1.00 15.52      A
ATOM   144  C   LEU A  20      30.264  44.108  91.923  1.00 15.38      A
ATOM   145  O   LEU A  20      31.424  43.852  92.227  1.00 19.23      A
ATOM   146  N   MET A  21      29.783  45.349  91.901  1.00 22.43      A
ATOM   147  CA  MET A  21      30.659  46.477  92.219  1.00 21.03      A
ATOM   148  CB  MET A  21      29.972  47.821  91.937  1.00 19.23      A
ATOM   149  CG  MET A  21      30.555  48.540  90.718  1.00 17.81      A
```

Figure 10 (4 of 142)

| ATOM | 150 | SD | MET | A | 21 | 30.471 | 47.518 | 89.207 | 1.00 | 17.41 | A |
| --- | --- | --- | --- | --- | --- | --- | --- | --- | --- | --- | --- |
| ATOM | 151 | CE | MET | A | 21 | 30.761 | 48.659 | 87.862 | 1.00 | 24.63 | A |
| ATOM | 152 | C | MET | A | 21 | 31.149 | 46.421 | 93.659 | 1.00 | 24.67 | A |
| ATOM | 153 | O | MET | A | 21 | 32.331 | 46.607 | 93.935 | 1.00 | 26.59 | A |
| ATOM | 154 | N | ALA | A | 22 | 30.245 | 46.149 | 94.583 | 1.00 | 18.53 | A |
| ATOM | 155 | CA | ALA | A | 22 | 30.634 | 46.072 | 95.976 | 1.00 | 12.26 | A |
| ATOM | 156 | CB | ALA | A | 22 | 29.390 | 45.794 | 96.838 | 1.00 | 12.26 | A |
| ATOM | 157 | C | ALA | A | 22 | 31.677 | 44.966 | 96.157 | 1.00 | 12.26 | A |
| ATOM | 158 | O | ALA | A | 22 | 32.724 | 45.170 | 96.767 | 1.00 | 12.26 | A |
| ATOM | 159 | N | ASN | A | 23 | 31.386 | 43.800 | 95.590 | 1.00 | 12.26 | A |
| ATOM | 160 | CA | ASN | A | 23 | 32.253 | 42.640 | 95.720 | 1.00 | 12.26 | A |
| ATOM | 161 | CB | ASN | A | 23 | 31.573 | 41.398 | 95.144 | 1.00 | 12.26 | A |
| ATOM | 162 | CG | ASN | A | 23 | 32.422 | 40.147 | 95.296 | 1.00 | 12.26 | A |
| ATOM | 163 | OD1 | ASN | A | 23 | 32.946 | 39.602 | 94.314 | 1.00 | 12.26 | A |
| ATOM | 164 | ND2 | ASN | A | 23 | 32.573 | 39.688 | 96.534 | 1.00 | 12.26 | A |
| ATOM | 165 | C | ASN | A | 23 | 33.600 | 42.825 | 95.073 | 1.00 | 12.26 | A |
| ATOM | 166 | O | ASN | A | 23 | 34.581 | 42.231 | 95.519 | 1.00 | 12.81 | A |
| ATOM | 167 | N | GLU | A | 24 | 33.644 | 43.630 | 94.014 | 1.00 | 12.26 | A |
| ATOM | 168 | CA | GLU | A | 24 | 34.895 | 43.912 | 93.303 | 1.00 | 12.26 | A |
| ATOM | 169 | CB | GLU | A | 24 | 34.634 | 44.359 | 91.869 | 1.00 | 12.26 | A |
| ATOM | 170 | CG | GLU | A | 24 | 34.034 | 43.304 | 90.957 | 1.00 | 17.06 | A |
| ATOM | 171 | CD | GLU | A | 24 | 34.951 | 42.115 | 90.784 | 1.00 | 17.79 | A |
| ATOM | 172 | OE1 | GLU | A | 24 | 36.188 | 42.352 | 90.786 | 1.00 | 13.68 | A |
| ATOM | 173 | OE2 | GLU | A | 24 | 34.436 | 40.967 | 90.644 | 1.00 | 20.22 | A |
| ATOM | 174 | C | GLU | A | 24 | 35.632 | 45.028 | 94.028 | 1.00 | 12.26 | A |
| ATOM | 175 | O | GLU | A | 24 | 36.838 | 44.962 | 94.218 | 1.00 | 16.18 | A |
| ATOM | 176 | N | VAL | A | 25 | 34.915 | 46.074 | 94.409 | 1.00 | 12.26 | A |
| ATOM | 177 | CA | VAL | A | 25 | 35.567 | 47.138 | 95.136 | 1.00 | 12.26 | A |
| ATOM | 178 | CB | VAL | A | 25 | 34.589 | 48.205 | 95.600 | 1.00 | 12.26 | A |
| ATOM | 179 | CG1 | VAL | A | 25 | 35.177 | 48.941 | 96.770 | 1.00 | 12.26 | A |
| ATOM | 180 | CG2 | VAL | A | 25 | 34.322 | 49.191 | 94.493 | 1.00 | 12.26 | A |
| ATOM | 181 | C | VAL | A | 25 | 36.149 | 46.484 | 96.373 | 1.00 | 12.26 | A |
| ATOM | 182 | O | VAL | A | 25 | 37.284 | 46.767 | 96.764 | 1.00 | 13.79 | A |
| ATOM | 183 | N | LEU | A | 26 | 35.360 | 45.597 | 96.983 | 1.00 | 13.63 | A |
| ATOM | 184 | CA | LEU | A | 26 | 35.784 | 44.907 | 98.193 | 1.00 | 12.26 | A |
| ATOM | 185 | CB | LEU | A | 26 | 34.883 | 43.707 | 98.497 | 1.00 | 17.52 | A |
| ATOM | 186 | CG | LEU | A | 26 | 35.284 | 42.869 | 99.730 | 1.00 | 16.70 | A |
| ATOM | 187 | CD1 | LEU | A | 26 | 35.141 | 43.689 | 101.005 | 1.00 | 12.26 | A |
| ATOM | 188 | CD2 | LEU | A | 26 | 34.421 | 41.623 | 99.802 | 1.00 | 18.84 | A |
| ATOM | 189 | C | LEU | A | 26 | 37.207 | 44.430 | 98.069 | 1.00 | 13.73 | A |
| ATOM | 190 | O | LEU | A | 26 | 38.011 | 44.688 | 98.958 | 1.00 | 15.80 | A |
| ATOM | 191 | N | TYR | A | 27 | 37.502 | 43.734 | 96.967 | 1.00 | 12.26 | A |
| ATOM | 192 | CA | TYR | A | 27 | 38.839 | 43.198 | 96.681 | 1.00 | 12.26 | A |
| ATOM | 193 | CB | TYR | A | 27 | 38.772 | 42.226 | 95.503 | 1.00 | 12.26 | A |
| ATOM | 194 | CG | TYR | A | 27 | 40.130 | 41.754 | 95.040 | 1.00 | 12.65 | A |
| ATOM | 195 | CD1 | TYR | A | 27 | 40.864 | 40.870 | 95.801 | 1.00 | 16.93 | A |
| ATOM | 196 | CE1 | TYR | A | 27 | 42.106 | 40.446 | 95.403 | 1.00 | 13.82 | A |
| ATOM | 197 | CD2 | TYR | A | 27 | 40.687 | 42.201 | 93.860 | 1.00 | 12.26 | A |
| ATOM | 198 | CE2 | TYR | A | 27 | 41.936 | 41.775 | 93.463 | 1.00 | 12.26 | A |
| ATOM | 199 | CZ | TYR | A | 27 | 42.629 | 40.898 | 94.242 | 1.00 | 12.26 | A |
| ATOM | 200 | OH | TYR | A | 27 | 43.849 | 40.439 | 93.871 | 1.00 | 14.74 | A |
| ATOM | 201 | C | TYR | A | 27 | 39.858 | 44.285 | 96.331 | 1.00 | 12.26 | A |
| ATOM | 202 | O | TYR | A | 27 | 40.903 | 44.429 | 96.973 | 1.00 | 12.26 | A |
| ATOM | 203 | N | GLN | A | 28 | 39.520 | 45.044 | 95.300 | 1.00 | 12.26 | A |
| ATOM | 204 | CA | GLN | A | 28 | 40.354 | 46.107 | 94.779 | 1.00 | 12.26 | A |
| ATOM | 205 | CB | GLN | A | 28 | 39.643 | 46.765 | 93.605 | 1.00 | 12.26 | A |
| ATOM | 206 | CG | GLN | A | 28 | 40.580 | 47.269 | 92.567 | 1.00 | 12.26 | A |
| ATOM | 207 | CD | GLN | A | 28 | 41.586 | 46.225 | 92.213 | 1.00 | 16.21 | A |
| ATOM | 208 | OE1 | GLN | A | 28 | 41.228 | 45.128 | 91.783 | 1.00 | 17.85 | A |
| ATOM | 209 | NE2 | GLN | A | 28 | 42.858 | 46.542 | 92.407 | 1.00 | 17.67 | A |
| ATOM | 210 | C | GLN | A | 28 | 40.809 | 47.176 | 95.759 | 1.00 | 12.26 | A |
| ATOM | 211 | O | GLN | A | 28 | 41.966 | 47.570 | 95.712 | 1.00 | 12.26 | A |
| ATOM | 212 | N | ALA | A | 29 | 39.916 | 47.668 | 96.620 | 1.00 | 12.26 | A |
| ATOM | 213 | CA | ALA | A | 29 | 40.292 | 48.697 | 97.597 | 1.00 | 12.26 | A |
| ATOM | 214 | CB | ALA | A | 29 | 39.082 | 49.567 | 97.946 | 1.00 | 12.26 | A |
| ATOM | 215 | C | ALA | A | 29 | 40.870 | 48.028 | 98.860 | 1.00 | 16.40 | A |

Figure 10 (5 of 142)

| ATOM | 216 | O | ALA | A | 29 | 41.218 | 48.700 | 99.843 | 1.00 | 17.65 | A |
| --- | --- | --- | --- | --- | --- | --- | --- | --- | --- | --- | --- |
| ATOM | 217 | N | GLY | A | 30 | 40.976 | 46.699 | 98.819 | 1.00 | 20.05 | A |
| ATOM | 218 | CA | GLY | A | 30 | 41.515 | 45.953 | 99.939 | 1.00 | 16.91 | A |
| ATOM | 219 | C | GLY | A | 30 | 40.727 | 46.115 | 101.226 | 1.00 | 16.67 | A |
| ATOM | 220 | O | GLY | A | 30 | 41.305 | 46.223 | 102.303 | 1.00 | 18.96 | A |
| ATOM | 221 | N | LEU | A | 31 | 39.406 | 46.095 | 101.129 | 1.00 | 12.26 | A |
| ATOM | 222 | CA | LEU | A | 31 | 38.567 | 46.271 | 102.298 | 1.00 | 12.26 | A |
| ATOM | 223 | CB | LEU | A | 31 | 37.262 | 46.932 | 101.872 | 1.00 | 12.26 | A |
| ATOM | 224 | CG | LEU | A | 31 | 37.393 | 48.221 | 101.056 | 1.00 | 12.26 | A |
| ATOM | 225 | CD1 | LEU | A | 31 | 35.995 | 48.691 | 100.652 | 1.00 | 12.26 | A |
| ATOM | 226 | CD2 | LEU | A | 31 | 38.148 | 49.281 | 101.846 | 1.00 | 12.26 | A |
| ATOM | 227 | C | LEU | A | 31 | 38.259 | 44.983 | 103.041 | 1.00 | 12.26 | A |
| ATOM | 228 | O | LEU | A | 31 | 38.463 | 43.903 | 102.519 | 1.00 | 16.68 | A |
| ATOM | 229 | N | ASP | A | 32 | 37.757 | 45.113 | 104.266 | 1.00 | 14.08 | A |
| ATOM | 230 | CA | ASP | A | 32 | 37.378 | 43.978 | 105.095 | 1.00 | 14.68 | A |
| ATOM | 231 | CB | ASP | A | 32 | 37.575 | 44.319 | 106.556 | 1.00 | 12.26 | A |
| ATOM | 232 | CG | ASP | A | 32 | 39.028 | 44.417 | 106.925 | 1.00 | 17.82 | A |
| ATOM | 233 | OD1 | ASP | A | 32 | 39.726 | 43.371 | 106.895 | 1.00 | 18.44 | A |
| ATOM | 234 | OD2 | ASP | A | 32 | 39.471 | 45.543 | 107.241 | 1.00 | 16.63 | A |
| ATOM | 235 | C | ASP | A | 32 | 35.921 | 43.620 | 104.863 | 1.00 | 15.01 | A |
| ATOM | 236 | O | ASP | A | 32 | 35.583 | 42.454 | 104.701 | 1.00 | 18.26 | A |
| ATOM | 237 | N | GLU | A | 33 | 35.054 | 44.624 | 104.861 | 1.00 | 12.26 | A |
| ATOM | 238 | CA | GLU | A | 33 | 33.642 | 44.389 | 104.623 | 1.00 | 15.69 | A |
| ATOM | 239 | CB | GLU | A | 33 | 32.943 | 44.016 | 105.932 | 1.00 | 19.11 | A |
| ATOM | 240 | CG | GLU | A | 33 | 33.763 | 44.321 | 107.175 | 1.00 | 29.42 | A |
| ATOM | 241 | CD | GLU | A | 33 | 33.112 | 43.813 | 108.457 | 1.00 | 34.24 | A |
| ATOM | 242 | OE1 | GLU | A | 33 | 32.077 | 44.394 | 108.865 | 1.00 | 33.31 | A |
| ATOM | 243 | OE2 | GLU | A | 33 | 33.639 | 42.831 | 109.049 | 1.00 | 38.40 | A |
| ATOM | 244 | C | GLU | A | 33 | 32.984 | 45.610 | 103.987 | 1.00 | 12.26 | A |
| ATOM | 245 | O | GLU | A | 33 | 33.372 | 46.754 | 104.224 | 1.00 | 13.71 | A |
| ATOM | 246 | N | ILE | A | 34 | 32.002 | 45.344 | 103.142 | 1.00 | 12.26 | A |
| ATOM | 247 | CA | ILE | A | 34 | 31.256 | 46.389 | 102.478 | 1.00 | 12.26 | A |
| ATOM | 248 | CB | ILE | A | 34 | 30.864 | 45.945 | 101.060 | 1.00 | 12.26 | A |
| ATOM | 249 | CG2 | ILE | A | 34 | 30.054 | 47.015 | 100.393 | 1.00 | 12.26 | A |
| ATOM | 250 | CG1 | ILE | A | 34 | 32.117 | 45.621 | 100.249 | 1.00 | 12.26 | A |
| ATOM | 251 | CD1 | ILE | A | 34 | 32.988 | 46.820 | 99.959 | 1.00 | 13.97 | A |
| ATOM | 252 | C | ILE | A | 34 | 29.995 | 46.578 | 103.312 | 1.00 | 13.08 | A |
| ATOM | 253 | O | ILE | A | 34 | 29.440 | 45.613 | 103.837 | 1.00 | 13.44 | A |
| ATOM | 254 | N | TRP | A | 35 | 29.556 | 47.819 | 103.458 | 1.00 | 12.26 | A |
| ATOM | 255 | CA | TRP | A | 35 | 28.342 | 48.098 | 104.216 | 1.00 | 13.75 | A |
| ATOM | 256 | CB | TRP | A | 35 | 28.629 | 49.083 | 105.336 | 1.00 | 12.26 | A |
| ATOM | 257 | CG | TRP | A | 35 | 29.412 | 48.511 | 106.431 | 1.00 | 12.26 | A |
| ATOM | 258 | CD2 | TRP | A | 35 | 29.762 | 49.163 | 107.651 | 1.00 | 12.26 | A |
| ATOM | 259 | CE2 | TRP | A | 35 | 30.573 | 48.277 | 108.381 | 1.00 | 12.26 | A |
| ATOM | 260 | CE3 | TRP | A | 35 | 29.503 | 50.432 | 108.181 | 1.00 | 16.14 | A |
| ATOM | 261 | CD1 | TRP | A | 35 | 29.981 | 47.274 | 106.479 | 1.00 | 12.40 | A |
| ATOM | 262 | NE1 | TRP | A | 35 | 30.681 | 47.124 | 107.653 | 1.00 | 13.42 | A |
| ATOM | 263 | CZ2 | TRP | A | 35 | 31.087 | 48.604 | 109.636 | 1.00 | 12.26 | A |
| ATOM | 264 | CZ3 | TRP | A | 35 | 30.025 | 50.757 | 109.438 | 1.00 | 14.13 | A |
| ATOM | 265 | CH2 | TRP | A | 35 | 30.819 | 49.853 | 110.135 | 1.00 | 12.26 | A |
| ATOM | 266 | C | TRP | A | 35 | 27.249 | 48.671 | 103.321 | 1.00 | 12.26 | A |
| ATOM | 267 | O | TRP | A | 35 | 27.361 | 49.791 | 102.822 | 1.00 | 17.68 | A |
| ATOM | 268 | N | PHE | A | 36 | 26.197 | 47.903 | 103.103 | 1.00 | 12.26 | A |
| ATOM | 269 | CA | PHE | A | 36 | 25.132 | 48.401 | 102.284 | 1.00 | 12.26 | A |
| ATOM | 270 | CB | PHE | A | 36 | 24.350 | 47.243 | 101.698 | 1.00 | 12.26 | A |
| ATOM | 271 | CG | PHE | A | 36 | 25.058 | 46.574 | 100.563 | 1.00 | 17.61 | A |
| ATOM | 272 | CD1 | PHE | A | 36 | 26.385 | 46.192 | 100.692 | 1.00 | 15.01 | A |
| ATOM | 273 | CD2 | PHE | A | 36 | 24.417 | 46.365 | 99.346 | 1.00 | 14.24 | A |
| ATOM | 274 | CE1 | PHE | A | 36 | 27.060 | 45.618 | 99.622 | 1.00 | 15.56 | A |
| ATOM | 275 | CE2 | PHE | A | 36 | 25.089 | 45.790 | 98.268 | 1.00 | 16.06 | A |
| ATOM | 276 | CZ | PHE | A | 36 | 26.405 | 45.417 | 98.401 | 1.00 | 12.26 | A |
| ATOM | 277 | C | PHE | A | 36 | 24.247 | 49.269 | 103.144 | 1.00 | 16.72 | A |
| ATOM | 278 | O | PHE | A | 36 | 23.473 | 48.759 | 103.946 | 1.00 | 15.59 | A |
| ATOM | 279 | N | MET | A | 37 | 24.378 | 50.583 | 102.965 | 1.00 | 18.11 | A |
| ATOM | 280 | CA | MET | A | 37 | 23.613 | 51.591 | 103.696 | 1.00 | 13.26 | A |
| ATOM | 281 | CB | MET | A | 37 | 24.581 | 52.708 | 104.085 | 1.00 | 12.26 | A |

Figure 10 (6 of 142)

```
ATOM    282  CG   MET A  37      24.115  53.648 105.173  1.00 12.26           A
ATOM    283  SD   MET A  37      25.502  54.661 105.844  1.00 12.26           A
ATOM    284  CE   MET A  37      25.659  55.783 104.558  1.00 12.26           A
ATOM    285  C    MET A  37      22.435  52.148 102.855  1.00 12.50           A
ATOM    286  O    MET A  37      22.646  52.865 101.872  1.00 18.49           A
ATOM    287  N    PRO A  38      21.179  51.806 103.224  1.00 12.52           A
ATOM    288  CD   PRO A  38      20.882  50.656 104.085  1.00 12.26           A
ATOM    289  CA   PRO A  38      19.943  52.247 102.544  1.00 14.25           A
ATOM    290  CB   PRO A  38      18.979  51.089 102.781  1.00 12.26           A
ATOM    291  CG   PRO A  38      19.863  49.963 103.266  1.00 12.26           A
ATOM    292  C    PRO A  38      19.357  53.570 103.086  1.00 17.06           A
ATOM    293  O    PRO A  38      19.249  53.773 104.297  1.00 21.88           A
ATOM    294  N    ASN A  39      18.969  54.461 102.181  1.00 16.46           A
ATOM    295  CA   ASN A  39      18.402  55.746 102.570  1.00 19.24           A
ATOM    296  CB   ASN A  39      18.209  56.627 101.361  1.00 26.19           A
ATOM    297  CG   ASN A  39      19.416  56.685 100.520  1.00 33.35           A
ATOM    298  OD1  ASN A  39      20.539  56.789 101.034  1.00 38.43           A
ATOM    299  ND2  ASN A  39      19.219  56.623  99.209  1.00 35.11           A
ATOM    300  C    ASN A  39      17.049  55.625 103.209  1.00 17.74           A
ATOM    301  O    ASN A  39      16.274  54.746 102.854  1.00 14.38           A
ATOM    302  N    GLN A  40      16.746  56.523 104.139  1.00 13.94           A
ATOM    303  CA   GLN A  40      15.431  56.487 104.733  1.00 12.56           A
ATOM    304  CB   GLN A  40      15.359  57.330 105.986  1.00 15.59           A
ATOM    305  CG   GLN A  40      14.032  57.146 106.686  1.00 22.96           A
ATOM    306  CD   GLN A  40      14.152  57.370 108.166  1.00 28.10           A
ATOM    307  OE1  GLN A  40      15.026  56.798 108.815  1.00 29.29           A
ATOM    308  NE2  GLN A  40      13.274  58.202 108.718  1.00 33.44           A
ATOM    309  C    GLN A  40      14.561  57.080 103.661  1.00 12.26           A
ATOM    310  O    GLN A  40      13.524  56.523 103.275  1.00 12.26           A
ATOM    311  N    ILE A  41      15.027  58.226 103.185  1.00 12.26           A
ATOM    312  CA   ILE A  41      14.399  58.961 102.110  1.00 16.75           A
ATOM    313  CB   ILE A  41      13.442  60.061 102.678  1.00 18.14           A
ATOM    314  CG2  ILE A  41      14.096  60.790 103.829  1.00 15.89           A
ATOM    315  CG1  ILE A  41      12.974  60.983 101.553  1.00 20.56           A
ATOM    316  CD1  ILE A  41      11.990  62.039 101.996  1.00 19.94           A
ATOM    317  C    ILE A  41      15.595  59.521 101.305  1.00 16.45           A
ATOM    318  O    ILE A  41      16.435  60.251 101.837  1.00 14.34           A
ATOM    319  N    PRO A  42      15.717  59.125 100.024  1.00 12.86           A
ATOM    320  CD   PRO A  42      14.779  58.280  99.269  1.00 14.92           A
ATOM    321  CA   PRO A  42      16.802  59.573  99.154  1.00 12.26           A
ATOM    322  CB   PRO A  42      16.433  58.967  97.806  1.00 12.26           A
ATOM    323  CG   PRO A  42      15.657  57.762  98.173  1.00 13.00           A
ATOM    324  C    PRO A  42      16.873  61.094  99.085  1.00 14.56           A
ATOM    325  O    PRO A  42      15.891  61.763  98.726  1.00 16.81           A
ATOM    326  N    PRO A  43      18.040  61.662  99.424  1.00 12.26           A
ATOM    327  CD   PRO A  43      19.266  60.976  99.864  1.00 12.26           A
ATOM    328  CA   PRO A  43      18.242  63.113  99.400  1.00 14.10           A
ATOM    329  CB   PRO A  43      19.677  63.279  99.908  1.00 12.26           A
ATOM    330  CG   PRO A  43      20.330  62.006  99.533  1.00 12.26           A
ATOM    331  C    PRO A  43      18.047  63.764  98.050  1.00 14.76           A
ATOM    332  O    PRO A  43      17.307  64.739  97.939  1.00 21.31           A
ATOM    333  N    HIS A  44      18.714  63.231  97.033  1.00 12.26           A
ATOM    334  CA   HIS A  44      18.618  63.795  95.706  1.00 12.26           A
ATOM    335  CB   HIS A  44      19.782  63.346  94.867  1.00 13.64           A
ATOM    336  CG   HIS A  44      19.918  61.868  94.811  1.00 19.28           A
ATOM    337  CD2  HIS A  44      20.265  61.038  93.799  1.00 20.62           A
ATOM    338  ND1  HIS A  44      19.705  61.069  95.912  1.00 20.17           A
ATOM    339  CE1  HIS A  44      19.911  59.807  95.580  1.00 22.66           A
ATOM    340  NE2  HIS A  44      20.250  59.762  94.304  1.00 21.85           A
ATOM    341  C    HIS A  44      17.329  63.495  94.966  1.00 12.26           A
ATOM    342  O    HIS A  44      17.160  63.943  93.839  1.00 19.85           A
ATOM    343  N    LYS A  45      16.415  62.752  95.590  1.00 12.26           A
ATOM    344  CA   LYS A  45      15.115  62.435  94.967  1.00 14.48           A
ATOM    345  CB   LYS A  45      15.194  61.096  94.203  1.00 16.55           A
ATOM    346  CG   LYS A  45      16.325  60.132  94.586  1.00 12.26           A
ATOM    347  CD   LYS A  45      16.663  59.222  93.413  1.00 15.82           A
```

Figure 10 (7 of 142)

| ATOM | 348 | CE  | LYS | A | 45 | 16.977 | 57.803 | 93.850  | 1.00 | 12.26 | A |
|------|-----|-----|-----|---|----|--------|--------|---------|------|-------|---|
| ATOM | 349 | NZ  | LYS | A | 45 | 17.291 | 56.943 | 92.678  | 1.00 | 12.26 | A |
| ATOM | 350 | C   | LYS | A | 45 | 13.897 | 62.396 | 95.893  | 1.00 | 16.37 | A |
| ATOM | 351 | O   | LYS | A | 45 | 13.432 | 61.315 | 96.219  | 1.00 | 12.26 | A |
| ATOM | 352 | N   | GLN | A | 46 | 13.396 | 63.546 | 96.307  | 1.00 | 21.23 | A |
| ATOM | 353 | CA  | GLN | A | 46 | 12.231 | 63.573 | 97.200  | 1.00 | 24.81 | A |
| ATOM | 354 | CB  | GLN | A | 46 | 12.530 | 64.374 | 98.452  | 1.00 | 27.31 | A |
| ATOM | 355 | CG  | GLN | A | 46 | 13.931 | 64.977 | 98.493  | 1.00 | 29.41 | A |
| ATOM | 356 | CD  | GLN | A | 46 | 14.229 | 65.602 | 99.841  | 1.00 | 20.59 | A |
| ATOM | 357 | OE1 | GLN | A | 46 | 15.321 | 66.137 | 100.087 | 1.00 | 20.59 | A |
| ATOM | 358 | NE2 | GLN | A | 46 | 13.254 | 65.531 | 100.738 | 1.00 | 20.59 | A |
| ATOM | 359 | C   | GLN | A | 46 | 11.193 | 64.272 | 96.355  | 1.00 | 27.65 | A |
| ATOM | 360 | O   | GLN | A | 46 | 10.922 | 65.450 | 96.525  | 1.00 | 26.89 | A |
| ATOM | 361 | N   | ASN | A | 47 | 10.673 | 63.536 | 95.388  | 1.00 | 20.59 | A |
| ATOM | 362 | CA  | ASN | A | 47 | 9.743  | 64.109 | 94.458  | 1.00 | 20.59 | A |
| ATOM | 363 | CB  | ASN | A | 47 | 10.402 | 65.454 | 94.055  | 1.00 | 20.59 | A |
| ATOM | 364 | CG  | ASN | A | 47 | 10.783 | 65.522 | 92.604  | 1.00 | 20.59 | A |
| ATOM | 365 | OD1 | ASN | A | 47 | 9.941  | 65.871 | 91.787  | 1.00 | 20.59 | A |
| ATOM | 366 | ND2 | ASN | A | 47 | 12.047 | 65.161 | 92.249  | 1.00 | 20.59 | A |
| ATOM | 367 | C   | ASN | A | 47 | 9.621  | 63.089 | 93.383  | 1.00 | 20.59 | A |
| ATOM | 368 | O   | ASN | A | 47 | 8.860  | 63.230 | 92.409  | 1.00 | 20.59 | A |
| ATOM | 369 | N   | GLU | A | 48 | 10.457 | 62.089 | 93.545  | 1.00 | 29.55 | A |
| ATOM | 370 | CA  | GLU | A | 48 | 10.459 | 60.916 | 92.684  | 1.00 | 31.31 | A |
| ATOM | 371 | CB  | GLU | A | 48 | 11.857 | 60.316 | 92.577  | 1.00 | 37.66 | A |
| ATOM | 372 | CG  | GLU | A | 48 | 12.288 | 59.832 | 91.192  | 1.00 | 44.07 | A |
| ATOM | 373 | CD  | GLU | A | 48 | 13.665 | 60.403 | 90.858  | 1.00 | 50.19 | A |
| ATOM | 374 | OE1 | GLU | A | 48 | 13.759 | 61.655 | 90.772  | 1.00 | 51.99 | A |
| ATOM | 375 | OE2 | GLU | A | 48 | 14.626 | 59.615 | 90.693  | 1.00 | 51.82 | A |
| ATOM | 376 | C   | GLU | A | 48 | 9.659  | 60.103 | 93.688  | 1.00 | 31.97 | A |
| ATOM | 377 | O   | GLU | A | 48 | 9.722  | 60.425 | 94.912  | 1.00 | 27.62 | A |
| ATOM | 378 | N   | ASP | A | 49 | 8.925  | 59.101 | 93.256  | 1.00 | 35.49 | A |
| ATOM | 379 | CA  | ASP | A | 49 | 8.074  | 58.270 | 94.104  | 1.00 | 39.65 | A |
| ATOM | 380 | CB  | ASP | A | 49 | 6.810  | 57.940 | 93.252  | 1.00 | 46.60 | A |
| ATOM | 381 | CG  | ASP | A | 49 | 5.505  | 57.948 | 94.039  | 1.00 | 52.63 | A |
| ATOM | 382 | OD1 | ASP | A | 49 | 4.887  | 59.033 | 94.237  | 1.00 | 54.24 | A |
| ATOM | 383 | OD2 | ASP | A | 49 | 5.181  | 56.851 | 94.525  | 1.00 | 58.53 | A |
| ATOM | 384 | C   | ASP | A | 49 | 8.833  | 56.996 | 94.528  | 1.00 | 38.99 | A |
| ATOM | 385 | O   | ASP | A | 49 | 8.414  | 55.916 | 94.125  | 1.00 | 46.62 | A |
| ATOM | 386 | N   | TYR | A | 50 | 9.876  | 57.107 | 95.353  | 1.00 | 32.72 | A |
| ATOM | 387 | CA  | TYR | A | 50 | 10.823 | 56.036 | 95.776  | 1.00 | 27.30 | A |
| ATOM | 388 | CB  | TYR | A | 50 | 12.056 | 56.703 | 96.361  | 1.00 | 20.34 | A |
| ATOM | 389 | CG  | TYR | A | 50 | 11.653 | 57.553 | 97.548  | 1.00 | 17.80 | A |
| ATOM | 390 | CD1 | TYR | A | 50 | 11.100 | 58.811 | 97.345  | 1.00 | 19.56 | A |
| ATOM | 391 | CE1 | TYR | A | 50 | 10.638 | 59.558 | 98.390  | 1.00 | 19.48 | A |
| ATOM | 392 | CD2 | TYR | A | 50 | 11.708 | 57.073 | 98.866  | 1.00 | 17.26 | A |
| ATOM | 393 | CE2 | TYR | A | 50 | 11.229 | 57.834 | 99.936  | 1.00 | 21.63 | A |
| ATOM | 394 | CZ  | TYR | A | 50 | 10.706 | 59.071 | 99.679  | 1.00 | 19.72 | A |
| ATOM | 395 | OH  | TYR | A | 50 | 10.218 | 59.808 | 100.726 | 1.00 | 24.12 | A |
| ATOM | 396 | C   | TYR | A | 50 | 10.455 | 54.868 | 96.721  | 1.00 | 23.73 | A |
| ATOM | 397 | O   | TYR | A | 50 | 10.964 | 54.857 | 97.841  | 1.00 | 24.04 | A |
| ATOM | 398 | N   | THR | A | 51 | 9.624  | 53.899 | 96.395  | 1.00 | 21.98 | A |
| ATOM | 399 | CA  | THR | A | 51 | 9.271  | 52.833 | 97.360  | 1.00 | 22.93 | A |
| ATOM | 400 | CB  | THR | A | 51 | 9.748  | 51.434 | 96.960  | 1.00 | 19.13 | A |
| ATOM | 401 | OG1 | THR | A | 51 | 11.115 | 51.304 | 97.231  | 1.00 | 22.74 | A |
| ATOM | 402 | CG2 | THR | A | 51 | 9.498  | 51.201 | 95.484  | 1.00 | 16.56 | A |
| ATOM | 403 | C   | THR | A | 51 | 9.576  | 52.978 | 98.858  | 1.00 | 22.35 | A |
| ATOM | 404 | O   | THR | A | 51 | 10.689 | 53.285 | 99.309  | 1.00 | 23.51 | A |
| ATOM | 405 | N   | ASP | A | 52 | 8.521  | 52.644 | 99.606  | 1.00 | 26.40 | A |
| ATOM | 406 | CA  | ASP | A | 52 | 8.365  | 52.703 | 101.056 | 1.00 | 32.18 | A |
| ATOM | 407 | CB  | ASP | A | 52 | 7.135  | 51.891 | 101.372 | 1.00 | 41.16 | A |
| ATOM | 408 | CG  | ASP | A | 52 | 5.916  | 52.442 | 100.664 | 1.00 | 47.31 | A |
| ATOM | 409 | OD1 | ASP | A | 52 | 5.449  | 53.541 | 101.066 | 1.00 | 52.43 | A |
| ATOM | 410 | OD2 | ASP | A | 52 | 5.448  | 51.789 | 99.700  | 1.00 | 52.03 | A |
| ATOM | 411 | C   | ASP | A | 52 | 9.447  | 52.411 | 102.058 | 1.00 | 29.43 | A |
| ATOM | 412 | O   | ASP | A | 52 | 9.177  | 52.543 | 103.252 | 1.00 | 27.19 | A |
| ATOM | 413 | N   | SER | A | 53 | 10.642 | 52.036 | 101.603 | 1.00 | 25.15 | A |

Figure 10 (8 of 142)

| | | | | | | | | | | |
|---|---|---|---|---|---|---|---|---|---|---|
| ATOM | 414 | CA | SER | A | 53 | 11.769 | 51.771 | 102.503 | 1.00 20.41 | A |
| ATOM | 415 | CB | SER | A | 53 | 11.809 | 52.769 | 103.667 | 1.00 17.53 | A |
| ATOM | 416 | OG | SER | A | 53 | 12.729 | 52.342 | 104.655 | 1.00 12.26 | A |
| ATOM | 417 | C | SER | A | 53 | 11.775 | 50.381 | 103.078 | 1.00 19.57 | A |
| ATOM | 418 | O | SER | A | 53 | 12.773 | 49.668 | 102.982 | 1.00 20.73 | A |
| ATOM | 419 | N | PHE | A | 54 | 10.675 | 50.001 | 103.706 | 1.00 19.07 | A |
| ATOM | 420 | CA | PHE | A | 54 | 10.577 | 48.666 | 104.282 | 1.00 18.54 | A |
| ATOM | 421 | CB | PHE | A | 54 | 9.168 | 48.429 | 104.850 | 1.00 18.27 | A |
| ATOM | 422 | CG | PHE | A | 54 | 8.956 | 47.040 | 105.379 | 1.00 17.57 | A |
| ATOM | 423 | CD1 | PHE | A | 54 | 9.786 | 46.535 | 106.364 | 1.00 16.60 | A |
| ATOM | 424 | CD2 | PHE | A | 54 | 7.932 | 46.233 | 104.883 | 1.00 18.17 | A |
| ATOM | 425 | CE1 | PHE | A | 54 | 9.603 | 45.250 | 106.852 | 1.00 13.65 | A |
| ATOM | 426 | CE2 | PHE | A | 54 | 7.743 | 44.939 | 105.369 | 1.00 15.76 | A |
| ATOM | 427 | CZ | PHE | A | 54 | 8.581 | 44.453 | 106.354 | 1.00 13.61 | A |
| ATOM | 428 | C | PHE | A | 54 | 10.880 | 47.617 | 103.203 | 1.00 15.98 | A |
| ATOM | 429 | O | PHE | A | 54 | 11.608 | 46.653 | 103.449 | 1.00 16.14 | A |
| ATOM | 430 | N | HIS | A | 55 | 10.340 | 47.811 | 102.006 | 1.00 12.26 | A |
| ATOM | 431 | CA | HIS | A | 55 | 10.582 | 46.834 | 100.959 | 1.00 14.16 | A |
| ATOM | 432 | CB | HIS | A | 55 | 9.548 | 47.011 | 99.854 | 1.00 17.37 | A |
| ATOM | 433 | CG | HIS | A | 55 | 8.147 | 46.901 | 100.356 | 1.00 19.12 | A |
| ATOM | 434 | CD2 | HIS | A | 55 | 7.671 | 46.719 | 101.612 | 1.00 20.78 | A |
| ATOM | 435 | ND1 | HIS | A | 55 | 7.046 | 47.004 | 99.534 | 1.00 19.34 | A |
| ATOM | 436 | CE1 | HIS | A | 55 | 5.951 | 46.892 | 100.265 | 1.00 22.22 | A |
| ATOM | 437 | NE2 | HIS | A | 55 | 6.303 | 46.719 | 101.528 | 1.00 22.45 | A |
| ATOM | 438 | C | HIS | A | 55 | 12.002 | 46.908 | 100.408 | 1.00 16.56 | A |
| ATOM | 439 | O | HIS | A | 55 | 12.550 | 45.899 | 99.916 | 1.00 18.35 | A |
| ATOM | 440 | N | ARG | A | 56 | 12.592 | 48.104 | 100.488 | 1.00 15.17 | A |
| ATOM | 441 | CA | ARG | A | 56 | 13.956 | 48.302 | 100.023 | 1.00 13.82 | A |
| ATOM | 442 | CB | ARG | A | 56 | 14.265 | 49.793 | 99.924 | 1.00 12.26 | A |
| ATOM | 443 | CG | ARG | A | 56 | 13.672 | 50.392 | 98.662 | 1.00 12.26 | A |
| ATOM | 444 | CD | ARG | A | 56 | 13.377 | 51.863 | 98.816 | 1.00 14.55 | A |
| ATOM | 445 | NE | ARG | A | 56 | 14.565 | 52.618 | 99.179 | 1.00 13.92 | A |
| ATOM | 446 | CZ | ARG | A | 56 | 14.611 | 53.482 | 100.188 | 1.00 14.09 | A |
| ATOM | 447 | NH1 | ARG | A | 56 | 13.526 | 53.678 | 100.921 | 1.00 12.26 | A |
| ATOM | 448 | NH2 | ARG | A | 56 | 15.731 | 54.157 | 100.452 | 1.00 19.04 | A |
| ATOM | 449 | C | ARG | A | 56 | 14.898 | 47.578 | 100.978 | 1.00 13.97 | A |
| ATOM | 450 | O | ARG | A | 56 | 15.768 | 46.804 | 100.550 | 1.00 15.46 | A |
| ATOM | 451 | N | VAL | A | 57 | 14.719 | 47.790 | 102.272 | 1.00 12.26 | A |
| ATOM | 452 | CA | VAL | A | 57 | 15.568 | 47.082 | 103.206 | 1.00 12.94 | A |
| ATOM | 453 | CB | VAL | A | 57 | 15.320 | 47.497 | 104.652 | 1.00 13.82 | A |
| ATOM | 454 | CG1 | VAL | A | 57 | 16.215 | 46.695 | 105.557 | 1.00 17.18 | A |
| ATOM | 455 | CG2 | VAL | A | 57 | 15.605 | 48.957 | 104.836 | 1.00 16.77 | A |
| ATOM | 456 | C | VAL | A | 57 | 15.307 | 45.572 | 103.093 | 1.00 14.79 | A |
| ATOM | 457 | O | VAL | A | 57 | 16.194 | 44.770 | 103.320 | 1.00 15.99 | A |
| ATOM | 458 | N | GLU | A | 58 | 14.097 | 45.166 | 102.745 | 1.00 16.99 | A |
| ATOM | 459 | CA | GLU | A | 58 | 13.846 | 43.728 | 102.618 | 1.00 20.41 | A |
| ATOM | 460 | CB | GLU | A | 58 | 12.335 | 43.414 | 102.480 | 1.00 23.67 | A |
| ATOM | 461 | CG | GLU | A | 58 | 11.570 | 43.363 | 103.811 | 1.00 27.15 | A |
| ATOM | 462 | CD | GLU | A | 58 | 12.326 | 42.564 | 104.877 | 1.00 32.20 | A |
| ATOM | 463 | OE1 | GLU | A | 58 | 12.372 | 41.312 | 104.766 | 1.00 32.93 | A |
| ATOM | 464 | OE2 | GLU | A | 58 | 12.888 | 43.196 | 105.809 | 1.00 34.84 | A |
| ATOM | 465 | C | GLU | A | 58 | 14.576 | 43.194 | 101.399 | 1.00 20.07 | A |
| ATOM | 466 | O | GLU | A | 58 | 15.341 | 42.227 | 101.489 | 1.00 23.29 | A |
| ATOM | 467 | N | MET | A | 59 | 14.338 | 43.830 | 100.254 | 1.00 17.97 | A |
| ATOM | 468 | CA | MET | A | 59 | 14.972 | 43.389 | 99.027 | 1.00 16.07 | A |
| ATOM | 469 | CB | MET | A | 59 | 14.550 | 44.286 | 97.843 | 1.00 12.26 | A |
| ATOM | 470 | CG | MET | A | 59 | 13.102 | 44.117 | 97.462 | 1.00 12.26 | A |
| ATOM | 471 | SD | MET | A | 59 | 12.713 | 44.700 | 95.867 | 1.00 12.26 | A |
| ATOM | 472 | CE | MET | A | 59 | 12.453 | 46.328 | 96.262 | 1.00 12.26 | A |
| ATOM | 473 | C | MET | A | 59 | 16.484 | 43.402 | 99.238 | 1.00 15.47 | A |
| ATOM | 474 | O | MET | A | 59 | 17.201 | 42.504 | 98.764 | 1.00 18.27 | A |
| ATOM | 475 | N | LEU | A | 60 | 16.953 | 44.397 | 99.992 | 1.00 12.26 | A |
| ATOM | 476 | CA | LEU | A | 60 | 18.371 | 44.520 | 100.233 | 1.00 12.26 | A |
| ATOM | 477 | CB | LEU | A | 60 | 18.710 | 45.806 | 100.986 | 1.00 12.26 | A |
| ATOM | 478 | CG | LEU | A | 60 | 19.851 | 46.671 | 100.392 | 1.00 15.55 | A |
| ATOM | 479 | CD1 | LEU | A | 60 | 20.524 | 47.477 | 101.501 | 1.00 13.77 | A |

Figure 10 (9 of 142)

```
ATOM    480  CD2 LEU A  60      20.917  45.803  99.700  1.00 14.48      A
ATOM    481  C   LEU A  60      18.889  43.342 101.010  1.00 13.32      A
ATOM    482  O   LEU A  60      19.933  42.788 100.671  1.00 17.32      A
ATOM    483  N   LYS A  61      18.163  42.951 102.053  1.00 16.10      A
ATOM    484  CA  LYS A  61      18.585  41.829 102.882  1.00 18.19      A
ATOM    485  CB  LYS A  61      17.659  41.681 104.077  1.00 16.02      A
ATOM    486  CG  LYS A  61      18.301  42.197 105.351  1.00 19.49      A
ATOM    487  CD  LYS A  61      17.285  42.768 106.337  1.00 21.51      A
ATOM    488  CE  LYS A  61      16.186  41.775 106.682  1.00 24.78      A
ATOM    489  NZ  LYS A  61      15.237  42.331 107.684  1.00 23.35      A
ATOM    490  C   LYS A  61      18.656  40.536 102.095  1.00 18.19      A
ATOM    491  O   LYS A  61      19.509  39.681 102.350  1.00 22.82      A
ATOM    492  N   LEU A  62      17.780  40.399 101.116  1.00 17.30      A
ATOM    493  CA  LEU A  62      17.803  39.206 100.320  1.00 19.64      A
ATOM    494  CB  LEU A  62      16.527  39.104  99.521  1.00 21.52      A
ATOM    495  CG  LEU A  62      15.311  38.852 100.386  1.00 20.74      A
ATOM    496  CD1 LEU A  62      14.057  39.207  99.616  1.00 26.62      A
ATOM    497  CD2 LEU A  62      15.299  37.407 100.791  1.00 21.20      A
ATOM    498  C   LEU A  62      18.982  39.205  99.372  1.00 18.99      A
ATOM    499  O   LEU A  62      19.622  38.174  99.175  1.00 26.17      A
ATOM    500  N   ALA A  63      19.275  40.359  98.784  1.00 16.47      A
ATOM    501  CA  ALA A  63      20.362  40.425  97.819  1.00 16.74      A
ATOM    502  CB  ALA A  63      20.297  41.713  97.020  1.00 15.06      A
ATOM    503  C   ALA A  63      21.736  40.280  98.419  1.00 17.19      A
ATOM    504  O   ALA A  63      22.689  39.995  97.691  1.00 21.99      A
ATOM    505  N   ILE A  64      21.870  40.450  99.726  1.00 12.26      A
ATOM    506  CA  ILE A  64      23.206  40.334 100.270  1.00 17.72      A
ATOM    507  CB  ILE A  64      23.640  41.635 100.901  1.00 14.27      A
ATOM    508  CG2 ILE A  64      23.500  42.750  99.909  1.00 15.98      A
ATOM    509  CG1 ILE A  64      22.769  41.942 102.100  1.00 12.26      A
ATOM    510  CD1 ILE A  64      23.298  43.076 102.907  1.00 12.26      A
ATOM    511  C   ILE A  64      23.449  39.231 101.272  1.00 18.56      A
ATOM    512  O   ILE A  64      24.558  39.096 101.799  1.00 19.52      A
ATOM    513  N   GLN A  65      22.437  38.420 101.534  1.00 23.19      A
ATOM    514  CA  GLN A  65      22.627  37.360 102.511  1.00 25.07      A
ATOM    515  CB  GLN A  65      21.339  36.536 102.685  1.00 29.84      A
ATOM    516  CG  GLN A  65      20.799  35.909 101.416  1.00 32.52      A
ATOM    517  CD  GLN A  65      19.518  35.129 101.666  1.00 36.51      A
ATOM    518  OE1 GLN A  65      18.526  35.663 102.184  1.00 35.15      A
ATOM    519  NE2 GLN A  65      19.534  33.852 101.299  1.00 41.10      A
ATOM    520  C   GLN A  65      23.784  36.429 102.179  1.00 21.74      A
ATOM    521  O   GLN A  65      24.664  36.201 103.009  1.00 21.10      A
ATOM    522  N   SER A  66      23.797  35.915 100.961  1.00 15.50      A
ATOM    523  CA  SER A  66      24.819  34.963 100.575  1.00 18.83      A
ATOM    524  CB  SER A  66      24.528  34.447  99.183  1.00 20.91      A
ATOM    525  OG  SER A  66      24.152  35.540  98.381  1.00 26.36      A
ATOM    526  C   SER A  66      26.261  35.404 100.639  1.00 18.34      A
ATOM    527  O   SER A  66      27.147  34.574 100.426  1.00 19.25      A
ATOM    528  N   ASN A  67      26.522  36.676 100.930  1.00 20.95      A
ATOM    529  CA  ASN A  67      27.912  37.128 100.997  1.00 19.64      A
ATOM    530  CB  ASN A  67      28.157  38.250  99.987  1.00 24.88      A
ATOM    531  CG  ASN A  67      29.638  38.547  99.790  1.00 27.90      A
ATOM    532  OD1 ASN A  67      30.045  39.046  98.739  1.00 31.20      A
ATOM    533  ND2 ASN A  67      30.445  38.258 100.803  1.00 27.64      A
ATOM    534  C   ASN A  67      28.316  37.565 102.399  1.00 17.04      A
ATOM    535  O   ASN A  67      27.895  38.604 102.890  1.00 12.26      A
ATOM    536  N   PRO A  68      29.169  36.763 103.051  1.00 16.02      A
ATOM    537  CD  PRO A  68      29.917  35.677 102.390  1.00 15.77      A
ATOM    538  CA  PRO A  68      29.678  36.992 104.407  1.00 15.73      A
ATOM    539  CB  PRO A  68      30.800  35.978 104.545  1.00 12.68      A
ATOM    540  CG  PRO A  68      30.426  34.899 103.563  1.00 17.17      A
ATOM    541  C   PRO A  68      30.217  38.382 104.586  1.00 16.02      A
ATOM    542  O   PRO A  68      30.043  38.978 105.645  1.00 18.07      A
ATOM    543  N   SER A  69      30.877  38.889 103.546  1.00 14.78      A
ATOM    544  CA  SER A  69      31.487  40.201 103.608  1.00 14.40      A
ATOM    545  CB  SER A  69      32.711  40.212 102.710  1.00 12.26      A
```

Figure 10 (10 of 142)

| ATOM | 546 | OG | SER | A | 69 | 33.674 | 39.329 | 103.262 | 1.00 | 12.26 | A |
| --- | --- | --- | --- | --- | --- | --- | --- | --- | --- | --- | --- |
| ATOM | 547 | C | SER | A | 69 | 30.586 | 41.394 | 103.343 | 1.00 | 18.73 | A |
| ATOM | 548 | O | SER | A | 69 | 31.024 | 42.539 | 103.402 | 1.00 | 20.65 | A |
| ATOM | 549 | N | PHE | A | 70 | 29.319 | 41.135 | 103.075 | 1.00 | 18.95 | A |
| ATOM | 550 | CA | PHE | A | 70 | 28.398 | 42.231 | 102.868 | 1.00 | 23.62 | A |
| ATOM | 551 | CB | PHE | A | 70 | 27.482 | 41.956 | 101.677 | 1.00 | 17.70 | A |
| ATOM | 552 | CG | PHE | A | 70 | 28.176 | 42.022 | 100.346 | 1.00 | 15.04 | A |
| ATOM | 553 | CD1 | PHE | A | 70 | 27.471 | 41.814 | 99.170 | 1.00 | 16.23 | A |
| ATOM | 554 | CD2 | PHE | A | 70 | 29.525 | 42.305 | 100.267 | 1.00 | 12.26 | A |
| ATOM | 555 | CE1 | PHE | A | 70 | 28.106 | 41.890 | 97.946 | 1.00 | 12.26 | A |
| ATOM | 556 | CE2 | PHE | A | 70 | 30.152 | 42.378 | 99.052 | 1.00 | 12.26 | A |
| ATOM | 557 | CZ | PHE | A | 70 | 29.446 | 42.173 | 97.894 | 1.00 | 12.26 | A |
| ATOM | 558 | C | PHE | A | 70 | 27.574 | 42.355 | 104.135 | 1.00 | 23.18 | A |
| ATOM | 559 | O | PHE | A | 70 | 27.109 | 41.350 | 104.682 | 1.00 | 22.28 | A |
| ATOM | 560 | N | LYS | A | 71 | 27.408 | 43.588 | 104.605 | 1.00 | 22.30 | A |
| ATOM | 561 | CA | LYS | A | 71 | 26.638 | 43.850 | 105.809 | 1.00 | 17.84 | A |
| ATOM | 562 | CB | LYS | A | 71 | 27.580 | 44.068 | 106.976 | 1.00 | 20.44 | A |
| ATOM | 563 | CG | LYS | A | 71 | 28.512 | 42.885 | 107.101 | 1.00 | 23.74 | A |
| ATOM | 564 | CD | LYS | A | 71 | 28.975 | 42.626 | 108.521 | 1.00 | 23.26 | A |
| ATOM | 565 | CE | LYS | A | 71 | 29.555 | 41.214 | 108.656 | 1.00 | 25.27 | A |
| ATOM | 566 | NZ | LYS | A | 71 | 28.532 | 40.172 | 108.320 | 1.00 | 20.24 | A |
| ATOM | 567 | C | LYS | A | 71 | 25.697 | 45.020 | 105.675 | 1.00 | 14.85 | A |
| ATOM | 568 | O | LYS | A | 71 | 26.045 | 46.045 | 105.092 | 1.00 | 13.94 | A |
| ATOM | 569 | N | LEU | A | 72 | 24.494 | 44.838 | 106.210 | 1.00 | 12.30 | A |
| ATOM | 570 | CA | LEU | A | 72 | 23.463 | 45.860 | 106.188 | 1.00 | 12.26 | A |
| ATOM | 571 | CB | LEU | A | 72 | 22.128 | 45.287 | 106.661 | 1.00 | 12.26 | A |
| ATOM | 572 | CG | LEU | A | 72 | 20.891 | 45.692 | 105.865 | 1.00 | 12.26 | A |
| ATOM | 573 | CD1 | LEU | A | 72 | 19.608 | 45.247 | 106.558 | 1.00 | 12.26 | A |
| ATOM | 574 | CD2 | LEU | A | 72 | 20.905 | 47.172 | 105.715 | 1.00 | 13.41 | A |
| ATOM | 575 | C | LEU | A | 72 | 23.892 | 46.934 | 107.159 | 1.00 | 12.26 | A |
| ATOM | 576 | O | LEU | A | 72 | 24.694 | 46.684 | 108.060 | 1.00 | 12.26 | A |
| ATOM | 577 | N | GLU | A | 73 | 23.382 | 48.138 | 106.954 | 1.00 | 14.45 | A |
| ATOM | 578 | CA | GLU | A | 73 | 23.652 | 49.260 | 107.838 | 1.00 | 12.26 | A |
| ATOM | 579 | CB | GLU | A | 73 | 24.934 | 49.992 | 107.447 | 1.00 | 12.26 | A |
| ATOM | 580 | CG | GLU | A | 73 | 25.136 | 51.295 | 108.213 | 1.00 | 27.82 | A |
| ATOM | 581 | CD | GLU | A | 73 | 25.021 | 51.108 | 109.708 | 1.00 | 29.53 | A |
| ATOM | 582 | OE1 | GLU | A | 73 | 25.969 | 50.574 | 110.332 | 1.00 | 32.62 | A |
| ATOM | 583 | OE2 | GLU | A | 73 | 23.961 | 51.488 | 110.247 | 1.00 | 31.16 | A |
| ATOM | 584 | C | GLU | A | 73 | 22.433 | 50.169 | 107.728 | 1.00 | 14.39 | A |
| ATOM | 585 | O | GLU | A | 73 | 22.172 | 50.791 | 106.685 | 1.00 | 19.18 | A |
| ATOM | 586 | N | LEU | A | 74 | 21.669 | 50.216 | 108.811 | 1.00 | 12.26 | A |
| ATOM | 587 | CA | LEU | A | 74 | 20.464 | 51.008 | 108.820 | 1.00 | 14.78 | A |
| ATOM | 588 | CB | LEU | A | 74 | 19.326 | 50.181 | 109.408 | 1.00 | 12.26 | A |
| ATOM | 589 | CG | LEU | A | 74 | 19.134 | 48.860 | 108.658 | 1.00 | 12.26 | A |
| ATOM | 590 | CD1 | LEU | A | 74 | 18.016 | 48.075 | 109.296 | 1.00 | 14.66 | A |
| ATOM | 591 | CD2 | LEU | A | 74 | 18.800 | 49.124 | 107.202 | 1.00 | 13.26 | A |
| ATOM | 592 | C | LEU | A | 74 | 20.623 | 52.326 | 109.560 | 1.00 | 14.55 | A |
| ATOM | 593 | O | LEU | A | 74 | 19.640 | 52.986 | 109.888 | 1.00 | 16.36 | A |
| ATOM | 594 | N | VAL | A | 75 | 21.866 | 52.722 | 109.791 | 1.00 | 12.26 | A |
| ATOM | 595 | CA | VAL | A | 75 | 22.131 | 53.962 | 110.494 | 1.00 | 13.47 | A |
| ATOM | 596 | CB | VAL | A | 75 | 23.617 | 54.324 | 110.455 | 1.00 | 12.26 | A |
| ATOM | 597 | CG1 | VAL | A | 75 | 24.088 | 54.445 | 108.999 | 1.00 | 12.26 | A |
| ATOM | 598 | CG2 | VAL | A | 75 | 23.842 | 55.635 | 111.223 | 1.00 | 12.26 | A |
| ATOM | 599 | C | VAL | A | 75 | 21.355 | 55.166 | 109.963 | 1.00 | 19.94 | A |
| ATOM | 600 | O | VAL | A | 75 | 21.038 | 56.092 | 110.723 | 1.00 | 18.88 | A |
| ATOM | 601 | N | GLU | A | 76 | 21.077 | 55.198 | 108.666 | 1.00 | 23.32 | A |
| ATOM | 602 | CA | GLU | A | 76 | 20.325 | 56.334 | 108.145 | 1.00 | 25.83 | A |
| ATOM | 603 | CB | GLU | A | 76 | 20.578 | 56.511 | 106.644 | 1.00 | 32.38 | A |
| ATOM | 604 | CG | GLU | A | 76 | 21.837 | 57.298 | 106.321 | 1.00 | 37.75 | A |
| ATOM | 605 | CD | GLU | A | 76 | 22.026 | 57.505 | 104.830 | 1.00 | 42.60 | A |
| ATOM | 606 | OE1 | GLU | A | 76 | 22.856 | 58.370 | 104.463 | 1.00 | 41.86 | A |
| ATOM | 607 | OE2 | GLU | A | 76 | 21.350 | 56.803 | 104.030 | 1.00 | 46.88 | A |
| ATOM | 608 | C | GLU | A | 76 | 18.836 | 56.139 | 108.426 | 1.00 | 23.36 | A |
| ATOM | 609 | O | GLU | A | 76 | 18.059 | 57.096 | 108.474 | 1.00 | 23.79 | A |
| ATOM | 610 | N | MET | A | 77 | 18.447 | 54.884 | 108.614 | 1.00 | 21.07 | A |
| ATOM | 611 | CA | MET | A | 77 | 17.072 | 54.549 | 108.909 | 1.00 | 23.31 | A |

Figure 10 (11 of 142)

| | | | | | | | | | | |
|---|---|---|---|---|---|---|---|---|---|---|
| ATOM | 612 | CB | MET | A | 77 | 16.856 | 53.067 | 108.712 | 1.00 18.58 | A |
| ATOM | 613 | CG | MET | A | 77 | 16.968 | 52.687 | 107.302 | 1.00 14.47 | A |
| ATOM | 614 | SD | MET | A | 77 | 15.358 | 52.667 | 106.621 | 1.00 16.84 | A |
| ATOM | 615 | CE | MET | A | 77 | 15.012 | 54.196 | 106.430 | 1.00 23.30 | A |
| ATOM | 616 | C | MET | A | 77 | 16.898 | 54.885 | 110.356 | 1.00 27.67 | A |
| ATOM | 617 | O | MET | A | 77 | 15.826 | 54.712 | 110.909 | 1.00 28.77 | A |
| ATOM | 618 | N | GLU | A | 78 | 17.964 | 55.378 | 110.970 | 1.00 36.25 | A |
| ATOM | 619 | CA | GLU | A | 78 | 17.924 | 55.694 | 112.379 | 1.00 45.54 | A |
| ATOM | 620 | CB | GLU | A | 78 | 19.334 | 55.826 | 112.936 | 1.00 48.37 | A |
| ATOM | 621 | CG | GLU | A | 78 | 19.531 | 55.089 | 114.254 | 1.00 49.43 | A |
| ATOM | 622 | CD | GLU | A | 78 | 20.956 | 54.615 | 114.441 | 1.00 49.39 | A |
| ATOM | 623 | OE1 | GLU | A | 78 | 21.850 | 55.485 | 114.453 | 1.00 49.96 | A |
| ATOM | 624 | OE2 | GLU | A | 78 | 21.182 | 53.388 | 114.563 | 1.00 47.45 | A |
| ATOM | 625 | C | GLU | A | 78 | 17.122 | 56.927 | 112.703 | 1.00 51.33 | A |
| ATOM | 626 | O | GLU | A | 78 | 17.406 | 57.604 | 113.689 | 1.00 50.23 | A |
| ATOM | 627 | N | ARG | A | 79 | 16.146 | 57.224 | 111.845 | 1.00 59.27 | A |
| ATOM | 628 | CA | ARG | A | 79 | 15.205 | 58.333 | 112.028 | 1.00 65.56 | A |
| ATOM | 629 | CB | ARG | A | 79 | 15.281 | 58.876 | 113.465 | 1.00 73.76 | A |
| ATOM | 630 | CG | ARG | A | 79 | 13.915 | 59.170 | 114.059 | 1.00 81.52 | A |
| ATOM | 631 | CD | ARG | A | 79 | 13.013 | 57.955 | 113.895 | 1.00 85.78 | A |
| ATOM | 632 | NE | ARG | A | 79 | 11.605 | 58.330 | 113.909 | 1.00 92.07 | A |
| ATOM | 633 | CZ | ARG | A | 79 | 10.610 | 57.507 | 113.599 | 1.00 93.99 | A |
| ATOM | 634 | NH1 | ARG | A | 79 | 10.873 | 56.255 | 113.253 | 1.00 93.48 | A |
| ATOM | 635 | NH2 | ARG | A | 79 | 9.353 | 57.937 | 113.625 | 1.00 95.75 | A |
| ATOM | 636 | C | ARG | A | 79 | 15.123 | 59.519 | 111.069 | 1.00 63.12 | A |
| ATOM | 637 | O | ARG | A | 79 | 16.117 | 60.100 | 110.643 | 1.00 60.28 | A |
| ATOM | 638 | N | GLU | A | 80 | 13.861 | 59.847 | 110.801 | 1.00 61.10 | A |
| ATOM | 639 | CA | GLU | A | 80 | 13.334 | 60.917 | 109.951 | 1.00 59.27 | A |
| ATOM | 640 | CB | GLU | A | 80 | 12.209 | 61.596 | 110.720 | 1.00 61.96 | A |
| ATOM | 641 | CG | GLU | A | 80 | 11.324 | 60.611 | 111.476 | 1.00 65.05 | A |
| ATOM | 642 | CD | GLU | A | 80 | 10.461 | 61.292 | 112.523 | 1.00 66.44 | A |
| ATOM | 643 | OE1 | GLU | A | 80 | 11.039 | 61.891 | 113.463 | 1.00 64.79 | A |
| ATOM | 644 | OE2 | GLU | A | 80 | 9.214 | 61.226 | 112.402 | 1.00 67.27 | A |
| ATOM | 645 | C | GLU | A | 80 | 14.193 | 62.006 | 109.322 | 1.00 56.64 | A |
| ATOM | 646 | O | GLU | A | 80 | 15.203 | 62.437 | 109.879 | 1.00 58.21 | A |
| ATOM | 647 | N | GLY | A | 81 | 13.730 | 62.473 | 108.164 | 1.00 50.13 | A |
| ATOM | 648 | CA | GLY | A | 81 | 14.408 | 63.530 | 107.436 | 1.00 44.38 | A |
| ATOM | 649 | C | GLY | A | 81 | 15.216 | 63.006 | 106.270 | 1.00 39.78 | A |
| ATOM | 650 | O | GLY | A | 81 | 15.635 | 61.851 | 106.295 | 1.00 44.37 | A |
| ATOM | 651 | N | PRO | A | 82 | 15.441 | 63.821 | 105.225 | 1.00 36.43 | A |
| ATOM | 652 | CD | PRO | A | 82 | 14.750 | 65.094 | 104.978 | 1.00 34.97 | A |
| ATOM | 653 | CA | PRO | A | 82 | 16.217 | 63.424 | 104.042 | 1.00 31.54 | A |
| ATOM | 654 | CB | PRO | A | 82 | 16.199 | 64.683 | 103.192 | 1.00 33.13 | A |
| ATOM | 655 | CG | PRO | A | 82 | 14.835 | 65.212 | 103.466 | 1.00 33.63 | A |
| ATOM | 656 | C | PRO | A | 82 | 17.627 | 62.983 | 104.425 | 1.00 27.80 | A |
| ATOM | 657 | O | PRO | A | 82 | 18.352 | 63.722 | 105.091 | 1.00 27.06 | A |
| ATOM | 658 | N | SER | A | 83 | 18.009 | 61.783 | 103.991 | 1.00 22.13 | A |
| ATOM | 659 | CA | SER | A | 83 | 19.304 | 61.205 | 104.323 | 1.00 20.64 | A |
| ATOM | 660 | CB | SER | A | 83 | 19.246 | 59.696 | 104.086 | 1.00 21.51 | A |
| ATOM | 661 | OG | SER | A | 83 | 18.228 | 59.092 | 104.870 | 1.00 24.87 | A |
| ATOM | 662 | C | SER | A | 83 | 20.530 | 61.790 | 103.618 | 1.00 18.35 | A |
| ATOM | 663 | O | SER | A | 83 | 21.013 | 61.241 | 102.625 | 1.00 21.90 | A |
| ATOM | 664 | N | TYR | A | 84 | 21.049 | 62.887 | 104.161 | 1.00 16.23 | A |
| ATOM | 665 | CA | TYR | A | 84 | 22.213 | 63.555 | 103.588 | 1.00 15.05 | A |
| ATOM | 666 | CB | TYR | A | 84 | 22.212 | 65.032 | 103.952 | 1.00 15.93 | A |
| ATOM | 667 | CG | TYR | A | 84 | 21.129 | 65.829 | 103.281 | 1.00 14.54 | A |
| ATOM | 668 | CD1 | TYR | A | 84 | 20.386 | 66.747 | 104.005 | 1.00 14.67 | A |
| ATOM | 669 | CE1 | TYR | A | 84 | 19.383 | 67.487 | 103.414 | 1.00 12.26 | A |
| ATOM | 670 | CD2 | TYR | A | 84 | 20.846 | 65.670 | 101.928 | 1.00 12.26 | A |
| ATOM | 671 | CE2 | TYR | A | 84 | 19.841 | 66.411 | 101.320 | 1.00 12.26 | A |
| ATOM | 672 | CZ | TYR | A | 84 | 19.108 | 67.321 | 102.071 | 1.00 12.26 | A |
| ATOM | 673 | OH | TYR | A | 84 | 18.093 | 68.063 | 101.483 | 1.00 12.26 | A |
| ATOM | 674 | C | TYR | A | 84 | 23.514 | 62.938 | 104.068 | 1.00 15.24 | A |
| ATOM | 675 | O | TYR | A | 84 | 23.842 | 62.995 | 105.252 | 1.00 12.26 | A |
| ATOM | 676 | N | THR | A | 85 | 24.272 | 62.383 | 103.135 | 1.00 14.17 | A |
| ATOM | 677 | CA | THR | A | 85 | 25.513 | 61.732 | 103.479 | 1.00 15.38 | A |

Figure 10 (12 of 142)

| ATOM | 678 | CB | THR | A | 85 | 26.274 | 61.350 | 102.220 | 1.00 | 15.69 | A |
|------|-----|-----|-----|---|----|--------|--------|---------|------|-------|---|
| ATOM | 679 | OG1 | THR | A | 85 | 25.400 | 60.595 | 101.379 | 1.00 | 15.02 | A |
| ATOM | 680 | CG2 | THR | A | 85 | 27.501 | 60.504 | 102.565 | 1.00 | 12.26 | A |
| ATOM | 681 | C | THR | A | 85 | 26.406 | 62.529 | 104.412 | 1.00 | 13.98 | A |
| ATOM | 682 | O | THR | A | 85 | 26.998 | 61.954 | 105.321 | 1.00 | 16.39 | A |
| ATOM | 683 | N | PHE | A | 86 | 26.509 | 63.838 | 104.223 | 1.00 | 12.26 | A |
| ATOM | 684 | CA | PHE | A | 86 | 27.375 | 64.585 | 105.126 | 1.00 | 12.26 | A |
| ATOM | 685 | CB | PHE | A | 86 | 27.337 | 66.080 | 104.891 | 1.00 | 12.26 | A |
| ATOM | 686 | CG | PHE | A | 86 | 27.963 | 66.851 | 106.019 | 1.00 | 12.26 | A |
| ATOM | 687 | CD1 | PHE | A | 86 | 29.345 | 66.916 | 106.143 | 1.00 | 18.19 | A |
| ATOM | 688 | CD2 | PHE | A | 86 | 27.180 | 67.406 | 107.027 | 1.00 | 18.47 | A |
| ATOM | 689 | CE1 | PHE | A | 86 | 29.944 | 67.513 | 107.245 | 1.00 | 18.19 | A |
| ATOM | 690 | CE2 | PHE | A | 86 | 27.774 | 68.004 | 108.135 | 1.00 | 21.24 | A |
| ATOM | 691 | CZ | PHE | A | 86 | 29.161 | 68.053 | 108.240 | 1.00 | 20.69 | A |
| ATOM | 692 | C | PHE | A | 86 | 26.966 | 64.374 | 106.564 | 1.00 | 16.16 | A |
| ATOM | 693 | O | PHE | A | 86 | 27.811 | 64.222 | 107.440 | 1.00 | 18.76 | A |
| ATOM | 694 | N | ASP | A | 87 | 25.659 | 64.420 | 106.802 | 1.00 | 21.71 | A |
| ATOM | 695 | CA | ASP | A | 87 | 25.115 | 64.224 | 108.134 | 1.00 | 22.50 | A |
| ATOM | 696 | CB | ASP | A | 87 | 23.610 | 64.478 | 108.133 | 1.00 | 26.20 | A |
| ATOM | 697 | CG | ASP | A | 87 | 23.273 | 65.945 | 108.208 | 1.00 | 27.39 | A |
| ATOM | 698 | OD1 | ASP | A | 87 | 22.079 | 66.281 | 108.093 | 1.00 | 27.30 | A |
| ATOM | 699 | OD2 | ASP | A | 87 | 24.202 | 66.760 | 108.391 | 1.00 | 28.01 | A |
| ATOM | 700 | C | ASP | A | 87 | 25.401 | 62.809 | 108.606 | 1.00 | 24.94 | A |
| ATOM | 701 | O | ASP | A | 87 | 25.892 | 62.617 | 109.716 | 1.00 | 26.59 | A |
| ATOM | 702 | N | THR | A | 88 | 25.108 | 61.820 | 107.759 | 1.00 | 19.13 | A |
| ATOM | 703 | CA | THR | A | 88 | 25.348 | 60.426 | 108.120 | 1.00 | 14.63 | A |
| ATOM | 704 | CB | THR | A | 88 | 24.819 | 59.452 | 107.048 | 1.00 | 12.26 | A |
| ATOM | 705 | OG1 | THR | A | 88 | 23.390 | 59.539 | 106.975 | 1.00 | 12.26 | A |
| ATOM | 706 | CG2 | THR | A | 88 | 25.193 | 58.023 | 107.407 | 1.00 | 12.26 | A |
| ATOM | 707 | C | THR | A | 88 | 26.824 | 60.139 | 108.379 | 1.00 | 14.37 | A |
| ATOM | 708 | O | THR | A | 88 | 27.196 | 59.752 | 109.486 | 1.00 | 19.32 | A |
| ATOM | 709 | N | VAL | A | 89 | 27.670 | 60.325 | 107.374 | 1.00 | 14.59 | A |
| ATOM | 710 | CA | VAL | A | 89 | 29.097 | 60.084 | 107.574 | 1.00 | 17.23 | A |
| ATOM | 711 | CB | VAL | A | 89 | 29.934 | 60.612 | 106.399 | 1.00 | 20.51 | A |
| ATOM | 712 | CG1 | VAL | A | 89 | 31.425 | 60.580 | 106.772 | 1.00 | 21.51 | A |
| ATOM | 713 | CG2 | VAL | A | 89 | 29.661 | 59.781 | 105.138 | 1.00 | 20.14 | A |
| ATOM | 714 | C | VAL | A | 89 | 29.594 | 60.755 | 108.858 | 1.00 | 15.92 | A |
| ATOM | 715 | O | VAL | A | 89 | 30.381 | 60.181 | 109.597 | 1.00 | 16.33 | A |
| ATOM | 716 | N | SER | A | 90 | 29.148 | 61.976 | 109.121 | 1.00 | 17.82 | A |
| ATOM | 717 | CA | SER | A | 90 | 29.563 | 62.658 | 110.338 | 1.00 | 17.58 | A |
| ATOM | 718 | CB | SER | A | 90 | 28.722 | 63.926 | 110.575 | 1.00 | 24.35 | A |
| ATOM | 719 | OG | SER | A | 90 | 28.898 | 64.920 | 109.573 | 1.00 | 25.89 | A |
| ATOM | 720 | C | SER | A | 90 | 29.315 | 61.685 | 111.484 | 1.00 | 17.43 | A |
| ATOM | 721 | O | SER | A | 90 | 30.240 | 61.256 | 112.184 | 1.00 | 18.25 | A |
| ATOM | 722 | N | LEU | A | 91 | 28.047 | 61.332 | 111.650 | 1.00 | 12.26 | A |
| ATOM | 723 | CA | LEU | A | 91 | 27.644 | 60.428 | 112.708 | 1.00 | 16.17 | A |
| ATOM | 724 | CB | LEU | A | 91 | 26.153 | 60.091 | 112.585 | 1.00 | 12.26 | A |
| ATOM | 725 | CG | LEU | A | 91 | 25.633 | 58.985 | 113.506 | 1.00 | 12.26 | A |
| ATOM | 726 | CD1 | LEU | A | 91 | 26.069 | 59.227 | 114.949 | 1.00 | 12.26 | A |
| ATOM | 727 | CD2 | LEU | A | 91 | 24.122 | 58.926 | 113.394 | 1.00 | 12.66 | A |
| ATOM | 728 | C | LEU | A | 91 | 28.475 | 59.154 | 112.715 | 1.00 | 17.98 | A |
| ATOM | 729 | O | LEU | A | 91 | 29.052 | 58.797 | 113.748 | 1.00 | 19.06 | A |
| ATOM | 730 | N | LEU | A | 92 | 28.547 | 58.476 | 111.570 | 1.00 | 17.16 | A |
| ATOM | 731 | CA | LEU | A | 92 | 29.313 | 57.236 | 111.479 | 1.00 | 16.51 | A |
| ATOM | 732 | CB | LEU | A | 92 | 29.320 | 56.705 | 110.035 | 1.00 | 13.13 | A |
| ATOM | 733 | CG | LEU | A | 92 | 27.958 | 56.172 | 109.555 | 1.00 | 12.26 | A |
| ATOM | 734 | CD1 | LEU | A | 92 | 27.982 | 55.876 | 108.065 | 1.00 | 13.23 | A |
| ATOM | 735 | CD2 | LEU | A | 92 | 27.592 | 54.910 | 110.334 | 1.00 | 12.27 | A |
| ATOM | 736 | C | LEU | A | 92 | 30.741 | 57.377 | 112.010 | 1.00 | 17.89 | A |
| ATOM | 737 | O | LEU | A | 92 | 31.168 | 56.568 | 112.829 | 1.00 | 18.97 | A |
| ATOM | 738 | N | LYS | A | 93 | 31.477 | 58.399 | 111.572 | 1.00 | 20.97 | A |
| ATOM | 739 | CA | LYS | A | 93 | 32.857 | 58.591 | 112.048 | 1.00 | 23.72 | A |
| ATOM | 740 | CB | LYS | A | 93 | 33.474 | 59.831 | 111.411 | 1.00 | 21.88 | A |
| ATOM | 741 | CG | LYS | A | 93 | 33.776 | 59.635 | 109.955 | 1.00 | 22.94 | A |
| ATOM | 742 | CD | LYS | A | 93 | 34.452 | 60.853 | 109.372 | 1.00 | 25.57 | A |
| ATOM | 743 | CE | LYS | A | 93 | 35.864 | 61.025 | 109.914 | 1.00 | 28.31 | A |

Figure 10 (13 of 142)

| | | | | | | | | | | |
|---|---|---|---|---|---|---|---|---|---|---|
| ATOM | 744 | NZ | LYS | A | 93 | 36.766 | 59.928 | 109.458 | 1.00 28.31 | A |
| ATOM | 745 | C | LYS | A | 93 | 32.947 | 58.700 | 113.571 | 1.00 26.02 | A |
| ATOM | 746 | O | LYS | A | 93 | 34.034 | 58.668 | 114.160 | 1.00 22.23 | A |
| ATOM | 747 | N | GLN | A | 94 | 31.786 | 58.827 | 114.201 | 1.00 25.21 | A |
| ATOM | 748 | CA | GLN | A | 94 | 31.715 | 58.928 | 115.642 | 1.00 26.60 | A |
| ATOM | 749 | CB | GLN | A | 94 | 30.587 | 59.872 | 116.023 | 1.00 30.00 | A |
| ATOM | 750 | CG | GLN | A | 94 | 30.927 | 60.709 | 117.220 | 1.00 42.54 | A |
| ATOM | 751 | CD | GLN | A | 94 | 29.925 | 61.816 | 117.434 | 1.00 49.34 | A |
| ATOM | 752 | OE1 | GLN | A | 94 | 28.717 | 61.562 | 117.555 | 1.00 50.37 | A |
| ATOM | 753 | NE2 | GLN | A | 94 | 30.415 | 63.063 | 117.480 | 1.00 52.04 | A |
| ATOM | 754 | C | GLN | A | 94 | 31.506 | 57.534 | 116.255 | 1.00 24.75 | A |
| ATOM | 755 | O | GLN | A | 94 | 32.241 | 57.128 | 117.152 | 1.00 23.05 | A |
| ATOM | 756 | N | ARG | A | 95 | 30.513 | 56.794 | 115.779 | 1.00 20.27 | A |
| ATOM | 757 | CA | ARG | A | 95 | 30.313 | 55.457 | 116.302 | 1.00 16.84 | A |
| ATOM | 758 | CB | ARG | A | 95 | 29.148 | 54.774 | 115.618 | 1.00 16.92 | A |
| ATOM | 759 | CG | ARG | A | 95 | 27.824 | 55.067 | 116.228 | 1.00 20.30 | A |
| ATOM | 760 | CD | ARG | A | 95 | 26.738 | 54.294 | 115.536 | 1.00 18.10 | A |
| ATOM | 761 | NE | ARG | A | 95 | 25.455 | 54.756 | 116.025 | 1.00 26.17 | A |
| ATOM | 762 | CZ | ARG | A | 95 | 24.294 | 54.299 | 115.587 | 1.00 29.01 | A |
| ATOM | 763 | NH1 | ARG | A | 95 | 24.260 | 53.367 | 114.640 | 1.00 28.91 | A |
| ATOM | 764 | NH2 | ARG | A | 95 | 23.166 | 54.755 | 116.115 | 1.00 34.93 | A |
| ATOM | 765 | C | ARG | A | 95 | 31.537 | 54.593 | 116.068 | 1.00 16.32 | A |
| ATOM | 766 | O | ARG | A | 95 | 31.878 | 53.759 | 116.888 | 1.00 22.75 | A |
| ATOM | 767 | N | TYR | A | 96 | 32.199 | 54.774 | 114.940 | 1.00 17.81 | A |
| ATOM | 768 | CA | TYR | A | 96 | 33.347 | 53.941 | 114.647 | 1.00 18.62 | A |
| ATOM | 769 | CB | TYR | A | 96 | 33.059 | 53.071 | 113.423 | 1.00 18.17 | A |
| ATOM | 770 | CG | TYR | A | 96 | 31.702 | 52.401 | 113.419 | 1.00 16.84 | A |
| ATOM | 771 | CD1 | TYR | A | 96 | 30.580 | 53.058 | 112.923 | 1.00 18.92 | A |
| ATOM | 772 | CE1 | TYR | A | 96 | 29.320 | 52.444 | 112.925 | 1.00 17.49 | A |
| ATOM | 773 | CD2 | TYR | A | 96 | 31.541 | 51.112 | 113.917 | 1.00 16.00 | A |
| ATOM | 774 | CE2 | TYR | A | 96 | 30.290 | 50.488 | 113.925 | 1.00 17.48 | A |
| ATOM | 775 | CZ | TYR | A | 96 | 29.183 | 51.160 | 113.428 | 1.00 17.09 | A |
| ATOM | 776 | OH | TYR | A | 96 | 27.943 | 50.555 | 113.435 | 1.00 21.83 | A |
| ATOM | 777 | C | TYR | A | 96 | 34.592 | 54.759 | 114.391 | 1.00 19.04 | A |
| ATOM | 778 | O | TYR | A | 96 | 35.002 | 54.933 | 113.250 | 1.00 21.44 | A |
| ATOM | 779 | N | PRO | A | 97 | 35.219 | 55.273 | 115.452 | 1.00 24.86 | A |
| ATOM | 780 | CD | PRO | A | 97 | 34.570 | 55.498 | 116.748 | 1.00 23.72 | A |
| ATOM | 781 | CA | PRO | A | 97 | 36.437 | 56.090 | 115.342 | 1.00 28.40 | A |
| ATOM | 782 | CB | PRO | A | 97 | 36.479 | 56.842 | 116.674 | 1.00 24.69 | A |
| ATOM | 783 | CG | PRO | A | 97 | 35.055 | 56.898 | 117.081 | 1.00 26.68 | A |
| ATOM | 784 | C | PRO | A | 97 | 37.728 | 55.320 | 115.099 | 1.00 29.56 | A |
| ATOM | 785 | O | PRO | A | 97 | 38.750 | 55.910 | 114.766 | 1.00 34.86 | A |
| ATOM | 786 | N | ASN | A | 98 | 37.697 | 54.007 | 115.257 | 1.00 33.21 | A |
| ATOM | 787 | CA | ASN | A | 98 | 38.914 | 53.228 | 115.064 | 1.00 35.46 | A |
| ATOM | 788 | CB | ASN | A | 98 | 39.128 | 52.306 | 116.257 | 1.00 40.42 | A |
| ATOM | 789 | CG | ASN | A | 98 | 39.608 | 53.058 | 117.479 | 1.00 42.73 | A |
| ATOM | 790 | OD1 | ASN | A | 98 | 38.998 | 54.046 | 117.906 | 1.00 42.91 | A |
| ATOM | 791 | ND2 | ASN | A | 98 | 40.711 | 52.598 | 118.048 | 1.00 45.88 | A |
| ATOM | 792 | C | ASN | A | 98 | 38.924 | 52.434 | 113.779 | 1.00 31.10 | A |
| ATOM | 793 | O | ASN | A | 98 | 39.891 | 51.733 | 113.465 | 1.00 34.66 | A |
| ATOM | 794 | N | ASP | A | 99 | 37.834 | 52.550 | 113.038 | 1.00 28.98 | A |
| ATOM | 795 | CA | ASP | A | 99 | 37.720 | 51.859 | 111.773 | 1.00 28.14 | A |
| ATOM | 796 | CB | ASP | A | 99 | 36.330 | 51.266 | 111.649 | 1.00 31.66 | A |
| ATOM | 797 | CG | ASP | A | 99 | 36.039 | 50.303 | 112.747 | 1.00 32.99 | A |
| ATOM | 798 | OD1 | ASP | A | 99 | 36.885 | 49.406 | 112.965 | 1.00 35.24 | A |
| ATOM | 799 | OD2 | ASP | A | 99 | 34.973 | 50.450 | 113.381 | 1.00 36.79 | A |
| ATOM | 800 | C | ASP | A | 99 | 38.027 | 52.796 | 110.602 | 1.00 26.57 | A |
| ATOM | 801 | O | ASP | A | 99 | 37.821 | 54.014 | 110.669 | 1.00 22.67 | A |
| ATOM | 802 | N | GLN | A | 100 | 38.541 | 52.216 | 109.529 | 1.00 22.65 | A |
| ATOM | 803 | CA | GLN | A | 100 | 38.892 | 52.988 | 108.358 | 1.00 21.65 | A |
| ATOM | 804 | CB | GLN | A | 100 | 40.108 | 52.340 | 107.713 | 1.00 25.16 | A |
| ATOM | 805 | CG | GLN | A | 100 | 41.141 | 53.311 | 107.189 | 1.00 30.74 | A |
| ATOM | 806 | CD | GLN | A | 100 | 42.402 | 52.601 | 106.742 | 1.00 36.39 | A |
| ATOM | 807 | OE1 | GLN | A | 100 | 43.139 | 52.044 | 107.568 | 1.00 36.23 | A |
| ATOM | 808 | NE2 | GLN | A | 100 | 42.653 | 52.598 | 105.429 | 1.00 38.69 | A |
| ATOM | 809 | C | GLN | A | 100 | 37.689 | 53.000 | 107.416 | 1.00 17.88 | A |

Figure 10 (14 of 142)

| ATOM | 810 | O   | GLN | A | 100 | 37.246 | 51.955 | 106.926 | 1.00 | 14.82 | A |
|------|-----|-----|-----|---|-----|--------|--------|---------|------|-------|---|
| ATOM | 811 | N   | LEU | A | 101 | 37.155 | 54.183 | 107.161 | 1.00 | 15.89 | A |
| ATOM | 812 | CA  | LEU | A | 101 | 35.987 | 54.261 | 106.308 | 1.00 | 16.67 | A |
| ATOM | 813 | CB  | LEU | A | 101 | 34.869 | 54.992 | 107.050 | 1.00 | 20.29 | A |
| ATOM | 814 | CG  | LEU | A | 101 | 34.524 | 54.503 | 108.456 | 1.00 | 22.68 | A |
| ATOM | 815 | CD1 | LEU | A | 101 | 33.339 | 55.290 | 108.982 | 1.00 | 22.70 | A |
| ATOM | 816 | CD2 | LEU | A | 101 | 34.206 | 53.022 | 108.426 | 1.00 | 19.45 | A |
| ATOM | 817 | C   | LEU | A | 101 | 36.164 | 54.883 | 104.928 | 1.00 | 17.33 | A |
| ATOM | 818 | O   | LEU | A | 101 | 36.827 | 55.915 | 104.758 | 1.00 | 18.24 | A |
| ATOM | 819 | N   | PHE | A | 102 | 35.550 | 54.230 | 103.945 | 1.00 | 16.29 | A |
| ATOM | 820 | CA  | PHE | A | 102 | 35.567 | 54.699 | 102.570 | 1.00 | 13.69 | A |
| ATOM | 821 | CB  | PHE | A | 102 | 36.415 | 53.799 | 101.682 | 1.00 | 12.26 | A |
| ATOM | 822 | CG  | PHE | A | 102 | 37.833 | 53.722 | 102.105 | 1.00 | 12.26 | A |
| ATOM | 823 | CD1 | PHE | A | 102 | 38.201 | 52.934 | 103.187 | 1.00 | 13.51 | A |
| ATOM | 824 | CD2 | PHE | A | 102 | 38.805 | 54.494 | 101.468 | 1.00 | 12.26 | A |
| ATOM | 825 | CE1 | PHE | A | 102 | 39.527 | 52.921 | 103.632 | 1.00 | 15.45 | A |
| ATOM | 826 | CE2 | PHE | A | 102 | 40.127 | 54.488 | 101.901 | 1.00 | 12.26 | A |
| ATOM | 827 | CZ  | PHE | A | 102 | 40.492 | 53.704 | 102.984 | 1.00 | 14.43 | A |
| ATOM | 828 | C   | PHE | A | 102 | 34.147 | 54.673 | 102.074 | 1.00 | 13.18 | A |
| ATOM | 829 | O   | PHE | A | 102 | 33.373 | 53.785 | 102.442 | 1.00 | 12.26 | A |
| ATOM | 830 | N   | PHE | A | 103 | 33.804 | 55.662 | 101.258 | 1.00 | 12.26 | A |
| ATOM | 831 | CA  | PHE | A | 103 | 32.478 | 55.731 | 100.680 | 1.00 | 12.26 | A |
| ATOM | 832 | CB  | PHE | A | 103 | 31.929 | 57.136 | 100.786 | 1.00 | 12.26 | A |
| ATOM | 833 | CG  | PHE | A | 103 | 30.455 | 57.195 | 100.685 | 1.00 | 12.26 | A |
| ATOM | 834 | CD1 | PHE | A | 103 | 29.675 | 57.038 | 101.811 | 1.00 | 12.26 | A |
| ATOM | 835 | CD2 | PHE | A | 103 | 29.839 | 57.364 | 99.460  | 1.00 | 12.26 | A |
| ATOM | 836 | CE1 | PHE | A | 103 | 28.298 | 57.047 | 101.728 | 1.00 | 12.26 | A |
| ATOM | 837 | CE2 | PHE | A | 103 | 28.462 | 57.371 | 99.368  | 1.00 | 12.92 | A |
| ATOM | 838 | CZ  | PHE | A | 103 | 27.688 | 57.211 | 100.510 | 1.00 | 13.60 | A |
| ATOM | 839 | C   | PHE | A | 103 | 32.594 | 55.314 | 99.210  | 1.00 | 12.26 | A |
| ATOM | 840 | O   | PHE | A | 103 | 33.578 | 55.616 | 98.542  | 1.00 | 12.26 | A |
| ATOM | 841 | N   | ILE | A | 104 | 31.590 | 54.628 | 98.696  | 1.00 | 12.26 | A |
| ATOM | 842 | CA  | ILE | A | 104 | 31.672 | 54.166 | 97.337  | 1.00 | 12.26 | A |
| ATOM | 843 | CB  | ILE | A | 104 | 31.711 | 52.657 | 97.335  | 1.00 | 12.26 | A |
| ATOM | 844 | CG2 | ILE | A | 104 | 31.791 | 52.137 | 95.888  | 1.00 | 12.26 | A |
| ATOM | 845 | CG1 | ILE | A | 104 | 32.880 | 52.182 | 98.211  | 1.00 | 12.26 | A |
| ATOM | 846 | CD1 | ILE | A | 104 | 32.878 | 50.684 | 98.467  | 1.00 | 12.26 | A |
| ATOM | 847 | C   | ILE | A | 104 | 30.544 | 54.625 | 96.432  | 1.00 | 18.28 | A |
| ATOM | 848 | O   | ILE | A | 104 | 29.361 | 54.551 | 96.791  | 1.00 | 23.15 | A |
| ATOM | 849 | N   | ILE | A | 105 | 30.909 | 55.091 | 95.239  | 1.00 | 15.72 | A |
| ATOM | 850 | CA  | ILE | A | 105 | 29.920 | 55.555 | 94.271  | 1.00 | 17.96 | A |
| ATOM | 851 | CB  | ILE | A | 105 | 29.817 | 57.092 | 94.235  | 1.00 | 17.35 | A |
| ATOM | 852 | CG2 | ILE | A | 105 | 29.090 | 57.598 | 95.492  | 1.00 | 23.31 | A |
| ATOM | 853 | CG1 | ILE | A | 105 | 31.218 | 57.689 | 94.077  | 1.00 | 19.98 | A |
| ATOM | 854 | CD1 | ILE | A | 105 | 31.221 | 59.168 | 93.726  | 1.00 | 20.57 | A |
| ATOM | 855 | C   | ILE | A | 105 | 30.313 | 55.089 | 92.894  | 1.00 | 14.65 | A |
| ATOM | 856 | O   | ILE | A | 105 | 31.465 | 54.773 | 92.660  | 1.00 | 13.45 | A |
| ATOM | 857 | N   | GLY | A | 106 | 29.345 | 55.043 | 91.989  | 1.00 | 12.26 | A |
| ATOM | 858 | CA  | GLY | A | 106 | 29.635 | 54.626 | 90.632  | 1.00 | 17.11 | A |
| ATOM | 859 | C   | GLY | A | 106 | 29.712 | 55.832 | 89.716  | 1.00 | 15.81 | A |
| ATOM | 860 | O   | GLY | A | 106 | 29.334 | 56.944 | 90.120  | 1.00 | 22.09 | A |
| ATOM | 861 | N   | ALA | A | 107 | 30.209 | 55.626 | 88.496  | 1.00 | 12.26 | A |
| ATOM | 862 | CA  | ALA | A | 107 | 30.324 | 56.706 | 87.513  | 1.00 | 12.26 | A |
| ATOM | 863 | CB  | ALA | A | 107 | 30.229 | 56.131 | 86.110  | 1.00 | 12.26 | A |
| ATOM | 864 | C   | ALA | A | 107 | 29.180 | 57.694 | 87.756  | 1.00 | 13.16 | A |
| ATOM | 865 | O   | ALA | A | 107 | 29.380 | 58.865 | 88.095  | 1.00 | 12.99 | A |
| ATOM | 866 | N   | ASP | A | 108 | 27.977 | 57.162 | 87.597  | 1.00 | 17.71 | A |
| ATOM | 867 | CA  | ASP | A | 108 | 26.729 | 57.855 | 87.794  | 1.00 | 12.26 | A |
| ATOM | 868 | CB  | ASP | A | 108 | 25.725 | 56.856 | 88.325  | 1.00 | 23.34 | A |
| ATOM | 869 | CG  | ASP | A | 108 | 24.370 | 57.422 | 88.404  | 1.00 | 28.83 | A |
| ATOM | 870 | OD1 | ASP | A | 108 | 24.206 | 58.583 | 87.967  | 1.00 | 37.84 | A |
| ATOM | 871 | OD2 | ASP | A | 108 | 23.469 | 56.712 | 88.893  | 1.00 | 38.94 | A |
| ATOM | 872 | C   | ASP | A | 108 | 26.837 | 59.015 | 88.759  | 1.00 | 20.40 | A |
| ATOM | 873 | O   | ASP | A | 108 | 26.844 | 60.176 | 88.349  | 1.00 | 26.78 | A |
| ATOM | 874 | N   | MET | A | 109 | 26.922 | 58.692 | 90.049  | 1.00 | 22.05 | A |
| ATOM | 875 | CA  | MET | A | 109 | 27.004 | 59.713 | 91.088  | 1.00 | 15.05 | A |

Figure 10 (15 of 142)

| | | | | | | | | | | |
|---|---|---|---|---|---|---|---|---|---|---|
| ATOM | 876 | CB | MET | A | 109 | 26.996 | 59.064 | 92.467 | 1.00 13.45 | A |
| ATOM | 877 | CG | MET | A | 109 | 25.620 | 58.665 | 92.953 | 1.00 12.26 | A |
| ATOM | 878 | SD | MET | A | 109 | 24.538 | 60.002 | 93.401 | 1.00 12.26 | A |
| ATOM | 879 | CE | MET | A | 109 | 23.539 | 60.040 | 91.986 | 1.00 12.26 | A |
| ATOM | 880 | C | MET | A | 109 | 28.225 | 60.599 | 90.952 | 1.00 15.05 | A |
| ATOM | 881 | O | MET | A | 109 | 28.192 | 61.773 | 91.315 | 1.00 16.55 | A |
| ATOM | 882 | N | ILE | A | 110 | 29.308 | 60.043 | 90.429 | 1.00 14.91 | A |
| ATOM | 883 | CA | ILE | A | 110 | 30.518 | 60.834 | 90.270 | 1.00 12.26 | A |
| ATOM | 884 | CB | ILE | A | 110 | 31.611 | 60.025 | 89.532 | 1.00 12.26 | A |
| ATOM | 885 | CG2 | ILE | A | 110 | 32.938 | 60.780 | 89.544 | 1.00 12.26 | A |
| ATOM | 886 | CG1 | ILE | A | 110 | 31.778 | 58.683 | 90.232 | 1.00 12.26 | A |
| ATOM | 887 | CD1 | ILE | A | 110 | 33.149 | 58.114 | 90.146 | 1.00 12.26 | A |
| ATOM | 888 | C | ILE | A | 110 | 30.187 | 62.129 | 89.522 | 1.00 12.26 | A |
| ATOM | 889 | O | ILE | A | 110 | 30.687 | 63.208 | 89.868 | 1.00 12.26 | A |
| ATOM | 890 | N | GLU | A | 111 | 29.313 | 62.004 | 88.523 | 1.00 12.26 | A |
| ATOM | 891 | CA | GLU | A | 111 | 28.880 | 63.123 | 87.703 | 1.00 13.92 | A |
| ATOM | 892 | CB | GLU | A | 111 | 28.002 | 62.621 | 86.541 | 1.00 12.26 | A |
| ATOM | 893 | CG | GLU | A | 111 | 28.733 | 62.187 | 85.264 | 1.00 24.15 | A |
| ATOM | 894 | CD | GLU | A | 111 | 27.779 | 61.880 | 84.087 | 1.00 26.81 | A |
| ATOM | 895 | OE1 | GLU | A | 111 | 26.805 | 62.634 | 83.859 | 1.00 29.85 | A |
| ATOM | 896 | OE2 | GLU | A | 111 | 28.012 | 60.887 | 83.369 | 1.00 33.32 | A |
| ATOM | 897 | C | GLU | A | 111 | 28.071 | 64.092 | 88.555 | 1.00 13.05 | A |
| ATOM | 898 | O | GLU | A | 111 | 28.028 | 65.291 | 88.285 | 1.00 18.83 | A |
| ATOM | 899 | N | TYR | A | 112 | 27.456 | 63.557 | 89.602 | 1.00 12.26 | A |
| ATOM | 900 | CA | TYR | A | 112 | 26.578 | 64.323 | 90.487 | 1.00 12.26 | A |
| ATOM | 901 | CB | TYR | A | 112 | 25.454 | 63.380 | 90.970 | 1.00 12.26 | A |
| ATOM | 902 | CG | TYR | A | 112 | 24.096 | 64.011 | 91.234 | 1.00 12.26 | A |
| ATOM | 903 | CD1 | TYR | A | 112 | 23.804 | 64.589 | 92.461 | 1.00 12.26 | A |
| ATOM | 904 | CE1 | TYR | A | 112 | 22.553 | 65.154 | 92.717 | 1.00 12.26 | A |
| ATOM | 905 | CD2 | TYR | A | 112 | 23.098 | 64.007 | 90.255 | 1.00 12.26 | A |
| ATOM | 906 | CE2 | TYR | A | 112 | 21.849 | 64.565 | 90.494 | 1.00 13.33 | A |
| ATOM | 907 | CZ | TYR | A | 112 | 21.582 | 65.138 | 91.728 | 1.00 14.00 | A |
| ATOM | 908 | OH | TYR | A | 112 | 20.344 | 65.687 | 91.978 | 1.00 17.49 | A |
| ATOM | 909 | C | TYR | A | 112 | 27.260 | 64.982 | 91.685 | 1.00 13.49 | A |
| ATOM | 910 | O | TYR | A | 112 | 26.639 | 65.743 | 92.415 | 1.00 12.26 | A |
| ATOM | 911 | N | LEU | A | 113 | 28.538 | 64.708 | 91.892 | 1.00 15.50 | A |
| ATOM | 912 | CA | LEU | A | 113 | 29.210 | 65.290 | 93.042 | 1.00 16.35 | A |
| ATOM | 913 | CB | LEU | A | 113 | 30.715 | 65.070 | 92.935 | 1.00 22.39 | A |
| ATOM | 914 | CG | LEU | A | 113 | 31.188 | 63.859 | 93.758 | 1.00 24.22 | A |
| ATOM | 915 | CD1 | LEU | A | 113 | 30.189 | 62.699 | 93.689 | 1.00 26.53 | A |
| ATOM | 916 | CD2 | LEU | A | 113 | 32.546 | 63.434 | 93.248 | 1.00 27.67 | A |
| ATOM | 917 | C | LEU | A | 113 | 28.861 | 66.749 | 93.263 | 1.00 12.26 | A |
| ATOM | 918 | O | LEU | A | 113 | 28.572 | 67.152 | 94.379 | 1.00 12.26 | A |
| ATOM | 919 | N | PRO | A | 114 | 28.884 | 67.561 | 92.207 | 1.00 12.26 | A |
| ATOM | 920 | CD | PRO | A | 114 | 29.453 | 67.340 | 90.877 | 1.00 12.26 | A |
| ATOM | 921 | CA | PRO | A | 114 | 28.539 | 68.967 | 92.389 | 1.00 12.26 | A |
| ATOM | 922 | CB | PRO | A | 114 | 28.644 | 69.533 | 90.972 | 1.00 12.26 | A |
| ATOM | 923 | CG | PRO | A | 114 | 28.709 | 68.326 | 90.086 | 1.00 12.26 | A |
| ATOM | 924 | C | PRO | A | 114 | 27.157 | 69.190 | 93.059 | 1.00 13.84 | A |
| ATOM | 925 | O | PRO | A | 114 | 27.069 | 69.871 | 94.085 | 1.00 12.79 | A |
| ATOM | 926 | N | LYS | A | 115 | 26.082 | 68.640 | 92.497 | 1.00 12.26 | A |
| ATOM | 927 | CA | LYS | A | 115 | 24.762 | 68.801 | 93.111 | 1.00 18.49 | A |
| ATOM | 928 | CB | LYS | A | 115 | 23.648 | 68.452 | 92.112 | 1.00 21.17 | A |
| ATOM | 929 | CG | LYS | A | 115 | 23.755 | 69.190 | 90.772 | 1.00 29.34 | A |
| ATOM | 930 | CD | LYS | A | 115 | 22.645 | 68.796 | 89.783 | 1.00 33.91 | A |
| ATOM | 931 | CE | LYS | A | 115 | 21.256 | 69.181 | 90.300 | 1.00 37.74 | A |
| ATOM | 932 | NZ | LYS | A | 115 | 20.183 | 68.903 | 89.304 | 1.00 41.49 | A |
| ATOM | 933 | C | LYS | A | 115 | 24.879 | 67.724 | 94.154 | 1.00 16.33 | A |
| ATOM | 934 | O | LYS | A | 115 | 24.817 | 66.563 | 93.807 | 1.00 28.99 | A |
| ATOM | 935 | N | TRP | A | 116 | 25.080 | 68.069 | 95.419 | 1.00 13.95 | A |
| ATOM | 936 | CA | TRP | A | 116 | 25.258 | 67.031 | 96.443 | 1.00 12.26 | A |
| ATOM | 937 | CB | TRP | A | 116 | 26.483 | 66.188 | 96.065 | 1.00 16.22 | A |
| ATOM | 938 | CG | TRP | A | 116 | 26.724 | 64.930 | 96.842 | 1.00 17.78 | A |
| ATOM | 939 | CD2 | TRP | A | 116 | 26.679 | 63.589 | 96.341 | 1.00 15.49 | A |
| ATOM | 940 | CE2 | TRP | A | 116 | 27.069 | 62.725 | 97.402 | 1.00 17.33 | A |
| ATOM | 941 | CE3 | TRP | A | 116 | 26.325 | 63.031 | 95.119 | 1.00 13.36 | A |

Figure 10 (16 of 142)

```
ATOM    942  CD1 TRP A 116      27.136  64.836  98.140  1.00 21.32      A
ATOM    943  NE1 TRP A 116      27.356  63.511  98.483  1.00 18.84      A
ATOM    944  CZ2 TRP A 116      27.143  61.345  97.264  1.00 17.13      A
ATOM    945  CZ3 TRP A 116      26.396  61.661  94.981  1.00 17.29      A
ATOM    946  CH2 TRP A 116      26.791  60.826  96.056  1.00 18.16      A
ATOM    947  C   TRP A 116      25.499  67.837  97.696  1.00 13.73      A
ATOM    948  O   TRP A 116      26.469  68.584  97.771  1.00 21.35      A
ATOM    949  N   TYR A 117      24.615  67.699  98.677  1.00 12.33      A
ATOM    950  CA  TYR A 117      24.690  68.505  99.900  1.00 12.26      A
ATOM    951  CB  TYR A 117      23.485  68.197 100.796  1.00 12.26      A
ATOM    952  CG  TYR A 117      23.405  69.067 102.029  1.00 12.26      A
ATOM    953  CD1 TYR A 117      23.282  70.449 101.925  1.00 12.26      A
ATOM    954  CE1 TYR A 117      23.184  71.256 103.070  1.00 12.26      A
ATOM    955  CD2 TYR A 117      23.434  68.502 103.311  1.00 15.89      A
ATOM    956  CE2 TYR A 117      23.335  69.293 104.461  1.00 14.46      A
ATOM    957  CZ  TYR A 117      23.207  70.670 104.332  1.00 17.82      A
ATOM    958  OH  TYR A 117      23.065  71.466 105.452  1.00 23.07      A
ATOM    959  C   TYR A 117      25.979  68.463 100.725  1.00 12.26      A
ATOM    960  O   TYR A 117      26.323  67.436 101.305  1.00 12.26      A
ATOM    961  N   LYS A 118      26.673  69.605 100.755  1.00 12.26      A
ATOM    962  CA  LYS A 118      27.917  69.784 101.509  1.00 16.19      A
ATOM    963  CB  LYS A 118      27.650  69.584 102.991  1.00 21.57      A
ATOM    964  CG  LYS A 118      27.064  70.786 103.671  1.00 24.82      A
ATOM    965  CD  LYS A 118      27.027  70.575 105.167  1.00 28.06      A
ATOM    966  CE  LYS A 118      26.455  71.796 105.865  1.00 28.44      A
ATOM    967  NZ  LYS A 118      26.342  71.595 107.335  1.00 32.28      A
ATOM    968  C   LYS A 118      29.127  68.940 101.129  1.00 16.10      A
ATOM    969  O   LYS A 118      29.939  68.584 101.981  1.00 12.26      A
ATOM    970  N   LEU A 119      29.263  68.643  99.846  1.00 19.90      A
ATOM    971  CA  LEU A 119      30.367  67.826  99.370  1.00 17.09      A
ATOM    972  CB  LEU A 119      30.350  67.762  97.851  1.00 19.08      A
ATOM    973  CG  LEU A 119      31.370  66.817  97.250  1.00 17.63      A
ATOM    974  CD1 LEU A 119      31.278  65.437  97.890  1.00 20.21      A
ATOM    975  CD2 LEU A 119      31.103  66.744  95.775  1.00 21.56      A
ATOM    976  C   LEU A 119      31.728  68.300  99.831  1.00 17.98      A
ATOM    977  O   LEU A 119      32.607  67.494 100.082  1.00 18.77      A
ATOM    978  N   ASP A 120      31.918  69.603  99.955  1.00 17.03      A
ATOM    979  CA  ASP A 120      33.225  70.069 100.358  1.00 21.15      A
ATOM    980  CB  ASP A 120      33.345  71.562 100.105  1.00 26.37      A
ATOM    981  CG  ASP A 120      33.526  71.876  98.624  1.00 30.61      A
ATOM    982  OD1 ASP A 120      34.649  71.654  98.105  1.00 32.82      A
ATOM    983  OD2 ASP A 120      32.543  72.327  97.976  1.00 31.75      A
ATOM    984  C   ASP A 120      33.569  69.733 101.788  1.00 19.66      A
ATOM    985  O   ASP A 120      34.738  69.579 102.124  1.00 23.86      A
ATOM    986  N   GLU A 121      32.559  69.598 102.633  1.00 16.96      A
ATOM    987  CA  GLU A 121      32.819  69.268 104.027  1.00 15.87      A
ATOM    988  CB  GLU A 121      31.672  69.751 104.925  1.00 21.59      A
ATOM    989  CG  GLU A 121      31.411  71.262 104.929  1.00 23.95      A
ATOM    990  CD  GLU A 121      30.885  71.790 103.596  1.00 27.50      A
ATOM    991  OE1 GLU A 121      30.173  71.036 102.882  1.00 27.70      A
ATOM    992  OE2 GLU A 121      31.178  72.969 103.277  1.00 27.30      A
ATOM    993  C   GLU A 121      32.947  67.756 104.129  1.00 12.26      A
ATOM    994  O   GLU A 121      33.795  67.231 104.849  1.00 12.26      A
ATOM    995  N   LEU A 122      32.092  67.067 103.379  1.00 12.26      A
ATOM    996  CA  LEU A 122      32.052  65.610 103.363  1.00 12.26      A
ATOM    997  CB  LEU A 122      30.933  65.142 102.442  1.00 12.26      A
ATOM    998  CG  LEU A 122      30.743  63.640 102.238  1.00 13.36      A
ATOM    999  CD1 LEU A 122      30.342  62.977 103.558  1.00 12.26      A
ATOM   1000  CD2 LEU A 122      29.674  63.414 101.146  1.00 12.26      A
ATOM   1001  C   LEU A 122      33.366  64.990 102.929  1.00 12.26      A
ATOM   1002  O   LEU A 122      33.857  64.081 103.579  1.00 12.26      A
ATOM   1003  N   LEU A 123      33.921  65.493 101.826  1.00 17.29      A
ATOM   1004  CA  LEU A 123      35.190  65.017 101.260  1.00 15.87      A
ATOM   1005  CB  LEU A 123      35.566  65.826 100.019  1.00 16.92      A
ATOM   1006  CG  LEU A 123      34.826  65.491  98.731  1.00 17.13      A
ATOM   1007  CD1 LEU A 123      35.163  66.531  97.678  1.00 19.31      A
```

Figure 10 (17 of 142)

| ATOM | 1008 | CD2 | LEU | A | 123 | 35.204 | 64.094 | 98.266 | 1.00 | 12.26 | A |
|---|---|---|---|---|---|---|---|---|---|---|---|
| ATOM | 1009 | C | LEU | A | 123 | 36.329 | 65.128 | 102.246 | 1.00 | 17.35 | A |
| ATOM | 1010 | O | LEU | A | 123 | 37.375 | 64.489 | 102.091 | 1.00 | 18.01 | A |
| ATOM | 1011 | N | ASN | A | 124 | 36.128 | 65.965 | 103.245 | 1.00 | 14.19 | A |
| ATOM | 1012 | CA | ASN | A | 124 | 37.121 | 66.179 | 104.267 | 1.00 | 22.18 | A |
| ATOM | 1013 | CB | ASN | A | 124 | 36.863 | 67.550 | 104.870 | 1.00 | 26.64 | A |
| ATOM | 1014 | CG | ASN | A | 124 | 38.008 | 68.055 | 105.704 | 1.00 | 31.94 | A |
| ATOM | 1015 | OD1 | ASN | A | 124 | 38.315 | 67.524 | 106.786 | 1.00 | 37.29 | A |
| ATOM | 1016 | ND2 | ASN | A | 124 | 38.646 | 69.108 | 105.213 | 1.00 | 35.80 | A |
| ATOM | 1017 | C | ASN | A | 124 | 36.953 | 65.064 | 105.314 | 1.00 | 21.05 | A |
| ATOM | 1018 | O | ASN | A | 124 | 37.902 | 64.631 | 105.964 | 1.00 | 14.58 | A |
| ATOM | 1019 | N | LEU | A | 125 | 35.731 | 64.589 | 105.462 | 1.00 | 21.05 | A |
| ATOM | 1020 | CA | LEU | A | 125 | 35.467 | 63.548 | 106.422 | 1.00 | 16.59 | A |
| ATOM | 1021 | CB | LEU | A | 125 | 33.980 | 63.498 | 106.745 | 1.00 | 14.33 | A |
| ATOM | 1022 | CG | LEU | A | 125 | 33.427 | 64.705 | 107.490 | 1.00 | 16.49 | A |
| ATOM | 1023 | CD1 | LEU | A | 125 | 31.922 | 64.585 | 107.633 | 1.00 | 16.28 | A |
| ATOM | 1024 | CD2 | LEU | A | 125 | 34.101 | 64.781 | 108.841 | 1.00 | 15.45 | A |
| ATOM | 1025 | C | LEU | A | 125 | 35.884 | 62.192 | 105.924 | 1.00 | 16.38 | A |
| ATOM | 1026 | O | LEU | A | 125 | 36.581 | 61.468 | 106.614 | 1.00 | 26.59 | A |
| ATOM | 1027 | N | ILE | A | 126 | 35.465 | 61.846 | 104.718 | 1.00 | 16.03 | A |
| ATOM | 1028 | CA | ILE | A | 126 | 35.749 | 60.524 | 104.182 | 1.00 | 15.13 | A |
| ATOM | 1029 | CB | ILE | A | 126 | 34.420 | 59.663 | 104.246 | 1.00 | 16.03 | A |
| ATOM | 1030 | CG2 | ILE | A | 126 | 33.367 | 60.205 | 103.230 | 1.00 | 12.26 | A |
| ATOM | 1031 | CG1 | ILE | A | 126 | 34.712 | 58.176 | 104.025 | 1.00 | 15.07 | A |
| ATOM | 1032 | CD1 | ILE | A | 126 | 33.482 | 57.303 | 104.220 | 1.00 | 12.26 | A |
| ATOM | 1033 | C | ILE | A | 126 | 36.334 | 60.538 | 102.765 | 1.00 | 12.26 | A |
| ATOM | 1034 | O | ILE | A | 126 | 36.204 | 61.510 | 102.032 | 1.00 | 12.26 | A |
| ATOM | 1035 | N | GLN | A | 127 | 36.993 | 59.448 | 102.398 | 1.00 | 15.20 | A |
| ATOM | 1036 | CA | GLN | A | 127 | 37.575 | 59.325 | 101.069 | 1.00 | 12.26 | A |
| ATOM | 1037 | CB | GLN | A | 127 | 38.875 | 58.532 | 101.125 | 1.00 | 18.28 | A |
| ATOM | 1038 | CG | GLN | A | 127 | 39.960 | 59.180 | 101.973 | 1.00 | 23.68 | A |
| ATOM | 1039 | CD | GLN | A | 127 | 41.116 | 58.242 | 102.232 | 1.00 | 23.69 | A |
| ATOM | 1040 | OE1 | GLN | A | 127 | 40.938 | 57.183 | 102.834 | 1.00 | 28.43 | A |
| ATOM | 1041 | NE2 | GLN | A | 127 | 42.303 | 58.619 | 101.776 | 1.00 | 24.71 | A |
| ATOM | 1042 | C | GLN | A | 127 | 36.607 | 58.603 | 100.159 | 1.00 | 12.26 | A |
| ATOM | 1043 | O | GLN | A | 127 | 35.949 | 57.659 | 100.584 | 1.00 | 12.26 | A |
| ATOM | 1044 | N | PHE | A | 128 | 36.529 | 59.042 | 98.908 | 1.00 | 12.26 | A |
| ATOM | 1045 | CA | PHE | A | 128 | 35.627 | 58.418 | 97.943 | 1.00 | 12.26 | A |
| ATOM | 1046 | CB | PHE | A | 128 | 34.906 | 59.480 | 97.116 | 1.00 | 12.26 | A |
| ATOM | 1047 | CG | PHE | A | 128 | 33.685 | 60.051 | 97.773 | 1.00 | 12.26 | A |
| ATOM | 1048 | CD1 | PHE | A | 128 | 33.788 | 60.826 | 98.913 | 1.00 | 12.26 | A |
| ATOM | 1049 | CD2 | PHE | A | 128 | 32.428 | 59.836 | 97.225 | 1.00 | 12.26 | A |
| ATOM | 1050 | CE1 | PHE | A | 128 | 32.645 | 61.389 | 99.500 | 1.00 | 13.47 | A |
| ATOM | 1051 | CE2 | PHE | A | 128 | 31.290 | 60.387 | 97.796 | 1.00 | 12.26 | A |
| ATOM | 1052 | CZ | PHE | A | 128 | 31.395 | 61.169 | 98.936 | 1.00 | 12.26 | A |
| ATOM | 1053 | C | PHE | A | 128 | 36.308 | 57.447 | 96.977 | 1.00 | 12.26 | A |
| ATOM | 1054 | O | PHE | A | 128 | 37.442 | 57.661 | 96.543 | 1.00 | 12.26 | A |
| ATOM | 1055 | N | ILE | A | 129 | 35.592 | 56.387 | 96.633 | 1.00 | 12.26 | A |
| ATOM | 1056 | CA | ILE | A | 129 | 36.095 | 55.388 | 95.711 | 1.00 | 12.26 | A |
| ATOM | 1057 | CB | ILE | A | 129 | 36.154 | 54.012 | 96.364 | 1.00 | 12.26 | A |
| ATOM | 1058 | CG2 | ILE | A | 129 | 36.467 | 52.964 | 95.326 | 1.00 | 12.26 | A |
| ATOM | 1059 | CG1 | ILE | A | 129 | 37.225 | 53.983 | 97.445 | 1.00 | 12.26 | A |
| ATOM | 1060 | CD1 | ILE | A | 129 | 37.321 | 52.626 | 98.131 | 1.00 | 12.26 | A |
| ATOM | 1061 | C | ILE | A | 129 | 35.127 | 55.327 | 94.539 | 1.00 | 16.78 | A |
| ATOM | 1062 | O | ILE | A | 129 | 33.928 | 55.129 | 94.726 | 1.00 | 16.76 | A |
| ATOM | 1063 | N | GLY | A | 130 | 35.649 | 55.490 | 93.329 | 1.00 | 17.25 | A |
| ATOM | 1064 | CA | GLY | A | 130 | 34.805 | 55.483 | 92.154 | 1.00 | 18.30 | A |
| ATOM | 1065 | C | GLY | A | 130 | 34.973 | 54.173 | 91.440 | 1.00 | 20.78 | A |
| ATOM | 1066 | O | GLY | A | 130 | 36.018 | 53.541 | 91.571 | 1.00 | 23.07 | A |
| ATOM | 1067 | N | VAL | A | 131 | 33.955 | 53.760 | 90.689 | 1.00 | 20.83 | A |
| ATOM | 1068 | CA | VAL | A | 131 | 34.028 | 52.501 | 89.986 | 1.00 | 22.51 | A |
| ATOM | 1069 | CB | VAL | A | 131 | 32.837 | 51.617 | 90.306 | 1.00 | 22.94 | A |
| ATOM | 1070 | CG1 | VAL | A | 131 | 32.828 | 50.439 | 89.375 | 1.00 | 28.95 | A |
| ATOM | 1071 | CG2 | VAL | A | 131 | 32.936 | 51.109 | 91.717 | 1.00 | 24.97 | A |
| ATOM | 1072 | C | VAL | A | 131 | 34.073 | 52.681 | 88.492 | 1.00 | 26.99 | A |
| ATOM | 1073 | O | VAL | A | 131 | 35.101 | 52.433 | 87.866 | 1.00 | 34.09 | A |

Figure 10 (18 of 142)

| ATOM | 1074 | N | LYS | A | 132 | 32.939 | 53.087 | 87.936 | 1.00 | 29.06 | A |
|---|---|---|---|---|---|---|---|---|---|---|---|
| ATOM | 1075 | CA | LYS | A | 132 | 32.751 | 53.315 | 86.500 | 1.00 | 34.00 | A |
| ATOM | 1076 | CB | LYS | A | 132 | 34.015 | 53.061 | 85.658 | 1.00 | 33.44 | A |
| ATOM | 1077 | CG | LYS | A | 132 | 33.796 | 53.459 | 84.204 | 1.00 | 41.27 | A |
| ATOM | 1078 | CD | LYS | A | 132 | 34.970 | 54.247 | 83.623 | 1.00 | 47.25 | A |
| ATOM | 1079 | CE | LYS | A | 132 | 34.542 | 54.990 | 82.334 | 1.00 | 48.96 | A |
| ATOM | 1080 | NZ | LYS | A | 132 | 35.673 | 55.512 | 81.496 | 1.00 | 46.33 | A |
| ATOM | 1081 | C | LYS | A | 132 | 31.609 | 52.461 | 85.965 | 1.00 | 34.50 | A |
| ATOM | 1082 | O | LYS | A | 132 | 31.708 | 51.240 | 85.781 | 1.00 | 34.25 | A |
| ATOM | 1083 | N | ARG | A | 133 | 30.510 | 53.148 | 85.720 | 1.00 | 35.33 | A |
| ATOM | 1084 | CA | ARG | A | 133 | 29.304 | 52.536 | 85.227 | 1.00 | 34.19 | A |
| ATOM | 1085 | CB | ARG | A | 133 | 28.121 | 53.076 | 86.031 | 1.00 | 33.33 | A |
| ATOM | 1086 | CG | ARG | A | 133 | 26.805 | 52.958 | 85.337 | 1.00 | 30.34 | A |
| ATOM | 1087 | CD | ARG | A | 133 | 25.770 | 52.353 | 86.245 | 1.00 | 26.70 | A |
| ATOM | 1088 | NE | ARG | A | 133 | 24.921 | 53.331 | 86.898 | 1.00 | 20.63 | A |
| ATOM | 1089 | CZ | ARG | A | 133 | 23.664 | 53.082 | 87.237 | 1.00 | 22.12 | A |
| ATOM | 1090 | NH1 | ARG | A | 133 | 23.124 | 51.888 | 86.987 | 1.00 | 21.22 | A |
| ATOM | 1091 | NH2 | ARG | A | 133 | 22.940 | 54.035 | 87.802 | 1.00 | 22.57 | A |
| ATOM | 1092 | C | ARG | A | 133 | 29.157 | 52.868 | 83.750 | 1.00 | 32.96 | A |
| ATOM | 1093 | O | ARG | A | 133 | 29.458 | 53.981 | 83.317 | 1.00 | 31.45 | A |
| ATOM | 1094 | N | PRO | A | 134 | 28.714 | 51.888 | 82.952 | 1.00 | 34.03 | A |
| ATOM | 1095 | CD | PRO | A | 134 | 28.511 | 50.479 | 83.319 | 1.00 | 35.82 | A |
| ATOM | 1096 | CA | PRO | A | 134 | 28.529 | 52.083 | 81.514 | 1.00 | 35.08 | A |
| ATOM | 1097 | CB | PRO | A | 134 | 28.142 | 50.691 | 81.017 | 1.00 | 32.82 | A |
| ATOM | 1098 | CG | PRO | A | 134 | 28.780 | 49.782 | 82.005 | 1.00 | 34.66 | A |
| ATOM | 1099 | C | PRO | A | 134 | 27.404 | 53.078 | 81.327 | 1.00 | 35.47 | A |
| ATOM | 1100 | O | PRO | A | 134 | 26.386 | 52.989 | 82.004 | 1.00 | 37.35 | A |
| ATOM | 1101 | N | GLY | A | 135 | 27.585 | 54.028 | 80.420 | 1.00 | 34.95 | A |
| ATOM | 1102 | CA | GLY | A | 135 | 26.539 | 55.009 | 80.194 | 1.00 | 37.76 | A |
| ATOM | 1103 | C | GLY | A | 135 | 26.898 | 56.331 | 80.835 | 1.00 | 39.38 | A |
| ATOM | 1104 | O | GLY | A | 135 | 26.468 | 57.402 | 80.403 | 1.00 | 42.22 | A |
| ATOM | 1105 | N | PHE | A | 136 | 27.685 | 56.255 | 81.896 | 1.00 | 39.80 | A |
| ATOM | 1106 | CA | PHE | A | 136 | 28.126 | 57.457 | 82.573 | 1.00 | 36.45 | A |
| ATOM | 1107 | CB | PHE | A | 136 | 27.698 | 57.443 | 84.039 | 1.00 | 35.58 | A |
| ATOM | 1108 | CG | PHE | A | 136 | 26.244 | 57.255 | 84.209 | 1.00 | 35.14 | A |
| ATOM | 1109 | CD1 | PHE | A | 136 | 25.680 | 56.018 | 83.988 | 1.00 | 36.09 | A |
| ATOM | 1110 | CD2 | PHE | A | 136 | 25.421 | 58.333 | 84.460 | 1.00 | 37.49 | A |
| ATOM | 1111 | CE1 | PHE | A | 136 | 24.312 | 55.852 | 84.003 | 1.00 | 39.21 | A |
| ATOM | 1112 | CE2 | PHE | A | 136 | 24.047 | 58.183 | 84.476 | 1.00 | 38.62 | A |
| ATOM | 1113 | CZ | PHE | A | 136 | 23.487 | 56.940 | 84.245 | 1.00 | 39.22 | A |
| ATOM | 1114 | C | PHE | A | 136 | 29.620 | 57.432 | 82.471 | 1.00 | 34.39 | A |
| ATOM | 1115 | O | PHE | A | 136 | 30.208 | 56.501 | 81.916 | 1.00 | 31.72 | A |
| ATOM | 1116 | N | HIS | A | 137 | 30.247 | 58.467 | 82.979 | 1.00 | 31.28 | A |
| ATOM | 1117 | CA | HIS | A | 137 | 31.676 | 58.461 | 82.946 | 1.00 | 33.48 | A |
| ATOM | 1118 | CB | HIS | A | 137 | 32.199 | 58.715 | 81.521 | 1.00 | 33.69 | A |
| ATOM | 1119 | CG | HIS | A | 137 | 31.837 | 60.053 | 80.960 | 1.00 | 36.16 | A |
| ATOM | 1120 | CD2 | HIS | A | 137 | 31.014 | 60.400 | 79.940 | 1.00 | 33.80 | A |
| ATOM | 1121 | ND1 | HIS | A | 137 | 32.363 | 61.231 | 81.450 | 1.00 | 34.99 | A |
| ATOM | 1122 | CE1 | HIS | A | 137 | 31.878 | 62.246 | 80.755 | 1.00 | 36.64 | A |
| ATOM | 1123 | NE2 | HIS | A | 137 | 31.056 | 61.769 | 79.834 | 1.00 | 33.28 | A |
| ATOM | 1124 | C | HIS | A | 137 | 32.228 | 59.432 | 83.956 | 1.00 | 35.16 | A |
| ATOM | 1125 | O | HIS | A | 137 | 31.669 | 60.507 | 84.210 | 1.00 | 28.30 | A |
| ATOM | 1126 | N | VAL | A | 138 | 33.312 | 58.976 | 84.570 | 1.00 | 38.73 | A |
| ATOM | 1127 | CA | VAL | A | 138 | 34.033 | 59.703 | 85.584 | 1.00 | 42.31 | A |
| ATOM | 1128 | CB | VAL | A | 138 | 34.816 | 58.717 | 86.427 | 1.00 | 41.76 | A |
| ATOM | 1129 | CG1 | VAL | A | 138 | 35.308 | 57.570 | 85.548 | 1.00 | 42.25 | A |
| ATOM | 1130 | CG2 | VAL | A | 138 | 35.959 | 59.427 | 87.092 | 1.00 | 44.14 | A |
| ATOM | 1131 | C | VAL | A | 138 | 34.971 | 60.742 | 84.959 | 1.00 | 48.81 | A |
| ATOM | 1132 | O | VAL | A | 138 | 35.364 | 60.624 | 83.788 | 1.00 | 51.12 | A |
| ATOM | 1133 | N | GLU | A | 139 | 35.331 | 61.758 | 85.737 | 1.00 | 50.87 | A |
| ATOM | 1134 | CA | GLU | A | 139 | 36.181 | 62.821 | 85.229 | 1.00 | 53.58 | A |
| ATOM | 1135 | CB | GLU | A | 139 | 35.494 | 63.501 | 84.036 | 1.00 | 58.81 | A |
| ATOM | 1136 | CG | GLU | A | 139 | 34.305 | 64.409 | 84.420 | 1.00 | 66.28 | A |
| ATOM | 1137 | CD | GLU | A | 139 | 33.186 | 64.405 | 83.379 | 1.00 | 70.65 | A |
| ATOM | 1138 | OE1 | GLU | A | 139 | 33.491 | 64.260 | 82.168 | 1.00 | 72.25 | A |
| ATOM | 1139 | OE2 | GLU | A | 139 | 32.005 | 64.559 | 83.777 | 1.00 | 69.87 | A |

Figure 10 (19 of 142)

| ATOM | 1140 | C   | GLU | A | 139 | 36.399 | 63.849 | 86.325 | 1.00 | 50.88 | A |
|------|------|-----|-----|---|-----|--------|--------|--------|------|-------|---|
| ATOM | 1141 | O   | GLU | A | 139 | 37.364 | 64.612 | 86.291 | 1.00 | 54.08 | A |
| ATOM | 1142 | N   | THR | A | 140 | 35.477 | 63.874 | 87.281 | 1.00 | 44.05 | A |
| ATOM | 1143 | CA  | THR | A | 140 | 35.512 | 64.796 | 88.414 | 1.00 | 33.18 | A |
| ATOM | 1144 | CB  | THR | A | 140 | 35.098 | 64.097 | 89.712 | 1.00 | 31.60 | A |
| ATOM | 1145 | OG1 | THR | A | 140 | 35.626 | 62.760 | 89.716 | 1.00 | 27.71 | A |
| ATOM | 1146 | CG2 | THR | A | 140 | 33.568 | 64.106 | 89.870 | 1.00 | 28.61 | A |
| ATOM | 1147 | C   | THR | A | 140 | 36.790 | 65.547 | 88.752 | 1.00 | 32.02 | A |
| ATOM | 1148 | O   | THR | A | 140 | 37.912 | 65.057 | 88.580 | 1.00 | 28.04 | A |
| ATOM | 1149 | N   | PRO | A | 141 | 36.620 | 66.766 | 89.258 | 1.00 | 25.10 | A |
| ATOM | 1150 | CD  | PRO | A | 141 | 35.391 | 67.574 | 89.163 | 1.00 | 24.36 | A |
| ATOM | 1151 | CA  | PRO | A | 141 | 37.748 | 67.597 | 89.641 | 1.00 | 21.56 | A |
| ATOM | 1152 | CB  | PRO | A | 141 | 37.278 | 68.975 | 89.225 | 1.00 | 22.83 | A |
| ATOM | 1153 | CG  | PRO | A | 141 | 35.850 | 68.934 | 89.644 | 1.00 | 23.25 | A |
| ATOM | 1154 | C   | PRO | A | 141 | 37.898 | 67.455 | 91.163 | 1.00 | 21.30 | A |
| ATOM | 1155 | O   | PRO | A | 141 | 38.558 | 68.262 | 91.815 | 1.00 | 27.58 | A |
| ATOM | 1156 | N   | TYR | A | 142 | 37.280 | 66.418 | 91.725 | 1.00 | 16.89 | A |
| ATOM | 1157 | CA  | TYR | A | 142 | 37.314 | 66.195 | 93.174 | 1.00 | 16.08 | A |
| ATOM | 1158 | CB  | TYR | A | 142 | 35.912 | 65.923 | 93.708 | 1.00 | 12.46 | A |
| ATOM | 1159 | CG  | TYR | A | 142 | 34.908 | 67.006 | 93.445 | 1.00 | 16.76 | A |
| ATOM | 1160 | CD1 | TYR | A | 142 | 34.793 | 68.102 | 94.292 | 1.00 | 12.26 | A |
| ATOM | 1161 | CE1 | TYR | A | 142 | 33.848 | 69.094 | 94.048 | 1.00 | 12.26 | A |
| ATOM | 1162 | CD2 | TYR | A | 142 | 34.057 | 66.931 | 92.347 | 1.00 | 17.50 | A |
| ATOM | 1163 | CE2 | TYR | A | 142 | 33.115 | 67.916 | 92.100 | 1.00 | 17.93 | A |
| ATOM | 1164 | CZ  | TYR | A | 142 | 33.015 | 68.991 | 92.952 | 1.00 | 12.26 | A |
| ATOM | 1165 | OH  | TYR | A | 142 | 32.075 | 69.961 | 92.720 | 1.00 | 12.26 | A |
| ATOM | 1166 | C   | TYR | A | 142 | 38.168 | 65.030 | 93.623 | 1.00 | 12.26 | A |
| ATOM | 1167 | O   | TYR | A | 142 | 38.282 | 64.026 | 92.929 | 1.00 | 14.74 | A |
| ATOM | 1168 | N   | PRO | A | 143 | 38.768 | 65.135 | 94.812 | 1.00 | 17.21 | A |
| ATOM | 1169 | CD  | PRO | A | 143 | 38.723 | 66.244 | 95.778 | 1.00 | 13.79 | A |
| ATOM | 1170 | CA  | PRO | A | 143 | 39.597 | 64.029 | 95.308 | 1.00 | 20.27 | A |
| ATOM | 1171 | CB  | PRO | A | 143 | 40.009 | 64.507 | 96.700 | 1.00 | 23.53 | A |
| ATOM | 1172 | CG  | PRO | A | 143 | 38.932 | 65.527 | 97.065 | 1.00 | 22.83 | A |
| ATOM | 1173 | C   | PRO | A | 143 | 38.810 | 62.698 | 95.336 | 1.00 | 18.62 | A |
| ATOM | 1174 | O   | PRO | A | 143 | 37.882 | 62.511 | 96.144 | 1.00 | 12.26 | A |
| ATOM | 1175 | N   | LEU | A | 144 | 39.201 | 61.775 | 94.456 | 1.00 | 15.96 | A |
| ATOM | 1176 | CA  | LEU | A | 144 | 38.523 | 60.487 | 94.345 | 1.00 | 12.26 | A |
| ATOM | 1177 | CB  | LEU | A | 144 | 37.313 | 60.673 | 93.430 | 1.00 | 12.26 | A |
| ATOM | 1178 | CG  | LEU | A | 144 | 36.197 | 59.653 | 93.451 | 1.00 | 12.56 | A |
| ATOM | 1179 | CD1 | LEU | A | 144 | 34.972 | 60.187 | 92.748 | 1.00 | 17.59 | A |
| ATOM | 1180 | CD2 | LEU | A | 144 | 36.696 | 58.416 | 92.767 | 1.00 | 12.69 | A |
| ATOM | 1181 | C   | LEU | A | 144 | 39.463 | 59.379 | 93.830 | 1.00 | 12.26 | A |
| ATOM | 1182 | O   | LEU | A | 144 | 40.190 | 59.554 | 92.848 | 1.00 | 12.26 | A |
| ATOM | 1183 | N   | LEU | A | 145 | 39.464 | 58.248 | 94.529 | 1.00 | 12.26 | A |
| ATOM | 1184 | CA  | LEU | A | 145 | 40.309 | 57.110 | 94.161 | 1.00 | 12.26 | A |
| ATOM | 1185 | CB  | LEU | A | 145 | 40.816 | 56.387 | 95.403 | 1.00 | 12.26 | A |
| ATOM | 1186 | CG  | LEU | A | 145 | 41.920 | 57.132 | 96.148 | 1.00 | 12.26 | A |
| ATOM | 1187 | CD1 | LEU | A | 145 | 42.376 | 56.310 | 97.335 | 1.00 | 12.26 | A |
| ATOM | 1188 | CD2 | LEU | A | 145 | 43.091 | 57.392 | 95.216 | 1.00 | 12.26 | A |
| ATOM | 1189 | C   | LEU | A | 145 | 39.526 | 56.140 | 93.299 | 1.00 | 13.70 | A |
| ATOM | 1190 | O   | LEU | A | 145 | 38.315 | 56.016 | 93.458 | 1.00 | 14.91 | A |
| ATOM | 1191 | N   | PHE | A | 146 | 40.206 | 55.434 | 92.400 | 1.00 | 12.26 | A |
| ATOM | 1192 | CA  | PHE | A | 146 | 39.491 | 54.539 | 91.508 | 1.00 | 12.26 | A |
| ATOM | 1193 | CB  | PHE | A | 146 | 39.767 | 54.902 | 90.050 | 1.00 | 12.26 | A |
| ATOM | 1194 | CG  | PHE | A | 146 | 39.233 | 56.253 | 89.673 | 1.00 | 22.90 | A |
| ATOM | 1195 | CD1 | PHE | A | 146 | 37.865 | 56.494 | 89.656 | 1.00 | 24.80 | A |
| ATOM | 1196 | CD2 | PHE | A | 146 | 40.100 | 57.314 | 89.412 | 1.00 | 27.09 | A |
| ATOM | 1197 | CE1 | PHE | A | 146 | 37.373 | 57.766 | 89.391 | 1.00 | 29.26 | A |
| ATOM | 1198 | CE2 | PHE | A | 146 | 39.610 | 58.594 | 89.147 | 1.00 | 28.57 | A |
| ATOM | 1199 | CZ  | PHE | A | 146 | 38.249 | 58.815 | 89.138 | 1.00 | 30.31 | A |
| ATOM | 1200 | C   | PHE | A | 146 | 39.761 | 53.096 | 91.732 | 1.00 | 12.26 | A |
| ATOM | 1201 | O   | PHE | A | 146 | 40.775 | 52.732 | 92.291 | 1.00 | 16.16 | A |
| ATOM | 1202 | N   | ALA | A | 147 | 38.816 | 52.272 | 91.312 | 1.00 | 12.26 | A |
| ATOM | 1203 | CA  | ALA | A | 147 | 38.946 | 50.850 | 91.454 | 1.00 | 12.26 | A |
| ATOM | 1204 | CB  | ALA | A | 147 | 38.121 | 50.383 | 92.616 | 1.00 | 12.26 | A |
| ATOM | 1205 | C   | ALA | A | 147 | 38.434 | 50.245 | 90.165 | 1.00 | 12.26 | A |

Figure 10 (20 of 142)

| | | | | | | | | | | |
|---|---|---|---|---|---|---|---|---|---|---|
| ATOM | 1206 | O   | ALA | A | 147 | 37.285 | 50.485 | 89.770 | 1.00 12.26 | A |
| ATOM | 1207 | N   | ASP | A | 148 | 39.293 | 49.498 | 89.477 | 1.00 12.26 | A |
| ATOM | 1208 | CA  | ASP | A | 148 | 38.850 | 48.853 | 88.261 | 1.00 22.94 | A |
| ATOM | 1209 | CB  | ASP | A | 148 | 39.987 | 48.173 | 87.538 | 1.00 35.87 | A |
| ATOM | 1210 | CG  | ASP | A | 148 | 40.789 | 49.141 | 86.739 | 1.00 38.19 | A |
| ATOM | 1211 | OD1 | ASP | A | 148 | 41.485 | 49.947 | 87.384 | 1.00 50.22 | A |
| ATOM | 1212 | OD2 | ASP | A | 148 | 40.712 | 49.117 | 85.486 | 1.00 39.53 | A |
| ATOM | 1213 | C   | ASP | A | 148 | 37.784 | 47.837 | 88.576 | 1.00 21.37 | A |
| ATOM | 1214 | O   | ASP | A | 148 | 37.948 | 46.953 | 89.412 | 1.00 13.76 | A |
| ATOM | 1215 | N   | VAL | A | 149 | 36.677 | 47.976 | 87.877 | 1.00 22.30 | A |
| ATOM | 1216 | CA  | VAL | A | 149 | 35.551 | 47.106 | 88.089 | 1.00 21.01 | A |
| ATOM | 1217 | CB  | VAL | A | 149 | 34.616 | 47.708 | 89.176 | 1.00 24.57 | A |
| ATOM | 1218 | CG1 | VAL | A | 149 | 33.354 | 46.874 | 89.322 | 1.00 35.61 | A |
| ATOM | 1219 | CG2 | VAL | A | 149 | 35.357 | 47.791 | 90.510 | 1.00 20.12 | A |
| ATOM | 1220 | C   | VAL | A | 149 | 34.793 | 46.907 | 86.786 | 1.00 19.02 | A |
| ATOM | 1221 | O   | VAL | A | 149 | 34.256 | 47.852 | 86.184 | 1.00 12.26 | A |
| ATOM | 1222 | N   | PRO | A | 150 | 34.730 | 45.660 | 86.342 | 1.00 12.26 | A |
| ATOM | 1223 | CD  | PRO | A | 150 | 35.088 | 44.427 | 87.062 | 1.00 12.26 | A |
| ATOM | 1224 | CA  | PRO | A | 150 | 34.029 | 45.361 | 85.106 | 1.00 12.26 | A |
| ATOM | 1225 | CB  | PRO | A | 150 | 33.758 | 43.871 | 85.239 | 1.00 12.26 | A |
| ATOM | 1226 | CG  | PRO | A | 150 | 34.977 | 43.394 | 85.977 | 1.00 13.05 | A |
| ATOM | 1227 | C   | PRO | A | 150 | 32.752 | 46.180 | 85.003 | 1.00 12.26 | A |
| ATOM | 1228 | O   | PRO | A | 150 | 32.002 | 46.305 | 85.973 | 1.00 12.26 | A |
| ATOM | 1229 | N   | GLU | A | 151 | 32.522 | 46.752 | 83.831 | 1.00 16.04 | A |
| ATOM | 1230 | CA  | GLU | A | 151 | 31.331 | 47.546 | 83.585 | 1.00 20.70 | A |
| ATOM | 1231 | CB  | GLU | A | 151 | 31.512 | 48.358 | 82.307 | 1.00 25.92 | A |
| ATOM | 1232 | CG  | GLU | A | 151 | 32.244 | 49.679 | 82.500 | 1.00 33.13 | A |
| ATOM | 1233 | CD  | GLU | A | 151 | 32.773 | 50.264 | 81.197 | 1.00 38.07 | A |
| ATOM | 1234 | OE1 | GLU | A | 151 | 33.228 | 51.439 | 81.230 | 1.00 34.78 | A |
| ATOM | 1235 | OE2 | GLU | A | 151 | 32.741 | 49.548 | 80.159 | 1.00 41.53 | A |
| ATOM | 1236 | C   | GLU | A | 151 | 30.130 | 46.629 | 83.431 | 1.00 12.92 | A |
| ATOM | 1237 | O   | GLU | A | 151 | 30.191 | 45.637 | 82.724 | 1.00 12.26 | A |
| ATOM | 1238 | N   | PHE | A | 152 | 29.039 | 46.941 | 84.106 | 1.00 12.26 | A |
| ATOM | 1239 | CA  | PHE | A | 152 | 27.854 | 46.120 | 83.978 | 1.00 14.04 | A |
| ATOM | 1240 | CB  | PHE | A | 152 | 27.672 | 45.257 | 85.218 | 1.00 19.32 | A |
| ATOM | 1241 | CG  | PHE | A | 152 | 26.580 | 44.226 | 85.092 | 1.00 24.40 | A |
| ATOM | 1242 | CD1 | PHE | A | 152 | 26.383 | 43.274 | 86.096 | 1.00 25.94 | A |
| ATOM | 1243 | CD2 | PHE | A | 152 | 25.722 | 44.220 | 83.994 | 1.00 25.47 | A |
| ATOM | 1244 | CE1 | PHE | A | 152 | 25.349 | 42.337 | 86.011 | 1.00 28.31 | A |
| ATOM | 1245 | CE2 | PHE | A | 152 | 24.683 | 43.285 | 83.902 | 1.00 22.32 | A |
| ATOM | 1246 | CZ  | PHE | A | 152 | 24.500 | 42.345 | 84.915 | 1.00 23.31 | A |
| ATOM | 1247 | C   | PHE | A | 152 | 26.700 | 47.089 | 83.815 | 1.00 16.98 | A |
| ATOM | 1248 | O   | PHE | A | 152 | 26.373 | 47.844 | 84.728 | 1.00 12.26 | A |
| ATOM | 1249 | N   | GLU | A | 153 | 26.093 | 47.070 | 82.637 | 1.00 15.97 | A |
| ATOM | 1250 | CA  | GLU | A | 153 | 25.006 | 47.974 | 82.328 | 1.00 16.04 | A |
| ATOM | 1251 | CB  | GLU | A | 153 | 24.880 | 48.150 | 80.826 | 1.00 19.67 | A |
| ATOM | 1252 | CG  | GLU | A | 153 | 23.855 | 49.178 | 80.462 | 1.00 21.93 | A |
| ATOM | 1253 | CD  | GLU | A | 153 | 23.654 | 49.272 | 78.985 | 1.00 26.71 | A |
| ATOM | 1254 | OE1 | GLU | A | 153 | 22.978 | 50.233 | 78.549 | 1.00 29.09 | A |
| ATOM | 1255 | OE2 | GLU | A | 153 | 24.168 | 48.381 | 78.263 | 1.00 31.76 | A |
| ATOM | 1256 | C   | GLU | A | 153 | 23.661 | 47.558 | 82.870 | 1.00 15.24 | A |
| ATOM | 1257 | O   | GLU | A | 153 | 22.872 | 46.928 | 82.180 | 1.00 17.88 | A |
| ATOM | 1258 | N   | VAL | A | 154 | 23.390 | 47.938 | 84.104 | 1.00 14.66 | A |
| ATOM | 1259 | CA  | VAL | A | 154 | 22.125 | 47.618 | 84.726 | 1.00 16.31 | A |
| ATOM | 1260 | CB  | VAL | A | 154 | 22.112 | 46.158 | 85.302 | 1.00 15.51 | A |
| ATOM | 1261 | CG1 | VAL | A | 154 | 23.316 | 45.921 | 86.224 | 1.00 18.15 | A |
| ATOM | 1262 | CG2 | VAL | A | 154 | 20.814 | 45.904 | 86.066 | 1.00 15.99 | A |
| ATOM | 1263 | C   | VAL | A | 154 | 21.897 | 48.629 | 85.834 | 1.00 19.89 | A |
| ATOM | 1264 | O   | VAL | A | 154 | 22.793 | 48.920 | 86.626 | 1.00 20.71 | A |
| ATOM | 1265 | N   | SER | A | 155 | 20.700 | 49.198 | 85.854 | 1.00 21.76 | A |
| ATOM | 1266 | CA  | SER | A | 155 | 20.319 | 50.160 | 86.881 | 1.00 22.35 | A |
| ATOM | 1267 | CB  | SER | A | 155 | 20.258 | 51.561 | 86.304 | 1.00 24.52 | A |
| ATOM | 1268 | OG  | SER | A | 155 | 19.200 | 51.639 | 85.375 | 1.00 31.03 | A |
| ATOM | 1269 | C   | SER | A | 155 | 18.927 | 49.741 | 87.352 | 1.00 22.40 | A |
| ATOM | 1270 | O   | SER | A | 155 | 18.211 | 49.020 | 86.650 | 1.00 23.26 | A |
| ATOM | 1271 | N   | SER | A | 156 | 18.543 | 50.175 | 88.544 | 1.00 20.73 | A |

Figure 10 (21 of 142)

| ATOM | 1272 | CA | SER | A | 156 | 17.232 | 49.814 | 89.063 | 1.00 | 19.21 | A |
|---|---|---|---|---|---|---|---|---|---|---|---|
| ATOM | 1273 | CB | SER | A | 156 | 16.996 | 50.492 | 90.410 | 1.00 | 15.95 | A |
| ATOM | 1274 | OG | SER | A | 156 | 16.809 | 51.883 | 90.211 | 1.00 | 23.28 | A |
| ATOM | 1275 | C | SER | A | 156 | 16.138 | 50.246 | 88.069 | 1.00 | 17.64 | A |
| ATOM | 1276 | O | SER | A | 156 | 15.300 | 49.444 | 87.642 | 1.00 | 20.89 | A |
| ATOM | 1277 | N | THR | A | 157 | 16.159 | 51.516 | 87.688 | 1.00 | 14.16 | A |
| ATOM | 1278 | CA | THR | A | 157 | 15.164 | 52.034 | 86.772 | 1.00 | 12.26 | A |
| ATOM | 1279 | CB | THR | A | 157 | 15.569 | 53.460 | 86.357 | 1.00 | 12.26 | A |
| ATOM | 1280 | OG1 | THR | A | 157 | 15.544 | 54.294 | 87.525 | 1.00 | 17.87 | A |
| ATOM | 1281 | CG2 | THR | A | 157 | 14.622 | 54.039 | 85.321 | 1.00 | 12.26 | A |
| ATOM | 1282 | C | THR | A | 157 | 14.915 | 51.115 | 85.561 | 1.00 | 15.23 | A |
| ATOM | 1283 | O | THR | A | 157 | 13.837 | 51.138 | 84.969 | 1.00 | 18.76 | A |
| ATOM | 1284 | N | MET | A | 158 | 15.897 | 50.290 | 85.214 | 1.00 | 17.05 | A |
| ATOM | 1285 | CA | MET | A | 158 | 15.765 | 49.351 | 84.095 | 1.00 | 20.31 | A |
| ATOM | 1286 | CB | MET | A | 158 | 17.088 | 48.628 | 83.854 | 1.00 | 25.96 | A |
| ATOM | 1287 | CG | MET | A | 158 | 17.034 | 47.460 | 82.872 | 1.00 | 31.01 | A |
| ATOM | 1288 | SD | MET | A | 158 | 18.683 | 46.701 | 82.699 | 1.00 | 34.21 | A |
| ATOM | 1289 | CE | MET | A | 158 | 19.738 | 48.133 | 82.728 | 1.00 | 38.55 | A |
| ATOM | 1290 | C | MET | A | 158 | 14.738 | 48.327 | 84.496 | 1.00 | 15.65 | A |
| ATOM | 1291 | O | MET | A | 158 | 13.692 | 48.172 | 83.858 | 1.00 | 21.71 | A |
| ATOM | 1292 | N | ILE | A | 159 | 15.093 | 47.623 | 85.565 | 1.00 | 14.34 | A |
| ATOM | 1293 | CA | ILE | A | 159 | 14.274 | 46.585 | 86.169 | 1.00 | 16.08 | A |
| ATOM | 1294 | CB | ILE | A | 159 | 14.893 | 46.124 | 87.541 | 1.00 | 17.23 | A |
| ATOM | 1295 | CG2 | ILE | A | 159 | 14.316 | 44.766 | 87.953 | 1.00 | 12.70 | A |
| ATOM | 1296 | CG1 | ILE | A | 159 | 16.426 | 45.997 | 87.425 | 1.00 | 12.26 | A |
| ATOM | 1297 | CD1 | ILE | A | 159 | 16.934 | 44.793 | 86.636 | 1.00 | 12.26 | A |
| ATOM | 1298 | C | ILE | A | 159 | 12.839 | 47.115 | 86.367 | 1.00 | 16.35 | A |
| ATOM | 1299 | O | ILE | A | 159 | 11.897 | 46.548 | 85.826 | 1.00 | 12.26 | A |
| ATOM | 1300 | N | ARG | A | 160 | 12.665 | 48.207 | 87.110 | 1.00 | 17.50 | A |
| ATOM | 1301 | CA | ARG | A | 160 | 11.324 | 48.739 | 87.308 | 1.00 | 22.89 | A |
| ATOM | 1302 | CB | ARG | A | 160 | 11.393 | 50.143 | 87.901 | 1.00 | 21.46 | A |
| ATOM | 1303 | CG | ARG | A | 160 | 12.234 | 50.186 | 89.158 | 1.00 | 25.86 | A |
| ATOM | 1304 | CD | ARG | A | 160 | 11.763 | 51.221 | 90.169 | 1.00 | 28.13 | A |
| ATOM | 1305 | NE | ARG | A | 160 | 12.795 | 52.212 | 90.456 | 1.00 | 27.22 | A |
| ATOM | 1306 | CZ | ARG | A | 160 | 12.999 | 53.307 | 89.729 | 1.00 | 29.50 | A |
| ATOM | 1307 | NH1 | ARG | A | 160 | 12.242 | 53.573 | 88.666 | 1.00 | 25.44 | A |
| ATOM | 1308 | NH2 | ARG | A | 160 | 13.974 | 54.136 | 90.058 | 1.00 | 34.14 | A |
| ATOM | 1309 | C | ARG | A | 160 | 10.536 | 48.744 | 85.997 | 1.00 | 25.79 | A |
| ATOM | 1310 | O | ARG | A | 160 | 9.425 | 48.234 | 85.938 | 1.00 | 25.30 | A |
| ATOM | 1311 | N | GLU | A | 161 | 11.105 | 49.297 | 84.937 | 1.00 | 30.36 | A |
| ATOM | 1312 | CA | GLU | A | 161 | 10.401 | 49.318 | 83.669 | 1.00 | 39.57 | A |
| ATOM | 1313 | CB | GLU | A | 161 | 11.119 | 50.229 | 82.694 | 1.00 | 48.38 | A |
| ATOM | 1314 | CG | GLU | A | 161 | 11.187 | 51.644 | 83.218 | 1.00 | 57.45 | A |
| ATOM | 1315 | CD | GLU | A | 161 | 11.455 | 52.656 | 82.132 | 1.00 | 62.11 | A |
| ATOM | 1316 | OE1 | GLU | A | 161 | 10.633 | 52.742 | 81.194 | 1.00 | 64.01 | A |
| ATOM | 1317 | OE2 | GLU | A | 161 | 12.482 | 53.364 | 82.221 | 1.00 | 67.28 | A |
| ATOM | 1318 | C | GLU | A | 161 | 10.303 | 47.915 | 83.118 | 1.00 | 40.21 | A |
| ATOM | 1319 | O | GLU | A | 161 | 9.311 | 47.539 | 82.509 | 1.00 | 41.97 | A |
| ATOM | 1320 | N | ARG | A | 162 | 11.345 | 47.136 | 83.335 | 1.00 | 43.54 | A |
| ATOM | 1321 | CA | ARG | A | 162 | 11.360 | 45.759 | 82.894 | 1.00 | 46.58 | A |
| ATOM | 1322 | CB | ARG | A | 162 | 12.662 | 45.120 | 83.358 | 1.00 | 51.01 | A |
| ATOM | 1323 | CG | ARG | A | 162 | 13.357 | 44.261 | 82.348 | 1.00 | 59.00 | A |
| ATOM | 1324 | CD | ARG | A | 162 | 14.263 | 45.090 | 81.490 | 1.00 | 65.18 | A |
| ATOM | 1325 | NE | ARG | A | 162 | 15.216 | 44.242 | 80.786 | 1.00 | 72.09 | A |
| ATOM | 1326 | CZ | ARG | A | 162 | 16.188 | 44.705 | 80.009 | 1.00 | 74.35 | A |
| ATOM | 1327 | NH1 | ARG | A | 162 | 16.336 | 46.018 | 79.837 | 1.00 | 77.12 | A |
| ATOM | 1328 | NH2 | ARG | A | 162 | 17.004 | 43.855 | 79.401 | 1.00 | 75.65 | A |
| ATOM | 1329 | C | ARG | A | 162 | 10.169 | 45.075 | 83.590 | 1.00 | 48.00 | A |
| ATOM | 1330 | O | ARG | A | 162 | 9.345 | 44.423 | 82.959 | 1.00 | 45.81 | A |
| ATOM | 1331 | N | PHE | A | 163 | 10.111 | 45.256 | 84.906 | 1.00 | 51.01 | A |
| ATOM | 1332 | CA | PHE | A | 163 | 9.083 | 44.698 | 85.794 | 1.00 | 53.32 | A |
| ATOM | 1333 | CB | PHE | A | 163 | 9.465 | 44.918 | 87.268 | 1.00 | 51.04 | A |
| ATOM | 1334 | CG | PHE | A | 163 | 10.079 | 43.733 | 87.941 | 1.00 | 49.60 | A |
| ATOM | 1335 | CD1 | PHE | A | 163 | 10.369 | 42.581 | 87.238 | 1.00 | 50.63 | A |
| ATOM | 1336 | CD2 | PHE | A | 163 | 10.398 | 43.787 | 89.287 | 1.00 | 48.45 | A |
| ATOM | 1337 | CE1 | PHE | A | 163 | 10.973 | 41.504 | 87.865 | 1.00 | 51.24 | A |

Figure 10 (22 of 142)

| ATOM | 1338 | CE2 | PHE A 163 | 11.001 | 42.715 | 89.920 | 1.00 | 50.41 | A |
| --- | --- | --- | --- | --- | --- | --- | --- | --- | --- |
| ATOM | 1339 | CZ | PHE A 163 | 11.289 | 41.573 | 89.207 | 1.00 | 52.33 | A |
| ATOM | 1340 | C | PHE A 163 | 7.747 | 45.371 | 85.595 | 1.00 | 54.80 | A |
| ATOM | 1341 | O | PHE A 163 | 6.930 | 45.378 | 86.507 | 1.00 | 61.06 | A |
| ATOM | 1342 | N | LYS A 164 | 7.528 | 45.960 | 84.432 | 1.00 | 54.72 | A |
| ATOM | 1343 | CA | LYS A 164 | 6.278 | 46.650 | 84.159 | 1.00 | 55.25 | A |
| ATOM | 1344 | CB | LYS A 164 | 6.237 | 47.986 | 84.887 | 1.00 | 58.20 | A |
| ATOM | 1345 | CG | LYS A 164 | 5.024 | 48.820 | 84.532 | 1.00 | 58.23 | A |
| ATOM | 1346 | CD | LYS A 164 | 3.819 | 48.499 | 85.420 | 1.00 | 59.36 | A |
| ATOM | 1347 | CE | LYS A 164 | 3.930 | 49.204 | 86.780 | 1.00 | 58.46 | A |
| ATOM | 1348 | NZ | LYS A 164 | 2.776 | 48.927 | 87.685 | 1.00 | 52.69 | A |
| ATOM | 1349 | C | LYS A 164 | 6.327 | 46.887 | 82.677 | 1.00 | 55.36 | A |
| ATOM | 1350 | O | LYS A 164 | 6.687 | 47.966 | 82.216 | 1.00 | 59.08 | A |
| ATOM | 1351 | N | SER A 165 | 5.960 | 45.855 | 81.941 | 1.00 | 55.39 | A |
| ATOM | 1352 | CA | SER A 165 | 5.992 | 45.835 | 80.490 | 1.00 | 54.56 | A |
| ATOM | 1353 | CB | SER A 165 | 7.049 | 46.798 | 79.952 | 1.00 | 55.28 | A |
| ATOM | 1354 | OG | SER A 165 | 7.101 | 46.751 | 78.544 | 1.00 | 60.24 | A |
| ATOM | 1355 | C | SER A 165 | 6.479 | 44.410 | 80.353 | 1.00 | 53.01 | A |
| ATOM | 1356 | O | SER A 165 | 6.822 | 43.933 | 79.274 | 1.00 | 51.15 | A |
| ATOM | 1357 | N | LYS A 166 | 6.503 | 43.759 | 81.512 | 1.00 | 51.61 | A |
| ATOM | 1358 | CA | LYS A 166 | 6.927 | 42.384 | 81.688 | 1.00 | 50.01 | A |
| ATOM | 1359 | CB | LYS A 166 | 5.707 | 41.466 | 81.642 | 1.00 | 52.05 | A |
| ATOM | 1360 | CG | LYS A 166 | 4.747 | 41.693 | 82.809 | 1.00 | 55.95 | A |
| ATOM | 1361 | CD | LYS A 166 | 5.423 | 41.458 | 84.167 | 1.00 | 59.02 | A |
| ATOM | 1362 | CE | LYS A 166 | 4.404 | 41.550 | 85.308 | 1.00 | 63.38 | A |
| ATOM | 1363 | NZ | LYS A 166 | 4.955 | 41.255 | 86.672 | 1.00 | 62.32 | A |
| ATOM | 1364 | C | LYS A 166 | 8.017 | 41.917 | 80.733 | 1.00 | 47.96 | A |
| ATOM | 1365 | O | LYS A 166 | 7.778 | 41.177 | 79.773 | 1.00 | 42.55 | A |
| ATOM | 1366 | N | LYS A 167 | 9.223 | 42.396 | 81.025 | 1.00 | 45.74 | A |
| ATOM | 1367 | CA | LYS A 167 | 10.424 | 42.067 | 80.288 | 1.00 | 44.78 | A |
| ATOM | 1368 | CB | LYS A 167 | 11.218 | 43.325 | 79.928 | 1.00 | 49.78 | A |
| ATOM | 1369 | CG | LYS A 167 | 11.180 | 43.675 | 78.461 | 1.00 | 55.61 | A |
| ATOM | 1370 | CD | LYS A 167 | 12.312 | 44.619 | 78.070 | 1.00 | 61.95 | A |
| ATOM | 1371 | CE | LYS A 167 | 12.222 | 44.981 | 76.584 | 1.00 | 68.88 | A |
| ATOM | 1372 | NZ | LYS A 167 | 13.332 | 45.834 | 76.061 | 1.00 | 70.67 | A |
| ATOM | 1373 | C | LYS A 167 | 11.234 | 41.215 | 81.247 | 1.00 | 44.80 | A |
| ATOM | 1374 | O | LYS A 167 | 11.057 | 41.278 | 82.449 | 1.00 | 40.80 | A |
| ATOM | 1375 | N | PRO A 168 | 12.140 | 40.412 | 80.715 | 1.00 | 46.64 | A |
| ATOM | 1376 | CD | PRO A 168 | 12.455 | 40.492 | 79.278 | 1.00 | 48.84 | A |
| ATOM | 1377 | CA | PRO A 168 | 13.049 | 39.488 | 81.382 | 1.00 | 46.28 | A |
| ATOM | 1378 | CB | PRO A 168 | 14.257 | 39.526 | 80.478 | 1.00 | 47.06 | A |
| ATOM | 1379 | CG | PRO A 168 | 13.590 | 39.495 | 79.129 | 1.00 | 50.98 | A |
| ATOM | 1380 | C | PRO A 168 | 13.426 | 39.666 | 82.846 | 1.00 | 45.63 | A |
| ATOM | 1381 | O | PRO A 168 | 13.006 | 38.874 | 83.691 | 1.00 | 46.96 | A |
| ATOM | 1382 | N | THR A 169 | 14.223 | 40.686 | 83.153 | 1.00 | 44.02 | A |
| ATOM | 1383 | CA | THR A 169 | 14.705 | 40.927 | 84.529 | 1.00 | 43.15 | A |
| ATOM | 1384 | CB | THR A 169 | 13.571 | 41.246 | 85.550 | 1.00 | 42.74 | A |
| ATOM | 1385 | OG1 | THR A 169 | 13.727 | 40.402 | 86.699 | 1.00 | 45.90 | A |
| ATOM | 1386 | CG2 | THR A 169 | 12.193 | 41.055 | 84.945 | 1.00 | 45.83 | A |
| ATOM | 1387 | C | THR A 169 | 15.527 | 39.771 | 85.119 | 1.00 | 38.19 | A |
| ATOM | 1388 | O | THR A 169 | 16.034 | 39.865 | 86.235 | 1.00 | 37.14 | A |
| ATOM | 1389 | N | ASP A 170 | 15.657 | 38.680 | 84.376 | 1.00 | 35.19 | A |
| ATOM | 1390 | CA | ASP A 170 | 16.436 | 37.556 | 84.860 | 1.00 | 35.76 | A |
| ATOM | 1391 | CB | ASP A 170 | 16.081 | 36.266 | 84.122 | 1.00 | 43.17 | A |
| ATOM | 1392 | CG | ASP A 170 | 14.690 | 35.760 | 84.458 | 1.00 | 48.82 | A |
| ATOM | 1393 | OD1 | ASP A 170 | 13.720 | 36.257 | 83.846 | 1.00 | 54.17 | A |
| ATOM | 1394 | OD2 | ASP A 170 | 14.558 | 34.873 | 85.337 | 1.00 | 51.36 | A |
| ATOM | 1395 | C | ASP A 170 | 17.900 | 37.839 | 84.650 | 1.00 | 30.43 | A |
| ATOM | 1396 | O | ASP A 170 | 18.287 | 38.450 | 83.661 | 1.00 | 31.21 | A |
| ATOM | 1397 | N | TYR A 171 | 18.712 | 37.368 | 85.582 | 1.00 | 27.96 | A |
| ATOM | 1398 | CA | TYR A 171 | 20.153 | 37.546 | 85.536 | 1.00 | 22.62 | A |
| ATOM | 1399 | CB | TYR A 171 | 20.735 | 37.000 | 84.227 | 1.00 | 21.32 | A |
| ATOM | 1400 | CG | TYR A 171 | 20.411 | 35.543 | 83.941 | 1.00 | 22.25 | A |
| ATOM | 1401 | CD1 | TYR A 171 | 19.393 | 35.192 | 83.044 | 1.00 | 24.91 | A |
| ATOM | 1402 | CE1 | TYR A 171 | 19.094 | 33.857 | 82.764 | 1.00 | 21.47 | A |
| ATOM | 1403 | CD2 | TYR A 171 | 21.119 | 34.518 | 84.554 | 1.00 | 20.23 | A |

Figure 10 (23 of 142)

| ATOM | 1404 | CE2 | TYR | A | 171 | 20.828 | 33.192 | 84.285 | 1.00 | 19.09 | A |
|---|---|---|---|---|---|---|---|---|---|---|---|
| ATOM | 1405 | CZ | TYR | A | 171 | 19.815 | 32.871 | 83.388 | 1.00 | 20.44 | A |
| ATOM | 1406 | OH | TYR | A | 171 | 19.531 | 31.557 | 83.111 | 1.00 | 23.01 | A |
| ATOM | 1407 | C | TYR | A | 171 | 20.537 | 39.011 | 85.703 | 1.00 | 21.99 | A |
| ATOM | 1408 | O | TYR | A | 171 | 21.659 | 39.401 | 85.383 | 1.00 | 27.12 | A |
| ATOM | 1409 | N | LEU | A | 172 | 19.608 | 39.818 | 86.208 | 1.00 | 16.64 | A |
| ATOM | 1410 | CA | LEU | A | 172 | 19.874 | 41.228 | 86.431 | 1.00 | 12.89 | A |
| ATOM | 1411 | CB | LEU | A | 172 | 18.941 | 42.103 | 85.601 | 1.00 | 15.79 | A |
| ATOM | 1412 | CG | LEU | A | 172 | 19.072 | 41.994 | 84.077 | 1.00 | 15.42 | A |
| ATOM | 1413 | CD1 | LEU | A | 172 | 18.157 | 42.988 | 83.414 | 1.00 | 21.84 | A |
| ATOM | 1414 | CD2 | LEU | A | 172 | 20.473 | 42.276 | 83.649 | 1.00 | 13.68 | A |
| ATOM | 1415 | C | LEU | A | 172 | 19.674 | 41.498 | 87.904 | 1.00 | 12.26 | A |
| ATOM | 1416 | O | LEU | A | 172 | 20.315 | 42.374 | 88.469 | 1.00 | 14.66 | A |
| ATOM | 1417 | N | ILE | A | 173 | 18.767 | 40.753 | 88.526 | 1.00 | 15.80 | A |
| ATOM | 1418 | CA | ILE | A | 173 | 18.527 | 40.870 | 89.970 | 1.00 | 18.88 | A |
| ATOM | 1419 | CB | ILE | A | 173 | 17.192 | 41.541 | 90.339 | 1.00 | 18.53 | A |
| ATOM | 1420 | CG2 | ILE | A | 173 | 17.286 | 43.028 | 90.143 | 1.00 | 23.42 | A |
| ATOM | 1421 | CG1 | ILE | A | 173 | 16.058 | 40.909 | 89.545 | 1.00 | 18.85 | A |
| ATOM | 1422 | CD1 | ILE | A | 173 | 14.732 | 41.591 | 89.743 | 1.00 | 20.85 | A |
| ATOM | 1423 | C | ILE | A | 173 | 18.454 | 39.454 | 90.493 | 1.00 | 19.13 | A |
| ATOM | 1424 | O | ILE | A | 173 | 18.053 | 38.545 | 89.768 | 1.00 | 21.75 | A |
| ATOM | 1425 | N | PRO | A | 174 | 18.851 | 39.243 | 91.755 | 1.00 | 20.59 | A |
| ATOM | 1426 | CD | PRO | A | 174 | 19.459 | 40.192 | 92.697 | 1.00 | 20.06 | A |
| ATOM | 1427 | CA | PRO | A | 174 | 18.807 | 37.904 | 92.335 | 1.00 | 23.17 | A |
| ATOM | 1428 | CB | PRO | A | 174 | 19.105 | 38.162 | 93.796 | 1.00 | 22.07 | A |
| ATOM | 1429 | CG | PRO | A | 174 | 20.090 | 39.265 | 93.707 | 1.00 | 20.29 | A |
| ATOM | 1430 | C | PRO | A | 174 | 17.438 | 37.313 | 92.123 | 1.00 | 22.76 | A |
| ATOM | 1431 | O | PRO | A | 174 | 16.452 | 38.038 | 92.046 | 1.00 | 23.21 | A |
| ATOM | 1432 | N | ASP | A | 175 | 17.380 | 35.995 | 92.019 | 1.00 | 29.67 | A |
| ATOM | 1433 | CA | ASP | A | 175 | 16.112 | 35.325 | 91.790 | 1.00 | 34.48 | A |
| ATOM | 1434 | CB | ASP | A | 175 | 16.377 | 33.850 | 91.445 | 1.00 | 43.32 | A |
| ATOM | 1435 | CG | ASP | A | 175 | 15.432 | 33.317 | 90.388 | 1.00 | 47.32 | A |
| ATOM | 1436 | OD1 | ASP | A | 175 | 14.285 | 32.965 | 90.747 | 1.00 | 52.06 | A |
| ATOM | 1437 | OD2 | ASP | A | 175 | 15.836 | 33.263 | 89.202 | 1.00 | 49.95 | A |
| ATOM | 1438 | C | ASP | A | 175 | 15.247 | 35.461 | 93.052 | 1.00 | 32.99 | A |
| ATOM | 1439 | O | ASP | A | 175 | 14.043 | 35.182 | 93.038 | 1.00 | 31.30 | A |
| ATOM | 1440 | N | LYS | A | 176 | 15.871 | 35.912 | 94.136 | 1.00 | 24.48 | A |
| ATOM | 1441 | CA | LYS | A | 176 | 15.172 | 36.069 | 95.396 | 1.00 | 23.71 | A |
| ATOM | 1442 | CB | LYS | A | 176 | 16.171 | 35.930 | 96.550 | 1.00 | 24.34 | A |
| ATOM | 1443 | CG | LYS | A | 176 | 16.654 | 34.490 | 96.749 | 1.00 | 26.03 | A |
| ATOM | 1444 | CD | LYS | A | 176 | 15.518 | 33.628 | 97.310 | 1.00 | 27.68 | A |
| ATOM | 1445 | CE | LYS | A | 176 | 15.599 | 32.175 | 96.868 | 1.00 | 27.55 | A |
| ATOM | 1446 | NZ | LYS | A | 176 | 14.465 | 31.373 | 97.436 | 1.00 | 25.75 | A |
| ATOM | 1447 | C | LYS | A | 176 | 14.491 | 37.425 | 95.424 | 1.00 | 26.44 | A |
| ATOM | 1448 | O | LYS | A | 176 | 13.376 | 37.578 | 95.937 | 1.00 | 24.56 | A |
| ATOM | 1449 | N | VAL | A | 177 | 15.167 | 38.409 | 94.850 | 1.00 | 23.34 | A |
| ATOM | 1450 | CA | VAL | A | 177 | 14.646 | 39.766 | 94.800 | 1.00 | 16.95 | A |
| ATOM | 1451 | CB | VAL | A | 177 | 15.791 | 40.749 | 94.397 | 1.00 | 15.89 | A |
| ATOM | 1452 | CG1 | VAL | A | 177 | 15.244 | 41.943 | 93.622 | 1.00 | 16.00 | A |
| ATOM | 1453 | CG2 | VAL | A | 177 | 16.529 | 41.222 | 95.666 | 1.00 | 14.10 | A |
| ATOM | 1454 | C | VAL | A | 177 | 13.467 | 39.841 | 93.831 | 1.00 | 19.35 | A |
| ATOM | 1455 | O | VAL | A | 177 | 12.531 | 40.601 | 94.038 | 1.00 | 16.15 | A |
| ATOM | 1456 | N | LYS | A | 178 | 13.513 | 39.024 | 92.785 | 1.00 | 25.32 | A |
| ATOM | 1457 | CA | LYS | A | 178 | 12.451 | 39.021 | 91.797 | 1.00 | 25.24 | A |
| ATOM | 1458 | CB | LYS | A | 178 | 12.795 | 38.085 | 90.630 | 1.00 | 25.50 | A |
| ATOM | 1459 | CG | LYS | A | 178 | 11.860 | 38.199 | 89.415 | 1.00 | 24.35 | A |
| ATOM | 1460 | CD | LYS | A | 178 | 12.339 | 37.352 | 88.226 | 1.00 | 28.76 | A |
| ATOM | 1461 | CE | LYS | A | 178 | 12.354 | 35.856 | 88.567 | 1.00 | 30.54 | A |
| ATOM | 1462 | NZ | LYS | A | 178 | 12.846 | 34.962 | 87.457 | 1.00 | 28.61 | A |
| ATOM | 1463 | C | LYS | A | 178 | 11.203 | 38.540 | 92.494 | 1.00 | 28.95 | A |
| ATOM | 1464 | O | LYS | A | 178 | 10.174 | 39.208 | 92.475 | 1.00 | 29.82 | A |
| ATOM | 1465 | N | LYS | A | 179 | 11.291 | 37.379 | 93.126 | 1.00 | 31.36 | A |
| ATOM | 1466 | CA | LYS | A | 179 | 10.130 | 36.846 | 93.823 | 1.00 | 30.77 | A |
| ATOM | 1467 | CB | LYS | A | 179 | 10.486 | 35.539 | 94.548 | 1.00 | 34.66 | A |
| ATOM | 1468 | CG | LYS | A | 179 | 10.892 | 34.393 | 93.608 | 1.00 | 36.95 | A |
| ATOM | 1469 | CD | LYS | A | 179 | 11.236 | 33.144 | 94.400 | 1.00 | 42.74 | A |

Figure 10 (24 of 142)

| ATOM | 1470 | CE | LYS | A | 179 | 11.861 | 32.067 | 93.532 | 1.00 | 43.98 | A |
|---|---|---|---|---|---|---|---|---|---|---|---|
| ATOM | 1471 | NZ | LYS | A | 179 | 12.260 | 30.894 | 94.370 | 1.00 | 49.01 | A |
| ATOM | 1472 | C | LYS | A | 179 | 9.545 | 37.866 | 94.806 | 1.00 | 27.23 | A |
| ATOM | 1473 | O | LYS | A | 179 | 8.349 | 38.145 | 94.750 | 1.00 | 20.33 | A |
| ATOM | 1474 | N | TYR | A | 180 | 10.369 | 38.442 | 95.683 | 1.00 | 23.36 | A |
| ATOM | 1475 | CA | TYR | A | 180 | 9.840 | 39.411 | 96.637 | 1.00 | 21.91 | A |
| ATOM | 1476 | CB | TYR | A | 180 | 10.947 | 40.142 | 97.367 | 1.00 | 20.44 | A |
| ATOM | 1477 | CG | TYR | A | 180 | 10.431 | 41.050 | 98.453 | 1.00 | 21.78 | A |
| ATOM | 1478 | CD1 | TYR | A | 180 | 10.664 | 40.753 | 99.789 | 1.00 | 27.34 | A |
| ATOM | 1479 | CE1 | TYR | A | 180 | 10.221 | 41.594 | 100.812 | 1.00 | 27.72 | A |
| ATOM | 1480 | CD2 | TYR | A | 180 | 9.731 | 42.219 | 98.152 | 1.00 | 24.59 | A |
| ATOM | 1481 | CE2 | TYR | A | 180 | 9.280 | 43.075 | 99.166 | 1.00 | 25.92 | A |
| ATOM | 1482 | CZ | TYR | A | 180 | 9.533 | 42.754 | 100.498 | 1.00 | 27.40 | A |
| ATOM | 1483 | OH | TYR | A | 180 | 9.141 | 43.591 | 101.527 | 1.00 | 27.58 | A |
| ATOM | 1484 | C | TYR | A | 180 | 8.987 | 40.440 | 95.925 | 1.00 | 25.02 | A |
| ATOM | 1485 | O | TYR | A | 180 | 7.883 | 40.742 | 96.356 | 1.00 | 29.71 | A |
| ATOM | 1486 | N | VAL | A | 181 | 9.500 | 40.993 | 94.837 | 1.00 | 25.02 | A |
| ATOM | 1487 | CA | VAL | A | 181 | 8.743 | 41.992 | 94.106 | 1.00 | 24.36 | A |
| ATOM | 1488 | CB | VAL | A | 181 | 9.514 | 42.492 | 92.844 | 1.00 | 26.22 | A |
| ATOM | 1489 | CG1 | VAL | A | 181 | 8.621 | 43.381 | 91.984 | 1.00 | 23.62 | A |
| ATOM | 1490 | CG2 | VAL | A | 181 | 10.737 | 43.280 | 93.268 | 1.00 | 28.03 | A |
| ATOM | 1491 | C | VAL | A | 181 | 7.385 | 41.442 | 93.697 | 1.00 | 25.82 | A |
| ATOM | 1492 | O | VAL | A | 181 | 6.362 | 41.964 | 94.133 | 1.00 | 30.45 | A |
| ATOM | 1493 | N | GLU | A | 182 | 7.368 | 40.389 | 92.879 | 1.00 | 26.44 | A |
| ATOM | 1494 | CA | GLU | A | 182 | 6.100 | 39.815 | 92.427 | 1.00 | 26.49 | A |
| ATOM | 1495 | CB | GLU | A | 182 | 6.326 | 38.511 | 91.651 | 1.00 | 33.22 | A |
| ATOM | 1496 | CG | GLU | A | 182 | 7.389 | 38.602 | 90.594 | 1.00 | 39.06 | A |
| ATOM | 1497 | CD | GLU | A | 182 | 7.526 | 37.319 | 89.800 | 1.00 | 42.61 | A |
| ATOM | 1498 | OE1 | GLU | A | 182 | 7.528 | 36.234 | 90.426 | 1.00 | 45.94 | A |
| ATOM | 1499 | OE2 | GLU | A | 182 | 7.642 | 37.403 | 88.552 | 1.00 | 45.29 | A |
| ATOM | 1500 | C | GLU | A | 182 | 5.202 | 39.533 | 93.630 | 1.00 | 24.83 | A |
| ATOM | 1501 | O | GLU | A | 182 | 4.016 | 39.883 | 93.632 | 1.00 | 19.71 | A |
| ATOM | 1502 | N | GLU | A | 183 | 5.781 | 38.913 | 94.654 | 1.00 | 24.59 | A |
| ATOM | 1503 | CA | GLU | A | 183 | 5.031 | 38.577 | 95.849 | 1.00 | 29.93 | A |
| ATOM | 1504 | CB | GLU | A | 183 | 5.902 | 37.827 | 96.855 | 1.00 | 34.71 | A |
| ATOM | 1505 | CG | GLU | A | 183 | 6.492 | 36.551 | 96.309 | 1.00 | 39.04 | A |
| ATOM | 1506 | CD | GLU | A | 183 | 6.958 | 35.626 | 97.400 | 1.00 | 40.05 | A |
| ATOM | 1507 | OE1 | GLU | A | 183 | 7.595 | 36.120 | 98.361 | 1.00 | 40.91 | A |
| ATOM | 1508 | OE2 | GLU | A | 183 | 6.687 | 34.409 | 97.283 | 1.00 | 42.09 | A |
| ATOM | 1509 | C | GLU | A | 183 | 4.469 | 39.817 | 96.499 | 1.00 | 31.54 | A |
| ATOM | 1510 | O | GLU | A | 183 | 3.263 | 39.973 | 96.575 | 1.00 | 36.58 | A |
| ATOM | 1511 | N | ASN | A | 184 | 5.334 | 40.709 | 96.958 | 1.00 | 32.28 | A |
| ATOM | 1512 | CA | ASN | A | 184 | 4.856 | 41.913 | 97.607 | 1.00 | 35.61 | A |
| ATOM | 1513 | CB | ASN | A | 184 | 5.915 | 42.431 | 98.572 | 1.00 | 41.92 | A |
| ATOM | 1514 | CG | ASN | A | 184 | 5.389 | 42.557 | 99.986 | 1.00 | 48.30 | A |
| ATOM | 1515 | OD1 | ASN | A | 184 | 6.155 | 42.553 | 100.948 | 1.00 | 54.64 | A |
| ATOM | 1516 | ND2 | ASN | A | 184 | 4.072 | 42.678 | 100.122 | 1.00 | 51.58 | A |
| ATOM | 1517 | C | ASN | A | 184 | 4.372 | 43.020 | 96.661 | 1.00 | 34.16 | A |
| ATOM | 1518 | O | ASN | A | 184 | 4.440 | 44.206 | 96.977 | 1.00 | 34.30 | A |
| ATOM | 1519 | N | GLY | A | 185 | 3.868 | 42.595 | 95.505 | 1.00 | 34.60 | A |
| ATOM | 1520 | CA | GLY | A | 185 | 3.305 | 43.492 | 94.505 | 1.00 | 39.89 | A |
| ATOM | 1521 | C | GLY | A | 185 | 4.035 | 44.717 | 93.980 | 1.00 | 41.18 | A |
| ATOM | 1522 | O | GLY | A | 185 | 3.431 | 45.536 | 93.284 | 1.00 | 44.80 | A |
| ATOM | 1523 | N | LEU | A | 186 | 5.318 | 44.858 | 94.281 | 1.00 | 38.23 | A |
| ATOM | 1524 | CA | LEU | A | 186 | 6.083 | 46.015 | 93.813 | 1.00 | 36.13 | A |
| ATOM | 1525 | CB | LEU | A | 186 | 7.533 | 45.898 | 94.283 | 1.00 | 30.40 | A |
| ATOM | 1526 | CG | LEU | A | 186 | 7.826 | 46.403 | 95.692 | 1.00 | 28.75 | A |
| ATOM | 1527 | CD1 | LEU | A | 186 | 7.896 | 47.890 | 95.666 | 1.00 | 25.59 | A |
| ATOM | 1528 | CD2 | LEU | A | 186 | 6.758 | 45.956 | 96.651 | 1.00 | 28.12 | A |
| ATOM | 1529 | C | LEU | A | 186 | 6.089 | 46.266 | 92.303 | 1.00 | 37.46 | A |
| ATOM | 1530 | O | LEU | A | 186 | 5.652 | 45.421 | 91.512 | 1.00 | 40.17 | A |
| ATOM | 1531 | N | TYR | A | 187 | 6.595 | 47.449 | 91.943 | 1.00 | 34.24 | A |
| ATOM | 1532 | CA | TYR | A | 187 | 6.762 | 47.917 | 90.567 | 1.00 | 34.30 | A |
| ATOM | 1533 | CB | TYR | A | 187 | 8.171 | 47.532 | 90.106 | 1.00 | 27.60 | A |
| ATOM | 1534 | CG | TYR | A | 187 | 9.240 | 47.757 | 91.172 | 1.00 | 23.20 | A |
| ATOM | 1535 | CD1 | TYR | A | 187 | 9.524 | 49.041 | 91.650 | 1.00 | 20.51 | A |

Figure 10 (25 of 142)

| | | | | | | | | | | |
|---|---|---|---|---|---|---|---|---|---|---|
| ATOM | 1536 | CE1 | TYR | A | 187 | 10.509 | 49.248 | 92.623 | 1.00 16.58 | A |
| ATOM | 1537 | CD2 | TYR | A | 187 | 9.973 | 46.686 | 91.698 | 1.00 21.63 | A |
| ATOM | 1538 | CE2 | TYR | A | 187 | 10.964 | 46.890 | 92.669 | 1.00 15.94 | A |
| ATOM | 1539 | CZ | TYR | A | 187 | 11.217 | 48.169 | 93.118 | 1.00 14.60 | A |
| ATOM | 1540 | OH | TYR | A | 187 | 12.190 | 48.365 | 94.055 | 1.00 17.26 | A |
| ATOM | 1541 | C | TYR | A | 187 | 5.714 | 47.424 | 89.550 | 1.00 34.86 | A |
| ATOM | 1542 | O | TYR | A | 187 | 4.788 | 48.200 | 89.251 | 1.00 40.21 | A |
| TER | 1543 | | TYR | A | 187 | | | | | |
| ATOM | 1544 | CB | LYS | B | 2 | 46.769 | 61.936 | 110.994 | 1.00 19.38 | B |
| ATOM | 1545 | CG | LYS | B | 2 | 47.691 | 63.013 | 110.444 | 1.00 20.95 | B |
| ATOM | 1546 | CD | LYS | B | 2 | 48.884 | 63.300 | 111.374 | 1.00 23.19 | B |
| ATOM | 1547 | CE | LYS | B | 2 | 49.598 | 64.600 | 110.985 | 1.00 19.52 | B |
| ATOM | 1548 | NZ | LYS | B | 2 | 50.918 | 64.794 | 111.639 | 1.00 16.08 | B |
| ATOM | 1549 | C | LYS | B | 2 | 45.990 | 60.840 | 108.875 | 1.00 19.68 | B |
| ATOM | 1550 | O | LYS | B | 2 | 47.038 | 60.191 | 108.890 | 1.00 18.90 | B |
| ATOM | 1551 | N | LYS | B | 2 | 44.504 | 60.962 | 110.931 | 1.00 13.82 | B |
| ATOM | 1552 | CA | LYS | B | 2 | 45.553 | 61.658 | 110.113 | 1.00 17.91 | B |
| ATOM | 1553 | N | LYS | B | 3 | 45.195 | 60.904 | 107.804 | 1.00 18.59 | B |
| ATOM | 1554 | CA | LYS | B | 3 | 45.436 | 60.153 | 106.562 | 1.00 17.74 | B |
| ATOM | 1555 | CB | LYS | B | 3 | 44.326 | 60.479 | 105.546 | 1.00 12.26 | B |
| ATOM | 1556 | CG | LYS | B | 3 | 42.892 | 60.322 | 106.073 | 1.00 12.26 | B |
| ATOM | 1557 | CD | LYS | B | 3 | 41.912 | 60.898 | 105.051 | 1.00 25.91 | B |
| ATOM | 1558 | CE | LYS | B | 3 | 40.589 | 61.396 | 105.663 | 1.00 24.93 | B |
| ATOM | 1559 | NZ | LYS | B | 3 | 39.768 | 62.172 | 104.647 | 1.00 27.93 | B |
| ATOM | 1560 | C | LYS | B | 3 | 46.817 | 60.374 | 105.918 | 1.00 16.39 | B |
| ATOM | 1561 | O | LYS | B | 3 | 47.084 | 61.432 | 105.347 | 1.00 18.24 | B |
| ATOM | 1562 | N | ILE | B | 4 | 47.681 | 59.363 | 105.983 | 1.00 19.47 | B |
| ATOM | 1563 | CA | ILE | B | 4 | 49.030 | 59.479 | 105.420 | 1.00 15.00 | B |
| ATOM | 1564 | CB | ILE | B | 4 | 50.083 | 59.268 | 106.518 | 1.00 14.62 | B |
| ATOM | 1565 | CG2 | ILE | B | 4 | 51.493 | 59.257 | 105.940 | 1.00 12.26 | B |
| ATOM | 1566 | CG1 | ILE | B | 4 | 49.955 | 60.407 | 107.521 | 1.00 17.34 | B |
| ATOM | 1567 | CD1 | ILE | B | 4 | 50.336 | 60.013 | 108.887 | 1.00 28.39 | B |
| ATOM | 1568 | C | ILE | B | 4 | 49.347 | 58.554 | 104.261 | 1.00 14.70 | B |
| ATOM | 1569 | O | ILE | B | 4 | 48.801 | 57.454 | 104.154 | 1.00 14.81 | B |
| ATOM | 1570 | N | GLY | B | 5 | 50.252 | 59.012 | 103.402 | 1.00 12.26 | B |
| ATOM | 1571 | CA | GLY | B | 5 | 50.644 | 58.238 | 102.241 | 1.00 12.26 | B |
| ATOM | 1572 | C | GLY | B | 5 | 52.140 | 58.026 | 102.190 | 1.00 12.59 | B |
| ATOM | 1573 | O | GLY | B | 5 | 52.890 | 58.908 | 101.772 | 1.00 12.26 | B |
| ATOM | 1574 | N | ILE | B | 6 | 52.570 | 56.846 | 102.634 | 1.00 14.44 | B |
| ATOM | 1575 | CA | ILE | B | 6 | 53.985 | 56.464 | 102.655 | 1.00 12.63 | B |
| ATOM | 1576 | CB | ILE | B | 6 | 54.176 | 55.111 | 103.334 | 1.00 12.26 | B |
| ATOM | 1577 | CG2 | ILE | B | 6 | 55.610 | 54.672 | 103.225 | 1.00 12.26 | B |
| ATOM | 1578 | CG1 | ILE | B | 6 | 53.732 | 55.222 | 104.781 | 1.00 12.97 | B |
| ATOM | 1579 | CD1 | ILE | B | 6 | 53.944 | 53.977 | 105.581 | 1.00 24.77 | B |
| ATOM | 1580 | C | ILE | B | 6 | 54.460 | 56.354 | 101.233 | 1.00 13.83 | B |
| ATOM | 1581 | O | ILE | B | 6 | 53.998 | 55.510 | 100.478 | 1.00 19.52 | B |
| ATOM | 1582 | N | PHE | B | 7 | 55.391 | 57.205 | 100.866 | 1.00 12.26 | B |
| ATOM | 1583 | CA | PHE | B | 7 | 55.895 | 57.208 | 99.505 | 1.00 12.26 | B |
| ATOM | 1584 | CB | PHE | B | 7 | 55.804 | 58.638 | 98.938 | 1.00 12.39 | B |
| ATOM | 1585 | CG | PHE | B | 7 | 56.179 | 58.757 | 97.484 | 1.00 12.26 | B |
| ATOM | 1586 | CD1 | PHE | B | 7 | 55.995 | 57.703 | 96.599 | 1.00 14.90 | B |
| ATOM | 1587 | CD2 | PHE | B | 7 | 56.651 | 59.950 | 96.985 | 1.00 12.26 | B |
| ATOM | 1588 | CE1 | PHE | B | 7 | 56.276 | 57.852 | 95.244 | 1.00 12.26 | B |
| ATOM | 1589 | CE2 | PHE | B | 7 | 56.932 | 60.097 | 95.627 | 1.00 12.26 | B |
| ATOM | 1590 | CZ | PHE | B | 7 | 56.743 | 59.048 | 94.762 | 1.00 12.26 | B |
| ATOM | 1591 | C | PHE | B | 7 | 57.324 | 56.692 | 99.434 | 1.00 16.68 | B |
| ATOM | 1592 | O | PHE | B | 7 | 58.261 | 57.450 | 99.222 | 1.00 19.00 | B |
| ATOM | 1593 | N | GLY | B | 8 | 57.490 | 55.392 | 99.601 | 1.00 15.53 | B |
| ATOM | 1594 | CA | GLY | B | 8 | 58.826 | 54.821 | 99.556 | 1.00 24.51 | B |
| ATOM | 1595 | C | GLY | B | 8 | 59.579 | 54.836 | 98.229 | 1.00 26.57 | B |
| ATOM | 1596 | O | GLY | B | 8 | 59.001 | 54.610 | 97.158 | 1.00 26.98 | B |
| ATOM | 1597 | N | GLY | B | 9 | 60.884 | 55.094 | 98.314 | 1.00 24.36 | B |
| ATOM | 1598 | CA | GLY | B | 9 | 61.736 | 55.118 | 97.131 | 1.00 24.88 | B |
| ATOM | 1599 | C | GLY | B | 9 | 63.214 | 55.215 | 97.492 | 1.00 27.12 | B |
| ATOM | 1600 | O | GLY | B | 9 | 63.538 | 55.559 | 98.631 | 1.00 31.18 | B |
| ATOM | 1601 | N | THR | B | 10 | 64.124 | 54.903 | 96.566 | 1.00 22.83 | B |

Figure 10 (26 of 142)

| | | | | | | | | | | |
|---|---|---|---|---|---|---|---|---|---|---|
| ATOM | 1602 | CA | THR | B | 10 | 65.546 | 55.022 | 96.903 | 1.00 19.88 | B |
| ATOM | 1603 | CB | THR | B | 10 | 66.482 | 54.002 | 96.160 | 1.00 20.87 | B |
| ATOM | 1604 | OG1 | THR | B | 10 | 66.792 | 54.491 | 94.856 | 1.00 24.29 | B |
| ATOM | 1605 | CG2 | THR | B | 10 | 65.839 | 52.658 | 96.018 | 1.00 19.00 | B |
| ATOM | 1606 | C | THR | B | 10 | 66.017 | 56.423 | 96.529 | 1.00 18.90 | B |
| ATOM | 1607 | O | THR | B | 10 | 67.128 | 56.812 | 96.878 | 1.00 21.26 | B |
| ATOM | 1608 | N | PHE | B | 11 | 65.167 | 57.159 | 95.809 | 1.00 17.93 | B |
| ATOM | 1609 | CA | PHE | B | 11 | 65.447 | 58.530 | 95.373 | 1.00 15.42 | B |
| ATOM | 1610 | CB | PHE | B | 11 | 64.970 | 59.523 | 96.424 | 1.00 12.26 | B |
| ATOM | 1611 | CG | PHE | B | 11 | 63.580 | 59.277 | 96.874 | 1.00 12.26 | B |
| ATOM | 1612 | CD1 | PHE | B | 11 | 63.328 | 58.512 | 98.007 | 1.00 12.26 | B |
| ATOM | 1613 | CD2 | PHE | B | 11 | 62.516 | 59.771 | 96.141 | 1.00 12.26 | B |
| ATOM | 1614 | CE1 | PHE | B | 11 | 62.034 | 58.244 | 98.405 | 1.00 12.26 | B |
| ATOM | 1615 | CE2 | PHE | B | 11 | 61.226 | 59.516 | 96.524 | 1.00 12.26 | B |
| ATOM | 1616 | CZ | PHE | B | 11 | 60.983 | 58.743 | 97.664 | 1.00 12.26 | B |
| ATOM | 1617 | C | PHE | B | 11 | 66.922 | 58.738 | 95.128 | 1.00 12.62 | B |
| ATOM | 1618 | O | PHE | B | 11 | 67.606 | 59.358 | 95.928 | 1.00 17.32 | B |
| ATOM | 1619 | N | ASP | B | 12 | 67.412 | 58.234 | 94.009 | 1.00 17.16 | B |
| ATOM | 1620 | CA | ASP | B | 12 | 68.829 | 58.341 | 93.702 | 1.00 23.02 | B |
| ATOM | 1621 | CB | ASP | B | 12 | 69.469 | 56.977 | 94.030 | 1.00 23.88 | B |
| ATOM | 1622 | CG | ASP | B | 12 | 70.903 | 56.856 | 93.563 | 1.00 26.42 | B |
| ATOM | 1623 | OD1 | ASP | B | 12 | 71.670 | 57.806 | 93.782 | 1.00 34.20 | B |
| ATOM | 1624 | OD2 | ASP | B | 12 | 71.273 | 55.806 | 92.987 | 1.00 26.92 | B |
| ATOM | 1625 | C | ASP | B | 12 | 69.033 | 58.776 | 92.236 | 1.00 15.04 | B |
| ATOM | 1626 | O | ASP | B | 12 | 69.432 | 57.988 | 91.364 | 1.00 15.36 | B |
| ATOM | 1627 | N | PRO | B | 13 | 68.795 | 60.073 | 91.960 | 1.00 12.26 | B |
| ATOM | 1628 | CD | PRO | B | 13 | 69.135 | 60.696 | 90.662 | 1.00 12.26 | B |
| ATOM | 1629 | CA | PRO | B | 13 | 68.369 | 61.102 | 92.921 | 1.00 14.29 | B |
| ATOM | 1630 | CB | PRO | B | 13 | 69.092 | 62.331 | 92.415 | 1.00 12.26 | B |
| ATOM | 1631 | CG | PRO | B | 13 | 68.866 | 62.180 | 90.919 | 1.00 12.26 | B |
| ATOM | 1632 | C | PRO | B | 13 | 66.872 | 61.328 | 92.898 | 1.00 12.26 | B |
| ATOM | 1633 | O | PRO | B | 13 | 66.154 | 60.654 | 92.168 | 1.00 14.89 | B |
| ATOM | 1634 | N | PRO | B | 14 | 66.384 | 62.286 | 93.708 | 1.00 12.26 | B |
| ATOM | 1635 | CD | PRO | B | 14 | 67.044 | 62.967 | 94.833 | 1.00 16.60 | B |
| ATOM | 1636 | CA | PRO | B | 14 | 64.949 | 62.567 | 93.726 | 1.00 12.26 | B |
| ATOM | 1637 | CB | PRO | B | 14 | 64.755 | 63.363 | 95.023 | 1.00 12.26 | B |
| ATOM | 1638 | CG | PRO | B | 14 | 65.931 | 63.005 | 95.852 | 1.00 14.34 | B |
| ATOM | 1639 | C | PRO | B | 14 | 64.772 | 63.459 | 92.520 | 1.00 12.26 | B |
| ATOM | 1640 | O | PRO | B | 14 | 65.729 | 64.113 | 92.109 | 1.00 15.52 | B |
| ATOM | 1641 | N | HIS | B | 15 | 63.588 | 63.475 | 91.925 | 1.00 12.26 | B |
| ATOM | 1642 | CA | HIS | B | 15 | 63.376 | 64.365 | 90.802 | 1.00 12.26 | B |
| ATOM | 1643 | CB | HIS | B | 15 | 63.784 | 63.717 | 89.492 | 1.00 12.26 | B |
| ATOM | 1644 | CG | HIS | B | 15 | 63.208 | 62.360 | 89.292 | 1.00 19.48 | B |
| ATOM | 1645 | CD2 | HIS | B | 15 | 63.797 | 61.168 | 89.050 | 1.00 12.26 | B |
| ATOM | 1646 | ND1 | HIS | B | 15 | 61.854 | 62.115 | 89.357 | 1.00 16.02 | B |
| ATOM | 1647 | CE1 | HIS | B | 15 | 61.634 | 60.827 | 89.166 | 1.00 20.47 | B |
| ATOM | 1648 | NE2 | HIS | B | 15 | 62.797 | 60.231 | 88.978 | 1.00 17.58 | B |
| ATOM | 1649 | C | HIS | B | 15 | 61.936 | 64.817 | 90.750 | 1.00 13.45 | B |
| ATOM | 1650 | O | HIS | B | 15 | 61.077 | 64.313 | 91.496 | 1.00 12.26 | B |
| ATOM | 1651 | N | ASN | B | 16 | 61.685 | 65.777 | 89.869 | 1.00 15.61 | B |
| ATOM | 1652 | CA | ASN | B | 16 | 60.375 | 66.369 | 89.736 | 1.00 19.18 | B |
| ATOM | 1653 | CB | ASN | B | 16 | 60.388 | 67.340 | 88.571 | 1.00 20.70 | B |
| ATOM | 1654 | CG | ASN | B | 16 | 61.314 | 68.514 | 88.823 | 1.00 21.21 | B |
| ATOM | 1655 | OD1 | ASN | B | 16 | 61.314 | 69.110 | 89.898 | 1.00 21.90 | B |
| ATOM | 1656 | ND2 | ASN | B | 16 | 62.101 | 68.853 | 87.829 | 1.00 20.72 | B |
| ATOM | 1657 | C | ASN | B | 16 | 59.229 | 65.384 | 89.627 | 1.00 21.48 | B |
| ATOM | 1658 | O | ASN | B | 16 | 58.166 | 65.589 | 90.223 | 1.00 27.30 | B |
| ATOM | 1659 | N | GLY | B | 17 | 59.448 | 64.308 | 88.880 | 1.00 17.36 | B |
| ATOM | 1660 | CA | GLY | B | 17 | 58.416 | 63.291 | 88.746 | 1.00 17.62 | B |
| ATOM | 1661 | C | GLY | B | 17 | 57.929 | 62.785 | 90.099 | 1.00 12.26 | B |
| ATOM | 1662 | O | GLY | B | 17 | 56.738 | 62.477 | 90.273 | 1.00 12.26 | B |
| ATOM | 1663 | N | HIS | B | 18 | 58.848 | 62.691 | 91.055 | 1.00 12.26 | B |
| ATOM | 1664 | CA | HIS | B | 18 | 58.508 | 62.243 | 92.380 | 1.00 12.26 | B |
| ATOM | 1665 | CB | HIS | B | 18 | 59.772 | 62.080 | 93.198 | 1.00 12.26 | B |
| ATOM | 1666 | CG | HIS | B | 18 | 60.640 | 60.944 | 92.748 | 1.00 13.74 | B |
| ATOM | 1667 | CD2 | HIS | B | 18 | 60.328 | 59.714 | 92.272 | 1.00 12.26 | B |

Figure 10 (27 of 142)

| | | | | | | | | | |
|---|---|---|---|---|---|---|---|---|---|
| ATOM | 1668 | ND1 | HIS B | 18 | 62.018 | 60.988 | 92.812 | 1.00 12.26 | B |
| ATOM | 1669 | CE1 | HIS B | 18 | 62.514 | 59.838 | 92.397 | 1.00 12.26 | B |
| ATOM | 1670 | NE2 | HIS B | 18 | 61.511 | 59.046 | 92.063 | 1.00 12.26 | B |
| ATOM | 1671 | C | HIS B | 18 | 57.612 | 63.296 | 93.003 | 1.00 12.26 | B |
| ATOM | 1672 | O | HIS B | 18 | 56.531 | 62.995 | 93.513 | 1.00 12.98 | B |
| ATOM | 1673 | N | LEU B | 19 | 58.065 | 64.538 | 92.936 | 1.00 12.97 | B |
| ATOM | 1674 | CA | LEU B | 19 | 57.341 | 65.674 | 93.483 | 1.00 12.26 | B |
| ATOM | 1675 | CB | LEU B | 19 | 58.145 | 66.922 | 93.183 | 1.00 12.26 | B |
| ATOM | 1676 | CG | LEU B | 19 | 59.537 | 66.821 | 93.807 | 1.00 14.22 | B |
| ATOM | 1677 | CD1 | LEU B | 19 | 60.426 | 67.958 | 93.327 | 1.00 18.32 | B |
| ATOM | 1678 | CD2 | LEU B | 19 | 59.384 | 66.826 | 95.336 | 1.00 16.10 | B |
| ATOM | 1679 | C | LEU B | 19 | 55.922 | 65.838 | 92.944 | 1.00 16.08 | B |
| ATOM | 1680 | O | LEU B | 19 | 54.981 | 66.135 | 93.700 | 1.00 12.26 | B |
| ATOM | 1681 | N | LEU B | 20 | 55.779 | 65.659 | 91.630 | 1.00 16.07 | B |
| ATOM | 1682 | CA | LEU B | 20 | 54.482 | 65.777 | 90.983 | 1.00 14.60 | B |
| ATOM | 1683 | CB | LEU B | 20 | 54.620 | 65.713 | 89.464 | 1.00 12.26 | B |
| ATOM | 1684 | CG | LEU B | 20 | 53.323 | 66.109 | 88.757 | 1.00 12.26 | B |
| ATOM | 1685 | CD1 | LEU B | 20 | 52.838 | 67.464 | 89.260 | 1.00 12.26 | B |
| ATOM | 1686 | CD2 | LEU B | 20 | 53.566 | 66.157 | 87.266 | 1.00 12.26 | B |
| ATOM | 1687 | C | LEU B | 20 | 53.558 | 64.672 | 91.458 | 1.00 13.64 | B |
| ATOM | 1688 | O | LEU B | 20 | 52.486 | 64.944 | 92.003 | 1.00 16.54 | B |
| ATOM | 1689 | N | MET B | 21 | 53.980 | 63.425 | 91.278 | 1.00 16.42 | B |
| ATOM | 1690 | CA | MET B | 21 | 53.149 | 62.305 | 91.701 | 1.00 15.93 | B |
| ATOM | 1691 | CB | MET B | 21 | 53.887 | 60.975 | 91.538 | 1.00 16.53 | B |
| ATOM | 1692 | CG | MET B | 21 | 53.464 | 60.196 | 90.316 | 1.00 12.26 | B |
| ATOM | 1693 | SD | MET B | 21 | 53.408 | 61.295 | 88.900 | 1.00 14.63 | B |
| ATOM | 1694 | CE | MET B | 21 | 52.892 | 60.224 | 87.587 | 1.00 28.01 | B |
| ATOM | 1695 | C | MET B | 21 | 52.692 | 62.444 | 93.132 | 1.00 12.26 | B |
| ATOM | 1696 | O | MET B | 21 | 51.513 | 62.292 | 93.423 | 1.00 12.26 | B |
| ATOM | 1697 | N | ALA B | 22 | 53.631 | 62.743 | 94.020 | 1.00 17.09 | B |
| ATOM | 1698 | CA | ALA B | 22 | 53.334 | 62.884 | 95.437 | 1.00 18.94 | B |
| ATOM | 1699 | CB | ALA B | 22 | 54.606 | 63.169 | 96.198 | 1.00 18.65 | B |
| ATOM | 1700 | C | ALA B | 22 | 52.323 | 63.976 | 95.714 | 1.00 18.11 | B |
| ATOM | 1701 | O | ALA B | 22 | 51.307 | 63.740 | 96.384 | 1.00 16.27 | B |
| ATOM | 1702 | N | ASN B | 23 | 52.608 | 65.166 | 95.193 | 1.00 12.26 | B |
| ATOM | 1703 | CA | ASN B | 23 | 51.747 | 66.316 | 95.401 | 1.00 12.26 | B |
| ATOM | 1704 | CB | ASN B | 23 | 52.465 | 67.578 | 94.897 | 1.00 12.26 | B |
| ATOM | 1705 | CG | ASN B | 23 | 51.678 | 68.847 | 95.173 | 1.00 13.87 | B |
| ATOM | 1706 | OD1 | ASN B | 23 | 50.974 | 69.368 | 94.286 | 1.00 15.48 | B |
| ATOM | 1707 | ND2 | ASN B | 23 | 51.772 | 69.349 | 96.408 | 1.00 12.26 | B |
| ATOM | 1708 | C | ASN B | 23 | 50.372 | 66.124 | 94.748 | 1.00 12.26 | B |
| ATOM | 1709 | O | ASN B | 23 | 49.384 | 66.721 | 95.169 | 1.00 15.17 | B |
| ATOM | 1710 | N | GLU B | 24 | 50.310 | 65.266 | 93.735 | 1.00 16.89 | B |
| ATOM | 1711 | CA | GLU B | 24 | 49.053 | 64.965 | 93.050 | 1.00 12.26 | B |
| ATOM | 1712 | CB | GLU B | 24 | 49.309 | 64.465 | 91.622 | 1.00 19.75 | B |
| ATOM | 1713 | CG | GLU B | 24 | 49.865 | 65.490 | 90.653 | 1.00 19.92 | B |
| ATOM | 1714 | CD | GLU B | 24 | 48.966 | 66.687 | 90.533 | 1.00 26.42 | B |
| ATOM | 1715 | OE1 | GLU B | 24 | 47.735 | 66.487 | 90.535 | 1.00 29.24 | B |
| ATOM | 1716 | OE2 | GLU B | 24 | 49.481 | 67.820 | 90.435 | 1.00 27.91 | B |
| ATOM | 1717 | C | GLU B | 24 | 48.310 | 63.870 | 93.812 | 1.00 12.26 | B |
| ATOM | 1718 | O | GLU B | 24 | 47.103 | 63.947 | 94.020 | 1.00 12.26 | B |
| ATOM | 1719 | N | VAL B | 25 | 49.025 | 62.829 | 94.206 | 1.00 12.26 | B |
| ATOM | 1720 | CA | VAL B | 25 | 48.375 | 61.766 | 94.931 | 1.00 12.26 | B |
| ATOM | 1721 | CB | VAL B | 25 | 49.349 | 60.663 | 95.346 | 1.00 12.26 | B |
| ATOM | 1722 | CG1 | VAL B | 25 | 48.732 | 59.842 | 96.448 | 1.00 13.03 | B |
| ATOM | 1723 | CG2 | VAL B | 25 | 49.653 | 59.757 | 94.164 | 1.00 12.26 | B |
| ATOM | 1724 | C | VAL B | 25 | 47.815 | 62.420 | 96.166 | 1.00 16.23 | B |
| ATOM | 1725 | O | VAL B | 25 | 46.663 | 62.187 | 96.537 | 1.00 22.73 | B |
| ATOM | 1726 | N | LEU B | 26 | 48.636 | 63.258 | 96.790 | 1.00 13.97 | B |
| ATOM | 1727 | CA | LEU B | 26 | 48.229 | 63.962 | 97.995 | 1.00 12.92 | B |
| ATOM | 1728 | CB | LEU B | 26 | 49.188 | 65.117 | 98.291 | 1.00 16.39 | B |
| ATOM | 1729 | CG | LEU B | 26 | 48.840 | 65.977 | 99.522 | 1.00 16.64 | B |
| ATOM | 1730 | CD1 | LEU B | 26 | 48.936 | 65.157 | 100.825 | 1.00 14.02 | B |
| ATOM | 1731 | CD2 | LEU B | 26 | 49.771 | 67.178 | 99.569 | 1.00 18.87 | B |
| ATOM | 1732 | C | LEU B | 26 | 46.820 | 64.504 | 97.864 | 1.00 12.26 | B |
| ATOM | 1733 | O | LEU B | 26 | 46.004 | 64.330 | 98.768 | 1.00 15.54 | B |

Figure 10 (28 of 142)

| ATOM | 1734 | N | TYR B | 27 | 46.543 | 65.166 | 96.744 | 1.00 | 12.26 | B |
|---|---|---|---|---|---|---|---|---|---|---|
| ATOM | 1735 | CA | TYR B | 27 | 45.221 | 65.731 | 96.488 | 1.00 | 12.26 | B |
| ATOM | 1736 | CB | TYR B | 27 | 45.257 | 66.677 | 95.281 | 1.00 | 12.26 | B |
| ATOM | 1737 | CG | TYR B | 27 | 43.893 | 67.216 | 94.934 | 1.00 | 12.26 | B |
| ATOM | 1738 | CD1 | TYR B | 27 | 43.239 | 68.085 | 95.786 | 1.00 | 14.57 | B |
| ATOM | 1739 | CE1 | TYR B | 27 | 41.977 | 68.581 | 95.478 | 1.00 | 16.72 | B |
| ATOM | 1740 | CD2 | TYR B | 27 | 43.252 | 66.847 | 93.763 | 1.00 | 12.26 | B |
| ATOM | 1741 | CE2 | TYR B | 27 | 41.990 | 67.335 | 93.447 | 1.00 | 14.72 | B |
| ATOM | 1742 | CZ | TYR B | 27 | 41.356 | 68.208 | 94.305 | 1.00 | 17.62 | B |
| ATOM | 1743 | OH | TYR B | 27 | 40.123 | 68.746 | 93.987 | 1.00 | 15.62 | B |
| ATOM | 1744 | C | TYR B | 27 | 44.170 | 64.652 | 96.218 | 1.00 | 12.26 | B |
| ATOM | 1745 | O | TYR B | 27 | 43.169 | 64.515 | 96.949 | 1.00 | 14.31 | B |
| ATOM | 1746 | N | GLN B | 28 | 44.425 | 63.891 | 95.159 | 1.00 | 15.12 | B |
| ATOM | 1747 | CA | GLN B | 28 | 43.545 | 62.837 | 94.692 | 1.00 | 13.42 | B |
| ATOM | 1748 | CB | GLN B | 28 | 44.204 | 62.158 | 93.500 | 1.00 | 12.26 | B |
| ATOM | 1749 | CG | GLN B | 28 | 43.222 | 61.779 | 92.431 | 1.00 | 12.26 | B |
| ATOM | 1750 | CD | GLN B | 28 | 42.261 | 62.904 | 92.123 | 1.00 | 17.40 | B |
| ATOM | 1751 | OE1 | GLN B | 28 | 42.675 | 64.035 | 91.866 | 1.00 | 19.55 | B |
| ATOM | 1752 | NE2 | GLN B | 28 | 40.965 | 62.601 | 92.145 | 1.00 | 22.83 | B |
| ATOM | 1753 | C | GLN B | 28 | 43.074 | 61.785 | 95.698 | 1.00 | 12.64 | B |
| ATOM | 1754 | O | GLN B | 28 | 41.894 | 61.421 | 95.692 | 1.00 | 12.26 | B |
| ATOM | 1755 | N | ALA B | 29 | 43.982 | 61.303 | 96.548 | 1.00 | 12.26 | B |
| ATOM | 1756 | CA | ALA B | 29 | 43.646 | 60.281 | 97.537 | 1.00 | 16.75 | B |
| ATOM | 1757 | CB | ALA B | 29 | 44.841 | 59.406 | 97.810 | 1.00 | 15.57 | B |
| ATOM | 1758 | C | ALA B | 29 | 43.148 | 60.888 | 98.830 | 1.00 | 19.13 | B |
| ATOM | 1759 | O | ALA B | 29 | 42.855 | 60.180 | 99.794 | 1.00 | 22.98 | B |
| ATOM | 1760 | N | GLY B | 30 | 43.060 | 62.212 | 98.840 | 1.00 | 27.07 | B |
| ATOM | 1761 | CA | GLY B | 30 | 42.567 | 62.920 | 100.002 | 1.00 | 22.14 | B |
| ATOM | 1762 | C | GLY B | 30 | 43.375 | 62.680 | 101.252 | 1.00 | 19.68 | B |
| ATOM | 1763 | O | GLY B | 30 | 42.814 | 62.449 | 102.330 | 1.00 | 23.56 | B |
| ATOM | 1764 | N | LEU B | 31 | 44.695 | 62.747 | 101.110 | 1.00 | 21.38 | B |
| ATOM | 1765 | CA | LEU B | 31 | 45.595 | 62.544 | 102.243 | 1.00 | 16.67 | B |
| ATOM | 1766 | CB | LEU B | 31 | 46.901 | 61.903 | 101.786 | 1.00 | 12.26 | B |
| ATOM | 1767 | CG | LEU B | 31 | 46.708 | 60.617 | 100.990 | 1.00 | 12.26 | B |
| ATOM | 1768 | CD1 | LEU B | 31 | 48.049 | 60.146 | 100.475 | 1.00 | 12.26 | B |
| ATOM | 1769 | CD2 | LEU B | 31 | 46.036 | 59.563 | 101.850 | 1.00 | 12.26 | B |
| ATOM | 1770 | C | LEU B | 31 | 45.908 | 63.861 | 102.913 | 1.00 | 12.27 | B |
| ATOM | 1771 | O | LEU B | 31 | 45.601 | 64.915 | 102.364 | 1.00 | 12.26 | B |
| ATOM | 1772 | N | ASP B | 32 | 46.514 | 63.777 | 104.099 | 1.00 | 16.78 | B |
| ATOM | 1773 | CA | ASP B | 32 | 46.914 | 64.943 | 104.894 | 1.00 | 17.81 | B |
| ATOM | 1774 | CB | ASP B | 32 | 46.724 | 64.662 | 106.385 | 1.00 | 24.39 | B |
| ATOM | 1775 | CG | ASP B | 32 | 45.277 | 64.694 | 106.796 | 1.00 | 25.67 | B |
| ATOM | 1776 | OD1 | ASP B | 32 | 44.637 | 65.771 | 106.685 | 1.00 | 29.03 | B |
| ATOM | 1777 | OD2 | ASP B | 32 | 44.786 | 63.635 | 107.227 | 1.00 | 26.09 | B |
| ATOM | 1778 | C | ASP B | 32 | 48.372 | 65.332 | 104.636 | 1.00 | 15.71 | B |
| ATOM | 1779 | O | ASP B | 32 | 48.710 | 66.510 | 104.508 | 1.00 | 21.17 | B |
| ATOM | 1780 | N | GLU B | 33 | 49.234 | 64.334 | 104.552 | 1.00 | 12.26 | B |
| ATOM | 1781 | CA | GLU B | 33 | 50.642 | 64.571 | 104.300 | 1.00 | 12.26 | B |
| ATOM | 1782 | CB | GLU B | 33 | 51.385 | 64.860 | 105.608 | 1.00 | 12.26 | B |
| ATOM | 1783 | CG | GLU B | 33 | 50.673 | 64.372 | 106.857 | 1.00 | 22.60 | B |
| ATOM | 1784 | CD | GLU B | 33 | 51.322 | 64.878 | 108.137 | 1.00 | 23.96 | B |
| ATOM | 1785 | OE1 | GLU B | 33 | 52.488 | 64.513 | 108.393 | 1.00 | 25.84 | B |
| ATOM | 1786 | OE2 | GLU B | 33 | 50.666 | 65.644 | 108.886 | 1.00 | 28.41 | B |
| ATOM | 1787 | C | GLU B | 33 | 51.252 | 63.359 | 103.636 | 1.00 | 12.26 | B |
| ATOM | 1788 | O | GLU B | 33 | 50.804 | 62.238 | 103.836 | 1.00 | 13.33 | B |
| ATOM | 1789 | N | ILE B | 34 | 52.267 | 63.589 | 102.823 | 1.00 | 12.26 | B |
| ATOM | 1790 | CA | ILE B | 34 | 52.947 | 62.499 | 102.154 | 1.00 | 13.29 | B |
| ATOM | 1791 | CB | ILE B | 34 | 53.185 | 62.818 | 100.666 | 1.00 | 16.74 | B |
| ATOM | 1792 | CG2 | ILE B | 34 | 53.927 | 61.678 | 100.014 | 1.00 | 12.26 | B |
| ATOM | 1793 | CG1 | ILE B | 34 | 51.853 | 63.041 | 99.959 | 1.00 | 16.99 | B |
| ATOM | 1794 | CD1 | ILE B | 34 | 51.031 | 61.796 | 99.839 | 1.00 | 20.85 | B |
| ATOM | 1795 | C | ILE B | 34 | 54.282 | 62.355 | 102.881 | 1.00 | 15.19 | B |
| ATOM | 1796 | O | ILE B | 34 | 54.872 | 63.351 | 103.310 | 1.00 | 19.11 | B |
| ATOM | 1797 | N | TRP B | 35 | 54.734 | 61.118 | 103.062 | 1.00 | 15.62 | B |
| ATOM | 1798 | CA | TRP B | 35 | 56.001 | 60.881 | 103.745 | 1.00 | 16.21 | B |
| ATOM | 1799 | CB | TRP B | 35 | 55.840 | 59.942 | 104.947 | 1.00 | 13.76 | B |

Figure 10 (29 of 142)

| ATOM | 1800 | CG | TRP | B | 35 | 55.059 | 60.485 | 106.105 | 1.00 | 12.26 | B |
|---|---|---|---|---|---|---|---|---|---|---|---|
| ATOM | 1801 | CD2 | TRP | B | 35 | 54.714 | 59.775 | 107.290 | 1.00 | 13.12 | B |
| ATOM | 1802 | CE2 | TRP | B | 35 | 53.835 | 60.596 | 108.031 | 1.00 | 12.26 | B |
| ATOM | 1803 | CE3 | TRP | B | 35 | 55.030 | 58.500 | 107.778 | 1.00 | 14.89 | B |
| ATOM | 1804 | CD1 | TRP | B | 35 | 54.431 | 61.695 | 106.191 | 1.00 | 14.47 | B |
| ATOM | 1805 | NE1 | TRP | B | 35 | 53.689 | 61.766 | 107.348 | 1.00 | 12.26 | B |
| ATOM | 1806 | CZ2 | TRP | B | 35 | 53.302 | 60.206 | 109.241 | 1.00 | 12.26 | B |
| ATOM | 1807 | CZ3 | TRP | B | 35 | 54.492 | 58.104 | 108.995 | 1.00 | 13.03 | B |
| ATOM | 1808 | CH2 | TRP | B | 35 | 53.620 | 58.953 | 109.703 | 1.00 | 12.26 | B |
| ATOM | 1809 | C | TRP | B | 35 | 56.934 | 60.220 | 102.778 | 1.00 | 13.64 | B |
| ATOM | 1810 | O | TRP | B | 35 | 56.681 | 59.103 | 102.357 | 1.00 | 18.06 | B |
| ATOM | 1811 | N | PHE | B | 36 | 58.004 | 60.907 | 102.414 | 1.00 | 12.26 | B |
| ATOM | 1812 | CA | PHE | B | 36 | 58.993 | 60.332 | 101.508 | 1.00 | 14.94 | B |
| ATOM | 1813 | CB | PHE | B | 36 | 59.801 | 61.423 | 100.828 | 1.00 | 12.26 | B |
| ATOM | 1814 | CG | PHE | B | 36 | 59.034 | 62.194 | 99.813 | 1.00 | 12.26 | B |
| ATOM | 1815 | CD1 | PHE | B | 36 | 57.882 | 62.893 | 100.165 | 1.00 | 12.83 | B |
| ATOM | 1816 | CD2 | PHE | B | 36 | 59.456 | 62.209 | 98.487 | 1.00 | 12.26 | B |
| ATOM | 1817 | CE1 | PHE | B | 36 | 57.153 | 63.599 | 99.199 | 1.00 | 12.26 | B |
| ATOM | 1818 | CE2 | PHE | B | 36 | 58.741 | 62.907 | 97.506 | 1.00 | 12.26 | B |
| ATOM | 1819 | CZ | PHE | B | 36 | 57.587 | 63.605 | 97.859 | 1.00 | 12.26 | B |
| ATOM | 1820 | C | PHE | B | 36 | 59.943 | 59.461 | 102.319 | 1.00 | 15.85 | B |
| ATOM | 1821 | O | PHE | B | 36 | 60.830 | 59.976 | 103.014 | 1.00 | 19.92 | B |
| ATOM | 1822 | N | MET | B | 37 | 59.765 | 58.146 | 102.209 | 1.00 | 17.01 | B |
| ATOM | 1823 | CA | MET | B | 37 | 60.577 | 57.164 | 102.943 | 1.00 | 24.48 | B |
| ATOM | 1824 | CB | MET | B | 37 | 59.651 | 56.042 | 103.465 | 1.00 | 22.81 | B |
| ATOM | 1825 | CG | MET | B | 37 | 60.286 | 55.009 | 104.393 | 1.00 | 12.26 | B |
| ATOM | 1826 | SD | MET | B | 37 | 59.008 | 54.061 | 105.192 | 1.00 | 12.26 | B |
| ATOM | 1827 | CE | MET | B | 37 | 58.674 | 53.002 | 103.987 | 1.00 | 12.26 | B |
| ATOM | 1828 | C | MET | B | 37 | 61.741 | 56.560 | 102.118 | 1.00 | 28.01 | B |
| ATOM | 1829 | O | MET | B | 37 | 61.528 | 55.732 | 101.221 | 1.00 | 37.91 | B |
| ATOM | 1830 | N | PRO | B | 38 | 62.988 | 56.961 | 102.428 | 1.00 | 22.32 | B |
| ATOM | 1831 | CD | PRO | B | 38 | 63.250 | 58.131 | 103.270 | 1.00 | 23.09 | B |
| ATOM | 1832 | CA | PRO | B | 38 | 64.227 | 56.523 | 101.774 | 1.00 | 20.80 | B |
| ATOM | 1833 | CB | PRO | B | 38 | 65.197 | 57.657 | 102.064 | 1.00 | 21.78 | B |
| ATOM | 1834 | CG | PRO | B | 38 | 64.318 | 58.802 | 102.482 | 1.00 | 24.90 | B |
| ATOM | 1835 | C | PRO | B | 38 | 64.780 | 55.196 | 102.271 | 1.00 | 26.00 | B |
| ATOM | 1836 | O | PRO | B | 38 | 64.848 | 54.942 | 103.480 | 1.00 | 21.24 | B |
| ATOM | 1837 | N | ASN | B | 39 | 65.198 | 54.369 | 101.315 | 1.00 | 31.44 | B |
| ATOM | 1838 | CA | ASN | B | 39 | 65.770 | 53.052 | 101.592 | 1.00 | 39.94 | B |
| ATOM | 1839 | CB | ASN | B | 39 | 65.915 | 52.236 | 100.306 | 1.00 | 46.17 | B |
| ATOM | 1840 | CG | ASN | B | 39 | 64.611 | 52.048 | 99.578 | 1.00 | 52.01 | B |
| ATOM | 1841 | OD1 | ASN | B | 39 | 63.564 | 51.834 | 100.191 | 1.00 | 57.15 | B |
| ATOM | 1842 | ND2 | ASN | B | 39 | 64.665 | 52.104 | 98.259 | 1.00 | 51.78 | B |
| ATOM | 1843 | C | ASN | B | 39 | 67.154 | 53.139 | 102.202 | 1.00 | 41.11 | B |
| ATOM | 1844 | O | ASN | B | 39 | 67.972 | 53.951 | 101.776 | 1.00 | 39.41 | B |
| ATOM | 1845 | N | GLN | B | 40 | 67.437 | 52.300 | 103.191 | 1.00 | 42.61 | B |
| ATOM | 1846 | CA | GLN | B | 40 | 68.771 | 52.329 | 103.750 | 1.00 | 41.74 | B |
| ATOM | 1847 | CB | GLN | B | 40 | 68.862 | 51.545 | 105.050 | 1.00 | 46.69 | B |
| ATOM | 1848 | CG | GLN | B | 40 | 70.156 | 51.841 | 105.783 | 1.00 | 51.03 | B |
| ATOM | 1849 | CD | GLN | B | 40 | 70.067 | 51.572 | 107.272 | 1.00 | 54.66 | B |
| ATOM | 1850 | OE1 | GLN | B | 40 | 69.126 | 52.006 | 107.948 | 1.00 | 52.05 | B |
| ATOM | 1851 | NE2 | GLN | B | 40 | 71.059 | 50.861 | 107.800 | 1.00 | 59.94 | B |
| ATOM | 1852 | C | GLN | B | 40 | 69.599 | 51.656 | 102.681 | 1.00 | 37.72 | B |
| ATOM | 1853 | O | GLN | B | 40 | 70.676 | 52.126 | 102.316 | 1.00 | 38.24 | B |
| ATOM | 1854 | N | ILE | B | 41 | 69.058 | 50.556 | 102.170 | 1.00 | 34.40 | B |
| ATOM | 1855 | CA | ILE | B | 41 | 69.678 | 49.770 | 101.108 | 1.00 | 36.25 | B |
| ATOM | 1856 | CB | ILE | B | 41 | 70.602 | 48.674 | 101.710 | 1.00 | 42.98 | B |
| ATOM | 1857 | CG2 | ILE | B | 41 | 69.853 | 47.840 | 102.732 | 1.00 | 44.96 | B |
| ATOM | 1858 | CG1 | ILE | B | 41 | 71.180 | 47.806 | 100.605 | 1.00 | 45.71 | B |
| ATOM | 1859 | CD1 | ILE | B | 41 | 72.099 | 46.729 | 101.142 | 1.00 | 46.52 | B |
| ATOM | 1860 | C | ILE | B | 41 | 68.475 | 49.179 | 100.360 | 1.00 | 34.54 | B |
| ATOM | 1861 | O | ILE | B | 41 | 67.676 | 48.442 | 100.943 | 1.00 | 29.35 | B |
| ATOM | 1862 | N | PRO | B | 42 | 68.314 | 49.534 | 99.071 | 1.00 | 29.98 | B |
| ATOM | 1863 | CD | PRO | B | 42 | 69.261 | 50.376 | 98.329 | 1.00 | 26.88 | B |
| ATOM | 1864 | CA | PRO | B | 42 | 67.226 | 49.095 | 98.184 | 1.00 | 27.85 | B |
| ATOM | 1865 | CB | PRO | B | 42 | 67.588 | 49.738 | 96.847 | 1.00 | 25.53 | B |

Figure 10 (30 of 142)

```
ATOM   1866  CG  PRO B  42      68.363  50.945  97.264  1.00 27.85      B
ATOM   1867  C   PRO B  42      67.095  47.584  98.072  1.00 27.99      B
ATOM   1868  O   PRO B  42      67.949  46.918  97.481  1.00 30.92      B
ATOM   1869  N   PRO B  43      65.996  47.023  98.609  1.00 22.77      B
ATOM   1870  CD  PRO B  43      64.806  47.701  99.154  1.00 21.18      B
ATOM   1871  CA  PRO B  43      65.780  45.584  98.567  1.00 21.79      B
ATOM   1872  CB  PRO B  43      64.383  45.421  99.183  1.00 18.98      B
ATOM   1873  CG  PRO B  43      63.720  46.692  98.879  1.00 19.45      B
ATOM   1874  C   PRO B  43      65.944  44.891  97.246  1.00 23.95      B
ATOM   1875  O   PRO B  43      66.611  43.840  97.198  1.00 26.69      B
ATOM   1876  N   HIS B  44      65.425  45.422  96.160  1.00 26.48      B
ATOM   1877  CA  HIS B  44      65.546  44.674  94.941  1.00 28.93      B
ATOM   1878  CB  HIS B  44      64.424  45.013  94.026  1.00 31.04      B
ATOM   1879  CG  HIS B  44      64.195  46.479  93.980  1.00 33.21      B
ATOM   1880  CD2 HIS B  44      63.801  47.304  92.990  1.00 33.60      B
ATOM   1881  ND1 HIS B  44      64.369  47.259  95.093  1.00 37.41      B
ATOM   1882  CE1 HIS B  44      64.100  48.525  94.809  1.00 38.08      B
ATOM   1883  NE2 HIS B  44      63.760  48.573  93.541  1.00 38.77      B
ATOM   1884  C   HIS B  44      66.832  45.085  94.273  1.00 30.90      B
ATOM   1885  O   HIS B  44      66.836  45.002  93.040  1.00 35.67      B
ATOM   1886  N   LYS B  45      67.874  45.606  94.908  1.00 33.32      B
ATOM   1887  CA  LYS B  45      68.956  45.845  93.994  1.00 41.45      B
ATOM   1888  CB  LYS B  45      68.625  46.753  92.948  1.00 43.43      B
ATOM   1889  CG  LYS B  45      68.313  48.137  93.330  1.00 48.64      B
ATOM   1890  CD  LYS B  45      67.664  48.854  92.153  1.00 54.67      B
ATOM   1891  CE  LYS B  45      66.704  49.904  92.699  1.00 56.10      B
ATOM   1892  NZ  LYS B  45      65.826  50.461  91.635  1.00 62.85      B
ATOM   1893  C   LYS B  45      70.141  46.253  94.607  1.00 45.59      B
ATOM   1894  O   LYS B  45      70.927  47.357  94.463  1.00 43.51      B
ATOM   1895  N   GLN B  46      70.522  45.157  95.206  1.00 21.23      B
ATOM   1896  CA  GLN B  46      71.502  44.915  96.150  1.00 24.81      B
ATOM   1897  CB  GLN B  46      70.917  43.634  96.893  1.00 27.31      B
ATOM   1898  CG  GLN B  46      70.131  44.019  97.865  1.00 29.41      B
ATOM   1899  CD  GLN B  46      69.607  43.014  98.758  1.00 20.59      B
ATOM   1900  OE1 GLN B  46      69.697  43.207  99.989  1.00 20.59      B
ATOM   1901  NE2 GLN B  46      68.980  41.998  98.238  1.00 20.59      B
ATOM   1902  C   GLN B  46      72.740  44.563  95.419  1.00 27.65      B
ATOM   1903  O   GLN B  46      73.993  44.445  95.838  1.00 26.89      B
ATOM   1904  N   ASN B  47      72.553  44.070  94.255  1.00 20.59      B
ATOM   1905  CA  ASN B  47      73.640  43.622  93.257  1.00 20.59      B
ATOM   1906  CB  ASN B  47      73.175  42.351  92.438  1.00 20.59      B
ATOM   1907  CG  ASN B  47      74.277  41.410  92.108  1.00 20.59      B
ATOM   1908  OD1 ASN B  47      74.273  40.853  91.001  1.00 20.59      B
ATOM   1909  ND2 ASN B  47      75.182  41.157  93.049  1.00 20.59      B
ATOM   1910  C   ASN B  47      73.793  44.686  92.193  1.00 20.59      B
ATOM   1911  O   ASN B  47      74.362  44.497  91.092  1.00 20.59      B
ATOM   1912  N   GLU B  48      73.152  45.770  92.543  1.00 29.55      B
ATOM   1913  CA  GLU B  48      73.042  46.938  91.665  1.00 31.31      B
ATOM   1914  CB  GLU B  48      71.675  47.594  91.961  1.00 37.66      B
ATOM   1915  CG  GLU B  48      71.192  48.510  90.869  1.00 44.07      B
ATOM   1916  CD  GLU B  48      70.548  47.734  89.735  1.00 50.19      B
ATOM   1917  OE1 GLU B  48      71.202  47.565  88.689  1.00 51.99      B
ATOM   1918  OE2 GLU B  48      69.390  47.303  89.911  1.00 51.82      B
ATOM   1919  C   GLU B  48      74.008  48.118  91.524  1.00 31.97      B
ATOM   1920  O   GLU B  48      74.311  48.390  90.426  1.00 27.62      B
ATOM   1921  N   ASP B  49      74.344  48.815  92.621  1.00 55.50      B
ATOM   1922  CA  ASP B  49      75.249  49.989  92.441  1.00 53.89      B
ATOM   1923  CB  ASP B  49      75.292  50.262  90.973  1.00 55.54      B
ATOM   1924  CG  ASP B  49      76.630  50.610  90.503  1.00 58.76      B
ATOM   1925  OD1 ASP B  49      77.189  51.693  90.824  1.00 60.76      B
ATOM   1926  OD2 ASP B  49      77.024  49.697  89.803  1.00 58.00      B
ATOM   1927  C   ASP B  49      74.558  51.115  93.096  1.00 54.69      B
ATOM   1928  O   ASP B  49      74.469  52.117  92.411  1.00 59.59      B
ATOM   1929  N   TYR B  50      73.992  51.070  94.267  1.00 47.12      B
ATOM   1930  CA  TYR B  50      73.266  52.289  94.676  1.00 44.32      B
ATOM   1931  CB  TYR B  50      72.091  51.912  95.568  1.00 43.23      B
```

Figure 10 (31 of 142)

```
ATOM   1932  CG   TYR B  50      72.566  51.004  96.643  1.00 42.35      B
ATOM   1933  CD1  TYR B  50      72.698  49.634  96.421  1.00 43.69      B
ATOM   1934  CE1  TYR B  50      73.153  48.776  97.447  1.00 46.88      B
ATOM   1935  CD2  TYR B  50      72.902  51.514  97.885  1.00 45.09      B
ATOM   1936  CE2  TYR B  50      73.354  50.686  98.904  1.00 49.55      B
ATOM   1937  CZ   TYR B  50      73.474  49.323  98.693  1.00 49.37      B
ATOM   1938  OH   TYR B  50      73.872  48.530  99.750  1.00 51.03      B
ATOM   1939  C    TYR B  50      74.084  53.411  95.388  1.00 43.09      B
ATOM   1940  O    TYR B  50      75.183  53.128  95.818  1.00 45.80      B
ATOM   1941  N    THR B  51      73.590  54.656  95.524  1.00 39.38      B
ATOM   1942  CA   THR B  51      74.419  55.659  96.217  1.00 37.40      B
ATOM   1943  CB   THR B  51      74.170  57.111  95.724  1.00 32.79      B
ATOM   1944  OG1  THR B  51      72.798  57.459  95.931  1.00 39.43      B
ATOM   1945  CG2  THR B  51      74.528  57.241  94.276  1.00 33.26      B
ATOM   1946  C    THR B  51      74.306  55.637  97.737  1.00 32.00      B
ATOM   1947  O    THR B  51      73.251  55.378  98.312  1.00 30.06      B
ATOM   1948  N    ASP B  52      75.442  55.933  98.348  1.00 35.02      B
ATOM   1949  CA   ASP B  52      75.685  55.949  99.780  1.00 40.49      B
ATOM   1950  CB   ASP B  52      76.936  56.792 100.025  1.00 49.44      B
ATOM   1951  CG   ASP B  52      78.177  56.181  99.398  1.00 53.62      B
ATOM   1952  OD1  ASP B  52      78.608  55.105  99.875  1.00 54.40      B
ATOM   1953  OD2  ASP B  52      78.714  56.765  98.428  1.00 57.60      B
ATOM   1954  C    ASP B  52      74.673  56.300 100.857  1.00 37.92      B
ATOM   1955  O    ASP B  52      75.048  56.265 102.031  1.00 41.39      B
ATOM   1956  N    SER B  53      73.424  56.616 100.523  1.00 31.68      B
ATOM   1957  CA   SER B  53      72.482  57.015 101.576  1.00 31.08      B
ATOM   1958  CB   SER B  53      72.512  56.021 102.737  1.00 31.27      B
ATOM   1959  OG   SER B  53      71.479  56.288 103.669  1.00 33.04      B
ATOM   1960  C    SER B  53      73.181  58.314 101.952  1.00 36.30      B
ATOM   1961  O    SER B  53      74.308  58.492 101.495  1.00 38.25      B
ATOM   1962  N    PHE B  54      72.610  59.224 102.754  1.00 39.91      B
ATOM   1963  CA   PHE B  54      73.322  60.505 102.998  1.00 41.10      B
ATOM   1964  CB   PHE B  54      74.605  60.215 103.785  1.00 41.66      B
ATOM   1965  CG   PHE B  54      75.702  61.234 103.638  1.00 47.16      B
ATOM   1966  CD1  PHE B  54      75.503  62.603 103.860  1.00 46.81      B
ATOM   1967  CD2  PHE B  54      76.994  60.781 103.379  1.00 48.77      B
ATOM   1968  CE1  PHE B  54      76.600  63.502 103.830  1.00 46.68      B
ATOM   1969  CE2  PHE B  54      78.084  61.655 103.349  1.00 47.65      B
ATOM   1970  CZ   PHE B  54      77.889  63.017 103.576  1.00 46.96      B
ATOM   1971  C    PHE B  54      73.476  60.868 101.502  1.00 41.02      B
ATOM   1972  O    PHE B  54      73.670  59.992 100.660  1.00 46.53      B
ATOM   1973  N    HIS B  55      73.355  62.126 101.112  1.00 41.85      B
ATOM   1974  CA   HIS B  55      73.273  62.335  99.663  1.00 35.77      B
ATOM   1975  CB   HIS B  55      74.257  61.464  98.837  1.00 37.02      B
ATOM   1976  CG   HIS B  55      75.712  61.696  99.118  1.00 38.15      B
ATOM   1977  CD2  HIS B  55      76.349  62.251 100.175  1.00 38.65      B
ATOM   1978  ND1  HIS B  55      76.700  61.290  98.244  1.00 42.52      B
ATOM   1979  CE1  HIS B  55      77.884  61.589  98.752  1.00 42.30      B
ATOM   1980  NE2  HIS B  55      77.699  62.171  99.923  1.00 42.42      B
ATOM   1981  C    HIS B  55      71.900  61.615  99.666  1.00 34.83      B
ATOM   1982  O    HIS B  55      71.468  61.155 100.733  1.00 36.51      B
ATOM   1983  N    ARG B  56      71.211  61.460  98.545  1.00 27.75      B
ATOM   1984  CA   ARG B  56      69.927  60.768  98.666  1.00 21.64      B
ATOM   1985  CB   ARG B  56      70.137  59.270  98.979  1.00 14.92      B
ATOM   1986  CG   ARG B  56      70.121  58.412  97.714  1.00 14.51      B
ATOM   1987  CD   ARG B  56      70.450  56.938  97.940  1.00 18.88      B
ATOM   1988  NE   ARG B  56      69.286  56.107  98.228  1.00 18.76      B
ATOM   1989  CZ   ARG B  56      69.276  55.133  99.134  1.00 22.98      B
ATOM   1990  NH1  ARG B  56      70.369  54.875  99.840  1.00 25.15      B
ATOM   1991  NH2  ARG B  56      68.175  54.416  99.338  1.00 22.63      B
ATOM   1992  C    ARG B  56      69.095  61.445  99.770  1.00 18.98      B
ATOM   1993  O    ARG B  56      68.265  62.313  99.485  1.00 13.07      B
ATOM   1994  N    VAL B  57      69.325  61.073 101.023  1.00 17.08      B
ATOM   1995  CA   VAL B  57      68.596  61.709 102.108  1.00 16.72      B
ATOM   1996  CB   VAL B  57      69.099  61.267 103.496  1.00 14.65      B
ATOM   1997  CG1  VAL B  57      68.439  62.116 104.562  1.00 21.20      B
```

Figure 10 (32 of 142)

| ATOM | 1998 | CG2 | VAL | B | 57 | 68.797 | 59.812 | 103.725 | 1.00 | 20.05 | B |
|---|---|---|---|---|---|---|---|---|---|---|---|
| ATOM | 1999 | C | VAL | B | 57 | 68.828 | 63.207 | 102.007 | 1.00 | 17.95 | B |
| ATOM | 2000 | O | VAL | B | 57 | 67.936 | 64.015 | 102.278 | 1.00 | 16.11 | B |
| ATOM | 2001 | N | GLU | B | 58 | 70.043 | 63.588 | 101.637 | 1.00 | 23.28 | B |
| ATOM | 2002 | CA | GLU | B | 58 | 70.318 | 65.007 | 101.533 | 1.00 | 26.13 | B |
| ATOM | 2003 | CB | GLU | B | 58 | 71.816 | 65.285 | 101.388 | 1.00 | 32.78 | B |
| ATOM | 2004 | CG | GLU | B | 58 | 72.563 | 65.343 | 102.732 | 1.00 | 34.07 | B |
| ATOM | 2005 | CD | GLU | B | 58 | 71.803 | 66.126 | 103.809 | 1.00 | 37.26 | B |
| ATOM | 2006 | OE1 | GLU | B | 58 | 71.477 | 67.323 | 103.579 | 1.00 | 36.64 | B |
| ATOM | 2007 | OE2 | GLU | B | 58 | 71.536 | 65.532 | 104.884 | 1.00 | 34.62 | B |
| ATOM | 2008 | C | GLU | B | 58 | 69.565 | 65.516 | 100.336 | 1.00 | 23.86 | B |
| ATOM | 2009 | O | GLU | B | 58 | 68.707 | 66.402 | 100.459 | 1.00 | 25.49 | B |
| ATOM | 2010 | N | MET | B | 59 | 69.875 | 64.946 | 99.178 | 1.00 | 19.67 | B |
| ATOM | 2011 | CA | MET | B | 59 | 69.183 | 65.343 | 97.964 | 1.00 | 20.11 | B |
| ATOM | 2012 | CB | MET | B | 59 | 69.525 | 64.361 | 96.835 | 1.00 | 21.05 | B |
| ATOM | 2013 | CG | MET | B | 59 | 71.022 | 64.356 | 96.475 | 1.00 | 13.29 | B |
| ATOM | 2014 | SD | MET | B | 59 | 71.384 | 63.651 | 94.859 | 1.00 | 12.26 | B |
| ATOM | 2015 | CE | MET | B | 59 | 70.955 | 61.969 | 95.329 | 1.00 | 12.26 | B |
| ATOM | 2016 | C | MET | B | 59 | 67.674 | 65.360 | 98.244 | 1.00 | 15.42 | B |
| ATOM | 2017 | O | MET | B | 59 | 66.950 | 66.292 | 97.872 | 1.00 | 19.51 | B |
| ATOM | 2018 | N | LEU | B | 60 | 67.222 | 64.327 | 98.935 | 1.00 | 14.76 | B |
| ATOM | 2019 | CA | LEU | B | 60 | 65.830 | 64.206 | 99.280 | 1.00 | 16.54 | B |
| ATOM | 2020 | CB | LEU | B | 60 | 65.605 | 62.939 | 100.099 | 1.00 | 18.39 | B |
| ATOM | 2021 | CG | LEU | B | 60 | 64.485 | 62.002 | 99.669 | 1.00 | 14.92 | B |
| ATOM | 2022 | CD1 | LEU | B | 60 | 63.761 | 61.575 | 100.944 | 1.00 | 15.32 | B |
| ATOM | 2023 | CD2 | LEU | B | 60 | 63.513 | 62.689 | 98.704 | 1.00 | 14.07 | B |
| ATOM | 2024 | C | LEU | B | 60 | 65.355 | 65.410 | 100.076 | 1.00 | 20.99 | B |
| ATOM | 2025 | O | LEU | B | 60 | 64.329 | 65.999 | 99.756 | 1.00 | 24.35 | B |
| ATOM | 2026 | N | LYS | B | 61 | 66.102 | 65.786 | 101.104 | 1.00 | 21.87 | B |
| ATOM | 2027 | CA | LYS | B | 61 | 65.693 | 66.898 | 101.941 | 1.00 | 29.94 | B |
| ATOM | 2028 | CB | LYS | B | 61 | 66.656 | 67.058 | 103.107 | 1.00 | 33.26 | B |
| ATOM | 2029 | CG | LYS | B | 61 | 66.004 | 66.768 | 104.452 | 1.00 | 36.62 | B |
| ATOM | 2030 | CD | LYS | B | 61 | 67.012 | 66.209 | 105.447 | 1.00 | 43.09 | B |
| ATOM | 2031 | CE | LYS | B | 61 | 68.205 | 67.133 | 105.585 | 1.00 | 49.26 | B |
| ATOM | 2032 | NZ | LYS | B | 61 | 69.270 | 66.526 | 106.413 | 1.00 | 53.52 | B |
| ATOM | 2033 | C | LYS | B | 61 | 65.569 | 68.197 | 101.182 | 1.00 | 31.31 | B |
| ATOM | 2034 | O | LYS | B | 61 | 64.731 | 69.036 | 101.518 | 1.00 | 35.78 | B |
| ATOM | 2035 | N | LEU | B | 62 | 66.390 | 68.358 | 100.151 | 1.00 | 28.37 | B |
| ATOM | 2036 | CA | LEU | B | 62 | 66.355 | 69.578 | 99.358 | 1.00 | 26.36 | B |
| ATOM | 2037 | CB | LEU | B | 62 | 67.578 | 69.648 | 98.446 | 1.00 | 27.38 | B |
| ATOM | 2038 | CG | LEU | B | 62 | 68.881 | 69.759 | 99.241 | 1.00 | 29.69 | B |
| ATOM | 2039 | CD1 | LEU | B | 62 | 70.088 | 69.464 | 98.355 | 1.00 | 28.80 | B |
| ATOM | 2040 | CD2 | LEU | B | 62 | 68.961 | 71.151 | 99.860 | 1.00 | 32.54 | B |
| ATOM | 2041 | C | LEU | B | 62 | 65.093 | 69.635 | 98.528 | 1.00 | 23.61 | B |
| ATOM | 2042 | O | LEU | B | 62 | 64.354 | 70.618 | 98.563 | 1.00 | 26.25 | B |
| ATOM | 2043 | N | ALA | B | 63 | 64.840 | 68.557 | 97.801 | 1.00 | 23.86 | B |
| ATOM | 2044 | CA | ALA | B | 63 | 63.684 | 68.476 | 96.929 | 1.00 | 22.35 | B |
| ATOM | 2045 | CB | ALA | B | 63 | 63.685 | 67.138 | 96.210 | 1.00 | 24.27 | B |
| ATOM | 2046 | C | ALA | B | 63 | 62.336 | 68.696 | 97.599 | 1.00 | 21.44 | B |
| ATOM | 2047 | O | ALA | B | 63 | 61.403 | 69.190 | 96.963 | 1.00 | 26.10 | B |
| ATOM | 2048 | N | ILE | B | 64 | 62.218 | 68.376 | 98.877 | 1.00 | 18.41 | B |
| ATOM | 2049 | CA | ILE | B | 64 | 60.920 | 68.511 | 99.500 | 1.00 | 19.74 | B |
| ATOM | 2050 | CB | ILE | B | 64 | 60.516 | 67.181 | 100.147 | 1.00 | 19.00 | B |
| ATOM | 2051 | CG2 | ILE | B | 64 | 60.616 | 66.059 | 99.108 | 1.00 | 17.18 | B |
| ATOM | 2052 | CG1 | ILE | B | 64 | 61.412 | 66.895 | 101.356 | 1.00 | 12.26 | B |
| ATOM | 2053 | CD1 | ILE | B | 64 | 60.795 | 65.919 | 102.338 | 1.00 | 14.27 | B |
| ATOM | 2054 | C | ILE | B | 64 | 60.746 | 69.614 | 100.523 | 1.00 | 18.03 | B |
| ATOM | 2055 | O | ILE | B | 64 | 59.682 | 69.724 | 101.145 | 1.00 | 21.84 | B |
| ATOM | 2056 | N | GLN | B | 65 | 61.757 | 70.451 | 100.696 | 1.00 | 14.88 | B |
| ATOM | 2057 | CA | GLN | B | 65 | 61.639 | 71.497 | 101.706 | 1.00 | 18.07 | B |
| ATOM | 2058 | CB | GLN | B | 65 | 62.922 | 72.294 | 101.813 | 1.00 | 20.06 | B |
| ATOM | 2059 | CG | GLN | B | 65 | 63.303 | 73.000 | 100.548 | 1.00 | 25.82 | B |
| ATOM | 2060 | CD | GLN | B | 65 | 64.573 | 73.815 | 100.730 | 1.00 | 29.10 | B |
| ATOM | 2061 | OE1 | GLN | B | 65 | 65.631 | 73.279 | 101.101 | 1.00 | 30.46 | B |
| ATOM | 2062 | NE2 | GLN | B | 65 | 64.475 | 75.122 | 100.479 | 1.00 | 35.98 | B |
| ATOM | 2063 | C | GLN | B | 65 | 60.481 | 72.459 | 101.508 | 1.00 | 17.86 | B |

Figure 10 (33 of 142)

| ATOM | 2064 | O | GLN | B | 65 | 59.665 | 72.640 | 102.411 | 1.00 | 20.54 | B |
|---|---|---|---|---|---|---|---|---|---|---|---|
| ATOM | 2065 | N | SER | B | 66 | 60.409 | 73.086 | 100.343 | 1.00 | 14.13 | B |
| ATOM | 2066 | CA | SER | B | 66 | 59.335 | 74.029 | 100.087 | 1.00 | 12.69 | B |
| ATOM | 2067 | CB | SER | B | 66 | 59.493 | 74.616 | 98.690 | 1.00 | 12.26 | B |
| ATOM | 2068 | OG | SER | B | 66 | 60.238 | 73.726 | 97.880 | 1.00 | 21.06 | B |
| ATOM | 2069 | C | SER | B | 66 | 57.916 | 73.492 | 100.271 | 1.00 | 12.26 | B |
| ATOM | 2070 | O | SER | B | 66 | 56.987 | 74.292 | 100.401 | 1.00 | 12.26 | B |
| ATOM | 2071 | N | ASN | B | 67 | 57.724 | 72.166 | 100.292 | 1.00 | 12.26 | B |
| ATOM | 2072 | CA | ASN | B | 67 | 56.366 | 71.644 | 100.468 | 1.00 | 16.80 | B |
| ATOM | 2073 | CB | ASN | B | 67 | 56.058 | 70.538 | 99.460 | 1.00 | 24.68 | B |
| ATOM | 2074 | CG | ASN | B | 67 | 54.553 | 70.246 | 99.337 | 1.00 | 26.58 | B |
| ATOM | 2075 | OD1 | ASN | B | 67 | 54.126 | 69.584 | 98.389 | 1.00 | 31.34 | B |
| ATOM | 2076 | ND2 | ASN | B | 67 | 53.750 | 70.732 | 100.291 | 1.00 | 30.11 | B |
| ATOM | 2077 | C | ASN | B | 67 | 55.992 | 71.166 | 101.871 | 1.00 | 16.45 | B |
| ATOM | 2078 | O | ASN | B | 67 | 56.433 | 70.116 | 102.335 | 1.00 | 12.26 | B |
| ATOM | 2079 | N | PRO | B | 68 | 55.147 | 71.955 | 102.554 | 1.00 | 13.10 | B |
| ATOM | 2080 | CD | PRO | B | 68 | 54.517 | 73.138 | 101.939 | 1.00 | 15.55 | B |
| ATOM | 2081 | CA | PRO | B | 68 | 54.622 | 71.737 | 103.902 | 1.00 | 12.26 | B |
| ATOM | 2082 | CB | PRO | B | 68 | 53.519 | 72.786 | 104.013 | 1.00 | 12.26 | B |
| ATOM | 2083 | CG | PRO | B | 68 | 54.009 | 73.876 | 103.135 | 1.00 | 17.03 | B |
| ATOM | 2084 | C | PRO | B | 68 | 54.059 | 70.314 | 104.053 | 1.00 | 16.10 | B |
| ATOM | 2085 | O | PRO | B | 68 | 54.402 | 69.591 | 104.994 | 1.00 | 17.70 | B |
| ATOM | 2086 | N | SER | B | 69 | 53.196 | 69.910 | 103.120 | 1.00 | 19.81 | B |
| ATOM | 2087 | CA | SER | B | 69 | 52.594 | 68.583 | 103.188 | 1.00 | 17.90 | B |
| ATOM | 2088 | CB | SER | B | 69 | 51.392 | 68.515 | 102.246 | 1.00 | 13.98 | B |
| ATOM | 2089 | OG | SER | B | 69 | 50.322 | 69.272 | 102.784 | 1.00 | 19.42 | B |
| ATOM | 2090 | C | SER | B | 69 | 53.580 | 67.442 | 102.916 | 1.00 | 15.05 | B |
| ATOM | 2091 | O | SER | B | 69 | 53.232 | 66.264 | 103.002 | 1.00 | 15.23 | B |
| ATOM | 2092 | N | PHE | B | 70 | 54.818 | 67.786 | 102.601 | 1.00 | 13.24 | B |
| ATOM | 2093 | CA | PHE | B | 70 | 55.798 | 66.747 | 102.366 | 1.00 | 18.88 | B |
| ATOM | 2094 | CB | PHE | B | 70 | 56.696 | 67.098 | 101.183 | 1.00 | 22.53 | B |
| ATOM | 2095 | CG | PHE | B | 70 | 56.059 | 66.838 | 99.853 | 1.00 | 19.01 | B |
| ATOM | 2096 | CD1 | PHE | B | 70 | 56.772 | 67.009 | 98.677 | 1.00 | 18.92 | B |
| ATOM | 2097 | CD2 | PHE | B | 70 | 54.743 | 66.399 | 99.779 | 1.00 | 21.81 | B |
| ATOM | 2098 | CE1 | PHE | B | 70 | 56.191 | 66.746 | 97.457 | 1.00 | 18.77 | B |
| ATOM | 2099 | CE2 | PHE | B | 70 | 54.160 | 66.135 | 98.561 | 1.00 | 19.44 | B |
| ATOM | 2100 | CZ | PHE | B | 70 | 54.887 | 66.310 | 97.397 | 1.00 | 20.51 | B |
| ATOM | 2101 | C | PHE | B | 70 | 56.608 | 66.591 | 103.626 | 1.00 | 23.66 | B |
| ATOM | 2102 | O | PHE | B | 70 | 56.926 | 67.582 | 104.282 | 1.00 | 26.67 | B |
| ATOM | 2103 | N | LYS | B | 71 | 56.926 | 65.350 | 103.977 | 1.00 | 20.92 | B |
| ATOM | 2104 | CA | LYS | B | 71 | 57.677 | 65.086 | 105.187 | 1.00 | 18.71 | B |
| ATOM | 2105 | CB | LYS | B | 71 | 56.722 | 64.831 | 106.349 | 1.00 | 18.74 | B |
| ATOM | 2106 | CG | LYS | B | 71 | 55.876 | 66.043 | 106.683 | 1.00 | 20.36 | B |
| ATOM | 2107 | CD | LYS | B | 71 | 55.073 | 65.816 | 107.926 | 1.00 | 21.71 | B |
| ATOM | 2108 | CE | LYS | B | 71 | 54.388 | 67.090 | 108.382 | 1.00 | 23.22 | B |
| ATOM | 2109 | NZ | LYS | B | 71 | 53.714 | 66.900 | 109.732 | 1.00 | 28.92 | B |
| ATOM | 2110 | C | LYS | B | 71 | 58.600 | 63.910 | 105.037 | 1.00 | 19.17 | B |
| ATOM | 2111 | O | LYS | B | 71 | 58.233 | 62.880 | 104.467 | 1.00 | 22.77 | B |
| ATOM | 2112 | N | LEU | B | 72 | 59.807 | 64.072 | 105.562 | 1.00 | 17.97 | B |
| ATOM | 2113 | CA | LEU | B | 72 | 60.814 | 63.020 | 105.523 | 1.00 | 14.09 | B |
| ATOM | 2114 | CB | LEU | B | 72 | 62.173 | 63.594 | 105.894 | 1.00 | 12.26 | B |
| ATOM | 2115 | CG | LEU | B | 72 | 63.334 | 63.071 | 105.062 | 1.00 | 19.48 | B |
| ATOM | 2116 | CD1 | LEU | B | 72 | 64.646 | 63.585 | 105.616 | 1.00 | 21.18 | B |
| ATOM | 2117 | CD2 | LEU | B | 72 | 63.305 | 61.574 | 105.074 | 1.00 | 23.17 | B |
| ATOM | 2118 | C | LEU | B | 72 | 60.461 | 61.917 | 106.520 | 1.00 | 14.63 | B |
| ATOM | 2119 | O | LEU | B | 72 | 59.721 | 62.135 | 107.485 | 1.00 | 18.16 | B |
| ATOM | 2120 | N | GLU | B | 73 | 60.998 | 60.729 | 106.296 | 1.00 | 15.11 | B |
| ATOM | 2121 | CA | GLU | B | 73 | 60.743 | 59.604 | 107.178 | 1.00 | 14.77 | B |
| ATOM | 2122 | CB | GLU | B | 73 | 59.507 | 58.831 | 106.730 | 1.00 | 17.57 | B |
| ATOM | 2123 | CG | GLU | B | 73 | 59.313 | 57.543 | 107.493 | 1.00 | 22.24 | B |
| ATOM | 2124 | CD | GLU | B | 73 | 59.412 | 57.744 | 108.987 | 1.00 | 24.57 | B |
| ATOM | 2125 | OE1 | GLU | B | 73 | 58.393 | 58.119 | 109.615 | 1.00 | 30.77 | B |
| ATOM | 2126 | OE2 | GLU | B | 73 | 60.517 | 57.539 | 109.528 | 1.00 | 25.88 | B |
| ATOM | 2127 | C | GLU | B | 73 | 61.956 | 58.727 | 107.059 | 1.00 | 16.54 | B |
| ATOM | 2128 | O | GLU | B | 73 | 62.161 | 58.070 | 106.039 | 1.00 | 17.42 | B |
| ATOM | 2129 | N | LEU | B | 74 | 62.775 | 58.718 | 108.098 | 1.00 | 16.28 | B |

Figure 10 (34 of 142)

| ATOM | 2130 | CA | LEU | B | 74 | 63.990 | 57.921 | 108.059 | 1.00 | 22.19 | B |
| --- | --- | --- | --- | --- | --- | --- | --- | --- | --- | --- | --- |
| ATOM | 2131 | CB | LEU | B | 74 | 65.175 | 58.793 | 108.507 | 1.00 | 20.13 | B |
| ATOM | 2132 | CG | LEU | B | 74 | 65.376 | 60.119 | 107.746 | 1.00 | 21.47 | B |
| ATOM | 2133 | CD1 | LEU | B | 74 | 66.435 | 60.984 | 108.392 | 1.00 | 18.77 | B |
| ATOM | 2134 | CD2 | LEU | B | 74 | 65.764 | 59.821 | 106.339 | 1.00 | 20.08 | B |
| ATOM | 2135 | C | LEU | B | 74 | 63.913 | 56.622 | 108.885 | 1.00 | 23.87 | B |
| ATOM | 2136 | O | LEU | B | 74 | 64.941 | 56.108 | 109.325 | 1.00 | 27.71 | B |
| ATOM | 2137 | N | VAL | B | 75 | 62.697 | 56.092 | 109.065 | 1.00 | 23.24 | B |
| ATOM | 2138 | CA | VAL | B | 75 | 62.458 | 54.862 | 109.833 | 1.00 | 21.42 | B |
| ATOM | 2139 | CB | VAL | B | 75 | 60.940 | 54.508 | 109.921 | 1.00 | 15.34 | B |
| ATOM | 2140 | CG1 | VAL | B | 75 | 60.385 | 54.142 | 108.534 | 1.00 | 15.49 | B |
| ATOM | 2141 | CG2 | VAL | B | 75 | 60.737 | 53.341 | 110.872 | 1.00 | 15.01 | B |
| ATOM | 2142 | C | VAL | B | 75 | 63.170 | 53.650 | 109.255 | 1.00 | 19.27 | B |
| ATOM | 2143 | O | VAL | B | 75 | 63.500 | 52.717 | 109.988 | 1.00 | 18.97 | B |
| ATOM | 2144 | N | GLU | B | 76 | 63.398 | 53.651 | 107.946 | 1.00 | 22.41 | B |
| ATOM | 2145 | CA | GLU | B | 76 | 64.070 | 52.520 | 107.325 | 1.00 | 31.30 | B |
| ATOM | 2146 | CB | GLU | B | 76 | 63.716 | 52.388 | 105.833 | 1.00 | 34.92 | B |
| ATOM | 2147 | CG | GLU | B | 76 | 62.338 | 51.769 | 105.565 | 1.00 | 38.31 | B |
| ATOM | 2148 | CD | GLU | B | 76 | 62.078 | 51.535 | 104.088 | 1.00 | 41.54 | B |
| ATOM | 2149 | OE1 | GLU | B | 76 | 61.023 | 50.964 | 103.748 | 1.00 | 40.74 | B |
| ATOM | 2150 | OE2 | GLU | B | 76 | 62.927 | 51.923 | 103.261 | 1.00 | 43.64 | B |
| ATOM | 2151 | C | GLU | B | 76 | 65.555 | 52.681 | 107.481 | 1.00 | 32.28 | B |
| ATOM | 2152 | O | GLU | B | 76 | 66.330 | 51.863 | 106.994 | 1.00 | 32.68 | B |
| ATOM | 2153 | N | MET | B | 77 | 65.949 | 53.733 | 108.184 | 1.00 | 32.09 | B |
| ATOM | 2154 | CA | MET | B | 77 | 67.361 | 54.008 | 108.398 | 1.00 | 37.51 | B |
| ATOM | 2155 | CB | MET | B | 77 | 67.649 | 55.456 | 108.051 | 1.00 | 34.81 | B |
| ATOM | 2156 | CG | MET | B | 77 | 67.414 | 55.705 | 106.615 | 1.00 | 31.27 | B |
| ATOM | 2157 | SD | MET | B | 77 | 68.878 | 56.312 | 105.870 | 1.00 | 37.65 | B |
| ATOM | 2158 | CE | MET | B | 77 | 69.666 | 54.896 | 105.407 | 1.00 | 32.03 | B |
| ATOM | 2159 | C | MET | B | 77 | 67.871 | 53.694 | 109.795 | 1.00 | 39.54 | B |
| ATOM | 2160 | O | MET | B | 77 | 69.035 | 53.940 | 110.109 | 1.00 | 41.00 | B |
| ATOM | 2161 | N | GLU | B | 78 | 66.996 | 53.153 | 110.629 | 1.00 | 41.83 | B |
| ATOM | 2162 | CA | GLU | B | 78 | 67.357 | 52.792 | 111.986 | 1.00 | 47.21 | B |
| ATOM | 2163 | CB | GLU | B | 78 | 66.248 | 53.201 | 112.951 | 1.00 | 47.43 | B |
| ATOM | 2164 | CG | GLU | B | 78 | 66.129 | 54.675 | 113.216 | 1.00 | 54.60 | B |
| ATOM | 2165 | CD | GLU | B | 78 | 64.698 | 55.153 | 113.132 | 1.00 | 57.35 | B |
| ATOM | 2166 | OE1 | GLU | B | 78 | 63.773 | 54.322 | 113.285 | 1.00 | 58.35 | B |
| ATOM | 2167 | OE2 | GLU | B | 78 | 64.498 | 56.367 | 112.919 | 1.00 | 62.05 | B |
| ATOM | 2168 | C | GLU | B | 78 | 67.394 | 51.286 | 111.949 | 1.00 | 52.77 | B |
| ATOM | 2169 | O | GLU | B | 78 | 67.036 | 50.637 | 112.935 | 1.00 | 55.17 | B |
| ATOM | 2170 | N | ARG | B | 79 | 67.847 | 50.699 | 110.848 | 1.00 | 56.11 | B |
| ATOM | 2171 | CA | ARG | B | 79 | 67.744 | 49.254 | 110.814 | 1.00 | 57.73 | B |
| ATOM | 2172 | CB | ARG | B | 79 | 66.352 | 48.913 | 110.271 | 1.00 | 58.47 | B |
| ATOM | 2173 | CG | ARG | B | 79 | 65.623 | 47.782 | 110.970 | 1.00 | 60.93 | B |
| ATOM | 2174 | CD | ARG | B | 79 | 64.840 | 46.939 | 109.960 | 1.00 | 62.47 | B |
| ATOM | 2175 | NE | ARG | B | 79 | 63.935 | 47.721 | 109.119 | 1.00 | 59.86 | B |
| ATOM | 2176 | CZ | ARG | B | 79 | 63.914 | 47.668 | 107.787 | 1.00 | 60.28 | B |
| ATOM | 2177 | NH1 | ARG | B | 79 | 64.754 | 46.878 | 107.126 | 1.00 | 60.07 | B |
| ATOM | 2178 | NH2 | ARG | B | 79 | 63.028 | 48.387 | 107.112 | 1.00 | 58.62 | B |
| ATOM | 2179 | C | ARG | B | 79 | 68.759 | 48.363 | 110.114 | 1.00 | 58.31 | B |
| ATOM | 2180 | O | ARG | B | 79 | 68.624 | 47.145 | 110.199 | 1.00 | 61.47 | B |
| ATOM | 2181 | N | GLU | B | 80 | 69.750 | 48.930 | 109.431 | 1.00 | 58.46 | B |
| ATOM | 2182 | CA | GLU | B | 80 | 70.760 | 48.135 | 108.702 | 1.00 | 59.09 | B |
| ATOM | 2183 | CB | GLU | B | 80 | 71.945 | 47.829 | 109.618 | 1.00 | 64.14 | B |
| ATOM | 2184 | CG | GLU | B | 80 | 72.080 | 46.379 | 110.018 | 1.00 | 68.07 | B |
| ATOM | 2185 | CD | GLU | B | 80 | 72.306 | 46.238 | 111.498 | 1.00 | 70.72 | B |
| ATOM | 2186 | OE1 | GLU | B | 80 | 71.348 | 46.471 | 112.270 | 1.00 | 72.94 | B |
| ATOM | 2187 | OE2 | GLU | B | 80 | 73.445 | 45.912 | 111.889 | 1.00 | 73.77 | B |
| ATOM | 2188 | C | GLU | B | 80 | 70.245 | 46.830 | 108.062 | 1.00 | 57.35 | B |
| ATOM | 2189 | O | GLU | B | 80 | 69.496 | 46.066 | 108.669 | 1.00 | 56.39 | B |
| ATOM | 2190 | N | GLY | B | 81 | 70.679 | 46.571 | 106.834 | 1.00 | 54.96 | B |
| ATOM | 2191 | CA | GLY | B | 81 | 70.230 | 45.383 | 106.134 | 1.00 | 55.73 | B |
| ATOM | 2192 | C | GLY | B | 81 | 69.105 | 45.819 | 105.216 | 1.00 | 51.15 | B |
| ATOM | 2193 | O | GLY | B | 81 | 68.500 | 46.855 | 105.469 | 1.00 | 57.34 | B |
| ATOM | 2194 | N | PRO | B | 82 | 68.785 | 45.062 | 104.160 | 1.00 | 49.49 | B |
| ATOM | 2195 | CD | PRO | B | 82 | 69.401 | 43.772 | 103.827 | 1.00 | 47.55 | B |

Figure 10 (35 of 142)

| | | | | | | | | | | |
|---|---|---|---|---|---|---|---|---|---|---|
| ATOM | 2196 | CA | PRO | B | 82 | 67.725 | 45.382 | 103.199 | 1.00 46.61 | B |
| ATOM | 2197 | CB | PRO | B | 82 | 67.672 | 44.134 | 102.338 | 1.00 46.49 | B |
| ATOM | 2198 | CG | PRO | B | 82 | 69.063 | 43.653 | 102.392 | 1.00 43.91 | B |
| ATOM | 2199 | C | PRO | B | 82 | 66.362 | 45.745 | 103.782 | 1.00 48.06 | B |
| ATOM | 2200 | O | PRO | B | 82 | 65.814 | 45.021 | 104.613 | 1.00 53.75 | B |
| ATOM | 2201 | N | SER | B | 83 | 65.816 | 46.863 | 103.311 | 1.00 48.08 | B |
| ATOM | 2202 | CA | SER | B | 83 | 64.523 | 47.365 | 103.774 | 1.00 47.23 | B |
| ATOM | 2203 | CB | SER | B | 83 | 64.524 | 48.894 | 103.706 | 1.00 54.78 | B |
| ATOM | 2204 | OG | SER | B | 83 | 65.614 | 49.353 | 102.921 | 1.00 57.97 | B |
| ATOM | 2205 | C | SER | B | 83 | 63.348 | 46.800 | 102.973 | 1.00 40.52 | B |
| ATOM | 2206 | O | SER | B | 83 | 62.961 | 47.337 | 101.940 | 1.00 40.30 | B |
| ATOM | 2207 | N | TYR | B | 84 | 62.752 | 45.742 | 103.501 | 1.00 36.80 | B |
| ATOM | 2208 | CA | TYR | B | 84 | 61.665 | 45.046 | 102.839 | 1.00 36.25 | B |
| ATOM | 2209 | CB | TYR | B | 84 | 61.732 | 43.597 | 103.268 | 1.00 37.76 | B |
| ATOM | 2210 | CG | TYR | B | 84 | 62.876 | 42.912 | 102.607 | 1.00 37.44 | B |
| ATOM | 2211 | CD1 | TYR | B | 84 | 63.877 | 42.315 | 103.351 | 1.00 40.27 | B |
| ATOM | 2212 | CE1 | TYR | B | 84 | 64.939 | 41.696 | 102.732 | 1.00 43.25 | B |
| ATOM | 2213 | CD2 | TYR | B | 84 | 62.963 | 42.876 | 101.222 | 1.00 36.21 | B |
| ATOM | 2214 | CE2 | TYR | B | 84 | 64.016 | 42.263 | 100.592 | 1.00 42.06 | B |
| ATOM | 2215 | CZ | TYR | B | 84 | 65.004 | 41.673 | 101.350 | 1.00 41.83 | B |
| ATOM | 2216 | OH | TYR | B | 84 | 66.068 | 41.065 | 100.718 | 1.00 48.12 | B |
| ATOM | 2217 | C | TYR | B | 84 | 60.210 | 45.509 | 102.862 | 1.00 34.13 | B |
| ATOM | 2218 | O | TYR | B | 84 | 59.294 | 44.706 | 102.619 | 1.00 38.00 | B |
| ATOM | 2219 | N | THR | B | 85 | 59.983 | 46.784 | 103.135 | 1.00 26.61 | B |
| ATOM | 2220 | CA | THR | B | 85 | 58.629 | 47.292 | 103.133 | 1.00 18.74 | B |
| ATOM | 2221 | CB | THR | B | 85 | 58.097 | 47.300 | 101.686 | 1.00 12.26 | B |
| ATOM | 2222 | OG1 | THR | B | 85 | 59.041 | 47.978 | 100.855 | 1.00 12.26 | B |
| ATOM | 2223 | CG2 | THR | B | 85 | 56.746 | 48.006 | 101.592 | 1.00 12.26 | B |
| ATOM | 2224 | C | THR | B | 85 | 57.684 | 46.525 | 104.062 | 1.00 17.79 | B |
| ATOM | 2225 | O | THR | B | 85 | 57.019 | 47.142 | 104.893 | 1.00 13.61 | B |
| ATOM | 2226 | N | PHE | B | 86 | 57.599 | 45.200 | 103.938 | 1.00 17.08 | B |
| ATOM | 2227 | CA | PHE | B | 86 | 56.719 | 44.469 | 104.837 | 1.00 20.23 | B |
| ATOM | 2228 | CB | PHE | B | 86 | 56.747 | 42.967 | 104.621 | 1.00 15.45 | B |
| ATOM | 2229 | CG | PHE | B | 86 | 56.124 | 42.205 | 105.762 | 1.00 14.55 | B |
| ATOM | 2230 | CD1 | PHE | B | 86 | 54.750 | 42.296 | 106.008 | 1.00 12.76 | B |
| ATOM | 2231 | CD2 | PHE | B | 86 | 56.912 | 41.454 | 106.636 | 1.00 16.35 | B |
| ATOM | 2232 | CE1 | PHE | B | 86 | 54.157 | 41.646 | 107.118 | 1.00 12.26 | B |
| ATOM | 2233 | CE2 | PHE | B | 86 | 56.346 | 40.802 | 107.742 | 1.00 15.83 | B |
| ATOM | 2234 | CZ | PHE | B | 86 | 54.958 | 40.899 | 107.985 | 1.00 13.72 | B |
| ATOM | 2235 | C | PHE | B | 86 | 57.241 | 44.729 | 106.227 | 1.00 22.39 | B |
| ATOM | 2236 | O | PHE | B | 86 | 56.508 | 45.150 | 107.118 | 1.00 29.56 | B |
| ATOM | 2237 | N | ASP | B | 87 | 58.528 | 44.468 | 106.407 | 1.00 27.12 | B |
| ATOM | 2238 | CA | ASP | B | 87 | 59.147 | 44.681 | 107.697 | 1.00 27.83 | B |
| ATOM | 2239 | CB | ASP | B | 87 | 60.641 | 44.372 | 107.615 | 1.00 31.15 | B |
| ATOM | 2240 | CG | ASP | B | 87 | 60.927 | 42.872 | 107.622 | 1.00 32.22 | B |
| ATOM | 2241 | OD1 | ASP | B | 87 | 61.957 | 42.459 | 107.043 | 1.00 33.64 | B |
| ATOM | 2242 | OD2 | ASP | B | 87 | 60.127 | 42.105 | 108.218 | 1.00 30.57 | B |
| ATOM | 2243 | C | ASP | B | 87 | 58.907 | 46.120 | 108.109 | 1.00 28.83 | B |
| ATOM | 2244 | O | ASP | B | 87 | 58.548 | 46.389 | 109.254 | 1.00 28.03 | B |
| ATOM | 2245 | N | THR | B | 88 | 59.055 | 47.037 | 107.155 | 1.00 24.78 | B |
| ATOM | 2246 | CA | THR | B | 88 | 58.874 | 48.459 | 107.424 | 1.00 17.11 | B |
| ATOM | 2247 | CB | THR | B | 88 | 59.384 | 49.312 | 106.250 | 1.00 14.30 | B |
| ATOM | 2248 | OG1 | THR | B | 88 | 60.808 | 49.171 | 106.129 | 1.00 12.26 | B |
| ATOM | 2249 | CG2 | THR | B | 88 | 59.031 | 50.777 | 106.478 | 1.00 12.41 | B |
| ATOM | 2250 | C | THR | B | 88 | 57.428 | 48.844 | 107.729 | 1.00 16.17 | B |
| ATOM | 2251 | O | THR | B | 88 | 57.136 | 49.475 | 108.752 | 1.00 17.57 | B |
| ATOM | 2252 | N | VAL | B | 89 | 56.520 | 48.490 | 106.834 | 1.00 15.00 | B |
| ATOM | 2253 | CA | VAL | B | 89 | 55.123 | 48.797 | 107.073 | 1.00 20.42 | B |
| ATOM | 2254 | CB | VAL | B | 89 | 54.239 | 48.298 | 105.931 | 1.00 24.62 | B |
| ATOM | 2255 | CG1 | VAL | B | 89 | 52.764 | 48.255 | 106.373 | 1.00 22.00 | B |
| ATOM | 2256 | CG2 | VAL | B | 89 | 54.415 | 49.215 | 104.739 | 1.00 21.88 | B |
| ATOM | 2257 | C | VAL | B | 89 | 54.691 | 48.130 | 108.377 | 1.00 22.97 | B |
| ATOM | 2258 | O | VAL | B | 89 | 53.814 | 48.635 | 109.088 | 1.00 26.54 | B |
| ATOM | 2259 | N | SER | B | 90 | 55.317 | 46.997 | 108.692 | 1.00 23.19 | B |
| ATOM | 2260 | CA | SER | B | 90 | 55.002 | 46.277 | 109.923 | 1.00 24.98 | B |
| ATOM | 2261 | CB | SER | B | 90 | 55.826 | 44.993 | 110.034 | 1.00 27.52 | B |

Figure 10 (36 of 142)

| | | | | | | | | | | |
|---|---|---|---|---|---|---|---|---|---|---|
| ATOM | 2262 | OG | SER | B | 90 | 55.416 | 44.025 | 109.089 | 1.00 30.97 | B |
| ATOM | 2263 | C | SER | B | 90 | 55.332 | 47.162 | 111.114 | 1.00 26.68 | B |
| ATOM | 2264 | O | SER | B | 90 | 54.472 | 47.448 | 111.959 | 1.00 28.02 | B |
| ATOM | 2265 | N | LEU | B | 91 | 56.593 | 47.582 | 111.166 | 1.00 27.08 | B |
| ATOM | 2266 | CA | LEU | B | 91 | 57.080 | 48.420 | 112.245 | 1.00 29.25 | B |
| ATOM | 2267 | CB | LEU | B | 91 | 58.553 | 48.756 | 112.042 | 1.00 31.81 | B |
| ATOM | 2268 | CG | LEU | B | 91 | 59.043 | 49.917 | 112.914 | 1.00 30.22 | B |
| ATOM | 2269 | CD1 | LEU | B | 91 | 58.647 | 49.718 | 114.399 | 1.00 34.00 | B |
| ATOM | 2270 | CD2 | LEU | B | 91 | 60.537 | 50.038 | 112.750 | 1.00 31.30 | B |
| ATOM | 2271 | C | LEU | B | 91 | 56.258 | 49.690 | 112.372 | 1.00 30.19 | B |
| ATOM | 2272 | O | LEU | B | 91 | 55.887 | 50.090 | 113.494 | 1.00 37.10 | B |
| ATOM | 2273 | N | LEU | B | 92 | 55.976 | 50.351 | 111.253 | 1.00 30.23 | B |
| ATOM | 2274 | CA | LEU | B | 92 | 55.126 | 51.514 | 111.355 | 1.00 29.49 | B |
| ATOM | 2275 | CB | LEU | B | 92 | 54.977 | 52.222 | 110.007 | 1.00 25.15 | B |
| ATOM | 2276 | CG | LEU | B | 92 | 56.251 | 52.646 | 109.281 | 1.00 21.52 | B |
| ATOM | 2277 | CD1 | LEU | B | 92 | 55.949 | 53.737 | 108.272 | 1.00 18.37 | B |
| ATOM | 2278 | CD2 | LEU | B | 92 | 57.215 | 53.167 | 110.288 | 1.00 19.31 | B |
| ATOM | 2279 | C | LEU | B | 92 | 53.835 | 50.800 | 111.743 | 1.00 35.16 | B |
| ATOM | 2280 | O | LEU | B | 92 | 53.867 | 49.764 | 112.391 | 1.00 37.35 | B |
| ATOM | 2281 | N | LYS | B | 93 | 52.695 | 51.319 | 111.334 | 1.00 37.84 | B |
| ATOM | 2282 | CA | LYS | B | 93 | 51.433 | 50.675 | 111.686 | 1.00 37.49 | B |
| ATOM | 2283 | CB | LYS | B | 93 | 51.134 | 49.491 | 110.754 | 1.00 32.81 | B |
| ATOM | 2284 | CG | LYS | B | 93 | 49.661 | 49.188 | 110.778 | 1.00 31.68 | B |
| ATOM | 2285 | CD | LYS | B | 93 | 49.196 | 48.111 | 109.858 | 1.00 32.51 | B |
| ATOM | 2286 | CE | LYS | B | 93 | 47.678 | 48.043 | 110.017 | 1.00 34.80 | B |
| ATOM | 2287 | NZ | LYS | B | 93 | 47.011 | 46.946 | 109.271 | 1.00 37.19 | B |
| ATOM | 2288 | C | LYS | B | 93 | 51.462 | 50.167 | 113.142 | 1.00 37.38 | B |
| ATOM | 2289 | O | LYS | B | 93 | 50.612 | 49.366 | 113.548 | 1.00 38.21 | B |
| ATOM | 2290 | N | GLN | B | 94 | 52.443 | 50.645 | 113.903 | 1.00 36.07 | B |
| ATOM | 2291 | CA | GLN | B | 94 | 52.615 | 50.299 | 115.296 | 1.00 43.38 | B |
| ATOM | 2292 | CB | GLN | B | 94 | 53.676 | 49.215 | 115.482 | 1.00 45.86 | B |
| ATOM | 2293 | CG | GLN | B | 94 | 53.250 | 47.818 | 115.008 | 1.00 56.30 | B |
| ATOM | 2294 | CD | GLN | B | 94 | 54.189 | 46.717 | 115.476 | 1.00 62.40 | B |
| ATOM | 2295 | OE1 | GLN | B | 94 | 54.115 | 45.577 | 115.008 | 1.00 66.15 | B |
| ATOM | 2296 | NE2 | GLN | B | 94 | 55.074 | 47.052 | 116.411 | 1.00 64.51 | B |
| ATOM | 2297 | C | GLN | B | 94 | 53.045 | 51.602 | 115.960 | 1.00 44.92 | B |
| ATOM | 2298 | O | GLN | B | 94 | 52.591 | 51.953 | 117.065 | 1.00 47.32 | B |
| ATOM | 2299 | N | ARG | B | 95 | 53.928 | 52.331 | 115.296 | 1.00 41.95 | B |
| ATOM | 2300 | CA | ARG | B | 95 | 54.340 | 53.623 | 115.839 | 1.00 36.34 | B |
| ATOM | 2301 | CB | ARG | B | 95 | 55.534 | 54.189 | 115.068 | 1.00 33.11 | B |
| ATOM | 2302 | CG | ARG | B | 95 | 56.898 | 53.764 | 115.570 | 1.00 35.44 | B |
| ATOM | 2303 | CD | ARG | B | 95 | 58.033 | 54.485 | 114.823 | 1.00 35.26 | B |
| ATOM | 2304 | NE | ARG | B | 95 | 59.337 | 53.902 | 115.156 | 1.00 39.36 | B |
| ATOM | 2305 | CZ | ARG | B | 95 | 60.496 | 54.306 | 114.641 | 1.00 35.11 | B |
| ATOM | 2306 | NH1 | ARG | B | 95 | 60.511 | 55.304 | 113.766 | 1.00 35.54 | B |
| ATOM | 2307 | NH2 | ARG | B | 95 | 61.635 | 53.708 | 114.987 | 1.00 37.61 | B |
| ATOM | 2308 | C | ARG | B | 95 | 53.138 | 54.555 | 115.641 | 1.00 36.35 | B |
| ATOM | 2309 | O | ARG | B | 95 | 52.950 | 55.518 | 116.379 | 1.00 36.57 | B |
| ATOM | 2310 | N | TYR | B | 96 | 52.327 | 54.262 | 114.632 | 1.00 40.20 | B |
| ATOM | 2311 | CA | TYR | B | 96 | 51.171 | 55.090 | 114.354 | 1.00 38.33 | B |
| ATOM | 2312 | CB | TYR | B | 96 | 51.420 | 55.933 | 113.109 | 1.00 40.61 | B |
| ATOM | 2313 | CG | TYR | B | 96 | 52.792 | 56.557 | 113.047 | 1.00 37.90 | B |
| ATOM | 2314 | CD1 | TYR | B | 96 | 53.888 | 55.830 | 112.583 | 1.00 41.56 | B |
| ATOM | 2315 | CE1 | TYR | B | 96 | 55.166 | 56.407 | 112.513 | 1.00 36.93 | B |
| ATOM | 2316 | CD2 | TYR | B | 96 | 53.000 | 57.881 | 113.447 | 1.00 36.93 | B |
| ATOM | 2317 | CE2 | TYR | B | 96 | 54.273 | 58.467 | 113.382 | 1.00 38.31 | B |
| ATOM | 2318 | CZ | TYR | B | 96 | 55.351 | 57.724 | 112.910 | 1.00 36.06 | B |
| ATOM | 2319 | OH | TYR | B | 96 | 56.601 | 58.300 | 112.802 | 1.00 32.26 | B |
| ATOM | 2320 | C | TYR | B | 96 | 49.925 | 54.238 | 114.161 | 1.00 41.23 | B |
| ATOM | 2321 | O | TYR | B | 96 | 49.487 | 53.997 | 113.039 | 1.00 43.91 | B |
| ATOM | 2322 | N | PRO | B | 97 | 49.346 | 53.756 | 115.263 | 1.00 45.56 | B |
| ATOM | 2323 | CD | PRO | B | 97 | 50.026 | 53.596 | 116.557 | 1.00 43.29 | B |
| ATOM | 2324 | CA | PRO | B | 97 | 48.139 | 52.922 | 115.210 | 1.00 44.67 | B |
| ATOM | 2325 | CB | PRO | B | 97 | 48.157 | 52.203 | 116.556 | 1.00 42.80 | B |
| ATOM | 2326 | CG | PRO | B | 97 | 49.615 | 52.207 | 116.936 | 1.00 44.91 | B |
| ATOM | 2327 | C | PRO | B | 97 | 46.847 | 53.709 | 115.019 | 1.00 44.67 | B |

Figure 10 (37 of 142)

| | | | | | | | | | |
|---|---|---|---|---|---|---|---|---|---|
| ATOM | 2328 | O | PRO | B | 97 | 45.789 | 53.117 | 114.785 | 1.00 49.86 B |
| ATOM | 2329 | N | ASN | B | 98 | 46.928 | 55.036 | 115.128 | 1.00 44.37 B |
| ATOM | 2330 | CA | ASN | B | 98 | 45.740 | 55.877 | 114.971 | 1.00 44.95 B |
| ATOM | 2331 | CB | ASN | B | 98 | 45.620 | 56.849 | 116.154 | 1.00 47.94 B |
| ATOM | 2332 | CG | ASN | B | 98 | 45.210 | 56.150 | 117.439 | 1.00 50.78 B |
| ATOM | 2333 | OD1 | ASN | B | 98 | 45.838 | 55.164 | 117.854 | 1.00 52.41 B |
| ATOM | 2334 | ND2 | ASN | B | 98 | 44.150 | 56.653 | 118.078 | 1.00 52.60 B |
| ATOM | 2335 | C | ASN | B | 98 | 45.696 | 56.647 | 113.651 | 1.00 40.12 B |
| ATOM | 2336 | O | ASN | B | 98 | 44.707 | 57.334 | 113.346 | 1.00 38.66 B |
| ATOM | 2337 | N | ASP | B | 99 | 46.767 | 56.528 | 112.872 | 1.00 36.20 B |
| ATOM | 2338 | CA | ASP | B | 99 | 46.837 | 57.194 | 111.579 | 1.00 30.88 B |
| ATOM | 2339 | CB | ASP | B | 99 | 48.231 | 57.749 | 111.339 | 1.00 29.74 B |
| ATOM | 2340 | CG | ASP | B | 99 | 48.597 | 58.814 | 112.319 | 1.00 36.68 B |
| ATOM | 2341 | OD1 | ASP | B | 99 | 47.715 | 59.628 | 112.668 | 1.00 40.66 B |
| ATOM | 2342 | OD2 | ASP | B | 99 | 49.772 | 58.843 | 112.731 | 1.00 41.68 B |
| ATOM | 2343 | C | ASP | B | 99 | 46.478 | 56.261 | 110.426 | 1.00 29.92 B |
| ATOM | 2344 | O | ASP | B | 99 | 46.749 | 55.051 | 110.468 | 1.00 28.47 B |
| ATOM | 2345 | N | GLN | B | 100 | 45.872 | 56.831 | 109.387 | 1.00 26.93 B |
| ATOM | 2346 | CA | GLN | B | 100 | 45.480 | 56.049 | 108.220 | 1.00 26.12 B |
| ATOM | 2347 | CB | GLN | B | 100 | 44.235 | 56.680 | 107.584 | 1.00 24.58 B |
| ATOM | 2348 | CG | GLN | B | 100 | 43.200 | 55.680 | 107.102 | 1.00 32.80 B |
| ATOM | 2349 | CD | GLN | B | 100 | 41.863 | 56.332 | 106.877 | 1.00 37.05 B |
| ATOM | 2350 | OE1 | GLN | B | 100 | 41.229 | 56.811 | 107.819 | 1.00 37.24 B |
| ATOM | 2351 | NE2 | GLN | B | 100 | 41.426 | 56.368 | 105.624 | 1.00 41.07 B |
| ATOM | 2352 | C | GLN | B | 100 | 46.664 | 56.012 | 107.241 | 1.00 21.49 B |
| ATOM | 2353 | O | GLN | B | 100 | 47.087 | 57.046 | 106.712 | 1.00 20.28 B |
| ATOM | 2354 | N | LEU | B | 101 | 47.212 | 54.817 | 107.026 | 1.00 19.32 B |
| ATOM | 2355 | CA | LEU | B | 101 | 48.354 | 54.669 | 106.129 | 1.00 20.00 B |
| ATOM | 2356 | CB | LEU | B | 101 | 49.467 | 53.907 | 106.824 | 1.00 19.19 B |
| ATOM | 2357 | CG | LEU | B | 101 | 49.745 | 54.425 | 108.228 | 1.00 20.41 B |
| ATOM | 2358 | CD1 | LEU | B | 101 | 50.958 | 53.712 | 108.764 | 1.00 21.10 B |
| ATOM | 2359 | CD2 | LEU | B | 101 | 49.982 | 55.928 | 108.206 | 1.00 15.15 B |
| ATOM | 2360 | C | LEU | B | 101 | 48.092 | 54.015 | 104.774 | 1.00 20.16 B |
| ATOM | 2361 | O | LEU | B | 101 | 47.397 | 52.993 | 104.652 | 1.00 21.79 B |
| ATOM | 2362 | N | PHE | B | 102 | 48.664 | 54.634 | 103.750 | 1.00 16.54 B |
| ATOM | 2363 | CA | PHE | B | 102 | 48.552 | 54.142 | 102.394 | 1.00 14.76 B |
| ATOM | 2364 | CB | PHE | B | 102 | 47.693 | 55.072 | 101.533 | 1.00 12.26 B |
| ATOM | 2365 | CG | PHE | B | 102 | 46.284 | 55.162 | 101.970 | 1.00 12.26 B |
| ATOM | 2366 | CD1 | PHE | B | 102 | 45.927 | 56.015 | 102.994 | 1.00 13.31 B |
| ATOM | 2367 | CD2 | PHE | B | 102 | 45.321 | 54.346 | 101.399 | 1.00 12.26 B |
| ATOM | 2368 | CE1 | PHE | B | 102 | 44.621 | 56.050 | 103.451 | 1.00 13.10 B |
| ATOM | 2369 | CE2 | PHE | B | 102 | 44.017 | 54.371 | 101.842 | 1.00 14.26 B |
| ATOM | 2370 | CZ | PHE | B | 102 | 43.661 | 55.222 | 102.875 | 1.00 14.85 B |
| ATOM | 2371 | C | PHE | B | 102 | 49.964 | 54.144 | 101.855 | 1.00 12.26 B |
| ATOM | 2372 | O | PHE | B | 102 | 50.774 | 54.982 | 102.245 | 1.00 12.26 B |
| ATOM | 2373 | N | PHE | B | 103 | 50.265 | 53.191 | 100.980 | 1.00 12.26 B |
| ATOM | 2374 | CA | PHE | B | 103 | 51.577 | 53.146 | 100.355 | 1.00 14.20 B |
| ATOM | 2375 | CB | PHE | B | 103 | 52.132 | 51.749 | 100.344 | 1.00 13.61 B |
| ATOM | 2376 | CG | PHE | B | 103 | 53.604 | 51.707 | 100.170 | 1.00 12.65 B |
| ATOM | 2377 | CD1 | PHE | B | 103 | 54.438 | 51.681 | 101.286 | 1.00 13.85 B |
| ATOM | 2378 | CD2 | PHE | B | 103 | 54.167 | 51.679 | 98.901 | 1.00 12.26 B |
| ATOM | 2379 | CE1 | PHE | B | 103 | 55.812 | 51.623 | 101.148 | 1.00 12.26 B |
| ATOM | 2380 | CE2 | PHE | B | 103 | 55.546 | 51.622 | 98.742 | 1.00 14.98 B |
| ATOM | 2381 | CZ | PHE | B | 103 | 56.373 | 51.592 | 99.871 | 1.00 15.27 B |
| ATOM | 2382 | C | PHE | B | 103 | 51.401 | 53.612 | 98.918 | 1.00 13.02 B |
| ATOM | 2383 | O | PHE | B | 103 | 50.321 | 53.461 | 98.322 | 1.00 16.72 B |
| ATOM | 2384 | N | ILE | B | 104 | 52.463 | 54.147 | 98.340 | 1.00 12.26 B |
| ATOM | 2385 | CA | ILE | B | 104 | 52.353 | 54.689 | 96.998 | 1.00 12.26 B |
| ATOM | 2386 | CB | ILE | B | 104 | 52.370 | 56.234 | 97.040 | 1.00 12.26 B |
| ATOM | 2387 | CG2 | ILE | B | 104 | 52.345 | 56.811 | 95.628 | 1.00 12.26 B |
| ATOM | 2388 | CG1 | ILE | B | 104 | 51.177 | 56.737 | 97.829 | 1.00 12.26 B |
| ATOM | 2389 | CD1 | ILE | B | 104 | 51.192 | 58.190 | 97.972 | 1.00 12.26 B |
| ATOM | 2390 | C | ILE | B | 104 | 53.421 | 54.242 | 96.036 | 1.00 17.27 B |
| ATOM | 2391 | O | ILE | B | 104 | 54.615 | 54.383 | 96.301 | 1.00 25.00 B |
| ATOM | 2392 | N | ILE | B | 105 | 52.984 | 53.731 | 94.896 | 1.00 18.24 B |
| ATOM | 2393 | CA | ILE | B | 105 | 53.911 | 53.275 | 93.875 | 1.00 17.94 B |

Figure 10 (38 of 142)

| | | | | | | | | | | |
|---|---|---|---|---|---|---|---|---|---|---|
| ATOM | 2394 | CB | ILE | B | 105 | 53.990 | 51.727 | 93.817 | 1.00 16.35 | B |
| ATOM | 2395 | CG2 | ILE | B | 105 | 54.515 | 51.166 | 95.133 | 1.00 23.25 | B |
| ATOM | 2396 | CG1 | ILE | B | 105 | 52.612 | 51.151 | 93.529 | 1.00 20.26 | B |
| ATOM | 2397 | CD1 | ILE | B | 105 | 52.656 | 49.705 | 93.250 | 1.00 15.19 | B |
| ATOM | 2398 | C | ILE | B | 105 | 53.448 | 53.763 | 92.515 | 1.00 14.95 | B |
| ATOM | 2399 | O | ILE | B | 105 | 52.272 | 54.073 | 92.326 | 1.00 15.12 | B |
| ATOM | 2400 | N | GLY | B | 106 | 54.379 | 53.828 | 91.571 | 1.00 16.32 | B |
| ATOM | 2401 | CA | GLY | B | 106 | 54.053 | 54.257 | 90.221 | 1.00 20.24 | B |
| ATOM | 2402 | C | GLY | B | 106 | 53.931 | 53.041 | 89.315 | 1.00 19.63 | B |
| ATOM | 2403 | O | GLY | B | 106 | 54.299 | 51.936 | 89.737 | 1.00 25.29 | B |
| ATOM | 2404 | N | ALA | B | 107 | 53.415 | 53.229 | 88.094 | 1.00 18.45 | B |
| ATOM | 2405 | CA | ALA | B | 107 | 53.245 | 52.132 | 87.128 | 1.00 20.47 | B |
| ATOM | 2406 | CB | ALA | B | 107 | 53.182 | 52.681 | 85.716 | 1.00 18.75 | B |
| ATOM | 2407 | C | ALA | B | 107 | 54.416 | 51.172 | 87.250 | 1.00 22.87 | B |
| ATOM | 2408 | O | ALA | B | 107 | 54.256 | 49.961 | 87.391 | 1.00 21.33 | B |
| ATOM | 2409 | N | ASP | B | 108 | 55.598 | 51.762 | 87.197 | 1.00 23.89 | B |
| ATOM | 2410 | CA | ASP | B | 108 | 56.855 | 51.070 | 87.321 | 1.00 24.68 | B |
| ATOM | 2411 | CB | ASP | B | 108 | 57.903 | 52.089 | 87.739 | 1.00 30.47 | B |
| ATOM | 2412 | CG | ASP | B | 108 | 59.254 | 51.494 | 87.835 | 1.00 35.86 | B |
| ATOM | 2413 | OD1 | ASP | B | 108 | 59.408 | 50.355 | 87.349 | 1.00 42.53 | B |
| ATOM | 2414 | OD2 | ASP | B | 108 | 60.161 | 52.154 | 88.381 | 1.00 41.63 | B |
| ATOM | 2415 | C | ASP | B | 108 | 56.792 | 49.915 | 88.323 | 1.00 23.12 | B |
| ATOM | 2416 | O | ASP | B | 108 | 56.759 | 48.761 | 87.919 | 1.00 32.33 | B |
| ATOM | 2417 | N | MET | B | 109 | 56.776 | 50.215 | 89.623 | 1.00 19.79 | B |
| ATOM | 2418 | CA | MET | B | 109 | 56.717 | 49.167 | 90.641 | 1.00 15.03 | B |
| ATOM | 2419 | CB | MET | B | 109 | 56.776 | 49.767 | 92.038 | 1.00 12.26 | B |
| ATOM | 2420 | CG | MET | B | 109 | 58.143 | 50.268 | 92.428 | 1.00 12.26 | B |
| ATOM | 2421 | SD | MET | B | 109 | 59.342 | 48.967 | 92.721 | 1.00 12.26 | B |
| ATOM | 2422 | CE | MET | B | 109 | 60.031 | 48.811 | 91.133 | 1.00 13.58 | B |
| ATOM | 2423 | C | MET | B | 109 | 55.479 | 48.290 | 90.534 | 1.00 14.64 | B |
| ATOM | 2424 | O | MET | B | 109 | 55.519 | 47.127 | 90.916 | 1.00 12.26 | B |
| ATOM | 2425 | N | ILE | B | 110 | 54.378 | 48.838 | 90.026 | 1.00 17.20 | B |
| ATOM | 2426 | CA | ILE | B | 110 | 53.149 | 48.059 | 89.876 | 1.00 12.58 | B |
| ATOM | 2427 | CB | ILE | B | 110 | 52.072 | 48.884 | 89.180 | 1.00 12.26 | B |
| ATOM | 2428 | CG2 | ILE | B | 110 | 50.841 | 48.047 | 88.948 | 1.00 12.26 | B |
| ATOM | 2429 | CG1 | ILE | B | 110 | 51.726 | 50.078 | 90.058 | 1.00 12.26 | B |
| ATOM | 2430 | CD1 | ILE | B | 110 | 50.380 | 50.646 | 89.775 | 1.00 12.26 | B |
| ATOM | 2431 | C | ILE | B | 110 | 53.403 | 46.758 | 89.106 | 1.00 12.26 | B |
| ATOM | 2432 | O | ILE | B | 110 | 52.843 | 45.703 | 89.429 | 1.00 16.41 | B |
| ATOM | 2433 | N | GLU | B | 111 | 54.274 | 46.843 | 88.106 | 1.00 12.26 | B |
| ATOM | 2434 | CA | GLU | B | 111 | 54.654 | 45.696 | 87.292 | 1.00 13.36 | B |
| ATOM | 2435 | CB | GLU | B | 111 | 55.438 | 46.151 | 86.070 | 1.00 18.93 | B |
| ATOM | 2436 | CG | GLU | B | 111 | 54.625 | 46.719 | 84.928 | 1.00 24.03 | B |
| ATOM | 2437 | CD | GLU | B | 111 | 55.504 | 47.025 | 83.716 | 1.00 25.81 | B |
| ATOM | 2438 | OE1 | GLU | B | 111 | 56.432 | 46.232 | 83.438 | 1.00 31.56 | B |
| ATOM | 2439 | OE2 | GLU | B | 111 | 55.270 | 48.047 | 83.035 | 1.00 31.76 | B |
| ATOM | 2440 | C | GLU | B | 111 | 55.546 | 44.748 | 88.077 | 1.00 12.26 | B |
| ATOM | 2441 | O | GLU | B | 111 | 55.663 | 43.561 | 87.762 | 1.00 12.26 | B |
| ATOM | 2442 | N | TYR | B | 112 | 56.178 | 45.292 | 89.101 | 1.00 12.26 | B |
| ATOM | 2443 | CA | TYR | B | 112 | 57.102 | 44.540 | 89.936 | 1.00 12.26 | B |
| ATOM | 2444 | CB | TYR | B | 112 | 58.170 | 45.508 | 90.424 | 1.00 16.43 | B |
| ATOM | 2445 | CG | TYR | B | 112 | 59.504 | 44.883 | 90.659 | 1.00 19.50 | B |
| ATOM | 2446 | CD1 | TYR | B | 112 | 59.857 | 44.405 | 91.908 | 1.00 24.19 | B |
| ATOM | 2447 | CE1 | TYR | B | 112 | 61.095 | 43.806 | 92.118 | 1.00 27.01 | B |
| ATOM | 2448 | CD2 | TYR | B | 112 | 60.416 | 44.753 | 89.622 | 1.00 25.19 | B |
| ATOM | 2449 | CE2 | TYR | B | 112 | 61.644 | 44.159 | 89.818 | 1.00 24.94 | B |
| ATOM | 2450 | CZ | TYR | B | 112 | 61.976 | 43.685 | 91.065 | 1.00 24.89 | B |
| ATOM | 2451 | OH | TYR | B | 112 | 63.179 | 43.058 | 91.252 | 1.00 30.70 | B |
| ATOM | 2452 | C | TYR | B | 112 | 56.468 | 43.822 | 91.134 | 1.00 13.54 | B |
| ATOM | 2453 | O | TYR | B | 112 | 57.101 | 42.953 | 91.742 | 1.00 12.71 | B |
| ATOM | 2454 | N | LEU | B | 113 | 55.220 | 44.182 | 91.460 | 1.00 12.26 | B |
| ATOM | 2455 | CA | LEU | B | 113 | 54.511 | 43.612 | 92.592 | 1.00 12.26 | B |
| ATOM | 2456 | CB | LEU | B | 113 | 53.008 | 43.843 | 92.412 | 1.00 12.26 | B |
| ATOM | 2457 | CG | LEU | B | 113 | 52.538 | 45.090 | 93.193 | 1.00 12.26 | B |
| ATOM | 2458 | CD1 | LEU | B | 113 | 53.512 | 46.180 | 92.959 | 1.00 12.26 | B |
| ATOM | 2459 | CD2 | LEU | B | 113 | 51.154 | 45.558 | 92.811 | 1.00 12.26 | B |

Figure 10 (39 of 142)

| ATOM | 2460 | C | LEU | B | 113 | 54.869 | 42.148 | 92.836 | 1.00 | 15.07 | B |
|---|---|---|---|---|---|---|---|---|---|---|---|
| ATOM | 2461 | O | LEU | B | 113 | 55.244 | 41.778 | 93.945 | 1.00 | 22.55 | B |
| ATOM | 2462 | N | PRO | B | 114 | 54.779 | 41.297 | 91.805 | 1.00 | 19.50 | B |
| ATOM | 2463 | CD | PRO | B | 114 | 54.267 | 41.569 | 90.458 | 1.00 | 12.26 | B |
| ATOM | 2464 | CA | PRO | B | 114 | 55.117 | 39.873 | 91.948 | 1.00 | 12.82 | B |
| ATOM | 2465 | CB | PRO | B | 114 | 55.077 | 39.360 | 90.515 | 1.00 | 12.26 | B |
| ATOM | 2466 | CG | PRO | B | 114 | 55.088 | 40.627 | 89.669 | 1.00 | 12.26 | B |
| ATOM | 2467 | C | PRO | B | 114 | 56.476 | 39.651 | 92.604 | 1.00 | 14.06 | B |
| ATOM | 2468 | O | PRO | B | 114 | 56.554 | 39.045 | 93.669 | 1.00 | 19.00 | B |
| ATOM | 2469 | N | LYS | B | 115 | 57.545 | 40.110 | 91.961 | 1.00 | 15.44 | B |
| ATOM | 2470 | CA | LYS | B | 115 | 58.884 | 39.994 | 92.545 | 1.00 | 22.62 | B |
| ATOM | 2471 | CB | LYS | B | 115 | 59.959 | 40.355 | 91.517 | 1.00 | 23.77 | B |
| ATOM | 2472 | CG | LYS | B | 115 | 59.859 | 39.614 | 90.206 | 1.00 | 30.61 | B |
| ATOM | 2473 | CD | LYS | B | 115 | 60.951 | 40.054 | 89.226 | 1.00 | 36.32 | B |
| ATOM | 2474 | CE | LYS | B | 115 | 62.324 | 39.597 | 89.693 | 1.00 | 43.57 | B |
| ATOM | 2475 | NZ | LYS | B | 115 | 63.391 | 39.856 | 88.686 | 1.00 | 48.04 | B |
| ATOM | 2476 | C | LYS | B | 115 | 58.873 | 41.068 | 93.631 | 1.00 | 18.78 | B |
| ATOM | 2477 | O | LYS | B | 115 | 59.041 | 42.232 | 93.326 | 1.00 | 27.54 | B |
| ATOM | 2478 | N | TRP | B | 116 | 58.687 | 40.700 | 94.889 | 1.00 | 17.92 | B |
| ATOM | 2479 | CA | TRP | B | 116 | 58.595 | 41.710 | 95.937 | 1.00 | 15.38 | B |
| ATOM | 2480 | CB | TRP | B | 116 | 57.426 | 42.640 | 95.593 | 1.00 | 19.49 | B |
| ATOM | 2481 | CG | TRP | B | 116 | 57.254 | 43.885 | 96.418 | 1.00 | 19.24 | B |
| ATOM | 2482 | CD2 | TRP | B | 116 | 57.241 | 45.242 | 95.941 | 1.00 | 18.79 | B |
| ATOM | 2483 | CE2 | TRP | B | 116 | 56.909 | 46.080 | 97.048 | 1.00 | 16.10 | B |
| ATOM | 2484 | CE3 | TRP | B | 116 | 57.483 | 45.829 | 94.701 | 1.00 | 15.03 | B |
| ATOM | 2485 | CD1 | TRP | B | 116 | 56.942 | 43.951 | 97.750 | 1.00 | 22.94 | B |
| ATOM | 2486 | NE1 | TRP | B | 116 | 56.728 | 45.268 | 98.133 | 1.00 | 21.28 | B |
| ATOM | 2487 | CZ2 | TRP | B | 116 | 56.797 | 47.460 | 96.949 | 1.00 | 12.26 | B |
| ATOM | 2488 | CZ3 | TRP | B | 116 | 57.376 | 47.206 | 94.598 | 1.00 | 16.24 | B |
| ATOM | 2489 | CH2 | TRP | B | 116 | 57.039 | 48.014 | 95.726 | 1.00 | 15.30 | B |
| ATOM | 2490 | C | TRP | B | 116 | 58.327 | 40.866 | 97.173 | 1.00 | 12.91 | B |
| ATOM | 2491 | O | TRP | B | 116 | 57.384 | 40.070 | 97.206 | 1.00 | 16.67 | B |
| ATOM | 2492 | N | TYR | B | 117 | 59.176 | 41.026 | 98.183 | 1.00 | 13.54 | B |
| ATOM | 2493 | CA | TYR | B | 117 | 59.110 | 40.223 | 99.396 | 1.00 | 12.26 | B |
| ATOM | 2494 | CB | TYR | B | 117 | 60.336 | 40.521 | 100.267 | 1.00 | 17.69 | B |
| ATOM | 2495 | CG | TYR | B | 117 | 60.424 | 39.718 | 101.546 | 1.00 | 12.37 | B |
| ATOM | 2496 | CD1 | TYR | B | 117 | 60.604 | 38.341 | 101.518 | 1.00 | 12.26 | B |
| ATOM | 2497 | CE1 | TYR | B | 117 | 60.659 | 37.591 | 102.701 | 1.00 | 12.26 | B |
| ATOM | 2498 | CD2 | TYR | B | 117 | 60.302 | 40.337 | 102.789 | 1.00 | 15.11 | B |
| ATOM | 2499 | CE2 | TYR | B | 117 | 60.353 | 39.605 | 103.976 | 1.00 | 12.26 | B |
| ATOM | 2500 | CZ | TYR | B | 117 | 60.533 | 38.229 | 103.933 | 1.00 | 12.26 | B |
| ATOM | 2501 | OH | TYR | B | 117 | 60.605 | 37.496 | 105.118 | 1.00 | 12.26 | B |
| ATOM | 2502 | C | TYR | B | 117 | 57.858 | 40.315 | 100.234 | 1.00 | 12.26 | B |
| ATOM | 2503 | O | TYR | B | 117 | 57.541 | 41.361 | 100.760 | 1.00 | 12.26 | B |
| ATOM | 2504 | N | LYS | B | 118 | 57.152 | 39.203 | 100.353 | 1.00 | 12.26 | B |
| ATOM | 2505 | CA | LYS | B | 118 | 55.967 | 39.143 | 101.181 | 1.00 | 12.26 | B |
| ATOM | 2506 | CB | LYS | B | 118 | 56.354 | 39.396 | 102.622 | 1.00 | 12.26 | B |
| ATOM | 2507 | CG | LYS | B | 118 | 57.067 | 38.239 | 103.257 | 1.00 | 16.08 | B |
| ATOM | 2508 | CD | LYS | B | 118 | 57.118 | 38.430 | 104.760 | 1.00 | 24.89 | B |
| ATOM | 2509 | CE | LYS | B | 118 | 57.685 | 37.207 | 105.463 | 1.00 | 31.64 | B |
| ATOM | 2510 | NZ | LYS | B | 118 | 57.823 | 37.419 | 106.930 | 1.00 | 41.72 | B |
| ATOM | 2511 | C | LYS | B | 118 | 54.844 | 40.074 | 100.818 | 1.00 | 12.26 | B |
| ATOM | 2512 | O | LYS | B | 118 | 54.266 | 40.719 | 101.687 | 1.00 | 12.26 | B |
| ATOM | 2513 | N | LEU | B | 119 | 54.494 | 40.122 | 99.545 | 1.00 | 12.45 | B |
| ATOM | 2514 | CA | LEU | B | 119 | 53.437 | 41.016 | 99.105 | 1.00 | 16.88 | B |
| ATOM | 2515 | CB | LEU | B | 119 | 53.361 | 41.029 | 97.583 | 1.00 | 18.18 | B |
| ATOM | 2516 | CG | LEU | B | 119 | 52.359 | 42.015 | 97.020 | 1.00 | 12.26 | B |
| ATOM | 2517 | CD1 | LEU | B | 119 | 52.681 | 43.396 | 97.562 | 1.00 | 12.26 | B |
| ATOM | 2518 | CD2 | LEU | B | 119 | 52.415 | 41.994 | 95.522 | 1.00 | 12.26 | B |
| ATOM | 2519 | C | LEU | B | 119 | 52.095 | 40.612 | 99.662 | 1.00 | 15.85 | B |
| ATOM | 2520 | O | LEU | B | 119 | 51.311 | 41.457 | 100.090 | 1.00 | 15.30 | B |
| ATOM | 2521 | N | ASP | B | 120 | 51.839 | 39.310 | 99.661 | 1.00 | 15.19 | B |
| ATOM | 2522 | CA | ASP | B | 120 | 50.571 | 38.800 | 100.132 | 1.00 | 18.76 | B |
| ATOM | 2523 | CB | ASP | B | 120 | 50.452 | 37.307 | 99.829 | 1.00 | 25.09 | B |
| ATOM | 2524 | CG | ASP | B | 120 | 50.356 | 37.025 | 98.322 | 1.00 | 28.44 | B |
| ATOM | 2525 | OD1 | ASP | B | 120 | 49.423 | 37.569 | 97.688 | 1.00 | 32.02 | B |

Figure 10 (40 of 142)

| ATOM | 2526 | OD2 | ASP | B | 120 | 51.204 | 36.279 | 97.761 | 1.00 | 28.43 | B |
|---|---|---|---|---|---|---|---|---|---|---|---|
| ATOM | 2527 | C | ASP | B | 120 | 50.302 | 39.071 | 101.586 | 1.00 | 21.15 | B |
| ATOM | 2528 | O | ASP | B | 120 | 49.145 | 39.039 | 101.990 | 1.00 | 28.50 | B |
| ATOM | 2529 | N | GLU | B | 121 | 51.341 | 39.347 | 102.376 | 1.00 | 17.97 | B |
| ATOM | 2530 | CA | GLU | B | 121 | 51.139 | 39.642 | 103.800 | 1.00 | 16.58 | B |
| ATOM | 2531 | CB | GLU | B | 121 | 52.221 | 39.013 | 104.674 | 1.00 | 22.37 | B |
| ATOM | 2532 | CG | GLU | B | 121 | 52.321 | 37.508 | 104.562 | 1.00 | 35.03 | B |
| ATOM | 2533 | CD | GLU | B | 121 | 52.891 | 37.080 | 103.221 | 1.00 | 43.82 | B |
| ATOM | 2534 | OE1 | GLU | B | 121 | 53.513 | 37.944 | 102.546 | 1.00 | 50.96 | B |
| ATOM | 2535 | OE2 | GLU | B | 121 | 52.728 | 35.888 | 102.850 | 1.00 | 49.75 | B |
| ATOM | 2536 | C | GLU | B | 121 | 51.171 | 41.145 | 103.984 | 1.00 | 15.63 | B |
| ATOM | 2537 | O | GLU | B | 121 | 50.613 | 41.696 | 104.946 | 1.00 | 18.11 | B |
| ATOM | 2538 | N | LEU | B | 122 | 51.840 | 41.803 | 103.046 | 1.00 | 14.08 | B |
| ATOM | 2539 | CA | LEU | B | 122 | 51.951 | 43.257 | 103.063 | 1.00 | 16.72 | B |
| ATOM | 2540 | CB | LEU | B | 122 | 53.066 | 43.712 | 102.102 | 1.00 | 12.98 | B |
| ATOM | 2541 | CG | LEU | B | 122 | 53.171 | 45.220 | 101.836 | 1.00 | 12.91 | B |
| ATOM | 2542 | CD1 | LEU | B | 122 | 53.475 | 45.956 | 103.130 | 1.00 | 14.11 | B |
| ATOM | 2543 | CD2 | LEU | B | 122 | 54.248 | 45.489 | 100.808 | 1.00 | 12.26 | B |
| ATOM | 2544 | C | LEU | B | 122 | 50.618 | 43.883 | 102.647 | 1.00 | 18.02 | B |
| ATOM | 2545 | O | LEU | B | 122 | 50.156 | 44.858 | 103.247 | 1.00 | 15.00 | B |
| ATOM | 2546 | N | LEU | B | 123 | 50.017 | 43.306 | 101.611 | 1.00 | 22.14 | B |
| ATOM | 2547 | CA | LEU | B | 123 | 48.751 | 43.775 | 101.087 | 1.00 | 22.98 | B |
| ATOM | 2548 | CB | LEU | B | 123 | 48.310 | 42.890 | 99.923 | 1.00 | 24.86 | B |
| ATOM | 2549 | CG | LEU | B | 123 | 49.039 | 43.146 | 98.609 | 1.00 | 26.82 | B |
| ATOM | 2550 | CD1 | LEU | B | 123 | 48.553 | 42.158 | 97.558 | 1.00 | 27.99 | B |
| ATOM | 2551 | CD2 | LEU | B | 123 | 48.780 | 44.581 | 98.158 | 1.00 | 28.66 | B |
| ATOM | 2552 | C | LEU | B | 123 | 47.711 | 43.738 | 102.184 | 1.00 | 22.18 | B |
| ATOM | 2553 | O | LEU | B | 123 | 46.769 | 44.531 | 102.193 | 1.00 | 27.61 | B |
| ATOM | 2554 | N | ASN | B | 124 | 47.903 | 42.824 | 103.121 | 1.00 | 22.13 | B |
| ATOM | 2555 | CA | ASN | B | 124 | 46.972 | 42.645 | 104.226 | 1.00 | 22.21 | B |
| ATOM | 2556 | CB | ASN | B | 124 | 47.201 | 41.253 | 104.843 | 1.00 | 30.83 | B |
| ATOM | 2557 | CG | ASN | B | 124 | 46.080 | 40.821 | 105.759 | 1.00 | 32.89 | B |
| ATOM | 2558 | OD1 | ASN | B | 124 | 45.905 | 41.372 | 106.845 | 1.00 | 35.93 | B |
| ATOM | 2559 | ND2 | ASN | B | 124 | 45.312 | 39.827 | 105.325 | 1.00 | 33.04 | B |
| ATOM | 2560 | C | ASN | B | 124 | 47.163 | 43.746 | 105.266 | 1.00 | 18.04 | B |
| ATOM | 2561 | O | ASN | B | 124 | 46.263 | 44.054 | 106.036 | 1.00 | 21.00 | B |
| ATOM | 2562 | N | LEU | B | 125 | 48.339 | 44.352 | 105.268 | 1.00 | 15.69 | B |
| ATOM | 2563 | CA | LEU | B | 125 | 48.643 | 45.410 | 106.213 | 1.00 | 14.60 | B |
| ATOM | 2564 | CB | LEU | B | 125 | 50.133 | 45.419 | 106.504 | 1.00 | 16.00 | B |
| ATOM | 2565 | CG | LEU | B | 125 | 50.617 | 44.316 | 107.431 | 1.00 | 16.07 | B |
| ATOM | 2566 | CD1 | LEU | B | 125 | 52.136 | 44.396 | 107.524 | 1.00 | 14.97 | B |
| ATOM | 2567 | CD2 | LEU | B | 125 | 49.955 | 44.468 | 108.817 | 1.00 | 12.26 | B |
| ATOM | 2568 | C | LEU | B | 125 | 48.263 | 46.807 | 105.770 | 1.00 | 14.17 | B |
| ATOM | 2569 | O | LEU | B | 125 | 47.671 | 47.577 | 106.518 | 1.00 | 18.51 | B |
| ATOM | 2570 | N | ILE | B | 126 | 48.630 | 47.144 | 104.550 | 1.00 | 13.04 | B |
| ATOM | 2571 | CA | ILE | B | 126 | 48.361 | 48.470 | 104.060 | 1.00 | 12.26 | B |
| ATOM | 2572 | CB | ILE | B | 126 | 49.678 | 49.283 | 104.098 | 1.00 | 12.26 | B |
| ATOM | 2573 | CG2 | ILE | B | 126 | 50.696 | 48.680 | 103.114 | 1.00 | 12.26 | B |
| ATOM | 2574 | CG1 | ILE | B | 126 | 49.413 | 50.757 | 103.787 | 1.00 | 19.42 | B |
| ATOM | 2575 | CD1 | ILE | B | 126 | 50.615 | 51.675 | 104.070 | 1.00 | 20.43 | B |
| ATOM | 2576 | C | ILE | B | 126 | 47.751 | 48.443 | 102.660 | 1.00 | 12.26 | B |
| ATOM | 2577 | O | ILE | B | 126 | 47.800 | 47.437 | 101.971 | 1.00 | 12.26 | B |
| ATOM | 2578 | N | GLN | B | 127 | 47.148 | 49.554 | 102.265 | 1.00 | 12.26 | B |
| ATOM | 2579 | CA | GLN | B | 127 | 46.525 | 49.660 | 100.964 | 1.00 | 12.26 | B |
| ATOM | 2580 | CB | GLN | B | 127 | 45.230 | 50.472 | 101.074 | 1.00 | 15.35 | B |
| ATOM | 2581 | CG | GLN | B | 127 | 44.139 | 49.737 | 101.847 | 1.00 | 22.27 | B |
| ATOM | 2582 | CD | GLN | B | 127 | 42.934 | 50.588 | 102.175 | 1.00 | 21.83 | B |
| ATOM | 2583 | OE1 | GLN | B | 127 | 43.064 | 51.679 | 102.724 | 1.00 | 26.91 | B |
| ATOM | 2584 | NE2 | GLN | B | 127 | 41.750 | 50.082 | 101.859 | 1.00 | 24.55 | B |
| ATOM | 2585 | C | GLN | B | 127 | 47.483 | 50.319 | 100.009 | 1.00 | 12.26 | B |
| ATOM | 2586 | O | GLN | B | 127 | 48.246 | 51.198 | 100.388 | 1.00 | 12.26 | B |
| ATOM | 2587 | N | PHE | B | 128 | 47.453 | 49.888 | 98.761 | 1.00 | 12.26 | B |
| ATOM | 2588 | CA | PHE | B | 128 | 48.329 | 50.471 | 97.756 | 1.00 | 13.23 | B |
| ATOM | 2589 | CB | PHE | B | 128 | 48.928 | 49.390 | 96.861 | 1.00 | 12.26 | B |
| ATOM | 2590 | CG | PHE | B | 128 | 50.158 | 48.751 | 97.410 | 1.00 | 14.51 | B |
| ATOM | 2591 | CD1 | PHE | B | 128 | 50.104 | 47.934 | 98.524 | 1.00 | 20.53 | B |

Figure 10 (41 of 142)

| ATOM | 2592 | CD2 | PHE | B | 128 | 51.379 | 48.955 | 96.797 | 1.00 | 13.44 | B |
|---|---|---|---|---|---|---|---|---|---|---|---|
| ATOM | 2593 | CE1 | PHE | B | 128 | 51.264 | 47.326 | 99.022 | 1.00 | 19.39 | B |
| ATOM | 2594 | CE2 | PHE | B | 128 | 52.537 | 48.357 | 97.283 | 1.00 | 20.20 | B |
| ATOM | 2595 | CZ | PHE | B | 128 | 52.479 | 47.540 | 98.396 | 1.00 | 20.13 | B |
| ATOM | 2596 | C | PHE | B | 128 | 47.619 | 51.455 | 96.847 | 1.00 | 12.26 | B |
| ATOM | 2597 | O | PHE | B | 128 | 46.482 | 51.217 | 96.426 | 1.00 | 16.69 | B |
| ATOM | 2598 | N | ILE | B | 129 | 48.307 | 52.552 | 96.540 | 1.00 | 12.26 | B |
| ATOM | 2599 | CA | ILE | B | 129 | 47.795 | 53.562 | 95.616 | 1.00 | 12.26 | B |
| ATOM | 2600 | CB | ILE | B | 129 | 47.721 | 54.958 | 96.254 | 1.00 | 12.26 | B |
| ATOM | 2601 | CG2 | ILE | B | 129 | 47.103 | 55.941 | 95.256 | 1.00 | 12.26 | B |
| ATOM | 2602 | CG1 | ILE | B | 129 | 46.858 | 54.915 | 97.512 | 1.00 | 12.26 | B |
| ATOM | 2603 | CD1 | ILE | B | 129 | 46.550 | 56.283 | 98.093 | 1.00 | 13.65 | B |
| ATOM | 2604 | C | ILE | B | 129 | 48.702 | 53.665 | 94.371 | 1.00 | 12.84 | B |
| ATOM | 2605 | O | ILE | B | 129 | 49.867 | 54.042 | 94.472 | 1.00 | 12.26 | B |
| ATOM | 2606 | N | GLY | B | 130 | 48.168 | 53.324 | 93.204 | 1.00 | 12.26 | B |
| ATOM | 2607 | CA | GLY | B | 130 | 48.956 | 53.400 | 91.992 | 1.00 | 12.26 | B |
| ATOM | 2608 | C | GLY | B | 130 | 48.779 | 54.737 | 91.297 | 1.00 | 12.66 | B |
| ATOM | 2609 | O | GLY | B | 130 | 47.819 | 55.470 | 91.555 | 1.00 | 18.49 | B |
| ATOM | 2610 | N | VAL | B | 131 | 49.694 | 55.057 | 90.390 | 1.00 | 15.31 | B |
| ATOM | 2611 | CA | VAL | B | 131 | 49.625 | 56.331 | 89.707 | 1.00 | 21.17 | B |
| ATOM | 2612 | CB | VAL | B | 131 | 50.860 | 57.171 | 90.000 | 1.00 | 20.55 | B |
| ATOM | 2613 | CG1 | VAL | B | 131 | 50.796 | 58.456 | 89.206 | 1.00 | 29.13 | B |
| ATOM | 2614 | CG2 | VAL | B | 131 | 50.946 | 57.478 | 91.462 | 1.00 | 27.60 | B |
| ATOM | 2615 | C | VAL | B | 131 | 49.554 | 56.224 | 88.203 | 1.00 | 24.63 | B |
| ATOM | 2616 | O | VAL | B | 131 | 48.629 | 56.740 | 87.555 | 1.00 | 31.07 | B |
| ATOM | 2617 | N | LYS | B | 132 | 50.590 | 55.589 | 87.675 | 1.00 | 25.39 | B |
| ATOM | 2618 | CA | LYS | B | 132 | 50.804 | 55.381 | 86.247 | 1.00 | 25.41 | B |
| ATOM | 2619 | CB | LYS | B | 132 | 49.556 | 55.618 | 85.390 | 1.00 | 30.83 | B |
| ATOM | 2620 | CG | LYS | B | 132 | 49.819 | 55.145 | 83.958 | 1.00 | 36.90 | B |
| ATOM | 2621 | CD | LYS | B | 132 | 48.588 | 54.593 | 83.244 | 1.00 | 42.23 | B |
| ATOM | 2622 | CE | LYS | B | 132 | 49.032 | 53.787 | 82.005 | 1.00 | 41.08 | B |
| ATOM | 2623 | NZ | LYS | B | 132 | 47.917 | 53.317 | 81.128 | 1.00 | 41.42 | B |
| ATOM | 2624 | C | LYS | B | 132 | 51.940 | 56.261 | 85.722 | 1.00 | 23.56 | B |
| ATOM | 2625 | O | LYS | B | 132 | 51.882 | 57.501 | 85.698 | 1.00 | 17.23 | B |
| ATOM | 2626 | N | ARG | B | 133 | 52.969 | 55.558 | 85.273 | 1.00 | 20.80 | B |
| ATOM | 2627 | CA | ARG | B | 133 | 54.198 | 56.130 | 84.755 | 1.00 | 16.29 | B |
| ATOM | 2628 | CB | ARG | B | 133 | 55.357 | 55.480 | 85.502 | 1.00 | 12.88 | B |
| ATOM | 2629 | CG | ARG | B | 133 | 56.665 | 55.633 | 84.825 | 1.00 | 12.26 | B |
| ATOM | 2630 | CD | ARG | B | 133 | 57.651 | 56.299 | 85.742 | 1.00 | 12.26 | B |
| ATOM | 2631 | NE | ARG | B | 133 | 58.548 | 55.367 | 86.421 | 1.00 | 12.26 | B |
| ATOM | 2632 | CZ | ARG | B | 133 | 59.843 | 55.603 | 86.622 | 1.00 | 12.26 | B |
| ATOM | 2633 | NH1 | ARG | B | 133 | 60.410 | 56.737 | 86.205 | 1.00 | 14.43 | B |
| ATOM | 2634 | NH2 | ARG | B | 133 | 60.580 | 54.697 | 87.236 | 1.00 | 12.26 | B |
| ATOM | 2635 | C | ARG | B | 133 | 54.321 | 55.852 | 83.254 | 1.00 | 16.34 | B |
| ATOM | 2636 | O | ARG | B | 133 | 54.018 | 54.737 | 82.813 | 1.00 | 16.44 | B |
| ATOM | 2637 | N | PRO | B | 134 | 54.758 | 56.858 | 82.452 | 1.00 | 16.76 | B |
| ATOM | 2638 | CD | PRO | B | 134 | 54.922 | 58.280 | 82.809 | 1.00 | 15.80 | B |
| ATOM | 2639 | CA | PRO | B | 134 | 54.913 | 56.690 | 81.000 | 1.00 | 15.27 | B |
| ATOM | 2640 | CB | PRO | B | 134 | 55.267 | 58.106 | 80.521 | 1.00 | 12.47 | B |
| ATOM | 2641 | CG | PRO | B | 134 | 54.569 | 58.976 | 81.488 | 1.00 | 12.47 | B |
| ATOM | 2642 | C | PRO | B | 134 | 56.031 | 55.697 | 80.714 | 1.00 | 17.08 | B |
| ATOM | 2643 | O | PRO | B | 134 | 57.134 | 55.862 | 81.223 | 1.00 | 17.52 | B |
| ATOM | 2644 | N | GLY | B | 135 | 55.757 | 54.671 | 79.912 | 1.00 | 19.45 | B |
| ATOM | 2645 | CA | GLY | B | 135 | 56.790 | 53.686 | 79.619 | 1.00 | 31.66 | B |
| ATOM | 2646 | C | GLY | B | 135 | 56.479 | 52.341 | 80.255 | 1.00 | 35.31 | B |
| ATOM | 2647 | O | GLY | B | 135 | 56.917 | 51.284 | 79.797 | 1.00 | 34.87 | B |
| ATOM | 2648 | N | PHE | B | 136 | 55.722 | 52.394 | 81.341 | 1.00 | 40.62 | B |
| ATOM | 2649 | CA | PHE | B | 136 | 55.292 | 51.204 | 82.047 | 1.00 | 40.51 | B |
| ATOM | 2650 | CB | PHE | B | 136 | 55.738 | 51.250 | 83.496 | 1.00 | 47.85 | B |
| ATOM | 2651 | CG | PHE | B | 136 | 57.187 | 51.491 | 83.648 | 1.00 | 52.52 | B |
| ATOM | 2652 | CD1 | PHE | B | 136 | 57.727 | 52.718 | 83.298 | 1.00 | 52.09 | B |
| ATOM | 2653 | CD2 | PHE | B | 136 | 58.028 | 50.475 | 84.079 | 1.00 | 53.38 | B |
| ATOM | 2654 | CE1 | PHE | B | 136 | 59.079 | 52.929 | 83.367 | 1.00 | 54.71 | B |
| ATOM | 2655 | CE2 | PHE | B | 136 | 59.391 | 50.671 | 84.153 | 1.00 | 55.89 | B |
| ATOM | 2656 | CZ | PHE | B | 136 | 59.922 | 51.899 | 83.796 | 1.00 | 57.18 | B |
| ATOM | 2657 | C | PHE | B | 136 | 53.799 | 51.298 | 82.002 | 1.00 | 35.57 | B |

Figure 10 (42 of 142)

```
ATOM   2658  O    PHE B 136      53.254  52.245  81.454  1.00 33.44           B
ATOM   2659  N    HIS B 137      53.121  50.327  82.575  1.00 33.40           B
ATOM   2660  CA   HIS B 137      51.677  50.396  82.584  1.00 38.63           B
ATOM   2661  CB   HIS B 137      51.124  50.130  81.185  1.00 42.12           B
ATOM   2662  CG   HIS B 137      51.533  48.809  80.626  1.00 46.02           B
ATOM   2663  CD2  HIS B 137      52.321  48.487  79.572  1.00 43.34           B
ATOM   2664  ND1  HIS B 137      51.129  47.615  81.187  1.00 44.08           B
ATOM   2665  CE1  HIS B 137      51.652  46.615  80.499  1.00 48.06           B
ATOM   2666  NE2  HIS B 137      52.379  47.116  79.515  1.00 46.05           B
ATOM   2667  C    HIS B 137      51.108  49.416  83.588  1.00 38.57           B
ATOM   2668  O    HIS B 137      51.585  48.282  83.716  1.00 34.94           B
ATOM   2669  N    VAL B 138      50.095  49.899  84.306  1.00 39.63           B
ATOM   2670  CA   VAL B 138      49.376  49.160  85.337  1.00 41.63           B
ATOM   2671  CB   VAL B 138      48.548  50.127  86.178  1.00 38.17           B
ATOM   2672  CG1  VAL B 138      48.016  51.258  85.300  1.00 37.61           B
ATOM   2673  CG2  VAL B 138      47.404  49.387  86.813  1.00 34.16           B
ATOM   2674  C    VAL B 138      48.438  48.090  84.765  1.00 47.41           B
ATOM   2675  O    VAL B 138      47.895  48.249  83.668  1.00 53.50           B
ATOM   2676  N    GLU B 139      48.237  47.008  85.513  1.00 48.56           B
ATOM   2677  CA   GLU B 139      47.363  45.934  85.047  1.00 47.10           B
ATOM   2678  CB   GLU B 139      47.963  45.282  83.802  1.00 53.95           B
ATOM   2679  CG   GLU B 139      49.081  44.279  84.115  1.00 58.45           B
ATOM   2680  CD   GLU B 139      50.149  44.193  83.017  1.00 60.70           B
ATOM   2681  OE1  GLU B 139      49.792  44.247  81.817  1.00 60.66           B
ATOM   2682  OE2  GLU B 139      51.349  44.060  83.355  1.00 63.17           B
ATOM   2683  C    GLU B 139      47.183  44.874  86.129  1.00 45.52           B
ATOM   2684  O    GLU B 139      46.231  44.096  86.105  1.00 47.46           B
ATOM   2685  N    THR B 140      48.119  44.851  87.067  1.00 40.03           B
ATOM   2686  CA   THR B 140      48.135  43.912  88.182  1.00 32.18           B
ATOM   2687  CB   THR B 140      48.610  44.608  89.422  1.00 35.65           B
ATOM   2688  OG1  THR B 140      47.983  45.894  89.486  1.00 29.00           B
ATOM   2689  CG2  THR B 140      50.111  44.750  89.404  1.00 29.76           B
ATOM   2690  C    THR B 140      46.883  43.150  88.597  1.00 34.26           B
ATOM   2691  O    THR B 140      45.743  43.603  88.421  1.00 36.72           B
ATOM   2692  N    PRO B 141      47.099  41.958  89.169  1.00 32.88           B
ATOM   2693  CD   PRO B 141      48.344  41.173  89.022  1.00 28.93           B
ATOM   2694  CA   PRO B 141      46.016  41.106  89.642  1.00 28.96           B
ATOM   2695  CB   PRO B 141      46.507  39.712  89.250  1.00 30.65           B
ATOM   2696  CG   PRO B 141      47.960  39.789  89.553  1.00 29.30           B
ATOM   2697  C    PRO B 141      45.934  41.306  91.164  1.00 23.97           B
ATOM   2698  O    PRO B 141      45.426  40.456  91.891  1.00 27.26           B
ATOM   2699  N    TYR B 142      46.432  42.443  91.633  1.00 19.76           B
ATOM   2700  CA   TYR B 142      46.471  42.733  93.056  1.00 15.33           B
ATOM   2701  CB   TYR B 142      47.900  43.039  93.490  1.00 15.71           B
ATOM   2702  CG   TYR B 142      48.942  42.007  93.165  1.00 16.14           B
ATOM   2703  CD1  TYR B 142      49.079  40.851  93.940  1.00 18.50           B
ATOM   2704  CE1  TYR B 142      50.065  39.902  93.653  1.00 18.42           B
ATOM   2705  CD2  TYR B 142      49.812  42.194  92.097  1.00 12.26           B
ATOM   2706  CE2  TYR B 142      50.799  41.256  91.807  1.00 17.52           B
ATOM   2707  CZ   TYR B 142      50.918  40.115  92.587  1.00 19.39           B
ATOM   2708  OH   TYR B 142      51.884  39.192  92.297  1.00 19.42           B
ATOM   2709  C    TYR B 142      45.634  43.911  93.519  1.00 15.39           B
ATOM   2710  O    TYR B 142      45.509  44.919  92.833  1.00 17.19           B
ATOM   2711  N    PRO B 143      45.086  43.815  94.727  1.00 12.82           B
ATOM   2712  CD   PRO B 143      45.262  42.838  95.803  1.00 16.55           B
ATOM   2713  CA   PRO B 143      44.294  44.941  95.190  1.00 15.32           B
ATOM   2714  CB   PRO B 143      43.948  44.540  96.619  1.00 22.31           B
ATOM   2715  CG   PRO B 143      45.093  43.708  97.011  1.00 20.85           B
ATOM   2716  C    PRO B 143      45.126  46.219  95.108  1.00 14.28           B
ATOM   2717  O    PRO B 143      46.190  46.330  95.719  1.00 16.22           B
ATOM   2718  N    LEU B 144      44.609  47.183  94.354  1.00 12.94           B
ATOM   2719  CA   LEU B 144      45.309  48.431  94.155  1.00 15.85           B
ATOM   2720  CB   LEU B 144      46.422  48.186  93.138  1.00 17.59           B
ATOM   2721  CG   LEU B 144      47.574  49.173  93.108  1.00 19.46           B
ATOM   2722  CD1  LEU B 144      48.676  48.599  92.280  1.00 20.23           B
ATOM   2723  CD2  LEU B 144      47.108  50.496  92.544  1.00 14.21           B
```

Figure 10 (43 of 142)

| ATOM | 2724 | C | LEU | B | 144 | 44.374 | 49.548 | 93.683 | 1.00 | 18.07 | B |
|---|---|---|---|---|---|---|---|---|---|---|---|
| ATOM | 2725 | O | LEU | B | 144 | 43.681 | 49.425 | 92.664 | 1.00 | 17.87 | B |
| ATOM | 2726 | N | LEU | B | 145 | 44.351 | 50.633 | 94.452 | 1.00 | 16.05 | B |
| ATOM | 2727 | CA | LEU | B | 145 | 43.518 | 51.796 | 94.135 | 1.00 | 12.26 | B |
| ATOM | 2728 | CB | LEU | B | 145 | 43.056 | 52.518 | 95.399 | 1.00 | 12.26 | B |
| ATOM | 2729 | CG | LEU | B | 145 | 41.907 | 51.838 | 96.122 | 1.00 | 12.26 | B |
| ATOM | 2730 | CD1 | LEU | B | 145 | 41.433 | 52.728 | 97.239 | 1.00 | 13.05 | B |
| ATOM | 2731 | CD2 | LEU | B | 145 | 40.780 | 51.554 | 95.136 | 1.00 | 12.26 | B |
| ATOM | 2732 | C | LEU | B | 145 | 44.332 | 52.748 | 93.291 | 1.00 | 12.26 | B |
| ATOM | 2733 | O | LEU | B | 145 | 45.539 | 52.847 | 93.453 | 1.00 | 12.26 | B |
| ATOM | 2734 | N | PHE | B | 146 | 43.663 | 53.477 | 92.411 | 1.00 | 12.26 | B |
| ATOM | 2735 | CA | PHE | B | 146 | 44.367 | 54.370 | 91.531 | 1.00 | 15.74 | B |
| ATOM | 2736 | CB | PHE | B | 146 | 44.037 | 53.991 | 90.105 | 1.00 | 24.44 | B |
| ATOM | 2737 | CG | PHE | B | 146 | 44.488 | 52.604 | 89.749 | 1.00 | 33.02 | B |
| ATOM | 2738 | CD1 | PHE | B | 146 | 45.838 | 52.322 | 89.619 | 1.00 | 34.65 | B |
| ATOM | 2739 | CD2 | PHE | B | 146 | 43.564 | 51.579 | 89.540 | 1.00 | 37.72 | B |
| ATOM | 2740 | CE1 | PHE | B | 146 | 46.267 | 51.051 | 89.287 | 1.00 | 41.46 | B |
| ATOM | 2741 | CE2 | PHE | B | 146 | 43.986 | 50.295 | 89.205 | 1.00 | 40.93 | B |
| ATOM | 2742 | CZ | PHE | B | 146 | 45.340 | 50.036 | 89.075 | 1.00 | 43.42 | B |
| ATOM | 2743 | C | PHE | B | 146 | 44.088 | 55.813 | 91.770 | 1.00 | 12.26 | B |
| ATOM | 2744 | O | PHE | B | 146 | 43.107 | 56.161 | 92.407 | 1.00 | 15.88 | B |
| ATOM | 2745 | N | ALA | B | 147 | 44.981 | 56.653 | 91.268 | 1.00 | 12.26 | B |
| ATOM | 2746 | CA | ALA | B | 147 | 44.847 | 58.095 | 91.404 | 1.00 | 12.26 | B |
| ATOM | 2747 | CB | ALA | B | 147 | 45.683 | 58.591 | 92.566 | 1.00 | 12.26 | B |
| ATOM | 2748 | C | ALA | B | 147 | 45.322 | 58.741 | 90.122 | 1.00 | 12.26 | B |
| ATOM | 2749 | O | ALA | B | 147 | 46.475 | 58.548 | 89.749 | 1.00 | 12.26 | B |
| ATOM | 2750 | N | ASP | B | 148 | 44.440 | 59.494 | 89.452 | 1.00 | 12.26 | B |
| ATOM | 2751 | CA | ASP | B | 148 | 44.790 | 60.177 | 88.200 | 1.00 | 12.26 | B |
| ATOM | 2752 | CB | ASP | B | 148 | 43.593 | 60.868 | 87.592 | 1.00 | 27.52 | B |
| ATOM | 2753 | CG | ASP | B | 148 | 42.723 | 59.910 | 86.865 | 1.00 | 29.35 | B |
| ATOM | 2754 | OD1 | ASP | B | 148 | 41.957 | 59.203 | 87.548 | 1.00 | 42.96 | B |
| ATOM | 2755 | OD2 | ASP | B | 148 | 42.824 | 59.836 | 85.621 | 1.00 | 35.68 | B |
| ATOM | 2756 | C | ASP | B | 148 | 45.899 | 61.174 | 88.389 | 1.00 | 13.72 | B |
| ATOM | 2757 | O | ASP | B | 148 | 45.819 | 62.093 | 89.202 | 1.00 | 12.26 | B |
| ATOM | 2758 | N | VAL | B | 149 | 46.940 | 61.002 | 87.604 | 1.00 | 16.19 | B |
| ATOM | 2759 | CA | VAL | B | 149 | 48.086 | 61.840 | 87.764 | 1.00 | 20.78 | B |
| ATOM | 2760 | CB | VAL | B | 149 | 49.064 | 61.167 | 88.747 | 1.00 | 22.74 | B |
| ATOM | 2761 | CG1 | VAL | B | 149 | 50.274 | 62.035 | 88.968 | 1.00 | 30.36 | B |
| ATOM | 2762 | CG2 | VAL | B | 149 | 48.362 | 60.877 | 90.062 | 1.00 | 29.38 | B |
| ATOM | 2763 | C | VAL | B | 149 | 48.778 | 62.064 | 86.446 | 1.00 | 20.85 | B |
| ATOM | 2764 | O | VAL | B | 149 | 49.265 | 61.134 | 85.812 | 1.00 | 23.25 | B |
| ATOM | 2765 | N | PRO | B | 150 | 48.846 | 63.315 | 86.023 | 1.00 | 12.26 | B |
| ATOM | 2766 | CD | PRO | B | 150 | 48.491 | 64.515 | 86.790 | 1.00 | 12.26 | B |
| ATOM | 2767 | CA | PRO | B | 150 | 49.491 | 63.665 | 84.770 | 1.00 | 12.26 | B |
| ATOM | 2768 | CB | PRO | B | 150 | 49.795 | 65.130 | 84.970 | 1.00 | 12.26 | B |
| ATOM | 2769 | CG | PRO | B | 150 | 48.621 | 65.582 | 85.772 | 1.00 | 12.26 | B |
| ATOM | 2770 | C | PRO | B | 150 | 50.755 | 62.852 | 84.593 | 1.00 | 12.66 | B |
| ATOM | 2771 | O | PRO | B | 150 | 51.598 | 62.842 | 85.483 | 1.00 | 15.34 | B |
| ATOM | 2772 | N | GLU | B | 151 | 50.886 | 62.162 | 83.462 | 1.00 | 14.88 | B |
| ATOM | 2773 | CA | GLU | B | 151 | 52.088 | 61.381 | 83.213 | 1.00 | 19.30 | B |
| ATOM | 2774 | CB | GLU | B | 151 | 51.933 | 60.548 | 81.943 | 1.00 | 18.88 | B |
| ATOM | 2775 | CG | GLU | B | 151 | 51.228 | 59.229 | 82.156 | 1.00 | 26.21 | B |
| ATOM | 2776 | CD | GLU | B | 151 | 50.602 | 58.697 | 80.879 | 1.00 | 35.03 | B |
| ATOM | 2777 | OE1 | GLU | B | 151 | 49.950 | 57.619 | 80.920 | 1.00 | 34.99 | B |
| ATOM | 2778 | OE2 | GLU | B | 151 | 50.760 | 59.372 | 79.833 | 1.00 | 39.18 | B |
| ATOM | 2779 | C | GLU | B | 151 | 53.269 | 62.331 | 83.062 | 1.00 | 12.26 | B |
| ATOM | 2780 | O | GLU | B | 151 | 53.138 | 63.405 | 82.500 | 1.00 | 12.26 | B |
| ATOM | 2781 | N | PHE | B | 152 | 54.417 | 61.944 | 83.592 | 1.00 | 12.26 | B |
| ATOM | 2782 | CA | PHE | B | 152 | 55.607 | 62.764 | 83.469 | 1.00 | 12.26 | B |
| ATOM | 2783 | CB | PHE | B | 152 | 55.806 | 63.590 | 84.741 | 1.00 | 12.26 | B |
| ATOM | 2784 | CG | PHE | B | 152 | 56.961 | 64.562 | 84.674 | 1.00 | 18.24 | B |
| ATOM | 2785 | CD1 | PHE | B | 152 | 57.238 | 65.412 | 85.748 | 1.00 | 19.52 | B |
| ATOM | 2786 | CD2 | PHE | B | 152 | 57.775 | 64.625 | 83.555 | 1.00 | 18.20 | B |
| ATOM | 2787 | CE1 | PHE | B | 152 | 58.310 | 66.308 | 85.700 | 1.00 | 18.94 | B |
| ATOM | 2788 | CE2 | PHE | B | 152 | 58.843 | 65.513 | 83.501 | 1.00 | 12.26 | B |
| ATOM | 2789 | CZ | PHE | B | 152 | 59.112 | 66.355 | 84.572 | 1.00 | 12.26 | B |

Figure 10 (44 of 142)

| ATOM | 2790 | C | PHE | B | 152 | 56.748 | 61.776 | 83.276 | 1.00 | 14.41 | B |
|---|---|---|---|---|---|---|---|---|---|---|---|
| ATOM | 2791 | O | PHE | B | 152 | 57.157 | 61.119 | 84.224 | 1.00 | 17.51 | B |
| ATOM | 2792 | N | GLU | B | 153 | 57.250 | 61.663 | 82.050 | 1.00 | 12.26 | B |
| ATOM | 2793 | CA | GLU | B | 153 | 58.327 | 60.727 | 81.755 | 1.00 | 15.87 | B |
| ATOM | 2794 | CB | GLU | B | 153 | 58.418 | 60.466 | 80.259 | 1.00 | 19.78 | B |
| ATOM | 2795 | CG | GLU | B | 153 | 59.435 | 59.400 | 79.900 | 1.00 | 21.55 | B |
| ATOM | 2796 | CD | GLU | B | 153 | 59.567 | 59.211 | 78.404 | 1.00 | 24.50 | B |
| ATOM | 2797 | OE1 | GLU | B | 153 | 60.190 | 58.206 | 77.970 | 1.00 | 24.99 | B |
| ATOM | 2798 | OE2 | GLU | B | 153 | 59.046 | 60.078 | 77.666 | 1.00 | 28.66 | B |
| ATOM | 2799 | C | GLU | B | 153 | 59.696 | 61.164 | 82.237 | 1.00 | 18.38 | B |
| ATOM | 2800 | O | GLU | B | 153 | 60.458 | 61.763 | 81.498 | 1.00 | 19.74 | B |
| ATOM | 2801 | N | VAL | B | 154 | 60.015 | 60.854 | 83.480 | 1.00 | 21.06 | B |
| ATOM | 2802 | CA | VAL | B | 154 | 61.306 | 61.194 | 84.033 | 1.00 | 21.03 | B |
| ATOM | 2803 | CB | VAL | B | 154 | 61.310 | 62.614 | 84.634 | 1.00 | 15.67 | B |
| ATOM | 2804 | CG1 | VAL | B | 154 | 60.068 | 62.829 | 85.479 | 1.00 | 15.64 | B |
| ATOM | 2805 | CG2 | VAL | B | 154 | 62.570 | 62.816 | 85.474 | 1.00 | 15.86 | B |
| ATOM | 2806 | C | VAL | B | 154 | 61.591 | 60.159 | 85.107 | 1.00 | 26.39 | B |
| ATOM | 2807 | O | VAL | B | 154 | 60.753 | 59.895 | 85.970 | 1.00 | 30.38 | B |
| ATOM | 2808 | N | SER | B | 155 | 62.766 | 59.547 | 85.019 | 1.00 | 29.61 | B |
| ATOM | 2809 | CA | SER | B | 155 | 63.202 | 58.523 | 85.970 | 1.00 | 35.68 | B |
| ATOM | 2810 | CB | SER | B | 155 | 63.239 | 57.161 | 85.302 | 1.00 | 36.78 | B |
| ATOM | 2811 | OG | SER | B | 155 | 64.422 | 57.074 | 84.529 | 1.00 | 35.74 | B |
| ATOM | 2812 | C | SER | B | 155 | 64.624 | 58.890 | 86.389 | 1.00 | 37.77 | B |
| ATOM | 2813 | O | SER | B | 155 | 65.358 | 59.487 | 85.603 | 1.00 | 37.71 | B |
| ATOM | 2814 | N | SER | B | 156 | 65.023 | 58.514 | 87.604 | 1.00 | 40.18 | B |
| ATOM | 2815 | CA | SER | B | 156 | 66.360 | 58.862 | 88.070 | 1.00 | 41.56 | B |
| ATOM | 2816 | CB | SER | B | 156 | 66.562 | 58.382 | 89.512 | 1.00 | 37.38 | B |
| ATOM | 2817 | OG | SER | B | 156 | 66.661 | 56.981 | 89.552 | 1.00 | 43.56 | B |
| ATOM | 2818 | C | SER | B | 156 | 67.459 | 58.312 | 87.145 | 1.00 | 39.77 | B |
| ATOM | 2819 | O | SER | B | 156 | 68.481 | 58.955 | 86.935 | 1.00 | 45.60 | B |
| ATOM | 2820 | N | THR | B | 157 | 67.243 | 57.145 | 86.559 | 1.00 | 40.46 | B |
| ATOM | 2821 | CA | THR | B | 157 | 68.257 | 56.573 | 85.682 | 1.00 | 46.10 | B |
| ATOM | 2822 | CB | THR | B | 157 | 67.953 | 55.087 | 85.418 | 1.00 | 46.47 | B |
| ATOM | 2823 | OG1 | THR | B | 157 | 68.034 | 54.371 | 86.662 | 1.00 | 46.33 | B |
| ATOM | 2824 | CG2 | THR | B | 157 | 68.936 | 54.488 | 84.422 | 1.00 | 46.74 | B |
| ATOM | 2825 | C | THR | B | 157 | 68.423 | 57.341 | 84.368 | 1.00 | 48.99 | B |
| ATOM | 2826 | O | THR | B | 157 | 69.265 | 57.011 | 83.549 | 1.00 | 51.28 | B |
| ATOM | 2827 | N | MET | B | 158 | 67.607 | 58.366 | 84.172 | 1.00 | 50.00 | B |
| ATOM | 2828 | CA | MET | B | 158 | 67.705 | 59.218 | 82.990 | 1.00 | 50.33 | B |
| ATOM | 2829 | CB | MET | B | 158 | 66.345 | 59.864 | 82.708 | 1.00 | 51.77 | B |
| ATOM | 2830 | CG | MET | B | 158 | 66.333 | 60.975 | 81.667 | 1.00 | 50.04 | B |
| ATOM | 2831 | SD | MET | B | 158 | 64.648 | 61.621 | 81.358 | 1.00 | 47.65 | B |
| ATOM | 2832 | CE | MET | B | 158 | 63.623 | 60.280 | 81.800 | 1.00 | 42.73 | B |
| ATOM | 2833 | C | MET | B | 158 | 68.714 | 60.278 | 83.426 | 1.00 | 50.40 | B |
| ATOM | 2834 | O | MET | B | 158 | 69.755 | 60.467 | 82.803 | 1.00 | 51.72 | B |
| ATOM | 2835 | N | ILE | B | 159 | 68.387 | 60.942 | 84.532 | 1.00 | 47.00 | B |
| ATOM | 2836 | CA | ILE | B | 159 | 69.221 | 61.978 | 85.118 | 1.00 | 46.04 | B |
| ATOM | 2837 | CB | ILE | B | 159 | 68.724 | 62.365 | 86.552 | 1.00 | 47.78 | B |
| ATOM | 2838 | CG2 | ILE | B | 159 | 69.494 | 63.591 | 87.069 | 1.00 | 49.89 | B |
| ATOM | 2839 | CG1 | ILE | B | 159 | 67.217 | 62.638 | 86.551 | 1.00 | 45.44 | B |
| ATOM | 2840 | CD1 | ILE | B | 159 | 66.814 | 63.930 | 85.895 | 1.00 | 46.56 | B |
| ATOM | 2841 | C | ILE | B | 159 | 70.665 | 61.489 | 85.235 | 1.00 | 49.35 | B |
| ATOM | 2842 | O | ILE | B | 159 | 71.579 | 62.140 | 84.756 | 1.00 | 48.65 | B |
| ATOM | 2843 | N | ARG | B | 160 | 70.861 | 60.337 | 85.869 | 1.00 | 50.58 | B |
| ATOM | 2844 | CA | ARG | B | 160 | 72.203 | 59.799 | 86.077 | 1.00 | 47.87 | B |
| ATOM | 2845 | CB | ARG | B | 160 | 72.134 | 58.387 | 86.688 | 1.00 | 49.09 | B |
| ATOM | 2846 | CG | ARG | B | 160 | 71.499 | 58.352 | 88.080 | 1.00 | 47.20 | B |
| ATOM | 2847 | CD | ARG | B | 160 | 72.090 | 57.267 | 88.978 | 1.00 | 47.99 | B |
| ATOM | 2848 | NE | ARG | B | 160 | 71.083 | 56.309 | 89.424 | 1.00 | 47.52 | B |
| ATOM | 2849 | CZ | ARG | B | 160 | 70.762 | 55.204 | 88.761 | 1.00 | 44.49 | B |
| ATOM | 2850 | NH1 | ARG | B | 160 | 71.378 | 54.908 | 87.627 | 1.00 | 44.68 | B |
| ATOM | 2851 | NH2 | ARG | B | 160 | 69.808 | 54.409 | 89.221 | 1.00 | 44.15 | B |
| ATOM | 2852 | C | ARG | B | 160 | 73.032 | 59.779 | 84.807 | 1.00 | 46.54 | B |
| ATOM | 2853 | O | ARG | B | 160 | 74.210 | 60.141 | 84.816 | 1.00 | 48.33 | B |
| ATOM | 2854 | N | GLU | B | 161 | 72.418 | 59.364 | 83.710 | 1.00 | 44.20 | B |
| ATOM | 2855 | CA | GLU | B | 161 | 73.129 | 59.305 | 82.443 | 1.00 | 48.15 | B |

Figure 10 (45 of 142)

```
ATOM   2856  CB   GLU B 161      72.401  58.355  81.511  1.00 54.51      B
ATOM   2857  CG   GLU B 161      72.102  57.046  82.234  1.00 60.59      B
ATOM   2858  CD   GLU B 161      71.781  55.896  81.299  1.00 64.51      B
ATOM   2859  OE1  GLU B 161      72.613  55.612  80.410  1.00 66.71      B
ATOM   2860  OE2  GLU B 161      70.705  55.272  81.456  1.00 65.36      B
ATOM   2861  C    GLU B 161      73.227  60.697  81.861  1.00 47.24      B
ATOM   2862  O    GLU B 161      74.187  61.036  81.181  1.00 43.24      B
ATOM   2863  N    ARG B 162      72.217  61.507  82.139  1.00 46.99      B
ATOM   2864  CA   ARG B 162      72.214  62.883  81.692  1.00 45.29      B
ATOM   2865  CB   ARG B 162      70.953  63.568  82.203  1.00 45.54      B
ATOM   2866  CG   ARG B 162      70.244  64.444  81.204  1.00 47.49      B
ATOM   2867  CD   ARG B 162      69.242  63.653  80.405  1.00 47.94      B
ATOM   2868  NE   ARG B 162      68.432  64.539  79.578  1.00 49.26      B
ATOM   2869  CZ   ARG B 162      67.366  64.142  78.900  1.00 50.47      B
ATOM   2870  NH1  ARG B 162      66.983  62.874  78.959  1.00 53.99      B
ATOM   2871  NH2  ARG B 162      66.694  65.002  78.156  1.00 50.90      B
ATOM   2872  C    ARG B 162      73.443  63.462  82.403  1.00 46.48      B
ATOM   2873  O    ARG B 162      74.370  63.932  81.764  1.00 47.88      B
ATOM   2874  N    PHE B 163      73.423  63.391  83.737  1.00 49.48      B
ATOM   2875  CA   PHE B 163      74.492  63.868  84.637  1.00 51.07      B
ATOM   2876  CB   PHE B 163      74.091  63.648  86.105  1.00 44.27      B
ATOM   2877  CG   PHE B 163      73.513  64.844  86.786  1.00 37.25      B
ATOM   2878  CD1  PHE B 163      73.292  66.028  86.101  1.00 35.39      B
ATOM   2879  CD2  PHE B 163      73.162  64.772  88.124  1.00 34.55      B
ATOM   2880  CE1  PHE B 163      72.726  67.128  86.740  1.00 35.61      B
ATOM   2881  CE2  PHE B 163      72.597  65.861  88.772  1.00 36.60      B
ATOM   2882  CZ   PHE B 163      72.378  67.046  88.078  1.00 38.39      B
ATOM   2883  C    PHE B 163      75.800  63.109  84.425  1.00 55.60      B
ATOM   2884  O    PHE B 163      76.525  62.838  85.381  1.00 59.50      B
ATOM   2885  N    LYS B 164      76.104  62.753  83.193  1.00 59.47      B
ATOM   2886  CA   LYS B 164      77.315  62.006  82.907  1.00 64.03      B
ATOM   2887  CB   LYS B 164      77.304  60.678  83.656  1.00 70.59      B
ATOM   2888  CG   LYS B 164      78.404  59.716  83.220  1.00 73.50      B
ATOM   2889  CD   LYS B 164      79.700  59.925  83.999  1.00 75.64      B
ATOM   2890  CE   LYS B 164      79.556  59.432  85.436  1.00 74.44      B
ATOM   2891  NZ   LYS B 164      80.804  59.571  86.227  1.00 74.36      B
ATOM   2892  C    LYS B 164      77.165  61.764  81.434  1.00 64.49      B
ATOM   2893  O    LYS B 164      76.690  60.714  81.007  1.00 68.66      B
ATOM   2894  N    SER B 165      77.578  62.760  80.670  1.00 62.50      B
ATOM   2895  CA   SER B 165      77.450  62.776  79.222  1.00 63.12      B
ATOM   2896  CB   SER B 165      76.336  61.815  78.791  1.00 58.78      B
ATOM   2897  OG   SER B 165      76.192  61.762  77.394  1.00 63.09      B
ATOM   2898  C    SER B 165      76.983  64.229  79.098  1.00 65.06      B
ATOM   2899  O    SER B 165      76.669  64.740  78.016  1.00 65.41      B
ATOM   2900  N    LYS B 166      76.964  64.875  80.265  1.00 65.52      B
ATOM   2901  CA   LYS B 166      76.529  66.256  80.452  1.00 63.06      B
ATOM   2902  CB   LYS B 166      77.699  67.226  80.308  1.00 66.92      B
ATOM   2903  CG   LYS B 166      79.015  66.568  80.001  1.00 69.77      B
ATOM   2904  CD   LYS B 166      79.938  66.625  81.200  1.00 72.35      B
ATOM   2905  CE   LYS B 166      80.145  68.059  81.668  1.00 74.83      B
ATOM   2906  NZ   LYS B 166      81.169  68.149  82.744  1.00 76.48      B
ATOM   2907  C    LYS B 166      75.395  66.683  79.532  1.00 60.97      B
ATOM   2908  O    LYS B 166      75.603  67.341  78.515  1.00 55.74      B
ATOM   2909  N    LYS B 167      74.191  66.276  79.901  1.00 62.99      B
ATOM   2910  CA   LYS B 167      73.003  66.627  79.162  1.00 67.50      B
ATOM   2911  CB   LYS B 167      72.190  65.376  78.812  1.00 71.98      B
ATOM   2912  CG   LYS B 167      72.572  64.705  77.493  1.00 75.83      B
ATOM   2913  CD   LYS B 167      71.404  63.857  76.968  1.00 80.54      B
ATOM   2914  CE   LYS B 167      71.661  63.301  75.567  1.00 81.68      B
ATOM   2915  NZ   LYS B 167      70.437  62.689  74.956  1.00 85.58      B
ATOM   2916  C    LYS B 167      72.213  67.542  80.091  1.00 68.34      B
ATOM   2917  O    LYS B 167      72.463  67.589  81.295  1.00 69.54      B
ATOM   2918  N    PRO B 168      71.259  68.290  79.539  1.00 67.71      B
ATOM   2919  CD   PRO B 168      70.881  68.192  78.116  1.00 65.31      B
ATOM   2920  CA   PRO B 168      70.386  69.234  80.232  1.00 63.98      B
ATOM   2921  CB   PRO B 168      69.147  69.220  79.353  1.00 64.93      B
```

Figure 10 (46 of 142)

| ATOM | 2922 | CG  | PRO | B | 168 | 69.759 | 69.202 | 77.993 | 1.00 | 66.35 | B |
| --- | --- | --- | --- | --- | --- | --- | --- | --- | --- | --- | --- |
| ATOM | 2923 | C   | PRO | B | 168 | 70.057 | 69.052 | 81.724 | 1.00 | 57.21 | B |
| ATOM | 2924 | O   | PRO | B | 168 | 70.511 | 69.843 | 82.552 | 1.00 | 59.42 | B |
| ATOM | 2925 | N   | THR | B | 169 | 69.281 | 68.022 | 82.065 | 1.00 | 49.93 | B |
| ATOM | 2926 | CA  | THR | B | 169 | 68.841 | 67.760 | 83.448 | 1.00 | 46.50 | B |
| ATOM | 2927 | CB  | THR | B | 169 | 70.019 | 67.504 | 84.457 | 1.00 | 46.04 | B |
| ATOM | 2928 | OG1 | THR | B | 169 | 69.868 | 68.361 | 85.600 | 1.00 | 46.95 | B |
| ATOM | 2929 | CG2 | THR | B | 169 | 71.377 | 67.734 | 83.814 | 1.00 | 47.79 | B |
| ATOM | 2930 | C   | THR | B | 169 | 67.983 | 68.877 | 84.031 | 1.00 | 41.81 | B |
| ATOM | 2931 | O   | THR | B | 169 | 67.376 | 68.705 | 85.085 | 1.00 | 42.05 | B |
| ATOM | 2932 | N   | ASP | B | 170 | 67.926 | 70.015 | 83.346 | 1.00 | 36.52 | B |
| ATOM | 2933 | CA  | ASP | B | 170 | 67.148 | 71.139 | 83.825 | 1.00 | 31.89 | B |
| ATOM | 2934 | CB  | ASP | B | 170 | 67.458 | 72.399 | 83.031 | 1.00 | 33.27 | B |
| ATOM | 2935 | CG  | ASP | B | 170 | 68.851 | 72.930 | 83.292 | 1.00 | 36.17 | B |
| ATOM | 2936 | OD1 | ASP | B | 170 | 69.813 | 72.403 | 82.704 | 1.00 | 38.78 | B |
| ATOM | 2937 | OD2 | ASP | B | 170 | 68.987 | 73.875 | 84.094 | 1.00 | 40.75 | B |
| ATOM | 2938 | C   | ASP | B | 170 | 65.688 | 70.830 | 83.680 | 1.00 | 27.06 | B |
| ATOM | 2939 | O   | ASP | B | 170 | 65.286 | 70.167 | 82.733 | 1.00 | 26.08 | B |
| ATOM | 2940 | N   | TYR | B | 171 | 64.903 | 71.324 | 84.628 | 1.00 | 29.55 | B |
| ATOM | 2941 | CA  | TYR | B | 171 | 63.464 | 71.132 | 84.639 | 1.00 | 26.56 | B |
| ATOM | 2942 | CB  | TYR | B | 171 | 62.845 | 71.651 | 83.330 | 1.00 | 31.77 | B |
| ATOM | 2943 | CG  | TYR | B | 171 | 63.155 | 73.113 | 83.026 | 1.00 | 34.74 | B |
| ATOM | 2944 | CD1 | TYR | B | 171 | 64.097 | 73.465 | 82.055 | 1.00 | 38.37 | B |
| ATOM | 2945 | CE1 | TYR | B | 171 | 64.390 | 74.798 | 81.785 | 1.00 | 36.62 | B |
| ATOM | 2946 | CD2 | TYR | B | 171 | 62.515 | 74.139 | 83.719 | 1.00 | 35.87 | B |
| ATOM | 2947 | CE2 | TYR | B | 171 | 62.802 | 75.470 | 83.455 | 1.00 | 38.83 | B |
| ATOM | 2948 | CZ  | TYR | B | 171 | 63.736 | 75.793 | 82.493 | 1.00 | 37.62 | B |
| ATOM | 2949 | OH  | TYR | B | 171 | 64.006 | 77.121 | 82.260 | 1.00 | 37.99 | B |
| ATOM | 2950 | C   | TYR | B | 171 | 63.085 | 69.674 | 84.864 | 1.00 | 22.03 | B |
| ATOM | 2951 | O   | TYR | B | 171 | 61.940 | 69.295 | 84.655 | 1.00 | 22.66 | B |
| ATOM | 2952 | N   | LEU | B | 172 | 64.045 | 68.859 | 85.295 | 1.00 | 16.53 | B |
| ATOM | 2953 | CA  | LEU | B | 172 | 63.798 | 67.442 | 85.574 | 1.00 | 17.20 | B |
| ATOM | 2954 | CB  | LEU | B | 172 | 64.693 | 66.558 | 84.715 | 1.00 | 13.10 | B |
| ATOM | 2955 | CG  | LEU | B | 172 | 64.404 | 66.541 | 83.223 | 1.00 | 12.26 | B |
| ATOM | 2956 | CD1 | LEU | B | 172 | 65.351 | 65.604 | 82.584 | 1.00 | 12.26 | B |
| ATOM | 2957 | CD2 | LEU | B | 172 | 63.019 | 66.076 | 82.954 | 1.00 | 12.26 | B |
| ATOM | 2958 | C   | LEU | B | 172 | 64.062 | 67.147 | 87.045 | 1.00 | 19.57 | B |
| ATOM | 2959 | O   | LEU | B | 172 | 63.497 | 66.216 | 87.632 | 1.00 | 19.96 | B |
| ATOM | 2960 | N   | ILE | B | 173 | 64.938 | 67.946 | 87.632 | 1.00 | 17.76 | B |
| ATOM | 2961 | CA  | ILE | B | 173 | 65.265 | 67.808 | 89.034 | 1.00 | 20.28 | B |
| ATOM | 2962 | CB  | ILE | B | 173 | 66.600 | 67.098 | 89.224 | 1.00 | 20.78 | B |
| ATOM | 2963 | CG2 | ILE | B | 173 | 66.445 | 65.636 | 88.916 | 1.00 | 23.74 | B |
| ATOM | 2964 | CG1 | ILE | B | 173 | 67.652 | 67.706 | 88.313 | 1.00 | 19.11 | B |
| ATOM | 2965 | CD1 | ILE | B | 173 | 68.979 | 67.037 | 88.465 | 1.00 | 21.29 | B |
| ATOM | 2966 | C   | ILE | B | 173 | 65.357 | 69.205 | 89.603 | 1.00 | 21.73 | B |
| ATOM | 2967 | O   | ILE | B | 173 | 65.754 | 70.131 | 88.893 | 1.00 | 22.51 | B |
| ATOM | 2968 | N   | PRO | B | 174 | 64.981 | 69.388 | 90.885 | 1.00 | 23.28 | B |
| ATOM | 2969 | CD  | PRO | B | 174 | 64.526 | 68.440 | 91.917 | 1.00 | 24.76 | B |
| ATOM | 2970 | CA  | PRO | B | 174 | 65.069 | 70.741 | 91.430 | 1.00 | 29.88 | B |
| ATOM | 2971 | CB  | PRO | B | 174 | 64.886 | 70.520 | 92.929 | 1.00 | 28.74 | B |
| ATOM | 2972 | CG  | PRO | B | 174 | 63.934 | 69.372 | 92.967 | 1.00 | 26.52 | B |
| ATOM | 2973 | C   | PRO | B | 174 | 66.418 | 71.348 | 91.093 | 1.00 | 34.61 | B |
| ATOM | 2974 | O   | PRO | B | 174 | 67.379 | 70.634 | 90.806 | 1.00 | 38.04 | B |
| ATOM | 2975 | N   | ASP | B | 175 | 66.487 | 72.670 | 91.104 | 1.00 | 42.99 | B |
| ATOM | 2976 | CA  | ASP | B | 175 | 67.746 | 73.317 | 90.812 | 1.00 | 46.97 | B |
| ATOM | 2977 | CB  | ASP | B | 175 | 67.508 | 74.783 | 90.450 | 1.00 | 54.30 | B |
| ATOM | 2978 | CG  | ASP | B | 175 | 68.501 | 75.291 | 89.421 | 1.00 | 59.12 | B |
| ATOM | 2979 | OD1 | ASP | B | 175 | 69.622 | 75.685 | 89.818 | 1.00 | 62.78 | B |
| ATOM | 2980 | OD2 | ASP | B | 175 | 68.164 | 75.281 | 88.211 | 1.00 | 62.82 | B |
| ATOM | 2981 | C   | ASP | B | 175 | 68.626 | 73.181 | 92.060 | 1.00 | 46.77 | B |
| ATOM | 2982 | O   | ASP | B | 175 | 69.831 | 73.375 | 91.993 | 1.00 | 45.39 | B |
| ATOM | 2983 | N   | LYS | B | 176 | 68.010 | 72.830 | 93.192 | 1.00 | 41.69 | B |
| ATOM | 2984 | CA  | LYS | B | 176 | 68.718 | 72.643 | 94.458 | 1.00 | 37.36 | B |
| ATOM | 2985 | CB  | LYS | B | 176 | 67.735 | 72.753 | 95.633 | 1.00 | 35.93 | B |
| ATOM | 2986 | CG  | LYS | B | 176 | 67.260 | 74.156 | 95.936 | 1.00 | 40.61 | B |
| ATOM | 2987 | CD  | LYS | B | 176 | 68.416 | 74.989 | 96.450 | 1.00 | 46.81 | B |

Figure 10 (47 of 142)

| ATOM | 2988 | CE  | LYS | B | 176 | 68.359 | 76.417 | 95.916  | 1.00 | 50.77 | B |
| ATOM | 2989 | NZ  | LYS | B | 176 | 69.546 | 77.227 | 96.337  | 1.00 | 56.61 | B |
| ATOM | 2990 | C   | LYS | B | 176 | 69.391 | 71.266 | 94.475  | 1.00 | 37.08 | B |
| ATOM | 2991 | O   | LYS | B | 176 | 70.446 | 71.074 | 95.079  | 1.00 | 38.05 | B |
| ATOM | 2992 | N   | VAL | B | 177 | 68.774 | 70.304 | 93.802  | 1.00 | 38.75 | B |
| ATOM | 2993 | CA  | VAL | B | 177 | 69.310 | 68.950 | 93.766  | 1.00 | 34.86 | B |
| ATOM | 2994 | CB  | VAL | B | 177 | 68.160 | 67.900 | 93.536  | 1.00 | 33.61 | B |
| ATOM | 2995 | CG1 | VAL | B | 177 | 68.693 | 66.657 | 92.843  | 1.00 | 32.38 | B |
| ATOM | 2996 | CG2 | VAL | B | 177 | 67.533 | 67.503 | 94.881  | 1.00 | 27.16 | B |
| ATOM | 2997 | C   | VAL | B | 177 | 70.385 | 68.834 | 92.697  | 1.00 | 36.20 | B |
| ATOM | 2998 | O   | VAL | B | 177 | 71.252 | 67.971 | 92.775  | 1.00 | 37.64 | B |
| ATOM | 2999 | N   | LYS | B | 178 | 70.348 | 69.718 | 91.708  | 1.00 | 36.28 | B |
| ATOM | 3000 | CA  | LYS | B | 178 | 71.355 | 69.658 | 90.662  | 1.00 | 36.57 | B |
| ATOM | 3001 | CB  | LYS | B | 178 | 70.988 | 70.546 | 89.480  | 1.00 | 38.55 | B |
| ATOM | 3002 | CG  | LYS | B | 178 | 72.004 | 70.528 | 88.342  | 1.00 | 36.34 | B |
| ATOM | 3003 | CD  | LYS | B | 178 | 71.547 | 71.427 | 87.186  | 1.00 | 40.74 | B |
| ATOM | 3004 | CE  | LYS | B | 178 | 71.447 | 72.899 | 87.621  | 1.00 | 46.47 | B |
| ATOM | 3005 | NZ  | LYS | B | 178 | 70.703 | 73.781 | 86.663  | 1.00 | 49.67 | B |
| ATOM | 3006 | C   | LYS | B | 178 | 72.636 | 70.153 | 91.270  | 1.00 | 39.46 | B |
| ATOM | 3007 | O   | LYS | B | 178 | 73.697 | 69.586 | 91.032  | 1.00 | 38.77 | B |
| ATOM | 3008 | N   | LYS | B | 179 | 72.531 | 71.216 | 92.063  | 1.00 | 40.24 | B |
| ATOM | 3009 | CA  | LYS | B | 179 | 73.707 | 71.781 | 92.716  | 1.00 | 40.52 | B |
| ATOM | 3010 | CB  | LYS | B | 179 | 73.338 | 73.037 | 93.515  | 1.00 | 41.01 | B |
| ATOM | 3011 | CG  | LYS | B | 179 | 72.950 | 74.208 | 92.616  | 1.00 | 46.99 | B |
| ATOM | 3012 | CD  | LYS | B | 179 | 72.452 | 75.422 | 93.385  | 1.00 | 50.98 | B |
| ATOM | 3013 | CE  | LYS | B | 179 | 71.896 | 76.460 | 92.424  | 1.00 | 50.54 | B |
| ATOM | 3014 | NZ  | LYS | B | 179 | 71.381 | 77.649 | 93.151  | 1.00 | 60.18 | B |
| ATOM | 3015 | C   | LYS | B | 179 | 74.348 | 70.749 | 93.630  | 1.00 | 39.16 | B |
| ATOM | 3016 | O   | LYS | B | 179 | 75.541 | 70.457 | 93.513  | 1.00 | 36.28 | B |
| ATOM | 3017 | N   | TYR | B | 180 | 73.555 | 70.180 | 94.530  | 1.00 | 34.20 | B |
| ATOM | 3018 | CA  | TYR | B | 180 | 74.100 | 69.186 | 95.434  | 1.00 | 29.98 | B |
| ATOM | 3019 | CB  | TYR | B | 180 | 73.005 | 68.457 | 96.179  | 1.00 | 27.31 | B |
| ATOM | 3020 | CG  | TYR | B | 180 | 73.562 | 67.562 | 97.253  | 1.00 | 28.38 | B |
| ATOM | 3021 | CD1 | TYR | B | 180 | 73.374 | 67.875 | 98.598  | 1.00 | 30.52 | B |
| ATOM | 3022 | CE1 | TYR | B | 180 | 73.833 | 67.037 | 99.607  | 1.00 | 25.97 | B |
| ATOM | 3023 | CD2 | TYR | B | 180 | 74.243 | 66.382 | 96.939  | 1.00 | 28.31 | B |
| ATOM | 3024 | CE2 | TYR | B | 180 | 74.712 | 65.538 | 97.941  | 1.00 | 25.62 | B |
| ATOM | 3025 | CZ  | TYR | B | 180 | 74.495 | 65.874 | 99.274  | 1.00 | 24.12 | B |
| ATOM | 3026 | OH  | TYR | B | 180 | 74.902 | 65.041 | 100.285 | 1.00 | 21.66 | B |
| ATOM | 3027 | C   | TYR | B | 180 | 74.933 | 68.149 | 94.699  | 1.00 | 28.74 | B |
| ATOM | 3028 | O   | TYR | B | 180 | 75.989 | 67.745 | 95.174  | 1.00 | 33.11 | B |
| ATOM | 3029 | N   | VAL | B | 181 | 74.457 | 67.699 | 93.548  | 1.00 | 27.22 | B |
| ATOM | 3030 | CA  | VAL | B | 181 | 75.190 | 66.691 | 92.803  | 1.00 | 23.13 | B |
| ATOM | 3031 | CB  | VAL | B | 181 | 74.402 | 66.235 | 91.576  | 1.00 | 22.57 | B |
| ATOM | 3032 | CG1 | VAL | B | 181 | 75.259 | 65.340 | 90.705  | 1.00 | 26.19 | B |
| ATOM | 3033 | CG2 | VAL | B | 181 | 73.163 | 65.497 | 92.019  | 1.00 | 24.60 | B |
| ATOM | 3034 | C   | VAL | B | 181 | 76.528 | 67.233 | 92.359  | 1.00 | 27.79 | B |
| ATOM | 3035 | O   | VAL | B | 181 | 77.580 | 66.697 | 92.720  | 1.00 | 25.29 | B |
| ATOM | 3036 | N   | GLU | B | 182 | 76.485 | 68.308 | 91.580  | 1.00 | 29.81 | B |
| ATOM | 3037 | CA  | GLU | B | 182 | 77.700 | 68.935 | 91.079  | 1.00 | 32.73 | B |
| ATOM | 3038 | CB  | GLU | B | 182 | 77.353 | 70.251 | 90.387  | 1.00 | 34.01 | B |
| ATOM | 3039 | CG  | GLU | B | 182 | 76.209 | 70.115 | 89.410  | 1.00 | 40.64 | B |
| ATOM | 3040 | CD  | GLU | B | 182 | 75.926 | 71.395 | 88.657  | 1.00 | 44.70 | B |
| ATOM | 3041 | OE1 | GLU | B | 182 | 75.765 | 72.439 | 89.324  | 1.00 | 46.78 | B |
| ATOM | 3042 | OE2 | GLU | B | 182 | 75.861 | 71.355 | 87.405  | 1.00 | 47.34 | B |
| ATOM | 3043 | C   | GLU | B | 182 | 78.642 | 69.188 | 92.251  | 1.00 | 34.00 | B |
| ATOM | 3044 | O   | GLU | B | 182 | 79.816 | 68.809 | 92.230  | 1.00 | 37.10 | B |
| ATOM | 3045 | N   | GLU | B | 183 | 78.105 | 69.811 | 93.290  | 1.00 | 36.28 | B |
| ATOM | 3046 | CA  | GLU | B | 183 | 78.900 | 70.120 | 94.458  | 1.00 | 41.18 | B |
| ATOM | 3047 | CB  | GLU | B | 183 | 78.065 | 70.879 | 95.485  | 1.00 | 45.78 | B |
| ATOM | 3048 | CG  | GLU | B | 183 | 77.503 | 72.176 | 94.971  | 1.00 | 57.46 | B |
| ATOM | 3049 | CD  | GLU | B | 183 | 77.228 | 73.159 | 96.086  | 1.00 | 61.90 | B |
| ATOM | 3050 | OE1 | GLU | B | 183 | 76.600 | 72.761 | 97.095  | 1.00 | 67.39 | B |
| ATOM | 3051 | OE2 | GLU | B | 183 | 77.638 | 74.331 | 95.951  | 1.00 | 65.50 | B |
| ATOM | 3052 | C   | GLU | B | 183 | 79.503 | 68.883 | 95.101  | 1.00 | 42.32 | B |
| ATOM | 3053 | O   | GLU | B | 183 | 80.718 | 68.771 | 95.182  | 1.00 | 41.76 | B |

Figure 10 (48 of 142)

| | | | | | | | | | | |
|---|---|---|---|---|---|---|---|---|---|---|
| ATOM | 3054 | N | ASN | B | 184 | 78.668 | 67.947 | 95.549 | 1.00 44.62 | B |
| ATOM | 3055 | CA | ASN | B | 184 | 79.176 | 66.758 | 96.202 | 1.00 47.17 | B |
| ATOM | 3056 | CB | ASN | B | 184 | 78.143 | 66.221 | 97.197 | 1.00 51.89 | B |
| ATOM | 3057 | CG | ASN | B | 184 | 78.670 | 66.218 | 98.629 | 1.00 57.95 | B |
| ATOM | 3058 | OD1 | ASN | B | 184 | 77.902 | 66.211 | 99.594 | 1.00 58.45 | B |
| ATOM | 3059 | ND2 | ASN | B | 184 | 79.994 | 66.211 | 98.769 | 1.00 62.08 | B |
| ATOM | 3060 | C | ASN | B | 184 | 79.658 | 65.671 | 95.253 | 1.00 45.97 | B |
| ATOM | 3061 | O | ASN | B | 184 | 79.644 | 64.492 | 95.594 | 1.00 46.91 | B |
| ATOM | 3062 | N | GLY | B | 185 | 80.090 | 66.096 | 94.063 | 1.00 47.43 | B |
| ATOM | 3063 | CA | GLY | B | 185 | 80.650 | 65.200 | 93.053 | 1.00 51.67 | B |
| ATOM | 3064 | C | GLY | B | 185 | 79.933 | 63.966 | 92.515 | 1.00 53.60 | B |
| ATOM | 3065 | O | GLY | B | 185 | 80.502 | 63.204 | 91.731 | 1.00 53.64 | B |
| ATOM | 3066 | N | LEU | B | 186 | 78.688 | 63.767 | 92.919 | 1.00 54.94 | B |
| ATOM | 3067 | CA | LEU | B | 186 | 77.880 | 62.626 | 92.480 | 1.00 53.26 | B |
| ATOM | 3068 | CB | LEU | B | 186 | 76.443 | 62.799 | 92.993 | 1.00 50.69 | B |
| ATOM | 3069 | CG | LEU | B | 186 | 76.127 | 62.371 | 94.428 | 1.00 50.59 | B |
| ATOM | 3070 | CD1 | LEU | B | 186 | 76.059 | 60.869 | 94.451 | 1.00 51.01 | B |
| ATOM | 3071 | CD2 | LEU | B | 186 | 77.169 | 62.871 | 95.417 | 1.00 49.98 | B |
| ATOM | 3072 | C | LEU | B | 186 | 77.836 | 62.324 | 90.970 | 1.00 53.27 | B |
| ATOM | 3073 | O | LEU | B | 186 | 78.471 | 63.004 | 90.150 | 1.00 55.79 | B |
| ATOM | 3074 | N | TYR | B | 187 | 77.056 | 61.288 | 90.648 | 1.00 48.71 | B |
| ATOM | 3075 | CA | TYR | B | 187 | 76.829 | 60.771 | 89.295 | 1.00 43.52 | B |
| ATOM | 3076 | CB | TYR | B | 187 | 75.397 | 61.094 | 88.845 | 1.00 33.44 | B |
| ATOM | 3077 | CG | TYR | B | 187 | 74.342 | 60.826 | 89.910 | 1.00 24.23 | B |
| ATOM | 3078 | CD1 | TYR | B | 187 | 74.166 | 59.552 | 90.439 | 1.00 20.23 | B |
| ATOM | 3079 | CE1 | TYR | B | 187 | 73.241 | 59.310 | 91.446 | 1.00 15.00 | B |
| ATOM | 3080 | CD2 | TYR | B | 187 | 73.553 | 61.861 | 90.418 | 1.00 19.71 | B |
| ATOM | 3081 | CE2 | TYR | B | 187 | 72.623 | 61.628 | 91.430 | 1.00 17.18 | B |
| ATOM | 3082 | CZ | TYR | B | 187 | 72.479 | 60.348 | 91.934 | 1.00 17.14 | B |
| ATOM | 3083 | OH | TYR | B | 187 | 71.581 | 60.097 | 92.941 | 1.00 15.09 | B |
| ATOM | 3084 | C | TYR | B | 187 | 77.825 | 61.267 | 88.253 | 1.00 45.16 | B |
| ATOM | 3085 | O | TYR | B | 187 | 78.627 | 60.459 | 87.767 | 1.00 49.95 | B |
| TER | 3086 | | TYR | B | 187 | | | | | |
| ATOM | 3087 | CB | LYS | C | 2 | 73.302 | 83.240 | 66.013 | 1.00 71.23 | C |
| ATOM | 3088 | CG | LYS | C | 2 | 73.044 | 83.295 | 67.520 | 1.00 72.16 | C |
| ATOM | 3089 | CD | LYS | C | 2 | 72.751 | 84.743 | 67.955 | 1.00 75.35 | C |
| ATOM | 3090 | CE | LYS | C | 2 | 72.726 | 84.928 | 69.472 | 1.00 74.80 | C |
| ATOM | 3091 | NZ | LYS | C | 2 | 72.379 | 86.333 | 69.866 | 1.00 75.90 | C |
| ATOM | 3092 | C | LYS | C | 2 | 72.467 | 81.040 | 65.134 | 1.00 65.53 | C |
| ATOM | 3093 | O | LYS | C | 2 | 71.566 | 81.507 | 64.441 | 1.00 65.03 | C |
| ATOM | 3094 | N | LYS | C | 2 | 74.458 | 82.091 | 64.165 | 1.00 69.30 | C |
| ATOM | 3095 | CA | LYS | C | 2 | 73.709 | 81.879 | 65.440 | 1.00 67.14 | C |
| ATOM | 3096 | N | LYS | C | 3 | 72.431 | 79.804 | 65.637 | 1.00 62.41 | C |
| ATOM | 3097 | CA | LYS | C | 3 | 71.293 | 78.893 | 65.417 | 1.00 59.58 | C |
| ATOM | 3098 | CB | LYS | C | 3 | 71.718 | 77.432 | 65.589 | 1.00 66.84 | C |
| ATOM | 3099 | CG | LYS | C | 3 | 72.876 | 76.975 | 64.713 | 1.00 72.95 | C |
| ATOM | 3100 | CD | LYS | C | 3 | 73.344 | 75.592 | 65.143 | 1.00 74.27 | C |
| ATOM | 3101 | CE | LYS | C | 3 | 74.819 | 75.398 | 64.854 | 1.00 75.31 | C |
| ATOM | 3102 | NZ | LYS | C | 3 | 75.333 | 74.183 | 65.533 | 1.00 71.91 | C |
| ATOM | 3103 | C | LYS | C | 3 | 70.180 | 79.193 | 66.410 | 1.00 53.76 | C |
| ATOM | 3104 | O | LYS | C | 3 | 70.317 | 78.930 | 67.608 | 1.00 51.14 | C |
| ATOM | 3105 | N | ILE | C | 4 | 69.066 | 79.705 | 65.899 | 1.00 44.20 | C |
| ATOM | 3106 | CA | ILE | C | 4 | 67.947 | 80.095 | 66.741 | 1.00 38.33 | C |
| ATOM | 3107 | CB | ILE | C | 4 | 67.700 | 81.605 | 66.585 | 1.00 37.73 | C |
| ATOM | 3108 | CG2 | ILE | C | 4 | 66.386 | 82.015 | 67.228 | 1.00 42.60 | C |
| ATOM | 3109 | CG1 | ILE | C | 4 | 68.871 | 82.356 | 67.211 | 1.00 40.26 | C |
| ATOM | 3110 | CD1 | ILE | C | 4 | 69.033 | 83.721 | 66.683 | 1.00 41.46 | C |
| ATOM | 3111 | C | ILE | C | 4 | 66.638 | 79.357 | 66.528 | 1.00 34.65 | C |
| ATOM | 3112 | O | ILE | C | 4 | 66.221 | 79.126 | 65.397 | 1.00 35.03 | C |
| ATOM | 3113 | N | GLY | C | 5 | 65.993 | 79.004 | 67.638 | 1.00 32.80 | C |
| ATOM | 3114 | CA | GLY | C | 5 | 64.719 | 78.322 | 67.586 | 1.00 24.71 | C |
| ATOM | 3115 | C | GLY | C | 5 | 63.592 | 79.211 | 68.081 | 1.00 18.79 | C |
| ATOM | 3116 | O | GLY | C | 5 | 63.522 | 79.536 | 69.266 | 1.00 26.01 | C |
| ATOM | 3117 | N | ILE | C | 6 | 62.720 | 79.628 | 67.168 | 1.00 19.49 | C |
| ATOM | 3118 | CA | ILE | C | 6 | 61.577 | 80.455 | 67.517 | 1.00 15.29 | C |
| ATOM | 3119 | CB | ILE | C | 6 | 61.048 | 81.188 | 66.281 | 1.00 12.26 | C |

Figure 10 (49 of 142)

```
ATOM   3120  CG2 ILE C   6      59.787  81.944  66.610  1.00 12.26           C
ATOM   3121  CG1 ILE C   6      62.112  82.164  65.795  1.00 14.27           C
ATOM   3122  CD1 ILE C   6      61.617  83.114  64.749  1.00 22.04           C
ATOM   3123  C   ILE C   6      60.521  79.507  68.092  1.00 16.62           C
ATOM   3124  O   ILE C   6      60.091  78.550  67.439  1.00 15.33           C
ATOM   3125  N   PHE C   7      60.110  79.777  69.322  1.00 14.08           C
ATOM   3126  CA  PHE C   7      59.167  78.924  70.009  1.00 12.78           C
ATOM   3127  CB  PHE C   7      59.879  78.382  71.256  1.00 18.73           C
ATOM   3128  CG  PHE C   7      59.048  77.488  72.117  1.00 22.98           C
ATOM   3129  CD1 PHE C   7      58.184  76.559  71.565  1.00 23.39           C
ATOM   3130  CD2 PHE C   7      59.201  77.520  73.493  1.00 25.69           C
ATOM   3131  CE1 PHE C   7      57.483  75.668  72.375  1.00 28.42           C
ATOM   3132  CE2 PHE C   7      58.507  76.638  74.304  1.00 23.17           C
ATOM   3133  CZ  PHE C   7      57.645  75.705  73.740  1.00 26.44           C
ATOM   3134  C   PHE C   7      57.926  79.721  70.351  1.00 12.26           C
ATOM   3135  O   PHE C   7      57.695  80.072  71.504  1.00 12.26           C
ATOM   3136  N   GLY C   8      57.130  80.023  69.335  1.00 14.43           C
ATOM   3137  CA  GLY C   8      55.909  80.787  69.560  1.00 14.79           C
ATOM   3138  C   GLY C   8      54.924  80.112  70.506  1.00 16.06           C
ATOM   3139  O   GLY C   8      54.905  78.879  70.627  1.00 20.15           C
ATOM   3140  N   GLY C   9      54.115  80.929  71.181  1.00 12.26           C
ATOM   3141  CA  GLY C   9      53.103  80.431  72.104  1.00 12.26           C
ATOM   3142  C   GLY C   9      52.315  81.596  72.682  1.00 12.26           C
ATOM   3143  O   GLY C   9      52.843  82.700  72.768  1.00 14.16           C
ATOM   3144  N   THR C  10      51.052  81.401  73.046  1.00 12.26           C
ATOM   3145  CA  THR C  10      50.312  82.513  73.654  1.00 12.26           C
ATOM   3146  CB  THR C  10      48.786  82.416  73.448  1.00 14.25           C
ATOM   3147  OG1 THR C  10      48.158  81.982  74.666  1.00 13.77           C
ATOM   3148  CG2 THR C  10      48.463  81.465  72.322  1.00 12.26           C
ATOM   3149  C   THR C  10      50.603  82.498  75.161  1.00 12.26           C
ATOM   3150  O   THR C  10      50.331  83.466  75.872  1.00 12.26           C
ATOM   3151  N   PHE C  11      51.153  81.375  75.626  1.00 12.26           C
ATOM   3152  CA  PHE C  11      51.532  81.183  77.024  1.00 14.66           C
ATOM   3153  CB  PHE C  11      52.911  81.796  77.233  1.00 12.26           C
ATOM   3154  CG  PHE C  11      53.915  81.318  76.227  1.00 12.26           C
ATOM   3155  CD1 PHE C  11      54.437  82.185  75.289  1.00 12.26           C
ATOM   3156  CD2 PHE C  11      54.289  79.974  76.177  1.00 12.26           C
ATOM   3157  CE1 PHE C  11      55.318  81.727  74.312  1.00 15.48           C
ATOM   3158  CE2 PHE C  11      55.170  79.505  75.205  1.00 12.26           C
ATOM   3159  CZ  PHE C  11      55.682  80.381  74.271  1.00 13.36           C
ATOM   3160  C   PHE C  11      50.518  81.750  78.002  1.00 14.84           C
ATOM   3161  O   PHE C  11      50.761  82.757  78.655  1.00 26.47           C
ATOM   3162  N   ASP C  12      49.391  81.060  78.126  1.00 12.26           C
ATOM   3163  CA  ASP C  12      48.313  81.522  78.965  1.00 12.67           C
ATOM   3164  CB  ASP C  12      47.237  82.086  78.030  1.00 17.14           C
ATOM   3165  CG  ASP C  12      46.056  82.669  78.758  1.00 17.87           C
ATOM   3166  OD1 ASP C  12      46.247  83.149  79.890  1.00 20.07           C
ATOM   3167  OD2 ASP C  12      44.941  82.669  78.180  1.00 14.23           C
ATOM   3168  C   ASP C  12      47.777  80.386  79.828  1.00 19.64           C
ATOM   3169  O   ASP C  12      46.699  79.852  79.576  1.00 23.57           C
ATOM   3170  N   PRO C  13      48.524  79.994  80.870  1.00 12.82           C
ATOM   3171  CD  PRO C  13      47.954  79.168  81.948  1.00 12.26           C
ATOM   3172  CA  PRO C  13      49.802  80.547  81.303  1.00 15.16           C
ATOM   3173  CB  PRO C  13      49.673  80.491  82.810  1.00 13.96           C
ATOM   3174  CG  PRO C  13      49.050  79.176  82.989  1.00 12.26           C
ATOM   3175  C   PRO C  13      50.937  79.661  80.819  1.00 12.26           C
ATOM   3176  O   PRO C  13      50.686  78.568  80.312  1.00 14.39           C
ATOM   3177  N   PRO C  14      52.198  80.127  80.951  1.00 12.26           C
ATOM   3178  CD  PRO C  14      52.629  81.462  81.386  1.00 12.26           C
ATOM   3179  CA  PRO C  14      53.358  79.327  80.529  1.00 12.26           C
ATOM   3180  CB  PRO C  14      54.525  80.315  80.579  1.00 12.26           C
ATOM   3181  CG  PRO C  14      53.876  81.655  80.565  1.00 13.48           C
ATOM   3182  C   PRO C  14      53.510  78.249  81.609  1.00 12.26           C
ATOM   3183  O   PRO C  14      53.032  78.422  82.726  1.00 13.82           C
ATOM   3184  N   HIS C  15      54.182  77.150  81.309  1.00 12.26           C
ATOM   3185  CA  HIS C  15      54.315  76.097  82.304  1.00 12.26           C
```

Figure 10 (50 of 142)

| ATOM | 3186 | CB | HIS | C | 15 | 53.052 | 75.273 | 82.308 | 1.00 | 12.26 | C |
|---|---|---|---|---|---|---|---|---|---|---|---|
| ATOM | 3187 | CG | HIS | C | 15 | 52.682 | 74.765 | 80.950 | 1.00 | 14.13 | C |
| ATOM | 3188 | CD2 | HIS | C | 15 | 51.522 | 74.840 | 80.253 | 1.00 | 16.05 | C |
| ATOM | 3189 | ND1 | HIS | C | 15 | 53.554 | 74.039 | 80.169 | 1.00 | 12.26 | C |
| ATOM | 3190 | CE1 | HIS | C | 15 | 52.944 | 73.681 | 79.054 | 1.00 | 12.26 | C |
| ATOM | 3191 | NE2 | HIS | C | 15 | 51.710 | 74.154 | 79.078 | 1.00 | 14.82 | C |
| ATOM | 3192 | C | HIS | C | 15 | 55.509 | 75.194 | 82.039 | 1.00 | 12.26 | C |
| ATOM | 3193 | O | HIS | C | 15 | 56.077 | 75.201 | 80.950 | 1.00 | 12.26 | C |
| ATOM | 3194 | N | ASN | C | 16 | 55.874 | 74.400 | 83.035 | 1.00 | 12.26 | C |
| ATOM | 3195 | CA | ASN | C | 16 | 57.018 | 73.515 | 82.913 | 1.00 | 12.26 | C |
| ATOM | 3196 | CB | ASN | C | 16 | 57.065 | 72.557 | 84.098 | 1.00 | 19.01 | C |
| ATOM | 3197 | CG | ASN | C | 16 | 57.044 | 73.276 | 85.435 | 1.00 | 24.65 | C |
| ATOM | 3198 | OD1 | ASN | C | 16 | 57.793 | 74.235 | 85.664 | 1.00 | 29.92 | C |
| ATOM | 3199 | ND2 | ASN | C | 16 | 56.195 | 72.804 | 86.334 | 1.00 | 25.51 | C |
| ATOM | 3200 | C | ASN | C | 16 | 57.015 | 72.725 | 81.613 | 1.00 | 12.26 | C |
| ATOM | 3201 | O | ASN | C | 16 | 58.062 | 72.299 | 81.128 | 1.00 | 12.26 | C |
| ATOM | 3202 | N | GLY | C | 17 | 55.832 | 72.511 | 81.053 | 1.00 | 12.26 | C |
| ATOM | 3203 | CA | GLY | C | 17 | 55.750 | 71.791 | 79.796 | 1.00 | 16.94 | C |
| ATOM | 3204 | C | GLY | C | 17 | 56.513 | 72.574 | 78.731 | 1.00 | 18.50 | C |
| ATOM | 3205 | O | GLY | C | 17 | 57.273 | 72.009 | 77.938 | 1.00 | 19.52 | C |
| ATOM | 3206 | N | HIS | C | 18 | 56.318 | 73.888 | 78.713 | 1.00 | 12.26 | C |
| ATOM | 3207 | CA | HIS | C | 18 | 57.002 | 74.728 | 77.748 | 1.00 | 12.26 | C |
| ATOM | 3208 | CB | HIS | C | 18 | 56.466 | 76.143 | 77.820 | 1.00 | 13.40 | C |
| ATOM | 3209 | CG | HIS | C | 18 | 54.999 | 76.242 | 77.560 | 1.00 | 13.91 | C |
| ATOM | 3210 | CD2 | HIS | C | 18 | 54.206 | 75.595 | 76.677 | 1.00 | 18.19 | C |
| ATOM | 3211 | ND1 | HIS | C | 18 | 54.173 | 77.099 | 78.260 | 1.00 | 15.08 | C |
| ATOM | 3212 | CE1 | HIS | C | 18 | 52.934 | 76.971 | 77.821 | 1.00 | 12.26 | C |
| ATOM | 3213 | NE2 | HIS | C | 18 | 52.927 | 76.065 | 76.860 | 1.00 | 12.26 | C |
| ATOM | 3214 | C | HIS | C | 18 | 58.490 | 74.740 | 78.032 | 1.00 | 12.26 | C |
| ATOM | 3215 | O | HIS | C | 18 | 59.295 | 74.497 | 77.141 | 1.00 | 12.26 | C |
| ATOM | 3216 | N | LEU | C | 19 | 58.854 | 75.018 | 79.282 | 1.00 | 12.26 | C |
| ATOM | 3217 | CA | LEU | C | 19 | 60.263 | 75.065 | 79.689 | 1.00 | 12.26 | C |
| ATOM | 3218 | CB | LEU | C | 19 | 60.362 | 75.360 | 81.186 | 1.00 | 12.26 | C |
| ATOM | 3219 | CG | LEU | C | 19 | 59.739 | 76.686 | 81.598 | 1.00 | 13.06 | C |
| ATOM | 3220 | CD1 | LEU | C | 19 | 59.469 | 76.696 | 83.079 | 1.00 | 12.26 | C |
| ATOM | 3221 | CD2 | LEU | C | 19 | 60.661 | 77.820 | 81.194 | 1.00 | 12.26 | C |
| ATOM | 3222 | C | LEU | C | 19 | 61.027 | 73.775 | 79.370 | 1.00 | 14.91 | C |
| ATOM | 3223 | O | LEU | C | 19 | 62.177 | 73.813 | 78.925 | 1.00 | 18.88 | C |
| ATOM | 3224 | N | LEU | C | 20 | 60.386 | 72.630 | 79.598 | 1.00 | 15.81 | C |
| ATOM | 3225 | CA | LEU | C | 20 | 61.035 | 71.355 | 79.328 | 1.00 | 13.14 | C |
| ATOM | 3226 | CB | LEU | C | 20 | 60.211 | 70.191 | 79.861 | 1.00 | 12.26 | C |
| ATOM | 3227 | CG | LEU | C | 20 | 60.980 | 68.884 | 79.652 | 1.00 | 12.26 | C |
| ATOM | 3228 | CD1 | LEU | C | 20 | 62.269 | 68.983 | 80.461 | 1.00 | 14.81 | C |
| ATOM | 3229 | CD2 | LEU | C | 20 | 60.148 | 67.660 | 80.069 | 1.00 | 12.26 | C |
| ATOM | 3230 | C | LEU | C | 20 | 61.257 | 71.146 | 77.842 | 1.00 | 15.50 | C |
| ATOM | 3231 | O | LEU | C | 20 | 62.349 | 70.845 | 77.428 | 1.00 | 17.82 | C |
| ATOM | 3232 | N | MET | C | 21 | 60.215 | 71.294 | 77.043 | 1.00 | 16.58 | C |
| ATOM | 3233 | CA | MET | C | 21 | 60.314 | 71.105 | 75.614 | 1.00 | 15.25 | C |
| ATOM | 3234 | CB | MET | C | 21 | 58.986 | 71.405 | 74.960 | 1.00 | 19.85 | C |
| ATOM | 3235 | CG | MET | C | 21 | 59.081 | 71.501 | 73.452 | 1.00 | 26.46 | C |
| ATOM | 3236 | SD | MET | C | 21 | 57.465 | 71.976 | 72.968 | 1.00 | 42.35 | C |
| ATOM | 3237 | CE | MET | C | 21 | 57.562 | 72.021 | 71.126 | 1.00 | 26.99 | C |
| ATOM | 3238 | C | MET | C | 21 | 61.361 | 71.977 | 74.983 | 1.00 | 13.55 | C |
| ATOM | 3239 | O | MET | C | 21 | 62.142 | 71.518 | 74.175 | 1.00 | 12.26 | C |
| ATOM | 3240 | N | ALA | C | 22 | 61.341 | 73.250 | 75.330 | 1.00 | 14.85 | C |
| ATOM | 3241 | CA | ALA | C | 22 | 62.290 | 74.190 | 74.769 | 1.00 | 15.15 | C |
| ATOM | 3242 | CB | ALA | C | 22 | 61.954 | 75.598 | 75.263 | 1.00 | 14.14 | C |
| ATOM | 3243 | C | ALA | C | 22 | 63.732 | 73.827 | 75.118 | 1.00 | 12.26 | C |
| ATOM | 3244 | O | ALA | C | 22 | 64.595 | 73.732 | 74.249 | 1.00 | 12.26 | C |
| ATOM | 3245 | N | ASN | C | 23 | 63.985 | 73.621 | 76.401 | 1.00 | 12.26 | C |
| ATOM | 3246 | CA | ASN | C | 23 | 65.325 | 73.291 | 76.863 | 1.00 | 17.76 | C |
| ATOM | 3247 | CB | ASN | C | 23 | 65.322 | 73.148 | 78.403 | 1.00 | 18.47 | C |
| ATOM | 3248 | CG | ASN | C | 23 | 66.726 | 72.937 | 78.992 | 1.00 | 17.49 | C |
| ATOM | 3249 | OD1 | ASN | C | 23 | 66.948 | 72.028 | 79.810 | 1.00 | 18.03 | C |
| ATOM | 3250 | ND2 | ASN | C | 23 | 67.669 | 73.782 | 78.591 | 1.00 | 15.86 | C |
| ATOM | 3251 | C | ASN | C | 23 | 65.848 | 72.008 | 76.200 | 1.00 | 17.44 | C |

Figure 10 (51 of 142)

| | | | | | | | | | | |
|---|---|---|---|---|---|---|---|---|---|---|
| ATOM | 3252 | O | ASN | C | 23 | 67.058 | 71.861 | 76.000 | 1.00 16.78 | C |
| ATOM | 3253 | N | GLU | C | 24 | 64.938 | 71.088 | 75.860 | 1.00 19.46 | C |
| ATOM | 3254 | CA | GLU | C | 24 | 65.309 | 69.813 | 75.234 | 1.00 27.80 | C |
| ATOM | 3255 | CB | GLU | C | 24 | 64.262 | 68.731 | 75.491 | 1.00 28.64 | C |
| ATOM | 3256 | CG | GLU | C | 24 | 64.185 | 68.249 | 76.922 | 1.00 34.57 | C |
| ATOM | 3257 | CD | GLU | C | 24 | 65.487 | 67.674 | 77.414 | 1.00 34.96 | C |
| ATOM | 3258 | OE1 | GLU | C | 24 | 66.058 | 66.823 | 76.692 | 1.00 33.76 | C |
| ATOM | 3259 | OE2 | GLU | C | 24 | 65.922 | 68.070 | 78.523 | 1.00 33.97 | C |
| ATOM | 3260 | C | GLU | C | 24 | 65.490 | 69.978 | 73.741 | 1.00 26.94 | C |
| ATOM | 3261 | O | GLU | C | 24 | 66.374 | 69.369 | 73.151 | 1.00 30.40 | C |
| ATOM | 3262 | N | VAL | C | 25 | 64.646 | 70.783 | 73.109 | 1.00 26.79 | C |
| ATOM | 3263 | CA | VAL | C | 25 | 64.830 | 71.003 | 71.684 | 1.00 29.41 | C |
| ATOM | 3264 | CB | VAL | C | 25 | 63.716 | 71.854 | 71.078 | 1.00 22.26 | C |
| ATOM | 3265 | CG1 | VAL | C | 25 | 64.041 | 72.148 | 69.636 | 1.00 21.40 | C |
| ATOM | 3266 | CG2 | VAL | C | 25 | 62.397 | 71.146 | 71.205 | 1.00 12.26 | C |
| ATOM | 3267 | C | VAL | C | 25 | 66.150 | 71.767 | 71.553 | 1.00 33.66 | C |
| ATOM | 3268 | O | VAL | C | 25 | 66.924 | 71.535 | 70.628 | 1.00 30.89 | C |
| ATOM | 3269 | N | LEU | C | 26 | 66.405 | 72.669 | 72.503 | 1.00 40.43 | C |
| ATOM | 3270 | CA | LEU | C | 26 | 67.634 | 73.473 | 72.510 | 1.00 47.52 | C |
| ATOM | 3271 | CB | LEU | C | 26 | 67.740 | 74.308 | 73.792 | 1.00 45.55 | C |
| ATOM | 3272 | CG | LEU | C | 26 | 69.104 | 74.971 | 74.016 | 1.00 47.75 | C |
| ATOM | 3273 | CD1 | LEU | C | 26 | 69.283 | 76.101 | 73.032 | 1.00 46.82 | C |
| ATOM | 3274 | CD2 | LEU | C | 26 | 69.199 | 75.490 | 75.437 | 1.00 49.89 | C |
| ATOM | 3275 | C | LEU | C | 26 | 68.875 | 72.597 | 72.410 | 1.00 53.58 | C |
| ATOM | 3276 | O | LEU | C | 26 | 69.854 | 72.955 | 71.755 | 1.00 58.54 | C |
| ATOM | 3277 | N | TYR | C | 27 | 68.836 | 71.461 | 73.093 | 1.00 55.57 | C |
| ATOM | 3278 | CA | TYR | C | 27 | 69.958 | 70.539 | 73.072 | 1.00 55.41 | C |
| ATOM | 3279 | CB | TYR | C | 27 | 69.992 | 69.713 | 74.366 | 1.00 66.71 | C |
| ATOM | 3280 | CG | TYR | C | 27 | 71.023 | 68.610 | 74.334 | 1.00 76.43 | C |
| ATOM | 3281 | CD1 | TYR | C | 27 | 72.383 | 68.899 | 74.429 | 1.00 78.36 | C |
| ATOM | 3282 | CE1 | TYR | C | 27 | 73.345 | 67.894 | 74.348 | 1.00 85.08 | C |
| ATOM | 3283 | CD2 | TYR | C | 27 | 70.643 | 67.283 | 74.159 | 1.00 76.61 | C |
| ATOM | 3284 | CE2 | TYR | C | 27 | 71.597 | 66.268 | 74.074 | 1.00 80.11 | C |
| ATOM | 3285 | CZ | TYR | C | 27 | 72.948 | 66.581 | 74.171 | 1.00 85.45 | C |
| ATOM | 3286 | OH | TYR | C | 27 | 73.898 | 65.584 | 74.101 | 1.00 87.30 | C |
| ATOM | 3287 | C | TYR | C | 27 | 69.861 | 69.605 | 71.861 | 1.00 46.02 | C |
| ATOM | 3288 | O | TYR | C | 27 | 70.788 | 69.505 | 71.059 | 1.00 48.01 | C |
| ATOM | 3289 | N | GLN | C | 28 | 68.718 | 68.941 | 71.737 | 1.00 43.91 | C |
| ATOM | 3290 | CA | GLN | C | 28 | 68.466 | 67.988 | 70.663 | 1.00 42.62 | C |
| ATOM | 3291 | CB | GLN | C | 28 | 67.043 | 67.425 | 70.779 | 1.00 50.17 | C |
| ATOM | 3292 | CG | GLN | C | 28 | 66.770 | 66.614 | 72.051 | 1.00 52.67 | C |
| ATOM | 3293 | CD | GLN | C | 28 | 67.752 | 65.468 | 72.242 | 1.00 47.38 | C |
| ATOM | 3294 | OE1 | GLN | C | 28 | 68.023 | 64.706 | 71.307 | 1.00 50.58 | C |
| ATOM | 3295 | NE2 | GLN | C | 28 | 68.285 | 65.338 | 73.459 | 1.00 49.85 | C |
| ATOM | 3296 | C | GLN | C | 28 | 68.665 | 68.509 | 69.249 | 1.00 45.26 | C |
| ATOM | 3297 | O | GLN | C | 28 | 69.031 | 67.744 | 68.358 | 1.00 39.39 | C |
| ATOM | 3298 | N | ALA | C | 29 | 68.421 | 69.796 | 69.029 | 1.00 44.17 | C |
| ATOM | 3299 | CA | ALA | C | 29 | 68.568 | 70.364 | 67.693 | 1.00 45.63 | C |
| ATOM | 3300 | CB | ALA | C | 29 | 67.343 | 71.202 | 67.353 | 1.00 44.90 | C |
| ATOM | 3301 | C | ALA | C | 29 | 69.838 | 71.188 | 67.525 | 1.00 41.35 | C |
| ATOM | 3302 | O | ALA | C | 29 | 70.021 | 71.863 | 66.514 | 1.00 37.95 | C |
| ATOM | 3303 | N | GLY | C | 30 | 70.712 | 71.123 | 68.523 | 1.00 42.46 | C |
| ATOM | 3304 | CA | GLY | C | 30 | 71.968 | 71.848 | 68.468 | 1.00 50.11 | C |
| ATOM | 3305 | C | GLY | C | 30 | 71.842 | 73.354 | 68.346 | 1.00 52.89 | C |
| ATOM | 3306 | O | GLY | C | 30 | 72.710 | 74.009 | 67.765 | 1.00 54.36 | C |
| ATOM | 3307 | N | LEU | C | 31 | 70.767 | 73.908 | 68.898 | 1.00 48.89 | C |
| ATOM | 3308 | CA | LEU | C | 31 | 70.548 | 75.345 | 68.850 | 1.00 42.02 | C |
| ATOM | 3309 | CB | LEU | C | 31 | 69.071 | 75.660 | 69.096 | 1.00 34.42 | C |
| ATOM | 3310 | CG | LEU | C | 31 | 68.025 | 74.910 | 68.274 | 1.00 32.26 | C |
| ATOM | 3311 | CD1 | LEU | C | 31 | 66.681 | 75.589 | 68.480 | 1.00 31.43 | C |
| ATOM | 3312 | CD2 | LEU | C | 31 | 68.390 | 74.909 | 66.806 | 1.00 30.95 | C |
| ATOM | 3313 | C | LEU | C | 31 | 71.406 | 76.079 | 69.883 | 1.00 43.07 | C |
| ATOM | 3314 | O | LEU | C | 31 | 71.970 | 75.470 | 70.800 | 1.00 44.14 | C |
| ATOM | 3315 | N | ASP | C | 32 | 71.501 | 77.392 | 69.720 | 1.00 44.19 | C |
| ATOM | 3316 | CA | ASP | C | 32 | 72.270 | 78.218 | 70.628 | 1.00 47.00 | C |
| ATOM | 3317 | CB | ASP | C | 32 | 72.992 | 79.305 | 69.850 | 1.00 52.73 | C |

Figure 10 (52 of 142)

| | | | | | | | | | | |
|---|---|---|---|---|---|---|---|---|---|---|
| ATOM | 3318 | CG | ASP | C | 32 | 73.970 | 78.743 | 68.860 | 1.00 51.14 | C |
| ATOM | 3319 | OD1 | ASP | C | 32 | 75.013 | 78.193 | 69.296 | 1.00 54.43 | C |
| ATOM | 3320 | OD2 | ASP | C | 32 | 73.686 | 78.849 | 67.647 | 1.00 48.79 | C |
| ATOM | 3321 | C | ASP | C | 32 | 71.333 | 78.849 | 71.639 | 1.00 44.32 | C |
| ATOM | 3322 | O | ASP | C | 32 | 71.678 | 78.993 | 72.814 | 1.00 49.97 | C |
| ATOM | 3323 | N | GLU | C | 33 | 70.141 | 79.220 | 71.178 | 1.00 37.04 | C |
| ATOM | 3324 | CA | GLU | C | 33 | 69.163 | 79.837 | 72.050 | 1.00 33.89 | C |
| ATOM | 3325 | CB | GLU | C | 33 | 69.502 | 81.323 | 72.269 | 1.00 36.13 | C |
| ATOM | 3326 | CG | GLU | C | 33 | 70.404 | 81.962 | 71.223 | 1.00 36.27 | C |
| ATOM | 3327 | CD | GLU | C | 33 | 70.738 | 83.401 | 71.559 | 1.00 37.80 | C |
| ATOM | 3328 | OE1 | GLU | C | 33 | 69.827 | 84.248 | 71.460 | 1.00 36.99 | C |
| ATOM | 3329 | OE2 | GLU | C | 33 | 71.904 | 83.684 | 71.928 | 1.00 38.22 | C |
| ATOM | 3330 | C | GLU | C | 33 | 67.731 | 79.706 | 71.572 | 1.00 30.80 | C |
| ATOM | 3331 | O | GLU | C | 33 | 67.449 | 79.794 | 70.389 | 1.00 29.44 | C |
| ATOM | 3332 | N | ILE | C | 34 | 66.830 | 79.477 | 72.515 | 1.00 24.83 | C |
| ATOM | 3333 | CA | ILE | C | 34 | 65.417 | 79.368 | 72.216 | 1.00 19.37 | C |
| ATOM | 3334 | CB | ILE | C | 34 | 64.733 | 78.373 | 73.153 | 1.00 15.92 | C |
| ATOM | 3335 | CG2 | ILE | C | 34 | 63.254 | 78.273 | 72.812 | 1.00 13.92 | C |
| ATOM | 3336 | CG1 | ILE | C | 34 | 65.413 | 77.019 | 73.044 | 1.00 12.26 | C |
| ATOM | 3337 | CD1 | ILE | C | 34 | 65.414 | 76.466 | 71.641 | 1.00 15.13 | C |
| ATOM | 3338 | C | ILE | C | 34 | 64.780 | 80.734 | 72.439 | 1.00 20.28 | C |
| ATOM | 3339 | O | ILE | C | 34 | 65.063 | 81.418 | 73.433 | 1.00 26.92 | C |
| ATOM | 3340 | N | TRP | C | 35 | 63.918 | 81.144 | 71.525 | 1.00 18.74 | C |
| ATOM | 3341 | CA | TRP | C | 35 | 63.254 | 82.424 | 71.689 | 1.00 17.99 | C |
| ATOM | 3342 | CB | TRP | C | 35 | 63.382 | 83.258 | 70.426 | 1.00 13.42 | C |
| ATOM | 3343 | CG | TRP | C | 35 | 64.753 | 83.782 | 70.188 | 1.00 12.26 | C |
| ATOM | 3344 | CD2 | TRP | C | 35 | 65.145 | 84.679 | 69.146 | 1.00 12.26 | C |
| ATOM | 3345 | CE2 | TRP | C | 35 | 66.527 | 84.921 | 69.305 | 1.00 15.84 | C |
| ATOM | 3346 | CE3 | TRP | C | 35 | 64.461 | 85.315 | 68.100 | 1.00 13.50 | C |
| ATOM | 3347 | CD1 | TRP | C | 35 | 65.881 | 83.510 | 70.910 | 1.00 12.26 | C |
| ATOM | 3348 | NE1 | TRP | C | 35 | 66.952 | 84.190 | 70.382 | 1.00 12.93 | C |
| ATOM | 3349 | CZ2 | TRP | C | 35 | 67.243 | 85.759 | 68.440 | 1.00 12.26 | C |
| ATOM | 3350 | CZ3 | TRP | C | 35 | 65.178 | 86.149 | 67.239 | 1.00 14.54 | C |
| ATOM | 3351 | CH2 | TRP | C | 35 | 66.555 | 86.367 | 67.424 | 1.00 12.26 | C |
| ATOM | 3352 | C | TRP | C | 35 | 61.797 | 82.213 | 71.985 | 1.00 14.71 | C |
| ATOM | 3353 | O | TRP | C | 35 | 61.077 | 81.662 | 71.155 | 1.00 18.41 | C |
| ATOM | 3354 | N | PHE | C | 36 | 61.355 | 82.629 | 73.164 | 1.00 18.93 | C |
| ATOM | 3355 | CA | PHE | C | 36 | 59.954 | 82.480 | 73.506 | 1.00 17.93 | C |
| ATOM | 3356 | CB | PHE | C | 36 | 59.760 | 82.429 | 75.014 | 1.00 18.28 | C |
| ATOM | 3357 | CG | PHE | C | 36 | 60.240 | 81.164 | 75.636 | 1.00 15.80 | C |
| ATOM | 3358 | CD1 | PHE | C | 36 | 61.579 | 80.798 | 75.569 | 1.00 15.93 | C |
| ATOM | 3359 | CD2 | PHE | C | 36 | 59.352 | 80.343 | 76.314 | 1.00 15.54 | C |
| ATOM | 3360 | CE1 | PHE | C | 36 | 62.023 | 79.629 | 76.171 | 1.00 19.61 | C |
| ATOM | 3361 | CE2 | PHE | C | 36 | 59.789 | 79.170 | 76.923 | 1.00 15.39 | C |
| ATOM | 3362 | CZ | PHE | C | 36 | 61.126 | 78.813 | 76.853 | 1.00 12.26 | C |
| ATOM | 3363 | C | PHE | C | 36 | 59.252 | 83.686 | 72.918 | 1.00 18.47 | C |
| ATOM | 3364 | O | PHE | C | 36 | 59.438 | 84.811 | 73.375 | 1.00 18.19 | C |
| ATOM | 3365 | N | MET | C | 37 | 58.449 | 83.444 | 71.889 | 1.00 14.81 | C |
| ATOM | 3366 | CA | MET | C | 37 | 57.754 | 84.524 | 71.226 | 1.00 16.31 | C |
| ATOM | 3367 | CB | MET | C | 37 | 58.089 | 84.480 | 69.731 | 1.00 16.91 | C |
| ATOM | 3368 | CG | MET | C | 37 | 57.528 | 85.634 | 68.950 | 1.00 15.88 | C |
| ATOM | 3369 | SD | MET | C | 37 | 57.893 | 85.434 | 67.254 | 1.00 17.82 | C |
| ATOM | 3370 | CE | MET | C | 37 | 56.773 | 84.123 | 66.886 | 1.00 13.47 | C |
| ATOM | 3371 | C | MET | C | 37 | 56.233 | 84.485 | 71.472 | 1.00 17.95 | C |
| ATOM | 3372 | O | MET | C | 37 | 55.514 | 83.612 | 70.951 | 1.00 21.90 | C |
| ATOM | 3373 | N | PRO | C | 38 | 55.732 | 85.444 | 72.283 | 1.00 16.25 | C |
| ATOM | 3374 | CD | PRO | C | 38 | 56.630 | 86.312 | 73.066 | 1.00 12.66 | C |
| ATOM | 3375 | CA | PRO | C | 38 | 54.331 | 85.652 | 72.700 | 1.00 14.32 | C |
| ATOM | 3376 | CB | PRO | C | 38 | 54.471 | 86.451 | 73.997 | 1.00 18.05 | C |
| ATOM | 3377 | CG | PRO | C | 38 | 55.949 | 86.312 | 74.385 | 1.00 16.44 | C |
| ATOM | 3378 | C | PRO | C | 38 | 53.414 | 86.387 | 71.701 | 1.00 17.10 | C |
| ATOM | 3379 | O | PRO | C | 38 | 53.810 | 87.394 | 71.114 | 1.00 21.18 | C |
| ATOM | 3380 | N | ASN | C | 39 | 52.180 | 85.906 | 71.545 | 1.00 22.76 | C |
| ATOM | 3381 | CA | ASN | C | 39 | 51.209 | 86.511 | 70.633 | 1.00 27.26 | C |
| ATOM | 3382 | CB | ASN | C | 39 | 50.084 | 85.548 | 70.367 | 1.00 33.63 | C |
| ATOM | 3383 | CG | ASN | C | 39 | 50.576 | 84.177 | 70.100 | 1.00 40.65 | C |

Figure 10 (53 of 142)

| | | | | | | | | | |
|---|---|---|---|---|---|---|---|---|---|
| ATOM | 3384 | OD1 | ASN | C | 39 | 51.549 | 83.994 | 69.361 | 1.00 45.86 | C |
| ATOM | 3385 | ND2 | ASN | C | 39 | 49.914 | 83.186 | 70.688 | 1.00 43.35 | C |
| ATOM | 3386 | C | ASN | C | 39 | 50.557 | 87.759 | 71.165 | 1.00 29.39 | C |
| ATOM | 3387 | O | ASN | C | 39 | 50.155 | 87.796 | 72.322 | 1.00 34.51 | C |
| ATOM | 3388 | N | GLN | C | 40 | 50.416 | 88.772 | 70.318 | 1.00 29.90 | C |
| ATOM | 3389 | CA | GLN | C | 40 | 49.734 | 89.998 | 70.727 | 1.00 30.39 | C |
| ATOM | 3390 | CB | GLN | C | 40 | 49.823 | 91.055 | 69.625 | 1.00 33.71 | C |
| ATOM | 3391 | CG | GLN | C | 40 | 48.897 | 92.253 | 69.788 | 1.00 36.42 | C |
| ATOM | 3392 | CD | GLN | C | 40 | 49.219 | 93.107 | 71.000 | 1.00 40.62 | C |
| ATOM | 3393 | OE1 | GLN | C | 40 | 48.808 | 94.268 | 71.078 | 1.00 44.62 | C |
| ATOM | 3394 | NE2 | GLN | C | 40 | 49.947 | 92.538 | 71.954 | 1.00 43.09 | C |
| ATOM | 3395 | C | GLN | C | 40 | 48.286 | 89.564 | 70.917 | 1.00 29.79 | C |
| ATOM | 3396 | O | GLN | C | 40 | 47.608 | 89.973 | 71.860 | 1.00 31.18 | C |
| ATOM | 3397 | N | ILE | C | 41 | 47.833 | 88.724 | 69.996 | 1.00 31.37 | C |
| ATOM | 3398 | CA | ILE | C | 41 | 46.495 | 88.168 | 70.018 | 1.00 39.03 | C |
| ATOM | 3399 | CB | ILE | C | 41 | 45.448 | 89.150 | 69.418 | 1.00 38.22 | C |
| ATOM | 3400 | CG2 | ILE | C | 41 | 45.977 | 89.782 | 68.144 | 1.00 39.17 | C |
| ATOM | 3401 | CG1 | ILE | C | 41 | 44.124 | 88.421 | 69.204 | 1.00 39.33 | C |
| ATOM | 3402 | CD1 | ILE | C | 41 | 43.030 | 89.289 | 68.639 | 1.00 41.83 | C |
| ATOM | 3403 | C | ILE | C | 41 | 46.577 | 86.879 | 69.200 | 1.00 40.57 | C |
| ATOM | 3404 | O | ILE | C | 41 | 46.835 | 86.908 | 67.997 | 1.00 44.43 | C |
| ATOM | 3405 | N | PRO | C | 42 | 46.387 | 85.717 | 69.857 | 1.00 38.77 | C |
| ATOM | 3406 | CD | PRO | C | 42 | 45.866 | 85.612 | 71.232 | 1.00 40.44 | C |
| ATOM | 3407 | CA | PRO | C | 42 | 46.439 | 84.394 | 69.222 | 1.00 38.27 | C |
| ATOM | 3408 | CB | PRO | C | 42 | 45.817 | 83.482 | 70.265 | 1.00 37.94 | C |
| ATOM | 3409 | CG | PRO | C | 42 | 46.142 | 84.159 | 71.562 | 1.00 39.36 | C |
| ATOM | 3410 | C | PRO | C | 42 | 45.656 | 84.375 | 67.910 | 1.00 41.92 | C |
| ATOM | 3411 | O | PRO | C | 42 | 44.500 | 84.740 | 67.844 | 1.00 41.14 | C |
| ATOM | 3412 | N | PRO | C | 43 | 46.272 | 83.882 | 66.837 | 1.00 43.51 | C |
| ATOM | 3413 | CD | PRO | C | 43 | 47.505 | 83.080 | 66.865 | 1.00 45.40 | C |
| ATOM | 3414 | CA | PRO | C | 43 | 45.649 | 83.805 | 65.518 | 1.00 45.63 | C |
| ATOM | 3415 | CB | PRO | C | 43 | 46.867 | 83.676 | 64.597 | 1.00 47.75 | C |
| ATOM | 3416 | CG | PRO | C | 43 | 47.805 | 82.851 | 65.426 | 1.00 44.92 | C |
| ATOM | 3417 | C | PRO | C | 43 | 44.624 | 82.696 | 65.292 | 1.00 45.84 | C |
| ATOM | 3418 | O | PRO | C | 43 | 43.924 | 82.685 | 64.283 | 1.00 47.29 | C |
| ATOM | 3419 | N | HIS | C | 44 | 44.466 | 81.824 | 66.259 | 1.00 46.00 | C |
| ATOM | 3420 | CA | HIS | C | 44 | 43.581 | 80.665 | 66.116 | 1.00 46.58 | C |
| ATOM | 3421 | CB | HIS | C | 44 | 44.447 | 79.456 | 65.885 | 1.00 47.36 | C |
| ATOM | 3422 | CG | HIS | C | 44 | 45.500 | 79.322 | 66.934 | 1.00 47.08 | C |
| ATOM | 3423 | CD2 | HIS | C | 44 | 46.051 | 80.260 | 67.732 | 1.00 44.43 | C |
| ATOM | 3424 | ND1 | HIS | C | 44 | 46.036 | 78.123 | 67.334 | 1.00 47.01 | C |
| ATOM | 3425 | CE1 | HIS | C | 44 | 46.864 | 78.309 | 68.352 | 1.00 45.17 | C |
| ATOM | 3426 | NE2 | HIS | C | 44 | 46.889 | 79.598 | 68.607 | 1.00 43.13 | C |
| ATOM | 3427 | C | HIS | C | 44 | 42.875 | 80.458 | 67.425 | 1.00 43.40 | C |
| ATOM | 3428 | O | HIS | C | 44 | 43.257 | 79.599 | 68.184 | 1.00 46.58 | C |
| ATOM | 3429 | N | LYS | C | 45 | 41.886 | 81.278 | 67.692 | 1.00 41.63 | C |
| ATOM | 3430 | CA | LYS | C | 45 | 41.092 | 81.195 | 68.902 | 1.00 43.27 | C |
| ATOM | 3431 | CB | LYS | C | 45 | 41.653 | 80.198 | 69.948 | 1.00 43.63 | C |
| ATOM | 3432 | CG | LYS | C | 45 | 42.673 | 80.811 | 70.920 | 1.00 44.76 | C |
| ATOM | 3433 | CD | LYS | C | 45 | 43.219 | 79.836 | 71.922 | 1.00 43.43 | C |
| ATOM | 3434 | CE | LYS | C | 45 | 44.108 | 78.842 | 71.224 | 1.00 41.36 | C |
| ATOM | 3435 | NZ | LYS | C | 45 | 45.257 | 78.464 | 72.078 | 1.00 37.73 | C |
| ATOM | 3436 | C | LYS | C | 45 | 41.099 | 82.608 | 69.437 | 1.00 44.93 | C |
| ATOM | 3437 | O | LYS | C | 45 | 41.760 | 82.910 | 70.417 | 1.00 43.12 | C |
| ATOM | 3438 | N | GLN | C | 46 | 40.411 | 83.484 | 68.728 | 1.00 21.23 | C |
| ATOM | 3439 | CA | GLN | C | 46 | 40.285 | 84.848 | 69.210 | 1.00 24.81 | C |
| ATOM | 3440 | CB | GLN | C | 46 | 40.578 | 85.874 | 68.117 | 1.00 27.31 | C |
| ATOM | 3441 | CG | GLN | C | 46 | 40.984 | 85.274 | 66.819 | 1.00 29.41 | C |
| ATOM | 3442 | CD | GLN | C | 46 | 41.125 | 86.372 | 65.786 | 1.00 20.59 | C |
| ATOM | 3443 | OE1 | GLN | C | 46 | 41.781 | 86.187 | 64.745 | 1.00 20.59 | C |
| ATOM | 3444 | NE2 | GLN | C | 46 | 40.456 | 87.517 | 66.029 | 1.00 20.59 | C |
| ATOM | 3445 | C | GLN | C | 46 | 38.858 | 84.843 | 69.611 | 1.00 27.65 | C |
| ATOM | 3446 | O | GLN | C | 46 | 38.283 | 85.858 | 70.041 | 1.00 26.89 | C |
| ATOM | 3447 | N | ASN | C | 47 | 38.240 | 83.698 | 69.368 | 1.00 20.59 | C |
| ATOM | 3448 | CA | ASN | C | 47 | 36.947 | 83.585 | 69.900 | 1.00 20.59 | C |
| ATOM | 3449 | CB | ASN | C | 47 | 35.814 | 83.386 | 68.942 | 1.00 20.59 | C |

Figure 10 (54 of 142)

```
ATOM   3450  CG   ASN C  47      34.925  84.649  68.894  1.00 20.59      C
ATOM   3451  OD1  ASN C  47      34.239  84.996  69.887  1.00 20.59      C
ATOM   3452  ND2  ASN C  47      34.968  85.372  67.759  1.00 20.59      C
ATOM   3453  C    ASN C  47      37.068  82.468  70.942  1.00 20.59      C
ATOM   3454  O    ASN C  47      36.534  81.347  70.912  1.00 20.59      C
ATOM   3455  N    GLU C  48      37.932  82.860  71.877  1.00 29.55      C
ATOM   3456  CA   GLU C  48      38.367  82.210  73.117  1.00 31.31      C
ATOM   3457  CB   GLU C  48      39.498  81.228  72.886  1.00 37.66      C
ATOM   3458  CG   GLU C  48      38.924  79.809  73.089  1.00 44.07      C
ATOM   3459  CD   GLU C  48      39.863  78.731  72.720  1.00 50.19      C
ATOM   3460  OE1  GLU C  48      40.791  78.479  73.524  1.00 51.99      C
ATOM   3461  OE2  GLU C  48      39.633  78.118  71.657  1.00 51.82      C
ATOM   3462  C    GLU C  48      38.710  83.471  73.849  1.00 31.97      C
ATOM   3463  O    GLU C  48      39.222  84.412  73.263  1.00 27.62      C
ATOM   3464  N    ASP C  49      38.353  83.459  75.111  1.00 56.29      C
ATOM   3465  CA   ASP C  49      38.543  84.626  75.926  1.00 52.02      C
ATOM   3466  CB   ASP C  49      37.674  84.483  77.218  1.00 53.90      C
ATOM   3467  CG   ASP C  49      38.455  84.122  78.495  1.00 58.14      C
ATOM   3468  OD1  ASP C  49      39.212  83.110  78.494  1.00 54.91      C
ATOM   3469  OD2  ASP C  49      38.262  84.822  79.524  1.00 62.47      C
ATOM   3470  C    ASP C  49      39.970  85.153  76.251  1.00 52.15      C
ATOM   3471  O    ASP C  49      40.079  86.166  76.935  1.00 58.72      C
ATOM   3472  N    TYR C  50      41.025  84.533  75.698  1.00 43.36      C
ATOM   3473  CA   TYR C  50      42.471  84.844  75.954  1.00 37.41      C
ATOM   3474  CB   TYR C  50      43.336  85.014  74.685  1.00 37.78      C
ATOM   3475  CG   TYR C  50      42.989  86.106  73.683  1.00 43.33      C
ATOM   3476  CD1  TYR C  50      42.016  85.896  72.702  1.00 44.77      C
ATOM   3477  CE1  TYR C  50      41.631  86.914  71.843  1.00 49.10      C
ATOM   3478  CD2  TYR C  50      43.582  87.379  73.749  1.00 45.35      C
ATOM   3479  CE2  TYR C  50      43.204  88.396  72.891  1.00 50.66      C
ATOM   3480  CZ   TYR C  50      42.224  88.163  71.950  1.00 52.24      C
ATOM   3481  OH   TYR C  50      41.761  89.188  71.154  1.00 56.83      C
ATOM   3482  C    TYR C  50      42.814  85.979  76.936  1.00 31.92      C
ATOM   3483  O    TYR C  50      42.123  86.972  77.030  1.00 27.33      C
ATOM   3484  N    THR C  51      43.888  85.803  77.693  1.00 26.21      C
ATOM   3485  CA   THR C  51      44.192  86.838  78.686  1.00 19.46      C
ATOM   3486  CB   THR C  51      44.885  86.261  79.939  1.00 12.26      C
ATOM   3487  OG1  THR C  51      46.147  85.718  79.571  1.00 17.90      C
ATOM   3488  CG2  THR C  51      44.034  85.203  80.605  1.00 12.26      C
ATOM   3489  C    THR C  51      44.997  87.996  78.154  1.00 23.42      C
ATOM   3490  O    THR C  51      45.920  87.832  77.368  1.00 25.73      C
ATOM   3491  N    ASP C  52      44.599  89.171  78.620  1.00 27.20      C
ATOM   3492  CA   ASP C  52      45.142  90.471  78.237  1.00 28.83      C
ATOM   3493  CB   ASP C  52      44.873  91.454  79.367  1.00 43.84      C
ATOM   3494  CG   ASP C  52      43.389  91.521  79.720  1.00 50.38      C
ATOM   3495  OD1  ASP C  52      42.592  92.000  78.863  1.00 54.06      C
ATOM   3496  OD2  ASP C  52      43.027  91.076  80.843  1.00 54.31      C
ATOM   3497  C    ASP C  52      46.546  90.690  77.701  1.00 23.76      C
ATOM   3498  O    ASP C  52      46.892  91.835  77.385  1.00 26.93      C
ATOM   3499  N    SER C  53      47.352  89.637  77.599  1.00 16.91      C
ATOM   3500  CA   SER C  53      48.703  89.771  77.031  1.00 18.76      C
ATOM   3501  CB   SER C  53      48.654  90.661  75.775  1.00 16.26      C
ATOM   3502  OG   SER C  53      49.940  91.117  75.406  1.00 19.33      C
ATOM   3503  C    SER C  53      49.791  90.296  77.970  1.00 19.73      C
ATOM   3504  O    SER C  53      50.836  89.661  78.144  1.00 12.92      C
ATOM   3505  N    PHE C  54      49.566  91.480  78.527  1.00 18.90      C
ATOM   3506  CA   PHE C  54      50.501  92.075  79.474  1.00 18.57      C
ATOM   3507  CB   PHE C  54      49.859  93.296  80.136  1.00 13.14      C
ATOM   3508  CG   PHE C  54      50.679  93.872  81.240  1.00 13.94      C
ATOM   3509  CD1  PHE C  54      51.947  94.376  80.981  1.00 17.85      C
ATOM   3510  CD2  PHE C  54      50.215  93.878  82.545  1.00 16.43      C
ATOM   3511  CE1  PHE C  54      52.745  94.875  82.013  1.00 21.25      C
ATOM   3512  CE2  PHE C  54      51.002  94.373  83.584  1.00 15.16      C
ATOM   3513  CZ   PHE C  54      52.266  94.870  83.317  1.00 16.87      C
ATOM   3514  C    PHE C  54      50.858  91.040  80.559  1.00 18.52      C
ATOM   3515  O    PHE C  54      52.012  90.924  80.997  1.00 26.14      C
```

Figure 10 (55 of 142)

| ATOM | 3516 | N   | HIS | C | 55 | 49.853 | 90.287 | 80.992 | 1.00 | 15.33 | C |
|------|------|-----|-----|---|----|--------|--------|--------|------|-------|---|
| ATOM | 3517 | CA  | HIS | C | 55 | 50.082 | 89.292 | 82.004 | 1.00 | 12.40 | C |
| ATOM | 3518 | CB  | HIS | C | 55 | 48.760 | 88.917 | 82.618 | 1.00 | 12.26 | C |
| ATOM | 3519 | CG  | HIS | C | 55 | 48.169 | 90.022 | 83.427 | 1.00 | 12.26 | C |
| ATOM | 3520 | CD2 | HIS | C | 55 | 48.671 | 91.228 | 83.780 | 1.00 | 13.39 | C |
| ATOM | 3521 | ND1 | HIS | C | 55 | 46.909 | 89.957 | 83.977 | 1.00 | 19.31 | C |
| ATOM | 3522 | CE1 | HIS | C | 55 | 46.656 | 91.076 | 84.633 | 1.00 | 18.94 | C |
| ATOM | 3523 | NE2 | HIS | C | 55 | 47.711 | 91.865 | 84.529 | 1.00 | 19.95 | C |
| ATOM | 3524 | C   | HIS | C | 55 | 50.800 | 88.109 | 81.406 | 1.00 | 12.26 | C |
| ATOM | 3525 | O   | HIS | C | 55 | 51.719 | 87.568 | 82.015 | 1.00 | 15.90 | C |
| ATOM | 3526 | N   | ARG | C | 56 | 50.408 | 87.720 | 80.201 | 1.00 | 12.26 | C |
| ATOM | 3527 | CA  | ARG | C | 56 | 51.077 | 86.608 | 79.563 | 1.00 | 12.26 | C |
| ATOM | 3528 | CB  | ARG | C | 56 | 50.459 | 86.334 | 78.197 | 1.00 | 12.26 | C |
| ATOM | 3529 | CG  | ARG | C | 56 | 49.163 | 85.554 | 78.298 | 1.00 | 12.26 | C |
| ATOM | 3530 | CD  | ARG | C | 56 | 48.227 | 85.890 | 77.157 | 1.00 | 13.98 | C |
| ATOM | 3531 | NE  | ARG | C | 56 | 48.769 | 85.515 | 75.852 | 1.00 | 19.51 | C |
| ATOM | 3532 | CZ  | ARG | C | 56 | 48.734 | 86.289 | 74.764 | 1.00 | 18.27 | C |
| ATOM | 3533 | NH1 | ARG | C | 56 | 48.184 | 87.502 | 74.808 | 1.00 | 14.74 | C |
| ATOM | 3534 | NH2 | ARG | C | 56 | 49.247 | 85.842 | 73.618 | 1.00 | 17.15 | C |
| ATOM | 3535 | C   | ARG | C | 56 | 52.567 | 86.910 | 79.448 | 1.00 | 12.26 | C |
| ATOM | 3536 | O   | ARG | C | 56 | 53.401 | 86.042 | 79.697 | 1.00 | 12.43 | C |
| ATOM | 3537 | N   | VAL | C | 57 | 52.915 | 88.141 | 79.101 | 1.00 | 12.26 | C |
| ATOM | 3538 | CA  | VAL | C | 57 | 54.326 | 88.475 | 78.994 | 1.00 | 12.50 | C |
| ATOM | 3539 | CB  | VAL | C | 57 | 54.520 | 89.803 | 78.257 | 1.00 | 12.26 | C |
| ATOM | 3540 | CG1 | VAL | C | 57 | 55.966 | 90.283 | 78.385 | 1.00 | 12.26 | C |
| ATOM | 3541 | CG2 | VAL | C | 57 | 54.166 | 89.617 | 76.800 | 1.00 | 14.47 | C |
| ATOM | 3542 | C   | VAL | C | 57 | 54.990 | 88.561 | 80.371 | 1.00 | 14.46 | C |
| ATOM | 3543 | O   | VAL | C | 57 | 56.182 | 88.298 | 80.512 | 1.00 | 12.68 | C |
| ATOM | 3544 | N   | GLU | C | 58 | 54.228 | 88.930 | 81.391 | 1.00 | 12.26 | C |
| ATOM | 3545 | CA  | GLU | C | 58 | 54.811 | 89.028 | 82.719 | 1.00 | 12.26 | C |
| ATOM | 3546 | CB  | GLU | C | 58 | 53.893 | 89.812 | 83.650 | 1.00 | 14.81 | C |
| ATOM | 3547 | CG  | GLU | C | 58 | 53.948 | 91.304 | 83.390 | 1.00 | 16.95 | C |
| ATOM | 3548 | CD  | GLU | C | 58 | 55.384 | 91.795 | 83.374 | 1.00 | 18.47 | C |
| ATOM | 3549 | OE1 | GLU | C | 58 | 56.106 | 91.481 | 84.336 | 1.00 | 20.58 | C |
| ATOM | 3550 | OE2 | GLU | C | 58 | 55.800 | 92.477 | 82.412 | 1.00 | 15.11 | C |
| ATOM | 3551 | C   | GLU | C | 58 | 55.050 | 87.638 | 83.257 | 1.00 | 12.26 | C |
| ATOM | 3552 | O   | GLU | C | 58 | 56.105 | 87.361 | 83.829 | 1.00 | 18.17 | C |
| ATOM | 3553 | N   | MET | C | 59 | 54.061 | 86.764 | 83.080 | 1.00 | 13.86 | C |
| ATOM | 3554 | CA  | MET | C | 59 | 54.198 | 85.381 | 83.525 | 1.00 | 14.72 | C |
| ATOM | 3555 | CB  | MET | C | 59 | 52.859 | 84.622 | 83.396 | 1.00 | 12.26 | C |
| ATOM | 3556 | CG  | MET | C | 59 | 51.779 | 85.112 | 84.331 | 1.00 | 12.26 | C |
| ATOM | 3557 | SD  | MET | C | 59 | 50.333 | 84.067 | 84.273 | 1.00 | 12.26 | C |
| ATOM | 3558 | CE  | MET | C | 59 | 49.714 | 84.441 | 82.726 | 1.00 | 12.26 | C |
| ATOM | 3559 | C   | MET | C | 59 | 55.287 | 84.682 | 82.686 | 1.00 | 16.60 | C |
| ATOM | 3560 | O   | MET | C | 59 | 55.955 | 83.756 | 83.161 | 1.00 | 21.32 | C |
| ATOM | 3561 | N   | LEU | C | 60 | 55.482 | 85.140 | 81.449 | 1.00 | 12.26 | C |
| ATOM | 3562 | CA  | LEU | C | 60 | 56.482 | 84.530 | 80.580 | 1.00 | 12.26 | C |
| ATOM | 3563 | CB  | LEU | C | 60 | 56.325 | 85.001 | 79.140 | 1.00 | 12.26 | C |
| ATOM | 3564 | CG  | LEU | C | 60 | 56.433 | 83.871 | 78.105 | 1.00 | 14.95 | C |
| ATOM | 3565 | CD1 | LEU | C | 60 | 56.902 | 84.417 | 76.775 | 1.00 | 12.26 | C |
| ATOM | 3566 | CD2 | LEU | C | 60 | 57.422 | 82.823 | 78.570 | 1.00 | 12.26 | C |
| ATOM | 3567 | C   | LEU | C | 60 | 57.879 | 84.873 | 81.043 | 1.00 | 12.26 | C |
| ATOM | 3568 | O   | LEU | C | 60 | 58.746 | 84.015 | 81.141 | 1.00 | 12.26 | C |
| ATOM | 3569 | N   | LYS | C | 61 | 58.103 | 86.147 | 81.301 | 1.00 | 15.66 | C |
| ATOM | 3570 | CA  | LYS | C | 61 | 59.406 | 86.613 | 81.775 | 1.00 | 14.30 | C |
| ATOM | 3571 | CB  | LYS | C | 61 | 59.337 | 88.121 | 82.065 | 1.00 | 12.26 | C |
| ATOM | 3572 | CG  | LYS | C | 61 | 60.138 | 88.955 | 81.110 | 1.00 | 12.26 | C |
| ATOM | 3573 | CD  | LYS | C | 61 | 59.442 | 90.256 | 80.812 | 1.00 | 12.26 | C |
| ATOM | 3574 | CE  | LYS | C | 61 | 59.204 | 91.069 | 82.063 | 1.00 | 12.26 | C |
| ATOM | 3575 | NZ  | LYS | C | 61 | 58.593 | 92.394 | 81.739 | 1.00 | 12.26 | C |
| ATOM | 3576 | C   | LYS | C | 61 | 59.845 | 85.868 | 83.046 | 1.00 | 12.26 | C |
| ATOM | 3577 | O   | LYS | C | 61 | 61.038 | 85.587 | 83.244 | 1.00 | 21.79 | C |
| ATOM | 3578 | N   | LEU | C | 62 | 58.868 | 85.559 | 83.898 | 1.00 | 12.26 | C |
| ATOM | 3579 | CA  | LEU | C | 62 | 59.133 | 84.890 | 85.162 | 1.00 | 12.26 | C |
| ATOM | 3580 | CB  | LEU | C | 62 | 57.877 | 84.927 | 86.038 | 1.00 | 15.03 | C |
| ATOM | 3581 | CG  | LEU | C | 62 | 57.442 | 86.320 | 86.488 | 1.00 | 12.26 | C |

Figure 10 (56 of 142)

```
ATOM   3582  CD1 LEU C  62      56.055  86.301  87.087  1.00 12.26           C
ATOM   3583  CD2 LEU C  62      58.459  86.811  87.490  1.00 17.66           C
ATOM   3584  C   LEU C  62      59.586  83.457  84.948  1.00 17.31           C
ATOM   3585  O   LEU C  62      60.650  83.055  85.422  1.00 23.47           C
ATOM   3586  N   ALA C  63      58.784  82.687  84.227  1.00 12.26           C
ATOM   3587  CA  ALA C  63      59.135  81.303  83.968  1.00 14.60           C
ATOM   3588  CB  ALA C  63      58.007  80.621  83.168  1.00 12.26           C
ATOM   3589  C   ALA C  63      60.488  81.132  83.236  1.00 15.40           C
ATOM   3590  O   ALA C  63      61.125  80.065  83.313  1.00 15.88           C
ATOM   3591  N   ILE C  64      60.964  82.170  82.555  1.00 15.20           C
ATOM   3592  CA  ILE C  64      62.207  81.983  81.824  1.00 18.33           C
ATOM   3593  CB  ILE C  64      62.006  82.176  80.318  1.00 18.97           C
ATOM   3594  CG2 ILE C  64      60.826  81.325  79.830  1.00 17.03           C
ATOM   3595  CG1 ILE C  64      61.743  83.651  80.015  1.00 18.77           C
ATOM   3596  CD1 ILE C  64      61.877  84.008  78.544  1.00 16.67           C
ATOM   3597  C   ILE C  64      63.384  82.829  82.198  1.00 17.82           C
ATOM   3598  O   ILE C  64      64.350  82.880  81.451  1.00 23.09           C
ATOM   3599  N   GLN C  65      63.324  83.494  83.337  1.00 20.44           C
ATOM   3600  CA  GLN C  65      64.440  84.334  83.737  1.00 24.64           C
ATOM   3601  CB  GLN C  65      64.044  85.188  84.950  1.00 27.86           C
ATOM   3602  CG  GLN C  65      63.524  84.376  86.114  1.00 35.99           C
ATOM   3603  CD  GLN C  65      63.058  85.235  87.263  1.00 37.99           C
ATOM   3604  OE1 GLN C  65      62.122  86.029  87.123  1.00 35.46           C
ATOM   3605  NE2 GLN C  65      63.707  85.080  88.417  1.00 44.12           C
ATOM   3606  C   GLN C  65      65.689  83.516  84.062  1.00 25.54           C
ATOM   3607  O   GLN C  65      66.798  83.865  83.666  1.00 20.47           C
ATOM   3608  N   SER C  66      65.489  82.410  84.763  1.00 25.54           C
ATOM   3609  CA  SER C  66      66.575  81.544  85.208  1.00 26.50           C
ATOM   3610  CB  SER C  66      66.023  80.540  86.216  1.00 28.50           C
ATOM   3611  OG  SER C  66      64.774  80.020  85.777  1.00 37.60           C
ATOM   3612  C   SER C  66      67.406  80.805  84.177  1.00 21.28           C
ATOM   3613  O   SER C  66      68.477  80.328  84.503  1.00 24.02           C
ATOM   3614  N   ASN C  67      66.930  80.684  82.945  1.00 23.88           C
ATOM   3615  CA  ASN C  67      67.698  79.978  81.913  1.00 26.51           C
ATOM   3616  CB  ASN C  67      66.808  79.005  81.143  1.00 32.74           C
ATOM   3617  CG  ASN C  67      67.581  78.170  80.134  1.00 29.16           C
ATOM   3618  OD1 ASN C  67      67.077  77.149  79.649  1.00 28.99           C
ATOM   3619  ND2 ASN C  67      68.803  78.596  79.812  1.00 34.23           C
ATOM   3620  C   ASN C  67      68.344  80.942  80.928  1.00 28.44           C
ATOM   3621  O   ASN C  67      67.662  81.584  80.125  1.00 34.20           C
ATOM   3622  N   PRO C  68      69.683  81.028  80.964  1.00 28.45           C
ATOM   3623  CD  PRO C  68      70.499  80.172  81.841  1.00 27.46           C
ATOM   3624  CA  PRO C  68      70.554  81.874  80.140  1.00 27.11           C
ATOM   3625  CB  PRO C  68      71.955  81.421  80.539  1.00 26.52           C
ATOM   3626  CG  PRO C  68      71.784  80.963  81.936  1.00 27.09           C
ATOM   3627  C   PRO C  68      70.326  81.700  78.651  1.00 24.65           C
ATOM   3628  O   PRO C  68      70.500  82.630  77.861  1.00 25.73           C
ATOM   3629  N   SER C  69      69.939  80.496  78.269  1.00 25.39           C
ATOM   3630  CA  SER C  69      69.713  80.212  76.873  1.00 26.22           C
ATOM   3631  CB  SER C  69      70.008  78.745  76.615  1.00 28.82           C
ATOM   3632  OG  SER C  69      71.342  78.437  76.981  1.00 32.39           C
ATOM   3633  C   SER C  69      68.307  80.553  76.413  1.00 24.33           C
ATOM   3634  O   SER C  69      67.995  80.405  75.248  1.00 26.02           C
ATOM   3635  N   PHE C  70      67.452  81.001  77.320  1.00 23.92           C
ATOM   3636  CA  PHE C  70      66.090  81.345  76.939  1.00 20.01           C
ATOM   3637  CB  PHE C  70      65.098  80.876  78.012  1.00 15.71           C
ATOM   3638  CG  PHE C  70      64.840  79.391  77.992  1.00 12.74           C
ATOM   3639  CD1 PHE C  70      63.973  78.802  78.915  1.00 15.69           C
ATOM   3640  CD2 PHE C  70      65.446  78.578  77.030  1.00 12.26           C
ATOM   3641  CE1 PHE C  70      63.713  77.432  78.882  1.00 12.26           C
ATOM   3642  CE2 PHE C  70      65.194  77.204  76.989  1.00 14.10           C
ATOM   3643  CZ  PHE C  70      64.325  76.633  77.918  1.00 12.26           C
ATOM   3644  C   PHE C  70      65.998  82.841  76.760  1.00 26.22           C
ATOM   3645  O   PHE C  70      66.558  83.603  77.558  1.00 27.47           C
ATOM   3646  N   LYS C  71      65.302  83.269  75.712  1.00 22.28           C
ATOM   3647  CA  LYS C  71      65.166  84.692  75.468  1.00 14.00           C
```

Figure 10 (57 of 142)

| | | | | | | | | | | |
|---|---|---|---|---|---|---|---|---|---|---|
| ATOM | 3648 | CB | LYS | C | 71 | 66.200 | 85.129 | 74.445 | 1.00 12.26 | C |
| ATOM | 3649 | CG | LYS | C | 71 | 67.588 | 84.924 | 75.016 | 1.00 12.26 | C |
| ATOM | 3650 | CD | LYS | C | 71 | 68.679 | 85.553 | 74.208 | 1.00 18.39 | C |
| ATOM | 3651 | CE | LYS | C | 71 | 70.025 | 85.339 | 74.890 | 1.00 18.57 | C |
| ATOM | 3652 | NZ | LYS | C | 71 | 71.158 | 85.783 | 74.008 | 1.00 25.84 | C |
| ATOM | 3653 | C | LYS | C | 71 | 63.798 | 85.129 | 75.044 | 1.00 12.26 | C |
| ATOM | 3654 | O | LYS | C | 71 | 63.154 | 84.469 | 74.248 | 1.00 12.26 | C |
| ATOM | 3655 | N | LEU | C | 72 | 63.348 | 86.251 | 75.578 | 1.00 12.26 | C |
| ATOM | 3656 | CA | LEU | C | 72 | 62.029 | 86.752 | 75.232 | 1.00 12.35 | C |
| ATOM | 3657 | CB | LEU | C | 72 | 61.556 | 87.759 | 76.287 | 1.00 12.26 | C |
| ATOM | 3658 | CG | LEU | C | 72 | 60.101 | 87.776 | 76.753 | 1.00 13.42 | C |
| ATOM | 3659 | CD1 | LEU | C | 72 | 59.830 | 89.091 | 77.451 | 1.00 12.26 | C |
| ATOM | 3660 | CD2 | LEU | C | 72 | 59.173 | 87.604 | 75.585 | 1.00 13.91 | C |
| ATOM | 3661 | C | LEU | C | 72 | 62.079 | 87.442 | 73.871 | 1.00 19.24 | C |
| ATOM | 3662 | O | LEU | C | 72 | 63.103 | 88.005 | 73.495 | 1.00 26.88 | C |
| ATOM | 3663 | N | GLU | C | 73 | 60.977 | 87.388 | 73.132 | 1.00 19.65 | C |
| ATOM | 3664 | CA | GLU | C | 73 | 60.881 | 88.050 | 71.833 | 1.00 18.51 | C |
| ATOM | 3665 | CB | GLU | C | 73 | 61.156 | 87.064 | 70.704 | 1.00 22.35 | C |
| ATOM | 3666 | CG | GLU | C | 73 | 60.925 | 87.698 | 69.350 | 1.00 27.76 | C |
| ATOM | 3667 | CD | GLU | C | 73 | 61.596 | 89.068 | 69.233 | 1.00 29.83 | C |
| ATOM | 3668 | OE1 | GLU | C | 73 | 62.831 | 89.114 | 69.040 | 1.00 36.46 | C |
| ATOM | 3669 | OE2 | GLU | C | 73 | 60.887 | 90.096 | 69.351 | 1.00 32.84 | C |
| ATOM | 3670 | C | GLU | C | 73 | 59.482 | 88.674 | 71.665 | 1.00 20.94 | C |
| ATOM | 3671 | O | GLU | C | 73 | 58.495 | 87.980 | 71.390 | 1.00 22.84 | C |
| ATOM | 3672 | N | LEU | C | 74 | 59.398 | 89.989 | 71.822 | 1.00 14.37 | C |
| ATOM | 3673 | CA | LEU | C | 74 | 58.109 | 90.649 | 71.729 | 1.00 21.31 | C |
| ATOM | 3674 | CB | LEU | C | 74 | 58.032 | 91.760 | 72.758 | 1.00 23.53 | C |
| ATOM | 3675 | CG | LEU | C | 74 | 58.206 | 91.296 | 74.199 | 1.00 24.03 | C |
| ATOM | 3676 | CD1 | LEU | C | 74 | 58.207 | 92.499 | 75.131 | 1.00 25.09 | C |
| ATOM | 3677 | CD2 | LEU | C | 74 | 57.085 | 90.329 | 74.559 | 1.00 28.66 | C |
| ATOM | 3678 | C | LEU | C | 74 | 57.804 | 91.220 | 70.366 | 1.00 24.29 | C |
| ATOM | 3679 | O | LEU | C | 74 | 57.033 | 92.179 | 70.242 | 1.00 23.35 | C |
| ATOM | 3680 | N | VAL | C | 75 | 58.410 | 90.628 | 69.345 | 1.00 24.80 | C |
| ATOM | 3681 | CA | VAL | C | 75 | 58.219 | 91.071 | 67.972 | 1.00 23.74 | C |
| ATOM | 3682 | CB | VAL | C | 75 | 58.974 | 90.174 | 66.993 | 1.00 17.89 | C |
| ATOM | 3683 | CG1 | VAL | C | 75 | 58.330 | 88.784 | 66.943 | 1.00 21.48 | C |
| ATOM | 3684 | CG2 | VAL | C | 75 | 58.966 | 90.805 | 65.636 | 1.00 18.99 | C |
| ATOM | 3685 | C | VAL | C | 75 | 56.752 | 91.108 | 67.547 | 1.00 21.54 | C |
| ATOM | 3686 | O | VAL | C | 75 | 56.332 | 92.013 | 66.820 | 1.00 21.05 | C |
| ATOM | 3687 | N | GLU | C | 76 | 55.972 | 90.119 | 67.980 | 1.00 23.01 | C |
| ATOM | 3688 | CA | GLU | C | 76 | 54.561 | 90.099 | 67.619 | 1.00 26.43 | C |
| ATOM | 3689 | CB | GLU | C | 76 | 53.989 | 88.683 | 67.781 | 1.00 30.33 | C |
| ATOM | 3690 | CG | GLU | C | 76 | 54.420 | 87.737 | 66.658 | 1.00 38.78 | C |
| ATOM | 3691 | CD | GLU | C | 76 | 53.724 | 86.381 | 66.716 | 1.00 42.00 | C |
| ATOM | 3692 | OE1 | GLU | C | 76 | 53.801 | 85.612 | 65.730 | 1.00 45.66 | C |
| ATOM | 3693 | OE2 | GLU | C | 76 | 53.100 | 86.077 | 67.755 | 1.00 47.50 | C |
| ATOM | 3694 | C | GLU | C | 76 | 53.743 | 91.139 | 68.407 | 1.00 23.72 | C |
| ATOM | 3695 | O | GLU | C | 76 | 52.638 | 91.506 | 68.008 | 1.00 26.38 | C |
| ATOM | 3696 | N | MET | C | 77 | 54.305 | 91.632 | 69.508 | 1.00 25.09 | C |
| ATOM | 3697 | CA | MET | C | 77 | 53.649 | 92.638 | 70.353 | 1.00 24.37 | C |
| ATOM | 3698 | CB | MET | C | 77 | 54.294 | 92.668 | 71.744 | 1.00 24.01 | C |
| ATOM | 3699 | CG | MET | C | 77 | 54.011 | 91.479 | 72.606 | 1.00 17.77 | C |
| ATOM | 3700 | SD | MET | C | 77 | 52.348 | 91.513 | 72.976 | 1.00 12.26 | C |
| ATOM | 3701 | CE | MET | C | 77 | 52.116 | 89.925 | 73.670 | 1.00 17.78 | C |
| ATOM | 3702 | C | MET | C | 77 | 53.840 | 94.008 | 69.711 | 1.00 24.30 | C |
| ATOM | 3703 | O | MET | C | 77 | 53.271 | 95.017 | 70.149 | 1.00 22.92 | C |
| ATOM | 3704 | N | GLU | C | 78 | 54.648 | 94.015 | 68.659 | 1.00 25.02 | C |
| ATOM | 3705 | CA | GLU | C | 78 | 55.022 | 95.221 | 67.928 | 1.00 28.46 | C |
| ATOM | 3706 | CB | GLU | C | 78 | 56.247 | 94.921 | 67.109 | 1.00 25.59 | C |
| ATOM | 3707 | CG | GLU | C | 78 | 57.403 | 95.781 | 67.421 | 1.00 36.75 | C |
| ATOM | 3708 | CD | GLU | C | 78 | 58.682 | 95.105 | 67.005 | 1.00 39.78 | C |
| ATOM | 3709 | OE1 | GLU | C | 78 | 58.764 | 94.729 | 65.814 | 1.00 42.94 | C |
| ATOM | 3710 | OE2 | GLU | C | 78 | 59.591 | 94.932 | 67.856 | 1.00 41.62 | C |
| ATOM | 3711 | C | GLU | C | 78 | 54.012 | 95.851 | 66.998 | 1.00 29.85 | C |
| ATOM | 3712 | O | GLU | C | 78 | 54.176 | 96.999 | 66.580 | 1.00 24.67 | C |
| ATOM | 3713 | N | ARG | C | 79 | 52.989 | 95.089 | 66.646 | 1.00 36.30 | C |

Figure 10 (58 of 142)

| | | | | | | | | | | |
|---|---|---|---|---|---|---|---|---|---|---|
| ATOM | 3714 | CA | ARG | C | 79 | 51.982 | 95.573 | 65.724 | 1.00 38.96 | C |
| ATOM | 3715 | CB | ARG | C | 79 | 52.423 | 95.294 | 64.274 | 1.00 37.65 | C |
| ATOM | 3716 | CG | ARG | C | 79 | 52.245 | 93.845 | 63.734 | 1.00 36.68 | C |
| ATOM | 3717 | CD | ARG | C | 79 | 53.038 | 92.788 | 64.497 | 1.00 34.98 | C |
| ATOM | 3718 | NE | ARG | C | 79 | 53.239 | 91.520 | 63.772 | 1.00 32.36 | C |
| ATOM | 3719 | CZ | ARG | C | 79 | 52.282 | 90.720 | 63.285 | 1.00 30.72 | C |
| ATOM | 3720 | NH1 | ARG | C | 79 | 50.994 | 91.031 | 63.414 | 1.00 30.65 | C |
| ATOM | 3721 | NH2 | ARG | C | 79 | 52.621 | 89.573 | 62.696 | 1.00 30.72 | C |
| ATOM | 3722 | C | ARG | C | 79 | 50.674 | 94.877 | 66.011 | 1.00 39.65 | C |
| ATOM | 3723 | O | ARG | C | 79 | 50.634 | 93.663 | 66.161 | 1.00 41.37 | C |
| ATOM | 3724 | N | GLU | C | 80 | 49.604 | 95.652 | 66.090 | 1.00 43.41 | C |
| ATOM | 3725 | CA | GLU | C | 80 | 48.284 | 95.110 | 66.361 | 1.00 51.43 | C |
| ATOM | 3726 | CB | GLU | C | 80 | 47.243 | 96.225 | 66.267 | 1.00 55.34 | C |
| ATOM | 3727 | CG | GLU | C | 80 | 47.435 | 97.137 | 65.063 | 1.00 64.16 | C |
| ATOM | 3728 | CD | GLU | C | 80 | 48.253 | 98.379 | 65.397 | 1.00 69.10 | C |
| ATOM | 3729 | OE1 | GLU | C | 80 | 47.792 | 99.163 | 66.261 | 1.00 72.87 | C |
| ATOM | 3730 | OE2 | GLU | C | 80 | 49.347 | 98.571 | 64.805 | 1.00 73.68 | C |
| ATOM | 3731 | C | GLU | C | 80 | 47.887 | 93.967 | 65.425 | 1.00 51.97 | C |
| ATOM | 3732 | O | GLU | C | 80 | 48.722 | 93.410 | 64.709 | 1.00 53.52 | C |
| ATOM | 3733 | N | GLY | C | 81 | 46.599 | 93.627 | 65.446 | 1.00 47.68 | C |
| ATOM | 3734 | CA | GLY | C | 81 | 46.084 | 92.564 | 64.605 | 1.00 41.59 | C |
| ATOM | 3735 | C | GLY | C | 81 | 46.582 | 91.171 | 64.950 | 1.00 39.63 | C |
| ATOM | 3736 | O | GLY | C | 81 | 47.676 | 91.004 | 65.488 | 1.00 44.09 | C |
| ATOM | 3737 | N | PRO | C | 82 | 45.782 | 90.139 | 64.640 | 1.00 41.48 | C |
| ATOM | 3738 | CD | PRO | C | 82 | 44.459 | 90.383 | 64.040 | 1.00 42.56 | C |
| ATOM | 3739 | CA | PRO | C | 82 | 45.994 | 88.698 | 64.843 | 1.00 39.60 | C |
| ATOM | 3740 | CB | PRO | C | 82 | 44.906 | 88.073 | 63.984 | 1.00 43.04 | C |
| ATOM | 3741 | CG | PRO | C | 82 | 43.775 | 89.038 | 64.191 | 1.00 42.79 | C |
| ATOM | 3742 | C | PRO | C | 82 | 47.386 | 88.247 | 64.429 | 1.00 40.99 | C |
| ATOM | 3743 | O | PRO | C | 82 | 47.769 | 88.343 | 63.258 | 1.00 43.37 | C |
| ATOM | 3744 | N | SER | C | 83 | 48.131 | 87.730 | 65.396 | 1.00 41.74 | C |
| ATOM | 3745 | CA | SER | C | 83 | 49.497 | 87.308 | 65.152 | 1.00 47.57 | C |
| ATOM | 3746 | CB | SER | C | 83 | 50.193 | 87.085 | 66.491 | 1.00 47.55 | C |
| ATOM | 3747 | OG | SER | C | 83 | 50.076 | 88.243 | 67.300 | 1.00 47.78 | C |
| ATOM | 3748 | C | SER | C | 83 | 49.683 | 86.093 | 64.258 | 1.00 48.12 | C |
| ATOM | 3749 | O | SER | C | 83 | 49.705 | 84.962 | 64.732 | 1.00 52.44 | C |
| ATOM | 3750 | N | TYR | C | 84 | 49.836 | 86.328 | 62.960 | 1.00 47.29 | C |
| ATOM | 3751 | CA | TYR | C | 84 | 50.044 | 85.225 | 62.036 | 1.00 48.67 | C |
| ATOM | 3752 | CB | TYR | C | 84 | 49.414 | 85.541 | 60.692 | 1.00 46.87 | C |
| ATOM | 3753 | CG | TYR | C | 84 | 47.918 | 85.623 | 60.752 | 1.00 45.36 | C |
| ATOM | 3754 | CD1 | TYR | C | 84 | 47.257 | 86.802 | 60.443 | 1.00 47.52 | C |
| ATOM | 3755 | CE1 | TYR | C | 84 | 45.878 | 86.887 | 60.490 | 1.00 51.28 | C |
| ATOM | 3756 | CD2 | TYR | C | 84 | 47.160 | 84.519 | 61.115 | 1.00 46.43 | C |
| ATOM | 3757 | CE2 | TYR | C | 84 | 45.774 | 84.592 | 61.168 | 1.00 50.80 | C |
| ATOM | 3758 | CZ | TYR | C | 84 | 45.141 | 85.785 | 60.852 | 1.00 51.36 | C |
| ATOM | 3759 | OH | TYR | C | 84 | 43.770 | 85.894 | 60.887 | 1.00 58.45 | C |
| ATOM | 3760 | C | TYR | C | 84 | 51.526 | 84.941 | 61.859 | 1.00 48.28 | C |
| ATOM | 3761 | O | TYR | C | 84 | 52.297 | 85.818 | 61.468 | 1.00 52.24 | C |
| ATOM | 3762 | N | THR | C | 85 | 51.914 | 83.704 | 62.142 | 1.00 49.00 | C |
| ATOM | 3763 | CA | THR | C | 85 | 53.302 | 83.299 | 62.042 | 1.00 50.90 | C |
| ATOM | 3764 | CB | THR | C | 85 | 53.446 | 81.815 | 62.339 | 1.00 49.80 | C |
| ATOM | 3765 | OG1 | THR | C | 85 | 52.710 | 81.504 | 63.527 | 1.00 49.67 | C |
| ATOM | 3766 | CG2 | THR | C | 85 | 54.902 | 81.465 | 62.552 | 1.00 49.05 | C |
| ATOM | 3767 | C | THR | C | 85 | 53.953 | 83.613 | 60.699 | 1.00 48.91 | C |
| ATOM | 3768 | O | THR | C | 85 | 55.142 | 83.928 | 60.656 | 1.00 45.29 | C |
| ATOM | 3769 | N | PHE | C | 86 | 53.206 | 83.523 | 59.600 | 1.00 49.90 | C |
| ATOM | 3770 | CA | PHE | C | 86 | 53.804 | 83.852 | 58.311 | 1.00 54.51 | C |
| ATOM | 3771 | CB | PHE | C | 86 | 52.803 | 83.707 | 57.164 | 1.00 56.04 | C |
| ATOM | 3772 | CG | PHE | C | 86 | 53.308 | 84.275 | 55.857 | 1.00 57.97 | C |
| ATOM | 3773 | CD1 | PHE | C | 86 | 54.423 | 83.722 | 55.219 | 1.00 59.17 | C |
| ATOM | 3774 | CD2 | PHE | C | 86 | 52.719 | 85.406 | 55.300 | 1.00 57.61 | C |
| ATOM | 3775 | CE1 | PHE | C | 86 | 54.943 | 84.296 | 54.047 | 1.00 57.20 | C |
| ATOM | 3776 | CE2 | PHE | C | 86 | 53.231 | 85.985 | 54.134 | 1.00 58.52 | C |
| ATOM | 3777 | CZ | PHE | C | 86 | 54.344 | 85.430 | 53.508 | 1.00 58.75 | C |
| ATOM | 3778 | C | PHE | C | 86 | 54.290 | 85.303 | 58.360 | 1.00 52.60 | C |
| ATOM | 3779 | O | PHE | C | 86 | 55.451 | 85.600 | 58.077 | 1.00 50.64 | C |

Figure 10 (59 of 142)

| ATOM | 3780 | N | ASP | C | 87 | 53.385 | 86.200 | 58.732 | 1.00 | 50.85 | C |
| --- | --- | --- | --- | --- | --- | --- | --- | --- | --- | --- | --- |
| ATOM | 3781 | CA | ASP | C | 87 | 53.697 | 87.616 | 58.824 | 1.00 | 45.90 | C |
| ATOM | 3782 | CB | ASP | C | 87 | 52.483 | 88.387 | 59.346 | 1.00 | 48.56 | C |
| ATOM | 3783 | CG | ASP | C | 87 | 51.435 | 88.618 | 58.278 | 1.00 | 50.45 | C |
| ATOM | 3784 | OD1 | ASP | C | 87 | 50.327 | 89.069 | 58.634 | 1.00 | 50.77 | C |
| ATOM | 3785 | OD2 | ASP | C | 87 | 51.721 | 88.360 | 57.087 | 1.00 | 52.35 | C |
| ATOM | 3786 | C | ASP | C | 87 | 54.892 | 87.875 | 59.725 | 1.00 | 40.00 | C |
| ATOM | 3787 | O | ASP | C | 87 | 55.750 | 88.694 | 59.411 | 1.00 | 45.69 | C |
| ATOM | 3788 | N | THR | C | 88 | 54.947 | 87.167 | 60.845 | 1.00 | 34.23 | C |
| ATOM | 3789 | CA | THR | C | 88 | 56.028 | 87.338 | 61.803 | 1.00 | 30.85 | C |
| ATOM | 3790 | CB | THR | C | 88 | 55.627 | 86.733 | 63.175 | 1.00 | 28.48 | C |
| ATOM | 3791 | OG1 | THR | C | 88 | 54.567 | 87.522 | 63.733 | 1.00 | 25.25 | C |
| ATOM | 3792 | CG2 | THR | C | 88 | 56.798 | 86.725 | 64.145 | 1.00 | 22.99 | C |
| ATOM | 3793 | C | THR | C | 88 | 57.348 | 86.758 | 61.298 | 1.00 | 28.29 | C |
| ATOM | 3794 | O | THR | C | 88 | 58.358 | 87.463 | 61.259 | 1.00 | 31.61 | C |
| ATOM | 3795 | N | VAL | C | 89 | 57.343 | 85.492 | 60.893 | 1.00 | 24.61 | C |
| ATOM | 3796 | CA | VAL | C | 89 | 58.560 | 84.853 | 60.388 | 1.00 | 24.42 | C |
| ATOM | 3797 | CB | VAL | C | 89 | 58.271 | 83.429 | 59.853 | 1.00 | 24.59 | C |
| ATOM | 3798 | CG1 | VAL | C | 89 | 59.546 | 82.792 | 59.350 | 1.00 | 26.26 | C |
| ATOM | 3799 | CG2 | VAL | C | 89 | 57.699 | 82.572 | 60.953 | 1.00 | 28.21 | C |
| ATOM | 3800 | C | VAL | C | 89 | 59.153 | 85.696 | 59.262 | 1.00 | 25.33 | C |
| ATOM | 3801 | O | VAL | C | 89 | 60.372 | 85.832 | 59.144 | 1.00 | 21.04 | C |
| ATOM | 3802 | N | SER | C | 90 | 58.275 | 86.254 | 58.433 | 1.00 | 28.08 | C |
| ATOM | 3803 | CA | SER | C | 90 | 58.702 | 87.108 | 57.328 | 1.00 | 27.27 | C |
| ATOM | 3804 | CB | SER | C | 90 | 57.496 | 87.807 | 56.683 | 1.00 | 27.25 | C |
| ATOM | 3805 | OG | SER | C | 90 | 56.583 | 86.883 | 56.104 | 1.00 | 30.70 | C |
| ATOM | 3806 | C | SER | C | 90 | 59.592 | 88.154 | 57.957 | 1.00 | 26.63 | C |
| ATOM | 3807 | O | SER | C | 90 | 60.822 | 88.093 | 57.871 | 1.00 | 30.09 | C |
| ATOM | 3808 | N | LEU | C | 91 | 58.942 | 89.107 | 58.612 | 1.00 | 24.56 | C |
| ATOM | 3809 | CA | LEU | C | 91 | 59.640 | 90.175 | 59.287 | 1.00 | 24.86 | C |
| ATOM | 3810 | CB | LEU | C | 91 | 58.744 | 90.801 | 60.357 | 1.00 | 22.31 | C |
| ATOM | 3811 | CG | LEU | C | 91 | 59.417 | 91.931 | 61.152 | 1.00 | 22.34 | C |
| ATOM | 3812 | CD1 | LEU | C | 91 | 60.121 | 92.858 | 60.188 | 1.00 | 25.50 | C |
| ATOM | 3813 | CD2 | LEU | C | 91 | 58.402 | 92.723 | 61.966 | 1.00 | 22.14 | C |
| ATOM | 3814 | C | LEU | C | 91 | 60.921 | 89.661 | 59.927 | 1.00 | 28.15 | C |
| ATOM | 3815 | O | LEU | C | 91 | 61.998 | 90.197 | 59.692 | 1.00 | 27.53 | C |
| ATOM | 3816 | N | LEU | C | 92 | 60.813 | 88.605 | 60.721 | 1.00 | 35.43 | C |
| ATOM | 3817 | CA | LEU | C | 92 | 61.986 | 88.060 | 61.387 | 1.00 | 42.88 | C |
| ATOM | 3818 | CB | LEU | C | 92 | 61.594 | 86.893 | 62.275 | 1.00 | 43.21 | C |
| ATOM | 3819 | CG | LEU | C | 92 | 60.909 | 87.366 | 63.554 | 1.00 | 40.03 | C |
| ATOM | 3820 | CD1 | LEU | C | 92 | 60.430 | 86.159 | 64.317 | 1.00 | 43.42 | C |
| ATOM | 3821 | CD2 | LEU | C | 92 | 61.876 | 88.198 | 64.401 | 1.00 | 37.74 | C |
| ATOM | 3822 | C | LEU | C | 92 | 63.118 | 87.634 | 60.480 | 1.00 | 47.35 | C |
| ATOM | 3823 | O | LEU | C | 92 | 64.280 | 87.827 | 60.818 | 1.00 | 52.42 | C |
| ATOM | 3824 | N | LYS | C | 93 | 62.799 | 87.049 | 59.334 | 1.00 | 51.36 | C |
| ATOM | 3825 | CA | LYS | C | 93 | 63.863 | 86.621 | 58.441 | 1.00 | 52.80 | C |
| ATOM | 3826 | CB | LYS | C | 93 | 63.308 | 85.842 | 57.250 | 1.00 | 57.98 | C |
| ATOM | 3827 | CG | LYS | C | 93 | 62.841 | 84.447 | 57.617 | 1.00 | 62.65 | C |
| ATOM | 3828 | CD | LYS | C | 93 | 62.530 | 83.601 | 56.394 | 1.00 | 65.25 | C |
| ATOM | 3829 | CE | LYS | C | 93 | 63.777 | 83.348 | 55.554 | 1.00 | 69.80 | C |
| ATOM | 3830 | NZ | LYS | C | 93 | 64.817 | 82.543 | 56.267 | 1.00 | 71.47 | C |
| ATOM | 3831 | C | LYS | C | 93 | 64.613 | 87.839 | 57.960 | 1.00 | 52.73 | C |
| ATOM | 3832 | O | LYS | C | 93 | 65.779 | 87.753 | 57.571 | 1.00 | 54.01 | C |
| ATOM | 3833 | N | GLN | C | 94 | 63.943 | 88.981 | 58.019 | 1.00 | 45.86 | C |
| ATOM | 3834 | CA | GLN | C | 94 | 64.534 | 90.230 | 57.573 | 1.00 | 48.41 | C |
| ATOM | 3835 | CB | GLN | C | 94 | 63.413 | 91.199 | 57.235 | 1.00 | 45.27 | C |
| ATOM | 3836 | CG | GLN | C | 94 | 63.694 | 92.116 | 56.089 | 1.00 | 48.24 | C |
| ATOM | 3837 | CD | GLN | C | 94 | 62.418 | 92.745 | 55.580 | 1.00 | 51.39 | C |
| ATOM | 3838 | OE1 | GLN | C | 94 | 61.741 | 93.484 | 56.299 | 1.00 | 50.72 | C |
| ATOM | 3839 | NE2 | GLN | C | 94 | 62.071 | 92.441 | 54.337 | 1.00 | 53.43 | C |
| ATOM | 3840 | C | GLN | C | 94 | 65.481 | 90.851 | 58.609 | 1.00 | 50.92 | C |
| ATOM | 3841 | O | GLN | C | 94 | 66.612 | 91.223 | 58.277 | 1.00 | 48.03 | C |
| ATOM | 3842 | N | ARG | C | 95 | 65.018 | 90.960 | 59.859 | 1.00 | 52.29 | C |
| ATOM | 3843 | CA | ARG | C | 95 | 65.824 | 91.546 | 60.934 | 1.00 | 50.09 | C |
| ATOM | 3844 | CB | ARG | C | 95 | 65.034 | 91.636 | 62.237 | 1.00 | 47.09 | C |
| ATOM | 3845 | CG | ARG | C | 95 | 64.184 | 92.855 | 62.359 | 1.00 | 52.84 | C |

Figure 10 (60 of 142)

| | | | | | | | | | | |
|---|---|---|---|---|---|---|---|---|---|---|
| ATOM | 3846 | CD  | ARG | C | 95  | 63.597 | 92.936 | 63.734 | 1.00 52.39 | C |
| ATOM | 3847 | NE  | ARG | C | 95  | 62.568 | 93.961 | 63.799 | 1.00 52.67 | C |
| ATOM | 3848 | CZ  | ARG | C | 95  | 61.752 | 94.117 | 64.833 | 1.00 55.10 | C |
| ATOM | 3849 | NH1 | ARG | C | 95  | 61.852 | 93.313 | 65.880 | 1.00 58.89 | C |
| ATOM | 3850 | NH2 | ARG | C | 95  | 60.836 | 95.069 | 64.821 | 1.00 59.65 | C |
| ATOM | 3851 | C   | ARG | C | 95  | 67.082 | 90.760 | 61.203 | 1.00 49.80 | C |
| ATOM | 3852 | O   | ARG | C | 95  | 68.118 | 91.325 | 61.529 | 1.00 52.51 | C |
| ATOM | 3853 | N   | TYR | C | 96  | 66.997 | 89.450 | 61.067 | 1.00 54.35 | C |
| ATOM | 3854 | CA  | TYR | C | 96  | 68.153 | 88.629 | 61.335 | 1.00 56.21 | C |
| ATOM | 3855 | CB  | TYR | C | 96  | 67.908 | 87.804 | 62.605 | 1.00 59.29 | C |
| ATOM | 3856 | CG  | TYR | C | 96  | 67.257 | 88.592 | 63.733 | 1.00 58.50 | C |
| ATOM | 3857 | CD1 | TYR | C | 96  | 65.893 | 88.878 | 63.711 | 1.00 59.94 | C |
| ATOM | 3858 | CE1 | TYR | C | 96  | 65.291 | 89.631 | 64.715 | 1.00 57.12 | C |
| ATOM | 3859 | CD2 | TYR | C | 96  | 68.010 | 89.079 | 64.800 | 1.00 55.93 | C |
| ATOM | 3860 | CE2 | TYR | C | 96  | 67.416 | 89.838 | 65.814 | 1.00 57.86 | C |
| ATOM | 3861 | CZ  | TYR | C | 96  | 66.050 | 90.112 | 65.760 | 1.00 58.15 | C |
| ATOM | 3862 | OH  | TYR | C | 96  | 65.426 | 90.878 | 66.727 | 1.00 55.46 | C |
| ATOM | 3863 | C   | TYR | C | 96  | 68.438 | 87.732 | 60.141 | 1.00 54.66 | C |
| ATOM | 3864 | O   | TYR | C | 96  | 68.065 | 86.559 | 60.124 | 1.00 55.94 | C |
| ATOM | 3865 | N   | PRO | C | 97  | 69.086 | 88.290 | 59.108 | 1.00 56.92 | C |
| ATOM | 3866 | CD  | PRO | C | 97  | 69.163 | 89.742 | 58.875 | 1.00 54.39 | C |
| ATOM | 3867 | CA  | PRO | C | 97  | 69.433 | 87.552 | 57.886 | 1.00 54.47 | C |
| ATOM | 3868 | CB  | PRO | C | 97  | 69.687 | 88.665 | 56.874 | 1.00 53.50 | C |
| ATOM | 3869 | CG  | PRO | C | 97  | 68.884 | 89.827 | 57.415 | 1.00 54.29 | C |
| ATOM | 3870 | C   | PRO | C | 97  | 70.650 | 86.635 | 58.018 | 1.00 53.70 | C |
| ATOM | 3871 | O   | PRO | C | 97  | 70.890 | 85.798 | 57.157 | 1.00 54.00 | C |
| ATOM | 3872 | N   | ASN | C | 98  | 71.422 | 86.793 | 59.089 | 1.00 54.62 | C |
| ATOM | 3873 | CA  | ASN | C | 98  | 72.617 | 85.972 | 59.275 | 1.00 59.73 | C |
| ATOM | 3874 | CB  | ASN | C | 98  | 73.806 | 86.861 | 59.635 | 1.00 63.81 | C |
| ATOM | 3875 | CG  | ASN | C | 98  | 74.273 | 87.685 | 58.468 | 1.00 67.83 | C |
| ATOM | 3876 | OD1 | ASN | C | 98  | 73.484 | 88.400 | 57.848 | 1.00 71.76 | C |
| ATOM | 3877 | ND2 | ASN | C | 98  | 75.561 | 87.592 | 58.154 | 1.00 69.51 | C |
| ATOM | 3878 | C   | ASN | C | 98  | 72.487 | 84.871 | 60.315 | 1.00 58.21 | C |
| ATOM | 3879 | O   | ASN | C | 98  | 73.437 | 84.122 | 60.566 | 1.00 56.60 | C |
| ATOM | 3880 | N   | ASP | C | 99  | 71.315 | 84.767 | 60.921 | 1.00 56.60 | C |
| ATOM | 3881 | CA  | ASP | C | 99  | 71.098 | 83.754 | 61.938 | 1.00 52.08 | C |
| ATOM | 3882 | CB  | ASP | C | 99  | 70.515 | 84.409 | 63.194 | 1.00 53.56 | C |
| ATOM | 3883 | CG  | ASP | C | 99  | 71.406 | 85.517 | 63.744 | 1.00 54.45 | C |
| ATOM | 3884 | OD1 | ASP | C | 99  | 72.581 | 85.228 | 64.050 | 1.00 55.16 | C |
| ATOM | 3885 | OD2 | ASP | C | 99  | 70.935 | 86.670 | 63.869 | 1.00 57.52 | C |
| ATOM | 3886 | C   | ASP | C | 99  | 70.148 | 82.687 | 61.400 | 1.00 46.76 | C |
| ATOM | 3887 | O   | ASP | C | 99  | 69.174 | 83.004 | 60.715 | 1.00 45.15 | C |
| ATOM | 3888 | N   | GLN | C | 100 | 70.431 | 81.424 | 61.697 | 1.00 43.08 | C |
| ATOM | 3889 | CA  | GLN | C | 100 | 69.561 | 80.367 | 61.219 | 1.00 41.10 | C |
| ATOM | 3890 | CB  | GLN | C | 100 | 70.324 | 79.054 | 61.137 | 1.00 42.91 | C |
| ATOM | 3891 | CG  | GLN | C | 100 | 69.534 | 77.986 | 60.419 | 1.00 45.17 | C |
| ATOM | 3892 | CD  | GLN | C | 100 | 70.418 | 76.979 | 59.717 | 1.00 47.00 | C |
| ATOM | 3893 | OE1 | GLN | C | 100 | 69.936 | 76.147 | 58.940 | 1.00 48.59 | C |
| ATOM | 3894 | NE2 | GLN | C | 100 | 71.720 | 77.040 | 59.991 | 1.00 47.19 | C |
| ATOM | 3895 | C   | GLN | C | 100 | 68.338 | 80.220 | 62.126 | 1.00 40.98 | C |
| ATOM | 3896 | O   | GLN | C | 100 | 68.461 | 79.999 | 63.333 | 1.00 41.26 | C |
| ATOM | 3897 | N   | LEU | C | 101 | 67.153 | 80.334 | 61.541 | 1.00 36.91 | C |
| ATOM | 3898 | CA  | LEU | C | 101 | 65.925 | 80.256 | 62.321 | 1.00 36.80 | C |
| ATOM | 3899 | CB  | LEU | C | 101 | 65.017 | 81.445 | 62.004 | 1.00 34.91 | C |
| ATOM | 3900 | CG  | LEU | C | 101 | 65.598 | 82.853 | 61.982 | 1.00 37.89 | C |
| ATOM | 3901 | CD1 | LEU | C | 101 | 64.459 | 83.846 | 61.789 | 1.00 36.82 | C |
| ATOM | 3902 | CD2 | LEU | C | 101 | 66.358 | 83.117 | 63.275 | 1.00 42.41 | C |
| ATOM | 3903 | C   | LEU | C | 101 | 65.086 | 78.999 | 62.146 | 1.00 34.69 | C |
| ATOM | 3904 | O   | LEU | C | 101 | 64.770 | 78.600 | 61.030 | 1.00 36.57 | C |
| ATOM | 3905 | N   | PHE | C | 102 | 64.699 | 78.397 | 63.263 | 1.00 34.04 | C |
| ATOM | 3906 | CA  | PHE | C | 102 | 63.843 | 77.226 | 63.236 | 1.00 33.31 | C |
| ATOM | 3907 | CB  | PHE | C | 102 | 64.583 | 76.009 | 63.769 | 1.00 30.82 | C |
| ATOM | 3908 | CG  | PHE | C | 102 | 65.847 | 75.695 | 63.031 | 1.00 29.21 | C |
| ATOM | 3909 | CD1 | PHE | C | 102 | 67.016 | 76.404 | 63.281 | 1.00 29.15 | C |
| ATOM | 3910 | CD2 | PHE | C | 102 | 65.884 | 74.636 | 62.131 | 1.00 26.64 | C |
| ATOM | 3911 | CE1 | PHE | C | 102 | 68.195 | 76.049 | 62.652 | 1.00 27.85 | C |

Figure 10 (61 of 142)

```
ATOM   3912  CE2 PHE C 102      67.060  74.274  61.496  1.00 24.55           C
ATOM   3913  CZ  PHE C 102      68.213  74.974  61.756  1.00 27.13           C
ATOM   3914  C   PHE C 102      62.633  77.521  64.129  1.00 35.22           C
ATOM   3915  O   PHE C 102      62.765  78.139  65.187  1.00 36.85           C
ATOM   3916  N   PHE C 103      61.451  77.103  63.699  1.00 33.83           C
ATOM   3917  CA  PHE C 103      60.254  77.319  64.495  1.00 33.60           C
ATOM   3918  CB  PHE C 103      59.063  77.590  63.581  1.00 31.33           C
ATOM   3919  CG  PHE C 103      57.958  78.358  64.239  1.00 30.70           C
ATOM   3920  CD1 PHE C 103      57.932  79.744  64.193  1.00 33.05           C
ATOM   3921  CD2 PHE C 103      56.940  77.698  64.906  1.00 32.12           C
ATOM   3922  CE1 PHE C 103      56.905  80.463  64.798  1.00 28.46           C
ATOM   3923  CE2 PHE C 103      55.907  78.416  65.518  1.00 33.01           C
ATOM   3924  CZ  PHE C 103      55.892  79.800  65.460  1.00 27.20           C
ATOM   3925  C   PHE C 103      60.032  76.030  65.291  1.00 34.14           C
ATOM   3926  O   PHE C 103      60.576  74.982  64.929  1.00 36.35           C
ATOM   3927  N   ILE C 104      59.253  76.092  66.371  1.00 28.65           C
ATOM   3928  CA  ILE C 104      59.002  74.896  67.175  1.00 22.58           C
ATOM   3929  CB  ILE C 104      59.925  74.854  68.382  1.00 15.11           C
ATOM   3930  CG2 ILE C 104      59.591  73.650  69.243  1.00 12.95           C
ATOM   3931  CG1 ILE C 104      61.374  74.788  67.899  1.00 13.26           C
ATOM   3932  CD1 ILE C 104      62.398  74.970  68.978  1.00 12.26           C
ATOM   3933  C   ILE C 104      57.567  74.720  67.652  1.00 23.46           C
ATOM   3934  O   ILE C 104      56.966  75.640  68.202  1.00 27.70           C
ATOM   3935  N   ILE C 105      57.032  73.519  67.449  1.00 29.14           C
ATOM   3936  CA  ILE C 105      55.658  73.169  67.823  1.00 32.46           C
ATOM   3937  CB  ILE C 105      54.746  73.143  66.574  1.00 32.01           C
ATOM   3938  CG2 ILE C 105      54.556  74.551  66.020  1.00 30.04           C
ATOM   3939  CG1 ILE C 105      55.382  72.226  65.520  1.00 33.40           C
ATOM   3940  CD1 ILE C 105      54.583  72.071  64.248  1.00 33.20           C
ATOM   3941  C   ILE C 105      55.615  71.771  68.460  1.00 35.69           C
ATOM   3942  O   ILE C 105      56.458  70.916  68.171  1.00 38.20           C
ATOM   3943  N   GLY C 106      54.627  71.551  69.322  1.00 41.19           C
ATOM   3944  CA  GLY C 106      54.467  70.260  69.970  1.00 42.73           C
ATOM   3945  C   GLY C 106      53.470  69.436  69.175  1.00 46.55           C
ATOM   3946  O   GLY C 106      52.858  69.958  68.236  1.00 49.88           C
ATOM   3947  N   ALA C 107      53.297  68.164  69.542  1.00 49.51           C
ATOM   3948  CA  ALA C 107      52.377  67.260  68.831  1.00 50.93           C
ATOM   3949  CB  ALA C 107      52.132  66.000  69.653  1.00 51.93           C
ATOM   3950  C   ALA C 107      51.050  67.926  68.522  1.00 53.49           C
ATOM   3951  O   ALA C 107      50.448  67.711  67.469  1.00 56.83           C
ATOM   3952  N   ASP C 108      50.614  68.734  69.474  1.00 56.78           C
ATOM   3953  CA  ASP C 108      49.371  69.475  69.408  1.00 58.97           C
ATOM   3954  CB  ASP C 108      49.321  70.385  70.631  1.00 63.63           C
ATOM   3955  CG  ASP C 108      48.162  71.331  70.606  1.00 65.03           C
ATOM   3956  OD1 ASP C 108      47.211  71.104  69.820  1.00 68.86           C
ATOM   3957  OD2 ASP C 108      48.206  72.304  71.390  1.00 71.21           C
ATOM   3958  C   ASP C 108      49.203  70.284  68.121  1.00 55.70           C
ATOM   3959  O   ASP C 108      48.284  70.046  67.332  1.00 59.46           C
ATOM   3960  N   MET C 109      50.099  71.244  67.928  1.00 54.38           C
ATOM   3961  CA  MET C 109      50.088  72.115  66.761  1.00 51.39           C
ATOM   3962  CB  MET C 109      51.109  73.234  66.956  1.00 46.92           C
ATOM   3963  CG  MET C 109      50.613  74.332  67.867  1.00 35.67           C
ATOM   3964  SD  MET C 109      49.206  75.241  67.157  1.00 28.10           C
ATOM   3965  CE  MET C 109      47.805  74.241  67.759  1.00 26.55           C
ATOM   3966  C   MET C 109      50.358  71.393  65.449  1.00 52.50           C
ATOM   3967  O   MET C 109      49.869  71.795  64.392  1.00 50.07           C
ATOM   3968  N   ILE C 110      51.143  70.327  65.518  1.00 55.08           C
ATOM   3969  CA  ILE C 110      51.463  69.554  64.329  1.00 56.62           C
ATOM   3970  CB  ILE C 110      52.401  68.368  64.689  1.00 57.28           C
ATOM   3971  CG2 ILE C 110      52.731  67.558  63.452  1.00 56.46           C
ATOM   3972  CG1 ILE C 110      53.699  68.909  65.300  1.00 54.11           C
ATOM   3973  CD1 ILE C 110      54.755  67.849  65.562  1.00 57.50           C
ATOM   3974  C   ILE C 110      50.165  69.053  63.680  1.00 60.53           C
ATOM   3975  O   ILE C 110      50.038  69.033  62.458  1.00 66.65           C
ATOM   3976  N   GLU C 111      49.200  68.660  64.507  1.00 61.79           C
ATOM   3977  CA  GLU C 111      47.907  68.188  64.022  1.00 63.90           C
```

Figure 10 (62 of 142)

| ATOM | 3978 | CB | GLU | C | 111 | 47.066 | 67.665 | 65.174 | 1.00 | 69.10 | C |
|---|---|---|---|---|---|---|---|---|---|---|---|
| ATOM | 3979 | CG | GLU | C | 111 | 47.261 | 66.229 | 65.556 | 1.00 | 74.02 | C |
| ATOM | 3980 | CD | GLU | C | 111 | 46.302 | 65.833 | 66.665 | 1.00 | 75.87 | C |
| ATOM | 3981 | OE1 | GLU | C | 111 | 45.118 | 66.240 | 66.591 | 1.00 | 76.62 | C |
| ATOM | 3982 | OE2 | GLU | C | 111 | 46.723 | 65.119 | 67.604 | 1.00 | 77.50 | C |
| ATOM | 3983 | C | GLU | C | 111 | 47.144 | 69.353 | 63.428 | 1.00 | 63.46 | C |
| ATOM | 3984 | O | GLU | C | 111 | 46.219 | 69.175 | 62.634 | 1.00 | 59.96 | C |
| ATOM | 3985 | N | TYR | C | 112 | 47.534 | 70.550 | 63.843 | 1.00 | 64.86 | C |
| ATOM | 3986 | CA | TYR | C | 112 | 46.873 | 71.770 | 63.422 | 1.00 | 63.38 | C |
| ATOM | 3987 | CB | TYR | C | 112 | 46.847 | 72.732 | 64.615 | 1.00 | 62.90 | C |
| ATOM | 3988 | CG | TYR | C | 112 | 45.636 | 73.634 | 64.684 | 1.00 | 61.28 | C |
| ATOM | 3989 | CD1 | TYR | C | 112 | 45.612 | 74.857 | 64.017 | 1.00 | 64.26 | C |
| ATOM | 3990 | CE1 | TYR | C | 112 | 44.487 | 75.689 | 64.070 | 1.00 | 64.81 | C |
| ATOM | 3991 | CD2 | TYR | C | 112 | 44.508 | 73.260 | 65.411 | 1.00 | 63.25 | C |
| ATOM | 3992 | CE2 | TYR | C | 112 | 43.381 | 74.081 | 65.470 | 1.00 | 62.45 | C |
| ATOM | 3993 | CZ | TYR | C | 112 | 43.376 | 75.292 | 64.797 | 1.00 | 62.44 | C |
| ATOM | 3994 | OH | TYR | C | 112 | 42.259 | 76.096 | 64.840 | 1.00 | 55.42 | C |
| ATOM | 3995 | C | TYR | C | 112 | 47.474 | 72.449 | 62.190 | 1.00 | 63.26 | C |
| ATOM | 3996 | O | TYR | C | 112 | 46.877 | 73.365 | 61.639 | 1.00 | 62.80 | C |
| ATOM | 3997 | N | LEU | C | 113 | 48.639 | 72.004 | 61.737 | 1.00 | 63.95 | C |
| ATOM | 3998 | CA | LEU | C | 113 | 49.251 | 72.628 | 60.567 | 1.00 | 68.62 | C |
| ATOM | 3999 | CB | LEU | C | 113 | 50.366 | 71.734 | 60.011 | 1.00 | 73.61 | C |
| ATOM | 4000 | CG | LEU | C | 113 | 51.770 | 72.104 | 60.511 | 1.00 | 76.93 | C |
| ATOM | 4001 | CD1 | LEU | C | 113 | 51.762 | 72.284 | 62.022 | 1.00 | 80.25 | C |
| ATOM | 4002 | CD2 | LEU | C | 113 | 52.758 | 71.029 | 60.104 | 1.00 | 79.19 | C |
| ATOM | 4003 | C | LEU | C | 113 | 48.253 | 72.998 | 59.463 | 1.00 | 68.95 | C |
| ATOM | 4004 | O | LEU | C | 113 | 48.256 | 74.131 | 58.989 | 1.00 | 67.51 | C |
| ATOM | 4005 | N | PRO | C | 114 | 47.384 | 72.058 | 59.040 | 1.00 | 71.82 | C |
| ATOM | 4006 | CD | PRO | C | 114 | 47.191 | 70.660 | 59.456 | 1.00 | 72.22 | C |
| ATOM | 4007 | CA | PRO | C | 114 | 46.427 | 72.414 | 57.985 | 1.00 | 70.15 | C |
| ATOM | 4008 | CB | PRO | C | 114 | 45.479 | 71.206 | 57.940 | 1.00 | 67.99 | C |
| ATOM | 4009 | CG | PRO | C | 114 | 45.711 | 70.492 | 59.242 | 1.00 | 71.35 | C |
| ATOM | 4010 | C | PRO | C | 114 | 45.700 | 73.733 | 58.242 | 1.00 | 67.54 | C |
| ATOM | 4011 | O | PRO | C | 114 | 45.854 | 74.683 | 57.481 | 1.00 | 63.91 | C |
| ATOM | 4012 | N | LYS | C | 115 | 44.893 | 73.790 | 59.296 | 1.00 | 69.60 | C |
| ATOM | 4013 | CA | LYS | C | 115 | 44.196 | 75.029 | 59.634 | 1.00 | 70.28 | C |
| ATOM | 4014 | CB | LYS | C | 115 | 43.148 | 74.785 | 60.725 | 1.00 | 70.53 | C |
| ATOM | 4015 | CG | LYS | C | 115 | 42.169 | 73.658 | 60.415 | 1.00 | 72.13 | C |
| ATOM | 4016 | CD | LYS | C | 115 | 41.205 | 73.370 | 61.577 | 1.00 | 69.98 | C |
| ATOM | 4017 | CE | LYS | C | 115 | 40.199 | 74.492 | 61.795 | 1.00 | 68.18 | C |
| ATOM | 4018 | NZ | LYS | C | 115 | 39.280 | 74.207 | 62.934 | 1.00 | 63.84 | C |
| ATOM | 4019 | C | LYS | C | 115 | 45.320 | 75.886 | 60.189 | 1.00 | 65.64 | C |
| ATOM | 4020 | O | LYS | C | 115 | 45.709 | 75.721 | 61.337 | 1.00 | 74.09 | C |
| ATOM | 4021 | N | TRP | C | 116 | 45.851 | 76.797 | 59.384 | 1.00 | 63.55 | C |
| ATOM | 4022 | CA | TRP | C | 116 | 46.978 | 77.622 | 59.824 | 1.00 | 62.78 | C |
| ATOM | 4023 | CB | TRP | C | 116 | 48.139 | 76.671 | 60.187 | 1.00 | 63.92 | C |
| ATOM | 4024 | CG | TRP | C | 116 | 49.380 | 77.238 | 60.823 | 1.00 | 57.37 | C |
| ATOM | 4025 | CD2 | TRP | C | 116 | 49.926 | 76.891 | 62.105 | 1.00 | 55.56 | C |
| ATOM | 4026 | CE2 | TRP | C | 116 | 51.170 | 77.557 | 62.231 | 1.00 | 53.61 | C |
| ATOM | 4027 | CE3 | TRP | C | 116 | 49.488 | 76.084 | 63.157 | 1.00 | 52.79 | C |
| ATOM | 4028 | CD1 | TRP | C | 116 | 50.284 | 78.077 | 60.245 | 1.00 | 59.12 | C |
| ATOM | 4029 | NE1 | TRP | C | 116 | 51.365 | 78.270 | 61.080 | 1.00 | 57.39 | C |
| ATOM | 4030 | CZ2 | TRP | C | 116 | 51.979 | 77.439 | 63.353 | 1.00 | 50.76 | C |
| ATOM | 4031 | CZ3 | TRP | C | 116 | 50.298 | 75.963 | 64.278 | 1.00 | 50.95 | C |
| ATOM | 4032 | CH2 | TRP | C | 116 | 51.530 | 76.642 | 64.366 | 1.00 | 50.07 | C |
| ATOM | 4033 | C | TRP | C | 116 | 47.301 | 78.515 | 58.625 | 1.00 | 60.75 | C |
| ATOM | 4034 | O | TRP | C | 116 | 47.637 | 78.034 | 57.547 | 1.00 | 61.57 | C |
| ATOM | 4035 | N | TYR | C | 117 | 47.174 | 79.818 | 58.819 | 1.00 | 60.14 | C |
| ATOM | 4036 | CA | TYR | C | 117 | 47.392 | 80.797 | 57.759 | 1.00 | 62.29 | C |
| ATOM | 4037 | CB | TYR | C | 117 | 47.242 | 82.199 | 58.336 | 1.00 | 66.36 | C |
| ATOM | 4038 | CG | TYR | C | 117 | 47.325 | 83.281 | 57.296 | 1.00 | 68.80 | C |
| ATOM | 4039 | CD1 | TYR | C | 117 | 46.367 | 83.380 | 56.296 | 1.00 | 70.45 | C |
| ATOM | 4040 | CE1 | TYR | C | 117 | 46.444 | 84.379 | 55.332 | 1.00 | 70.58 | C |
| ATOM | 4041 | CD2 | TYR | C | 117 | 48.364 | 84.206 | 57.308 | 1.00 | 70.65 | C |
| ATOM | 4042 | CE2 | TYR | C | 117 | 48.451 | 85.209 | 56.350 | 1.00 | 71.91 | C |
| ATOM | 4043 | CZ | TYR | C | 117 | 47.494 | 85.290 | 55.367 | 1.00 | 71.09 | C |

Figure 10 (63 of 142)

| ATOM | 4044 | OH  | TYR | C | 117 | 47.600 | 86.276 | 54.416 | 1.00 | 71.94 | C |
| ATOM | 4045 | C   | TYR | C | 117 | 48.686 | 80.748 | 56.949 | 1.00 | 61.39 | C |
| ATOM | 4046 | O   | TYR | C | 117 | 49.761 | 81.030 | 57.468 | 1.00 | 61.51 | C |
| ATOM | 4047 | N   | LYS | C | 118 | 48.562 | 80.415 | 55.666 | 1.00 | 61.30 | C |
| ATOM | 4048 | CA  | LYS | C | 118 | 49.694 | 80.362 | 54.746 | 1.00 | 62.21 | C |
| ATOM | 4049 | CB  | LYS | C | 118 | 50.303 | 81.751 | 54.606 | 1.00 | 63.38 | C |
| ATOM | 4050 | CG  | LYS | C | 118 | 49.492 | 82.705 | 53.776 | 1.00 | 69.38 | C |
| ATOM | 4051 | CD  | LYS | C | 118 | 50.313 | 83.939 | 53.455 | 1.00 | 73.31 | C |
| ATOM | 4052 | CE  | LYS | C | 118 | 49.543 | 84.899 | 52.567 | 1.00 | 75.37 | C |
| ATOM | 4053 | NZ  | LYS | C | 118 | 50.288 | 86.166 | 52.349 | 1.00 | 79.95 | C |
| ATOM | 4054 | C   | LYS | C | 118 | 50.819 | 79.376 | 55.049 | 1.00 | 63.98 | C |
| ATOM | 4055 | O   | LYS | C | 118 | 51.992 | 79.671 | 54.800 | 1.00 | 61.75 | C |
| ATOM | 4056 | N   | LEU | C | 119 | 50.477 | 78.201 | 55.554 | 1.00 | 66.74 | C |
| ATOM | 4057 | CA  | LEU | C | 119 | 51.502 | 77.227 | 55.884 | 1.00 | 70.64 | C |
| ATOM | 4058 | CB  | LEU | C | 119 | 50.862 | 75.914 | 56.325 | 1.00 | 70.08 | C |
| ATOM | 4059 | CG  | LEU | C | 119 | 51.853 | 74.913 | 56.907 | 1.00 | 72.28 | C |
| ATOM | 4060 | CD1 | LEU | C | 119 | 52.677 | 75.578 | 57.994 | 1.00 | 74.62 | C |
| ATOM | 4061 | CD2 | LEU | C | 119 | 51.100 | 73.734 | 57.463 | 1.00 | 73.25 | C |
| ATOM | 4062 | C   | LEU | C | 119 | 52.450 | 76.971 | 54.721 | 1.00 | 71.40 | C |
| ATOM | 4063 | O   | LEU | C | 119 | 53.672 | 77.004 | 54.879 | 1.00 | 72.88 | C |
| ATOM | 4064 | N   | ASP | C | 120 | 51.882 | 76.739 | 53.545 | 1.00 | 72.54 | C |
| ATOM | 4065 | CA  | ASP | C | 120 | 52.679 | 76.449 | 52.360 | 1.00 | 72.29 | C |
| ATOM | 4066 | CB  | ASP | C | 120 | 51.739 | 76.217 | 51.177 | 1.00 | 74.54 | C |
| ATOM | 4067 | CG  | ASP | C | 120 | 50.887 | 74.969 | 51.357 | 1.00 | 76.54 | C |
| ATOM | 4068 | OD1 | ASP | C | 120 | 51.460 | 73.851 | 51.409 | 1.00 | 77.27 | C |
| ATOM | 4069 | OD2 | ASP | C | 120 | 49.648 | 75.108 | 51.455 | 1.00 | 75.57 | C |
| ATOM | 4070 | C   | ASP | C | 120 | 53.764 | 77.478 | 52.016 | 1.00 | 69.36 | C |
| ATOM | 4071 | O   | ASP | C | 120 | 54.830 | 77.116 | 51.502 | 1.00 | 67.65 | C |
| ATOM | 4072 | N   | GLU | C | 121 | 53.509 | 78.749 | 52.313 | 1.00 | 67.01 | C |
| ATOM | 4073 | CA  | GLU | C | 121 | 54.482 | 79.803 | 52.029 | 1.00 | 64.17 | C |
| ATOM | 4074 | CB  | GLU | C | 121 | 53.793 | 81.167 | 51.908 | 1.00 | 69.26 | C |
| ATOM | 4075 | CG  | GLU | C | 121 | 52.685 | 81.269 | 50.858 | 1.00 | 73.00 | C |
| ATOM | 4076 | CD  | GLU | C | 121 | 51.504 | 80.352 | 51.151 | 1.00 | 75.36 | C |
| ATOM | 4077 | OE1 | GLU | C | 121 | 51.279 | 80.035 | 52.339 | 1.00 | 78.29 | C |
| ATOM | 4078 | OE2 | GLU | C | 121 | 50.793 | 79.957 | 50.201 | 1.00 | 74.30 | C |
| ATOM | 4079 | C   | GLU | C | 121 | 55.481 | 79.862 | 53.169 | 1.00 | 61.16 | C |
| ATOM | 4080 | O   | GLU | C | 121 | 56.675 | 80.088 | 52.972 | 1.00 | 56.97 | C |
| ATOM | 4081 | N   | LEU | C | 122 | 54.961 | 79.665 | 54.371 | 1.00 | 60.26 | C |
| ATOM | 4082 | CA  | LEU | C | 122 | 55.765 | 79.689 | 55.578 | 1.00 | 64.53 | C |
| ATOM | 4083 | CB  | LEU | C | 122 | 54.843 | 79.603 | 56.799 | 1.00 | 67.98 | C |
| ATOM | 4084 | CG  | LEU | C | 122 | 55.456 | 79.634 | 58.203 | 1.00 | 68.99 | C |
| ATOM | 4085 | CD1 | LEU | C | 122 | 56.073 | 81.000 | 58.491 | 1.00 | 69.31 | C |
| ATOM | 4086 | CD2 | LEU | C | 122 | 54.373 | 79.321 | 59.220 | 1.00 | 70.65 | C |
| ATOM | 4087 | C   | LEU | C | 122 | 56.782 | 78.545 | 55.601 | 1.00 | 66.42 | C |
| ATOM | 4088 | O   | LEU | C | 122 | 57.966 | 78.763 | 55.863 | 1.00 | 66.95 | C |
| ATOM | 4089 | N   | LEU | C | 123 | 56.319 | 77.328 | 55.328 | 1.00 | 67.01 | C |
| ATOM | 4090 | CA  | LEU | C | 123 | 57.191 | 76.157 | 55.334 | 1.00 | 66.90 | C |
| ATOM | 4091 | CB  | LEU | C | 123 | 56.434 | 74.935 | 54.836 | 1.00 | 69.08 | C |
| ATOM | 4092 | CG  | LEU | C | 123 | 55.525 | 74.295 | 55.876 | 1.00 | 71.25 | C |
| ATOM | 4093 | CD1 | LEU | C | 123 | 54.749 | 73.157 | 55.253 | 1.00 | 72.35 | C |
| ATOM | 4094 | CD2 | LEU | C | 123 | 56.378 | 73.795 | 57.028 | 1.00 | 72.27 | C |
| ATOM | 4095 | C   | LEU | C | 123 | 58.390 | 76.395 | 54.453 | 1.00 | 69.81 | C |
| ATOM | 4096 | O   | LEU | C | 123 | 59.444 | 75.775 | 54.609 | 1.00 | 66.22 | C |
| ATOM | 4097 | N   | ASN | C | 124 | 58.203 | 77.312 | 53.517 | 1.00 | 73.11 | C |
| ATOM | 4098 | CA  | ASN | C | 124 | 59.237 | 77.679 | 52.575 | 1.00 | 76.37 | C |
| ATOM | 4099 | CB  | ASN | C | 124 | 58.580 | 78.325 | 51.353 | 1.00 | 81.73 | C |
| ATOM | 4100 | CG  | ASN | C | 124 | 59.538 | 78.503 | 50.198 | 1.00 | 88.58 | C |
| ATOM | 4101 | OD1 | ASN | C | 124 | 60.524 | 79.243 | 50.294 | 1.00 | 91.71 | C |
| ATOM | 4102 | ND2 | ASN | C | 124 | 59.256 | 77.821 | 49.091 | 1.00 | 91.64 | C |
| ATOM | 4103 | C   | ASN | C | 124 | 60.203 | 78.655 | 53.251 | 1.00 | 73.69 | C |
| ATOM | 4104 | O   | ASN | C | 124 | 61.400 | 78.668 | 52.958 | 1.00 | 74.68 | C |
| ATOM | 4105 | N   | LEU | C | 125 | 59.669 | 79.457 | 54.168 | 1.00 | 73.04 | C |
| ATOM | 4106 | CA  | LEU | C | 125 | 60.455 | 80.451 | 54.893 | 1.00 | 70.26 | C |
| ATOM | 4107 | CB  | LEU | C | 125 | 59.533 | 81.494 | 55.516 | 1.00 | 70.07 | C |
| ATOM | 4108 | CG  | LEU | C | 125 | 58.847 | 82.460 | 54.561 | 1.00 | 70.89 | C |
| ATOM | 4109 | CD1 | LEU | C | 125 | 57.938 | 83.403 | 55.329 | 1.00 | 70.84 | C |

Figure 10 (64 of 142)

| | | | | | | | | | | |
|---|---|---|---|---|---|---|---|---|---|---|
| ATOM | 4110 | CD2 | LEU | C | 125 | 59.909 | 83.243 | 53.819 | 1.00 | 73.35 | C |
| ATOM | 4111 | C | LEU | C | 125 | 61.349 | 79.897 | 55.991 | 1.00 | 66.88 | C |
| ATOM | 4112 | O | LEU | C | 125 | 62.542 | 80.208 | 56.035 | 1.00 | 68.75 | C |
| ATOM | 4113 | N | ILE | C | 126 | 60.769 | 79.093 | 56.881 | 1.00 | 63.73 | C |
| ATOM | 4114 | CA | ILE | C | 126 | 61.509 | 78.524 | 58.002 | 1.00 | 65.03 | C |
| ATOM | 4115 | CB | ILE | C | 126 | 61.204 | 79.317 | 59.303 | 1.00 | 60.33 | C |
| ATOM | 4116 | CG2 | ILE | C | 126 | 59.724 | 79.236 | 59.618 | 1.00 | 59.29 | C |
| ATOM | 4117 | CG1 | ILE | C | 126 | 62.040 | 78.783 | 60.468 | 1.00 | 63.33 | C |
| ATOM | 4118 | CD1 | ILE | C | 126 | 61.864 | 79.564 | 61.753 | 1.00 | 60.77 | C |
| ATOM | 4119 | C | ILE | C | 126 | 61.178 | 77.054 | 58.218 | 1.00 | 60.38 | C |
| ATOM | 4120 | O | ILE | C | 126 | 60.073 | 76.613 | 57.920 | 1.00 | 56.90 | C |
| ATOM | 4121 | N | GLN | C | 127 | 62.147 | 76.301 | 58.734 | 1.00 | 57.99 | C |
| ATOM | 4122 | CA | GLN | C | 127 | 61.967 | 74.875 | 59.002 | 1.00 | 53.90 | C |
| ATOM | 4123 | CB | GLN | C | 127 | 63.320 | 74.168 | 59.060 | 1.00 | 59.02 | C |
| ATOM | 4124 | CG | GLN | C | 127 | 64.166 | 74.346 | 57.829 | 1.00 | 67.74 | C |
| ATOM | 4125 | CD | GLN | C | 127 | 65.590 | 73.881 | 58.040 | 1.00 | 71.84 | C |
| ATOM | 4126 | OE1 | GLN | C | 127 | 66.383 | 74.535 | 58.730 | 1.00 | 74.85 | C |
| ATOM | 4127 | NE2 | GLN | C | 127 | 65.924 | 72.741 | 57.454 | 1.00 | 75.78 | C |
| ATOM | 4128 | C | GLN | C | 127 | 61.266 | 74.674 | 60.336 | 1.00 | 49.32 | C |
| ATOM | 4129 | O | GLN | C | 127 | 61.490 | 75.427 | 61.279 | 1.00 | 51.48 | C |
| ATOM | 4130 | N | PHE | C | 128 | 60.424 | 73.656 | 60.418 | 1.00 | 40.31 | C |
| ATOM | 4131 | CA | PHE | C | 128 | 59.730 | 73.370 | 61.654 | 1.00 | 36.32 | C |
| ATOM | 4132 | CB | PHE | C | 128 | 58.293 | 72.994 | 61.370 | 1.00 | 31.30 | C |
| ATOM | 4133 | CG | PHE | C | 128 | 57.397 | 74.168 | 61.173 | 1.00 | 33.31 | C |
| ATOM | 4134 | CD1 | PHE | C | 128 | 57.700 | 75.140 | 60.228 | 1.00 | 30.21 | C |
| ATOM | 4135 | CD2 | PHE | C | 128 | 56.216 | 74.288 | 61.914 | 1.00 | 29.84 | C |
| ATOM | 4136 | CE1 | PHE | C | 128 | 56.832 | 76.217 | 60.017 | 1.00 | 33.69 | C |
| ATOM | 4137 | CE2 | PHE | C | 128 | 55.342 | 75.364 | 61.708 | 1.00 | 31.82 | C |
| ATOM | 4138 | CZ | PHE | C | 128 | 55.648 | 76.325 | 60.760 | 1.00 | 31.59 | C |
| ATOM | 4139 | C | PHE | C | 128 | 60.381 | 72.233 | 62.404 | 1.00 | 36.88 | C |
| ATOM | 4140 | O | PHE | C | 128 | 60.989 | 71.353 | 61.798 | 1.00 | 43.36 | C |
| ATOM | 4141 | N | ILE | C | 129 | 60.274 | 72.266 | 63.727 | 1.00 | 36.56 | C |
| ATOM | 4142 | CA | ILE | C | 129 | 60.803 | 71.187 | 64.541 | 1.00 | 32.72 | C |
| ATOM | 4143 | CB | ILE | C | 129 | 61.942 | 71.619 | 65.467 | 1.00 | 29.71 | C |
| ATOM | 4144 | CG2 | ILE | C | 129 | 62.409 | 70.416 | 66.272 | 1.00 | 27.63 | C |
| ATOM | 4145 | CG1 | ILE | C | 129 | 63.110 | 72.164 | 64.644 | 1.00 | 28.37 | C |
| ATOM | 4146 | CD1 | ILE | C | 129 | 64.329 | 72.526 | 65.469 | 1.00 | 29.50 | C |
| ATOM | 4147 | C | ILE | C | 129 | 59.637 | 70.714 | 65.381 | 1.00 | 32.53 | C |
| ATOM | 4148 | O | ILE | C | 129 | 58.929 | 71.512 | 65.975 | 1.00 | 33.87 | C |
| ATOM | 4149 | N | GLY | C | 130 | 59.419 | 69.409 | 65.397 | 1.00 | 39.67 | C |
| ATOM | 4150 | CA | GLY | C | 130 | 58.319 | 68.859 | 66.157 | 1.00 | 42.90 | C |
| ATOM | 4151 | C | GLY | C | 130 | 58.856 | 68.102 | 67.340 | 1.00 | 46.93 | C |
| ATOM | 4152 | O | GLY | C | 130 | 60.005 | 67.666 | 67.360 | 1.00 | 47.85 | C |
| ATOM | 4153 | N | VAL | C | 131 | 58.024 | 67.939 | 68.344 | 1.00 | 51.66 | C |
| ATOM | 4154 | CA | VAL | C | 131 | 58.494 | 67.248 | 69.502 | 1.00 | 66.13 | C |
| ATOM | 4155 | CB | VAL | C | 131 | 58.459 | 68.203 | 70.696 | 1.00 | 63.29 | C |
| ATOM | 4156 | CG1 | VAL | C | 131 | 58.535 | 67.443 | 72.001 | 1.00 | 66.43 | C |
| ATOM | 4157 | CG2 | VAL | C | 131 | 59.629 | 69.158 | 70.581 | 1.00 | 65.95 | C |
| ATOM | 4158 | C | VAL | C | 131 | 57.648 | 66.017 | 69.711 | 1.00 | 65.95 | C |
| ATOM | 4159 | O | VAL | C | 131 | 58.041 | 64.905 | 69.327 | 1.00 | 67.83 | C |
| ATOM | 4160 | N | LYS | C | 132 | 56.479 | 66.236 | 70.299 | 1.00 | 74.58 | C |
| ATOM | 4161 | CA | LYS | C | 132 | 55.513 | 65.186 | 70.599 | 1.00 | 81.96 | C |
| ATOM | 4162 | CB | LYS | C | 132 | 56.116 | 63.774 | 70.444 | 1.00 | 83.06 | C |
| ATOM | 4163 | CG | LYS | C | 132 | 55.087 | 62.670 | 70.651 | 1.00 | 84.23 | C |
| ATOM | 4164 | CD | LYS | C | 132 | 55.422 | 61.397 | 69.900 | 1.00 | 85.21 | C |
| ATOM | 4165 | CE | LYS | C | 132 | 54.221 | 60.454 | 69.930 | 1.00 | 84.61 | C |
| ATOM | 4166 | NZ | LYS | C | 132 | 54.399 | 59.215 | 69.118 | 1.00 | 83.26 | C |
| ATOM | 4167 | C | LYS | C | 132 | 54.965 | 65.359 | 72.012 | 1.00 | 85.22 | C |
| ATOM | 4168 | O | LYS | C | 132 | 55.651 | 65.115 | 73.013 | 1.00 | 83.99 | C |
| ATOM | 4169 | N | ARG | C | 133 | 53.716 | 65.798 | 72.074 | 1.00 | 89.89 | C |
| ATOM | 4170 | CA | ARG | C | 133 | 53.036 | 65.999 | 73.333 | 1.00 | 97.24 | C |
| ATOM | 4171 | CB | ARG | C | 133 | 52.190 | 67.281 | 73.290 | 1.00 | 104.01 | C |
| ATOM | 4172 | CG | ARG | C | 133 | 51.052 | 67.290 | 74.310 | 1.00 | 108.05 | C |
| ATOM | 4173 | CD | ARG | C | 133 | 50.914 | 68.602 | 75.072 | 1.00 | 111.92 | C |
| ATOM | 4174 | NE | ARG | C | 133 | 50.074 | 69.592 | 74.396 | 1.00 | 116.36 | C |
| ATOM | 4175 | CZ | ARG | C | 133 | 49.579 | 70.675 | 74.994 | 1.00 | 118.27 | C |

Figure 10 (65 of 142)

| | | | | | | | | | |
|---|---|---|---|---|---|---|---|---|---|
| ATOM | 4176 | NH1 | ARG | C | 133 | 49.843 | 70.901 | 76.275 | 1.00 119.70 | C |
| ATOM | 4177 | NH2 | ARG | C | 133 | 48.819 | 71.530 | 74.320 | 1.00 119.55 | C |
| ATOM | 4178 | C | ARG | C | 133 | 52.150 | 64.796 | 73.623 | 1.00 99.13 | C |
| ATOM | 4179 | O | ARG | C | 133 | 51.657 | 64.127 | 72.712 | 1.00 97.73 | C |
| ATOM | 4180 | N | PRO | C | 134 | 51.959 | 64.495 | 74.909 | 1.00 98.28 | C |
| ATOM | 4181 | CD | PRO | C | 134 | 52.645 | 65.126 | 76.050 | 1.00 95.88 | C |
| ATOM | 4182 | CA | PRO | C | 134 | 51.131 | 63.372 | 75.351 | 1.00 96.74 | C |
| ATOM | 4183 | CB | PRO | C | 134 | 51.411 | 63.303 | 76.849 | 1.00 97.63 | C |
| ATOM | 4184 | CG | PRO | C | 134 | 52.744 | 63.991 | 77.002 | 1.00 95.80 | C |
| ATOM | 4185 | C | PRO | C | 134 | 49.665 | 63.692 | 75.076 | 1.00 101.90 | C |
| ATOM | 4186 | O | PRO | C | 134 | 49.189 | 64.771 | 75.440 | 1.00 104.33 | C |
| ATOM | 4187 | N | GLY | C | 135 | 48.956 | 62.760 | 74.442 | 1.00 104.74 | C |
| ATOM | 4188 | CA | GLY | C | 135 | 47.546 | 62.971 | 74.143 | 1.00 108.75 | C |
| ATOM | 4189 | C | GLY | C | 135 | 47.300 | 63.268 | 72.675 | 1.00 109.12 | C |
| ATOM | 4190 | O | GLY | C | 135 | 46.267 | 62.903 | 72.105 | 1.00 108.82 | C |
| ATOM | 4191 | N | PHE | C | 136 | 48.257 | 63.957 | 72.070 | 1.00 109.73 | C |
| ATOM | 4192 | CA | PHE | C | 136 | 48.183 | 64.297 | 70.664 | 1.00 108.13 | C |
| ATOM | 4193 | CB | PHE | C | 136 | 48.568 | 65.758 | 70.435 | 1.00 112.83 | C |
| ATOM | 4194 | CG | PHE | C | 136 | 47.770 | 66.727 | 71.248 | 1.00 116.55 | C |
| ATOM | 4195 | CD1 | PHE | C | 136 | 48.020 | 66.891 | 72.609 | 1.00 116.84 | C |
| ATOM | 4196 | CD2 | PHE | C | 136 | 46.742 | 67.455 | 70.662 | 1.00 117.15 | C |
| ATOM | 4197 | CE1 | PHE | C | 136 | 47.253 | 67.765 | 73.374 | 1.00 118.98 | C |
| ATOM | 4198 | CE2 | PHE | C | 136 | 45.972 | 68.330 | 71.416 | 1.00 119.09 | C |
| ATOM | 4199 | CZ | PHE | C | 136 | 46.227 | 68.486 | 72.776 | 1.00 120.05 | C |
| ATOM | 4200 | C | PHE | C | 136 | 49.223 | 63.409 | 70.034 | 1.00 102.62 | C |
| ATOM | 4201 | O | PHE | C | 136 | 49.910 | 62.662 | 70.729 | 1.00 100.88 | C |
| ATOM | 4202 | N | HIS | C | 137 | 49.345 | 63.479 | 68.719 | 1.00 98.21 | C |
| ATOM | 4203 | CA | HIS | C | 137 | 50.349 | 62.678 | 68.055 | 1.00 96.91 | C |
| ATOM | 4204 | CB | HIS | C | 137 | 49.944 | 61.182 | 68.046 | 1.00 98.45 | C |
| ATOM | 4205 | CG | HIS | C | 137 | 48.701 | 60.874 | 67.268 | 1.00 99.94 | C |
| ATOM | 4206 | CD2 | HIS | C | 137 | 47.482 | 60.439 | 67.670 | 1.00 99.90 | C |
| ATOM | 4207 | ND1 | HIS | C | 137 | 48.640 | 60.965 | 65.894 | 1.00 98.79 | C |
| ATOM | 4208 | CE1 | HIS | C | 137 | 47.439 | 60.598 | 65.483 | 1.00 100.92 | C |
| ATOM | 4209 | NE2 | HIS | C | 137 | 46.717 | 60.274 | 66.540 | 1.00 100.60 | C |
| ATOM | 4210 | C | HIS | C | 137 | 50.686 | 63.193 | 66.661 | 1.00 95.22 | C |
| ATOM | 4211 | O | HIS | C | 137 | 49.841 | 63.746 | 65.948 | 1.00 88.94 | C |
| ATOM | 4212 | N | VAL | C | 138 | 51.961 | 63.030 | 66.322 | 1.00 95.20 | C |
| ATOM | 4213 | CA | VAL | C | 138 | 52.543 | 63.448 | 65.055 | 1.00 99.28 | C |
| ATOM | 4214 | CB | VAL | C | 138 | 54.063 | 63.718 | 65.246 | 1.00 97.34 | C |
| ATOM | 4215 | CG1 | VAL | C | 138 | 54.665 | 62.688 | 66.191 | 1.00 99.18 | C |
| ATOM | 4216 | CG2 | VAL | C | 138 | 54.775 | 63.668 | 63.922 | 1.00 98.66 | C |
| ATOM | 4217 | C | VAL | C | 138 | 52.317 | 62.425 | 63.933 | 1.00 98.04 | C |
| ATOM | 4218 | O | VAL | C | 138 | 52.180 | 61.222 | 64.184 | 1.00 100.09 | C |
| ATOM | 4219 | N | GLU | C | 139 | 52.280 | 62.916 | 62.696 | 1.00 99.36 | C |
| ATOM | 4220 | CA | GLU | C | 139 | 52.052 | 62.066 | 61.533 | 1.00 98.04 | C |
| ATOM | 4221 | CB | GLU | C | 139 | 50.669 | 61.419 | 61.642 | 1.00 98.73 | C |
| ATOM | 4222 | CG | GLU | C | 139 | 49.510 | 62.408 | 61.445 | 1.00 99.30 | C |
| ATOM | 4223 | CD | GLU | C | 139 | 48.341 | 62.179 | 62.402 | 1.00 97.88 | C |
| ATOM | 4224 | OE1 | GLU | C | 139 | 48.101 | 61.014 | 62.790 | 1.00 95.98 | C |
| ATOM | 4225 | OE2 | GLU | C | 139 | 47.653 | 63.165 | 62.755 | 1.00 94.59 | C |
| ATOM | 4226 | C | GLU | C | 139 | 52.125 | 62.879 | 60.236 | 1.00 97.56 | C |
| ATOM | 4227 | O | GLU | C | 139 | 52.395 | 62.327 | 59.172 | 1.00 101.02 | C |
| ATOM | 4228 | N | THR | C | 140 | 51.886 | 64.188 | 60.350 | 1.00 93.38 | C |
| ATOM | 4229 | CA | THR | C | 140 | 51.871 | 65.144 | 59.227 | 1.00 85.60 | C |
| ATOM | 4230 | CB | THR | C | 140 | 52.445 | 66.543 | 59.598 | 1.00 87.57 | C |
| ATOM | 4231 | OG1 | THR | C | 140 | 53.723 | 66.397 | 60.231 | 1.00 86.86 | C |
| ATOM | 4232 | CG2 | THR | C | 140 | 51.480 | 67.307 | 60.477 | 1.00 86.66 | C |
| ATOM | 4233 | C | THR | C | 140 | 52.530 | 64.812 | 57.905 | 1.00 78.98 | C |
| ATOM | 4234 | O | THR | C | 140 | 53.553 | 64.127 | 57.838 | 1.00 77.33 | C |
| ATOM | 4235 | N | PRO | C | 141 | 51.947 | 65.344 | 56.823 | 1.00 74.05 | C |
| ATOM | 4236 | CD | PRO | C | 141 | 50.617 | 65.987 | 56.852 | 1.00 71.47 | C |
| ATOM | 4237 | CA | PRO | C | 141 | 52.400 | 65.175 | 55.447 | 1.00 69.46 | C |
| ATOM | 4238 | CB | PRO | C | 141 | 51.103 | 65.240 | 54.670 | 1.00 70.41 | C |
| ATOM | 4239 | CG | PRO | C | 141 | 50.383 | 66.333 | 55.396 | 1.00 71.06 | C |
| ATOM | 4240 | C | PRO | C | 141 | 53.317 | 66.331 | 55.094 | 1.00 60.53 | C |
| ATOM | 4241 | O | PRO | C | 141 | 53.727 | 66.481 | 53.951 | 1.00 62.94 | C |

Figure 10 (66 of 142)

```
ATOM   4242  N    TYR C 142      53.634  67.148  56.087  1.00 54.46           C
ATOM   4243  CA   TYR C 142      54.480  68.307  55.865  1.00 49.03           C
ATOM   4244  CB   TYR C 142      53.951  69.477  56.669  1.00 44.11           C
ATOM   4245  CG   TYR C 142      52.510  69.797  56.415  1.00 40.14           C
ATOM   4246  CD1  TYR C 142      52.133  70.603  55.343  1.00 40.07           C
ATOM   4247  CE1  TYR C 142      50.789  70.929  55.113  1.00 39.51           C
ATOM   4248  CD2  TYR C 142      51.518  69.308  57.259  1.00 40.67           C
ATOM   4249  CE2  TYR C 142      50.169  69.618  57.045  1.00 42.43           C
ATOM   4250  CZ   TYR C 142      49.804  70.433  55.966  1.00 42.03           C
ATOM   4251  OH   TYR C 142      48.466  70.741  55.751  1.00 36.83           C
ATOM   4252  C    TYR C 142      55.936  68.088  56.237  1.00 48.19           C
ATOM   4253  O    TYR C 142      56.253  67.279  57.111  1.00 47.20           C
ATOM   4254  N    PRO C 143      56.843  68.826  55.575  1.00 42.82           C
ATOM   4255  CD   PRO C 143      56.540  69.905  54.618  1.00 43.65           C
ATOM   4256  CA   PRO C 143      58.286  68.738  55.820  1.00 47.23           C
ATOM   4257  CB   PRO C 143      58.868  69.654  54.750  1.00 46.24           C
ATOM   4258  CG   PRO C 143      57.819  70.707  54.619  1.00 44.02           C
ATOM   4259  C    PRO C 143      58.523  69.269  57.226  1.00 53.14           C
ATOM   4260  O    PRO C 143      58.357  70.461  57.477  1.00 57.80           C
ATOM   4261  N    LEU C 144      58.920  68.402  58.145  1.00 51.04           C
ATOM   4262  CA   LEU C 144      59.102  68.839  59.515  1.00 48.24           C
ATOM   4263  CB   LEU C 144      57.760  68.645  60.212  1.00 51.44           C
ATOM   4264  CG   LEU C 144      57.311  69.395  61.451  1.00 53.11           C
ATOM   4265  CD1  LEU C 144      55.820  69.150  61.669  1.00 52.79           C
ATOM   4266  CD2  LEU C 144      58.113  68.918  62.641  1.00 58.62           C
ATOM   4267  C    LEU C 144      60.181  67.965  60.121  1.00 47.46           C
ATOM   4268  O    LEU C 144      60.273  66.793  59.777  1.00 49.67           C
ATOM   4269  N    LEU C 145      61.011  68.519  60.997  1.00 48.20           C
ATOM   4270  CA   LEU C 145      62.065  67.722  61.624  1.00 53.15           C
ATOM   4271  CB   LEU C 145      63.373  68.501  61.673  1.00 55.98           C
ATOM   4272  CG   LEU C 145      64.148  68.565  60.356  1.00 54.86           C
ATOM   4273  CD1  LEU C 145      65.351  69.495  60.524  1.00 55.66           C
ATOM   4274  CD2  LEU C 145      64.589  67.151  59.945  1.00 56.93           C
ATOM   4275  C    LEU C 145      61.647  67.330  63.024  1.00 51.05           C
ATOM   4276  O    LEU C 145      60.764  67.950  63.587  1.00 53.88           C
ATOM   4277  N    PHE C 146      62.283  66.316  63.602  1.00 54.38           C
ATOM   4278  CA   PHE C 146      61.892  65.880  64.939  1.00 58.82           C
ATOM   4279  CB   PHE C 146      61.176  64.538  64.833  1.00 64.14           C
ATOM   4280  CG   PHE C 146      59.903  64.605  64.047  1.00 63.90           C
ATOM   4281  CD1  PHE C 146      58.839  65.375  64.495  1.00 63.48           C
ATOM   4282  CD2  PHE C 146      59.773  63.927  62.844  1.00 66.05           C
ATOM   4283  CE1  PHE C 146      57.667  65.466  63.755  1.00 62.66           C
ATOM   4284  CE2  PHE C 146      58.604  64.014  62.100  1.00 63.16           C
ATOM   4285  CZ   PHE C 146      57.551  64.786  62.556  1.00 62.63           C
ATOM   4286  C    PHE C 146      62.974  65.797  66.011  1.00 56.71           C
ATOM   4287  O    PHE C 146      64.127  65.472  65.738  1.00 59.57           C
ATOM   4288  N    ALA C 147      62.571  66.100  67.242  1.00 50.30           C
ATOM   4289  CA   ALA C 147      63.464  66.059  68.395  1.00 47.35           C
ATOM   4290  CB   ALA C 147      63.794  67.477  68.846  1.00 45.30           C
ATOM   4291  C    ALA C 147      62.808  65.279  69.537  1.00 47.75           C
ATOM   4292  O    ALA C 147      61.706  65.611  69.979  1.00 44.50           C
ATOM   4293  N    ASP C 148      63.475  64.228  69.999  1.00 50.79           C
ATOM   4294  CA   ASP C 148      62.938  63.431  71.097  1.00 53.24           C
ATOM   4295  CB   ASP C 148      63.785  62.178  71.339  1.00 64.01           C
ATOM   4296  CG   ASP C 148      63.505  61.080  70.331  1.00 67.25           C
ATOM   4297  OD1  ASP C 148      63.819  61.272  69.136  1.00 73.16           C
ATOM   4298  OD2  ASP C 148      62.965  60.027  70.738  1.00 70.44           C
ATOM   4299  C    ASP C 148      62.901  64.267  72.366  1.00 47.42           C
ATOM   4300  O    ASP C 148      63.913  64.850  72.773  1.00 50.15           C
ATOM   4301  N    VAL C 149      61.724  64.312  72.983  1.00 42.29           C
ATOM   4302  CA   VAL C 149      61.494  65.072  74.206  1.00 38.25           C
ATOM   4303  CB   VAL C 149      60.901  66.467  73.911  1.00 39.55           C
ATOM   4304  CG1  VAL C 149      60.609  67.204  75.207  1.00 33.55           C
ATOM   4305  CG2  VAL C 149      61.859  67.260  73.059  1.00 40.00           C
ATOM   4306  C    VAL C 149      60.516  64.362  75.122  1.00 36.08           C
ATOM   4307  O    VAL C 149      59.365  64.136  74.757  1.00 37.86           C
```

Figure 10 (67 of 142)

| | | | | | | | | | | |
|---|---|---|---|---|---|---|---|---|---|---|
| ATOM | 4308 | N | PRO | C | 150 | 60.962 | 64.018 | 76.337 | 1.00 30.80 | C |
| ATOM | 4309 | CD | PRO | C | 150 | 62.291 | 64.352 | 76.870 | 1.00 33.05 | C |
| ATOM | 4310 | CA | PRO | C | 150 | 60.174 | 63.335 | 77.359 | 1.00 28.73 | C |
| ATOM | 4311 | CB | PRO | C | 150 | 60.929 | 63.671 | 78.634 | 1.00 25.04 | C |
| ATOM | 4312 | CG | PRO | C | 150 | 62.316 | 63.585 | 78.187 | 1.00 31.15 | C |
| ATOM | 4313 | C | PRO | C | 150 | 58.758 | 63.866 | 77.386 | 1.00 25.60 | C |
| ATOM | 4314 | O | PRO | C | 150 | 58.555 | 65.067 | 77.510 | 1.00 27.22 | C |
| ATOM | 4315 | N | GLU | C | 151 | 57.782 | 62.974 | 77.265 | 1.00 24.81 | C |
| ATOM | 4316 | CA | GLU | C | 151 | 56.387 | 63.390 | 77.272 | 1.00 25.33 | C |
| ATOM | 4317 | CB | GLU | C | 151 | 55.477 | 62.212 | 76.893 | 1.00 28.41 | C |
| ATOM | 4318 | CG | GLU | C | 151 | 54.636 | 61.688 | 78.047 | 1.00 46.51 | C |
| ATOM | 4319 | CD | GLU | C | 151 | 53.646 | 60.616 | 77.632 | 1.00 55.18 | C |
| ATOM | 4320 | OE1 | GLU | C | 151 | 54.083 | 59.500 | 77.261 | 1.00 56.33 | C |
| ATOM | 4321 | OE2 | GLU | C | 151 | 52.427 | 60.893 | 77.679 | 1.00 57.12 | C |
| ATOM | 4322 | C | GLU | C | 151 | 56.007 | 63.923 | 78.653 | 1.00 20.66 | C |
| ATOM | 4323 | O | GLU | C | 151 | 56.294 | 63.299 | 79.675 | 1.00 15.71 | C |
| ATOM | 4324 | N | PHE | C | 152 | 55.368 | 65.084 | 78.683 | 1.00 16.85 | C |
| ATOM | 4325 | CA | PHE | C | 152 | 54.951 | 65.688 | 79.947 | 1.00 15.01 | C |
| ATOM | 4326 | CB | PHE | C | 152 | 55.881 | 66.856 | 80.278 | 1.00 14.21 | C |
| ATOM | 4327 | CG | PHE | C | 152 | 55.723 | 67.409 | 81.657 | 1.00 16.67 | C |
| ATOM | 4328 | CD1 | PHE | C | 152 | 56.643 | 68.330 | 82.141 | 1.00 15.72 | C |
| ATOM | 4329 | CD2 | PHE | C | 152 | 54.668 | 67.020 | 82.472 | 1.00 19.82 | C |
| ATOM | 4330 | CE1 | PHE | C | 152 | 56.522 | 68.855 | 83.414 | 1.00 12.26 | C |
| ATOM | 4331 | CE2 | PHE | C | 152 | 54.531 | 67.545 | 83.763 | 1.00 19.16 | C |
| ATOM | 4332 | CZ | PHE | C | 152 | 55.462 | 68.463 | 84.232 | 1.00 12.26 | C |
| ATOM | 4333 | C | PHE | C | 152 | 53.510 | 66.150 | 79.726 | 1.00 14.71 | C |
| ATOM | 4334 | O | PHE | C | 152 | 53.242 | 67.135 | 79.048 | 1.00 25.78 | C |
| ATOM | 4335 | N | GLU | C | 153 | 52.577 | 65.403 | 80.290 | 1.00 12.83 | C |
| ATOM | 4336 | CA | GLU | C | 153 | 51.175 | 65.699 | 80.117 | 1.00 17.68 | C |
| ATOM | 4337 | CB | GLU | C | 153 | 50.338 | 64.486 | 80.529 | 1.00 22.91 | C |
| ATOM | 4338 | CG | GLU | C | 153 | 48.847 | 64.617 | 80.247 | 1.00 34.92 | C |
| ATOM | 4339 | CD | GLU | C | 153 | 48.040 | 63.436 | 80.790 | 1.00 34.75 | C |
| ATOM | 4340 | OE1 | GLU | C | 153 | 46.819 | 63.383 | 80.515 | 1.00 39.59 | C |
| ATOM | 4341 | OE2 | GLU | C | 153 | 48.623 | 62.568 | 81.490 | 1.00 38.50 | C |
| ATOM | 4342 | C | GLU | C | 153 | 50.742 | 66.924 | 80.895 | 1.00 19.43 | C |
| ATOM | 4343 | O | GLU | C | 153 | 50.151 | 66.813 | 81.960 | 1.00 13.93 | C |
| ATOM | 4344 | N | VAL | C | 154 | 51.044 | 68.100 | 80.359 | 1.00 20.59 | C |
| ATOM | 4345 | CA | VAL | C | 154 | 50.633 | 69.341 | 81.002 | 1.00 21.51 | C |
| ATOM | 4346 | CB | VAL | C | 154 | 51.685 | 69.866 | 81.986 | 1.00 17.56 | C |
| ATOM | 4347 | CG1 | VAL | C | 154 | 52.981 | 70.194 | 81.278 | 1.00 16.18 | C |
| ATOM | 4348 | CG2 | VAL | C | 154 | 51.150 | 71.084 | 82.647 | 1.00 13.95 | C |
| ATOM | 4349 | C | VAL | C | 154 | 50.350 | 70.408 | 79.957 | 1.00 23.33 | C |
| ATOM | 4350 | O | VAL | C | 154 | 51.139 | 70.610 | 79.029 | 1.00 29.19 | C |
| ATOM | 4351 | N | SER | C | 155 | 49.209 | 71.076 | 80.113 | 1.00 26.03 | C |
| ATOM | 4352 | CA | SER | C | 155 | 48.757 | 72.115 | 79.182 | 1.00 28.51 | C |
| ATOM | 4353 | CB | SER | C | 155 | 47.618 | 71.589 | 78.303 | 1.00 30.92 | C |
| ATOM | 4354 | OG | SER | C | 155 | 46.429 | 71.405 | 79.064 | 1.00 27.07 | C |
| ATOM | 4355 | C | SER | C | 155 | 48.218 | 73.257 | 80.005 | 1.00 28.92 | C |
| ATOM | 4356 | O | SER | C | 155 | 47.840 | 73.056 | 81.152 | 1.00 35.21 | C |
| ATOM | 4357 | N | SER | C | 156 | 48.149 | 74.447 | 79.424 | 1.00 27.40 | C |
| ATOM | 4358 | CA | SER | C | 156 | 47.644 | 75.595 | 80.166 | 1.00 27.22 | C |
| ATOM | 4359 | CB | SER | C | 156 | 47.852 | 76.856 | 79.365 | 1.00 23.78 | C |
| ATOM | 4360 | OG | SER | C | 156 | 46.831 | 76.902 | 78.405 | 1.00 30.38 | C |
| ATOM | 4361 | C | SER | C | 156 | 46.153 | 75.475 | 80.487 | 1.00 25.19 | C |
| ATOM | 4362 | O | SER | C | 156 | 45.682 | 75.901 | 81.550 | 1.00 30.97 | C |
| ATOM | 4363 | N | THR | C | 157 | 45.404 | 74.905 | 79.558 | 1.00 23.15 | C |
| ATOM | 4364 | CA | THR | C | 157 | 43.983 | 74.745 | 79.776 | 1.00 30.50 | C |
| ATOM | 4365 | CB | THR | C | 157 | 43.289 | 74.215 | 78.508 | 1.00 31.08 | C |
| ATOM | 4366 | OG1 | THR | C | 157 | 43.447 | 75.169 | 77.452 | 1.00 27.88 | C |
| ATOM | 4367 | CG2 | THR | C | 157 | 41.799 | 73.993 | 78.759 | 1.00 26.11 | C |
| ATOM | 4368 | C | THR | C | 157 | 43.784 | 73.778 | 80.933 | 1.00 31.21 | C |
| ATOM | 4369 | O | THR | C | 157 | 42.660 | 73.507 | 81.346 | 1.00 39.95 | C |
| ATOM | 4370 | N | MET | C | 158 | 44.882 | 73.239 | 81.445 | 1.00 31.53 | C |
| ATOM | 4371 | CA | MET | C | 158 | 44.816 | 72.338 | 82.582 | 1.00 29.78 | C |
| ATOM | 4372 | CB | MET | C | 158 | 46.018 | 71.397 | 82.570 | 1.00 33.57 | C |
| ATOM | 4373 | CG | MET | C | 158 | 46.171 | 70.517 | 83.791 | 1.00 26.47 | C |

Figure 10 (68 of 142)

| ATOM | 4374 | SD | MET | C | 158 | 47.691 | 69.577 | 83.664 | 1.00 | 20.31 | C |
|---|---|---|---|---|---|---|---|---|---|---|---|
| ATOM | 4375 | CE | MET | C | 158 | 47.387 | 68.746 | 82.086 | 1.00 | 23.82 | C |
| ATOM | 4376 | C | MET | C | 158 | 44.899 | 73.276 | 83.769 | 1.00 | 25.13 | C |
| ATOM | 4377 | O | MET | C | 158 | 44.015 | 73.302 | 84.636 | 1.00 | 32.81 | C |
| ATOM | 4378 | N | ILE | C | 159 | 45.967 | 74.071 | 83.757 | 1.00 | 12.26 | C |
| ATOM | 4379 | CA | ILE | C | 159 | 46.261 | 75.036 | 84.802 | 1.00 | 15.60 | C |
| ATOM | 4380 | CB | ILE | C | 159 | 47.460 | 75.921 | 84.423 | 1.00 | 12.26 | C |
| ATOM | 4381 | CG2 | ILE | C | 159 | 47.906 | 76.727 | 85.652 | 1.00 | 12.26 | C |
| ATOM | 4382 | CG1 | ILE | C | 159 | 48.599 | 75.059 | 83.886 | 1.00 | 12.26 | C |
| ATOM | 4383 | CD1 | ILE | C | 159 | 49.118 | 74.051 | 84.878 | 1.00 | 24.23 | C |
| ATOM | 4384 | C | ILE | C | 159 | 45.078 | 75.942 | 85.102 | 1.00 | 17.31 | C |
| ATOM | 4385 | O | ILE | C | 159 | 44.705 | 76.150 | 86.266 | 1.00 | 16.19 | C |
| ATOM | 4386 | N | ARG | C | 160 | 44.477 | 76.479 | 84.049 | 1.00 | 18.75 | C |
| ATOM | 4387 | CA | ARG | C | 160 | 43.360 | 77.374 | 84.245 | 1.00 | 18.50 | C |
| ATOM | 4388 | CB | ARG | C | 160 | 42.834 | 77.824 | 82.890 | 1.00 | 13.82 | C |
| ATOM | 4389 | CG | ARG | C | 160 | 43.947 | 78.204 | 81.949 | 1.00 | 15.43 | C |
| ATOM | 4390 | CD | ARG | C | 160 | 43.633 | 79.483 | 81.193 | 1.00 | 21.09 | C |
| ATOM | 4391 | NE | ARG | C | 160 | 43.970 | 79.354 | 79.779 | 1.00 | 25.84 | C |
| ATOM | 4392 | CZ | ARG | C | 160 | 43.323 | 78.564 | 78.928 | 1.00 | 25.33 | C |
| ATOM | 4393 | NH1 | ARG | C | 160 | 42.298 | 77.829 | 79.343 | 1.00 | 27.80 | C |
| ATOM | 4394 | NH2 | ARG | C | 160 | 43.700 | 78.508 | 77.659 | 1.00 | 24.80 | C |
| ATOM | 4395 | C | ARG | C | 160 | 42.254 | 76.714 | 85.070 | 1.00 | 17.76 | C |
| ATOM | 4396 | O | ARG | C | 160 | 41.750 | 77.291 | 86.042 | 1.00 | 20.84 | C |
| ATOM | 4397 | N | GLU | C | 161 | 41.883 | 75.496 | 84.700 | 1.00 | 19.67 | C |
| ATOM | 4398 | CA | GLU | C | 161 | 40.825 | 74.822 | 85.414 | 1.00 | 23.09 | C |
| ATOM | 4399 | CB | GLU | C | 161 | 40.363 | 73.596 | 84.637 | 1.00 | 32.71 | C |
| ATOM | 4400 | CG | GLU | C | 161 | 39.896 | 73.905 | 83.208 | 1.00 | 43.99 | C |
| ATOM | 4401 | CD | GLU | C | 161 | 39.289 | 72.682 | 82.499 | 1.00 | 48.78 | C |
| ATOM | 4402 | OE1 | GLU | C | 161 | 38.186 | 72.251 | 82.910 | 1.00 | 51.37 | C |
| ATOM | 4403 | OE2 | GLU | C | 161 | 39.910 | 72.146 | 81.541 | 1.00 | 50.12 | C |
| ATOM | 4404 | C | GLU | C | 161 | 41.337 | 74.432 | 86.777 | 1.00 | 25.25 | C |
| ATOM | 4405 | O | GLU | C | 161 | 40.595 | 74.425 | 87.760 | 1.00 | 25.88 | C |
| ATOM | 4406 | N | ARG | C | 162 | 42.616 | 74.099 | 86.838 | 1.00 | 23.69 | C |
| ATOM | 4407 | CA | ARG | C | 162 | 43.216 | 73.724 | 88.099 | 1.00 | 23.96 | C |
| ATOM | 4408 | CB | ARG | C | 162 | 44.663 | 73.353 | 87.851 | 1.00 | 20.93 | C |
| ATOM | 4409 | CG | ARG | C | 162 | 45.140 | 72.161 | 88.608 | 1.00 | 27.39 | C |
| ATOM | 4410 | CD | ARG | C | 162 | 45.050 | 70.896 | 87.781 | 1.00 | 30.77 | C |
| ATOM | 4411 | NE | ARG | C | 162 | 45.964 | 69.886 | 88.322 | 1.00 | 33.24 | C |
| ATOM | 4412 | CZ | ARG | C | 162 | 46.102 | 68.659 | 87.838 | 1.00 | 34.15 | C |
| ATOM | 4413 | NH1 | ARG | C | 162 | 45.378 | 68.270 | 86.791 | 1.00 | 37.45 | C |
| ATOM | 4414 | NH2 | ARG | C | 162 | 46.980 | 67.831 | 88.395 | 1.00 | 32.82 | C |
| ATOM | 4415 | C | ARG | C | 162 | 43.102 | 74.986 | 88.969 | 1.00 | 27.53 | C |
| ATOM | 4416 | O | ARG | C | 162 | 42.565 | 74.953 | 90.080 | 1.00 | 29.16 | C |
| ATOM | 4417 | N | PHE | C | 163 | 43.593 | 76.099 | 88.427 | 1.00 | 33.01 | C |
| ATOM | 4418 | CA | PHE | C | 163 | 43.550 | 77.410 | 89.083 | 1.00 | 37.14 | C |
| ATOM | 4419 | CB | PHE | C | 163 | 44.357 | 78.439 | 88.284 | 1.00 | 34.44 | C |
| ATOM | 4420 | CG | PHE | C | 163 | 45.767 | 78.598 | 88.734 | 1.00 | 32.43 | C |
| ATOM | 4421 | CD1 | PHE | C | 163 | 46.208 | 78.011 | 89.894 | 1.00 | 36.69 | C |
| ATOM | 4422 | CD2 | PHE | C | 163 | 46.656 | 79.362 | 88.003 | 1.00 | 32.41 | C |
| ATOM | 4423 | CE1 | PHE | C | 163 | 47.520 | 78.184 | 90.321 | 1.00 | 38.71 | C |
| ATOM | 4424 | CE2 | PHE | C | 163 | 47.967 | 79.540 | 88.424 | 1.00 | 35.07 | C |
| ATOM | 4425 | CZ | PHE | C | 163 | 48.396 | 78.953 | 89.579 | 1.00 | 36.72 | C |
| ATOM | 4426 | C | PHE | C | 163 | 42.117 | 77.917 | 89.145 | 1.00 | 41.71 | C |
| ATOM | 4427 | O | PHE | C | 163 | 41.879 | 79.120 | 89.055 | 1.00 | 48.11 | C |
| ATOM | 4428 | N | LYS | C | 164 | 41.164 | 77.010 | 89.274 | 1.00 | 42.66 | C |
| ATOM | 4429 | CA | LYS | C | 164 | 39.764 | 77.387 | 89.319 | 1.00 | 44.25 | C |
| ATOM | 4430 | CB | LYS | C | 164 | 39.337 | 77.992 | 87.981 | 1.00 | 48.65 | C |
| ATOM | 4431 | CG | LYS | C | 164 | 37.944 | 78.616 | 87.980 | 1.00 | 55.56 | C |
| ATOM | 4432 | CD | LYS | C | 164 | 36.851 | 77.563 | 88.137 | 1.00 | 58.62 | C |
| ATOM | 4433 | CE | LYS | C | 164 | 35.459 | 78.174 | 88.201 | 1.00 | 58.16 | C |
| ATOM | 4434 | NZ | LYS | C | 164 | 34.417 | 77.127 | 88.428 | 1.00 | 57.75 | C |
| ATOM | 4435 | C | LYS | C | 164 | 39.075 | 76.074 | 89.545 | 1.00 | 41.21 | C |
| ATOM | 4436 | O | LYS | C | 164 | 38.610 | 75.429 | 88.617 | 1.00 | 41.73 | C |
| ATOM | 4437 | N | SER | C | 165 | 39.034 | 75.689 | 90.804 | 1.00 | 38.26 | C |
| ATOM | 4438 | CA | SER | C | 165 | 38.469 | 74.431 | 91.266 | 1.00 | 35.39 | C |
| ATOM | 4439 | CB | SER | C | 165 | 38.346 | 73.383 | 90.160 | 1.00 | 34.41 | C |

Figure 10 (69 of 142)

```
ATOM   4440  OG   SER C 165      37.617  72.260  90.645  1.00 39.16           C
ATOM   4441  C    SER C 165      39.576  74.031  92.208  1.00 29.52           C
ATOM   4442  O    SER C 165      39.744  72.872  92.563  1.00 32.19           C
ATOM   4443  N    LYS C 166      40.347  75.048  92.563  1.00 24.43           C
ATOM   4444  CA   LYS C 166      41.454  74.946  93.475  1.00 18.11           C
ATOM   4445  CB   LYS C 166      40.992  75.319  94.876  1.00 28.40           C
ATOM   4446  CG   LYS C 166      39.557  75.859  94.966  1.00 32.23           C
ATOM   4447  CD   LYS C 166      39.517  77.393  95.022  1.00 41.89           C
ATOM   4448  CE   LYS C 166      40.412  77.922  96.150  1.00 50.53           C
ATOM   4449  NZ   LYS C 166      40.476  79.412  96.192  1.00 55.48           C
ATOM   4450  C    LYS C 166      42.093  73.580  93.522  1.00 13.46           C
ATOM   4451  O    LYS C 166      41.967  72.878  94.521  1.00 12.26           C
ATOM   4452  N    LYS C 167      42.753  73.182  92.441  1.00 12.26           C
ATOM   4453  CA   LYS C 167      43.457  71.911  92.418  1.00 12.26           C
ATOM   4454  CB   LYS C 167      43.159  71.152  91.143  1.00 12.26           C
ATOM   4455  CG   LYS C 167      41.982  70.234  91.237  1.00 12.26           C
ATOM   4456  CD   LYS C 167      42.114  69.141  90.206  1.00 12.26           C
ATOM   4457  CE   LYS C 167      41.086  68.092  90.478  1.00 12.26           C
ATOM   4458  NZ   LYS C 167      41.391  66.771  89.857  1.00 21.69           C
ATOM   4459  C    LYS C 167      44.938  72.270  92.474  1.00 12.26           C
ATOM   4460  O    LYS C 167      45.316  73.346  92.065  1.00 16.32           C
ATOM   4461  N    PRO C 168      45.794  71.363  92.966  1.00 12.26           C
ATOM   4462  CD   PRO C 168      45.410  69.961  93.205  1.00 12.26           C
ATOM   4463  CA   PRO C 168      47.243  71.509  93.118  1.00 12.26           C
ATOM   4464  CB   PRO C 168      47.735  70.094  92.897  1.00 12.26           C
ATOM   4465  CG   PRO C 168      46.713  69.324  93.654  1.00 12.26           C
ATOM   4466  C    PRO C 168      48.059  72.541  92.333  1.00 14.15           C
ATOM   4467  O    PRO C 168      48.597  73.491  92.927  1.00 17.60           C
ATOM   4468  N    THR C 169      48.157  72.382  91.019  1.00 12.26           C
ATOM   4469  CA   THR C 169      48.971  73.295  90.198  1.00 15.37           C
ATOM   4470  CB   THR C 169      48.499  74.759  90.225  1.00 14.88           C
ATOM   4471  OG1  THR C 169      49.553  75.571  90.756  1.00 13.30           C
ATOM   4472  CG2  THR C 169      47.279  74.939  91.081  1.00 19.29           C
ATOM   4473  C    THR C 169      50.472  73.354  90.552  1.00 18.49           C
ATOM   4474  O    THR C 169      51.242  73.951  89.805  1.00 23.56           C
ATOM   4475  N    ASP C 170      50.898  72.776  91.675  1.00 19.57           C
ATOM   4476  CA   ASP C 170      52.324  72.781  92.025  1.00 18.97           C
ATOM   4477  CB   ASP C 170      52.542  72.459  93.499  1.00 23.62           C
ATOM   4478  CG   ASP C 170      52.013  73.533  94.406  1.00 27.13           C
ATOM   4479  OD1  ASP C 170      50.781  73.579  94.617  1.00 33.83           C
ATOM   4480  OD2  ASP C 170      52.830  74.336  94.900  1.00 27.81           C
ATOM   4481  C    ASP C 170      53.082  71.759  91.195  1.00 15.36           C
ATOM   4482  O    ASP C 170      52.568  70.674  90.910  1.00 20.42           C
ATOM   4483  N    TYR C 171      54.313  72.103  90.833  1.00 12.26           C
ATOM   4484  CA   TYR C 171      55.162  71.249  90.010  1.00 12.71           C
ATOM   4485  CB   TYR C 171      55.266  69.841  90.599  1.00 12.26           C
ATOM   4486  CG   TYR C 171      55.760  69.835  92.023  1.00 14.11           C
ATOM   4487  CD1  TYR C 171      54.887  69.557  93.088  1.00 14.49           C
ATOM   4488  CE1  TYR C 171      55.336  69.573  94.412  1.00 17.34           C
ATOM   4489  CD2  TYR C 171      57.093  70.128  92.315  1.00 12.26           C
ATOM   4490  CE2  TYR C 171      57.556  70.150  93.629  1.00 12.26           C
ATOM   4491  CZ   TYR C 171      56.680  69.873  94.671  1.00 20.35           C
ATOM   4492  OH   TYR C 171      57.169  69.896  95.955  1.00 19.50           C
ATOM   4493  C    TYR C 171      54.676  71.165  88.557  1.00 12.26           C
ATOM   4494  O    TYR C 171      55.110  70.289  87.805  1.00 14.76           C
ATOM   4495  N    LEU C 172      53.781  72.080  88.176  1.00 12.26           C
ATOM   4496  CA   LEU C 172      53.256  72.141  86.817  1.00 12.26           C
ATOM   4497  CB   LEU C 172      51.739  71.984  86.829  1.00 12.26           C
ATOM   4498  CG   LEU C 172      51.266  70.647  87.374  1.00 12.26           C
ATOM   4499  CD1  LEU C 172      49.766  70.602  87.355  1.00 12.26           C
ATOM   4500  CD2  LEU C 172      51.843  69.535  86.530  1.00 12.26           C
ATOM   4501  C    LEU C 172      53.657  73.493  86.222  1.00 16.83           C
ATOM   4502  O    LEU C 172      53.957  73.605  85.026  1.00 12.26           C
ATOM   4503  N    ILE C 173      53.678  74.516  87.075  1.00 21.15           C
ATOM   4504  CA   ILE C 173      54.058  75.874  86.676  1.00 18.88           C
ATOM   4505  CB   ILE C 173      52.849  76.856  86.656  1.00 12.26           C
```

Figure 10 (70 of 142)

| | | | | | | | | | | |
|---|---|---|---|---|---|---|---|---|---|---|
| ATOM | 4506 | CG2 | ILE | C | 173 | 51.888 | 76.497 | 85.574 | 1.00 12.26 | C |
| ATOM | 4507 | CG1 | ILE | C | 173 | 52.155 | 76.855 | 88.006 | 1.00 12.26 | C |
| ATOM | 4508 | CD1 | ILE | C | 173 | 51.063 | 77.852 | 88.087 | 1.00 12.26 | C |
| ATOM | 4509 | C | ILE | C | 173 | 55.060 | 76.402 | 87.701 | 1.00 22.07 | C |
| ATOM | 4510 | O | ILE | C | 173 | 54.955 | 76.077 | 88.889 | 1.00 23.77 | C |
| ATOM | 4511 | N | PRO | C | 174 | 56.045 | 77.215 | 87.261 | 1.00 18.78 | C |
| ATOM | 4512 | CD | PRO | C | 174 | 56.248 | 77.678 | 85.881 | 1.00 16.84 | C |
| ATOM | 4513 | CA | PRO | C | 174 | 57.065 | 77.792 | 88.144 | 1.00 18.52 | C |
| ATOM | 4514 | CB | PRO | C | 174 | 57.703 | 78.845 | 87.271 | 1.00 19.93 | C |
| ATOM | 4515 | CG | PRO | C | 174 | 57.640 | 78.211 | 85.933 | 1.00 18.14 | C |
| ATOM | 4516 | C | PRO | C | 174 | 56.402 | 78.397 | 89.354 | 1.00 17.88 | C |
| ATOM | 4517 | O | PRO | C | 174 | 55.352 | 79.026 | 89.227 | 1.00 17.47 | C |
| ATOM | 4518 | N | ASP | C | 175 | 57.006 | 78.235 | 90.521 | 1.00 22.09 | C |
| ATOM | 4519 | CA | ASP | C | 175 | 56.350 | 78.759 | 91.697 | 1.00 25.67 | C |
| ATOM | 4520 | CB | ASP | C | 175 | 57.073 | 78.356 | 92.981 | 1.00 36.56 | C |
| ATOM | 4521 | CG | ASP | C | 175 | 56.105 | 77.869 | 94.046 | 1.00 37.92 | C |
| ATOM | 4522 | OD1 | ASP | C | 175 | 55.449 | 78.725 | 94.696 | 1.00 39.57 | C |
| ATOM | 4523 | OD2 | ASP | C | 175 | 55.984 | 76.627 | 94.206 | 1.00 43.25 | C |
| ATOM | 4524 | C | ASP | C | 175 | 56.232 | 80.250 | 91.583 | 1.00 22.64 | C |
| ATOM | 4525 | O | ASP | C | 175 | 55.433 | 80.879 | 92.285 | 1.00 25.57 | C |
| ATOM | 4526 | N | LYS | C | 176 | 57.005 | 80.821 | 90.670 | 1.00 16.63 | C |
| ATOM | 4527 | CA | LYS | C | 176 | 56.944 | 82.259 | 90.485 | 1.00 15.72 | C |
| ATOM | 4528 | CB | LYS | C | 176 | 58.185 | 82.757 | 89.749 | 1.00 15.28 | C |
| ATOM | 4529 | CG | LYS | C | 176 | 59.421 | 82.741 | 90.624 | 1.00 17.77 | C |
| ATOM | 4530 | CD | LYS | C | 176 | 60.633 | 83.355 | 89.940 | 1.00 19.84 | C |
| ATOM | 4531 | CE | LYS | C | 176 | 61.364 | 84.283 | 90.898 | 1.00 20.91 | C |
| ATOM | 4532 | NZ | LYS | C | 176 | 60.415 | 85.263 | 91.514 | 1.00 27.89 | C |
| ATOM | 4533 | C | LYS | C | 176 | 55.687 | 82.601 | 89.712 | 1.00 20.05 | C |
| ATOM | 4534 | O | LYS | C | 176 | 55.006 | 83.581 | 90.010 | 1.00 21.51 | C |
| ATOM | 4535 | N | VAL | C | 177 | 55.365 | 81.771 | 88.731 | 1.00 16.31 | C |
| ATOM | 4536 | CA | VAL | C | 177 | 54.199 | 82.016 | 87.925 | 1.00 12.26 | C |
| ATOM | 4537 | CB | VAL | C | 177 | 54.190 | 81.078 | 86.705 | 1.00 12.26 | C |
| ATOM | 4538 | CG1 | VAL | C | 177 | 52.837 | 81.109 | 86.019 | 1.00 12.56 | C |
| ATOM | 4539 | CG2 | VAL | C | 177 | 55.255 | 81.526 | 85.720 | 1.00 12.26 | C |
| ATOM | 4540 | C | VAL | C | 177 | 52.963 | 81.842 | 88.782 | 1.00 12.26 | C |
| ATOM | 4541 | O | VAL | C | 177 | 52.026 | 82.631 | 88.696 | 1.00 12.26 | C |
| ATOM | 4542 | N | LYS | C | 178 | 52.964 | 80.828 | 89.637 | 1.00 16.94 | C |
| ATOM | 4543 | CA | LYS | C | 178 | 51.803 | 80.616 | 90.489 | 1.00 14.96 | C |
| ATOM | 4544 | CB | LYS | C | 178 | 51.990 | 79.441 | 91.459 | 1.00 12.26 | C |
| ATOM | 4545 | CG | LYS | C | 178 | 50.696 | 79.105 | 92.213 | 1.00 13.93 | C |
| ATOM | 4546 | CD | LYS | C | 178 | 50.790 | 77.828 | 93.021 | 1.00 19.63 | C |
| ATOM | 4547 | CE | LYS | C | 178 | 51.768 | 77.976 | 94.168 | 1.00 24.17 | C |
| ATOM | 4548 | NZ | LYS | C | 178 | 51.890 | 76.687 | 94.911 | 1.00 22.19 | C |
| ATOM | 4549 | C | LYS | C | 178 | 51.524 | 81.885 | 91.282 | 1.00 15.78 | C |
| ATOM | 4550 | O | LYS | C | 178 | 50.372 | 82.333 | 91.336 | 1.00 15.50 | C |
| ATOM | 4551 | N | LYS | C | 179 | 52.563 | 82.473 | 91.885 | 1.00 12.26 | C |
| ATOM | 4552 | CA | LYS | C | 179 | 52.366 | 83.701 | 92.662 | 1.00 12.26 | C |
| ATOM | 4553 | CB | LYS | C | 179 | 53.670 | 84.208 | 93.278 | 1.00 12.26 | C |
| ATOM | 4554 | CG | LYS | C | 179 | 54.232 | 83.314 | 94.368 | 1.00 19.00 | C |
| ATOM | 4555 | CD | LYS | C | 179 | 53.258 | 83.098 | 95.536 | 1.00 20.29 | C |
| ATOM | 4556 | CE | LYS | C | 179 | 53.803 | 82.021 | 96.489 | 1.00 22.39 | C |
| ATOM | 4557 | NZ | LYS | C | 179 | 52.931 | 81.817 | 97.683 | 1.00 26.19 | C |
| ATOM | 4558 | C | LYS | C | 179 | 51.770 | 84.803 | 91.808 | 1.00 12.26 | C |
| ATOM | 4559 | O | LYS | C | 179 | 50.796 | 85.440 | 92.202 | 1.00 12.26 | C |
| ATOM | 4560 | N | TYR | C | 180 | 52.334 | 85.027 | 90.629 | 1.00 15.49 | C |
| ATOM | 4561 | CA | TYR | C | 180 | 51.801 | 86.072 | 89.778 | 1.00 12.26 | C |
| ATOM | 4562 | CB | TYR | C | 180 | 52.513 | 86.088 | 88.443 | 1.00 12.26 | C |
| ATOM | 4563 | CG | TYR | C | 180 | 52.107 | 87.254 | 87.575 | 1.00 12.26 | C |
| ATOM | 4564 | CD1 | TYR | C | 180 | 52.907 | 88.392 | 87.475 | 1.00 15.42 | C |
| ATOM | 4565 | CE1 | TYR | C | 180 | 52.529 | 89.465 | 86.676 | 1.00 12.26 | C |
| ATOM | 4566 | CD2 | TYR | C | 180 | 50.912 | 87.222 | 86.853 | 1.00 12.32 | C |
| ATOM | 4567 | CE2 | TYR | C | 180 | 50.525 | 88.291 | 86.055 | 1.00 14.90 | C |
| ATOM | 4568 | CZ | TYR | C | 180 | 51.338 | 89.400 | 85.975 | 1.00 12.26 | C |
| ATOM | 4569 | OH | TYR | C | 180 | 50.935 | 90.441 | 85.194 | 1.00 13.44 | C |
| ATOM | 4570 | C | TYR | C | 180 | 50.303 | 85.884 | 89.549 | 1.00 12.26 | C |
| ATOM | 4571 | O | TYR | C | 180 | 49.529 | 86.838 | 89.646 | 1.00 12.26 | C |

Figure 10 (71 of 142)

| | | | | | | | | | | |
|---|---|---|---|---|---|---|---|---|---|---|
| ATOM | 4572 | N | VAL | C | 181 | 49.885 | 84.663 | 89.235 | 1.00 12.26 | C |
| ATOM | 4573 | CA | VAL | C | 181 | 48.465 | 84.441 | 89.021 | 1.00 12.26 | C |
| ATOM | 4574 | CB | VAL | C | 181 | 48.138 | 82.988 | 88.637 | 1.00 12.26 | C |
| ATOM | 4575 | CG1 | VAL | C | 181 | 46.634 | 82.817 | 88.586 | 1.00 12.26 | C |
| ATOM | 4576 | CG2 | VAL | C | 181 | 48.733 | 82.649 | 87.296 | 1.00 12.26 | C |
| ATOM | 4577 | C | VAL | C | 181 | 47.678 | 84.793 | 90.280 | 1.00 12.26 | C |
| ATOM | 4578 | O | VAL | C | 181 | 46.723 | 85.574 | 90.217 | 1.00 12.76 | C |
| ATOM | 4579 | N | GLU | C | 182 | 48.072 | 84.227 | 91.419 | 1.00 12.26 | C |
| ATOM | 4580 | CA | GLU | C | 182 | 47.367 | 84.507 | 92.653 | 1.00 12.26 | C |
| ATOM | 4581 | CB | GLU | C | 182 | 48.045 | 83.807 | 93.818 | 1.00 12.26 | C |
| ATOM | 4582 | CG | GLU | C | 182 | 48.137 | 82.330 | 93.616 | 1.00 16.48 | C |
| ATOM | 4583 | CD | GLU | C | 182 | 48.784 | 81.593 | 94.792 | 1.00 20.75 | C |
| ATOM | 4584 | OE1 | GLU | C | 182 | 49.875 | 82.018 | 95.274 | 1.00 16.84 | C |
| ATOM | 4585 | OE2 | GLU | C | 182 | 48.192 | 80.568 | 95.218 | 1.00 23.25 | C |
| ATOM | 4586 | C | GLU | C | 182 | 47.321 | 86.006 | 92.892 | 1.00 12.26 | C |
| ATOM | 4587 | O | GLU | C | 182 | 46.244 | 86.592 | 93.019 | 1.00 12.26 | C |
| ATOM | 4588 | N | GLU | C | 183 | 48.486 | 86.632 | 92.911 | 1.00 12.26 | C |
| ATOM | 4589 | CA | GLU | C | 183 | 48.549 | 88.060 | 93.162 | 1.00 13.15 | C |
| ATOM | 4590 | CB | GLU | C | 183 | 49.998 | 88.562 | 93.106 | 1.00 16.91 | C |
| ATOM | 4591 | CG | GLU | C | 183 | 50.967 | 87.775 | 93.996 | 1.00 28.07 | C |
| ATOM | 4592 | CD | GLU | C | 183 | 52.337 | 88.436 | 94.173 | 1.00 28.21 | C |
| ATOM | 4593 | OE1 | GLU | C | 183 | 52.855 | 89.022 | 93.206 | 1.00 30.71 | C |
| ATOM | 4594 | OE2 | GLU | C | 183 | 52.908 | 88.352 | 95.282 | 1.00 32.82 | C |
| ATOM | 4595 | C | GLU | C | 183 | 47.688 | 88.895 | 92.220 | 1.00 15.59 | C |
| ATOM | 4596 | O | GLU | C | 183 | 46.826 | 89.643 | 92.668 | 1.00 13.27 | C |
| ATOM | 4597 | N | ASN | C | 184 | 47.891 | 88.772 | 90.915 | 1.00 19.23 | C |
| ATOM | 4598 | CA | ASN | C | 184 | 47.122 | 89.594 | 89.992 | 1.00 23.10 | C |
| ATOM | 4599 | CB | ASN | C | 184 | 47.960 | 89.855 | 88.733 | 1.00 33.14 | C |
| ATOM | 4600 | CG | ASN | C | 184 | 48.517 | 91.280 | 88.689 | 1.00 42.68 | C |
| ATOM | 4601 | OD1 | ASN | C | 184 | 49.661 | 91.497 | 88.276 | 1.00 49.09 | C |
| ATOM | 4602 | ND2 | ASN | C | 184 | 47.700 | 92.263 | 89.103 | 1.00 48.84 | C |
| ATOM | 4603 | C | ASN | C | 184 | 45.699 | 89.126 | 89.639 | 1.00 19.82 | C |
| ATOM | 4604 | O | ASN | C | 184 | 45.146 | 89.484 | 88.591 | 1.00 25.03 | C |
| ATOM | 4605 | N | GLY | C | 185 | 45.098 | 88.353 | 90.532 | 1.00 16.55 | C |
| ATOM | 4606 | CA | GLY | C | 185 | 43.748 | 87.874 | 90.304 | 1.00 17.72 | C |
| ATOM | 4607 | C | GLY | C | 185 | 43.440 | 87.069 | 89.042 | 1.00 18.67 | C |
| ATOM | 4608 | O | GLY | C | 185 | 42.282 | 87.020 | 88.624 | 1.00 16.54 | C |
| ATOM | 4609 | N | LEU | C | 186 | 44.440 | 86.428 | 88.438 | 1.00 16.99 | C |
| ATOM | 4610 | CA | LEU | C | 186 | 44.234 | 85.623 | 87.229 | 1.00 16.70 | C |
| ATOM | 4611 | CB | LEU | C | 186 | 45.568 | 85.317 | 86.570 | 1.00 12.26 | C |
| ATOM | 4612 | CG | LEU | C | 186 | 46.211 | 86.266 | 85.565 | 1.00 12.26 | C |
| ATOM | 4613 | CD1 | LEU | C | 186 | 45.425 | 86.264 | 84.285 | 1.00 12.26 | C |
| ATOM | 4614 | CD2 | LEU | C | 186 | 46.282 | 87.639 | 86.142 | 1.00 12.26 | C |
| ATOM | 4615 | C | LEU | C | 186 | 43.513 | 84.286 | 87.450 | 1.00 18.49 | C |
| ATOM | 4616 | O | LEU | C | 186 | 43.397 | 83.805 | 88.579 | 1.00 21.09 | C |
| ATOM | 4617 | N | TYR | C | 187 | 43.057 | 83.702 | 86.337 | 1.00 19.29 | C |
| ATOM | 4618 | CA | TYR | C | 187 | 42.347 | 82.416 | 86.275 | 1.00 21.80 | C |
| ATOM | 4619 | CB | TYR | C | 187 | 43.385 | 81.329 | 86.105 | 1.00 13.72 | C |
| ATOM | 4620 | CG | TYR | C | 187 | 44.380 | 81.691 | 85.030 | 1.00 12.98 | C |
| ATOM | 4621 | CD1 | TYR | C | 187 | 43.963 | 81.932 | 83.714 | 1.00 12.26 | C |
| ATOM | 4622 | CE1 | TYR | C | 187 | 44.878 | 82.225 | 82.699 | 1.00 12.26 | C |
| ATOM | 4623 | CD2 | TYR | C | 187 | 45.741 | 81.760 | 85.310 | 1.00 12.26 | C |
| ATOM | 4624 | CE2 | TYR | C | 187 | 46.671 | 82.051 | 84.305 | 1.00 12.26 | C |
| ATOM | 4625 | CZ | TYR | C | 187 | 46.230 | 82.279 | 82.997 | 1.00 13.26 | C |
| ATOM | 4626 | OH | TYR | C | 187 | 47.145 | 82.524 | 81.995 | 1.00 23.65 | C |
| ATOM | 4627 | C | TYR | C | 187 | 41.362 | 82.035 | 87.394 | 1.00 26.85 | C |
| ATOM | 4628 | O | TYR | C | 187 | 40.144 | 81.965 | 87.123 | 1.00 34.42 | C |
| TER | 4629 | | TYR | C | 187 | | | | | |
| ATOM | 4630 | CB | LYS | D | 2 | 9.687 | 25.197 | 67.027 | 1.00 44.32 | D |
| ATOM | 4631 | CG | LYS | D | 2 | 10.122 | 25.109 | 68.480 | 1.00 36.94 | D |
| ATOM | 4632 | CD | LYS | D | 2 | 10.407 | 23.657 | 68.888 | 1.00 35.66 | D |
| ATOM | 4633 | CE | LYS | D | 2 | 10.652 | 23.520 | 70.396 | 1.00 33.81 | D |
| ATOM | 4634 | NZ | LYS | D | 2 | 10.921 | 22.101 | 70.792 | 1.00 33.25 | D |
| ATOM | 4635 | C | LYS | D | 2 | 10.532 | 27.470 | 66.341 | 1.00 39.93 | D |
| ATOM | 4636 | O | LYS | D | 2 | 11.510 | 27.042 | 65.705 | 1.00 35.59 | D |
| ATOM | 4637 | N | LYS | D | 2 | 8.454 | 26.476 | 65.304 | 1.00 46.15 | D |

Figure 10 (72 of 142)

| ATOM | 4638 | CA | LYS | D | 2 | 9.278 | 26.594 | 66.557 | 1.00 | 40.81 | D |
|------|------|----|----|---|---|-------|--------|--------|------|-------|---|
| ATOM | 4639 | N | LYS | D | 3 | 10.495 | 28.691 | 66.879 | 1.00 | 33.72 | D |
| ATOM | 4640 | CA | LYS | D | 3 | 11.592 | 29.649 | 66.736 | 1.00 | 33.14 | D |
| ATOM | 4641 | CB | LYS | D | 3 | 11.067 | 31.079 | 66.929 | 1.00 | 39.21 | D |
| ATOM | 4642 | CG | LYS | D | 3 | 9.772 | 31.443 | 66.165 | 1.00 | 42.57 | D |
| ATOM | 4643 | CD | LYS | D | 3 | 9.385 | 32.890 | 66.474 | 1.00 | 41.30 | D |
| ATOM | 4644 | CE | LYS | D | 3 | 7.901 | 33.174 | 66.294 | 1.00 | 41.08 | D |
| ATOM | 4645 | NZ | LYS | D | 3 | 7.524 | 34.498 | 66.924 | 1.00 | 30.52 | D |
| ATOM | 4646 | C | LYS | D | 3 | 12.735 | 29.381 | 67.726 | 1.00 | 30.83 | D |
| ATOM | 4647 | O | LYS | D | 3 | 12.594 | 29.588 | 68.938 | 1.00 | 26.95 | D |
| ATOM | 4648 | N | ILE | D | 4 | 13.871 | 28.946 | 67.178 | 1.00 | 27.62 | D |
| ATOM | 4649 | CA | ILE | D | 4 | 15.067 | 28.599 | 67.945 | 1.00 | 20.26 | D |
| ATOM | 4650 | CB | ILE | D | 4 | 15.433 | 27.153 | 67.695 | 1.00 | 22.38 | D |
| ATOM | 4651 | CG2 | ILE | D | 4 | 16.794 | 26.836 | 68.280 | 1.00 | 24.22 | D |
| ATOM | 4652 | CG1 | ILE | D | 4 | 14.342 | 26.271 | 68.270 | 1.00 | 28.19 | D |
| ATOM | 4653 | CD1 | ILE | D | 4 | 14.208 | 24.996 | 67.526 | 1.00 | 35.83 | D |
| ATOM | 4654 | C | ILE | D | 4 | 16.312 | 29.427 | 67.649 | 1.00 | 19.84 | D |
| ATOM | 4655 | O | ILE | D | 4 | 16.603 | 29.740 | 66.499 | 1.00 | 18.57 | D |
| ATOM | 4656 | N | GLY | D | 5 | 17.049 | 29.755 | 68.705 | 1.00 | 19.81 | D |
| ATOM | 4657 | CA | GLY | D | 5 | 18.272 | 30.512 | 68.553 | 1.00 | 16.90 | D |
| ATOM | 4658 | C | GLY | D | 5 | 19.472 | 29.659 | 68.937 | 1.00 | 18.04 | D |
| ATOM | 4659 | O | GLY | D | 5 | 19.694 | 29.398 | 70.120 | 1.00 | 28.70 | D |
| ATOM | 4660 | N | ILE | D | 6 | 20.228 | 29.192 | 67.945 | 1.00 | 16.63 | D |
| ATOM | 4661 | CA | ILE | D | 6 | 21.425 | 28.404 | 68.210 | 1.00 | 12.26 | D |
| ATOM | 4662 | CB | ILE | D | 6 | 21.954 | 27.768 | 66.947 | 1.00 | 12.26 | D |
| ATOM | 4663 | CG2 | ILE | D | 6 | 23.246 | 27.023 | 67.247 | 1.00 | 12.26 | D |
| ATOM | 4664 | CG1 | ILE | D | 6 | 20.864 | 26.861 | 66.377 | 1.00 | 12.26 | D |
| ATOM | 4665 | CD1 | ILE | D | 6 | 21.321 | 25.874 | 65.333 | 1.00 | 12.26 | D |
| ATOM | 4666 | C | ILE | D | 6 | 22.475 | 29.348 | 68.767 | 1.00 | 12.26 | D |
| ATOM | 4667 | O | ILE | D | 6 | 22.855 | 30.345 | 68.140 | 1.00 | 12.26 | D |
| ATOM | 4668 | N | PHE | D | 7 | 22.953 | 29.017 | 69.953 | 1.00 | 12.26 | D |
| ATOM | 4669 | CA | PHE | D | 7 | 23.911 | 29.859 | 70.641 | 1.00 | 12.26 | D |
| ATOM | 4670 | CB | PHE | D | 7 | 23.267 | 30.286 | 71.971 | 1.00 | 12.26 | D |
| ATOM | 4671 | CG | PHE | D | 7 | 24.048 | 31.302 | 72.751 | 1.00 | 12.26 | D |
| ATOM | 4672 | CD1 | PHE | D | 7 | 24.855 | 32.235 | 72.122 | 1.00 | 12.26 | D |
| ATOM | 4673 | CD2 | PHE | D | 7 | 23.911 | 31.369 | 74.129 | 1.00 | 12.26 | D |
| ATOM | 4674 | CE1 | PHE | D | 7 | 25.502 | 33.215 | 72.860 | 1.00 | 12.26 | D |
| ATOM | 4675 | CE2 | PHE | D | 7 | 24.553 | 32.346 | 74.869 | 1.00 | 12.26 | D |
| ATOM | 4676 | CZ | PHE | D | 7 | 25.345 | 33.267 | 74.237 | 1.00 | 12.26 | D |
| ATOM | 4677 | C | PHE | D | 7 | 25.204 | 29.095 | 70.843 | 1.00 | 12.26 | D |
| ATOM | 4678 | O | PHE | D | 7 | 25.484 | 28.590 | 71.916 | 1.00 | 12.26 | D |
| ATOM | 4679 | N | GLY | D | 8 | 25.993 | 29.007 | 69.789 | 1.00 | 12.26 | D |
| ATOM | 4680 | CA | GLY | D | 8 | 27.241 | 28.280 | 69.880 | 1.00 | 12.26 | D |
| ATOM | 4681 | C | GLY | D | 8 | 28.329 | 28.984 | 70.660 | 1.00 | 12.26 | D |
| ATOM | 4682 | O | GLY | D | 8 | 28.474 | 30.198 | 70.585 | 1.00 | 12.26 | D |
| ATOM | 4683 | N | GLY | D | 9 | 29.107 | 28.201 | 71.401 | 1.00 | 12.26 | D |
| ATOM | 4684 | CA | GLY | D | 9 | 30.213 | 28.730 | 72.184 | 1.00 | 12.26 | D |
| ATOM | 4685 | C | GLY | D | 9 | 31.048 | 27.558 | 72.671 | 1.00 | 15.73 | D |
| ATOM | 4686 | O | GLY | D | 9 | 30.577 | 26.425 | 72.596 | 1.00 | 21.21 | D |
| ATOM | 4687 | N | THR | D | 10 | 32.277 | 27.782 | 73.135 | 1.00 | 15.12 | D |
| ATOM | 4688 | CA | THR | D | 10 | 33.062 | 26.652 | 73.630 | 1.00 | 13.41 | D |
| ATOM | 4689 | CB | THR | D | 10 | 34.582 | 26.790 | 73.391 | 1.00 | 12.26 | D |
| ATOM | 4690 | OG1 | THR | D | 10 | 35.184 | 27.387 | 74.540 | 1.00 | 19.90 | D |
| ATOM | 4691 | CG2 | THR | D | 10 | 34.877 | 27.642 | 72.177 | 1.00 | 13.19 | D |
| ATOM | 4692 | C | THR | D | 10 | 32.830 | 26.580 | 75.133 | 1.00 | 12.73 | D |
| ATOM | 4693 | O | THR | D | 10 | 33.112 | 25.549 | 75.758 | 1.00 | 12.26 | D |
| ATOM | 4694 | N | PHE | D | 11 | 32.315 | 27.690 | 75.686 | 1.00 | 13.07 | D |
| ATOM | 4695 | CA | PHE | D | 11 | 31.989 | 27.843 | 77.115 | 1.00 | 13.76 | D |
| ATOM | 4696 | CB | PHE | D | 11 | 30.648 | 27.176 | 77.414 | 1.00 | 12.26 | D |
| ATOM | 4697 | CG | PHE | D | 11 | 29.559 | 27.607 | 76.499 | 1.00 | 12.26 | D |
| ATOM | 4698 | CD1 | PHE | D | 11 | 29.063 | 26.753 | 75.526 | 1.00 | 12.26 | D |
| ATOM | 4699 | CD2 | PHE | D | 11 | 29.051 | 28.900 | 76.582 | 1.00 | 15.05 | D |
| ATOM | 4700 | CE1 | PHE | D | 11 | 28.063 | 27.189 | 74.647 | 1.00 | 12.26 | D |
| ATOM | 4701 | CE2 | PHE | D | 11 | 28.056 | 29.352 | 75.716 | 1.00 | 12.26 | D |
| ATOM | 4702 | CZ | PHE | D | 11 | 27.562 | 28.499 | 74.745 | 1.00 | 13.58 | D |
| ATOM | 4703 | C | PHE | D | 11 | 33.052 | 27.284 | 78.052 | 1.00 | 13.88 | D |

Figure 10 (73 of 142)

| ATOM | 4704 | O | PHE | D | 11 | 32.828 | 26.264 | 78.707 | 1.00 | 16.95 | D |
|---|---|---|---|---|---|---|---|---|---|---|---|
| ATOM | 4705 | N | ASP | D | 12 | 34.190 | 27.974 | 78.137 | 1.00 | 12.26 | D |
| ATOM | 4706 | CA | ASP | D | 12 | 35.309 | 27.520 | 78.955 | 1.00 | 12.26 | D |
| ATOM | 4707 | CB | ASP | D | 12 | 36.392 | 27.026 | 77.998 | 1.00 | 12.26 | D |
| ATOM | 4708 | CG | ASP | D | 12 | 37.606 | 26.479 | 78.702 | 1.00 | 12.26 | D |
| ATOM | 4709 | OD1 | ASP | D | 12 | 37.433 | 25.802 | 79.734 | 1.00 | 12.26 | D |
| ATOM | 4710 | OD2 | ASP | D | 12 | 38.726 | 26.709 | 78.194 | 1.00 | 12.26 | D |
| ATOM | 4711 | C | ASP | D | 12 | 35.876 | 28.591 | 79.892 | 1.00 | 12.26 | D |
| ATOM | 4712 | O | ASP | D | 12 | 36.995 | 29.050 | 79.700 | 1.00 | 13.29 | D |
| ATOM | 4713 | N | PRO | D | 13 | 35.150 | 28.936 | 80.976 | 1.00 | 12.26 | D |
| ATOM | 4714 | CD | PRO | D | 13 | 35.732 | 29.787 | 82.033 | 1.00 | 12.26 | D |
| ATOM | 4715 | CA | PRO | D | 13 | 33.839 | 28.425 | 81.404 | 1.00 | 12.28 | D |
| ATOM | 4716 | CB | PRO | D | 13 | 33.966 | 28.452 | 82.915 | 1.00 | 12.26 | D |
| ATOM | 4717 | CG | PRO | D | 13 | 34.648 | 29.774 | 83.113 | 1.00 | 12.26 | D |
| ATOM | 4718 | C | PRO | D | 13 | 32.668 | 29.275 | 80.958 | 1.00 | 12.26 | D |
| ATOM | 4719 | O | PRO | D | 13 | 32.849 | 30.354 | 80.396 | 1.00 | 12.26 | D |
| ATOM | 4720 | N | PRO | D | 14 | 31.442 | 28.789 | 81.201 | 1.00 | 12.26 | D |
| ATOM | 4721 | CD | PRO | D | 14 | 31.085 | 27.442 | 81.660 | 1.00 | 12.99 | D |
| ATOM | 4722 | CA | PRO | D | 14 | 30.234 | 29.527 | 80.832 | 1.00 | 12.26 | D |
| ATOM | 4723 | CB | PRO | D | 14 | 29.119 | 28.489 | 80.984 | 1.00 | 12.26 | D |
| ATOM | 4724 | CG | PRO | D | 14 | 29.819 | 27.201 | 80.890 | 1.00 | 14.53 | D |
| ATOM | 4725 | C | PRO | D | 14 | 30.130 | 30.586 | 81.911 | 1.00 | 12.26 | D |
| ATOM | 4726 | O | PRO | D | 14 | 30.530 | 30.342 | 83.046 | 1.00 | 12.26 | D |
| ATOM | 4727 | N | HIS | D | 15 | 29.614 | 31.755 | 81.579 | 1.00 | 12.26 | D |
| ATOM | 4728 | CA | HIS | D | 15 | 29.493 | 32.761 | 82.604 | 1.00 | 12.26 | D |
| ATOM | 4729 | CB | HIS | D | 15 | 30.706 | 33.662 | 82.579 | 1.00 | 15.43 | D |
| ATOM | 4730 | CG | HIS | D | 15 | 31.039 | 34.190 | 81.218 | 1.00 | 13.70 | D |
| ATOM | 4731 | CD2 | HIS | D | 15 | 32.173 | 34.108 | 80.485 | 1.00 | 17.40 | D |
| ATOM | 4732 | ND1 | HIS | D | 15 | 30.169 | 34.975 | 80.492 | 1.00 | 13.63 | D |
| ATOM | 4733 | CE1 | HIS | D | 15 | 30.757 | 35.359 | 79.374 | 1.00 | 12.26 | D |
| ATOM | 4734 | NE2 | HIS | D | 15 | 31.974 | 34.847 | 79.346 | 1.00 | 12.72 | D |
| ATOM | 4735 | C | HIS | D | 15 | 28.218 | 33.555 | 82.437 | 1.00 | 12.44 | D |
| ATOM | 4736 | O | HIS | D | 15 | 27.504 | 33.389 | 81.445 | 1.00 | 12.26 | D |
| ATOM | 4737 | N | ASN | D | 16 | 27.932 | 34.411 | 83.409 | 1.00 | 12.26 | D |
| ATOM | 4738 | CA | ASN | D | 16 | 26.713 | 35.189 | 83.370 | 1.00 | 12.26 | D |
| ATOM | 4739 | CB | ASN | D | 16 | 26.651 | 36.159 | 84.537 | 1.00 | 16.24 | D |
| ATOM | 4740 | CG | ASN | D | 16 | 26.545 | 35.449 | 85.876 | 1.00 | 19.23 | D |
| ATOM | 4741 | OD1 | ASN | D | 16 | 25.676 | 34.608 | 86.090 | 1.00 | 20.91 | D |
| ATOM | 4742 | ND2 | ASN | D | 16 | 27.428 | 35.797 | 86.790 | 1.00 | 20.08 | D |
| ATOM | 4743 | C | ASN | D | 16 | 26.519 | 35.934 | 82.076 | 1.00 | 12.26 | D |
| ATOM | 4744 | O | ASN | D | 16 | 25.405 | 35.994 | 81.558 | 1.00 | 12.26 | D |
| ATOM | 4745 | N | GLY | D | 17 | 27.588 | 36.506 | 81.543 | 1.00 | 12.26 | D |
| ATOM | 4746 | CA | GLY | D | 17 | 27.458 | 37.215 | 80.284 | 1.00 | 18.64 | D |
| ATOM | 4747 | C | GLY | D | 17 | 26.684 | 36.366 | 79.283 | 1.00 | 21.39 | D |
| ATOM | 4748 | O | GLY | D | 17 | 25.767 | 36.840 | 78.602 | 1.00 | 20.52 | D |
| ATOM | 4749 | N | HIS | D | 18 | 27.053 | 35.096 | 79.203 | 1.00 | 18.74 | D |
| ATOM | 4750 | CA | HIS | D | 18 | 26.401 | 34.176 | 78.305 | 1.00 | 18.15 | D |
| ATOM | 4751 | CB | HIS | D | 18 | 27.032 | 32.799 | 78.436 | 1.00 | 18.94 | D |
| ATOM | 4752 | CG | HIS | D | 18 | 28.470 | 32.758 | 78.018 | 1.00 | 15.85 | D |
| ATOM | 4753 | CD2 | HIS | D | 18 | 29.125 | 33.393 | 77.015 | 1.00 | 17.93 | D |
| ATOM | 4754 | ND1 | HIS | D | 18 | 29.406 | 31.974 | 78.656 | 1.00 | 17.70 | D |
| ATOM | 4755 | CE1 | HIS | D | 18 | 30.575 | 32.127 | 78.063 | 1.00 | 12.26 | D |
| ATOM | 4756 | NE2 | HIS | D | 18 | 30.432 | 32.982 | 77.064 | 1.00 | 12.26 | D |
| ATOM | 4757 | C | HIS | D | 18 | 24.937 | 34.107 | 78.662 | 1.00 | 17.49 | D |
| ATOM | 4758 | O | HIS | D | 18 | 24.079 | 34.382 | 77.828 | 1.00 | 27.18 | D |
| ATOM | 4759 | N | LEU | D | 19 | 24.657 | 33.755 | 79.911 | 1.00 | 15.96 | D |
| ATOM | 4760 | CA | LEU | D | 19 | 23.288 | 33.631 | 80.392 | 1.00 | 16.56 | D |
| ATOM | 4761 | CB | LEU | D | 19 | 23.301 | 33.310 | 81.884 | 1.00 | 19.33 | D |
| ATOM | 4762 | CG | LEU | D | 19 | 24.020 | 31.993 | 82.180 | 1.00 | 15.96 | D |
| ATOM | 4763 | CD1 | LEU | D | 19 | 24.343 | 31.934 | 83.621 | 1.00 | 19.42 | D |
| ATOM | 4764 | CD2 | LEU | D | 19 | 23.181 | 30.806 | 81.783 | 1.00 | 12.26 | D |
| ATOM | 4765 | C | LEU | D | 19 | 22.475 | 34.892 | 80.121 | 1.00 | 16.68 | D |
| ATOM | 4766 | O | LEU | D | 19 | 21.335 | 34.830 | 79.657 | 1.00 | 17.02 | D |
| ATOM | 4767 | N | LEU | D | 20 | 23.062 | 36.042 | 80.394 | 1.00 | 12.26 | D |
| ATOM | 4768 | CA | LEU | D | 20 | 22.368 | 37.298 | 80.162 | 1.00 | 12.26 | D |
| ATOM | 4769 | CB | LEU | D | 20 | 23.222 | 38.458 | 80.664 | 1.00 | 12.26 | D |

Figure 10 (74 of 142)

| | | | | | | | | | |
|---|---|---|---|---|---|---|---|---|---|
| ATOM | 4770 | CG  | LEU | D | 20 | 22.641 | 39.869 | 80.592 | 1.00 12.26 | D |
| ATOM | 4771 | CD1 | LEU | D | 20 | 21.344 | 39.980 | 81.386 | 1.00 15.91 | D |
| ATOM | 4772 | CD2 | LEU | D | 20 | 23.675 | 40.822 | 81.140 | 1.00 12.26 | D |
| ATOM | 4773 | C   | LEU | D | 20 | 22.045 | 37.510 | 78.682 | 1.00 12.26 | D |
| ATOM | 4774 | O   | LEU | D | 20 | 20.897 | 37.704 | 78.301 | 1.00 12.26 | D |
| ATOM | 4775 | N   | MET | D | 21 | 23.061 | 37.483 | 77.840 | 1.00 12.26 | D |
| ATOM | 4776 | CA  | MET | D | 21 | 22.809 | 37.690 | 76.428 | 1.00 14.70 | D |
| ATOM | 4777 | CB  | MET | D | 21 | 24.088 | 37.492 | 75.610 | 1.00 17.70 | D |
| ATOM | 4778 | CG  | MET | D | 21 | 24.652 | 38.796 | 75.083 | 1.00 22.46 | D |
| ATOM | 4779 | SD  | MET | D | 21 | 24.862 | 40.002 | 76.421 | 1.00 30.18 | D |
| ATOM | 4780 | CE  | MET | D | 21 | 25.361 | 41.527 | 75.541 | 1.00 32.25 | D |
| ATOM | 4781 | C   | MET | D | 21 | 21.722 | 36.778 | 75.902 | 1.00 12.26 | D |
| ATOM | 4782 | O   | MET | D | 21 | 20.750 | 37.237 | 75.323 | 1.00 12.26 | D |
| ATOM | 4783 | N   | ALA | D | 22 | 21.882 | 35.482 | 76.111 | 1.00 12.26 | D |
| ATOM | 4784 | CA  | ALA | D | 22 | 20.912 | 34.521 | 75.617 | 1.00 12.26 | D |
| ATOM | 4785 | CB  | ALA | D | 22 | 21.325 | 33.122 | 76.036 | 1.00 17.29 | D |
| ATOM | 4786 | C   | ALA | D | 22 | 19.483 | 34.800 | 76.066 | 1.00 12.26 | D |
| ATOM | 4787 | O   | ALA | D | 22 | 18.555 | 34.787 | 75.255 | 1.00 13.44 | D |
| ATOM | 4788 | N   | ASN | D | 23 | 19.307 | 35.051 | 77.354 | 1.00 12.26 | D |
| ATOM | 4789 | CA  | ASN | D | 23 | 17.983 | 35.300 | 77.896 | 1.00 12.26 | D |
| ATOM | 4790 | CB  | ASN | D | 23 | 18.073 | 35.403 | 79.420 | 1.00 14.75 | D |
| ATOM | 4791 | CG  | ASN | D | 23 | 16.711 | 35.457 | 80.099 | 1.00 12.26 | D |
| ATOM | 4792 | OD1 | ASN | D | 23 | 16.468 | 36.343 | 80.913 | 1.00 14.33 | D |
| ATOM | 4793 | ND2 | ASN | D | 23 | 15.830 | 34.510 | 79.785 | 1.00 12.26 | D |
| ATOM | 4794 | C   | ASN | D | 23 | 17.362 | 36.564 | 77.302 | 1.00 17.04 | D |
| ATOM | 4795 | O   | ASN | D | 23 | 16.137 | 36.664 | 77.200 | 1.00 21.87 | D |
| ATOM | 4796 | N   | GLU | D | 24 | 18.212 | 37.517 | 76.906 | 1.00 15.81 | D |
| ATOM | 4797 | CA  | GLU | D | 24 | 17.772 | 38.788 | 76.309 | 1.00 19.23 | D |
| ATOM | 4798 | CB  | GLU | D | 24 | 18.891 | 39.837 | 76.349 | 1.00 17.00 | D |
| ATOM | 4799 | CG  | GLU | D | 24 | 19.196 | 40.397 | 77.718 | 1.00 17.27 | D |
| ATOM | 4800 | CD  | GLU | D | 24 | 17.974 | 40.998 | 78.338 | 1.00 23.27 | D |
| ATOM | 4801 | OE1 | GLU | D | 24 | 17.152 | 41.536 | 77.579 | 1.00 26.00 | D |
| ATOM | 4802 | OE2 | GLU | D | 24 | 17.824 | 40.942 | 79.571 | 1.00 27.40 | D |
| ATOM | 4803 | C   | GLU | D | 24 | 17.374 | 38.569 | 74.860 | 1.00 18.44 | D |
| ATOM | 4804 | O   | GLU | D | 24 | 16.280 | 38.944 | 74.438 | 1.00 17.34 | D |
| ATOM | 4805 | N   | VAL | D | 25 | 18.281 | 37.967 | 74.100 | 1.00 16.46 | D |
| ATOM | 4806 | CA  | VAL | D | 25 | 18.030 | 37.680 | 72.698 | 1.00 15.59 | D |
| ATOM | 4807 | CB  | VAL | D | 25 | 19.149 | 36.844 | 72.092 | 1.00 12.87 | D |
| ATOM | 4808 | CG1 | VAL | D | 25 | 18.729 | 36.367 | 70.707 | 1.00 12.26 | D |
| ATOM | 4809 | CG2 | VAL | D | 25 | 20.434 | 37.674 | 72.028 | 1.00 15.97 | D |
| ATOM | 4810 | C   | VAL | D | 25 | 16.750 | 36.884 | 72.573 | 1.00 23.66 | D |
| ATOM | 4811 | O   | VAL | D | 25 | 15.976 | 37.071 | 71.636 | 1.00 27.41 | D |
| ATOM | 4812 | N   | LEU | D | 26 | 16.547 | 35.980 | 73.524 | 1.00 27.60 | D |
| ATOM | 4813 | CA  | LEU | D | 26 | 15.362 | 35.133 | 73.553 | 1.00 23.79 | D |
| ATOM | 4814 | CB  | LEU | D | 26 | 15.386 | 34.252 | 74.797 | 1.00 30.77 | D |
| ATOM | 4815 | CG  | LEU | D | 26 | 14.108 | 33.450 | 75.036 | 1.00 33.63 | D |
| ATOM | 4816 | CD1 | LEU | D | 26 | 13.944 | 32.418 | 73.934 | 1.00 35.67 | D |
| ATOM | 4817 | CD2 | LEU | D | 26 | 14.172 | 32.787 | 76.399 | 1.00 35.65 | D |
| ATOM | 4818 | C   | LEU | D | 26 | 14.096 | 35.979 | 73.568 | 1.00 22.70 | D |
| ATOM | 4819 | O   | LEU | D | 26 | 13.058 | 35.604 | 73.011 | 1.00 22.87 | D |
| ATOM | 4820 | N   | TYR | D | 27 | 14.183 | 37.116 | 74.237 | 1.00 18.14 | D |
| ATOM | 4821 | CA  | TYR | D | 27 | 13.055 | 38.009 | 74.317 | 1.00 17.04 | D |
| ATOM | 4822 | CB  | TYR | D | 27 | 13.171 | 38.878 | 75.562 | 1.00 18.91 | D |
| ATOM | 4823 | CG  | TYR | D | 27 | 12.101 | 39.931 | 75.654 | 1.00 23.18 | D |
| ATOM | 4824 | CD1 | TYR | D | 27 | 10.777 | 39.583 | 75.898 | 1.00 25.65 | D |
| ATOM | 4825 | CE1 | TYR | D | 27 |  9.772 | 40.552 | 75.975 | 1.00 32.59 | D |
| ATOM | 4826 | CD2 | TYR | D | 27 | 12.406 | 41.275 | 75.484 | 1.00 23.92 | D |
| ATOM | 4827 | CE2 | TYR | D | 27 | 11.410 | 42.251 | 75.556 | 1.00 28.27 | D |
| ATOM | 4828 | CZ  | TYR | D | 27 | 10.090 | 41.886 | 75.805 | 1.00 33.26 | D |
| ATOM | 4829 | OH  | TYR | D | 27 |  9.093 | 42.841 | 75.904 | 1.00 37.00 | D |
| ATOM | 4830 | C   | TYR | D | 27 | 13.070 | 38.892 | 73.082 | 1.00 18.94 | D |
| ATOM | 4831 | O   | TYR | D | 27 | 12.182 | 38.826 | 72.228 | 1.00 25.81 | D |
| ATOM | 4832 | N   | GLN | D | 28 | 14.113 | 39.707 | 72.992 | 1.00 16.59 | D |
| ATOM | 4833 | CA  | GLN | D | 28 | 14.284 | 40.652 | 71.898 | 1.00 14.59 | D |
| ATOM | 4834 | CB  | GLN | D | 28 | 15.708 | 41.240 | 71.980 | 1.00 17.41 | D |
| ATOM | 4835 | CG  | GLN | D | 28 | 15.766 | 42.750 | 71.794 | 1.00 29.94 | D |

Figure 10 (75 of 142)

| ATOM | 4836 | CD | GLN | D | 28 | 14.650 | 43.482 | 72.540 | 1.00 | 32.26 | D |
| --- | --- | --- | --- | --- | --- | --- | --- | --- | --- | --- | --- |
| ATOM | 4837 | OE1 | GLN | D | 28 | 14.667 | 43.591 | 73.770 | 1.00 | 33.45 | D |
| ATOM | 4838 | NE2 | GLN | D | 28 | 13.668 | 43.979 | 71.790 | 1.00 | 37.48 | D |
| ATOM | 4839 | C | GLN | D | 28 | 13.972 | 40.109 | 70.482 | 1.00 | 15.88 | D |
| ATOM | 4840 | O | GLN | D | 28 | 13.401 | 40.816 | 69.653 | 1.00 | 12.66 | D |
| ATOM | 4841 | N | ALA | D | 29 | 14.321 | 38.858 | 70.213 | 1.00 | 13.34 | D |
| ATOM | 4842 | CA | ALA | D | 29 | 14.081 | 38.282 | 68.893 | 1.00 | 16.41 | D |
| ATOM | 4843 | CB | ALA | D | 29 | 15.293 | 37.491 | 68.444 | 1.00 | 20.52 | D |
| ATOM | 4844 | C | ALA | D | 29 | 12.858 | 37.388 | 68.890 | 1.00 | 12.26 | D |
| ATOM | 4845 | O | ALA | D | 29 | 12.647 | 36.619 | 67.950 | 1.00 | 12.26 | D |
| ATOM | 4846 | N | GLY | D | 30 | 12.070 | 37.484 | 69.961 | 1.00 | 20.12 | D |
| ATOM | 4847 | CA | GLY | D | 30 | 10.845 | 36.708 | 70.089 | 1.00 | 17.73 | D |
| ATOM | 4848 | C | GLY | D | 30 | 10.954 | 35.220 | 69.835 | 1.00 | 17.28 | D |
| ATOM | 4849 | O | GLY | D | 30 | 10.063 | 34.622 | 69.232 | 1.00 | 19.64 | D |
| ATOM | 4850 | N | LEU | D | 31 | 12.052 | 34.624 | 70.296 | 1.00 | 25.55 | D |
| ATOM | 4851 | CA | LEU | D | 31 | 12.298 | 33.182 | 70.143 | 1.00 | 22.52 | D |
| ATOM | 4852 | CB | LEU | D | 31 | 13.791 | 32.882 | 70.276 | 1.00 | 19.95 | D |
| ATOM | 4853 | CG | LEU | D | 31 | 14.730 | 33.617 | 69.330 | 1.00 | 22.29 | D |
| ATOM | 4854 | CD1 | LEU | D | 31 | 16.173 | 33.240 | 69.677 | 1.00 | 19.67 | D |
| ATOM | 4855 | CD2 | LEU | D | 31 | 14.399 | 33.235 | 67.879 | 1.00 | 21.27 | D |
| ATOM | 4856 | C | LEU | D | 31 | 11.544 | 32.327 | 71.171 | 1.00 | 22.58 | D |
| ATOM | 4857 | O | LEU | D | 31 | 10.983 | 32.834 | 72.151 | 1.00 | 28.99 | D |
| ATOM | 4858 | N | ASP | D | 32 | 11.551 | 31.019 | 70.958 | 1.00 | 21.27 | D |
| ATOM | 4859 | CA | ASP | D | 32 | 10.852 | 30.131 | 71.868 | 1.00 | 22.01 | D |
| ATOM | 4860 | CB | ASP | D | 32 | 10.154 | 29.028 | 71.089 | 1.00 | 31.67 | D |
| ATOM | 4861 | CG | ASP | D | 32 | 9.049 | 29.558 | 70.211 | 1.00 | 33.11 | D |
| ATOM | 4862 | OD1 | ASP | D | 32 | 8.015 | 29.996 | 70.768 | 1.00 | 36.72 | D |
| ATOM | 4863 | OD2 | ASP | D | 32 | 9.217 | 29.550 | 68.968 | 1.00 | 37.05 | D |
| ATOM | 4864 | C | ASP | D | 32 | 11.814 | 29.524 | 72.853 | 1.00 | 20.47 | D |
| ATOM | 4865 | O | ASP | D | 32 | 11.455 | 29.235 | 73.987 | 1.00 | 21.98 | D |
| ATOM | 4866 | N | GLU | D | 33 | 13.046 | 29.321 | 72.418 | 1.00 | 16.37 | D |
| ATOM | 4867 | CA | GLU | D | 33 | 14.052 | 28.743 | 73.285 | 1.00 | 15.99 | D |
| ATOM | 4868 | CB | GLU | D | 33 | 13.779 | 27.248 | 73.518 | 1.00 | 14.78 | D |
| ATOM | 4869 | CG | GLU | D | 33 | 13.010 | 26.531 | 72.410 | 1.00 | 23.10 | D |
| ATOM | 4870 | CD | GLU | D | 33 | 12.649 | 25.078 | 72.760 | 1.00 | 24.37 | D |
| ATOM | 4871 | OE1 | GLU | D | 33 | 13.495 | 24.177 | 72.536 | 1.00 | 26.04 | D |
| ATOM | 4872 | OE2 | GLU | D | 33 | 11.521 | 24.839 | 73.263 | 1.00 | 26.85 | D |
| ATOM | 4873 | C | GLU | D | 33 | 15.425 | 28.936 | 72.682 | 1.00 | 16.03 | D |
| ATOM | 4874 | O | GLU | D | 33 | 15.571 | 29.022 | 71.455 | 1.00 | 20.72 | D |
| ATOM | 4875 | N | ILE | D | 34 | 16.424 | 29.022 | 73.561 | 1.00 | 12.60 | D |
| ATOM | 4876 | CA | ILE | D | 34 | 17.812 | 29.189 | 73.165 | 1.00 | 12.26 | D |
| ATOM | 4877 | CB | ILE | D | 34 | 18.494 | 30.221 | 74.039 | 1.00 | 14.19 | D |
| ATOM | 4878 | CG2 | ILE | D | 34 | 19.893 | 30.461 | 73.522 | 1.00 | 12.26 | D |
| ATOM | 4879 | CG1 | ILE | D | 34 | 17.665 | 31.507 | 74.073 | 1.00 | 12.26 | D |
| ATOM | 4880 | CD1 | ILE | D | 34 | 17.587 | 32.214 | 72.777 | 1.00 | 19.46 | D |
| ATOM | 4881 | C | ILE | D | 34 | 18.509 | 27.851 | 73.367 | 1.00 | 12.26 | D |
| ATOM | 4882 | O | ILE | D | 34 | 18.312 | 27.220 | 74.399 | 1.00 | 12.26 | D |
| ATOM | 4883 | N | TRP | D | 35 | 19.292 | 27.407 | 72.380 | 1.00 | 12.26 | D |
| ATOM | 4884 | CA | TRP | D | 35 | 20.025 | 26.131 | 72.479 | 1.00 | 15.65 | D |
| ATOM | 4885 | CB | TRP | D | 35 | 19.873 | 25.272 | 71.242 | 1.00 | 13.03 | D |
| ATOM | 4886 | CG | TRP | D | 35 | 18.563 | 24.724 | 71.037 | 1.00 | 12.26 | D |
| ATOM | 4887 | CD2 | TRP | D | 35 | 18.177 | 23.913 | 69.944 | 1.00 | 12.26 | D |
| ATOM | 4888 | CE2 | TRP | D | 35 | 16.807 | 23.626 | 70.101 | 1.00 | 12.26 | D |
| ATOM | 4889 | CE3 | TRP | D | 35 | 18.849 | 23.429 | 68.818 | 1.00 | 12.26 | D |
| ATOM | 4890 | CD1 | TRP | D | 35 | 17.464 | 24.882 | 71.821 | 1.00 | 14.71 | D |
| ATOM | 4891 | NE1 | TRP | D | 35 | 16.395 | 24.217 | 71.264 | 1.00 | 13.96 | D |
| ATOM | 4892 | CZ2 | TRP | D | 35 | 16.104 | 22.833 | 69.191 | 1.00 | 18.71 | D |
| ATOM | 4893 | CZ3 | TRP | D | 35 | 18.157 | 22.646 | 67.912 | 1.00 | 12.26 | D |
| ATOM | 4894 | CH2 | TRP | D | 35 | 16.790 | 22.367 | 68.094 | 1.00 | 14.14 | D |
| ATOM | 4895 | C | TRP | D | 35 | 21.501 | 26.353 | 72.635 | 1.00 | 14.24 | D |
| ATOM | 4896 | O | TRP | D | 35 | 22.172 | 26.729 | 71.680 | 1.00 | 17.25 | D |
| ATOM | 4897 | N | PHE | D | 36 | 22.006 | 26.095 | 73.830 | 1.00 | 12.26 | D |
| ATOM | 4898 | CA | PHE | D | 36 | 23.413 | 26.274 | 74.082 | 1.00 | 12.26 | D |
| ATOM | 4899 | CB | PHE | D | 36 | 23.650 | 26.296 | 75.578 | 1.00 | 12.26 | D |
| ATOM | 4900 | CG | PHE | D | 36 | 23.272 | 27.585 | 76.214 | 1.00 | 12.47 | D |
| ATOM | 4901 | CD1 | PHE | D | 36 | 21.963 | 28.056 | 76.147 | 1.00 | 13.70 | D |

Figure 10 (76 of 142)

| | | | | | | | | | | |
|---|---|---|---|---|---|---|---|---|---|---|
| ATOM | 4902 | CD2 | PHE | D | 36 | 24.235 | 28.360 | 76.842 | 1.00 12.26 | D |
| ATOM | 4903 | CE1 | PHE | D | 36 | 21.617 | 29.306 | 76.699 | 1.00 16.44 | D |
| ATOM | 4904 | CE2 | PHE | D | 36 | 23.908 | 29.599 | 77.396 | 1.00 12.76 | D |
| ATOM | 4905 | CZ | PHE | D | 36 | 22.596 | 30.076 | 77.323 | 1.00 12.26 | D |
| ATOM | 4906 | C | PHE | D | 36 | 24.173 | 25.148 | 73.423 | 1.00 12.26 | D |
| ATOM | 4907 | O | PHE | D | 36 | 24.078 | 24.007 | 73.856 | 1.00 17.43 | D |
| ATOM | 4908 | N | MET | D | 37 | 24.937 | 25.472 | 72.386 | 1.00 12.26 | D |
| ATOM | 4909 | CA | MET | D | 37 | 25.679 | 24.463 | 71.641 | 1.00 12.26 | D |
| ATOM | 4910 | CB | MET | D | 37 | 25.323 | 24.595 | 70.161 | 1.00 13.61 | D |
| ATOM | 4911 | CG | MET | D | 37 | 25.973 | 23.595 | 69.241 | 1.00 13.73 | D |
| ATOM | 4912 | SD | MET | D | 37 | 25.112 | 23.616 | 67.655 | 1.00 14.79 | D |
| ATOM | 4913 | CE | MET | D | 37 | 25.872 | 25.008 | 66.914 | 1.00 18.22 | D |
| ATOM | 4914 | C | MET | D | 37 | 27.201 | 24.471 | 71.828 | 1.00 13.79 | D |
| ATOM | 4915 | O | MET | D | 37 | 27.916 | 25.263 | 71.212 | 1.00 18.14 | D |
| ATOM | 4916 | N | PRO | D | 38 | 27.714 | 23.554 | 72.668 | 1.00 19.36 | D |
| ATOM | 4917 | CD | PRO | D | 38 | 26.865 | 22.653 | 73.458 | 1.00 17.78 | D |
| ATOM | 4918 | CA | PRO | D | 38 | 29.130 | 23.353 | 73.023 | 1.00 17.68 | D |
| ATOM | 4919 | CB | PRO | D | 38 | 29.056 | 22.508 | 74.297 | 1.00 17.86 | D |
| ATOM | 4920 | CG | PRO | D | 38 | 27.611 | 22.625 | 74.743 | 1.00 17.73 | D |
| ATOM | 4921 | C | PRO | D | 38 | 29.972 | 22.645 | 71.948 | 1.00 16.95 | D |
| ATOM | 4922 | O | PRO | D | 38 | 29.577 | 21.593 | 71.431 | 1.00 22.02 | D |
| ATOM | 4923 | N | ASN | D | 39 | 31.148 | 23.199 | 71.649 | 1.00 21.81 | D |
| ATOM | 4924 | CA | ASN | D | 39 | 32.034 | 22.625 | 70.638 | 1.00 27.39 | D |
| ATOM | 4925 | CB | ASN | D | 39 | 33.102 | 23.606 | 70.244 | 1.00 30.68 | D |
| ATOM | 4926 | CG | ASN | D | 39 | 32.572 | 24.971 | 70.108 | 1.00 35.47 | D |
| ATOM | 4927 | OD1 | ASN | D | 39 | 31.530 | 25.183 | 69.472 | 1.00 39.94 | D |
| ATOM | 4928 | ND2 | ASN | D | 39 | 33.268 | 25.931 | 70.701 | 1.00 36.83 | D |
| ATOM | 4929 | C | ASN | D | 39 | 32.747 | 21.413 | 71.121 | 1.00 26.44 | D |
| ATOM | 4930 | O | ASN | D | 39 | 33.032 | 21.291 | 72.303 | 1.00 29.35 | D |
| ATOM | 4931 | N | GLN | D | 40 | 33.073 | 20.519 | 70.206 | 1.00 24.83 | D |
| ATOM | 4932 | CA | GLN | D | 40 | 33.801 | 19.341 | 70.624 | 1.00 29.11 | D |
| ATOM | 4933 | CB | GLN | D | 40 | 33.678 | 18.220 | 69.603 | 1.00 32.50 | D |
| ATOM | 4934 | CG | GLN | D | 40 | 34.301 | 16.935 | 70.083 | 1.00 37.37 | D |
| ATOM | 4935 | CD | GLN | D | 40 | 33.635 | 15.765 | 69.455 | 1.00 44.10 | D |
| ATOM | 4936 | OE1 | GLN | D | 40 | 32.408 | 15.727 | 69.381 | 1.00 47.74 | D |
| ATOM | 4937 | NE2 | GLN | D | 40 | 34.421 | 14.792 | 68.992 | 1.00 49.60 | D |
| ATOM | 4938 | C | GLN | D | 40 | 35.242 | 19.791 | 70.725 | 1.00 27.92 | D |
| ATOM | 4939 | O | GLN | D | 40 | 35.974 | 19.418 | 71.653 | 1.00 29.33 | D |
| ATOM | 4940 | N | ILE | D | 41 | 35.628 | 20.599 | 69.741 | 1.00 30.38 | D |
| ATOM | 4941 | CA | ILE | D | 41 | 36.962 | 21.187 | 69.643 | 1.00 32.78 | D |
| ATOM | 4942 | CB | ILE | D | 41 | 37.959 | 20.270 | 68.906 | 1.00 32.85 | D |
| ATOM | 4943 | CG2 | ILE | D | 41 | 37.335 | 19.697 | 67.644 | 1.00 34.75 | D |
| ATOM | 4944 | CG1 | ILE | D | 41 | 39.224 | 21.057 | 68.596 | 1.00 34.84 | D |
| ATOM | 4945 | CD1 | ILE | D | 41 | 40.330 | 20.219 | 68.028 | 1.00 36.29 | D |
| ATOM | 4946 | C | ILE | D | 41 | 36.790 | 22.491 | 68.880 | 1.00 31.35 | D |
| ATOM | 4947 | O | ILE | D | 41 | 36.570 | 22.489 | 67.669 | 1.00 31.86 | D |
| ATOM | 4948 | N | PRO | D | 42 | 36.892 | 23.628 | 69.594 | 1.00 34.19 | D |
| ATOM | 4949 | CD | PRO | D | 42 | 37.520 | 23.732 | 70.924 | 1.00 37.38 | D |
| ATOM | 4950 | CA | PRO | D | 42 | 36.741 | 24.963 | 69.015 | 1.00 34.51 | D |
| ATOM | 4951 | CB | PRO | D | 42 | 37.337 | 25.879 | 70.088 | 1.00 35.40 | D |
| ATOM | 4952 | CG | PRO | D | 42 | 37.148 | 25.126 | 71.339 | 1.00 35.00 | D |
| ATOM | 4953 | C | PRO | D | 42 | 37.483 | 25.092 | 67.697 | 1.00 33.57 | D |
| ATOM | 4954 | O | PRO | D | 42 | 38.695 | 24.898 | 67.641 | 1.00 36.09 | D |
| ATOM | 4955 | N | PRO | D | 43 | 36.763 | 25.414 | 66.614 | 1.00 29.97 | D |
| ATOM | 4956 | CD | PRO | D | 43 | 35.324 | 25.720 | 66.552 | 1.00 31.24 | D |
| ATOM | 4957 | CA | PRO | D | 43 | 37.385 | 25.567 | 65.294 | 1.00 31.49 | D |
| ATOM | 4958 | CB | PRO | D | 43 | 36.204 | 25.918 | 64.395 | 1.00 32.20 | D |
| ATOM | 4959 | CG | PRO | D | 43 | 35.249 | 26.614 | 65.336 | 1.00 32.15 | D |
| ATOM | 4960 | C | PRO | D | 43 | 38.478 | 26.640 | 65.254 | 1.00 33.37 | D |
| ATOM | 4961 | O | PRO | D | 43 | 39.620 | 26.361 | 64.860 | 1.00 34.99 | D |
| ATOM | 4962 | N | HIS | D | 44 | 38.129 | 27.860 | 65.672 | 1.00 32.32 | D |
| ATOM | 4963 | CA | HIS | D | 44 | 39.056 | 28.989 | 65.675 | 1.00 32.57 | D |
| ATOM | 4964 | CB | HIS | D | 44 | 38.287 | 30.283 | 65.820 | 1.00 32.20 | D |
| ATOM | 4965 | CG | HIS | D | 44 | 37.469 | 30.341 | 67.066 | 1.00 33.55 | D |
| ATOM | 4966 | CD2 | HIS | D | 44 | 36.944 | 31.386 | 67.749 | 1.00 31.11 | D |
| ATOM | 4967 | ND1 | HIS | D | 44 | 37.029 | 29.204 | 67.704 | 1.00 33.40 | D |

Figure 10 (77 of 142)

| | | | | | | | | | |
|---|---|---|---|---|---|---|---|---|---|
| ATOM | 4968 | CE1 | HIS | D | 44 | 36.264 | 29.543 | 68.726 | 1.00 31.63 | D |
| ATOM | 4969 | NE2 | HIS | D | 44 | 36.195 | 30.861 | 68.774 | 1.00 31.06 | D |
| ATOM | 4970 | C | HIS | D | 44 | 40.177 | 28.986 | 66.702 | 1.00 32.09 | D |
| ATOM | 4971 | O | HIS | D | 44 | 40.913 | 29.956 | 66.796 | 1.00 37.05 | D |
| ATOM | 4972 | N | LYS | D | 45 | 40.322 | 27.927 | 67.483 | 1.00 29.18 | D |
| ATOM | 4973 | CA | LYS | D | 45 | 41.422 | 27.903 | 68.427 | 1.00 31.58 | D |
| ATOM | 4974 | CB | LYS | D | 45 | 41.081 | 28.750 | 69.661 | 1.00 28.87 | D |
| ATOM | 4975 | CG | LYS | D | 45 | 39.911 | 28.268 | 70.461 | 1.00 27.60 | D |
| ATOM | 4976 | CD | LYS | D | 45 | 39.641 | 29.166 | 71.656 | 1.00 27.21 | D |
| ATOM | 4977 | CE | LYS | D | 45 | 38.788 | 30.369 | 71.282 | 1.00 28.63 | D |
| ATOM | 4978 | NZ | LYS | D | 45 | 37.689 | 30.616 | 72.270 | 1.00 30.31 | D |
| ATOM | 4979 | C | LYS | D | 45 | 41.805 | 26.469 | 68.784 | 1.00 38.46 | D |
| ATOM | 4980 | O | LYS | D | 45 | 41.803 | 26.075 | 69.941 | 1.00 40.14 | D |
| ATOM | 4981 | N | GLN | D | 46 | 42.145 | 25.701 | 67.761 | 1.00 21.23 | D |
| ATOM | 4982 | CA | GLN | D | 46 | 42.510 | 24.300 | 67.952 | 1.00 24.81 | D |
| ATOM | 4983 | CB | GLN | D | 46 | 42.497 | 23.575 | 66.605 | 1.00 27.31 | D |
| ATOM | 4984 | CG | GLN | D | 46 | 41.349 | 23.952 | 65.698 | 1.00 29.41 | D |
| ATOM | 4985 | CD | GLN | D | 46 | 41.558 | 23.454 | 64.275 | 1.00 20.59 | D |
| ATOM | 4986 | OE1 | GLN | D | 46 | 41.365 | 24.230 | 63.320 | 1.00 20.59 | D |
| ATOM | 4987 | NE2 | GLN | D | 46 | 41.967 | 22.169 | 64.109 | 1.00 20.59 | D |
| ATOM | 4988 | C | GLN | D | 46 | 43.901 | 24.144 | 68.574 | 1.00 27.65 | D |
| ATOM | 4989 | O | GLN | D | 46 | 44.300 | 23.013 | 68.988 | 1.00 26.89 | D |
| ATOM | 4990 | N | ASN | D | 47 | 44.683 | 25.219 | 68.605 | 1.00 20.59 | D |
| ATOM | 4991 | CA | ASN | D | 47 | 45.988 | 25.088 | 69.198 | 1.00 20.59 | D |
| ATOM | 4992 | CB | ASN | D | 47 | 47.153 | 25.360 | 68.277 | 1.00 20.59 | D |
| ATOM | 4993 | CG | ASN | D | 47 | 47.788 | 24.036 | 67.780 | 1.00 20.59 | D |
| ATOM | 4994 | OD1 | ASN | D | 47 | 48.806 | 23.547 | 68.321 | 1.00 20.59 | D |
| ATOM | 4995 | ND2 | ASN | D | 47 | 47.070 | 23.357 | 66.868 | 1.00 20.59 | D |
| ATOM | 4996 | C | ASN | D | 47 | 46.099 | 25.806 | 70.493 | 1.00 20.59 | D |
| ATOM | 4997 | O | ASN | D | 47 | 47.141 | 26.282 | 70.923 | 1.00 20.59 | D |
| ATOM | 4998 | N | GLU | D | 48 | 44.990 | 25.770 | 71.204 | 1.00 29.55 | D |
| ATOM | 4999 | CA | GLU | D | 48 | 45.093 | 26.268 | 72.542 | 1.00 31.31 | D |
| ATOM | 5000 | CB | GLU | D | 48 | 44.273 | 27.509 | 72.913 | 1.00 37.66 | D |
| ATOM | 5001 | CG | GLU | D | 48 | 43.869 | 28.429 | 71.903 | 1.00 44.07 | D |
| ATOM | 5002 | CD | GLU | D | 48 | 44.104 | 29.832 | 72.370 | 1.00 50.19 | D |
| ATOM | 5003 | OE1 | GLU | D | 48 | 45.250 | 30.127 | 72.797 | 1.00 51.99 | D |
| ATOM | 5004 | OE2 | GLU | D | 48 | 43.119 | 30.593 | 72.311 | 1.00 51.82 | D |
| ATOM | 5005 | C | GLU | D | 48 | 44.657 | 25.147 | 73.396 | 1.00 31.97 | D |
| ATOM | 5006 | O | GLU | D | 48 | 44.585 | 24.026 | 72.967 | 1.00 27.62 | D |
| ATOM | 5007 | N | ASP | D | 49 | 44.167 | 25.590 | 74.511 | 1.00 60.89 | D |
| ATOM | 5008 | CA | ASP | D | 49 | 43.997 | 24.691 | 75.572 | 1.00 59.60 | D |
| ATOM | 5009 | CB | ASP | D | 49 | 44.665 | 25.255 | 76.775 | 1.00 63.31 | D |
| ATOM | 5010 | CG | ASP | D | 49 | 45.801 | 24.384 | 77.225 | 1.00 65.91 | D |
| ATOM | 5011 | OD1 | ASP | D | 49 | 45.764 | 23.141 | 76.947 | 1.00 65.20 | D |
| ATOM | 5012 | OD2 | ASP | D | 49 | 46.716 | 24.906 | 77.865 | 1.00 68.11 | D |
| ATOM | 5013 | C | ASP | D | 49 | 42.707 | 24.215 | 76.051 | 1.00 58.02 | D |
| ATOM | 5014 | O | ASP | D | 49 | 42.710 | 23.456 | 77.030 | 1.00 64.56 | D |
| ATOM | 5015 | N | TYR | D | 50 | 41.609 | 24.483 | 75.362 | 1.00 50.18 | D |
| ATOM | 5016 | CA | TYR | D | 50 | 40.313 | 24.148 | 75.951 | 1.00 42.68 | D |
| ATOM | 5017 | CB | TYR | D | 50 | 39.260 | 23.743 | 74.932 | 1.00 42.26 | D |
| ATOM | 5018 | CG | TYR | D | 50 | 39.738 | 23.091 | 73.700 | 1.00 43.33 | D |
| ATOM | 5019 | CD1 | TYR | D | 50 | 40.395 | 23.826 | 72.722 | 1.00 41.37 | D |
| ATOM | 5020 | CE1 | TYR | D | 50 | 40.966 | 23.206 | 71.643 | 1.00 40.71 | D |
| ATOM | 5021 | CD2 | TYR | D | 50 | 39.649 | 21.713 | 73.559 | 1.00 43.67 | D |
| ATOM | 5022 | CE2 | TYR | D | 50 | 40.212 | 21.082 | 72.496 | 1.00 41.75 | D |
| ATOM | 5023 | CZ | TYR | D | 50 | 40.873 | 21.826 | 71.542 | 1.00 39.89 | D |
| ATOM | 5024 | OH | TYR | D | 50 | 41.478 | 21.173 | 70.503 | 1.00 38.74 | D |
| ATOM | 5025 | C | TYR | D | 50 | 40.409 | 23.060 | 76.977 | 1.00 37.75 | D |
| ATOM | 5026 | O | TYR | D | 50 | 41.295 | 22.190 | 76.959 | 1.00 36.99 | D |
| ATOM | 5027 | N | THR | D | 51 | 39.367 | 22.966 | 77.774 | 1.00 33.97 | D |
| ATOM | 5028 | CA | THR | D | 51 | 39.491 | 22.033 | 78.834 | 1.00 33.77 | D |
| ATOM | 5029 | CB | THR | D | 51 | 39.024 | 22.703 | 80.102 | 1.00 27.20 | D |
| ATOM | 5030 | OG1 | THR | D | 51 | 37.614 | 22.585 | 80.107 | 1.00 29.23 | D |
| ATOM | 5031 | CG2 | THR | D | 51 | 39.410 | 24.182 | 80.023 | 1.00 20.37 | D |
| ATOM | 5032 | C | THR | D | 51 | 38.620 | 20.881 | 78.405 | 1.00 33.23 | D |
| ATOM | 5033 | O | THR | D | 51 | 37.430 | 21.033 | 78.247 | 1.00 33.63 | D |

Figure 10 (78 of 142)

| ATOM | 5034 | N | ASP | D | 52 | 39.279 | 19.785 | 78.137 | 1.00 | 38.85 | D |
|---|---|---|---|---|---|---|---|---|---|---|---|
| ATOM | 5035 | CA | ASP | D | 52 | 38.674 | 18.521 | 77.794 | 1.00 | 44.11 | D |
| ATOM | 5036 | CB | ASP | D | 52 | 38.945 | 17.580 | 78.991 | 1.00 | 53.63 | D |
| ATOM | 5037 | CG | ASP | D | 52 | 40.426 | 17.457 | 79.284 | 1.00 | 57.58 | D |
| ATOM | 5038 | OD1 | ASP | D | 52 | 41.127 | 16.932 | 78.396 | 1.00 | 59.96 | D |
| ATOM | 5039 | OD2 | ASP | D | 52 | 40.860 | 17.872 | 80.392 | 1.00 | 61.33 | D |
| ATOM | 5040 | C | ASP | D | 52 | 37.186 | 18.333 | 77.352 | 1.00 | 37.77 | D |
| ATOM | 5041 | O | ASP | D | 52 | 36.779 | 17.199 | 77.087 | 1.00 | 36.03 | D |
| ATOM | 5042 | N | SER | D | 53 | 36.378 | 19.391 | 77.309 | 1.00 | 33.45 | D |
| ATOM | 5043 | CA | SER | D | 53 | 34.974 | 19.255 | 76.864 | 1.00 | 30.49 | D |
| ATOM | 5044 | CB | SER | D | 53 | 34.896 | 18.337 | 75.622 | 1.00 | 26.85 | D |
| ATOM | 5045 | OG | SER | D | 53 | 33.569 | 18.093 | 75.182 | 1.00 | 23.03 | D |
| ATOM | 5046 | C | SER | D | 53 | 33.990 | 18.744 | 77.917 | 1.00 | 30.72 | D |
| ATOM | 5047 | O | SER | D | 53 | 33.027 | 19.429 | 78.279 | 1.00 | 29.26 | D |
| ATOM | 5048 | N | PHE | D | 54 | 34.227 | 17.528 | 78.388 | 1.00 | 24.89 | D |
| ATOM | 5049 | CA | PHE | D | 54 | 33.382 | 16.928 | 79.403 | 1.00 | 24.51 | D |
| ATOM | 5050 | CB | PHE | D | 54 | 34.057 | 15.702 | 79.998 | 1.00 | 21.81 | D |
| ATOM | 5051 | CG | PHE | D | 54 | 33.275 | 15.083 | 81.100 | 1.00 | 20.89 | D |
| ATOM | 5052 | CD1 | PHE | D | 54 | 31.964 | 14.671 | 80.889 | 1.00 | 22.54 | D |
| ATOM | 5053 | CD2 | PHE | D | 54 | 33.824 | 14.933 | 82.355 | 1.00 | 22.33 | D |
| ATOM | 5054 | CE1 | PHE | D | 54 | 31.218 | 14.116 | 81.928 | 1.00 | 26.13 | D |
| ATOM | 5055 | CE2 | PHE | D | 54 | 33.087 | 14.385 | 83.390 | 1.00 | 20.10 | D |
| ATOM | 5056 | CZ | PHE | D | 54 | 31.786 | 13.977 | 83.179 | 1.00 | 23.09 | D |
| ATOM | 5057 | C | PHE | D | 54 | 33.072 | 17.917 | 80.522 | 1.00 | 24.27 | D |
| ATOM | 5058 | O | PHE | D | 54 | 31.967 | 17.938 | 81.062 | 1.00 | 31.24 | D |
| ATOM | 5059 | N | HIS | D | 55 | 34.045 | 18.744 | 80.873 | 1.00 | 21.36 | D |
| ATOM | 5060 | CA | HIS | D | 55 | 33.818 | 19.709 | 81.926 | 1.00 | 17.81 | D |
| ATOM | 5061 | CB | HIS | D | 55 | 35.149 | 20.116 | 82.523 | 1.00 | 19.00 | D |
| ATOM | 5062 | CG | HIS | D | 55 | 35.860 | 18.971 | 83.163 | 1.00 | 19.83 | D |
| ATOM | 5063 | CD2 | HIS | D | 55 | 35.432 | 17.720 | 83.461 | 1.00 | 17.72 | D |
| ATOM | 5064 | ND1 | HIS | D | 55 | 37.179 | 19.027 | 83.552 | 1.00 | 22.00 | D |
| ATOM | 5065 | CE1 | HIS | D | 55 | 37.537 | 17.860 | 84.058 | 1.00 | 22.02 | D |
| ATOM | 5066 | NE2 | HIS | D | 55 | 36.495 | 17.049 | 84.014 | 1.00 | 23.66 | D |
| ATOM | 5067 | C | HIS | D | 55 | 33.061 | 20.896 | 81.404 | 1.00 | 14.19 | D |
| ATOM | 5068 | O | HIS | D | 55 | 32.266 | 21.502 | 82.113 | 1.00 | 12.26 | D |
| ATOM | 5069 | N | ARG | D | 56 | 33.291 | 21.222 | 80.149 | 1.00 | 12.26 | D |
| ATOM | 5070 | CA | ARG | D | 56 | 32.584 | 22.332 | 79.580 | 1.00 | 12.26 | D |
| ATOM | 5071 | CB | ARG | D | 56 | 33.135 | 22.619 | 78.187 | 1.00 | 12.26 | D |
| ATOM | 5072 | CG | ARG | D | 56 | 34.485 | 23.339 | 78.264 | 1.00 | 12.26 | D |
| ATOM | 5073 | CD | ARG | D | 56 | 35.367 | 23.080 | 77.070 | 1.00 | 12.26 | D |
| ATOM | 5074 | NE | ARG | D | 56 | 34.716 | 23.525 | 75.851 | 1.00 | 15.44 | D |
| ATOM | 5075 | CZ | ARG | D | 56 | 34.710 | 22.821 | 74.728 | 1.00 | 16.89 | D |
| ATOM | 5076 | NH1 | ARG | D | 56 | 35.331 | 21.638 | 74.685 | 1.00 | 16.53 | D |
| ATOM | 5077 | NH2 | ARG | D | 56 | 34.066 | 23.292 | 73.659 | 1.00 | 18.07 | D |
| ATOM | 5078 | C | ARG | D | 56 | 31.110 | 21.988 | 79.563 | 1.00 | 12.26 | D |
| ATOM | 5079 | O | ARG | D | 56 | 30.270 | 22.809 | 79.927 | 1.00 | 12.26 | D |
| ATOM | 5080 | N | VAL | D | 57 | 30.789 | 20.763 | 79.179 | 1.00 | 12.26 | D |
| ATOM | 5081 | CA | VAL | D | 57 | 29.394 | 20.372 | 79.136 | 1.00 | 12.54 | D |
| ATOM | 5082 | CB | VAL | D | 57 | 29.207 | 19.033 | 78.381 | 1.00 | 12.29 | D |
| ATOM | 5083 | CG1 | VAL | D | 57 | 27.755 | 18.526 | 78.481 | 1.00 | 12.26 | D |
| ATOM | 5084 | CG2 | VAL | D | 57 | 29.557 | 19.248 | 76.938 | 1.00 | 12.26 | D |
| ATOM | 5085 | C | VAL | D | 57 | 28.858 | 20.262 | 80.546 | 1.00 | 12.26 | D |
| ATOM | 5086 | O | VAL | D | 57 | 27.680 | 20.501 | 80.792 | 1.00 | 12.26 | D |
| ATOM | 5087 | N | GLU | D | 58 | 29.714 | 19.920 | 81.489 | 1.00 | 12.26 | D |
| ATOM | 5088 | CA | GLU | D | 58 | 29.214 | 19.801 | 82.831 | 1.00 | 12.26 | D |
| ATOM | 5089 | CB | GLU | D | 58 | 30.192 | 19.030 | 83.698 | 1.00 | 21.74 | D |
| ATOM | 5090 | CG | GLU | D | 58 | 30.143 | 17.530 | 83.438 | 1.00 | 24.00 | D |
| ATOM | 5091 | CD | GLU | D | 58 | 28.722 | 16.974 | 83.490 | 1.00 | 25.49 | D |
| ATOM | 5092 | OE1 | GLU | D | 58 | 28.116 | 17.026 | 84.579 | 1.00 | 24.62 | D |
| ATOM | 5093 | OE2 | GLU | D | 58 | 28.214 | 16.492 | 82.447 | 1.00 | 16.28 | D |
| ATOM | 5094 | C | GLU | D | 58 | 28.941 | 21.164 | 83.400 | 1.00 | 12.26 | D |
| ATOM | 5095 | O | GLU | D | 58 | 27.893 | 21.392 | 83.985 | 1.00 | 12.26 | D |
| ATOM | 5096 | N | MET | D | 59 | 29.887 | 22.077 | 83.231 | 1.00 | 12.55 | D |
| ATOM | 5097 | CA | MET | D | 59 | 29.707 | 23.438 | 83.719 | 1.00 | 12.26 | D |
| ATOM | 5098 | CB | MET | D | 59 | 30.994 | 24.264 | 83.508 | 1.00 | 12.26 | D |
| ATOM | 5099 | CG | MET | D | 59 | 32.187 | 23.837 | 84.354 | 1.00 | 12.26 | D |

Figure 10 (79 of 142)

| ATOM | 5100 | SD | MET | D | 59 | 33.575 | 24.954 | 84.214 | 1.00 | 12.26 | D |
| --- | --- | --- | --- | --- | --- | --- | --- | --- | --- | --- | --- |
| ATOM | 5101 | CE | MET | D | 59 | 34.135 | 24.580 | 82.558 | 1.00 | 12.26 | D |
| ATOM | 5102 | C | MET | D | 59 | 28.526 | 24.089 | 82.978 | 1.00 | 12.26 | D |
| ATOM | 5103 | O | MET | D | 59 | 27.689 | 24.769 | 83.574 | 1.00 | 12.26 | D |
| ATOM | 5104 | N | LEU | D | 60 | 28.456 | 23.864 | 81.673 | 1.00 | 12.26 | D |
| ATOM | 5105 | CA | LEU | D | 60 | 27.381 | 24.434 | 80.886 | 1.00 | 12.26 | D |
| ATOM | 5106 | CB | LEU | D | 60 | 27.473 | 23.972 | 79.436 | 1.00 | 12.26 | D |
| ATOM | 5107 | CG | LEU | D | 60 | 27.215 | 25.041 | 78.370 | 1.00 | 15.74 | D |
| ATOM | 5108 | CD1 | LEU | D | 60 | 26.610 | 24.371 | 77.144 | 1.00 | 12.26 | D |
| ATOM | 5109 | CD2 | LEU | D | 60 | 26.270 | 26.113 | 78.896 | 1.00 | 15.19 | D |
| ATOM | 5110 | C | LEU | D | 60 | 26.036 | 24.018 | 81.453 | 1.00 | 14.45 | D |
| ATOM | 5111 | O | LEU | D | 60 | 25.128 | 24.833 | 81.584 | 1.00 | 12.26 | D |
| ATOM | 5112 | N | LYS | D | 61 | 25.924 | 22.738 | 81.793 | 1.00 | 16.67 | D |
| ATOM | 5113 | CA | LYS | D | 61 | 24.688 | 22.173 | 82.318 | 1.00 | 14.49 | D |
| ATOM | 5114 | CB | LYS | D | 61 | 24.837 | 20.657 | 82.487 | 1.00 | 12.26 | D |
| ATOM | 5115 | CG | LYS | D | 61 | 24.037 | 19.873 | 81.469 | 1.00 | 12.26 | D |
| ATOM | 5116 | CD | LYS | D | 61 | 24.580 | 18.468 | 81.275 | 1.00 | 12.99 | D |
| ATOM | 5117 | CE | LYS | D | 61 | 24.543 | 17.632 | 82.537 | 1.00 | 12.26 | D |
| ATOM | 5118 | NZ | LYS | D | 61 | 25.136 | 16.309 | 82.255 | 1.00 | 12.26 | D |
| ATOM | 5119 | C | LYS | D | 61 | 24.246 | 22.803 | 83.615 | 1.00 | 12.26 | D |
| ATOM | 5120 | O | LYS | D | 61 | 23.054 | 22.923 | 83.879 | 1.00 | 20.14 | D |
| ATOM | 5121 | N | LEU | D | 62 | 25.205 | 23.223 | 84.417 | 1.00 | 12.26 | D |
| ATOM | 5122 | CA | LEU | D | 62 | 24.859 | 23.823 | 85.685 | 1.00 | 12.26 | D |
| ATOM | 5123 | CB | LEU | D | 62 | 26.084 | 23.911 | 86.584 | 1.00 | 12.26 | D |
| ATOM | 5124 | CG | LEU | D | 62 | 26.655 | 22.555 | 86.984 | 1.00 | 12.26 | D |
| ATOM | 5125 | CD1 | LEU | D | 62 | 28.045 | 22.710 | 87.515 | 1.00 | 12.26 | D |
| ATOM | 5126 | CD2 | LEU | D | 62 | 25.737 | 21.921 | 88.000 | 1.00 | 12.26 | D |
| ATOM | 5127 | C | LEU | D | 62 | 24.292 | 25.196 | 85.457 | 1.00 | 12.26 | D |
| ATOM | 5128 | O | LEU | D | 62 | 23.199 | 25.502 | 85.918 | 1.00 | 22.88 | D |
| ATOM | 5129 | N | ALA | D | 63 | 25.034 | 26.020 | 84.732 | 1.00 | 15.11 | D |
| ATOM | 5130 | CA | ALA | D | 63 | 24.617 | 27.385 | 84.430 | 1.00 | 14.13 | D |
| ATOM | 5131 | CB | ALA | D | 63 | 25.569 | 27.968 | 83.399 | 1.00 | 12.26 | D |
| ATOM | 5132 | C | ALA | D | 63 | 23.160 | 27.567 | 83.949 | 1.00 | 15.41 | D |
| ATOM | 5133 | O | ALA | D | 63 | 22.433 | 28.476 | 84.394 | 1.00 | 20.18 | D |
| ATOM | 5134 | N | ILE | D | 64 | 22.727 | 26.691 | 83.051 | 1.00 | 21.32 | D |
| ATOM | 5135 | CA | ILE | D | 64 | 21.396 | 26.815 | 82.487 | 1.00 | 25.70 | D |
| ATOM | 5136 | CB | ILE | D | 64 | 21.428 | 26.565 | 80.959 | 1.00 | 22.90 | D |
| ATOM | 5137 | CG2 | ILE | D | 64 | 22.357 | 27.569 | 80.275 | 1.00 | 19.62 | D |
| ATOM | 5138 | CG1 | ILE | D | 64 | 21.880 | 25.128 | 80.685 | 1.00 | 16.71 | D |
| ATOM | 5139 | CD1 | ILE | D | 64 | 21.636 | 24.682 | 79.263 | 1.00 | 20.24 | D |
| ATOM | 5140 | C | ILE | D | 64 | 20.298 | 25.937 | 83.054 | 1.00 | 25.72 | D |
| ATOM | 5141 | O | ILE | D | 64 | 19.241 | 25.836 | 82.442 | 1.00 | 29.64 | D |
| ATOM | 5142 | N | GLN | D | 65 | 20.494 | 25.310 | 84.205 | 1.00 | 29.00 | D |
| ATOM | 5143 | CA | GLN | D | 65 | 19.434 | 24.439 | 84.700 | 1.00 | 30.82 | D |
| ATOM | 5144 | CB | GLN | D | 65 | 19.922 | 23.622 | 85.872 | 1.00 | 34.16 | D |
| ATOM | 5145 | CG | GLN | D | 65 | 20.737 | 22.446 | 85.432 | 1.00 | 42.45 | D |
| ATOM | 5146 | CD | GLN | D | 65 | 21.423 | 21.779 | 86.589 | 1.00 | 45.83 | D |
| ATOM | 5147 | OE1 | GLN | D | 65 | 21.341 | 22.244 | 87.736 | 1.00 | 45.38 | D |
| ATOM | 5148 | NE2 | GLN | D | 65 | 22.117 | 20.680 | 86.304 | 1.00 | 48.04 | D |
| ATOM | 5149 | C | GLN | D | 65 | 18.158 | 25.135 | 85.078 | 1.00 | 28.13 | D |
| ATOM | 5150 | O | GLN | D | 65 | 17.071 | 24.716 | 84.693 | 1.00 | 25.87 | D |
| ATOM | 5151 | N | SER | D | 66 | 18.306 | 26.212 | 85.828 | 1.00 | 25.29 | D |
| ATOM | 5152 | CA | SER | D | 66 | 17.173 | 27.000 | 86.305 | 1.00 | 28.93 | D |
| ATOM | 5153 | CB | SER | D | 66 | 17.654 | 27.993 | 87.367 | 1.00 | 28.88 | D |
| ATOM | 5154 | OG | SER | D | 66 | 18.871 | 28.610 | 86.977 | 1.00 | 40.62 | D |
| ATOM | 5155 | C | SER | D | 66 | 16.342 | 27.754 | 85.269 | 1.00 | 26.95 | D |
| ATOM | 5156 | O | SER | D | 66 | 15.342 | 28.366 | 85.626 | 1.00 | 27.27 | D |
| ATOM | 5157 | N | ASN | D | 67 | 16.748 | 27.731 | 84.002 | 1.00 | 28.50 | D |
| ATOM | 5158 | CA | ASN | D | 67 | 15.999 | 28.429 | 82.971 | 1.00 | 25.80 | D |
| ATOM | 5159 | CB | ASN | D | 67 | 16.913 | 29.341 | 82.165 | 1.00 | 32.29 | D |
| ATOM | 5160 | CG | ASN | D | 67 | 16.156 | 30.166 | 81.141 | 1.00 | 35.07 | D |
| ATOM | 5161 | OD1 | ASN | D | 67 | 16.695 | 31.127 | 80.581 | 1.00 | 38.46 | D |
| ATOM | 5162 | ND2 | ASN | D | 67 | 14.905 | 29.797 | 80.884 | 1.00 | 37.11 | D |
| ATOM | 5163 | C | ASN | D | 67 | 15.349 | 27.422 | 82.055 | 1.00 | 22.23 | D |
| ATOM | 5164 | O | ASN | D | 67 | 16.022 | 26.729 | 81.306 | 1.00 | 26.35 | D |
| ATOM | 5165 | N | PRO | D | 68 | 14.021 | 27.327 | 82.115 | 1.00 | 19.93 | D |

Figure 10 (80 of 142)

| ATOM | 5166 | CD  | PRO D | 68 | 13.207 | 28.064 | 83.094 | 1.00 | 17.97 | D |
|------|------|-----|-------|----|--------|--------|--------|------|-------|---|
| ATOM | 5167 | CA  | PRO D | 68 | 13.188 | 26.427 | 81.321 | 1.00 | 18.64 | D |
| ATOM | 5168 | CB  | PRO D | 68 | 11.782 | 26.765 | 81.793 | 1.00 | 21.70 | D |
| ATOM | 5169 | CG  | PRO D | 68 | 12.007 | 27.188 | 83.217 | 1.00 | 19.70 | D |
| ATOM | 5170 | C   | PRO D | 68 | 13.346 | 26.628 | 79.818 | 1.00 | 16.29 | D |
| ATOM | 5171 | O   | PRO D | 68 | 13.155 | 25.690 | 79.043 | 1.00 | 17.90 | D |
| ATOM | 5172 | N   | SER D | 69 | 13.699 | 27.840 | 79.402 | 1.00 | 13.99 | D |
| ATOM | 5173 | CA  | SER D | 69 | 13.861 | 28.118 | 77.986 | 1.00 | 16.56 | D |
| ATOM | 5174 | CB  | SER D | 69 | 13.430 | 29.543 | 77.679 | 1.00 | 20.26 | D |
| ATOM | 5175 | OG  | SER D | 69 | 12.069 | 29.730 | 78.017 | 1.00 | 25.64 | D |
| ATOM | 5176 | C   | SER D | 69 | 15.262 | 27.892 | 77.452 | 1.00 | 16.14 | D |
| ATOM | 5177 | O   | SER D | 69 | 15.493 | 28.093 | 76.268 | 1.00 | 19.24 | D |
| ATOM | 5178 | N   | PHE D | 70 | 16.201 | 27.502 | 78.312 | 1.00 | 14.41 | D |
| ATOM | 5179 | CA  | PHE D | 70 | 17.569 | 27.225 | 77.869 | 1.00 | 12.26 | D |
| ATOM | 5180 | CB  | PHE D | 70 | 18.604 | 27.714 | 78.870 | 1.00 | 12.26 | D |
| ATOM | 5181 | CG  | PHE D | 70 | 18.803 | 29.202 | 78.851 | 1.00 | 12.26 | D |
| ATOM | 5182 | CD1 | PHE D | 70 | 19.732 | 29.800 | 79.695 | 1.00 | 12.26 | D |
| ATOM | 5183 | CD2 | PHE D | 70 | 18.039 | 30.015 | 78.010 | 1.00 | 12.26 | D |
| ATOM | 5184 | CE1 | PHE D | 70 | 19.898 | 31.186 | 79.709 | 1.00 | 12.26 | D |
| ATOM | 5185 | CE2 | PHE D | 70 | 18.195 | 31.397 | 78.013 | 1.00 | 12.26 | D |
| ATOM | 5186 | CZ  | PHE D | 70 | 19.129 | 31.983 | 78.869 | 1.00 | 12.26 | D |
| ATOM | 5187 | C   | PHE D | 70 | 17.717 | 25.745 | 77.704 | 1.00 | 12.26 | D |
| ATOM | 5188 | O   | PHE D | 70 | 17.305 | 24.990 | 78.560 | 1.00 | 12.26 | D |
| ATOM | 5189 | N   | LYS D | 71 | 18.315 | 25.325 | 76.603 | 1.00 | 12.26 | D |
| ATOM | 5190 | CA  | LYS D | 71 | 18.465 | 23.906 | 76.349 | 1.00 | 15.38 | D |
| ATOM | 5191 | CB  | LYS D | 71 | 17.380 | 23.460 | 75.367 | 1.00 | 13.56 | D |
| ATOM | 5192 | CG  | LYS D | 71 | 16.002 | 23.836 | 75.875 | 1.00 | 17.16 | D |
| ATOM | 5193 | CD  | LYS D | 71 | 14.885 | 23.008 | 75.286 | 1.00 | 22.23 | D |
| ATOM | 5194 | CE  | LYS D | 71 | 13.638 | 23.278 | 76.087 | 1.00 | 28.69 | D |
| ATOM | 5195 | NZ  | LYS D | 71 | 14.020 | 23.209 | 77.526 | 1.00 | 27.55 | D |
| ATOM | 5196 | C   | LYS D | 71 | 19.841 | 23.555 | 75.827 | 1.00 | 15.01 | D |
| ATOM | 5197 | O   | LYS D | 71 | 20.466 | 24.329 | 75.106 | 1.00 | 24.38 | D |
| ATOM | 5198 | N   | LEU D | 72 | 20.315 | 22.382 | 76.210 | 1.00 | 12.26 | D |
| ATOM | 5199 | CA  | LEU D | 72 | 21.619 | 21.921 | 75.783 | 1.00 | 12.26 | D |
| ATOM | 5200 | CB  | LEU D | 72 | 22.161 | 20.936 | 76.820 | 1.00 | 12.26 | D |
| ATOM | 5201 | CG  | LEU D | 72 | 23.654 | 20.856 | 77.115 | 1.00 | 12.26 | D |
| ATOM | 5202 | CD1 | LEU D | 72 | 23.932 | 19.583 | 77.830 | 1.00 | 12.26 | D |
| ATOM | 5203 | CD2 | LEU D | 72 | 24.444 | 20.883 | 75.843 | 1.00 | 13.91 | D |
| ATOM | 5204 | C   | LEU D | 72 | 21.503 | 21.226 | 74.420 | 1.00 | 12.26 | D |
| ATOM | 5205 | O   | LEU D | 72 | 20.505 | 20.579 | 74.126 | 1.00 | 13.68 | D |
| ATOM | 5206 | N   | GLU D | 73 | 22.520 | 21.371 | 73.583 | 1.00 | 15.73 | D |
| ATOM | 5207 | CA  | GLU D | 73 | 22.537 | 20.732 | 72.271 | 1.00 | 12.26 | D |
| ATOM | 5208 | CB  | GLU D | 73 | 22.192 | 21.723 | 71.153 | 1.00 | 12.26 | D |
| ATOM | 5209 | CG  | GLU D | 73 | 22.334 | 21.082 | 69.786 | 1.00 | 16.63 | D |
| ATOM | 5210 | CD  | GLU D | 73 | 21.698 | 19.702 | 69.751 | 1.00 | 18.66 | D |
| ATOM | 5211 | OE1 | GLU D | 73 | 20.450 | 19.634 | 69.816 | 1.00 | 23.11 | D |
| ATOM | 5212 | OE2 | GLU D | 73 | 22.438 | 18.694 | 69.686 | 1.00 | 16.77 | D |
| ATOM | 5213 | C   | GLU D | 73 | 23.937 | 20.184 | 72.036 | 1.00 | 17.38 | D |
| ATOM | 5214 | O   | GLU D | 73 | 24.877 | 20.942 | 71.751 | 1.00 | 18.32 | D |
| ATOM | 5215 | N   | LEU D | 74 | 24.076 | 18.868 | 72.154 | 1.00 | 12.26 | D |
| ATOM | 5216 | CA  | LEU D | 74 | 25.380 | 18.251 | 71.981 | 1.00 | 16.42 | D |
| ATOM | 5217 | CB  | LEU D | 74 | 25.576 | 17.144 | 73.001 | 1.00 | 12.26 | D |
| ATOM | 5218 | CG  | LEU D | 74 | 25.488 | 17.579 | 74.461 | 1.00 | 14.90 | D |
| ATOM | 5219 | CD1 | LEU D | 74 | 25.693 | 16.337 | 75.350 | 1.00 | 12.26 | D |
| ATOM | 5220 | CD2 | LEU D | 74 | 26.530 | 18.668 | 74.755 | 1.00 | 17.69 | D |
| ATOM | 5221 | C   | LEU D | 74 | 25.615 | 17.695 | 70.596 | 1.00 | 15.43 | D |
| ATOM | 5222 | O   | LEU D | 74 | 26.428 | 16.788 | 70.409 | 1.00 | 20.44 | D |
| ATOM | 5223 | N   | VAL D | 75 | 24.906 | 18.243 | 69.622 | 1.00 | 14.54 | D |
| ATOM | 5224 | CA  | VAL D | 75 | 25.059 | 17.779 | 68.252 | 1.00 | 12.44 | D |
| ATOM | 5225 | CB  | VAL D | 75 | 24.224 | 18.625 | 67.276 | 1.00 | 12.26 | D |
| ATOM | 5226 | CG1 | VAL D | 75 | 24.665 | 20.074 | 67.320 | 1.00 | 12.26 | D |
| ATOM | 5227 | CG2 | VAL D | 75 | 24.396 | 18.092 | 65.879 | 1.00 | 12.26 | D |
| ATOM | 5228 | C   | VAL D | 75 | 26.518 | 17.821 | 67.798 | 1.00 | 12.26 | D |
| ATOM | 5229 | O   | VAL D | 75 | 27.019 | 16.865 | 67.193 | 1.00 | 12.26 | D |
| ATOM | 5230 | N   | GLU D | 76 | 27.197 | 18.933 | 68.086 | 1.00 | 13.44 | D |
| ATOM | 5231 | CA  | GLU D | 76 | 28.595 | 19.064 | 67.683 | 1.00 | 21.28 | D |

Figure 10 (81 of 142)

| | | | | | | | | | | |
|---|---|---|---|---|---|---|---|---|---|---|
| ATOM | 5232 | CB | GLU | D | 76 | 29.091 | 20.497 | 67.923 | 1.00 22.16 | D |
| ATOM | 5233 | CG | GLU | D | 76 | 28.640 | 21.452 | 66.820 | 1.00 27.56 | D |
| ATOM | 5234 | CD | GLU | D | 76 | 29.398 | 22.777 | 66.815 | 1.00 30.01 | D |
| ATOM | 5235 | OE1 | GLU | D | 76 | 29.275 | 23.542 | 65.829 | 1.00 30.86 | D |
| ATOM | 5236 | OE2 | GLU | D | 76 | 30.117 | 23.060 | 67.798 | 1.00 33.76 | D |
| ATOM | 5237 | C | GLU | D | 76 | 29.513 | 18.033 | 68.363 | 1.00 21.65 | D |
| ATOM | 5238 | O | GLU | D | 76 | 30.572 | 17.677 | 67.833 | 1.00 26.50 | D |
| ATOM | 5239 | N | MET | D | 77 | 29.080 | 17.531 | 69.517 | 1.00 23.90 | D |
| ATOM | 5240 | CA | MET | D | 77 | 29.833 | 16.541 | 70.288 | 1.00 25.26 | D |
| ATOM | 5241 | CB | MET | D | 77 | 29.313 | 16.474 | 71.716 | 1.00 26.15 | D |
| ATOM | 5242 | CG | MET | D | 77 | 29.514 | 17.712 | 72.522 | 1.00 20.43 | D |
| ATOM | 5243 | SD | MET | D | 77 | 31.209 | 17.933 | 72.893 | 1.00 12.74 | D |
| ATOM | 5244 | CE | MET | D | 77 | 31.717 | 16.259 | 73.127 | 1.00 12.26 | D |
| ATOM | 5245 | C | MET | D | 77 | 29.679 | 15.152 | 69.707 | 1.00 26.84 | D |
| ATOM | 5246 | O | MET | D | 77 | 30.290 | 14.201 | 70.196 | 1.00 31.02 | D |
| ATOM | 5247 | N | GLU | D | 78 | 28.847 | 15.026 | 68.682 | 1.00 28.00 | D |
| ATOM | 5248 | CA | GLU | D | 78 | 28.587 | 13.719 | 68.110 | 1.00 30.04 | D |
| ATOM | 5249 | CB | GLU | D | 78 | 27.093 | 13.399 | 68.268 | 1.00 34.15 | D |
| ATOM | 5250 | CG | GLU | D | 78 | 26.347 | 13.056 | 67.017 | 1.00 36.91 | D |
| ATOM | 5251 | CD | GLU | D | 78 | 25.049 | 13.812 | 66.908 | 1.00 38.62 | D |
| ATOM | 5252 | OE1 | GLU | D | 78 | 24.573 | 13.972 | 65.769 | 1.00 42.02 | D |
| ATOM | 5253 | OE2 | GLU | D | 78 | 24.506 | 14.239 | 67.952 | 1.00 41.16 | D |
| ATOM | 5254 | C | GLU | D | 78 | 29.056 | 13.703 | 66.681 | 1.00 30.95 | D |
| ATOM | 5255 | O | GLU | D | 78 | 28.304 | 13.943 | 65.745 | 1.00 27.51 | D |
| ATOM | 5256 | N | ARG | D | 79 | 30.343 | 13.418 | 66.560 | 1.00 32.83 | D |
| ATOM | 5257 | CA | ARG | D | 79 | 31.079 | 13.380 | 65.305 | 1.00 34.93 | D |
| ATOM | 5258 | CB | ARG | D | 79 | 30.241 | 13.991 | 64.151 | 1.00 33.12 | D |
| ATOM | 5259 | CG | ARG | D | 79 | 30.892 | 15.108 | 63.304 | 1.00 31.96 | D |
| ATOM | 5260 | CD | ARG | D | 79 | 30.967 | 16.418 | 64.039 | 1.00 25.76 | D |
| ATOM | 5261 | NE | ARG | D | 79 | 30.169 | 17.498 | 63.467 | 1.00 22.92 | D |
| ATOM | 5262 | CZ | ARG | D | 79 | 30.702 | 18.576 | 62.896 | 1.00 23.45 | D |
| ATOM | 5263 | NH1 | ARG | D | 79 | 32.026 | 18.683 | 62.808 | 1.00 23.60 | D |
| ATOM | 5264 | NH2 | ARG | D | 79 | 29.931 | 19.585 | 62.490 | 1.00 18.77 | D |
| ATOM | 5265 | C | ARG | D | 79 | 32.347 | 14.194 | 65.631 | 1.00 36.65 | D |
| ATOM | 5266 | O | ARG | D | 79 | 32.274 | 15.342 | 66.077 | 1.00 35.38 | D |
| ATOM | 5267 | N | GLU | D | 80 | 33.504 | 13.566 | 65.440 | 1.00 40.56 | D |
| ATOM | 5268 | CA | GLU | D | 80 | 34.800 | 14.173 | 65.740 | 1.00 46.67 | D |
| ATOM | 5269 | CB | GLU | D | 80 | 35.911 | 13.124 | 65.624 | 1.00 51.11 | D |
| ATOM | 5270 | CG | GLU | D | 80 | 35.822 | 12.235 | 64.377 | 1.00 58.97 | D |
| ATOM | 5271 | CD | GLU | D | 80 | 34.702 | 11.208 | 64.477 | 1.00 62.49 | D |
| ATOM | 5272 | OE1 | GLU | D | 80 | 34.488 | 10.710 | 65.604 | 1.00 66.70 | D |
| ATOM | 5273 | OE2 | GLU | D | 80 | 34.052 | 10.893 | 63.451 | 1.00 64.55 | D |
| ATOM | 5274 | C | GLU | D | 80 | 35.209 | 15.391 | 64.931 | 1.00 48.38 | D |
| ATOM | 5275 | O | GLU | D | 80 | 34.402 | 16.024 | 64.240 | 1.00 49.93 | D |
| ATOM | 5276 | N | GLY | D | 81 | 36.492 | 15.716 | 65.053 | 1.00 47.86 | D |
| ATOM | 5277 | CA | GLY | D | 81 | 37.064 | 16.844 | 64.346 | 1.00 42.99 | D |
| ATOM | 5278 | C | GLY | D | 81 | 36.528 | 18.223 | 64.692 | 1.00 39.68 | D |
| ATOM | 5279 | O | GLY | D | 81 | 35.446 | 18.364 | 65.275 | 1.00 42.87 | D |
| ATOM | 5280 | N | PRO | D | 82 | 37.289 | 19.273 | 64.332 | 1.00 42.06 | D |
| ATOM | 5281 | CD | PRO | D | 82 | 38.608 | 19.086 | 63.695 | 1.00 43.52 | D |
| ATOM | 5282 | CA | PRO | D | 82 | 37.016 | 20.704 | 64.533 | 1.00 41.44 | D |
| ATOM | 5283 | CB | PRO | D | 82 | 38.042 | 21.374 | 63.627 | 1.00 42.65 | D |
| ATOM | 5284 | CG | PRO | D | 82 | 39.233 | 20.483 | 63.797 | 1.00 42.75 | D |
| ATOM | 5285 | C | PRO | D | 82 | 35.589 | 21.074 | 64.166 | 1.00 41.45 | D |
| ATOM | 5286 | O | PRO | D | 82 | 35.172 | 20.946 | 63.008 | 1.00 45.73 | D |
| ATOM | 5287 | N | SER | D | 83 | 34.857 | 21.554 | 65.162 | 1.00 39.00 | D |
| ATOM | 5288 | CA | SER | D | 83 | 33.455 | 21.904 | 64.996 | 1.00 42.02 | D |
| ATOM | 5289 | CB | SER | D | 83 | 32.811 | 22.012 | 66.382 | 1.00 41.70 | D |
| ATOM | 5290 | OG | SER | D | 83 | 33.052 | 20.835 | 67.140 | 1.00 41.04 | D |
| ATOM | 5291 | C | SER | D | 83 | 33.161 | 23.159 | 64.167 | 1.00 41.12 | D |
| ATOM | 5292 | O | SER | D | 83 | 32.965 | 24.240 | 64.718 | 1.00 44.46 | D |
| ATOM | 5293 | N | TYR | D | 84 | 33.097 | 23.002 | 62.843 | 1.00 40.13 | D |
| ATOM | 5294 | CA | TYR | D | 84 | 32.827 | 24.125 | 61.932 | 1.00 36.62 | D |
| ATOM | 5295 | CB | TYR | D | 84 | 33.399 | 23.830 | 60.544 | 1.00 37.42 | D |
| ATOM | 5296 | CG | TYR | D | 84 | 34.912 | 23.785 | 60.482 | 1.00 36.28 | D |
| ATOM | 5297 | CD1 | TYR | D | 84 | 35.592 | 22.602 | 60.196 | 1.00 36.80 | D |

Figure 10 (82 of 142)

| ATOM | 5298 | CE1 | TYR | D | 84 | 36.980 | 22.568 | 60.141 | 1.00 | 39.05 | D |
|---|---|---|---|---|---|---|---|---|---|---|---|
| ATOM | 5299 | CD2 | TYR | D | 84 | 35.662 | 24.932 | 60.711 | 1.00 | 35.92 | D |
| ATOM | 5300 | CE2 | TYR | D | 84 | 37.049 | 24.909 | 60.658 | 1.00 | 37.08 | D |
| ATOM | 5301 | CZ | TYR | D | 84 | 37.702 | 23.726 | 60.375 | 1.00 | 38.80 | D |
| ATOM | 5302 | OH | TYR | D | 84 | 39.077 | 23.707 | 60.347 | 1.00 | 41.50 | D |
| ATOM | 5303 | C | TYR | D | 84 | 31.333 | 24.405 | 61.812 | 1.00 | 34.35 | D |
| ATOM | 5304 | O | TYR | D | 84 | 30.564 | 23.535 | 61.392 | 1.00 | 33.37 | D |
| ATOM | 5305 | N | THR | D | 85 | 30.932 | 25.627 | 62.159 | 1.00 | 28.94 | D |
| ATOM | 5306 | CA | THR | D | 85 | 29.524 | 26.008 | 62.132 | 1.00 | 27.13 | D |
| ATOM | 5307 | CB | THR | D | 85 | 29.337 | 27.480 | 62.494 | 1.00 | 28.05 | D |
| ATOM | 5308 | OG1 | THR | D | 85 | 29.845 | 27.693 | 63.812 | 1.00 | 27.33 | D |
| ATOM | 5309 | CG2 | THR | D | 85 | 27.854 | 27.863 | 62.470 | 1.00 | 29.11 | D |
| ATOM | 5310 | C | THR | D | 85 | 28.781 | 25.723 | 60.848 | 1.00 | 26.69 | D |
| ATOM | 5311 | O | THR | D | 85 | 27.566 | 25.550 | 60.865 | 1.00 | 24.97 | D |
| ATOM | 5312 | N | PHE | D | 86 | 29.490 | 25.679 | 59.728 | 1.00 | 30.33 | D |
| ATOM | 5313 | CA | PHE | D | 86 | 28.821 | 25.366 | 58.473 | 1.00 | 32.79 | D |
| ATOM | 5314 | CB | PHE | D | 86 | 29.771 | 25.537 | 57.291 | 1.00 | 34.65 | D |
| ATOM | 5315 | CG | PHE | D | 86 | 29.224 | 24.999 | 55.991 | 1.00 | 36.97 | D |
| ATOM | 5316 | CD1 | PHE | D | 86 | 28.070 | 25.544 | 55.423 | 1.00 | 37.20 | D |
| ATOM | 5317 | CD2 | PHE | D | 86 | 29.864 | 23.940 | 55.336 | 1.00 | 35.56 | D |
| ATOM | 5318 | CE1 | PHE | D | 86 | 27.564 | 25.048 | 54.222 | 1.00 | 36.19 | D |
| ATOM | 5319 | CE2 | PHE | D | 86 | 29.369 | 23.439 | 54.138 | 1.00 | 35.81 | D |
| ATOM | 5320 | CZ | PHE | D | 86 | 28.218 | 23.993 | 53.580 | 1.00 | 39.30 | D |
| ATOM | 5321 | C | PHE | D | 86 | 28.356 | 23.911 | 58.558 | 1.00 | 27.54 | D |
| ATOM | 5322 | O | PHE | D | 86 | 27.161 | 23.630 | 58.551 | 1.00 | 25.64 | D |
| ATOM | 5323 | N | ASP | D | 87 | 29.314 | 22.998 | 58.660 | 1.00 | 28.78 | D |
| ATOM | 5324 | CA | ASP | D | 87 | 29.020 | 21.574 | 58.753 | 1.00 | 28.93 | D |
| ATOM | 5325 | CB | ASP | D | 87 | 30.255 | 20.814 | 59.246 | 1.00 | 32.80 | D |
| ATOM | 5326 | CG | ASP | D | 87 | 31.276 | 20.559 | 58.150 | 1.00 | 32.06 | D |
| ATOM | 5327 | OD1 | ASP | D | 87 | 32.415 | 20.166 | 58.508 | 1.00 | 27.50 | D |
| ATOM | 5328 | OD2 | ASP | D | 87 | 30.941 | 20.734 | 56.952 | 1.00 | 37.49 | D |
| ATOM | 5329 | C | ASP | D | 87 | 27.854 | 21.285 | 59.696 | 1.00 | 28.68 | D |
| ATOM | 5330 | O | ASP | D | 87 | 26.917 | 20.564 | 59.350 | 1.00 | 32.14 | D |
| ATOM | 5331 | N | THR | D | 88 | 27.919 | 21.851 | 60.894 | 1.00 | 24.94 | D |
| ATOM | 5332 | CA | THR | D | 88 | 26.886 | 21.644 | 61.903 | 1.00 | 24.69 | D |
| ATOM | 5333 | CB | THR | D | 88 | 27.338 | 22.231 | 63.264 | 1.00 | 23.13 | D |
| ATOM | 5334 | OG1 | THR | D | 88 | 28.490 | 21.505 | 63.718 | 1.00 | 21.28 | D |
| ATOM | 5335 | CG2 | THR | D | 88 | 26.223 | 22.131 | 64.308 | 1.00 | 20.13 | D |
| ATOM | 5336 | C | THR | D | 88 | 25.524 | 22.217 | 61.512 | 1.00 | 22.88 | D |
| ATOM | 5337 | O | THR | D | 88 | 24.534 | 21.485 | 61.477 | 1.00 | 22.74 | D |
| ATOM | 5338 | N | VAL | D | 89 | 25.471 | 23.514 | 61.222 | 1.00 | 22.35 | D |
| ATOM | 5339 | CA | VAL | D | 89 | 24.217 | 24.142 | 60.831 | 1.00 | 25.08 | D |
| ATOM | 5340 | CB | VAL | D | 89 | 24.422 | 25.620 | 60.434 | 1.00 | 29.14 | D |
| ATOM | 5341 | CG1 | VAL | D | 89 | 23.132 | 26.200 | 59.854 | 1.00 | 31.79 | D |
| ATOM | 5342 | CG2 | VAL | D | 89 | 24.831 | 26.426 | 61.659 | 1.00 | 30.45 | D |
| ATOM | 5343 | C | VAL | D | 89 | 23.620 | 23.370 | 59.662 | 1.00 | 25.88 | D |
| ATOM | 5344 | O | VAL | D | 89 | 22.399 | 23.270 | 59.535 | 1.00 | 25.82 | D |
| ATOM | 5345 | N | SER | D | 90 | 24.480 | 22.827 | 58.806 | 1.00 | 24.69 | D |
| ATOM | 5346 | CA | SER | D | 90 | 24.017 | 22.021 | 57.677 | 1.00 | 21.21 | D |
| ATOM | 5347 | CB | SER | D | 90 | 25.192 | 21.349 | 56.960 | 1.00 | 23.66 | D |
| ATOM | 5348 | OG | SER | D | 90 | 26.076 | 22.298 | 56.380 | 1.00 | 30.11 | D |
| ATOM | 5349 | C | SER | D | 90 | 23.167 | 20.929 | 58.288 | 1.00 | 22.65 | D |
| ATOM | 5350 | O | SER | D | 90 | 21.946 | 20.896 | 58.119 | 1.00 | 25.98 | D |
| ATOM | 5351 | N | LEU | D | 91 | 23.843 | 20.036 | 59.004 | 1.00 | 17.71 | D |
| ATOM | 5352 | CA | LEU | D | 91 | 23.187 | 18.931 | 59.678 | 1.00 | 17.34 | D |
| ATOM | 5353 | CB | LEU | D | 91 | 24.145 | 18.292 | 60.678 | 1.00 | 12.26 | D |
| ATOM | 5354 | CG | LEU | D | 91 | 23.601 | 17.111 | 61.480 | 1.00 | 12.26 | D |
| ATOM | 5355 | CD1 | LEU | D | 91 | 22.831 | 16.177 | 60.571 | 1.00 | 17.72 | D |
| ATOM | 5356 | CD2 | LEU | D | 91 | 24.760 | 16.379 | 62.143 | 1.00 | 12.26 | D |
| ATOM | 5357 | C | LEU | D | 91 | 21.921 | 19.406 | 60.390 | 1.00 | 19.56 | D |
| ATOM | 5358 | O | LEU | D | 91 | 20.839 | 18.883 | 60.152 | 1.00 | 23.11 | D |
| ATOM | 5359 | N | LEU | D | 92 | 22.044 | 20.401 | 61.255 | 1.00 | 26.64 | D |
| ATOM | 5360 | CA | LEU | D | 92 | 20.875 | 20.907 | 61.957 | 1.00 | 29.49 | D |
| ATOM | 5361 | CB | LEU | D | 92 | 21.235 | 22.161 | 62.740 | 1.00 | 26.79 | D |
| ATOM | 5362 | CG | LEU | D | 92 | 21.990 | 21.837 | 64.024 | 1.00 | 22.79 | D |
| ATOM | 5363 | CD1 | LEU | D | 92 | 22.513 | 23.125 | 64.623 | 1.00 | 21.90 | D |

Figure 10 (83 of 142)

| ATOM | 5364 | CD2 | LEU | D | 92 | 21.071 | 21.079 | 65.007 | 1.00 | 20.25 | D |
| --- | --- | --- | --- | --- | --- | --- | --- | --- | --- | --- | --- |
| ATOM | 5365 | C | LEU | D | 92 | 19.696 | 21.204 | 61.042 | 1.00 | 35.33 | D |
| ATOM | 5366 | O | LEU | D | 92 | 18.585 | 20.731 | 61.283 | 1.00 | 40.36 | D |
| ATOM | 5367 | N | LYS | D | 93 | 19.926 | 21.988 | 59.996 | 1.00 | 41.56 | D |
| ATOM | 5368 | CA | LYS | D | 93 | 18.845 | 22.326 | 59.077 | 1.00 | 46.85 | D |
| ATOM | 5369 | CB | LYS | D | 93 | 19.340 | 23.238 | 57.965 | 1.00 | 52.97 | D |
| ATOM | 5370 | CG | LYS | D | 93 | 19.737 | 24.612 | 58.432 | 1.00 | 58.79 | D |
| ATOM | 5371 | CD | LYS | D | 93 | 19.989 | 25.526 | 57.249 | 1.00 | 64.20 | D |
| ATOM | 5372 | CE | LYS | D | 93 | 18.705 | 25.788 | 56.474 | 1.00 | 69.09 | D |
| ATOM | 5373 | NZ | LYS | D | 93 | 17.708 | 26.549 | 57.279 | 1.00 | 69.56 | D |
| ATOM | 5374 | C | LYS | D | 93 | 18.227 | 21.092 | 58.449 | 1.00 | 46.84 | D |
| ATOM | 5375 | O | LYS | D | 93 | 17.280 | 21.197 | 57.671 | 1.00 | 49.34 | D |
| ATOM | 5376 | N | GLN | D | 94 | 18.760 | 19.922 | 58.781 | 1.00 | 44.22 | D |
| ATOM | 5377 | CA | GLN | D | 94 | 18.241 | 18.682 | 58.230 | 1.00 | 44.03 | D |
| ATOM | 5378 | CB | GLN | D | 94 | 19.391 | 17.814 | 57.749 | 1.00 | 49.01 | D |
| ATOM | 5379 | CG | GLN | D | 94 | 19.020 | 16.900 | 56.616 | 1.00 | 57.86 | D |
| ATOM | 5380 | CD | GLN | D | 94 | 20.241 | 16.296 | 55.960 | 1.00 | 62.33 | D |
| ATOM | 5381 | OE1 | GLN | D | 94 | 20.999 | 15.554 | 56.593 | 1.00 | 65.16 | D |
| ATOM | 5382 | NE2 | GLN | D | 94 | 20.447 | 16.617 | 54.686 | 1.00 | 65.78 | D |
| ATOM | 5383 | C | GLN | D | 94 | 17.411 | 17.920 | 59.254 | 1.00 | 41.55 | D |
| ATOM | 5384 | O | GLN | D | 94 | 16.362 | 17.366 | 58.923 | 1.00 | 42.49 | D |
| ATOM | 5385 | N | ARG | D | 95 | 17.893 | 17.888 | 60.492 | 1.00 | 35.59 | D |
| ATOM | 5386 | CA | ARG | D | 95 | 17.184 | 17.208 | 61.565 | 1.00 | 31.87 | D |
| ATOM | 5387 | CB | ARG | D | 95 | 18.039 | 17.119 | 62.814 | 1.00 | 28.84 | D |
| ATOM | 5388 | CG | ARG | D | 95 | 19.066 | 16.049 | 62.784 | 1.00 | 26.95 | D |
| ATOM | 5389 | CD | ARG | D | 95 | 19.807 | 16.077 | 64.082 | 1.00 | 24.93 | D |
| ATOM | 5390 | NE | ARG | D | 95 | 20.726 | 14.961 | 64.209 | 1.00 | 26.58 | D |
| ATOM | 5391 | CZ | ARG | D | 95 | 21.530 | 14.792 | 65.250 | 1.00 | 24.18 | D |
| ATOM | 5392 | NH1 | ARG | D | 95 | 21.518 | 15.678 | 66.231 | 1.00 | 27.23 | D |
| ATOM | 5393 | NH2 | ARG | D | 95 | 22.316 | 13.728 | 65.332 | 1.00 | 23.83 | D |
| ATOM | 5394 | C | ARG | D | 95 | 15.932 | 17.970 | 61.920 | 1.00 | 33.50 | D |
| ATOM | 5395 | O | ARG | D | 95 | 14.926 | 17.377 | 62.305 | 1.00 | 31.71 | D |
| ATOM | 5396 | N | TYR | D | 96 | 15.995 | 19.292 | 61.803 | 1.00 | 37.45 | D |
| ATOM | 5397 | CA | TYR | D | 96 | 14.851 | 20.122 | 62.141 | 1.00 | 43.44 | D |
| ATOM | 5398 | CB | TYR | D | 96 | 15.183 | 20.987 | 63.357 | 1.00 | 45.29 | D |
| ATOM | 5399 | CG | TYR | D | 96 | 15.825 | 20.182 | 64.450 | 1.00 | 47.15 | D |
| ATOM | 5400 | CD1 | TYR | D | 96 | 17.185 | 19.928 | 64.429 | 1.00 | 48.82 | D |
| ATOM | 5401 | CE1 | TYR | D | 96 | 17.773 | 19.120 | 65.376 | 1.00 | 47.27 | D |
| ATOM | 5402 | CD2 | TYR | D | 96 | 15.059 | 19.607 | 65.460 | 1.00 | 46.22 | D |
| ATOM | 5403 | CE2 | TYR | D | 96 | 15.636 | 18.795 | 66.416 | 1.00 | 47.30 | D |
| ATOM | 5404 | CZ | TYR | D | 96 | 16.998 | 18.552 | 66.370 | 1.00 | 47.94 | D |
| ATOM | 5405 | OH | TYR | D | 96 | 17.599 | 17.746 | 67.314 | 1.00 | 47.18 | D |
| ATOM | 5406 | C | TYR | D | 96 | 14.479 | 20.988 | 60.955 | 1.00 | 44.24 | D |
| ATOM | 5407 | O | TYR | D | 96 | 14.904 | 22.137 | 60.854 | 1.00 | 51.19 | D |
| ATOM | 5408 | N | PRO | D | 97 | 13.689 | 20.433 | 60.027 | 1.00 | 43.33 | D |
| ATOM | 5409 | CD | PRO | D | 97 | 13.580 | 18.984 | 59.816 | 1.00 | 42.30 | D |
| ATOM | 5410 | CA | PRO | D | 97 | 13.254 | 21.145 | 58.829 | 1.00 | 41.71 | D |
| ATOM | 5411 | CB | PRO | D | 97 | 12.921 | 20.017 | 57.858 | 1.00 | 40.84 | D |
| ATOM | 5412 | CG | PRO | D | 97 | 13.780 | 18.891 | 58.332 | 1.00 | 42.35 | D |
| ATOM | 5413 | C | PRO | D | 97 | 12.074 | 22.061 | 59.038 | 1.00 | 42.90 | D |
| ATOM | 5414 | O | PRO | D | 97 | 11.832 | 22.946 | 58.225 | 1.00 | 44.43 | D |
| ATOM | 5415 | N | ASN | D | 98 | 11.340 | 21.875 | 60.124 | 1.00 | 46.93 | D |
| ATOM | 5416 | CA | ASN | D | 98 | 10.168 | 22.721 | 60.339 | 1.00 | 53.11 | D |
| ATOM | 5417 | CB | ASN | D | 98 | 8.957 | 21.858 | 60.666 | 1.00 | 57.41 | D |
| ATOM | 5418 | CG | ASN | D | 98 | 8.565 | 20.965 | 59.517 | 1.00 | 62.60 | D |
| ATOM | 5419 | OD1 | ASN | D | 98 | 9.370 | 20.157 | 59.034 | 1.00 | 63.54 | D |
| ATOM | 5420 | ND2 | ASN | D | 98 | 7.323 | 21.105 | 59.064 | 1.00 | 65.82 | D |
| ATOM | 5421 | C | ASN | D | 98 | 10.318 | 23.783 | 61.402 | 1.00 | 52.04 | D |
| ATOM | 5422 | O | ASN | D | 98 | 9.360 | 24.485 | 61.732 | 1.00 | 53.89 | D |
| ATOM | 5423 | N | ASP | D | 99 | 11.515 | 23.910 | 61.945 | 1.00 | 50.91 | D |
| ATOM | 5424 | CA | ASP | D | 99 | 11.715 | 24.905 | 62.970 | 1.00 | 48.67 | D |
| ATOM | 5425 | CB | ASP | D | 99 | 12.434 | 24.279 | 64.161 | 1.00 | 48.32 | D |
| ATOM | 5426 | CG | ASP | D | 99 | 11.650 | 23.128 | 64.747 | 1.00 | 48.97 | D |
| ATOM | 5427 | OD1 | ASP | D | 99 | 10.520 | 23.364 | 65.221 | 1.00 | 50.23 | D |
| ATOM | 5428 | OD2 | ASP | D | 99 | 12.146 | 21.984 | 64.715 | 1.00 | 51.13 | D |
| ATOM | 5429 | C | ASP | D | 99 | 12.476 | 26.071 | 62.403 | 1.00 | 46.41 | D |

Figure 10 (84 of 142)

| | | | | | | | | | |
|---|---|---|---|---|---|---|---|---|---|
| ATOM | 5430 | O | ASP | D | 99 | 13.228 | 25.928 | 61.435 | 1.00 45.99 | D |
| ATOM | 5431 | N | GLN | D | 100 | 12.249 | 27.231 | 63.002 | 1.00 42.46 | D |
| ATOM | 5432 | CA | GLN | D | 100 | 12.897 | 28.443 | 62.576 | 1.00 42.80 | D |
| ATOM | 5433 | CB | GLN | D | 100 | 11.984 | 29.602 | 62.893 | 1.00 43.44 | D |
| ATOM | 5434 | CG | GLN | D | 100 | 12.089 | 30.715 | 61.903 | 1.00 53.06 | D |
| ATOM | 5435 | CD | GLN | D | 100 | 10.918 | 31.654 | 62.001 | 1.00 57.02 | D |
| ATOM | 5436 | OE1 | GLN | D | 100 | 9.759 | 31.242 | 61.834 | 1.00 57.78 | D |
| ATOM | 5437 | NE2 | GLN | D | 100 | 11.201 | 32.931 | 62.271 | 1.00 58.68 | D |
| ATOM | 5438 | C | GLN | D | 100 | 14.212 | 28.565 | 63.334 | 1.00 41.04 | D |
| ATOM | 5439 | O | GLN | D | 100 | 14.211 | 28.639 | 64.554 | 1.00 40.94 | D |
| ATOM | 5440 | N | LEU | D | 101 | 15.329 | 28.588 | 62.609 | 1.00 35.77 | D |
| ATOM | 5441 | CA | LEU | D | 101 | 16.645 | 28.656 | 63.234 | 1.00 31.55 | D |
| ATOM | 5442 | CB | LEU | D | 101 | 17.528 | 27.507 | 62.730 | 1.00 31.22 | D |
| ATOM | 5443 | CG | LEU | D | 101 | 17.012 | 26.071 | 62.759 | 1.00 34.64 | D |
| ATOM | 5444 | CD1 | LEU | D | 101 | 18.122 | 25.114 | 62.357 | 1.00 37.09 | D |
| ATOM | 5445 | CD2 | LEU | D | 101 | 16.520 | 25.745 | 64.145 | 1.00 37.40 | D |
| ATOM | 5446 | C | LEU | D | 101 | 17.430 | 29.944 | 63.042 | 1.00 28.83 | D |
| ATOM | 5447 | O | LEU | D | 101 | 17.593 | 30.429 | 61.929 | 1.00 32.51 | D |
| ATOM | 5448 | N | PHE | D | 102 | 17.946 | 30.480 | 64.136 | 1.00 28.76 | D |
| ATOM | 5449 | CA | PHE | D | 102 | 18.779 | 31.671 | 64.078 | 1.00 26.51 | D |
| ATOM | 5450 | CB | PHE | D | 102 | 18.099 | 32.857 | 64.738 | 1.00 26.90 | D |
| ATOM | 5451 | CG | PHE | D | 102 | 16.841 | 33.246 | 64.079 | 1.00 28.35 | D |
| ATOM | 5452 | CD1 | PHE | D | 102 | 15.688 | 32.508 | 64.288 | 1.00 31.32 | D |
| ATOM | 5453 | CD2 | PHE | D | 102 | 16.809 | 34.325 | 63.211 | 1.00 28.79 | D |
| ATOM | 5454 | CE1 | PHE | D | 102 | 14.518 | 32.832 | 63.641 | 1.00 33.55 | D |
| ATOM | 5455 | CE2 | PHE | D | 102 | 15.650 | 34.661 | 62.555 | 1.00 29.81 | D |
| ATOM | 5456 | CZ | PHE | D | 102 | 14.494 | 33.912 | 62.770 | 1.00 33.27 | D |
| ATOM | 5457 | C | PHE | D | 102 | 20.064 | 31.390 | 64.815 | 1.00 25.82 | D |
| ATOM | 5458 | O | PHE | D | 102 | 20.070 | 30.665 | 65.803 | 1.00 30.45 | D |
| ATOM | 5459 | N | PHE | D | 103 | 21.165 | 31.937 | 64.333 | 1.00 20.61 | D |
| ATOM | 5460 | CA | PHE | D | 103 | 22.402 | 31.738 | 65.048 | 1.00 20.63 | D |
| ATOM | 5461 | CB | PHE | D | 103 | 23.546 | 31.472 | 64.093 | 1.00 17.67 | D |
| ATOM | 5462 | CG | PHE | D | 103 | 24.670 | 30.738 | 64.719 | 1.00 15.72 | D |
| ATOM | 5463 | CD1 | PHE | D | 103 | 24.746 | 29.364 | 64.613 | 1.00 16.36 | D |
| ATOM | 5464 | CD2 | PHE | D | 103 | 25.657 | 31.417 | 65.405 | 1.00 16.76 | D |
| ATOM | 5465 | CE1 | PHE | D | 103 | 25.791 | 28.666 | 65.174 | 1.00 20.30 | D |
| ATOM | 5466 | CE2 | PHE | D | 103 | 26.710 | 30.732 | 65.976 | 1.00 25.21 | D |
| ATOM | 5467 | CZ | PHE | D | 103 | 26.781 | 29.344 | 65.858 | 1.00 23.26 | D |
| ATOM | 5468 | C | PHE | D | 103 | 22.661 | 33.023 | 65.837 | 1.00 23.05 | D |
| ATOM | 5469 | O | PHE | D | 103 | 22.123 | 34.091 | 65.521 | 1.00 25.47 | D |
| ATOM | 5470 | N | ILE | D | 104 | 23.490 | 32.929 | 66.867 | 1.00 20.66 | D |
| ATOM | 5471 | CA | ILE | D | 104 | 23.767 | 34.107 | 67.671 | 1.00 19.19 | D |
| ATOM | 5472 | CB | ILE | D | 104 | 22.918 | 34.064 | 68.955 | 1.00 19.61 | D |
| ATOM | 5473 | CG2 | ILE | D | 104 | 23.238 | 35.263 | 69.851 | 1.00 16.25 | D |
| ATOM | 5474 | CG1 | ILE | D | 104 | 21.440 | 34.039 | 68.564 | 1.00 12.70 | D |
| ATOM | 5475 | CD1 | ILE | D | 104 | 20.522 | 33.837 | 69.714 | 1.00 13.06 | D |
| ATOM | 5476 | C | ILE | D | 104 | 25.244 | 34.309 | 68.019 | 1.00 16.63 | D |
| ATOM | 5477 | O | ILE | D | 104 | 25.946 | 33.375 | 68.438 | 1.00 20.96 | D |
| ATOM | 5478 | N | ILE | D | 105 | 25.710 | 35.540 | 67.835 | 1.00 19.53 | D |
| ATOM | 5479 | CA | ILE | D | 105 | 27.090 | 35.869 | 68.129 | 1.00 14.69 | D |
| ATOM | 5480 | CB | ILE | D | 105 | 27.944 | 35.929 | 66.857 | 1.00 15.68 | D |
| ATOM | 5481 | CG2 | ILE | D | 105 | 28.090 | 34.551 | 66.257 | 1.00 19.30 | D |
| ATOM | 5482 | CG1 | ILE | D | 105 | 27.297 | 36.868 | 65.847 | 1.00 12.26 | D |
| ATOM | 5483 | CD1 | ILE | D | 105 | 28.134 | 37.084 | 64.639 | 1.00 12.26 | D |
| ATOM | 5484 | C | ILE | D | 105 | 27.152 | 37.225 | 68.774 | 1.00 19.54 | D |
| ATOM | 5485 | O | ILE | D | 105 | 26.227 | 38.028 | 68.655 | 1.00 19.41 | D |
| ATOM | 5486 | N | GLY | D | 106 | 28.251 | 37.475 | 69.467 | 1.00 23.53 | D |
| ATOM | 5487 | CA | GLY | D | 106 | 28.435 | 38.768 | 70.091 | 1.00 28.07 | D |
| ATOM | 5488 | C | GLY | D | 106 | 29.425 | 39.575 | 69.265 | 1.00 28.08 | D |
| ATOM | 5489 | O | GLY | D | 106 | 30.127 | 39.028 | 68.403 | 1.00 31.96 | D |
| ATOM | 5490 | N | ALA | D | 107 | 29.481 | 40.879 | 69.524 | 1.00 35.30 | D |
| ATOM | 5491 | CA | ALA | D | 107 | 30.387 | 41.782 | 68.813 | 1.00 36.26 | D |
| ATOM | 5492 | CB | ALA | D | 107 | 30.564 | 43.072 | 69.600 | 1.00 38.86 | D |
| ATOM | 5493 | C | ALA | D | 107 | 31.731 | 41.115 | 68.611 | 1.00 37.95 | D |
| ATOM | 5494 | O | ALA | D | 107 | 32.407 | 41.332 | 67.614 | 1.00 36.86 | D |
| ATOM | 5495 | N | ASP | D | 108 | 32.101 | 40.306 | 69.589 | 1.00 39.01 | D |

Figure 10 (85 of 142)

| | | | | | | | | | | |
|---|---|---|---|---|---|---|---|---|---|---|
| ATOM | 5496 | CA | ASP | D | 108 | 33.340 | 39.552 | 69.577 | 1.00 44.25 | D |
| ATOM | 5497 | CB | ASP | D | 108 | 33.304 | 38.567 | 70.748 | 1.00 46.98 | D |
| ATOM | 5498 | CG | ASP | D | 108 | 34.507 | 37.664 | 70.797 | 1.00 51.22 | D |
| ATOM | 5499 | OD1 | ASP | D | 108 | 35.460 | 37.879 | 70.017 | 1.00 53.45 | D |
| ATOM | 5500 | OD2 | ASP | D | 108 | 34.498 | 36.735 | 71.633 | 1.00 57.10 | D |
| ATOM | 5501 | C | ASP | D | 108 | 33.468 | 38.802 | 68.251 | 1.00 39.73 | D |
| ATOM | 5502 | O | ASP | D | 108 | 34.320 | 39.105 | 67.410 | 1.00 42.99 | D |
| ATOM | 5503 | N | MET | D | 109 | 32.596 | 37.822 | 68.079 | 1.00 35.52 | D |
| ATOM | 5504 | CA | MET | D | 109 | 32.586 | 37.009 | 66.887 | 1.00 29.46 | D |
| ATOM | 5505 | CB | MET | D | 109 | 31.555 | 35.909 | 67.048 | 1.00 20.42 | D |
| ATOM | 5506 | CG | MET | D | 109 | 32.038 | 34.837 | 67.977 | 1.00 14.34 | D |
| ATOM | 5507 | SD | MET | D | 109 | 33.454 | 33.988 | 67.225 | 1.00 14.47 | D |
| ATOM | 5508 | CE | MET | D | 109 | 34.788 | 34.905 | 67.838 | 1.00 22.52 | D |
| ATOM | 5509 | C | MET | D | 109 | 32.317 | 37.790 | 65.623 | 1.00 32.33 | D |
| ATOM | 5510 | O | MET | D | 109 | 32.908 | 37.505 | 64.587 | 1.00 34.77 | D |
| ATOM | 5511 | N | ILE | D | 110 | 31.427 | 38.769 | 65.704 | 1.00 30.87 | D |
| ATOM | 5512 | CA | ILE | D | 110 | 31.085 | 39.575 | 64.543 | 1.00 25.61 | D |
| ATOM | 5513 | CB | ILE | D | 110 | 30.234 | 40.756 | 64.975 | 1.00 32.08 | D |
| ATOM | 5514 | CG2 | ILE | D | 110 | 29.891 | 41.625 | 63.781 | 1.00 31.57 | D |
| ATOM | 5515 | CG1 | ILE | D | 110 | 28.977 | 40.221 | 65.656 | 1.00 32.45 | D |
| ATOM | 5516 | CD1 | ILE | D | 110 | 27.905 | 41.268 | 65.903 | 1.00 37.79 | D |
| ATOM | 5517 | C | ILE | D | 110 | 32.319 | 40.066 | 63.790 | 1.00 30.81 | D |
| ATOM | 5518 | O | ILE | D | 110 | 32.416 | 39.926 | 62.562 | 1.00 26.85 | D |
| ATOM | 5519 | N | GLU | D | 111 | 33.258 | 40.636 | 64.547 | 1.00 36.07 | D |
| ATOM | 5520 | CA | GLU | D | 111 | 34.519 | 41.157 | 64.010 | 1.00 35.19 | D |
| ATOM | 5521 | CB | GLU | D | 111 | 35.410 | 41.704 | 65.146 | 1.00 42.65 | D |
| ATOM | 5522 | CG | GLU | D | 111 | 35.199 | 43.174 | 65.524 | 1.00 40.93 | D |
| ATOM | 5523 | CD | GLU | D | 111 | 36.119 | 43.636 | 66.660 | 1.00 40.94 | D |
| ATOM | 5524 | OE1 | GLU | D | 111 | 37.323 | 43.279 | 66.677 | 1.00 40.38 | D |
| ATOM | 5525 | OE2 | GLU | D | 111 | 35.629 | 44.374 | 67.537 | 1.00 41.43 | D |
| ATOM | 5526 | C | GLU | D | 111 | 35.259 | 40.024 | 63.313 | 1.00 36.01 | D |
| ATOM | 5527 | O | GLU | D | 111 | 35.975 | 40.234 | 62.336 | 1.00 34.38 | D |
| ATOM | 5528 | N | TYR | D | 112 | 35.058 | 38.820 | 63.829 | 1.00 38.72 | D |
| ATOM | 5529 | CA | TYR | D | 112 | 35.711 | 37.613 | 63.336 | 1.00 40.72 | D |
| ATOM | 5530 | CB | TYR | D | 112 | 35.842 | 36.636 | 64.517 | 1.00 43.73 | D |
| ATOM | 5531 | CG | TYR | D | 112 | 37.036 | 35.718 | 64.470 | 1.00 45.83 | D |
| ATOM | 5532 | CD1 | TYR | D | 112 | 36.910 | 34.401 | 64.025 | 1.00 48.78 | D |
| ATOM | 5533 | CE1 | TYR | D | 112 | 38.008 | 33.533 | 64.001 | 1.00 53.04 | D |
| ATOM | 5534 | CD2 | TYR | D | 112 | 38.289 | 36.156 | 64.888 | 1.00 48.61 | D |
| ATOM | 5535 | CE2 | TYR | D | 112 | 39.393 | 35.303 | 64.869 | 1.00 50.42 | D |
| ATOM | 5536 | CZ | TYR | D | 112 | 39.246 | 33.988 | 64.424 | 1.00 51.77 | D |
| ATOM | 5537 | OH | TYR | D | 112 | 40.318 | 33.117 | 64.408 | 1.00 52.24 | D |
| ATOM | 5538 | C | TYR | D | 112 | 35.028 | 36.922 | 62.143 | 1.00 39.60 | D |
| ATOM | 5539 | O | TYR | D | 112 | 35.574 | 35.973 | 61.584 | 1.00 39.12 | D |
| ATOM | 5540 | N | LEU | D | 113 | 33.852 | 37.388 | 61.740 | 1.00 33.63 | D |
| ATOM | 5541 | CA | LEU | D | 113 | 33.163 | 36.746 | 60.625 | 1.00 29.92 | D |
| ATOM | 5542 | CB | LEU | D | 113 | 32.001 | 37.613 | 60.151 | 1.00 30.94 | D |
| ATOM | 5543 | CG | LEU | D | 113 | 30.644 | 37.146 | 60.685 | 1.00 31.68 | D |
| ATOM | 5544 | CD1 | LEU | D | 113 | 30.722 | 36.926 | 62.171 | 1.00 35.17 | D |
| ATOM | 5545 | CD2 | LEU | D | 113 | 29.587 | 38.172 | 60.365 | 1.00 32.98 | D |
| ATOM | 5546 | C | LEU | D | 113 | 34.067 | 36.383 | 59.451 | 1.00 30.55 | D |
| ATOM | 5547 | O | LEU | D | 113 | 34.016 | 35.267 | 58.957 | 1.00 28.06 | D |
| ATOM | 5548 | N | PRO | D | 114 | 34.894 | 37.324 | 58.978 | 1.00 30.27 | D |
| ATOM | 5549 | CD | PRO | D | 114 | 34.953 | 38.765 | 59.251 | 1.00 30.89 | D |
| ATOM | 5550 | CA | PRO | D | 114 | 35.771 | 36.983 | 57.860 | 1.00 25.31 | D |
| ATOM | 5551 | CB | PRO | D | 114 | 36.624 | 38.242 | 57.678 | 1.00 24.54 | D |
| ATOM | 5552 | CG | PRO | D | 114 | 36.380 | 39.061 | 58.913 | 1.00 30.64 | D |
| ATOM | 5553 | C | PRO | D | 114 | 36.594 | 35.716 | 58.081 | 1.00 28.71 | D |
| ATOM | 5554 | O | PRO | D | 114 | 36.405 | 34.742 | 57.359 | 1.00 23.71 | D |
| ATOM | 5555 | N | LYS | D | 115 | 37.514 | 35.712 | 59.043 | 1.00 35.65 | D |
| ATOM | 5556 | CA | LYS | D | 115 | 38.293 | 34.494 | 59.303 | 1.00 40.95 | D |
| ATOM | 5557 | CB | LYS | D | 115 | 39.411 | 34.763 | 60.325 | 1.00 40.12 | D |
| ATOM | 5558 | CG | LYS | D | 115 | 40.255 | 36.000 | 60.028 | 1.00 40.69 | D |
| ATOM | 5559 | CD | LYS | D | 115 | 41.264 | 36.306 | 61.141 | 1.00 45.08 | D |
| ATOM | 5560 | CE | LYS | D | 115 | 42.365 | 35.231 | 61.247 | 1.00 43.99 | D |
| ATOM | 5561 | NZ | LYS | D | 115 | 43.415 | 35.559 | 62.272 | 1.00 44.40 | D |

Figure 10 (86 of 142)

| ATOM | 5562 | C | LYS | D | 115 | 37.238 | 33.576 | 59.909 | 1.00 | 38.44 | D |
|---|---|---|---|---|---|---|---|---|---|---|---|
| ATOM | 5563 | O | LYS | D | 115 | 37.013 | 33.615 | 61.110 | 1.00 | 52.18 | D |
| ATOM | 5564 | N | TRP | D | 116 | 36.577 | 32.768 | 59.090 | 1.00 | 38.80 | D |
| ATOM | 5565 | CA | TRP | D | 116 | 35.510 | 31.906 | 59.592 | 1.00 | 43.17 | D |
| ATOM | 5566 | CB | TRP | D | 116 | 34.345 | 32.798 | 60.015 | 1.00 | 48.38 | D |
| ATOM | 5567 | CG | TRP | D | 116 | 33.239 | 32.159 | 60.776 | 1.00 | 49.02 | D |
| ATOM | 5568 | CD2 | TRP | D | 116 | 32.773 | 32.532 | 62.079 | 1.00 | 50.61 | D |
| ATOM | 5569 | CE2 | TRP | D | 116 | 31.628 | 31.749 | 62.359 | 1.00 | 52.34 | D |
| ATOM | 5570 | CE3 | TRP | D | 116 | 33.211 | 33.449 | 63.037 | 1.00 | 51.09 | D |
| ATOM | 5571 | CD1 | TRP | D | 116 | 32.392 | 31.192 | 60.331 | 1.00 | 49.85 | D |
| ATOM | 5572 | NE1 | TRP | D | 116 | 31.416 | 30.940 | 61.274 | 1.00 | 51.52 | D |
| ATOM | 5573 | CZ2 | TRP | D | 116 | 30.910 | 31.860 | 63.548 | 1.00 | 55.05 | D |
| ATOM | 5574 | CZ3 | TRP | D | 116 | 32.499 | 33.562 | 64.222 | 1.00 | 53.65 | D |
| ATOM | 5575 | CH2 | TRP | D | 116 | 31.360 | 32.767 | 64.469 | 1.00 | 54.91 | D |
| ATOM | 5576 | C | TRP | D | 116 | 35.097 | 30.953 | 58.478 | 1.00 | 41.76 | D |
| ATOM | 5577 | O | TRP | D | 116 | 34.467 | 31.360 | 57.502 | 1.00 | 42.36 | D |
| ATOM | 5578 | N | TYR | D | 117 | 35.457 | 29.685 | 58.639 | 1.00 | 41.97 | D |
| ATOM | 5579 | CA | TYR | D | 117 | 35.194 | 28.650 | 57.646 | 1.00 | 40.85 | D |
| ATOM | 5580 | CB | TYR | D | 117 | 35.444 | 27.277 | 58.252 | 1.00 | 43.88 | D |
| ATOM | 5581 | CG | TYR | D | 117 | 35.412 | 26.178 | 57.220 | 1.00 | 48.42 | D |
| ATOM | 5582 | CD1 | TYR | D | 117 | 36.418 | 26.063 | 56.259 | 1.00 | 52.03 | D |
| ATOM | 5583 | CE1 | TYR | D | 117 | 36.390 | 25.048 | 55.301 | 1.00 | 52.65 | D |
| ATOM | 5584 | CD2 | TYR | D | 117 | 34.377 | 25.254 | 57.193 | 1.00 | 52.09 | D |
| ATOM | 5585 | CE2 | TYR | D | 117 | 34.343 | 24.234 | 56.236 | 1.00 | 55.61 | D |
| ATOM | 5586 | CZ | TYR | D | 117 | 35.353 | 24.135 | 55.296 | 1.00 | 53.36 | D |
| ATOM | 5587 | OH | TYR | D | 117 | 35.340 | 23.106 | 54.378 | 1.00 | 57.15 | D |
| ATOM | 5588 | C | TYR | D | 117 | 33.840 | 28.623 | 56.946 | 1.00 | 40.13 | D |
| ATOM | 5589 | O | TYR | D | 117 | 32.829 | 28.246 | 57.531 | 1.00 | 41.12 | D |
| ATOM | 5590 | N | LYS | D | 118 | 33.852 | 29.002 | 55.672 | 1.00 | 36.83 | D |
| ATOM | 5591 | CA | LYS | D | 118 | 32.670 | 29.021 | 54.821 | 1.00 | 32.16 | D |
| ATOM | 5592 | CB | LYS | D | 118 | 32.082 | 27.627 | 54.700 | 1.00 | 32.46 | D |
| ATOM | 5593 | CG | LYS | D | 118 | 32.818 | 26.757 | 53.727 | 1.00 | 35.21 | D |
| ATOM | 5594 | CD | LYS | D | 118 | 31.972 | 25.571 | 53.301 | 1.00 | 35.19 | D |
| ATOM | 5595 | CE | LYS | D | 118 | 32.768 | 24.680 | 52.377 | 1.00 | 36.83 | D |
| ATOM | 5596 | NZ | LYS | D | 118 | 32.196 | 23.311 | 52.263 | 1.00 | 39.84 | D |
| ATOM | 5597 | C | LYS | D | 118 | 31.545 | 29.960 | 55.172 | 1.00 | 32.67 | D |
| ATOM | 5598 | O | LYS | D | 118 | 30.386 | 29.642 | 54.917 | 1.00 | 31.07 | D |
| ATOM | 5599 | N | LEU | D | 119 | 31.871 | 31.118 | 55.729 | 1.00 | 34.38 | D |
| ATOM | 5600 | CA | LEU | D | 119 | 30.843 | 32.071 | 56.108 | 1.00 | 40.71 | D |
| ATOM | 5601 | CB | LEU | D | 119 | 31.482 | 33.394 | 56.514 | 1.00 | 40.06 | D |
| ATOM | 5602 | CG | LEU | D | 119 | 30.444 | 34.459 | 56.853 | 1.00 | 39.47 | D |
| ATOM | 5603 | CD1 | LEU | D | 119 | 29.424 | 33.868 | 57.825 | 1.00 | 41.78 | D |
| ATOM | 5604 | CD2 | LEU | D | 119 | 31.136 | 35.679 | 57.447 | 1.00 | 39.98 | D |
| ATOM | 5605 | C | LEU | D | 119 | 29.815 | 32.324 | 55.009 | 1.00 | 46.08 | D |
| ATOM | 5606 | O | LEU | D | 119 | 28.605 | 32.201 | 55.225 | 1.00 | 46.56 | D |
| ATOM | 5607 | N | ASP | D | 120 | 30.307 | 32.668 | 53.828 | 1.00 | 50.95 | D |
| ATOM | 5608 | CA | ASP | D | 120 | 29.439 | 32.964 | 52.704 | 1.00 | 54.56 | D |
| ATOM | 5609 | CB | ASP | D | 120 | 30.285 | 33.193 | 51.448 | 1.00 | 58.81 | D |
| ATOM | 5610 | CG | ASP | D | 120 | 31.063 | 34.507 | 51.500 | 1.00 | 63.77 | D |
| ATOM | 5611 | OD1 | ASP | D | 120 | 30.415 | 35.578 | 51.497 | 1.00 | 68.15 | D |
| ATOM | 5612 | OD2 | ASP | D | 120 | 32.316 | 34.473 | 51.546 | 1.00 | 64.17 | D |
| ATOM | 5613 | C | ASP | D | 120 | 28.359 | 31.922 | 52.440 | 1.00 | 53.18 | D |
| ATOM | 5614 | O | ASP | D | 120 | 27.247 | 32.284 | 52.077 | 1.00 | 52.96 | D |
| ATOM | 5615 | N | GLU | D | 121 | 28.673 | 30.639 | 52.622 | 1.00 | 55.77 | D |
| ATOM | 5616 | CA | GLU | D | 121 | 27.686 | 29.576 | 52.392 | 1.00 | 55.54 | D |
| ATOM | 5617 | CB | GLU | D | 121 | 28.360 | 28.222 | 52.096 | 1.00 | 64.32 | D |
| ATOM | 5618 | CG | GLU | D | 121 | 29.367 | 28.201 | 50.950 | 1.00 | 73.99 | D |
| ATOM | 5619 | CD | GLU | D | 121 | 30.607 | 29.019 | 51.254 | 1.00 | 79.68 | D |
| ATOM | 5620 | OE1 | GLU | D | 121 | 30.948 | 29.153 | 52.454 | 1.00 | 84.61 | D |
| ATOM | 5621 | OE2 | GLU | D | 121 | 31.243 | 29.517 | 50.295 | 1.00 | 83.32 | D |
| ATOM | 5622 | C | GLU | D | 121 | 26.812 | 29.419 | 53.631 | 1.00 | 54.28 | D |
| ATOM | 5623 | O | GLU | D | 121 | 25.629 | 29.093 | 53.528 | 1.00 | 52.86 | D |
| ATOM | 5624 | N | LEU | D | 122 | 27.404 | 29.646 | 54.801 | 1.00 | 52.45 | D |
| ATOM | 5625 | CA | LEU | D | 122 | 26.683 | 29.530 | 56.060 | 1.00 | 54.44 | D |
| ATOM | 5626 | CB | LEU | D | 122 | 27.643 | 29.671 | 57.243 | 1.00 | 61.33 | D |
| ATOM | 5627 | CG | LEU | D | 122 | 27.098 | 29.465 | 58.662 | 1.00 | 63.15 | D |

Figure 10 (87 of 142)

| ATOM | 5628 | CD1 | LEU | D | 122 | 26.586 | 28.045 | 58.847 | 1.00 | 63.53 | D |
|------|------|-----|-----|---|-----|--------|--------|--------|------|-------|---|
| ATOM | 5629 | CD2 | LEU | D | 122 | 28.207 | 29.741 | 59.653 | 1.00 | 66.10 | D |
| ATOM | 5630 | C | LEU | D | 122 | 25.639 | 30.622 | 56.114 | 1.00 | 54.15 | D |
| ATOM | 5631 | O | LEU | D | 122 | 24.480 | 30.362 | 56.415 | 1.00 | 54.00 | D |
| ATOM | 5632 | N | LEU | D | 123 | 26.060 | 31.845 | 55.808 | 1.00 | 52.77 | D |
| ATOM | 5633 | CA | LEU | D | 123 | 25.160 | 32.992 | 55.810 | 1.00 | 50.81 | D |
| ATOM | 5634 | CB | LEU | D | 123 | 25.874 | 34.220 | 55.258 | 1.00 | 51.33 | D |
| ATOM | 5635 | CG | LEU | D | 123 | 26.878 | 34.817 | 56.231 | 1.00 | 52.19 | D |
| ATOM | 5636 | CD1 | LEU | D | 123 | 27.549 | 36.012 | 55.602 | 1.00 | 52.61 | D |
| ATOM | 5637 | CD2 | LEU | D | 123 | 26.165 | 35.213 | 57.516 | 1.00 | 52.17 | D |
| ATOM | 5638 | C | LEU | D | 123 | 23.927 | 32.710 | 54.974 | 1.00 | 52.19 | D |
| ATOM | 5639 | O | LEU | D | 123 | 22.853 | 33.276 | 55.184 | 1.00 | 50.74 | D |
| ATOM | 5640 | N | ASN | D | 124 | 24.094 | 31.821 | 54.014 | 1.00 | 53.23 | D |
| ATOM | 5641 | CA | ASN | D | 124 | 23.005 | 31.456 | 53.144 | 1.00 | 54.37 | D |
| ATOM | 5642 | CB | ASN | D | 124 | 23.575 | 30.762 | 51.908 | 1.00 | 60.67 | D |
| ATOM | 5643 | CG | ASN | D | 124 | 22.556 | 30.604 | 50.803 | 1.00 | 63.61 | D |
| ATOM | 5644 | OD1 | ASN | D | 124 | 21.608 | 29.824 | 50.925 | 1.00 | 65.68 | D |
| ATOM | 5645 | ND2 | ASN | D | 124 | 22.741 | 31.349 | 49.711 | 1.00 | 64.94 | D |
| ATOM | 5646 | C | ASN | D | 124 | 22.064 | 30.526 | 53.903 | 1.00 | 54.26 | D |
| ATOM | 5647 | O | ASN | D | 124 | 20.845 | 30.640 | 53.789 | 1.00 | 61.17 | D |
| ATOM | 5648 | N | LEU | D | 125 | 22.640 | 29.626 | 54.696 | 1.00 | 50.26 | D |
| ATOM | 5649 | CA | LEU | D | 125 | 21.878 | 28.654 | 55.472 | 1.00 | 46.52 | D |
| ATOM | 5650 | CB | LEU | D | 125 | 22.832 | 27.631 | 56.077 | 1.00 | 45.49 | D |
| ATOM | 5651 | CG | LEU | D | 125 | 23.433 | 26.642 | 55.092 | 1.00 | 47.35 | D |
| ATOM | 5652 | CD1 | LEU | D | 125 | 24.455 | 25.755 | 55.787 | 1.00 | 47.05 | D |
| ATOM | 5653 | CD2 | LEU | D | 125 | 22.305 | 25.807 | 54.500 | 1.00 | 49.82 | D |
| ATOM | 5654 | C | LEU | D | 125 | 20.986 | 29.186 | 56.588 | 1.00 | 46.49 | D |
| ATOM | 5655 | O | LEU | D | 125 | 19.813 | 28.834 | 56.672 | 1.00 | 43.47 | D |
| ATOM | 5656 | N | ILE | D | 126 | 21.545 | 30.026 | 57.450 | 1.00 | 45.80 | D |
| ATOM | 5657 | CA | ILE | D | 126 | 20.800 | 30.542 | 58.589 | 1.00 | 44.58 | D |
| ATOM | 5658 | CB | ILE | D | 126 | 21.128 | 29.700 | 59.850 | 1.00 | 46.34 | D |
| ATOM | 5659 | CG2 | ILE | D | 126 | 22.625 | 29.720 | 60.105 | 1.00 | 47.23 | D |
| ATOM | 5660 | CG1 | ILE | D | 126 | 20.357 | 30.219 | 61.061 | 1.00 | 47.96 | D |
| ATOM | 5661 | CD1 | ILE | D | 126 | 20.497 | 29.341 | 62.283 | 1.00 | 42.01 | D |
| ATOM | 5662 | C | ILE | D | 126 | 21.105 | 32.003 | 58.861 | 1.00 | 38.76 | D |
| ATOM | 5663 | O | ILE | D | 126 | 22.146 | 32.509 | 58.454 | 1.00 | 39.32 | D |
| ATOM | 5664 | N | GLN | D | 127 | 20.190 | 32.670 | 59.557 | 1.00 | 35.84 | D |
| ATOM | 5665 | CA | GLN | D | 127 | 20.338 | 34.085 | 59.886 | 1.00 | 36.53 | D |
| ATOM | 5666 | CB | GLN | D | 127 | 18.974 | 34.761 | 59.968 | 1.00 | 40.40 | D |
| ATOM | 5667 | CG | GLN | D | 127 | 18.131 | 34.588 | 58.731 | 1.00 | 51.53 | D |
| ATOM | 5668 | CD | GLN | D | 127 | 16.683 | 34.954 | 58.971 | 1.00 | 55.25 | D |
| ATOM | 5669 | OE1 | GLN | D | 127 | 16.033 | 34.382 | 59.840 | 1.00 | 60.10 | D |
| ATOM | 5670 | NE2 | GLN | D | 127 | 16.169 | 35.906 | 58.200 | 1.00 | 59.60 | D |
| ATOM | 5671 | C | GLN | D | 127 | 21.029 | 34.269 | 61.215 | 1.00 | 37.09 | D |
| ATOM | 5672 | O | GLN | D | 127 | 20.729 | 33.574 | 62.174 | 1.00 | 39.07 | D |
| ATOM | 5673 | N | PHE | D | 128 | 21.948 | 35.220 | 61.272 | 1.00 | 31.99 | D |
| ATOM | 5674 | CA | PHE | D | 128 | 22.674 | 35.504 | 62.495 | 1.00 | 24.62 | D |
| ATOM | 5675 | CB | PHE | D | 128 | 24.095 | 35.975 | 62.156 | 1.00 | 17.69 | D |
| ATOM | 5676 | CG | PHE | D | 128 | 25.042 | 34.863 | 61.816 | 1.00 | 17.84 | D |
| ATOM | 5677 | CD1 | PHE | D | 128 | 24.714 | 33.899 | 60.867 | 1.00 | 14.77 | D |
| ATOM | 5678 | CD2 | PHE | D | 128 | 26.275 | 34.786 | 62.448 | 1.00 | 16.38 | D |
| ATOM | 5679 | CE1 | PHE | D | 128 | 25.602 | 32.875 | 60.551 | 1.00 | 18.44 | D |
| ATOM | 5680 | CE2 | PHE | D | 128 | 27.175 | 33.766 | 62.141 | 1.00 | 18.33 | D |
| ATOM | 5681 | CZ | PHE | D | 128 | 26.837 | 32.805 | 61.189 | 1.00 | 18.02 | D |
| ATOM | 5682 | C | PHE | D | 128 | 21.948 | 36.591 | 63.278 | 1.00 | 22.86 | D |
| ATOM | 5683 | O | PHE | D | 128 | 21.135 | 37.327 | 62.731 | 1.00 | 26.95 | D |
| ATOM | 5684 | N | ILE | D | 129 | 22.210 | 36.661 | 64.574 | 1.00 | 22.41 | D |
| ATOM | 5685 | CA | ILE | D | 129 | 21.636 | 37.711 | 65.395 | 1.00 | 21.02 | D |
| ATOM | 5686 | CB | ILE | D | 129 | 20.560 | 37.203 | 66.357 | 1.00 | 21.53 | D |
| ATOM | 5687 | CG2 | ILE | D | 129 | 20.219 | 38.296 | 67.360 | 1.00 | 16.48 | D |
| ATOM | 5688 | CG1 | ILE | D | 129 | 19.297 | 36.839 | 65.579 | 1.00 | 22.37 | D |
| ATOM | 5689 | CD1 | ILE | D | 129 | 18.163 | 36.306 | 66.451 | 1.00 | 14.93 | D |
| ATOM | 5690 | C | ILE | D | 129 | 22.827 | 38.210 | 66.184 | 1.00 | 27.47 | D |
| ATOM | 5691 | O | ILE | D | 129 | 23.472 | 37.438 | 66.894 | 1.00 | 30.21 | D |
| ATOM | 5692 | N | GLY | D | 130 | 23.136 | 39.493 | 66.038 | 1.00 | 28.40 | D |
| ATOM | 5693 | CA | GLY | D | 130 | 24.281 | 40.059 | 66.725 | 1.00 | 27.21 | D |

Figure 10 (88 of 142)

| | | | | | | | | | | |
|---|---|---|---|---|---|---|---|---|---|---|
| ATOM | 5694 | C   | GLY | D | 130 | 23.871 | 40.764 | 67.986 | 1.00 26.00 | D |
| ATOM | 5695 | O   | GLY | D | 130 | 22.757 | 41.274 | 68.082 | 1.00 31.85 | D |
| ATOM | 5696 | N   | VAL | D | 131 | 24.773 | 40.802 | 68.954 | 1.00 27.37 | D |
| ATOM | 5697 | CA  | VAL | D | 131 | 24.455 | 41.444 | 70.204 | 1.00 35.29 | D |
| ATOM | 5698 | CB  | VAL | D | 131 | 24.685 | 40.467 | 71.353 | 1.00 36.48 | D |
| ATOM | 5699 | CG1 | VAL | D | 131 | 24.492 | 41.167 | 72.674 | 1.00 37.83 | D |
| ATOM | 5700 | CG2 | VAL | D | 131 | 23.697 | 39.308 | 71.226 | 1.00 31.06 | D |
| ATOM | 5701 | C   | VAL | D | 131 | 25.209 | 42.750 | 70.429 | 1.00 32.41 | D |
| ATOM | 5702 | O   | VAL | D | 131 | 24.652 | 43.825 | 70.221 | 1.00 37.31 | D |
| ATOM | 5703 | N   | LYS | D | 132 | 26.465 | 42.645 | 70.849 | 1.00 37.47 | D |
| ATOM | 5704 | CA  | LYS | D | 132 | 27.354 | 43.783 | 71.130 | 1.00 47.24 | D |
| ATOM | 5705 | CB  | LYS | D | 132 | 26.632 | 45.148 | 71.091 | 1.00 46.54 | D |
| ATOM | 5706 | CG  | LYS | D | 132 | 25.743 | 45.461 | 72.291 | 1.00 45.00 | D |
| ATOM | 5707 | CD  | LYS | D | 132 | 25.108 | 46.852 | 72.201 | 1.00 43.98 | D |
| ATOM | 5708 | CE  | LYS | D | 132 | 24.168 | 47.108 | 73.392 | 1.00 46.13 | D |
| ATOM | 5709 | NZ  | LYS | D | 132 | 23.422 | 48.416 | 73.367 | 1.00 44.45 | D |
| ATOM | 5710 | C   | LYS | D | 132 | 27.948 | 43.557 | 72.514 | 1.00 54.68 | D |
| ATOM | 5711 | O   | LYS | D | 132 | 27.250 | 43.586 | 73.530 | 1.00 59.43 | D |
| ATOM | 5712 | N   | ARG | D | 133 | 29.245 | 43.290 | 72.541 | 1.00 60.51 | D |
| ATOM | 5713 | CA  | ARG | D | 133 | 29.941 | 43.050 | 73.789 | 1.00 65.38 | D |
| ATOM | 5714 | CB  | ARG | D | 133 | 30.739 | 41.739 | 73.712 | 1.00 69.16 | D |
| ATOM | 5715 | CG  | ARG | D | 133 | 31.990 | 41.743 | 74.574 | 1.00 72.47 | D |
| ATOM | 5716 | CD  | ARG | D | 133 | 32.198 | 40.459 | 75.334 | 1.00 75.44 | D |
| ATOM | 5717 | NE  | ARG | D | 133 | 32.857 | 39.420 | 74.555 | 1.00 78.28 | D |
| ATOM | 5718 | CZ  | ARG | D | 133 | 33.426 | 38.355 | 75.107 | 1.00 79.50 | D |
| ATOM | 5719 | NH1 | ARG | D | 133 | 33.407 | 38.217 | 76.426 | 1.00 82.02 | D |
| ATOM | 5720 | NH2 | ARG | D | 133 | 34.007 | 37.428 | 74.360 | 1.00 79.47 | D |
| ATOM | 5721 | C   | ARG | D | 133 | 30.865 | 44.230 | 74.053 | 1.00 68.50 | D |
| ATOM | 5722 | O   | ARG | D | 133 | 31.438 | 44.797 | 73.126 | 1.00 65.93 | D |
| ATOM | 5723 | N   | PRO | D | 134 | 31.008 | 44.630 | 75.325 | 1.00 70.93 | D |
| ATOM | 5724 | CD  | PRO | D | 134 | 30.284 | 44.207 | 76.533 | 1.00 70.50 | D |
| ATOM | 5725 | CA  | PRO | D | 134 | 31.887 | 45.760 | 75.622 | 1.00 70.57 | D |
| ATOM | 5726 | CB  | PRO | D | 134 | 31.605 | 46.044 | 77.099 | 1.00 71.44 | D |
| ATOM | 5727 | CG  | PRO | D | 134 | 30.239 | 45.487 | 77.310 | 1.00 69.62 | D |
| ATOM | 5728 | C   | PRO | D | 134 | 33.345 | 45.383 | 75.375 | 1.00 73.68 | D |
| ATOM | 5729 | O   | PRO | D | 134 | 33.805 | 44.336 | 75.827 | 1.00 76.10 | D |
| ATOM | 5730 | N   | GLY | D | 135 | 34.065 | 46.235 | 74.656 | 1.00 78.36 | D |
| ATOM | 5731 | CA  | GLY | D | 135 | 35.464 | 45.968 | 74.374 | 1.00 83.89 | D |
| ATOM | 5732 | C   | GLY | D | 135 | 35.675 | 45.751 | 72.892 | 1.00 86.32 | D |
| ATOM | 5733 | O   | GLY | D | 135 | 36.712 | 46.108 | 72.326 | 1.00 85.53 | D |
| ATOM | 5734 | N   | PHE | D | 136 | 34.671 | 45.150 | 72.269 | 1.00 86.87 | D |
| ATOM | 5735 | CA  | PHE | D | 136 | 34.691 | 44.876 | 70.845 | 1.00 82.36 | D |
| ATOM | 5736 | CB  | PHE | D | 136 | 34.325 | 43.417 | 70.587 | 1.00 85.22 | D |
| ATOM | 5737 | CG  | PHE | D | 136 | 35.133 | 42.448 | 71.391 | 1.00 88.41 | D |
| ATOM | 5738 | CD1 | PHE | D | 136 | 34.907 | 42.292 | 72.756 | 1.00 89.52 | D |
| ATOM | 5739 | CD2 | PHE | D | 136 | 36.169 | 41.735 | 70.798 | 1.00 91.22 | D |
| ATOM | 5740 | CE1 | PHE | D | 136 | 35.706 | 41.444 | 73.518 | 1.00 93.47 | D |
| ATOM | 5741 | CE2 | PHE | D | 136 | 36.975 | 40.886 | 71.549 | 1.00 90.91 | D |
| ATOM | 5742 | CZ  | PHE | D | 136 | 36.744 | 40.741 | 72.912 | 1.00 91.70 | D |
| ATOM | 5743 | C   | PHE | D | 136 | 33.620 | 45.769 | 70.267 | 1.00 80.90 | D |
| ATOM | 5744 | O   | PHE | D | 136 | 33.021 | 46.568 | 70.987 | 1.00 80.97 | D |
| ATOM | 5745 | N   | HIS | D | 137 | 33.381 | 45.654 | 68.969 | 1.00 76.54 | D |
| ATOM | 5746 | CA  | HIS | D | 137 | 32.328 | 46.445 | 68.358 | 1.00 77.70 | D |
| ATOM | 5747 | CB  | HIS | D | 137 | 32.679 | 47.938 | 68.382 | 1.00 79.98 | D |
| ATOM | 5748 | CG  | HIS | D | 137 | 33.839 | 48.304 | 67.516 | 1.00 84.10 | D |
| ATOM | 5749 | CD2 | HIS | D | 137 | 35.036 | 48.859 | 67.819 | 1.00 83.57 | D |
| ATOM | 5750 | ND1 | HIS | D | 137 | 33.830 | 48.126 | 66.149 | 1.00 82.78 | D |
| ATOM | 5751 | CE1 | HIS | D | 137 | 34.973 | 48.557 | 65.647 | 1.00 86.65 | D |
| ATOM | 5752 | NE2 | HIS | D | 137 | 35.723 | 49.006 | 66.639 | 1.00 86.78 | D |
| ATOM | 5753 | C   | HIS | D | 137 | 31.947 | 45.989 | 66.954 | 1.00 75.53 | D |
| ATOM | 5754 | O   | HIS | D | 137 | 32.792 | 45.624 | 66.127 | 1.00 69.61 | D |
| ATOM | 5755 | N   | VAL | D | 138 | 30.637 | 46.002 | 66.733 | 1.00 74.79 | D |
| ATOM | 5756 | CA  | VAL | D | 138 | 29.999 | 45.590 | 65.492 | 1.00 76.11 | D |
| ATOM | 5757 | CB  | VAL | D | 138 | 28.513 | 45.247 | 65.773 | 1.00 75.38 | D |
| ATOM | 5758 | CG1 | VAL | D | 138 | 27.874 | 46.339 | 66.633 | 1.00 76.39 | D |
| ATOM | 5759 | CG2 | VAL | D | 138 | 27.766 | 45.085 | 64.480 | 1.00 75.70 | D |

Figure 10 (89 of 142)

| | | | | | | | | | | |
|---|---|---|---|---|---|---|---|---|---|---|
| ATOM | 5760 | C   | VAL | D | 138 | 30.098 | 46.632 | 64.370 | 1.00 77.10 | D |
| ATOM | 5761 | O   | VAL | D | 138 | 30.122 | 47.840 | 64.623 | 1.00 80.52 | D |
| ATOM | 5762 | N   | GLU | D | 139 | 30.154 | 46.153 | 63.129 | 1.00 76.69 | D |
| ATOM | 5763 | CA  | GLU | D | 139 | 30.263 | 47.041 | 61.972 | 1.00 73.74 | D |
| ATOM | 5764 | CB  | GLU | D | 139 | 31.606 | 47.777 | 62.014 | 1.00 74.51 | D |
| ATOM | 5765 | CG  | GLU | D | 139 | 32.803 | 46.897 | 61.647 | 1.00 73.78 | D |
| ATOM | 5766 | CD  | GLU | D | 139 | 34.014 | 47.152 | 62.528 | 1.00 75.12 | D |
| ATOM | 5767 | OE1 | GLU | D | 139 | 34.305 | 48.339 | 62.805 | 1.00 74.02 | D |
| ATOM | 5768 | OE2 | GLU | D | 139 | 34.675 | 46.165 | 62.935 | 1.00 74.60 | D |
| ATOM | 5769 | C   | GLU | D | 139 | 30.159 | 46.271 | 60.647 | 1.00 72.86 | D |
| ATOM | 5770 | O   | GLU | D | 139 | 29.872 | 46.858 | 59.601 | 1.00 76.58 | D |
| ATOM | 5771 | N   | THR | D | 140 | 30.400 | 44.960 | 60.709 | 1.00 68.43 | D |
| ATOM | 5772 | CA  | THR | D | 140 | 30.370 | 44.054 | 59.551 | 1.00 58.36 | D |
| ATOM | 5773 | CB  | THR | D | 140 | 29.844 | 42.655 | 59.933 | 1.00 59.56 | D |
| ATOM | 5774 | OG1 | THR | D | 140 | 28.622 | 42.790 | 60.672 | 1.00 55.77 | D |
| ATOM | 5775 | CG2 | THR | D | 140 | 30.902 | 41.879 | 60.733 | 1.00 55.53 | D |
| ATOM | 5776 | C   | THR | D | 140 | 29.624 | 44.432 | 58.278 | 1.00 55.47 | D |
| ATOM | 5777 | O   | THR | D | 140 | 28.626 | 45.145 | 58.302 | 1.00 54.52 | D |
| ATOM | 5778 | N   | PRO | D | 141 | 30.115 | 43.927 | 57.138 | 1.00 53.18 | D |
| ATOM | 5779 | CD  | PRO | D | 141 | 31.466 | 43.339 | 57.055 | 1.00 55.27 | D |
| ATOM | 5780 | CA  | PRO | D | 141 | 29.586 | 44.129 | 55.795 | 1.00 47.90 | D |
| ATOM | 5781 | CB  | PRO | D | 141 | 30.847 | 44.231 | 54.968 | 1.00 52.44 | D |
| ATOM | 5782 | CG  | PRO | D | 141 | 31.658 | 43.126 | 55.555 | 1.00 51.92 | D |
| ATOM | 5783 | C   | PRO | D | 141 | 28.790 | 42.892 | 55.420 | 1.00 44.03 | D |
| ATOM | 5784 | O   | PRO | D | 141 | 28.597 | 42.604 | 54.242 | 1.00 43.19 | D |
| ATOM | 5785 | N   | TYR | D | 142 | 28.361 | 42.145 | 56.433 | 1.00 42.79 | D |
| ATOM | 5786 | CA  | TYR | D | 142 | 27.586 | 40.925 | 56.223 | 1.00 40.37 | D |
| ATOM | 5787 | CB  | TYR | D | 142 | 28.202 | 39.777 | 57.021 | 1.00 39.73 | D |
| ATOM | 5788 | CG  | TYR | D | 142 | 29.674 | 39.536 | 56.759 | 1.00 37.93 | D |
| ATOM | 5789 | CD1 | TYR | D | 142 | 30.101 | 38.818 | 55.635 | 1.00 39.31 | D |
| ATOM | 5790 | CE1 | TYR | D | 142 | 31.469 | 38.564 | 55.405 | 1.00 35.66 | D |
| ATOM | 5791 | CD2 | TYR | D | 142 | 30.645 | 40.002 | 57.649 | 1.00 37.52 | D |
| ATOM | 5792 | CE2 | TYR | D | 142 | 32.009 | 39.756 | 57.427 | 1.00 38.81 | D |
| ATOM | 5793 | CZ  | TYR | D | 142 | 32.411 | 39.038 | 56.306 | 1.00 38.60 | D |
| ATOM | 5794 | OH  | TYR | D | 142 | 33.748 | 38.807 | 56.085 | 1.00 36.14 | D |
| ATOM | 5795 | C   | TYR | D | 142 | 26.140 | 41.144 | 56.680 | 1.00 39.72 | D |
| ATOM | 5796 | O   | TYR | D | 142 | 25.856 | 42.058 | 57.462 | 1.00 39.45 | D |
| ATOM | 5797 | N   | PRO | D | 143 | 25.201 | 40.320 | 56.178 | 1.00 38.38 | D |
| ATOM | 5798 | CD  | PRO | D | 143 | 25.431 | 39.313 | 55.128 | 1.00 36.44 | D |
| ATOM | 5799 | CA  | PRO | D | 143 | 23.772 | 40.401 | 56.526 | 1.00 36.46 | D |
| ATOM | 5800 | CB  | PRO | D | 143 | 23.119 | 39.522 | 55.466 | 1.00 36.45 | D |
| ATOM | 5801 | CG  | PRO | D | 143 | 24.174 | 38.500 | 55.188 | 1.00 36.42 | D |
| ATOM | 5802 | C   | PRO | D | 143 | 23.537 | 39.899 | 57.965 | 1.00 36.72 | D |
| ATOM | 5803 | O   | PRO | D | 143 | 23.536 | 38.693 | 58.242 | 1.00 39.65 | D |
| ATOM | 5804 | N   | LEU | D | 144 | 23.316 | 40.829 | 58.882 | 1.00 35.06 | D |
| ATOM | 5805 | CA  | LEU | D | 144 | 23.163 | 40.456 | 60.273 | 1.00 37.74 | D |
| ATOM | 5806 | CB  | LEU | D | 144 | 24.525 | 40.662 | 60.934 | 1.00 42.74 | D |
| ATOM | 5807 | CG  | LEU | D | 144 | 25.031 | 39.989 | 62.198 | 1.00 45.52 | D |
| ATOM | 5808 | CD1 | LEU | D | 144 | 26.524 | 40.251 | 62.326 | 1.00 47.33 | D |
| ATOM | 5809 | CD2 | LEU | D | 144 | 24.302 | 40.537 | 63.393 | 1.00 49.69 | D |
| ATOM | 5810 | C   | LEU | D | 144 | 22.093 | 41.313 | 60.933 | 1.00 39.55 | D |
| ATOM | 5811 | O   | LEU | D | 144 | 21.941 | 42.490 | 60.600 | 1.00 36.85 | D |
| ATOM | 5812 | N   | LEU | D | 145 | 21.339 | 40.715 | 61.853 | 1.00 38.90 | D |
| ATOM | 5813 | CA  | LEU | D | 145 | 20.283 | 41.438 | 62.576 | 1.00 34.67 | D |
| ATOM | 5814 | CB  | LEU | D | 145 | 19.001 | 40.609 | 62.682 | 1.00 34.02 | D |
| ATOM | 5815 | CG  | LEU | D | 145 | 18.098 | 40.577 | 61.446 | 1.00 32.17 | D |
| ATOM | 5816 | CD1 | LEU | D | 145 | 16.891 | 39.700 | 61.698 | 1.00 32.89 | D |
| ATOM | 5817 | CD2 | LEU | D | 145 | 17.648 | 41.985 | 61.114 | 1.00 34.45 | D |
| ATOM | 5818 | C   | LEU | D | 145 | 20.766 | 41.754 | 63.970 | 1.00 28.74 | D |
| ATOM | 5819 | O   | LEU | D | 145 | 21.601 | 41.036 | 64.505 | 1.00 32.09 | D |
| ATOM | 5820 | N   | PHE | D | 146 | 20.231 | 42.807 | 64.575 | 1.00 28.65 | D |
| ATOM | 5821 | CA  | PHE | D | 146 | 20.684 | 43.169 | 65.902 | 1.00 29.23 | D |
| ATOM | 5822 | CB  | PHE | D | 146 | 21.327 | 44.541 | 65.847 | 1.00 34.27 | D |
| ATOM | 5823 | CG  | PHE | D | 146 | 22.559 | 44.557 | 65.004 | 1.00 35.83 | D |
| ATOM | 5824 | CD1 | PHE | D | 146 | 23.676 | 43.810 | 65.384 | 1.00 36.47 | D |
| ATOM | 5825 | CD2 | PHE | D | 146 | 22.584 | 45.227 | 63.787 | 1.00 36.79 | D |

Figure 10 (90 of 142)

| ATOM | 5826 | CE1 | PHE | D | 146 | 24.799 | 43.724 | 64.565 | 1.00 | 36.79 | D |
|---|---|---|---|---|---|---|---|---|---|---|---|
| ATOM | 5827 | CE2 | PHE | D | 146 | 23.705 | 45.150 | 62.955 | 1.00 | 38.11 | D |
| ATOM | 5828 | CZ | PHE | D | 146 | 24.812 | 44.393 | 63.347 | 1.00 | 37.69 | D |
| ATOM | 5829 | C | PHE | D | 146 | 19.664 | 43.090 | 66.997 | 1.00 | 28.34 | D |
| ATOM | 5830 | O | PHE | D | 146 | 18.478 | 43.298 | 66.778 | 1.00 | 28.75 | D |
| ATOM | 5831 | N | ALA | D | 147 | 20.151 | 42.761 | 68.184 | 1.00 | 21.38 | D |
| ATOM | 5832 | CA | ALA | D | 147 | 19.309 | 42.632 | 69.352 | 1.00 | 19.77 | D |
| ATOM | 5833 | CB | ALA | D | 147 | 19.186 | 41.171 | 69.720 | 1.00 | 14.12 | D |
| ATOM | 5834 | C | ALA | D | 147 | 19.929 | 43.418 | 70.489 | 1.00 | 21.15 | D |
| ATOM | 5835 | O | ALA | D | 147 | 21.011 | 43.088 | 70.960 | 1.00 | 19.68 | D |
| ATOM | 5836 | N | ASP | D | 148 | 19.256 | 44.474 | 70.924 | 1.00 | 30.29 | D |
| ATOM | 5837 | CA | ASP | D | 148 | 19.796 | 45.274 | 72.016 | 1.00 | 36.56 | D |
| ATOM | 5838 | CB | ASP | D | 148 | 18.886 | 46.453 | 72.340 | 1.00 | 48.19 | D |
| ATOM | 5839 | CG | ASP | D | 148 | 19.229 | 47.695 | 71.531 | 1.00 | 55.40 | D |
| ATOM | 5840 | OD1 | ASP | D | 148 | 19.065 | 47.679 | 70.289 | 1.00 | 62.92 | D |
| ATOM | 5841 | OD2 | ASP | D | 148 | 19.666 | 48.693 | 72.143 | 1.00 | 58.59 | D |
| ATOM | 5842 | C | ASP | D | 148 | 19.967 | 44.431 | 73.256 | 1.00 | 35.61 | D |
| ATOM | 5843 | O | ASP | D | 148 | 19.038 | 43.762 | 73.703 | 1.00 | 39.43 | D |
| ATOM | 5844 | N | VAL | D | 149 | 21.162 | 44.471 | 73.822 | 1.00 | 33.32 | D |
| ATOM | 5845 | CA | VAL | D | 149 | 21.444 | 43.685 | 75.002 | 1.00 | 36.58 | D |
| ATOM | 5846 | CB | VAL | D | 149 | 21.993 | 42.315 | 74.620 | 1.00 | 41.19 | D |
| ATOM | 5847 | CG1 | VAL | D | 149 | 22.298 | 41.534 | 75.870 | 1.00 | 44.21 | D |
| ATOM | 5848 | CG2 | VAL | D | 149 | 20.975 | 41.566 | 73.748 | 1.00 | 45.33 | D |
| ATOM | 5849 | C | VAL | D | 149 | 22.455 | 44.368 | 75.892 | 1.00 | 30.22 | D |
| ATOM | 5850 | O | VAL | D | 149 | 23.589 | 44.577 | 75.487 | 1.00 | 28.95 | D |
| ATOM | 5851 | N | PRO | D | 150 | 22.056 | 44.688 | 77.132 | 1.00 | 26.73 | D |
| ATOM | 5852 | CD | PRO | D | 150 | 20.842 | 44.147 | 77.759 | 1.00 | 29.71 | D |
| ATOM | 5853 | CA | PRO | D | 150 | 22.865 | 45.353 | 78.147 | 1.00 | 26.80 | D |
| ATOM | 5854 | CB | PRO | D | 150 | 22.195 | 44.932 | 79.441 | 1.00 | 20.77 | D |
| ATOM | 5855 | CG | PRO | D | 150 | 20.809 | 44.902 | 79.069 | 1.00 | 26.95 | D |
| ATOM | 5856 | C | PRO | D | 150 | 24.288 | 44.896 | 78.103 | 1.00 | 22.30 | D |
| ATOM | 5857 | O | PRO | D | 150 | 24.550 | 43.697 | 78.138 | 1.00 | 16.78 | D |
| ATOM | 5858 | N | GLU | D | 151 | 25.201 | 45.856 | 78.027 | 1.00 | 20.63 | D |
| ATOM | 5859 | CA | GLU | D | 151 | 26.615 | 45.549 | 77.991 | 1.00 | 25.53 | D |
| ATOM | 5860 | CB | GLU | D | 151 | 27.405 | 46.804 | 77.585 | 1.00 | 34.78 | D |
| ATOM | 5861 | CG | GLU | D | 151 | 27.350 | 47.039 | 76.060 | 1.00 | 49.95 | D |
| ATOM | 5862 | CD | GLU | D | 151 | 27.817 | 48.424 | 75.615 | 1.00 | 54.82 | D |
| ATOM | 5863 | OE1 | GLU | D | 151 | 27.900 | 48.662 | 74.373 | 1.00 | 55.32 | D |
| ATOM | 5864 | OE2 | GLU | D | 151 | 28.089 | 49.268 | 76.509 | 1.00 | 56.48 | D |
| ATOM | 5865 | C | GLU | D | 151 | 27.067 | 44.988 | 79.339 | 1.00 | 18.46 | D |
| ATOM | 5866 | O | GLU | D | 151 | 26.762 | 45.531 | 80.396 | 1.00 | 15.37 | D |
| ATOM | 5867 | N | PHE | D | 152 | 27.757 | 43.857 | 79.285 | 1.00 | 15.49 | D |
| ATOM | 5868 | CA | PHE | D | 152 | 28.259 | 43.198 | 80.477 | 1.00 | 12.26 | D |
| ATOM | 5869 | CB | PHE | D | 152 | 27.383 | 41.997 | 80.791 | 1.00 | 15.65 | D |
| ATOM | 5870 | CG | PHE | D | 152 | 27.673 | 41.370 | 82.103 | 1.00 | 14.04 | D |
| ATOM | 5871 | CD1 | PHE | D | 152 | 26.860 | 40.369 | 82.590 | 1.00 | 12.26 | D |
| ATOM | 5872 | CD2 | PHE | D | 152 | 28.749 | 41.792 | 82.862 | 1.00 | 17.34 | D |
| ATOM | 5873 | CE1 | PHE | D | 152 | 27.113 | 39.803 | 83.811 | 1.00 | 12.26 | D |
| ATOM | 5874 | CE2 | PHE | D | 152 | 29.007 | 41.223 | 84.091 | 1.00 | 17.83 | D |
| ATOM | 5875 | CZ | PHE | D | 152 | 28.187 | 40.228 | 84.566 | 1.00 | 12.26 | D |
| ATOM | 5876 | C | PHE | D | 152 | 29.686 | 42.751 | 80.176 | 1.00 | 12.26 | D |
| ATOM | 5877 | O | PHE | D | 152 | 29.918 | 41.739 | 79.530 | 1.00 | 12.26 | D |
| ATOM | 5878 | N | GLU | D | 153 | 30.648 | 43.519 | 80.650 | 1.00 | 12.26 | D |
| ATOM | 5879 | CA | GLU | D | 153 | 32.041 | 43.215 | 80.390 | 1.00 | 13.99 | D |
| ATOM | 5880 | CB | GLU | D | 153 | 32.905 | 44.427 | 80.731 | 1.00 | 13.11 | D |
| ATOM | 5881 | CG | GLU | D | 153 | 34.349 | 44.225 | 80.363 | 1.00 | 22.49 | D |
| ATOM | 5882 | CD | GLU | D | 153 | 35.258 | 45.317 | 80.891 | 1.00 | 27.85 | D |
| ATOM | 5883 | OE1 | GLU | D | 153 | 36.454 | 45.326 | 80.524 | 1.00 | 31.79 | D |
| ATOM | 5884 | OE2 | GLU | D | 153 | 34.788 | 46.165 | 81.678 | 1.00 | 32.73 | D |
| ATOM | 5885 | C | GLU | D | 153 | 32.544 | 42.010 | 81.162 | 1.00 | 15.52 | D |
| ATOM | 5886 | O | GLU | D | 153 | 33.145 | 42.164 | 82.213 | 1.00 | 15.42 | D |
| ATOM | 5887 | N | VAL | D | 154 | 32.309 | 40.812 | 80.649 | 1.00 | 19.97 | D |
| ATOM | 5888 | CA | VAL | D | 154 | 32.783 | 39.611 | 81.333 | 1.00 | 22.04 | D |
| ATOM | 5889 | CB | VAL | D | 154 | 31.777 | 39.110 | 82.389 | 1.00 | 20.48 | D |
| ATOM | 5890 | CG1 | VAL | D | 154 | 30.387 | 38.949 | 81.767 | 1.00 | 21.59 | D |
| ATOM | 5891 | CG2 | VAL | D | 154 | 32.269 | 37.795 | 82.958 | 1.00 | 12.26 | D |

Figure 10 (91 of 142)

| ATOM | 5892 | C | VAL | D | 154 | 33.047 | 38.481 | 80.359 | 1.00 | 22.56 | D |
|---|---|---|---|---|---|---|---|---|---|---|---|
| ATOM | 5893 | O | VAL | D | 154 | 32.155 | 38.063 | 79.621 | 1.00 | 31.12 | D |
| ATOM | 5894 | N | SER | D | 155 | 34.274 | 37.981 | 80.366 | 1.00 | 20.11 | D |
| ATOM | 5895 | CA | SER | D | 155 | 34.655 | 36.887 | 79.473 | 1.00 | 23.96 | D |
| ATOM | 5896 | CB | SER | D | 155 | 35.752 | 37.340 | 78.510 | 1.00 | 32.00 | D |
| ATOM | 5897 | OG | SER | D | 155 | 36.975 | 37.550 | 79.200 | 1.00 | 31.79 | D |
| ATOM | 5898 | C | SER | D | 155 | 35.177 | 35.694 | 80.253 | 1.00 | 23.51 | D |
| ATOM | 5899 | O | SER | D | 155 | 35.604 | 35.826 | 81.400 | 1.00 | 20.92 | D |
| ATOM | 5900 | N | SER | D | 156 | 35.162 | 34.528 | 79.626 | 1.00 | 22.19 | D |
| ATOM | 5901 | CA | SER | D | 156 | 35.672 | 33.342 | 80.294 | 1.00 | 23.85 | D |
| ATOM | 5902 | CB | SER | D | 156 | 35.437 | 32.123 | 79.420 | 1.00 | 17.44 | D |
| ATOM | 5903 | OG | SER | D | 156 | 36.269 | 32.203 | 78.291 | 1.00 | 27.81 | D |
| ATOM | 5904 | C | SER | D | 156 | 37.181 | 33.501 | 80.586 | 1.00 | 25.94 | D |
| ATOM | 5905 | O | SER | D | 156 | 37.670 | 33.099 | 81.649 | 1.00 | 32.90 | D |
| ATOM | 5906 | N | THR | D | 157 | 37.911 | 34.089 | 79.639 | 1.00 | 24.31 | D |
| ATOM | 5907 | CA | THR | D | 157 | 39.343 | 34.321 | 79.798 | 1.00 | 22.10 | D |
| ATOM | 5908 | CB | THR | D | 157 | 39.922 | 34.941 | 78.537 | 1.00 | 25.45 | D |
| ATOM | 5909 | OG1 | THR | D | 157 | 39.802 | 33.997 | 77.468 | 1.00 | 26.02 | D |
| ATOM | 5910 | CG2 | THR | D | 157 | 41.376 | 35.294 | 78.729 | 1.00 | 18.91 | D |
| ATOM | 5911 | C | THR | D | 157 | 39.610 | 35.227 | 80.996 | 1.00 | 26.19 | D |
| ATOM | 5912 | O | THR | D | 157 | 40.727 | 35.260 | 81.524 | 1.00 | 32.52 | D |
| ATOM | 5913 | N | MET | D | 158 | 38.578 | 35.967 | 81.411 | 1.00 | 27.64 | D |
| ATOM | 5914 | CA | MET | D | 158 | 38.657 | 36.835 | 82.589 | 1.00 | 23.12 | D |
| ATOM | 5915 | CB | MET | D | 158 | 37.413 | 37.718 | 82.695 | 1.00 | 23.05 | D |
| ATOM | 5916 | CG | MET | D | 158 | 37.356 | 38.592 | 83.949 | 1.00 | 19.08 | D |
| ATOM | 5917 | SD | MET | D | 158 | 35.876 | 39.602 | 83.997 | 1.00 | 12.26 | D |
| ATOM | 5918 | CE | MET | D | 158 | 35.945 | 40.386 | 82.310 | 1.00 | 12.26 | D |
| ATOM | 5919 | C | MET | D | 158 | 38.655 | 35.852 | 83.748 | 1.00 | 21.84 | D |
| ATOM | 5920 | O | MET | D | 158 | 39.609 | 35.754 | 84.521 | 1.00 | 27.41 | D |
| ATOM | 5921 | N | ILE | D | 159 | 37.560 | 35.109 | 83.834 | 1.00 | 16.34 | D |
| ATOM | 5922 | CA | ILE | D | 159 | 37.393 | 34.107 | 84.859 | 1.00 | 12.34 | D |
| ATOM | 5923 | CB | ILE | D | 159 | 36.191 | 33.213 | 84.548 | 1.00 | 12.26 | D |
| ATOM | 5924 | CG2 | ILE | D | 159 | 35.949 | 32.250 | 85.726 | 1.00 | 12.26 | D |
| ATOM | 5925 | CG1 | ILE | D | 159 | 34.976 | 34.079 | 84.216 | 1.00 | 12.26 | D |
| ATOM | 5926 | CD1 | ILE | D | 159 | 34.615 | 35.050 | 85.300 | 1.00 | 12.26 | D |
| ATOM | 5927 | C | ILE | D | 159 | 38.621 | 33.205 | 85.007 | 1.00 | 16.01 | D |
| ATOM | 5928 | O | ILE | D | 159 | 39.169 | 33.052 | 86.097 | 1.00 | 17.64 | D |
| ATOM | 5929 | N | ARG | D | 160 | 39.051 | 32.596 | 83.912 | 1.00 | 12.26 | D |
| ATOM | 5930 | CA | ARG | D | 160 | 40.195 | 31.708 | 83.990 | 1.00 | 12.26 | D |
| ATOM | 5931 | CB | ARG | D | 160 | 40.632 | 31.284 | 82.596 | 1.00 | 12.26 | D |
| ATOM | 5932 | CG | ARG | D | 160 | 39.529 | 30.562 | 81.854 | 1.00 | 12.26 | D |
| ATOM | 5933 | CD | ARG | D | 160 | 40.072 | 29.541 | 80.851 | 1.00 | 12.26 | D |
| ATOM | 5934 | NE | ARG | D | 160 | 39.665 | 29.873 | 79.496 | 1.00 | 12.26 | D |
| ATOM | 5935 | CZ | ARG | D | 160 | 40.331 | 30.699 | 78.704 | 1.00 | 13.89 | D |
| ATOM | 5936 | NH1 | ARG | D | 160 | 41.446 | 31.265 | 79.119 | 1.00 | 17.71 | D |
| ATOM | 5937 | NH2 | ARG | D | 160 | 39.862 | 30.989 | 77.505 | 1.00 | 18.76 | D |
| ATOM | 5938 | C | ARG | D | 160 | 41.347 | 32.358 | 84.738 | 1.00 | 13.72 | D |
| ATOM | 5939 | O | ARG | D | 160 | 41.887 | 31.769 | 85.669 | 1.00 | 18.14 | D |
| ATOM | 5940 | N | GLU | D | 161 | 41.711 | 33.579 | 84.354 | 1.00 | 15.51 | D |
| ATOM | 5941 | CA | GLU | D | 161 | 42.814 | 34.268 | 85.014 | 1.00 | 15.92 | D |
| ATOM | 5942 | CB | GLU | D | 161 | 43.150 | 35.559 | 84.276 | 1.00 | 25.17 | D |
| ATOM | 5943 | CG | GLU | D | 161 | 43.514 | 35.365 | 82.818 | 1.00 | 37.10 | D |
| ATOM | 5944 | CD | GLU | D | 161 | 44.165 | 36.609 | 82.216 | 1.00 | 43.33 | D |
| ATOM | 5945 | OE1 | GLU | D | 161 | 45.232 | 37.019 | 82.728 | 1.00 | 48.30 | D |
| ATOM | 5946 | OE2 | GLU | D | 161 | 43.621 | 37.183 | 81.240 | 1.00 | 46.42 | D |
| ATOM | 5947 | C | GLU | D | 161 | 42.446 | 34.594 | 86.446 | 1.00 | 13.17 | D |
| ATOM | 5948 | O | GLU | D | 161 | 43.286 | 34.543 | 87.343 | 1.00 | 12.26 | D |
| ATOM | 5949 | N | ARG | D | 162 | 41.178 | 34.949 | 86.638 | 1.00 | 13.24 | D |
| ATOM | 5950 | CA | ARG | D | 162 | 40.648 | 35.296 | 87.945 | 1.00 | 13.54 | D |
| ATOM | 5951 | CB | ARG | D | 162 | 39.172 | 35.621 | 87.804 | 1.00 | 17.07 | D |
| ATOM | 5952 | CG | ARG | D | 162 | 38.704 | 36.821 | 88.586 | 1.00 | 27.51 | D |
| ATOM | 5953 | CD | ARG | D | 162 | 38.715 | 38.083 | 87.759 | 1.00 | 28.78 | D |
| ATOM | 5954 | NE | ARG | D | 162 | 37.886 | 39.110 | 88.380 | 1.00 | 33.44 | D |
| ATOM | 5955 | CZ | ARG | D | 162 | 37.840 | 40.369 | 87.963 | 1.00 | 42.99 | D |
| ATOM | 5956 | NH1 | ARG | D | 162 | 38.585 | 40.750 | 86.921 | 1.00 | 46.17 | D |
| ATOM | 5957 | NH2 | ARG | D | 162 | 37.051 | 41.244 | 88.581 | 1.00 | 44.67 | D |

Figure 10 (92 of 142)

| ATOM | 5958 | C | ARG | D | 162 | 40.845 | 34.054 | 88.800 | 1.00 | 15.39 | D |
|---|---|---|---|---|---|---|---|---|---|---|---|
| ATOM | 5959 | O | ARG | D | 162 | 41.454 | 34.116 | 89.865 | 1.00 | 16.61 | D |
| ATOM | 5960 | N | PHE | D | 163 | 40.345 | 32.927 | 88.290 | 1.00 | 22.21 | D |
| ATOM | 5961 | CA | PHE | D | 163 | 40.448 | 31.614 | 88.930 | 1.00 | 26.87 | D |
| ATOM | 5962 | CB | PHE | D | 163 | 39.638 | 30.574 | 88.159 | 1.00 | 27.89 | D |
| ATOM | 5963 | CG | PHE | D | 163 | 38.267 | 30.352 | 88.681 | 1.00 | 25.69 | D |
| ATOM | 5964 | CD1 | PHE | D | 163 | 37.902 | 30.796 | 89.932 | 1.00 | 27.09 | D |
| ATOM | 5965 | CD2 | PHE | D | 163 | 37.338 | 29.662 | 87.920 | 1.00 | 27.04 | D |
| ATOM | 5966 | CE1 | PHE | D | 163 | 36.624 | 30.554 | 90.418 | 1.00 | 30.61 | D |
| ATOM | 5967 | CE2 | PHE | D | 163 | 36.061 | 29.413 | 88.398 | 1.00 | 26.17 | D |
| ATOM | 5968 | CZ | PHE | D | 163 | 35.701 | 29.858 | 89.643 | 1.00 | 28.11 | D |
| ATOM | 5969 | C | PHE | D | 163 | 41.880 | 31.134 | 88.892 | 1.00 | 30.46 | D |
| ATOM | 5970 | O | PHE | D | 163 | 42.119 | 29.958 | 88.646 | 1.00 | 38.06 | D |
| ATOM | 5971 | N | LYS | D | 164 | 42.838 | 32.009 | 89.130 | 1.00 | 29.64 | D |
| ATOM | 5972 | CA | LYS | D | 164 | 44.222 | 31.589 | 89.046 | 1.00 | 31.77 | D |
| ATOM | 5973 | CB | LYS | D | 164 | 44.509 | 31.011 | 87.652 | 1.00 | 39.15 | D |
| ATOM | 5974 | CG | LYS | D | 164 | 45.944 | 30.600 | 87.439 | 1.00 | 47.42 | D |
| ATOM | 5975 | CD | LYS | D | 164 | 46.168 | 29.852 | 86.132 | 1.00 | 50.69 | D |
| ATOM | 5976 | CE | LYS | D | 164 | 47.578 | 29.208 | 86.136 | 1.00 | 54.27 | D |
| ATOM | 5977 | NZ | LYS | D | 164 | 47.929 | 28.402 | 84.916 | 1.00 | 52.12 | D |
| ATOM | 5978 | C | LYS | D | 164 | 44.986 | 32.856 | 89.239 | 1.00 | 29.47 | D |
| ATOM | 5979 | O | LYS | D | 164 | 45.555 | 33.405 | 88.302 | 1.00 | 32.76 | D |
| ATOM | 5980 | N | SER | D | 165 | 44.961 | 33.317 | 90.474 | 1.00 | 23.69 | D |
| ATOM | 5981 | CA | SER | D | 165 | 45.591 | 34.558 | 90.924 | 1.00 | 18.35 | D |
| ATOM | 5982 | CB | SER | D | 165 | 45.673 | 35.598 | 89.807 | 1.00 | 17.88 | D |
| ATOM | 5983 | OG | SER | D | 165 | 44.378 | 36.005 | 89.418 | 1.00 | 17.33 | D |
| ATOM | 5984 | C | SER | D | 165 | 44.500 | 34.933 | 91.907 | 1.00 | 15.08 | D |
| ATOM | 5985 | O | SER | D | 165 | 44.344 | 36.079 | 92.337 | 1.00 | 12.26 | D |
| ATOM | 5986 | N | LYS | D | 166 | 43.744 | 33.891 | 92.230 | 1.00 | 13.97 | D |
| ATOM | 5987 | CA | LYS | D | 166 | 42.630 | 33.938 | 93.136 | 1.00 | 12.26 | D |
| ATOM | 5988 | CB | LYS | D | 166 | 43.040 | 33.382 | 94.490 | 1.00 | 12.26 | D |
| ATOM | 5989 | CG | LYS | D | 166 | 44.517 | 33.025 | 94.610 | 1.00 | 12.26 | D |
| ATOM | 5990 | CD | LYS | D | 166 | 44.740 | 31.488 | 94.738 | 1.00 | 12.26 | D |
| ATOM | 5991 | CE | LYS | D | 166 | 43.969 | 30.870 | 95.936 | 1.00 | 17.53 | D |
| ATOM | 5992 | NZ | LYS | D | 166 | 43.959 | 29.369 | 95.949 | 1.00 | 15.05 | D |
| ATOM | 5993 | C | LYS | D | 166 | 41.998 | 35.295 | 93.317 | 1.00 | 12.26 | D |
| ATOM | 5994 | O | LYS | D | 166 | 42.196 | 35.933 | 94.334 | 1.00 | 12.26 | D |
| ATOM | 5995 | N | LYS | D | 167 | 41.258 | 35.734 | 92.303 | 1.00 | 12.26 | D |
| ATOM | 5996 | CA | LYS | D | 167 | 40.515 | 36.981 | 92.343 | 1.00 | 12.26 | D |
| ATOM | 5997 | CB | LYS | D | 167 | 40.775 | 37.807 | 91.092 | 1.00 | 12.26 | D |
| ATOM | 5998 | CG | LYS | D | 167 | 41.899 | 38.814 | 91.216 | 1.00 | 12.26 | D |
| ATOM | 5999 | CD | LYS | D | 167 | 41.736 | 39.859 | 90.115 | 1.00 | 14.80 | D |
| ATOM | 6000 | CE | LYS | D | 167 | 42.685 | 41.031 | 90.273 | 1.00 | 21.78 | D |
| ATOM | 6001 | NZ | LYS | D | 167 | 42.307 | 42.225 | 89.434 | 1.00 | 22.77 | D |
| ATOM | 6002 | C | LYS | D | 167 | 39.034 | 36.547 | 92.428 | 1.00 | 12.26 | D |
| ATOM | 6003 | O | LYS | D | 167 | 38.698 | 35.412 | 92.096 | 1.00 | 12.26 | D |
| ATOM | 6004 | N | PRO | D | 168 | 38.143 | 37.442 | 92.877 | 1.00 | 12.26 | D |
| ATOM | 6005 | CD | PRO | D | 168 | 38.547 | 38.840 | 93.092 | 1.00 | 12.26 | D |
| ATOM | 6006 | CA | PRO | D | 168 | 36.702 | 37.319 | 93.083 | 1.00 | 12.26 | D |
| ATOM | 6007 | CB | PRO | D | 168 | 36.226 | 38.736 | 92.886 | 1.00 | 12.26 | D |
| ATOM | 6008 | CG | PRO | D | 168 | 37.271 | 39.467 | 93.630 | 1.00 | 12.26 | D |
| ATOM | 6009 | C | PRO | D | 168 | 35.823 | 36.322 | 92.366 | 1.00 | 12.26 | D |
| ATOM | 6010 | O | PRO | D | 168 | 35.248 | 35.446 | 93.008 | 1.00 | 12.26 | D |
| ATOM | 6011 | N | THR | D | 169 | 35.675 | 36.452 | 91.059 | 1.00 | 12.26 | D |
| ATOM | 6012 | CA | THR | D | 169 | 34.809 | 35.536 | 90.298 | 1.00 | 12.90 | D |
| ATOM | 6013 | CB | THR | D | 169 | 35.325 | 34.049 | 90.312 | 1.00 | 12.26 | D |
| ATOM | 6014 | OG1 | THR | D | 169 | 34.456 | 33.233 | 91.126 | 1.00 | 12.26 | D |
| ATOM | 6015 | CG2 | THR | D | 169 | 36.755 | 33.973 | 90.845 | 1.00 | 12.26 | D |
| ATOM | 6016 | C | THR | D | 169 | 33.336 | 35.507 | 90.749 | 1.00 | 14.10 | D |
| ATOM | 6017 | O | THR | D | 169 | 32.475 | 34.978 | 90.038 | 1.00 | 15.93 | D |
| ATOM | 6018 | N | ASP | D | 170 | 33.035 | 36.055 | 91.920 | 1.00 | 16.32 | D |
| ATOM | 6019 | CA | ASP | D | 170 | 31.655 | 36.056 | 92.401 | 1.00 | 19.28 | D |
| ATOM | 6020 | CB | ASP | D | 170 | 31.580 | 36.474 | 93.867 | 1.00 | 26.72 | D |
| ATOM | 6021 | CG | ASP | D | 170 | 32.180 | 35.446 | 94.796 | 1.00 | 29.90 | D |
| ATOM | 6022 | OD1 | ASP | D | 170 | 33.427 | 35.399 | 94.916 | 1.00 | 35.42 | D |
| ATOM | 6023 | OD2 | ASP | D | 170 | 31.398 | 34.679 | 95.401 | 1.00 | 33.19 | D |

Figure 10 (93 of 142)

```
ATOM   6024  C    ASP D 170      30.824  37.019  91.589  1.00 15.31           D
ATOM   6025  O    ASP D 170      31.277  38.121  91.271  1.00 24.72           D
ATOM   6026  N    TYR D 171      29.605  36.606  91.270  1.00 12.26           D
ATOM   6027  CA   TYR D 171      28.695  37.437  90.487  1.00 15.22           D
ATOM   6028  CB   TYR D 171      28.623  38.858  91.061  1.00 12.26           D
ATOM   6029  CG   TYR D 171      28.231  38.895  92.514  1.00 12.26           D
ATOM   6030  CD1  TYR D 171      29.170  39.174  93.498  1.00 15.73           D
ATOM   6031  CE1  TYR D 171      28.826  39.177  94.839  1.00 20.43           D
ATOM   6032  CD2  TYR D 171      26.932  38.619  92.905  1.00 12.26           D
ATOM   6033  CE2  TYR D 171      26.577  38.615  94.238  1.00 18.86           D
ATOM   6034  CZ   TYR D 171      27.526  38.891  95.202  1.00 23.70           D
ATOM   6035  OH   TYR D 171      27.168  38.841  96.530  1.00 27.51           D
ATOM   6036  C    TYR D 171      29.040  37.499  88.991  1.00 14.22           D
ATOM   6037  O    TYR D 171      28.384  38.221  88.232  1.00 15.49           D
ATOM   6038  N    LEU D 172      30.063  36.748  88.577  1.00 14.77           D
ATOM   6039  CA   LEU D 172      30.453  36.687  87.175  1.00 12.26           D
ATOM   6040  CB   LEU D 172      31.946  36.875  87.028  1.00 12.26           D
ATOM   6041  CG   LEU D 172      32.468  38.170  87.613  1.00 12.26           D
ATOM   6042  CD1  LEU D 172      33.945  38.194  87.378  1.00 17.53           D
ATOM   6043  CD2  LEU D 172      31.805  39.374  86.975  1.00 13.26           D
ATOM   6044  C    LEU D 172      30.053  35.322  86.611  1.00 12.26           D
ATOM   6045  O    LEU D 172      29.725  35.195  85.424  1.00 12.26           D
ATOM   6046  N    ILE D 173      30.074  34.299  87.465  1.00 15.08           D
ATOM   6047  CA   ILE D 173      29.685  32.952  87.052  1.00 15.94           D
ATOM   6048  CB   ILE D 173      30.890  32.021  86.940  1.00 17.31           D
ATOM   6049  CG2  ILE D 173      31.804  32.486  85.842  1.00 20.91           D
ATOM   6050  CG1  ILE D 173      31.655  32.009  88.245  1.00 12.26           D
ATOM   6051  CD1  ILE D 173      32.796  31.048  88.227  1.00 12.26           D
ATOM   6052  C    ILE D 173      28.750  32.353  88.077  1.00 18.15           D
ATOM   6053  O    ILE D 173      28.914  32.596  89.266  1.00 21.36           D
ATOM   6054  N    PRO D 174      27.744  31.571  87.635  1.00 19.95           D
ATOM   6055  CD   PRO D 174      27.424  31.139  86.262  1.00 17.51           D
ATOM   6056  CA   PRO D 174      26.814  30.959  88.587  1.00 22.06           D
ATOM   6057  CB   PRO D 174      26.169  29.857  87.762  1.00 20.94           D
ATOM   6058  CG   PRO D 174      26.063  30.500  86.429  1.00 15.55           D
ATOM   6059  C    PRO D 174      27.616  30.407  89.742  1.00 20.94           D
ATOM   6060  O    PRO D 174      28.739  29.968  89.548  1.00 23.66           D
ATOM   6061  N    ASP D 175      27.066  30.428  90.943  1.00 24.74           D
ATOM   6062  CA   ASP D 175      27.834  29.919  92.059  1.00 28.31           D
ATOM   6063  CB   ASP D 175      27.146  30.244  93.378  1.00 34.04           D
ATOM   6064  CG   ASP D 175      28.127  30.634  94.442  1.00 35.85           D
ATOM   6065  OD1  ASP D 175      28.774  29.727  95.023  1.00 37.58           D
ATOM   6066  OD2  ASP D 175      28.255  31.856  94.675  1.00 41.49           D
ATOM   6067  C    ASP D 175      28.005  28.416  91.903  1.00 30.17           D
ATOM   6068  O    ASP D 175      28.915  27.821  92.489  1.00 31.27           D
ATOM   6069  N    LYS D 176      27.141  27.803  91.095  1.00 26.34           D
ATOM   6070  CA   LYS D 176      27.226  26.362  90.884  1.00 25.37           D
ATOM   6071  CB   LYS D 176      25.952  25.810  90.241  1.00 27.71           D
ATOM   6072  CG   LYS D 176      24.712  25.872  91.124  1.00 31.72           D
ATOM   6073  CD   LYS D 176      23.504  25.327  90.373  1.00 31.44           D
ATOM   6074  CE   LYS D 176      22.241  25.351  91.215  1.00 29.37           D
ATOM   6075  NZ   LYS D 176      21.075  24.873  90.414  1.00 29.41           D
ATOM   6076  C    LYS D 176      28.393  26.105  89.972  1.00 26.66           D
ATOM   6077  O    LYS D 176      29.041  25.069  90.060  1.00 27.56           D
ATOM   6078  N    VAL D 177      28.668  27.061  89.098  1.00 23.32           D
ATOM   6079  CA   VAL D 177      29.761  26.899  88.170  1.00 18.76           D
ATOM   6080  CB   VAL D 177      29.612  27.893  87.014  1.00 19.32           D
ATOM   6081  CG1  VAL D 177      30.951  28.134  86.343  1.00 23.67           D
ATOM   6082  CG2  VAL D 177      28.598  27.347  86.018  1.00 16.44           D
ATOM   6083  C    VAL D 177      31.104  27.048  88.871  1.00 22.83           D
ATOM   6084  O    VAL D 177      32.070  26.373  88.519  1.00 26.19           D
ATOM   6085  N    LYS D 178      31.152  27.911  89.883  1.00 25.19           D
ATOM   6086  CA   LYS D 178      32.387  28.142  90.631  1.00 19.02           D
ATOM   6087  CB   LYS D 178      32.223  29.284  91.640  1.00 20.13           D
ATOM   6088  CG   LYS D 178      33.465  29.520  92.474  1.00 18.73           D
ATOM   6089  CD   LYS D 178      33.368  30.797  93.276  1.00 23.45           D
```

Figure 10 (94 of 142)

| | | | | | | | | | | |
|---|---|---|---|---|---|---|---|---|---|---|
| ATOM | 6090 | CE | LYS | D | 178 | 32.286 | 30.701 | 94.339 | 1.00 24.22 | D |
| ATOM | 6091 | NZ | LYS | D | 178 | 32.237 | 31.942 | 95.176 | 1.00 21.37 | D |
| ATOM | 6092 | C | LYS | D | 178 | 32.752 | 26.874 | 91.373 | 1.00 17.67 | D |
| ATOM | 6093 | O | LYS | D | 178 | 33.916 | 26.445 | 91.392 | 1.00 18.38 | D |
| ATOM | 6094 | N | LYS | D | 179 | 31.743 | 26.264 | 91.978 | 1.00 14.64 | D |
| ATOM | 6095 | CA | LYS | D | 179 | 31.993 | 25.056 | 92.722 | 1.00 15.49 | D |
| ATOM | 6096 | CB | LYS | D | 179 | 30.717 | 24.585 | 93.417 | 1.00 12.26 | D |
| ATOM | 6097 | CG | LYS | D | 179 | 30.335 | 25.464 | 94.590 | 1.00 13.62 | D |
| ATOM | 6098 | CD | LYS | D | 179 | 28.993 | 25.059 | 95.157 | 1.00 16.68 | D |
| ATOM | 6099 | CE | LYS | D | 179 | 28.421 | 26.163 | 96.052 | 1.00 22.56 | D |
| ATOM | 6100 | NZ | LYS | D | 179 | 27.014 | 25.855 | 96.483 | 1.00 30.05 | D |
| ATOM | 6101 | C | LYS | D | 179 | 32.563 | 23.985 | 91.805 | 1.00 12.65 | D |
| ATOM | 6102 | O | LYS | D | 179 | 33.632 | 23.439 | 92.088 | 1.00 12.26 | D |
| ATOM | 6103 | N | TYR | D | 180 | 31.887 | 23.702 | 90.695 | 1.00 12.26 | D |
| ATOM | 6104 | CA | TYR | D | 180 | 32.393 | 22.680 | 89.799 | 1.00 12.26 | D |
| ATOM | 6105 | CB | TYR | D | 180 | 31.696 | 22.729 | 88.454 | 1.00 12.26 | D |
| ATOM | 6106 | CG | TYR | D | 180 | 32.063 | 21.564 | 87.554 | 1.00 12.26 | D |
| ATOM | 6107 | CD1 | TYR | D | 180 | 31.210 | 20.466 | 87.426 | 1.00 12.26 | D |
| ATOM | 6108 | CE1 | TYR | D | 180 | 31.534 | 19.398 | 86.615 | 1.00 12.26 | D |
| ATOM | 6109 | CD2 | TYR | D | 180 | 33.263 | 21.556 | 86.835 | 1.00 12.26 | D |
| ATOM | 6110 | CE2 | TYR | D | 180 | 33.599 | 20.492 | 86.016 | 1.00 17.55 | D |
| ATOM | 6111 | CZ | TYR | D | 180 | 32.728 | 19.417 | 85.913 | 1.00 14.16 | D |
| ATOM | 6112 | OH | TYR | D | 180 | 33.061 | 18.355 | 85.110 | 1.00 17.65 | D |
| ATOM | 6113 | C | TYR | D | 180 | 33.879 | 22.902 | 89.574 | 1.00 16.62 | D |
| ATOM | 6114 | O | TYR | D | 180 | 34.681 | 21.991 | 89.774 | 1.00 18.10 | D |
| ATOM | 6115 | N | VAL | D | 181 | 34.252 | 24.115 | 89.173 | 1.00 12.42 | D |
| ATOM | 6116 | CA | VAL | D | 181 | 35.657 | 24.412 | 88.911 | 1.00 12.26 | D |
| ATOM | 6117 | CB | VAL | D | 181 | 35.879 | 25.899 | 88.633 | 1.00 12.26 | D |
| ATOM | 6118 | CG1 | VAL | D | 181 | 37.349 | 26.171 | 88.473 | 1.00 12.26 | D |
| ATOM | 6119 | CG2 | VAL | D | 181 | 35.156 | 26.301 | 87.386 | 1.00 12.26 | D |
| ATOM | 6120 | C | VAL | D | 181 | 36.532 | 24.018 | 90.087 | 1.00 14.13 | D |
| ATOM | 6121 | O | VAL | D | 181 | 37.488 | 23.230 | 89.957 | 1.00 12.26 | D |
| ATOM | 6122 | N | GLU | D | 182 | 36.193 | 24.573 | 91.242 | 1.00 12.26 | D |
| ATOM | 6123 | CA | GLU | D | 182 | 36.952 | 24.303 | 92.446 | 1.00 12.26 | D |
| ATOM | 6124 | CB | GLU | D | 182 | 36.325 | 25.043 | 93.618 | 1.00 13.27 | D |
| ATOM | 6125 | CG | GLU | D | 182 | 36.055 | 26.500 | 93.294 | 1.00 23.27 | D |
| ATOM | 6126 | CD | GLU | D | 182 | 35.675 | 27.303 | 94.516 | 1.00 27.23 | D |
| ATOM | 6127 | OE1 | GLU | D | 182 | 34.960 | 26.733 | 95.384 | 1.00 29.87 | D |
| ATOM | 6128 | OE2 | GLU | D | 182 | 36.086 | 28.493 | 94.595 | 1.00 28.88 | D |
| ATOM | 6129 | C | GLU | D | 182 | 37.023 | 22.819 | 92.738 | 1.00 12.26 | D |
| ATOM | 6130 | O | GLU | D | 182 | 38.094 | 22.264 | 92.955 | 1.00 12.26 | D |
| ATOM | 6131 | N | GLU | D | 183 | 35.882 | 22.164 | 92.724 | 1.00 12.26 | D |
| ATOM | 6132 | CA | GLU | D | 183 | 35.900 | 20.766 | 93.021 | 1.00 12.26 | D |
| ATOM | 6133 | CB | GLU | D | 183 | 34.492 | 20.204 | 93.049 | 1.00 14.47 | D |
| ATOM | 6134 | CG | GLU | D | 183 | 33.567 | 20.900 | 94.010 | 1.00 26.79 | D |
| ATOM | 6135 | CD | GLU | D | 183 | 32.270 | 20.140 | 94.230 | 1.00 31.20 | D |
| ATOM | 6136 | OE1 | GLU | D | 183 | 31.622 | 19.711 | 93.236 | 1.00 35.68 | D |
| ATOM | 6137 | OE2 | GLU | D | 183 | 31.903 | 19.990 | 95.417 | 1.00 38.20 | D |
| ATOM | 6138 | C | GLU | D | 183 | 36.716 | 20.002 | 92.015 | 1.00 12.26 | D |
| ATOM | 6139 | O | GLU | D | 183 | 37.607 | 19.256 | 92.403 | 1.00 14.54 | D |
| ATOM | 6140 | N | ASN | D | 184 | 36.436 | 20.188 | 90.724 | 1.00 12.64 | D |
| ATOM | 6141 | CA | ASN | D | 184 | 37.144 | 19.423 | 89.692 | 1.00 16.02 | D |
| ATOM | 6142 | CB | ASN | D | 184 | 36.248 | 19.243 | 88.450 | 1.00 19.59 | D |
| ATOM | 6143 | CG | ASN | D | 184 | 35.852 | 17.784 | 88.222 | 1.00 29.36 | D |
| ATOM | 6144 | OD1 | ASN | D | 184 | 34.700 | 17.487 | 87.884 | 1.00 35.20 | D |
| ATOM | 6145 | ND2 | ASN | D | 184 | 36.810 | 16.864 | 88.399 | 1.00 34.60 | D |
| ATOM | 6146 | C | ASN | D | 184 | 38.546 | 19.910 | 89.301 | 1.00 14.31 | D |
| ATOM | 6147 | O | ASN | D | 184 | 39.083 | 19.529 | 88.253 | 1.00 17.48 | D |
| ATOM | 6148 | N | GLY | D | 185 | 39.139 | 20.723 | 90.173 | 1.00 12.26 | D |
| ATOM | 6149 | CA | GLY | D | 185 | 40.477 | 21.246 | 89.957 | 1.00 13.51 | D |
| ATOM | 6150 | C | GLY | D | 185 | 40.777 | 22.059 | 88.702 | 1.00 14.25 | D |
| ATOM | 6151 | O | GLY | D | 185 | 41.947 | 22.188 | 88.305 | 1.00 13.62 | D |
| ATOM | 6152 | N | LEU | D | 186 | 39.741 | 22.627 | 88.086 | 1.00 13.92 | D |
| ATOM | 6153 | CA | LEU | D | 186 | 39.903 | 23.398 | 86.852 | 1.00 12.26 | D |
| ATOM | 6154 | CB | LEU | D | 186 | 38.541 | 23.676 | 86.226 | 1.00 12.26 | D |
| ATOM | 6155 | CG | LEU | D | 186 | 37.874 | 22.713 | 85.249 | 1.00 12.26 | D |

Figure 10 (95 of 142)

| ATOM | 6156 | CD1 | LEU | D | 186 | 38.691 | 22.671 | 83.978 | 1.00 | 12.83 | D |
|------|------|-----|-----|---|-----|--------|--------|--------|------|-------|---|
| ATOM | 6157 | CD2 | LEU | D | 186 | 37.741 | 21.349 | 85.861 | 1.00 | 12.26 | D |
| ATOM | 6158 | C | LEU | D | 186 | 40.593 | 24.720 | 87.076 | 1.00 | 12.26 | D |
| ATOM | 6159 | O | LEU | D | 186 | 40.713 | 25.163 | 88.214 | 1.00 | 12.26 | D |
| ATOM | 6160 | N | TYR | D | 187 | 41.028 | 25.333 | 85.976 | 1.00 | 14.70 | D |
| ATOM | 6161 | CA | TYR | D | 187 | 41.695 | 26.649 | 85.938 | 1.00 | 15.00 | D |
| ATOM | 6162 | CB | TYR | D | 187 | 40.620 | 27.722 | 85.766 | 1.00 | 15.46 | D |
| ATOM | 6163 | CG | TYR | D | 187 | 39.574 | 27.366 | 84.736 | 1.00 | 16.08 | D |
| ATOM | 6164 | CD1 | TYR | D | 187 | 39.912 | 27.158 | 83.389 | 1.00 | 12.26 | D |
| ATOM | 6165 | CE1 | TYR | D | 187 | 38.946 | 26.834 | 82.436 | 1.00 | 15.10 | D |
| ATOM | 6166 | CD2 | TYR | D | 187 | 38.244 | 27.238 | 85.102 | 1.00 | 14.12 | D |
| ATOM | 6167 | CE2 | TYR | D | 187 | 37.265 | 26.913 | 84.159 | 1.00 | 18.76 | D |
| ATOM | 6168 | CZ | TYR | D | 187 | 37.626 | 26.713 | 82.826 | 1.00 | 19.91 | D |
| ATOM | 6169 | OH | TYR | D | 187 | 36.655 | 26.387 | 81.900 | 1.00 | 25.83 | D |
| ATOM | 6170 | C | TYR | D | 187 | 42.657 | 27.082 | 87.077 | 1.00 | 15.38 | D |
| ATOM | 6171 | O | TYR | D | 187 | 43.895 | 27.012 | 86.902 | 1.00 | 21.48 | D |
| TER | 6172 | | TYR | D | 187 | | | | | | |
| ATOM | 6173 | CB | LYS | E | 2 | 48.160 | 23.074 | 126.304 | 1.00 | 84.10 | E |
| ATOM | 6174 | CG | LYS | E | 2 | 48.253 | 22.043 | 127.425 | 1.00 | 87.80 | E |
| ATOM | 6175 | CD | LYS | E | 2 | 47.022 | 22.107 | 128.326 | 1.00 | 92.92 | E |
| ATOM | 6176 | CE | LYS | E | 2 | 47.174 | 21.202 | 129.541 | 1.00 | 94.89 | E |
| ATOM | 6177 | NZ | LYS | E | 2 | 45.957 | 21.171 | 130.408 | 1.00 | 95.79 | E |
| ATOM | 6178 | C | LYS | E | 2 | 49.331 | 21.901 | 124.391 | 1.00 | 72.33 | E |
| ATOM | 6179 | O | LYS | E | 2 | 48.261 | 21.452 | 123.962 | 1.00 | 67.78 | E |
| ATOM | 6180 | N | LYS | E | 2 | 49.364 | 24.406 | 124.599 | 1.00 | 79.29 | E |
| ATOM | 6181 | CA | LYS | E | 2 | 49.364 | 23.111 | 125.351 | 1.00 | 76.25 | E |
| ATOM | 6182 | N | LYS | E | 3 | 50.514 | 21.379 | 124.067 | 1.00 | 64.43 | E |
| ATOM | 6183 | CA | LYS | E | 3 | 50.653 | 20.239 | 123.158 | 1.00 | 60.69 | E |
| ATOM | 6184 | CB | LYS | E | 3 | 52.138 | 19.995 | 122.849 | 1.00 | 61.48 | E |
| ATOM | 6185 | CG | LYS | E | 3 | 52.892 | 21.230 | 122.346 | 1.00 | 62.27 | E |
| ATOM | 6186 | CD | LYS | E | 3 | 54.389 | 20.937 | 122.190 | 1.00 | 58.27 | E |
| ATOM | 6187 | CE | LYS | E | 3 | 55.243 | 22.214 | 122.125 | 1.00 | 56.43 | E |
| ATOM | 6188 | NZ | LYS | E | 3 | 56.723 | 21.954 | 122.236 | 1.00 | 50.57 | E |
| ATOM | 6189 | C | LYS | E | 3 | 50.020 | 18.960 | 123.717 | 1.00 | 62.47 | E |
| ATOM | 6190 | O | LYS | E | 3 | 50.549 | 18.330 | 124.635 | 1.00 | 57.82 | E |
| ATOM | 6191 | N | ILE | E | 4 | 48.893 | 18.567 | 123.139 | 1.00 | 59.90 | E |
| ATOM | 6192 | CA | ILE | E | 4 | 48.186 | 17.386 | 123.602 | 1.00 | 55.79 | E |
| ATOM | 6193 | CB | ILE | E | 4 | 46.796 | 17.777 | 124.096 | 1.00 | 59.81 | E |
| ATOM | 6194 | CG2 | ILE | E | 4 | 45.962 | 16.532 | 124.378 | 1.00 | 64.71 | E |
| ATOM | 6195 | CG1 | ILE | E | 4 | 46.953 | 18.667 | 125.330 | 1.00 | 62.20 | E |
| ATOM | 6196 | CD1 | ILE | E | 4 | 45.801 | 19.602 | 125.571 | 1.00 | 63.36 | E |
| ATOM | 6197 | C | ILE | E | 4 | 48.045 | 16.292 | 122.561 | 1.00 | 55.73 | E |
| ATOM | 6198 | O | ILE | E | 4 | 47.826 | 16.564 | 121.381 | 1.00 | 53.12 | E |
| ATOM | 6199 | N | GLY | E | 5 | 48.166 | 15.049 | 123.013 | 1.00 | 57.96 | E |
| ATOM | 6200 | CA | GLY | E | 5 | 48.039 | 13.925 | 122.110 | 1.00 | 54.60 | E |
| ATOM | 6201 | C | GLY | E | 5 | 46.839 | 13.070 | 122.458 | 1.00 | 53.25 | E |
| ATOM | 6202 | O | GLY | E | 5 | 46.855 | 12.345 | 123.451 | 1.00 | 55.81 | E |
| ATOM | 6203 | N | ILE | E | 6 | 45.792 | 13.165 | 121.650 | 1.00 | 55.16 | E |
| ATOM | 6204 | CA | ILE | E | 6 | 44.594 | 12.373 | 121.879 | 1.00 | 53.06 | E |
| ATOM | 6205 | CB | ILE | E | 6 | 43.439 | 12.826 | 120.980 | 1.00 | 57.94 | E |
| ATOM | 6206 | CG2 | ILE | E | 6 | 42.305 | 11.818 | 121.033 | 1.00 | 58.25 | E |
| ATOM | 6207 | CG1 | ILE | E | 6 | 42.943 | 14.193 | 121.439 | 1.00 | 58.76 | E |
| ATOM | 6208 | CD1 | ILE | E | 6 | 41.672 | 14.639 | 120.746 | 1.00 | 59.69 | E |
| ATOM | 6209 | C | ILE | E | 6 | 44.892 | 10.921 | 121.570 | 1.00 | 56.77 | E |
| ATOM | 6210 | O | ILE | E | 6 | 45.287 | 10.594 | 120.454 | 1.00 | 56.62 | E |
| ATOM | 6211 | N | PHE | E | 7 | 44.690 | 10.052 | 122.556 | 1.00 | 57.64 | E |
| ATOM | 6212 | CA | PHE | E | 7 | 44.953 | 8.623 | 122.395 | 1.00 | 62.81 | E |
| ATOM | 6213 | CB | PHE | E | 7 | 45.992 | 8.177 | 123.437 | 1.00 | 60.67 | E |
| ATOM | 6214 | CG | PHE | E | 7 | 46.490 | 6.765 | 123.255 | 1.00 | 60.58 | E |
| ATOM | 6215 | CD1 | PHE | E | 7 | 46.494 | 6.159 | 122.006 | 1.00 | 56.41 | E |
| ATOM | 6216 | CD2 | PHE | E | 7 | 47.005 | 6.060 | 124.332 | 1.00 | 61.57 | E |
| ATOM | 6217 | CE1 | PHE | E | 7 | 47.006 | 4.883 | 121.837 | 1.00 | 59.95 | E |
| ATOM | 6218 | CE2 | PHE | E | 7 | 47.521 | 4.777 | 124.165 | 1.00 | 58.28 | E |
| ATOM | 6219 | CZ | PHE | E | 7 | 47.518 | 4.189 | 122.913 | 1.00 | 59.30 | E |
| ATOM | 6220 | C | PHE | E | 7 | 43.655 | 7.839 | 122.552 | 1.00 | 64.66 | E |
| ATOM | 6221 | O | PHE | E | 7 | 43.352 | 7.333 | 123.628 | 1.00 | 65.93 | E |

Figure 10 (96 of 142)

| | | | | | | | | | | |
|---|---|---|---|---|---|---|---|---|---|---|
| ATOM | 6222 | N | GLY | E | 8 | 42.891 | 7.746 | 121.467 | 1.00 71.61 | E |
| ATOM | 6223 | CA | GLY | E | 8 | 41.622 | 7.041 | 121.505 | 1.00 74.63 | E |
| ATOM | 6224 | C | GLY | E | 8 | 41.750 | 5.536 | 121.436 | 1.00 79.11 | E |
| ATOM | 6225 | O | GLY | E | 8 | 42.649 | 5.015 | 120.778 | 1.00 80.04 | E |
| ATOM | 6226 | N | GLY | E | 9 | 40.842 | 4.843 | 122.120 | 1.00 85.43 | E |
| ATOM | 6227 | CA | GLY | E | 9 | 40.842 | 3.389 | 122.140 | 1.00 88.73 | E |
| ATOM | 6228 | C | GLY | E | 9 | 39.660 | 2.830 | 122.912 | 1.00 92.34 | E |
| ATOM | 6229 | O | GLY | E | 9 | 39.090 | 3.518 | 123.764 | 1.00 91.08 | E |
| ATOM | 6230 | N | THR | E | 10 | 39.272 | 1.592 | 122.613 | 1.00 92.89 | E |
| ATOM | 6231 | CA | THR | E | 10 | 38.155 | 0.982 | 123.322 | 1.00 95.64 | E |
| ATOM | 6232 | CB | THR | E | 10 | 37.571 | -0.249 | 122.579 | 1.00 100.83 | E |
| ATOM | 6233 | OG1 | THR | E | 10 | 38.388 | -1.400 | 122.825 | 1.00 102.54 | E |
| ATOM | 6234 | CG2 | THR | E | 10 | 37.508 | 0.005 | 121.092 | 1.00 104.42 | E |
| ATOM | 6235 | C | THR | E | 10 | 38.677 | 0.519 | 124.670 | 1.00 94.05 | E |
| ATOM | 6236 | O | THR | E | 10 | 37.924 | 0.420 | 125.627 | 1.00 94.13 | E |
| ATOM | 6237 | N | PHE | E | 11 | 39.978 | 0.245 | 124.735 | 1.00 93.55 | E |
| ATOM | 6238 | CA | PHE | E | 11 | 40.626 | -0.208 | 125.966 | 1.00 92.58 | E |
| ATOM | 6239 | CB | PHE | E | 11 | 40.761 | 0.964 | 126.944 | 1.00 95.50 | E |
| ATOM | 6240 | CG | PHE | E | 11 | 41.486 | 2.152 | 126.369 | 1.00 97.04 | E |
| ATOM | 6241 | CD1 | PHE | E | 11 | 40.805 | 3.334 | 126.088 | 1.00 95.07 | E |
| ATOM | 6242 | CD2 | PHE | E | 11 | 42.851 | 2.089 | 126.108 | 1.00 94.32 | E |
| ATOM | 6243 | CE1 | PHE | E | 11 | 41.473 | 4.439 | 125.554 | 1.00 95.33 | E |
| ATOM | 6244 | CE2 | PHE | E | 11 | 43.531 | 3.186 | 125.574 | 1.00 95.07 | E |
| ATOM | 6245 | CZ | PHE | E | 11 | 42.840 | 4.364 | 125.298 | 1.00 96.85 | E |
| ATOM | 6246 | C | PHE | E | 11 | 39.848 | -1.350 | 126.623 | 1.00 88.07 | E |
| ATOM | 6247 | O | PHE | E | 11 | 39.428 | -1.248 | 127.776 | 1.00 89.36 | E |
| ATOM | 6248 | N | ASP | E | 12 | 39.679 | -2.445 | 125.890 | 1.00 83.83 | E |
| ATOM | 6249 | CA | ASP | E | 12 | 38.930 | -3.587 | 126.392 | 1.00 83.52 | E |
| ATOM | 6250 | CB | ASP | E | 12 | 37.671 | -3.764 | 125.543 | 1.00 88.93 | E |
| ATOM | 6251 | CG | ASP | E | 12 | 36.803 | -4.905 | 126.015 | 1.00 93.05 | E |
| ATOM | 6252 | OD1 | ASP | E | 12 | 36.498 | -4.955 | 127.229 | 1.00 98.17 | E |
| ATOM | 6253 | OD2 | ASP | E | 12 | 36.422 | -5.744 | 125.166 | 1.00 95.70 | E |
| ATOM | 6254 | C | ASP | E | 12 | 39.738 | -4.887 | 126.410 | 1.00 79.36 | E |
| ATOM | 6255 | O | ASP | E | 12 | 39.547 | -5.766 | 125.569 | 1.00 77.56 | E |
| ATOM | 6256 | N | PRO | E | 13 | 40.630 | -5.039 | 127.398 | 1.00 73.58 | E |
| ATOM | 6257 | CD | PRO | E | 13 | 41.254 | -6.333 | 127.742 | 1.00 74.39 | E |
| ATOM | 6258 | CA | PRO | E | 13 | 40.872 | -4.050 | 128.449 | 1.00 72.20 | E |
| ATOM | 6259 | CB | PRO | E | 13 | 41.101 | -4.925 | 129.665 | 1.00 73.30 | E |
| ATOM | 6260 | CG | PRO | E | 13 | 41.949 | -6.033 | 129.067 | 1.00 74.33 | E |
| ATOM | 6261 | C | PRO | E | 13 | 42.096 | -3.214 | 128.135 | 1.00 68.69 | E |
| ATOM | 6262 | O | PRO | E | 13 | 42.746 | -3.401 | 127.114 | 1.00 64.57 | E |
| ATOM | 6263 | N | PRO | E | 14 | 42.420 | -2.267 | 129.015 | 1.00 68.73 | E |
| ATOM | 6264 | CD | PRO | E | 14 | 41.609 | -1.756 | 130.130 | 1.00 69.10 | E |
| ATOM | 6265 | CA | PRO | E | 14 | 43.595 | -1.423 | 128.797 | 1.00 69.97 | E |
| ATOM | 6266 | CB | PRO | E | 14 | 43.380 | -0.264 | 129.770 | 1.00 70.64 | E |
| ATOM | 6267 | CG | PRO | E | 14 | 41.905 | -0.295 | 130.073 | 1.00 69.85 | E |
| ATOM | 6268 | C | PRO | E | 14 | 44.808 | -2.251 | 129.221 | 1.00 69.51 | E |
| ATOM | 6269 | O | PRO | E | 14 | 44.719 | -2.989 | 130.203 | 1.00 73.96 | E |
| ATOM | 6270 | N | HIS | E | 15 | 45.929 | -2.151 | 128.509 | 1.00 68.53 | E |
| ATOM | 6271 | CA | HIS | E | 15 | 47.115 | -2.898 | 128.918 | 1.00 70.23 | E |
| ATOM | 6272 | CB | HIS | E | 15 | 47.248 | -4.215 | 128.123 | 1.00 73.37 | E |
| ATOM | 6273 | CG | HIS | E | 15 | 47.123 | -4.071 | 126.638 | 1.00 77.97 | E |
| ATOM | 6274 | CD2 | HIS | E | 15 | 46.210 | -4.573 | 125.772 | 1.00 79.19 | E |
| ATOM | 6275 | ND1 | HIS | E | 15 | 48.051 | -3.401 | 125.872 | 1.00 78.64 | E |
| ATOM | 6276 | CE1 | HIS | E | 15 | 47.716 | -3.499 | 124.596 | 1.00 81.62 | E |
| ATOM | 6277 | NE2 | HIS | E | 15 | 46.603 | -4.206 | 124.508 | 1.00 80.20 | E |
| ATOM | 6278 | C | HIS | E | 15 | 48.417 | -2.096 | 128.890 | 1.00 65.27 | E |
| ATOM | 6279 | O | HIS | E | 15 | 48.426 | -0.925 | 128.512 | 1.00 59.24 | E |
| ATOM | 6280 | N | ASN | E | 16 | 49.504 | -2.725 | 129.335 | 1.00 67.14 | E |
| ATOM | 6281 | CA | ASN | E | 16 | 50.809 | -2.073 | 129.378 | 1.00 71.06 | E |
| ATOM | 6282 | CB | ASN | E | 16 | 51.871 | -3.027 | 129.959 | 1.00 76.96 | E |
| ATOM | 6283 | CG | ASN | E | 16 | 51.652 | -3.335 | 131.449 | 1.00 81.15 | E |
| ATOM | 6284 | OD1 | ASN | E | 16 | 51.449 | -2.431 | 132.263 | 1.00 85.63 | E |
| ATOM | 6285 | ND2 | ASN | E | 16 | 51.718 | -4.616 | 131.805 | 1.00 85.37 | E |
| ATOM | 6286 | C | ASN | E | 16 | 51.220 | -1.598 | 127.981 | 1.00 67.62 | E |
| ATOM | 6287 | O | ASN | E | 16 | 51.853 | -0.544 | 127.836 | 1.00 63.55 | E |

Figure 10 (97 of 142)

| ATOM | 6288 | N | GLY | E | 17 | 50.864 | -2.371 | 126.957 | 1.00 | 66.80 | E |
| ATOM | 6289 | CA | GLY | E | 17 | 51.194 | -1.959 | 125.609 | 1.00 | 64.91 | E |
| ATOM | 6290 | C | GLY | E | 17 | 50.782 | -0.503 | 125.478 | 1.00 | 65.09 | E |
| ATOM | 6291 | O | GLY | E | 17 | 51.599 | 0.356 | 125.154 | 1.00 | 66.64 | E |
| ATOM | 6292 | N | HIS | E | 18 | 49.511 | -0.228 | 125.767 | 1.00 | 61.98 | E |
| ATOM | 6293 | CA | HIS | E | 18 | 48.951 | 1.121 | 125.688 | 1.00 | 58.13 | E |
| ATOM | 6294 | CB | HIS | E | 18 | 47.526 | 1.139 | 126.240 | 1.00 | 55.98 | E |
| ATOM | 6295 | CG | HIS | E | 18 | 46.580 | 0.244 | 125.502 | 1.00 | 52.71 | E |
| ATOM | 6296 | CD2 | HIS | E | 18 | 46.559 | -0.166 | 124.212 | 1.00 | 53.24 | E |
| ATOM | 6297 | ND1 | HIS | E | 18 | 45.477 | -0.328 | 126.099 | 1.00 | 54.18 | E |
| ATOM | 6298 | CE1 | HIS | E | 18 | 44.819 | -1.051 | 125.209 | 1.00 | 55.10 | E |
| ATOM | 6299 | NE2 | HIS | E | 18 | 45.455 | -0.969 | 124.055 | 1.00 | 52.99 | E |
| ATOM | 6300 | C | HIS | E | 18 | 49.798 | 2.084 | 126.486 | 1.00 | 53.75 | E |
| ATOM | 6301 | O | HIS | E | 18 | 50.293 | 3.079 | 125.968 | 1.00 | 59.05 | E |
| ATOM | 6302 | N | LEU | E | 19 | 49.956 | 1.772 | 127.761 | 1.00 | 54.84 | E |
| ATOM | 6303 | CA | LEU | E | 19 | 50.735 | 2.587 | 128.679 | 1.00 | 53.76 | E |
| ATOM | 6304 | CB | LEU | E | 19 | 50.875 | 1.848 | 130.002 | 1.00 | 55.32 | E |
| ATOM | 6305 | CG | LEU | E | 19 | 49.585 | 1.755 | 130.803 | 1.00 | 50.55 | E |
| ATOM | 6306 | CD1 | LEU | E | 19 | 49.794 | 0.872 | 132.007 | 1.00 | 52.54 | E |
| ATOM | 6307 | CD2 | LEU | E | 19 | 49.165 | 3.150 | 131.212 | 1.00 | 51.55 | E |
| ATOM | 6308 | C | LEU | E | 19 | 52.115 | 2.964 | 128.164 | 1.00 | 51.29 | E |
| ATOM | 6309 | O | LEU | E | 19 | 52.550 | 4.109 | 128.325 | 1.00 | 46.68 | E |
| ATOM | 6310 | N | LEU | E | 20 | 52.796 | 1.999 | 127.550 | 1.00 | 51.48 | E |
| ATOM | 6311 | CA | LEU | E | 20 | 54.136 | 2.227 | 127.019 | 1.00 | 58.71 | E |
| ATOM | 6312 | CB | LEU | E | 20 | 54.800 | 0.895 | 126.663 | 1.00 | 55.84 | E |
| ATOM | 6313 | CG | LEU | E | 20 | 56.231 | 1.000 | 126.124 | 1.00 | 55.49 | E |
| ATOM | 6314 | CD1 | LEU | E | 20 | 57.093 | 1.823 | 127.072 | 1.00 | 55.91 | E |
| ATOM | 6315 | CD2 | LEU | E | 20 | 56.801 | -0.390 | 125.938 | 1.00 | 56.85 | E |
| ATOM | 6316 | C | LEU | E | 20 | 54.152 | 3.148 | 125.805 | 1.00 | 59.50 | E |
| ATOM | 6317 | O | LEU | E | 20 | 54.928 | 4.106 | 125.765 | 1.00 | 59.86 | E |
| ATOM | 6318 | N | MET | E | 21 | 53.305 | 2.861 | 124.818 | 1.00 | 61.01 | E |
| ATOM | 6319 | CA | MET | E | 21 | 53.248 | 3.685 | 123.618 | 1.00 | 62.82 | E |
| ATOM | 6320 | CB | MET | E | 21 | 52.166 | 3.186 | 122.664 | 1.00 | 61.14 | E |
| ATOM | 6321 | CG | MET | E | 21 | 52.724 | 2.455 | 121.465 | 1.00 | 61.88 | E |
| ATOM | 6322 | SD | MET | E | 21 | 53.795 | 1.126 | 121.961 | 1.00 | 63.56 | E |
| ATOM | 6323 | CE | MET | E | 21 | 54.461 | 0.525 | 120.421 | 1.00 | 58.08 | E |
| ATOM | 6324 | C | MET | E | 21 | 52.979 | 5.126 | 123.985 | 1.00 | 62.02 | E |
| ATOM | 6325 | O | MET | E | 21 | 53.727 | 6.019 | 123.609 | 1.00 | 61.39 | E |
| ATOM | 6326 | N | ALA | E | 22 | 51.912 | 5.347 | 124.735 | 1.00 | 64.51 | E |
| ATOM | 6327 | CA | ALA | E | 22 | 51.558 | 6.690 | 125.154 | 1.00 | 61.41 | E |
| ATOM | 6328 | CB | ALA | E | 22 | 50.325 | 6.648 | 126.055 | 1.00 | 60.72 | E |
| ATOM | 6329 | C | ALA | E | 22 | 52.701 | 7.400 | 125.873 | 1.00 | 60.65 | E |
| ATOM | 6330 | O | ALA | E | 22 | 53.033 | 8.534 | 125.539 | 1.00 | 62.44 | E |
| ATOM | 6331 | N | ASN | E | 23 | 53.313 | 6.746 | 126.856 | 1.00 | 60.65 | E |
| ATOM | 6332 | CA | ASN | E | 23 | 54.386 | 7.402 | 127.592 | 1.00 | 63.65 | E |
| ATOM | 6333 | CB | ASN | E | 23 | 54.811 | 6.574 | 128.803 | 1.00 | 63.42 | E |
| ATOM | 6334 | CG | ASN | E | 23 | 55.857 | 7.282 | 129.652 | 1.00 | 65.24 | E |
| ATOM | 6335 | OD1 | ASN | E | 23 | 56.981 | 6.805 | 129.799 | 1.00 | 67.35 | E |
| ATOM | 6336 | ND2 | ASN | E | 23 | 55.490 | 8.431 | 130.210 | 1.00 | 65.36 | E |
| ATOM | 6337 | C | ASN | E | 23 | 55.591 | 7.673 | 126.714 | 1.00 | 63.04 | E |
| ATOM | 6338 | O | ASN | E | 23 | 56.371 | 8.590 | 126.984 | 1.00 | 60.39 | E |
| ATOM | 6339 | N | GLU | E | 24 | 55.742 | 6.872 | 125.663 | 1.00 | 64.37 | E |
| ATOM | 6340 | CA | GLU | E | 24 | 56.858 | 7.039 | 124.747 | 1.00 | 67.00 | E |
| ATOM | 6341 | CB | GLU | E | 24 | 57.146 | 5.740 | 123.989 | 1.00 | 67.10 | E |
| ATOM | 6342 | CG | GLU | E | 24 | 57.792 | 4.640 | 124.830 | 1.00 | 66.50 | E |
| ATOM | 6343 | CD | GLU | E | 24 | 59.076 | 5.093 | 125.513 | 1.00 | 69.89 | E |
| ATOM | 6344 | OE1 | GLU | E | 24 | 59.909 | 5.750 | 124.849 | 1.00 | 65.80 | E |
| ATOM | 6345 | OE2 | GLU | E | 24 | 59.257 | 4.783 | 126.713 | 1.00 | 67.80 | E |
| ATOM | 6346 | C | GLU | E | 24 | 56.551 | 8.155 | 123.770 | 1.00 | 59.50 | E |
| ATOM | 6347 | O | GLU | E | 24 | 57.372 | 9.040 | 123.575 | 1.00 | 60.00 | E |
| ATOM | 6348 | N | VAL | E | 25 | 55.373 | 8.114 | 123.153 | 1.00 | 56.46 | E |
| ATOM | 6349 | CA | VAL | E | 25 | 54.981 | 9.166 | 122.216 | 1.00 | 60.03 | E |
| ATOM | 6350 | CB | VAL | E | 25 | 53.503 | 9.028 | 121.729 | 1.00 | 51.62 | E |
| ATOM | 6351 | CG1 | VAL | E | 25 | 53.021 | 10.338 | 121.144 | 1.00 | 48.27 | E |
| ATOM | 6352 | CG2 | VAL | E | 25 | 53.386 | 7.945 | 120.672 | 1.00 | 48.44 | E |
| ATOM | 6353 | C | VAL | E | 25 | 55.102 | 10.468 | 122.979 | 1.00 | 53.31 | E |

Figure 10 (98 of 142)

| | | | | | | | | | | |
|---|---|---|---|---|---|---|---|---|---|---|
| ATOM | 6354 | O | VAL | E | 25 | 55.702 | 11.418 | 122.494 | 1.00 57.22 | E |
| ATOM | 6355 | N | LEU | E | 26 | 54.541 | 10.495 | 124.185 | 1.00 53.52 | E |
| ATOM | 6356 | CA | LEU | E | 26 | 54.575 | 11.692 | 125.022 | 1.00 55.11 | E |
| ATOM | 6357 | CB | LEU | E | 26 | 54.308 | 11.341 | 126.490 | 1.00 57.98 | E |
| ATOM | 6358 | CG | LEU | E | 26 | 54.401 | 12.563 | 127.421 | 1.00 58.46 | E |
| ATOM | 6359 | CD1 | LEU | E | 26 | 53.261 | 13.522 | 127.120 | 1.00 58.30 | E |
| ATOM | 6360 | CD2 | LEU | E | 26 | 54.344 | 12.135 | 128.865 | 1.00 60.29 | E |
| ATOM | 6361 | C | LEU | E | 26 | 55.918 | 12.406 | 124.914 | 1.00 53.64 | E |
| ATOM | 6362 | O | LEU | E | 26 | 55.985 | 13.617 | 124.701 | 1.00 52.75 | E |
| ATOM | 6363 | N | TYR | E | 27 | 56.988 | 11.640 | 125.071 | 1.00 50.31 | E |
| ATOM | 6364 | CA | TYR | E | 27 | 58.336 | 12.180 | 124.980 | 1.00 49.22 | E |
| ATOM | 6365 | CB | TYR | E | 27 | 59.337 | 11.187 | 125.570 | 1.00 51.47 | E |
| ATOM | 6366 | CG | TYR | E | 27 | 60.787 | 11.581 | 125.390 | 1.00 51.26 | E |
| ATOM | 6367 | CD1 | TYR | E | 27 | 61.346 | 12.619 | 126.133 | 1.00 52.54 | E |
| ATOM | 6368 | CE1 | TYR | E | 27 | 62.687 | 12.958 | 126.000 | 1.00 52.52 | E |
| ATOM | 6369 | CD2 | TYR | E | 27 | 61.610 | 10.894 | 124.503 | 1.00 49.83 | E |
| ATOM | 6370 | CE2 | TYR | E | 27 | 62.953 | 11.227 | 124.365 | 1.00 50.26 | E |
| ATOM | 6371 | CZ | TYR | E | 27 | 63.481 | 12.257 | 125.120 | 1.00 51.43 | E |
| ATOM | 6372 | OH | TYR | E | 27 | 64.809 | 12.569 | 125.015 | 1.00 50.40 | E |
| ATOM | 6373 | C | TYR | E | 27 | 58.717 | 12.459 | 123.528 | 1.00 50.69 | E |
| ATOM | 6374 | O | TYR | E | 27 | 58.882 | 13.609 | 123.120 | 1.00 50.91 | E |
| ATOM | 6375 | N | GLN | E | 28 | 58.850 | 11.386 | 122.757 | 1.00 52.11 | E |
| ATOM | 6376 | CA | GLN | E | 28 | 59.237 | 11.474 | 121.362 | 1.00 52.44 | E |
| ATOM | 6377 | CB | GLN | E | 28 | 58.974 | 10.135 | 120.669 | 1.00 56.77 | E |
| ATOM | 6378 | CG | GLN | E | 28 | 60.045 | 9.781 | 119.670 | 1.00 61.46 | E |
| ATOM | 6379 | CD | GLN | E | 28 | 61.421 | 10.146 | 120.188 | 1.00 59.67 | E |
| ATOM | 6380 | OE1 | GLN | E | 28 | 61.872 | 9.618 | 121.199 | 1.00 64.39 | E |
| ATOM | 6381 | NE2 | GLN | E | 28 | 62.089 | 11.063 | 119.505 | 1.00 61.59 | E |
| ATOM | 6382 | C | GLN | E | 28 | 58.552 | 12.610 | 120.610 | 1.00 57.21 | E |
| ATOM | 6383 | O | GLN | E | 28 | 59.206 | 13.351 | 119.879 | 1.00 55.97 | E |
| ATOM | 6384 | N | ALA | E | 29 | 57.246 | 12.760 | 120.800 | 1.00 58.30 | E |
| ATOM | 6385 | CA | ALA | E | 29 | 56.496 | 13.810 | 120.120 | 1.00 62.34 | E |
| ATOM | 6386 | CB | ALA | E | 29 | 55.093 | 13.322 | 119.803 | 1.00 64.87 | E |
| ATOM | 6387 | C | ALA | E | 29 | 56.430 | 15.110 | 120.917 | 1.00 63.96 | E |
| ATOM | 6388 | O | ALA | E | 29 | 55.633 | 15.993 | 120.613 | 1.00 63.84 | E |
| ATOM | 6389 | N | GLY | E | 30 | 57.265 | 15.219 | 121.942 | 1.00 66.77 | E |
| ATOM | 6390 | CA | GLY | E | 30 | 57.304 | 16.424 | 122.754 | 1.00 72.65 | E |
| ATOM | 6391 | C | GLY | E | 30 | 55.976 | 16.984 | 123.238 | 1.00 75.91 | E |
| ATOM | 6392 | O | GLY | E | 30 | 55.808 | 18.200 | 123.316 | 1.00 76.79 | E |
| ATOM | 6393 | N | LEU | E | 31 | 55.039 | 16.109 | 123.584 | 1.00 78.35 | E |
| ATOM | 6394 | CA | LEU | E | 31 | 53.730 | 16.545 | 124.066 | 1.00 78.55 | E |
| ATOM | 6395 | CB | LEU | E | 31 | 52.699 | 15.440 | 123.820 | 1.00 79.69 | E |
| ATOM | 6396 | CG | LEU | E | 31 | 52.670 | 14.883 | 122.395 | 1.00 83.59 | E |
| ATOM | 6397 | CD1 | LEU | E | 31 | 51.604 | 13.813 | 122.267 | 1.00 84.15 | E |
| ATOM | 6398 | CD2 | LEU | E | 31 | 52.398 | 16.008 | 121.428 | 1.00 84.89 | E |
| ATOM | 6399 | C | LEU | E | 31 | 53.755 | 16.898 | 125.557 | 1.00 80.46 | E |
| ATOM | 6400 | O | LEU | E | 31 | 54.697 | 16.543 | 126.268 | 1.00 80.19 | E |
| ATOM | 6401 | N | ASP | E | 32 | 52.714 | 17.592 | 126.022 | 1.00 80.55 | E |
| ATOM | 6402 | CA | ASP | E | 32 | 52.590 | 17.991 | 127.434 | 1.00 80.38 | E |
| ATOM | 6403 | CB | ASP | E | 32 | 51.915 | 19.366 | 127.555 | 1.00 84.15 | E |
| ATOM | 6404 | CG | ASP | E | 32 | 52.768 | 20.494 | 126.999 | 1.00 88.23 | E |
| ATOM | 6405 | OD1 | ASP | E | 32 | 53.875 | 20.735 | 127.533 | 1.00 89.57 | E |
| ATOM | 6406 | OD2 | ASP | E | 32 | 52.329 | 21.143 | 126.026 | 1.00 89.78 | E |
| ATOM | 6407 | C | ASP | E | 32 | 51.773 | 16.967 | 128.225 | 1.00 77.52 | E |
| ATOM | 6408 | O | ASP | E | 32 | 52.001 | 16.762 | 129.417 | 1.00 75.75 | E |
| ATOM | 6409 | N | GLU | E | 33 | 50.810 | 16.339 | 127.557 | 1.00 75.31 | E |
| ATOM | 6410 | CA | GLU | E | 33 | 49.968 | 15.332 | 128.184 | 1.00 70.55 | E |
| ATOM | 6411 | CB | GLU | E | 33 | 48.929 | 15.986 | 129.102 | 1.00 72.97 | E |
| ATOM | 6412 | CG | GLU | E | 33 | 48.744 | 17.484 | 128.900 | 1.00 77.35 | E |
| ATOM | 6413 | CD | GLU | E | 33 | 47.727 | 18.084 | 129.861 | 1.00 79.77 | E |
| ATOM | 6414 | OE1 | GLU | E | 33 | 46.523 | 17.751 | 129.748 | 1.00 79.45 | E |
| ATOM | 6415 | OE2 | GLU | E | 33 | 48.136 | 18.887 | 130.731 | 1.00 77.55 | E |
| ATOM | 6416 | C | GLU | E | 33 | 49.265 | 14.484 | 127.141 | 1.00 70.00 | E |
| ATOM | 6417 | O | GLU | E | 33 | 48.915 | 14.969 | 126.068 | 1.00 67.82 | E |
| ATOM | 6418 | N | ILE | E | 34 | 49.081 | 13.207 | 127.455 | 1.00 69.81 | E |
| ATOM | 6419 | CA | ILE | E | 34 | 48.402 | 12.276 | 126.560 | 1.00 67.79 | E |

Figure 10 (99 of 142)

| | | | | | | | | | |
|---|---|---|---|---|---|---|---|---|---|
| ATOM | 6420 | CB | ILE | E | 34 | 49.094 | 10.905 | 126.524 | 1.00 68.20 | E |
| ATOM | 6421 | CG2 | ILE | E | 34 | 48.343 | 9.974 | 125.593 | 1.00 64.96 | E |
| ATOM | 6422 | CG1 | ILE | E | 34 | 50.554 | 11.062 | 126.098 | 1.00 66.51 | E |
| ATOM | 6423 | CD1 | ILE | E | 34 | 50.738 | 11.592 | 124.704 | 1.00 66.41 | E |
| ATOM | 6424 | C | ILE | E | 34 | 47.020 | 12.076 | 127.155 | 1.00 70.13 | E |
| ATOM | 6425 | O | ILE | E | 34 | 46.899 | 11.906 | 128.371 | 1.00 73.70 | E |
| ATOM | 6426 | N | TRP | E | 35 | 45.986 | 12.096 | 126.315 | 1.00 71.86 | E |
| ATOM | 6427 | CA | TRP | E | 35 | 44.611 | 11.927 | 126.788 | 1.00 75.71 | E |
| ATOM | 6428 | CB | TRP | E | 35 | 43.702 | 13.055 | 126.284 | 1.00 79.95 | E |
| ATOM | 6429 | CG | TRP | E | 35 | 43.998 | 14.433 | 126.827 | 1.00 79.49 | E |
| ATOM | 6430 | CD2 | TRP | E | 35 | 43.296 | 15.635 | 126.501 | 1.00 74.41 | E |
| ATOM | 6431 | CE2 | TRP | E | 35 | 43.909 | 16.687 | 127.220 | 1.00 78.88 | E |
| ATOM | 6432 | CE3 | TRP | E | 35 | 42.207 | 15.926 | 125.668 | 1.00 79.61 | E |
| ATOM | 6433 | CD1 | TRP | E | 35 | 44.983 | 14.793 | 127.711 | 1.00 77.99 | E |
| ATOM | 6434 | NE1 | TRP | E | 35 | 44.935 | 16.148 | 127.950 | 1.00 78.11 | E |
| ATOM | 6435 | CZ2 | TRP | E | 35 | 43.465 | 18.007 | 127.129 | 1.00 76.72 | E |
| ATOM | 6436 | CZ3 | TRP | E | 35 | 41.767 | 17.236 | 125.578 | 1.00 80.49 | E |
| ATOM | 6437 | CH2 | TRP | E | 35 | 42.396 | 18.262 | 126.305 | 1.00 78.56 | E |
| ATOM | 6438 | C | TRP | E | 35 | 44.037 | 10.613 | 126.313 | 1.00 71.42 | E |
| ATOM | 6439 | O | TRP | E | 35 | 43.901 | 10.389 | 125.113 | 1.00 77.58 | E |
| ATOM | 6440 | N | PHE | E | 36 | 43.702 | 9.740 | 127.253 | 1.00 73.09 | E |
| ATOM | 6441 | CA | PHE | E | 36 | 43.123 | 8.463 | 126.880 | 1.00 77.82 | E |
| ATOM | 6442 | CB | PHE | E | 36 | 43.376 | 7.401 | 127.951 | 1.00 75.94 | E |
| ATOM | 6443 | CG | PHE | E | 36 | 44.809 | 6.939 | 128.032 | 1.00 72.17 | E |
| ATOM | 6444 | CD1 | PHE | E | 36 | 45.826 | 7.827 | 128.381 | 1.00 72.87 | E |
| ATOM | 6445 | CD2 | PHE | E | 36 | 45.134 | 5.606 | 127.803 | 1.00 70.10 | E |
| ATOM | 6446 | CE1 | PHE | E | 36 | 47.147 | 7.392 | 128.508 | 1.00 70.07 | E |
| ATOM | 6447 | CE2 | PHE | E | 36 | 46.453 | 5.160 | 127.927 | 1.00 69.83 | E |
| ATOM | 6448 | CZ | PHE | E | 36 | 47.461 | 6.056 | 128.281 | 1.00 69.21 | E |
| ATOM | 6449 | C | PHE | E | 36 | 41.633 | 8.665 | 126.682 | 1.00 77.84 | E |
| ATOM | 6450 | O | PHE | E | 36 | 40.884 | 8.896 | 127.633 | 1.00 78.11 | E |
| ATOM | 6451 | N | MET | E | 37 | 41.216 | 8.590 | 125.425 | 1.00 79.25 | E |
| ATOM | 6452 | CA | MET | E | 37 | 39.821 | 8.770 | 125.074 | 1.00 84.40 | E |
| ATOM | 6453 | CB | MET | E | 37 | 39.692 | 9.770 | 123.925 | 1.00 81.48 | E |
| ATOM | 6454 | CG | MET | E | 37 | 38.258 | 10.029 | 123.494 | 1.00 81.24 | E |
| ATOM | 6455 | SD | MET | E | 37 | 38.115 | 11.369 | 122.304 | 1.00 76.64 | E |
| ATOM | 6456 | CE | MET | E | 37 | 38.556 | 10.538 | 120.842 | 1.00 77.13 | E |
| ATOM | 6457 | C | MET | E | 37 | 39.156 | 7.457 | 124.698 | 1.00 83.92 | E |
| ATOM | 6458 | O | MET | E | 37 | 39.369 | 6.913 | 123.614 | 1.00 79.34 | E |
| ATOM | 6459 | N | PRO | E | 38 | 38.332 | 6.933 | 125.607 | 1.00 85.48 | E |
| ATOM | 6460 | CD | PRO | E | 38 | 38.260 | 7.419 | 126.993 | 1.00 87.60 | E |
| ATOM | 6461 | CA | PRO | E | 38 | 37.588 | 5.679 | 125.456 | 1.00 86.69 | E |
| ATOM | 6462 | CB | PRO | E | 38 | 37.275 | 5.289 | 126.902 | 1.00 90.35 | E |
| ATOM | 6463 | CG | PRO | E | 38 | 38.249 | 6.139 | 127.743 | 1.00 88.11 | E |
| ATOM | 6464 | C | PRO | E | 38 | 36.318 | 5.872 | 124.631 | 1.00 83.05 | E |
| ATOM | 6465 | O | PRO | E | 38 | 35.648 | 6.893 | 124.752 | 1.00 85.26 | E |
| ATOM | 6466 | N | ASN | E | 39 | 35.986 | 4.891 | 123.799 | 1.00 81.89 | E |
| ATOM | 6467 | CA | ASN | E | 39 | 34.783 | 4.966 | 122.968 | 1.00 87.08 | E |
| ATOM | 6468 | CB | ASN | E | 39 | 34.833 | 3.933 | 121.840 | 1.00 91.67 | E |
| ATOM | 6469 | CG | ASN | E | 39 | 36.146 | 3.936 | 121.114 | 1.00 95.10 | E |
| ATOM | 6470 | OD1 | ASN | E | 39 | 36.707 | 4.994 | 120.835 | 1.00 99.60 | E |
| ATOM | 6471 | ND2 | ASN | E | 39 | 36.645 | 2.751 | 120.787 | 1.00 97.59 | E |
| ATOM | 6472 | C | ASN | E | 39 | 33.533 | 4.687 | 123.792 | 1.00 88.60 | E |
| ATOM | 6473 | O | ASN | E | 39 | 33.603 | 4.048 | 124.845 | 1.00 85.23 | E |
| ATOM | 6474 | N | GLN | E | 40 | 32.385 | 5.165 | 123.319 | 1.00 88.40 | E |
| ATOM | 6475 | CA | GLN | E | 40 | 31.131 | 4.897 | 124.012 | 1.00 88.30 | E |
| ATOM | 6476 | CB | GLN | E | 40 | 30.088 | 5.978 | 123.716 | 1.00 88.04 | E |
| ATOM | 6477 | CG | GLN | E | 40 | 28.786 | 5.761 | 124.480 | 1.00 94.12 | E |
| ATOM | 6478 | CD | GLN | E | 40 | 27.974 | 7.028 | 124.649 | 1.00 99.36 | E |
| ATOM | 6479 | OE1 | GLN | E | 40 | 28.503 | 8.067 | 125.037 | 1.00100.22 | E |
| ATOM | 6480 | NE2 | GLN | E | 40 | 26.678 | 6.944 | 124.376 | 1.00 99.21 | E |
| ATOM | 6481 | C | GLN | E | 40 | 30.680 | 3.563 | 123.445 | 1.00 85.40 | E |
| ATOM | 6482 | O | GLN | E | 40 | 30.131 | 2.710 | 124.145 | 1.00 85.33 | E |
| ATOM | 6483 | N | ILE | E | 41 | 30.947 | 3.411 | 122.152 | 1.00 89.45 | E |
| ATOM | 6484 | CA | ILE | E | 41 | 30.643 | 2.212 | 121.388 | 1.00104.64 | E |
| ATOM | 6485 | CB | ILE | E | 41 | 29.162 | 2.180 | 120.910 | 1.00102.30 | E |

Figure 10 (100 of 142)

```
ATOM   6486  CG2 ILE E  41      28.767   3.516 120.332  1.00 104.07      E
ATOM   6487  CG1 ILE E  41      28.969   1.066 119.878  1.00 106.90      E
ATOM   6488  CD1 ILE E  41      27.559   0.951 119.344  1.00 110.91      E
ATOM   6489  C   ILE E  41      31.575   2.221 120.177  1.00 102.47      E
ATOM   6490  O   ILE E  41      31.578   3.169 119.388  1.00  97.71      E
ATOM   6491  N   ASP E  52      30.649  -3.357 128.187  1.00  89.37      E
ATOM   6492  CA  ASP E  52      29.644  -2.407 128.658  1.00  93.24      E
ATOM   6493  CB  ASP E  52      29.014  -2.888 129.977  1.00 100.68      E
ATOM   6494  CG  ASP E  52      28.215  -4.162 129.813  1.00  99.85      E
ATOM   6495  OD1 ASP E  52      27.185  -4.131 129.102  1.00 101.69      E
ATOM   6496  OD2 ASP E  52      28.626  -5.190 130.394  1.00 101.17      E
ATOM   6497  C   ASP E  52      30.123  -0.964 128.836  1.00  92.59      E
ATOM   6498  O   ASP E  52      29.315  -0.103 129.168  1.00  90.58      E
ATOM   6499  N   SER E  53      31.412  -0.694 128.638  1.00  89.40      E
ATOM   6500  CA  SER E  53      31.941   0.679 128.775  1.00  89.67      E
ATOM   6501  CB  SER E  53      30.962   1.707 128.170  1.00  87.11      E
ATOM   6502  OG  SER E  53      31.238   3.028 128.633  1.00  82.22      E
ATOM   6503  C   SER E  53      32.301   1.148 130.186  1.00  93.08      E
ATOM   6504  O   SER E  53      33.415   1.628 130.426  1.00  94.29      E
ATOM   6505  N   PHE E  54      31.351   1.043 131.110  1.00  94.22      E
ATOM   6506  CA  PHE E  54      31.591   1.467 132.479  1.00  99.35      E
ATOM   6507  CB  PHE E  54      30.363   1.197 133.347  1.00  95.24      E
ATOM   6508  CG  PHE E  54      30.592   1.456 134.806  1.00  93.74      E
ATOM   6509  CD1 PHE E  54      30.906   2.737 135.257  1.00  90.67      E
ATOM   6510  CD2 PHE E  54      30.536   0.413 135.724  1.00  90.52      E
ATOM   6511  CE1 PHE E  54      31.163   2.976 136.606  1.00  88.96      E
ATOM   6512  CE2 PHE E  54      30.792   0.640 137.071  1.00  88.26      E
ATOM   6513  CZ  PHE E  54      31.107   1.924 137.515  1.00  88.50      E
ATOM   6514  C   PHE E  54      32.800   0.743 133.062  1.00 102.95      E
ATOM   6515  O   PHE E  54      33.524   1.297 133.889  1.00 106.94      E
ATOM   6516  N   HIS E  55      33.012  -0.497 132.623  1.00 105.75      E
ATOM   6517  CA  HIS E  55      34.137  -1.303 133.098  1.00 103.59      E
ATOM   6518  CB  HIS E  55      33.853  -2.794 132.886  1.00 101.89      E
ATOM   6519  CG  HIS E  55      32.734  -3.318 133.729  1.00  99.37      E
ATOM   6520  CD2 HIS E  55      31.923  -2.695 134.616  1.00  97.73      E
ATOM   6521  ND1 HIS E  55      32.338  -4.638 133.709  1.00  98.58      E
ATOM   6522  CE1 HIS E  55      31.331  -4.805 134.547  1.00  97.47      E
ATOM   6523  NE2 HIS E  55      31.060  -3.641 135.110  1.00  98.76      E
ATOM   6524  C   HIS E  55      35.417  -0.917 132.377  1.00 102.88      E
ATOM   6525  O   HIS E  55      36.516  -1.048 132.914  1.00 102.68      E
ATOM   6526  N   ARG E  56      35.267  -0.452 131.146  1.00 102.62      E
ATOM   6527  CA  ARG E  56      36.412  -0.036 130.369  1.00  97.72      E
ATOM   6528  CB  ARG E  56      35.996   0.138 128.910  1.00  99.51      E
ATOM   6529  CG  ARG E  56      35.739  -1.195 128.202  1.00 102.72      E
ATOM   6530  CD  ARG E  56      34.713  -1.045 127.097  1.00 107.51      E
ATOM   6531  NE  ARG E  56      35.134  -0.066 126.098  1.00 116.35      E
ATOM   6532  CZ  ARG E  56      34.302   0.731 125.432  1.00 115.46      E
ATOM   6533  NH1 ARG E  56      32.996   0.667 125.659  1.00 117.93      E
ATOM   6534  NH2 ARG E  56      34.774   1.594 124.541  1.00 117.56      E
ATOM   6535  C   ARG E  56      36.922   1.266 130.978  1.00  97.28      E
ATOM   6536  O   ARG E  56      38.130   1.445 131.154  1.00  93.53      E
ATOM   6537  N   VAL E  57      35.994   2.157 131.327  1.00  90.69      E
ATOM   6538  CA  VAL E  57      36.345   3.443 131.938  1.00  88.60      E
ATOM   6539  CB  VAL E  57      35.129   4.401 132.041  1.00  87.29      E
ATOM   6540  CG1 VAL E  57      35.539   5.675 132.766  1.00  90.11      E
ATOM   6541  CG2 VAL E  57      34.597   4.738 130.667  1.00  91.18      E
ATOM   6542  C   VAL E  57      36.882   3.266 133.355  1.00  85.63      E
ATOM   6543  O   VAL E  57      37.634   4.105 133.854  1.00  84.34      E
ATOM   6544  N   GLU E  58      36.470   2.186 134.010  1.00  85.73      E
ATOM   6545  CA  GLU E  58      36.919   1.931 135.368  1.00  82.90      E
ATOM   6546  CB  GLU E  58      35.987   0.938 136.066  1.00  83.33      E
ATOM   6547  CG  GLU E  58      34.789   1.625 136.697  1.00  84.50      E
ATOM   6548  CD  GLU E  58      35.190   2.913 137.407  1.00  88.08      E
ATOM   6549  OE1 GLU E  58      36.000   2.850 138.360  1.00  89.39      E
ATOM   6550  OE2 GLU E  58      34.705   3.993 137.004  1.00  86.68      E
ATOM   6551  C   GLU E  58      38.359   1.454 135.393  1.00  80.78      E
```

Figure 10 (101 of 142)

| ATOM | 6552 | O | GLU | E | 58 | 39.158 | 1.959 | 136.182 | 1.00 | 78.21 | E |
|---|---|---|---|---|---|---|---|---|---|---|---|
| ATOM | 6553 | N | MET | E | 59 | 38.695 | 0.488 | 134.539 | 1.00 | 77.22 | E |
| ATOM | 6554 | CA | MET | E | 59 | 40.070 | 0.013 | 134.458 | 1.00 | 73.00 | E |
| ATOM | 6555 | CB | MET | E | 59 | 40.225 | -0.927 | 133.264 | 1.00 | 66.30 | E |
| ATOM | 6556 | CG | MET | E | 59 | 39.042 | -1.870 | 133.149 | 1.00 | 56.17 | E |
| ATOM | 6557 | SD | MET | E | 59 | 39.438 | -3.525 | 132.625 | 1.00 | 52.37 | E |
| ATOM | 6558 | CE | MET | E | 59 | 37.972 | -4.021 | 131.749 | 1.00 | 41.47 | E |
| ATOM | 6559 | C | MET | E | 59 | 40.829 | 1.323 | 134.260 | 1.00 | 73.23 | E |
| ATOM | 6560 | O | MET | E | 59 | 41.514 | 1.787 | 135.160 | 1.00 | 70.46 | E |
| ATOM | 6561 | N | LEU | E | 60 | 40.679 | 1.944 | 133.098 | 1.00 | 72.74 | E |
| ATOM | 6562 | CA | LEU | E | 60 | 41.307 | 3.238 | 132.885 | 1.00 | 73.27 | E |
| ATOM | 6563 | CB | LEU | E | 60 | 40.770 | 3.857 | 131.600 | 1.00 | 75.13 | E |
| ATOM | 6564 | CG | LEU | E | 60 | 41.758 | 4.044 | 130.452 | 1.00 | 73.00 | E |
| ATOM | 6565 | CD1 | LEU | E | 60 | 41.000 | 4.138 | 129.149 | 1.00 | 73.57 | E |
| ATOM | 6566 | CD2 | LEU | E | 60 | 42.585 | 5.295 | 130.689 | 1.00 | 74.43 | E |
| ATOM | 6567 | C | LEU | E | 60 | 40.907 | 4.091 | 134.109 | 1.00 | 71.98 | E |
| ATOM | 6568 | O | LEU | E | 60 | 39.774 | 4.000 | 134.587 | 1.00 | 73.00 | E |
| ATOM | 6569 | N | LYS | E | 61 | 41.850 | 4.898 | 134.601 | 1.00 | 71.88 | E |
| ATOM | 6570 | CA | LYS | E | 61 | 41.723 | 5.768 | 135.792 | 1.00 | 72.23 | E |
| ATOM | 6571 | CB | LYS | E | 61 | 40.356 | 5.645 | 136.481 | 1.00 | 72.06 | E |
| ATOM | 6572 | CG | LYS | E | 61 | 40.023 | 6.837 | 137.369 | 1.00 | 67.65 | E |
| ATOM | 6573 | CD | LYS | E | 61 | 38.549 | 7.223 | 137.276 | 1.00 | 67.23 | E |
| ATOM | 6574 | CE | LYS | E | 61 | 37.666 | 6.431 | 138.235 | 1.00 | 66.32 | E |
| ATOM | 6575 | NZ | LYS | E | 61 | 36.236 | 6.837 | 138.111 | 1.00 | 68.27 | E |
| ATOM | 6576 | C | LYS | E | 61 | 42.819 | 5.202 | 136.688 | 1.00 | 75.65 | E |
| ATOM | 6577 | O | LYS | E | 61 | 43.249 | 5.810 | 137.668 | 1.00 | 71.34 | E |
| ATOM | 6578 | N | LEU | E | 62 | 43.228 | 3.995 | 136.304 | 1.00 | 80.31 | E |
| ATOM | 6579 | CA | LEU | E | 62 | 44.307 | 3.232 | 136.907 | 1.00 | 84.54 | E |
| ATOM | 6580 | CB | LEU | E | 62 | 43.815 | 1.868 | 137.399 | 1.00 | 87.11 | E |
| ATOM | 6581 | CG | LEU | E | 62 | 43.540 | 0.764 | 136.374 | 1.00 | 90.45 | E |
| ATOM | 6582 | CD1 | LEU | E | 62 | 44.791 | -0.059 | 136.165 | 1.00 | 92.18 | E |
| ATOM | 6583 | CD2 | LEU | E | 62 | 42.405 | -0.124 | 136.875 | 1.00 | 94.16 | E |
| ATOM | 6584 | C | LEU | E | 62 | 45.158 | 3.081 | 135.652 | 1.00 | 84.48 | E |
| ATOM | 6585 | O | LEU | E | 62 | 44.644 | 3.250 | 134.542 | 1.00 | 87.22 | E |
| ATOM | 6586 | N | ALA | E | 63 | 46.433 | 2.756 | 135.807 | 1.00 | 85.69 | E |
| ATOM | 6587 | CA | ALA | E | 63 | 47.320 | 2.661 | 134.654 | 1.00 | 84.45 | E |
| ATOM | 6588 | CB | ALA | E | 63 | 46.590 | 2.049 | 133.435 | 1.00 | 86.43 | E |
| ATOM | 6589 | C | ALA | E | 63 | 47.713 | 4.111 | 134.376 | 1.00 | 81.76 | E |
| ATOM | 6590 | O | ALA | E | 63 | 48.898 | 4.445 | 134.328 | 1.00 | 85.94 | E |
| ATOM | 6591 | N | ILE | E | 64 | 46.709 | 4.971 | 134.219 | 1.00 | 79.70 | E |
| ATOM | 6592 | CA | ILE | E | 64 | 46.943 | 6.387 | 133.976 | 1.00 | 81.54 | E |
| ATOM | 6593 | CB | ILE | E | 64 | 45.948 | 6.969 | 132.937 | 1.00 | 78.83 | E |
| ATOM | 6594 | CG2 | ILE | E | 64 | 45.609 | 5.901 | 131.914 | 1.00 | 78.42 | E |
| ATOM | 6595 | CG1 | ILE | E | 64 | 44.663 | 7.461 | 133.612 | 1.00 | 75.33 | E |
| ATOM | 6596 | CD1 | ILE | E | 64 | 43.677 | 8.097 | 132.641 | 1.00 | 74.64 | E |
| ATOM | 6597 | C | ILE | E | 64 | 46.756 | 7.093 | 135.298 | 1.00 | 74.95 | E |
| ATOM | 6598 | O | ILE | E | 64 | 46.787 | 8.319 | 135.369 | 1.00 | 75.06 | E |
| ATOM | 6599 | N | GLN | E | 65 | 46.549 | 6.299 | 136.345 | 1.00 | 74.73 | E |
| ATOM | 6600 | CA | GLN | E | 65 | 46.358 | 6.834 | 137.687 | 1.00 | 78.59 | E |
| ATOM | 6601 | CB | GLN | E | 65 | 45.742 | 5.779 | 138.620 | 1.00 | 82.66 | E |
| ATOM | 6602 | CG | GLN | E | 65 | 46.727 | 4.787 | 139.250 | 1.00 | 89.06 | E |
| ATOM | 6603 | CD | GLN | E | 65 | 46.806 | 4.935 | 140.764 | 1.00 | 90.23 | E |
| ATOM | 6604 | OE1 | GLN | E | 65 | 45.780 | 4.944 | 141.447 | 1.00 | 93.69 | E |
| ATOM | 6605 | NE2 | GLN | E | 65 | 48.024 | 5.047 | 141.295 | 1.00 | 91.75 | E |
| ATOM | 6606 | C | GLN | E | 65 | 47.720 | 7.230 | 138.218 | 1.00 | 77.66 | E |
| ATOM | 6607 | O | GLN | E | 65 | 47.899 | 8.308 | 138.786 | 1.00 | 72.55 | E |
| ATOM | 6608 | N | SER | E | 66 | 48.677 | 6.336 | 138.014 | 1.00 | 73.76 | E |
| ATOM | 6609 | CA | SER | E | 66 | 50.037 | 6.539 | 138.468 | 1.00 | 73.39 | E |
| ATOM | 6610 | CB | SER | E | 66 | 50.759 | 5.193 | 138.501 | 1.00 | 71.18 | E |
| ATOM | 6611 | OG | SER | E | 66 | 50.342 | 4.389 | 137.417 | 1.00 | 68.96 | E |
| ATOM | 6612 | C | SER | E | 66 | 50.815 | 7.535 | 137.616 | 1.00 | 75.02 | E |
| ATOM | 6613 | O | SER | E | 66 | 51.848 | 8.057 | 138.056 | 1.00 | 73.98 | E |
| ATOM | 6614 | N | ASN | E | 67 | 50.323 | 7.805 | 136.408 | 1.00 | 78.12 | E |
| ATOM | 6615 | CA | ASN | E | 67 | 51.007 | 8.736 | 135.512 | 1.00 | 83.75 | E |
| ATOM | 6616 | CB | ASN | E | 67 | 51.073 | 8.153 | 134.093 | 1.00 | 83.64 | E |
| ATOM | 6617 | CG | ASN | E | 67 | 52.076 | 8.876 | 133.207 | 1.00 | 82.06 | E |

Figure 10 (102 of 142)

| | | | | | | | | | |
|---|---|---|---|---|---|---|---|---|---|
| ATOM | 6618 | OD1 | ASN | E | 67 | 52.440 | 8.383 | 132.147 | 1.00 80.47 | E |
| ATOM | 6619 | ND2 | ASN | E | 67 | 52.521 | 10.051 | 133.638 | 1.00 81.68 | E |
| ATOM | 6620 | C | ASN | E | 67 | 50.366 | 10.125 | 135.484 | 1.00 85.35 | E |
| ATOM | 6621 | O | ASN | E | 67 | 49.243 | 10.301 | 135.003 | 1.00 85.57 | E |
| ATOM | 6622 | N | PRO | E | 68 | 51.085 | 11.132 | 136.012 | 1.00 91.05 | E |
| ATOM | 6623 | CD | PRO | E | 68 | 52.396 | 10.985 | 136.670 | 1.00 89.71 | E |
| ATOM | 6624 | CA | PRO | E | 68 | 50.630 | 12.524 | 136.068 | 1.00 94.17 | E |
| ATOM | 6625 | CB | PRO | E | 68 | 51.812 | 13.246 | 136.715 | 1.00 92.00 | E |
| ATOM | 6626 | CG | PRO | E | 68 | 52.436 | 12.186 | 137.571 | 1.00 90.30 | E |
| ATOM | 6627 | C | PRO | E | 68 | 50.316 | 13.086 | 134.682 | 1.00 92.74 | E |
| ATOM | 6628 | O | PRO | E | 68 | 49.393 | 13.879 | 134.514 | 1.00 96.92 | E |
| ATOM | 6629 | N | SER | E | 69 | 51.098 | 12.666 | 133.694 | 1.00 94.40 | E |
| ATOM | 6630 | CA | SER | E | 69 | 50.932 | 13.134 | 132.326 | 1.00 99.35 | E |
| ATOM | 6631 | CB | SER | E | 69 | 52.259 | 12.997 | 131.581 | 1.00 96.32 | E |
| ATOM | 6632 | OG | SER | E | 69 | 53.285 | 13.711 | 132.253 | 1.00 92.74 | E |
| ATOM | 6633 | C | SER | E | 69 | 49.821 | 12.416 | 131.561 | 1.00 101.78 | E |
| ATOM | 6634 | O | SER | E | 69 | 49.563 | 12.715 | 130.394 | 1.00 102.95 | E |
| ATOM | 6635 | N | PHE | E | 70 | 49.171 | 11.464 | 132.216 | 1.00 103.02 | E |
| ATOM | 6636 | CA | PHE | E | 70 | 48.075 | 10.733 | 131.596 | 1.00 100.52 | E |
| ATOM | 6637 | CB | PHE | E | 70 | 48.205 | 9.232 | 131.876 | 1.00 100.16 | E |
| ATOM | 6638 | CG | PHE | E | 70 | 49.252 | 8.543 | 131.047 | 1.00 97.69 | E |
| ATOM | 6639 | CD1 | PHE | E | 70 | 49.382 | 7.158 | 131.088 | 1.00 100.75 | E |
| ATOM | 6640 | CD2 | PHE | E | 70 | 50.094 | 9.270 | 130.216 | 1.00 100.47 | E |
| ATOM | 6641 | CE1 | PHE | E | 70 | 50.329 | 6.507 | 130.312 | 1.00 102.70 | E |
| ATOM | 6642 | CE2 | PHE | E | 70 | 51.043 | 8.631 | 129.436 | 1.00 97.32 | E |
| ATOM | 6643 | CZ | PHE | E | 70 | 51.162 | 7.244 | 129.484 | 1.00 99.09 | E |
| ATOM | 6644 | C | PHE | E | 70 | 46.749 | 11.258 | 132.147 | 1.00 99.34 | E |
| ATOM | 6645 | O | PHE | E | 70 | 46.571 | 11.378 | 133.363 | 1.00 102.66 | E |
| ATOM | 6646 | N | LYS | E | 71 | 45.821 | 11.576 | 131.249 | 1.00 92.62 | E |
| ATOM | 6647 | CA | LYS | E | 71 | 44.527 | 12.100 | 131.657 | 1.00 84.46 | E |
| ATOM | 6648 | CB | LYS | E | 71 | 44.485 | 13.607 | 131.428 | 1.00 80.08 | E |
| ATOM | 6649 | CG | LYS | E | 71 | 45.727 | 14.275 | 131.939 | 1.00 74.96 | E |
| ATOM | 6650 | CD | LYS | E | 71 | 45.472 | 15.684 | 132.374 | 1.00 76.54 | E |
| ATOM | 6651 | CE | LYS | E | 71 | 46.529 | 16.103 | 133.378 | 1.00 77.10 | E |
| ATOM | 6652 | NZ | LYS | E | 71 | 46.534 | 15.176 | 134.544 | 1.00 81.60 | E |
| ATOM | 6653 | C | LYS | E | 71 | 43.387 | 11.435 | 130.919 | 1.00 81.64 | E |
| ATOM | 6654 | O | LYS | E | 71 | 43.483 | 11.131 | 129.734 | 1.00 81.84 | E |
| ATOM | 6655 | N | LEU | E | 72 | 42.304 | 11.195 | 131.642 | 1.00 82.59 | E |
| ATOM | 6656 | CA | LEU | E | 72 | 41.131 | 10.582 | 131.051 | 1.00 83.59 | E |
| ATOM | 6657 | CB | LEU | E | 72 | 40.252 | 9.970 | 132.139 | 1.00 88.02 | E |
| ATOM | 6658 | CG | LEU | E | 72 | 39.573 | 8.633 | 131.834 | 1.00 88.73 | E |
| ATOM | 6659 | CD1 | LEU | E | 72 | 38.531 | 8.344 | 132.911 | 1.00 92.31 | E |
| ATOM | 6660 | CD2 | LEU | E | 72 | 38.926 | 8.668 | 130.461 | 1.00 89.65 | E |
| ATOM | 6661 | C | LEU | E | 72 | 40.372 | 11.709 | 130.368 | 1.00 83.19 | E |
| ATOM | 6662 | O | LEU | E | 72 | 40.581 | 12.881 | 130.683 | 1.00 81.56 | E |
| ATOM | 6663 | N | GLU | E | 73 | 39.500 | 11.350 | 129.433 | 1.00 84.58 | E |
| ATOM | 6664 | CA | GLU | E | 73 | 38.679 | 12.310 | 128.700 | 1.00 87.72 | E |
| ATOM | 6665 | CB | GLU | E | 73 | 39.453 | 12.921 | 127.528 | 1.00 90.08 | E |
| ATOM | 6666 | CG | GLU | E | 73 | 40.595 | 13.855 | 127.929 | 1.00 94.74 | E |
| ATOM | 6667 | CD | GLU | E | 73 | 40.119 | 15.086 | 128.686 | 1.00 96.02 | E |
| ATOM | 6668 | OE1 | GLU | E | 73 | 39.235 | 15.798 | 128.165 | 1.00 96.88 | E |
| ATOM | 6669 | OE2 | GLU | E | 73 | 40.633 | 15.342 | 129.797 | 1.00 100.16 | E |
| ATOM | 6670 | C | GLU | E | 73 | 37.486 | 11.523 | 128.177 | 1.00 89.27 | E |
| ATOM | 6671 | O | GLU | E | 73 | 37.607 | 10.751 | 127.221 | 1.00 90.32 | E |
| ATOM | 6672 | N | LEU | E | 74 | 36.335 | 11.715 | 128.812 | 1.00 91.39 | E |
| ATOM | 6673 | CA | LEU | E | 74 | 35.129 | 10.987 | 128.435 | 1.00 96.84 | E |
| ATOM | 6674 | CB | LEU | E | 74 | 34.357 | 10.619 | 129.700 | 1.00 97.73 | E |
| ATOM | 6675 | CG | LEU | E | 74 | 35.189 | 9.844 | 130.724 | 1.00 97.30 | E |
| ATOM | 6676 | CD1 | LEU | E | 74 | 34.464 | 9.802 | 132.062 | 1.00 98.64 | E |
| ATOM | 6677 | CD2 | LEU | E | 74 | 35.463 | 8.440 | 130.193 | 1.00 99.87 | E |
| ATOM | 6678 | C | LEU | E | 74 | 34.229 | 11.751 | 127.477 | 1.00 96.79 | E |
| ATOM | 6679 | O | LEU | E | 74 | 33.007 | 11.610 | 127.515 | 1.00 98.58 | E |
| ATOM | 6680 | N | VAL | E | 75 | 34.834 | 12.544 | 126.603 | 1.00 97.30 | E |
| ATOM | 6681 | CA | VAL | E | 75 | 34.070 | 13.325 | 125.644 | 1.00 98.55 | E |
| ATOM | 6682 | CB | VAL | E | 75 | 35.000 | 14.223 | 124.818 | 1.00 95.46 | E |
| ATOM | 6683 | CG1 | VAL | E | 75 | 35.955 | 13.366 | 124.003 | 1.00 95.05 | E |

Figure 10 (103 of 142)

```
ATOM   6684  CG2 VAL E  75      34.183  15.138 123.922  1.00 97.62       E
ATOM   6685  C   VAL E  75      33.218  12.472 124.695  1.00 97.48       E
ATOM   6686  O   VAL E  75      32.126  12.880 124.308  1.00100.44       E
ATOM   6687  N   GLU E  76      33.702  11.295 124.313  1.00 97.24       E
ATOM   6688  CA  GLU E  76      32.932  10.439 123.416  1.00 98.46       E
ATOM   6689  CB  GLU E  76      33.841   9.414 122.733  1.00 99.53       E
ATOM   6690  CG  GLU E  76      34.703   9.976 121.616  1.00102.17       E
ATOM   6691  CD  GLU E  76      35.516   8.903 120.913  1.00102.09       E
ATOM   6692  OE1 GLU E  76      36.115   9.206 119.860  1.00103.98       E
ATOM   6693  OE2 GLU E  76      35.560   7.758 121.413  1.00103.48       E
ATOM   6694  C   GLU E  76      31.830   9.709 124.174  1.00 97.46       E
ATOM   6695  O   GLU E  76      30.864   9.230 123.580  1.00 97.54       E
ATOM   6696  N   MET E  77      31.995   9.626 125.489  1.00 95.87       E
ATOM   6697  CA  MET E  77      31.043   8.960 126.378  1.00 94.44       E
ATOM   6698  CB  MET E  77      31.740   8.583 127.687  1.00 96.61       E
ATOM   6699  CG  MET E  77      32.820   7.545 127.546  1.00 93.60       E
ATOM   6700  SD  MET E  77      32.252   5.969 128.178  1.00 93.11       E
ATOM   6701  CE  MET E  77      31.076   5.525 126.972  1.00 89.04       E
ATOM   6702  C   MET E  77      29.899   9.912 126.694  1.00 91.89       E
ATOM   6703  O   MET E  77      28.911   9.539 127.328  1.00 90.25       E
ATOM   6704  N   GLU E  78      30.061  11.148 126.241  1.00 89.74       E
ATOM   6705  CA  GLU E  78      29.110  12.229 126.460  1.00 87.28       E
ATOM   6706  CB  GLU E  78      29.871  13.541 126.335  1.00 89.17       E
ATOM   6707  CG  GLU E  78      29.298  14.729 127.036  1.00 90.64       E
ATOM   6708  CD  GLU E  78      29.872  15.990 126.449  1.00 93.42       E
ATOM   6709  OE1 GLU E  78      29.281  16.518 125.479  1.00 94.94       E
ATOM   6710  OE2 GLU E  78      30.929  16.437 126.938  1.00 95.63       E
ATOM   6711  C   GLU E  78      27.978  12.197 125.431  1.00 84.52       E
ATOM   6712  O   GLU E  78      26.980  12.911 125.559  1.00 85.31       E
ATOM   6713  N   ARG E  79      28.141  11.360 124.416  1.00 81.10       E
ATOM   6714  CA  ARG E  79      27.169  11.262 123.342  1.00 76.78       E
ATOM   6715  CB  ARG E  79      27.887  11.111 122.006  1.00 75.13       E
ATOM   6716  CG  ARG E  79      28.591  12.364 121.523  1.00 68.96       E
ATOM   6717  CD  ARG E  79      29.095  12.158 120.099  1.00 65.54       E
ATOM   6718  NE  ARG E  79      30.448  11.605 120.033  1.00 60.62       E
ATOM   6719  CZ  ARG E  79      30.888  10.823 119.048  1.00 58.65       E
ATOM   6720  NH1 ARG E  79      30.080  10.488 118.048  1.00 55.85       E
ATOM   6721  NH2 ARG E  79      32.143  10.388 119.051  1.00 55.26       E
ATOM   6722  C   ARG E  79      26.154  10.149 123.465  1.00 78.24       E
ATOM   6723  O   ARG E  79      25.529   9.973 124.508  1.00 79.53       E
ATOM   6724  N   GLU E  80      26.000   9.409 122.368  1.00 77.58       E
ATOM   6725  CA  GLU E  80      25.049   8.304 122.266  1.00 81.28       E
ATOM   6726  CB  GLU E  80      23.666   8.776 122.724  1.00 81.37       E
ATOM   6727  CG  GLU E  80      22.836   7.750 123.496  1.00 79.48       E
ATOM   6728  CD  GLU E  80      21.515   8.342 123.984  1.00 77.00       E
ATOM   6729  OE1 GLU E  80      20.708   8.773 123.127  1.00 77.52       E
ATOM   6730  OE2 GLU E  80      21.284   8.379 125.215  1.00 76.34       E
ATOM   6731  C   GLU E  80      25.007   7.942 120.781  1.00 83.17       E
ATOM   6732  O   GLU E  80      24.485   8.704 119.970  1.00 82.89       E
ATOM   6733  N   GLY E  81      25.546   6.779 120.434  1.00 86.03       E
ATOM   6734  CA  GLY E  81      25.596   6.358 119.044  1.00 89.62       E
ATOM   6735  C   GLY E  81      27.036   5.946 118.785  1.00 88.64       E
ATOM   6736  O   GLY E  81      27.826   5.962 119.729  1.00 92.68       E
ATOM   6737  N   PRO E  82      27.425   5.590 117.544  1.00 90.62       E
ATOM   6738  CD  PRO E  82      26.566   5.452 116.359  1.00 89.70       E
ATOM   6739  CA  PRO E  82      28.804   5.178 117.230  1.00 90.33       E
ATOM   6740  CB  PRO E  82      28.696   4.671 115.790  1.00 87.23       E
ATOM   6741  CG  PRO E  82      27.242   4.327 115.634  1.00 87.63       E
ATOM   6742  C   PRO E  82      29.838   6.302 117.363  1.00 92.66       E
ATOM   6743  O   PRO E  82      29.649   7.390 116.814  1.00 93.35       E
ATOM   6744  N   SER E  83      30.932   6.030 118.077  1.00 96.28       E
ATOM   6745  CA  SER E  83      31.990   7.023 118.284  1.00 96.36       E
ATOM   6746  CB  SER E  83      32.774   6.705 119.564  1.00 97.72       E
ATOM   6747  OG  SER E  83      31.990   6.947 120.721  1.00 98.14       E
ATOM   6748  C   SER E  83      32.952   7.140 117.098  1.00 94.81       E
ATOM   6749  O   SER E  83      33.954   6.424 117.008  1.00 91.32       E
```

Figure 10 (104 of 142)

| | | | | | | | | | | |
|---|---|---|---|---|---|---|---|---|---|---|
| ATOM | 6750 | N | TYR | E | 84 | 32.622 | 8.063 | 116.197 | 1.00 94.06 | E |
| ATOM | 6751 | CA | TYR | E | 84 | 33.401 | 8.330 | 114.997 | 1.00 93.31 | E |
| ATOM | 6752 | CB | TYR | E | 84 | 32.460 | 8.726 | 113.866 | 1.00 95.09 | E |
| ATOM | 6753 | CG | TYR | E | 84 | 31.659 | 7.569 | 113.320 | 1.00 95.35 | E |
| ATOM | 6754 | CD1 | TYR | E | 84 | 30.281 | 7.661 | 113.168 | 1.00 97.45 | E |
| ATOM | 6755 | CE1 | TYR | E | 84 | 29.552 | 6.614 | 112.616 | 1.00 99.97 | E |
| ATOM | 6756 | CD2 | TYR | E | 84 | 32.291 | 6.397 | 112.912 | 1.00 94.16 | E |
| ATOM | 6757 | CE2 | TYR | E | 84 | 31.574 | 5.347 | 112.361 | 1.00 98.37 | E |
| ATOM | 6758 | CZ | TYR | E | 84 | 30.206 | 5.461 | 112.212 | 1.00 100.45 | E |
| ATOM | 6759 | OH | TYR | E | 84 | 29.501 | 4.422 | 111.646 | 1.00 103.19 | E |
| ATOM | 6760 | C | TYR | E | 84 | 34.406 | 9.440 | 115.260 | 1.00 91.32 | E |
| ATOM | 6761 | O | TYR | E | 84 | 34.041 | 10.542 | 115.681 | 1.00 93.89 | E |
| ATOM | 6762 | N | THR | E | 85 | 35.672 | 9.148 | 114.995 | 1.00 87.30 | E |
| ATOM | 6763 | CA | THR | E | 85 | 36.734 | 10.102 | 115.251 | 1.00 85.96 | E |
| ATOM | 6764 | CB | THR | E | 85 | 38.075 | 9.567 | 114.776 | 1.00 86.12 | E |
| ATOM | 6765 | OG1 | THR | E | 85 | 38.224 | 8.212 | 115.214 | 1.00 87.96 | E |
| ATOM | 6766 | CG2 | THR | E | 85 | 39.201 | 10.400 | 115.354 | 1.00 85.51 | E |
| ATOM | 6767 | C | THR | E | 85 | 36.500 | 11.454 | 114.619 | 1.00 85.77 | E |
| ATOM | 6768 | O | THR | E | 85 | 36.795 | 12.482 | 115.228 | 1.00 80.22 | E |
| ATOM | 6769 | N | PHE | E | 86 | 35.973 | 11.474 | 113.402 | 1.00 86.17 | E |
| ATOM | 6770 | CA | PHE | E | 86 | 35.743 | 12.765 | 112.777 | 1.00 92.48 | E |
| ATOM | 6771 | CB | PHE | E | 86 | 35.067 | 12.622 | 111.409 | 1.00 91.11 | E |
| ATOM | 6772 | CG | PHE | E | 86 | 34.670 | 13.944 | 110.808 | 1.00 93.36 | E |
| ATOM | 6773 | CD1 | PHE | E | 86 | 35.635 | 14.889 | 110.468 | 1.00 93.67 | E |
| ATOM | 6774 | CD2 | PHE | E | 86 | 33.328 | 14.279 | 110.661 | 1.00 95.03 | E |
| ATOM | 6775 | CE1 | PHE | E | 86 | 35.270 | 16.149 | 109.998 | 1.00 91.49 | E |
| ATOM | 6776 | CE2 | PHE | E | 86 | 32.953 | 15.539 | 110.192 | 1.00 91.62 | E |
| ATOM | 6777 | CZ | PHE | E | 86 | 33.928 | 16.476 | 109.862 | 1.00 91.31 | E |
| ATOM | 6778 | C | PHE | E | 86 | 34.880 | 13.645 | 113.679 | 1.00 91.20 | E |
| ATOM | 6779 | O | PHE | E | 86 | 35.291 | 14.732 | 114.091 | 1.00 91.80 | E |
| ATOM | 6780 | N | ASP | E | 87 | 33.685 | 13.159 | 113.991 | 1.00 94.95 | E |
| ATOM | 6781 | CA | ASP | E | 87 | 32.745 | 13.896 | 114.828 | 1.00 93.62 | E |
| ATOM | 6782 | CB | ASP | E | 87 | 31.519 | 13.023 | 115.127 | 1.00 92.07 | E |
| ATOM | 6783 | CG | ASP | E | 87 | 30.638 | 12.801 | 113.902 | 1.00 89.48 | E |
| ATOM | 6784 | OD1 | ASP | E | 87 | 29.883 | 11.805 | 113.893 | 1.00 87.17 | E |
| ATOM | 6785 | OD2 | ASP | E | 87 | 30.689 | 13.622 | 112.956 | 1.00 89.30 | E |
| ATOM | 6786 | C | ASP | E | 87 | 33.378 | 14.362 | 116.133 | 1.00 88.91 | E |
| ATOM | 6787 | O | ASP | E | 87 | 33.213 | 15.513 | 116.542 | 1.00 96.18 | E |
| ATOM | 6788 | N | THR | E | 88 | 34.109 | 13.464 | 116.779 | 1.00 83.97 | E |
| ATOM | 6789 | CA | THR | E | 88 | 34.749 | 13.784 | 118.046 | 1.00 81.85 | E |
| ATOM | 6790 | CB | THR | E | 88 | 35.395 | 12.542 | 118.677 | 1.00 79.68 | E |
| ATOM | 6791 | OG1 | THR | E | 88 | 34.409 | 11.512 | 118.817 | 1.00 73.71 | E |
| ATOM | 6792 | CG2 | THR | E | 88 | 35.985 | 12.887 | 120.048 | 1.00 73.23 | E |
| ATOM | 6793 | C | THR | E | 88 | 35.819 | 14.841 | 117.885 | 1.00 80.57 | E |
| ATOM | 6794 | O | THR | E | 88 | 35.821 | 15.848 | 118.592 | 1.00 76.94 | E |
| ATOM | 6795 | N | VAL | E | 89 | 36.742 | 14.599 | 116.961 | 1.00 78.70 | E |
| ATOM | 6796 | CA | VAL | E | 89 | 37.812 | 15.549 | 116.724 | 1.00 76.83 | E |
| ATOM | 6797 | CB | VAL | E | 89 | 38.689 | 15.121 | 115.523 | 1.00 73.04 | E |
| ATOM | 6798 | CG1 | VAL | E | 89 | 39.704 | 16.201 | 115.208 | 1.00 74.90 | E |
| ATOM | 6799 | CG2 | VAL | E | 89 | 39.408 | 13.827 | 115.849 | 1.00 75.05 | E |
| ATOM | 6800 | C | VAL | E | 89 | 37.150 | 16.893 | 116.450 | 1.00 76.51 | E |
| ATOM | 6801 | O | VAL | E | 89 | 37.560 | 17.920 | 116.990 | 1.00 76.93 | E |
| ATOM | 6802 | N | SER | E | 90 | 36.104 | 16.871 | 115.631 | 1.00 73.55 | E |
| ATOM | 6803 | CA | SER | E | 90 | 35.383 | 18.089 | 115.299 | 1.00 72.70 | E |
| ATOM | 6804 | CB | SER | E | 90 | 34.091 | 17.752 | 114.558 | 1.00 75.31 | E |
| ATOM | 6805 | OG | SER | E | 90 | 34.359 | 16.993 | 113.391 | 1.00 76.42 | E |
| ATOM | 6806 | C | SER | E | 90 | 35.055 | 18.841 | 116.578 | 1.00 72.22 | E |
| ATOM | 6807 | O | SER | E | 90 | 35.497 | 19.975 | 116.777 | 1.00 72.90 | E |
| ATOM | 6808 | N | LEU | E | 91 | 34.288 | 18.193 | 117.450 | 1.00 73.96 | E |
| ATOM | 6809 | CA | LEU | E | 91 | 33.891 | 18.798 | 118.719 | 1.00 74.62 | E |
| ATOM | 6810 | CB | LEU | E | 91 | 33.031 | 17.816 | 119.535 | 1.00 74.98 | E |
| ATOM | 6811 | CG | LEU | E | 91 | 32.684 | 18.206 | 120.986 | 1.00 72.96 | E |
| ATOM | 6812 | CD1 | LEU | E | 91 | 32.014 | 19.566 | 121.025 | 1.00 72.61 | E |
| ATOM | 6813 | CD2 | LEU | E | 91 | 31.770 | 17.153 | 121.604 | 1.00 72.18 | E |
| ATOM | 6814 | C | LEU | E | 91 | 35.093 | 19.238 | 119.550 | 1.00 75.84 | E |
| ATOM | 6815 | O | LEU | E | 91 | 35.124 | 20.347 | 120.089 | 1.00 76.36 | E |

Figure 10 (105 of 142)

```
ATOM   6816  N    LEU E  92      36.084  18.363 119.640  1.00 76.29           E
ATOM   6817  CA   LEU E  92      37.274  18.643 120.425  1.00 78.29           E
ATOM   6818  CB   LEU E  92      38.211  17.439 120.362  1.00 75.19           E
ATOM   6819  CG   LEU E  92      37.708  16.290 121.233  1.00 73.58           E
ATOM   6820  CD1  LEU E  92      38.516  15.036 120.984  1.00 71.14           E
ATOM   6821  CD2  LEU E  92      37.800  16.722 122.688  1.00 71.82           E
ATOM   6822  C    LEU E  92      38.025  19.920 120.065  1.00 82.18           E
ATOM   6823  O    LEU E  92      38.357  20.716 120.950  1.00 83.87           E
ATOM   6824  N    LYS E  93      38.288  20.116 118.774  1.00 87.35           E
ATOM   6825  CA   LYS E  93      39.013  21.302 118.317  1.00 88.89           E
ATOM   6826  CB   LYS E  93      39.236  21.247 116.794  1.00 91.91           E
ATOM   6827  CG   LYS E  93      40.197  20.141 116.341  1.00 95.34           E
ATOM   6828  CD   LYS E  93      40.403  20.120 114.827  1.00 96.67           E
ATOM   6829  CE   LYS E  93      41.061  21.396 114.328  1.00 97.16           E
ATOM   6830  NZ   LYS E  93      42.397  21.612 114.937  1.00 94.88           E
ATOM   6831  C    LYS E  93      38.249  22.568 118.700  1.00 87.98           E
ATOM   6832  O    LYS E  93      38.837  23.646 118.855  1.00 84.35           E
ATOM   6833  N    GLN E  94      36.938  22.417 118.871  1.00 88.12           E
ATOM   6834  CA   GLN E  94      36.075  23.530 119.237  1.00 92.05           E
ATOM   6835  CB   GLN E  94      34.627  23.179 118.908  1.00 90.22           E
ATOM   6836  CG   GLN E  94      33.785  24.360 118.496  1.00 89.95           E
ATOM   6837  CD   GLN E  94      32.502  23.928 117.818  1.00 90.05           E
ATOM   6838  OE1  GLN E  94      31.597  23.379 118.452  1.00 87.05           E
ATOM   6839  NE2  GLN E  94      32.423  24.164 116.514  1.00 89.15           E
ATOM   6840  C    GLN E  94      36.223  23.851 120.722  1.00 97.14           E
ATOM   6841  O    GLN E  94      36.323  25.020 121.105  1.00 95.37           E
ATOM   6842  N    ARG E  95      36.239  22.810 121.553  1.00102.43           E
ATOM   6843  CA   ARG E  95      36.387  22.984 122.994  1.00109.37           E
ATOM   6844  CB   ARG E  95      36.189  21.656 123.722  1.00109.69           E
ATOM   6845  CG   ARG E  95      34.749  21.270 123.920  1.00113.87           E
ATOM   6846  CD   ARG E  95      34.648  20.058 124.802  1.00114.44           E
ATOM   6847  NE   ARG E  95      33.266  19.809 125.175  1.00115.51           E
ATOM   6848  CZ   ARG E  95      32.863  18.764 125.881  1.00114.92           E
ATOM   6849  NH1  ARG E  95      33.743  17.860 126.290  1.00115.86           E
ATOM   6850  NH2  ARG E  95      31.579  18.628 126.178  1.00116.46           E
ATOM   6851  C    ARG E  95      37.757  23.543 123.349  1.00110.42           E
ATOM   6852  O    ARG E  95      37.878  24.395 124.225  1.00112.09           E
ATOM   6853  N    TYR E  96      38.786  23.058 122.666  1.00114.36           E
ATOM   6854  CA   TYR E  96      40.144  23.513 122.921  1.00114.58           E
ATOM   6855  CB   TYR E  96      41.002  22.344 123.404  1.00121.52           E
ATOM   6856  CG   TYR E  96      40.311  21.490 124.439  1.00126.84           E
ATOM   6857  CD1  TYR E  96      39.356  20.542 124.066  1.00130.17           E
ATOM   6858  CE1  TYR E  96      38.689  19.779 125.019  1.00129.18           E
ATOM   6859  CD2  TYR E  96      40.583  21.652 125.794  1.00127.60           E
ATOM   6860  CE2  TYR E  96      39.921  20.897 126.756  1.00127.81           E
ATOM   6861  CZ   TYR E  96      38.976  19.964 126.362  1.00127.19           E
ATOM   6862  OH   TYR E  96      38.315  19.225 127.315  1.00128.29           E
ATOM   6863  C    TYR E  96      40.732  24.104 121.650  1.00111.61           E
ATOM   6864  O    TYR E  96      41.473  23.439 120.930  1.00114.27           E
ATOM   6865  N    PRO E  97      40.387  25.361 121.345  1.00107.73           E
ATOM   6866  CD   PRO E  97      39.177  26.047 121.820  1.00104.60           E
ATOM   6867  CA   PRO E  97      40.900  26.019 120.143  1.00102.34           E
ATOM   6868  CB   PRO E  97      39.888  27.142 119.908  1.00100.91           E
ATOM   6869  CG   PRO E  97      38.640  26.622 120.543  1.00102.49           E
ATOM   6870  C    PRO E  97      42.331  26.547 120.270  1.00 99.99           E
ATOM   6871  O    PRO E  97      42.975  26.845 119.262  1.00100.49           E
ATOM   6872  N    ASN E  98      42.834  26.660 121.496  1.00 96.87           E
ATOM   6873  CA   ASN E  98      44.191  27.169 121.701  1.00 93.50           E
ATOM   6874  CB   ASN E  98      44.196  28.222 122.809  1.00 93.79           E
ATOM   6875  CG   ASN E  98      43.450  29.482 122.416  1.00 95.47           E
ATOM   6876  OD1  ASN E  98      42.275  29.431 122.043  1.00 96.16           E
ATOM   6877  ND2  ASN E  98      44.128  30.623 122.503  1.00 95.50           E
ATOM   6878  C    ASN E  98      45.217  26.092 122.033  1.00 89.48           E
ATOM   6879  O    ASN E  98      46.371  26.399 122.348  1.00 88.53           E
ATOM   6880  N    ASP E  99      44.791  24.834 121.961  1.00 86.15           E
ATOM   6881  CA   ASP E  99      45.668  23.704 122.252  1.00 80.69           E
```

Figure 10 (106 of 142)

| | | | | | | | | | | |
|---|---|---|---|---|---|---|---|---|---|---|
| ATOM | 6882 | CB | ASP | E | 99 | 45.053 | 22.823 | 123.342 | 1.00 85.83 | E |
| ATOM | 6883 | CG | ASP | E | 99 | 44.787 | 23.585 | 124.621 | 1.00 85.38 | E |
| ATOM | 6884 | OD1 | ASP | E | 99 | 45.739 | 24.190 | 125.160 | 1.00 86.11 | E |
| ATOM | 6885 | OD2 | ASP | E | 99 | 43.625 | 23.583 | 125.084 | 1.00 87.74 | E |
| ATOM | 6886 | C | ASP | E | 99 | 45.975 | 22.856 | 121.019 | 1.00 73.64 | E |
| ATOM | 6887 | O | ASP | E | 99 | 45.085 | 22.481 | 120.247 | 1.00 71.54 | E |
| ATOM | 6888 | N | GLN | E | 100 | 47.260 | 22.566 | 120.857 | 1.00 65.73 | E |
| ATOM | 6889 | CA | GLN | E | 100 | 47.771 | 21.775 | 119.753 | 1.00 57.86 | E |
| ATOM | 6890 | CB | GLN | E | 100 | 49.302 | 21.824 | 119.792 | 1.00 58.48 | E |
| ATOM | 6891 | CG | GLN | E | 100 | 50.001 | 21.930 | 118.442 | 1.00 58.78 | E |
| ATOM | 6892 | CD | GLN | E | 100 | 51.458 | 22.399 | 118.559 | 1.00 57.79 | E |
| ATOM | 6893 | OE1 | GLN | E | 100 | 51.733 | 23.478 | 119.092 | 1.00 57.41 | E |
| ATOM | 6894 | NE2 | GLN | E | 100 | 52.389 | 21.589 | 118.053 | 1.00 57.22 | E |
| ATOM | 6895 | C | GLN | E | 100 | 47.277 | 20.349 | 119.953 | 1.00 55.56 | E |
| ATOM | 6896 | O | GLN | E | 100 | 47.598 | 19.720 | 120.957 | 1.00 52.15 | E |
| ATOM | 6897 | N | LEU | E | 101 | 46.494 | 19.840 | 119.009 | 1.00 51.57 | E |
| ATOM | 6898 | CA | LEU | E | 101 | 45.973 | 18.481 | 119.123 | 1.00 51.98 | E |
| ATOM | 6899 | CB | LEU | E | 101 | 44.447 | 18.488 | 119.006 | 1.00 49.90 | E |
| ATOM | 6900 | CG | LEU | E | 101 | 43.671 | 19.470 | 119.875 | 1.00 51.76 | E |
| ATOM | 6901 | CD1 | LEU | E | 101 | 42.202 | 19.105 | 119.837 | 1.00 49.22 | E |
| ATOM | 6902 | CD2 | LEU | E | 101 | 44.183 | 19.418 | 121.293 | 1.00 52.80 | E |
| ATOM | 6903 | C | LEU | E | 101 | 46.531 | 17.504 | 118.088 | 1.00 52.35 | E |
| ATOM | 6904 | O | LEU | E | 101 | 46.621 | 17.817 | 116.898 | 1.00 51.72 | E |
| ATOM | 6905 | N | PHE | E | 102 | 46.904 | 16.313 | 118.545 | 1.00 53.51 | E |
| ATOM | 6906 | CA | PHE | E | 102 | 47.408 | 15.284 | 117.644 | 1.00 51.55 | E |
| ATOM | 6907 | CB | PHE | E | 102 | 48.901 | 15.033 | 117.860 | 1.00 48.21 | E |
| ATOM | 6908 | CG | PHE | E | 102 | 49.765 | 16.228 | 117.603 | 1.00 47.61 | E |
| ATOM | 6909 | CD1 | PHE | E | 102 | 49.896 | 17.225 | 118.558 | 1.00 50.87 | E |
| ATOM | 6910 | CD2 | PHE | E | 102 | 50.467 | 16.348 | 116.408 | 1.00 49.33 | E |
| ATOM | 6911 | CE1 | PHE | E | 102 | 50.721 | 18.325 | 118.326 | 1.00 50.48 | E |
| ATOM | 6912 | CE2 | PHE | E | 102 | 51.290 | 17.443 | 116.169 | 1.00 45.38 | E |
| ATOM | 6913 | CZ | PHE | E | 102 | 51.420 | 18.432 | 117.126 | 1.00 47.26 | E |
| ATOM | 6914 | C | PHE | E | 102 | 46.646 | 14.004 | 117.936 | 1.00 52.79 | E |
| ATOM | 6915 | O | PHE | E | 102 | 46.066 | 13.852 | 119.013 | 1.00 52.40 | E |
| ATOM | 6916 | N | PHE | E | 103 | 46.615 | 13.095 | 116.971 | 1.00 50.26 | E |
| ATOM | 6917 | CA | PHE | E | 103 | 45.941 | 11.830 | 117.197 | 1.00 54.58 | E |
| ATOM | 6918 | CB | PHE | E | 103 | 44.862 | 11.572 | 116.154 | 1.00 56.56 | E |
| ATOM | 6919 | CG | PHE | E | 103 | 43.795 | 10.629 | 116.635 | 1.00 65.59 | E |
| ATOM | 6920 | CD1 | PHE | E | 103 | 42.788 | 11.079 | 117.490 | 1.00 68.65 | E |
| ATOM | 6921 | CD2 | PHE | E | 103 | 43.827 | 9.283 | 116.286 | 1.00 66.57 | E |
| ATOM | 6922 | CE1 | PHE | E | 103 | 41.828 | 10.201 | 117.989 | 1.00 68.62 | E |
| ATOM | 6923 | CE2 | PHE | E | 103 | 42.869 | 8.396 | 116.781 | 1.00 69.53 | E |
| ATOM | 6924 | CZ | PHE | E | 103 | 41.869 | 8.857 | 117.636 | 1.00 69.38 | E |
| ATOM | 6925 | C | PHE | E | 103 | 46.987 | 10.724 | 117.142 | 1.00 52.65 | E |
| ATOM | 6926 | O | PHE | E | 103 | 47.920 | 10.797 | 116.348 | 1.00 55.06 | E |
| ATOM | 6927 | N | ILE | E | 104 | 46.824 | 9.694 | 117.969 | 1.00 45.43 | E |
| ATOM | 6928 | CA | ILE | E | 104 | 47.799 | 8.612 | 118.036 | 1.00 35.74 | E |
| ATOM | 6929 | CB | ILE | E | 104 | 48.434 | 8.567 | 119.425 | 1.00 29.32 | E |
| ATOM | 6930 | CG2 | ILE | E | 104 | 49.455 | 7.451 | 119.494 | 1.00 29.24 | E |
| ATOM | 6931 | CG1 | ILE | E | 104 | 49.053 | 9.926 | 119.740 | 1.00 27.59 | E |
| ATOM | 6932 | CD1 | ILE | E | 104 | 49.619 | 10.046 | 121.141 | 1.00 28.22 | E |
| ATOM | 6933 | C | ILE | E | 104 | 47.249 | 7.234 | 117.741 | 1.00 30.41 | E |
| ATOM | 6934 | O | ILE | E | 104 | 46.358 | 6.754 | 118.440 | 1.00 32.15 | E |
| ATOM | 6935 | N | ILE | E | 105 | 47.803 | 6.591 | 116.718 | 1.00 30.07 | E |
| ATOM | 6936 | CA | ILE | E | 105 | 47.382 | 5.244 | 116.331 | 1.00 32.11 | E |
| ATOM | 6937 | CB | ILE | E | 105 | 46.595 | 5.247 | 115.010 | 1.00 34.45 | E |
| ATOM | 6938 | CG2 | ILE | E | 105 | 45.327 | 6.047 | 115.174 | 1.00 37.47 | E |
| ATOM | 6939 | CG1 | ILE | E | 105 | 47.451 | 5.843 | 113.889 | 1.00 38.49 | E |
| ATOM | 6940 | CD1 | ILE | E | 105 | 46.786 | 5.818 | 112.521 | 1.00 37.91 | E |
| ATOM | 6941 | C | ILE | E | 105 | 48.597 | 4.349 | 116.152 | 1.00 31.27 | E |
| ATOM | 6942 | O | ILE | E | 105 | 49.701 | 4.837 | 115.933 | 1.00 34.70 | E |
| ATOM | 6943 | N | GLY | E | 106 | 48.387 | 3.038 | 116.225 | 1.00 27.98 | E |
| ATOM | 6944 | CA | GLY | E | 106 | 49.488 | 2.100 | 116.083 | 1.00 24.10 | E |
| ATOM | 6945 | C | GLY | E | 106 | 49.468 | 1.440 | 114.728 | 1.00 19.24 | E |
| ATOM | 6946 | O | GLY | E | 106 | 48.486 | 1.575 | 114.003 | 1.00 21.82 | E |
| ATOM | 6947 | N | ALA | E | 107 | 50.540 | 0.727 | 114.387 | 1.00 24.66 | E |

Figure 10 (107 of 142)

```
ATOM   6948  CA   ALA E 107      50.649   0.054 113.090  1.00 23.91           E
ATOM   6949  CB   ALA E 107      51.885  -0.836 113.070  1.00 24.65           E
ATOM   6950  C    ALA E 107      49.406  -0.762 112.737  1.00 28.58           E
ATOM   6951  O    ALA E 107      49.177  -1.101 111.572  1.00 30.54           E
ATOM   6952  N    ASP E 108      48.608  -1.066 113.758  1.00 34.83           E
ATOM   6953  CA   ASP E 108      47.373  -1.830 113.596  1.00 46.24           E
ATOM   6954  CB   ASP E 108      46.814  -2.226 114.969  1.00 45.59           E
ATOM   6955  CG   ASP E 108      46.800  -1.062 115.954  1.00 44.86           E
ATOM   6956  OD1  ASP E 108      47.135   0.073 115.561  1.00 47.43           E
ATOM   6957  OD2  ASP E 108      46.456  -1.275 117.132  1.00 46.02           E
ATOM   6958  C    ASP E 108      46.349  -0.991 112.841  1.00 52.29           E
ATOM   6959  O    ASP E 108      45.946  -1.342 111.731  1.00 51.28           E
ATOM   6960  N    MET E 109      45.950   0.122 113.454  1.00 58.13           E
ATOM   6961  CA   MET E 109      44.990   1.052 112.877  1.00 62.17           E
ATOM   6962  CB   MET E 109      44.654   2.147 113.889  1.00 58.73           E
ATOM   6963  CG   MET E 109      43.691   1.704 114.964  1.00 55.07           E
ATOM   6964  SD   MET E 109      42.096   1.268 114.261  1.00 51.78           E
ATOM   6965  CE   MET E 109      42.357  -0.436 113.690  1.00 46.30           E
ATOM   6966  C    MET E 109      45.518   1.685 111.604  1.00 63.67           E
ATOM   6967  O    MET E 109      44.780   1.874 110.646  1.00 61.50           E
ATOM   6968  N    ILE E 110      46.797   2.027 111.598  1.00 66.65           E
ATOM   6969  CA   ILE E 110      47.389   2.627 110.418  1.00 67.09           E
ATOM   6970  CB   ILE E 110      48.921   2.713 110.573  1.00 68.36           E
ATOM   6971  CG2  ILE E 110      49.548   3.220 109.299  1.00 71.83           E
ATOM   6972  CG1  ILE E 110      49.247   3.624 111.762  1.00 67.38           E
ATOM   6973  CD1  ILE E 110      50.686   4.056 111.873  1.00 64.69           E
ATOM   6974  C    ILE E 110      46.988   1.805 109.188  1.00 69.71           E
ATOM   6975  O    ILE E 110      46.646   2.360 108.143  1.00 73.23           E
ATOM   6976  N    GLU E 111      47.000   0.481 109.329  1.00 73.49           E
ATOM   6977  CA   GLU E 111      46.610  -0.414 108.239  1.00 76.74           E
ATOM   6978  CB   GLU E 111      46.778  -1.879 108.649  1.00 84.81           E
ATOM   6979  CG   GLU E 111      48.163  -2.471 108.479  1.00 88.28           E
ATOM   6980  CD   GLU E 111      48.178  -3.971 108.755  1.00 87.92           E
ATOM   6981  OE1  GLU E 111      47.368  -4.703 108.138  1.00 87.32           E
ATOM   6982  OE2  GLU E 111      49.000  -4.417 109.586  1.00 89.62           E
ATOM   6983  C    GLU E 111      45.142  -0.193 107.936  1.00 76.17           E
ATOM   6984  O    GLU E 111      44.686  -0.339 106.805  1.00 72.74           E
ATOM   6985  N    TYR E 112      44.413   0.161 108.982  1.00 77.01           E
ATOM   6986  CA   TYR E 112      42.981   0.373 108.923  1.00 81.15           E
ATOM   6987  CB   TYR E 112      42.411   0.116 110.320  1.00 84.63           E
ATOM   6988  CG   TYR E 112      41.032  -0.462 110.315  1.00 89.73           E
ATOM   6989  CD1  TYR E 112      39.917   0.339 110.527  1.00 91.95           E
ATOM   6990  CE1  TYR E 112      38.632  -0.196 110.494  1.00 99.81           E
ATOM   6991  CD2  TYR E 112      40.837  -1.816 110.069  1.00 93.90           E
ATOM   6992  CE2  TYR E 112      39.562  -2.365 110.032  1.00 97.01           E
ATOM   6993  CZ   TYR E 112      38.461  -1.551 110.247  1.00 98.44           E
ATOM   6994  OH   TYR E 112      37.197  -2.099 110.228  1.00104.94           E
ATOM   6995  C    TYR E 112      42.499   1.736 108.404  1.00 81.29           E
ATOM   6996  O    TYR E 112      41.328   1.885 108.073  1.00 84.06           E
ATOM   6997  N    LEU E 113      43.381   2.727 108.321  1.00 77.82           E
ATOM   6998  CA   LEU E 113      42.967   4.044 107.856  1.00 73.99           E
ATOM   6999  CB   LEU E 113      44.194   4.878 107.498  1.00 74.08           E
ATOM   7000  CG   LEU E 113      44.661   5.785 108.645  1.00 76.10           E
ATOM   7001  CD1  LEU E 113      44.553   5.081 109.977  1.00 76.42           E
ATOM   7002  CD2  LEU E 113      46.085   6.208 108.389  1.00 78.05           E
ATOM   7003  C    LEU E 113      41.946   4.037 106.714  1.00 70.63           E
ATOM   7004  O    LEU E 113      40.921   4.693 106.818  1.00 71.99           E
ATOM   7005  N    PRO E 114      42.197   3.297 105.618  1.00 72.48           E
ATOM   7006  CD   PRO E 114      43.302   2.377 105.326  1.00 67.55           E
ATOM   7007  CA   PRO E 114      41.212   3.283 104.525  1.00 70.81           E
ATOM   7008  CB   PRO E 114      41.709   2.164 103.617  1.00 64.29           E
ATOM   7009  CG   PRO E 114      42.598   1.342 104.511  1.00 67.01           E
ATOM   7010  C    PRO E 114      39.798   3.033 105.045  1.00 73.71           E
ATOM   7011  O    PRO E 114      38.903   3.849 104.841  1.00 73.95           E
ATOM   7012  N    LYS E 115      39.594   1.897 105.699  1.00 77.05           E
ATOM   7013  CA   LYS E 115      38.297   1.587 106.295  1.00 82.11           E
```

Figure 10 (108 of 142)

```
ATOM   7014  CB   LYS E 115      38.227   0.108 106.695  1.00 83.71      E
ATOM   7015  CG   LYS E 115      38.521  -0.866 105.556  1.00 85.54      E
ATOM   7016  CD   LYS E 115      38.449  -2.322 106.010  1.00 89.31      E
ATOM   7017  CE   LYS E 115      37.036  -2.713 106.412  1.00 89.91      E
ATOM   7018  NZ   LYS E 115      36.943  -4.162 106.737  1.00 90.83      E
ATOM   7019  C    LYS E 115      38.288   2.471 107.544  1.00 75.58      E
ATOM   7020  O    LYS E 115      38.912   2.145 108.547  1.00 81.08      E
ATOM   7021  N    TRP E 116      37.590   3.594 107.486  1.00 75.06      E
ATOM   7022  CA   TRP E 116      37.582   4.518 108.608  1.00 75.89      E
ATOM   7023  CB   TRP E 116      39.030   5.009 108.798  1.00 74.19      E
ATOM   7024  CG   TRP E 116      39.397   5.757 110.056  1.00 68.42      E
ATOM   7025  CD2  TRP E 116      40.312   5.330 111.086  1.00 69.20      E
ATOM   7026  CE2  TRP E 116      40.438   6.403 112.008  1.00 67.07      E
ATOM   7027  CE3  TRP E 116      41.040   4.153 111.316  1.00 68.83      E
ATOM   7028  CD1  TRP E 116      39.015   7.022 110.394  1.00 67.13      E
ATOM   7029  NE1  TRP E 116      39.637   7.420 111.559  1.00 66.16      E
ATOM   7030  CZ2  TRP E 116      41.258   6.337 113.147  1.00 67.99      E
ATOM   7031  CZ3  TRP E 116      41.860   4.084 112.452  1.00 69.93      E
ATOM   7032  CH2  TRP E 116      41.960   5.176 113.353  1.00 69.45      E
ATOM   7033  C    TRP E 116      36.633   5.605 108.103  1.00 76.47      E
ATOM   7034  O    TRP E 116      36.715   6.009 106.948  1.00 78.89      E
ATOM   7035  N    TYR E 117      35.712   6.045 108.953  1.00 77.77      E
ATOM   7036  CA   TYR E 117      34.717   7.049 108.579  1.00 78.51      E
ATOM   7037  CB   TYR E 117      33.578   7.045 109.603  1.00 81.09      E
ATOM   7038  CG   TYR E 117      32.512   8.077 109.326  1.00 82.39      E
ATOM   7039  CD1  TYR E 117      31.675   7.961 108.216  1.00 83.88      E
ATOM   7040  CE1  TYR E 117      30.722   8.938 107.930  1.00 81.72      E
ATOM   7041  CD2  TYR E 117      32.368   9.192 110.149  1.00 83.62      E
ATOM   7042  CE2  TYR E 117      31.421  10.174 109.874  1.00 83.61      E
ATOM   7043  CZ   TYR E 117      30.604  10.044 108.764  1.00 82.14      E
ATOM   7044  OH   TYR E 117      29.689  11.036 108.484  1.00 82.93      E
ATOM   7045  C    TYR E 117      35.212   8.485 108.402  1.00 79.13      E
ATOM   7046  O    TYR E 117      35.516   9.171 109.384  1.00 75.77      E
ATOM   7047  N    LYS E 118      35.263   8.934 107.147  1.00 79.16      E
ATOM   7048  CA   LYS E 118      35.685  10.294 106.803  1.00 81.44      E
ATOM   7049  CB   LYS E 118      34.828  11.318 107.557  1.00 82.45      E
ATOM   7050  CG   LYS E 118      33.487  11.626 106.919  1.00 86.50      E
ATOM   7051  CD   LYS E 118      32.842  12.825 107.602  1.00 88.29      E
ATOM   7052  CE   LYS E 118      31.478  13.146 107.017  1.00 90.23      E
ATOM   7053  NZ   LYS E 118      30.834  14.283 107.726  1.00 90.37      E
ATOM   7054  C    LYS E 118      37.152  10.637 107.048  1.00 82.74      E
ATOM   7055  O    LYS E 118      37.465  11.750 107.478  1.00 85.50      E
ATOM   7056  N    LEU E 119      38.056   9.711 106.757  1.00 84.01      E
ATOM   7057  CA   LEU E 119      39.465   9.980 107.005  1.00 85.28      E
ATOM   7058  CB   LEU E 119      40.331   8.808 106.527  1.00 86.63      E
ATOM   7059  CG   LEU E 119      41.816   8.879 106.908  1.00 88.95      E
ATOM   7060  CD1  LEU E 119      41.967   9.158 108.395  1.00 89.31      E
ATOM   7061  CD2  LEU E 119      42.497   7.573 106.542  1.00 90.53      E
ATOM   7062  C    LEU E 119      39.921  11.273 106.345  1.00 85.54      E
ATOM   7063  O    LEU E 119      40.493  12.151 106.997  1.00 84.18      E
ATOM   7064  N    ASP E 120      39.641  11.393 105.053  1.00 84.18      E
ATOM   7065  CA   ASP E 120      40.043  12.565 104.291  1.00 79.11      E
ATOM   7066  CB   ASP E 120      39.470  12.478 102.876  1.00 81.74      E
ATOM   7067  CG   ASP E 120      40.098  11.358 102.071  1.00 84.63      E
ATOM   7068  OD1  ASP E 120      41.325  11.404 101.839  1.00 85.78      E
ATOM   7069  OD2  ASP E 120      39.368  10.428 101.675  1.00 85.01      E
ATOM   7070  C    ASP E 120      39.686  13.907 104.930  1.00 75.05      E
ATOM   7071  O    ASP E 120      40.422  14.883 104.774  1.00 78.32      E
ATOM   7072  N    GLU E 121      38.575  13.957 105.661  1.00 71.67      E
ATOM   7073  CA   GLU E 121      38.152  15.203 106.304  1.00 68.40      E
ATOM   7074  CB   GLU E 121      36.625  15.248 106.460  1.00 73.77      E
ATOM   7075  CG   GLU E 121      35.818  15.058 105.173  1.00 76.74      E
ATOM   7076  CD   GLU E 121      35.913  13.644 104.613  1.00 77.49      E
ATOM   7077  OE1  GLU E 121      36.278  12.729 105.381  1.00 80.21      E
ATOM   7078  OE2  GLU E 121      35.610  13.442 103.413  1.00 75.39      E
ATOM   7079  C    GLU E 121      38.788  15.350 107.681  1.00 67.57      E
```

Figure 10 (109 of 142)

| ATOM | 7080 | O | GLU | E | 121 | 39.070 | 16.462 | 108.148 | 1.00 | 61.30 | E |
|---|---|---|---|---|---|---|---|---|---|---|---|
| ATOM | 7081 | N | LEU | E | 122 | 39.002 | 14.211 | 108.324 | 1.00 | 68.92 | E |
| ATOM | 7082 | CA | LEU | E | 122 | 39.586 | 14.174 | 109.652 | 1.00 | 73.40 | E |
| ATOM | 7083 | CB | LEU | E | 122 | 39.425 | 12.768 | 110.239 | 1.00 | 81.00 | E |
| ATOM | 7084 | CG | LEU | E | 122 | 39.968 | 12.439 | 111.632 | 1.00 | 83.96 | E |
| ATOM | 7085 | CD1 | LEU | E | 122 | 39.245 | 13.243 | 112.683 | 1.00 | 86.72 | E |
| ATOM | 7086 | CD2 | LEU | E | 122 | 39.785 | 10.958 | 111.896 | 1.00 | 87.58 | E |
| ATOM | 7087 | C | LEU | E | 122 | 41.052 | 14.557 | 109.571 | 1.00 | 72.02 | E |
| ATOM | 7088 | O | LEU | E | 122 | 41.528 | 15.388 | 110.341 | 1.00 | 72.26 | E |
| ATOM | 7089 | N | LEU | E | 123 | 41.757 | 13.948 | 108.623 | 1.00 | 70.76 | E |
| ATOM | 7090 | CA | LEU | E | 123 | 43.172 | 14.216 | 108.433 | 1.00 | 72.32 | E |
| ATOM | 7091 | CB | LEU | E | 123 | 43.669 | 13.515 | 107.173 | 1.00 | 75.14 | E |
| ATOM | 7092 | CG | LEU | E | 123 | 43.934 | 12.021 | 107.317 | 1.00 | 78.44 | E |
| ATOM | 7093 | CD1 | LEU | E | 123 | 44.197 | 11.412 | 105.946 | 1.00 | 80.59 | E |
| ATOM | 7094 | CD2 | LEU | E | 123 | 45.122 | 11.816 | 108.249 | 1.00 | 80.76 | E |
| ATOM | 7095 | C | LEU | E | 123 | 43.396 | 15.707 | 108.310 | 1.00 | 75.23 | E |
| ATOM | 7096 | O | LEU | E | 123 | 44.429 | 16.238 | 108.732 | 1.00 | 68.00 | E |
| ATOM | 7097 | N | ASN | E | 124 | 42.409 | 16.379 | 107.730 | 1.00 | 77.16 | E |
| ATOM | 7098 | CA | ASN | E | 124 | 42.470 | 17.817 | 107.537 | 1.00 | 77.28 | E |
| ATOM | 7099 | CB | ASN | E | 124 | 41.346 | 18.248 | 106.591 | 1.00 | 80.85 | E |
| ATOM | 7100 | CG | ASN | E | 124 | 41.504 | 19.670 | 106.111 | 1.00 | 84.55 | E |
| ATOM | 7101 | OD1 | ASN | E | 124 | 41.294 | 20.618 | 106.865 | 1.00 | 86.76 | E |
| ATOM | 7102 | ND2 | ASN | E | 124 | 41.890 | 19.828 | 104.849 | 1.00 | 88.44 | E |
| ATOM | 7103 | C | ASN | E | 124 | 42.337 | 18.521 | 108.887 | 1.00 | 73.88 | E |
| ATOM | 7104 | O | ASN | E | 124 | 42.906 | 19.595 | 109.106 | 1.00 | 75.95 | E |
| ATOM | 7105 | N | LEU | E | 125 | 41.601 | 17.893 | 109.798 | 1.00 | 75.50 | E |
| ATOM | 7106 | CA | LEU | E | 125 | 41.373 | 18.453 | 111.127 | 1.00 | 78.01 | E |
| ATOM | 7107 | CB | LEU | E | 125 | 40.114 | 17.837 | 111.732 | 1.00 | 82.89 | E |
| ATOM | 7108 | CG | LEU | E | 125 | 38.794 | 18.130 | 111.015 | 1.00 | 82.33 | E |
| ATOM | 7109 | CD1 | LEU | E | 125 | 37.676 | 17.379 | 111.710 | 1.00 | 83.70 | E |
| ATOM | 7110 | CD2 | LEU | E | 125 | 38.511 | 19.628 | 111.032 | 1.00 | 84.87 | E |
| ATOM | 7111 | C | LEU | E | 125 | 42.528 | 18.284 | 112.108 | 1.00 | 77.00 | E |
| ATOM | 7112 | O | LEU | E | 125 | 42.918 | 19.229 | 112.790 | 1.00 | 74.50 | E |
| ATOM | 7113 | N | ILE | E | 126 | 43.069 | 17.075 | 112.185 | 1.00 | 75.11 | E |
| ATOM | 7114 | CA | ILE | E | 126 | 44.161 | 16.808 | 113.106 | 1.00 | 75.28 | E |
| ATOM | 7115 | CB | ILE | E | 126 | 43.616 | 16.105 | 114.381 | 1.00 | 74.23 | E |
| ATOM | 7116 | CG2 | ILE | E | 126 | 43.082 | 14.728 | 114.023 | 1.00 | 73.46 | E |
| ATOM | 7117 | CG1 | ILE | E | 126 | 44.705 | 16.025 | 115.454 | 1.00 | 76.88 | E |
| ATOM | 7118 | CD1 | ILE | E | 126 | 44.193 | 15.625 | 116.834 | 1.00 | 75.12 | E |
| ATOM | 7119 | C | ILE | E | 126 | 45.286 | 15.973 | 112.483 | 1.00 | 71.83 | E |
| ATOM | 7120 | O | ILE | E | 126 | 45.068 | 15.197 | 111.547 | 1.00 | 70.57 | E |
| ATOM | 7121 | N | GLN | E | 127 | 46.493 | 16.160 | 113.013 | 1.00 | 67.78 | E |
| ATOM | 7122 | CA | GLN | E | 127 | 47.686 | 15.449 | 112.560 | 1.00 | 62.87 | E |
| ATOM | 7123 | CB | GLN | E | 127 | 48.921 | 16.297 | 112.828 | 1.00 | 66.41 | E |
| ATOM | 7124 | CG | GLN | E | 127 | 48.912 | 17.636 | 112.133 | 1.00 | 71.59 | E |
| ATOM | 7125 | CD | GLN | E | 127 | 50.047 | 18.511 | 112.598 | 1.00 | 74.15 | E |
| ATOM | 7126 | OE1 | GLN | E | 127 | 50.109 | 18.885 | 113.764 | 1.00 | 77.60 | E |
| ATOM | 7127 | NE2 | GLN | E | 127 | 50.958 | 18.837 | 111.696 | 1.00 | 77.70 | E |
| ATOM | 7128 | C | GLN | E | 127 | 47.847 | 14.102 | 113.268 | 1.00 | 64.17 | E |
| ATOM | 7129 | O | GLN | E | 127 | 47.805 | 14.021 | 114.502 | 1.00 | 63.81 | E |
| ATOM | 7130 | N | PHE | E | 128 | 48.050 | 13.049 | 112.485 | 1.00 | 56.48 | E |
| ATOM | 7131 | CA | PHE | E | 128 | 48.211 | 11.717 | 113.046 | 1.00 | 54.57 | E |
| ATOM | 7132 | CB | PHE | E | 128 | 47.709 | 10.670 | 112.048 | 1.00 | 56.46 | E |
| ATOM | 7133 | CG | PHE | E | 128 | 46.232 | 10.435 | 112.125 | 1.00 | 64.20 | E |
| ATOM | 7134 | CD1 | PHE | E | 128 | 45.348 | 11.499 | 112.074 | 1.00 | 61.41 | E |
| ATOM | 7135 | CD2 | PHE | E | 128 | 45.724 | 9.152 | 112.296 | 1.00 | 61.40 | E |
| ATOM | 7136 | CE1 | PHE | E | 128 | 43.977 | 11.290 | 112.198 | 1.00 | 65.31 | E |
| ATOM | 7137 | CE2 | PHE | E | 128 | 44.352 | 8.936 | 112.419 | 1.00 | 64.34 | E |
| ATOM | 7138 | CZ | PHE | E | 128 | 43.480 | 10.007 | 112.372 | 1.00 | 65.61 | E |
| ATOM | 7139 | C | PHE | E | 128 | 49.642 | 11.399 | 113.446 | 1.00 | 51.91 | E |
| ATOM | 7140 | O | PHE | E | 128 | 50.588 | 11.925 | 112.868 | 1.00 | 54.52 | E |
| ATOM | 7141 | N | ILE | E | 129 | 49.786 | 10.553 | 114.460 | 1.00 | 49.50 | E |
| ATOM | 7142 | CA | ILE | E | 129 | 51.090 | 10.114 | 114.929 | 1.00 | 40.41 | E |
| ATOM | 7143 | CB | ILE | E | 129 | 51.422 | 10.671 | 116.298 | 1.00 | 38.92 | E |
| ATOM | 7144 | CG2 | ILE | E | 129 | 52.782 | 10.181 | 116.721 | 1.00 | 41.73 | E |
| ATOM | 7145 | CG1 | ILE | E | 129 | 51.401 | 12.194 | 116.246 | 1.00 | 41.67 | E |

Figure 10 (110 of 142)

| ATOM | 7146 | CD1 | ILE | E | 129 | 51.906 | 12.868 | 117.513 | 1.00 | 42.38 | E |
|---|---|---|---|---|---|---|---|---|---|---|---|
| ATOM | 7147 | C | ILE | E | 129 | 51.041 | 8.600 | 115.015 | 1.00 | 37.79 | E |
| ATOM | 7148 | O | ILE | E | 129 | 50.208 | 8.039 | 115.725 | 1.00 | 37.61 | E |
| ATOM | 7149 | N | GLY | E | 130 | 51.924 | 7.948 | 114.267 | 1.00 | 39.46 | E |
| ATOM | 7150 | CA | GLY | E | 130 | 51.973 | 6.499 | 114.243 | 1.00 | 40.43 | E |
| ATOM | 7151 | C | GLY | E | 130 | 53.088 | 6.014 | 115.139 | 1.00 | 46.00 | E |
| ATOM | 7152 | O | GLY | E | 130 | 54.008 | 6.774 | 115.461 | 1.00 | 44.16 | E |
| ATOM | 7153 | N | VAL | E | 131 | 53.011 | 4.755 | 115.555 | 1.00 | 46.10 | E |
| ATOM | 7154 | CA | VAL | E | 131 | 54.031 | 4.197 | 116.429 | 1.00 | 50.36 | E |
| ATOM | 7155 | CB | VAL | E | 131 | 53.426 | 3.740 | 117.765 | 1.00 | 50.28 | E |
| ATOM | 7156 | CG1 | VAL | E | 131 | 54.511 | 3.157 | 118.633 | 1.00 | 50.00 | E |
| ATOM | 7157 | CG2 | VAL | E | 131 | 52.755 | 4.905 | 118.468 | 1.00 | 47.71 | E |
| ATOM | 7158 | C | VAL | E | 131 | 54.688 | 3.002 | 115.760 | 1.00 | 50.41 | E |
| ATOM | 7159 | O | VAL | E | 131 | 55.858 | 3.057 | 115.387 | 1.00 | 53.26 | E |
| ATOM | 7160 | N | LYS | E | 132 | 53.898 | 1.941 | 115.609 | 1.00 | 56.91 | E |
| ATOM | 7161 | CA | LYS | E | 132 | 54.300 | 0.669 | 115.015 | 1.00 | 63.09 | E |
| ATOM | 7162 | CB | LYS | E | 132 | 55.729 | 0.709 | 114.468 | 1.00 | 66.40 | E |
| ATOM | 7163 | CG | LYS | E | 132 | 56.181 | -0.619 | 113.897 | 1.00 | 65.48 | E |
| ATOM | 7164 | CD | LYS | E | 132 | 57.307 | -0.425 | 112.909 | 1.00 | 66.87 | E |
| ATOM | 7165 | CE | LYS | E | 132 | 57.407 | -1.615 | 111.967 | 1.00 | 68.19 | E |
| ATOM | 7166 | NZ | LYS | E | 132 | 58.408 | -1.383 | 110.884 | 1.00 | 70.10 | E |
| ATOM | 7167 | C | LYS | E | 132 | 54.199 | -0.431 | 116.068 | 1.00 | 69.53 | E |
| ATOM | 7168 | O | LYS | E | 132 | 54.922 | -0.424 | 117.067 | 1.00 | 71.37 | E |
| ATOM | 7169 | N | ARG | E | 133 | 53.280 | -1.365 | 115.843 | 1.00 | 75.45 | E |
| ATOM | 7170 | CA | ARG | E | 133 | 53.072 | -2.485 | 116.751 | 1.00 | 82.73 | E |
| ATOM | 7171 | CB | ARG | E | 133 | 51.576 | -2.642 | 117.068 | 1.00 | 83.41 | E |
| ATOM | 7172 | CG | ARG | E | 133 | 51.154 | -4.084 | 117.301 | 1.00 | 82.30 | E |
| ATOM | 7173 | CD | ARG | E | 133 | 50.150 | -4.229 | 118.417 | 1.00 | 81.82 | E |
| ATOM | 7174 | NE | ARG | E | 133 | 48.764 | -4.127 | 117.979 | 1.00 | 85.83 | E |
| ATOM | 7175 | CZ | ARG | E | 133 | 47.732 | -4.435 | 118.755 | 1.00 | 86.41 | E |
| ATOM | 7176 | NH1 | ARG | E | 133 | 47.952 | -4.854 | 119.992 | 1.00 | 88.76 | E |
| ATOM | 7177 | NH2 | ARG | E | 133 | 46.489 | -4.340 | 118.304 | 1.00 | 85.73 | E |
| ATOM | 7178 | C | ARG | E | 133 | 53.614 | -3.775 | 116.128 | 1.00 | 86.05 | E |
| ATOM | 7179 | O | ARG | E | 133 | 53.661 | -3.914 | 114.901 | 1.00 | 87.84 | E |
| ATOM | 7180 | N | PRO | E | 134 | 54.053 | -4.726 | 116.970 | 1.00 | 88.43 | E |
| ATOM | 7181 | CD | PRO | E | 134 | 54.358 | -4.556 | 118.402 | 1.00 | 85.33 | E |
| ATOM | 7182 | CA | PRO | E | 134 | 54.586 | -6.000 | 116.478 | 1.00 | 87.43 | E |
| ATOM | 7183 | CB | PRO | E | 134 | 55.229 | -6.610 | 117.727 | 1.00 | 86.49 | E |
| ATOM | 7184 | CG | PRO | E | 134 | 55.581 | -5.414 | 118.560 | 1.00 | 86.57 | E |
| ATOM | 7185 | C | PRO | E | 134 | 53.459 | -6.873 | 115.919 | 1.00 | 87.01 | E |
| ATOM | 7186 | O | PRO | E | 134 | 52.456 | -7.112 | 116.594 | 1.00 | 86.39 | E |
| ATOM | 7187 | N | GLY | E | 135 | 53.627 | -7.342 | 114.689 | 1.00 | 87.66 | E |
| ATOM | 7188 | CA | GLY | E | 135 | 52.609 | -8.176 | 114.080 | 1.00 | 91.73 | E |
| ATOM | 7189 | C | GLY | E | 135 | 51.959 | -7.451 | 112.921 | 1.00 | 96.15 | E |
| ATOM | 7190 | O | GLY | E | 135 | 51.563 | -8.060 | 111.924 | 1.00 | 96.71 | E |
| ATOM | 7191 | N | PHE | E | 136 | 51.847 | -6.136 | 113.056 | 1.00 | 96.79 | E |
| ATOM | 7192 | CA | PHE | E | 136 | 51.256 | -5.314 | 112.013 | 1.00 | 97.48 | E |
| ATOM | 7193 | CB | PHE | E | 136 | 50.197 | -4.389 | 112.608 | 1.00 | 102.50 | E |
| ATOM | 7194 | CG | PHE | E | 136 | 49.144 | -5.118 | 113.379 | 1.00 | 108.39 | E |
| ATOM | 7195 | CD1 | PHE | E | 136 | 49.435 | -5.663 | 114.628 | 1.00 | 108.92 | E |
| ATOM | 7196 | CD2 | PHE | E | 136 | 47.886 | -5.333 | 112.829 | 1.00 | 111.76 | E |
| ATOM | 7197 | CE1 | PHE | E | 136 | 48.490 | -6.418 | 115.314 | 1.00 | 114.75 | E |
| ATOM | 7198 | CE2 | PHE | E | 136 | 46.933 | -6.086 | 113.507 | 1.00 | 112.71 | E |
| ATOM | 7199 | CZ | PHE | E | 136 | 47.235 | -6.632 | 114.751 | 1.00 | 114.24 | E |
| ATOM | 7200 | C | PHE | E | 136 | 52.383 | -4.516 | 111.401 | 1.00 | 94.48 | E |
| ATOM | 7201 | O | PHE | E | 136 | 53.536 | -4.668 | 111.806 | 1.00 | 94.19 | E |
| ATOM | 7202 | N | HIS | E | 137 | 52.070 | -3.673 | 110.426 | 1.00 | 90.38 | E |
| ATOM | 7203 | CA | HIS | E | 137 | 53.120 | -2.892 | 109.806 | 1.00 | 88.47 | E |
| ATOM | 7204 | CB | HIS | E | 137 | 53.902 | -3.773 | 108.828 | 1.00 | 92.96 | E |
| ATOM | 7205 | CG | HIS | E | 137 | 55.212 | -3.186 | 108.408 | 1.00 | 98.05 | E |
| ATOM | 7206 | CD2 | HIS | E | 137 | 56.398 | -3.094 | 109.056 | 1.00 | 99.09 | E |
| ATOM | 7207 | ND1 | HIS | E | 137 | 55.391 | -2.566 | 107.190 | 1.00 | 96.97 | E |
| ATOM | 7208 | CE1 | HIS | E | 137 | 56.631 | -2.117 | 107.106 | 1.00 | 100.56 | E |
| ATOM | 7209 | NE2 | HIS | E | 137 | 57.262 | -2.424 | 108.225 | 1.00 | 100.48 | E |
| ATOM | 7210 | C | HIS | E | 137 | 52.626 | -1.627 | 109.117 | 1.00 | 82.99 | E |
| ATOM | 7211 | O | HIS | E | 137 | 51.622 | -1.633 | 108.403 | 1.00 | 79.87 | E |

Figure 10 (111 of 142)

| ATOM | 7212 | N   | VAL | E | 138 | 53.364 | -0.546 | 109.354 | 1.00 | 78.83 | E |
|------|------|-----|-----|---|-----|--------|--------|---------|------|-------|---|
| ATOM | 7213 | CA  | VAL | E | 138 | 53.079 | 0.776  | 108.811 | 1.00 | 76.96 | E |
| ATOM | 7214 | CB  | VAL | E | 138 | 53.725 | 1.863  | 109.692 | 1.00 | 72.57 | E |
| ATOM | 7215 | CG1 | VAL | E | 138 | 55.108 | 1.416  | 110.155 | 1.00 | 69.17 | E |
| ATOM | 7216 | CG2 | VAL | E | 138 | 53.844 | 3.146  | 108.906 | 1.00 | 72.67 | E |
| ATOM | 7217 | C   | VAL | E | 138 | 53.588 | 0.963  | 107.385 | 1.00 | 74.36 | E |
| ATOM | 7218 | O   | VAL | E | 138 | 54.724 | 0.598  | 107.085 | 1.00 | 73.77 | E |
| ATOM | 7219 | N   | GLU | E | 139 | 52.759 | 1.547  | 106.520 | 1.00 | 75.31 | E |
| ATOM | 7220 | CA  | GLU | E | 139 | 53.144 | 1.785  | 105.131 | 1.00 | 74.90 | E |
| ATOM | 7221 | CB  | GLU | E | 139 | 53.067 | 0.494  | 104.318 | 1.00 | 76.22 | E |
| ATOM | 7222 | CG  | GLU | E | 139 | 53.995 | -0.608 | 104.791 | 1.00 | 73.81 | E |
| ATOM | 7223 | CD  | GLU | E | 139 | 53.926 | -1.847 | 103.924 | 1.00 | 73.60 | E |
| ATOM | 7224 | OE1 | GLU | E | 139 | 52.865 | -2.077 | 103.293 | 1.00 | 72.48 | E |
| ATOM | 7225 | OE2 | GLU | E | 139 | 54.930 | -2.594 | 103.890 | 1.00 | 71.93 | E |
| ATOM | 7226 | C   | GLU | E | 139 | 52.271 | 2.825  | 104.453 | 1.00 | 74.96 | E |
| ATOM | 7227 | O   | GLU | E | 139 | 52.653 | 3.404  | 103.440 | 1.00 | 77.62 | E |
| ATOM | 7228 | N   | THR | E | 140 | 51.090 | 3.038  | 105.013 | 1.00 | 73.12 | E |
| ATOM | 7229 | CA  | THR | E | 140 | 50.106 | 3.985  | 104.497 | 1.00 | 71.59 | E |
| ATOM | 7230 | CB  | THR | E | 140 | 49.433 | 4.753  | 105.648 | 1.00 | 74.28 | E |
| ATOM | 7231 | OG1 | THR | E | 140 | 50.415 | 5.095  | 106.640 | 1.00 | 69.56 | E |
| ATOM | 7232 | CG2 | THR | E | 140 | 48.315 | 3.930  | 106.254 | 1.00 | 71.04 | E |
| ATOM | 7233 | C   | THR | E | 140 | 50.491 | 5.051  | 103.474 | 1.00 | 70.22 | E |
| ATOM | 7234 | O   | THR | E | 140 | 51.635 | 5.483  | 103.387 | 1.00 | 73.19 | E |
| ATOM | 7235 | N   | PRO | E | 141 | 49.508 | 5.483  | 102.673 | 1.00 | 67.57 | E |
| ATOM | 7236 | CD  | PRO | E | 141 | 48.318 | 4.654  | 102.401 | 1.00 | 66.00 | E |
| ATOM | 7237 | CA  | PRO | E | 141 | 49.650 | 6.510  | 101.642 | 1.00 | 64.49 | E |
| ATOM | 7238 | CB  | PRO | E | 141 | 48.902 | 5.903  | 100.470 | 1.00 | 62.78 | E |
| ATOM | 7239 | CG  | PRO | E | 141 | 47.727 | 5.304  | 101.152 | 1.00 | 63.49 | E |
| ATOM | 7240 | C   | PRO | E | 141 | 48.957 | 7.771  | 102.197 | 1.00 | 57.78 | E |
| ATOM | 7241 | O   | PRO | E | 141 | 48.420 | 8.586  | 101.453 | 1.00 | 62.11 | E |
| ATOM | 7242 | N   | TYR | E | 142 | 48.969 | 7.913  | 103.520 | 1.00 | 55.15 | E |
| ATOM | 7243 | CA  | TYR | E | 142 | 48.332 | 9.045  | 104.180 | 1.00 | 56.26 | E |
| ATOM | 7244 | CB  | TYR | E | 142 | 47.234 | 8.542  | 105.110 | 1.00 | 53.80 | E |
| ATOM | 7245 | CG  | TYR | E | 142 | 46.152 | 7.744  | 104.418 | 1.00 | 51.74 | E |
| ATOM | 7246 | CD1 | TYR | E | 142 | 45.101 | 8.383  | 103.756 | 1.00 | 50.96 | E |
| ATOM | 7247 | CE1 | TYR | E | 142 | 44.086 | 7.649  | 103.133 | 1.00 | 48.54 | E |
| ATOM | 7248 | CD2 | TYR | E | 142 | 46.168 | 6.344  | 104.439 | 1.00 | 51.70 | E |
| ATOM | 7249 | CE2 | TYR | E | 142 | 45.157 | 5.599  | 103.816 | 1.00 | 52.42 | E |
| ATOM | 7250 | CZ  | TYR | E | 142 | 44.120 | 6.260  | 103.166 | 1.00 | 51.24 | E |
| ATOM | 7251 | OH  | TYR | E | 142 | 43.123 | 5.538  | 102.547 | 1.00 | 45.01 | E |
| ATOM | 7252 | C   | TYR | E | 142 | 49.333 | 9.862  | 104.979 | 1.00 | 53.36 | E |
| ATOM | 7253 | O   | TYR | E | 142 | 50.384 | 9.369  | 105.371 | 1.00 | 55.37 | E |
| ATOM | 7254 | N   | PRO | E | 143 | 49.012 | 11.132 | 105.235 | 1.00 | 45.17 | E |
| ATOM | 7255 | CD  | PRO | E | 143 | 47.766 | 11.839 | 104.901 | 1.00 | 47.67 | E |
| ATOM | 7256 | CA  | PRO | E | 143 | 49.910 | 11.996 | 105.991 | 1.00 | 46.10 | E |
| ATOM | 7257 | CB  | PRO | E | 143 | 49.281 | 13.371 | 105.809 | 1.00 | 52.54 | E |
| ATOM | 7258 | CG  | PRO | E | 143 | 47.830 | 13.058 | 105.797 | 1.00 | 49.99 | E |
| ATOM | 7259 | C   | PRO | E | 143 | 49.950 | 11.547 | 107.441 | 1.00 | 47.77 | E |
| ATOM | 7260 | O   | PRO | E | 143 | 48.946 | 11.621 | 108.157 | 1.00 | 50.92 | E |
| ATOM | 7261 | N   | LEU | E | 144 | 51.114 | 11.085 | 107.876 | 1.00 | 40.79 | E |
| ATOM | 7262 | CA  | LEU | E | 144 | 51.257 | 10.611 | 109.239 | 1.00 | 38.13 | E |
| ATOM | 7263 | CB  | LEU | E | 144 | 50.964 | 9.115  | 109.268 | 1.00 | 44.65 | E |
| ATOM | 7264 | CG  | LEU | E | 144 | 50.228 | 8.514  | 110.459 | 1.00 | 44.83 | E |
| ATOM | 7265 | CD1 | LEU | E | 144 | 49.734 | 7.128  | 110.085 | 1.00 | 48.72 | E |
| ATOM | 7266 | CD2 | LEU | E | 144 | 51.137 | 8.463  | 111.649 | 1.00 | 46.42 | E |
| ATOM | 7267 | C   | LEU | E | 144 | 52.678 | 10.867 | 109.684 | 1.00 | 38.87 | E |
| ATOM | 7268 | O   | LEU | E | 144 | 53.588 | 10.799 | 108.876 | 1.00 | 36.16 | E |
| ATOM | 7269 | N   | LEU | E | 145 | 52.872 | 11.187 | 110.955 | 1.00 | 35.63 | E |
| ATOM | 7270 | CA  | LEU | E | 145 | 54.217 | 11.401 | 111.468 | 1.00 | 36.25 | E |
| ATOM | 7271 | CB  | LEU | E | 145 | 54.288 | 12.695 | 112.271 | 1.00 | 31.57 | E |
| ATOM | 7272 | CG  | LEU | E | 145 | 54.218 | 13.953 | 111.402 | 1.00 | 30.09 | E |
| ATOM | 7273 | CD1 | LEU | E | 145 | 54.365 | 15.179 | 112.273 | 1.00 | 30.14 | E |
| ATOM | 7274 | CD2 | LEU | E | 145 | 55.323 | 13.928 | 110.371 | 1.00 | 29.48 | E |
| ATOM | 7275 | C   | LEU | E | 145 | 54.516 | 10.195 | 112.342 | 1.00 | 36.53 | E |
| ATOM | 7276 | O   | LEU | E | 145 | 53.598 | 9.550  | 112.827 | 1.00 | 41.06 | E |
| ATOM | 7277 | N   | PHE | E | 146 | 55.782 | 9.862  | 112.538 | 1.00 | 40.59 | E |

Figure 10 (112 of 142)

```
ATOM   7278  CA   PHE E 146      56.095   8.694 113.348  1.00 39.28           E
ATOM   7279  CB   PHE E 146      56.806   7.652 112.505  1.00 36.34           E
ATOM   7280  CG   PHE E 146      55.980   7.160 111.384  1.00 37.82           E
ATOM   7281  CD1  PHE E 146      54.932   6.292 111.621  1.00 39.36           E
ATOM   7282  CD2  PHE E 146      56.194   7.616 110.090  1.00 43.85           E
ATOM   7283  CE1  PHE E 146      54.099   5.885 110.583  1.00 41.19           E
ATOM   7284  CE2  PHE E 146      55.365   7.214 109.040  1.00 41.31           E
ATOM   7285  CZ   PHE E 146      54.316   6.348 109.288  1.00 40.38           E
ATOM   7286  C    PHE E 146      56.918   8.978 114.572  1.00 41.06           E
ATOM   7287  O    PHE E 146      57.569  10.020 114.680  1.00 43.86           E
ATOM   7288  N    ALA E 147      56.878   8.030 115.496  1.00 38.44           E
ATOM   7289  CA   ALA E 147      57.620   8.126 116.734  1.00 39.86           E
ATOM   7290  CB   ALA E 147      56.704   8.543 117.856  1.00 36.52           E
ATOM   7291  C    ALA E 147      58.199   6.754 117.017  1.00 40.04           E
ATOM   7292  O    ALA E 147      57.491   5.753 116.949  1.00 41.75           E
ATOM   7293  N    ASP E 148      59.492   6.703 117.310  1.00 47.05           E
ATOM   7294  CA   ASP E 148      60.127   5.438 117.613  1.00 54.72           E
ATOM   7295  CB   ASP E 148      61.637   5.582 117.601  1.00 64.76           E
ATOM   7296  CG   ASP E 148      62.190   5.596 116.213  1.00 70.46           E
ATOM   7297  OD1  ASP E 148      62.040   6.623 115.523  1.00 75.38           E
ATOM   7298  OD2  ASP E 148      62.760   4.564 115.806  1.00 76.55           E
ATOM   7299  C    ASP E 148      59.680   4.969 118.976  1.00 57.51           E
ATOM   7300  O    ASP E 148      59.854   5.669 119.975  1.00 57.87           E
ATOM   7301  N    VAL E 149      59.090   3.783 119.012  1.00 58.94           E
ATOM   7302  CA   VAL E 149      58.621   3.225 120.260  1.00 61.96           E
ATOM   7303  CB   VAL E 149      57.124   3.479 120.446  1.00 63.88           E
ATOM   7304  CG1  VAL E 149      56.668   2.934 121.789  1.00 64.57           E
ATOM   7305  CG2  VAL E 149      56.848   4.975 120.356  1.00 65.28           E
ATOM   7306  C    VAL E 149      58.887   1.734 120.288  1.00 58.73           E
ATOM   7307  O    VAL E 149      58.469   1.000 119.394  1.00 65.51           E
ATOM   7308  N    PRO E 150      59.592   1.271 121.327  1.00 55.77           E
ATOM   7309  CD   PRO E 150      59.954   2.049 122.522  1.00 51.54           E
ATOM   7310  CA   PRO E 150      59.937  -0.137 121.506  1.00 53.40           E
ATOM   7311  CB   PRO E 150      60.343  -0.192 122.961  1.00 48.31           E
ATOM   7312  CG   PRO E 150      60.934   1.154 123.180  1.00 50.84           E
ATOM   7313  C    PRO E 150      58.747  -1.028 121.229  1.00 49.78           E
ATOM   7314  O    PRO E 150      57.719  -0.884 121.874  1.00 49.95           E
ATOM   7315  N    GLU E 151      58.881  -1.935 120.269  1.00 50.20           E
ATOM   7316  CA   GLU E 151      57.801  -2.851 119.932  1.00 58.69           E
ATOM   7317  CB   GLU E 151      58.223  -3.737 118.767  1.00 61.32           E
ATOM   7318  CG   GLU E 151      58.263  -2.999 117.442  1.00 78.46           E
ATOM   7319  CD   GLU E 151      58.927  -3.801 116.344  1.00 84.56           E
ATOM   7320  OE1  GLU E 151      58.787  -3.423 115.159  1.00 86.26           E
ATOM   7321  OE2  GLU E 151      59.599  -4.805 116.669  1.00 86.67           E
ATOM   7322  C    GLU E 151      57.470  -3.698 121.151  1.00 60.63           E
ATOM   7323  O    GLU E 151      58.368  -4.113 121.872  1.00 58.15           E
ATOM   7324  N    PHE E 152      56.181  -3.933 121.387  1.00 62.21           E
ATOM   7325  CA   PHE E 152      55.708  -4.728 122.527  1.00 65.16           E
ATOM   7326  CB   PHE E 152      55.335  -3.807 123.700  1.00 68.47           E
ATOM   7327  CG   PHE E 152      54.986  -4.536 124.977  1.00 73.88           E
ATOM   7328  CD1  PHE E 152      54.726  -3.825 126.145  1.00 75.11           E
ATOM   7329  CD2  PHE E 152      54.918  -5.924 125.018  1.00 76.19           E
ATOM   7330  CE1  PHE E 152      54.403  -4.484 127.329  1.00 75.65           E
ATOM   7331  CE2  PHE E 152      54.594  -6.589 126.200  1.00 74.39           E
ATOM   7332  CZ   PHE E 152      54.337  -5.866 127.354  1.00 75.20           E
ATOM   7333  C    PHE E 152      54.482  -5.505 122.058  1.00 63.90           E
ATOM   7334  O    PHE E 152      53.382  -4.967 121.983  1.00 64.63           E
ATOM   7335  N    GLU E 153      54.684  -6.778 121.747  1.00 70.73           E
ATOM   7336  CA   GLU E 153      53.613  -7.635 121.246  1.00 74.90           E
ATOM   7337  CB   GLU E 153      54.214  -8.933 120.707  1.00 79.29           E
ATOM   7338  CG   GLU E 153      53.245  -9.825 119.952  1.00 82.57           E
ATOM   7339  CD   GLU E 153      53.859 -11.169 119.579  1.00 82.18           E
ATOM   7340  OE1  GLU E 153      53.232 -11.918 118.798  1.00 82.07           E
ATOM   7341  OE2  GLU E 153      54.965 -11.486 120.069  1.00 80.49           E
ATOM   7342  C    GLU E 153      52.551  -7.966 122.282  1.00 76.71           E
ATOM   7343  O    GLU E 153      52.537  -9.066 122.823  1.00 76.68           E
```

Figure 10 (113 of 142)

| ATOM | 7344 | N   | VAL E 154 | 51.652 | -7.025  | 122.540 | 1.00 | 75.86  | E |
|------|------|-----|-----------|--------|---------|---------|------|--------|---|
| ATOM | 7345 | CA  | VAL E 154 | 50.596 | -7.246  | 123.513 | 1.00 | 80.74  | E |
| ATOM | 7346 | CB  | VAL E 154 | 51.017 | -6.744  | 124.904 | 1.00 | 77.85  | E |
| ATOM | 7347 | CG1 | VAL E 154 | 51.530 | -5.312  | 124.815 | 1.00 | 75.87  | E |
| ATOM | 7348 | CG2 | VAL E 154 | 49.836 | -6.830  | 125.855 | 1.00 | 77.57  | E |
| ATOM | 7349 | C   | VAL E 154 | 49.293 | -6.563  | 123.126 | 1.00 | 79.88  | E |
| ATOM | 7350 | O   | VAL E 154 | 49.243 | -5.343  | 122.984 | 1.00 | 83.57  | E |
| ATOM | 7351 | N   | SER E 155 | 48.240 | -7.356  | 122.962 | 1.00 | 80.53  | E |
| ATOM | 7352 | CA  | SER E 155 | 46.927 | -6.826  | 122.600 | 1.00 | 84.01  | E |
| ATOM | 7353 | CB  | SER E 155 | 46.495 | -7.357  | 121.231 | 1.00 | 85.81  | E |
| ATOM | 7354 | OG  | SER E 155 | 46.352 | -8.767  | 121.246 | 1.00 | 78.26  | E |
| ATOM | 7355 | C   | SER E 155 | 45.913 | -7.258  | 123.638 | 1.00 | 86.32  | E |
| ATOM | 7356 | O   | SER E 155 | 46.129 | -8.243  | 124.340 | 1.00 | 87.33  | E |
| ATOM | 7357 | N   | SER E 156 | 44.803 | -6.536  | 123.739 | 1.00 | 91.75  | E |
| ATOM | 7358 | CA  | SER E 156 | 43.782 | -6.910  | 124.712 | 1.00 | 94.37  | E |
| ATOM | 7359 | CB  | SER E 156 | 42.635 | -5.903  | 124.713 | 1.00 | 93.14  | E |
| ATOM | 7360 | OG  | SER E 156 | 41.765 | -6.146  | 123.625 | 1.00 | 93.35  | E |
| ATOM | 7361 | C   | SER E 156 | 43.235 | -8.299  | 124.372 | 1.00 | 94.18  | E |
| ATOM | 7362 | O   | SER E 156 | 43.072 | -9.137  | 125.259 | 1.00 | 98.84  | E |
| ATOM | 7363 | N   | THR E 157 | 42.965 | -8.540  | 123.088 | 1.00 | 95.25  | E |
| ATOM | 7364 | CA  | THR E 157 | 42.429 | -9.826  | 122.622 | 1.00 | 103.66 | E |
| ATOM | 7365 | CB  | THR E 157 | 42.141 | -9.797  | 121.101 | 1.00 | 101.55 | E |
| ATOM | 7366 | OG1 | THR E 157 | 41.181 | -8.770  | 120.822 | 1.00 | 100.08 | E |
| ATOM | 7367 | CG2 | THR E 157 | 41.572 | -11.136 | 120.630 | 1.00 | 97.61  | E |
| ATOM | 7368 | C   | THR E 157 | 43.354 | -11.003 | 122.938 | 1.00 | 104.46 | E |
| ATOM | 7369 | O   | THR E 157 | 43.065 | -12.162 | 122.618 | 1.00 | 109.40 | E |
| ATOM | 7370 | N   | MET E 158 | 44.480 | -10.684 | 123.555 | 1.00 | 106.73 | E |
| ATOM | 7371 | CA  | MET E 158 | 45.437 | -11.685 | 123.977 | 1.00 | 108.32 | E |
| ATOM | 7372 | CB  | MET E 158 | 46.834 | -11.086 | 123.954 | 1.00 | 106.34 | E |
| ATOM | 7373 | CG  | MET E 158 | 47.874 | -11.840 | 124.742 | 1.00 | 106.58 | E |
| ATOM | 7374 | SD  | MET E 158 | 49.328 | -10.797 | 124.909 | 1.00 | 104.48 | E |
| ATOM | 7375 | CE  | MET E 158 | 49.621 | -10.380 | 123.165 | 1.00 | 101.90 | E |
| ATOM | 7376 | C   | MET E 158 | 44.992 | -11.933 | 125.408 | 1.00 | 108.87 | E |
| ATOM | 7377 | O   | MET E 158 | 44.704 | -13.062 | 125.804 | 1.00 | 109.86 | E |
| ATOM | 7378 | N   | ILE E 159 | 44.910 | -10.837 | 126.159 | 1.00 | 104.71 | E |
| ATOM | 7379 | CA  | ILE E 159 | 44.492 | -10.857 | 127.552 | 1.00 | 98.32  | E |
| ATOM | 7380 | CB  | ILE E 159 | 44.338 | -9.420  | 128.119 | 1.00 | 97.42  | E |
| ATOM | 7381 | CG2 | ILE E 159 | 44.041 | -9.482  | 129.613 | 1.00 | 98.38  | E |
| ATOM | 7382 | CG1 | ILE E 159 | 45.606 | -8.598  | 127.853 | 1.00 | 96.45  | E |
| ATOM | 7383 | CD1 | ILE E 159 | 46.854 | -9.089  | 128.565 | 1.00 | 95.48  | E |
| ATOM | 7384 | C   | ILE E 159 | 43.153 | -11.568 | 127.688 | 1.00 | 99.01  | E |
| ATOM | 7385 | O   | ILE E 159 | 43.032 | -12.538 | 128.429 | 1.00 | 99.85  | E |
| ATOM | 7386 | N   | ARG E 160 | 42.146 | -11.086 | 126.969 | 1.00 | 98.83  | E |
| ATOM | 7387 | CA  | ARG E 160 | 40.817 | -11.686 | 127.031 | 1.00 | 95.12  | E |
| ATOM | 7388 | CB  | ARG E 160 | 39.929 | -11.123 | 125.916 | 1.00 | 98.89  | E |
| ATOM | 7389 | CG  | ARG E 160 | 39.818 | -9.604  | 125.942 | 1.00 | 103.66 | E |
| ATOM | 7390 | CD  | ARG E 160 | 38.410 | -9.133  | 125.608 | 1.00 | 108.10 | E |
| ATOM | 7391 | NE  | ARG E 160 | 38.392 | -8.201  | 124.483 | 1.00 | 114.10 | E |
| ATOM | 7392 | CZ  | ARG E 160 | 38.595 | -8.552  | 123.218 | 1.00 | 115.21 | E |
| ATOM | 7393 | NH1 | ARG E 160 | 38.829 | -9.820  | 122.903 | 1.00 | 117.60 | E |
| ATOM | 7394 | NH2 | ARG E 160 | 38.567 | -7.632  | 122.265 | 1.00 | 117.22 | E |
| ATOM | 7395 | C   | ARG E 160 | 40.862 | -13.216 | 126.953 | 1.00 | 91.05  | E |
| ATOM | 7396 | O   | ARG E 160 | 40.243 | -13.900 | 127.771 | 1.00 | 89.23  | E |
| ATOM | 7397 | N   | GLU E 161 | 41.596 | -13.747 | 125.977 | 1.00 | 86.46  | E |
| ATOM | 7398 | CA  | GLU E 161 | 41.717 | -15.193 | 125.821 | 1.00 | 84.42  | E |
| ATOM | 7399 | CB  | GLU E 161 | 42.325 | -15.539 | 124.471 | 1.00 | 82.99  | E |
| ATOM | 7400 | CG  | GLU E 161 | 42.411 | -17.018 | 124.225 | 1.00 | 84.20  | E |
| ATOM | 7401 | CD  | GLU E 161 | 42.984 | -17.316 | 122.875 | 1.00 | 85.66  | E |
| ATOM | 7402 | OE1 | GLU E 161 | 43.097 | -16.365 | 122.076 | 1.00 | 85.09  | E |
| ATOM | 7403 | OE2 | GLU E 161 | 43.315 | -18.491 | 122.609 | 1.00 | 85.63  | E |
| ATOM | 7404 | C   | GLU E 161 | 42.598 | -15.750 | 126.932 | 1.00 | 82.49  | E |
| ATOM | 7405 | O   | GLU E 161 | 42.426 | -16.887 | 127.371 | 1.00 | 79.32  | E |
| ATOM | 7406 | N   | ARG E 162 | 43.555 | -14.938 | 127.367 | 1.00 | 83.35  | E |
| ATOM | 7407 | CA  | ARG E 162 | 44.455 | -15.311 | 128.452 | 1.00 | 84.94  | E |
| ATOM | 7408 | CB  | ARG E 162 | 45.494 | -14.207 | 128.683 | 1.00 | 83.52  | E |
| ATOM | 7409 | CG  | ARG E 162 | 46.924 | -14.674 | 128.916 | 1.00 | 82.42  | E |

Figure 10 (114 of 142)

| ATOM | 7410 | CD  | ARG | E | 162 | 47.636 | -14.935 | 127.597 | 1.00 | 80.91  | E |
|------|------|-----|-----|---|-----|--------|---------|---------|------|--------|---|
| ATOM | 7411 | NE  | ARG | E | 162 | 49.078 | -15.048 | 127.779 | 1.00 | 81.39  | E |
| ATOM | 7412 | CZ  | ARG | E | 162 | 49.953 | -15.127 | 126.784 | 1.00 | 81.02  | E |
| ATOM | 7413 | NH1 | ARG | E | 162 | 49.538 | -15.105 | 125.528 | 1.00 | 81.27  | E |
| ATOM | 7414 | NH2 | ARG | E | 162 | 51.246 | -15.230 | 127.045 | 1.00 | 80.99  | E |
| ATOM | 7415 | C   | ARG | E | 162 | 43.549 | -15.411 | 129.680 | 1.00 | 86.69  | E |
| ATOM | 7416 | O   | ARG | E | 162 | 43.612 | -16.377 | 130.443 | 1.00 | 88.23  | E |
| ATOM | 7417 | N   | PHE | E | 163 | 42.703 | -14.392 | 129.841 | 1.00 | 87.89  | E |
| ATOM | 7418 | CA  | PHE | E | 163 | 41.742 | -14.274 | 130.937 | 1.00 | 90.90  | E |
| ATOM | 7419 | CB  | PHE | E | 163 | 41.242 | -12.823 | 131.032 | 1.00 | 90.50  | E |
| ATOM | 7420 | CG  | PHE | E | 163 | 41.949 | -11.982 | 132.069 | 1.00 | 91.24  | E |
| ATOM | 7421 | CD1 | PHE | E | 163 | 43.040 | -12.471 | 132.782 | 1.00 | 91.75  | E |
| ATOM | 7422 | CD2 | PHE | E | 163 | 41.501 | -10.694 | 132.343 | 1.00 | 90.93  | E |
| ATOM | 7423 | CE1 | PHE | E | 163 | 43.671 | -11.682 | 133.756 | 1.00 | 93.40  | E |
| ATOM | 7424 | CE2 | PHE | E | 163 | 42.122 |  -9.902 | 133.309 | 1.00 | 90.55  | E |
| ATOM | 7425 | CZ  | PHE | E | 163 | 43.206 | -10.395 | 134.017 | 1.00 | 92.67  | E |
| ATOM | 7426 | C   | PHE | E | 163 | 40.543 | -15.200 | 130.721 | 1.00 | 90.48  | E |
| ATOM | 7427 | O   | PHE | E | 163 | 39.447 | -14.928 | 131.203 | 1.00 | 90.14  | E |
| ATOM | 7428 | N   | LYS | E | 164 | 40.762 | -16.289 | 129.989 | 1.00 | 89.28  | E |
| ATOM | 7429 | CA  | LYS | E | 164 | 39.723 | -17.275 | 129.678 | 1.00 | 86.48  | E |
| ATOM | 7430 | CB  | LYS | E | 164 | 38.691 | -16.686 | 128.705 | 1.00 | 83.35  | E |
| ATOM | 7431 | CG  | LYS | E | 164 | 37.641 | -17.678 | 128.195 | 1.00 | 73.08  | E |
| ATOM | 7432 | CD  | LYS | E | 164 | 36.455 | -17.790 | 129.135 | 1.00 | 67.25  | E |
| ATOM | 7433 | CE  | LYS | E | 164 | 35.634 | -16.518 | 129.116 | 1.00 | 60.08  | E |
| ATOM | 7434 | NZ  | LYS | E | 164 | 34.482 | -16.575 | 130.056 | 1.00 | 56.29  | E |
| ATOM | 7435 | C   | LYS | E | 164 | 40.446 | -18.443 | 129.022 | 1.00 | 85.39  | E |
| ATOM | 7436 | O   | LYS | E | 164 | 40.499 | -18.549 | 127.800 | 1.00 | 87.76  | E |
| ATOM | 7437 | N   | SER | E | 165 | 40.991 | -19.306 | 129.871 | 1.00 | 88.29  | E |
| ATOM | 7438 | CA  | SER | E | 165 | 41.779 | -20.482 | 129.509 | 1.00 | 88.13  | E |
| ATOM | 7439 | CB  | SER | E | 165 | 42.318 | -20.393 | 128.083 | 1.00 | 90.95  | E |
| ATOM | 7440 | OG  | SER | E | 165 | 43.246 | -21.433 | 127.825 | 1.00 | 94.17  | E |
| ATOM | 7441 | C   | SER | E | 165 | 42.909 | -20.268 | 130.489 | 1.00 | 88.68  | E |
| ATOM | 7442 | O   | SER | E | 165 | 44.010 | -20.808 | 130.353 | 1.00 | 85.25  | E |
| ATOM | 7443 | N   | LYS | E | 166 | 42.586 | -19.428 | 131.471 | 1.00 | 87.68  | E |
| ATOM | 7444 | CA  | LYS | E | 166 | 43.467 | -19.011 | 132.553 | 1.00 | 87.44  | E |
| ATOM | 7445 | CB  | LYS | E | 166 | 43.133 | -19.764 | 133.848 | 1.00 | 93.87  | E |
| ATOM | 7446 | CG  | LYS | E | 166 | 42.116 | -20.885 | 133.713 | 1.00 | 99.68  | E |
| ATOM | 7447 | CD  | LYS | E | 166 | 40.827 | -20.536 | 134.438 | 1.00 | 105.12 | E |
| ATOM | 7448 | CE  | LYS | E | 166 | 41.077 | -20.219 | 135.909 | 1.00 | 109.52 | E |
| ATOM | 7449 | NZ  | LYS | E | 166 | 39.835 | -19.785 | 136.614 | 1.00 | 111.24 | E |
| ATOM | 7450 | C   | LYS | E | 166 | 44.961 | -19.110 | 132.281 | 1.00 | 84.40  | E |
| ATOM | 7451 | O   | LYS | E | 166 | 45.632 | -20.043 | 132.736 | 1.00 | 80.67  | E |
| ATOM | 7452 | N   | LYS | E | 167 | 45.472 | -18.142 | 131.529 | 1.00 | 82.27  | E |
| ATOM | 7453 | CA  | LYS | E | 167 | 46.890 | -18.077 | 131.228 | 1.00 | 83.75  | E |
| ATOM | 7454 | CB  | LYS | E | 167 | 47.126 | -17.916 | 129.729 | 1.00 | 84.87  | E |
| ATOM | 7455 | CG  | LYS | E | 167 | 47.306 | -19.240 | 129.010 | 1.00 | 86.27  | E |
| ATOM | 7456 | CD  | LYS | E | 167 | 47.984 | -19.028 | 127.670 | 1.00 | 89.83  | E |
| ATOM | 7457 | CE  | LYS | E | 167 | 48.437 | -20.341 | 127.056 | 1.00 | 91.75  | E |
| ATOM | 7458 | NZ  | LYS | E | 167 | 49.174 | -20.097 | 125.780 | 1.00 | 94.98  | E |
| ATOM | 7459 | C   | LYS | E | 167 | 47.453 | -16.892 | 132.002 | 1.00 | 83.19  | E |
| ATOM | 7460 | O   | LYS | E | 167 | 46.704 | -16.041 | 132.466 | 1.00 | 84.09  | E |
| ATOM | 7461 | N   | PRO | E | 168 | 48.781 | -16.830 | 132.152 | 1.00 | 83.46  | E |
| ATOM | 7462 | CD  | PRO | E | 168 | 49.695 | -17.690 | 131.377 | 1.00 | 82.01  | E |
| ATOM | 7463 | CA  | PRO | E | 168 | 49.539 | -15.798 | 132.864 | 1.00 | 82.93  | E |
| ATOM | 7464 | CB  | PRO | E | 168 | 50.843 | -15.762 | 132.097 | 1.00 | 82.84  | E |
| ATOM | 7465 | CG  | PRO | E | 168 | 51.059 | -17.214 | 131.823 | 1.00 | 84.40  | E |
| ATOM | 7466 | C   | PRO | E | 168 | 48.955 | -14.407 | 133.056 | 1.00 | 79.08  | E |
| ATOM | 7467 | O   | PRO | E | 168 | 48.613 | -14.038 | 134.179 | 1.00 | 80.60  | E |
| ATOM | 7468 | N   | THR | E | 169 | 48.852 | -13.642 | 131.969 | 1.00 | 77.02  | E |
| ATOM | 7469 | CA  | THR | E | 169 | 48.355 | -12.258 | 131.991 | 1.00 | 77.12  | E |
| ATOM | 7470 | CB  | THR | E | 169 | 46.856 | -12.134 | 132.416 | 1.00 | 78.03  | E |
| ATOM | 7471 | OG1 | THR | E | 169 | 46.747 | -11.235 | 133.531 | 1.00 | 78.04  | E |
| ATOM | 7472 | CG2 | THR | E | 169 | 46.266 | -13.474 | 132.791 | 1.00 | 79.19  | E |
| ATOM | 7473 | C   | THR | E | 169 | 49.163 | -11.327 | 132.903 | 1.00 | 76.08  | E |
| ATOM | 7474 | O   | THR | E | 169 | 48.887 | -10.130 | 132.976 | 1.00 | 73.46  | E |
| ATOM | 7475 | N   | ASP | E | 170 | 50.154 | -11.866 | 133.605 | 1.00 | 76.11  | E |

Figure 10 (115 of 142)

```
ATOM   7476  CA   ASP E 170      50.970 -11.037 134.484  1.00 79.07      E
ATOM   7477  CB   ASP E 170      51.639 -11.878 135.580  1.00 80.55      E
ATOM   7478  CG   ASP E 170      50.647 -12.455 136.562  1.00 78.34      E
ATOM   7479  OD1  ASP E 170      50.085 -13.540 136.291  1.00 75.78      E
ATOM   7480  OD2  ASP E 170      50.433 -11.807 137.606  1.00 78.78      E
ATOM   7481  C    ASP E 170      52.039 -10.327 133.664  1.00 79.35      E
ATOM   7482  O    ASP E 170      52.627 -10.911 132.744  1.00 77.40      E
ATOM   7483  N    TYR E 171      52.279  -9.064 134.002  1.00 83.73      E
ATOM   7484  CA   TYR E 171      53.273  -8.250 133.311  1.00 88.88      E
ATOM   7485  CB   TYR E 171      54.601  -9.008 133.226  1.00 95.83      E
ATOM   7486  CG   TYR E 171      55.116  -9.472 134.568  1.00101.95      E
ATOM   7487  CD1  TYR E 171      55.171 -10.829 134.883  1.00103.49      E
ATOM   7488  CE1  TYR E 171      55.664 -11.265 136.109  1.00110.07      E
ATOM   7489  CD2  TYR E 171      55.563  -8.555 135.517  1.00103.27      E
ATOM   7490  CE2  TYR E 171      56.056  -8.980 136.746  1.00105.60      E
ATOM   7491  CZ   TYR E 171      56.107 -10.337 137.033  1.00110.88      E
ATOM   7492  OH   TYR E 171      56.620 -10.770 138.233  1.00112.74      E
ATOM   7493  C    TYR E 171      52.813  -7.834 131.909  1.00 83.27      E
ATOM   7494  O    TYR E 171      53.622  -7.431 131.072  1.00 86.08      E
ATOM   7495  N    LEU E 172      51.511  -7.942 131.661  1.00 80.00      E
ATOM   7496  CA   LEU E 172      50.932  -7.553 130.377  1.00 78.61      E
ATOM   7497  CB   LEU E 172      50.195  -8.728 129.724  1.00 81.70      E
ATOM   7498  CG   LEU E 172      51.000  -9.959 129.314  1.00 80.99      E
ATOM   7499  CD1  LEU E 172      50.093 -10.955 128.620  1.00 79.61      E
ATOM   7500  CD2  LEU E 172      52.115  -9.547 128.388  1.00 84.65      E
ATOM   7501  C    LEU E 172      49.948  -6.421 130.637  1.00 80.15      E
ATOM   7502  O    LEU E 172      49.781  -5.534 129.810  1.00 75.47      E
ATOM   7503  N    ILE E 173      49.305  -6.475 131.801  1.00 77.66      E
ATOM   7504  CA   ILE E 173      48.326  -5.483 132.238  1.00 77.74      E
ATOM   7505  CB   ILE E 173      46.896  -6.044 132.195  1.00 77.77      E
ATOM   7506  CG2  ILE E 173      46.493  -6.332 130.768  1.00 79.75      E
ATOM   7507  CG1  ILE E 173      46.818  -7.320 133.036  1.00 80.71      E
ATOM   7508  CD1  ILE E 173      45.477  -8.034 132.966  1.00 87.97      E
ATOM   7509  C    ILE E 173      48.656  -5.185 133.683  1.00 77.60      E
ATOM   7510  O    ILE E 173      49.151  -6.056 134.391  1.00 78.73      E
ATOM   7511  N    PRO E 174      48.389  -3.954 134.145  1.00 80.04      E
ATOM   7512  CD   PRO E 174      47.837  -2.800 133.419  1.00 82.16      E
ATOM   7513  CA   PRO E 174      48.683  -3.593 135.537  1.00 82.24      E
ATOM   7514  CB   PRO E 174      48.052  -2.217 135.673  1.00 82.39      E
ATOM   7515  CG   PRO E 174      48.247  -1.645 134.309  1.00 83.03      E
ATOM   7516  C    PRO E 174      48.077  -4.601 136.501  1.00 82.95      E
ATOM   7517  O    PRO E 174      47.144  -5.324 136.143  1.00 84.50      E
ATOM   7518  N    ASP E 175      48.605  -4.656 137.720  1.00 82.21      E
ATOM   7519  CA   ASP E 175      48.088  -5.599 138.702  1.00 82.11      E
ATOM   7520  CB   ASP E 175      49.073  -5.754 139.877  1.00 83.44      E
ATOM   7521  CG   ASP E 175      49.257  -7.214 140.309  1.00 84.17      E
ATOM   7522  OD1  ASP E 175      48.391  -7.742 141.040  1.00 85.40      E
ATOM   7523  OD2  ASP E 175      50.266  -7.839 139.910  1.00 85.65      E
ATOM   7524  C    ASP E 175      46.747  -5.058 139.175  1.00 78.94      E
ATOM   7525  O    ASP E 175      45.932  -5.783 139.735  1.00 77.51      E
ATOM   7526  N    LYS E 176      46.508  -3.778 138.919  1.00 76.87      E
ATOM   7527  CA   LYS E 176      45.259  -3.158 139.328  1.00 74.35      E
ATOM   7528  CB   LYS E 176      45.447  -1.644 139.452  1.00 74.65      E
ATOM   7529  CG   LYS E 176      46.325  -1.233 140.624  1.00 76.32      E
ATOM   7530  CD   LYS E 176      45.637  -1.547 141.943  1.00 78.68      E
ATOM   7531  CE   LYS E 176      46.646  -1.805 143.052  1.00 81.09      E
ATOM   7532  NZ   LYS E 176      45.988  -2.032 144.374  1.00 83.42      E
ATOM   7533  C    LYS E 176      44.114  -3.472 138.369  1.00 74.88      E
ATOM   7534  O    LYS E 176      42.951  -3.518 138.769  1.00 77.57      E
ATOM   7535  N    VAL E 177      44.441  -3.683 137.099  1.00 75.58      E
ATOM   7536  CA   VAL E 177      43.418  -3.998 136.108  1.00 75.22      E
ATOM   7537  CB   VAL E 177      43.868  -3.612 134.663  1.00 78.74      E
ATOM   7538  CG1  VAL E 177      43.265  -4.580 133.635  1.00 75.78      E
ATOM   7539  CG2  VAL E 177      43.417  -2.187 134.339  1.00 75.41      E
ATOM   7540  C    VAL E 177      43.110  -5.480 136.161  1.00 72.58      E
ATOM   7541  O    VAL E 177      41.973  -5.889 135.928  1.00 71.45      E
```

Figure 10 (116 of 142)

| ATOM | 7542 | N | LYS | E | 178 | 44.125 | -6.287 | 136.453 | 1.00 | 73.97 | E |
|---|---|---|---|---|---|---|---|---|---|---|---|
| ATOM | 7543 | CA | LYS | E | 178 | 43.895 | -7.716 | 136.540 | 1.00 | 73.83 | E |
| ATOM | 7544 | CB | LYS | E | 178 | 45.183 | -8.480 | 136.868 | 1.00 | 75.74 | E |
| ATOM | 7545 | CG | LYS | E | 178 | 44.997 | -10.005 | 136.855 | 1.00 | 70.58 | E |
| ATOM | 7546 | CD | LYS | E | 178 | 46.290 | -10.742 | 137.137 | 1.00 | 70.10 | E |
| ATOM | 7547 | CE | LYS | E | 178 | 46.817 | -10.419 | 138.525 | 1.00 | 68.79 | E |
| ATOM | 7548 | NZ | LYS | E | 178 | 48.147 | -11.034 | 138.766 | 1.00 | 71.67 | E |
| ATOM | 7549 | C | LYS | E | 178 | 42.875 | -7.928 | 137.651 | 1.00 | 75.62 | E |
| ATOM | 7550 | O | LYS | E | 178 | 41.895 | -8.656 | 137.471 | 1.00 | 77.22 | E |
| ATOM | 7551 | N | LYS | E | 179 | 43.101 | -7.281 | 138.795 | 1.00 | 72.24 | E |
| ATOM | 7552 | CA | LYS | E | 179 | 42.190 | -7.409 | 139.924 | 1.00 | 72.03 | E |
| ATOM | 7553 | CB | LYS | E | 179 | 42.671 | -6.578 | 141.115 | 1.00 | 70.37 | E |
| ATOM | 7554 | CG | LYS | E | 179 | 43.871 | -7.176 | 141.831 | 1.00 | 69.89 | E |
| ATOM | 7555 | CD | LYS | E | 179 | 44.320 | -6.316 | 143.008 | 1.00 | 70.20 | E |
| ATOM | 7556 | CE | LYS | E | 179 | 45.605 | -6.864 | 143.616 | 1.00 | 71.93 | E |
| ATOM | 7557 | NZ | LYS | E | 179 | 46.154 | -5.992 | 144.692 | 1.00 | 72.96 | E |
| ATOM | 7558 | C | LYS | E | 179 | 40.783 | -6.988 | 139.542 | 1.00 | 74.12 | E |
| ATOM | 7559 | O | LYS | E | 179 | 39.835 | -7.704 | 139.840 | 1.00 | 73.34 | E |
| ATOM | 7560 | N | TYR | E | 180 | 40.640 | -5.845 | 138.872 | 1.00 | 78.64 | E |
| ATOM | 7561 | CA | TYR | E | 180 | 39.314 | -5.378 | 138.475 | 1.00 | 86.39 | E |
| ATOM | 7562 | CB | TYR | E | 180 | 39.399 | -4.091 | 137.651 | 1.00 | 87.89 | E |
| ATOM | 7563 | CG | TYR | E | 180 | 38.033 | -3.512 | 137.341 | 1.00 | 89.53 | E |
| ATOM | 7564 | CD1 | TYR | E | 180 | 37.501 | -2.476 | 138.110 | 1.00 | 88.51 | E |
| ATOM | 7565 | CE1 | TYR | E | 180 | 36.221 | -1.984 | 137.866 | 1.00 | 86.64 | E |
| ATOM | 7566 | CD2 | TYR | E | 180 | 37.245 | -4.043 | 136.313 | 1.00 | 86.64 | E |
| ATOM | 7567 | CE2 | TYR | E | 180 | 35.963 | -3.564 | 136.063 | 1.00 | 86.15 | E |
| ATOM | 7568 | CZ | TYR | E | 180 | 35.456 | -2.534 | 136.840 | 1.00 | 89.22 | E |
| ATOM | 7569 | OH | TYR | E | 180 | 34.188 | -2.056 | 136.581 | 1.00 | 83.41 | E |
| ATOM | 7570 | C | TYR | E | 180 | 38.529 | -6.421 | 137.673 | 1.00 | 86.45 | E |
| ATOM | 7571 | O | TYR | E | 180 | 37.327 | -6.586 | 137.882 | 1.00 | 89.92 | E |
| ATOM | 7572 | N | VAL | E | 181 | 39.203 | -7.108 | 136.753 | 1.00 | 90.00 | E |
| ATOM | 7573 | CA | VAL | E | 181 | 38.567 | -8.131 | 135.914 | 1.00 | 90.57 | E |
| ATOM | 7574 | CB | VAL | E | 181 | 39.536 | -8.673 | 134.848 | 1.00 | 92.54 | E |
| ATOM | 7575 | CG1 | VAL | E | 181 | 38.892 | -9.852 | 134.120 | 1.00 | 93.11 | E |
| ATOM | 7576 | CG2 | VAL | E | 181 | 39.908 | -7.572 | 133.873 | 1.00 | 94.32 | E |
| ATOM | 7577 | C | VAL | E | 181 | 38.059 | -9.336 | 136.699 | 1.00 | 93.34 | E |
| ATOM | 7578 | O | VAL | E | 181 | 36.933 | -9.790 | 136.498 | 1.00 | 94.67 | E |
| ATOM | 7579 | N | GLU | E | 182 | 38.913 | -9.870 | 137.565 | 1.00 | 92.70 | E |
| ATOM | 7580 | CA | GLU | E | 182 | 38.559 | -11.019 | 138.383 | 1.00 | 93.24 | E |
| ATOM | 7581 | CB | GLU | E | 182 | 39.780 | -11.473 | 139.191 | 1.00 | 96.56 | E |
| ATOM | 7582 | CG | GLU | E | 182 | 41.064 | -11.599 | 138.367 | 1.00 | 102.53 | E |
| ATOM | 7583 | CD | GLU | E | 182 | 42.246 | -12.139 | 139.169 | 1.00 | 106.48 | E |
| ATOM | 7584 | OE1 | GLU | E | 182 | 42.557 | -11.575 | 140.246 | 1.00 | 108.77 | E |
| ATOM | 7585 | OE2 | GLU | E | 182 | 42.869 | -13.125 | 138.712 | 1.00 | 109.93 | E |
| ATOM | 7586 | C | GLU | E | 182 | 37.407 | -10.650 | 139.323 | 1.00 | 90.59 | E |
| ATOM | 7587 | O | GLU | E | 182 | 36.434 | -11.396 | 139.447 | 1.00 | 87.88 | E |
| ATOM | 7588 | N | GLU | E | 183 | 37.517 | -9.488 | 139.969 | 1.00 | 91.84 | E |
| ATOM | 7589 | CA | GLU | E | 183 | 36.497 | -9.004 | 140.905 | 1.00 | 93.38 | E |
| ATOM | 7590 | CB | GLU | E | 183 | 36.930 | -7.677 | 141.551 | 1.00 | 93.85 | E |
| ATOM | 7591 | CG | GLU | E | 183 | 38.246 | -7.737 | 142.301 | 1.00 | 99.75 | E |
| ATOM | 7592 | CD | GLU | E | 183 | 38.430 | -6.566 | 143.242 | 1.00 | 101.82 | E |
| ATOM | 7593 | OE1 | GLU | E | 183 | 38.196 | -5.411 | 142.824 | 1.00 | 101.24 | E |
| ATOM | 7594 | OE2 | GLU | E | 183 | 38.817 | -6.803 | 144.405 | 1.00 | 105.07 | E |
| ATOM | 7595 | C | GLU | E | 183 | 35.125 | -8.801 | 140.268 | 1.00 | 92.04 | E |
| ATOM | 7596 | O | GLU | E | 183 | 34.144 | -9.423 | 140.681 | 1.00 | 92.76 | E |
| ATOM | 7597 | N | ASN | E | 184 | 35.059 | -7.929 | 139.266 | 1.00 | 90.05 | E |
| ATOM | 7598 | CA | ASN | E | 184 | 33.795 | -7.635 | 138.605 | 1.00 | 87.56 | E |
| ATOM | 7599 | CB | ASN | E | 184 | 33.840 | -6.222 | 138.022 | 1.00 | 88.54 | E |
| ATOM | 7600 | CG | ASN | E | 184 | 32.789 | -5.321 | 138.632 | 1.00 | 92.48 | E |
| ATOM | 7601 | OD1 | ASN | E | 184 | 32.913 | -4.095 | 138.618 | 1.00 | 94.77 | E |
| ATOM | 7602 | ND2 | ASN | E | 184 | 31.734 | -5.929 | 139.166 | 1.00 | 95.22 | E |
| ATOM | 7603 | C | ASN | E | 184 | 33.330 | -8.633 | 137.546 | 1.00 | 85.44 | E |
| ATOM | 7604 | O | ASN | E | 184 | 32.554 | -8.283 | 136.660 | 1.00 | 85.67 | E |
| ATOM | 7605 | N | GLY | E | 185 | 33.808 | -9.872 | 137.650 | 1.00 | 86.47 | E |
| ATOM | 7606 | CA | GLY | E | 185 | 33.418 | -10.939 | 136.736 | 1.00 | 87.30 | E |
| ATOM | 7607 | C | GLY | E | 185 | 33.750 | -10.900 | 135.249 | 1.00 | 89.95 | E |

Figure 10 (117 of 142)

```
ATOM   7608  O    GLY E 185      33.270 -11.754 134.504  1.00 90.65      E
ATOM   7609  N    LEU E 186      34.575  -9.951 134.813  1.00 91.18      E
ATOM   7610  CA   LEU E 186      34.938  -9.809 133.395  1.00 91.58      E
ATOM   7611  CB   LEU E 186      35.780  -8.538 133.197  1.00 85.79      E
ATOM   7612  CG   LEU E 186      35.125  -7.159 133.014  1.00 83.46      E
ATOM   7613  CD1  LEU E 186      34.309  -7.134 131.718  1.00 81.21      E
ATOM   7614  CD2  LEU E 186      34.253  -6.832 134.206  1.00 83.48      E
ATOM   7615  C    LEU E 186      35.656 -10.965 132.684  1.00 92.67      E
ATOM   7616  O    LEU E 186      36.145 -11.911 133.308  1.00 97.53      E
ATOM   7617  N    TYR E 187      35.697 -10.841 131.358  1.00 92.50      E
ATOM   7618  CA   TYR E 187      36.345 -11.767 130.425  1.00 92.47      E
ATOM   7619  CB   TYR E 187      37.790 -11.286 130.189  1.00 92.95      E
ATOM   7620  CG   TYR E 187      37.881  -9.790 129.919  1.00 91.98      E
ATOM   7621  CD1  TYR E 187      37.180  -9.211 128.862  1.00 91.41      E
ATOM   7622  CE1  TYR E 187      37.190  -7.827 128.660  1.00 89.25      E
ATOM   7623  CD2  TYR E 187      38.609  -8.944 130.765  1.00 90.65      E
ATOM   7624  CE2  TYR E 187      38.625  -7.555 130.570  1.00 90.10      E
ATOM   7625  CZ   TYR E 187      37.910  -7.007 129.521  1.00 91.58      E
ATOM   7626  OH   TYR E 187      37.881  -5.642 129.362  1.00 86.63      E
ATOM   7627  C    TYR E 187      36.318 -13.268 130.761  1.00 90.13      E
ATOM   7628  O    TYR E 187      35.599 -14.006 130.059  1.00 87.06      E
TER    7629       TYR E 187
ATOM   7630  CB   LYS F   2      58.872 -29.128 144.337  1.00 78.63      F
ATOM   7631  CG   LYS F   2      58.556 -27.658 144.552  1.00 73.01      F
ATOM   7632  CD   LYS F   2      59.231 -27.126 145.814  1.00 72.94      F
ATOM   7633  CE   LYS F   2      58.640 -25.789 146.232  1.00 72.60      F
ATOM   7634  NZ   LYS F   2      59.306 -25.180 147.419  1.00 73.57      F
ATOM   7635  C    LYS F   2      59.129 -29.245 141.852  1.00 79.94      F
ATOM   7636  O    LYS F   2      60.336 -29.028 141.981  1.00 82.69      F
ATOM   7637  N    LYS F   2      58.331 -31.215 143.113  1.00 83.78      F
ATOM   7638  CA   LYS F   2      58.299 -29.720 143.047  1.00 78.98      F
ATOM   7639  N    LYS F   3      58.477 -29.082 140.698  1.00 75.97      F
ATOM   7640  CA   LYS F   3      59.137 -28.651 139.458  1.00 74.29      F
ATOM   7641  CB   LYS F   3      58.170 -28.817 138.293  1.00 76.04      F
ATOM   7642  CG   LYS F   3      57.374 -30.107 138.360  1.00 77.14      F
ATOM   7643  CD   LYS F   3      56.247 -30.086 137.346  1.00 79.53      F
ATOM   7644  CE   LYS F   3      55.268 -31.228 137.554  1.00 81.14      F
ATOM   7645  NZ   LYS F   3      54.048 -31.036 136.721  1.00 81.58      F
ATOM   7646  C    LYS F   3      59.602 -27.200 139.549  1.00 73.54      F
ATOM   7647  O    LYS F   3      58.784 -26.289 139.660  1.00 71.79      F
ATOM   7648  N    ILE F   4      60.915 -26.990 139.481  1.00 70.35      F
ATOM   7649  CA   ILE F   4      61.495 -25.654 139.603  1.00 67.97      F
ATOM   7650  CB   ILE F   4      62.373 -25.581 140.874  1.00 69.58      F
ATOM   7651  CG2  ILE F   4      63.097 -24.248 140.943  1.00 74.62      F
ATOM   7652  CG1  ILE F   4      61.494 -25.785 142.109  1.00 73.48      F
ATOM   7653  CD1  ILE F   4      62.233 -26.326 143.305  1.00 74.04      F
ATOM   7654  C    ILE F   4      62.318 -25.175 138.402  1.00 66.98      F
ATOM   7655  O    ILE F   4      63.117 -25.927 137.836  1.00 65.44      F
ATOM   7656  N    GLY F   5      62.115 -23.910 138.030  1.00 67.51      F
ATOM   7657  CA   GLY F   5      62.832 -23.320 136.912  1.00 62.60      F
ATOM   7658  C    GLY F   5      63.872 -22.300 137.348  1.00 60.23      F
ATOM   7659  O    GLY F   5      63.531 -21.183 137.742  1.00 64.12      F
ATOM   7660  N    ILE F   6      65.144 -22.685 137.286  1.00 64.14      F
ATOM   7661  CA   ILE F   6      66.238 -21.801 137.673  1.00 68.56      F
ATOM   7662  CB   ILE F   6      67.544 -22.595 137.908  1.00 69.11      F
ATOM   7663  CG2  ILE F   6      68.704 -21.635 138.187  1.00 68.92      F
ATOM   7664  CG1  ILE F   6      67.341 -23.571 139.073  1.00 67.78      F
ATOM   7665  CD1  ILE F   6      68.562 -24.394 139.432  1.00 70.60      F
ATOM   7666  C    ILE F   6      66.464 -20.764 136.584  1.00 68.44      F
ATOM   7667  O    ILE F   6      66.850 -21.099 135.463  1.00 69.12      F
ATOM   7668  N    PHE F   7      66.227 -19.504 136.941  1.00 69.34      F
ATOM   7669  CA   PHE F   7      66.352 -18.375 136.028  1.00 73.48      F
ATOM   7670  CB   PHE F   7      65.018 -17.618 135.999  1.00 78.17      F
ATOM   7671  CG   PHE F   7      64.951 -16.492 134.995  1.00 81.06      F
ATOM   7672  CD1  PHE F   7      65.474 -16.633 133.712  1.00 78.39      F
ATOM   7673  CD2  PHE F   7      64.282 -15.313 135.315  1.00 83.96      F
```

Figure 10 (118 of 142)

| | | | | | | | | | |
|---|---|---|---|---|---|---|---|---|---|
| ATOM | 7674 | CE1 | PHE | F | 7 | 65.325 | -15.618 | 132.765 | 1.00 81.97 | F |
| ATOM | 7675 | CE2 | PHE | F | 7 | 64.130 | -14.297 | 134.374 | 1.00 78.08 | F |
| ATOM | 7676 | CZ | PHE | F | 7 | 64.652 | -14.451 | 133.097 | 1.00 80.08 | F |
| ATOM | 7677 | C | PHE | F | 7 | 67.479 | -17.445 | 136.451 | 1.00 70.56 | F |
| ATOM | 7678 | O | PHE | F | 7 | 67.239 | -16.339 | 136.927 | 1.00 68.43 | F |
| ATOM | 7679 | N | GLY | F | 8 | 68.713 | -17.909 | 136.275 | 1.00 71.41 | F |
| ATOM | 7680 | CA | GLY | F | 8 | 69.869 | -17.104 | 136.630 | 1.00 66.90 | F |
| ATOM | 7681 | C | GLY | F | 8 | 70.123 | -15.957 | 135.660 | 1.00 65.82 | F |
| ATOM | 7682 | O | GLY | F | 8 | 69.815 | -16.056 | 134.476 | 1.00 68.65 | F |
| ATOM | 7683 | N | GLY | F | 9 | 70.690 | -14.869 | 136.166 | 1.00 61.92 | F |
| ATOM | 7684 | CA | GLY | F | 9 | 70.979 | -13.715 | 135.344 | 1.00 57.43 | F |
| ATOM | 7685 | C | GLY | F | 9 | 71.646 | -12.694 | 136.227 | 1.00 60.88 | F |
| ATOM | 7686 | O | GLY | F | 9 | 71.584 | -12.812 | 137.445 | 1.00 61.40 | F |
| ATOM | 7687 | N | THR | F | 10 | 72.283 | -11.692 | 135.643 | 1.00 58.71 | F |
| ATOM | 7688 | CA | THR | F | 10 | 72.953 | -10.702 | 136.465 | 1.00 57.58 | F |
| ATOM | 7689 | CB | THR | F | 10 | 74.151 | -10.079 | 135.745 | 1.00 58.20 | F |
| ATOM | 7690 | OG1 | THR | F | 10 | 73.793 | -8.784 | 135.245 | 1.00 60.62 | F |
| ATOM | 7691 | CG2 | THR | F | 10 | 74.588 | -10.969 | 134.597 | 1.00 59.48 | F |
| ATOM | 7692 | C | THR | F | 10 | 71.985 | -9.604 | 136.833 | 1.00 57.99 | F |
| ATOM | 7693 | O | THR | F | 10 | 72.242 | -8.824 | 137.747 | 1.00 61.61 | F |
| ATOM | 7694 | N | PHE | F | 11 | 70.873 | -9.545 | 136.115 | 1.00 55.55 | F |
| ATOM | 7695 | CA | PHE | F | 11 | 69.858 | -8.539 | 136.369 | 1.00 56.21 | F |
| ATOM | 7696 | CB | PHE | F | 11 | 68.883 | -9.081 | 137.413 | 1.00 55.84 | F |
| ATOM | 7697 | CG | PHE | F | 11 | 68.438 | -10.496 | 137.141 | 1.00 55.28 | F |
| ATOM | 7698 | CD1 | PHE | F | 11 | 69.022 | -11.572 | 137.803 | 1.00 52.04 | F |
| ATOM | 7699 | CD2 | PHE | F | 11 | 67.473 | -10.757 | 136.177 | 1.00 53.15 | F |
| ATOM | 7700 | CE1 | PHE | F | 11 | 68.653 | -12.888 | 137.498 | 1.00 53.20 | F |
| ATOM | 7701 | CE2 | PHE | F | 11 | 67.097 | -12.068 | 135.864 | 1.00 51.76 | F |
| ATOM | 7702 | CZ | PHE | F | 11 | 67.690 | -13.132 | 136.525 | 1.00 53.04 | F |
| ATOM | 7703 | C | PHE | F | 11 | 70.478 | -7.203 | 136.816 | 1.00 55.02 | F |
| ATOM | 7704 | O | PHE | F | 11 | 70.481 | -6.858 | 137.997 | 1.00 54.14 | F |
| ATOM | 7705 | N | ASP | F | 12 | 71.021 | -6.457 | 135.859 | 1.00 57.47 | F |
| ATOM | 7706 | CA | ASP | F | 12 | 71.628 | -5.180 | 136.152 | 1.00 66.30 | F |
| ATOM | 7707 | CB | ASP | F | 12 | 73.149 | -5.305 | 136.150 | 1.00 65.88 | F |
| ATOM | 7708 | CG | ASP | F | 12 | 73.838 | -3.962 | 136.207 | 1.00 72.10 | F |
| ATOM | 7709 | OD1 | ASP | F | 12 | 73.518 | -3.169 | 137.120 | 1.00 77.42 | F |
| ATOM | 7710 | OD2 | ASP | F | 12 | 74.692 | -3.693 | 135.338 | 1.00 77.02 | F |
| ATOM | 7711 | C | ASP | F | 12 | 71.236 | -4.046 | 135.199 | 1.00 65.48 | F |
| ATOM | 7712 | O | ASP | F | 12 | 71.998 | -3.703 | 134.299 | 1.00 65.37 | F |
| ATOM | 7713 | N | PRO | F | 13 | 70.004 | -3.512 | 135.326 | 1.00 66.70 | F |
| ATOM | 7714 | CD | PRO | F | 13 | 69.649 | -2.224 | 134.688 | 1.00 69.43 | F |
| ATOM | 7715 | CA | PRO | F | 13 | 69.003 | -3.828 | 136.344 | 1.00 75.34 | F |
| ATOM | 7716 | CB | PRO | F | 13 | 68.377 | -2.489 | 136.647 | 1.00 68.74 | F |
| ATOM | 7717 | CG | PRO | F | 13 | 68.267 | -1.924 | 135.286 | 1.00 70.27 | F |
| ATOM | 7718 | C | PRO | F | 13 | 67.967 | -4.807 | 135.769 | 1.00 73.17 | F |
| ATOM | 7719 | O | PRO | F | 13 | 67.933 | -5.062 | 134.560 | 1.00 70.22 | F |
| ATOM | 7720 | N | PRO | F | 14 | 67.100 | -5.345 | 136.641 | 1.00 80.69 | F |
| ATOM | 7721 | CD | PRO | F | 14 | 66.966 | -5.091 | 138.085 | 1.00 83.20 | F |
| ATOM | 7722 | CA | PRO | F | 14 | 66.075 | -6.285 | 136.186 | 1.00 80.83 | F |
| ATOM | 7723 | CB | PRO | F | 14 | 65.518 | -6.863 | 137.489 | 1.00 82.19 | F |
| ATOM | 7724 | CG | PRO | F | 14 | 66.511 | -6.426 | 138.570 | 1.00 84.04 | F |
| ATOM | 7725 | C | PRO | F | 14 | 65.040 | -5.455 | 135.471 | 1.00 67.86 | F |
| ATOM | 7726 | O | PRO | F | 14 | 64.994 | -4.239 | 135.654 | 1.00 70.29 | F |
| ATOM | 7727 | N | HIS | F | 15 | 64.209 | -6.091 | 134.664 | 1.00 61.92 | F |
| ATOM | 7728 | CA | HIS | F | 15 | 63.182 | -5.346 | 133.969 | 1.00 62.81 | F |
| ATOM | 7729 | CB | HIS | F | 15 | 63.762 | -4.711 | 132.714 | 1.00 64.24 | F |
| ATOM | 7730 | CG | HIS | F | 15 | 64.464 | -5.682 | 131.824 | 1.00 66.62 | F |
| ATOM | 7731 | CD2 | HIS | F | 15 | 65.770 | -5.802 | 131.493 | 1.00 67.82 | F |
| ATOM | 7732 | ND1 | HIS | F | 15 | 63.801 | -6.689 | 131.159 | 1.00 61.61 | F |
| ATOM | 7733 | CE1 | HIS | F | 15 | 64.671 | -7.387 | 130.452 | 1.00 67.63 | F |
| ATOM | 7734 | NE2 | HIS | F | 15 | 65.872 | -6.869 | 130.637 | 1.00 66.25 | F |
| ATOM | 7735 | C | HIS | F | 15 | 62.021 | -6.251 | 133.627 | 1.00 59.12 | F |
| ATOM | 7736 | O | HIS | F | 15 | 62.151 | -7.472 | 133.652 | 1.00 57.34 | F |
| ATOM | 7737 | N | ASN | F | 16 | 60.884 | -5.641 | 133.320 | 1.00 55.83 | F |
| ATOM | 7738 | CA | ASN | F | 16 | 59.682 | -6.383 | 132.990 | 1.00 56.45 | F |
| ATOM | 7739 | CB | ASN | F | 16 | 58.604 | -5.428 | 132.478 | 1.00 63.30 | F |

Figure 10 (119 of 142)

| | | | | | | | | | |
|---|---|---|---|---|---|---|---|---|---|
| ATOM | 7740 | CG | ASN | F | 16 | 58.351 | -4.262 | 133.432 | 1.00 67.85 | F |
| ATOM | 7741 | OD1 | ASN | F | 16 | 58.240 | -4.443 | 134.643 | 1.00 68.98 | F |
| ATOM | 7742 | ND2 | ASN | F | 16 | 58.246 | -3.062 | 132.882 | 1.00 72.23 | F |
| ATOM | 7743 | C | ASN | F | 16 | 59.963 | -7.471 | 131.964 | 1.00 54.66 | F |
| ATOM | 7744 | O | ASN | F | 16 | 59.283 | -8.490 | 131.941 | 1.00 51.34 | F |
| ATOM | 7745 | N | GLY | F | 17 | 60.967 | -7.265 | 131.119 | 1.00 52.46 | F |
| ATOM | 7746 | CA | GLY | F | 17 | 61.286 | -8.280 | 130.135 | 1.00 57.24 | F |
| ATOM | 7747 | C | GLY | F | 17 | 61.485 | -9.615 | 130.830 | 1.00 56.46 | F |
| ATOM | 7748 | O | GLY | F | 17 | 60.893 | -10.636 | 130.469 | 1.00 59.16 | F |
| ATOM | 7749 | N | HIS | F | 18 | 62.335 | -9.602 | 131.847 | 1.00 55.01 | F |
| ATOM | 7750 | CA | HIS | F | 18 | 62.615 | -10.801 | 132.615 | 1.00 54.45 | F |
| ATOM | 7751 | CB | HIS | F | 18 | 63.569 | -10.462 | 133.761 | 1.00 56.50 | F |
| ATOM | 7752 | CG | HIS | F | 18 | 64.912 | -9.981 | 133.309 | 1.00 58.33 | F |
| ATOM | 7753 | CD2 | HIS | F | 18 | 65.788 | -10.494 | 132.413 | 1.00 55.71 | F |
| ATOM | 7754 | ND1 | HIS | F | 18 | 65.510 | -8.853 | 133.829 | 1.00 59.29 | F |
| ATOM | 7755 | CE1 | HIS | F | 18 | 66.698 | -8.694 | 133.273 | 1.00 58.11 | F |
| ATOM | 7756 | NE2 | HIS | F | 18 | 66.891 | -9.677 | 132.410 | 1.00 57.23 | F |
| ATOM | 7757 | C | HIS | F | 18 | 61.299 | -11.316 | 133.178 | 1.00 51.14 | F |
| ATOM | 7758 | O | HIS | F | 18 | 60.892 | -12.455 | 132.930 | 1.00 47.60 | F |
| ATOM | 7759 | N | LEU | F | 19 | 60.637 | -10.443 | 133.930 | 1.00 55.20 | F |
| ATOM | 7760 | CA | LEU | F | 19 | 59.367 | -10.747 | 134.566 | 1.00 56.36 | F |
| ATOM | 7761 | CB | LEU | F | 19 | 58.761 | -9.461 | 135.110 | 1.00 59.93 | F |
| ATOM | 7762 | CG | LEU | F | 19 | 59.600 | -8.797 | 136.196 | 1.00 59.09 | F |
| ATOM | 7763 | CD1 | LEU | F | 19 | 59.069 | -7.404 | 136.484 | 1.00 60.81 | F |
| ATOM | 7764 | CD2 | LEU | F | 19 | 59.573 | -9.667 | 137.442 | 1.00 60.77 | F |
| ATOM | 7765 | C | LEU | F | 19 | 58.375 | -11.466 | 133.659 | 1.00 59.04 | F |
| ATOM | 7766 | O | LEU | F | 19 | 57.694 | -12.383 | 134.105 | 1.00 62.41 | F |
| ATOM | 7767 | N | LEU | F | 20 | 58.266 | -11.058 | 132.397 | 1.00 60.07 | F |
| ATOM | 7768 | CA | LEU | F | 20 | 57.350 | -11.753 | 131.498 | 1.00 64.72 | F |
| ATOM | 7769 | CB | LEU | F | 20 | 57.244 | -11.050 | 130.156 | 1.00 65.27 | F |
| ATOM | 7770 | CG | LEU | F | 20 | 56.346 | -9.828 | 130.060 | 1.00 65.90 | F |
| ATOM | 7771 | CD1 | LEU | F | 20 | 57.172 | -8.563 | 130.198 | 1.00 67.84 | F |
| ATOM | 7772 | CD2 | LEU | F | 20 | 55.654 | -9.856 | 128.709 | 1.00 67.08 | F |
| ATOM | 7773 | C | LEU | F | 20 | 57.944 | -13.123 | 131.279 | 1.00 67.39 | F |
| ATOM | 7774 | O | LEU | F | 20 | 57.337 | -14.143 | 131.590 | 1.00 64.57 | F |
| ATOM | 7775 | N | MET | F | 21 | 59.149 | -13.117 | 130.733 | 1.00 71.89 | F |
| ATOM | 7776 | CA | MET | F | 21 | 59.898 | -14.327 | 130.468 | 1.00 76.55 | F |
| ATOM | 7777 | CB | MET | F | 21 | 61.380 | -14.017 | 130.507 | 1.00 74.94 | F |
| ATOM | 7778 | CG | MET | F | 21 | 62.041 | -14.015 | 129.176 | 1.00 75.53 | F |
| ATOM | 7779 | SD | MET | F | 21 | 63.699 | -14.547 | 129.463 | 1.00 73.65 | F |
| ATOM | 7780 | CE | MET | F | 21 | 63.764 | -16.095 | 128.568 | 1.00 65.58 | F |
| ATOM | 7781 | C | MET | F | 21 | 59.606 | -15.402 | 131.495 | 1.00 78.88 | F |
| ATOM | 7782 | O | MET | F | 21 | 59.222 | -16.528 | 131.164 | 1.00 77.86 | F |
| ATOM | 7783 | N | ALA | F | 22 | 59.807 | -15.041 | 132.753 | 1.00 82.38 | F |
| ATOM | 7784 | CA | ALA | F | 22 | 59.568 | -15.955 | 133.851 | 1.00 79.47 | F |
| ATOM | 7785 | CB | ALA | F | 22 | 59.919 | -15.273 | 135.169 | 1.00 79.85 | F |
| ATOM | 7786 | C | ALA | F | 22 | 58.108 | -16.358 | 133.853 | 1.00 78.13 | F |
| ATOM | 7787 | O | ALA | F | 22 | 57.764 | -17.487 | 133.517 | 1.00 80.96 | F |
| ATOM | 7788 | N | ASN | F | 23 | 57.256 | -15.401 | 134.203 | 1.00 76.46 | F |
| ATOM | 7789 | CA | ASN | F | 23 | 55.824 | -15.634 | 134.288 | 1.00 77.37 | F |
| ATOM | 7790 | CB | ASN | F | 23 | 55.083 | -14.305 | 134.498 | 1.00 78.60 | F |
| ATOM | 7791 | CG | ASN | F | 23 | 53.664 | -14.494 | 135.047 | 1.00 75.15 | F |
| ATOM | 7792 | OD1 | ASN | F | 23 | 52.680 | -14.258 | 134.348 | 1.00 77.40 | F |
| ATOM | 7793 | ND2 | ASN | F | 23 | 53.561 | -14.915 | 136.303 | 1.00 74.63 | F |
| ATOM | 7794 | C | ASN | F | 23 | 55.229 | -16.393 | 133.110 | 1.00 74.68 | F |
| ATOM | 7795 | O | ASN | F | 23 | 54.163 | -16.964 | 133.233 | 1.00 76.02 | F |
| ATOM | 7796 | N | GLU | F | 24 | 55.891 | -16.404 | 131.965 | 1.00 72.45 | F |
| ATOM | 7797 | CA | GLU | F | 24 | 55.342 | -17.150 | 130.838 | 1.00 75.76 | F |
| ATOM | 7798 | CB | GLU | F | 24 | 55.647 | -16.452 | 129.512 | 1.00 73.48 | F |
| ATOM | 7799 | CG | GLU | F | 24 | 54.891 | -15.156 | 129.244 | 1.00 72.19 | F |
| ATOM | 7800 | CD | GLU | F | 24 | 53.403 | -15.367 | 129.078 | 1.00 72.64 | F |
| ATOM | 7801 | OE1 | GLU | F | 24 | 53.012 | -16.358 | 128.420 | 1.00 67.03 | F |
| ATOM | 7802 | OE2 | GLU | F | 24 | 52.629 | -14.532 | 129.596 | 1.00 72.48 | F |
| ATOM | 7803 | C | GLU | F | 24 | 55.970 | -18.537 | 130.835 | 1.00 72.29 | F |
| ATOM | 7804 | O | GLU | F | 24 | 55.270 | -19.548 | 130.716 | 1.00 73.64 | F |
| ATOM | 7805 | N | VAL | F | 25 | 57.298 | -18.564 | 130.971 | 1.00 70.50 | F |

Figure 10 (120 of 142)

| ATOM | 7806 | CA | VAL | F | 25 | 58.081 | -19.805 | 131.001 | 1.00 | 74.59 | F |
|---|---|---|---|---|---|---|---|---|---|---|---|
| ATOM | 7807 | CB | VAL | F | 25 | 59.558 | -19.550 | 131.413 | 1.00 | 64.24 | F |
| ATOM | 7808 | CG1 | VAL | F | 25 | 60.180 | -20.848 | 131.881 | 1.00 | 65.32 | F |
| ATOM | 7809 | CG2 | VAL | F | 25 | 60.358 | -19.005 | 130.242 | 1.00 | 64.02 | F |
| ATOM | 7810 | C | VAL | F | 25 | 57.507 | -20.824 | 131.979 | 1.00 | 66.18 | F |
| ATOM | 7811 | O | VAL | F | 25 | 57.492 | -22.019 | 131.695 | 1.00 | 67.03 | F |
| ATOM | 7812 | N | LEU | F | 26 | 57.090 | -20.341 | 133.146 | 1.00 | 64.49 | F |
| ATOM | 7813 | CA | LEU | F | 26 | 56.496 | -21.180 | 134.171 | 1.00 | 67.02 | F |
| ATOM | 7814 | CB | LEU | F | 26 | 55.974 | -20.258 | 135.288 | 1.00 | 65.12 | F |
| ATOM | 7815 | CG | LEU | F | 26 | 55.187 | -20.608 | 136.554 | 1.00 | 63.46 | F |
| ATOM | 7816 | CD1 | LEU | F | 26 | 55.699 | -21.874 | 137.184 | 1.00 | 62.18 | F |
| ATOM | 7817 | CD2 | LEU | F | 26 | 55.308 | -19.425 | 137.532 | 1.00 | 60.99 | F |
| ATOM | 7818 | C | LEU | F | 26 | 55.385 | -21.911 | 133.418 | 1.00 | 72.28 | F |
| ATOM | 7819 | O | LEU | F | 26 | 55.644 | -22.857 | 132.691 | 1.00 | 69.98 | F |
| ATOM | 7820 | N | TYR | F | 27 | 54.163 | -21.439 | 133.563 | 1.00 | 73.06 | F |
| ATOM | 7821 | CA | TYR | F | 27 | 52.984 | -21.983 | 132.899 | 1.00 | 79.25 | F |
| ATOM | 7822 | CB | TYR | F | 27 | 52.052 | -20.812 | 132.583 | 1.00 | 84.46 | F |
| ATOM | 7823 | CG | TYR | F | 27 | 52.022 | -19.810 | 133.724 | 1.00 | 91.14 | F |
| ATOM | 7824 | CD1 | TYR | F | 27 | 53.198 | -19.222 | 134.178 | 1.00 | 91.00 | F |
| ATOM | 7825 | CE1 | TYR | F | 27 | 53.213 | -18.369 | 135.265 | 1.00 | 91.62 | F |
| ATOM | 7826 | CD2 | TYR | F | 27 | 50.841 | -19.499 | 134.397 | 1.00 | 87.60 | F |
| ATOM | 7827 | CE2 | TYR | F | 27 | 50.848 | -18.628 | 135.499 | 1.00 | 88.57 | F |
| ATOM | 7828 | CZ | TYR | F | 27 | 52.049 | -18.074 | 135.922 | 1.00 | 92.74 | F |
| ATOM | 7829 | OH | TYR | F | 27 | 52.114 | -17.232 | 137.008 | 1.00 | 88.93 | F |
| ATOM | 7830 | C | TYR | F | 27 | 53.188 | -22.854 | 131.651 | 1.00 | 77.13 | F |
| ATOM | 7831 | O | TYR | F | 27 | 52.792 | -24.020 | 131.644 | 1.00 | 75.91 | F |
| ATOM | 7832 | N | GLN | F | 28 | 53.788 | -22.310 | 130.595 | 1.00 | 82.44 | F |
| ATOM | 7833 | CA | GLN | F | 28 | 53.978 | -23.106 | 129.382 | 1.00 | 86.04 | F |
| ATOM | 7834 | CB | GLN | F | 28 | 54.536 | -22.236 | 128.245 | 1.00 | 89.18 | F |
| ATOM | 7835 | CG | GLN | F | 28 | 54.342 | -22.836 | 126.848 | 1.00 | 92.88 | F |
| ATOM | 7836 | CD | GLN | F | 28 | 52.918 | -23.335 | 126.601 | 1.00 | 91.82 | F |
| ATOM | 7837 | OE1 | GLN | F | 28 | 51.950 | -22.583 | 126.739 | 1.00 | 92.05 | F |
| ATOM | 7838 | NE2 | GLN | F | 28 | 52.787 | -24.616 | 126.242 | 1.00 | 90.76 | F |
| ATOM | 7839 | C | GLN | F | 28 | 54.886 | -24.313 | 129.634 | 1.00 | 90.43 | F |
| ATOM | 7840 | O | GLN | F | 28 | 54.877 | -25.275 | 128.871 | 1.00 | 83.10 | F |
| ATOM | 7841 | N | ALA | F | 29 | 55.657 | -24.259 | 130.716 | 1.00 | 94.34 | F |
| ATOM | 7842 | CA | ALA | F | 29 | 56.560 | -25.347 | 131.085 | 1.00 | 98.49 | F |
| ATOM | 7843 | CB | ALA | F | 29 | 57.965 | -24.800 | 131.341 | 1.00 | 101.33 | F |
| ATOM | 7844 | C | ALA | F | 29 | 56.047 | -26.086 | 132.327 | 1.00 | 97.55 | F |
| ATOM | 7845 | O | ALA | F | 29 | 56.739 | -26.933 | 132.885 | 1.00 | 98.81 | F |
| ATOM | 7846 | N | GLY | F | 30 | 54.837 | -25.747 | 132.763 | 1.00 | 98.31 | F |
| ATOM | 7847 | CA | GLY | F | 30 | 54.234 | -26.396 | 133.919 | 1.00 | 98.85 | F |
| ATOM | 7848 | C | GLY | F | 30 | 55.037 | -26.444 | 135.205 | 1.00 | 98.22 | F |
| ATOM | 7849 | O | GLY | F | 30 | 54.927 | -27.406 | 135.967 | 1.00 | 98.70 | F |
| ATOM | 7850 | N | LEU | F | 31 | 55.828 | -25.405 | 135.459 | 1.00 | 95.56 | F |
| ATOM | 7851 | CA | LEU | F | 31 | 56.644 | -25.338 | 136.666 | 1.00 | 90.39 | F |
| ATOM | 7852 | CB | LEU | F | 31 | 57.809 | -24.369 | 136.463 | 1.00 | 90.20 | F |
| ATOM | 7853 | CG | LEU | F | 31 | 58.644 | -24.631 | 135.213 | 1.00 | 90.79 | F |
| ATOM | 7854 | CD1 | LEU | F | 31 | 59.834 | -23.700 | 135.207 | 1.00 | 91.29 | F |
| ATOM | 7855 | CD2 | LEU | F | 31 | 59.106 | -26.074 | 135.191 | 1.00 | 91.74 | F |
| ATOM | 7856 | C | LEU | F | 31 | 55.833 | -24.896 | 137.875 | 1.00 | 89.40 | F |
| ATOM | 7857 | O | LEU | F | 31 | 54.729 | -24.374 | 137.741 | 1.00 | 88.70 | F |
| ATOM | 7858 | N | ASP | F | 32 | 56.389 | -25.102 | 139.060 | 1.00 | 88.25 | F |
| ATOM | 7859 | CA | ASP | F | 32 | 55.711 | -24.708 | 140.281 | 1.00 | 87.92 | F |
| ATOM | 7860 | CB | ASP | F | 32 | 56.032 | -25.708 | 141.395 | 1.00 | 95.44 | F |
| ATOM | 7861 | CG | ASP | F | 32 | 55.432 | -27.077 | 141.126 | 1.00 | 98.43 | F |
| ATOM | 7862 | OD1 | ASP | F | 32 | 54.190 | -27.207 | 141.191 | 1.00 | 101.78 | F |
| ATOM | 7863 | OD2 | ASP | F | 32 | 56.197 | -28.020 | 140.834 | 1.00 | 99.70 | F |
| ATOM | 7864 | C | ASP | F | 32 | 56.159 | -23.298 | 140.647 | 1.00 | 86.71 | F |
| ATOM | 7865 | O | ASP | F | 32 | 55.336 | -22.430 | 140.944 | 1.00 | 84.45 | F |
| ATOM | 7866 | N | GLU | F | 33 | 57.467 | -23.068 | 140.601 | 1.00 | 81.50 | F |
| ATOM | 7867 | CA | GLU | F | 33 | 58.017 | -21.758 | 140.915 | 1.00 | 81.48 | F |
| ATOM | 7868 | CB | GLU | F | 33 | 58.389 | -21.668 | 142.408 | 1.00 | 80.92 | F |
| ATOM | 7869 | CG | GLU | F | 33 | 58.109 | -22.932 | 143.234 | 1.00 | 84.82 | F |
| ATOM | 7870 | CD | GLU | F | 33 | 58.224 | -22.708 | 144.744 | 1.00 | 84.95 | F |
| ATOM | 7871 | OE1 | GLU | F | 33 | 59.325 | -22.385 | 145.239 | 1.00 | 81.65 | F |

Figure 10 (121 of 142)

| | | | | | | | | | |
|---|---|---|---|---|---|---|---|---|---|
| ATOM | 7872 | OE2 | GLU | F | 33 | 57.202 | -22.861 | 145.442 | 1.00 83.18 | F |
| ATOM | 7873 | C | GLU | F | 33 | 59.236 | -21.461 | 140.047 | 1.00 80.55 | F |
| ATOM | 7874 | O | GLU | F | 33 | 59.862 | -22.369 | 139.506 | 1.00 76.10 | F |
| ATOM | 7875 | N | ILE | F | 34 | 59.545 | -20.176 | 139.900 | 1.00 83.33 | F |
| ATOM | 7876 | CA | ILE | F | 34 | 60.697 | -19.724 | 139.118 | 1.00 85.38 | F |
| ATOM | 7877 | CB | ILE | F | 34 | 60.320 | -18.615 | 138.104 | 1.00 81.32 | F |
| ATOM | 7878 | CG2 | ILE | F | 34 | 61.557 | -18.174 | 137.356 | 1.00 79.81 | F |
| ATOM | 7879 | CG1 | ILE | F | 34 | 59.270 | -19.116 | 137.114 | 1.00 80.42 | F |
| ATOM | 7880 | CD1 | ILE | F | 34 | 59.761 | -20.235 | 136.227 | 1.00 82.36 | F |
| ATOM | 7881 | C | ILE | F | 34 | 61.669 | -19.106 | 140.113 | 1.00 80.13 | F |
| ATOM | 7882 | O | ILE | F | 34 | 61.269 | -18.277 | 140.928 | 1.00 89.58 | F |
| ATOM | 7883 | N | TRP | F | 35 | 62.936 | -19.495 | 140.062 | 1.00 79.93 | F |
| ATOM | 7884 | CA | TRP | F | 35 | 63.903 | -18.932 | 140.995 | 1.00 88.49 | F |
| ATOM | 7885 | CB | TRP | F | 35 | 64.724 | -20.048 | 141.665 | 1.00100.58 | F |
| ATOM | 7886 | CG | TRP | F | 35 | 63.946 | -20.977 | 142.588 | 1.00102.25 | F |
| ATOM | 7887 | CD2 | TRP | F | 35 | 64.448 | -22.152 | 143.237 | 1.00 98.73 | F |
| ATOM | 7888 | CE2 | TRP | F | 35 | 63.383 | -22.712 | 143.975 | 1.00101.73 | F |
| ATOM | 7889 | CE3 | TRP | F | 35 | 65.696 | -22.783 | 143.263 | 1.00101.34 | F |
| ATOM | 7890 | CD1 | TRP | F | 35 | 62.632 | -20.876 | 142.955 | 1.00101.03 | F |
| ATOM | 7891 | NE1 | TRP | F | 35 | 62.287 | -21.915 | 143.786 | 1.00104.01 | F |
| ATOM | 7892 | CZ2 | TRP | F | 35 | 63.527 | -23.876 | 144.730 | 1.00100.66 | F |
| ATOM | 7893 | CZ3 | TRP | F | 35 | 65.840 | -23.942 | 144.014 | 1.00102.00 | F |
| ATOM | 7894 | CH2 | TRP | F | 35 | 64.758 | -24.476 | 144.738 | 1.00100.32 | F |
| ATOM | 7895 | C | TRP | F | 35 | 64.835 | -17.953 | 140.289 | 1.00 79.17 | F |
| ATOM | 7896 | O | TRP | F | 35 | 65.553 | -18.327 | 139.367 | 1.00 77.89 | F |
| ATOM | 7897 | N | PHE | F | 36 | 64.809 | -16.695 | 140.721 | 1.00 73.83 | F |
| ATOM | 7898 | CA | PHE | F | 36 | 65.664 | -15.664 | 140.141 | 1.00 69.04 | F |
| ATOM | 7899 | CB | PHE | F | 36 | 65.029 | -14.289 | 140.327 | 1.00 69.15 | F |
| ATOM | 7900 | CG | PHE | F | 36 | 63.903 | -14.014 | 139.380 | 1.00 66.14 | F |
| ATOM | 7901 | CD1 | PHE | F | 36 | 62.759 | -14.794 | 139.401 | 1.00 67.86 | F |
| ATOM | 7902 | CD2 | PHE | F | 36 | 63.991 | -12.979 | 138.460 | 1.00 63.80 | F |
| ATOM | 7903 | CE1 | PHE | F | 36 | 61.720 | -14.549 | 138.521 | 1.00 67.65 | F |
| ATOM | 7904 | CE2 | PHE | F | 36 | 62.959 | -12.728 | 137.577 | 1.00 65.17 | F |
| ATOM | 7905 | CZ | PHE | F | 36 | 61.821 | -13.514 | 137.606 | 1.00 64.94 | F |
| ATOM | 7906 | C | PHE | F | 36 | 67.041 | -15.686 | 140.790 | 1.00 65.70 | F |
| ATOM | 7907 | O | PHE | F | 36 | 67.234 | -15.115 | 141.861 | 1.00 68.94 | F |
| ATOM | 7908 | N | MET | F | 37 | 67.996 | -16.317 | 140.111 | 1.00 58.75 | F |
| ATOM | 7909 | CA | MET | F | 37 | 69.362 | -16.491 | 140.610 | 1.00 60.40 | F |
| ATOM | 7910 | CB | MET | F | 37 | 69.819 | -17.918 | 140.276 | 1.00 53.84 | F |
| ATOM | 7911 | CG | MET | F | 37 | 71.200 | -18.285 | 140.743 | 1.00 45.37 | F |
| ATOM | 7912 | SD | MET | F | 37 | 71.393 | -20.059 | 140.682 | 1.00 42.97 | F |
| ATOM | 7913 | CE | MET | F | 37 | 71.911 | -20.300 | 138.985 | 1.00 46.46 | F |
| ATOM | 7914 | C | MET | F | 37 | 70.430 | -15.484 | 140.162 | 1.00 59.93 | F |
| ATOM | 7915 | O | MET | F | 37 | 71.127 | -15.695 | 139.182 | 1.00 63.60 | F |
| ATOM | 7916 | N | PRO | F | 38 | 70.589 | -14.387 | 140.908 | 1.00 61.69 | F |
| ATOM | 7917 | CD | PRO | F | 38 | 69.826 | -14.057 | 142.121 | 1.00 66.67 | F |
| ATOM | 7918 | CA | PRO | F | 38 | 71.566 | -13.339 | 140.612 | 1.00 66.15 | F |
| ATOM | 7919 | CB | PRO | F | 38 | 71.293 | -12.297 | 141.695 | 1.00 66.62 | F |
| ATOM | 7920 | CG | PRO | F | 38 | 69.874 | -12.571 | 142.110 | 1.00 65.71 | F |
| ATOM | 7921 | C | PRO | F | 38 | 72.995 | -13.876 | 140.698 | 1.00 64.91 | F |
| ATOM | 7922 | O | PRO | F | 38 | 73.317 | -14.657 | 141.591 | 1.00 68.20 | F |
| ATOM | 7923 | N | ASN | F | 39 | 73.848 | -13.429 | 139.782 | 1.00 68.37 | F |
| ATOM | 7924 | CA | ASN | F | 39 | 75.250 | -13.853 | 139.727 | 1.00 73.96 | F |
| ATOM | 7925 | CB | ASN | F | 39 | 75.806 | -13.656 | 138.326 | 1.00 81.07 | F |
| ATOM | 7926 | CG | ASN | F | 39 | 75.206 | -14.596 | 137.338 | 1.00 83.24 | F |
| ATOM | 7927 | OD1 | ASN | F | 39 | 74.468 | -15.511 | 137.711 | 1.00 84.17 | F |
| ATOM | 7928 | ND2 | ASN | F | 39 | 75.514 | -14.388 | 136.061 | 1.00 87.34 | F |
| ATOM | 7929 | C | ASN | F | 39 | 76.224 | -13.183 | 140.683 | 1.00 74.57 | F |
| ATOM | 7930 | O | ASN | F | 39 | 75.914 | -12.921 | 141.848 | 1.00 76.47 | F |
| ATOM | 7931 | N | GLN | F | 40 | 77.418 | -12.914 | 140.161 | 1.00 71.45 | F |
| ATOM | 7932 | CA | GLN | F | 40 | 78.473 | -12.289 | 140.934 | 1.00 74.41 | F |
| ATOM | 7933 | CB | GLN | F | 40 | 79.424 | -13.358 | 141.469 | 1.00 80.48 | F |
| ATOM | 7934 | CG | GLN | F | 40 | 79.573 | -13.334 | 142.976 | 1.00 91.73 | F |
| ATOM | 7935 | CD | GLN | F | 40 | 79.348 | -14.695 | 143.592 | 1.00 97.48 | F |
| ATOM | 7936 | OE1 | GLN | F | 40 | 79.147 | -14.816 | 144.801 | 1.00102.37 | F |
| ATOM | 7937 | NE2 | GLN | F | 40 | 79.378 | -15.733 | 142.761 | 1.00102.97 | F |

Figure 10 (122 of 142)

| ATOM | 7938 | C | GLN | F | 40 | 79.262 | -11.279 | 140.121 | 1.00 | 71.92 | F |
| --- | --- | --- | --- | --- | --- | --- | --- | --- | --- | --- | --- |
| ATOM | 7939 | O | GLN | F | 40 | 78.863 | -10.121 | 139.991 | 1.00 | 67.51 | F |
| ATOM | 7940 | N | ILE | F | 41 | 80.391 | -11.728 | 139.581 | 1.00 | 71.05 | F |
| ATOM | 7941 | CA | ILE | F | 41 | 81.255 | -10.856 | 138.798 | 1.00 | 75.32 | F |
| ATOM | 7942 | CB | ILE | F | 41 | 82.733 | -10.914 | 139.279 | 1.00 | 78.01 | F |
| ATOM | 7943 | CG2 | ILE | F | 41 | 83.376 | -12.245 | 138.872 | 1.00 | 79.79 | F |
| ATOM | 7944 | CG1 | ILE | F | 41 | 83.488 | -9.697 | 138.723 | 1.00 | 85.21 | F |
| ATOM | 7945 | CD1 | ILE | F | 41 | 84.936 | -9.942 | 138.365 | 1.00 | 89.88 | F |
| ATOM | 7946 | C | ILE | F | 41 | 81.211 | -11.237 | 137.331 | 1.00 | 73.30 | F |
| ATOM | 7947 | O | ILE | F | 41 | 80.478 | -10.629 | 136.552 | 1.00 | 70.76 | F |
| ATOM | 7948 | N | ASP | F | 52 | 77.433 | -3.420 | 141.636 | 1.00 | 77.47 | F |
| ATOM | 7949 | CA | ASP | F | 52 | 78.072 | -3.814 | 142.889 | 1.00 | 81.59 | F |
| ATOM | 7950 | CB | ASP | F | 52 | 78.068 | -2.647 | 143.873 | 1.00 | 89.11 | F |
| ATOM | 7951 | CG | ASP | F | 52 | 79.178 | -1.656 | 143.601 | 1.00 | 94.06 | F |
| ATOM | 7952 | OD1 | ASP | F | 52 | 80.363 | -2.037 | 143.712 | 1.00 | 99.22 | F |
| ATOM | 7953 | OD2 | ASP | F | 52 | 78.869 | -0.493 | 143.277 | 1.00 | 99.09 | F |
| ATOM | 7954 | C | ASP | F | 52 | 77.413 | -5.024 | 143.541 | 1.00 | 79.17 | F |
| ATOM | 7955 | O | ASP | F | 52 | 77.774 | -5.407 | 144.652 | 1.00 | 79.17 | F |
| ATOM | 7956 | N | SER | F | 53 | 76.454 | -5.612 | 142.831 | 1.00 | 77.59 | F |
| ATOM | 7957 | CA | SER | F | 53 | 75.700 | -6.788 | 143.269 | 1.00 | 74.47 | F |
| ATOM | 7958 | CB | SER | F | 53 | 76.641 | -7.937 | 143.702 | 1.00 | 70.81 | F |
| ATOM | 7959 | OG | SER | F | 53 | 77.293 | -7.695 | 144.934 | 1.00 | 70.96 | F |
| ATOM | 7960 | C | SER | F | 53 | 74.656 | -6.515 | 144.350 | 1.00 | 77.25 | F |
| ATOM | 7961 | O | SER | F | 53 | 73.540 | -7.026 | 144.271 | 1.00 | 80.30 | F |
| ATOM | 7962 | N | PHE | F | 54 | 74.991 | -5.709 | 145.351 | 1.00 | 76.26 | F |
| ATOM | 7963 | CA | PHE | F | 54 | 74.022 | -5.422 | 146.403 | 1.00 | 80.32 | F |
| ATOM | 7964 | CB | PHE | F | 54 | 74.645 | -4.543 | 147.495 | 1.00 | 82.43 | F |
| ATOM | 7965 | CG | PHE | F | 54 | 73.671 | -4.123 | 148.569 | 1.00 | 86.12 | F |
| ATOM | 7966 | CD1 | PHE | F | 54 | 72.988 | -5.076 | 149.325 | 1.00 | 84.47 | F |
| ATOM | 7967 | CD2 | PHE | F | 54 | 73.429 | -2.774 | 148.816 | 1.00 | 85.27 | F |
| ATOM | 7968 | CE1 | PHE | F | 54 | 72.079 | -4.692 | 150.307 | 1.00 | 83.65 | F |
| ATOM | 7969 | CE2 | PHE | F | 54 | 72.523 | -2.380 | 149.796 | 1.00 | 84.87 | F |
| ATOM | 7970 | CZ | PHE | F | 54 | 71.846 | -3.342 | 150.542 | 1.00 | 84.51 | F |
| ATOM | 7971 | C | PHE | F | 54 | 72.796 | -4.727 | 145.821 | 1.00 | 77.14 | F |
| ATOM | 7972 | O | PHE | F | 54 | 71.665 | -5.019 | 146.196 | 1.00 | 77.13 | F |
| ATOM | 7973 | N | HIS | F | 55 | 73.026 | -3.813 | 144.890 | 1.00 | 77.78 | F |
| ATOM | 7974 | CA | HIS | F | 55 | 71.931 | -3.081 | 144.283 | 1.00 | 71.33 | F |
| ATOM | 7975 | CB | HIS | F | 55 | 72.475 | -1.840 | 143.584 | 1.00 | 70.98 | F |
| ATOM | 7976 | CG | HIS | F | 55 | 73.202 | -0.914 | 144.508 | 1.00 | 69.78 | F |
| ATOM | 7977 | CD2 | HIS | F | 55 | 73.376 | -0.958 | 145.850 | 1.00 | 69.60 | F |
| ATOM | 7978 | ND1 | HIS | F | 55 | 73.870 | 0.209 | 144.074 | 1.00 | 71.71 | F |
| ATOM | 7979 | CE1 | HIS | F | 55 | 74.427 | 0.817 | 145.107 | 1.00 | 68.99 | F |
| ATOM | 7980 | NE2 | HIS | F | 55 | 74.142 | 0.128 | 146.197 | 1.00 | 70.31 | F |
| ATOM | 7981 | C | HIS | F | 55 | 71.144 | -3.946 | 143.323 | 1.00 | 68.67 | F |
| ATOM | 7982 | O | HIS | F | 55 | 69.952 | -3.733 | 143.134 | 1.00 | 69.46 | F |
| ATOM | 7983 | N | ARG | F | 56 | 71.808 | -4.931 | 142.727 | 1.00 | 66.26 | F |
| ATOM | 7984 | CA | ARG | F | 56 | 71.150 | -5.836 | 141.787 | 1.00 | 66.61 | F |
| ATOM | 7985 | CB | ARG | F | 56 | 72.199 | -6.661 | 141.018 | 1.00 | 65.73 | F |
| ATOM | 7986 | CG | ARG | F | 56 | 73.061 | -5.859 | 140.024 | 1.00 | 60.13 | F |
| ATOM | 7987 | CD | ARG | F | 56 | 74.425 | -6.513 | 139.803 | 1.00 | 57.84 | F |
| ATOM | 7988 | NE | ARG | F | 56 | 74.301 | -7.934 | 139.494 | 1.00 | 57.59 | F |
| ATOM | 7989 | CZ | ARG | F | 56 | 75.211 | -8.852 | 139.812 | 1.00 | 57.69 | F |
| ATOM | 7990 | NH1 | ARG | F | 56 | 76.318 | -8.496 | 140.449 | 1.00 | 57.52 | F |
| ATOM | 7991 | NH2 | ARG | F | 56 | 75.010 | -10.129 | 139.509 | 1.00 | 54.87 | F |
| ATOM | 7992 | C | ARG | F | 56 | 70.181 | -6.759 | 142.539 | 1.00 | 70.80 | F |
| ATOM | 7993 | O | ARG | F | 56 | 69.061 | -6.998 | 142.076 | 1.00 | 64.91 | F |
| ATOM | 7994 | N | VAL | F | 57 | 70.611 | -7.270 | 143.696 | 1.00 | 74.68 | F |
| ATOM | 7995 | CA | VAL | F | 57 | 69.763 | -8.146 | 144.510 | 1.00 | 79.58 | F |
| ATOM | 7996 | CB | VAL | F | 57 | 70.533 | -8.799 | 145.694 | 1.00 | 79.79 | F |
| ATOM | 7997 | CG1 | VAL | F | 57 | 69.554 | -9.548 | 146.602 | 1.00 | 83.74 | F |
| ATOM | 7998 | CG2 | VAL | F | 57 | 71.596 | -9.754 | 145.172 | 1.00 | 83.38 | F |
| ATOM | 7999 | C | VAL | F | 57 | 68.620 | -7.321 | 145.090 | 1.00 | 80.99 | F |
| ATOM | 8000 | O | VAL | F | 57 | 67.510 | -7.821 | 145.264 | 1.00 | 85.35 | F |
| ATOM | 8001 | N | GLU | F | 58 | 68.897 | -6.058 | 145.396 | 1.00 | 82.35 | F |
| ATOM | 8002 | CA | GLU | F | 58 | 67.875 | -5.179 | 145.940 | 1.00 | 82.93 | F |
| ATOM | 8003 | CB | GLU | F | 58 | 68.496 | -3.870 | 146.424 | 1.00 | 83.80 | F |

Figure 10 (123 of 142)

| ATOM | 8004 | CG | GLU | F | 58 | 69.165 | -4.014 | 147.775 | 1.00 | 91.15 | F |
|---|---|---|---|---|---|---|---|---|---|---|---|
| ATOM | 8005 | CD | GLU | F | 58 | 68.306 | -4.815 | 148.741 | 1.00 | 93.97 | F |
| ATOM | 8006 | OE1 | GLU | F | 58 | 67.135 | -4.431 | 148.944 | 1.00 | 95.43 | F |
| ATOM | 8007 | OE2 | GLU | F | 58 | 68.795 | -5.828 | 149.288 | 1.00 | 93.03 | F |
| ATOM | 8008 | C | GLU | F | 58 | 66.825 | -4.900 | 144.887 | 1.00 | 84.31 | F |
| ATOM | 8009 | O | GLU | F | 58 | 65.631 | -5.087 | 145.129 | 1.00 | 77.96 | F |
| ATOM | 8010 | N | MET | F | 59 | 67.280 | -4.457 | 143.717 | 1.00 | 85.23 | F |
| ATOM | 8011 | CA | MET | F | 59 | 66.376 | -4.164 | 142.616 | 1.00 | 82.81 | F |
| ATOM | 8012 | CB | MET | F | 59 | 67.145 | -3.665 | 141.384 | 1.00 | 77.31 | F |
| ATOM | 8013 | CG | MET | F | 59 | 67.864 | -2.329 | 141.567 | 1.00 | 76.07 | F |
| ATOM | 8014 | SD | MET | F | 59 | 68.465 | -1.623 | 140.010 | 1.00 | 69.15 | F |
| ATOM | 8015 | CE | MET | F | 59 | 70.005 | -2.438 | 139.786 | 1.00 | 67.58 | F |
| ATOM | 8016 | C | MET | F | 59 | 65.604 | -5.429 | 142.257 | 1.00 | 79.76 | F |
| ATOM | 8017 | O | MET | F | 59 | 64.417 | -5.364 | 141.937 | 1.00 | 81.83 | F |
| ATOM | 8018 | N | LEU | F | 60 | 66.272 | -6.579 | 142.322 | 1.00 | 75.29 | F |
| ATOM | 8019 | CA | LEU | F | 60 | 65.625 | -7.848 | 141.992 | 1.00 | 69.96 | F |
| ATOM | 8020 | CB | LEU | F | 60 | 66.650 | -8.983 | 141.979 | 1.00 | 67.08 | F |
| ATOM | 8021 | CG | LEU | F | 60 | 66.686 | -9.871 | 140.729 | 1.00 | 64.48 | F |
| ATOM | 8022 | CD1 | LEU | F | 60 | 67.286 | -11.211 | 141.083 | 1.00 | 65.25 | F |
| ATOM | 8023 | CD2 | LEU | F | 60 | 65.293 | -10.084 | 140.189 | 1.00 | 63.28 | F |
| ATOM | 8024 | C | LEU | F | 60 | 64.480 | -8.209 | 142.948 | 1.00 | 64.67 | F |
| ATOM | 8025 | O | LEU | F | 60 | 63.435 | -8.692 | 142.512 | 1.00 | 63.89 | F |
| ATOM | 8026 | N | LYS | F | 61 | 64.682 | -7.981 | 144.247 | 1.00 | 61.74 | F |
| ATOM | 8027 | CA | LYS | F | 61 | 63.660 | -8.278 | 145.256 | 1.00 | 57.71 | F |
| ATOM | 8028 | CB | LYS | F | 61 | 64.192 | -7.978 | 146.671 | 1.00 | 58.37 | F |
| ATOM | 8029 | CG | LYS | F | 61 | 64.500 | -9.236 | 147.505 | 1.00 | 58.16 | F |
| ATOM | 8030 | CD | LYS | F | 61 | 65.797 | -9.118 | 148.335 | 1.00 | 58.73 | F |
| ATOM | 8031 | CE | LYS | F | 61 | 65.746 | -7.993 | 149.362 | 1.00 | 56.69 | F |
| ATOM | 8032 | NZ | LYS | F | 61 | 66.943 | -7.982 | 150.245 | 1.00 | 51.37 | F |
| ATOM | 8033 | C | LYS | F | 61 | 62.435 | -7.428 | 144.969 | 1.00 | 55.38 | F |
| ATOM | 8034 | O | LYS | F | 61 | 61.309 | -7.934 | 144.921 | 1.00 | 50.95 | F |
| ATOM | 8035 | N | LEU | F | 62 | 62.675 | -6.133 | 144.769 | 1.00 | 52.16 | F |
| ATOM | 8036 | CA | LEU | F | 62 | 61.608 | -5.186 | 144.474 | 1.00 | 53.06 | F |
| ATOM | 8037 | CB | LEU | F | 62 | 62.197 | -3.800 | 144.170 | 1.00 | 50.49 | F |
| ATOM | 8038 | CG | LEU | F | 62 | 62.908 | -3.075 | 145.323 | 1.00 | 49.58 | F |
| ATOM | 8039 | CD1 | LEU | F | 62 | 63.639 | -1.830 | 144.808 | 1.00 | 47.71 | F |
| ATOM | 8040 | CD2 | LEU | F | 62 | 61.886 | -2.692 | 146.382 | 1.00 | 51.38 | F |
| ATOM | 8041 | C | LEU | F | 62 | 60.784 | -5.663 | 143.285 | 1.00 | 53.75 | F |
| ATOM | 8042 | O | LEU | F | 62 | 59.556 | -5.674 | 143.331 | 1.00 | 53.26 | F |
| ATOM | 8043 | N | ALA | F | 63 | 61.473 | -6.082 | 142.231 | 1.00 | 55.97 | F |
| ATOM | 8044 | CA | ALA | F | 63 | 60.822 | -6.538 | 141.011 | 1.00 | 58.16 | F |
| ATOM | 8045 | CB | ALA | F | 63 | 61.863 | -6.763 | 139.940 | 1.00 | 60.22 | F |
| ATOM | 8046 | C | ALA | F | 63 | 59.953 | -7.781 | 141.134 | 1.00 | 57.87 | F |
| ATOM | 8047 | O | ALA | F | 63 | 58.919 | -7.884 | 140.477 | 1.00 | 59.57 | F |
| ATOM | 8048 | N | ILE | F | 64 | 60.351 | -8.729 | 141.968 | 1.00 | 60.47 | F |
| ATOM | 8049 | CA | ILE | F | 64 | 59.556 | -9.943 | 142.077 | 1.00 | 69.18 | F |
| ATOM | 8050 | CB | ILE | F | 64 | 60.453 | -11.196 | 141.936 | 1.00 | 65.47 | F |
| ATOM | 8051 | CG2 | ILE | F | 64 | 61.143 | -11.182 | 140.584 | 1.00 | 67.62 | F |
| ATOM | 8052 | CG1 | ILE | F | 64 | 61.476 | -11.238 | 143.074 | 1.00 | 66.27 | F |
| ATOM | 8053 | CD1 | ILE | F | 64 | 62.217 | -12.554 | 143.189 | 1.00 | 64.73 | F |
| ATOM | 8054 | C | ILE | F | 64 | 58.695 | -10.087 | 143.341 | 1.00 | 68.12 | F |
| ATOM | 8055 | O | ILE | F | 64 | 57.930 | -11.050 | 143.460 | 1.00 | 69.24 | F |
| ATOM | 8056 | N | GLN | F | 65 | 58.793 | -9.138 | 144.270 | 1.00 | 71.17 | F |
| ATOM | 8057 | CA | GLN | F | 65 | 58.015 | -9.233 | 145.501 | 1.00 | 75.57 | F |
| ATOM | 8058 | CB | GLN | F | 65 | 58.099 | -7.928 | 146.298 | 1.00 | 73.89 | F |
| ATOM | 8059 | CG | GLN | F | 65 | 57.556 | -6.706 | 145.589 | 1.00 | 82.62 | F |
| ATOM | 8060 | CD | GLN | F | 65 | 57.625 | -5.456 | 146.455 | 1.00 | 86.34 | F |
| ATOM | 8061 | OE1 | GLN | F | 65 | 58.695 | -5.079 | 146.939 | 1.00 | 87.97 | F |
| ATOM | 8062 | NE2 | GLN | F | 65 | 56.481 | -4.806 | 146.650 | 1.00 | 89.24 | F |
| ATOM | 8063 | C | GLN | F | 65 | 56.558 | -9.584 | 145.227 | 1.00 | 75.29 | F |
| ATOM | 8064 | O | GLN | F | 65 | 56.042 | -10.574 | 145.744 | 1.00 | 75.60 | F |
| ATOM | 8065 | N | SER | F | 66 | 55.912 | -8.783 | 144.391 | 1.00 | 75.53 | F |
| ATOM | 8066 | CA | SER | F | 66 | 54.509 | -8.970 | 144.035 | 1.00 | 77.60 | F |
| ATOM | 8067 | CB | SER | F | 66 | 54.076 | -7.835 | 143.100 | 1.00 | 80.70 | F |
| ATOM | 8068 | OG | SER | F | 66 | 55.082 | -7.542 | 142.139 | 1.00 | 79.82 | F |
| ATOM | 8069 | C | SER | F | 66 | 54.097 | -10.313 | 143.419 | 1.00 | 77.08 | F |

Figure 10 (124 of 142)

| ATOM | 8070 | O | SER | F | 66 | 52.902 | -10.559 | 143.233 | 1.00 | 78.65 | F |
|---|---|---|---|---|---|---|---|---|---|---|---|
| ATOM | 8071 | N | ASN | F | 67 | 55.056 | -11.184 | 143.104 | 1.00 | 77.97 | F |
| ATOM | 8072 | CA | ASN | F | 67 | 54.699 | -12.469 | 142.503 | 1.00 | 80.40 | F |
| ATOM | 8073 | CB | ASN | F | 67 | 55.511 | -12.701 | 141.215 | 1.00 | 84.78 | F |
| ATOM | 8074 | CG | ASN | F | 67 | 54.917 | -13.801 | 140.324 | 1.00 | 85.93 | F |
| ATOM | 8075 | OD1 | ASN | F | 67 | 55.339 | -13.976 | 139.179 | 1.00 | 87.09 | F |
| ATOM | 8076 | ND2 | ASN | F | 67 | 53.944 | -14.545 | 140.849 | 1.00 | 87.80 | F |
| ATOM | 8077 | C | ASN | F | 67 | 54.866 | -13.658 | 143.457 | 1.00 | 80.23 | F |
| ATOM | 8078 | O | ASN | F | 67 | 55.969 | -13.950 | 143.921 | 1.00 | 79.17 | F |
| ATOM | 8079 | N | PRO | F | 68 | 53.752 | -14.350 | 143.766 | 1.00 | 77.08 | F |
| ATOM | 8080 | CD | PRO | F | 68 | 52.390 | -13.978 | 143.347 | 1.00 | 75.64 | F |
| ATOM | 8081 | CA | PRO | F | 68 | 53.716 | -15.517 | 144.652 | 1.00 | 75.74 | F |
| ATOM | 8082 | CB | PRO | F | 68 | 52.243 | -15.951 | 144.602 | 1.00 | 74.68 | F |
| ATOM | 8083 | CG | PRO | F | 68 | 51.706 | -15.310 | 143.347 | 1.00 | 74.65 | F |
| ATOM | 8084 | C | PRO | F | 68 | 54.681 | -16.635 | 144.246 | 1.00 | 75.12 | F |
| ATOM | 8085 | O | PRO | F | 68 | 55.012 | -17.502 | 145.056 | 1.00 | 76.54 | F |
| ATOM | 8086 | N | SER | F | 69 | 55.125 | -16.614 | 142.994 | 1.00 | 75.30 | F |
| ATOM | 8087 | CA | SER | F | 69 | 56.065 | -17.610 | 142.486 | 1.00 | 78.30 | F |
| ATOM | 8088 | CB | SER | F | 69 | 55.528 | -18.222 | 141.192 | 1.00 | 72.77 | F |
| ATOM | 8089 | OG | SER | F | 69 | 54.230 | -18.753 | 141.384 | 1.00 | 71.63 | F |
| ATOM | 8090 | C | SER | F | 69 | 57.412 | -16.932 | 142.213 | 1.00 | 81.41 | F |
| ATOM | 8091 | O | SER | F | 69 | 58.146 | -17.332 | 141.310 | 1.00 | 79.58 | F |
| ATOM | 8092 | N | PHE | F | 70 | 57.728 | -15.905 | 143.003 | 1.00 | 87.31 | F |
| ATOM | 8093 | CA | PHE | F | 70 | 58.970 | -15.153 | 142.831 | 1.00 | 88.80 | F |
| ATOM | 8094 | CB | PHE | F | 70 | 58.878 | -13.777 | 143.535 | 1.00 | 91.66 | F |
| ATOM | 8095 | CG | PHE | F | 70 | 58.908 | -13.820 | 145.060 | 1.00 | 91.58 | F |
| ATOM | 8096 | CD1 | PHE | F | 70 | 59.878 | -13.092 | 145.755 | 1.00 | 95.69 | F |
| ATOM | 8097 | CD2 | PHE | F | 70 | 57.951 | -14.519 | 145.796 | 1.00 | 96.43 | F |
| ATOM | 8098 | CE1 | PHE | F | 70 | 59.903 | -13.056 | 147.149 | 1.00 | 95.32 | F |
| ATOM | 8099 | CE2 | PHE | F | 70 | 57.969 | -14.489 | 147.198 | 1.00 | 94.81 | F |
| ATOM | 8100 | CZ | PHE | F | 70 | 58.944 | -13.753 | 147.872 | 1.00 | 95.15 | F |
| ATOM | 8101 | C | PHE | F | 70 | 60.215 | -15.918 | 143.271 | 1.00 | 87.74 | F |
| ATOM | 8102 | O | PHE | F | 70 | 60.892 | -16.515 | 142.448 | 1.00 | 88.61 | F |
| ATOM | 8103 | N | LYS | F | 71 | 60.522 | -15.891 | 144.562 | 1.00 | 84.30 | F |
| ATOM | 8104 | CA | LYS | F | 71 | 61.671 | -16.609 | 145.093 | 1.00 | 77.81 | F |
| ATOM | 8105 | CB | LYS | F | 71 | 61.504 | -18.114 | 144.838 | 1.00 | 79.27 | F |
| ATOM | 8106 | CG | LYS | F | 71 | 61.299 | -18.946 | 146.107 | 1.00 | 79.19 | F |
| ATOM | 8107 | CD | LYS | F | 71 | 60.252 | -18.341 | 147.061 | 1.00 | 77.46 | F |
| ATOM | 8108 | CE | LYS | F | 71 | 58.838 | -18.854 | 146.803 | 1.00 | 74.62 | F |
| ATOM | 8109 | NZ | LYS | F | 71 | 57.864 | -18.253 | 147.759 | 1.00 | 72.22 | F |
| ATOM | 8110 | C | LYS | F | 71 | 63.020 | -16.158 | 144.546 | 1.00 | 72.63 | F |
| ATOM | 8111 | O | LYS | F | 71 | 63.369 | -16.451 | 143.402 | 1.00 | 68.06 | F |
| ATOM | 8112 | N | LEU | F | 72 | 63.785 | -15.446 | 145.365 | 1.00 | 68.01 | F |
| ATOM | 8113 | CA | LEU | F | 72 | 65.116 | -15.034 | 144.944 | 1.00 | 65.67 | F |
| ATOM | 8114 | CB | LEU | F | 72 | 65.762 | -14.079 | 145.958 | 1.00 | 72.47 | F |
| ATOM | 8115 | CG | LEU | F | 72 | 65.994 | -12.635 | 145.497 | 1.00 | 72.27 | F |
| ATOM | 8116 | CD1 | LEU | F | 72 | 66.811 | -11.864 | 146.522 | 1.00 | 76.24 | F |
| ATOM | 8117 | CD2 | LEU | F | 72 | 66.725 | -12.653 | 144.178 | 1.00 | 75.02 | F |
| ATOM | 8118 | C | LEU | F | 72 | 65.895 | -16.344 | 144.929 | 1.00 | 61.33 | F |
| ATOM | 8119 | O | LEU | F | 72 | 65.326 | -17.410 | 144.722 | 1.00 | 62.90 | F |
| ATOM | 8120 | N | GLU | F | 73 | 67.201 | -16.256 | 145.137 | 1.00 | 59.84 | F |
| ATOM | 8121 | CA | GLU | F | 73 | 68.089 | -17.423 | 145.189 | 1.00 | 60.92 | F |
| ATOM | 8122 | CB | GLU | F | 73 | 67.843 | -18.405 | 144.030 | 1.00 | 57.90 | F |
| ATOM | 8123 | CG | GLU | F | 73 | 68.769 | -19.620 | 144.075 | 1.00 | 59.29 | F |
| ATOM | 8124 | CD | GLU | F | 73 | 68.847 | -20.270 | 145.459 | 1.00 | 62.46 | F |
| ATOM | 8125 | OE1 | GLU | F | 73 | 67.865 | -20.924 | 145.877 | 1.00 | 65.27 | F |
| ATOM | 8126 | OE2 | GLU | F | 73 | 69.888 | -20.112 | 146.137 | 1.00 | 66.29 | F |
| ATOM | 8127 | C | GLU | F | 73 | 69.504 | -16.891 | 145.145 | 1.00 | 63.90 | F |
| ATOM | 8128 | O | GLU | F | 73 | 70.069 | -16.688 | 144.078 | 1.00 | 62.89 | F |
| ATOM | 8129 | N | LEU | F | 74 | 70.071 | -16.665 | 146.323 | 1.00 | 64.11 | F |
| ATOM | 8130 | CA | LEU | F | 74 | 71.404 | -16.104 | 146.414 | 1.00 | 64.16 | F |
| ATOM | 8131 | CB | LEU | F | 74 | 71.425 | -15.081 | 147.555 | 1.00 | 63.87 | F |
| ATOM | 8132 | CG | LEU | F | 74 | 70.258 | -14.076 | 147.459 | 1.00 | 64.13 | F |
| ATOM | 8133 | CD1 | LEU | F | 74 | 70.189 | -13.194 | 148.703 | 1.00 | 65.90 | F |
| ATOM | 8134 | CD2 | LEU | F | 74 | 70.414 | -13.232 | 146.197 | 1.00 | 66.25 | F |
| ATOM | 8135 | C | LEU | F | 74 | 72.484 | -17.158 | 146.598 | 1.00 | 58.96 | F |

Figure 10 (125 of 142)

| | | | | | | | | | |
|---|---|---|---|---|---|---|---|---|---|
| ATOM | 8136 | O | LEU | F | 74 | 73.577 -16.856 147.077 | 1.00 | 62.24 | F |
| ATOM | 8137 | N | VAL | F | 75 | 72.179 -18.390 146.202 | 1.00 | 56.04 | F |
| ATOM | 8138 | CA | VAL | F | 75 | 73.129 -19.492 146.327 | 1.00 | 56.13 | F |
| ATOM | 8139 | CB | VAL | F | 75 | 72.571 -20.795 145.701 | 1.00 | 53.90 | F |
| ATOM | 8140 | CG1 | VAL | F | 75 | 72.163 -20.547 144.272 | 1.00 | 53.59 | F |
| ATOM | 8141 | CG2 | VAL | F | 75 | 73.619 -21.897 145.751 | 1.00 | 53.03 | F |
| ATOM | 8142 | C | VAL | F | 75 | 74.437 -19.148 145.634 | 1.00 | 55.26 | F |
| ATOM | 8143 | O | VAL | F | 75 | 75.515 -19.587 146.032 | 1.00 | 54.04 | F |
| ATOM | 8144 | N | GLU | F | 76 | 74.339 -18.338 144.598 | 1.00 | 57.92 | F |
| ATOM | 8145 | CA | GLU | F | 76 | 75.520 -17.971 143.845 | 1.00 | 62.13 | F |
| ATOM | 8146 | CB | GLU | F | 76 | 75.104 -17.515 142.452 | 1.00 | 61.41 | F |
| ATOM | 8147 | CG | GLU | F | 76 | 76.131 -17.774 141.384 | 1.00 | 60.52 | F |
| ATOM | 8148 | CD | GLU | F | 76 | 75.560 -18.636 140.293 | 1.00 | 61.31 | F |
| ATOM | 8149 | OE1 | GLU | F | 76 | 76.147 -19.697 140.003 | 1.00 | 62.12 | F |
| ATOM | 8150 | OE2 | GLU | F | 76 | 74.515 -18.251 139.728 | 1.00 | 64.09 | F |
| ATOM | 8151 | C | GLU | F | 76 | 76.313 -16.862 144.507 | 1.00 | 62.52 | F |
| ATOM | 8152 | O | GLU | F | 76 | 77.463 -16.630 144.165 | 1.00 | 65.51 | F |
| ATOM | 8153 | N | MET | F | 77 | 75.696 -16.187 145.462 | 1.00 | 65.32 | F |
| ATOM | 8154 | CA | MET | F | 77 | 76.338 -15.069 146.117 | 1.00 | 70.22 | F |
| ATOM | 8155 | CB | MET | F | 77 | 75.263 -14.091 146.577 | 1.00 | 74.23 | F |
| ATOM | 8156 | CG | MET | F | 77 | 74.281 -13.751 145.458 | 1.00 | 71.72 | F |
| ATOM | 8157 | SD | MET | F | 77 | 74.340 -12.043 144.879 | 1.00 | 72.99 | F |
| ATOM | 8158 | CE | MET | F | 77 | 76.068 -11.847 144.529 | 1.00 | 70.22 | F |
| ATOM | 8159 | C | MET | F | 77 | 77.264 -15.436 147.260 | 1.00 | 74.16 | F |
| ATOM | 8160 | O | MET | F | 77 | 78.249 -14.740 147.497 | 1.00 | 72.81 | F |
| ATOM | 8161 | N | GLU | F | 78 | 76.957 -16.518 147.966 | 1.00 | 75.92 | F |
| ATOM | 8162 | CA | GLU | F | 78 | 77.786 -16.982 149.084 | 1.00 | 77.67 | F |
| ATOM | 8163 | CB | GLU | F | 78 | 77.453 -18.456 149.378 | 1.00 | 77.21 | F |
| ATOM | 8164 | CG | GLU | F | 78 | 76.027 -18.750 149.854 | 1.00 | 78.27 | F |
| ATOM | 8165 | CD | GLU | F | 78 | 75.486 -20.087 149.345 | 1.00 | 77.61 | F |
| ATOM | 8166 | OE1 | GLU | F | 78 | 76.278 -21.018 149.085 | 1.00 | 78.06 | F |
| ATOM | 8167 | OE2 | GLU | F | 78 | 74.255 -20.213 149.215 | 1.00 | 76.37 | F |
| ATOM | 8168 | C | GLU | F | 78 | 79.295 -16.872 148.762 | 1.00 | 77.59 | F |
| ATOM | 8169 | O | GLU | F | 78 | 80.007 -15.953 149.189 | 1.00 | 80.04 | F |
| ATOM | 8170 | N | ARG | F | 79 | 79.729 -17.864 147.996 | 1.00 | 76.91 | F |
| ATOM | 8171 | CA | ARG | F | 79 | 81.079 -18.122 147.492 | 1.00 | 74.77 | F |
| ATOM | 8172 | CB | ARG | F | 79 | 80.901 -19.094 146.324 | 1.00 | 71.12 | F |
| ATOM | 8173 | CG | ARG | F | 79 | 79.500 -19.746 146.403 | 1.00 | 67.24 | F |
| ATOM | 8174 | CD | ARG | F | 79 | 78.946 -20.271 145.081 | 1.00 | 59.63 | F |
| ATOM | 8175 | NE | ARG | F | 79 | 79.037 -21.725 145.002 | 1.00 | 55.74 | F |
| ATOM | 8176 | CZ | ARG | F | 79 | 78.590 -22.463 143.989 | 1.00 | 56.00 | F |
| ATOM | 8177 | NH1 | ARG | F | 79 | 78.013 -21.895 142.941 | 1.00 | 54.47 | F |
| ATOM | 8178 | NH2 | ARG | F | 79 | 78.698 -23.783 144.034 | 1.00 | 53.21 | F |
| ATOM | 8179 | C | ARG | F | 79 | 82.036 -16.979 147.097 | 1.00 | 78.88 | F |
| ATOM | 8180 | O | ARG | F | 79 | 83.065 -16.779 147.744 | 1.00 | 80.43 | F |
| ATOM | 8181 | N | GLU | F | 80 | 81.712 -16.254 146.031 | 1.00 | 80.40 | F |
| ATOM | 8182 | CA | GLU | F | 80 | 82.556 -15.166 145.527 | 1.00 | 85.39 | F |
| ATOM | 8183 | CB | GLU | F | 80 | 82.814 -14.101 146.604 | 1.00 | 82.67 | F |
| ATOM | 8184 | CG | GLU | F | 80 | 84.119 -13.294 146.411 | 1.00 | 83.28 | F |
| ATOM | 8185 | CD | GLU | F | 80 | 84.227 -12.568 145.071 | 1.00 | 82.43 | F |
| ATOM | 8186 | OE1 | GLU | F | 80 | 85.369 -12.316 144.618 | 1.00 | 82.70 | F |
| ATOM | 8187 | OE2 | GLU | F | 80 | 83.180 -12.239 144.476 | 1.00 | 83.41 | F |
| ATOM | 8188 | C | GLU | F | 80 | 83.888 -15.588 144.880 | 1.00 | 90.18 | F |
| ATOM | 8189 | O | GLU | F | 80 | 84.851 -16.039 145.519 | 1.00 | 90.65 | F |
| ATOM | 8190 | N | GLY | F | 81 | 83.884 -15.378 143.575 | 1.00 | 94.29 | F |
| ATOM | 8191 | CA | GLY | F | 81 | 84.963 -15.662 142.656 | 1.00 | 98.68 | F |
| ATOM | 8192 | C | GLY | F | 81 | 83.975 -15.526 141.524 | 1.00 | 99.32 | F |
| ATOM | 8193 | O | GLY | F | 81 | 83.439 -14.431 141.318 | 1.00 | 100.80 | F |
| ATOM | 8194 | N | PRO | F | 82 | 83.726 -16.589 140.752 | 1.00 | 104.43 | F |
| ATOM | 8195 | CD | PRO | F | 82 | 84.601 -17.732 140.409 | 1.00 | 102.63 | F |
| ATOM | 8196 | CA | PRO | F | 82 | 82.730 -16.370 139.710 | 1.00 | 101.02 | F |
| ATOM | 8197 | CB | PRO | F | 82 | 83.388 -16.973 138.480 | 1.00 | 102.30 | F |
| ATOM | 8198 | CG | PRO | F | 82 | 84.049 -18.205 139.040 | 1.00 | 101.73 | F |
| ATOM | 8199 | C | PRO | F | 82 | 81.611 -17.250 140.260 | 1.00 | 101.80 | F |
| ATOM | 8200 | O | PRO | F | 82 | 80.997 -16.937 141.278 | 1.00 | 104.08 | F |
| ATOM | 8201 | N | SER | F | 83 | 81.412 -18.376 139.592 | 1.00 | 104.45 | F |

Figure 10 (126 of 142)

```
ATOM   8202  CA   SER F  83      80.441 -19.390 139.944  1.00 106.20      F
ATOM   8203  CB   SER F  83      79.404 -18.889 140.950  1.00 105.74      F
ATOM   8204  OG   SER F  83      79.089 -19.924 141.873  1.00 107.16      F
ATOM   8205  C    SER F  83      79.774 -19.800 138.664  1.00 106.70      F
ATOM   8206  O    SER F  83      78.687 -19.328 138.327  1.00 106.00      F
ATOM   8207  N    TYR F  84      80.474 -20.654 137.930  1.00 107.16      F
ATOM   8208  CA   TYR F  84      79.960 -21.177 136.687  1.00 107.18      F
ATOM   8209  CB   TYR F  84      80.835 -22.340 136.231  1.00 104.78      F
ATOM   8210  CG   TYR F  84      82.279 -21.955 136.032  1.00 103.53      F
ATOM   8211  CD1  TYR F  84      82.624 -20.988 135.099  1.00 105.24      F
ATOM   8212  CE1  TYR F  84      83.947 -20.627 134.890  1.00 103.37      F
ATOM   8213  CD2  TYR F  84      83.300 -22.561 136.763  1.00 104.76      F
ATOM   8214  CE2  TYR F  84      84.638 -22.208 136.561  1.00 106.50      F
ATOM   8215  CZ   TYR F  84      84.952 -21.241 135.616  1.00 105.08      F
ATOM   8216  OH   TYR F  84      86.267 -20.911 135.366  1.00 106.52      F
ATOM   8217  C    TYR F  84      78.583 -21.681 137.048  1.00 107.25      F
ATOM   8218  O    TYR F  84      78.295 -21.860 138.229  1.00 109.98      F
ATOM   8219  N    THR F  85      77.721 -21.886 136.059  1.00 107.59      F
ATOM   8220  CA   THR F  85      76.395 -22.418 136.351  1.00 106.14      F
ATOM   8221  CB   THR F  85      75.634 -22.741 135.047  1.00 106.68      F
ATOM   8222  OG1  THR F  85      75.881 -21.703 134.092  1.00 108.19      F
ATOM   8223  CG2  THR F  85      74.139 -22.817 135.297  1.00 108.22      F
ATOM   8224  C    THR F  85      76.788 -23.712 137.063  1.00 100.35      F
ATOM   8225  O    THR F  85      77.197 -23.694 138.219  1.00  99.41      F
ATOM   8226  N    PHE F  86      76.662 -24.828 136.365  1.00  94.61      F
ATOM   8227  CA   PHE F  86      77.076 -26.125 136.880  1.00  91.31      F
ATOM   8228  CB   PHE F  86      78.225 -26.595 136.003  1.00  89.64      F
ATOM   8229  CG   PHE F  86      78.919 -27.809 136.502  1.00  87.46      F
ATOM   8230  CD1  PHE F  86      78.336 -29.063 136.379  1.00  86.37      F
ATOM   8231  CD2  PHE F  86      80.186 -27.706 137.064  1.00  86.53      F
ATOM   8232  CE1  PHE F  86      79.014 -30.203 136.798  1.00  82.42      F
ATOM   8233  CE2  PHE F  86      80.871 -28.837 137.484  1.00  85.11      F
ATOM   8234  CZ   PHE F  86      80.282 -30.089 137.353  1.00  83.94      F
ATOM   8235  C    PHE F  86      77.475 -26.199 138.368  1.00  86.66      F
ATOM   8236  O    PHE F  86      76.886 -26.959 139.121  1.00  85.67      F
ATOM   8237  N    ASP F  87      78.488 -25.437 138.777  1.00  84.34      F
ATOM   8238  CA   ASP F  87      78.930 -25.420 140.173  1.00  77.92      F
ATOM   8239  CB   ASP F  87      79.934 -24.290 140.398  1.00  78.45      F
ATOM   8240  CG   ASP F  87      81.355 -24.697 140.066  1.00  77.62      F
ATOM   8241  OD1  ASP F  87      82.235 -23.805 140.085  1.00  77.47      F
ATOM   8242  OD2  ASP F  87      81.590 -25.900 139.800  1.00  72.37      F
ATOM   8243  C    ASP F  87      77.757 -25.231 141.128  1.00  77.39      F
ATOM   8244  O    ASP F  87      77.599 -25.970 142.097  1.00  79.01      F
ATOM   8245  N    THR F  88      76.942 -24.225 140.849  1.00  71.24      F
ATOM   8246  CA   THR F  88      75.779 -23.942 141.670  1.00  66.46      F
ATOM   8247  CB   THR F  88      75.106 -22.639 141.235  1.00  65.56      F
ATOM   8248  OG1  THR F  88      76.042 -21.564 141.359  1.00  62.96      F
ATOM   8249  CG2  THR F  88      73.884 -22.354 142.098  1.00  63.23      F
ATOM   8250  C    THR F  88      74.771 -25.068 141.535  1.00  68.37      F
ATOM   8251  O    THR F  88      74.363 -25.662 142.530  1.00  67.76      F
ATOM   8252  N    VAL F  89      74.370 -25.352 140.298  1.00  68.36      F
ATOM   8253  CA   VAL F  89      73.403 -26.413 140.032  1.00  71.86      F
ATOM   8254  CB   VAL F  89      73.209 -26.647 138.509  1.00  67.49      F
ATOM   8255  CG1  VAL F  89      72.330 -27.871 138.268  1.00  71.80      F
ATOM   8256  CG2  VAL F  89      72.568 -25.420 137.876  1.00  72.30      F
ATOM   8257  C    VAL F  89      73.872 -27.704 140.683  1.00  68.32      F
ATOM   8258  O    VAL F  89      73.062 -28.500 141.144  1.00  69.03      F
ATOM   8259  N    SER F  90      75.183 -27.905 140.726  1.00  69.60      F
ATOM   8260  CA   SER F  90      75.742 -29.100 141.340  1.00  70.81      F
ATOM   8261  CB   SER F  90      77.268 -29.099 141.226  1.00  70.41      F
ATOM   8262  OG   SER F  90      77.689 -29.181 139.875  1.00  72.31      F
ATOM   8263  C    SER F  90      75.352 -29.123 142.809  1.00  71.73      F
ATOM   8264  O    SER F  90      74.816 -30.109 143.314  1.00  69.30      F
ATOM   8265  N    LEU F  91      75.635 -28.018 143.488  1.00  71.59      F
ATOM   8266  CA   LEU F  91      75.332 -27.883 144.901  1.00  74.30      F
ATOM   8267  CB   LEU F  91      75.879 -26.554 145.425  1.00  71.08      F
```

Figure 10 (127 of 142)

| ATOM | 8268 | CG  | LEU | F | 91 | 75.446 | -26.128 | 146.828 | 1.00 | 68.17  | F |
| ATOM | 8269 | CD1 | LEU | F | 91 | 75.639 | -27.257 | 147.821 | 1.00 | 67.65  | F |
| ATOM | 8270 | CD2 | LEU | F | 91 | 76.251 | -24.915 | 147.231 | 1.00 | 68.74  | F |
| ATOM | 8271 | C   | LEU | F | 91 | 73.829 | -27.961 | 145.134 | 1.00 | 76.52  | F |
| ATOM | 8272 | O   | LEU | F | 91 | 73.384 | -28.551 | 146.114 | 1.00 | 80.62  | F |
| ATOM | 8273 | N   | LEU | F | 92 | 73.052 | -27.373 | 144.227 | 1.00 | 79.49  | F |
| ATOM | 8274 | CA  | LEU | F | 92 | 71.599 | -27.384 | 144.342 | 1.00 | 79.55  | F |
| ATOM | 8275 | CB  | LEU | F | 92 | 70.971 | -26.373 | 143.383 | 1.00 | 78.22  | F |
| ATOM | 8276 | CG  | LEU | F | 92 | 71.150 | -24.884 | 143.695 | 1.00 | 74.47  | F |
| ATOM | 8277 | CD1 | LEU | F | 92 | 70.514 | -24.043 | 142.587 | 1.00 | 72.35  | F |
| ATOM | 8278 | CD2 | LEU | F | 92 | 70.526 | -24.559 | 145.046 | 1.00 | 72.89  | F |
| ATOM | 8279 | C   | LEU | F | 92 | 71.055 | -28.771 | 144.052 | 1.00 | 82.61  | F |
| ATOM | 8280 | O   | LEU | F | 92 | 70.224 | -29.282 | 144.805 | 1.00 | 83.84  | F |
| ATOM | 8281 | N   | LYS | F | 93 | 71.509 | -29.382 | 142.958 | 1.00 | 85.61  | F |
| ATOM | 8282 | CA  | LYS | F | 93 | 71.064 | -30.731 | 142.623 | 1.00 | 87.24  | F |
| ATOM | 8283 | CB  | LYS | F | 93 | 71.786 | -31.272 | 141.388 | 1.00 | 90.00  | F |
| ATOM | 8284 | CG  | LYS | F | 93 | 71.231 | -30.767 | 140.071 | 1.00 | 95.40  | F |
| ATOM | 8285 | CD  | LYS | F | 93 | 71.725 | -31.612 | 138.919 | 1.00 | 99.09  | F |
| ATOM | 8286 | CE  | LYS | F | 93 | 71.196 | -33.040 | 139.011 | 1.00 | 100.76 | F |
| ATOM | 8287 | NZ  | LYS | F | 93 | 69.715 | -33.124 | 138.853 | 1.00 | 102.01 | F |
| ATOM | 8288 | C   | LYS | F | 93 | 71.402 | -31.596 | 143.820 | 1.00 | 86.58  | F |
| ATOM | 8289 | O   | LYS | F | 93 | 70.923 | -32.721 | 143.948 | 1.00 | 83.99  | F |
| ATOM | 8290 | N   | GLN | F | 94 | 72.246 | -31.051 | 144.691 | 1.00 | 86.51  | F |
| ATOM | 8291 | CA  | GLN | F | 94 | 72.656 | -31.738 | 145.903 | 1.00 | 88.41  | F |
| ATOM | 8292 | CB  | GLN | F | 94 | 74.142 | -31.483 | 146.183 | 1.00 | 87.23  | F |
| ATOM | 8293 | CG  | GLN | F | 94 | 74.813 | -32.576 | 147.001 | 1.00 | 88.95  | F |
| ATOM | 8294 | CD  | GLN | F | 94 | 76.324 | -32.434 | 147.051 | 1.00 | 91.48  | F |
| ATOM | 8295 | OE1 | GLN | F | 94 | 76.860 | -31.586 | 147.763 | 1.00 | 89.76  | F |
| ATOM | 8296 | NE2 | GLN | F | 94 | 77.021 | -33.265 | 146.280 | 1.00 | 92.46  | F |
| ATOM | 8297 | C   | GLN | F | 94 | 71.790 | -31.207 | 147.045 | 1.00 | 88.97  | F |
| ATOM | 8298 | O   | GLN | F | 94 | 71.423 | -31.954 | 147.948 | 1.00 | 86.95  | F |
| ATOM | 8299 | N   | ARG | F | 95 | 71.457 | -29.918 | 146.992 | 1.00 | 90.49  | F |
| ATOM | 8300 | CA  | ARG | F | 95 | 70.622 | -29.293 | 148.017 | 1.00 | 93.65  | F |
| ATOM | 8301 | CB  | ARG | F | 95 | 70.793 | -27.776 | 148.004 | 1.00 | 95.54  | F |
| ATOM | 8302 | CG  | ARG | F | 95 | 71.969 | -27.267 | 148.796 | 1.00 | 101.07 | F |
| ATOM | 8303 | CD  | ARG | F | 95 | 71.965 | -25.762 | 148.804 | 1.00 | 103.41 | F |
| ATOM | 8304 | NE  | ARG | F | 95 | 73.038 | -25.215 | 149.619 | 1.00 | 107.70 | F |
| ATOM | 8305 | CZ  | ARG | F | 95 | 73.265 | -23.915 | 149.756 | 1.00 | 108.30 | F |
| ATOM | 8306 | NH1 | ARG | F | 95 | 72.493 | -23.041 | 149.129 | 1.00 | 112.61 | F |
| ATOM | 8307 | NH2 | ARG | F | 95 | 74.255 | -23.488 | 150.519 | 1.00 | 112.92 | F |
| ATOM | 8308 | C   | ARG | F | 95 | 69.138 | -29.621 | 147.858 | 1.00 | 94.24  | F |
| ATOM | 8309 | O   | ARG | F | 95 | 68.384 | -29.571 | 148.827 | 1.00 | 96.36  | F |
| ATOM | 8310 | N   | TYR | F | 96 | 68.716 | -29.935 | 146.635 | 1.00 | 94.10  | F |
| ATOM | 8311 | CA  | TYR | F | 96 | 67.321 | -30.278 | 146.362 | 1.00 | 92.46  | F |
| ATOM | 8312 | CB  | TYR | F | 96 | 66.599 | -29.097 | 145.710 | 1.00 | 89.45  | F |
| ATOM | 8313 | CG  | TYR | F | 96 | 66.853 | -27.781 | 146.411 | 1.00 | 85.41  | F |
| ATOM | 8314 | CD1 | TYR | F | 96 | 68.079 | -27.130 | 146.278 | 1.00 | 84.04  | F |
| ATOM | 8315 | CE1 | TYR | F | 96 | 68.341 | -25.940 | 146.954 | 1.00 | 80.50  | F |
| ATOM | 8316 | CD2 | TYR | F | 96 | 65.886 | -27.205 | 147.240 | 1.00 | 82.73  | F |
| ATOM | 8317 | CE2 | TYR | F | 96 | 66.138 | -26.008 | 147.924 | 1.00 | 78.16  | F |
| ATOM | 8318 | CZ  | TYR | F | 96 | 67.369 | -25.382 | 147.776 | 1.00 | 79.40  | F |
| ATOM | 8319 | OH  | TYR | F | 96 | 67.633 | -24.204 | 148.442 | 1.00 | 73.68  | F |
| ATOM | 8320 | C   | TYR | F | 96 | 67.311 | -31.484 | 145.432 | 1.00 | 93.21  | F |
| ATOM | 8321 | O   | TYR | F | 96 | 67.082 | -31.359 | 144.230 | 1.00 | 93.56  | F |
| ATOM | 8322 | N   | PRO | F | 97 | 67.584 | -32.675 | 145.987 | 1.00 | 99.75  | F |
| ATOM | 8323 | CD  | PRO | F | 97 | 68.141 | -32.853 | 147.335 | 1.00 | 99.92  | F |
| ATOM | 8324 | CA  | PRO | F | 97 | 67.628 | -33.944 | 145.251 | 1.00 | 100.46 | F |
| ATOM | 8325 | CB  | PRO | F | 97 | 68.363 | -34.883 | 146.212 | 1.00 | 98.80  | F |
| ATOM | 8326 | CG  | PRO | F | 97 | 69.139 | -33.948 | 147.097 | 1.00 | 102.38 | F |
| ATOM | 8327 | C   | PRO | F | 97 | 66.262 | -34.497 | 144.875 | 1.00 | 96.70  | F |
| ATOM | 8328 | O   | PRO | F | 97 | 66.161 | -35.413 | 144.059 | 1.00 | 96.60  | F |
| ATOM | 8329 | N   | ASN | F | 98 | 65.213 | -33.949 | 145.472 | 1.00 | 96.15  | F |
| ATOM | 8330 | CA  | ASN | F | 98 | 63.868 | -34.430 | 145.187 | 1.00 | 97.06  | F |
| ATOM | 8331 | CB  | ASN | F | 98 | 63.165 | -34.810 | 146.489 | 1.00 | 95.25  | F |
| ATOM | 8332 | CG  | ASN | F | 98 | 63.753 | -36.056 | 147.121 | 1.00 | 99.96  | F |
| ATOM | 8333 | OD1 | ASN | F | 98 | 64.956 | -36.126 | 147.395 | 1.00 | 102.06 | F |

Figure 10 (128 of 142)

| ATOM | 8334 | ND2 | ASN | F | 98 | 62.905 | -37.050 | 147.354 | 1.00 | 99.72 | F |
|---|---|---|---|---|---|---|---|---|---|---|---|
| ATOM | 8335 | C | ASN | F | 98 | 63.031 | -33.427 | 144.415 | 1.00 | 95.12 | F |
| ATOM | 8336 | O | ASN | F | 98 | 61.823 | -33.605 | 144.259 | 1.00 | 93.90 | F |
| ATOM | 8337 | N | ASP | F | 99 | 63.674 | -32.368 | 143.936 | 1.00 | 94.73 | F |
| ATOM | 8338 | CA | ASP | F | 99 | 62.979 | -31.349 | 143.163 | 1.00 | 93.27 | F |
| ATOM | 8339 | CB | ASP | F | 99 | 63.291 | -29.947 | 143.709 | 1.00 | 94.25 | F |
| ATOM | 8340 | CG | ASP | F | 99 | 62.884 | -29.781 | 145.166 | 1.00 | 97.67 | F |
| ATOM | 8341 | OD1 | ASP | F | 99 | 61.709 | -30.051 | 145.495 | 1.00 | 99.38 | F |
| ATOM | 8342 | OD2 | ASP | F | 99 | 63.737 | -29.378 | 145.984 | 1.00 | 98.19 | F |
| ATOM | 8343 | C | ASP | F | 99 | 63.441 | -31.476 | 141.716 | 1.00 | 91.31 | F |
| ATOM | 8344 | O | ASP | F | 99 | 64.601 | -31.800 | 141.452 | 1.00 | 91.23 | F |
| ATOM | 8345 | N | GLN | F | 100 | 62.518 | -31.243 | 140.789 | 1.00 | 91.15 | F |
| ATOM | 8346 | CA | GLN | F | 100 | 62.785 | -31.321 | 139.352 | 1.00 | 88.73 | F |
| ATOM | 8347 | CB | GLN | F | 100 | 61.479 | -31.646 | 138.622 | 1.00 | 93.72 | F |
| ATOM | 8348 | CG | GLN | F | 100 | 61.608 | -32.376 | 137.299 | 1.00 | 100.01 | F |
| ATOM | 8349 | CD | GLN | F | 100 | 60.249 | -32.813 | 136.761 | 1.00 | 103.68 | F |
| ATOM | 8350 | OE1 | GLN | F | 100 | 59.541 | -33.606 | 137.389 | 1.00 | 107.72 | F |
| ATOM | 8351 | NE2 | GLN | F | 100 | 59.878 | -32.291 | 135.599 | 1.00 | 105.16 | F |
| ATOM | 8352 | C | GLN | F | 100 | 63.290 | -29.942 | 138.939 | 1.00 | 84.81 | F |
| ATOM | 8353 | O | GLN | F | 100 | 62.564 | -28.955 | 139.050 | 1.00 | 85.01 | F |
| ATOM | 8354 | N | LEU | F | 101 | 64.527 | -29.862 | 138.462 | 1.00 | 79.98 | F |
| ATOM | 8355 | CA | LEU | F | 101 | 65.080 | -28.567 | 138.087 | 1.00 | 78.87 | F |
| ATOM | 8356 | CB | LEU | F | 101 | 66.446 | -28.369 | 138.762 | 1.00 | 78.66 | F |
| ATOM | 8357 | CG | LEU | F | 101 | 66.516 | -28.554 | 140.280 | 1.00 | 76.98 | F |
| ATOM | 8358 | CD1 | LEU | F | 101 | 67.908 | -28.214 | 140.781 | 1.00 | 75.59 | F |
| ATOM | 8359 | CD2 | LEU | F | 101 | 65.485 | -27.665 | 140.947 | 1.00 | 78.44 | F |
| ATOM | 8360 | C | LEU | F | 101 | 65.215 | -28.340 | 136.584 | 1.00 | 78.13 | F |
| ATOM | 8361 | O | LEU | F | 101 | 65.489 | -29.268 | 135.818 | 1.00 | 73.43 | F |
| ATOM | 8362 | N | PHE | F | 102 | 65.010 | -27.092 | 136.175 | 1.00 | 76.14 | F |
| ATOM | 8363 | CA | PHE | F | 102 | 65.131 | -26.702 | 134.780 | 1.00 | 73.19 | F |
| ATOM | 8364 | CB | PHE | F | 102 | 63.760 | -26.555 | 134.121 | 1.00 | 75.01 | F |
| ATOM | 8365 | CG | PHE | F | 102 | 62.930 | -27.800 | 134.131 | 1.00 | 75.05 | F |
| ATOM | 8366 | CD1 | PHE | F | 102 | 62.263 | -28.203 | 135.284 | 1.00 | 74.78 | F |
| ATOM | 8367 | CD2 | PHE | F | 102 | 62.765 | -28.540 | 132.966 | 1.00 | 78.47 | F |
| ATOM | 8368 | CE1 | PHE | F | 102 | 61.436 | -29.326 | 135.275 | 1.00 | 77.80 | F |
| ATOM | 8369 | CE2 | PHE | F | 102 | 61.943 | -29.662 | 132.941 | 1.00 | 74.17 | F |
| ATOM | 8370 | CZ | PHE | F | 102 | 61.274 | -30.058 | 134.099 | 1.00 | 75.52 | F |
| ATOM | 8371 | C | PHE | F | 102 | 65.830 | -25.353 | 134.719 | 1.00 | 75.38 | F |
| ATOM | 8372 | O | PHE | F | 102 | 65.539 | -24.460 | 135.513 | 1.00 | 74.94 | F |
| ATOM | 8373 | N | PHE | F | 103 | 66.757 | -25.194 | 133.786 | 1.00 | 73.11 | F |
| ATOM | 8374 | CA | PHE | F | 103 | 67.426 | -23.912 | 133.659 | 1.00 | 74.67 | F |
| ATOM | 8375 | CB | PHE | F | 103 | 68.900 | -24.081 | 133.304 | 1.00 | 70.86 | F |
| ATOM | 8376 | CG | PHE | F | 103 | 69.734 | -22.900 | 133.680 | 1.00 | 70.35 | F |
| ATOM | 8377 | CD1 | PHE | F | 103 | 70.184 | -22.749 | 134.984 | 1.00 | 70.80 | F |
| ATOM | 8378 | CD2 | PHE | F | 103 | 70.019 | -21.908 | 132.752 | 1.00 | 69.74 | F |
| ATOM | 8379 | CE1 | PHE | F | 103 | 70.903 | -21.626 | 135.366 | 1.00 | 69.57 | F |
| ATOM | 8380 | CE2 | PHE | F | 103 | 70.737 | -20.780 | 133.123 | 1.00 | 69.60 | F |
| ATOM | 8381 | CZ | PHE | F | 103 | 71.181 | -20.638 | 134.436 | 1.00 | 69.28 | F |
| ATOM | 8382 | C | PHE | F | 103 | 66.721 | -23.139 | 132.551 | 1.00 | 79.23 | F |
| ATOM | 8383 | O | PHE | F | 103 | 66.195 | -23.729 | 131.603 | 1.00 | 79.57 | F |
| ATOM | 8384 | N | ILE | F | 104 | 66.719 | -21.817 | 132.666 | 1.00 | 80.79 | F |
| ATOM | 8385 | CA | ILE | F | 104 | 66.056 | -20.981 | 131.679 | 1.00 | 77.25 | F |
| ATOM | 8386 | CB | ILE | F | 104 | 64.812 | -20.318 | 132.288 | 1.00 | 71.39 | F |
| ATOM | 8387 | CG2 | ILE | F | 104 | 64.186 | -19.359 | 131.292 | 1.00 | 75.34 | F |
| ATOM | 8388 | CG1 | ILE | F | 104 | 63.812 | -21.399 | 132.697 | 1.00 | 68.80 | F |
| ATOM | 8389 | CD1 | ILE | F | 104 | 62.738 | -20.916 | 133.640 | 1.00 | 61.82 | F |
| ATOM | 8390 | C | ILE | F | 104 | 66.957 | -19.908 | 131.096 | 1.00 | 77.53 | F |
| ATOM | 8391 | O | ILE | F | 104 | 67.649 | -19.182 | 131.814 | 1.00 | 82.11 | F |
| ATOM | 8392 | N | ILE | F | 105 | 66.926 | -19.824 | 129.773 | 1.00 | 83.49 | F |
| ATOM | 8393 | CA | ILE | F | 105 | 67.716 | -18.867 | 129.017 | 1.00 | 89.92 | F |
| ATOM | 8394 | CB | ILE | F | 105 | 68.991 | -19.516 | 128.466 | 1.00 | 89.26 | F |
| ATOM | 8395 | CG2 | ILE | F | 105 | 69.900 | -19.949 | 129.608 | 1.00 | 89.50 | F |
| ATOM | 8396 | CG1 | ILE | F | 105 | 68.604 | -20.717 | 127.601 | 1.00 | 88.24 | F |
| ATOM | 8397 | CD1 | ILE | F | 105 | 69.733 | -21.273 | 126.782 | 1.00 | 88.47 | F |
| ATOM | 8398 | C | ILE | F | 105 | 66.884 | -18.414 | 127.826 | 1.00 | 94.83 | F |
| ATOM | 8399 | O | ILE | F | 105 | 66.034 | -19.157 | 127.341 | 1.00 | 95.88 | F |

Figure 10 (129 of 142)

| ATOM | 8400 | N | GLY | F | 106 | 67.131 | -17.200 | 127.349 | 1.00 | 102.39 | F |
|---|---|---|---|---|---|---|---|---|---|---|---|
| ATOM | 8401 | CA | GLY | F | 106 | 66.389 | -16.701 | 126.207 | 1.00 | 100.93 | F |
| ATOM | 8402 | C | GLY | F | 106 | 67.239 | -16.821 | 124.963 | 1.00 | 103.65 | F |
| ATOM | 8403 | O | GLY | F | 106 | 68.413 | -17.182 | 125.047 | 1.00 | 108.80 | F |
| ATOM | 8404 | N | ALA | F | 107 | 66.653 | -16.520 | 123.811 | 1.00 | 110.82 | F |
| ATOM | 8405 | CA | ALA | F | 107 | 67.372 | -16.589 | 122.544 | 1.00 | 110.65 | F |
| ATOM | 8406 | CB | ALA | F | 107 | 66.643 | -15.760 | 121.502 | 1.00 | 113.56 | F |
| ATOM | 8407 | C | ALA | F | 107 | 68.818 | -16.106 | 122.681 | 1.00 | 116.74 | F |
| ATOM | 8408 | O | ALA | F | 107 | 69.757 | -16.804 | 122.293 | 1.00 | 113.67 | F |
| ATOM | 8409 | N | ASP | F | 108 | 68.977 | -14.905 | 123.234 | 1.00 | 117.91 | F |
| ATOM | 8410 | CA | ASP | F | 108 | 70.281 | -14.284 | 123.451 | 1.00 | 125.29 | F |
| ATOM | 8411 | CB | ASP | F | 108 | 70.132 | -13.154 | 124.485 | 1.00 | 124.17 | F |
| ATOM | 8412 | CG | ASP | F | 108 | 71.454 | -12.486 | 124.835 | 1.00 | 125.25 | F |
| ATOM | 8413 | OD1 | ASP | F | 108 | 72.411 | -12.589 | 124.039 | 1.00 | 128.22 | F |
| ATOM | 8414 | OD2 | ASP | F | 108 | 71.531 | -11.843 | 125.905 | 1.00 | 129.68 | F |
| ATOM | 8415 | C | ASP | F | 108 | 71.339 | -15.297 | 123.901 | 1.00 | 125.79 | F |
| ATOM | 8416 | O | ASP | F | 108 | 72.294 | -15.569 | 123.169 | 1.00 | 124.34 | F |
| ATOM | 8417 | N | MET | F | 109 | 71.155 | -15.854 | 125.096 | 1.00 | 128.57 | F |
| ATOM | 8418 | CA | MET | F | 109 | 72.076 | -16.842 | 125.659 | 1.00 | 127.66 | F |
| ATOM | 8419 | CB | MET | F | 109 | 71.683 | -17.180 | 127.101 | 1.00 | 120.23 | F |
| ATOM | 8420 | CG | MET | F | 109 | 72.410 | -16.349 | 128.121 | 1.00 | 113.31 | F |
| ATOM | 8421 | SD | MET | F | 109 | 74.191 | -16.364 | 127.778 | 1.00 | 102.85 | F |
| ATOM | 8422 | CE | MET | F | 109 | 74.422 | -14.700 | 127.047 | 1.00 | 98.24 | F |
| ATOM | 8423 | C | MET | F | 109 | 72.176 | -18.139 | 124.864 | 1.00 | 128.74 | F |
| ATOM | 8424 | O | MET | F | 109 | 73.230 | -18.781 | 124.845 | 1.00 | 126.57 | F |
| ATOM | 8425 | N | ILE | F | 110 | 71.081 | -18.532 | 124.218 | 1.00 | 126.04 | F |
| ATOM | 8426 | CA | ILE | F | 110 | 71.069 | -19.764 | 123.437 | 1.00 | 117.19 | F |
| ATOM | 8427 | CB | ILE | F | 110 | 69.720 | -19.969 | 122.717 | 1.00 | 116.89 | F |
| ATOM | 8428 | CG2 | ILE | F | 110 | 69.681 | -21.346 | 122.087 | 1.00 | 115.91 | F |
| ATOM | 8429 | CG1 | ILE | F | 110 | 68.567 | -19.827 | 123.715 | 1.00 | 113.90 | F |
| ATOM | 8430 | CD1 | ILE | F | 110 | 67.202 | -20.188 | 123.149 | 1.00 | 111.38 | F |
| ATOM | 8431 | C | ILE | F | 110 | 72.174 | -19.689 | 122.399 | 1.00 | 119.68 | F |
| ATOM | 8432 | O | ILE | F | 110 | 72.800 | -20.693 | 122.060 | 1.00 | 120.53 | F |
| ATOM | 8433 | N | GLU | F | 111 | 72.406 | -18.474 | 121.914 | 1.00 | 120.38 | F |
| ATOM | 8434 | CA | GLU | F | 111 | 73.428 | -18.197 | 120.915 | 1.00 | 117.99 | F |
| ATOM | 8435 | CB | GLU | F | 111 | 73.282 | -16.765 | 120.401 | 1.00 | 124.50 | F |
| ATOM | 8436 | CG | GLU | F | 111 | 72.225 | -16.565 | 119.336 | 1.00 | 120.59 | F |
| ATOM | 8437 | CD | GLU | F | 111 | 72.259 | -15.162 | 118.774 | 1.00 | 119.80 | F |
| ATOM | 8438 | OE1 | GLU | F | 111 | 73.374 | -14.678 | 118.483 | 1.00 | 117.61 | F |
| ATOM | 8439 | OE2 | GLU | F | 111 | 71.184 | -14.545 | 118.620 | 1.00 | 117.27 | F |
| ATOM | 8440 | C | GLU | F | 111 | 74.852 | -18.371 | 121.442 | 1.00 | 119.86 | F |
| ATOM | 8441 | O | GLU | F | 111 | 75.772 | -18.661 | 120.676 | 1.00 | 115.98 | F |
| ATOM | 8442 | N | TYR | F | 112 | 75.035 | -18.190 | 122.745 | 1.00 | 114.99 | F |
| ATOM | 8443 | CA | TYR | F | 112 | 76.360 | -18.296 | 123.356 | 1.00 | 112.75 | F |
| ATOM | 8444 | CB | TYR | F | 112 | 76.380 | -17.509 | 124.672 | 1.00 | 112.68 | F |
| ATOM | 8445 | CG | TYR | F | 112 | 77.159 | -16.213 | 124.610 | 1.00 | 112.83 | F |
| ATOM | 8446 | CD1 | TYR | F | 112 | 77.493 | -15.524 | 125.778 | 1.00 | 110.61 | F |
| ATOM | 8447 | CE1 | TYR | F | 112 | 78.239 | -14.351 | 125.731 | 1.00 | 113.02 | F |
| ATOM | 8448 | CD2 | TYR | F | 112 | 77.589 | -15.689 | 123.388 | 1.00 | 111.96 | F |
| ATOM | 8449 | CE2 | TYR | F | 112 | 78.333 | -14.519 | 123.333 | 1.00 | 110.02 | F |
| ATOM | 8450 | CZ | TYR | F | 112 | 78.657 | -13.856 | 124.510 | 1.00 | 110.97 | F |
| ATOM | 8451 | OH | TYR | F | 112 | 79.419 | -12.710 | 124.469 | 1.00 | 112.91 | F |
| ATOM | 8452 | C | TYR | F | 112 | 76.873 | -19.725 | 123.607 | 1.00 | 109.34 | F |
| ATOM | 8453 | O | TYR | F | 112 | 77.836 | -20.159 | 122.981 | 1.00 | 110.15 | F |
| ATOM | 8454 | N | LEU | F | 113 | 76.227 | -20.425 | 124.534 | 1.00 | 108.59 | F |
| ATOM | 8455 | CA | LEU | F | 113 | 76.549 | -21.791 | 124.952 | 1.00 | 105.57 | F |
| ATOM | 8456 | CB | LEU | F | 113 | 75.480 | -22.736 | 124.357 | 1.00 | 107.71 | F |
| ATOM | 8457 | CG | LEU | F | 113 | 75.038 | -23.928 | 125.217 | 1.00 | 106.95 | F |
| ATOM | 8458 | CD1 | LEU | F | 113 | 75.084 | -23.565 | 126.685 | 1.00 | 108.70 | F |
| ATOM | 8459 | CD2 | LEU | F | 113 | 73.634 | -24.333 | 124.818 | 1.00 | 104.99 | F |
| ATOM | 8460 | C | LEU | F | 113 | 78.030 | -22.325 | 124.829 | 1.00 | 103.51 | F |
| ATOM | 8461 | O | LEU | F | 113 | 78.960 | -21.528 | 124.857 | 1.00 | 104.16 | F |
| ATOM | 8462 | N | PRO | F | 114 | 78.253 | -23.651 | 124.620 | 1.00 | 105.67 | F |
| ATOM | 8463 | CD | PRO | F | 114 | 77.622 | -23.664 | 123.290 | 1.00 | 101.99 | F |
| ATOM | 8464 | CA | PRO | F | 114 | 79.403 | -24.588 | 124.484 | 1.00 | 103.43 | F |
| ATOM | 8465 | CB | PRO | F | 114 | 79.517 | -24.815 | 122.979 | 1.00 | 99.18 | F |

Figure 10 (130 of 142)

| | | | | | | | | | |
|---|---|---|---|---|---|---|---|---|---|
| ATOM | 8466 | CG | PRO | F | 114 | 78.805 | -23.688 | 122.400 | 1.00 101.84 | F |
| ATOM | 8467 | C | PRO | F | 114 | 80.785 | -24.300 | 125.109 | 1.00 101.25 | F |
| ATOM | 8468 | O | PRO | F | 114 | 81.414 | -25.207 | 125.674 | 1.00 99.15 | F |
| ATOM | 8469 | N | LYS | F | 115 | 81.274 | -23.067 | 124.992 | 1.00 100.30 | F |
| ATOM | 8470 | CA | LYS | F | 115 | 82.553 | -22.683 | 125.584 | 1.00 104.06 | F |
| ATOM | 8471 | CB | LYS | F | 115 | 82.983 | -21.330 | 125.011 | 1.00 100.88 | F |
| ATOM | 8472 | CG | LYS | F | 115 | 84.126 | -20.648 | 125.759 | 1.00 98.68 | F |
| ATOM | 8473 | CD | LYS | F | 115 | 85.363 | -20.419 | 124.885 | 1.00 97.81 | F |
| ATOM | 8474 | CE | LYS | F | 115 | 85.194 | -19.278 | 123.882 | 1.00 93.36 | F |
| ATOM | 8475 | NZ | LYS | F | 115 | 84.279 | -19.627 | 122.766 | 1.00 95.22 | F |
| ATOM | 8476 | C | LYS | F | 115 | 82.241 | -22.568 | 127.077 | 1.00 102.87 | F |
| ATOM | 8477 | O | LYS | F | 115 | 83.079 | -22.191 | 127.892 | 1.00 103.86 | F |
| ATOM | 8478 | N | TRP | F | 116 | 81.000 | -22.927 | 127.385 | 1.00 106.00 | F |
| ATOM | 8479 | CA | TRP | F | 116 | 80.366 | -22.901 | 128.698 | 1.00 105.73 | F |
| ATOM | 8480 | CB | TRP | F | 116 | 78.929 | -23.363 | 128.473 | 1.00 104.92 | F |
| ATOM | 8481 | CG | TRP | F | 116 | 77.939 | -23.240 | 129.583 | 1.00 102.80 | F |
| ATOM | 8482 | CD2 | TRP | F | 116 | 76.778 | -22.414 | 129.586 | 1.00 103.28 | F |
| ATOM | 8483 | CE2 | TRP | F | 116 | 76.034 | -22.710 | 130.747 | 1.00 102.60 | F |
| ATOM | 8484 | CE3 | TRP | F | 116 | 76.246 | -21.482 | 128.677 | 1.00 101.01 | F |
| ATOM | 8485 | CD1 | TRP | F | 116 | 77.892 | -23.960 | 130.746 | 1.00 104.36 | F |
| ATOM | 8486 | NE1 | TRP | F | 116 | 76.758 | -23.651 | 131.457 | 1.00 104.46 | F |
| ATOM | 8487 | CZ2 | TRP | F | 116 | 74.839 | -22.074 | 131.072 | 1.00 100.59 | F |
| ATOM | 8488 | CZ3 | TRP | F | 116 | 75.051 | -20.849 | 128.989 | 1.00 99.56 | F |
| ATOM | 8489 | CH2 | TRP | F | 116 | 74.347 | -21.167 | 130.166 | 1.00 99.41 | F |
| ATOM | 8490 | C | TRP | F | 116 | 81.010 | -23.671 | 129.856 | 1.00 105.39 | F |
| ATOM | 8491 | O | TRP | F | 116 | 80.309 | -24.256 | 130.668 | 1.00 107.85 | F |
| ATOM | 8492 | N | TYR | F | 117 | 82.335 | -23.666 | 129.943 | 1.00 103.80 | F |
| ATOM | 8493 | CA | TYR | F | 117 | 83.034 | -24.349 | 131.038 | 1.00 104.96 | F |
| ATOM | 8494 | CB | TYR | F | 117 | 83.364 | -23.330 | 132.139 | 1.00 111.47 | F |
| ATOM | 8495 | CG | TYR | F | 117 | 83.788 | -21.958 | 131.614 | 1.00 116.46 | F |
| ATOM | 8496 | CD1 | TYR | F | 117 | 84.962 | -21.345 | 132.056 | 1.00 116.75 | F |
| ATOM | 8497 | CE1 | TYR | F | 117 | 85.310 | -20.051 | 131.635 | 1.00 114.14 | F |
| ATOM | 8498 | CD2 | TYR | F | 117 | 82.980 | -21.245 | 130.726 | 1.00 116.77 | F |
| ATOM | 8499 | CE2 | TYR | F | 117 | 83.319 | -19.958 | 130.298 | 1.00 117.52 | F |
| ATOM | 8500 | CZ | TYR | F | 117 | 84.481 | -19.367 | 130.757 | 1.00 117.28 | F |
| ATOM | 8501 | OH | TYR | F | 117 | 84.797 | -18.088 | 130.357 | 1.00 113.81 | F |
| ATOM | 8502 | C | TYR | F | 117 | 82.161 | -25.493 | 131.574 | 1.00 97.87 | F |
| ATOM | 8503 | O | TYR | F | 117 | 81.359 | -25.327 | 132.499 | 1.00 91.06 | F |
| ATOM | 8504 | N | LYS | F | 118 | 82.341 | -26.651 | 130.951 | 1.00 93.11 | F |
| ATOM | 8505 | CA | LYS | F | 118 | 81.593 | -27.863 | 131.231 | 1.00 86.80 | F |
| ATOM | 8506 | CB | LYS | F | 118 | 81.502 | -28.167 | 132.729 | 1.00 83.75 | F |
| ATOM | 8507 | CG | LYS | F | 118 | 81.102 | -29.615 | 133.017 | 1.00 83.77 | F |
| ATOM | 8508 | CD | LYS | F | 118 | 81.575 | -30.069 | 134.398 | 1.00 86.51 | F |
| ATOM | 8509 | CE | LYS | F | 118 | 83.103 | -30.080 | 134.534 | 1.00 85.18 | F |
| ATOM | 8510 | NZ | LYS | F | 118 | 83.558 | -30.370 | 135.934 | 1.00 89.75 | F |
| ATOM | 8511 | C | LYS | F | 118 | 80.205 | -27.696 | 130.636 | 1.00 89.00 | F |
| ATOM | 8512 | O | LYS | F | 118 | 79.678 | -26.585 | 130.529 | 1.00 89.19 | F |
| ATOM | 8513 | N | LEU | F | 119 | 79.643 | -28.816 | 130.210 | 1.00 92.04 | F |
| ATOM | 8514 | CA | LEU | F | 119 | 78.322 | -28.864 | 129.604 | 1.00 97.81 | F |
| ATOM | 8515 | CB | LEU | F | 119 | 78.367 | -28.477 | 128.125 | 1.00 102.25 | F |
| ATOM | 8516 | CG | LEU | F | 119 | 77.462 | -27.337 | 127.665 | 1.00 105.17 | F |
| ATOM | 8517 | CD1 | LEU | F | 119 | 76.160 | -27.346 | 128.431 | 1.00 107.48 | F |
| ATOM | 8518 | CD2 | LEU | F | 119 | 78.172 | -26.053 | 127.892 | 1.00 108.61 | F |
| ATOM | 8519 | C | LEU | F | 119 | 77.977 | -30.317 | 129.701 | 1.00 98.60 | F |
| ATOM | 8520 | O | LEU | F | 119 | 77.270 | -30.726 | 130.615 | 1.00 95.07 | F |
| ATOM | 8521 | N | ASP | F | 120 | 78.508 | -31.086 | 128.750 | 1.00 101.24 | F |
| ATOM | 8522 | CA | ASP | F | 120 | 78.301 | -32.527 | 128.685 | 1.00 100.48 | F |
| ATOM | 8523 | CB | ASP | F | 120 | 79.607 | -33.246 | 128.283 | 1.00 106.95 | F |
| ATOM | 8524 | CG | ASP | F | 120 | 80.843 | -32.355 | 128.408 | 1.00 112.14 | F |
| ATOM | 8525 | OD1 | ASP | F | 120 | 80.906 | -31.534 | 129.347 | 1.00 116.03 | F |
| ATOM | 8526 | OD2 | ASP | F | 120 | 81.758 | -32.482 | 127.567 | 1.00 113.79 | F |
| ATOM | 8527 | C | ASP | F | 120 | 77.813 | -33.042 | 130.029 | 1.00 95.23 | F |
| ATOM | 8528 | O | ASP | F | 120 | 76.811 | -33.754 | 130.114 | 1.00 95.52 | F |
| ATOM | 8529 | N | GLU | F | 121 | 78.515 | -32.643 | 131.084 | 1.00 89.16 | F |
| ATOM | 8530 | CA | GLU | F | 121 | 78.167 | -33.048 | 132.436 | 1.00 82.92 | F |
| ATOM | 8531 | CB | GLU | F | 121 | 79.306 | -32.694 | 133.395 | 1.00 89.75 | F |

Figure 10 (131 of 142)

```
ATOM   8532  CG  GLU F 121      79.715 -33.866 134.265  1.00 91.09      F
ATOM   8533  CD  GLU F 121      81.152 -33.779 134.719  1.00 92.81      F
ATOM   8534  OE1 GLU F 121      82.001 -33.287 133.939  1.00 91.28      F
ATOM   8535  OE2 GLU F 121      81.441 -34.221 135.849  1.00 90.77      F
ATOM   8536  C   GLU F 121      76.878 -32.377 132.877  1.00 78.19      F
ATOM   8537  O   GLU F 121      75.868 -33.043 133.059  1.00 68.64      F
ATOM   8538  N   LEU F 122      76.914 -31.057 133.023  1.00 70.47      F
ATOM   8539  CA  LEU F 122      75.741 -30.305 133.456  1.00 68.09      F
ATOM   8540  CB  LEU F 122      75.927 -28.814 133.174  1.00 63.52      F
ATOM   8541  CG  LEU F 122      74.730 -27.917 133.520  1.00 62.62      F
ATOM   8542  CD1 LEU F 122      74.376 -28.067 134.996  1.00 59.72      F
ATOM   8543  CD2 LEU F 122      75.061 -26.469 133.181  1.00 61.88      F
ATOM   8544  C   LEU F 122      74.425 -30.764 132.840  1.00 67.59      F
ATOM   8545  O   LEU F 122      73.409 -30.848 133.527  1.00 68.98      F
ATOM   8546  N   LEU F 123      74.444 -31.045 131.542  1.00 71.59      F
ATOM   8547  CA  LEU F 123      73.252 -31.499 130.834  1.00 72.75      F
ATOM   8548  CB  LEU F 123      73.559 -31.677 129.348  1.00 77.09      F
ATOM   8549  CG  LEU F 123      73.614 -30.419 128.477  1.00 78.00      F
ATOM   8550  CD1 LEU F 123      74.113 -30.786 127.086  1.00 79.91      F
ATOM   8551  CD2 LEU F 123      72.230 -29.787 128.407  1.00 79.82      F
ATOM   8552  C   LEU F 123      72.736 -32.814 131.408  1.00 72.94      F
ATOM   8553  O   LEU F 123      71.534 -33.080 131.395  1.00 72.72      F
ATOM   8554  N   ASN F 124      73.658 -33.635 131.900  1.00 71.43      F
ATOM   8555  CA  ASN F 124      73.327 -34.925 132.501  1.00 74.13      F
ATOM   8556  CB  ASN F 124      74.604 -35.776 132.592  1.00 75.30      F
ATOM   8557  CG  ASN F 124      74.348 -37.253 132.381  1.00 73.79      F
ATOM   8558  OD1 ASN F 124      73.599 -37.642 131.482  1.00 75.67      F
ATOM   8559  ND2 ASN F 124      74.989 -38.090 133.196  1.00 74.41      F
ATOM   8560  C   ASN F 124      72.769 -34.655 133.900  1.00 73.23      F
ATOM   8561  O   ASN F 124      72.481 -35.575 134.668  1.00 75.35      F
ATOM   8562  N   LEU F 125      72.624 -33.375 134.219  1.00 75.97      F
ATOM   8563  CA  LEU F 125      72.137 -32.961 135.523  1.00 77.40      F
ATOM   8564  CB  LEU F 125      73.207 -32.139 136.255  1.00 80.75      F
ATOM   8565  CG  LEU F 125      74.642 -32.650 136.458  1.00 77.92      F
ATOM   8566  CD1 LEU F 125      75.408 -31.632 137.303  1.00 78.08      F
ATOM   8567  CD2 LEU F 125      74.652 -34.014 137.138  1.00 79.08      F
ATOM   8568  C   LEU F 125      70.874 -32.118 135.417  1.00 78.82      F
ATOM   8569  O   LEU F 125      69.929 -32.309 136.181  1.00 80.49      F
ATOM   8570  N   ILE F 126      70.859 -31.183 134.472  1.00 83.57      F
ATOM   8571  CA  ILE F 126      69.709 -30.304 134.312  1.00 89.03      F
ATOM   8572  CB  ILE F 126      70.043 -28.888 134.851  1.00 89.85      F
ATOM   8573  CG2 ILE F 126      70.796 -28.100 133.790  1.00 85.36      F
ATOM   8574  CG1 ILE F 126      68.761 -28.154 135.250  1.00 90.81      F
ATOM   8575  CD1 ILE F 126      68.990 -26.970 136.192  1.00 89.55      F
ATOM   8576  C   ILE F 126      69.257 -30.198 132.856  1.00 93.98      F
ATOM   8577  O   ILE F 126      69.931 -30.682 131.946  1.00 95.40      F
ATOM   8578  N   GLN F 127      68.106 -29.563 132.652  1.00 94.89      F
ATOM   8579  CA  GLN F 127      67.548 -29.362 131.319  1.00 94.50      F
ATOM   8580  CB  GLN F 127      66.209 -30.093 131.191  1.00 98.71      F
ATOM   8581  CG  GLN F 127      66.313 -31.602 131.284  1.00106.38      F
ATOM   8582  CD  GLN F 127      64.954 -32.280 131.277  1.00110.26      F
ATOM   8583  OE1 GLN F 127      64.155 -32.103 132.197  1.00115.84      F
ATOM   8584  NE2 GLN F 127      64.685 -33.059 130.234  1.00114.96      F
ATOM   8585  C   GLN F 127      67.353 -27.872 131.065  1.00 95.27      F
ATOM   8586  O   GLN F 127      66.982 -27.124 131.971  1.00 93.14      F
ATOM   8587  N   PHE F 128      67.607 -27.448 129.832  1.00 92.83      F
ATOM   8588  CA  PHE F 128      67.464 -26.047 129.468  1.00 94.97      F
ATOM   8589  CB  PHE F 128      68.621 -25.599 128.587  1.00 94.91      F
ATOM   8590  CG  PHE F 128      69.869 -25.278 129.340  1.00 97.14      F
ATOM   8591  CD1 PHE F 128      70.519 -26.250 130.089  1.00 92.69      F
ATOM   8592  CD2 PHE F 128      70.413 -24.004 129.282  1.00 91.78      F
ATOM   8593  CE1 PHE F 128      71.695 -25.953 130.768  1.00 93.10      F
ATOM   8594  CE2 PHE F 128      71.588 -23.698 129.956  1.00 93.29      F
ATOM   8595  CZ  PHE F 128      72.231 -24.674 130.700  1.00 94.54      F
ATOM   8596  C   PHE F 128      66.170 -25.750 128.741  1.00 95.27      F
ATOM   8597  O   PHE F 128      65.677 -26.562 127.959  1.00 97.77      F
```

Figure 10 (132 of 142)

| ATOM | 8598 | N | ILE | F | 129 | 65.629 | -24.569 | 129.003 | 1.00 | 97.80 | F |
| --- | --- | --- | --- | --- | --- | --- | --- | --- | --- | --- | --- |
| ATOM | 8599 | CA | ILE | F | 129 | 64.403 | -24.133 | 128.361 | 1.00 | 96.37 | F |
| ATOM | 8600 | CB | ILE | F | 129 | 63.274 | -23.936 | 129.393 | 1.00 | 100.35 | F |
| ATOM | 8601 | CG2 | ILE | F | 129 | 62.029 | -23.413 | 128.703 | 1.00 | 104.40 | F |
| ATOM | 8602 | CG1 | ILE | F | 129 | 62.976 | -25.269 | 130.096 | 1.00 | 101.61 | F |
| ATOM | 8603 | CD1 | ILE | F | 129 | 61.872 | -25.206 | 131.158 | 1.00 | 99.81 | F |
| ATOM | 8604 | C | ILE | F | 129 | 64.714 | -22.811 | 127.665 | 1.00 | 95.14 | F |
| ATOM | 8605 | O | ILE | F | 129 | 65.233 | -21.884 | 128.285 | 1.00 | 97.67 | F |
| ATOM | 8606 | N | GLY | F | 130 | 64.420 | -22.744 | 126.369 | 1.00 | 93.63 | F |
| ATOM | 8607 | CA | GLY | F | 130 | 64.674 | -21.540 | 125.598 | 1.00 | 84.46 | F |
| ATOM | 8608 | C | GLY | F | 130 | 63.388 | -20.792 | 125.313 | 1.00 | 84.91 | F |
| ATOM | 8609 | O | GLY | F | 130 | 62.338 | -21.410 | 125.131 | 1.00 | 83.64 | F |
| ATOM | 8610 | N | VAL | F | 131 | 63.464 | -19.465 | 125.269 | 1.00 | 81.65 | F |
| ATOM | 8611 | CA | VAL | F | 131 | 62.284 | -18.645 | 125.023 | 1.00 | 77.05 | F |
| ATOM | 8612 | CB | VAL | F | 131 | 62.119 | -17.580 | 126.137 | 1.00 | 77.22 | F |
| ATOM | 8613 | CG1 | VAL | F | 131 | 60.987 | -16.623 | 125.801 | 1.00 | 71.83 | F |
| ATOM | 8614 | CG2 | VAL | F | 131 | 61.832 | -18.268 | 127.460 | 1.00 | 70.30 | F |
| ATOM | 8615 | C | VAL | F | 131 | 62.347 | -17.963 | 123.662 | 1.00 | 76.76 | F |
| ATOM | 8616 | O | VAL | F | 131 | 61.571 | -18.287 | 122.760 | 1.00 | 77.46 | F |
| ATOM | 8617 | N | VAL | F | 138 | 67.218 | -18.098 | 117.943 | 1.00 | 120.67 | F |
| ATOM | 8618 | CA | VAL | F | 138 | 67.450 | -19.470 | 118.382 | 1.00 | 121.75 | F |
| ATOM | 8619 | CB | VAL | F | 138 | 66.235 | -20.016 | 119.187 | 1.00 | 122.96 | F |
| ATOM | 8620 | CG1 | VAL | F | 138 | 64.941 | -19.777 | 118.417 | 1.00 | 122.59 | F |
| ATOM | 8621 | CG2 | VAL | F | 138 | 66.420 | -21.498 | 119.470 | 1.00 | 120.40 | F |
| ATOM | 8622 | C | VAL | F | 138 | 67.731 | -20.393 | 117.198 | 1.00 | 119.80 | F |
| ATOM | 8623 | O | VAL | F | 138 | 67.274 | -20.141 | 116.076 | 1.00 | 117.99 | F |
| ATOM | 8624 | N | GLU | F | 139 | 68.487 | -21.460 | 117.461 | 1.00 | 120.71 | F |
| ATOM | 8625 | CA | GLU | F | 139 | 68.851 | -22.429 | 116.432 | 1.00 | 118.91 | F |
| ATOM | 8626 | CB | GLU | F | 139 | 69.645 | -21.718 | 115.329 | 1.00 | 119.08 | F |
| ATOM | 8627 | CG | GLU | F | 139 | 71.048 | -21.291 | 115.741 | 1.00 | 108.11 | F |
| ATOM | 8628 | CD | GLU | F | 139 | 71.409 | -19.910 | 115.236 | 1.00 | 105.03 | F |
| ATOM | 8629 | OE1 | GLU | F | 139 | 70.887 | -19.505 | 114.177 | 1.00 | 99.11 | F |
| ATOM | 8630 | OE2 | GLU | F | 139 | 72.224 | -19.234 | 115.896 | 1.00 | 100.63 | F |
| ATOM | 8631 | C | GLU | F | 139 | 69.670 | -23.605 | 116.989 | 1.00 | 118.83 | F |
| ATOM | 8632 | O | GLU | F | 139 | 69.598 | -24.718 | 116.465 | 1.00 | 118.51 | F |
| ATOM | 8633 | N | THR | F | 140 | 70.436 | -23.332 | 118.049 | 1.00 | 119.51 | F |
| ATOM | 8634 | CA | THR | F | 140 | 71.322 | -24.286 | 118.742 | 1.00 | 121.01 | F |
| ATOM | 8635 | CB | THR | F | 140 | 71.172 | -24.167 | 120.292 | 1.00 | 123.17 | F |
| ATOM | 8636 | OG1 | THR | F | 140 | 69.794 | -23.960 | 120.638 | 1.00 | 118.88 | F |
| ATOM | 8637 | CG2 | THR | F | 140 | 72.026 | -23.029 | 120.831 | 1.00 | 116.36 | F |
| ATOM | 8638 | C | THR | F | 140 | 71.306 | -25.788 | 118.412 | 1.00 | 121.78 | F |
| ATOM | 8639 | O | THR | F | 140 | 70.247 | -26.382 | 118.195 | 1.00 | 124.40 | F |
| ATOM | 8640 | N | PRO | F | 141 | 72.503 | -26.415 | 118.380 | 1.00 | 121.57 | F |
| ATOM | 8641 | CD | PRO | F | 141 | 73.790 | -25.691 | 118.309 | 1.00 | 119.09 | F |
| ATOM | 8642 | CA | PRO | F | 141 | 72.708 | -27.841 | 118.096 | 1.00 | 119.78 | F |
| ATOM | 8643 | CB | PRO | F | 141 | 74.069 | -27.854 | 117.416 | 1.00 | 118.56 | F |
| ATOM | 8644 | CG | PRO | F | 141 | 74.810 | -26.818 | 118.195 | 1.00 | 119.31 | F |
| ATOM | 8645 | C | PRO | F | 141 | 72.711 | -28.668 | 119.386 | 1.00 | 118.97 | F |
| ATOM | 8646 | O | PRO | F | 141 | 73.159 | -29.817 | 119.396 | 1.00 | 117.69 | F |
| ATOM | 8647 | N | TYR | F | 142 | 72.209 | -28.067 | 120.466 | 1.00 | 119.29 | F |
| ATOM | 8648 | CA | TYR | F | 142 | 72.156 | -28.704 | 121.787 | 1.00 | 118.83 | F |
| ATOM | 8649 | CB | TYR | F | 142 | 72.772 | -27.774 | 122.852 | 1.00 | 119.61 | F |
| ATOM | 8650 | CG | TYR | F | 142 | 74.151 | -27.251 | 122.504 | 1.00 | 118.42 | F |
| ATOM | 8651 | CD1 | TYR | F | 142 | 75.280 | -28.061 | 122.638 | 1.00 | 118.27 | F |
| ATOM | 8652 | CE1 | TYR | F | 142 | 76.535 | -27.620 | 122.225 | 1.00 | 116.77 | F |
| ATOM | 8653 | CD2 | TYR | F | 142 | 74.314 | -25.974 | 121.956 | 1.00 | 118.77 | F |
| ATOM | 8654 | CE2 | TYR | F | 142 | 75.565 | -25.525 | 121.538 | 1.00 | 118.79 | F |
| ATOM | 8655 | CZ | TYR | F | 142 | 76.668 | -26.360 | 121.672 | 1.00 | 119.56 | F |
| ATOM | 8656 | OH | TYR | F | 142 | 77.895 | -25.969 | 121.203 | 1.00 | 118.16 | F |
| ATOM | 8657 | C | TYR | F | 142 | 70.724 | -29.037 | 122.214 | 1.00 | 118.44 | F |
| ATOM | 8658 | O | TYR | F | 142 | 69.770 | -28.382 | 121.791 | 1.00 | 120.68 | F |
| ATOM | 8659 | N | PRO | F | 143 | 70.562 | -30.061 | 123.068 | 1.00 | 115.35 | F |
| ATOM | 8660 | CD | PRO | F | 143 | 71.647 | -30.872 | 123.646 | 1.00 | 112.88 | F |
| ATOM | 8661 | CA | PRO | F | 143 | 69.256 | -30.497 | 123.577 | 1.00 | 107.02 | F |
| ATOM | 8662 | CB | PRO | F | 143 | 69.607 | -31.737 | 124.389 | 1.00 | 111.23 | F |
| ATOM | 8663 | CG | PRO | F | 143 | 70.993 | -31.429 | 124.876 | 1.00 | 110.21 | F |

Figure 10 (133 of 142)

| ATOM | 8664 | C | PRO | F | 143 | 68.669 | -29.378 | 124.437 | 1.00 | 107.05 | F |
|---|---|---|---|---|---|---|---|---|---|---|---|
| ATOM | 8665 | O | PRO | F | 143 | 69.142 | -29.117 | 125.540 | 1.00 | 105.82 | F |
| ATOM | 8666 | N | LEU | F | 144 | 67.635 | -28.721 | 123.927 | 1.00 | 104.02 | F |
| ATOM | 8667 | CA | LEU | F | 144 | 67.024 | -27.600 | 124.628 | 1.00 | 102.63 | F |
| ATOM | 8668 | CB | LEU | F | 144 | 67.658 | -26.308 | 124.096 | 1.00 | 108.95 | F |
| ATOM | 8669 | CG | LEU | F | 144 | 67.585 | -24.947 | 124.786 | 1.00 | 111.58 | F |
| ATOM | 8670 | CD1 | LEU | F | 144 | 68.428 | -23.956 | 123.995 | 1.00 | 115.21 | F |
| ATOM | 8671 | CD2 | LEU | F | 144 | 66.164 | -24.466 | 124.865 | 1.00 | 115.66 | F |
| ATOM | 8672 | C | LEU | F | 144 | 65.521 | -27.610 | 124.361 | 1.00 | 102.11 | F |
| ATOM | 8673 | O | LEU | F | 144 | 65.101 | -27.727 | 123.212 | 1.00 | 100.14 | F |
| ATOM | 8674 | N | LEU | F | 145 | 64.708 | -27.504 | 125.408 | 1.00 | 98.97 | F |
| ATOM | 8675 | CA | LEU | F | 145 | 63.259 | -27.490 | 125.222 | 1.00 | 96.39 | F |
| ATOM | 8676 | CB | LEU | F | 145 | 62.544 | -28.095 | 126.428 | 1.00 | 94.87 | F |
| ATOM | 8677 | CG | LEU | F | 145 | 62.594 | -29.621 | 126.445 | 1.00 | 96.94 | F |
| ATOM | 8678 | CD1 | LEU | F | 145 | 61.891 | -30.153 | 127.680 | 1.00 | 98.36 | F |
| ATOM | 8679 | CD2 | LEU | F | 145 | 61.946 | -30.158 | 125.177 | 1.00 | 98.84 | F |
| ATOM | 8680 | C | LEU | F | 145 | 62.813 | -26.063 | 125.023 | 1.00 | 94.03 | F |
| ATOM | 8681 | O | LEU | F | 145 | 63.474 | -25.139 | 125.487 | 1.00 | 97.79 | F |
| ATOM | 8682 | N | PHE | F | 146 | 61.694 | -25.871 | 124.338 | 1.00 | 95.10 | F |
| ATOM | 8683 | CA | PHE | F | 146 | 61.221 | -24.520 | 124.098 | 1.00 | 96.13 | F |
| ATOM | 8684 | CB | PHE | F | 146 | 61.200 | -24.249 | 122.597 | 1.00 | 99.59 | F |
| ATOM | 8685 | CG | PHE | F | 146 | 62.564 | -24.230 | 121.979 | 1.00 | 99.92 | F |
| ATOM | 8686 | CD1 | PHE | F | 146 | 63.456 | -23.199 | 122.273 | 1.00 | 99.68 | F |
| ATOM | 8687 | CD2 | PHE | F | 146 | 62.973 | -25.249 | 121.122 | 1.00 | 98.71 | F |
| ATOM | 8688 | CE1 | PHE | F | 146 | 64.741 | -23.181 | 121.728 | 1.00 | 98.91 | F |
| ATOM | 8689 | CE2 | PHE | F | 146 | 64.255 | -25.244 | 120.569 | 1.00 | 98.25 | F |
| ATOM | 8690 | CZ | PHE | F | 146 | 65.142 | -24.206 | 120.873 | 1.00 | 100.45 | F |
| ATOM | 8691 | C | PHE | F | 146 | 59.872 | -24.196 | 124.714 | 1.00 | 94.39 | F |
| ATOM | 8692 | O | PHE | F | 146 | 59.055 | -25.079 | 124.984 | 1.00 | 95.54 | F |
| ATOM | 8693 | N | ALA | F | 147 | 59.658 | -22.910 | 124.947 | 1.00 | 90.37 | F |
| ATOM | 8694 | CA | ALA | F | 147 | 58.420 | -22.438 | 125.527 | 1.00 | 90.62 | F |
| ATOM | 8695 | CB | ALA | F | 147 | 58.617 | -22.161 | 127.015 | 1.00 | 91.68 | F |
| ATOM | 8696 | C | ALA | F | 147 | 58.029 | -21.163 | 124.794 | 1.00 | 90.47 | F |
| ATOM | 8697 | O | ALA | F | 147 | 58.775 | -20.176 | 124.824 | 1.00 | 88.15 | F |
| ATOM | 8698 | N | ASP | F | 148 | 56.882 | -21.187 | 124.117 | 1.00 | 96.80 | F |
| ATOM | 8699 | CA | ASP | F | 148 | 56.415 | -20.014 | 123.389 | 1.00 | 100.30 | F |
| ATOM | 8700 | CB | ASP | F | 148 | 55.112 | -20.315 | 122.652 | 1.00 | 109.34 | F |
| ATOM | 8701 | CG | ASP | F | 148 | 55.341 | -20.981 | 121.309 | 1.00 | 111.00 | F |
| ATOM | 8702 | OD1 | ASP | F | 148 | 55.736 | -22.167 | 121.272 | 1.00 | 114.39 | F |
| ATOM | 8703 | OD2 | ASP | F | 148 | 55.141 | -20.296 | 120.285 | 1.00 | 114.69 | F |
| ATOM | 8704 | C | ASP | F | 148 | 56.217 | -18.861 | 124.342 | 1.00 | 97.72 | F |
| ATOM | 8705 | O | ASP | F | 148 | 55.472 | -18.937 | 125.328 | 1.00 | 97.31 | F |
| ATOM | 8706 | N | VAL | F | 149 | 56.937 | -17.789 | 124.050 | 1.00 | 97.04 | F |
| ATOM | 8707 | CA | VAL | F | 149 | 56.861 | -16.579 | 124.893 | 1.00 | 101.33 | F |
| ATOM | 8708 | CB | VAL | F | 149 | 57.788 | -16.708 | 126.133 | 1.00 | 107.83 | F |
| ATOM | 8709 | CG1 | VAL | F | 149 | 57.421 | -15.599 | 127.170 | 1.00 | 109.91 | F |
| ATOM | 8710 | CG2 | VAL | F | 149 | 57.584 | -18.045 | 126.784 | 1.00 | 111.50 | F |
| ATOM | 8711 | C | VAL | F | 149 | 57.179 | -15.377 | 123.901 | 1.00 | 97.64 | F |
| ATOM | 8712 | O | VAL | F | 149 | 57.993 | -15.415 | 123.097 | 1.00 | 96.81 | F |
| ATOM | 8713 | N | PRO | F | 150 | 56.647 | -14.215 | 124.180 | 1.00 | 88.34 | F |
| ATOM | 8714 | CD | PRO | F | 150 | 57.822 | -14.134 | 125.063 | 1.00 | 84.13 | F |
| ATOM | 8715 | CA | PRO | F | 150 | 56.245 | -12.817 | 123.877 | 1.00 | 83.01 | F |
| ATOM | 8716 | CB | PRO | F | 150 | 56.388 | -12.134 | 125.227 | 1.00 | 78.99 | F |
| ATOM | 8717 | CG | PRO | F | 150 | 57.692 | -12.793 | 125.712 | 1.00 | 83.21 | F |
| ATOM | 8718 | C | PRO | F | 150 | 57.331 | -12.221 | 122.963 | 1.00 | 84.32 | F |
| ATOM | 8719 | O | PRO | F | 150 | 58.494 | -12.704 | 122.816 | 1.00 | 83.75 | F |
| ATOM | 8720 | N | GLU | F | 151 | 56.996 | -11.109 | 122.355 | 1.00 | 80.80 | F |
| ATOM | 8721 | CA | GLU | F | 151 | 58.000 | -10.409 | 121.575 | 1.00 | 74.71 | F |
| ATOM | 8722 | CB | GLU | F | 151 | 57.702 | -10.395 | 120.075 | 1.00 | 79.13 | F |
| ATOM | 8723 | CG | GLU | F | 151 | 58.935 | -10.745 | 119.198 | 1.00 | 88.06 | F |
| ATOM | 8724 | CD | GLU | F | 151 | 60.239 | -10.109 | 119.680 | 1.00 | 93.84 | F |
| ATOM | 8725 | OE1 | GLU | F | 151 | 60.181 | -8.996 | 120.246 | 1.00 | 91.81 | F |
| ATOM | 8726 | OE2 | GLU | F | 151 | 61.326 | -10.708 | 119.479 | 1.00 | 93.75 | F |
| ATOM | 8727 | C | GLU | F | 151 | 57.990 | -9.016 | 122.161 | 1.00 | 66.14 | F |
| ATOM | 8728 | O | GLU | F | 151 | 57.282 | -8.116 | 121.720 | 1.00 | 62.86 | F |
| ATOM | 8729 | N | PHE | F | 152 | 58.751 | -8.898 | 123.232 | 1.00 | 65.03 | F |

Figure 10 (134 of 142)

| | | | | | | | | | |
|---|---|---|---|---|---|---|---|---|---|
| ATOM | 8730 | CA | PHE | F | 152 | 58.919 | -7.655 | 123.933 | 1.00 67.79 | F |
| ATOM | 8731 | CB | PHE | F | 152 | 58.910 | -7.928 | 125.438 | 1.00 71.66 | F |
| ATOM | 8732 | CG | PHE | F | 152 | 58.715 | -6.697 | 126.290 | 1.00 74.22 | F |
| ATOM | 8733 | CD1 | PHE | F | 152 | 57.877 | -6.735 | 127.409 | 1.00 73.19 | F |
| ATOM | 8734 | CD2 | PHE | F | 152 | 59.399 | -5.519 | 126.010 | 1.00 72.42 | F |
| ATOM | 8735 | CE1 | PHE | F | 152 | 57.714 | -5.609 | 128.225 | 1.00 72.57 | F |
| ATOM | 8736 | CE2 | PHE | F | 152 | 59.245 | -4.392 | 126.817 | 1.00 72.06 | F |
| ATOM | 8737 | CZ | PHE | F | 152 | 58.404 | -4.439 | 127.929 | 1.00 74.08 | F |
| ATOM | 8738 | C | PHE | F | 152 | 60.309 | -7.264 | 123.430 | 1.00 66.12 | F |
| ATOM | 8739 | O | PHE | F | 152 | 61.053 | -8.103 | 122.906 | 1.00 66.32 | F |
| ATOM | 8740 | N | GLU | F | 153 | 60.645 | -5.990 | 123.559 | 1.00 65.81 | F |
| ATOM | 8741 | CA | GLU | F | 153 | 61.932 | -5.488 | 123.117 | 1.00 68.92 | F |
| ATOM | 8742 | CB | GLU | F | 153 | 61.761 | -4.638 | 121.854 | 1.00 67.85 | F |
| ATOM | 8743 | CG | GLU | F | 153 | 62.755 | -3.487 | 121.738 | 1.00 70.54 | F |
| ATOM | 8744 | CD | GLU | F | 153 | 62.847 | -2.887 | 120.350 | 1.00 70.26 | F |
| ATOM | 8745 | OE1 | GLU | F | 153 | 63.586 | -1.887 | 120.190 | 1.00 67.40 | F |
| ATOM | 8746 | OE2 | GLU | F | 153 | 62.195 | -3.418 | 119.420 | 1.00 67.01 | F |
| ATOM | 8747 | C | GLU | F | 153 | 62.590 | -4.677 | 124.218 | 1.00 69.98 | F |
| ATOM | 8748 | O | GLU | F | 153 | 62.604 | -3.446 | 124.195 | 1.00 62.71 | F |
| ATOM | 8749 | N | VAL | F | 154 | 63.137 | -5.377 | 125.197 | 1.00 71.85 | F |
| ATOM | 8750 | CA | VAL | F | 154 | 63.791 | -4.686 | 126.279 | 1.00 74.34 | F |
| ATOM | 8751 | CB | VAL | F | 154 | 62.791 | -4.350 | 127.396 | 1.00 72.17 | F |
| ATOM | 8752 | CG1 | VAL | F | 154 | 62.254 | -5.633 | 128.013 | 1.00 74.98 | F |
| ATOM | 8753 | CG2 | VAL | F | 154 | 63.461 | -3.468 | 128.434 | 1.00 70.74 | F |
| ATOM | 8754 | C | VAL | F | 154 | 64.950 | -5.473 | 126.854 | 1.00 70.36 | F |
| ATOM | 8755 | O | VAL | F | 154 | 64.863 | -6.687 | 127.055 | 1.00 76.60 | F |
| ATOM | 8756 | N | SER | F | 155 | 66.047 | -4.768 | 127.091 | 1.00 68.23 | F |
| ATOM | 8757 | CA | SER | F | 155 | 67.231 | -5.369 | 127.674 | 1.00 70.10 | F |
| ATOM | 8758 | CB | SER | F | 155 | 68.305 | -5.612 | 126.619 | 1.00 73.67 | F |
| ATOM | 8759 | OG | SER | F | 155 | 68.875 | -4.390 | 126.196 | 1.00 71.77 | F |
| ATOM | 8760 | C | SER | F | 155 | 67.687 | -4.316 | 128.652 | 1.00 70.40 | F |
| ATOM | 8761 | O | SER | F | 155 | 67.368 | -3.137 | 128.481 | 1.00 64.47 | F |
| ATOM | 8762 | N | SER | F | 156 | 68.415 | -4.731 | 129.683 | 1.00 71.04 | F |
| ATOM | 8763 | CA | SER | F | 156 | 68.866 | -3.778 | 130.679 | 1.00 69.23 | F |
| ATOM | 8764 | CB | SER | F | 156 | 69.609 | -4.493 | 131.821 | 1.00 69.76 | F |
| ATOM | 8765 | OG | SER | F | 156 | 70.904 | -4.922 | 131.437 | 1.00 74.50 | F |
| ATOM | 8766 | C | SER | F | 156 | 69.748 | -2.714 | 130.040 | 1.00 65.39 | F |
| ATOM | 8767 | O | SER | F | 156 | 69.574 | -1.527 | 130.304 | 1.00 66.73 | F |
| ATOM | 8768 | N | THR | F | 157 | 70.671 | -3.135 | 129.179 | 1.00 64.52 | F |
| ATOM | 8769 | CA | THR | F | 157 | 71.583 | -2.203 | 128.524 | 1.00 66.69 | F |
| ATOM | 8770 | CB | THR | F | 157 | 72.485 | -2.924 | 127.516 | 1.00 68.60 | F |
| ATOM | 8771 | OG1 | THR | F | 157 | 73.150 | -4.008 | 128.171 | 1.00 69.39 | F |
| ATOM | 8772 | CG2 | THR | F | 157 | 73.533 | -1.974 | 126.973 | 1.00 65.97 | F |
| ATOM | 8773 | C | THR | F | 157 | 70.834 | -1.079 | 127.823 | 1.00 65.96 | F |
| ATOM | 8774 | O | THR | F | 157 | 71.420 | -0.053 | 127.470 | 1.00 69.84 | F |
| ATOM | 8775 | N | MET | F | 158 | 69.537 | -1.285 | 127.610 | 1.00 62.80 | F |
| ATOM | 8776 | CA | MET | F | 158 | 68.690 | -0.264 | 126.999 | 1.00 60.91 | F |
| ATOM | 8777 | CB | MET | F | 158 | 67.333 | -0.850 | 126.609 | 1.00 56.92 | F |
| ATOM | 8778 | CG | MET | F | 158 | 66.242 | 0.195 | 126.421 | 1.00 57.03 | F |
| ATOM | 8779 | SD | MET | F | 158 | 64.619 | -0.536 | 126.230 | 1.00 57.27 | F |
| ATOM | 8780 | CE | MET | F | 158 | 64.993 | -1.974 | 125.180 | 1.00 59.27 | F |
| ATOM | 8781 | C | MET | F | 158 | 68.478 | 0.773 | 128.092 | 1.00 63.41 | F |
| ATOM | 8782 | O | MET | F | 158 | 68.841 | 1.945 | 127.947 | 1.00 62.29 | F |
| ATOM | 8783 | N | ILE | F | 159 | 67.888 | 0.299 | 129.190 | 1.00 60.69 | F |
| ATOM | 8784 | CA | ILE | F | 159 | 67.598 | 1.104 | 130.363 | 1.00 51.63 | F |
| ATOM | 8785 | CB | ILE | F | 159 | 67.158 | 0.214 | 131.529 | 1.00 51.29 | F |
| ATOM | 8786 | CG2 | ILE | F | 159 | 66.679 | 1.084 | 132.676 | 1.00 54.99 | F |
| ATOM | 8787 | CG1 | ILE | F | 159 | 66.063 | -0.750 | 131.075 | 1.00 49.34 | F |
| ATOM | 8788 | CD1 | ILE | F | 159 | 64.733 | -0.096 | 130.838 | 1.00 43.89 | F |
| ATOM | 8789 | C | ILE | F | 159 | 68.829 | 1.894 | 130.797 | 1.00 52.64 | F |
| ATOM | 8790 | O | ILE | F | 159 | 68.776 | 3.111 | 130.887 | 1.00 51.59 | F |
| ATOM | 8791 | N | ARG | F | 160 | 69.937 | 1.199 | 131.055 | 1.00 54.21 | F |
| ATOM | 8792 | CA | ARG | F | 160 | 71.168 | 1.856 | 131.490 | 1.00 55.05 | F |
| ATOM | 8793 | CB | ARG | F | 160 | 72.355 | 0.905 | 131.394 | 1.00 54.65 | F |
| ATOM | 8794 | CG | ARG | F | 160 | 72.172 | -0.344 | 132.187 | 1.00 53.04 | F |
| ATOM | 8795 | CD | ARG | F | 160 | 73.497 | -0.856 | 132.687 | 1.00 52.88 | F |

Figure 10 135 of 142)

| | | | | | | | | | |
|---|---|---|---|---|---|---|---|---|---|
| ATOM | 8796 | NE | ARG | F | 160 | 73.687 | -2.252 | 132.325 | 1.00 51.17 | F |
| ATOM | 8797 | CZ | ARG | F | 160 | 74.302 | -2.658 | 131.221 | 1.00 46.59 | F |
| ATOM | 8798 | NH1 | ARG | F | 160 | 74.798 | -1.766 | 130.366 | 1.00 43.79 | F |
| ATOM | 8799 | NH2 | ARG | F | 160 | 74.412 | -3.956 | 130.975 | 1.00 42.40 | F |
| ATOM | 8800 | C | ARG | F | 160 | 71.468 | 3.099 | 130.681 | 1.00 58.75 | F |
| ATOM | 8801 | O | ARG | F | 160 | 71.864 | 4.127 | 131.228 | 1.00 58.07 | F |
| ATOM | 8802 | N | GLU | F | 161 | 71.288 | 3.005 | 129.370 | 1.00 64.19 | F |
| ATOM | 8803 | CA | GLU | F | 161 | 71.541 | 4.143 | 128.509 | 1.00 68.13 | F |
| ATOM | 8804 | CB | GLU | F | 161 | 71.735 | 3.658 | 127.076 | 1.00 70.95 | F |
| ATOM | 8805 | CG | GLU | F | 161 | 72.863 | 2.633 | 126.986 | 1.00 74.96 | F |
| ATOM | 8806 | CD | GLU | F | 161 | 73.324 | 2.368 | 125.567 | 1.00 77.98 | F |
| ATOM | 8807 | OE1 | GLU | F | 161 | 73.701 | 3.342 | 124.866 | 1.00 75.79 | F |
| ATOM | 8808 | OE2 | GLU | F | 161 | 73.313 | 1.182 | 125.161 | 1.00 76.26 | F |
| ATOM | 8809 | C | GLU | F | 161 | 70.337 | 5.055 | 128.654 | 1.00 67.51 | F |
| ATOM | 8810 | O | GLU | F | 161 | 70.461 | 6.270 | 128.760 | 1.00 61.01 | F |
| ATOM | 8811 | N | ARG | F | 162 | 69.163 | 4.449 | 128.688 | 1.00 71.32 | F |
| ATOM | 8812 | CA | ARG | F | 162 | 67.941 | 5.206 | 128.866 | 1.00 78.16 | F |
| ATOM | 8813 | CB | ARG | F | 162 | 66.790 | 4.247 | 129.158 | 1.00 78.33 | F |
| ATOM | 8814 | CG | ARG | F | 162 | 65.522 | 4.492 | 128.368 | 1.00 83.90 | F |
| ATOM | 8815 | CD | ARG | F | 162 | 65.643 | 3.977 | 126.958 | 1.00 86.83 | F |
| ATOM | 8816 | NE | ARG | F | 162 | 64.346 | 3.959 | 126.302 | 1.00 90.20 | F |
| ATOM | 8817 | CZ | ARG | F | 162 | 64.121 | 3.429 | 125.106 | 1.00 94.30 | F |
| ATOM | 8818 | NH1 | ARG | F | 162 | 65.113 | 2.866 | 124.419 | 1.00 94.25 | F |
| ATOM | 8819 | NH2 | ARG | F | 162 | 62.895 | 3.454 | 124.603 | 1.00 96.34 | F |
| ATOM | 8820 | C | ARG | F | 162 | 68.187 | 6.091 | 130.084 | 1.00 81.77 | F |
| ATOM | 8821 | O | ARG | F | 162 | 68.155 | 7.317 | 130.007 | 1.00 80.11 | F |
| ATOM | 8822 | N | PHE | F | 163 | 68.453 | 5.429 | 131.206 | 1.00 90.35 | F |
| ATOM | 8823 | CA | PHE | F | 163 | 68.716 | 6.060 | 132.497 | 1.00 97.95 | F |
| ATOM | 8824 | CB | PHE | F | 163 | 68.859 | 4.982 | 133.581 | 1.00103.83 | F |
| ATOM | 8825 | CG | PHE | F | 163 | 67.590 | 4.675 | 134.334 | 1.00108.36 | F |
| ATOM | 8826 | CD1 | PHE | F | 163 | 66.428 | 5.399 | 134.117 | 1.00110.02 | F |
| ATOM | 8827 | CD2 | PHE | F | 163 | 67.575 | 3.670 | 135.295 | 1.00110.31 | F |
| ATOM | 8828 | CE1 | PHE | F | 163 | 65.275 | 5.125 | 134.849 | 1.00111.15 | F |
| ATOM | 8829 | CE2 | PHE | F | 163 | 66.427 | 3.393 | 136.027 | 1.00111.67 | F |
| ATOM | 8830 | CZ | PHE | F | 163 | 65.278 | 4.123 | 135.802 | 1.00111.93 | F |
| ATOM | 8831 | C | PHE | F | 163 | 69.980 | 6.922 | 132.508 | 1.00 99.62 | F |
| ATOM | 8832 | O | PHE | F | 163 | 70.522 | 7.223 | 133.575 | 1.00101.00 | F |
| ATOM | 8833 | N | LYS | F | 164 | 70.455 | 7.301 | 131.329 | 1.00 98.93 | F |
| ATOM | 8834 | CA | LYS | F | 164 | 71.657 | 8.125 | 131.196 | 1.00 98.35 | F |
| ATOM | 8835 | CB | LYS | F | 164 | 72.926 | 7.282 | 131.335 | 1.00102.02 | F |
| ATOM | 8836 | CG | LYS | F | 164 | 74.227 | 8.042 | 131.047 | 1.00100.44 | F |
| ATOM | 8837 | CD | LYS | F | 164 | 74.769 | 8.780 | 132.275 | 1.00100.79 | F |
| ATOM | 8838 | CE | LYS | F | 164 | 75.293 | 7.806 | 133.329 | 1.00100.65 | F |
| ATOM | 8839 | NZ | LYS | F | 164 | 75.987 | 8.500 | 134.442 | 1.00 97.85 | F |
| ATOM | 8840 | C | LYS | F | 164 | 71.567 | 8.659 | 129.794 | 1.00 94.46 | F |
| ATOM | 8841 | O | LYS | F | 164 | 72.091 | 8.065 | 128.856 | 1.00 95.73 | F |
| ATOM | 8842 | N | SER | F | 165 | 70.892 | 9.790 | 129.682 | 1.00 92.27 | F |
| ATOM | 8843 | CA | SER | F | 165 | 70.621 | 10.469 | 128.426 | 1.00 87.33 | F |
| ATOM | 8844 | CB | SER | F | 165 | 70.785 | 9.532 | 127.225 | 1.00 89.71 | F |
| ATOM | 8845 | OG | SER | F | 165 | 70.785 | 10.251 | 126.005 | 1.00 92.01 | F |
| ATOM | 8846 | C | SER | F | 165 | 69.155 | 10.708 | 128.694 | 1.00 84.29 | F |
| ATOM | 8847 | O | SER | F | 165 | 68.375 | 11.070 | 127.818 | 1.00 83.18 | F |
| ATOM | 8848 | N | LYS | F | 166 | 68.814 | 10.458 | 129.953 | 1.00 79.08 | F |
| ATOM | 8849 | CA | LYS | F | 166 | 67.477 | 10.609 | 130.494 | 1.00 76.64 | F |
| ATOM | 8850 | CB | LYS | F | 166 | 67.334 | 11.971 | 131.176 | 1.00 80.44 | F |
| ATOM | 8851 | CG | LYS | F | 166 | 68.547 | 12.882 | 131.057 | 1.00 80.25 | F |
| ATOM | 8852 | CD | LYS | F | 166 | 69.136 | 13.195 | 132.430 | 1.00 79.88 | F |
| ATOM | 8853 | CE | LYS | F | 166 | 68.088 | 13.800 | 133.358 | 1.00 82.23 | F |
| ATOM | 8854 | NZ | LYS | F | 166 | 68.581 | 13.935 | 134.751 | 1.00 78.77 | F |
| ATOM | 8855 | C | LYS | F | 166 | 66.308 | 10.420 | 129.548 | 1.00 74.62 | F |
| ATOM | 8856 | O | LYS | F | 166 | 65.652 | 11.388 | 129.167 | 1.00 68.35 | F |
| ATOM | 8857 | N | LYS | F | 167 | 66.049 | 9.174 | 129.173 | 1.00 73.27 | F |
| ATOM | 8858 | CA | LYS | F | 167 | 64.915 | 8.865 | 128.318 | 1.00 75.95 | F |
| ATOM | 8859 | CB | LYS | F | 167 | 65.327 | 7.910 | 127.185 | 1.00 80.63 | F |
| ATOM | 8860 | CG | LYS | F | 167 | 65.780 | 8.622 | 125.904 | 1.00 77.98 | F |
| ATOM | 8861 | CD | LYS | F | 167 | 65.915 | 7.645 | 124.738 | 1.00 79.17 | F |

Figure 10 (136 of 142)

| ATOM | 8862 | CE | LYS | F | 167 | 66.135 | 8.370 | 123.416 | 1.00 | 79.41 | F |
|---|---|---|---|---|---|---|---|---|---|---|---|
| ATOM | 8863 | NZ | LYS | F | 167 | 66.269 | 7.417 | 122.270 | 1.00 | 80.28 | F |
| ATOM | 8864 | C | LYS | F | 167 | 63.882 | 8.226 | 129.255 | 1.00 | 75.53 | F |
| ATOM | 8865 | O | LYS | F | 167 | 64.203 | 7.886 | 130.383 | 1.00 | 77.16 | F |
| ATOM | 8866 | N | PRO | F | 168 | 62.630 | 8.078 | 128.809 | 1.00 | 74.08 | F |
| ATOM | 8867 | CD | PRO | F | 168 | 62.262 | 8.414 | 127.423 | 1.00 | 74.78 | F |
| ATOM | 8868 | CA | PRO | F | 168 | 61.474 | 7.507 | 129.510 | 1.00 | 70.75 | F |
| ATOM | 8869 | CB | PRO | F | 168 | 60.622 | 7.002 | 128.367 | 1.00 | 73.35 | F |
| ATOM | 8870 | CG | PRO | F | 168 | 60.772 | 8.115 | 127.396 | 1.00 | 74.93 | F |
| ATOM | 8871 | C | PRO | F | 168 | 61.631 | 6.454 | 130.613 | 1.00 | 67.65 | F |
| ATOM | 8872 | O | PRO | F | 168 | 61.375 | 6.750 | 131.781 | 1.00 | 68.34 | F |
| ATOM | 8873 | N | THR | F | 169 | 62.018 | 5.230 | 130.246 | 1.00 | 64.87 | F |
| ATOM | 8874 | CA | THR | F | 169 | 62.197 | 4.091 | 131.181 | 1.00 | 62.59 | F |
| ATOM | 8875 | CB | THR | F | 169 | 63.288 | 4.351 | 132.274 | 1.00 | 58.62 | F |
| ATOM | 8876 | OG1 | THR | F | 169 | 62.769 | 3.997 | 133.560 | 1.00 | 58.62 | F |
| ATOM | 8877 | CG2 | THR | F | 169 | 63.736 | 5.789 | 132.290 | 1.00 | 62.04 | F |
| ATOM | 8878 | C | THR | F | 169 | 60.948 | 3.559 | 131.904 | 1.00 | 60.16 | F |
| ATOM | 8879 | O | THR | F | 169 | 61.004 | 2.523 | 132.579 | 1.00 | 55.65 | F |
| ATOM | 8880 | N | ASP | F | 170 | 59.829 | 4.258 | 131.765 | 1.00 | 57.99 | F |
| ATOM | 8881 | CA | ASP | F | 170 | 58.588 | 3.821 | 132.385 | 1.00 | 54.84 | F |
| ATOM | 8882 | CB | ASP | F | 170 | 57.567 | 4.950 | 132.378 | 1.00 | 55.12 | F |
| ATOM | 8883 | CG | ASP | F | 170 | 58.021 | 6.141 | 133.176 | 1.00 | 56.47 | F |
| ATOM | 8884 | OD1 | ASP | F | 170 | 58.967 | 6.836 | 132.755 | 1.00 | 57.67 | F |
| ATOM | 8885 | OD2 | ASP | F | 170 | 57.428 | 6.377 | 134.240 | 1.00 | 57.52 | F |
| ATOM | 8886 | C | ASP | F | 170 | 58.035 | 2.646 | 131.600 | 1.00 | 52.52 | F |
| ATOM | 8887 | O | ASP | F | 170 | 58.235 | 2.552 | 130.397 | 1.00 | 58.25 | F |
| ATOM | 8888 | N | TYR | F | 171 | 57.343 | 1.747 | 132.280 | 1.00 | 54.09 | F |
| ATOM | 8889 | CA | TYR | F | 171 | 56.754 | 0.596 | 131.616 | 1.00 | 59.86 | F |
| ATOM | 8890 | CB | TYR | F | 171 | 55.825 | 1.067 | 130.507 | 1.00 | 66.66 | F |
| ATOM | 8891 | CG | TYR | F | 171 | 54.793 | 2.062 | 130.978 | 1.00 | 68.17 | F |
| ATOM | 8892 | CD1 | TYR | F | 171 | 54.887 | 3.412 | 130.638 | 1.00 | 69.83 | F |
| ATOM | 8893 | CE1 | TYR | F | 171 | 53.927 | 4.326 | 131.055 | 1.00 | 70.02 | F |
| ATOM | 8894 | CD2 | TYR | F | 171 | 53.713 | 1.655 | 131.755 | 1.00 | 67.77 | F |
| ATOM | 8895 | CE2 | TYR | F | 171 | 52.753 | 2.563 | 132.179 | 1.00 | 68.56 | F |
| ATOM | 8896 | CZ | TYR | F | 171 | 52.865 | 3.892 | 131.822 | 1.00 | 70.35 | F |
| ATOM | 8897 | OH | TYR | F | 171 | 51.897 | 4.778 | 132.217 | 1.00 | 68.57 | F |
| ATOM | 8898 | C | TYR | F | 171 | 57.776 | -0.383 | 131.050 | 1.00 | 59.16 | F |
| ATOM | 8899 | O | TYR | F | 171 | 57.423 | -1.335 | 130.352 | 1.00 | 58.55 | F |
| ATOM | 8900 | N | LEU | F | 172 | 59.045 | -0.141 | 131.341 | 1.00 | 60.34 | F |
| ATOM | 8901 | CA | LEU | F | 172 | 60.098 | -1.035 | 130.892 | 1.00 | 66.96 | F |
| ATOM | 8902 | CB | LEU | F | 172 | 61.249 | -0.235 | 130.295 | 1.00 | 67.96 | F |
| ATOM | 8903 | CG | LEU | F | 172 | 60.917 | 0.342 | 128.926 | 1.00 | 68.84 | F |
| ATOM | 8904 | CD1 | LEU | F | 172 | 62.085 | 1.153 | 128.420 | 1.00 | 71.00 | F |
| ATOM | 8905 | CD2 | LEU | F | 172 | 60.598 | -0.797 | 127.975 | 1.00 | 71.23 | F |
| ATOM | 8906 | C | LEU | F | 172 | 60.561 | -1.805 | 132.121 | 1.00 | 70.37 | F |
| ATOM | 8907 | O | LEU | F | 172 | 60.834 | -3.007 | 132.060 | 1.00 | 66.98 | F |
| ATOM | 8908 | N | ILE | F | 173 | 60.622 | -1.090 | 133.239 | 1.00 | 71.39 | F |
| ATOM | 8909 | CA | ILE | F | 173 | 61.024 | -1.640 | 134.527 | 1.00 | 77.83 | F |
| ATOM | 8910 | CB | ILE | F | 173 | 62.344 | -1.017 | 134.998 | 1.00 | 77.38 | F |
| ATOM | 8911 | CG2 | ILE | F | 173 | 63.501 | -1.593 | 134.199 | 1.00 | 80.83 | F |
| ATOM | 8912 | CG1 | ILE | F | 173 | 62.244 | 0.511 | 134.890 | 1.00 | 79.34 | F |
| ATOM | 8913 | CD1 | ILE | F | 173 | 63.477 | 1.258 | 135.330 | 1.00 | 86.27 | F |
| ATOM | 8914 | C | ILE | F | 173 | 59.938 | -1.266 | 135.528 | 1.00 | 76.37 | F |
| ATOM | 8915 | O | ILE | F | 173 | 59.249 | -0.264 | 135.344 | 1.00 | 79.73 | F |
| ATOM | 8916 | N | PRO | F | 174 | 59.764 | -2.064 | 136.598 | 1.00 | 78.79 | F |
| ATOM | 8917 | CD | PRO | F | 174 | 60.480 | -3.289 | 136.993 | 1.00 | 77.94 | F |
| ATOM | 8918 | CA | PRO | F | 174 | 58.735 | -1.733 | 137.587 | 1.00 | 81.97 | F |
| ATOM | 8919 | CB | PRO | F | 174 | 58.978 | -2.757 | 138.692 | 1.00 | 79.19 | F |
| ATOM | 8920 | CG | PRO | F | 174 | 59.502 | -3.922 | 137.953 | 1.00 | 77.62 | F |
| ATOM | 8921 | C | PRO | F | 174 | 58.978 | -0.307 | 138.068 | 1.00 | 82.28 | F |
| ATOM | 8922 | O | PRO | F | 174 | 60.103 | 0.187 | 137.992 | 1.00 | 84.22 | F |
| ATOM | 8923 | N | ASP | F | 175 | 57.936 | 0.358 | 138.553 | 1.00 | 84.74 | F |
| ATOM | 8924 | CA | ASP | F | 175 | 58.085 | 1.727 | 139.035 | 1.00 | 89.47 | F |
| ATOM | 8925 | CB | ASP | F | 175 | 56.705 | 2.342 | 139.306 | 1.00 | 91.77 | F |
| ATOM | 8926 | CG | ASP | F | 175 | 56.650 | 3.830 | 138.979 | 1.00 | 91.50 | F |
| ATOM | 8927 | OD1 | ASP | F | 175 | 57.176 | 4.650 | 139.764 | 1.00 | 91.15 | F |

Figure 10 (137 of 142)

| ATOM | 8928 | OD2 | ASP | F | 175 | 56.084 | 4.178 | 137.920 | 1.00 | 93.41 | F |
|---|---|---|---|---|---|---|---|---|---|---|---|
| ATOM | 8929 | C | ASP | F | 175 | 58.936 | 1.710 | 140.308 | 1.00 | 87.07 | F |
| ATOM | 8930 | O | ASP | F | 175 | 59.501 | 2.730 | 140.715 | 1.00 | 84.82 | F |
| ATOM | 8931 | N | LYS | F | 176 | 59.028 | 0.532 | 140.918 | 1.00 | 86.49 | F |
| ATOM | 8932 | CA | LYS | F | 176 | 59.805 | 0.340 | 142.139 | 1.00 | 85.87 | F |
| ATOM | 8933 | CB | LYS | F | 176 | 59.357 | -0.950 | 142.845 | 1.00 | 85.51 | F |
| ATOM | 8934 | CG | LYS | F | 176 | 57.951 | -0.860 | 143.417 | 1.00 | 86.90 | F |
| ATOM | 8935 | CD | LYS | F | 176 | 57.908 | 0.183 | 144.524 | 1.00 | 89.14 | F |
| ATOM | 8936 | CE | LYS | F | 176 | 56.593 | 0.937 | 144.540 | 1.00 | 88.52 | F |
| ATOM | 8937 | NZ | LYS | F | 176 | 56.577 | 1.979 | 145.606 | 1.00 | 93.01 | F |
| ATOM | 8938 | C | LYS | F | 176 | 61.301 | 0.283 | 141.828 | 1.00 | 89.51 | F |
| ATOM | 8939 | O | LYS | F | 176 | 62.125 | 0.838 | 142.567 | 1.00 | 86.45 | F |
| ATOM | 8940 | N | VAL | F | 177 | 61.644 | -0.387 | 140.729 | 1.00 | 86.43 | F |
| ATOM | 8941 | CA | VAL | F | 177 | 63.035 | -0.511 | 140.312 | 1.00 | 81.52 | F |
| ATOM | 8942 | CB | VAL | F | 177 | 63.176 | -1.532 | 139.153 | 1.00 | 81.01 | F |
| ATOM | 8943 | CG1 | VAL | F | 177 | 64.557 | -1.434 | 138.527 | 1.00 | 82.95 | F |
| ATOM | 8944 | CG2 | VAL | F | 177 | 62.959 | -2.939 | 139.678 | 1.00 | 81.57 | F |
| ATOM | 8945 | C | VAL | F | 177 | 63.580 | 0.850 | 139.886 | 1.00 | 82.61 | F |
| ATOM | 8946 | O | VAL | F | 177 | 64.747 | 1.168 | 140.130 | 1.00 | 80.31 | F |
| ATOM | 8947 | N | LYS | F | 178 | 62.726 | 1.654 | 139.257 | 1.00 | 84.21 | F |
| ATOM | 8948 | CA | LYS | F | 178 | 63.122 | 2.984 | 138.806 | 1.00 | 80.62 | F |
| ATOM | 8949 | CB | LYS | F | 178 | 61.966 | 3.685 | 138.072 | 1.00 | 81.07 | F |
| ATOM | 8950 | CG | LYS | F | 178 | 62.328 | 5.074 | 137.512 | 1.00 | 82.31 | F |
| ATOM | 8951 | CD | LYS | F | 178 | 61.272 | 5.626 | 136.544 | 1.00 | 80.95 | F |
| ATOM | 8952 | CE | LYS | F | 178 | 59.968 | 5.989 | 137.248 | 1.00 | 75.44 | F |
| ATOM | 8953 | NZ | LYS | F | 178 | 58.932 | 6.488 | 136.291 | 1.00 | 74.40 | F |
| ATOM | 8954 | C | LYS | F | 178 | 63.529 | 3.813 | 140.008 | 1.00 | 80.69 | F |
| ATOM | 8955 | O | LYS | F | 178 | 64.654 | 4.310 | 140.095 | 1.00 | 76.47 | F |
| ATOM | 8956 | N | LYS | F | 179 | 62.597 | 3.949 | 140.939 | 1.00 | 77.98 | F |
| ATOM | 8957 | CA | LYS | F | 179 | 62.841 | 4.716 | 142.135 | 1.00 | 76.01 | F |
| ATOM | 8958 | CB | LYS | F | 179 | 61.665 | 4.529 | 143.077 | 1.00 | 73.20 | F |
| ATOM | 8959 | CG | LYS | F | 179 | 60.360 | 4.991 | 142.448 | 1.00 | 73.73 | F |
| ATOM | 8960 | CD | LYS | F | 179 | 59.193 | 4.762 | 143.387 | 1.00 | 74.08 | F |
| ATOM | 8961 | CE | LYS | F | 179 | 57.898 | 5.365 | 142.849 | 1.00 | 72.64 | F |
| ATOM | 8962 | NZ | LYS | F | 179 | 56.750 | 5.168 | 143.799 | 1.00 | 68.57 | F |
| ATOM | 8963 | C | LYS | F | 179 | 64.163 | 4.332 | 142.795 | 1.00 | 76.70 | F |
| ATOM | 8964 | O | LYS | F | 179 | 64.997 | 5.203 | 143.057 | 1.00 | 74.39 | F |
| ATOM | 8965 | N | TYR | F | 180 | 64.374 | 3.037 | 143.029 | 1.00 | 80.34 | F |
| ATOM | 8966 | CA | TYR | F | 180 | 65.616 | 2.565 | 143.663 | 1.00 | 88.55 | F |
| ATOM | 8967 | CB | TYR | F | 180 | 65.659 | 1.025 | 143.708 | 1.00 | 90.24 | F |
| ATOM | 8968 | CG | TYR | F | 180 | 66.865 | 0.442 | 144.440 | 1.00 | 91.52 | F |
| ATOM | 8969 | CD1 | TYR | F | 180 | 66.733 | -0.121 | 145.706 | 1.00 | 91.26 | F |
| ATOM | 8970 | CE1 | TYR | F | 180 | 67.834 | -0.650 | 146.377 | 1.00 | 89.49 | F |
| ATOM | 8971 | CD2 | TYR | F | 180 | 68.139 | 0.459 | 143.862 | 1.00 | 90.45 | F |
| ATOM | 8972 | CE2 | TYR | F | 180 | 69.246 | -0.068 | 144.529 | 1.00 | 89.53 | F |
| ATOM | 8973 | CZ | TYR | F | 180 | 69.083 | -0.619 | 145.784 | 1.00 | 91.09 | F |
| ATOM | 8974 | OH | TYR | F | 180 | 70.170 | -1.136 | 146.446 | 1.00 | 84.65 | F |
| ATOM | 8975 | C | TYR | F | 180 | 66.880 | 3.084 | 142.964 | 1.00 | 90.03 | F |
| ATOM | 8976 | O | TYR | F | 180 | 67.844 | 3.486 | 143.622 | 1.00 | 88.90 | F |
| ATOM | 8977 | N | VAL | F | 181 | 66.885 | 3.064 | 141.634 | 1.00 | 92.58 | F |
| ATOM | 8978 | CA | VAL | F | 181 | 68.048 | 3.531 | 140.897 | 1.00 | 92.43 | F |
| ATOM | 8979 | CB | VAL | F | 181 | 67.898 | 3.288 | 139.391 | 1.00 | 92.58 | F |
| ATOM | 8980 | CG1 | VAL | F | 181 | 69.072 | 3.920 | 138.653 | 1.00 | 94.64 | F |
| ATOM | 8981 | CG2 | VAL | F | 181 | 67.835 | 1.792 | 139.108 | 1.00 | 93.89 | F |
| ATOM | 8982 | C | VAL | F | 181 | 68.235 | 5.015 | 141.125 | 1.00 | 91.99 | F |
| ATOM | 8983 | O | VAL | F | 181 | 69.336 | 5.473 | 141.426 | 1.00 | 93.73 | F |
| ATOM | 8984 | N | GLU | F | 182 | 67.146 | 5.760 | 140.980 | 1.00 | 90.67 | F |
| ATOM | 8985 | CA | GLU | F | 182 | 67.181 | 7.201 | 141.160 | 1.00 | 92.62 | F |
| ATOM | 8986 | CB | GLU | F | 182 | 65.795 | 7.796 | 140.912 | 1.00 | 96.98 | F |
| ATOM | 8987 | CG | GLU | F | 182 | 65.178 | 7.410 | 139.573 | 1.00 | 97.22 | F |
| ATOM | 8988 | CD | GLU | F | 182 | 63.872 | 8.141 | 139.299 | 1.00 | 96.92 | F |
| ATOM | 8989 | OE1 | GLU | F | 182 | 63.010 | 8.168 | 140.203 | 1.00 | 98.15 | F |
| ATOM | 8990 | OE2 | GLU | F | 182 | 63.705 | 8.681 | 138.181 | 1.00 | 98.85 | F |
| ATOM | 8991 | C | GLU | F | 182 | 67.650 | 7.583 | 142.557 | 1.00 | 91.50 | F |
| ATOM | 8992 | O | GLU | F | 182 | 68.455 | 8.498 | 142.721 | 1.00 | 90.96 | F |
| ATOM | 8993 | N | GLU | F | 183 | 67.144 | 6.873 | 143.560 | 1.00 | 89.31 | F |

Figure 10 (138 of 142)

| | | | | | | | | | |
|---|---|---|---|---|---|---|---|---|---|
| ATOM | 8994 | CA | GLU | F | 183 | 67.498 | 7.154 | 144.947 | 1.00 92.77 | F |
| ATOM | 8995 | CB | GLU | F | 183 | 66.553 | 6.401 | 145.895 | 1.00 94.70 | F |
| ATOM | 8996 | CG | GLU | F | 183 | 65.062 | 6.586 | 145.599 | 1.00 99.42 | F |
| ATOM | 8997 | CD | GLU | F | 183 | 64.154 | 6.114 | 146.738 | 1.00100.52 | F |
| ATOM | 8998 | OE1 | GLU | F | 183 | 64.243 | 4.934 | 147.146 | 1.00100.93 | F |
| ATOM | 8999 | OE2 | GLU | F | 183 | 63.343 | 6.932 | 147.225 | 1.00100.78 | F |
| ATOM | 9000 | C | GLU | F | 183 | 68.943 | 6.800 | 145.303 | 1.00 92.33 | F |
| ATOM | 9001 | O | GLU | F | 183 | 69.710 | 7.654 | 145.761 | 1.00 90.35 | F |
| ATOM | 9002 | N | ASN | F | 184 | 69.307 | 5.539 | 145.086 | 1.00 93.09 | F |
| ATOM | 9003 | CA | ASN | F | 184 | 70.641 | 5.050 | 145.415 | 1.00 90.09 | F |
| ATOM | 9004 | CB | ASN | F | 184 | 70.565 | 3.552 | 145.722 | 1.00 94.98 | F |
| ATOM | 9005 | CG | ASN | F | 184 | 71.144 | 3.203 | 147.081 | 1.00 97.65 | F |
| ATOM | 9006 | OD1 | ASN | F | 184 | 70.902 | 2.118 | 147.612 | 1.00100.50 | F |
| ATOM | 9007 | ND2 | ASN | F | 184 | 71.921 | 4.123 | 147.650 | 1.00103.11 | F |
| ATOM | 9008 | C | ASN | F | 184 | 71.688 | 5.304 | 144.337 | 1.00 84.02 | F |
| ATOM | 9009 | O | ASN | F | 184 | 72.548 | 4.420 | 144.133 | 1.00 82.12 | F |
| TER | 9010 | | ASN | F | 184 | | | | | |
| ATOM | 9011 | C1 | NAA | H | 1 | 64.531 | -13.365 | 126.676 | 1.00146.15 | H |
| ATOM | 9012 | N2 | NAA | H | 1 | 65.571 | -13.538 | 127.545 | 1.00145.79 | H |
| ATOM | 9013 | C3 | NAA | H | 1 | 66.097 | -12.411 | 128.123 | 1.00143.87 | H |
| ATOM | 9014 | C4 | NAA | H | 1 | 65.583 | -11.111 | 127.834 | 1.00144.65 | H |
| ATOM | 9015 | C5 | NAA | H | 1 | 64.508 | -11.065 | 126.979 | 1.00145.90 | H |
| ATOM | 9016 | N6 | NAA | H | 1 | 63.984 | -12.160 | 126.372 | 1.00146.83 | H |
| ATOM | 9017 | N7 | NAA | H | 1 | 67.154 | -12.241 | 129.044 | 1.00143.95 | H |
| ATOM | 9018 | N8 | NAA | H | 1 | 63.912 | -9.901 | 126.719 | 1.00146.10 | H |
| ATOM | 9019 | C12 | NAA | H | 1 | 68.022 | -13.295 | 129.678 | 1.00141.94 | H |
| ATOM | 9020 | C13 | NAA | H | 1 | 67.938 | -14.736 | 129.154 | 1.00140.09 | H |
| ATOM | 9021 | C14 | NAA | H | 1 | 68.385 | -15.599 | 130.344 | 1.00140.49 | H |
| ATOM | 9022 | C15 | NAA | H | 1 | 68.389 | -14.616 | 131.545 | 1.00140.40 | H |
| ATOM | 9023 | O16 | NAA | H | 1 | 67.755 | -13.452 | 131.055 | 1.00141.28 | H |
| ATOM | 9024 | O18 | NAA | H | 1 | 68.796 | -14.967 | 128.060 | 1.00140.84 | H |
| ATOM | 9025 | O20 | NAA | H | 1 | 69.676 | -16.115 | 130.022 | 1.00138.65 | H |
| ATOM | 9026 | C24 | NAA | H | 1 | 69.816 | -14.303 | 132.097 | 1.00141.23 | H |
| ATOM | 9027 | O26 | NAA | H | 1 | 70.086 | -12.886 | 132.210 | 1.00138.59 | H |
| ATOM | 9028 | P29 | NAA | H | 1 | 71.407 | -12.283 | 131.583 | 1.00136.79 | H |
| ATOM | 9029 | O30 | NAA | H | 1 | 71.981 | -11.211 | 132.453 | 1.00136.27 | H |
| ATOM | 9030 | O31 | NAA | H | 1 | 70.998 | -11.748 | 130.155 | 1.00137.99 | H |
| ATOM | 9031 | O32 | NAA | H | 1 | 72.378 | -13.451 | 131.373 | 1.00134.28 | H |
| ATOM | 9032 | P34 | NAA | H | 1 | 73.908 | -13.625 | 131.329 | 1.00131.86 | H |
| ATOM | 9033 | O35 | NAA | H | 1 | 74.587 | -12.939 | 132.465 | 1.00131.99 | H |
| ATOM | 9034 | O36 | NAA | H | 1 | 74.461 | -13.087 | 129.954 | 1.00131.77 | H |
| ATOM | 9035 | O38 | NAA | H | 1 | 74.226 | -15.174 | 131.342 | 1.00131.20 | H |
| ATOM | 9036 | C39 | NAA | H | 1 | 73.117 | -16.099 | 131.480 | 1.00130.36 | H |
| ATOM | 9037 | C40 | NAA | H | 1 | 73.322 | -17.044 | 132.668 | 1.00128.82 | H |
| ATOM | 9038 | C43 | NAA | H | 1 | 74.021 | -16.386 | 133.861 | 1.00129.05 | H |
| ATOM | 9039 | C44 | NAA | H | 1 | 75.071 | -17.399 | 134.292 | 1.00128.74 | H |
| ATOM | 9040 | C45 | NAA | H | 1 | 75.186 | -18.377 | 133.111 | 1.00129.15 | H |
| ATOM | 9041 | O46 | NAA | H | 1 | 74.134 | -18.104 | 132.222 | 1.00128.57 | H |
| ATOM | 9042 | O48 | NAA | H | 1 | 73.167 | -16.127 | 134.960 | 1.00128.48 | H |
| ATOM | 9043 | O50 | NAA | H | 1 | 74.585 | -18.105 | 135.418 | 1.00127.90 | H |
| ATOM | 9044 | C54 | NAA | H | 1 | 77.414 | -19.208 | 132.489 | 1.00135.40 | H |
| ATOM | 9045 | C55 | NAA | H | 1 | 78.612 | -19.245 | 131.758 | 1.00137.35 | H |
| ATOM | 9046 | C56 | NAA | H | 1 | 78.793 | -18.287 | 130.725 | 1.00136.12 | H |
| ATOM | 9047 | C57 | NAA | H | 1 | 77.780 | -17.333 | 130.462 | 1.00134.71 | H |
| ATOM | 9048 | C58 | NAA | H | 1 | 76.612 | -17.371 | 131.247 | 1.00133.62 | H |
| ATOM | 9049 | C61 | NAA | H | 1 | 79.639 | -20.250 | 132.069 | 1.00139.11 | H |
| ATOM | 9050 | O62 | NAA | H | 1 | 79.188 | -21.440 | 132.532 | 1.00140.76 | H |
| ATOM | 9051 | O63 | NAA | H | 1 | 80.788 | -20.011 | 131.930 | 1.00142.32 | H |
| ATOM | 9052 | C65 | NAA | H | 1 | 67.244 | -10.886 | 129.194 | 1.00143.62 | H |
| ATOM | 9053 | N66 | NAA | H | 1 | 66.325 | -10.171 | 128.513 | 1.00143.80 | H |
| ATOM | 9054 | N68 | NAA | H | 1 | 76.414 | -18.305 | 132.262 | 1.00132.73 | H |
| ATOM | 9055 | C1 | NAA | J | 1 | 51.060 | 0.134 | 120.054 | 1.00115.65 | J |
| ATOM | 9056 | N2 | NAA | J | 1 | 49.734 | 0.413 | 120.030 | 1.00115.76 | J |
| ATOM | 9057 | C3 | NAA | J | 1 | 48.881 | -0.572 | 120.429 | 1.00114.92 | J |
| ATOM | 9058 | C4 | NAA | J | 1 | 49.360 | -1.841 | 120.859 | 1.00116.05 | J |
| ATOM | 9059 | C5 | NAA | J | 1 | 50.729 | -2.012 | 120.836 | 1.00116.74 | J |

Figure 10 (139 of 142)

```
ATOM   9060  N6  NAA J  1   51.594  -1.050 120.447  1.00115.86   J
ATOM   9061  N7  NAA J  1   47.471  -0.604 120.518  1.00114.19   J
ATOM   9062  N8  NAA J  1   51.264  -3.179 121.200  1.00117.49   J
ATOM   9063  C12 NAA J  1   46.491   0.483 120.181  1.00111.87   J
ATOM   9064  C13 NAA J  1   46.998   1.664 119.371  1.00111.58   J
ATOM   9065  C14 NAA J  1   45.906   2.710 119.567  1.00110.32   J
ATOM   9066  C15 NAA J  1   45.285   2.318 120.936  1.00107.71   J
ATOM   9067  O16 NAA J  1   45.941   1.123 121.313  1.00109.98   J
ATOM   9068  O18 NAA J  1   47.131   1.361 118.003  1.00114.55   J
ATOM   9069  O20 NAA J  1   45.011   2.582 118.469  1.00109.68   J
ATOM   9070  C24 NAA J  1   43.748   2.134 120.894  1.00104.30   J
ATOM   9071  O26 NAA J  1   43.326   0.908 121.509  1.00 96.95   J
ATOM   9072  P29 NAA J  1   42.502  -0.127 120.665  1.00 93.22   J
ATOM   9073  O30 NAA J  1   41.422  -0.730 121.487  1.00 93.51   J
ATOM   9074  O31 NAA J  1   43.529  -1.219 120.166  1.00 92.48   J
ATOM   9075  O32 NAA J  1   41.958   0.642 119.422  1.00 95.68   J
ATOM   9076  P34 NAA J  1   40.781   0.445 118.413  1.00 98.55   J
ATOM   9077  O35 NAA J  1   39.484   0.351 119.129  1.00 98.94   J
ATOM   9078  O36 NAA J  1   41.008  -0.868 117.544  1.00 97.72   J
ATOM   9079  O38 NAA J  1   40.737   1.643 117.359  1.00 95.99   J
ATOM   9080  C39 NAA J  1   41.544   2.818 117.581  1.00 94.89   J
ATOM   9081  C40 NAA J  1   40.677   4.085 117.737  1.00 93.22   J
ATOM   9082  C43 NAA J  1   39.316   3.853 118.385  1.00 93.20   J
ATOM   9083  C44 NAA J  1   38.403   4.861 117.693  1.00 91.46   J
ATOM   9084  C45 NAA J  1   39.093   5.140 116.342  1.00 90.42   J
ATOM   9085  O46 NAA J  1   40.425   4.648 116.455  1.00 92.43   J
ATOM   9086  O48 NAA J  1   39.295   4.113 119.765  1.00 93.25   J
ATOM   9087  O50 NAA J  1   38.383   6.055 118.458  1.00 89.69   J
ATOM   9088  C54 NAA J  1   37.658   5.155 114.292  1.00 90.78   J
ATOM   9089  C55 NAA J  1   37.091   4.593 113.113  1.00 91.22   J
ATOM   9090  C56 NAA J  1   37.444   3.257 112.781  1.00 90.35   J
ATOM   9091  C57 NAA J  1   38.328   2.530 113.606  1.00 89.50   J
ATOM   9092  C58 NAA J  1   38.845   3.158 114.753  1.00 91.05   J
ATOM   9093  C61 NAA J  1   36.162   5.366 112.249  1.00 93.86   J
ATOM   9094  O62 NAA J  1   36.015   6.685 112.556  1.00 93.06   J
ATOM   9095  O63 NAA J  1   35.582   4.840 111.336  1.00 94.31   J
ATOM   9096  C65 NAA J  1   47.203  -1.849 120.992  1.00115.43   J
ATOM   9097  N66 NAA J  1   48.285  -2.627 121.209  1.00116.15   J
ATOM   9098  N68 NAA J  1   38.533   4.467 115.115  1.00 91.67   J
ATOM   9099  C1  NAA K  1   27.771  38.913  74.729  1.00 14.32   K
ATOM   9100  N2  NAA K  1   28.346  37.792  74.221  1.00 12.26   K
ATOM   9101  C3  NAA K  1   29.398  37.272  74.914  1.00 12.26   K
ATOM   9102  C4  NAA K  1   29.889  37.864  76.113  1.00 12.26   K
ATOM   9103  C5  NAA K  1   29.228  38.978  76.556  1.00 12.26   K
ATOM   9104  N6  NAA K  1   28.179  39.535  75.886  1.00 12.26   K
ATOM   9105  N7  NAA K  1   30.186  36.151  74.671  1.00 14.28   K
ATOM   9106  N8  NAA K  1   29.611  39.560  77.703  1.00 12.26   K
ATOM   9107  C12 NAA K  1   30.070  35.193  73.565  1.00 15.50   K
ATOM   9108  C13 NAA K  1   29.354  35.666  72.315  1.00 16.57   K
ATOM   9109  C14 NAA K  1   28.907  34.371  71.658  1.00 15.66   K
ATOM   9110  C15 NAA K  1   28.898  33.362  72.834  1.00 15.81   K
ATOM   9111  O16 NAA K  1   29.354  34.068  73.953  1.00 14.62   K
ATOM   9112  O18 NAA K  1   30.211  36.374  71.453  1.00 19.39   K
ATOM   9113  O20 NAA K  1   29.864  34.074  70.649  1.00 17.84   K
ATOM   9114  C24 NAA K  1   29.767  32.116  72.606  1.00 18.08   K
ATOM   9115  O26 NAA K  1   30.650  31.908  73.701  1.00 20.05   K
ATOM   9116  P29 NAA K  1   32.166  31.755  73.414  1.00 22.06   K
ATOM   9117  O30 NAA K  1   32.745  30.595  74.173  1.00 20.70   K
ATOM   9118  O31 NAA K  1   32.804  33.156  73.803  1.00 23.36   K
ATOM   9119  O32 NAA K  1   32.331  31.549  71.894  1.00 23.37   K
ATOM   9120  P34 NAA K  1   33.537  31.368  70.964  1.00 25.47   K
ATOM   9121  O35 NAA K  1   34.388  30.239  71.418  1.00 24.52   K
ATOM   9122  O36 NAA K  1   34.386  32.708  70.932  1.00 23.63   K
ATOM   9123  O38 NAA K  1   32.986  31.106  69.481  1.00 31.50   K
ATOM   9124  C39 NAA K  1   31.592  31.407  69.169  1.00 32.75   K
ATOM   9125  C40 NAA K  1   30.917  30.331  68.287  1.00 35.77   K
```

Figure 10 (140 of 142)

| | | | | | | | | | | |
|---|---|---|---|---|---|---|---|---|---|---|
| ATOM | 9126 | C43 | NAA | K | 1 | 31.353 | 28.901 | 68.551 | 1.00 38.30 | K |
| ATOM | 9127 | C44 | NAA | K | 1 | 31.518 | 28.256 | 67.185 | 1.00 36.71 | K |
| ATOM | 9128 | C45 | NAA | K | 1 | 31.499 | 29.420 | 66.201 | 1.00 38.66 | K |
| ATOM | 9129 | O46 | NAA | K | 1 | 31.168 | 30.594 | 66.918 | 1.00 35.91 | K |
| ATOM | 9130 | O48 | NAA | K | 1 | 30.389 | 28.159 | 69.232 | 1.00 43.85 | K |
| ATOM | 9131 | O50 | NAA | K | 1 | 30.390 | 27.422 | 66.942 | 1.00 37.05 | K |
| ATOM | 9132 | C54 | NAA | K | 1 | 32.942 | 29.166 | 64.202 | 1.00 40.96 | K |
| ATOM | 9133 | C55 | NAA | K | 1 | 34.090 | 29.393 | 63.408 | 1.00 39.70 | K |
| ATOM | 9134 | C56 | NAA | K | 1 | 35.088 | 30.231 | 63.938 | 1.00 39.98 | K |
| ATOM | 9135 | C57 | NAA | K | 1 | 34.921 | 30.805 | 65.214 | 1.00 39.82 | K |
| ATOM | 9136 | C58 | NAA | K | 1 | 33.757 | 30.527 | 65.942 | 1.00 41.16 | K |
| ATOM | 9137 | C61 | NAA | K | 1 | 34.235 | 28.779 | 62.070 | 1.00 39.54 | K |
| ATOM | 9138 | O62 | NAA | K | 1 | 33.086 | 28.312 | 61.524 | 1.00 39.49 | K |
| ATOM | 9139 | O63 | NAA | K | 1 | 35.305 | 28.708 | 61.511 | 1.00 36.76 | K |
| ATOM | 9140 | C65 | NAA | K | 1 | 31.096 | 36.142 | 75.672 | 1.00 16.07 | K |
| ATOM | 9141 | N66 | NAA | K | 1 | 30.961 | 37.136 | 76.565 | 1.00 15.24 | K |
| ATOM | 9142 | N68 | NAA | K | 1 | 32.755 | 29.724 | 65.453 | 1.00 40.43 | K |
| ATOM | 9143 | C1 | NAA | L | 1 | 55.251 | 69.801 | 74.289 | 1.00 23.75 | L |
| ATOM | 9144 | N2 | NAA | L | 1 | 54.675 | 70.967 | 73.845 | 1.00 23.25 | L |
| ATOM | 9145 | C3 | NAA | L | 1 | 53.770 | 71.579 | 74.672 | 1.00 21.49 | L |
| ATOM | 9146 | C4 | NAA | L | 1 | 53.427 | 71.041 | 75.950 | 1.00 24.78 | L |
| ATOM | 9147 | C5 | NAA | L | 1 | 54.058 | 69.861 | 76.311 | 1.00 28.01 | L |
| ATOM | 9148 | N6 | NAA | L | 1 | 54.976 | 69.219 | 75.503 | 1.00 26.30 | L |
| ATOM | 9149 | N7 | NAA | L | 1 | 53.021 | 72.751 | 74.522 | 1.00 19.05 | L |
| ATOM | 9150 | N8 | NAA | L | 1 | 53.751 | 69.293 | 77.498 | 1.00 23.89 | L |
| ATOM | 9151 | C12 | NAA | L | 1 | 53.010 | 73.690 | 73.385 | 1.00 25.95 | L |
| ATOM | 9152 | C13 | NAA | L | 1 | 53.649 | 73.249 | 72.068 | 1.00 27.21 | L |
| ATOM | 9153 | C14 | NAA | L | 1 | 53.874 | 74.582 | 71.362 | 1.00 27.48 | L |
| ATOM | 9154 | C15 | NAA | L | 1 | 54.013 | 75.588 | 72.537 | 1.00 25.17 | L |
| ATOM | 9155 | O16 | NAA | L | 1 | 53.701 | 74.866 | 73.697 | 1.00 27.12 | L |
| ATOM | 9156 | O18 | NAA | L | 1 | 52.794 | 72.425 | 71.279 | 1.00 31.03 | L |
| ATOM | 9157 | O20 | NAA | L | 1 | 52.730 | 74.802 | 70.550 | 1.00 29.24 | L |
| ATOM | 9158 | C24 | NAA | L | 1 | 53.107 | 76.828 | 72.414 | 1.00 24.83 | L |
| ATOM | 9159 | O26 | NAA | L | 1 | 52.255 | 76.961 | 73.552 | 1.00 19.71 | L |
| ATOM | 9160 | P29 | NAA | L | 1 | 50.742 | 77.114 | 73.311 | 1.00 19.68 | L |
| ATOM | 9161 | O30 | NAA | L | 1 | 50.115 | 77.946 | 74.397 | 1.00 18.78 | L |
| ATOM | 9162 | O31 | NAA | L | 1 | 50.132 | 75.641 | 73.249 | 1.00 23.53 | L |
| ATOM | 9163 | O32 | NAA | L | 1 | 50.610 | 77.738 | 71.918 | 1.00 22.14 | L |
| ATOM | 9164 | P34 | NAA | L | 1 | 49.442 | 77.866 | 70.961 | 1.00 23.36 | L |
| ATOM | 9165 | O35 | NAA | L | 1 | 48.547 | 78.995 | 71.333 | 1.00 25.21 | L |
| ATOM | 9166 | O36 | NAA | L | 1 | 48.604 | 76.542 | 70.962 | 1.00 25.07 | L |
| ATOM | 9167 | O38 | NAA | L | 1 | 49.994 | 78.044 | 69.491 | 1.00 27.88 | L |
| ATOM | 9168 | C39 | NAA | L | 1 | 51.402 | 77.897 | 69.237 | 1.00 30.97 | L |
| ATOM | 9169 | C40 | NAA | L | 1 | 51.936 | 79.052 | 68.361 | 1.00 38.43 | L |
| ATOM | 9170 | C43 | NAA | L | 1 | 51.295 | 80.407 | 68.619 | 1.00 41.27 | L |
| ATOM | 9171 | C44 | NAA | L | 1 | 51.373 | 81.102 | 67.275 | 1.00 41.19 | L |
| ATOM | 9172 | C45 | NAA | L | 1 | 51.391 | 79.957 | 66.268 | 1.00 43.57 | L |
| ATOM | 9173 | O46 | NAA | L | 1 | 51.716 | 78.777 | 66.988 | 1.00 41.01 | L |
| ATOM | 9174 | O48 | NAA | L | 1 | 52.001 | 81.195 | 69.535 | 1.00 47.69 | L |
| ATOM | 9175 | O50 | NAA | L | 1 | 52.610 | 81.785 | 67.193 | 1.00 45.52 | L |
| ATOM | 9176 | C54 | NAA | L | 1 | 49.834 | 80.351 | 64.370 | 1.00 44.96 | L |
| ATOM | 9177 | C55 | NAA | L | 1 | 48.657 | 80.143 | 63.596 | 1.00 46.09 | L |
| ATOM | 9178 | C56 | NAA | L | 1 | 47.739 | 79.179 | 64.049 | 1.00 46.71 | L |
| ATOM | 9179 | C57 | NAA | L | 1 | 48.010 | 78.466 | 65.230 | 1.00 46.60 | L |
| ATOM | 9180 | C58 | NAA | L | 1 | 49.195 | 78.736 | 65.945 | 1.00 46.07 | L |
| ATOM | 9181 | C61 | NAA | L | 1 | 48.398 | 80.905 | 62.351 | 1.00 45.20 | L |
| ATOM | 9182 | O62 | NAA | L | 1 | 49.429 | 81.655 | 61.894 | 1.00 43.93 | L |
| ATOM | 9183 | O63 | NAA | L | 1 | 47.338 | 80.848 | 61.788 | 1.00 45.42 | L |
| ATOM | 9184 | C65 | NAA | L | 1 | 52.293 | 72.850 | 75.662 | 1.00 21.55 | L |
| ATOM | 9185 | N66 | NAA | L | 1 | 52.491 | 71.864 | 76.550 | 1.00 23.41 | L |
| ATOM | 9186 | N68 | NAA | L | 1 | 50.118 | 79.664 | 65.531 | 1.00 44.19 | L |
| ATOM | 9187 | C1 | NAA | M | 1 | 55.452 | 57.798 | 88.726 | 1.00 12.26 | M |
| ATOM | 9188 | N2 | NAA | M | 1 | 56.258 | 57.223 | 89.654 | 1.00 13.33 | M |
| ATOM | 9189 | C3 | NAA | M | 1 | 57.591 | 57.411 | 89.508 | 1.00 15.56 | M |
| ATOM | 9190 | C4 | NAA | M | 1 | 58.130 | 58.178 | 88.444 | 1.00 16.72 | M |
| ATOM | 9191 | C5 | NAA | M | 1 | 57.243 | 58.727 | 87.587 | 1.00 14.98 | M |

Figure 10 (141 of 142)

```
ATOM   9192  N6   NAA M  1     55.906  58.549  87.679  1.00 12.26      M
ATOM   9193  N7   NAA M  1     58.666  56.957  90.266  1.00 21.66      M
ATOM   9194  N8   NAA M  1     57.691  59.487  86.596  1.00 15.12      M
ATOM   9195  C12  NAA M  1     58.644  56.124  91.485  1.00 22.40      M
ATOM   9196  C13  NAA M  1     57.353  55.389  91.831  1.00 20.38      M
ATOM   9197  C14  NAA M  1     57.491  55.111  93.340  1.00 22.62      M
ATOM   9198  C15  NAA M  1     58.632  56.090  93.772  1.00 28.32      M
ATOM   9199  O16  NAA M  1     58.883  56.879  92.634  1.00 24.73      M
ATOM   9200  O18  NAA M  1     57.198  54.188  91.099  1.00 16.34      M
ATOM   9201  O20  NAA M  1     57.817  53.736  93.493  1.00 27.32      M
ATOM   9202  C24  NAA M  1     59.937  55.397  94.238  1.00 28.29      M
ATOM   9203  O26  NAA M  1     61.096  55.929  93.556  1.00 25.77      M
ATOM   9204  P29  NAA M  1     62.267  54.960  93.149  1.00 18.68      M
ATOM   9205  O30  NAA M  1     63.609  55.599  93.361  1.00 28.53      M
ATOM   9206  O31  NAA M  1     62.032  54.579  91.624  1.00 28.75      M
ATOM   9207  O32  NAA M  1     62.091  53.688  94.026  1.00 33.25      M
ATOM   9208  P34  NAA M  1     62.444  52.194  93.847  1.00 23.43      M
ATOM   9209  O35  NAA M  1     63.836  51.938  94.281  1.00 29.62      M
ATOM   9210  O36  NAA M  1     62.293  51.758  92.341  1.00 30.09      M
ATOM   9211  O38  NAA M  1     61.425  51.291  94.665  1.00 24.18      M
ATOM   9212  C39  NAA M  1     60.282  51.880  95.323  1.00 27.94      M
ATOM   9213  C40  NAA M  1     60.170  51.412  96.789  1.00 26.56      M
ATOM   9214  C43  NAA M  1     61.504  51.163  97.466  1.00 23.41      M
ATOM   9215  C44  NAA M  1     61.199  50.102  98.518  1.00 22.90      M
ATOM   9216  C45  NAA M  1     59.991  49.355  97.925  1.00 16.48      M
ATOM   9217  O46  NAA M  1     59.447  50.178  96.888  1.00 21.26      M
ATOM   9218  O48  NAA M  1     62.009  52.296  98.107  1.00 31.92      M
ATOM   9219  O50  NAA M  1     60.809  50.736  99.729  1.00 21.27      M
ATOM   9220  C54  NAA M  1     60.198  46.886  98.111  1.00 12.26      M
ATOM   9221  C55  NAA M  1     60.421  45.587  97.619  1.00 12.29      M
ATOM   9222  C56  NAA M  1     60.736  45.466  96.242  1.00 17.19      M
ATOM   9223  C57  NAA M  1     60.819  46.604  95.415  1.00 15.62      M
ATOM   9224  C58  NAA M  1     60.579  47.854  95.985  1.00 12.26      M
ATOM   9225  C61  NAA M  1     60.332  44.382  98.486  1.00 15.51      M
ATOM   9226  O62  NAA M  1     59.664  44.528  99.661  1.00 12.26      M
ATOM   9227  O63  NAA M  1     60.811  43.338  98.141  1.00 19.98      M
ATOM   9228  C65  NAA M  1     59.756  57.444  89.624  1.00 22.63      M
ATOM   9229  N66  NAA M  1     59.492  58.183  88.532  1.00 21.95      M
ATOM   9230  N68  NAA M  1     60.256  48.018  97.311  1.00 12.26      M
ATOM   9231  C1   NAA N  1     28.343  50.516  89.371  1.00 12.26      N
ATOM   9232  N2   NAA N  1     27.519  51.177  90.229  1.00 12.26      N
ATOM   9233  C3   NAA N  1     26.195  51.095  89.991  1.00 14.72      N
ATOM   9234  C4   NAA N  1     25.665  50.352  88.907  1.00 12.26      N
ATOM   9235  C5   NAA N  1     26.568  49.713  88.104  1.00 12.26      N
ATOM   9236  N6   NAA N  1     27.915  49.780  88.302  1.00 12.26      N
ATOM   9237  N7   NAA N  1     25.126  51.651  90.659  1.00 17.42      N
ATOM   9238  N8   NAA N  1     26.125  48.985  87.060  1.00 14.05      N
ATOM   9239  C12  NAA N  1     25.147  52.502  91.853  1.00 18.78      N
ATOM   9240  C13  NAA N  1     26.414  53.298  92.158  1.00 19.57      N
ATOM   9241  C14  NAA N  1     26.333  53.515  93.676  1.00 20.69      N
ATOM   9242  C15  NAA N  1     25.261  52.484  94.152  1.00 18.17      N
ATOM   9243  O16  NAA N  1     24.937  51.744  93.010  1.00 21.22      N
ATOM   9244  O18  NAA N  1     26.454  54.545  91.484  1.00 26.83      N
ATOM   9245  O20  NAA N  1     25.973  54.863  93.886  1.00 12.26      N
ATOM   9246  C24  NAA N  1     23.987  53.096  94.793  1.00 20.83      N
ATOM   9247  O26  NAA N  1     22.783  52.579  94.195  1.00 18.31      N
ATOM   9248  P29  NAA N  1     21.634  53.591  93.867  1.00 19.09      N
ATOM   9249  O30  NAA N  1     20.315  53.176  94.495  1.00 16.91      N
ATOM   9250  O31  NAA N  1     21.531  53.671  92.260  1.00 15.06      N
ATOM   9251  O32  NAA N  1     22.145  54.939  94.428  1.00 14.17      N
ATOM   9252  P34  NAA N  1     21.558  56.328  94.429  1.00 12.26      N
ATOM   9253  O35  NAA N  1     20.150  56.261  94.919  1.00 15.68      N
ATOM   9254  O36  NAA N  1     21.597  56.937  92.957  1.00 17.07      N
ATOM   9255  O38  NAA N  1     22.410  57.321  95.320  1.00 17.43      N
ATOM   9256  C39  NAA N  1     23.741  56.996  95.738  1.00 16.16      N
ATOM   9257  C40  NAA N  1     23.989  57.440  97.207  1.00 16.17      N
```

Figure 10 (142 of 142)

```
ATOM   9258  C43  NAA N   1      22.738  57.608   98.042  1.00 16.06           N
ATOM   9259  C44  NAA N   1      23.111  58.672   99.052  1.00 17.53           N
ATOM   9260  C45  NAA N   1      24.194  59.485   98.350  1.00 13.67           N
ATOM   9261  O46  NAA N   1      24.657  58.698   97.260  1.00 12.26           N
ATOM   9262  O48  NAA N   1      22.398  56.445   98.748  1.00 34.16           N
ATOM   9263  O50  NAA N   1      23.685  58.043  100.159  1.00 20.07           N
ATOM   9264  C54  NAA N   1      23.903  61.932   98.594  1.00 12.56           N
ATOM   9265  C55  NAA N   1      23.526  63.217   98.193  1.00 16.56           N
ATOM   9266  C56  NAA N   1      22.974  63.364   96.894  1.00 19.23           N
ATOM   9267  C57  NAA N   1      22.819  62.246   96.058  1.00 12.26           N
ATOM   9268  C58  NAA N   1      23.209  60.992   96.538  1.00 12.34           N
ATOM   9269  C61  NAA N   1      23.708  64.376   99.099  1.00 16.51           N
ATOM   9270  O62  NAA N   1      24.031  64.077  100.381  1.00 21.71           N
ATOM   9271  O63  NAA N   1      23.590  65.501   98.707  1.00 22.61           N
ATOM   9272  C65  NAA N   1      24.044  51.238   89.976  1.00 18.39           N
ATOM   9273  N66  NAA N   1      24.306  50.461   88.917  1.00 16.10           N
ATOM   9274  N68  NAA N   1      23.764  60.816   97.799  1.00 12.26           N
END
```

CRYSTAL STRUCTURE OF YQEJ AND USES THEREOF

CROSS REFERENCE TO RELATED APPLICATIONS

This application claims the benefit of U.S. Provisional Application No. 60/313,153, filed Aug. 17, 2001 and U.S. Provisional Application No. 60/340,613, filed Dec. 7, 2001.

FIELD OF THE INVENTION

The present invention relates to the identification of *Bacillus subtilis* yqeJ as a NaMN AT, the determination of the crystal structures of yqeJ alone and bound to NaAD, and the use of the structures for designing new antimicrobial agents.

BACKGROUND OF THE INVENTION

Nicotinamide adenine dinucleotide (NAD) is an essential molecule in cells. In addition to its role in oxidation-reduction reactions, in which NAD(H) and its phosphorylated form, NADP(H), act as hydride donors and acceptors, NAD is also important for other cellular processes, such as the activity of NAD-dependent DNA ligases, mono and poly ADP-ribosylation of proteins, and production of the intracellular calcium-mobilizing molecules cADPR and NaADP (1), (2).

NAD is synthesized via a multi-step de novo pathway or via a pyridine salvage pathway. The enzyme nicotinic acid mononucleotide adenylyl transferase (NaMN AT, EC 2.7.7.18) sits at the convergence of these two pathways. NaMN AT catalyzes the conversion of ATP and nicotinic acid mononucleotide (NaMN) to nicotinic acid adenine dinucleotide (NaAD) (FIG. 1), which is directly processed to NAD by NAD synthetase. The nadD gene, encoding NaMN AT, was the first enzyme demonstrated to be essential of NAD biosynthesis by both the de novo and salvage pathways (3). A number of enzymes demonstrating in vitro adenylyltransferase activity for NaMN and NMN have been identified in eukarya, archaea and bacteria (4), (5), (6), (7), (8), (9), (10), (11). Along with sequence homology, the specificity of these enzymes for NMN versus NaMN provides a useful method for classifying new genes within this family.

While there is sequence conservation between the eubacterial nadD genes (FIG. 2), sequence alignment of nadD NaMN ATs to the eukaryotic enzymes or archeal enzymes is difficult outside of the region surrounding the (H/T)XGH (SEQ ID NO:18) nucleotidyl transferase consensus sequence. Adenylyltransferases encoded by the nadD gene prefer the nicotinic acid containing NaMN over NMN as a substrate by a factor that ranges from 6–1 to 2000–1 (12), (13), (4). Eubacteria also contain enzymes that demonstrate higher specificity for the nicotinamide containing NMN. This group the products of the nadR gene, which in addition to its regulatory role in NAD biosynthesis, also contains NMN AT activity (14). The eukaryotic and archeal NMN AT (EC 2.7.7.1), such as those from human (15), *Methanococcus jannaschii* (16) and *Methanobacterium thermoautotrophicum* (17), either demonstrate higher specificity for NMN as a substrate, as compared to NaMN, or show little preference for either substrate (4).

Primary sequence studies indicate that NaMN AT belongs to the nucleotidyltransferase α/β phosphodiesterases superfamily of enzymes that contain the (H/T)XGH (SEQ ID NO:18) signature motif. Members of this family share the same basic catalytic mechanism, involving direct nucleophilic attack upon an α-phosphate followed by the release of pyrophosphate, while the enzyme provides stabilization of the transition state prior to the formation of a new phosphodiester bond. The recent structure determination of NMN ATs, from *Methanococcus jannaschii* and *Methanobacterium thermoautotrophicum*, has allowed this sequence and functional homology to be extended to the structural conservation of residues involved in substrate binding and catalysis (16), (17).

Genes that have been identified to be essential for bacterial survival are currently being evaluated for their potential as targets for anti-microbial chemotherapy. Understanding the biochemical, physical and structural properties of these essential enzymes and placing them in a larger biological context are the first steps in exploring this potential. The present invention is based on the identification of an unassigned reading frame in *B. subtilis* (yqeJ) as a NaMN AT. The recombinant enzyme was expressed in *E. coli* and shown to prefer NaMN as a substrate to NMN, allowing the assignment of it as the nadD gene of *B. subtilis*. It differs from the NMN ATs from *Metanococcus jannaschii* and *Methanobacterium thermoautotrophicum* both in its substrate specificity and oligomeric state. It is homodimeric as opposed to a homo-hexamer (16), (17). The three dimensional structure of NaMN AT from *B. subtilis* has been determined to 2.2 Å and 3.2 Å with the NaAD bound. This has allowed the identification of key residues in substrate binding and catalysis. These structures will provide invaluable information in the ongoing development of anti-microbial agents targeting NAD biosynthesis.

SUMMARY OF THE INVENTION

The present invention provides a crystallized yqeJ having four molecules of yqeJ (molecules A, B, C and D as set forth in FIG. 9) in the asymmetric unit. The present invention also provides a crystallized complex of yqeJ and NaAD, that includes six molecules of yqeJ (molecules A, B, C, D, E and F as set forth in FIG. 10) in the asymmetric unit.

The present invention also provides a three dimensional model of yqeJ as derived by x-ray diffraction data of the yqeJ crystal. Specifically, the three dimensional model of yqeJ is defined by the relative structural coordinates for molecules A, B, C and/or D of yqeJ (SEQ ID NO:26) according to FIG. 9, ± a root mean square deviation from the backbone atoms of said amino acids of not more than 1.5 Å. The three dimensional model of yqeJ is useful for a number of applications, including, but not limited to, the visualization, identification and characterization of various active sites of yqeJ, including the substrate binding sites of yqeJ. The active site structures may then be used to design various agents which interact with yqeJ, as well as yqeJ complexed with a substrate or related molecules.

The present invention also provides a three dimensional model of yqeJ as derived by x-ray diffraction data of the yqeJ/NaAD crystal. Specifically, the three dimensional model of yqeJ is defined by the reactive structural coordinates for molecules A, B, C, D, E and/or F of yqeJ (SEQ ID NO:26) according to FIG. 10, ± a root mean square deviation from the backbone atoms of said amino acids of not more than 1.5 Å. The three dimensional model of yqeJ is useful for a number of applications, including, but not limited to, the visualization, identification and characterization of various active sites of yqeJ, including the substrate binding sites of yqeJ. The active site structures may then be used to design various agents which interact with yqeJ, as well as yqeJ complexed with NaAD, other substrates or related molecules.

The present invention is also directed to an active site of yqeJ, and preferably the substrate binding site of yqeJ, which is most preferably NaAD. More preferably, the active site comprises the relative structural coordinates of amino acid residues Ile6, Phe7, Gly8, Gly9, Thr10, Phe11, Asp12, Pro13, Pro14, His15, Asn16, Gly17, His18, Leu19, Leu20, Met21, Ala22, Val25, Phe36, Met37, Pro38, Asn39, Glu40, Ile41, Pro42, Pro43, His44, Lys45, Tyr50, Thr51, Arg56, Glu76, Pro82, Ser83, Tyr84, Thr85, Phe86, Asp87, Thr88, Phe103, Ile104, Ile105, Gly106, Ala107, Asp108, Met109, Ile110, Tyr112, Leu113, Pro114, Lys115, Trp116, Tyr117, Lys118, Leu119, Leu122, Phe128, Ile129, Gly130, Val131, Lys132, Arg133, Pro134, Phe136, Val149, Pro150, Glu151, Phe152, Glu153, Val154, Ser155, Ser156, Thr157, Met158, Ile159, Arg160 and Tyr187 for molecules A, B, C or D of yqeJ (SEQ ID NO:26) according to FIG. 9 or 10, ± a root mean square deviation from the backbone atoms of said amino acids of not more than 1.5 Å. The active site may correspond to the configuration of yqeJ in its state of association with its substrate (e.g, NaAD) or in its unbound state.

In addition, the present invention provides a method for identifying an agent that interacts with yqeJ, comprising the steps of: (a) generating a three dimensional model of molecules A, B, C and/or D of yqeJ (SEQ ID NO:26) using the relative structural coordinates according to FIG. 9, ± a root mean square deviation from the backbone atoms of said amino acids of not more than 1.5 Å; and (b) employing said three-dimensional model to design or select an agent that interacts with yqeJ.

The present invention also provides a method for identifying an agent that interacts with yqeJ, comprising the steps of: (a) generating a three dimensional model of molecules A, B, C, D, E and/or F of yqeJ (SEQ ID NO:26) using the relative structural coordinates according to FIG. 10, ± a root mean square deviation from the backbone atoms of said amino acids of not more than 1.5 Å; and (b) employing said three-dimensional model to design or select an agent that interacts with yqeJ.

Still further, the present invention provides a method for identifying a potential inhibitor of yqeJ, comprising the steps of: (a) generating a three dimensional model of said molecule comprising a substrate binding site using the relative structural coordinates of amino acid residues Ile6, Phe7, Gly8, Gly9, Thr10, Phe11, Asp12, Pro13, Pro14, His15, Asn16, Gly17, His18, Leu19, Leu20, Met21, Ala22, Val25, Phe36, Met37, Pro38, Asn39, Glu40, Ile41, Pro42, Pro43, His44, Lys45, Tyr50, Thr51, Arg56, Glu76, Pro82, Ser83, Tyr84, Thr85, Phe86, Asp87, Thr88, Phe103, Ile104, Ile105, Gly106, Ala107, Asp108, Met109, Ile110, Tyr112, Leu113, Pro114, Lys115, Trp116, Tyr117, Lys118, Leu119, Leu122, Phe128, Ile129, Gly130, Val131, Lys132, Arg133, Pro134, Phe136, Val149, Pro150, Glu151, Phe152, Glu153, Val154, Ser155, Ser156, Thr157, Met158, Ile159, Arg160 and Tyr187 for molecules A, B, C or D of yqeJ (SEQ ID NO:26) according to FIG. 9 or 10, ± a root mean square deviation from the backbone atoms of said amino acids of not more than 1.5 Å; and (b) selecting or designing a candidate agent by performing computer fitting analysis of the candidate inhibitor with the three dimensional model generated in step (a).

Finally, the present intention provides agents or inhibitors identified using the foregoing methods. Small molecules or other agents which inhibit or otherwise interfere with substrate binding to yqeJ may be useful as antimicrobial agents.

Additional objects of the present invention will be apparent from the description which follows.

BRIEF DESCRIPTION OF THE FIGURES

FIG. 2 provides a sequence alignment of *Bacillus subtilis* yqeJ (SEQ ID NO:1) with known eubacterial nadD genes: *Escherichia coli* (SEQ ID NO:2), *Bacillus halodurans* (SEQ ID NO:3), *Lactococcus lactis* (SEQ ID NO:4), *Mycobacterium leprae* (SEQ ID NO:5), *Streptomyces coelicolor* (SEQ ID NO:6), *Mycobacterium tuberculosis* (SEQ ID NO:7), *Treponema pallidum* (SEQ ID NO:8), *Borrelia burgdorferi* (SEQ ID NO:9), *Neisseria meningitides* (SEQ ID NO:10), and *Pseudomonas aeruginosa* (SEQ ID NO:11). Residues that are highlighted in bold are identical, residues that are boxed (beginning at H) designate the nucleotidyl transferase consensus sequence, while the residues in the box (beginning at S) designate the SXXXXR/K motif (SEQ ID NO:20). The secondary structure elements of *B. subtilis* NaMN AT (SEQ ID NO:1) are overlaid on the sequence with the arrows and cylinders representing the β strands and α helices, respectively.

FIG. 8A is an α-carbon trace of NaMN AT monomer bound to NaAD. Inset: electron density from a 3f°–2f$_c$ composite omit map is contoured at 1 σ.

FIG. 9 provides the atomic structural coordinates for yqeJ NaMN AT (SEQ ID NO:26) as derived by X-ray diffraction of a yqeJ crystal. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location in the unit cell (Å). "Occ" indicates the occupancy factor. "B" indicates the "B-value", which is a measure of how mobile the atom is in the atomic structure (Å$^2$). Under "Residue type", "A," "B," "C" and "D" refer to each molecule of yqeJ, and "S" refers to water molecules.

FIG. 10 provides the atomic structural coordinates for yqeJ NaMN AT (SEQ ID NO:26) and NaAD as derived by X-ray diffraction of the crystal complex of yqeJ NaMN AT (SEQ ID NO:26) with NaAD. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location in the unit cell (Å). "Occ" indicates the occupancy factor. "B" indicates the "B-value", which is a measure of how mobile the atom is in the atomic structure (Å$^2$). Under "Residue type", "A," "B," "C," "D," "E," and "F" refer to each molecule of yqeJ, and "H," "J," "K," "L," "M" and "N" refer to NaAD molecules.

DETAILED DESCRIPTION OF THE INVENTION

As used herein, the following terms and phrases shall have the meanings set forth below:

Unless otherwise noted, yqeJ is NaMNATase and catalyzes the reversible addition of ATP to NAMN or NMN to yield pyrophosphate and NAAD or NAD, respectively. Preferably, yqeJ comprises the amino acid sequences for *Bacillus subtilis* depicted in FIG. 2 (SEQ ID NO:1), FIG. 9 (SEQ ID NO:26) or FIG. 10 (SEQ ID NO:26), including conservative substitutions. "YqeJ activity" refers to the ability of yqeJ to catalyze the aforementioned reaction.

Figure 1:
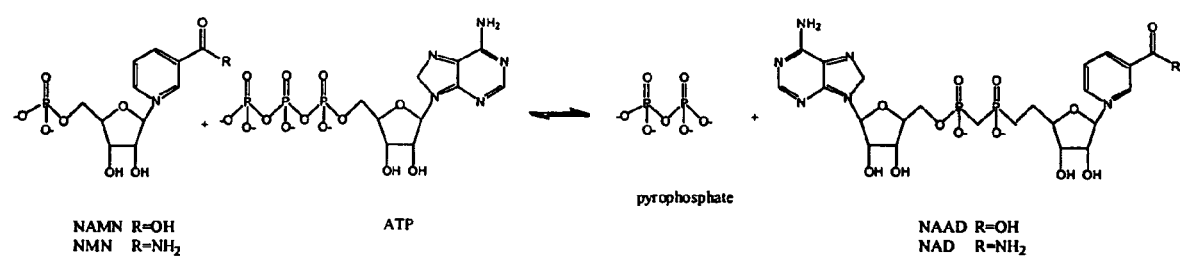
FIG. 1 depicts the reaction catalyzed by yqeJ NaMN AT. NaMN AT catalyzes the reversible addition of Nicotinic Acid Mononucleotide (NaMN) or Nicotinamide Mononucleotide (NMN) to ATP yielding pyrophosphate and Nicotinic Acid Adenine Dinucleotide (NaAD) or Nicotinamide Adenine Dinucleotide (NAD), respectively.

A "substrate" is a compound or molecule involved in a reaction in which yqeJ acts as a catalyst, and binds to yqeJ. Preferably, the reaction is set forth in FIG. 1, and the substrate is NAMN, NMN and ATP, as well as the product of the reaction, namely, NaAD and NAD.

Unless otherwise indicated, "protein" or "molecule" shall include a protein, protein domain, polypeptide or peptide.

"Structural coordinates" are the Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. The structural coordinates of the present invention may be modified from the original sets provided in FIGS. 9 and 10 by mathematical manipulation, such as by inversion or integer additions or subtractions. As such, it is recognized that the structural coordinates of the present invention are relative, and are in no way specifically limited by the actual x, y, z coordinates of FIGS. 9 and 10.

An "agent" shall include a protein, polypeptide, peptide, nucleic acid (including DNA or RNA), molecule, compound or drug.

"Root mean square deviation" is the square root of the arithmetic mean of the squares of the deviations from the mean, and is a way of expressing deviation or variation from the structural coordinates described herein. The present invention includes all embodiments comprising conservative substitutions of the noted amino acid residues resulting in same structural coordinates within the stated root mean square deviation. It will be obvious to the skilled practitioner that the numbering of the amino acid residues of yqeJ may be different than that set forth herein, and may contain certain conservative amino acid substitutions that yield the same three dimensional structures as those defined by FIGS. 9 and 10 herein. Corresponding amino acids and conservative substitutions in other isoforms or analogues are easily identified by visual inspection of the relevant amino acid sequences or by using commercially available homology software programs (e.g., MODELLAR, MSI, San Diego, Calif.).

"Conservative substitutions" are those amino acid substitutions which are functionally equivalent to the substituted amino acid residue, either by way of having similar polarity, steric arrangement, or by belonging to the same class as the substituted residue (e.g., hydrophobic, acidic or basic), and includes substitutions having an inconsequential effect on the three dimensional structure of yqeJ with respect to the use of said structures for the identification and design of agents which interact with yqeJ and a substrate, as well as other proteins, peptides, molecules or molecular complexes comprising a substrate binding site, for molecular replacement analyses and/or for homology modeling.

An "active site" refers to a region of a molecule or molecular complex that, as a result of its shape and charge potential, favorably interacts or associates with another agent (including, without limitation, a protein, polypeptide, peptide, nucleic acid, including DNA or RNA, molecule, compound or drug) via various covalent and/or non-covalent binding forces. As such, an active site of the present invention may include, for example, the actual site of substrate binding with yqeJ, as well as accessory binding sites adjacent or proximal to the actual site of substrate binding that nonetheless may affect yqeJ activity upon interaction or association with a particular agent, either by direct interference with the actual site of substrate binding or by indirectly affecting the steric conformation or charge potential of the yqeJ and thereby preventing or reducing binding of substrate to yqeJ at the actual site of substrate binding. As used herein, an "active site" also includes analog residues of yqeJ, which exhibit observable NMR perturbations in the presence of a binding ligand, such as the substrate. While such residues exhibiting observable NMR perturbations may not necessarily be in direct contact with or immediately proximate to ligand binding residues, they may be critical yqeJ residues for rational drug design protocols.

The present invention first provides a crystallized yqeJ that includes four molecules of yqeJ, namely, molecules A, B, C and D, in the asymmetric unit. In a particular embodiment, the amino acid sequence of each molecule of yqeJ (SEQ ID NO:1) is set forth in FIG. 2, and includes conservative substitutions. The crystal of the present invention effectively diffracts X-rays for the determination of the structural coordinates of yqeJ, and is characterized as having space group $P2_1$, unit cell parameters of a=43.98 Å, b=126.10 Å, c=70.58 Å and β=92.73°. Each molecule of yqeJ is further characterized as having the secondary structure in which β and α strands are configured in trace order as β2 1, αA, β2, αB, β3, αC, β4, αD, β5, β6, αE and αF. More preferably, the β and α strands correspond to amino acid residues of each molecule of yqeJ (SEQ ID NO:1) as follows: β1 (3–9), αA (16–28), β2 (33–38), αB (53–64), β3 (70–72), αC (85–95), β4 (100–106), αD (117–125), β5 (127–132), β6 (145–148), αE (156–165) and αF (175–183).

The present invention also provides a crystallized complex of yqeJ and NaAD. The crystallized complex is preferably characterized as having space group $P2_12_12_1$ with unit cell parameters a=78.39 Å, b=108.90 Å, c=178.09 Å, α=β=γ=90.00° and contains six molecules of yqeJ for each molecule of NaAD in the asymmetric unit. Here again, it is preferred that the amino acid sequence of each molecule of yqeJ (SEQ ID NO:1) is set forth in FIG. 2, and includes conservative substitutions.

Using the crystals of the present invention, X-ray diffraction data can be collected by a variety of means in order to obtain the atomic coordinates of the molecules in the crystals. With the aid of specifically designed computer software, such crystallographic data can be used to generate a three dimensional structure. Various methods used to generate and refine a three dimensional structure of a molecular structure are well known to those skilled in the art, and include, without limitation, multiwavelength anomalous dispersion (MAD), multiple isomorphous replacement, reciprocal space solvent flattening, molecular replacement, and single isomorphous replacement with anomalous scattering (SIRAS).

Accordingly, the present invention also provides a three dimensional model of yqeJ as derived by x-ray diffraction data of the yqeJ crystal. The three dimensional model of yqeJ is preferably defined by the structural coordinates shown in FIG. 9 for molecules A, B, C and/or D, ± a root mean square deviation from the backbone atoms of the amino acids of not more than 1.5 Å, preferably not more than 1.0 Å, and most preferably not more than 0.5 Å. The three dimensional model may include all four molecules of yqeJ, each molecule alone, as well as combinations of the molecules (e.g., molecules A/B, A/C, A/D, B/C and B/D). The three dimensional model of yqeJ is useful for a number of applications, including, but not limited to, the visualization, identification and characterization of various active sites of yqeJ, including the substrate binding sites. The active site structures may then be used to design agents with interact with yqeJ, as well as yqeJ complexed with a substrate or related molecules.

The present invention also provides a three dimensional model of yqeJ as derived by x-ray diffraction data of the yqeJ/NaAD crystal complex. The three dimensional model of yqeJ is preferably defined by the structural coordinates shown in FIG. 10 for molecules A, B, C, D, E and/or F, ± a root mean square deviation from the backbone atoms of the amino acids of not more than 1.5 Å, preferably not more than 1.0 Å, and most preferably not more than 0.5 Å. The three dimensional model may include all six molecules of yqeJ, each molecule alone, as well as combinations of the molecules (e.g., molecules A/B, A/C, A/D, B/C and B/D, etc). However, when the model is used to define the active binding site, it is preferred that the three dimensional model is defined by the structural coordinates of the individual molecules A, B, C or D in FIG. 10 since the coordinates for these molecules are more resolved than molecules E and F. The three dimensional model of yqeJ is useful for a number of applications, including, but not limited to, the visualization, identification and characterization of various active sites of yqeJ, including the substrate binding sites. The active site structures may then be used to design agents with interact with yqeJ, as well as yqeJ complexed with NaAD, other substrates or related molecules.

The present invention is also directed to an active site of yqeJ, and preferably the substrate binding site of yqeJ. More preferably, the active site comprises the relative structural coordinates of amino acid residues Ile6, Phe7, Gly8, Gly9, Thr10, Phe11, Asp12, Pro13, Pro14, His15, Asn16, Gly17, His18, Leu19, Leu20, Met21, Ala22, Val25, Phe36, Met37, Pro38, Asn39, Glu40, Ile41, Pro42, Pro43, His44, Lys45, Tyr50, Thr51, Arg56, Glu76, Pro82, Ser83, Tyr84, Thr85, Phe86, Asp87, Thr88, Phe103, Ile104, Ile105, Gly106, Ala107, Asp108, Met109, Ile110, Tyr112, Leu113, Pro114, Lys115, Trp116, Tyr117, Lys118, Leu119, Leu122, Phe128, Ile129, Gly130, Val131, Lys132, Arg133, Pro134, Phe136, Val149, Pro150, Glu151, Phe152, Glu153, Val154, Ser155, Ser156, Thr157, Met158, Ile159, Arg160 and Tyr187 for molecules A, B, C or D of yqeJ (SEQ ID NO:26) according to FIG. 9 or 10, ± a root mean square deviation from the backbone atoms of said amino acids of not more than 1.5 Å, preferably not more than 1.0 Å, and most preferably not more than 0.5 Å. The active site may correspond to the configuration of yqeJ in its state of association with a substrate such as NaAD, or in its unbound state.

Another aspect of the present invention is directed to a method for identifying an agent that interacts with yqeJ, comprising the steps of: (a) generating a three dimensional model of molecules A, B, C or D of yqeJ (SEQ ID NO:26) using the relative structural coordinates according to FIG. 9, ± a root mean square deviation from the backbone atoms of said amino acids of not more than 1.5 Å, preferably not more than 1.0 Å, and most preferably not more than 0.5 Å; and (b) employing said three-dimensional model to design or select an agent that interacts with yqeJ.

In another embodiment, the present invention is directed to a method for identifying an agent that interacts with yqeJ, comprising the steps of: (a) generating a three dimensional model of molecules A, B, C, D, E and/or F of yqeJ (SEQ ID NO:26) using the relative structural coordinates according to FIG. 10, ± a root mean square deviation from the backbone atoms of said amino acids of not more than 1.5 Å, preferably not more than 1.0 Å, and most preferably not more than 0.5 Å; and (b) employing said three-dimensional model to design or select an agent that interacts with yqeJ.

In the foregoing methods, the agent may be identified using computer fitting analyses utilizing various computer software programs that evaluate the "fit" between the putative active site and the identified agent, by (a) generating a three dimensional model of the putative active site of a molecule or molecular complex using homology modeling or the atomic structural coordinates of the active site, and (b) determining the degree of association between the putative active site and the identified agent. Three dimensional models of the putative active site may be generated using any one of a number of methods known in the art, and include, but are not limited to, homology modeling as well as computer analysis of raw date generated using crystallographic or spectroscopy data. Computer programs used to generate such three dimensional models and/or perform the necessary fitting analyses include, but are not limited to: GRID (Oxford University, Oxford, UK), MCSS (Molecular Simulations, San Diego, Calif.), AUTODOCK (Scripps Research Institute, La Jolla, Calif.), DOCK (University of California, San Francisco, Calif.), Flo99 (Thistlesoft, Morris Township, N.J.), Ludi (Molecular Simulations, San Diego, Calif.), QUANTA (Molecular Simulations, San Diego, Calif.), Insight (Molecular Simulations, San Diego, Calif.), SYBYL (TRIPOS, Inc., St. Louis. Mo.) and LEAPFROG (TRIPOS, Inc., St. Louis, Mo.). The structural coordinates also may be used to visualize the three-dimensional structure of yqeJ using MOLSCRIPT (Kraulis, P J, J. Appl. Crystallogr. 24: 946–950 (1991)) and RASTER3D (Bacon, D. J. and Anderson, W. F., J. Mol. Graph. 6: 219–220 (1998)), for example.

The effect of such an agent identified by computer fitting analyses on yqeJ activity may be further evaluated by contacting the identified agent with yqeJ and measuring the effect of the agent on yqeJ activity. Depending upon the action of the agent on the active site of yqeJ, the agent may act either as an inhibitor or activator of yqeJ activity. For example, enzymatic assays may be performed and the results analyzed to determine whether the agent is an inhibitor of yqeJ and a substrate (i.e., the agent may reduce or prevent binding affinity between yqeJ and a substrate) or an activator of yqeJ and a substrate (i.e., the agent may increase binding affinity between yqeJ and a substrate). However, in the preferred embodiment, the agent is an inhibitor of yqeJ activity. In this regard, the candidate inhibitor can be tested by obtaining the inhibitor and introducing the inhibitor in a reaction with yqeJ, NAMN (or MMN) and ATP, and determining the effect the candidate inhibitor has on the reaction. Alternatively, the candidate inhibitor can be tested by introducing the candidate inhibitor in a reaction with yqeJ, NAAD (or NAD) and pyrophosphate, and determining the effect the candidate inhibitor has on the reaction. The specific adenylyl trasferase assays that can be used are described in Example 1 below. Once a candidate inhibitor has been tested and shown to inhibit the reaction, further tests may be performed to evaluate the potential therapeutic efficacy of the agent as an antimicrobial agent.

Still further, the present invention provides a method for identifying a potential inhibitor of yqeJ, comprising the steps of: (a) generating a three dimensional model of said molecule comprising a substrate binding site using the relative structural coordinates of amino acid residues Ile6, Phe7, Gly8, Gly9, Thr10, Phe11, Asp12, Pro13, Pro14, His15, Asn16, Gly17, His18, Leu19, Leu20, Met21, Ala22, Val25, Phe36, Met37, Pro38, Asn39, Glu40, Ile41, Pro42, Pro43, His44, Lys45, Tyr50, Thr51, Arg56, Glu76, Pro82, Ser83, Tyr84, Thr85, Phe86, Asp87, Thr88, Phe103, Ile104, Ile105, Gly106, Ala107, Asp108, Met109, Ile110, Tyr112, Leu113, Pro114, Lys115, Trp116, Tyr117, Lys118, Leu119, Leu122, Phe128, Ile129, Gly130, Val131, Lys132, Arg133, Pro134, Phe136, Val149, Pro150, Glu151, Phe152, Glu153, Val154, Ser155, Ser156, Thr157, Met158, Ile159, Arg160 and Tyr187 for molecules A, B, C or D of yqeJ (SEQ ID NO:26) according to FIG. 9 or 10, ± a root mean square deviation from the backbone atoms of said amino acids of not more than 1.5 Å, preferably not more than 1.0 Å, and most preferably not more than 0.5 Å; and (b) selecting or designing a candidate agent by performing computer fitting analysis of the candidate inhibitor with the three dimensional model generated in step (a). Here again, once the candidate inhibitor is obtained or synthesized, the candidate inhibitor may be analyzed in various assays as discussed above.

Various molecular analysis and rational drug design techniques are further disclosed in U.S. Pat. Nos. 5,834,228, 5,939,528 and 5,865,116, as well as in PCT Application No. PCT/US98/16879, published WO 99/09148, the contents of which are hereby incorporated by reference.

The present invention is also directed to the agents or inhibitors identified using the foregoing methods. Such agents or inhibitors may be a protein, polypeptide, peptide, nucleic acid, including DNA or RNA, molecule, compound, or drug. Small molecules or other agents which inhibit or otherwise interfere with yqeJ and a substrate may be useful in the treatment of diseases or conditions associated with bacterial infection.

The present invention may be better understood by reference to the following non-limiting Example. The following Example is presented in order to more fully illustrate the preferred embodiments of the invention, and should in no way be construed as limiting the scope of the present invention.

EXAMPLE 1

1. Methods and Methods

Cloning and expression of B. subtilis NaMN AT. The B. subtilis yqeJ gene was PCR cloned into a modified version of pET16b to yield pML208. This E. coli expression vector has the yqeJ coding sequence downstream of the T7 RNA polymerase promoter. The expressed protein contains the peptide MGHHHHHHHHHHSSGHIEGRHMPGGS (SEQ ID NO:12) fused to Lys-2 of the native sequence. This provides a purification tag and contains the cleavage site for Factor Xa, between Arg-20 and His-21 of the peptide, resulting in the cleaved protein having an extra six amino acids on its amino termini. To produce selenomethionine labeled yqeJ, the protein was expressed in BL21(DE3) Escherichia coli at 25° C. Cultures were grown in shake flasks in LeMaster's media and induced at log phase with 0.5 mM IPTG. Cultures were harvested 4 hours post induction. Unlabelled yqeJ was also expressed in BL21DE3 E. coli, but at 37° C. High density expression was carried out in a Biostat C-10 bioreactor (B. Braun Biotech). The culture was induced with 1.0 mM IPTG (final) at 4.6 $OD_{600}$. Cells were harvested 4 hours post induction at 9.0 $OD_{600}$.

Purification and cleavage of B. subtilis NaMN AT. The purification, unless otherwise stated was performed at 4° C. Bacteria were resuspended in buffer (50 mM Hepes pH 7.5, 500 mM NaCl) and lysed by passage through a Microfluidics microfluidizer. The lysate was collected and centrifuged at 20,000×g for 30 min. The supernatant, containing 40% of the expressed yqeJ NaMN AT (the remainder being insoluble), was applied to a Poros PI column (Applied Biosystems) that was coupled to a Ni-NTA column (Qiagen). The Ni-NTA column was washed with 50 mM imidazole and the protein was eluted with a 50–800 mM imidazole gradient. 10 mM EDTA was added to the fraction containing yqeJ NaMN AT, for 6 hours, followed by dialysis against 50 mM Tris pH 8.0, 50 mM NaCl, 2 mM $CaCl_2$. The His-tag was removed from yqeJ NaMN AT by a six hour digestion with Factor Xa (New England Biolabs) at room temperature. The reaction was applied to a Poros HQ 50 column and the bound protein was eluted with a 0–1 M NaCl gradient. The peak fraction containing yqeJ NaMN AT was diluted and applied to a Poros S column. The flow through, containing yqeJ NaMN AT, was applied to TSK-Gel G3000 SW column (TosoHaas), equilibrated with 50 mM Hepes pH 7.5, 50 mM NaCl. Protein purity was >95%.

Adenylyl Trasferase Assays

Discontinuous HPLC assay. The discontinuous HPLC assay is based upon the assays published by Mehl et al. (12)

and Balducci et al. (18). Reaction conditions were 20 mM Hepes, pH 7.4, 10 mM $MgCl_2$, and 0.36 or 0.18 mg/ml yqeJ protein incubated at 37° C. For the forward reaction, the incubations contained 1 mM ATP and 1 mM NaMN or NMN. For the reverse reaction, the incubations contained or 1 mM sodium pyrophosphate and 0.5 mM NaAD or NAD. The reactants and products were separated by chromatography on a 3.9×150 mm C18 column (Novapack 5 μm, Waters Inc). Buffer A 100 mM potassium phosphate pH 7.5. Buffer B 100 mM potassium phosphate pH 7.5 in 20% MeOH. The elution conditions were: 0 to 3 min in 100% A, 3.0 to 3.1 min to 100% B, 3.1 to 7 min 100% B. The absorbance of reactants and products was detected at 254 nm. Under these conditions NAMN eluted at 1.16 min., NMN at 1.29 min., ATP at 2.12 min., NaAD at 5.37 min. and NAD at 5.47 min.

Continuous assay. A continuous assay to monitor the reaction in the forward direction was based upon the EnzChek pyrophosphate assay from Molecular Probes (Eugene Oreg.) In this assay, inorganic pyrophosphate produced in the forward reaction of yqeJ is cleaved by inorganic pyrophosphatase to phosphate, which is used by the second coupling enzyme, purine nucleoside phosphorylase (PNP), to convert the chromogenic substrate 2-amino-6-mercapto-7-methylpurine ribonucleoside (MESG) to ribose-1-phosphate and 2-amino-6-mercapto-7methylpurine ($E_{360}$=11,000 $M^{-1}cm^{-1}$). The reaction conditions were 20 mM Hepes pH 7.5, 10 mM $MgCl_2$, 0.2 mM MESG, 1 U PNP, 0.01 U inorganic pyrophosphatase, and 0.03 μg/mL yqeJ. The reaction volume was 125 μL and was carried out in a 96 well plate at room temperature using spectamax384 plus plate reader recording continuously at 360 nm (Molecular Devices, Sunnyvale Calif.). For the $K_M$ determinations, NaMN was varied from 25 to 500 μM with ATP held at 2 mM and ATP was varied from 50 to 1000 μM with NaMN held constant at 1 mM. All kinetic constants were determined from non-linear fits of the experimental data using the enzyme kinetic module of Sigmaplot 7.0 (SPSS, Inc. San Rafael Calif.). The reaction conditions were the same for the $K_M$ determinations for NMN except the $MgCl_2$ concentration was increased to 50 mM and the yqeJ concentration was increased to 75 μg/mL due to the lower activity against this substrate. Substrate inhibition was seen in assays using NMN as a substrate, with the double reciprocal plots curving sharply upwards above 5 mM. The data was fit to a model of substrate inhibition using the equation: $v=Vmax/(1+K_M/S+S/Ki)$. The Ki determined for NMN was 17+/-3 mM. NMN was varied from 0.5 to 10 mM with ATP held constant at 0.6 mM. The kinetic constants of yqeJ using NMN and ATP substrates also was determined with a second coupled assay system, one coupling NAD production to its reduction by alcohol dehydrogenase. This assay was described by Balducci et al (Balducci et al, 1995a) and has been used to characterize other NMN ATase. Using this assay, very similar values of $K_M$ and Vmax for NMN were obtained as was determined with the PNP coupled assay described above. The alcohol dehydrogenase coupled assay was not suitable to assays NaMN as a substrate, presumably because NaAD is not a good substrate for alcohol dehydrogenase.

The back reaction for yqeJ NaMN AT was monitored using the coupled enzyme assay of hexokinase and glucose-6-phosphate dehydrogenase (from yeast). YqeJ NaMN AT converts pyrophosphate and NaAD (or NAD) to NaMN (or NMN) and ATP. The ATP is then used by hexokinase to phosphorylate glucose to give glucose-6-phosphate and ADP. Glucose-6-phosphate is oxidized to 6-phospho-glucono-δ-lactone by glucose-6-phosphate dehydrogenase and NADP is reduced to NADPH. The assay is followed by the absorbance of NADPH at 340 nm. Glucose-6-phosphate dehydrogenase from baker's yeast was used because this enzyme prefers NADP to NAD as a co-substrate. Assay conditions were: 20 mM HEPES pH 7.5, 50 mM $MgCl_2$, 1 mM NaPPi, 10 mM KCl, 5 U hexokinase, 5 U glucose-6-phosphate dehydrogenase, 1 mM glucose, 0.5 mM NADP+. YqeJ concentration is 0.0015 mg/ml for NaAD determination and 0.0075 mg/ml for NAD determination. For $K_M$ determinations, NaAD was varied from 5 to 100 μM holding PPi at 1 mM, NAD was varied from 1 to 10 mM holding PPi at 1 mM and PPi was varied from 0.1 to 2 mM holding NaAD at 500 μM. At high concentration of NaPPi a precipitate was observed. This limited the concentrations of PPi that could be used in the assays.

Crystallization. Crystals were grown by hanging drop vapor diffusion at 18° C. in drops containing 1.5 μl of protein stock solution (14 mg/ml protein, 50 mM HEPES pH 7.5, 50 mM NaCl) mixed with 1.5 μl of well solution (8% PEG 3350, 100 mM $MgCl_2$) and equilibrated against 1 ml of well solution. Block shaped crystals grew in 3 weeks, measuring approximately 50 μm across. NaAD-NaMN At complex co-crystals were grown at 18° C. in drops containing 1.0 μl of protein stock solution (14 mg/ml protein, 2 mM NaAD, 50 mM HEPES pH 7.5, 50 mM NaCl) mixed with 1.0 μl of well solution (20% PEG 3350, 100 mM MgAcetate) and 0.3 μl of xylitol (30% w/v). Plate-like crystals grew in 1–3 weeks to approximately 200 μm×50 μm ×20 μm.

Data collection and processing. Crystals of the apo-form belong to the space group $P2_1$ with unit cell parameters a=43.98 Å, b=126.10 Å, c=70.58 Å and β92.73° (α and γ=90°) and contain four molecules of NaMN AT in the asymmetric unit, implying a solvent content of 58.5%. To harvest crystals, an equal volume of a solution of 35% PEG 3350, 100 mM $MgCl_2$ was added to drops, and after equilibration for several minutes crystals were swiped through another drop of this solution and cooled rapidly in liquid nitrogen. Data collection statistics are shown in Table II. MAD data were recorded at the 5.0.2 beamline of the Advanced Light Source at Lawrence Berkeley National Laboratory using a Quantum-4 detector. Data was collected at two energies chosen based on the measured absorption at the selinium K edge: 12661 eV (λ=0.97920 Å) and 12959 eV (λ=0.9567 Å) corresponding to maximum f" and a remote energy, respectively. Intensities were integrated and scaled using the programs Denzo and Scalepack (19).

Crystals of the NaAD bound form belong to the space group $P2_12_12_1$ with unit cell parameters a=78.39 Å b=108.90 Å c=178.09 Å, α=β=γ=90.00° and contain six molecules of yqeJ in the asymmetric unit, implying a solvent content of 55.6%. To harvest crystals, ethylene glycol was added to the drops to 20% and after mixing, the crystals were cooled rapidly in liquid nitrogen. Data collection statistics are shown in Table II. MAD data were recorded at the 5.0.2 beamline of the Advanced Light Source at Lawrence Berkeley National Laboratory using a Quantum-4 detector. Data was collected at two consecutive energies, based on the measured absorption at the selenium K edge: 12662 eV (λ=0.97910 Å) and 12863 eV (λ=0.96388 Å) and corresponding to maximum f" and a remote energy. Intensities were integrated and scaled using the programs Denzo and Scalepack (19).

Phasing, model building and refinement. The apo structure was determined by the multiple wavelength anomalous dispersion (MAD) method. Initially 22 selenium sites were found with the program SOLVE (20), and phasing with these sites in CNS (21) revealed two additional sites by means of a difference fourier map. Phases were calculated from these 24 sites in CNS and SHARP (22) and improved by solvent modification with Solomon (22). ARP/WARP (23) was used to partially trace the α-carbon backbone. The complete model, with the exception of residues 42–52 in all molecules and residues 118–126 in molecules A and C, was built into the experimental map. After several iterative cycles of refinement using CNS and model improvement, water molecules were placed automatically in CNS. A simulated annealing composite-omit map was calculated to check the final model. Final $R_{work}$ and $R_{free}$ values of 22.21% and 25.44% were obtained.

The NaAD-NaMN AT complex structure was determined using a combination of MAD phases and molecular replacement using the apo enzyme structure. Initially 21 selenium sites found using the program ShakeNBake (24), and phasing with these sites in MLPhare (25) revealed 13 additional sites by means of a difference fourier map. Phases were calculated from these 34 sites and improved with solvent flattening and fourfold averaging with DM (25). This experimental map was used to build four of the six molecules in the asymmetric unit, employing strict NCS restraints. At this point, the refined structure of the apo-enzyme become available. The complex model was edited such that fragments of the high-resolution apo model were substituted wherever the apo model was in good agreement with electron density in the experimental map. MAD phases were then combined with model phases to generate improved maps, and two more molecules were identified. Density for the first four molecules found is significantly stronger than for the final two, however density for the bound NaAD is good in all 6 molecules. The final R values after releasing NCS restraints and rebuilding are $R_{free}=0.2798$ and $R_{work}=0.2787$.

Size exclusion chromotagraphy. 90 µg of *B. subtilis* NaMN AT was run on a Pharmacia superose 12 H/R 10/30 column in Tris buffered Saline pH 7.5 at a flow rate of 0.5 ml/min. The retention time of *B. subtilis* NaMN AT was 27.3 min. To determine the apparent molecular weight of *B. subtilis* NaMN AT, the standards Thyroglobin 670,000, Gamma globulin 158,000, Ovalbumin 44,000, Myoglobin 17,000 and Vitamin B-12 1,350 (Biorad) were also run on the column under the same conditions.

Analytical Ultracentrifugation. Protein was pre-equilibrated by dialysis at $4_C$°C in 20 mM HEPES and 10 mM $MgCl_2$, pH 7.2. The partial specific volume of *B. subtilis* NaMN AT was calculated based on the amino acid composition, and the density of the solvent was calculated from the chemical composition of the buffer using the computer program SEDNTERP and adjusted for temperature. Sedimentation velocity experiments were performed on a Beckman XL1/XLA Analytical Ultracentrifuge operating at a rotor speed of 30,000 rpm using 400 µl samples loaded into two-channel carbon-Epon centerpieces in an An-60 Ti titanium rotor preequilibrated to temperature at least 1 hour prior to each experiment. The sedimentation coefficients and molecular weights were obtained by fitting the data to the program SVEDBERG (26). Sedimentation equilibrium experiments were performed at 4° C. and 20° C. using a rotor speed of 18,000 rpm. Samples (400 µl) were loaded into two-channel cells at 3 different protein concentrations. Scans were recorded at 4° C. and 20° C., and signal was detected using absorbance optics (280 nm) and interference optics. Equilibrium was judged to be achieved when no deviations in a plot of the difference between successive scans taken 3 hrs apart were observed, usually within 24 hours. Although, temperature and ligand did have a minor effect upon the apparent molecular weight as determined by analytical ultracentrifugation. The variation between the velocity and equilibrium values at the different protein concentrations can be attributed to hydrodynamic effects.

Equations. The molecular weight of the protein in the presence and absence of ligand was obtained from sedimentation equilibrium experiments using the following equation:

1) $C_r = C_o \exp[m(1-v\rho)\omega^2(r^2-r_o^2)/2RT] + \text{base}$

Where $C_r$ is absorbance at radius r; $C_0$ is absorbance at reference radius $r_0$; M is the molar mass of the macromolecule; v is the partial specific volume of the macromolecule (mL/g); ρ is the density of the solvent; ω is the angular velocity of the rotor; R is gas constant; T is temperature; and base is baseline offset. The molecular weight of yqeJ NaMN AT was obtained from sedimentation velocity experiments using equation 2:

2) $M = (sRT)/(1-v\rho)D$

Where s is the sedimentation coefficient and D is the diffusion coefficeint obtained by fitting the data to the program SVEDBERG (26).

Figure 3:
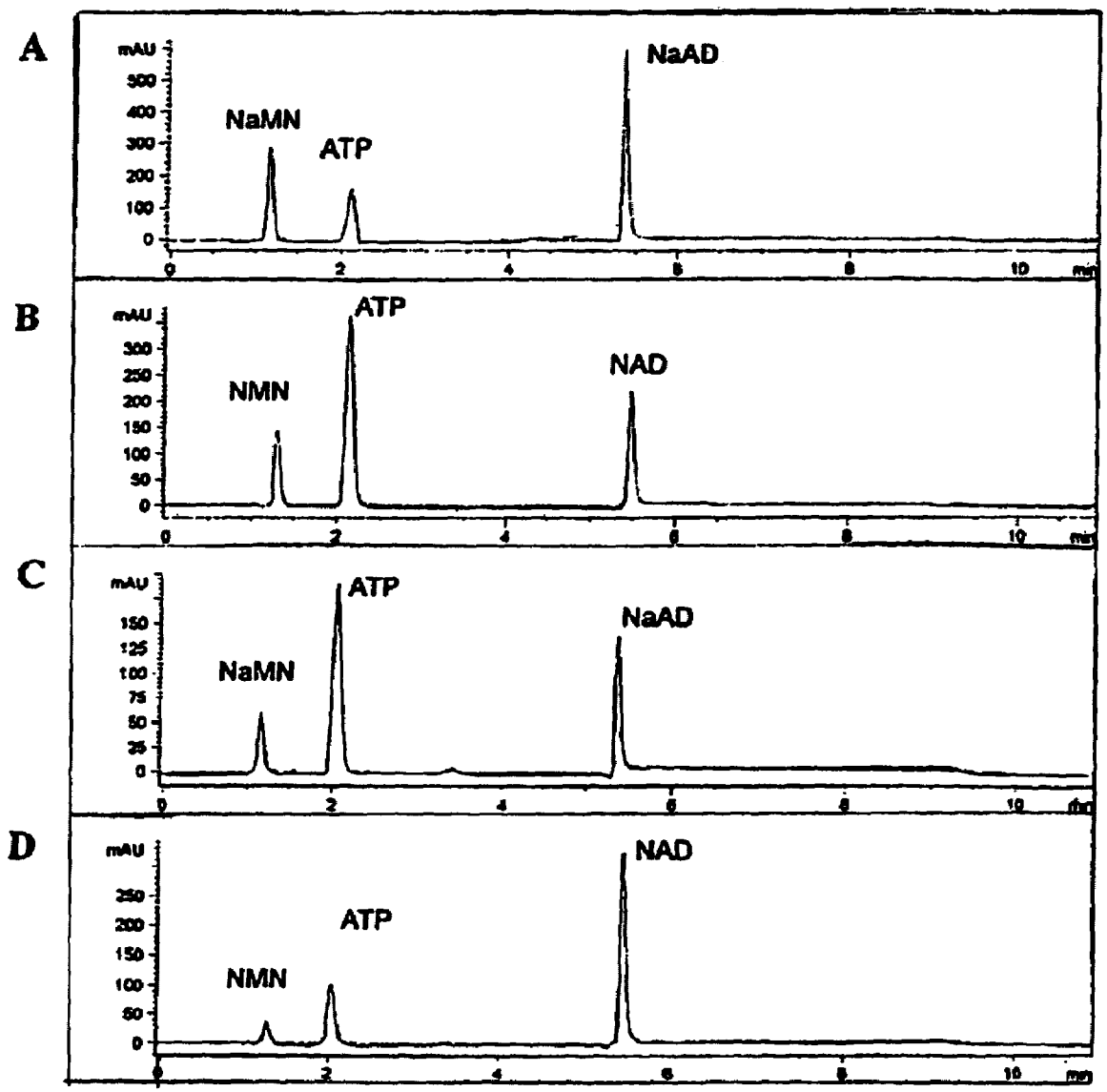
FIGS. 3A, 3B, 3C and 3D provides the results of HPLC analysis of yqeJ NaMN AT adenylyl transferase activity. 0.36 mg/ml yqeJ NaMN AT was incubated with 1 mM ATP and 1 mM NaMN (3A) or 1 mM NMN (3B) for 30 minutes. The reverse reaction with 0.18 mg/ml yqeJ NaMN AT was assayed with 1 mM sodium pyrophosphate and either 0.5 mM NaAD (3C) or 0.5 mM NAD (3D) for 30 minutes. Under these conditions NaMN eluted at 1.16 min, NMN at 1.29 min, ATP at 2.12 min, NaAD at 5.37, and NAD at 5.47 min.
Figure 4:
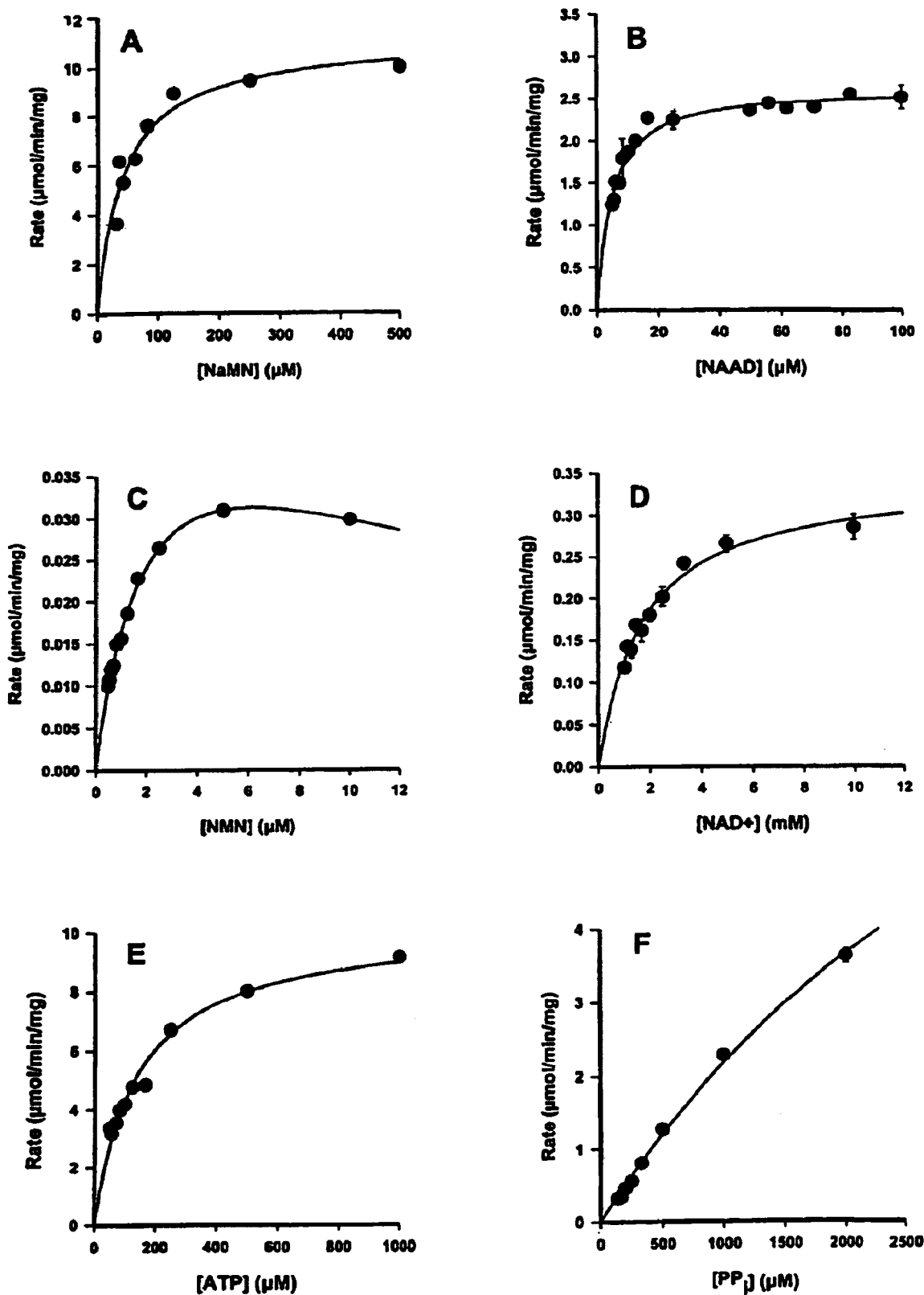
FIGS. 4A–4F provide representative data of *B. subtilis* NaMN AT activity. Plots show rate vs. substrate concentration: (4A) NaMN, (4B) NAAD, (4C) NMN, (4D) NAD, (4E) ATP and (4F) pyrophosphate. Lines represent fit to rate equation indicated in Methods. Forward reaction, graphs 4A, 4C and 4E, uses purine ribonucleoside phosphorylase coupled assay system. Back reaction, graphs 4B, 4D and 4F, uses the hexokinase/glucose-6-phosphate dehydrogenase coupled enzyme assay system.

2. Results yqeJ encodes NaMN AT nadD. The *S. pneumonia* genome was sequenced and searched for essential genes that may be suitable targets for the development of anti-microbial agents. Those genes identified were then tested in *B. subtilis* and *E. coli*. An unassigned open reading frame, yqeJ that was essential in all three organisms was identified in *B. subtilis*. Comparisons of its amino acid sequence to genbank using the program Blast (27) revealed it has homology to a number of putative adenylyl transferases including the recently assigned nadD gene of *E. coli* (SEQ ID NO:2) (12). yqeJ (SEQ ID NO:1) contains the signature nucleotidyl transferase consensus sequence (H/T)XGH (SEQ ID NO:18). As can be seen in FIG. 2, *B. subtilis* yqeJ is closely related to *E. coli* nadD (SEQ ID NO:2) and other putative eubacterial NaMN ATs. The *B. subtilis* enzyme is more distantly related to *E. coli* nadR and other eukaryotic and archeal NMN ATs. Alignment of the *B. subtilis* NaMN AT (SEQ ID NO:1) to these species was difficult owing to little homology outside of the region around the H/TXGH (SEQ ID NO:18) consensus sequence. This later group of enzymes includes the NMN AT from *M. jannaschii* and *M. thermoautotrophicum* for which three-dimensional structures have recently been determined (17), (16). Thus, it appears that the sequence of the *B. subtilis* enzyme is more closely related to the group of eubacterial enzymes that prefer NaMN as a substrate than to the archeal or eukaryotic enzymes that show little preference among the substrates or prefer NMN over NaMN (13), (12), (4). To confirm that yqeJ was indeed a NaMN AT recombinant protein was expressed in *E. coli* and purified (see Methods). Adenylyl transferase assays were performed to determine the activity and substrate specificity of yqeJ NaMN AT. Incubation of the enzyme with NaMN and ATP led to the formation of a new peak as detected by HPLC that eluted with the NaAD standard, the expected product of the forward reaction of NaMN AT (FIG. 3A). Similarly, the enzyme was able to convert NMN and ATP to a new peak that eluted with NAD (FIG. 3B). Using the same assay system, we were able to demonstrate that yqeJ protein was also able to catalyze the reverse reaction. FIG. 3C shows NaAD being converted to NaMN and ATP and FIG. 3D shows NAD being converted to NMN and ATP.

No product was formed under any of these reaction conditions in the absence of yqeJ protein.

To better understand the substrate specificity of *B. subtilis* yqeJ, the catalytic constants for substrates were determined in the forward and reverse reactions using a coupled enzyme assays as described in the methods section. The data are summarized in Table I and shown in graph form in FIGS. 4A–4F. Comparing the $V_{max}/K_M$ ratio for the different substrates in the forward and reverse reactions we see the *B. subtilis* enzyme has a clear preference for nicotinic acid containing substrates (NaMN and NaAD) over nicotinamide containing ones (NMN and NAD) by factors of 12,900 to 1 for the forward reaction and 2,000 to 1 for the reverse reaction. This same substrate preference is shared with nadD enzymes from other eubacterial sources (13), (12) and allows us to assign yqeJ as the nadD gene in *B. subtilis*.

The crystal structure of NaMN AT. NaMN AT was crystallized both empty and with NaAD bound. For the apo structure good data were collected to 2.1 Å, while anistrophic data of the NaAD bound form were collected to 3.2 Å (Table II). The apo structure of NaMN AT was determined using experimental phases derived from selenium substituted methionine protein crystals by the MAD technique (see methods). The final model of NaMN AT (SEQ ID NO:26) contains four molecules in the asymmetric unit of which residues 42–52 are disordered in all molecules, and residues 118–126 are disordered in molecules A and C. The NaAD bound structure of NaMN AT was determined using experimental MAD phases combined with phases from molecular replacement using fragments from the apo structure. The crystal structure of NaAD bound NaMN AT contains six molecules in the asymmetric unit (two are predominantly disordered) all of which show clear density for the bound NaAD (FIG. 8A).

Figure 5:
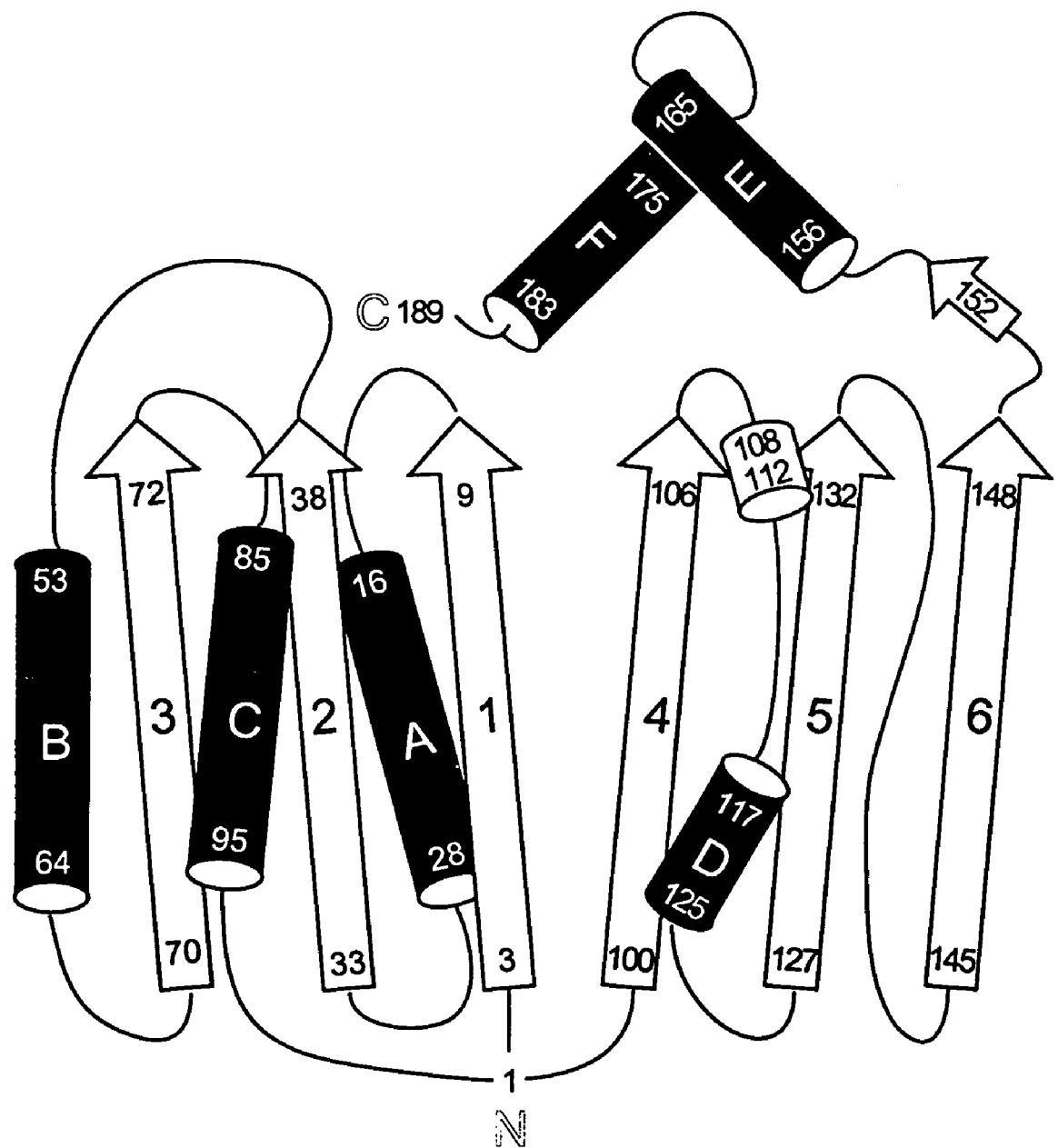
FIG. 5 provides a topology diagram of the secondary structure elements of yqeJ NaMN AT. Grey arrows and black cylinders represent β-sheets and α-helices, respectively. The white cylinder represents an α-helical turn and the white arrow an isolated β bridge that is part of the dimer interface.
Figure 6:
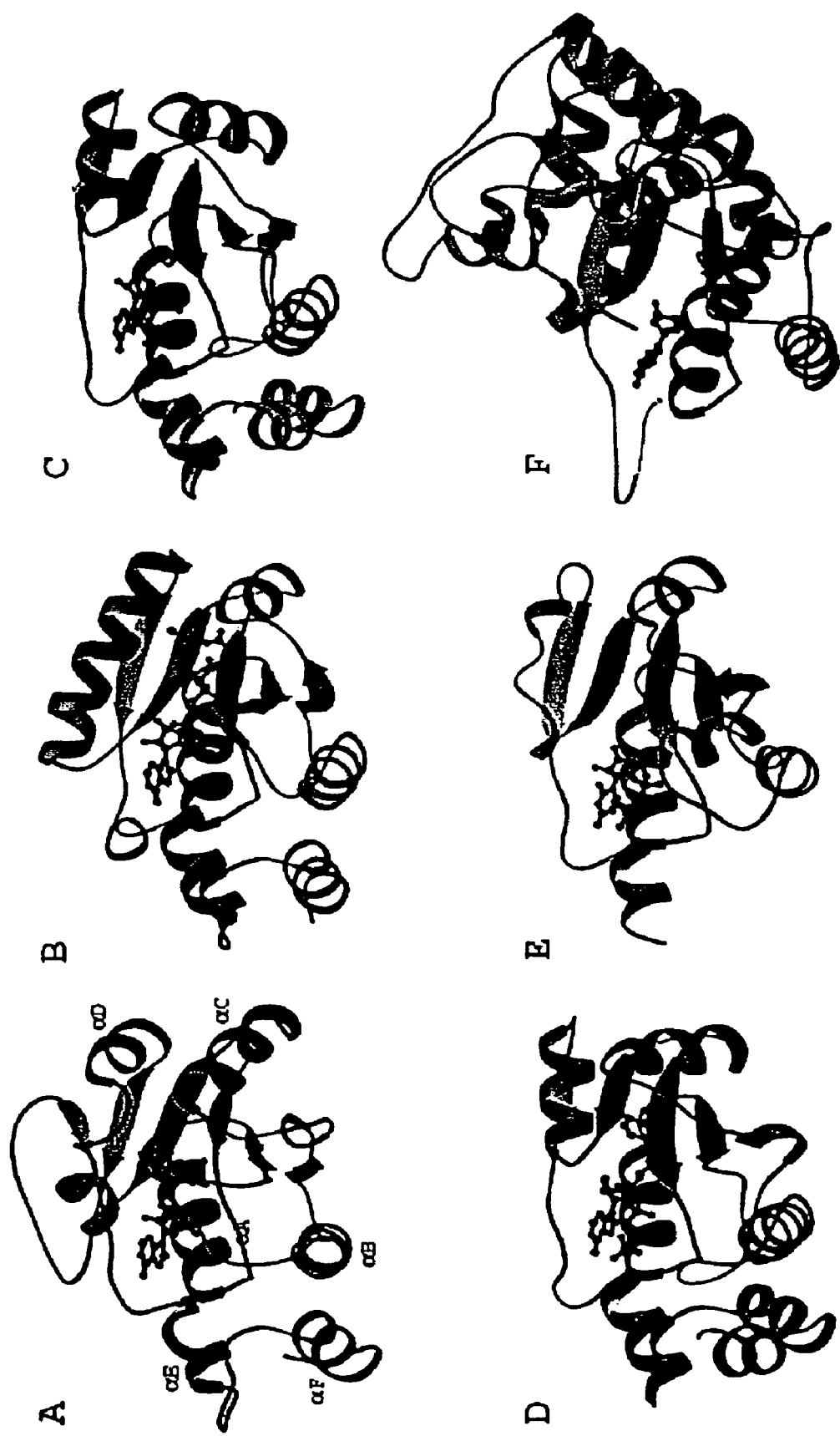
FIGS. 6A–6F show a comparison of enzymes of the nucleotidyl-transferase α/β phosphodiesterases. 6A) *B. subtilis* NaMN AT, 6B) *E. coli* phosphopantetheine adenylyltransferase, 6C) *M. jannaschii* NMN AT, 6D) *M. thermoautotrophicum* NMN AT, 6E (*B. subtilis* glycerol-3-phosphate cytidyltransferase, and 6F) *E. coli* glytaminyl tRNA synthetase. Strands of the central parallel β-sheet, the HXGH motif (SEQ ID NO:19) and the SxxxxR/K motif (SEQ ID NO:20) are also shown.

Subunit Structure. NaMN AT (SEQ ID NO:26) contains 6 β-strands and 6 α-helices that form a single large domain with a smaller C-terminal lobe domain (FIG. 5). The core of the large domain is a twisted, parallel β-sheet formed by 6 β-strands (of order: 321456); a classic nucleotide-binding Rossman fold (28). Two α-helices (α-helix C and α-helix D) above and two (α-helix A and α-helix B) below the central β-sheet form characteristic right-handed β/α/β super secondary structure elements. The C-terminal lobe domain is formed by the last 33 amino acids and comprises two α-helices (E and F). Significant structural similarities place NaMN AT in the superfamily of nucleotidyl-transferase α/β phosphodiesterases (29)(FIG. 6).

The prototypical member of the nucleotidyltransferase superfamily is the class I aminoacyl-tRNA synthetase, other members include phosphopantetheine adenylyltransferase (PPAT), (29), glycerol-3-phosphate cytidylyltransferase (GCT) (30), and nicotinamide mononucleotide adenylyltransferases from *M. jannaschii* (NMN AT mj) (16) and *M. thermoautotrophicum* (NMN ATmt) (17). The RMS deviation of NaMN AT to PPAT is 2.4 Å, to NMN ATmj it is 2.9 Å, and to GCT is 3.0 Å for all $C_α$ atoms (31). All these enzymes catalyze the same chemical reaction; the formation of a phosphodiester bond by the nucleophilic attack on the α-phosphate of ATP or CTP (for GCT) resulting in the loss of pyrophosphate and the adenylation (cytidylation) of a unique moiety (an amino acid in the case of aminoacyl-tRNA synthetases, a phosphopanteine for PPAT, glycerol-3-phosphate for GCT and a nicotinamide for the NMN ATs).

In comparison to other members of this superfamily, a striking difference of NaMN AT is the presence of a sixth strand. Since the central interactions of an important dimerization interface occur directly after β-strand 6 (see below), it is possible that the additional β-strand allows the loops following β-strand 4 and 5 the necessary flexibility to participate in substrate/product coordination. Other differences mimic the main differences between empty and NaAD bound structures of NaMN AT and center around a reordering of residues after β-strand 4 and before α-helix E. This suggests that the conformation of this region is dependent on occupation of the active site.

Figure 7:
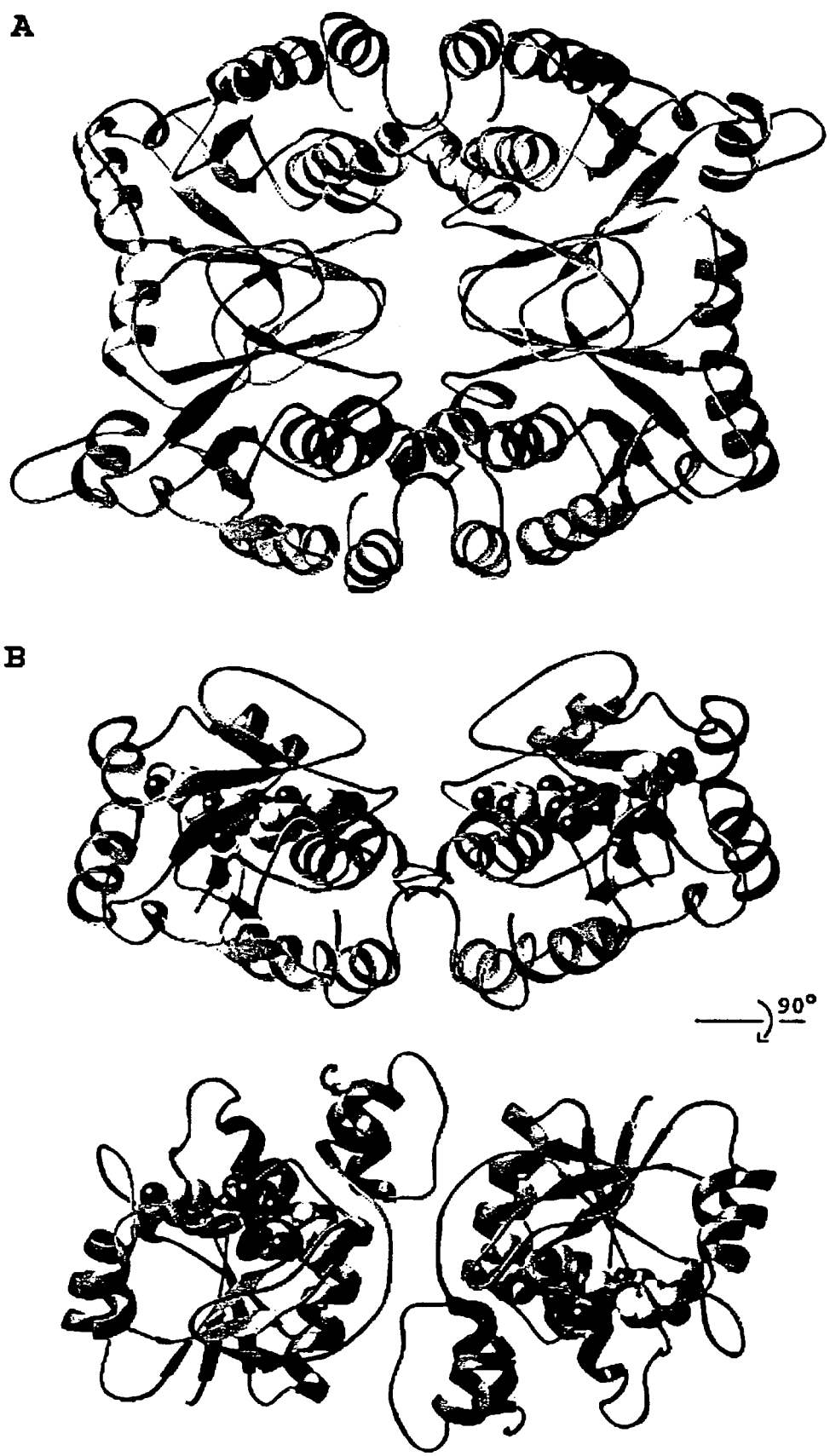
FIGS. 7A and 7B represent ribbon diagrams of NaMN AT. A) Dimer of dimers observed in the apo crystal structure, the two 'functional' dimers are shown. B) The 'functional' dimer (lower structure from FIG. 7A) is shown bound to NaAD.

A Functional Dimer. The NaAD-NaMN AT complex crystal structures reveals that NaAD binds in an extended conformation to a 20 Å long channel, almost perpendicular to the β-sheet. A large cleft at the C-terminal of β-strands 1 and 4 accommodates the di-phosphate moiety of NaAD. In the apo-NaMN AT crystal this channel is occupied, and its conformation distorted, by non-crystallographic interactions of one of the two dimers present in the asymmetric unit (FIG. 7A). This 'handshake' dimer buries a total surface area of 2034 Å$^2$ per monomer with interactions that involve residues from 102 to 146 of SEQ ID NO:26 and results in the burying of an extensive hydrophobic surface and the formation of three salt-bridges. Based on the extent of the surfaces area and shape complementarity ($S_c$=0.71 (32)), and in the absence of other structural data, this dimer would likely be interpreted as being physiological relevant. It is, however, the second ('functional') dimer, which buries only 848 Å$^2$ per monomer ($S_c$=0.64), that is seen to be conserved in the NaAD bound NaMN AT crystal (FIG. 7B). The independent crystal packing of the complex crystal structure of NaAD-NaMN AT environment presents three 'functional' dimers, one of which is partially disordered. The 'functional' dimer is formed by a pseudo-twofold symmetry operation centered around an anti-parallel β-sheet interaction from residues 151–153 of SEQ ID NO:26 (β-bridge at residue 152). In addition, the aromatic ring of Phe$^{152}$ stacks with Phe$^{152}$ from the other monomer and the side-chain of Glu$^{153}$ interacts with its dimer equivalent backbone amide group and Pro$^{150}$. An analysis of nadD sequences reveals the conservation of Pro$^{150}$ and a hydrophobic residue at position 152. The 'functional' dimer interface is further composed of interactions of residues from a loop at the C-terminus of β-strand 5, the loop between α-helices E and F (in the lobe domain) and α-helix A. Residues which are sequentially proximal to the dimer interface form part of the ATP binding pocket (see below) suggesting a possible role for dimer formation prior to productive substrate binding.

Temperature sensitive lethal mutations in nadD from *Salmonella typhimurium* had also suggested a multimeric enzyme (3). The quaternary organization of *B. subtilis* NaMN AT was further investigated with biophysical techniques. The results of size exclusion chromatography and analytical ultracentrifugation experiments both indicate a molecular weight consistent with a dimer (Table III), a conclusion which was not affected by the addition of NaAD. These results clearly distinguished *B. subtilis* NaMN AT from the eight other N(a)MN ATs for which the multimeric state of the enzyme has been investigated. Two of the enzymes, from *M. jannaschii* (16) and *M. thermoautotrophicum* (17) have been shown to crystallize as homohexamers, and a third from *Synechocystits* was identified as a homohexamer by size exclusion chromatography (33). The remaining five, *E. coli* nadR (14), and the NMN ATs from *S. solfataricus* (11), *S. cerevisiae* (7), (8), Bull testes (5), and human (9,10) appear to be trimers or tetramers by size exclusion chromatography. If the two crystal structures presented here reflect the physiological oligomeric state of NaMN AT, then the 'functional' dimer which is conserved in the independent crystal environments of the apo and NaAD bound form is proposed to be the dimer observed in solution. This is a surprising finding, given the large, intimate interface of the 'handshake' dimer. It clearly provides a caveat to the over interpretation of oligomeric states observed by crystallography and emphasizes the necessity of independent determination of quaternary structures.

NaAD binding. NaAD is seen bound in an extended conformation (the adenine $C_6$ to nicotinate $C_2$ distance is 16 Å (34)) to NaMN AT (SEQ ID NO:26). The NaAD is buried in a large enclosed cavity (FIG. 8A) with solvent channels to the di-phosphate and nicotinic acid moieties, such that release of product would require a rearrangement of the protein. The adenylate ribose and di-phosphate moiety of NaAD bind across a groove formed by the C-terminal splitting of β-strand 1 and β-strand 4. Comparing the apo and NaAD bound NaMN AT crystal structures reveals a conformational flexibility of regions that interact with the upper binding surface of the adenylate ribose and diphosphate moiety of NaAD (FIG. 8A). However, interpretation of these conformational changes must be tempered by the extensive non-crystallographic contacts made by the formation of the handshake dimer in the apo crystal structure.

Figure 8B:
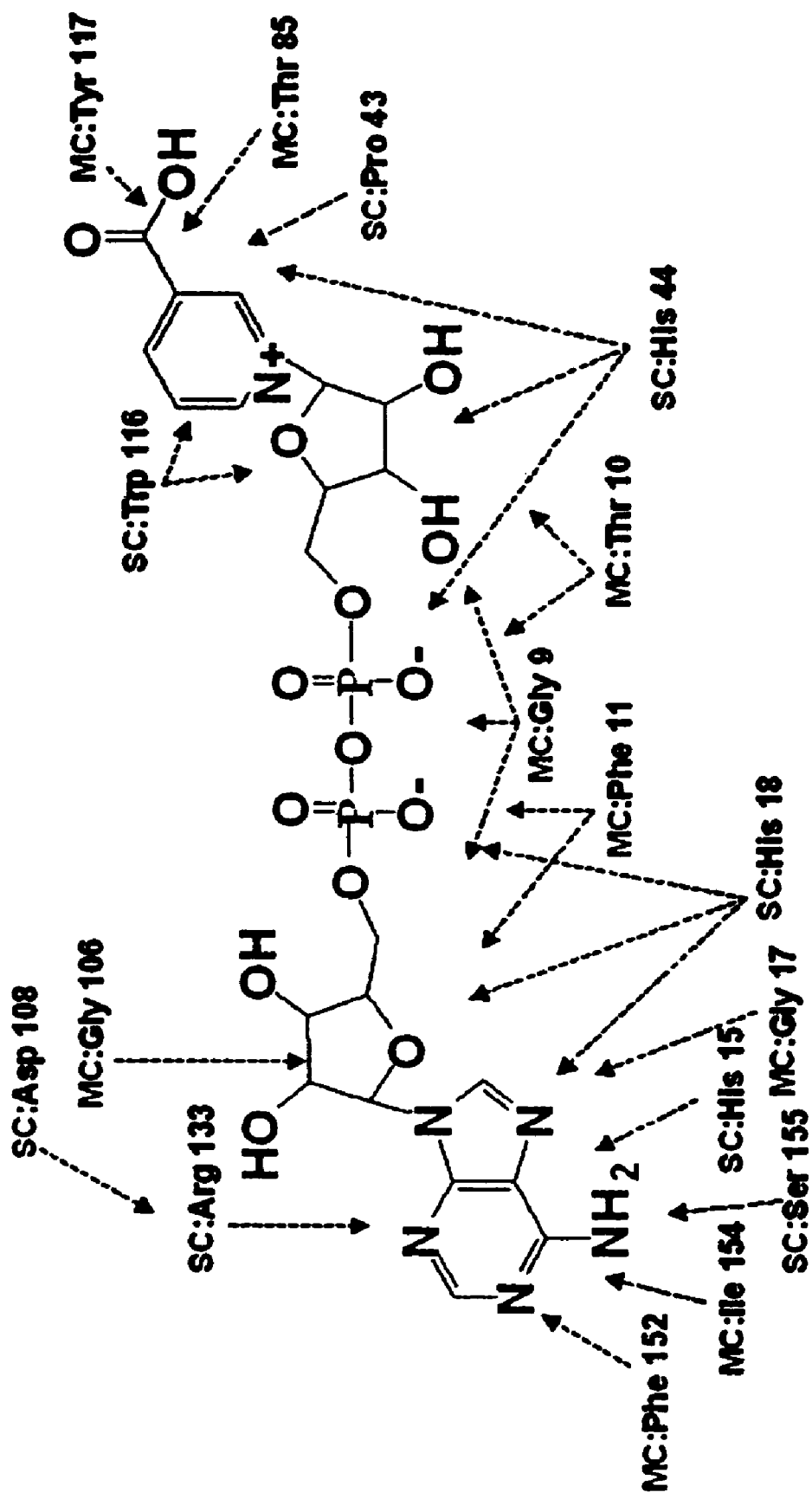
FIG. 8B is a schematic of selected active site interactions of NaAD with NaMN AT. MC: indicates main chain interaction, SC: indicates side chain interaction.

The classic alternating β strand-α helix motif of the Rossman fold unit is repeated in NaMN AT (SEQ ID NO:26) such that β-strands 4, 5 and 6 compose a modified second binding motif (FIG. 8A). It is this structural unit which is seen to have the greatest mobility upon binding of NaAD. At the C-terminal end of β-strand 4, $Gly^{106}$ and $Asp^{108}$ are highly conserved in nadD proteins. $Gly^{106}$ interacts with the adenyl ribose ring and the side-chain of $Asp^{108}$ is within hydrogen bonding distance with the guanadinium group of $Arg^{133}$, another conserved residue (FIG. 8B). The aliphatic portion of the side-chain of $Arg^{133}$ stacks on top of the adenine ring in a similar position of $Arg^{260}$ of glutaminyl-tRNA (35) and also $Arg^{113}$ of GCT. The positive charge of these conserved arginines are positioned to play a role in stabilizing the β-phosphate of the tri-phosphate substrates (36). However, $Met^{118}$ and $Leu^{124}$ in NMN ATmj and NMN ATmt, respectively, replace the hydrophobic stacking on the adenine ring but are positioned 3 amino acids before a conserved arginine ($Arg^{121}$ and $Arg^{127}$ respectively), which retains the proposed charge-charge interaction to the ATP.

More striking differences between NaMN AT and the NMN AT structures are present in the loop following β-strand 4. The NaAD bound structure of NaMN AT (SEQ ID NO:26) has a small α-helical turn prior to α-helix D. The α-helical turn starts after $Asp^{108}$ and finishes before $Trp^{116}$, both of which are conserved in nadD proteins (FIG. 2). The indole ring of $Trp^{116}$, stacks in a parallel fashion against the lower (i.e. class B hydride transfer) surface of the pyridinic ring. A similar interaction of the pyridinic ring is seen in complexes of NMN ATmt (17). Here the bound NAD and NMN π-stack with the indole ring of $Trp^{87}$, positioned on α-helix C. In NaMN AT, the dipole moment of α-helix C is positioned to complement the negative charge on the nicotinic acid. Because these critical tryptophan residues occur in different parts of the structure, the NaAD in NaMN AT has considerable conformational variation (centered mainly on the $β_N$ and $v_N$ torsion angles (IUPAC convention for NAD)) from the NMN and NAD bound to NMN ATmt. The most significant interactions that enable specificity for NaMN are the positioning of the nicotinic acid oxygens within hydrogen bonding distance to the backbone amides of $Tyr^{117}$ and $Thr^{85}$. The only other deamido-NAD bound protein structure available is that of NH3-dependent NAD+ synthetase from Bacillus subtilis (37), where the nicotinic group is disordered.

The loop from β-strand 2 to α-helix B becomes ordered by its interactions with NaAD. This loop contains a partially conserved $P^{42}P^{43}H^{44}K^{45}$ motif (SEQ ID NO:25) that interacts with both the nicotinic ring, through $Pro^{43}$ and $His^{44}$, and the modeled γ-phosphate of ATP through $His^{44}$ and $Lys^{45}$. Residues that form the floor of this pocket remain invariant in the apo and NaAD bound structures. These include $Gly^9$, $Thr^{10}$ and $Phe^{11}$, at the end of β-strand 1 that interact with the di-phosphate group. The main chain oxygens of $Phe^{152}$ and $Ile^{154}$, immobilized at the dimerization interface, are directed towards the adenine ring. The aromatic ring of $Phe^7$ fixes the orientation of imidazole group of $His^{18}$ in an edge-on interaction. The adenine then rests on a platform comprising $His^{15}$, $His^{18}$, and $Gly^{17}$ of the HXGH (SEQ ID NO:19) signature motif on one face and with $Arg^{133}$ layered on the other.

Conserved motifs in the nucleotidyl-transferase α/β phosphodiesterases. The signature sequence motif HXGH (SEQ ID NO:19), first seen in class I aminoacyl-tRNA synthetases has been identified as being conserved in all nucleotidyl-transferase α/β phosphodiesterases (17). In B. subtilis NaMN AT (SEQ ID NO:1) this conserved motif is $H^{15}N^{16}G^{17}H^{18}$ (SEQ ID NO:24). The apo crystal structure of NaMN AT (SEQ ID NO:26) shows this loop to be unchanged in its confirmation to that of NaAD bound. The two imidazole rings of $His^{15}$ and $His^{18}$ stack on each other in a parallel (π—π) fashion and the backbone amide of $His^{15}$ hydrogen bonds to the hydroxyl of $His^{18}$. The arrangement of this loop results in a similar conformation seen in all other adenylyl transferase structures. The side-chain of $His^{18}$ makes extensive interactions with the adenyl ribose and the side-chain of $His^{15}$ is positioned to interact with the modeled β-phosphate of ATP. Site-directed mutagenesis studies of NMN ATmt and other adenylyl transferases have implicated $His^{15}$ in the loss of enzymatic activity and in the stabilization of the transition state (17).

In addition to the HXGH motif (SEQ ID NO:19), class I aminoacyl-tRNA synthetases are characterized by a KMSKS (SEQ ID NO:27) region. The core functionality of this region can now be extended to the whole super-family by the observation that the serine stabilizes a loop at the N-terminal end of an α-helix proximal to the ATP's phosphate binding site for all known members. In NaMN AT, the tri-phosphate of ATP would be stabilized by the N-terminal dipole of α-helix E. It has been previously noted that this second conserved sequence motif seen in tRNA synthetases ($K^{230}$FGKT (SEQ ID NO:21) in tyrosyl- and $V^{267}$MSKR (SEQ ID NO:22) in glutaminyl-tRNA synthetase) has a structurally equivalent $R^{113}$TXGISTT motif (SEQ ID NO:23) in the GCT family (30). Both these sequences lie at the N-terminal end of an α-helix and make direct interactions to the β- and γ-phosphates of bound ATP. Comparison of the current complex structure with the two published NMN AT structures shows a similar set of structural interactions from conservatively mutated sequences and suggests an equivalent sequence motif (FIG. 6). The key residues of this motif for cytidylyl transferase and adneylyltransferases appear to be the initial serine and the terminal arginine/lysine and suggest a $S^n$xxxxR/$K^{n+5}$ (SEQ ID NO:20) minimal consensus sequence (Table IV). The main chain carbonyl preceding the seminal serine is within hydrogen-bonding distance to the exocyclic nitrogen of adenine and the Oγ of this serine (at position n) is within hydrogen-bonding distance to the n+3 main-chain nitrogen. This appears to cap the N-terminal of an α-helix whose dipole moment stabilizes the tri-phosphate binding pocket. Further, this α-helix is not part of the β/α/β dinucleotide binding fold, but occurs in a distinct domain. The positive charge at position n+5 of this motif appears to coordinate the γ-phosphate of ATP in NMN ATmj, consistent with modeling studies for Arg[160] of NaMN AT (SEQ ID NO:1). In GCT, however, Lys[123] is built pointing away from the catalytic active site, but the higher temperature factor for the side chain may indicate a high degree mobility. In pantothenate synthetase (PS), this motif occurs in a region that is believed to show dramatic structural rearrangement (37). The crystal strucuter of glutaminyl-tRNA synthetase complexed with tRNA and ATP shows that the positively charged residue is on the same face of the α-helix, but positioned only a half-turn from the seminal serine. Further studies should reveal whether the composition of this α-helix plays a role in catalysis.

se residues are structurally conserved among known structures in this superfamily, other contributors to the active site vary. As arginine from β-strand 1 in NMN ATmj and NMN ATmt (Arg[8] and Arg[11], respectively) contributes to stabilization of the tri-phosphate group of ATP. In contrast PPAT, GCT and NaMN AT (SEQ ID NO:1) lack this residue, but the conserved Lys[42] in PPAT (Lys[46] of GCT and Lys[45] of NaMN AT (SEQ ID NO:1) is thought to play a similar role.

In conclusion, the *B. subtilis* yqeJ gene encoding NaMN AT has been identified as an essential part of the NAD synthesis pathway exhibiting structural homology to other known adneylytransferases. The biochemical and structural characterization of substrate specificity (NaMN vs NMN) may provide an exciting new target for anti-microbial therapies. Further studies are needed to elucidate the function of NaMN AT dimerizatino and the role of the conserved sequence and structural motifs in catalysis.

TABLE I

Kinetic constants for NaMN AT

| Substrate | $K_M$ (mM) | $V_{max}$ (μmol/min/mg) | $V_{max}/K_M$ |
|---|---|---|---|
| NaMN[a] | 0.043 +/− 0.009 | 11.1 +/− 0.7 | 258 |
| NMN[a,b] | 2.3 +/− 0.2 | 0.054 +/− 0.003 | 0.02 |
| ATP[a,c] | 0.135 +/− 0.013 | 10.1 +/− 0.4 | |
| NAAD[d,e] | 0.0068 +/− 0.0012 | 2.8 +/− 0.2 | 412 |
| NAD[d,e] | 1.7 +/− 0.2 | 0.34 +/− 0.01 | 0.2 |
| PPi[d,f] | 4.2 +/− 0.6 | 11.5 +/− 1.3 | |

[a] kinetic constants for forward reaction.
[b] Data for NMN was fit to the equation for substrate inhibition: v = Vmax/(1 + $K_M$/S + S/Ki); Ki NMN = 17 +/− 3 mM.
[c] at saturating concentrations of NaMN.
[d] kinetic constants for back reaction.
[e] at subsaturating concentrations of PPi.
[f] at saturating concentrations of NaAD.

TABLE II

Statistics for Data Collection, Phase Determination, and Refinement

| Data Collection | peak | remote |
|---|---|---|
| empty yqeJ(SEQ ID NO:26) | | |
| wavelength (Å) | 0.9792 | 0.9567 |
| resolution range (Å) | 20–2.2 | 20–2.0 |
| $R_{merge}$[a] (%) | 10.3 (45.3) | 7.9 (47.0) |
| completeness (%) | 100.0 (100.0) | 99.9 (99.8) |
| total reflections | 286583 | 196259 |
| unique reflections | 38710 | 51680 |
| I/σ(I) | 22.7 (3.3) | 16.4 (2.4) |
| NAAD bound yqeJ (SEQ ID NO:26) | | |
| wavelength (Å) | 0.9791 | 0.9639 |
| resolution range (Å) | 15.0–3.2 | 15.0–3.4 |

TABLE II-continued

Statistics for Data Collection, Phase Determination, and Refinement

| $R_{merge}$[a] (%) | 14.7 (28.9) | 11.1 (27.6) |
|---|---|---|
| completeness (%) | 96.5 (84.0) | 96.8 (79.0) |
| total reflections | 80499 | 99889 |
| unique reflections | 24599 | 20850 |
| I/σ(I) | 16.0 (5.6) | 12.3 (4.8) |

| Model Refinement | NaMN AT | NAAD-NaMN AT |
|---|---|---|
| maximum resolution (Å) | 2.1 | 3.2 |
| $R_{work}$[b] (%) | 22.21 | 27.87 |
| $R_{free}$ (%) | 25.44 | 27.98 |
| RMS deviations from ideal geometry for: | | |
| bonds (Å) | 0.009 | 0.012 |
| angles (°) | 1.347 | 1.913 |
| non-hydrogen protein atom | 7848 | 9051 |
| water molecules | 139 | 0 |

[a] $R_{merge} = |I_h - \langle I_h \rangle|/I_h$, where $\langle I_h \rangle$ is the average intensity over symmetry equivalents. Numbers in parentheses reflect statistics for the last shell.
[b] $R_{work} = | |F_{obs}| - |F_{calc}| |/|F_{obs}|$
[c] $R_{free}$ is equivalent to $R_{work}$, but calculated for a randomly chosen 5% of reflections omitted from the refinement process.

TABLE III

Apparent Molecular Weights of NaMN AT

| Conditions | Method | Temp. | MW, app |
|---|---|---|---|
| 79 μM[a] | SEC[b] | 20° C. | 42758 |
| 44 μM | equilibrium[c] | 20° C. | 47622 ± 224 |
| 44 μM | velocity | 20° C. | 41200 |
| 22 μM | equilibrium | 20° C. | 48182 ± 467 |
| 22 μM | velocity | 20° C. | 43400 |
| 4.4 μM | equilibrium | 20° C. | 49138 ± 570 |
| 16 μM | equilibrium | 4° C. | 42502 ± 209 |
| 16 μM | velocity | 4° C. | 41500 |
| 133 μM + 1 mM NAAD | equilibrium | 4° C. | 36370 ± 221 |
| 16 μM + 1 mM NAAD | equilibrium | 4° C. | 39545 ± 169 |

[a] concentration based on monomer molecular weight
[b] size exclusion chromatography
[c] Results obtained from a fit of the data to a single ideal species model

TABLE IV

SXXXXR/K motif (SEQ ID NO:20) in cytidylyl transferase and adenylyl transferase families

| | | | | | | | SEQ ID NO: |
|---|---|---|---|---|---|---|---|
| B. subtilis NaMN AT | S[155] | S[156] | T[157] | M[158] | I[159] | R[160] | 13 |
| NMN ATmj | S[125] | G[126] | T[127] | E[128] | I[129] | R[130] | 14 |
| NMN ATmt | S[131] | G[132] | T[133] | E[134] | V[135] | R[136] | 15 |
| PPAT | S[128] | S[129] | S[130] | L[131] | V[132] | K[133] | 16 |
| GCT | S[118] | T[119] | T[120] | K[121] | I[122] | K[123] | 17 |
| glutaminyl-tRNA synth. | S[269] | K[270] | — | — | — | R[271] | |
| PS | S[187] | S[188] | — | — | — | R[189] | |
| consensus | S | X | X | X | X | R/K | (SEQ ID NO: 20) |

TABLE V

Residues from YQEJ (SEQ ID NO:26) which are within 8 Å of NaAD and modeled phosphates of ATP.

Ile6, Phe7, Gly8, Gly9, Thr10, Phe11, Asp12, Pro13, Pro14, His15, Asn16, Gly17, His18, Leu19, Leu20, Met21, Ala22, Val25, Phe36, Met37, Pro38, Asn39, Glu40, Ile41, Pro42, Pro43, His44, Lys45, Tyr50, Thr51, Arg56, Glu76, Pro82, Ser83, Tyr84, Thr85, Phe86, Asp87, Thr88, Phe103, Ile104, Ile105, Gly106, Ala107, Asp108, Met109, Ile110, Tyr112, Leu113, Pro114, Lys115, Trp116, Tyr117, Lys118, Leu119, Leu122, Phe128, Ile129, Gly130, Val131, Lys132, Arg133, Pro134, Phe136, Val149, Pro150, Glu151, Phe152, Glu153, Val154, Ser155, Ser156, Thr157, Met158, Ile159, Arg160, Tyr187

REFERENCES

1. Ziegler, M. (2000) *Eur J Biochem* 267(6), 1550–64.
2. Petit, M. A., and Ehrlich, S. D. (2000) *Nucleic Acids Res* 28(23), 4642–8.
3. Hughes, K. T., Ladika, D., Roth, J. R., and Olivera, B. M. (1983) *J Bacteriol* 155(1), 213–21.
4. Magni, G., Amici, A., Emanuelli, M., Raffaelli, N., and Ruggieri, S. (1999) *Adv Enzymol Relat Areas Mol Biol* 73, 135–82.
5. Balducci, E., Orsomando, G., Polzonetti, V., Vita, A., Emanuelli, M., Raffaelli, N., Ruggieri, S., Magni, G., and Natalini, P. (1995) *Biochem J* 310(Pt 2), 395–400.
6. Raffaelli, N., Emanuelli, M., Pisani, F. M., Amici, A., Lorenzi, T., Ruggieri, S., and Magni, G. (1999) *Mol Cell Biochem* 193(1–2), 99–102.
7. Natalini, P., Ruggieri, S., Raffaelli, N., and Magni, G. (1986) *Biochemistry* 25(12), 3725–9.
8. Emanuelli, M., Carnevali, F., Lorenzi, M., Raffaelli, N., Amici, A., Ruggieri, S., and Magni, G. (1999) *FEBS Lett* 455(1–2), 13–7.
9. Emanuelli, M., Natalini, P., Raffaelli, N., Ruggieri, S., Vita, A., and Magni, G. (1992) *Arch Biochem Biophys* 298(1), 29–34.
10. Emanuelli, M., Carnevali, F., Saccucci, F., Pierella, F., Amici, A., Raffaelli, N., and Magni, G. (2001) *J Biol Chem* 276(1), 406–12.
11. Raffaelli, N., Pisani, F. M., Lorenzi, T., Emanuelli, M., Amici, A., Ruggieri, S., and Magni, G. (1997) *J Bacteriol* 179(24), 7718–23.
12. Mehl, R. A., Kinsland, C., and Begley, T. P. (2000) *J Bacteriol* 182(15), 4372–4.
13. Begley, T. P., Kinsland, C., Mehl, R. A., Osterman, A., and Dorrestein, P. (2001) *Vitam Horm* 61, 103–19.
14. Raffaelli, N., Lorenzi, T., Mariani, P. L., Emanuelli, M., Amici, A., Ruggieri, S., and Magni, G. (1999) *J Bacteriol* 181(17), 5509–11.
15. Schweiger, M., Hennig, K., Lerner, F., Niere, M., Hirsch-Kauffmann, M., Specht, T., Weise, C., Oei, S. L., and Ziegler, M. (2001) *FEBS Lett* 492(1–2), 95–100.
16. D'Angelo, I., Raffaelli, N., Dabusti, V., Lorenzi, T., Magni, G., and Rizzi, M. (2000) *Structure Fold Des* 8(9), 993–1004.
17. Saridakis, V., Christendat, D., Kimber, M. S., Dharamsi, A., Edwards, A. M., and Pai, E. F. (2001) *J Biol Chem* 276(10), 7225–32.
18. Balducci, E., Emanuelli, M., Raffaelli, N., Ruggieri, S., Amici, A., Magni, G., Orsomando, G., Polzonetti, V., and Natalini, P. (1995) *Anal Biochem* 228(1), 64–8.
19. Otwinowski, Z., and Minor, W. (1997) *Methods Enzymol.* 276, 307–326
20. Terwilliger, T. C., and Berendzen, J. (1999) *Acta Crystallogr D Biol Crystallogr* 55(Pt 4), 849–61.
21. Brunger, A. T., Adams, P. D., Clore, G. M., DeLano, W. L., Gros, P., Grosse-Kunstleve, R. W., Jiang, J. S., Kuszewski, J., Nilges, M., and Pannu, N. S. (1998) *Act Crystallographica* D54, 905–921.
22. De La Fortelle, E., and Bricogne, G. (1997) *Methods Enzymol.* 276, 4772–494.
23. Perrakis, A., Morris, R. J., and Lamzin, V. S. (1999) *Nature Struct. Biol.* 6, 458–463.
24. Weeks, C. M., and Miller, R. (1999) *Journal of Applied Crystallography* 32, 120–124.
25. CCP4 (1994) *Acta Crystallographica. Section D.* 50, 760–763.
26. Philo, J. S. (1994) *Modern Analytical Ultracentrifugation* (Schuster, T. M. a. L., T. M., Ed.), Birkhauser, Boston, Mass.
27. Altschol, S. F., Gish, W., Miller, W., Myers, E. W., and Lipman, D. J. (1990) *J. Mol. Biol.* 215, 403–410.
28. Rossmann, M. G., Liljas, A., Branden, C. I., and Banaszak, L. J. (1975) in *The Enzymes*, pp. 61–102, Academic Press, New York.
29. Izard, T., and Geerlof, A. (1999) *Embo J* 18(8), 2021–30.
30. Weber, C. H., Park, Y. S., Sanker, S., Kent, C., and Ludwig, M. L. (1999) *Structure* 7, 1113–1124.
31. Holm, L., and Sander, C. (1995) *Trends Biochem. Sci.* 20, 478–480.
32. Lawrence, M. C., and Colman, P. M. (1993) *J. Mol. Biol.* 234, 946–950.
33. Raffaelli, et al., (1999) *FEBS Lett* 444(2–3), 222–6.
34. Bell, C. E., Yeates, T. O., and Eisenberg, D. (1997) *Protein Sci.* 6(10), 2084–2096.
35. Rould, M. A., Perona, J. J., and Steitz, T. A. (1991) *Nature* 352(6332), 213–8.
36. Brick, P., et al., (1988) *J. Mol. Biol.* 208, 83–98.
37. Rizzi, M., et al., (1996) *Embo J* 15(19), 5125–34.
38. von Delft, F., et al.,(2001) *Structure (Camb)* 9(5), 439–50.

All publications mentioned herein above, whether to issued patents, pending applications, published articles, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for identifying an agent that interacts with *Bacillus subtilis* nicotinic acid mononucleotide adenylyl transferase yqeJ, comprising:
   obtaining a crystallized yqeJ of SEQ ID NO:26 comprising four molecules of yqeJ of SEQ ID NO:26, wherein the crystallized yqeJ belongs to space group $P2_1$ with unit cell parameters a=43.98 Å, b=126.10 Å, c=70.58 Å, and β=92.73 Å;
   determining the three dimensional structure of yqeJ;
   employing said three-dimensional structure to design or select an agent that interacts with yqeJ; and
   obtaining the agent.

2. The method of claim 1, wherein the three dimensional structure comprises the relative structural coordinates of yqeJ of SEQ ID NO:26 as represented in FIG. 9, ± a root mean square deviation from the backbone atoms of yqeJ of SEQ ID NO:26 of not more than 1.5 Å.

3. The method of claim 2, wherein the ± a root mean square deviation from the backbone atoms of yqeJ of SEQ ID NO:26 is not more than 1.0 Å.

4. The method of claim 2, wherein the ± a root mean square deviation from the backbone atoms of yqeJ of SEQ ID NO:26 is not more than 0.5 Å.

5. The method of claim 1, further comprising: contacting the identified agent with yqeJ in order to determine the effect the agent has on yqeJ activity.

6. A method for identifying an agent that interacts with *Bacillus subtilis* nicotinic acid mononucleotide adenylyl transferase yqeJ, comprising:
   obtaining a crystallized complex comprising six molecules of yqeJ of SEQ ID NO:26 and six molecules of nicotinic acid adenine dinucleotide (NaAD), wherein the crystallized complex belongs to space group $P2_12_12_1$ with unit cell parameters a=78.39 Å, b=108.90 Å, c=178.09 Å;
   determining the three dimensional structure of the crystallized complex;
   employing said three-dimensional structure to design or select an agent that interacts with yqeJ; and
   obtaining the agent.

7. The method of claim 6, wherein the three dimensional structure comprises the relative structural coordinates of yqeJ of SEQ ID NO:26 and NaAD as represented in FIG. 10, ± a root mean square deviation from the backbone atoms of yqeJ of SEQ ID NO:26 of not more than 1.5 Å.

8. The method of claim 7, wherein the ± a root mean square deviation from the backbone atoms of yqeJ of SEQ ID NO:26 is not more than 1.0 Å.

9. The method of claim 7, wherein the ± a root mean square deviation from the backbone atoms of yqeJ of SEQ ID NO:26 is not more than 0.5 Å.

10. The method of claim 6, further comprising: contacting the identified agent with yqeJ in order to determine the effect the agent has on yqeJ activity.

11. A method for identifying a potential inhibitor of *Bacillus subtilis* nicotinic acid mononucleotide adenylyl transferase yqeJ, comprising:
    obtaining (i) a crystallized yqeJ of SEQ ID NO:26 comprising four molecules of yqeJ of SEQ ID NO:26, wherein the crystallized yqeJ belongs to space group $P2_1$ with unit cell parameters a=43.98 Å, b=126.10 Å, c=70.58 Å, and β=92.73 Å, or (ii) a crystallized complex comprising six molecules of yqeJ of SEQ ID NO:26 and six molecules of NaAD, wherein the crystallized complex belongs to space group $P2_12_12_1$ with unit cell parameters a=78.39 Å, b=108.90 Å, c=178.09 Å;
    determining the three dimensional structure of (i) the crystallized yqeJ or (ii) the crystallized complex of yqeJ and NaAD;
    selecting or designing a candidate inhibitor by performing computer fitting analysis of the candidate inhibitor with the three dimensional structure; and
    obtaining the candidate inhibitor.

12. The method of claim 11, wherein the three dimensional structure of (i) the crystallized yqeJ or (ii) the crystallized complex of yqeJ and NaAD comprises the relative structural coordinates of amino acid residues Ile6, Phe7, Gly8, Gly9, Thr10, Phe11, Asp12, Pro13, Pro14, His15, Asn16, Gly17, His18, Leu19, Leu20, Met21, Ala22, Val25, Phe36, Met37, Pro38, Asn39, Glu40, Ile41, Pro42, Pro43, His44, Lys45, Tyr50, Thr51, Arg56, Glu76, Pro82, Ser83, Tyr84, Thr85, Phe86, Asp87, Thr88, Phe103, Ile104, Ile105, Gly106, Ala107, Asp108, Met109, Ile110, Tyr112, Leu113, Pro114, Lys115, Trp116, Tyr117, Lys118, Leu119, Leu122, Phe128, Ile129, Gly130, Val131, Lys132, Arg133, Pro134, Phe136, Val149, Pro150, Glu151, Phe152, Glu153, Val154, Ser155, Ser156, Thr157, Met158, Ile159, Arg160 and Tyr187 of yqeJ of SEQ ID NO:26 according to FIG. 9 or 10, ± a root mean square deviation from the backbone atoms of yqeJ of SEQ ID NO:26 of not more than 1.5 Å.

13. The method of claim 12, wherein the ± a root mean square deviation from the backbone atoms of yqeJ of SEQ ID NO:26 is not more than 1.0 Å.

14. The method of claim 12, wherein the ± a root mean square deviation from the backbone atoms of yqeJ of SEQ ID NO:26 is not more than 0.5 Å.

15. The method of claim 11, which further comprises:
introducing the candidate inhibitor in a reaction with (i) yqeJ, (ii) nicotinic acid mononucleotide (NAMN) or nicotinamide mononucleotide (NMN), and (iii) ATP; and determining the effect the candidate inhibitor has on the reaction.

16. The method of claim 11, which further comprises:
introducing the candidate inhibitor in a reaction with (i) yqeJ, (ii) nicotinic acid adenine dinucleotide (NAAD) or nicotinomide adenine dinucleotide (NAD), and (iii) pyrophosphate; and
determining the effect the candidate inhibitor has on the reaction.

* * * * *

SEQUENCE LISTING

<160> NUMBER OF SEQ ID NOS: 27

<210> SEQ ID NO 1

```
<211> LENGTH: 189
<212> TYPE: PRT
<213> ORGANISM: Bacillus subtilis

<400> SEQUENCE: 1

Met Lys Lys Ile Gly Ile Phe Gly Gly Thr Phe Asp Pro His Asn
 1               5                  10                  15

Gly His Leu Leu Met Ala Asn Glu Val Leu Tyr Gln Ala Gly Leu Asp
                20                  25                  30

Glu Ile Trp Phe Met Pro Asn Gln Ile Pro Pro His Lys Gln Asn Glu
            35                  40                  45

Asp Tyr Thr Asp Ser Phe His Arg Val Glu Met Leu Lys Leu Ala Ile
 50                  55                  60

Gln Ser Asn Pro Ser Phe Lys Leu Glu Leu Val Glu Met Glu Arg Glu
65                  70                  75                  80

Gly Pro Ser Tyr Thr Phe Asp Thr Val Ser Leu Leu Lys Gln Arg Tyr
                85                  90                  95

Pro Asn Asp Gln Leu Phe Phe Ile Ile Gly Ala Asp Met Ile Glu Tyr
            100                 105                 110

Leu Pro Lys Trp Tyr Lys Leu Asp Glu Leu Leu Asn Leu Ile Gln Phe
        115                 120                 125

Ile Gly Val Lys Arg Pro Gly Phe His Val Glu Thr Pro Tyr Pro Leu
130                 135                 140

Leu Phe Ala Asp Val Pro Glu Phe Glu Val Ser Ser Thr Met Ile Arg
145                 150                 155                 160

Glu Arg Phe Lys Ser Lys Lys Pro Thr Asp Tyr Leu Ile Pro Asp Lys
                165                 170                 175

Val Lys Tyr Val Glu Glu Asn Gly Leu Tyr Glu Ser
            180                 185

<210> SEQ ID NO 2
<211> LENGTH: 213
<212> TYPE: PRT
<213> ORGANISM: Escherichia coli

<400> SEQUENCE: 2

Met Lys Ser Leu Gln Ala Leu Phe Gly Gly Thr Phe Asp Pro Val His
 1               5                  10                  15

Tyr Gly His Leu Lys Pro Val Glu Thr Leu Ala Asn Leu Ile Gly Leu
                20                  25                  30

Thr Arg Val Thr Ile Ile Pro Asn Asn Val Pro Pro His Arg Pro Gln
            35                  40                  45

Pro Glu Ala Asn Ser Val Gln Arg Lys His Met Leu Glu Leu Ala Ile
 50                  55                  60

Ala Asp Lys Pro Leu Phe Thr Leu Asp Glu Arg Glu Leu Lys Arg Asn
65                  70                  75                  80

Ala Pro Ser Tyr Thr Ala Gln Thr Leu Lys Glu Trp Arg Gln Glu Gln
                85                  90                  95

Gly Pro Asp Val Pro Leu Ala Phe Ile Ile Gly Gln Asp Ser Leu Leu
            100                 105                 110

Thr Phe Pro Thr Trp Tyr Glu Tyr Glu Thr Ile Leu Asp Asn Ala His
        115                 120                 125

Leu Ile Val Cys Arg Arg Pro Gly Tyr Pro Leu Glu Met Ala Gln Pro
130                 135                 140

Gln Tyr Gln Gln Trp Leu Glu Asp His Leu Thr His Asn Pro Glu Asp
145                 150                 155                 160
```

-continued

Leu His Leu Gln Pro Ala Gly Lys Ile Tyr Leu Ala Glu Thr Pro Trp
                165                 170                 175

Phe Asn Ile Ser Ala Thr Ile Ile Arg Glu Arg Leu Gln Asn Gly Glu
            180                 185                 190

Ser Cys Glu Asp Leu Leu Pro Glu Pro Val Leu Thr Tyr Ile Asn Gln
        195                 200                 205

Gln Gly Leu Tyr Arg
    210

<210> SEQ ID NO 3
<211> LENGTH: 160
<212> TYPE: PRT
<213> ORGANISM: Bacillus halodurans

<400> SEQUENCE: 3

Met Lys Arg Ile Gly Leu Leu Gly Gly Thr Phe Asp Pro Pro His Ile
1               5                   10                  15

Gly His Leu Leu Leu Ala Gln Glu Ala Ile His Cys Ala Asp Leu Asp
            20                  25                  30

Glu Val Trp Phe Val Pro Val Gly Ile Pro Pro His Lys Glu Arg Glu
        35                  40                  45

Glu Ile Ala Ser Asn Asp Asp Arg Leu Ala Met Ile Lys Arg Ala Ile
50                  55                  60

Lys Gly Lys Glu Thr Leu Phe Asn Ile Cys Thr Ile Glu Leu Glu Arg
65                  70                  75                  80

Glu Gly Lys Ser Tyr Thr Ile Asp Thr Val Arg Thr Leu Thr Lys Lys
                85                  90                  95

His Pro Asp Val Arg Phe Phe Ile Ile Gly Gly Asp Met Val Lys
            100                 105                 110

Ser Leu Pro Thr Trp Lys Gly Ile Asp Glu Leu Leu Ala Thr Val Thr
        115                 120                 125

Phe Ile Gly Phe Lys Arg Pro Gly Val Leu Leu Asp Ser Pro Tyr Gln
    130                 135                 140

Asp Gln Leu Met Leu Val Glu Gly Pro Glu Val Asn Val Ser Ser Thr
145                 150                 155                 160

<210> SEQ ID NO 4
<211> LENGTH: 195
<212> TYPE: PRT
<213> ORGANISM: Lactococcus lactis

<400> SEQUENCE: 4

Met Asp Lys Gly Asn Arg Lys Lys Val Gly Leu Leu Gly Gly Asn Phe
1               5                   10                  15

Asn Pro Ile His His Ala His Leu Met Met Ala Asp Gln Val Ala Gln
            20                  25                  30

Gln Met Asn Leu Asp Lys Val Leu Leu Met Pro Glu Asn Ile Pro Pro
        35                  40                  45

His Val Asp Glu Lys Glu Thr Ile Ser Ala Lys His Arg Val Lys Met
50                  55                  60

Leu Glu Leu Ala Ile Lys Glu Asn Pro Arg Leu Gly Leu Glu Leu Ile
65                  70                  75                  80

Glu Ile Glu Arg Gly Gly Lys Ser Tyr Ser Tyr Asp Thr Leu Lys Leu
                85                  90                  95

Leu Thr Glu Ala Asn Pro Asp Thr Asp Tyr Tyr Phe Ile Ile Gly Ser
            100                 105                 110

```
Asp Met Val Glu Tyr Leu Pro Lys Trp Tyr Lys Ile Asp Glu Leu Leu
        115                 120                 125

Lys Leu Val Thr Phe Ile Ala Leu Arg Arg Lys Asp Thr Ile Ser Lys
130                 135                 140

Ser Pro Tyr Pro Val Thr Trp Leu Asp Ala Pro Leu Leu Pro Ile Ser
145                 150                 155                 160

Ser Thr Met Leu Arg Glu Met Phe Ala Lys Asn Ile Glu Pro Thr Tyr
                165                 170                 175

Phe Leu Pro Gln Asn Val Ile Asp Tyr Ile Lys Thr Glu Lys Leu Tyr
            180                 185                 190

Lys Lys Arg
        195

<210> SEQ ID NO 5
<211> LENGTH: 234
<212> TYPE: PRT
<213> ORGANISM: Mycobacterium leprae

<400> SEQUENCE: 5

Met Gly Gly Thr Phe Asp Pro Ile His Tyr Gly His Leu Val Ala Ala
1               5                   10                  15

Ser Glu Val Ala His Met Phe Glu Leu Asp Glu Val Met Phe Val Pro
            20                  25                  30

Ser Gly Gln Pro Trp Gln Lys Gly Arg His Val Ser Ala Ala Glu Asp
        35                  40                  45

Arg Tyr Leu Met Thr Val Ile Ala Thr Ala Ser Asn Pro Arg Phe Ser
    50                  55                  60

Val Ser Arg Val Asp Ile Asp Arg Thr Gly Pro Thr Tyr Thr Arg Asp
65                  70                  75                  80

Thr Val His Asp Leu His Ala Leu Asn Pro Asp Ser Glu Leu Tyr Phe
                85                  90                  95

Ile Thr Gly Ala Asp Ala Leu Ala Ser Ile Leu Ser Trp Gln Gly Trp
            100                 105                 110

Asp Glu Leu Phe Asp Leu Ala Arg Phe Val Gly Val Ser Arg Pro Gly
        115                 120                 125

Tyr Glu Leu Gly Gln Glu His Ile Thr Gly Val Met Gly Glu Leu Pro
    130                 135                 140

Ala Asp Ala Leu Thr Leu Val Glu Ile Pro Ala Leu Ala Ile Ser Ser
145                 150                 155                 160

Thr Asp Cys Arg Gln Arg Val Glu Gln Arg Gln Pro Leu Trp Tyr Leu
                165                 170                 175

Met Pro Asp Gly Val Val Gln Tyr Val Phe Lys Arg Arg Leu Tyr Arg
            180                 185                 190

Gly Pro His Gly Val Ala Gly Thr Gly Arg Leu Thr Thr Pro Ser Leu
        195                 200                 205

Val Val Gly Asn Asn Thr Met Ile Arg Glu Arg Met Thr Glu Gly Lys
    210                 215                 220

Pro Ile Ser Tyr Leu Leu Pro Leu Asp Val
225                 230

<210> SEQ ID NO 6
<211> LENGTH: 238
<212> TYPE: PRT
<213> ORGANISM: Streptomyces coelicolor

<400> SEQUENCE: 6
```

```
Met Gly Glu His Asp Thr Pro Thr Gly Pro Ala His Ala Pro Ala Arg
 1               5                  10                  15

Gly Thr Gln Asn Ala Val Pro Ala Arg Ala Thr Gly Pro Val Gln Gly
                20                  25                  30

Pro Val Asn Gly Pro Ala Asp Gly Pro Ser Ala Gly Lys Arg Arg Leu
            35                  40                  45

Gly Val Met Gly Gly Thr Phe Asp Pro Ile His His Gly His Leu Val
        50                  55                  60

Ala Ala Ser Glu Val Ala Ala Gln Phe Gln Leu Asp Glu Val Val Phe
65                  70                  75                  80

Val Pro Thr Gly Gln Pro Trp Gln Lys Ser His Arg Ala Val Ser Ala
                85                  90                  95

Ala Glu Asp Arg Tyr Leu Met Thr Val Ala Thr Val Glu Asn Pro
                100                 105                 110

Gln Phe Ser Val Ser Arg Ile Asp Ile Asp Arg Gly Gly Pro Thr Tyr
            115                 120                 125

Thr Val Asp Thr Leu Arg Asp Leu Arg Ala Leu Asn Pro Asp Ala Asp
    130                 135                 140

Leu Phe Phe Ile Thr Gly Ala Asp Ala Leu Ala Gln Ile Leu Thr Trp
145                 150                 155                 160

Arg Asp Ser Glu Glu Leu Phe Ser Leu Ala His Phe Ile Gly Val Thr
                165                 170                 175

Arg Pro Gly His Thr Leu Thr Asp Ala Gly Leu Pro Lys Gly Gly Val
            180                 185                 190

Ser Leu Val Glu Val Pro Ala Leu Ala Ile Ser Ser Thr Asp Cys Arg
        195                 200                 205

Ala Arg Val Ala Lys Gly Asp Pro Val Trp Tyr Leu Val Pro Asp Gly
    210                 215                 220

Val Val Arg Tyr Ile Asp Lys Arg His Leu Tyr Arg Gly Glu
225                 230                 235

<210> SEQ ID NO 7
<211> LENGTH: 144
<212> TYPE: PRT
<213> ORGANISM: Mycobacterium tuberculosis

<400> SEQUENCE: 7

Met Gly Gly Thr Phe Asp Pro Ile His Tyr Gly His Leu Val Ala Ala
 1               5                  10                  15

Ser Glu Val Ala Asp Leu Phe Asp Leu Asp Glu Val Val Phe Val Pro
                20                  25                  30

Ser Gly Gln Pro Trp Gln Lys Gly Arg Gln Val Ser Ala Ala Glu His
            35                  40                  45

Arg Tyr Leu Met Thr Val Ile Ala Thr Ala Ser Asn Pro Arg Phe Ser
50                  55                  60

Val Ser Arg Val Asp Ile Asp Arg Gly Gly Pro Thr Tyr Thr Lys Asp
65                  70                  75                  80

Thr Leu Ala Asp Leu His Ala Leu His Pro Asp Ser Glu Leu Tyr Phe
                85                  90                  95

Thr Thr Gly Ala Asp Ala Leu Ala Ser Ile Met Ser Trp Gln Gly Trp
            100                 105                 110

Glu Glu Leu Phe Glu Leu Ala Arg Phe Val Gly Val Ser Arg Pro Gly
        115                 120                 125

Tyr Glu Leu Arg Asn Glu His Ile Thr Ser Leu Leu Gly Gln Leu Ala
```

130                 135                 140

<210> SEQ ID NO 8
<211> LENGTH: 144
<212> TYPE: PRT
<213> ORGANISM: Treponema pallidum

<400> SEQUENCE: 8

Met Lys Leu Ala Leu Phe Gly Gly Ser Tyr Asp Pro Val His Leu Gly
 1               5                  10                  15

His Leu Leu Ala Asp Ala Val His Arg His Ala Gly Tyr Asp Arg
            20                  25                  30

Val Leu Phe Val Pro Thr Phe Val Ser Pro Phe Lys Glu Lys Glu Gly
            35                  40                  45

Ser Ala Ser Ala His Asp Arg Val Arg Met Leu His Leu Ala Ile Gly
        50                  55                  60

Thr Thr Pro Tyr Phe Ser Val Glu Glu Cys Glu Ile Arg Arg Gly Gly
65                  70                  75                  80

Ile Ser Tyr Thr Ala Glu Thr Val Gln His Val Arg Glu Lys Tyr Gly
                85                  90                  95

Ala Gln Leu Glu Gly Lys Leu Ala Leu Val Leu Gly Glu Asp Ala Ala
            100                 105                 110

Arg Ser Val Pro His Trp His Ala Phe Asp Ser Trp Ser Thr His Val
        115                 120                 125

Asp Phe Val Val Gly Ala Arg Pro Val Thr Ser Gly Asp Gly Gly Asn
    130                 135                 140

<210> SEQ ID NO 9
<211> LENGTH: 144
<212> TYPE: PRT
<213> ORGANISM: Borrellia burgdorferi

<400> SEQUENCE: 9

Met Arg Ile Ala Ile Leu Gly Gly Thr Tyr Asn Pro Val His Ile Gly
 1               5                  10                  15

His Ile Phe Leu Ala Lys Glu Ile Glu Tyr Leu Leu Asn Ile Asp Arg
            20                  25                  30

Val Ile Phe Ile Pro Thr Cys Asn Pro Ala His Lys Leu Ile Asp Glu
            35                  40                  45

Asn Val Ser Val Ser Asn Arg Ile Asp Met Leu Lys Leu Ala Leu Glu
        50                  55                  60

Asn Glu Asp Lys Met Phe Ile Asp Asp Cys Asp Ile Ile Asn Gly Gly
65                  70                  75                  80

Ile Thr Tyr Thr Val Asp Thr Ile Ser Cys Val Lys Lys Lys Tyr Lys
                85                  90                  95

Asn Asp Lys Leu Phe Leu Ile Ile Gly Asp Asp Leu Phe Gln Asn Phe
            100                 105                 110

Asp Ser Trp Lys Asp Pro Gln Ser Ile Val Ser Ser Val Glu Leu Val
        115                 120                 125

Val Ala His Arg Ile Tyr Lys Glu Arg Leu Lys Ser Ser Phe Lys His
    130                 135                 140

<210> SEQ ID NO 10
<211> LENGTH: 144
<212> TYPE: PRT
<213> ORGANISM: Neisseria meningitidis

<400> SEQUENCE: 10

```
Met Lys Lys Ile Gly Leu Phe Gly Gly Thr Phe Asp Pro Ile His Asn
  1               5                  10                  15

Gly His Leu His Ile Ala Arg Ala Phe Ala Asp Glu Ile Gly Leu Asp
             20                  25                  30

Ala Val Phe Leu Pro Thr Gly Pro Tyr His Lys Asp Ala Ala
         35                  40                  45

Ser Ala Ser Ala Ala Asp Arg Leu Ala Met Val Glu Leu Ala Thr Ala
 50                      55                  60

Glu Asp Ala Arg Phe Ala Val Ser Asp Cys Asp Ile Val Arg Glu Gly
 65                  70                  75                  80

Ala Thr Tyr Thr Phe Asp Thr Val Gln Ile Phe Arg Gln Gln Phe Pro
                 85                  90                  95

Ser Ala Gln Leu Trp Trp Leu Met Gly Ser Asp Ser Leu Met Lys Leu
            100                 105                 110

His Thr Trp Lys Lys Trp Gln Met Leu Val Arg Glu Thr Asn Ile Ala
            115                 120                 125

Val Ala Met Arg Gln Gly Asp Ser Leu His Gln Thr Pro Arg Glu Leu
    130                 135                 140

<210> SEQ ID NO 11
<211> LENGTH: 214
<212> TYPE: PRT
<213> ORGANISM: Pseudomonas aeruginosa

<400> SEQUENCE: 11

Met Gly Lys Arg Ile Gly Leu Phe Gly Gly Thr Phe Asp Pro Val His
  1               5                  10                  15

Ile Gly His Met Arg Ser Ala Val Glu Met Ala Glu Gln Phe Ala Leu
             20                  25                  30

Asp Glu Leu Arg Leu Leu Pro Asn Ala Arg Pro Pro His Arg Glu Thr
             35                  40                  45

Pro Gln Val Ser Ala Ala Gln Arg Leu Ala Met Val Glu Arg Ala Val
 50                      55                  60

Ala Gly Val Glu Arg Leu Thr Val Asp Pro Arg Glu Leu Gln Arg Asp
 65                  70                  75                  80

Lys Pro Ser Tyr Thr Ile Asp Thr Leu Glu Ser Val Arg Ala Glu Leu
                 85                  90                  95

Ala Ala Asp Asp Gln Leu Phe Met Leu Ile Gly Trp Asp Ala Phe Cys
            100                 105                 110

Gly Leu Pro Thr Trp His Arg Trp Glu Ala Leu Leu Asp His Cys His
            115                 120                 125

Ile Val Val Leu Gln Arg Pro Asp Ala Asp Ser Glu Pro Pro Glu Ser
    130                 135                 140

Leu Arg Asp Leu Leu Ala Ala Arg Ser Val Ala Asp Pro Gln Ala Leu
145                 150                 155                 160

Lys Gly Pro Gly Gly Gln Ile Thr Phe Val Trp Gln Thr Pro Leu Ala
                165                 170                 175

Val Ser Ala Thr Gln Ile Arg Ala Leu Leu Gly Ala Gly Arg Ser Val
            180                 185                 190

Arg Phe Leu Val Pro Asp Ala Val Leu Asn Tyr Ile Glu Ala His His
        195                 200                 205

Leu Tyr Arg Ala Pro His
    210
```

```
<210> SEQ ID NO 12
<211> LENGTH: 26
<212> TYPE: PRT
<213> ORGANISM: Artificial Sequence
<220> FEATURE:
<223> OTHER INFORMATION: Synthetically generated peptide

<400> SEQUENCE: 12

Met Gly His His His His His His His His His Ser Ser Gly His
 1               5                  10                  15

Ile Glu Gly Arg His Met Pro Gly Gly Ser
            20                  25

<210> SEQ ID NO 13
<211> LENGTH: 6
<212> TYPE: PRT
<213> ORGANISM: Bacillus subtilis

<400> SEQUENCE: 13

Ser Ser Thr Met Ile Arg
 1               5

<210> SEQ ID NO 14
<211> LENGTH: 6
<212> TYPE: PRT
<213> ORGANISM: M. jannaschii

<400> SEQUENCE: 14

Ser Gly Thr Glu Ile Arg
 1               5

<210> SEQ ID NO 15
<211> LENGTH: 6
<212> TYPE: PRT
<213> ORGANISM: M. thermoautotrophicum

<400> SEQUENCE: 15

Ser Gly Thr Glu Val Arg
 1               5

<210> SEQ ID NO 16
<211> LENGTH: 6
<212> TYPE: PRT
<213> ORGANISM: Bacillus subtilis

<400> SEQUENCE: 16

Ser Ser Ser Leu Val Lys
 1               5

<210> SEQ ID NO 17
<211> LENGTH: 6
<212> TYPE: PRT
<213> ORGANISM: Bacillus subtilis

<400> SEQUENCE: 17

Ser Thr Thr Lys Ile Lys
 1               5

<210> SEQ ID NO 18
<211> LENGTH: 4
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
```

```
<222> LOCATION: 1
<223> OTHER INFORMATION: Xaa = His or Thr
<220> FEATURE:
<221> NAME/KEY: VARIANT
<222> LOCATION: 2
<223> OTHER INFORMATION: Xaa = any amino acid

<400> SEQUENCE: 18

Xaa Xaa Gly His
 1

<210> SEQ ID NO 19
<211> LENGTH: 4
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 2
<223> OTHER INFORMATION: Xaa = any amino acid

<400> SEQUENCE: 19

His Xaa Gly His
 1

<210> SEQ ID NO 20
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 2, 3, 4, 5
<223> OTHER INFORMATION: Xaa = any amino acid
<220> FEATURE:
<221> NAME/KEY: VARIANT
<222> LOCATION: 6
<223> OTHER INFORMATION: Xaa = Arg or Lys

<400> SEQUENCE: 20

Ser Xaa Xaa Xaa Xaa Xaa
 1               5

<210> SEQ ID NO 21
<211> LENGTH: 5
<212> TYPE: PRT
<213> ORGANISM: Artificial Sequence
<220> FEATURE:
<223> OTHER INFORMATION: Conserved motif

<400> SEQUENCE: 21

Lys Phe Gly Lys Thr
 1               5

<210> SEQ ID NO 22
<211> LENGTH: 5
<212> TYPE: PRT
<213> ORGANISM: Artificial Sequence
<220> FEATURE:
<223> OTHER INFORMATION: Conserved motif

<400> SEQUENCE: 22

Val Met Ser Lys Arg
 1               5

<210> SEQ ID NO 23
<211> LENGTH: 8
```

```
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = any amino acid

<400> SEQUENCE: 23

Arg Thr Xaa Gly Ile Ser Thr Thr
 1               5

<210> SEQ ID NO 24
<211> LENGTH: 4
<212> TYPE: PRT
<213> ORGANISM: Bacillus subtilis

<400> SEQUENCE: 24

His Asn Gly His
 1

<210> SEQ ID NO 25
<211> LENGTH: 4
<212> TYPE: PRT
<213> ORGANISM: Artificial Sequence
<220> FEATURE:
<223> OTHER INFORMATION: Conserved motif

<400> SEQUENCE: 25

Pro Pro His Lys
 1

<210> SEQ ID NO 26
<211> LENGTH: 189
<212> TYPE: PRT
<213> ORGANISM: Bacillus subtilis

<400> SEQUENCE: 26

Ser Lys Lys Ile Gly Ile Phe Gly Gly Thr Phe Asp Pro Pro His Asn
 1               5                  10                  15

Gly His Leu Leu Met Ala Asn Glu Val Leu Tyr Gln Ala Gly Leu Asp
             20                  25                  30

Glu Ile Trp Phe Met Pro Asn Gln Ile Pro Pro His Lys Gln Asn Glu
         35                  40                  45

Asp Tyr Thr Asp Ser Phe His Arg Val Glu Met Leu Lys Leu Ala Ile
     50                  55                  60

Gln Ser Asn Pro Ser Phe Lys Leu Glu Leu Val Glu Met Glu Arg Glu
65                  70                  75                  80

Gly Pro Ser Tyr Thr Phe Asp Thr Val Ser Leu Leu Lys Gln Arg Tyr
                 85                  90                  95

Pro Asn Asp Gln Leu Phe Phe Ile Ile Gly Ala Asp Met Ile Glu Tyr
            100                 105                 110

Leu Pro Lys Trp Tyr Lys Leu Asp Glu Leu Leu Asn Leu Ile Gln Phe
        115                 120                 125

Ile Gly Val Lys Arg Pro Gly Phe His Val Glu Thr Pro Tyr Pro Leu
    130                 135                 140

Leu Phe Ala Asp Val Pro Glu Phe Glu Val Ser Ser Thr Met Ile Arg
145                 150                 155                 160

Glu Arg Phe Lys Ser Lys Lys Pro Thr Asp Tyr Leu Ile Pro Asp Lys
                165                 170                 175
```

```
Val Lys Lys Tyr Val Glu Glu Asn Gly Leu Tyr Glu Ser
            180                 185

<210> SEQ ID NO 27
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 27

Lys Met Ser Lys Ser
 1               5
```